US012790375B2

(12) United States Patent
Krivega et al.

(10) Patent No.: US 12,790,375 B2
(45) Date of Patent: Nov. 10, 2026

(54) METHODS AND COMPOSITIONS FOR IMPROVED DELIVERY VIA ULTRASOUND

(71) Applicant: SonoThera, Inc., South San Francisco, CA (US)

(72) Inventors: Ivan Krivega, Burlingame, CA (US); Margarita Krivega, South San Francisco, CA (US); Steven B. Feinstein, Highland Park, IL (US); Kenneth Greenberg, Berkeley, CA (US)

(73) Assignee: SonoThera, Inc., South San Francisco, CA (US)

( * ) Notice: Subject to any disclaimer, the term of this patent is extended or adjusted under 35 U.S.C. 154(b) by 0 days.

(21) Appl. No.: 19/418,762

(22) Filed: Dec. 12, 2025

(65) Prior Publication Data

US 2026/0176312 A1 Jun. 25, 2026

Related U.S. Application Data

(63) Continuation of application No. PCT/US2025/055812, filed on Nov. 17, 2025.

(60) Provisional application No. 63/894,540, filed on Oct. 6, 2025, provisional application No. 63/805,758, filed on May 14, 2025, provisional application No. 63/774,082, filed on Mar. 18, 2025, provisional application No. 63/722,046, filed on Nov. 18, 2024, provisional application No. 63/722,045, filed on Nov. 18, 2024.

(51) Int. Cl.
*C07K 14/47* (2006.01)
*C12N 15/85* (2006.01)

(52) U.S. Cl.
CPC .......... *C07K 14/4708* (2013.01); *C12N 15/85* (2013.01); *C12N 2830/008* (2013.01)

(58) Field of Classification Search
None
See application file for complete search history.

(56) References Cited

U.S. PATENT DOCUMENTS 5,190,766 A 3/1993 Ishihara
5,498,421 A 3/1996 Grinstaff et al.
5,542,935 A 8/1996 Unger et al.
5,558,092 A 9/1996 Unger et al.
5,580,575 A 12/1996 Unger et al.
5,770,222 A 6/1998 Unger et al.
5,849,727 A 12/1998 Porter et al.
5,961,459 A 10/1999 Kaul et al.
6,048,903 A 4/2000 Toppo
6,066,123 A 5/2000 Li et al.
6,068,857 A 5/2000 Weitschies et al.
6,071,495 A 6/2000 Unger et al.
6,117,858 A 9/2000 Porter et al.
6,120,751 A 9/2000 Unger
RE36,939 E 10/2000 Tachibana et al.
6,135,976 A 10/2000 Tachibana et al.
6,139,819 A 10/2000 Unger et al.
6,265,387 B1 7/2001 Wolff et al.
6,575,956 B1 6/2003 Brisken et al.
6,743,779 B1 6/2004 Unger et al.
7,211,248 B2 5/2007 Davidson
7,351,535 B2 4/2008 Lawn et al.
7,892,824 B2 2/2011 Duan et al.
9,303,078 B2 4/2016 Garcia
9,393,328 B2 7/2016 Coles et al.
9,804,151 B2 10/2017 Shroff
10,266,827 B2 4/2019 Wilton et al.
10,351,611 B2 7/2019 Lai et al.
10,947,540 B2 3/2021 Bitoun et al.
RE48,960 E 3/2022 Wilton et al.
11,473,071 B2 10/2022 Yoshimi et al.
11,479,772 B2 10/2022 Caruthers et al.
11,597,931 B2 3/2023 Xia et al.
11,685,916 B2 6/2023 Zhang et al.
11,732,259 B2 8/2023 Hanson
11,872,287 B2 1/2024 Geall et al.
11,958,888 B2 4/2024 Chamberlain et al.

(Continued)

FOREIGN PATENT DOCUMENTS

EP 2704749 A1 3/2014
EP 3327127 A1 5/2018

(Continued)

OTHER PUBLICATIONS

Abstract and Case Policies and Procedures. American College of Cardiology 74th Annual Scientific Session & Expo. pp. 1-8. (2024).
Antoniou, Michael. et al. Efficient 3'-end Formation of Human beta-globin mRNA in Vivo Requires Sequences Within the Last Intron but Occurs Independently of the Splicing Reaction. Nucleic Acids Research 26(3):721-729 (1998).
ASH Abstract Acceptance: Poster Presentation (Abstract #2232); Email from Surabhi Rao dated Oct. 2, 2024. pp. 1-6. (2024).
Beekman, Chantal, et al. Use of capillary Western immunoassay (Wes) for quantification of dystrophin levels in skeletal muscle of healthy controls and individuals with Becker and Duchenne muscular dystrophy. PloS one 13.4: e0195850. (2018).

(Continued)

*Primary Examiner* — Manjunath N Rao
*Assistant Examiner* — Jae W Lee
(74) *Attorney, Agent, or Firm* — WILSON SONSINI GOODRICH & ROSATI

(57) ABSTRACT

Provided are methods and compositions for expressing a functional dystrophin protein or a functional fragment thereof in a subject. The method can include administering a nucleic acid encoding the dystrophin protein to the subject, administering a sonoactive agent to the subject, and applying ultrasound energy the cell. Also provided are use of a nucleic acid encoding a functional dystrophin protein and a sonoactive agent in a method of treating a subject having a dystrophinopathy disorder requiring a dystrophin gene therapy or a dystrophin protein replacement therapy.

19 Claims, 29 Drawing Sheets

Specification includes a Sequence Listing.

(56) References Cited

U.S. PATENT DOCUMENTS

| | | | |
|---|---|---|---|
| 11,959,094 | B2 | 4/2024 | Izpisua Belmonte et al. |
| 12,012,439 | B2 | 6/2024 | Dickson et al. |
| 12,053,441 | B2 | 8/2024 | Hekimi et al. |
| 12,076,419 | B2 | 9/2024 | Ren |
| 12,104,152 | B2 | 10/2024 | Khurana et al. |
| 12,163,148 | B2 | 12/2024 | Yeo et al. |
| 12,171,843 | B2 | 12/2024 | Mingozzi et al. |
| 12,221,636 | B2 | 2/2025 | Zhang et al. |
| 2001/0008758 | A1 | 7/2001 | McHale et al. |
| 2001/0009904 | A1 | 7/2001 | Wolff et al. |
| 2002/0165191 | A1 | 11/2002 | Moonen |
| 2004/0266663 | A1 | 12/2004 | Schwartz et al. |
| 2007/0196283 | A1 | 8/2007 | Davidson |
| 2019/0134221 | A1 | 5/2019 | Bumcrot et al. |
| 2019/0151476 | A1 | 5/2019 | Gersbach et al. |
| 2019/0338311 | A1 | 11/2019 | Amoasii et al. |
| 2020/0282074 | A1 | 9/2020 | Levin et al. |
| 2020/0332272 | A1 | 10/2020 | Zhang et al. |
| 2020/0405824 | A1 | 12/2020 | Odom et al. |
| 2021/0002665 | A1 | 1/2021 | Gersbach et al. |
| 2021/0024907 | A1 | 1/2021 | Angel et al. |
| 2021/0087555 | A1 | 3/2021 | Li et al. |
| 2021/0130800 | A1 | 5/2021 | Zhang et al. |
| 2021/0139550 | A1 | 5/2021 | Duan et al. |
| 2021/0238597 | A1 | 8/2021 | Turunen et al. |
| 2021/0253563 | A1 | 8/2021 | Morgan et al. |
| 2021/0254062 | A1 | 8/2021 | Zhang et al. |
| 2021/0276991 | A1 | 9/2021 | Morgan et al. |
| 2021/0290772 | A1 | 9/2021 | Wolfe et al. |
| 2021/0315994 | A1 | 10/2021 | Liu et al. |
| 2021/0361779 | A1 | 11/2021 | Zhang et al. |
| 2021/0388379 | A1 | 12/2021 | Kotin et al. |
| 2021/0395729 | A1 | 12/2021 | Woolf |
| 2021/0395770 | A1 | 12/2021 | Vandendriessche et al. |
| 2021/0403947 | A1 | 12/2021 | Banks et al. |
| 2022/0031865 | A1 | 2/2022 | Ramu et al. |
| 2022/0096606 | A1 | 3/2022 | Gromada et al. |
| 2022/0145347 | A1 | 5/2022 | Bachmann et al. |
| 2022/0162640 | A1 | 5/2022 | Ronzitti et al. |
| 2022/0170013 | A1 | 6/2022 | Liu et al. |
| 2022/0177879 | A1 | 6/2022 | Gersbach et al. |
| 2022/0195406 | A1 | 6/2022 | Gersbach et al. |
| 2022/0204448 | A1 | 6/2022 | Zhi et al. |
| 2022/0220468 | A1 | 7/2022 | Sheen et al. |
| 2022/0238182 | A1 | 7/2022 | Shen et al. |
| 2022/0243228 | A1 | 8/2022 | Angel et al. |
| 2022/0249701 | A1 | 8/2022 | Regev et al. |
| 2022/0280652 | A1 | 9/2022 | Whitehead et al. |
| 2022/0306573 | A1 | 9/2022 | Zhang et al. |
| 2023/0024301 | A1 | 1/2023 | Kupatt et al. |
| 2023/0032846 | A1 | 2/2023 | Gersbach et al. |
| 2023/0036370 | A1 | 2/2023 | Mali et al. |
| 2023/0040544 | A1 | 2/2023 | Pozsgai et al. |
| 2023/0044997 | A1 | 2/2023 | Bojjireddy et al. |
| 2023/0046606 | A1 | 2/2023 | Bojjireddy et al. |
| 2023/0174977 | A1 | 6/2023 | Packard et al. |
| 2023/0183740 | A1 | 6/2023 | Ozsolak et al. |
| 2023/0193266 | A1 | 6/2023 | Caruthers et al. |
| 2023/0212577 | A1 | 7/2023 | Burge et al. |
| 2023/0257723 | A1 | 8/2023 | Gersbach et al. |
| 2023/0270886 | A1 | 8/2023 | Qiao et al. |
| 2023/0272378 | A1 | 8/2023 | Lueck et al. |
| 2023/0272428 | A1 | 8/2023 | Wagers |
| 2023/0277686 | A1 | 9/2023 | Lostal et al. |
| 2023/0287419 | A1 | 9/2023 | Chang et al. |
| 2023/0313186 | A1 | 10/2023 | Khurana |
| 2023/0332144 | A1 | 10/2023 | Liu et al. |
| 2023/0348870 | A1 | 11/2023 | Gersbach et al. |
| 2023/0357795 | A1 | 11/2023 | Flanigan et al. |
| 2023/0383270 | A1 | 11/2023 | Gersbach et al. |
| 2023/0392132 | A1 | 12/2023 | Gersbach et al. |
| 2023/0407317 | A1 | 12/2023 | Chang et al. |
| 2023/0407331 | A1 | 12/2023 | Banks et al. |
| 2024/0002859 | A1 | 1/2024 | Khurana |
| 2024/0091379 | A1 | 3/2024 | Lek et al. |
| 2024/0100190 | A1 | 3/2024 | He et al. |
| 2024/0108753 | A1 | 4/2024 | Kwok |
| 2024/0116993 | A1 | 4/2024 | Jaskula-Ranga |
| 2024/0141339 | A1 | 5/2024 | Van Deutekom et al. |
| 2024/0141384 | A1 | 5/2024 | Wang et al. |
| 2024/0148904 | A1 | 5/2024 | Duan et al. |
| 2024/0150718 | A1 | 5/2024 | Spuler et al. |
| 2024/0156919 | A1 | 5/2024 | Jantz et al. |
| 2024/0165271 | A1 | 5/2024 | Olson et al. |
| 2024/0200066 | A1 | 6/2024 | Wein et al. |
| 2024/0209360 | A1 | 6/2024 | Flanigan et al. |
| 2024/0226334 | A1 | 7/2024 | Olson et al. |
| 2024/0240185 | A1 | 7/2024 | Mehle et al. |
| 2024/0252683 | A1 | 8/2024 | Fulga et al. |
| 2024/0254509 | A1 | 8/2024 | Flanigan et al. |
| 2024/0269329 | A1 | 8/2024 | Sweeney |
| 2024/0287547 | A1 | 8/2024 | Kuang et al. |
| 2024/0309364 | A1 | 9/2024 | Khurana et al. |
| 2024/0325454 | A1 | 10/2024 | Olson et al. |
| 2024/0327831 | A1 | 10/2024 | Chanda et al. |
| 2024/0350670 | A1 | 10/2024 | Ronzitti et al. |
| 2024/0350674 | A1 | 10/2024 | Brown et al. |
| 2024/0358736 | A1 | 10/2024 | Levin et al. |
| 2024/0358857 | A1 | 10/2024 | Danos et al. |
| 2024/0360452 | A1 | 10/2024 | Van Deutekom |
| 2024/0368596 | A1 | 11/2024 | Hartl et al. |
| 2024/0384249 | A1 | 11/2024 | Harrington et al. |
| 2024/0390522 | A1 | 11/2024 | Sweeney |
| 2024/0391969 | A1 | 11/2024 | Wang et al. |
| 2024/0398993 | A1 | 12/2024 | Foight et al. |
| 2024/0401037 | A1 | 12/2024 | Belayew et al. |
| 2024/0409955 | A1 | 12/2024 | Abbadi et al. |
| 2024/0415984 | A1 | 12/2024 | Fulga et al. |
| 2025/0009904 | A1 | 1/2025 | Savva et al. |
| 2025/0011777 | A1 | 1/2025 | Schissel et al. |
| 2025/0025569 | A1 | 1/2025 | Williams et al. |
| 2025/0032628 | A1 | 1/2025 | Sun et al. |
| 2025/0034536 | A1 | 1/2025 | Owens et al. |
| 2025/0042933 | A1 | 2/2025 | Watanabe et al. |
| 2025/0043269 | A1 | 2/2025 | Lopez et al. |
| 2025/0066496 | A1 | 2/2025 | Subramanian et al. |
| 2025/0099621 | A1 | 3/2025 | Horhota et al. |

FOREIGN PATENT DOCUMENTS

| | | | | |
|---|---|---|---|---|
| EP | 3230445 | A4 | 9/2018 | |
| EP | 3765615 | A1 | 1/2021 | |
| EP | 3765616 | A1 | 1/2021 | |
| EP | 3327127 | B1 | 3/2021 | |
| EP | 3864161 | A1 | 8/2021 | |
| EP | 3997227 | A1 | 5/2022 | |
| EP | 3814370 | A4 | 6/2022 | |
| EP | 3935179 | A4 | 11/2022 | |
| EP | 4146812 | A1 | 3/2023 | |
| EP | 4211242 | A1 | 7/2023 | |
| EP | 4240338 | A1 | 9/2023 | |
| EP | 4247778 | A1 | 9/2023 | |
| EP | 4255495 | A1 | 10/2023 | |
| EP | 4274894 | A2 | 11/2023 | |
| EP | 4352234 | A2 | 4/2024 | |
| EP | 4362954 | A1 | 5/2024 | |
| EP | 4373528 | A2 | 5/2024 | |
| EP | 4402267 | A2 | 7/2024 | |
| EP | 4423266 | A1 | 9/2024 | |
| EP | 4423278 | A1 | 9/2024 | |
| EP | 4475856 | A2 | 12/2024 | |
| EP | 4479536 | A1 | 12/2024 | |
| EP | 4434997 | A3 | 1/2025 | |
| EP | 4489772 | A1 | 1/2025 | |
| EP | 4490292 | A1 | 1/2025 | |
| EP | 4493226 | A1 | 1/2025 | |
| EP | 4511489 | A2 | 2/2025 | |
| WO | WO-2012150960 | A1 | 11/2012 | |
| WO | WO-2020210432 | A1 | 10/2020 | |
| WO | WO-2021007453 | A2 | 1/2021 | |
| WO | WO-2021097157 | A1 | 5/2021 | |
| WO | WO-2021165350 | A1 | 8/2021 | |
| WO | WO-2023141586 | A1 * | 7/2023 | ............ C12N 15/85 |
| WO | WO-2024064913 | A1 | 3/2024 | |

(56) References Cited

FOREIGN PATENT DOCUMENTS

| | | | |
|---|---|---|---|
| WO | WO-2024067885 | A1 | 4/2024 |
| WO | WO-2024064237 | A3 | 5/2024 |
| WO | WO-2024129982 | A3 | 7/2024 |
| WO | WO-2024149282 | A1 | 7/2024 |
| WO | WO-2024155745 | A1 | 7/2024 |
| WO | WO-2024173671 | A2 | 8/2024 |
| WO | WO-2024178172 | A1 | 8/2024 |
| WO | WO-2024182358 | A1 | 9/2024 |
| WO | WO-2024193704 | A1 | 9/2024 |
| WO | WO-2024192281 | A3 | 10/2024 |
| WO | WO-2024197951 | A1 | 10/2024 |
| WO | WO-2024206891 | A1 | 10/2024 |
| WO | WO-2024216116 | A1 | 10/2024 |
| WO | WO-2024216118 | A1 | 10/2024 |
| WO | WO-2024229028 | A2 | 11/2024 |
| WO | WO-2024254519 | A2 | 12/2024 |
| WO | WO-2024254709 | A1 | 12/2024 |
| WO | WO-2024155741 | A9 | 1/2025 |
| WO | WO-2024238595 | A3 | 1/2025 |
| WO | WO-2025007916 | A1 | 1/2025 |
| WO | WO-2025017168 | A1 | 1/2025 |
| WO | WO-2025017169 | A1 | 1/2025 |
| WO | WO-2025019273 | A1 | 1/2025 |
| WO | WO-2025030099 | A1 | 2/2025 |

OTHER PUBLICATIONS

Benthall, Katie, et al. Cellular Phenotyping of Non-Human Primate and Mouse Kidney and Liver Following a Novel Targeted Transcutaneous Ultrasound-Mediated Gene Delivery Demonstrates Gene Expression in Clinically Relevant Cell Types. Molecular Therapy. vol. 32. No. 4. Cell Press. (2024).

Benthall, Katie; et al. Development of a Non-viral Gene Therapy for X-linked Alport Syndrome by Targeted Transcutaneous Ultrasound-Mediated Gene Delivery: TH-OR90. Journal of the American Society of Nephrology 35(10S):10.1681/ASN.2024qxx815yr. (2024).

Campbell, Barry, et al. Non-viral Gene Delivery Utilizing Transcutaneous Ultrasound Enables Rapid and Robust Gene Expression. American Society of Gene & Cell Therapy. pp. 1. (2023).

Castle, Jason W., et al. Therapeutic ultrasound: increased HDL-cholesterol following infusions of acoustic microspheres and apolipoprotein AI plasmids. Atherosclerosis 241.1: 92-99. (2015).

Chan, Jonathan, et al. Non-viral, Ultrasound Mediated Gene Delivery to the Heart of Mice and Macaques. Toxicology Research Laboratory & SonoThera, Sessions 2024. pp. 1-3. (2024).

Chan, Jonathan, et al. Non-viral, Ultrasound Mediated Gene Delivery to the Heart of Mice and Non-Human Primates. American Heart Association. pp. 1. (2024).

Chen, Shuyuan, et al. Optimization of ultrasound parameters for cardiac gene delivery of adenoviral or plasmid deoxyribonucleic acid by ultrasound-targeted microbubble destruction. Journal of the American College of Cardiology 42.2: 301-308. (2003).

Chen, Shuyuan, et al. Successful ß cells islet regeneration in streptozotocin-induced diabetic baboons using ultrasound-targeted microbubble gene therapy with cyclinD2/CDK4/GLP1. Cell Cycle 13.7: 1145-1151. (2014).

Danialou, Gawiyou. et al. Ultrasound Increases Plasmid-mediated Gene Transfer to Dystrophic Muscles Without Collateral Damage. Molecular therapy 6(5):687-693 (2002).

Dittmar, Kristin M., et al. Pulsed high-intensity focused ultrasound enhances systemic administration of naked DNA in squamous cell carcinoma model: initial experience. Radiology 235.2: 541-546. (2005).

Frederich, Bert, et al. Kidney-targeted non-viral gene delivery using a novel, noninvasive, transcutaneous, ultrasound delivery platform enables redosable, titratable, and durable gene expression in healthy mice and NHPs, and polycystic kidneys mouse model. American Society of Gene & Cell Therapy. pp. 1. (2024).

Frederich, Bert J., et al. Kidney-Targeted Delivery of Non-viral Nucleic Acids Using Noninvasive Transcutaneous Ultrasound Enables Safe, Re-dosable, Titratable, and Durable Gene Expression in Mice and Nonhuman Primates. American Society of Nephrology. pp. 1. (2024).

Frederich, Bert J., et al. Kidney-Targeted Non-Viral Gene Delivery Using a Novel Noninvasive Transcutaneous Ultrasound Delivery Platform Enables Redosable, Titratable, and Durable Gene Expression in Healthy Mice and NHPs, and Polycystic Kidneys Mouse Model. Molecular Therapy. vol. 32. No. 4. Cell Press. (2024).

Goossens, Remko, et al. DMD antisense oligonucleotide mediated exon skipping efficiency correlates with flanking intron retention time and target position within the exon. RNA biology 20.1: 693-702. (2023).

Haddad-Mashadrizeh, Aliakbar. et al. A Systematic Study of the Function of the Human Beta-globin Introns on the Expression of the Human Coagulation Factor IX in Cultured Chinese Hamster Ovary Cells. The Journal of Gene Medicine 11(10):941-950 (2009).

Helfield, Brandon, et al. Biophysical insight into mechanisms of sonoporation. Proceedings of the National Academy of Sciences 113.36: 9983-9988. (2016).

Huber, P. E. et al. Focused ultrasound (HIFU) induces localized enhancement of reporter gene expression in rabbit carotid artery. Gene Therapy 10(18):1600-1607 (2003).

Krivega, Ivan, et al. Development of a non-viral genetic medicine for Hemophilia A by targeted transcutaneous ultrasound-mediated gene delivery. ESGCT, SonoThera. pp. 1-15. (2024).

Krivega, Ivan, et al. Development of a non-viral genetic medicine for X-linked Alport syndrome by targeted transcutaneous ultrasound-mediated gene delivery. European Society of Gene & Cell Therapy. pp. 1. (2024).

Krivega, Ivan, et al. Engineering FVIII Protein for Enhancing Expression and Secretion Profile to Achieve Normal Level of FVIII in Plasma Utilizing Noninvasive Transcutaneous Ultrasound Mediated Gene Delivery. Blood 144. Supplement 1: 7458-7458. (2024).

Krivega, Ivan, et al. Engineering FVIII protein for enhancing expression and secretion profile to achieve normal level of FVIII in plasma utilizing noninvasive transcutaneous ultrasound mediated gene delivery. International Society on Thrombosis and Haemostasis, Inc. pp. 1-15. (2024).

Krivega, Ivan, et al. Non-Viral Gene Therapy for DMD Allowing Full-Length Dystrophin Delivery to Skeletal, Cardiac, and Diaphragm Muscles. MDA conference 2025. pp. 1-14. (2025).

Krivega, Ivan, et al. Non-Viral Genetic Medicine for Targeted Delivery of Full-Length Dystrophin to Skeletal, Cardiac, and Diaphragm Muscles in DMD Mouse Models and Non-Human Primates. American Society of Gene & Cell Therapy 2025 Annual Meeting. pp. 1. (2025).

Krivega, Margarita, et al. Development of a Next-Generation Non-Viral Human FVIII Therapeutic Administered through Targeted Transcutaneous Ultrasound Enables Normal Physiological Levels of FVIII Transgene Expression in a Redosable and Titratable Manner. Molecular Therapy. vol. 32. No. 4.: Cell Press. (2024).

Krivega, Margarita, et al. Development of a non-viral genetic medicine for ADPKD administered through targeted transcutaneous ultrasound mediated delivery. American Society of Nephrology. pp. 1. (2024).

Krivega, Margarita, et al. Development of a Non-viral Genetic Medicine for ADPKD Administered through Targeted Transcutaneous Ultrasound-Mediated Delivery: TH-PO431. Journal of the American Society of Nephrology 35.10S: 10-1681. (2024).

Krivega, Margot, et al. Development of a next-generation non-viral human FVIII therapeutic administered through targeted transcutaneous ultrasound enables normal physiological levels of FVIII transgene expression in a redosable and titratable manner. American Society of Gene & Cell Therapy. pp. 1. (2024).

Manson, M. et al. Transcutaneous ultrasound-mediated gene delivery into canine livers achieves therapeutic levels of factor VIII expression. blood advances: vol. 6, No. 12, 3557-3568 (2022).

Mehier-Humbert, Sophie, et al. Ultrasound-mediated gene delivery: kinetics of plasmid internalization and gene expression. Journal of Controlled Release 104.1: 203-211. (2005).

Miao, Carol H., et al. Enhanced Gene Expression of Factor VIII by Ultrasound-Mediated Gene Delivery in Dogs. Molecular Therapy 23: S107. (2015).

(56) References Cited

OTHER PUBLICATIONS

Miao, Carol H., et al. High-level factor VIII gene expression in vivo achieved by nonviral liver-specific gene therapy vectors. Human gene therapy 14.14: 1297-1305. (2003).
Miao, Carol H., et al. Ultrasound enhances gene delivery of human factor IX plasmid. Human gene therapy 16.7: 893-905. (2005).
Moonkyung, Kang. et al. Human Beta-globin Second Intron Highly Enhances Expression of Foreign Genes from Murine Cytomegalovirus Immediate-early Promoter. Journal of Microbiology and Biotechnology 15(3): 544-550. (2005).
Morisaka, Hiroyuki, et al. CRISPR-Cas3 induces broad and unidirectional genome editing in human cells. Nature communications 10.1: 5302. (2019).
Noble, Misty L., et al. Improved luciferase gene expression using ultrasound targeted microbubble destruction therapy in swine. AIP Conference Proceedings. vol. 1503. No. 1. American Institute of Physics. (2012).
Noble-Vranish, Misty L., et al. Ultrasound-mediated gene therapy in swine livers using single-element, multi-lensed, high-intensity ultrasound transducers. Molecular Therapy Methods & Clinical Development 10: 179-188. (2018).
PCT/US2025/055812 International Search Report and Written Opinion dated Feb. 6, 2026.
Rao, Surabhi, et al. Targeted non-viral gene delivery through transcutaneous ultrasound enables rapid, robust, redosable, titratable, and durable gene expression in the liver in murine and NHP models. American Society of Gene & Cell Therapy 2024. pp. 1. (2024).
Rao, Surabhi et al. Targeted non-viral gene delivery through transcutaneous ultrasound enables rapid, robust, redosable, titratable, and durable gene expression in the liver in murine and NHP models. SonoThera Inc. pp. 1-2. (2024).
Rao, Surabhi, et al. Targeted Non-Viral Gene Delivery through Transcutaneous Ultrasound Enables Robust, Redosable, Titratable, and Durable FVIII and FIX Gene Expression in the Liver in Murine Models. Emerging Tools, Techniques, and Artificial Intelligence in Hematology. 2232, pp. 1. (2024).
Schultz, Christopher W. et al. Selecting the optimal parameters for sonoporation of pancreatic cancer in a pre-clinical model. Cancer Biology & Therapy 22(3):204-215 (2021).
Shimamura, Munehisa, et al. Gene transfer into adult rat spinal cord using naked plasmid DNA and ultrasound microbubbles. The Journal of Gene Medicine: A cross-disciplinary journal for research on the science of gene transfer and its clinical applications 7.11: 1468-1474. (2005).
Shohet, Ralph V. et al. Echocardiographic Destruction of Albumin Microbubbles Directs Gene Delivery to the Myocardium. Circulation 101(22):2554-2556 (2000).
Song, Shuxian, et al. Ultrasound-mediated gene delivery of factor VIII plasmids for hemophilia A gene therapy in mice. Molecular Therapy-Nucleic Acids 27: 916-926. (2022).
Song, Zhaojun, et al. Noninvasive, targeted gene therapy for acute spinal cord injury using LIFU-mediated BDNF-loaded cationic nanobubble destruction. Biochemical and biophysical research communications 496.3: 911-920. (2018).
Wang, Guo-zhong. et al. Ultrasonic Destruction of Albumin Microbubbles Enhances Gene Transfection and Expression in Cardiac Myocytes. Chinese Medical Journal 124(9):1395-1400 (2011).
Zhang, G., et al. Hydroporation as the mechanism of hydrodynamic delivery. Gene therapy 11.8: 675-682. (2004).
U.S. Appl. No. 19/391,999 Office Action dated Jun. 3, 2026.
Walsh, Aidan P.G. et al. Ultrasonic Particles: an Approach for Targeted Gene Delivery. Advanced Drug Delivery Reviews 179:113998, 1-20 (2021).

* cited by examiner one-time treated MDX skeletal muscle; arrows indicate positive myofibers treated MDX skeletal muscle without ultrasound (no US)

one-time treated MDX heart muscle; arrows indicate positive myocytes one-time treated MDX heart muscle without ultrasound (no US)

one-time treated MDX diaphragm muscle; arrows/oval indicate positive myocytes naïve MDX diaphragm muscle

Ultrasound mediated gene delivery treated tissue

Naïve tissue

Blue: DAPI stained nuclei
Yellow: human full-length dystrophin

Blue: DAPI stained nuclei
Yellow: human full-length dystrophin

Blue: DAPI stained nuclei
Yellow: human full-length dystrophin

SEQUENCE LISTING

Sequence total quantity: 51
SEQ ID NO: 1 moltype = DNA length = 11061
FEATURE Location/Qualifiers
source 1..11061
mol_type = other DNA
note = DMD-WT
organism = synthetic construct
SEQUENCE: 1

```
atgctttggt gggaagaagt agaggactgt tatgaaagag aagatgttca aaagaaaaca  60
ttcacaaaat gggtaaatgc acaattttct aagtttggga agcagcatat tgagaacctc  120
ttcagtgacc tacaggatgg gaggcgcctc ctagacctcc tcgaaggcct gacagggcaa  180
aaactgccaa aagaaaaagg atccacaaga gttcatgccc tgaacaatgt caacaaggca  240
ctgcgggttt tgcagaacaa taatgttgat ttagtgaata ttggaagtac tgacatcgta  300
gatggaaatc ataaactgac tcttggtttg atttggaata taatcctcca ctggcaggtc  360
aaaaatgtaa tgaaaaatat catggctgga ttgcaacaaa ccaacagtga aaagattctc  420
ctgagctggg tccgacaatc aactcgtaat tatccacagg ttaatgtaat caacttcacc  480
accagctggt ctgatggcct ggctttgaat gctctcatcc atagtcatag gccagaccta  540
tttgactgga atagtgtggt ttgccagcag tcagccacac aacgactgga acatgcattc  600
aacatcgcca gatatcaatt aggcatagag aaactactcg atcctgaaga tgttgatacc  660
acctatccag ataagaagtc catcttaatg tacatcacat cactcttcca agttttgcct  720
caacaagtga gcattgaagc catccaggaa gtggaaatgt tgccaaggcc acctaaagtg  780
actaaagaag aacattttca gttacatcat caaatgcact attctcaaca gatcacggtc  840
agtctagcac agggatatga gagaacttct tcccctaagc ctcgattcaa gagctatgcc  900
tacacacagg ctgcttatgt caccacctct gaccctacac ggagcccatt tccttcacag  960
catttggaag ctcctgaaga caagtcattt ggcagttcat tgatggagag tgaagtaaac  1020
ctggaccgtt atcaaacagc tttagaagaa gtattatcgt ggcttctttc tgctgaggac  1080
acattgcaag cacaaggaga gatttctaat gatgtggaag tggtgaaaga ccagtttcat  1140
actcatgagg ggtacatgat ggatttgaca gcccatcagg gccgggttgg taatattcta  1200
caattgggaa gtaagctgat tggaacagga aaattatcag aagatgaaga aactgaagta  1260
caagagcaga tgaatctcct aaattcaaga tgggaatgcc tcagggtagc tagcatggaa  1320
aaacaaagca atttacatag agttttaatg gatctccaga atcagaaact gaaagagttg  1380
aatgactggc taacaaaaac agaagaaaga acaaggaaaa tggaggaaga gcctcttgga  1440
cctgatcttg aagacctaaa acgccaagta caacaacata aggtgcttca agaagatcta  1500
```

```
gaacaagaac aagtcagggt caattctctc actcacatgg tggtggtagt tgatgaatct  1560
agtggagatc acgcaactgc tgctttggaa gaacaactta aggtattggg agatcgatgg  1620
gcaaacatct gtagatggac agaagaccgc tgggttcttt tacaagacat ccttctcaaa  1680
tggcaacgtc ttactgaaga acagtgcctt tttagtgcat ggctttcaga aaaagaagat  1740
gcagtgaaca agattcacac aactggcttt aaagatcaaa atgaaatgtt atcaagtctt  1800
caaaaactgg ccgttttaaa agcggatcta gaaaagaaaa agcaatccat gggcaaactg  1860
tattcactca aacaagatct tctttcaaca ctgaagaata agtcagtgac ccagaagacg  1920
gaagcatggc tggataactt tgcccggtgt tgggataatt tagtccaaaa acttgaaaag  1980
agtacagcac agatttcaca ggctgtcacc accactcagc catcactaac acagacaact  2040
gtaatggaaa cagtaactac ggtgaccaca agggaacaga tcctggtaaa gcatgctcaa  2100
gaggaacttc caccaccacc tccccaaaag aagaggcaga ttactgtgga ttctgaaatt  2160
aggaaaaggt tggatgttga tataactgaa cttcacagct ggattactcg ctcagaagct  2220
gtgttgcaga gtcctgaatt tgcaatcttt cggaaggaag gcaacttctc agacttaaaa  2280
gaaaaagtca atgccataga gcgagaaaaa gctgagaagt tcagaaaact gcaagatgcc  2340
agcagatcag ctcaggccct ggtggaacag atggtgaatg agggtgttaa tgcagatagc  2400
atcaaacaag cctcagaaca actgaacagc cggtggatcg aattctgcca gttgctaagt  2460
gagagactta actggctgga gtatcagaac aacatcatcg ctttctataa tcagctacaa  2520
caattggagc agatgacaac tactgctgaa aactggttga aaatccaacc caccacccca  2580
tcagagccaa cagcaattaa aagtcagtta aaaatttgta aggatgaagt caaccggcta  2640
tcagatcttc aacctcaaat tgaacgatta aaaattcaaa gcatagccct gaaagagaaa  2700
ggacaaggac ccatgttcct ggatgcagac tttgtggcct ttacaaatca ttttaagcaa  2760
gtcttttctg atgtgcaggc cagagagaaa gagctacaga caatttttga cactttgcca  2820
ccaatgcgct atcaggaaac catgagtgcc atcaggacat gggtccagca gtcagaaacc  2880
aaactctcca tacctcaact tagtgtcacc gactatgaaa tcatggagca gagactcggg  2940
gaattgcagg ctttacaaag ttctctgcaa gagcaacaaa gtggcctata ctatctcagc  3000
accactgtga aagagatgtc gaagaaagcg ccctctgaaa ttagccggaa atatcaatca  3060
gaatttgaag aaattgaggg acgctggaag aagctctcct cccagctggt tgagcattgt  3120
caaaagctag aggagcaaat gaataaactc cgaaaaattc agaatcacat acaaaccctg  3180
aagaaatgga tggctgaagt tgatgttttt ctgaaggagg aatggcctgc ccttggggat  3240
tcagaaattc taaaaaagca gctgaaacag tgcagacttt tagtcagtga tattcagaca  3300
attcagccca gtctaaacag tgtcaatgaa ggtgggcaga agataaagaa tgaagcagag  3360
ccagagtttg cttcgagact tgagacagaa ctcaaagaac ttaacactca gtgggatcac  3420
atgtgccaac aggtctatgc cagaaaggag gccttgaagg gaggtttgga gaaaactgta  3480
agcctccaga aagatctatc agagatgcac gaatggatga cacaagctga agaagagtat  3540
cttgagagag attttgaata taaaactcca gatgaattac agaaagcagt tgaagagatg  3600
aagagagcta aagaagaggc ccaacaaaaa gaagcgaaag tgaaactcct tactgagtct  3660
gtaaatagtg tcatagctca agctccacct gtagcacaag aggccttaaa aaaggaactt  3720
gaaactctaa ccaccaacta ccagtggctc tgcactaggc tgaatgggaa atgcaagact  3780
ttggaagaag tttgggcatg ttggcatgag ttattgtcat acttggagaa agcaaacaag  3840
tggctaaatg aagtagaatt taaacttaaa accactgaaa acattcctgg cggagctgag  3900
gaaatctctg aggtgctaga ttcacttgaa aatttgatgc gacattcaga ggataaccca  3960
aatcagattc gcatattggc acagaccta acagatggcg gagtcatgga tgagctaatc  4020
aatgaggaac ttgagacatt taattctcgt tggagggaac tacatgaaga ggctgtaagg  4080
aggcaaaagt tgcttgaaca gagcatccag tctgcccagg agactgaaaa atccttacac  4140
ttaatccagg agtccctcac attcattgac aagcagttgg cagcttatat tgcagacaag  4200
gtggacgcag ctcaaatgcc tcaggaagcc cagaaaatcc aatctgattt gacaagtcat  4260
gagatcagtt tagaagaaat gaagaaacat aatcagggga aggaggctgc ccaaagagtc  4320
ctgtctcaga ttgatgttgc acagaaaaaa ttacaagatg tctccatgaa gtttcgatta  4380
ttccagaaac cagccaattt tgagcagcgt ctacaagaaa gtaagatgat tttagatgaa  4440
gtgaagatgc acttgcctgc attggaaaca aagagtgtgg aacaggaagt agtacagtca  4500
cagctaaatc attgtgtgaa cttgtataaa agtctgagtg aagtgaagtc tgaagtggaa  4560
atggtgataa agactggacg tcagattgta cagaaaaagc agacggaaaa tcccaaagaa  4620
cttgatgaaa gagtaacagc tttgaaattg cattataatg agctgggagc aaaggtaaca  4680
gaaagaaagc aacagttgga gaaatgcttg aaattgtccc gtaagatgcg aaaggaaatg  4740
aatgtcttga cagaatggct ggcagctaca gatatggaat tgacaaagag atcagcagtt  4800
gaaggaatgc ctagtaattt ggattctgaa gttgcctggg gaaaggctac tcaaaaagag  4860
attgagaaac agaaggtgca cctgaagagt atcacagagg taggagaggc cttgaaaaca  4920
gttttgggca agaaggagac gttggtggaa gataaactca gtcttctgaa tagtaactgg  4980
atagctgtca cctcccgagc agaagagtgg ttaaatcttt tgttggaata ccagaaacac  5040
atggaaactt ttgaccagaa tgtggaccac atcacaaagt ggatcattca ggctgacaca  5100
cttttggatg aatcagagaa aaagaaaccc cagcaaaaag aagacgtgct taagcgttta  5160
aaggcagaac tgaatgacat acgcccaaag gtggactcta cacgtgacca agcagcaaac  5220
ttgatggcaa accgcggtga ccactgcagg aaattagtag agccccaaat ctcagagctc  5280
aaccatcgat ttgcagccat ttcacacaga attaagactg gaaaggcctc cattcctttg  5340
aaggaattgg agcagtttaa ctcagatata caaaaattgc ttgaaccact ggaggctgaa  5400
attcagcagg gggtgaatct gaaagaggaa gacttcaata aagatatgaa tgaagacaat  5460
gagggtactg taaaagaatt gttgcaaaga ggagacaact tacaacaaag aatcacagat  5520
gagagaaagc gagaggaaat aaagataaaa cagcagctgt tacagacaaa acataatgct  5580
ctcaaggatt tgaggagcca aagaagaaaa aaggctctag aaatttctca tcagtggtat  5640
cagtacaaga ggcaggctga tgatctcctg aaatgcttgg atgacattga aaaaaaatta  5700
gccagcctac ctgagcccag agatgaaagg aaaataaagg aaattgatcg ggaattgcag  5760
aagaagaaag aggagctgaa tgcagtgcgt aggcaagctg agggcttgtc tgaggatggg  5820
gccgcaatgg cagtggagcc aactcagatc cagctcagca agcgctggcg ggaaattgag  5880
agcaaatttg ctcagtttcg aagactcaac tttgcacaaa ttcacactgt ccgtgaagaa  5940
acgatgatgg tgatgactga agacatgcct ttggaaattt cttatgtgcc ttctacttat  6000
ttgactgaaa tcactcatgt ctcacaagcc ctattagaag tggaacaact tctcaatgct  6060
cctgacctct gtgctaagga ctttgaagat ctctttaagc aagaggagtc tctgaagaat  6120
ataaaagata gtctacaaca aagctcaggt cggattgaca ttattcatag caagaagaca  6180
gcagcattgc aaagtgcaac gcctgtggaa agggtgaagc tacaggaagc tctctcccag  6240
```

```
cttgatttcc aatgggaaaa agttaacaaa atgtacaagg accgacaagg gcgatttgac  6300
agatctgttg agaaatggcg gcgttttcat tatgatataa agatatttaa tcagtggcta  6360
acagaagctg aacagtttct cagaaagaca caaattcctg agaattggga acatgctaaa  6420
tacaaatggt atcttaagga actccaggat ggcattgggc agcggcaaac tgttgtcaga  6480
acattgaatg caactgggga agaaataatt cagcaatcct caaaaacaga tgccagtatt  6540
ctacaggaaa aattgggaag cctgaatctg cggtggcagg aggtctgcaa acagctgtca  6600
gacagaaaaa agaggctaga agaacaaaag aatatcttgt cagaatttca aagagattta  6660
aatgaatttg ttttatggtt ggaggaagca gataacattg ctagtatccc acttgaacct  6720
ggaaaagagc agcaactaaa agaaaagctt gagcaagtca agttactggt ggaagagttg  6780
cccctgcgcc agggaattct caaacaatta aatgaaactg gaggacccgt gcttgtaagt  6840
gctcccataa gcccagaaga gcaagataaa cttgaaaata agctcaagca gacaaatctc  6900
cagtggataa aggtttccag agctttacct gagaaacaag gagaaattga agctcaaata  6960
aaagaccttg ggcagcttga aaaaaagctt gaagaccttg aagagcagtt aaatcatctg  7020
ctgctgtggt tatctcctat taggaatcag ttggaaattt ataaccaacc aaaccaagaa  7080
ggaccatttg acgttaagga aactgaaata gcagttcaag ctaaacaacc ggatgtggaa  7140
gagattttgt ctaaagggca gcatttgtac aaggaaaaac cagccactca gccagtgaag  7200
aggaagttag aagatctgag ctctgagtgg aaggcggtaa accgtttact tcaagagctg  7260
agggcaaagc agcctgacct agctcctgga ctgaccacta ttggagcctc tcctactcag  7320
actgttactc tggtgacaca acctgtggtt actaaggaaa ctgccatctc caaactagaa  7380
atgccatctt ccttgatgtt ggaggtacct gctctggcag atttcaaccg ggcttggaca  7440
gaacttaccg actggctttc tctgcttgat caagttataa aatcacagag ggtgatggtg  7500
ggtgaccttg aggatatcaa cgagatgatc atcaagcaga aggcaacaat gcaggatttg  7560
gaacagaggc gtccccagtt ggaagaactc attaccgctg cccaaaattt gaaaaacaag  7620
accagcaatc aagaggctag aacaatcatt acggatcgaa ttgaaagaat tcagaatcag  7680
tgggatgaag tacaagaaca ccttcagaac cggaggcaac agttgaatga aatgttaaag  7740
gattcaacac aatggctgga agctaaggaa gaagctgagc aggtcttagg acaggccaga  7800
gccaagcttg agtcatggaa ggagggtccc tatacagtag atgcaatcca aaagaaaatc  7860
acagaaacca agcagttggc caaagacctc cgccagtggc agacaaatgt agatgtggca  7920
aatgacttgg ccctgaaact tctccgggat tattctgcag atgataccag aaaagtccac  7980
atgataacag agaatatcaa tgcctcttgg agaagcattc ataaaagggt gagtgagcga  8040
gaggctgctt tggaagaaac tcatagatta ctgcaacagt tcccccctgga cctggaaaag  8100
tttcttgcct ggcttacaga agctgaaaca actgccaatg tcctacagga tgctacccgt  8160
aaggaaaggc tcctagaaga ctccaaggga gtaaaagagc tgatgaaaca atggcaagac  8220
ctccaaggtg aaattgaagc tcacacagat gtttatcaca acctggatga aaacagccaa  8280
aaaatcctga gatccctgga aggttccgat gatgcagtcc tgttacaaag acgtttggat  8340
aacatgaact tcaagtggag tgaacttcgg aaaaagtctc tcaacattag gtcccatttg  8400
gaagccagtt ctgaccagtg gaagcgtctg cacctttctc tgcaggaact tctggtgtgg  8460
ctacagctga aagatgatga attaagccgg caggcaccta ttggaggcga ctttccagca  8520
gttcagaagc agaacgatgt acatagggcc ttcaagaggg aattgaaaac taaagaacct  8580
gtaatcatga gtactcttga gactgtacga atatttctga cagagcagcc tttggaagga  8640
ctagagaaac tctaccagga gcccagagag ctgcctcctg aggagagagc ccagaatgtc  8700
actcggcttc tacgaaagca ggctgaggag gtcaatactg agtgggaaaa attgaacctg  8760
cactccgctg actggcagag aaaaatagat gaaacccttg aaagactccg ggaacttcaa  8820
gaggccacgg atgagctgga cctcaagctg cgccaagctg aggtgatcaa gggatcctgg  8880
cagcccgtgg gcgatctcct cattgactct ctccaagatc acctggagaa agtcaaggca  8940
cttcgaggag aaattgcgcc tctgaaagag aacgtgagcc acgtcaatga ccttgctcgc  9000
cagcttacca ctttgggcat tcagctctca ccgtataacc tcagcactct ggaagacctg  9060
aacaccagat ggaagcttct gcaggtggcc gtcgaggacc gagtcaggca gctgcatgaa  9120
gcccacaggg actttggtcc agcatctcag cactttcttt ccacgtctgt ccagggtccc  9180
tgggagagag ccatctcgcc aaacaaagtg ccctactata tcaaccacga gactcaaaca  9240
acttgctggg accatcccaa aatgacagag ctctaccagt ctttagctga cctgaataat  9300
gtcagattct cagcttatag gactgccatg aaactccgaa gactgcagaa ggccctttgc  9360
ttggatctct tgagcctgtc agctgcatgt gatgccttgg accagcacaa cctcaagcaa  9420
aatgaccagc ccatggatat cctgcagatt attaattgtt tgaccactat ttatgaccgc  9480
ctggagcaag agcacaacaa tttggtcaac gtccctctct gcgtggatat gtgtctgaac  9540
tggctgctga atgtttatga tacgggacga acagggagga tccgtgtcct gtcttttaaa  9600
actggcatca tttccctgtg taaagcacat ttggaagaca agtacagata cctttttcaag  9660
caagtggcaa gttcaacagg attttgtgac cagcgcaggc tgggcctcct tctgcatgat  9720
tctatccaaa ttccaagaca gttgggtgaa gttgcatcct ttgggggcag taacattgag  9780
ccaagtgtcc ggagctgctt ccaatttgct aataataagc cagagatcga agcggccctc  9840
ttcctagact ggatgagact ggaacccccag tccatggtgt ggctgcccgt cctgcacaga  9900
gtggctgctg cagaaactgc caagcatcag gccaaatgta acatctgcaa agagtgtcca  9960
atcattggat tcaggtacag gagtctaaag cactttaatt atgacatctg ccaaagctgc  10020
tttttttctg gtcgagttgc aaaaggccat aaaatgcact atcccatggt ggaatattgc  10080
actccgacta catcaggaga agatgttcga gactttgcca aggtactaaa aaacaaattt  10140
cgaaccaaaa ggtattttgc gaagcatccc cgaatgggct acctgccagt gcagactgtc  10200
ttagaggggg acaacatgga aactcccgtt actctgatca acttctggcc agtagattct  10260
gcgcctgcct cgtcccctca gctttcacac gatgatactc attcacgcat tgaacattat  10320
gctagcaggc tagcagaaat ggaaaacagc aatggatctt atctaaatga tagcatctct  10380
cctaatgaga gcatagatga tgaacatttg ttaatccagc attactgcca aagtttgaac  10440
caggactccc ccctgagcca gcctcgtagt cctgcccaga tcttgatttc cttagagagt  10500
gaggaaagag gggagctaga gagaatccta gcagatcttg aggaagaaaa caggaatctg  10560
caagcagaat atgaccgtct aaagcagcag cacgaacata aaggcctgtc cccactgccg  10620
tcccctcctg aaatgatgcc cacctctccc cagagtcccc gggatgctga gctcattgct  10680
gaggccaagc tactgcgtca acacaaaggc cgcctggaag ccaggatgca aatcctggaa  10740
gaccacaata aacagctgga gtcacagtta cacaggctaa ggcagctgct ggagcaaccc  10800
caggcagagg ccaaagtgaa tggcacaacg gtgtcctctc cttctacctc tctacagagg  10860
tccgacagca gtcagcctat gctgctccga gtggttggca gtcaaacttc ggactccatg  10920
ggtgaggaag atcttctcag tcctccccag gacacaagca cagggttaga ggaggtgatg  10980
```

```
gagcaactca acaactcctt ccctagttca agaggaagaa atacccctgg aaagccaatg  11040
agagaggaca caatgtagta a                                             11061

SEQ ID NO: 2            moltype = DNA  length = 11061
FEATURE                 Location/Qualifiers
source                  1..11061
                        mol_type = other DNA
                        note = DMD-3
                        organism = synthetic construct
SEQUENCE: 2
atgctgtggt gggaagaggt ggaggactgt tacgagagag aggacgtgca gaagaagaca  60
ttcaccaagt gggtgaacgc tcagttcagc aagttcggca agcagcacat cgagaacctg  120
tttagcgatc tacaagatgg cagaagactg ctggacctgc tggagggcct gaccgggcag  180
aagctgccca aagaaaaggg gtctacaaga gtgcacgccc tgaacaacgt gaacaaggcc  240
ctgagagtgc tgcagaacaa caacgtggac ctggtgaaca tcggcagcac cgacatcgtg  300
gacggcaacc acaagctgac cctgggcctg atctggaaca tcatcctgca ctggcaagtg  360
aagaacgtga tgaagaacat catggccggc ctgcagcaga ccaacagcga gaagatcctg  420
ctgagctggg tgagacagag cacaagaaac tacccccaag tgaacgtgat caacttcacc  480
acaagctgga gcgacggcct ggccctgaac gccctgatcc acagccacag acccgacctg  540
ttcgactgga acagcgtggt gtgtcagcag agcgccacac agagactgga gcacgccttc  600
aacatcgcta gatatcagct gggcatcgag aagttactgg accccgaaga tgtggacacc  660
acctaccccg acaagaagag catcctgatg tacatcacaa gcctgttcca agtgctgcct  720
cagcaagtga gcatcgaggc catccaagaa gtcgagatgc tgcctagacc ccccaaggtg  780
accaaggagg agcactttca gctgcaccat cagatgcact actctcagca gatcacagtc  840
agcttggcac aaggctacga gagaacaagc agccccaagc ctagattcaa gagctacgcc  900
tacacccaag ccgcctacgt gaccacaagt gaccccacaa gaagcccctt cccttctcag  960
cacctggagg cccccgagga caagagcttc ggcagcagcc tgatggagag cgaggtgaac  1020
ctggacagat atcagaccgc gttagaagaa gtgttgagct ggctgctgag cgccgaggac  1080
accctgcaag cccaaggcga gatcagcaac gatgtggagg tggtgaagga tcagttccac  1140
acccacgagg gctacatgat ggacctgacc gcccaccaag gcagagtggg caacatcctg  1200
cagctgggca gcaagctgat cggcaccggc aagctgagcg aggacgagga aaccgaggtt  1260
caagagcaaa tgaacctgct aaacagcaga tgggagtgcc tgagagtggc tagcatggaa  1320
aagcagagta acctgcacag agtgctgatg gacctgcaga atcagaaatt gaaagaactt  1380
aatgattggc tgaccaagac cgaggagaga acaagaaaga tggaggagga gcccctgggc  1440
cccgacctgg aggacctgaa gagacaagtg cagcagcaca aggtgctgca agaggacctg  1500
gagcaagagc aagtgagagt gaactctctg acacacatgg tggtggtagt ggacgagagc  1560
agcggcgatc acgctaccgc ggcgctggaa gagcagctga aagtgctggg cgacagatgg  1620
gccaacatct gcagatggac cgaggacaga tgggtgctgc tgcaagacat cctgctgaag  1680
tggcagagac tgaccgagga gcagtgcctg ttcagcgcct ggctgagcga gaaggaagac  1740
gctgtgaaca agatccacac caccggcttc aaggatcaga acgagatgct gagctccctc  1800
caaaagctcg cagtgctgaa ggccgacctg gaaaagaaaa aacagtcgat gggcaagctg  1860
tacagcctga agcaagacct gctgagcacc ctgaagaaca agagcgtgac acagaagacc  1920
gaggcctggc tggacaactt cgctagatgc tgggacaacc tggtacagaa gttagagaag  1980
tctaccgctc agatcagcca agccgtaacc accacacaac ctagcctgac tcagaccacc  2040
gtgatggaaa ccgtgaccac cgtgacaacc cgtgagcaga tcctggtgaa gcacgcccaa  2100
gaggagctgc cccccccccc ccctcagaag aagagacaga tcaccgtgga ctcagagatt  2160
cgcaagagac tggacgtgga catcaccgag ctgcacagct ggatcacaag aagcgaggcc  2220
gtgctgcaga gccctgagtt cgcgatcttt agaaaggagg gcaacttcag cgacttgaag  2280
gagaaagtga acgccatcga gagagagaag gccgagaagt tcagaaagtt gcaagacgcc  2340
tcaagaagcg cccaagccct ggtggagcag atggttaacg aaggcgtgaa tgccgacagc  2400
atcaagcaag ctagcgagca gctgaatagc cggtggattg aattctgtca gctgctgagc  2460
gagagattaa actggctgga gtatcagaac aacatcatcg ccttctacaa tcagctgcag  2520
caactagaac aaatgaccac caccgccgag aactggctaa agattcagcc caccacccct  2580
agcgagccca ccgccatcaa atctcagctg aaaatttgca aggacgaagt gaacagactg  2640
tcggacctgc agcctcaaat cgaaagactg aaaattcaga gcatcgcact taaggagaag  2700
ggccaaggac ccatgttcct ggacgccgac ttcgtggcct tcaccaacca cttcaagcaa  2760
gtgttcagcg acgtgcaagc tagagagaag gagctgcaga ccatcttcga caccctgccc  2820
cccatgagat accaagaaac catgagcgcc atcagaacct gggtgcagca gagcgaaacc  2880
aagctgagca tccctcagct gagcgtgacc gactacgaga tcatggagca aagactggga  2940
gagctgcaag ccctgcagag cagcctgcaa gagcagcaga gcggcctgta ctacctgagc  3000
accaccgtga aggagatgtc gaagaaagcc ccgtcggaga tcagcagaaa gtatcagagc  3060
gagttcgagg agatcgaggg cagatggaag aagctgagca gccaactggt ggaacactgt  3120
cagaaattag aagaacagat gaacaagctg agaaagattc agaaccacat tcagaccctg  3180
aagaagtgga tggccgaggt ggacgtgttc ctgaaagagg agtggcccgc cctgggcgat  3240
tccgaaatct taaaaaagca gctgaagcag tgcagactgc tggtgtcaga tatccaaacc  3300
attcaaccaa gcctgaacag cgtgaacgaa ggcgggcaga agatcaagaa cgaggccgag  3360
cccgagttcg ctagcagact ggaaaccgag ctgaaggagc tgaatacaca gtgggaccac  3420
atgtgtcagc aagtgtacgc tagaaaggaa gcgctgaagg gcgggctgga gaagaccgtt  3480
agcctgcaaa aggatctgag cgagatgcac gagtggatga cccaagccga ggaggagtac  3540
ctggagagag acttcgagta caagaccccc gacgagctgc agaaggccgt cgaggaaatg  3600
aagagagcga aggaggaggc tcagcagaag gaagccaagg tgaagctgct gactgaatct  3660
gtcaacagtg tgatagctca agcacccccc gttgcccaag aggcactaaa gaaggagctg  3720
gaaactctga ccaccaacta tcagtggctg tgcacaagac tgaacggcaa gtgcaagacc  3780
ctggaggaag tgtgggcctg ctggcacgag ctgctgagct acctggagaa ggccaacaag  3840
tggctgaacg aggtggagtt caagctgaag accaccgaga acatccccgg cggcgccgag  3900
gagatcagcg aggtgctgga cagcctggag aacctgatga gacacagcga ggacaacccc  3960
aatcagatca gaatcctggc tcagaccctg accgacggcg gcgtgatgga cgagctgatc  4020
aacgaggagc tggaaacctt taactctaga tggcgagaac tgcacgagga ggccgtgaga  4080
agacagaagc tgctggagca aagcattcag agcgcccaag aaaccgagaa gagcctgcac  4140
```

-continued

```
ctgatccaag agagcctgac cttcatcgac aagcagctgg ccgcctacat cgccgacaag 4200
gtggacgccg ctcagatgcc acaagaggct cagaagattc agtccgatct gacaagccac 4260
gagatcagcc tggaggagat gaaaaaacac aaccaaggca aggaggccgc tcagagagtg 4320
ctgtctcaga tcgacgtggc tcagaagaag ctgcaagacg tgagcatgaa gttcagactg 4380
tttcagaagc ccgccaactt cgagcagcga ctgcaagaga gcaagatgat cctggacgag 4440
gtgaagatgc acctgcccgc cctggaaacc aagagcgtgg agcaagaggt ggtgcagtct 4500
cagttgaacc actgcgtgaa cctgtacaag agcctgtcgg aggtcaagag tgaggtcgag 4560
atggtgatca aaactgggag acagatcgtg caaaaaaagc agaccgagaa ccccaaggag 4620
ctggacgagc gtgttaccgc cctgaagctg cactacaacg agctgggcgc caaggtgacc 4680
gagagaaagc agcagctgga gaagtgcctg aagctgagca gaaagatgag aaaggagatg 4740
aacgtgctga ccgagtggct ggccgccacc gacatggagc tgaccaagag aagcgccgtg 4800
gagggcatgc ctagcaacct ggacagcgag gtggcctggg gcaaggccac acagaaggag 4860
atcgagaagc agaaggtgca cctgaagagc atcaccgagg tgggcgaggc cctgaagacc 4920
gtgctgggca agaaggaaac cctggtggag gacaagctga gcctgctgaa ctcgaactgg 4980
atcgccgtga caagcagagc cgaggagtgg ctgaacctgc tgttagagta ccaaaaacac 5040
atggaaacct tcgatcagaa cgtggaccac atcaccaagt ggatcatcca agccgacacc 5100
ctgctggacg aaagcgaaaa gaagaagccg caacaaaagg aggatgtgct gaagagactg 5160
aaggccgaac tgaacgatat cagacccaag gtggacagca cacgggacca agccgccaac 5220
ctgatggcca acagaggcga ccactgcaga aaactggtgg agcctcagat cagcgagctg 5280
aaccacagat tcgccgccat cagccacaga atcaaaaccg gcaaagcgag catccccttg 5340
aaggaactgg agcaatttaa cagcgacatc caaaaattgc tcgaaccact ggaggccgag 5400
attcagcaag gcgtgaacct gaaggaagag gacttcaaca aggacatgaa cgaggacaac 5460
gagggcaccg tgaaagaact gctgcagaga ggcgacaacc tgcagcagag aatcaccgac 5520
gagagaaaga gagaggagat caagatcaag cagcagctgc tgcagactaa gcacaacgcc 5580
ctgaaggatc tgagatctca gaggagaaaa aaggctctgg aaatttcaca tcagtggtat 5640
cagtacaaga gacaagcaga cgacctgctg aagtgcctgg acgacatcga gaagaagtta 5700
gctagcctgc ccgagcctag agacgagaga aagatcaagg agatcgacag agagttacaa 5760
aagaagaagg aggagctgaa tgcggtaaga agacaagcgg aaggcctgtc cgaggacggc 5820
gcagccatgg ccgtggagcc cacacagatt cagctcagca agagatggag agagatcgag 5880
agcaagttcg ctcagttcag aagactgaac ttcgctcaga tccacaccgt gagagaggaa 5940
accatgatgg tgatgaccga ggacatgccc ctggagatct catacgttcc tagcacctac 6000
ctgaccgaga tcacccacgt gagccaagcc ctgctggagg tggagcagct gctgaacgcc 6060
cccgacctgt gcgccaagga cttcgaggac ctgttcaaac aagaggagag cctgaagaac 6120
atcaaggaca gcctgcagca aagtagcggc agaatcgaca tcatccacag caagaagacc 6180
gccgccctgc agagcgccac ccccgtggag agagtgaagc ttcaagaggc cctttcgcag 6240
ctggattttc agtgggagaa ggtgaacaaa atgtacaagg acagacaagg cagattcgac 6300
agaagcgtgg agaagtggag aagattccac tacgacatca agatcttcaa tcagtggctg 6360
accgaggcag agcagttcct gagaaagaca cagatccccg agaactggga gcacgccaag 6420
tacaagtggt acctgaagga gctgcaagac ggcatcgggc agagacagac cgtggtgaga 6480
accctgaacg ccaccggcga ggagatcatc caacaaagct ccaaaaccga cgctagcatc 6540
ctgcaagaga aactgggcag cctgaacctg agatggcaag aggtgtgcaa gcagctgagc 6600
gaccgcaaaa aacggttaga ggagcagaag aacatcctga gcgagtttca gcgggacctg 6660
aacgagttcg tgctgtggct ggaggaggcc gataacatcg ctagcatccc cctggagccc 6720
ggcaaggagc agcagttaaa agaaaaactt gagcaagtga agctgctggt ggaggagctg 6780
cccctgagac aaggcatcct gaagcagctg aacgagactg gcggccccgt gctggtgagc 6840
gcccccatca gccccgagga gcaagacaag ctggagaaca agctgaagca gaccaacctg 6900
cagtggatca aggtgagcag agccctgccc gagaagcaag gcgaaatcga ggcccaaata 6960
aaggacctgg gcagctggga gaagaaactc gaagacttgg aagaacaact caaccacttg 7020
ctgctgtggc tgagccccat cagaaatcag ctggagatct acaatcagcc caaccaagag 7080
gggccattcg acgtgaagga aaccgagatc gccgtgcaag ccaagcagcc cgatgtggag 7140
gagatcctga gcaaggggca gcacctgtac aaggagaagc ccgccacaca gcccgtcaag 7200
cgtaaactag aggatctttc ctctgagtgg aaggccgtga accgtctgct acaagagctg 7260
cgggctaagc aacccgactt agcgcccggc ctgaccacca tcggtgcaag ccccacgcag 7320
accgtgaccc tggtgaccca acccgtggtg accaaggaaa ccgccatcag caagctggag 7380
atgcctagca gcctgatgct ggaggtgccc gccctggccg acttcaacag agcctggacc 7440
gagctgaccg actggctgag cctgctggac caagtgatca agtctcagag agtgatggtg 7500
ggcgatctgg aggacatcaa tgagatgatc atcaagcaga aggccaccat gcaagacctg 7560
gagcagagaa gacctcagct ggaggagctg atcaccgccg ctcagaacct gaaaaacaag 7620
acgagcaacc aagaggctag aaccatcatc accgacagaa tcgagagaat tcagaatcag 7680
tgggacgagg tgcaagagca cctgcagaac agaagacagc aactaaacga aatgctcaag 7740
gacagcacac agtggctgga ggccaaggag gaggcggagc aagtgttggg ccaagctaga 7800
gccaagctgg agagctggaa ggagggaccc tacaccgtgg acgccattca gaagaagatc 7860
accgaaacca agcagctggc caaggacctg cgacagtggc agaccaacgt ggacgtggcc 7920
aacgatcttg ccctgaagct gctgcgcgac tatagcgccg acgacacaag aaaggtgcac 7980
atgatcaccg agaacatcaa cgctagctgg cgtagcatcc acaagagagt gagcgagaga 8040
gaggcggctt tggaggaaac ccatagactg ctgcagcagt ttcccctgga cctggagaag 8100
ttcctggcct ggctgaccga agccgaaaca accgccaacg tgctgcaaga cgccacaaga 8160
aaggagagac tgctggagga cagcaagggc gtgaaggagc tgatgaagca gtggcaagac 8220
ctgcaaggcg agatcgaagc gcacaccgac gtgtaccaca acctggacga gaactctcag 8280
aagatcctga gaagcctgga gggcagcgac gacgccgtgc tgttacagag aaggctggac 8340
aacatgaact tcaagtggag cgagctgaga aagaagagcc tgaacatcag aagccacctg 8400
gaggctagca gcgatcagtg gaagagactg cacctgagcc tgcaagagct gctggtctgg 8460
cttcagttga aggacgatga gctgagcaga caagccccca tcggcggcga cttccccgcc 8520
gtgcagaagc agaacgacgt gcatagagcc ttcaagagag agctgaagac caaggagccc 8580
gtgatcatga gcaccctgga aacggtgaga atcttcctga ccgagcagcc cctggagggc 8640
ctggagaagc tgtaccaaga gcctagagag ctgcccccg aggagagagc tcagaacgtg 8700
acaagactgc tgagaaagca agccgaagag gtgaacaccg agtgggagaa gctgaacctg 8760
cacagcgccg actggcagag aaagatcgac gaaaccctgg agagactgag agaattgcaa 8820
gaggcgaccg acgagctgga cctgaagctg agacaagccg aggtcatcaa gggcagctgg 8880
```

```
cagcccgtgg gcgatctatt aattgactct ctacaagacc acctggagaa agtgaaggcc  8940
ctgagaggcg agatcgcccc cctgaaggag aacgtgagcc acgtgaatga tctggcacgt  9000
cagctgacca ccctgggcat acaactgtcc ccctataacc tgagcacact ggaggatttg  9060
aatactagat ggaagctgct gcaagtggcc gtggaggaca gagtaagaca attacatgag  9120
gcccacagag acttcggccc cgcttctcag cacttcctga gcacaagcgt gcaaggcccc  9180
tgggagagag ccatttcccc caacaaggtc ccctactaca tcaaccacga gacacagacc  9240
acctgctggg accaccccaa gatgaccgag ctgtatcaga gcctcgccga tctgaacaat  9300
gtgagattca gcgcctacag aaccgccatg aagctgagaa gactgcagaa ggccctgtgc  9360
ctggacttat taagcctgag cgccgcctgc gacgccctgg atcagcacaa cctgaagcaa  9420
aacgaccaac ccatggacat cctgcagatc atcaactgcc tcaccaccat atacgacaga  9480
ctggaacaag agcacaacaa cctggtgaac gtgcccctgt gcgtggacat gtgcctgaac  9540
tggctgctga acgtgtacga caccggcaga accggcagaa tcagagtgct gagcttcaag  9600
accggcatca tcagcctgtg caaggcccac ctggaggaca aatacagata ccttttcaaa  9660
caagtggcta gcagcaccgg cttctgcgac caaagaagac tgggtctgct gctgcacgac  9720
agcattcaga tccctagaca gctgggcgag gtggctagct tcggcggcag caacatcgag  9780
cctagcgtga gaagctgctt tcagttcgcc aacaacaagc ccgagataga ggcagccctc  9840
ttcttagact ggatgagact ggagcctcag agcatggtat ggctgccggt cctgcacaga  9900
gtggccgccg ccgaaaccgc caagcaccaa gccaagtgca acatctgcaa ggagtgcccc  9960
atcatcggct tcagatacag aagcctgaag cacttcaact acgacatctg tcagagctgc  10020
ttcttcagcg gcagagtggc caagggccac aagatgcact accccatggt ggagtactgc  10080
acccccacca caagcggcga ggacgtgaga gacttcgcca aggtgttgaa gaataagttt  10140
agaaccaaga gatacttcgc caagcaccct agaatgggct acctgcccgt gcagaccgtg  10200
ctggagggcg acaacatgga aacccccgtg accctgatca acttctggcc cgtggacagc  10260
gcccccgcta gcagccctca gctgagccac gacgacaccc acagcagaat cgagcactac  10320
gctagcagac tggccgagat ggagaacagc aacggcagct acctgaacga cagcatcagc  10380
ccgaatgaga gcatcgacga cgagcacctg ctgattcagc actactgtca gagcctgaac  10440
caagacagcc ccctgtctca gcctagaagc cccgctcaga tcctgatcag cctggagagc  10500
gaggagagag gcgagctgga gagaatccta gcagatctgg aggaagagaa cagaaacctg  10560
caagccgagt atgaccgact gaaacagcaa catgagcaca aaggcctgag cccactgccc  10620
tcccccccg agatgatgcc cacaagccct cagagcccta gagacgccga gctgatcgct  10680
gaagcgaagt tacttagaca acacaagggc agactggagg ctagaatgca gatcctggag  10740
gaccacaaca agcagctgga gtctcagctg cacagactga ggcagctgct ggaacagccc  10800
caagccgagg ccaaagtgaa cggcaccacc gtgagcagtc ctagcacaag cctgcagaga  10860
agcgacagct ctcagcccat gctgctgaga gtggtgggct ctcagacaag cgacagcatg  10920
ggcgaggagg atctgctgag tccgccccaa gacacaagca ccggcctgga agaggtgatg  10980
gagcaactga acaatagctt ccctagcagc agaggcagaa acacccccgg caagcccatg  11040
agagaggaca ccatgtgatg a                                            11061
```

```
SEQ ID NO: 3            moltype = DNA  length = 11061
FEATURE                 Location/Qualifiers
source                  1..11061
                        mol_type = other DNA
                        note = DMD-4
                        organism = synthetic construct
SEQUENCE: 3
atgctttggt gggaagaagt cgaggactgc tacgagcgcg aggacgtgca gaagaaaacc  60
ttcaccaaat gggtcaacgc ccagttcagc aagttcggca agcagcacat cgagaacctg  120
ttcagcgacc tgcaggatgg cagaaggctg ctggatctgc tggaaggcct gacaggacag  180
aagctgccca aagagaaggg cagcacaaga gtgcacgccc tgaacaacgt gaacaaggcc  240
ctgagagtgc tgcagaacaa caacgtggac ctggtcaaca tcggcagcac cgacatcgtg  300
gacggcaacc acaaactgac cctgggcctg atctggaaca tcatcctgca ctggcaagtg  360
aagaacgtga tgaagaacat catggccggc ctgcagcaga ccaacagcga gaagattctg  420
ctgagctggg tccgacagag cacccggaat taccctcaag tgaacgtgat caacttcacc  480
acctcttgga gcgacggact ggccctgaat gccctgatcc acagccacag acctgacctg  540
ttcgactgga acagcgtcgt gtgtcagcag agcgccacac agaggctgga acacgccttc  600
aatatcgcca gataccagct gggcatcgag aaactgctgg accccgagga tgtggacacc  660
acctatcctg acaagaaatc catcctcatg tacatcacca gcctgttcca ggtgctgccc  720
cagcaggttt ccatcgaggc cattcaagag gtcgagatgc tgcccagacc tcctaaagtg  780
accaaagagg aacacttcca gctgcaccac cagatgcact actctcagca gatcaccgtg  840
tctctggccc agggctacga gagaacaagc agccccaagc ctcggttcaa gagctacgcc  900
tatacacagg ccgcctacgt gaccaccagc gatcctacaa gaagcccatt tcctagccag  960
catctggaag cccctgagga caagagcttt ggcagcagcc tgatggaaag cgaagtgaac  1020
ctggaccgct accagacagc cctggaagag gttctgagct ggctgctgtc tgccgaggat  1080
acactgcagg ctcagggcga gatcagcaac gacgtggaag tggtcaagga ccagtttcac  1140
acccacgagg gctacatgat ggacctgaca gcccaccagg gcagagtggg caatattctg  1200
cagctgggct ccaagctgat cggcacaggc aagctgagcg aggacgaaga gacagaggtg  1260
caagagcaga tgaacctgct gaacagcaga tgggagtgtc tgagagtggc cagcatggaa  1320
aagcagagca acctgcaccg ggtgctgatg gatctccaga accagaagct gaaagagctg  1380
aacgactggc tgaccaagac cgaggaacgg acccggaaga tggaagagga acctctggga  1440
cccgacctgg aagatctgaa aagacaggtg cagcagcata aggtgctgca agaggacctc  1500
gaacaagagc aagtgcgcgt gaacagcctg acacacatgg tggtggtcgt ggatgagagc  1560
agcggagatc atgccacagc cgctctggaa gaacagctga aggtgctggg agacagatgg  1620
gccaatatct gccggtggac cgaggataga tgggtgctgc tccaggacat cctgctgaag  1680
tggcagcggc tgacagagga acagtgcctg tttagcgcct ggctgtccga gaaagaggac  1740
gccgtcaaca agatccacac caccggcttc aaggatcaga atgagatgct gagcagcctg  1800
cagaaactgg ccgtgctgaa ggctgacctg gaaaagaaaa agcagtccat gggcaagctg  1860
tactccctga agcaggacct gctgagcaca ctgaagaaca agtctgtgac ccagaaaacc  1920
gaggcctggc tggacaactt cgcccggtgt tgggataacc tggtgcagaa gctggaaaag  1980
tccaccgctc agatctctca ggccgtgacc acaacacagc cttctctgac ccagaccacc  2040
```

-continued

```
gtgatggaaa cagtgaccac agtgacaacc cgcgagcaga tcctggtcaa gcacgcccaa  2100
gaagaactgc ctcctccacc tcctcagaag aaacggcaga tcacagtgga cagcgagatc  2160
cggaagagac tggacgtgga catcaccgag ctgcacagct ggatcaccag atccgaagcc  2220
gtgctgcagt cccctgagtt cgccatcttc agaaaagagg gcaacttctc cgacctgaaa  2280
gagaaagtca acgccatcga gagagagaag gccgagaagt tccggaagct gcaggacgcc  2340
tctagatctg cccaggctct ggtggaacag atggtcaacg aaggcgtgaa cgccgacagc  2400
atcaagcagg cctcagagca gctgaactcc cggtggatcg agttctgtca gctcctgagc  2460
gagagactga actggctgga ataccagaac aatatcattg ccttctacaa ccagctccag  2520
cagctcgaac agatgaccac cacagccgag aattggctga agatccagcc taccacacct  2580
agcgagccca ccgccattaa gagccagctg aaaatctgca aggacgaagt gaatcggctg  2640
agcgatctgc agccccagat cgaaagactg aaaatccagt ctatcgccct caaagagaaa  2700
ggacagggcc ccatgttcct ggacgccgat tttgtggcct ttaccaacca cttcaaacag  2760
gtgttctccg acgtgcaggc ccgggaaaaa gagctgcaga ccatcttcga caccctgcct  2820
ccaatgagat accaagagac aatgagcgcc atccggacct gggtgcagca aagcgagaca  2880
aagctgagca tcccacagct gagcgtgacc gactacgaga tcatggaaca gagactgggc  2940
gaactgcagg ccctccagtc tagcctgcaa gaacagcagt ccggcctgta ctacctgagc  3000
acaaccgtga aagagatgag caagaaggcc cctagcgaga tctcccggaa gtaccagagc  3060
gagttcgaag agatcgaagg ccggtggaag aagctgtcta gccagctggt tgagcactgc  3120
cagaaactcg aagaacaaat gaacaagctg cgcaagatcc agaatcacat ccagacgctg  3180
aagaaatgga tggccgaggt ggacgtgttc ctgaaagaag agtggcccgc tctgggcgac  3240
tccgagattc tgaagaaaca gctcaaacag tgccggctgc tggtgtccga tatccagaca  3300
atccagccaa gcctgaactc cgtgaatgaa ggcggccaga agatcaagaa cgaggccgag  3360
cctgagtttg ccagcagact ggaaaccgaa ctgaaagaac tcaacaccca gtgggaccac  3420
atgtgccagc aagtgtacgc ccggaaagag gccctgaaag gcggactcga aaagactgtg  3480
tctctgcaga aagacctgtc tgagatgcac gagtggatga cccaggccga agaggaatac  3540
ctggaacggg acttcgagta caagacccct gatgagctgc aaaaagccgt cgaggaaatg  3600
aagcgggcca aagaagaggc ccagcagaaa gaagccaaag tcaagctgct gaccgagtcc  3660
gtgaatagcg ttatcgctca ggcccctcct gtggctcaag aggctctcaa gaaagaactg  3720
gaaactctga ccaccaacta ccagtggctg tgcaccagac tgaacggcaa gtgcaagaca  3780
ctggaagaag tgtgggcctg ctggcacgaa ctgctgtcct atctggaaaa ggccaacaag  3840
tggctgaacg aggtggaatt caagctgaaa accaccgaga acatccctgg cggcgctgaa  3900
gagattagcg aggtgctgga cagcctggaa aacctgatga gacacagcga ggacaacccc  3960
aatcagatca gaatcctggc tcagaccctg accgatggcg gcgtgatgga cgagctgatc  4020
aacgaggaac tcgaaacctt caacagccgg tggcgggaac tgcacgagga agctgttcgg  4080
aggcagaagt tgctggaaca gtctatccag agcgcacaag aaaccgagaa gtccctgcac  4140
ctgatccaag agagcctgac cttcatcgac aagcagctgg ccgcttatat cgccgacaag  4200
gtggacgctg ctcagatgcc ccaagaggca cagaagattc agagcgacct gaccagccac  4260
gagattagcc tggaagaaat gaagaagcac aaccagggca aagaggccgc tcagagagtc  4320
ctgagccaga tcgatgtggc acagaaaaag ctccaggatg tgtccatgaa gtttcggctg  4380
tttcagaagc ccgccaactt cgagcagaga ctgcaagagt ccaagatgat cctggacgaa  4440
gtcaaaatgc atctgcccgc actggaaaca aagtccgtgg aacaagaagt ggtgcagtcc  4500
cagctgaacc actgcgtgaa cctgtacaag agcctgtccg aagtgaagtc tgaggtggaa  4560
atggtcatca agaccggcag gcagatcgtc cagaagaagc agaccgagaa tcccaaagaa  4620
ctcgacgaga gagtgaccgc tctgaagctg cactacaatg agctgggcgc caaagtgacc  4680
gagcggaagc aacagcttga gaagtgcctg aaactgtctc ggaagatgcg gaaagaaatg  4740
aacgtgctga cagagtggct ggccgccacc gatatggaac tgactaagag aagcgccgtg  4800
gaaggcatgc ccagcaacct ggatagtgaa gtggcctggg gcaaagccac tcagaaagag  4860
attgagaagc agaaggtcca cctgaagtcc atcaccgaag tgggcgaagc cctgaaaacc  4920
gtgctgggaa agaaagagac actggtcgag gacaagctgt ccctgctgaa ttccaactgg  4980
atcgccgtga cctccagagc tgaggaatgg ctgaatctgc tgcttgagta ccagaaacac  5040
atggaaacgt tcgaccagaa cgtcgaccac atcacaaagt ggatcatcca ggctgatacc  5100
ctgctggacg agtccgagaa gaagaaaccc caacaaaaag aagatgtgct gaagcggctg  5160
aaagccgagc tgaatgacat ccggcctaag gtggacagca ccagagatca ggcagccaac  5220
ctgatggcca acagaggcga ccactgtcgg aagctcgtgg aacctcagat cagcgagctt  5280
aaccacagat ttgccgccat cagccaccgg atcaagacag gcaaggccag cattcctctc  5340
aaagagcttg agcagttcaa cagcgacatc caaaagctgc tcgaacccct ggaagccgag  5400
atccaacagg gcgtcaacct caaagaagaa gatttcaaca aggacatgaa cgaggacaat  5460
gagggcaccg tcaaagaact gctgcagcgg ggcgataatc tgcagcagcg gattaccgat  5520
gagcgcaagc gggaagagat caagattaag cagcagctgc tgcagaccaa gcacaacgcc  5580
ctgaaggacc tgcggagcca gagaagaaag aaggccctgg aaatcagcca ccagtggtat  5640
cagtacaagc ggcaggccga cgacctgctg aagtgcctgg atgacatcga gaagaagctg  5700
gcctctctgc ccgagcctag ggacgagaga aagatcaaag agatcgaccg cgagctgcag  5760
aaaaagaaag aggaactgaa cgccgtccgc agacaggccg aaggactttc tgaagatggc  5820
gccgctatgg ccgtggaacc cacacagatt cagctgagca agcggtggcg ggaaatcgag  5880
agcaagttcg cccagttccg gcggctgaat ttcgcccaga tccacaccgt gcgggaagag  5940
acaatgatgg tcatgacaga ggacatgccc cttgagatca gctacgtgcc cagcacctac  6000
ctgaccgaga tcacccatgt gtctcaggcc ctgctggaag tggaacagct gctgaatgcc  6060
cctgacctgt gcgccaagga cttcgaggac ctgttcaagc aagaggaaag cctgaagaac  6120
atcaaggaca gcctgcagca gagcagcggc cggatcgata tcatccacag caagaaaacc  6180
gccgcactgc agagcgccac acctgtggaa agagtgaagc tgcaagaggc cctgagccag  6240
ctggatttcc agtgggagaa agtgaacaag atgtacaagg accggcaggg cagattcgac  6300
cgcagcgttg aaaagtggcg gcggttccac tacgacatca agatcttcaa ccagtggctg  6360
accgaggccg agcagttcct gagaaagaca cagatccccg agaactggga gcacgccaag  6420
tacaagtggt atctgaaaga gctgcaggac ggcatcggcc agagacagac agtcgtgcgg  6480
acactgaatg ccaccggcga ggaaatcatc cagcagtcca gcaagaccga cgccagcatc  6540
ctgcaagaga agctgggcag cctgaacctg cggtggcaag aagtgtgcaa gcagctgagc  6600
gaccggaaga agcggctgga agaacagaag aatatcctga gcgagttcca gcgggacctg  6660
aacgagttcg tgctgtggct cgaagaggcc gacaatatcg ccagcattcc cctggaacct  6720
ggcaaagagc agcagctgaa agaaaagctg gaacaagtga aactgctggt cgaggaactg  6780
```

```
ccccctgagac agggaatcct gaaacagctg aacgagacag gcggccctgt gctggtgtct  6840
gcccctattt ctcccgagga acaggacaag ctggaaaaca agctgaagca gaccaacctg  6900
cagtggatca aggtgtccag agcactgcct gagaagcagg gcgagatcga ggcccagatc  6960
aaggacctgg gacagctcga aaagaagctt gaggacctcg aagaacagct caaccatctg  7020
ctgctttggc tgagccccat ccggaaccag ctggaaatct acaaccagcc taatcaagag  7080
ggcccccttcg acgtgaaaga aaccgagatt gccgtgcagg ccaagcagcc cgatgtggaa  7140
gagatcctgt ctaagggcca gcacctgtac aaagagaagc ccgccacaca gcccgtgaag  7200
cggaaactgg aagatctgag cagcgagtgg aaggccgtga accggctgct gcaagaactg  7260
agagccaaac agcctgatct ggcccctggc ctgacaacaa ttggcgcctc tcctacacag  7320
accgtgacac tggtcacaca gcctgtggtc accaaagaga cagccatcag caaactggaa  7380
atgcccagca gtctgatgct cgaagtgccc gcactggccg acttcaatag agcctggacc  7440
gagctgaccg actggctcag tctgctggac caagtcatca agtcccagag agtgatggtc  7500
ggagatcttg aggacatcaa cgagatgatc attaagcaga aagccaccat gcaggacctt  7560
gagcagagaa ggccccagct tgaagaactg atcaccgccg ctcagaacct gaaaaacaag  7620
accagcaatc aagaagcccg gaccatcatc accgaccgga tcgagagaat ccagaaccag  7680
tgggacgaag tgcaagagca tctgcagaac agacggcagc agctcaatga gatgctgaag  7740
gacagcacac agtggctgga agccaaagaa gaagccgagc aggttctcgg acaggccaga  7800
gctaagctgg aatcttggaa agagggaccc tacaccgtcg acgccatcca gaagaagatc  7860
accgagacaa agcagctggc caaggatctg agacagtggc agaccaatgt ggacgtggcc  7920
aacgacctgg ctctgaagct gctgagagac tacagcgccg acgacaccag aaaggtgcac  7980
atgatcaccg aaaacatcaa cgcctcttgg cggagcatcc acaagcgggt gtcagagaga  8040
gaagccgctc tggaagaaac acatagactg ctccagcagt tcccactcga cctggaaaag  8100
ttcctggcct ggctgacaga agccgaaacc accgctaacg tgctccagga tgccaccaga  8160
aaagagcggc tgttggagga cagcaagggc gtcaaagaac tcatgaagca gtggcaggat  8220
ctgcaagggg agattgaagc ccacaccgac gtgtaccaca acctggacga gaacagccag  8280
aagatcctgc ggtccctgga aggctctgat gatgctgtgc tgcttcagag gcggctggac  8340
aacatgaact tcaagtggag cgagctgcgg aagaagtccc tgaacatcag aagccacctg  8400
gaagcctcca gcgaccagtg gaaaagactg cacctgtctc tccaagagct gctcgtgtgg  8460
ctgcagctga aggatgacga gctgagtaga caggccccta tcggcggaga ttttcccgcc  8520
gtgcagaaac agaacgacgt gcaccgggcc ttcaagagag agctgaaaac aaaagaaccc  8580
gtcatcatga gcaccctgga aaccgtgcgg atctttctga ccgagcagcc tctggaagga  8640
ctggaaaagc tgtaccaaga gcctagagag ctgcctcctg aagaaagggc ccagaacgtg  8700
acacggctgc ttagaaagca ggccgaggaa gtgaacaccg aatgggagaa gctgaacctc  8760
cactccgccg actggcagcg gaagatcgat gagacactgg aacggctgcg ggaactgcaa  8820
gaagccacag acgagctgga cctgaaactg cggcaggctg aagtgatcaa aggctcctgg  8880
cagccagtgg gcgatctgct gatcgatagc ctgcaggacc atctggaaaa agtcaaggcc  8940
ctgcggggag agatcgcccc tctcaaagaa aacgtgtccc acgtgaacga tctggccagg  9000
cagctgacaa cactgggcat ccagctgagc ccttacaacc tgtctacctt ggaggacctg  9060
aatacccggt ggaagctgct ccaagtggcc gtcgaggata gagtgcggca gctgcatgag  9120
gctcacagag attttggacc cgccagccag cacttcctga gcacatctgt tcaaggcccc  9180
tgggagagag ctatcagccc taacaaggtg ccctactaca tcaaccacga gacacagacc  9240
acctgttggg atcaccccaa gatgaccgaa ctgtatcagt ccctggccga cctgaacaac  9300
gtgcggttta gcgcctaccg gaccgccatg aagctgcgca gactgcagaa agctctgtgc  9360
ctggacctgc tgtctctgag cgctgcttgt gatgccctgg accagcataa cctcaagcag  9420
aacgaccagc ctatggacat cctgcagatc atcaactgcc tgaccaccat ctacgaccgg  9480
ctcgaacaag agcacaacaa cctggtcaac gtgcccctgt gcgtggacat gtgcctgaat  9540
tggctgctga acgtgtacga caccggcaga accggcagga tcagagtgct gagcttcaag  9600
accggcatca tctccctgtg caaggcccac cttgaggata agtaccgcta cctgtttaag  9660
caggtcgcca gcagcaccgg cttttgcgac caaagaaggc tgggactgct gctccacgac  9720
agcattcaga tccctagaca gctgggcgaa gtggcctctt tcggcggctc taatatcgag  9780
cctagcgtgc ggagctgctt ccagttcgcc aacaacaagc ccgagattga ggccgcactg  9840
ttcctggact ggatgagact ggaaccccag agcatggtct ggctgcctgt gctgcataga  9900
gtggccgcag ccgaaacagc caagcaccag gccaagtgca acatctgcaa agagtgcccc  9960
atcatcggct tccggtacag atccctgaag cacttcaact acgatatctg ccagtcctgc  10020
ttcttcagcg gcagagtggc caagggccac aagatgcact accccatggt ggaatactgc  10080
acccctacca cctctggcga ggacgtgcgg gattttgcca aggtgctcaa gaacaagttc  10140
cggaccaagc gctacttcgc taagcacccc agaatgggct acctgccagt gcagacagtg  10200
cttgagggcg acaacatgga aacccctgtg actctgatca acttctggcc cgtggatagc  10260
gcccctgcta gttctcctca gctgtctcac gacgataccc acagcagaat cgagcactac  10320
gcctccagac tggccgagat ggaaaacagc aacggcagct acctgaatga cagcatcagc  10380
cccaacgaga gcatcgacga cgaacatctg ctcattcagc actactgcca gagcctgaat  10440
caggacagcc ctctgtctca gcctagaagc cctgcacaga tcctgatcag cctggaaagc  10500
gaggaacgcg gcgagctgga aagaatcctg gcagacctgg aagaggaaaa ccggaacctg  10560
caggccgaat acgacagact caagcagcag cacgagcaca agggactgtc tccactgcct  10620
tctccacctg aaatgatgcc cacctctcca cagagcccca gagatgccga gctgattgcc  10680
gaagccaaac tgctgaggca gcacaaaggc agactcgaag ccagaatgca gattctcgaa  10740
gatcacaaca agcagctcga atcccagctg cacagactta ggcagctgct ggaacagcct  10800
caggcagagg ccaaagtgaa tggcaccacc gtgtctagcc ctagcacaag cctgcagaga  10860
tccgacagca gccagccaat gcttctgaga gtcgtgggct cccagaccag cgattctatg  10920
ggcgaagagg acctgctcag ccctcctcag gatacaagca ccggcctgga agaagtgatg  10980
gaacaactga acaacagctt ccccagcagc agaggcagaa acacccctgg caagcccatg  11040
cgcgaggaca ccatgtgata a                                              11061
```

```
SEQ ID NO: 4           moltype = DNA  length = 1051
FEATURE                Location/Qualifiers
source                 1..1051
                       mol_type = other DNA
                       note = MHCK Promoter
                       organism = synthetic construct
```

```
SEQUENCE: 4
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccact acgggtctag  240
gctgcccatg taaggaggca aggcctgggg acacccgaga tgcctggtta taattaaccc  300
agacatgtgg ctgccccccc cccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac c                                 1051

SEQ ID NO: 5            moltype = DNA  length = 855
FEATURE                 Location/Qualifiers
source                  1..855
                        mol_type = other DNA
                        note = MHCK Promoter SF
                        organism = synthetic construct
SEQUENCE: 5
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccact acgggtctag  240
gctgcccatg taaggaggca aggcctgggg acacccgaga tgcctggtta taattaaccc  300
agacatgtgg ctgccccccc cccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatc                                                   855

SEQ ID NO: 6            moltype = DNA  length = 12889
FEATURE                 Location/Qualifiers
source                  1..12889
                        mol_type = other DNA
                        note = MHCK7-hBGi-DMD-3-WPRE3-DTS
                        organism = synthetic construct
SEQUENCE: 6
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccact acgggtctag  240
gctgcccatg taaggaggca aggcctgggg acacccgaga tgcctggtta taattaaccc  300
agacatgtgg ctgccccccc cccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctgtgg tgggaagagg tggaggactg  1080
ttacgagaga gaggacgtgc agaagaagac attcaccaag tgggtgaacg ctcagttcag  1140
caagttcggc aagcagcaca tcgagaacct gtttagcgat ctacaagatg gcagaagact  1200
gctggacctg ctggagggcc tgaccgggca gaagctgccc aaagaaaagg ggtctacaag  1260
agtgcacgcc ctgaacaacg tgaacaaggc cctgagagtg ctgcagaaca acaacgtgga  1320
cctggtgaac atcggcagca ccgacatcgt ggacggcaac cacaagctga ccctgggcct  1380
gatctggaac atcatcctgc actggcaagt gaagaacgtg atgaagaaca tcatggccgg  1440
cctgcagcag accaacagcg agaagatcct gctgagctgg gtgagacaga gcacaagaaa  1500
ctacccccaa gtgaacgtga tcaacttcac cacaagctgg agcgacggcc tggccctgaa  1560
cgccctgatc cacagccaca gacccgacct gttcgactgg aacagcgtgg tgtgtcagca  1620
gagcgccaca cagagactgg agcacgcctt caacatcgct agatatcagc tgggcatcga  1680
gaagttactg gaccccgaag atgtggacac cacctacccc gacaagaaga gcatcctgat  1740
```

-continued

```
gtacatcaca agcctgttcc aagtgctgcc tcagcaagtg agcatcgagg ccatccaaga 1800
agtcgagatg ctgcctagac cccccaaggt gaccaaggag gagcactttc agctgcacca 1860
tcagatgcac tactctcagc agatcacagt cagcttggca caaggctacg agagaacaag 1920
cagccccaag cctagattca agagctacgc ctacacccaa gccgcctacg tgaccacaag 1980
tgaccccaca agaagcccct tcccttctca gcacctggag gcccccgagg acaagagctt 2040
cggcagcagc ctgatggaga gcgaggtgaa cctggacaga tatcagaccg cgttagaaga 2100
agtgttgagc tggctgctga gcgccgagga caccctgcaa gcccaaggcg agatcagcaa 2160
cgatgtggag gtggtgaagg atcagttcca cacccacgag ggctacatga tggacctgac 2220
cgcccaccaa ggcagagtgg gcaacatcct gcagctgggc agcaagctga tcggcaccgg 2280
caagctgagc gaggacgagg aaaccgaggt tcaagagcaa atgaacctgc taaacagcag 2340
atgggagtgc ctgagagtgg ctagcatgga aaagcagagt aacctgcaca gagtgctgat 2400
ggacctgcag aatcagaaat tgaaagaact taatgattgg ctgaccaaga ccgaggagag 2460
aacaagaaag atggaggagg agcccctggg ccccgacctg gaggacctga agagacaagt 2520
gcagcagcac aaggtgctgc aagaggacct ggagcaagag caagtgagag tgaactctct 2580
gacacacatg gtggtggtag tggacgagag cagcggcgat cacgctaccg cggcgctgga 2640
agagcagctg aaagtgctgg gcgacagatg ggccaacatc tgcagatgga ccgaggacag 2700
atgggtgctg ctgcaagaca tcctgctgaa gtggcagaga ctgaccgagg agcagtgcct 2760
gttcagcgcc tggctgagcg agaaggaaga cgctgtgaac aagatccaca ccaccggctt 2820
caaggatcag aacgagatgc tgagctccct ccaaaagctc gcagtgctga aggccgacct 2880
ggaaaagaaa aaacagtcga tgggcaagct gtacagcctg aagcaagacc tgctgagcac 2940
cctgaagaac aagagcgtga cacagaagac cgaggcctgg ctggacaact tcgctagatg 3000
ctgggacaac ctggtacaga agttagagaa gtctaccgct cagatcagcc aagccgtaac 3060
caccacacaa cctagcctga ctcagaccac cgtgatggaa accgtgacca ccgtgacaac 3120
ccgtgagcag atcctggtga agcacgccca agaggagctg cccccccccc cccctcagaa 3180
gaagagacag atcaccgtgg actcagagat tcgcaagaga ctggacgtgg acatcaccga 3240
gctgcacagc tggatcacaa gaagcgaggc cgtgctgcag agccctgagt tcgcgatctt 3300
tagaaaggag ggcaacttca gcgacttgaa ggagaaagtg aacgccatcg agagagagaa 3360
ggccgagaag ttcagaaagt tgcaagacgc ctcaagaagc gcccaagccc tggtggagca 3420
gatggttaac gaaggcgtga atgccgacag catcaagcaa gctagcgagc agctgaatag 3480
ccggtggatt gaattctgtc agctgctgag cgagagatta aactggctgg agtatcagaa 3540
caacatcatc gccttctaca atcagctgca gcaactagaa caaatgacca ccaccgccga 3600
gaactggcta aagattcagc ccaccacccc tagcgagccc accgccatca aatctcagct 3660
gaaaatttgc aaggacgaag tgaacagact gtcggacctg cagcctcaaa tcgaaagact 3720
gaaaattcag agcatcgcac ttaaggagaa gggccaagga cccatgttcc tggacgccga 3780
cttcgtggcc ttcaccaacc acttcaagca agtgttcagc gacgtgcaag ctagagagaa 3840
ggagctgcag accatcttcg acaccctgcc ccccatgaga taccaagaaa ccatgagcgc 3900
catcagaacc tgggtgcagc agagcgaaac caagctgagc atccctcagc tgagcgtgac 3960
cgactacgag atcatggagc aaagactggg agagctgcaa gccctgcaga gcagcctgca 4020
agagcagcag agcggcctgt actacctgag caccaccgtg aaggagatgt cgaagaaagc 4080
cccgtcggag atcagcagaa agtatcagag cgagttcgag gagatcgagg gcagatggaa 4140
gaagctgagc agccaactgg tggaacactg tcagaaatta gaagaacaga tgaacaagct 4200
gagaaagatt cagaaccaca ttcagaccct gaagaagtgg atggccgagg tggacgtgtt 4260
cctgaaagag gagtggcccg ccctgggcga ttccgaaatc ttaaaaaagc agctgaagca 4320
gtgcagactg ctggtgtcag atatccaaac cattcaacca agcctgaaca gcgtgaacga 4380
aggcgggcag aagatcaaga acgaggccga gcccgagttc gctagcagac tggaaaccga 4440
gctgaaggag ctgaatacac agtgggacca catgtgtcag caagtgtacg ctagaaagga 4500
agcgctgaag ggcgggctgg agaagaccgt tagcctgcaa aaggatctga gcgagatgca 4560
cgagtggatg acccaagccg aggaggagta cctggagaga gacttcgagt acaagacccc 4620
cgacgagctg cagaaggccg tcgaggaaat gaagagagcg aaggaggagg ctcagcagaa 4680
ggaagccaag ggtgaagctgc tgactgaatc tgtcaacagt gtgatagctc aagcaccccc 4740
cgttgcccaa gaggcactaa agaaggagct ggaaactctg accaccaact atcagtggct 4800
gtgcacaaga ctgaacggca agtgcaagac cctggaggaa gtgtgggcct gctggcacga 4860
gctgctgagc tacctggaga aggccaacaa gtggctgaac gaggtggagt tcaagctgaa 4920
gaccaccgag aacatccccg gcggcgccga ggagatcagc gaggtgctgg acagcctgga 4980
gaacctgatg agacacagcg aggacaaccc caatcagatc agaatcctgg ctcagaccct 5040
gaccgacggc ggcgtgatgg acgagctgat caacgaggag ctggaaacct ttaactctag 5100
atggcgagaa ctgcacgagg aggccgtgag aagacagaag ctgctggagc aaagcattca 5160
gagcgcccaa gaaaccgaga agagcctgca cctgatccaa gagagcctga ccttcatcga 5220
caagcagctg gccgcctaca tcgccgacaa ggtggacgcc gctcagatgc cacaagaggc 5280
tcagaagatt cagtccgatc tgacaagcca cgagatcagc ctggaggaga tgaaaaaaca 5340
caaccaaggc aaggaggccg ctcagagagt gctgtctcag atcgacgtgg ctcagaagaa 5400
gctgcaagac gtgagcatga agttcagact gtttcagaag cccgccaact tcgagcagcg 5460
actgcaagag agcaagatga tcctggacga ggtgaagatg cacctgcccg ccctggaaac 5520
caagagcgtg gagcaagagg tggtgcagtc tcagttgaac cactgcgtga acctgtacaa 5580
gagcctgtcg gaggtcaaga gtgaggtcga gatggtgatc aaaactggga gacagatcgt 5640
gcaaaaaaag cagaccgaga accccaagga gctggacgag cgtgttaccg ccctgaagct 5700
gcactacaac gagctgggcg ccaaggtgac cgagagaaag cagcagctgg agaagtgcct 5760
gaagctgagc agaaagatga gaaaggagat gaacgtgctg accgagtggc tggccgccac 5820
cgacatggag ctgaccaaga gaagcgccgt ggagggcatg cctagcaacc tggacagcga 5880
ggtggcctgg ggcaaggcca cacagaagga gatcgagaag cagaaggtgc acctgaagag 5940
catcaccgag gtgggcgagg ccctgaagac cgtgctgggc aagaaggaaa ccctggtgga 6000
ggacaagctg agcctgctga actcgaactg gatcgccgtg acaagcagag ccgaggagtg 6060
gctgaacctg ctgttagagt accaaaaaca catggaaacc ttcgatcaga acgtggacca 6120
catcaccaag tggatcatcc aagccgacac cctgctggac gaaagcgaaa agaagaagcc 6180
gcaacaaaag gaggatgtgc tgaagagact gaaggccgaa ctgaacgata tcagacccaa 6240
ggtggacagc acacgggacc aagccgccaa cctgatggcc aacagaggcg accactgcag 6300
aaaactggtg gagcctcaga tcagcgagct gaaccacaga ttcgccgcca tcagccacag 6360
aatcaaaacc ggcaaagcga gcatcccctt gaaggaactg gagcaattta acagcgacat 6420
ccaaaaattg ctcgaaccac tggaggccga gattcagcaa ggcgtgaacc tgaaggaaga 6480
```

```
ggacttcaac aaggacatga acgaggacaa cgagggcacc gtgaaagaac tgctgcagag  6540
aggcgacaac ctgcagcaga gaatcaccga cgagagaaag agagaggaga tcaagatcaa  6600
gcagcagctg ctgcagacta agcacaacgc cctgaaggat ctgagatctc agaggagaaa  6660
aaaggctctg gaaatttcac atcagtggta tcagtacaag agacaagcag acgacctgct  6720
gaagtgcctg gacgacatcg agaagaagtt agctagcctg cccgagccta gagacgagag  6780
aaagatcaag gagatcgaca gagagttaca aaagaagaag gaggagctga atgcggtaag  6840
aagacaagcg gaaggcctgt ccgaggacgg cgcagccatg gccgtggagc ccacacagat  6900
tcagctcagc aagagatgga gagagatcga gagcaagttc gctcagttca gaagactgaa  6960
cttcgctcag atccacaccg tgagagagga aaccatgatg gtgatgaccg aggacatgcc  7020
cctggagatc tcatacgttc ctagcaccta cctgaccgag atcacccacg tgagccaagc  7080
cctgctggag gtggagcagc tgctgaacgc ccccgacctg tgcgccaagg acttcgagga  7140
cctgttcaaa caagaggaga gcctgaagaa catcaaggac agcctgcagc aaagtagcgg  7200
cagaatcgac atcatccaca gcaagaagac cgccgccctg cagagcgcca cccccgtgga  7260
gagagtgaag cttcaagagg ccctttcgca gctggatttt cagtgggaga aggtgaacaa  7320
aatgtacaag gacagacaag gcagattcga cagaagcgtg gagaagtgga gaagattcca  7380
ctacgacatc aagatcttca atcagtggct gaccgaggca gagcagttcc tgagaaagac  7440
acagatcccc gagaactggg agcacgccaa gtacaagtgg tacctgaagg agctgcaaga  7500
cggcatcggg cagagacaga ccgtggtgag aaccctgaac gccaccggcg aggagatcat  7560
ccaacaaagc tccaaaaccg acgctagcat cctgcaagag aaactgggca gcctgaacct  7620
gagatggcaa gaggtgtgca agcagctgag cgaccgcaaa aaacggttag aggagcagaa  7680
gaacatcctg agcgagtttc agcgggacct gaacgagttc gtgctgtggc tggaggaggc  7740
cgataacatc gctagcatcc ccctggagcc cggcaaggag cagcagttaa aagaaaaact  7800
tgagcaagtg aagctgctgg tggaggagct gcccctgaga caaggcatcc tgaagcagct  7860
gaacgagact ggcggccccg tgctggtgag cgcccccatc agccccgagg agcaagacaa  7920
gctggagaac aagctgaagc agaccaacct gcagtggatc aaggtgagca gagccctgcc  7980
cgagaagcaa ggcgaaatcg aggcccaaat aaaggacctg gggcagctgg agaagaaact  8040
cgaagacttg gaagaacaac tcaaccactt gctgctgtgg ctgagcccca tcagaaatca  8100
gctggagatc tacaatcagc ccaaccaaga ggggccattc gacgtgaagg aaaccgagat  8160
cgccgtgcaa gccaagcagc ccgatgtgga ggagatcctg agcaaggggc agcacctgta  8220
caaggagaag cccgccacac agcccgtcaa gcgtaaacta gaggatcttt cctctgagtg  8280
gaaggccgtg aaccgtctgc tacaagagct gcgggctaag caacccgact tagcgcccgg  8340
cctgaccacc atcggtgcaa gccccacgca gaccgtgacc ctggtgaccc aacccgtggt  8400
gaccaaggaa accgccatca gcaagctgga gatgcctagc agcctgatgc tggaggtgcc  8460
cgccctggcc gacttcaaca gagcctggac cgagctgacc gactggctga gcctgctgga  8520
ccaagtgatc aagtctcaga gagtgatggt gggcgatctg gaggacatca atgagatgat  8580
catcaagcag aaggccacca tgcaagacct ggagcagaga agacctcagc tggaggagct  8640
gatcaccgcc gctcagaacc tgaaaaacaa gacgagcaac caagaggcta gaaccatcat  8700
caccgacaga atcgagagaa ttcagaatca gtgggacgag gtgcaagagc acctgcagaa  8760
cagaagacag caactaaacg aaatgctcaa ggacagcaca cagtggctgg aggccaagga  8820
ggaggcggag caagtgttgg gccaagctag agccaagctg gagagctgga aggagggacc  8880
ctacaccgtg gacgccattc agaagaagat caccgaaacc aagcagctgg ccaaggacct  8940
gcgacagtgg cagaccaacg tggacgtggc caacgatctt gccctgaagc tgctgcgcga  9000
ctatagcgcc gacgacacaa gaaaggtgca catgatcacc gagaacatca acgctagctg  9060
gcgtagcatc cacaagagag tgagcgagag agaggcggct ttggaggaaa cccatagact  9120
gctgcagcag tttcccctgg acctggagaa gttcctggcc tggctgaccg aagccgaaac  9180
aaccgccaac gtgctgcaag acgccacaag aaaggagaga ctgctggagg acagcaaggg  9240
cgtgaaggag ctgatgaagc agtggcaaga cctgcaaggc gagatcgaag cgcacaccga  9300
cgtgtaccac aacctggacg agaactctca gaagatcctg agaagcctgg agggcagcga  9360
cgacgccgtg ctgttacaga gaaggctgga caacatgaac ttcaagtgga gcgagctgag  9420
aaagaagagc ctgaacatca gaagccacct ggaggctagc agcgatcagt ggaagagact  9480
gcacctgagc ctgcaagagc tgctggtctg gcttcagttg aaggacgatg agctgagcag  9540
acaagccccc atcggcggcg acttccccgc cgtgcagaag cagaacgacg tgcatagagc  9600
cttcaagaga gagctgaaga ccaaggagcc cgtgatcatg agcaccctgg aaacggtgag  9660
aatcttcctg accgagcagc ccctggaggg cctggagaag ctgtaccaag agcctagaga  9720
gctgcccccc gaggagagag ctcagaacgt gacaagactg ctgagaaagc aagccgaaga  9780
ggtgaacacc gagtgggaga agctgaacct gcacagcgcc gactggcaga gaaagatcga  9840
cgaaaccctg gagagactga gagaattgca agaggcgacc gacgagctgg acctgaagct  9900
gagacaagcc gaggtcatca agggcagctg gcagcccgtg ggcgatctat taattgactc  9960
tctacaagac cacctggaga aagtgaaggc cctgagaggc gagatcgccc ccctgaagga  10020
gaacgtgagc cacgtgaatg atctggcacg tcagctgacc accctgggca tacaactgtc  10080
cccctataac ctgagcacac tggaggattt gaatactaga tggaagctgc tgcaagtggc  10140
cgtggaggac agagtaagac aattacatga ggcccacaga gacttcggcc ccgcttctca  10200
gcacttcctg agcacaagcg tgcaaggccc ctgggagaga gccatttccc ccaacaaggt  10260
cccctactac atcaaccacg agacacagac cacctgctgg gaccacccca agatgaccga  10320
gctgtatcag agcctcgccg atctgaacaa tgtgagattc agcgcctaca gaaccgccat  10380
gaagctgaga agactgcaga aggccctgtg cctggactta ttagcctga gcgccgcctg  10440
cgacgccctg gatcagcaca acctgaagca aaacgaccaa cccatggaca tcctgcagat  10500
catcaactgc ctcaccacca tatacgacag actggaacaa gagcacaaca acctggtgaa  10560
cgtgcccctg tgcgtggaca tgtgcctgaa ctggctgctg aacgtgtacg acaccggcag  10620
aaccggcaga atcagagtgc tgagcttcaa gaccggcatc atcagcctgt gcaaggccca  10680
cctggaggac aaatacagat accttttcaa acaagtggct agcagcaccg gcttctgcga  10740
ccaaagaaga ctgggtctgc tgctgcacga cagcattcag atccctagac agctgggcga  10800
ggtggctagc ttcggcggca gcaacatcga gcctagcgtg agaagctgct ttcagttcgc  10860
caacaacaag cccgagatag aggcagccct cttcttagac tggatgagac tggagcctca  10920
gagcatggta tggctgccgg tcctgcacag agtggccgcc gccgaaaccg ccaagcacca  10980
agccaagtgc aacatctgca aggagtgccc catcatcggc ttcagataca gaagcctgaa  11040
gcacttcaac tacgacatct gtcagagctg cttcttcagc ggcagagtgg ccaagggcca  11100
caagatgcac taccccatgg tggagtactg cacccccacc acaagcggcg aggacgtgag  11160
agacttcgcc aaggtgttga agaataagtt tagaaccaag agatacttcg ccaagcaccc  11220
```

```
tagaatgggc tacctgcccg tgcagaccgt gctggagggc gacaacatgg aaacccccgt  11280
gaccctgatc aacttctggc ccgtggacag cgcccccgct agcagccctc agctgagcca  11340
cgacgacacc cacagcagaa tcgagcacta cgctagcaga ctggccgaga tggagaacag  11400
caacggcagc tacctgaacg acagcatcag cccgaatgag agcatcgacg acgagcacct  11460
gctgattcag cactactgtc agagcctgaa ccaagacagc cccctgtctc agcctagaag  11520
ccccgctcag atcctgatca gcctggagag cgaggagaga ggcgagctgg agagaatcct  11580
agcagatctg gaggaagaga acagaaacct gcaagccgag tatgaccgac tgaaacagca  11640
acatgagcac aaaggcctga gcccactgcc ctccccccc gagatgatgc ccacaagccc  11700
tcagagccct agagacgccg agctgatcgc tgaagcgaag ttacttagac aacacaaggg  11760
cagactggag gctagaatgc agatcctgga ggaccacaac aagcagctgg agtctcagct  11820
gcacagactg aggcagctgc tggaacagcc ccaagccgag gccaaagtga acggcaccac  11880
cgtgagcagt cctagcacaa gcctgcagag aagcgacagc tctcagccca tgctgctgag  11940
agtggtgggc tctcagacaa gcgacagcat gggcgaggag gatctgctga gtccgcccca  12000
agacacaagc accggcctgg aagaggtgat ggagcaactg aacaatagct tccctagcag  12060
cagaggcaga aacacccccg gcaagcccat gagagaggac accatgtgat gactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg tgtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgggaag atgtctactg agctgtgcga tccctgctgg ggactttccg ctggggactt  12780
tccgctgggg actttccgcc ttcagctaag gaagctacca atatttagag gtacattttg  12840
ttctagaaca aaatgtaccg gtacattttg ttctggtaca ttttgttct             12889

SEQ ID NO: 7           moltype = DNA  length = 12889
FEATURE                Location/Qualifiers
source                 1..12889
                       mol_type = other DNA
                       note = MHCK7-hBGi-DMD-4-WPRE3-DTS
                       organism = synthetic construct
SEQUENCE: 7
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccact acgggtctag  240
gctgcccatg taaggaggca aggcctgggg acacccgaga tgcctggtta taattaaccc  300
agacatgtgg ctgccccccc cccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctttgg tgggaagaag tcgaggactg  1080
ctacgagcgc gaggacgtgc agaagaaaac cttcaccaaa tgggtcaacg cccagttcag  1140
caagttcggc aagcagcaca tcgagaacct gttcagcgac ctgcaggatg gcagaaggct  1200
gctggatctg ctggaaggcc tgacaggaca gaagctgccc aaagagaagg gcagcacaag  1260
agtgcacgcc ctgaacaacg tgaacaaggc cctgagagtg ctgcagaaca acaacgtgga  1320
cctggtcaac atcggcagca ccgacatcgt ggacggcaac cacaaactga ccctgggcct  1380
gatctggaac atcatcctgc actggcaagt gaagaacgtg atgaagaaca tcatggccgg  1440
cctgcagcag accaacagcg agaagattct gctgagctgg gtccgacaga gcacccggaa  1500
ttaccctcaa gtgaacgtga tcaacttcac cacctcttgg agcgacggac tggccctgaa  1560
tgccctgatc cacagccaca gacctgacct gttcgactgg aacagcgtcg tgtgtcagca  1620
gagcgccaca cagaggctgg aacacgcctt caatatcgcc agataccagc tgggcatcga  1680
gaaactgctg gaccccgagg atgtggacac cacctatcct gacaagaaat ccatcctcat  1740
gtacatcacc agcctgttcc aggtgctgcc ccagcaggtt tccatcgagg ccattcaaga  1800
ggtcgagatg ctgcccagac ctcctaaagt gaccaaagag gaacacttcc agctgcacca  1860
ccagatgcac tactctcagc agatcaccgt gtctctggcc cagggctacg agagaacaag  1920
cagccccaag cctcggttca agagctacgc ctatacacag gccgcctacg tgaccaccag  1980
cgatcctaca agaagcccat ttcctagcca gcatctggaa gcccctgagg acaagagctt  2040
tggcagcagc ctgatggaaa gcgaagtgaa cctggaccgc taccagacag ccctggaaga  2100
ggttctgagc tggctgctgt ctgccgagga tacactgcag gctcagggcg agatcagcaa  2160
cgacgtggaa gtggtcaagg accagtttca cacccacgag ggctacatga tggacctgac  2220
agcccaccag ggcagagtgg gcaatattct gcagctgggc tccaagctga tcggcacagg  2280
caagctgagc gaggacgaag agacagaggt gcaagagcag atgaacctgc tgaacagcag  2340
atgggagtgt ctgagagtgg ccagcatgga aaagcagagc aacctgcacc gggtgctgat  2400
ggatctccag aaccagaagc tgaaagagct gaacgactgg ctgaccaaga ccgaggaacg  2460
gacccggaag atggaagagg aacctctggg acccgacctg gaagatctga aaagacaggt  2520
gcagcagcat aaggtgctgc aagaggacct cgaacaagag caagtgcgcg tgaacagcct  2580
```

```
gacacacatg gtggtggtcg tggatgagag cagcggagat catgccacag ccgctctgga  2640
agaacagctg aaggtgctgg gagacagatg ggccaatatc tgccggtgga ccgaggatag  2700
atgggtgctg ctccaggaca tcctgctgaa gtggcagcgg ctgacagagg aacagtgcct  2760
gtttagcgcc tggctgtccg agaaagagga cgccgtcaac aagatccaca ccaccggctt  2820
caaggatcag aatgagatgc tgagcagcct gcagaaactg gccgtgctga aggctgacct  2880
ggaaaagaaa aagcagtcca tgggcaagct gtactccctg aagcaggacc tgctgagcac  2940
actgaagaac aagtctgtga cccagaaaac cgaggcctgg ctggacaact tcgcccggtg  3000
ttgggataac ctggtgcaga agctggaaaa gtccaccgct cagatctctc aggccgtgac  3060
cacaacacag ccttctctga cccagaccac cgtgatggaa acagtgacca cagtgacaac  3120
ccgcgagcag atcctggtca agcacgccca agaagaactg cctcctccac ctcctcagaa  3180
gaaacggcag atcacagtgg acagcgagat ccggaagaga ctggacgtgg acatcaccga  3240
gctgcacagc tggatcacca gatccgaagc cgtgctgcag tcccctgagt tcgccatctt  3300
cagaaaagag ggcaacttct ccgacctgaa agagaaagtc aacgccatcg agagagagaa  3360
ggccgagaag ttccggaagc tgcaggacgc ctctagatct gcccaggctc tggtggaaca  3420
gatggtcaac gaaggcgtga acgccgacag catcaagcag gcctcagagc agctgaactc  3480
ccggtggatc gagttctgtc agctcctgag cgagagactg aactggctgg aataccagaa  3540
caatatcatt gccttctaca accagctcca gcagctcgaa cagatgacca ccacagccga  3600
gaattggctg aagatccagc ctaccacacc tagcgagccc accgccatta agagccagct  3660
gaaaatctgc aaggacgaag tgaatcggct gagcgatctg cagccccaga tcgaaagact  3720
gaaaatccag tctatcgccc tcaaagagaa aggacagggc cccatgttcc tggacgccga  3780
ttttgtggcc tttaccaacc acttcaaaca ggtgttctcc gacgtgcagg cccgggaaaa  3840
agagctgcag accatcttcg acaccctgcc tccaatgaga taccaagaga caatgagcgc  3900
catccggacc tgggtgcagc aaagcgagac aaagctgagc atcccacagc tgagcgtgac  3960
cgactacgag atcatggaac agagactggg cgaactgcag gccctccagt ctagcctgca  4020
agaacagcag tccggcctgt actacctgag cacaaccgtg aaagagatga gcaagaaggc  4080
ccctagcgag atctcccgga agtaccagag cgagttcgaa gagatcgaag gccggtggaa  4140
gaagctgtct agccagctgg ttgagcactg ccagaaactc gaagaacaaa tgaacaagct  4200
gcgcaagatc cagaatcaca tccagacgct gaagaaatgg atggccgagg tggacgtgtt  4260
cctgaaagaa gagtggcccg ctctgggcga ctccgagatt ctgaagaaac agctcaaaca  4320
gtgccggctg ctggtgtccg atatccagac aatccagcca agcctgaact ccgtgaatga  4380
aggcggccag aagatcaaga acgaggccga gcctgagttt gccagcagac tggaaaccga  4440
actgaaagaa ctcaacaccc agtgggacca catgtgccag caagtgtacg cccggaaaga  4500
ggccctgaaa ggcggactcg aaaagactgt gtctctgcag aaagacctgt ctgagatgca  4560
cgagtggatg acccaggccg aagaggaata cctggaacgg gacttcgagt acaagacccc  4620
tgatgagctg caaaaagccg tcgaggaaat gaagcgggcc aaagaagagg cccagcagaa  4680
agaagccaaa gtcaagctgc tgaccgagtc cgtgaatagc gttatcgctc aggcccctcc  4740
tgtggctcaa gaggctctca agaaagaact ggaaactctg accaccaact accagtggct  4800
gtgcaccaga ctgaacggca agtgcaagac actggaagaa gtgtgggcct gctggcacga  4860
actgctgtcc tatctggaaa aggccaacaa gtggctgaac gaggtggaat tcaagctgaa  4920
aaccaccgag aacatccctg gcggcgctga agagattagc gaggtgctgg acagcctgga  4980
aaacctgatg agacacagcg aggacaaccc caatcagatc agaatcctgg ctcagaccct  5040
gaccgatggc ggcgtgatgg acgagctgat caacgaggaa ctcgaaacct tcaacagccg  5100
gtggcgggaa ctgcacgagg aagctgttcg gaggcagaag ttgctggaac agtctatcca  5160
gagcgcacaa gaaaccgaga agtccctgca cctgatccaa gagagcctga ccttcatcga  5220
caagcagctg gccgcttata tcgccgacaa ggtggacgct gctcagatgc cccaagaggc  5280
acagaagatt cagagcgacc tgaccagcca cgagattagc ctggaagaaa tgaagaagca  5340
caaccagggc aaagaggccg ctcagagagt cctgagccag atcgatgtgg cacagaaaaa  5400
gctccaggat gtgtccatga agtttcggct gtttcagaag cccgccaact tcgagcagag  5460
actgcaagag tccaagatga tcctggacga agtcaaaatg catctgcccg cactggaaac  5520
aaagtccgtg gaacaagaag tggtgcagtc ccagctgaac cactgcgtga acctgtacaa  5580
gagcctgtcc gaagtgaagt ctgaggtgga aatggtcatc aagaccggca ggcagatcgt  5640
ccagaagaag cagaccgaga atcccaaaga actcgacgag agagtgaccg ctctgaagct  5700
gcactacaat gagctgggcg ccaaagtgac cgagcggaag caacagcttg agaagtgcct  5760
gaaactgtct cggaagatgc ggaaagaaat gaacgtgctg acagagtggc tggccgccac  5820
cgatatggaa ctgactaaga gaagcgccgt ggaaggcatg cccagcaacc tggatagtga  5880
agtggcctgg ggcaaagcca ctcagaaaga gattgagaag cagaaggtcc acctgaagtc  5940
catcaccgaa gtgggcgaag ccctgaaaac cgtgctggga aagaaagaga cactggtcga  6000
ggacaagctg tccctgctga attccaactg gatcgccgtg acctccagag ctgaggaatg  6060
gctgaatctg ctgcttgagt accagaaaca catggaaacg ttcgaccaga acgtcgacca  6120
catcacaaag tggatcatcc aggctgatac cctgctggac gagtccgaga agaagaaacc  6180
ccaacaaaaa gaagatgtgc tgaagcggct gaaagccgag ctgaatgaca tccggcctaa  6240
ggtggacagc accagagatc aggcagccaa cctgatggcc aacagaggcg accactgtcg  6300
gaagctcgtg gaacctcaga tcagcgagct taaccacaga tttgccgcca tcagccaccg  6360
gatcaagaca ggcaaggcca gcattcctct caaagagctt gagcagttca acagcgacat  6420
ccaaaagctg ctcgaacccc tggaagccga gatccaacag ggcgtcaacc tcaaagaaga  6480
agatttcaac aaggacatga acgaggacaa tgagggcacc gtcaaagaac tgctgcagcg  6540
gggcgataat ctgcagcagc ggattaccga tgagcgcaag cgggaagaga tcaagattaa  6600
gcagcagctg ctgcagacca agcacaacgc cctgaaggac ctgcggagcc agagaagaaa  6660
gaaggccctg gaaatcagcc accagtggta tcagtacaag cggcaggccg acgacctgct  6720
gaagtgcctg gatgacatcg agaagaagct ggcctctctg cccgagccta gggacgagag  6780
aaagatcaaa gagatcgacc gcgagctgca gaaaaagaaa gaggaactga acgccgtccg  6840
cagacaggcc gaaggacttt ctgaagatgg cgccgctatg gccgtggaac ccacacagat  6900
tcagctgagc aagcggtggc gggaaatcga gagcaagttc gcccagttcc ggcggctgaa  6960
tttcgcccag atccacaccg tgcgggaaga gacaatgatg gtcatgacag aggacatgcc  7020
ccttgagatc agctacgtgc ccagcaccta cctgaccgag atcacccatg tgtctcaggc  7080
cctgctggaa gtggaacagc tgctgaatgc ccctgacctg tgcgccaagg acttcgagga  7140
cctgttcaag caagaggaaa gcctgaagaa catcaaggac agcctgcagc agagcagcgg  7200
ccggatcgat atcatccaca gcaagaaaac cgccgcactg cagagcgcca cacctgtgga  7260
aagagtgaag ctgcaagagg ccctgagcca gctggatttc cagtgggaga aagtgaacaa  7320
```

```
gatgtacaag gaccggcagg gcagattcga ccgcagcgtt gaaaagtggc ggcggttcca  7380
ctacgacatc aagatcttca accagtggct gaccgaggcc gagcagttcc tgagaaagac  7440
acagatcccc gagaactggg agcacgccaa gtacaagtgg tatctgaaag agctgcagga  7500
cggcatcggc cagagacaga cagtcgtgcg gacactgaat gccaccggcg aggaaatcat  7560
ccagcagtcc agcaagaccg acgccagcat cctgcaagag aagctgggca gcctgaacct  7620
gcggtggcaa gaagtgtgca agcagctgag cgaccggaag aagcggctgg aagaacagaa  7680
gaatatcctg agcgagttcc agcgggacct gaacgagttc gtgctgtggc tcgaagaggc  7740
cgacaatatc gccagcattc ccctggaacc tggcaaagag cagcagctga aagaaaagct  7800
ggaacaagtg aaactgctgg tcgaggaact gcccctgaga cagggaatcc tgaaacagct  7860
gaacgagaca ggcggccctg tgctggtgtc tgcccctatt tctcccgagg aacaggacaa  7920
gctggaaaac aagctgaagc agaccaacct gcagtggatc aaggtgtcca gagcactgcc  7980
tgagaagcag ggcgagatcg aggcccagat caaggacctg ggacagctcg aaaagaagct  8040
tgaggacctc gaagaacagc tcaaccatct gctgctttgg ctgagcccca tccggaacca  8100
gctggaaatc tacaaccagc ctaatcaaga gggccccttc gacgtgaaag aaaccgagat  8160
tgccgtgcag gccaagcagc ccgatgtgga agagatcctg tctaagggcc agcacctgta  8220
caaagagaag cccgccacac agcccgtgaa gcggaaactg gaagatctga gcagcgagtg  8280
gaaggccgtg aaccggctgc tgcaagaact gagagccaaa cagcctgatc tggcccctgg  8340
cctgacaaca attggcgcct ctcctacaca gaccgtgaca ctggtcacac agcctgtggt  8400
caccaaagag acagccatca gcaaactgga aatgcccagc agtctgatgc tcgaagtgcc  8460
cgcactggcc gacttcaata gagcctggac cgagctgacc gactggctca gtctgctgga  8520
ccaagtcatc aagtcccaga gagtgatggt cggagatctt gaggacatca acgagatgat  8580
cattaagcag aaagccacca tgcaggacct tgagcagaga aggccccagc ttgaagaact  8640
gatcaccgcc gctcagaacc tgaaaaacaa gaccagcaat caagaagccc ggaccatcat  8700
caccgaccgg atcgagagaa tccagaacca gtgggacgaa gtgcaagagc atctgcagaa  8760
cagacggcag cagctcaatg agatgctgaa ggacagcaca cagtggctgg aagccaaaga  8820
agaagccgag caggttctcg gacaggccag agctaagctg gaatcttgga aagagggacc  8880
ctacaccgtc gacgccatcc agaagaagat caccgagaca aagcagctgg ccaaggatct  8940
gagacagtgg cagaccaatg tggacgtggc caacgacctg gctctgaagc tgctgagaga  9000
ctacagcgcc gacgacacca gaaaggtgca catgatcacc gaaaacatca acgcctcttg  9060
gcggagcatc cacaagcggg tgtcagagag agaagccgct ctggaagaaa cacatagact  9120
gctccagcag ttcccactcg acctggaaaa gttcctggcc tggctgacag aagccgaaac  9180
caccgctaac gtgctccagg atgccaccag aaaagagcgg ctgttggagg acagcaaggg  9240
cgtcaaagaa ctcatgaagc agtggcagga tctgcaaggg gagattgaag cccacaccga  9300
cgtgtaccac aacctggacg agaacagcca gaagatcctg cggtccctgg aaggctctga  9360
tgatgctgtg ctgcttcaga ggcggctgga caacatgaac ttcaagtgga gcgagctgcg  9420
gaagaagtcc ctgaacatca gaagccacct ggaagcctcc agcgaccagt ggaaaagact  9480
gcacctgtct ctccaagagc tgctcgtgtg gctgcagctg aaggatgacg agctgagtag  9540
acaggcccct atcggcggag attttcccgc cgtgcagaaa cagaacgacg tgcaccgggc  9600
cttcaagaga gagctgaaaa caaaagaacc cgtcatcatg agcaccctgg aaaccgtgcg  9660
gatctttctg accgagcagc ctctggaagg actggaaaag ctgtaccaag agcctagaga  9720
gctgcctcct gaagaaaggg cccagaacgt gacacggctg cttagaaagc aggccgagga  9780
agtgaacacc gaatgggaga agctgaacct ccactccgcc gactggcagc ggaagatcga  9840
tgagacactg gaacggctgc gggaactgca agaagccaca gacgagctgg acctgaaact  9900
gcggcaggct gaagtgatca aaggctcctg gcagccagtg ggcgatctgc tgatcgatag  9960
cctgcaggac catctggaaa aagtcaaggc cctgcgggga gagatcgccc ctctcaaaga  10020
aaacgtgtcc cacgtgaacg atctggccag gcagctgaca acactgggca tccagctgag  10080
ccccttacaac ctgtctacct tggaggacct gaatacccgg tggaagctgc tccaagtggc  10140
cgtcgaggat agagtgcggc agctgcatga ggctcacaga gattttggac ccgccagcca  10200
gcacttcctg agcacatctg ttcaaggccc ctgggagaga gctatcagcc ctaacaaggt  10260
gccctactac atcaaccacg agacacagac cacctgttgg gatcacccca agatgaccga  10320
actgtatcag tccctggccg acctgaacaa cgtgcggttt agcgcctacc ggaccgccat  10380
gaagctgcgc agactgcaga aagctctgtg cctggacctg ctgtctctga gcgctgcttg  10440
tgatgccctg gaccagcata acctcaagca gaacgaccag cctatggaca tcctgcagat  10500
catcaactgc ctgaccacca tctacgaccg gctcgaacaa gagcacaaca acctggtcaa  10560
cgtgcccctg tgcgtggaca tgtgcctgaa ttggctgctg aacgtgtacg acaccggcag  10620
aaccggcagg atcagagtgc tgagcttcaa gaccggcatc atctccctgt gcaaggccca  10680
ccttgaggat aagtaccgct acctgtttaa gcaggtcgcc agcagcaccg gcttttgcga  10740
ccaaagaagg ctgggactgc tgctccacga cagcattcag atccctagac agctgggcga  10800
agtggcctct ttcggcggct ctaatatcga gcctagcgtg cggagctgct tccagttcgc  10860
caacaacaag cccgagattg aggccgcact gttcctggac tggatgagac tggaacccca  10920
gagcatggtc tggctgcctg tgctgcatag agtggccgca gccgaaacag ccaagcacca  10980
ggccaagtgc aacatctgca aagagtgccc catcatcggc ttccggtaca gatccctgaa  11040
gcacttcaac tacgatatct gccagtcctg cttcttcagc ggcagagtgg ccaagggcca  11100
caagatgcac taccccatgg tggaatactg cacccctacc acctctggcg aggacgtgcg  11160
ggattttgcc aaggtgctca agaacaagtt ccggaccaag cgctacttcg ctaagcaccc  11220
cagaatgggc tacctgccag tgcagacagt gcttgagggc gacaacatgg aaacccctgt  11280
gactctgatc aacttctggc ccgtggatag cgcccctgct agttctcctc agctgtctca  11340
cgacgatacc cacagcagaa tcgagcacta cgcctccaga ctggccgaga tggaaaacag  11400
caacggcagc tacctgaatg acagcatcag ccccaacgag agcatcgacg acgaacatct  11460
gctcattcag cactactgcc agagcctgaa tcaggacagc cctctgtctc agcctagaag  11520
ccctgcacag atcctgatca gcctggaaag cgaggaacgc ggcgagctgg aaagaatcct  11580
ggcagacctg gaagaggaaa accggaacct gcaggccgaa tacgacagac tcaagcagca  11640
gcacgagcac aagggactgt ctccactgcc ttctccacct gaaatgatgc ccacctctcc  11700
acagagcccc agagatgccg agctgattgc cgaagccaaa ctgctgaggc agcacaaagg  11760
cagactcgaa gccagaatgc agattctcga agatcacaac aagcagctcg aatcccagct  11820
gcacagactt aggcagctgc tggaacagcc tcaggcagag gccaaagtga atggcaccac  11880
cgtgtctagc cctagcacaa gcctgcagag atccgacagc agccagccaa tgcttctgag  11940
agtcgtgggc tcccagacca gcgattctat gggcgaagag gacctgctca gccctcctca  12000
ggatacaagc accggcctgg aagaagtgat ggaacaactg aacaacagct tccccagcag  12060
```

```
cagaggcaga aacacccctg gcaagcccat gcgcgaggac accatgtgat aactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg ggtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgggaag atgtctactg agctgtgcga tccctgctgg ggactttccg ctggggactt  12780
tccgctgggg actttccgcc ttcagctaag gaagctacca atatttagag gtacattttg  12840
ttctagaaca aaatgtaccg gtacattttg ttctggtaca ttttgttct              12889
```

```
SEQ ID NO: 8           moltype = DNA  length = 382
FEATURE                Location/Qualifiers
source                 1..382
                       mol_type = other DNA
                       note = WPRE3
                       organism = synthetic construct
SEQUENCE: 8
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt gg                                           382
```

```
SEQ ID NO: 9           moltype = DNA  length = 224
FEATURE                Location/Qualifiers
source                 1..224
                       mol_type = other DNA
                       note = PolyA
                       organism = synthetic construct
SEQUENCE: 9
tgtgccttct agttgccagc catctgttgt ttgcccctcc cccgtgcctt ccttgaccct  60
ggaaggtgcc actcccactg tcctttccta ataaaatgag gaaattgcat cgcattgtct  120
gagtaggtgt cattctattc tggggggtgg ggtggggcag gacagcaagg gggaggattg  180
ggaagacaat agcaggcatg ctggggatgc ggtgggctct atgg                   224
```

```
SEQ ID NO: 10          moltype = DNA  length = 608
FEATURE                Location/Qualifiers
source                 1..608
                       mol_type = other DNA
                       note = Post-Tx Reg.
                       organism = synthetic construct
SEQUENCE: 10
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggggtgtgcc ttctagttgc cagccatctg ttgtttgccc  420
ctcccccgtg ccttccttga ccctggaagg tgccactccc actgtccttt cctaataaaa  480
tgaggaaatt gcatcgcatt gtctgagtag gtgtcattct attctggggg gtggggtggg  540
gcaggacagc aagggggagg attgggaaga caatagcagg catgctgggg atgcggtggg  600
ctctatgg                                                           608
```

```
SEQ ID NO: 11          moltype = DNA  length = 150
FEATURE                Location/Qualifiers
source                 1..150
                       mol_type = other DNA
                       note = DTS
                       organism = synthetic construct
SEQUENCE: 11
gagctgtgcg atccctgctg gggactttcc gctggggact ttccgctggg gactttccgc  60
cttcagctaa ggaagctacc aatatttaga ggtacatttt gttctagaac aaaatgtacc  120
ggtacatttt gttctggtac attttgttct                                   150
```

```
SEQ ID NO: 12          moltype = DNA  length = 771
FEATURE                Location/Qualifiers
source                 1..771
                       mol_type = other DNA
                       note = Post-Tx Reg. DTS
                       organism = synthetic construct
SEQUENCE: 12
```

```
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcc ttctagttgc cagccatctg ttgtttgccc  420
ctcccccgtg ccttccttga ccctggaagg tgccactccc actgtccttt cctaataaaa  480
tgaggaaatt gcatcgcatt gtctgagtag gtgtcattct attctggggg gtggggtggg  540
gcaggacagc aagggggagg attgggaaga caatagcagg catgctgggg atgcggtggg  600
ctctatggga agatgtctac tgagctgtgc gatccctgct ggggactttc cgctggggac  660
tttccgctgg ggactttccg ccttcagcta aggaagctac caatatttag aggtacattt  720
tgttctagaa caaaatgtac cggtacattt tgttctggta cattttgttc t          771

SEQ ID NO: 13          moltype = AA  length = 3685
FEATURE                Location/Qualifiers
source                 1..3685
                       mol_type = protein
                       note = Dystrophin -WT
                       organism = synthetic construct
SEQUENCE: 13
MLWWEEVEDC YEREDVQKKT FTKWVNAQFS KFGKQHIENL FSDLQDGRRL LDLLEGLTGQ  60
KLPKEKGSTR VHALNNVNKA LRVLQNNNVD LVNIGSTDIV DGNHKLTLGL IWNIILHWQV  120
KNVMKNIMAG LQQTNSEKIL LSWVRQSTRN YPQVNVINFT TSWSDGLALN ALIHSHRPDL  180
FDWNSVVCQQ SATQRLEHAF NIARYQLGIE KLLDPEDVDT TYPDKKSILM YITSLFQVLP  240
QQVSIEAIQE VEMLPRPPKV TKEEHFQLHH QMHYSQQITV SLAQGYERTS SPKPRFKSYA  300
YTQAAYVTTS DPTRSPFPSQ HLEAPEDKSF GSSLMESEVN LDRYQTALEE VLSWLLSAED  360
TLQAQGEISN DVEVVKDQFH THEGYMMDLT AHQGRVGNIL QLGSKLIGTG KLSEDEETEV  420
QEQMNLLNSR WECLRVASME KQSNLHRVLM DLQNQKLKEL NDWLTKTEER TRKMEEEPLG  480
PDLEDLKRQV QQHKVLQEDL EQEQVRVNSL THMVVVVDES SGDHATAALE EQLKVLGDRW  540
ANICRWTEDR WVLLQDILLK WQRLTEEQCL FSAWLSEKED AVNKIHTTGF KDQNEMLSSL  600
QKLAVLKADL EKKKQSMGKL YSLKQDLLST LKNKSVTQKT EAWLDNFARC WDNLVQKLEK  660
STAQISQAVT TTQPSLTQTT VMETVTTVTT REQILVKHAQ EELPPPPPQK KRQITVDSEI  720
RKRLDVDITE LHSWITRSEA VLQSPEFAIF RKEGNFSDLK EKVNAIEREK AEKFRKLQDA  780
SRSAQALVEQ MVNEGVNADS IKQASEQLNS RWIEFCQLLS ERLNWLEYQN NIIAFYNQLQ  840
QLEQMTTTAE NWLKIQPTTP SEPTAIKSQL KICKDEVNRL SDLQPQIERL KIQSIALKEK  900
GQGPMFLDAD FVAFTNHFKQ VFSDVQAREK ELQTIFDTLP PMRYQETMSA IRTWVQQSET  960
KLSIPQLSVT DYEIMEQRLG ELQALQSSLQ EQQSGLYYLS TTVKEMSKKA PSEISRKYQS  1020
EFEEIEGRWK KLSSQLVEHC QKLEEQMNKL RKIQNHIQTL KKWMAEVDVF LKEEWPALGD  1080
SEILKKQLKQ CRLLVSDIQT IQPSLNSVNE GGQKIKNEAE PEFASRLETE LKELNTQWDH  1140
MCQQVYARKE ALKGGLEKTV SLQKDLSEMH EWMTQAEEEY LERDFEYKTP DELQKAVEEM  1200
KRAKEEAQQK EAKVKLLTES VNSVIAQAPP VAQEALKKEL ETLTTNYQWL CTRLNGKCKT  1260
LEEVWACWHE LLSYLEKANK WLNEVEFKLK TTENIPGGAE EISEVLDSLE NLMRHSEDNP  1320
NQIRILAQTL TDGGVMDELI NEELETFNSR WRELHEEAVR RQKLLEQSIQ SAQETEKSLH  1380
LIQESLTFID KQLAAYIADK VDAAQMPQEA QKIQSDLTSH EISLEEMKKH NQGKEAAQRV  1440
LSQIDVAQKK LQDVSMKFRL FQKPANFEQR LQESKMILDE VKMHLPALET KSVEQEVVQS  1500
QLNHCVNLYK SLSEVKSEVE MVIKTGRQIV QKKQTENPKE LDERVTALKL HYNELGAKVT  1560
ERKQQLEKCL KLSRKMRKEM NVLTEWLAAT DMELTKRSAV EGMPSNLDSE VAWGKATQKE  1620
IEKQKVHLKS ITEVGEALKT VLGKKETLVE DKLSLLNSNW IAVTSRAEEW LNLLLEYQKH  1680
METFDQNVDH ITKWIIQADT LLDESEKKKP QQKEDVLKRL KAELNDIRPK VDSTRDQAAN  1740
LMANRGDHCR KLVEPQISEL NHRFAAISHR IKTGKASIPL KELEQFNSDI QKLLEPLEAE  1800
IQQGVNLKEE DFNKDMNEDN EGTVKELLQR GDNLQQRITD ERKREEIKIK QQLLQTKHNA  1860
LKDLRSQRRK KALEISHQWY QYKRQADDLL KCLDDIEKKL ASLPEPRDER KIKEIDRELQ  1920
KKKEELNAVR RQAEGLSEDG AAMAVEPTQI QLSKRWREIE SKFAQFRRLN FAQIHTVREE  1980
TMMVMTEDMP LEISYVPSTY LTEITHVSQA LLEVEQLLNA PDLCAKDFED LFKQEESLKN  2040
IKDSLQQSSG RIDIIHSKKT AALQSATPVE RVKLQEALSQ LDFQWEKVNK MYKDRQGRFD  2100
RSVEKWRRFH YDIKIFNQWL TEAEQFLRKT QIPENWEHAK YKWYLKELQD GIGQRQTVVR  2160
TLNATGEEII QQSSKTDASI LQEKLGSLNL RWQEVCKQLS DRKKRLEEQK NILSEFQRDL  2220
NEFVLWLEEA DNIASIPLEP GKEQQLKEKL EQVKLLVEEL PLRQGILKQL NETGGPVLVS  2280
APISPEEQDK LENKLKQTNL QWIKVSRALP EKQGEIEAQI KDLGQLEKKL EDLEEQLNHL  2340
LLWLSPIRNQ LEIYNQPNQE GPFDVKETEI AVQAKQPDVE EILSKGQHLY KEKPATQPVK  2400
RKLEDLSSEW KAVNRLLQEL RAKQPDLAPG LTTIGASPTQ TVTLVTQPVV TKETAISKLE  2460
MPSSLMLEVP ALADFNRAWT ELTDWLSLLD QVIKSQRVMV GDLEDINEMI IKQKATMQDL  2520
EQRRPQLEEL ITAAQNLKNK TSNQEARTII TDRIERIQNQ WDEVQEHLQN RRQQLNEMLK  2580
DSTQWLEAKE EAEQVLGQAR AKLESWKEGP YTVDAIQKKI TETKQLAKDL RQWQTNVDVA  2640
NDLALKLLRD YSADDTRKVH MITENINASW RSIHKRVSER EAALEETHRL LQQFPLDLEK  2700
FLAWLTEAET TANVLQDATR KERLLEDSKG VKELMKQWQD LQGEIEAHTD VYHNLDENSQ  2760
KILRSLEGSD DAVLLQRRLD NMNFKWSELR KKSLNIRSHL EASSDQWKRL HLSLQELLVW  2820
LQLKDDELSR QAPIGGDFPA VQKQNDVHRA FKRELKTKEP VIMSTLETVR IFLTEQPLEG  2880
LEKLYQEPRE LPPEERAQNV TRLLRKQAEE VNTEWEKLNL HSADWQRKID ETLERLRELQ  2940
EATDELDLKL RQAEVIKGSW QPVGDLLIDS LQDHLEKVKA LRGEIAPLKE NVSHVNDLAR  3000
QLTTLGIQLS PYNLSTLEDL NTRWKLLQVA VEDRVRQLHE AHRDFGPASQ HFLSTSVQGP  3060
WERAISPNKV PYYINHETQT TCWDHPKMTE LYQSLADLNN VRFSAYRTAM KLRRLQKALC  3120
LDLLSLSAAC DALDQHNLKQ NDQPMDILQI INCLTTIYDR LEQEHNNLVN VPLCVDMCLN  3180
WLLNVYDTGR TGRIRVLSFK TGIISLCKAH LEDKYRYLFK QVASSTGFCD QRRLGLLLHD  3240
SIQIPRQLGE VASFGGSNIE PSVRSCFQFA NNKPEIEAAL FLDWMRLEPQ SMVWLPVLHR  3300
VAAAETAKHQ AKCNICKECP IIGFRYRSLK HFNYDICQSC FFSGRVAKGH KMHYPMVEYC  3360
TPTTSGEDVR DFAKVLKNKF RTKRYFAKHP RMGYLPVQTV LEGDNMETPV TLINFWPVDS  3420
APASSPQLSH DDTHSRIEHY ASRLAEMENS NGSYLNDSIS PNESIDDEHL LIQHYCQSLN  3480
```

```
QDSPLSQPRS PAQILISLES EERGELERIL ADLEEENRNL QAEYDRLKQQ HEHKGLSPLP  3540
SPPEMMPTSP QSPRDAELIA EAKLLRQHKG RLEARMQILE DHNKQLESQL HRLRQLLEQP  3600
QAEAKVNGTT VSSPSTSLQR SDSSQPMLLR VVGSQTSDSM GEEDLLSPPQ DTSTGLEEVM  3660
EQLNNSFPSS RGRNTPGKPM REDTM                                        3685

SEQ ID NO: 14          moltype = DNA  length = 13222
FEATURE                Location/Qualifiers
source                 1..13222
                       mol_type = other DNA
                       note = NP-CBA-hBGi-DMD-3-WPRE3-DTS
                       organism = synthetic construct
SEQUENCE: 14
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac catgctgtgg tgggaagagg  300
tggaggactg ttacgagaga gaggacgtgc agaagaagac attcaccaag tgggtgaacg  360
ctcagttcag caagttcggc aagcagcaca tcgagaacct gtttagcgat ctacaagatg  420
gcagaagact gctggacctg ctggagggcc tgaccgggca gaagctgccc aaagaaaagg  480
ggtctacaag agtgcacgcc ctgaacaacg tgaacaaggc cctgagagtg ctgcagaaca  540
acaacgtgga cctggtgaac atcggcagca ccgacatcgt ggacggcaac cacaagctga  600
ccctgggcct gatctggaac atcatcctgc actggcaagt gaagaacgtg atgaagaaca  660
tcatggccgg cctgcagcag accaacagcg agaagatcct gctgagctgg gtgagacaga  720
gcacaagaaa ctacccccaa gtgaacgtga tcaacttcac cacaagctgg agcgacggcc  780
tggccctgaa cgccctgatc cacagccaca gacccgacct gttcgactgg aacagcgtgg  840
tgtgtcagca gagcgccaca cagagactgg agcacgcctt caacatcgct agatatcagc  900
tgggcatcga gaagttactg gaccccgaag atgtggacac cacctacccc gacaagaaga  960
gcatcctgat gtacatcaca agcctgttcc aagtgctgcc tcagcaagtg agcatcgagg  1020
ccatccaaga agtcgagatg ctgcctagac cccccaaggt gaccaaggag gagcactttc  1080
agctgcacca tcagatgcac tactctcagc agatcacagt cagcttggca caaggctacg  1140
agagaacaag cagccccaag cctagattca agagctacgc ctacacccaa gccgcctacg  1200
tgaccacaag tgaccccaca agaagcccct tcccttctca gcacctggag gcccccgagg  1260
acaagagctt cggcagcagc ctgatggaga gcgaggtgaa cctggacaga tatcagaccg  1320
cgttagaaga agtgttgagc tggctgctga gcgccgagga caccctgcaa gcccaaggcg  1380
agatcagcaa cgatgtggag gtggtgaagg atcagttcca cacccacgag ggctacatga  1440
tggacctgac cgcccaccaa ggcagagtgg gcaacatcct gcagctgggc agcaagctga  1500
tcggcaccgg caagctgagc gaggacgagg aaaccgaggt tcaagagcaa atgaacctgc  1560
taaacagcag atgggagtgc ctgagagtgg ctagcatgga aaagcagagt aacctgcaca  1620
gagtgctgat ggacctgcag aatcagaaat tgaaagaact taatgattgg ctgaccaaga  1680
ccgaggagag aacaagaaag atggaggagg agcccctggg ccccgacctg gaggacctga  1740
agagacaagt gcagcagcac aaggtgctgc aagaggacct ggagcaagag caagtgagag  1800
tgaactctct gacacacatg gtggtggtag tggacgagag cagcggcgat cacgctaccg  1860
cggcgctgga agagcagctg aaagtgctgg gcgacagatg ggccaacatc tgcagatgga  1920
ccgaggacag atgggtgctg ctgcaagaca tcctgctgaa gtggcagaga ctgaccgagg  1980
agcagtgcct gttcagcgcc tggctgagcg agaaggaaga cgctgtgaac aagatccaca  2040
ccaccggctt caaggatcag aacgagatgc tgagctccct ccaaaagctc gcagtgctga  2100
aggccgacct ggaaaagaaa aaacagtcga tgggcaagct gtacagcctg aagcaagacc  2160
tgctgagcac cctgaagaac aagagcgtga cacagaagac cgaggcctgg ctggacaact  2220
tcgctagatg ctgggacaac ctggtacaga agttagagaa gtctaccgct cagatcagcc  2280
aagccgtaac caccacacaa cctagcctga ctcagaccac cgtgatggaa accgtgacca  2340
ccgtgacaac ccgtgagcag atcctggtga agcacgccca agaggagctg cccccccccc  2400
cccctcagaa gaagagacag atcaccgtgg actcagagat tcgcaagaga ctggacgtgg  2460
acatcaccga gctgcacagc tggatcacaa gaagcgaggc cgtgctgcag agccctgagt  2520
tcgcgatctt tagaaaggag ggcaacttca gcgacttgaa ggagaaagtg aacgccatcg  2580
agagagagaa ggccgagaag ttcagaaagt tgcaagacgc ctcaagaagc gcccaagccc  2640
tggtggagca gatggttaac gaaggcgtga atgccgacag catcaagcaa gctagcgagc  2700
agctgaatag ccggtggatt gaattctgtc agctgctgag cgagagatta aactggctgg  2760
agtatcagaa caacatcatc gccttctaca atcagctgca gcaactagaa caaatgacca  2820
ccaccgccga gaactggcta aagattcagc ccaccacccc tagcgagccc accgccatca  2880
aatctcagct gaaaatttgc aaggacgaag tgaacagact gtcggacctg cagcctcaaa  2940
tcgaaagact gaaaattcag agcatcgcac ttaaggagaa gggccaagga cccatgttcc  3000
tggacgccga cttcgtggcc ttcaccaacc acttcaagca agtgttcagc gacgtgcaag  3060
ctagagagaa ggagctgcag accatcttcg acaccctgcc ccccatgaga taccaagaaa  3120
ccatgagcgc catcagaacc tgggtgcagc agagcgaaac caagctgagc atccctcagc  3180
tgagcgtgac cgactacgag atcatggagc aaagactggg agagctgcaa gccctgcaga  3240
gcagcctgca agagcagcag agcggcctgt actacctgag caccaccgtg aaggagatgt  3300
cgaagaaagc ccccgtcggag atcagcagaa agtatcagag cgagttcgag gagatcgagg  3360
gcagatggaa gaagctgagc agccaactgg tggaacactg tcagaaatta gaagaacaga  3420
tgaacaagct gagaaagatt cagaaccaca ttcagaccct gaagaagtgg atggccgagg  3480
tggacgtgtt cctgaaagag gagtggcccg ccctgggcga ttccgaaatc ttaaaaaagc  3540
agctgaagca gtgcagactg ctggtgtcag atatccaaac cattcaacca agcctgaaca  3600
gcgtgaacga aggcgggcag aagatcaaga acgaggccga gcccgagttc gctagcagac  3660
tggaaaccga gctgaaggag ctgaatacac agtgggacca catgtgtcag caagtgtacg  3720
ctagaaagga agcgctgaag ggcgggctgg agaagaccgt tagcctgcaa aaggatctga  3780
gcgagatgca cgaggtggatg acccaagccg aggaggagta cctggagaga gacttcgagt  3840
acaagacccc cgacgagctg cagaaggccg tcgaggaaat gaagagagcg aaggaggagg  3900
ctcagcagaa ggaagccaag gtgaagctgc tgactgaatc tgtcaacagt gtgatagctc  3960
aagcaccccc cgttgcccaa gaggcactaa agaaggagct ggaaactctg accaccaact  4020
```

```
atcagtggct gtgcacaaga ctgaacggca agtgcaagac cctggaggaa gtgtgggcct  4080
gctggcacga gctgctgagc tacctggaga aggccaacaa gtggctgaac gaggtggagt  4140
tcaagctgaa gaccaccgag aacatccccg gcggcgccga ggagatcagc gaggtgctgg  4200
acagcctgga gaacctgatg agacacagcg aggacaaccc caatcagatc agaatcctgg  4260
ctcagaccct gaccgacggc ggcgtgatgg acgagctgat caacgaggag ctggaaacct  4320
ttaactctag atggcgagaa ctgcacgagg aggccgtgag aagacagaag ctgctggagc  4380
aaagcattca gagcgcccaa gaaaccgaga agagcctgca cctgatccaa gagagcctga  4440
ccttcatcga caagcagctg gccgcctaca tcgccgacaa ggtggacgcc gctcagatgc  4500
cacaagaggc tcagaagatt cagtccgatc tgacaagcca cgagatcagc ctggaggaga  4560
tgaaaaaaca caaccaaggc aaggaggccg ctcagagagt gctgtctcag atcgacgtgg  4620
ctcagaagaa gctgcaagac gtgagcatga agttcagact gtttcagaag cccgccaact  4680
tcgagcagcg actgcaagag agcaagatga tcctggacga ggtgaagatg cacctgcccg  4740
ccctggaaac caagagcgtg gagcaagagg tggtgcagtc tcagttgaac cactgcgtga  4800
acctgtacaa gagcctgtcg gaggtcaaga gtgaggtcga gatggtgatc aaaactggga  4860
gacagatcgt gcaaaaaaag cagaccgaga accccaagga gctggacgag cgtgttaccg  4920
ccctgaagct gcactacaac gagctgggcg ccaaggtgac cgagagaaag cagcagctgg  4980
agaagtgcct gaagctgagc agaaagatga gaaaggagat gaacgtgctg accgagtggc  5040
tggccgccac cgacatggag ctgaccaaga gaagcgccgt ggagggcatg cctagcaacc  5100
tggacagcga ggtggcctgg ggcaaggcca cacagaagga gatcgagaag cagaaggtgc  5160
acctgaagag catcaccgag gtgggcgagg ccctgaagac cgtgctgggc aagaaggaaa  5220
ccctggtgga ggacaagctg agcctgctga actcgaactg gatcgccgtg acaagcagag  5280
ccgaggagtg gctgaacctg ctgttagagt accaaaaaca catggaaacc ttcgatcaga  5340
acgtggacca catcaccaag tggatcatcc aagccgacac cctgctggac gaaagcgaaa  5400
agaagaagcc gcaacaaaag gaggatgtgc tgaagagact gaaggccgaa ctgaacgata  5460
tcagacccaa ggtggacagc acacgggacc aagccgccaa cctgatggcc aacagaggcg  5520
accactgcag aaaactggtg gagcctcaga tcagcgagct gaaccacaga ttcgccgcca  5580
tcagccacag aatcaaaacc ggcaaagcga gcatcccctt gaaggaactg gagcaattta  5640
acagcgacat ccaaaaattg ctcgaaccac tggaggccga gattcagcaa ggcgtgaacc  5700
tgaaggaaga ggacttcaac aaggacatga acgaggacaa cgagggcacc gtgaaagaac  5760
tgctgcagag aggcgacaac ctgcagcaga gaatcaccga cgagagaaag agagaggaga  5820
tcaagatcaa gcagcagctg ctgcagacta agcacaacgc cctgaaggat ctgagatctc  5880
agaggagaaa aaaggctctg gaaatttcac atcagtggta tcagtacaag agacaagcag  5940
acgacctgct gaagtgcctg gacgacatcg agaagaagtt agctagcctg cccgagccta  6000
gagacgagag aaagatcaag gagatcgaca gagagttaca aaagaagaag gaggagctga  6060
atgcggtaag aagacaagcg gaaggcctgt ccgaggacgg cgcagccatg gccgtggagc  6120
ccacacagat tcagctcagc aagagatgga gagagatcga gagcaagttc gctcagttca  6180
gaagactgaa cttcgctcag atccacaccg tgagagagga aaccatgatg gtgatgaccg  6240
aggacatgcc cctggagatc tcatacgttc ctagcaccta cctgaccgag atcacccacg  6300
tgagccaagc cctgctggag gtggagcagc tgctgaacgc ccccgacctg tgcgccaagg  6360
acttcgagga cctgttcaaa caagaggaga gcctgaagaa catcaaggac agcctgcagc  6420
aaagtagcgg cagaatcgac atcatccaca gcaagaagac cgccgccctg cagagcgcca  6480
cccccgtgga gagagtgaag cttcaagagg ccctttcgca gctggatttt cagtgggaga  6540
aggtgaacaa aatgtacaag gacagacaag gcagattcga cagaagcgtg gagaagtgga  6600
gaagattcca ctacgacatc aagatcttca atcagtggct gaccgaggca gagcagttcc  6660
tgagaaagac acagatcccc gagaactggg agcacgccaa gtacaagtgg tacctgaagg  6720
agctgcaaga cggcatcggg cagagacaga ccgtggtgag aaccctgaac gccaccggcg  6780
aggagatcat ccaacaaagc tccaaaaccg acgctagcat cctgcaagag aaactgggca  6840
gcctgaacct gagatggcaa gaggtgtgca agcagctgag cgaccgcaaa aaacggttag  6900
aggagcagaa gaacatcctg agcgagtttc agcgggacct gaacgagttc gtgctgtggc  6960
tggaggaggc cgataacatc gctagcatcc ccctggagcc cggcaaggag cagcagttaa  7020
aagaaaaact tgagcaagtg aagctgctgg tggaggagct gcccctgaga caaggcatcc  7080
tgaagcagct gaacgagact ggcggccccg tgctggtgag cgcccccatc agccccgagg  7140
agcaagacaa gctggagaac aagctgaagc agaccaacct gcagtggatc aaggtgagca  7200
gagccctgcc cgagaagcaa ggcgaaatcg aggcccaaat aaaggacctg gggcagctgg  7260
agaagaaact cgaagacttg gaagaacaac tcaaccactt gctgctgtgg ctgagcccca  7320
tcagaaatca gctggagatc tacaatcagc ccaaccaaga ggggccattc gacgtgaagg  7380
aaaccgagat cgccgtgcaa gccaagcagc ccgatgtgga ggagatcctg agcaaggggc  7440
agcacctgta caaggagaag cccgccacac agcccgtcaa gcgtaaacta gaggatcttt  7500
cctctgagtg gaaggccgtg aaccgtctgc tacaagagct gcgggctaag caacccgact  7560
tagcgcccgg cctgaccacc atcggtgcaa gccccacgca gaccgtgacc ctggtgaccc  7620
aacccgtggt gaccaaggaa accgccatca gcaagctgga gatgcctagc agcctgatgc  7680
tggaggtgcc cgccctggcc gacttcaaca gagcctggac cgagctgacc gactggctga  7740
gcctgctgga ccaagtgatc aagtctcaga gagtgatggt gggcgatctg gaggacatca  7800
atgagatgat catcaagcag aaggccacca tgcaagacct ggagcagaga agacctcagc  7860
tggaggagct gatcaccgcc gctcagaacc tgaaaaacaa gacgagcaac caagaggcta  7920
gaaccatcat caccgacaga atcgagagaa ttcagaatca gtgggacgag gtgcaagagc  7980
acctgcagaa cagaagacag caactaaacg aaatgctcaa ggacagcaca cagtggctgg  8040
aggccaagga ggaggcggag caagtgttgg gccaagctag agccaagctg gagagctgga  8100
aggagggacc ctacaccgtg gacgccattc agaagaagat caccgaaacc aagcagctgg  8160
ccaaggacct gcgacagtgg cagaccaacg tggacgtggc caacgatctt gccctgaagc  8220
tgctgcgcga ctatagcgcc gacgacacaa gaaaggtgca catgatcacc gagaacatca  8280
acgctagctg gcgtagcatc cacaagagag tgagcgagag agaggcggct ttggaggaaa  8340
cccatagact gctgcagcag tttcccctgg acctggagaa gttcctggcc tggctgaccg  8400
aagccgaaac aaccgccaac gtgctgcaag acgccacaag aaaggagaga ctgctggagg  8460
acagcaaggg cgtgaaggag ctgatgaagc agtggcaaga cctgcaaggc gagatcgaag  8520
cgcacaccga cgtgtaccac aacctggacg agaactctca gaagatcctg agaagcctgg  8580
agggcagcga cgacgccgtg ctgttacaga gaaggctgga caacatgaac ttcaagtgga  8640
gcgagctgag aaagaagagc ctgaacatca gaagccacct ggaggctagc agcgatcagt  8700
ggaagagact gcacctgagc ctgcaagagc tgctggtctg gcttcagttg aaggacgatg  8760
```

-continued

```
agctgagcag acaagccccc atcggcggcg acttccccgc cgtgcagaag cagaacgacg  8820
tgcatagagc cttcaagaga gagctgaaga ccaaggagcc cgtgatcatg agcaccctgg  8880
aaacggtgag aatcttcctg accgagcagc ccctggaggg cctggagaag ctgtaccaag  8940
agcctagaga gctgcccccc gaggagagag ctcagaacgt gacaagactg ctgagaaagc  9000
aagccgaaga ggtgaacacc gagtgggaga agctgaacct gcacagcgcc gactggcaga  9060
gaaagatcga cgaaaccctg gagagactga gagaattgca agaggcgacc gacgagctgg  9120
acctgaagct gagacaagcc gaggtcatca agggcagctg gcagcccgtg ggcgatctat  9180
taattgactc tctacaagac cacctggaga aagtgaaggc cctgagaggc gagatcgccc  9240
ccctgaagga gaacgtgagc cacgtgaatg atctggcacg tcagctgacc accctgggca  9300
tacaactgtc cccctataac ctgagcacac tggaggattt gaatactaga tggaagctgc  9360
tgcaagtggc cgtggaggac agagtaagac aattacatga ggcccacaga gacttcggcc  9420
ccgcttctca gcacttcctg agcacaagcg tgcaaggccc ctgggagaga gccatttccc  9480
ccaacaaggt cccctactac atcaaccacg agacacagac cacctgctgg gaccacccca  9540
agatgaccga gctgtatcag agcctcgccg atctgaacaa tgtgagattc agcgcctaca  9600
gaaccgccat gaagctgaga agactgcaga aggccctgtg cctggactta ttaagcctga  9660
gcgccgcctg cgacgccctg gatcagcaca acctgaagca aaacgaccaa cccatggaca  9720
tcctgcagat catcaactgc ctcaccacca tatacgacag actggaacaa gagcacaaca  9780
acctggtgaa cgtgcccctg tgcgtggaca tgtgcctgaa ctggctgctg aacgtgtacg  9840
acaccggcag aaccggcaga atcagagtgc tgagcttcaa gaccggcatc atcagcctgt  9900
gcaaggccca cctggaggac aaatacagat accttttcaa acaagtggct agcagcaccg  9960
gcttctgcga ccaaagaaga ctgggtctgc tgctgcacga cagcattcag atccctagac  10020
agctgggcga ggtggctagc ttcggcggca gcaacatcga gcctagcgtg agaagctgct  10080
ttcagttcgc caacaacaag cccgagatag aggcagccct cttcttagac tggatgagac  10140
tggagcctca gagcatggta tggctgccgg tcctgcacag agtggccgcc gccgaaaccg  10200
ccaagcacca agccaagtgc aacatctgca aggagtgccc catcatcggc ttcagataca  10260
gaagcctgaa gcacttcaac tacgacatct gtcagagctg cttcttcagc ggcagagtgg  10320
ccaagggcca caagatgcac taccccatgg tggagtactg cacccccacc acaagcggcg  10380
aggacgtgag agacttcgcc aaggtgttga agaataagtt tagaaccaag agatacttcg  10440
ccaagcaccc tagaatgggc tacctgcccg tgcagaccgt gctggagggc gacaacatgg  10500
aaacccccgt gaccctgatc aacttctggc ccgtggacag cgcccccgct agcagccctc  10560
agctgagcca cgacgacacc cacagcagaa tcgagcacta cgctagcaga ctggccgaga  10620
tggagaacag caacggcagc tacctgaacg acagcatcag cccgaatgag agcatcgacg  10680
acgagcacct gctgattcag cactactgtc agagcctgaa ccaagacagc cccctgtctc  10740
agcctagaag ccccgctcag atcctgatca gcctggagag cgaggagaga ggcgagctgg  10800
agagaatcct agcagatctg gaggaagaga acagaaacct gcaagccgag tatgaccgac  10860
tgaaacagca acatgagcac aaaggcctga gcccactgcc ctcccccccc gagatgatgc  10920
ccacaagccc tcagagccct agagacgccg agctgatcgc tgaagcgaag ttacttagac  10980
aacacaaggg cagactggag gctagaatgc agatcctgga ggaccacaac aagcagctgg  11040
agtctcagct gcacagactg aggcagctgc tggaacagcc ccaagccgag gccaaagtga  11100
acggcaccac cgtgagcagt cctagcacaa gcctgcagag aagcgacagc tctcagccca  11160
tgctgctgag agtggtgggc tctcagacaa gcgacagcat gggcgaggag gatctgctga  11220
gtccgcccca agacacaagc accggcctgg aagaggtgat ggagcaactg aacaatagct  11280
tccctagcag cagaggcaga aacacccccg gcaagcccat gagagaggac accatgtgat  11340
gactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acgtggcgcc atcggatccc gggcccgtgg  12180
cttgttgtcc acaaccatta aaccttaaaa gctttaaaag ccttatatat tcttttttt  12240
cttataaaac ttaaaacctt agaggctatt taagttgctg atttatatta attttattgt  12300
tcaaacatga gagcttagta cgtgaaacat gagagcttag tacattagcc atgagagctt  12360
agtacattag ccatgagggt ttagttcatt aaacatgaga gcttagtaca ttaaacatga  12420
gagcttagta cattaaacat gagagcttag tacatactat caacaggttg aactgctgat  12480
ctgtacagta gaattggtaa agagagttgt gtaaaatatt gagttcgcac atcttgttgt  12540
ctgattattg atttttggcg aaaccatttg atcatatgac aagatgtgta tctaccttaa  12600
cttaatgatt ttgataaaaa tcattatgcg gccgccgtta cataacttac ggtaaatggc  12660
ccgcctggct gaccgcccaa cgacccccgc ccattgacgt caataatgac gtatgttccc  12720
atagtaacgc caatagggac tttccattga cgtcaatggg tggagtattt acggtaaact  12780
gcccacttgg cagtacatca agtgtatcat atgccaagta cgccccctat tgacgtcaat  12840
gacggtaaat ggcccgcctg gcattatgcc cagtacatga ccttatggga ctttcctact  12900
tggcagtaca tctacgtatt agtcatcgct attaccatgg tcgaggtgag ccccacgttc  12960
tgcttcactc tccccatctc ccccccctcc ccacccccaa ttttgtattt atttattttt  13020
taattatttt gtgcagcgat gggggcgggg gggggggggg cgcgcgccag gcggggcggg  13080
gcggggcgag gggcggggcg gggcgaggcg gagaggtgcg gcggcagcca atcagagcgg  13140
cgcgctccga aagtttcctt ttatggcgag gcggcggcgg cggcggccct ataaaaagcg  13200
aagcgcgcgg cgggcgggag tc                                          13222
```

```
SEQ ID NO: 15          moltype = DNA  length = 13210
FEATURE                Location/Qualifiers
source                 1..13210
```

```
                        mol_type = other DNA
                        note = NP-CBA-hBGi-DMD-4-WPRE3-DTS
                        organism = synthetic construct
SEQUENCE: 15
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac catgctttgg tgggaagaag  300
tcgaggactg ctacgagcgc gaggacgtgc agaagaaaac cttcaccaaa tgggtcaacg  360
cccagttcag caagttcggc aagcagcaca tcgagaacct gttcagcgac ctgcaggatg  420
gcagaaggct gctggatctg ctggaaggcc tgacaggaca gaagctgccc aaagagaagg  480
gcagcacaag agtgcacgcc ctgaacaacg tgaacaaggc cctgagagtg ctgcagaaca  540
acaacgtgga cctggtcaac atcggcagca ccgacatcgt ggacggcaac cacaaactga  600
ccctgggcct gatctggaac atcatcctgc actggcaagt gaagaacgtg atgaagaaca  660
tcatggccgg cctgcagcag accaacagcg agaagattct gctgagctgg gtccgacaga  720
gcacccggaa ttaccctcaa gtgaacgtga tcaacttcac cacctcttgg agcgacggac  780
tggccctgaa tgccctgatc cacagccaca gacctgacct gttcgactgg aacagcgtcg  840
tgtgtcagca gagcgccaca cagaggctgg aacacgcctt caatatcgcc agataccagc  900
tgggcatcga gaaactgctg gaccccgagg atgtggacac cacctatcct gacaagaaat  960
ccatcctcat gtacatcacc agcctgttcc aggtgctgcc ccagcaggtt tccatcgagg  1020
ccattcaaga ggtcgagatg ctgcccagac ctcctaaagt gaccaaagag gaacacttcc  1080
agctgcacca ccagatgcac tactctcagc agatcaccgt gtctctggcc cagggctacg  1140
agagaacaag cagccccaag cctcggttca agagctacgc ctatacacag gccgcctacg  1200
tgaccaccag cgatcctaca agaagcccat ttcctagcca gcatctggaa gcccctgagg  1260
acaagagctt tggcagcagc ctgatggaaa gcgaagtgaa cctggaccgc taccagacag  1320
ccctggaaga ggttctgagc tggctgctgt ctgccgagga tacactgcag gctcagggcg  1380
agatcagcaa cgacgtggaa gtggtcaagg accagtttca cacccacgag ggctacatga  1440
tggacctgac agcccaccag ggcagagtgg gcaatattct gcagctgggc tccaagctga  1500
tcggcacagg caagctgagc gaggacgaag agacagaggt gcaagagcag atgaacctgc  1560
tgaacagcag atgggagtgt ctgagagtgg ccagcatgga aaagcagagc aacctgcacc  1620
gggtgctgat ggatctccag aaccagaagc tgaaagagct gaacgactgg ctgaccaaga  1680
ccgaggaacg gacccggaag atggaagagg aacctctggg acccgacctg gaagatctga  1740
aaagacaggt gcagcagcat aaggtgctgc aagaggacct cgaacaagag caagtgcgcg  1800
tgaacagcct gacacacatg gtggtggtcg tggatgagag cagcggagat catgccacag  1860
ccgctctgga agaacagctg aaggtgctgg gagacagatg ggccaatatc tgccggtgga  1920
ccgaggatag atgggtgctg ctccaggaca tcctgctgaa gtggcagcgg ctgacagagg  1980
aacagtgcct gtttagcgcc tggctgtccg agaaagagga cgccgtcaac aagatccaca  2040
ccaccggctt caaggatcag aatgagatgc tgagcagcct gcagaaactg gccgtgctga  2100
aggctgacct ggaaaagaaa aagcagtcca tgggcaagct gtactccctg aagcaggacc  2160
tgctgagcac actgaagaac aagtctgtga cccagaaaac cgaggcctgg ctggacaact  2220
tcgcccggtg ttgggataac ctggtgcaga agctggaaaa gtccaccgct cagatctctc  2280
aggccgtgac cacaacacag ccttctctga cccagaccac cgtgatggaa acagtgacca  2340
cagtgacaac ccgcgagcag atcctggtca agcacgccca agaagaactg cctcctccac  2400
ctcctcagaa gaaacggcag atcacagtgg acagcgagat ccggaagaga ctggacgtgg  2460
acatcaccga gctgcacagc tggatcacca gatccgaagc cgtgctgcag tcccctgagt  2520
tcgccatctt cagaaaagag ggcaacttct ccgacctgaa agagaaagtc aacgccatcg  2580
agagagagaa ggccgagaag ttccggaagc tgcaggacgc ctctagatct gcccaggctc  2640
tggtggaaca gatggtcaac gaaggcgtga acgccgacag catcaagcag gcctcagagc  2700
agctgaactc ccggtggatc gagttctgtc agctcctgag cgagagactg aactggctgg  2760
aataccagaa caatatcatt gccttctaca accagctcca gcagctcgaa cagatgacca  2820
ccacagccga gaattggctg aagatccagc ctaccacacc tagcgagccc accgccatta  2880
agagccagct gaaaatctgc aaggacgaag tgaatcggct gagcgatctg cagccccaga  2940
tcgaaagact gaaaatccag tctatcgccc tcaaagagaa aggacagggc cccatgttcc  3000
tggacgccga ttttgtggcc tttaccaacc acttcaaaca ggtgttctcc gacgtgcagg  3060
cccgggaaaa agagctgcag accatcttcg acaccctgcc tccaatgaga taccaagaga  3120
caatgagcgc catccggacc tgggtgcagc aaagcgagac aaagctgagc atcccacagc  3180
tgagcgtgac cgactacgag atcatggaac agagactggg cgaactgcag gccctccagt  3240
ctagcctgca agaacagcag tccggcctgt actacctgag cacaaccgtg aaagagatga  3300
gcaagaaggc ccctagcgag atctcccgga agtaccagag cgagttcgaa gagatcgaag  3360
gccggtggaa gaagctgtct agccagctgg ttgagcactg ccagaaactc gaagaacaaa  3420
tgaacaagct gcgcaagatc cagaatcaca tccagacgct gaagaaatgg atggccgagg  3480
tggacgtgtt cctgaaagaa gagtggcccg ctctgggcga ctccgagatt ctgaagaaac  3540
agctcaaaca gtgccggctg ctggtgtccg atatccagac aatccagcca agcctgaact  3600
ccgtgaatga aggcggccag aagatcaaga acgaggccga gcctgagttt gccagcagac  3660
tggaaaccga actgaaagaa ctcaacaccc agtgggacca catgtgccag caagtgtacg  3720
cccggaaaga ggccctgaaa ggcggactcg aaaagactgt gtctctgcag aaagacctgt  3780
ctgagatgca cgagtggatg acccaggccg aagaggaata cctggaacgg gacttcgagt  3840
acaagacccc tgatgagctg caaaaagccg tcgaggaaat gaagcgggcc aaagaagagg  3900
cccagcagaa agaagccaaa gtcaagctgc tgaccgagtc cgtgaatagc gttatcgctc  3960
aggcccctcc tgtggctcaa gaggctctca agaaagaact ggaaactctg accaccaact  4020
accagtggct gtgcaccaga ctgaacggca agtgcaagac actggaagaa gtgtgggcct  4080
gctggcacga actgctgtcc tatctggaaa aggccaacaa gtggctgaac gaggtggaat  4140
tcaagctgaa aaccaccgag aacatccctg gcggcgctga agagattagc gaggtgctgg  4200
acagcctgga aaacctgatg agacacagcg aggacaaccc caatcagatc agaatcctgg  4260
ctcagaccct gaccgatggc ggcgtgatgg acgagctgat caacgaggaa ctcgaaacct  4320
tcaacagccg gtggcgggaa ctgcacgagg aagctgttcg gaggcagaag ttgctggaac  4380
agtctatcca gagcgcacaa gaaaccgaga agtccctgca cctgatccaa gagagcctga  4440
ccttcatcga caagcagctg gccgcttata tcgccgacaa ggtggacgct gctcagatgc  4500
```

-continued

```
cccaagaggc acagaagatt cagagcgacc tgaccagcca cgagattagc ctggaagaaa  4560
tgaagaagca caaccagggc aaagaggccg ctcagagagt cctgagccag atcgatgtgg  4620
cacagaaaaa gctccaggat gtgtccatga agtttcggct gtttcagaag cccgccaact  4680
tcgagcagag actgcaagag tccaagatga tcctggacga agtcaaaatg catctgcccg  4740
cactggaaac aaagtccgtg gaacaagaag tggtgcagtc ccagctgaac cactgcgtga  4800
acctgtacaa gagcctgtcc gaagtgaagt ctgaggtgga aatggtcatc aagaccggca  4860
ggcagatcgt ccagaagaag cagaccgaga atcccaaaga actcgacgag agagtgaccg  4920
ctctgaagct gcactacaat gagctgggcg ccaaagtgac cgagcggaag caacagcttg  4980
agaagtgcct gaaactgtct cggaagatgc ggaaagaaat gaacgtgctg acagagtggc  5040
tggccgccac cgatatggaa ctgactaaga gaagcgccgt ggaaggcatg cccagcaacc  5100
tggatagtga agtggcctgg ggcaaagcca ctcagaaaga gattgagaag cagaaggtcc  5160
acctgaagtc catcaccgaa gtgggcgaag ccctgaaaac cgtgctggga aagaaagaga  5220
cactggtcga ggacaagctg tccctgctga attccaactg gatcgccgtg acctccagag  5280
ctgaggaatg gctgaatctg ctgcttgagt accagaaaca catggaaacg ttcgaccaga  5340
acgtcgacca catcacaaag tggatcatcc aggctgatac cctgctggac gagtccgaga  5400
agaagaaacc ccaacaaaaa gaagatgtgc tgaagcggct gaaagccgag ctgaatgaca  5460
tccggcctaa ggtggacagc accagagatc aggcagccaa cctgatggcc aacagaggcg  5520
accactgtcg gaagctcgtg gaacctcaga tcagcgagct taaccacaga tttgccgcca  5580
tcagccaccg gatcaagaca ggcaaggcca gcattcctct caaagagctt gagcagttca  5640
acagcgacat ccaaaagctg ctcgaacccc tggaagccga gatccaacag ggcgtcaacc  5700
tcaaagaaga agatttcaac aaggacatga acgaggacaa tgagggcacc gtcaaagaac  5760
tgctgcagcg gggcgataat ctgcagcagc ggattaccga tgagcgcaag cgggaagaga  5820
tcaagattaa gcagcagctg ctgcagacca agcacaacgc cctgaaggac ctgcggagcc  5880
agagaagaaa gaaggccctg gaaatcagcc accagtggta tcagtacaag cggcaggccg  5940
acgacctgct gaagtgcctg gatgacatcg agaagaagct ggcctctctg cccgagccta  6000
gggacgagag aaagatcaaa gagatcgacc gcgagctgca gaaaaagaaa gaggaactga  6060
acgccgtccg cagacaggcc gaaggacttt ctgaagatgg cgccgctatg gccgtggaac  6120
ccacacagat tcagctgagc aagcggtggc gggaaatcga gagcaagttc gcccagttcc  6180
ggcggctgaa tttcgcccag atccacaccg tgcgggaaga gacaatgatg gtcatgacag  6240
aggacatgcc ccttgagatc agctacgtgc ccagcaccta cctgaccgag atcacccatg  6300
tgtctcaggc cctgctggaa gtggaacagc tgctgaatgc ccctgacctg tgcgccaagg  6360
acttcgagga cctgttcaag caagaggaaa gcctgaagaa catcaaggac agcctgcagc  6420
agagcagcgg ccggatcgat atcatccaca gcaagaaaac cgccgcactg cagagcgcca  6480
cacctgtgga aagagtgaag ctgcaagagg ccctgagcca gctggatttc cagtgggaga  6540
aagtgaacaa gatgtacaag gaccggcagg gcagattcga ccgcagcgtt gaaaagtggc  6600
ggcggttcca ctacgacatc aagatcttca accagtggct gaccgaggcc gagcagttcc  6660
tgagaaagac acagatcccc gagaactggg agcacgccaa gtacaagtgg tatctgaaag  6720
agctgcagga cggcatcggc cagagacaga cagtcgtgcg gacactgaat gccaccggcg  6780
aggaaatcat ccagcagtcc agcaagaccg acgccagcat cctgcaagag aagctgggca  6840
gcctgaacct gcggtggcaa gaagtgtgca agcagctgag cgaccggaag aagcggctgg  6900
aagaacagaa gaatatcctg agcgagttcc agcgggacct gaacgagttc gtgctgtggc  6960
tcgaagaggc cgacaatatc gccagcattc ccctggaacc tggcaaagag cagcagctga  7020
aagaaaagct ggaacaagtg aaactgctgg tcgaggaact gcccctgaga cagggaatcc  7080
tgaaacagct gaacgagaca ggcggccctg tgctggtgtc tgcccctatt tctcccgagg  7140
aacaggacaa gctggaaaac aagctgaagc agaccaacct gcagtggatc aaggtgtcca  7200
gagcactgcc tgagaagcag ggcgagatcg aggcccagat caaggacctg ggacagctcg  7260
aaaagaagct tgaggacctc gaagaacagc tcaaccatct gctgctttgg ctgagcccca  7320
tccggaacca gctggaaatc tacaaccagc ctaatcaaga gggccccttc gacgtgaaag  7380
aaaccgagat tgccgtgcag gccaagcagc ccgatgtgga agagatcctg tctaagggcc  7440
agcacctgta caaagagaag cccgccacac agcccgtgaa gcggaaactg gaagatctga  7500
gcagcgagtg gaaggccgtg aaccggctgc tgcaagaact gagagccaaa cagcctgatc  7560
tggcccctgg cctgacaaca attggcgcct ctcctacaca gaccgtgaca ctggtcacac  7620
agcctgtggt caccaaagag acagccatca gcaaactgga aatgcccagc agtctgatgc  7680
tcgaagtgcc cgcactggcc gacttcaata gagcctggac cgagctgacc gactggctca  7740
gtctgctgga ccaagtcatc aagtcccaga gagtgatggt cggagatctt gaggacatca  7800
acgagatgat cattaagcag aaagccacca tgcaggacct tgagcagaga aggccccagc  7860
ttgaagaact gatcaccgcc gctcagaacc tgaaaaacaa gaccagcaat caagaagccc  7920
ggaccatcat caccgaccgg atcgagagaa tccagaacca gtgggacgaa gtgcaagagc  7980
atctgcagaa cagacggcag cagctcaatg agatgctgaa ggacagcaca cagtggctgg  8040
aagccaaaga agaagccgag caggttctcg gacaggccag agctaagctg gaatcttgga  8100
aagagggacc ctacaccgtc gacgccatcc agaagaagat caccgagaca aagcagctgg  8160
ccaaggatct gagacagtgg cagaccaatg tggacgtggc caacgacctg gctctgaagc  8220
tgctgagaga ctacagcgcc gacgacacca gaaaggtgca catgatcacc gaaaacatca  8280
acgcctcttg gcggagcatc cacaagcggg tgtcagagag agaagccgct ctggaagaaa  8340
cacatagact gctccagcag ttcccactcg acctggaaaa gttcctggcc tggctgacag  8400
aagccgaaac caccgctaac gtgctccagg atgccaccag aaaagagcgg ctgttggagg  8460
acagcaaggg cgtcaaagaa ctcatgaagc agtggcagga tctgcaaggg gagattgaag  8520
cccacaccga cgtgtaccac aacctggacg agaacagcca gaagatcctg cggtccctgg  8580
aaggctctga tgatgctgtg ctgcttcaga ggcggctgga caacatgaac ttcaagtgga  8640
gcgagctgcg gaagaagtcc ctgaacatca gaagccacct ggaagcctcc agcgaccagt  8700
ggaaaagact gcacctgtct ctccaagagc tgctcgtgtg gctgcagctg aaggatgacg  8760
agctgagtag acaggcccct atcggcggag attttcccgc cgtgcagaaa cagaacgacg  8820
tgcaccgggc cttcaagaga gagctgaaaa caaaagaacc cgtcatcatg agcaccctgg  8880
aaaccgtgcg gatctttctg accgagcagc ctctggaagg actggaaaag ctgtaccaag  8940
agcctagaga gctgcctcct gaagaaaggg cccagaacgt gacacggctg cttagaaagc  9000
aggccgagga agtgaacacc gaatgggaga agctgaacct ccactccgcc gactggcagc  9060
ggaagatcga tgagacactg gaacggctgc gggaactgca agaagccaca gacgagctgg  9120
acctgaaact gcggcaggct gaagtgatca aaggctcctg gcagccagtg ggcgatctgc  9180
tgatcgatag cctgcaggac catctggaaa aagtcaaggc cctgcgggga gagatcgccc  9240
```

```
ctctcaaaga aaacgtgtcc cacgtgaacg atctggccag gcagctgaca acactgggca  9300
tccagctgag cccttacaac ctgtctacct tggaggacct gaatacccgg tggaagctgc  9360
tccaagtggc cgtcgaggat agagtgcggc agctgcatga ggctcacaga gattttggac  9420
ccgccagcca gcacttcctg agcacatctg ttcaaggccc ctgggagaga gctatcagcc  9480
ctaacaaggt gccctactac atcaaccacg agacacagac cacctgttgg gatcacccca  9540
agatgaccga actgtatcag tccctggccg acctgaacaa cgtgcggttt agcgcctacc  9600
ggaccgccat gaagctgcgc agactgcaga aagctctgtg cctggacctg ctgtctctga  9660
gcgctgcttg tgatgccctg gaccagcata acctcaagca gaacgaccag cctatggaca  9720
tcctgcagat catcaactgc ctgaccacca tctacgaccg gctcgaacaa gagcacaaca  9780
acctggtcaa cgtgcccctg tgcgtggaca tgtgcctgaa ttggctgctg aacgtgtacg  9840
acaccggcag aaccggcagg atcagagtgc tgagcttcaa gaccggcatc atctccctgt  9900
gcaaggccca ccttgaggat aagtaccgct acctgtttaa gcaggtcgcc agcagcaccg  9960
gcttttgcga ccaaagaagg ctgggactgc tgctccacga cagcattcag atccctagac  10020
agctgggcga agtggcctct ttcggcggct ctaatatcga gcctagcgtg cggagctgct  10080
tccagttcgc caacaacaag cccgagattg aggccgcact gttcctggac tggatgagac  10140
tggaacccca gagcatggtc tggctgcctg tgctgcatag agtggccgca gccgaaacag  10200
ccaagcacca ggccaagtgc aacatctgca aagagtgccc catcatcggc ttccggtaca  10260
gatccctgaa gcacttcaac tacgatatct gccagtcctg cttcttcagc ggcagagtgg  10320
ccaagggcca caagatgcac taccccatgg tggaatactg caccccctacc acctctggcg  10380
aggacgtgcg ggattttgcc aaggtgctca agaacaagtt ccggaccaag cgctacttcg  10440
ctaagcaccc cagaatgggc tacctgccag tgcagacagt gcttgagggc gacaacatgg  10500
aaacccctgt gactctgatc aacttctggc ccgtggatag cgcccctgct agttctcctc  10560
agctgtctca cgacgatacc cacagcagaa tcgagcacta cgcctccaga ctggccgaga  10620
tggaaaacag caacggcagc tacctgaatg acagcatcag ccccaacgag agcatcgacg  10680
acgaacatct gctcattcag cactactgcc agagcctgaa tcaggacagc cctctgtctc  10740
agcctagaag ccctgcacag atcctgatca gcctggaaag cgaggaacgc ggcgagctgg  10800
aaagaatcct ggcagacctg gaagaggaaa accggaacct gcaggccgaa tacgacagac  10860
tcaagcagca gcacgagcac aagggactgt ctccactgcc ttctccacct gaaatgatgc  10920
ccacctctcc acagagcccc agagatgccg agctgattgc cgaagccaaa ctgctgaggc  10980
agcacaaagg cagactcgaa gccagaatgc agattctcga agatcacaac aagcagctcg  11040
aatcccagct gcacagactt aggcagctgc tggaacagcc tcaggcagag gccaaagtga  11100
atggcaccac cgtgtctagc cctagcacaa gcctgcagag atccgacagc agccagccaa  11160
tgcttctgag agtcgtgggc tcccagacca gcgattctat gggcgaagag gacctgctca  11220
gccctcctca ggatacaagc accggcctgg aagaagtgat ggaacaactg aacaacagct  11280
tccccagcag cagaggcaga aacacccctg gcaagcccat gcgcgaggac accatgtgat  11340
aactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acctagctgg cttgttgtcc acaaccatta  12180
aaccttaaaa gctttaaaag ccttatatat tctttttttt cttataaaac ttaaaacctt  12240
agaggctatt taagttgctg atttatatta attttattgt tcaaacatga gagcttagta  12300
cgtgaaacat gagagcttag tacattagcc atgagagctt agtacattag ccatgagggt  12360
ttagttcatt aaacatgaga gcttagtaca ttaaacatga gagcttagta cattaaacat  12420
gagagcttag tacatactat caacaggttg aactgctgat ctgtacagta gaattggtaa  12480
agagagttgt gtaaaatatt gagttcgcac atcttgttgt ctgattattg atttttggcg  12540
aaaccatttg atcatatgac aagatgtgta tctaccttaa cttaatgatt ttgataaaaa  12600
tcattacgaa tgcatgcggc cgccgttaca taacttacgg taaatggccc gcctggctga  12660
ccgcccaacg acccccgccc attgacgtca ataatgacgt atgttcccat agtaacgcca  12720
atagggactt tccattgacg tcaatgggtg gagtatttac ggtaaactgc ccacttggca  12780
gtacatcaag tgtatcatat gccaagtacg ccccctattg acgtcaatga cggtaaatgg  12840
cccgcctggc attatgccca gtacatgacc ttatgggact ttcctacttg gcagtacatc  12900
tacgtattag tcatcgctat taccatggtc gaggtgagcc ccacgttctg cttcactctc  12960
cccatctccc ccccctcccc acccccaatt ttgtatttat ttatttttta attattttgt  13020
gcagcgatgg gggcgggggg gggggggcg cgcgccaggc ggggcggggc ggggcgaggg  13080
gcggggcggg gcgaggcgga gaggtgcggc ggcagccaat cagagcggcg cgctccgaaa  13140
gtttcctttt atggcgaggc ggcggcggcg gcggccctat aaaaagcgaa gcgcgcggcg  13200
ggcgggagtc                                                         13210
```

```
SEQ ID NO: 16           moltype = DNA  length = 13397
FEATURE                 Location/Qualifiers
source                  1..13397
                        mol_type = other DNA
                        note = NP-MHCK7-hBGi-DMD-3-WPRE3-DTS
                        organism = synthetic construct
SEQUENCE: 16
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggccctttg  180
ctaatcatgt tcatacctct tatcttcctc ccacagctcc tgggcaacgt gctggtctgt  240
```

-continued gtgctggccc atcactttgg caaagaattg cgatcgccac catgctgtgg tgggaagagg 300
tggaggactg ttacgagaga gaggacgtgc agaagaagac attcaccaag tgggtgaacg 360
ctcagttcag caagttcggc aagcagcaca tcgagaacct gtttagcgat ctacaagatg 420
gcagaagact gctggacctg ctggagggcc tgaccgggca gaagctgccc aaagaaaagg 480
ggtctacaag agtgcacgcc ctgaacaacg tgaacaaggc cctgagagtg ctgcagaaca 540
acaacgtgga cctggtgaac atcggcagca ccgacatcgt ggacggcaac cacaagctga 600
ccctgggcct gatctggaac atcatcctgc actggcaagt gaagaacgtg atgaagaaca 660
tcatggccgg cctgcagcag accaacagcg agaagatcct gctgagctgg gtgagacaga 720
gcacaagaaa ctacccccaa gtgaacgtga tcaacttcac cacaagctgg agcgacggcc 780
tggccctgaa cgccctgatc cacagccaca gacccgacct gttcgactgg aacagcgtgg 840
tgtgtcagca gagcgccaca cagagactgg agcacgcctt caacatcgct agatatcagc 900
tgggcatcga gaagttactg gaccccgaag atgtggacac cacctacccc gacaagaaga 960
gcatcctgat gtacatcaca agcctgttcc aagtgctgcc tcagcaagtg agcatcgagg 1020
ccatccaaga agtcgagatg ctgcctagac cccccaaggt gaccaaggag gagcactttc 1080
agctgcacca tcagatgcac tactctcagc agatcacagt cagcttggca caaggctacg 1140
agagaacaag cagccccaag cctagattca agagctacgc ctacacccaa gccgcctacg 1200
tgaccacaag tgaccccaca agaagcccct tcccttctca gcacctggag gcccccgagg 1260
acaagagctt cggcagcagc ctgatggaga gcgaggtgaa cctggacaga tatcagaccg 1320
cgttagaaga agtgttgagc tggctgctga gcgccgagga caccctgcaa gcccaaggcg 1380
agatcagcaa cgatgtggag gtggtgaagg atcagttcca cacccacgag ggctacatga 1440
tggacctgac cgcccaccaa ggcagagtgg gcaacatcct gcagctgggc agcaagctga 1500
tcggcaccgg caagctgagc gaggacgagg aaaccgaggt tcaagagcaa atgaacctgc 1560
taaacagcag atgggagtgc ctgagagtgg ctagcatgga aaagcagagt aacctgcaca 1620
gagtgctgat ggacctgcag aatcagaaat tgaaagaact taatgattgg ctgaccaaga 1680
ccgaggagag aacaagaaag atggaggagg agcccctggg ccccgacctg gaggacctga 1740
agagacaagt gcagcagcac aaggtgctgc aagaggacct ggagcaagag caagtgagag 1800
tgaactctct gacacacatg gtggtggtag tggacgagag cagcggcgat cacgctaccg 1860
cggcgctgga agagcagctg aaagtgctgg gcgacagatg ggccaacatc tgcagatgga 1920
ccgaggacag atgggtgctg ctgcaagaca tcctgctgaa gtggcagaga ctgaccgagg 1980
agcagtgcct gttcagcgcc tggctgagcg agaaggaaga cgctgtgaac aagatccaca 2040
ccaccggctt caaggatcag aacgagatgc tgagctccct ccaaaagctc gcagtgctga 2100
aggccgacct ggaaaagaaa aaacagtcga tgggcaagct gtacagcctg aagcaagacc 2160
tgctgagcac cctgaagaac aagagcgtga cacagaagac cgaggcctgg ctggacaact 2220
tcgctagatg ctgggacaac ctggtacaga agttagagaa gtctaccgct cagatcagcc 2280
aagccgtaac caccacacaa cctagcctga ctcagaccac cgtgatggaa accgtgacca 2340
ccgtgacaac ccgtgagcag atcctggtga agcacgccca agaggagctg cccccccccc 2400
cccctcagaa gaagagacag atcaccgtgg actcagagat tcgcaagaga ctggacgtgg 2460
acatcaccga gctgcacagc tggatcacaa gaagcgaggc cgtgctgcag agccctgagt 2520
tcgcgatctt tagaaaggag ggcaacttca gcgacttgaa ggagaaagtg aacgccatcg 2580
agagagagaa ggccgagaag ttcagaaagt tgcaagacgc ctcaagaagc gcccaagccc 2640
tggtggagca gatggttaac gaaggcgtga atgccgacag catcaagcaa gctagcgagc 2700
agctgaatag ccggtggatt gaattctgtc agctgctgag cgagagatta aactggctgg 2760
agtatcagaa caacatcatc gccttctaca atcagctgca gcaactagaa caaatgacca 2820
ccaccgccga gaactggcta aagattcagc ccaccacccc tagcgagccc accgccatca 2880
aatctcagct gaaaatttgc aaggacgaag tgaacagact gtcggacctg cagcctcaaa 2940
tcgaaagact gaaaattcag agcatcgcac ttaaggagaa gggccaagga cccatgttcc 3000
tggacgccga cttcgtggcc ttcaccaacc acttcaagca agtgttcagc gacgtgcaag 3060
ctagagagaa ggagctgcag accatcttcg acaccctgcc ccccatgaga taccaagaaa 3120
ccatgagcgc catcagaacc tgggtgcagc agagcgaaac caagctgagc atccctcagc 3180
tgagcgtgac cgactacgag atcatggagc aaagactggg agagctgcaa gccctgcaga 3240
gcagcctgca agagcagcag agcggcctgt actacctgag caccaccgtg aaggagatgt 3300
cgaagaaagc ccgtcggag atcagcagaa agtatcagag cgagttcgag gagatcgagg 3360
gcagatggaa gaagctgagc agccaactgg tggaacactg tcagaaatta gaagaacaga 3420
tgaacaagct gagaaagatt cagaaccaca ttcagaccct gaagaagtgg atggccgagg 3480
tggacgtgtt cctgaaagag gagtggcccg ccctgggcga ttccgaaatc ttaaaaaagc 3540
agctgaagca gtgcagactg ctggtgtcag atatccaaac cattcaacca agcctgaaca 3600
gcgtgaacga aggcgggcag aagatcaaga acgaggccga gcccgagttc gctagcagac 3660
tggaaaccga gctgaaggag ctgaatacac agtgggacca catgtgtcag caagtgtacg 3720
ctagaaagga agcgctgaag ggcgggctgg agaagaccgt tagcctgcaa aaggatctga 3780
gcgagatgca cgagtggatg acccaagccg aggaggagta cctggagaga gacttcgagt 3840
acaagacccc cgacgagctg cagaaggccg tcgaggaaat gaagagagcg aaggaggagg 3900
ctcagcagaa ggaagccaag gtgaagctgc tgactgaatc tgtcaacagt gtgatagctc 3960
aagcaccccc cgttgcccaa gaggcactaa agaaggagct ggaaactctg accaccaact 4020
atcagtggct gtgcacaaga ctgaacggca agtgcaagac cctggaggaa gtgtgggcct 4080
gctggcacga gctgctgagc tacctggaga aggccaacaa gtggctgaac gaggtggagt 4140
tcaagctgaa gaccaccgag aacatccccg gcggcgccga ggagatcagc gaggtgctgg 4200
acagcctgga gaacctgatg agacacagcg aggacaaccc caatcagatc agaatcctgg 4260
ctcagaccct gaccgacggc ggcgtgatgg acgagctgat caacgaggag ctggaaacct 4320
ttaactctag atggcgagaa ctgcacgagg aggccgtgag aagacagaag ctgctggagc 4380
aaagcattca gagcgcccaa gaaaccgaga agagcctgca cctgatccaa gagagcctga 4440
ccttcatcga caagcagctg gccgcctaca tcgccgacaa ggtggacgcc gctcagatgc 4500
cacaagaggc tcagaagatt cagtccgatc tgacaagcca cgagatcagc ctggaggaga 4560
tgaaaaaaca caaccaaggc aaggaggccg ctcagagagt gctgtctcag atcgacgtgg 4620
ctcagaagaa gctgcaagac gtgagcatga agttcagact gtttcagaag cccgccaact 4680
tcgagcagcg actgcaagag agcaagatga tcctggacga ggtgaagatg cacctgcccg 4740
ccctggaaac caagagcgtg gagcaagagg tggtgcagtc tcagttgaac cactgcgtga 4800
acctgtacaa gagcctgtcg gaggtcaaga gtgaggtcga gatggtgatc aaaactggga 4860
gacagatcgt gcaaaaaaag cagaccgaga accccaagga gctggacgag cgtgttaccg 4920
ccctgaagct gcactacaac gagctgggcg ccaaggtgac cgagagaaag cagcagctgg 4980

-continued

```
agaagtgcct gaagctgagc agaaagatga gaaaggagat gaacgtgctg accgagtggc  5040
tggccgccac cgacatggag ctgaccaaga gaagcgccgt ggagggcatg cctagcaacc  5100
tggacagcga ggtggcctgg ggcaaggcca cacagaagga gatcgagaag cagaaggtgc  5160
acctgaagag catcaccgag gtgggcgagg ccctgaagac cgtgctgggc aagaaggaaa  5220
ccctggtgga ggacaagctg agcctgctga actcgaactg gatcgccgtg acaagcagag  5280
ccgaggagtg gctgaacctg ctgttagagt accaaaaaca catggaaacc ttcgatcaga  5340
acgtggacca catcaccaag tggatcatcc aagccgacac cctgctggac gaaagcgaaa  5400
agaagaagcc gcaacaaaag gaggatgtgc tgaagagact gaaggccgaa ctgaacgata  5460
tcagacccaa ggtggacagc acacgggacc aagccgccaa cctgatggcc aacagaggcg  5520
accactgcag aaaactggtg gagcctcaga tcagcgagct gaaccacaga ttcgccgcca  5580
tcagccacag aatcaaaacc ggcaaagcga gcatcccctt gaaggaactg gagcaattta  5640
acagcgacat ccaaaaattg ctcgaaccac tggaggccga gattcagcaa ggcgtgaacc  5700
tgaaggaaga ggacttcaac aaggacatga acgaggacaa cgagggcacc gtgaaagaac  5760
tgctgcagag aggcgacaac ctgcagcaga gaatcaccga cgagagaaag agagaggaga  5820
tcaagatcaa gcagcagctg ctgcagacta agcacaacgc cctgaaggat ctgagatctc  5880
agaggagaaa aaaggctctg gaaatttcac atcagtggta tcagtacaag agacaagcag  5940
acgacctgct gaagtgcctg gacgacatcg agaagaagtt agctagcctg cccgagccta  6000
gagacgagag aaagatcaag gagatcgaca gagagttaca aaagaagaag gaggagctga  6060
atgcggtaag aagacaagcg gaaggcctgt ccgaggacgg cgcagccatg gccgtggagc  6120
ccacacagat tcagctcagc aagagatgga gagagatcga gagcaagttc gctcagttca  6180
gaagactgaa cttcgctcag atccacaccg tgagagagga aaccatgatg gtgatgaccg  6240
aggacatgcc cctggagatc tcatacgttc ctagcaccta cctgaccgag atcacccacg  6300
tgagccaagc cctgctggag gtggagcagc tgctgaacgc ccccgacctg tgcgccaagg  6360
acttcgagga cctgttcaaa caagaggaga gcctgaagaa catcaaggac agcctgcagc  6420
aaagtagcgg cagaatcgac atcatccaca gcaagaagac cgccgccctg cagagcgcca  6480
cccccgtgga gagagtgaag cttcaagagg ccctttcgca gctggatttt cagtgggaga  6540
aggtgaacaa aatgtacaag gacagacaag gcagattcga cagaagcgtg gagaagtgga  6600
gaagattcca ctacgacatc aagatcttca atcagtggct gaccgaggca gagcagttcc  6660
tgagaaagac acagatcccc gagaactggg agcacgccaa gtacaagtgg tacctgaagg  6720
agctgcaaga cggcatcggg cagagacaga ccgtggtgag aaccctgaac gccaccggcg  6780
aggagatcat ccaacaaagc tccaaaaccg acgctagcat cctgcaagag aaactgggca  6840
gcctgaacct gagatggcaa gaggtgtgca agcagctgag cgaccgcaaa aaacggttag  6900
aggagcagaa gaacatcctg agcgagtttc agcgggacct gaacgagttc gtgctgtggc  6960
tggaggaggc cgataacatc gctagcatcc ccctggagcc cggcaaggag cagcagttaa  7020
aagaaaaact tgagcaagtg aagctgctgg tggaggagct gcccctgaga caaggcatcc  7080
tgaagcagct gaacgagact ggcggccccg tgctggtgag cgccccccatc agccccgagg  7140
agcaagacaa gctggagaac aagctgaagc agaccaacct gcagtggatc aaggtgagca  7200
gagccctgcc cgagaagcaa ggcgaaatcg aggcccaaat aaaggacctg gggcagctgg  7260
agaagaaact cgaagacttg gaagaacaac tcaaccactt gctgctgtgg ctgagcccca  7320
tcagaaatca gctggagatc tacaatcagc ccaaccaaga ggggccattc gacgtgaagg  7380
aaaccgagat cgccgtgcaa gccaagcagc ccgatgtgga ggagatcctg agcaaggggc  7440
agcacctgta caaggagaag cccgccacac agcccgtcaa gcgtaaacta gaggatcttt  7500
cctctgagtg gaaggccgtg aaccgtctgc tacaagagct gcgggctaag caacccgact  7560
tagcgcccgg cctgaccacc atcggtgcaa gccccacgca gaccgtgacc ctggtgaccc  7620
aacccgtggt gaccaaggaa accgccatca gcaagctgga gatgcctagc agcctgatgc  7680
tggaggtgcc cgccctggcc gacttcaaca gagcctggac cgagctgacc gactggctga  7740
gcctgctgga ccaagtgatc aagtctcaga gagtgatggt gggcgatctg gaggacatca  7800
atgagatgat catcaagcag aaggccacca tgcaagacct ggagcagaga agacctcagc  7860
tggaggagct gatcaccgcc gctcagaacc tgaaaaacaa gacgagcaac caagaggcta  7920
gaaccatcat caccgacaga atcgagagaa ttcagaatca gtgggacgag gtgcaagagc  7980
acctgcagaa cagaagacag caactaaacg aaatgctcaa ggacagcaca cagtggctgg  8040
aggccaagga ggaggcggag caagtgttgg gccaagctag agccaagctg gagagctgga  8100
aggagggacc ctacaccgtg gacgccattc agaagaagat caccgaaacc aagcagctgg  8160
ccaaggacct gcgacagtgg cagaccaacg tggacgtggc caacgatctt gccctgaagc  8220
tgctgcgcga ctatagcgcc gacgacacaa gaaaggtgca catgatcacc gagaacatca  8280
acgctagctg gcgtagcatc cacaagagag tgagcgagag agaggcggct ttggaggaaa  8340
cccatagact gctgcagcag tttcccctgg acctggagaa gttcctggcc tggctgaccg  8400
aagccgaaac aaccgccaac gtgctgcaag acgccacaag aaaggagaga ctgctggagg  8460
acagcaaggg cgtgaaggag ctgatgaagc agtggcaaga cctgcaaggc gagatcgaag  8520
cgcacaccga cgtgtaccac aacctggacg agaactctca gaagatcctg agaagcctgg  8580
agggcagcga cgacgccgtg ctgttacaga gaaggctgga caacatgaac ttcaagtgga  8640
gcgagctgag aaagaagagc ctgaacatca gaagccacct ggaggctagc agcgatcagt  8700
ggaagagact gcacctgagc ctgcaagagc tgctggtctg gcttcagttg aaggacgatg  8760
agctgagcag acaagccccc atcggcggcg acttccccgc cgtgcagaag cagaacgacg  8820
tgcatagagc cttcaagaga gagctgaaga ccaaggagcc cgtgatcatg agcaccctgg  8880
aaacggtgag aatcttcctg accgagcagc ccctggaggg cctggagaag ctgtaccaag  8940
agcctagaga gctgcccccc gaggagagag ctcagaacgt gacaagactg ctgagaaagc  9000
aagccgaaga ggtgaacacc gagtgggaga agctgaacct gcacagcgcc gactggcaga  9060
gaaagatcga cgaaaccctg gagagactga gagaattgca agaggcgacc gacgagctgg  9120
acctgaagct gagacaagcc gaggtcatca agggcagctg gcagcccgtg ggcgatctat  9180
taattgactc tctacaagac cacctggaga aagtgaaggc cctgagaggc gagatcgccc  9240
ccctgaagga gaacgtgagc cacgtgaatg atctggcacg tcagctgacc accctgggca  9300
tacaactgtc cccctataac ctgagcacac tggaggattt gaatactaga tggaagctgc  9360
tgcaagtggc cgtggaggac agagtaagac aattacatga ggcccacaga gacttcggcc  9420
ccgcttctca gcacttcctg agcacaagcg tgcaaggccc ctgggagaga gccatttccc  9480
ccaacaaggt cccctactac atcaaccacg agacacagac cacctgctgg gaccacccca  9540
agatgaccga gctgtatcag agcctcgccg atctgaacaa tgtgagattc agcgcctaca  9600
gaaccgccat gaagctgaga agactgcaga aggccctgtg cctggactta ttaagcctga  9660
gcgccgcctg cgacgccctg gatcagcaca acctgaagca aaacgaccaa cccatggaca  9720
```

```
tcctgcagat catcaactgc ctcaccacca tatacgacag actggaacaa gagcacaaca  9780
acctggtgaa cgtgcccctg tgcgtggaca tgtgcctgaa ctggctgctg aacgtgtacg  9840
acaccggcag aaccggcaga atcagagtgc tgagcttcaa gaccggcatc atcagcctgt  9900
gcaaggccca cctggaggac aaatacagat accttttcaa acaagtggct agcagcaccg  9960
gcttctgcga ccaaagaaga ctgggtctgc tgctgcacga cagcattcag atccctagac  10020
agctgggcga ggtggctagc ttcggcggca gcaacatcga gcctagcgtg agaagctgct  10080
ttcagttcgc caacaacaag cccgagatag aggcagccct cttcttagac tggatgagac  10140
tggagcctca gagcatggta tggctgccgg tcctgcacag agtggccgcc gccgaaaccg  10200
ccaagcacca agccaagtgc aacatctgca aggagtgccc catcatcggc ttcagataca  10260
gaagcctgaa gcacttcaac tacgacatct gtcagagctg cttcttcagc ggcagagtgg  10320
ccaagggcca caagatgcac taccccatgg tggagtactg cacccccacc acaagcggcg  10380
aggacgtgag agacttcgcc aaggtgttga agaataagtt tagaaccaag agatacttcg  10440
ccaagcaccc tagaatgggc tacctgcccg tgcagaccgt gctggagggc gacaacatgg  10500
aaacccccgt gaccctgatc aacttctggc ccgtggacag cgcccccgct agcagccctc  10560
agctgagcca cgacgacacc cacagcagaa tcgagcacta cgctagcaga ctggccgaga  10620
tggagaacag caacggcagc tacctgaacg acagcatcag cccgaatgag agcatcgacg  10680
acgagcacct gctgattcag cactactgtc agagcctgaa ccaagacagc cccctgtctc  10740
agcctagaag ccccgctcag atcctgatca gcctggagag cgaggagaga ggcgagctgg  10800
agagaatcct agcagatctg gaggaagaga acagaaacct gcaagccgag tatgaccgac  10860
tgaaacagca acatgagcac aaaggcctga gcccactgcc ctcccccccc gagatgatgc  10920
ccacaagccc tcagagccct agagacgccg agctgatcgc tgaagcgaag ttacttagac  10980
aacacaaggg cagactggag gctagaatgc agatcctgga ggaccacaac aagcagctgg  11040
agtctcagct gcacagactg aggcagctgc tggaacagcc ccaagccgag gccaaagtga  11100
acggcaccac cgtgagcagt cctagcacaa gcctgcagag aagcgacagc tctcagccca  11160
tgctgctgag agtggtgggc tctcagacaa gcgacagcat gggcgaggag gatctgctga  11220
gtccgcccca agacacaagc accggcctgg aagaggtgat ggagcaactg aacaatagct  11280
tccctagcag cagaggcaga aacacccccg gcaagcccat gagagaggac accatgtgat  11340
gactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acgtggcgcc atcggatccc gggcccgtgg  12180
cttgttgtcc acaaccatta aaccttaaaa gctttaaaag ccttatatat tcttttttt  12240
cttataaaac ttaaaacctt agaggctatt taagttgctg atttatatta attttattgt  12300
tcaaacatga gagcttagta cgtgaaacat gagagcttag tacattagcc atgagagctt  12360
agtacattag ccatgagggt ttagttcatt aaacatgaga gcttagtaca ttaaacatga  12420
gagcttagta cattaaacat gagagcttag tacatactat caacaggttg aactgctgat  12480
ctgtacagta gaattggtaa agagagttgt gtaaaatatt gagttcgcac atcttgttgt  12540
ctgattattg atttttggcg aaaccatttg atcatatgac aagatgtgta tctaccttaa  12600
cttaatgatt ttgataaaaa tcattatcta gaagctgcat gtctaagcta gacccttcag  12660
attaaaaata actgaggtaa gggcctgggt aggggaggtg gtgtgagacg ctcctgtctc  12720
tcctctatct gcccatcggc cctttgggga ggaggaatgt gcccaaggac taaaaaaagg  12780
ccatggagcc agaggggcga gggcaacaga cctttcatgg gcaaaccttg gggccctgct  12840
gtctagcatg ccccactacg ggtctaggct gcccatgtaa ggaggcaagg cctggggaca  12900
cccgagatgc ctggttataa ttaacccaga catgtggctg cccccccccc cccaacacct  12960
gctgcctcta aaaataaccc tgtccctggt ggatcccctg catgcgaaga tcttcgaaca  13020
aggctgtggg ggactgaggg caggctgtaa caggcttggg ggccagggct tatacgtgcc  13080
tgggactccc aaagtattac tgttccatgt tcccggcgaa gggccagctg tcccccgcca  13140
gctagactca gcacttagtt taggaaccag tgagcaagtc agcccttggg gcagcccata  13200
caaggccatg gggctgggca agctgcacgc ctgggtccgg ggtgggcacg gtgcccgggc  13260
aacgagctga aagctcatct gctctcaggg gcccctccct ggggacagcc cctcctggct  13320
agtcacaccc tgtaggctcc tctatataac ccaggggcac aggggctgcc ctcattctac  13380
caccacctcc acagcac                                                 13397
```

```
SEQ ID NO: 17          moltype = DNA  length = 13385
FEATURE                Location/Qualifiers
source                 1..13385
                       mol_type = other DNA
                       note = NP-MHCK7-hBGi-DMD-4-WPRE3-DTS
                       organism = synthetic construct
SEQUENCE: 17
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac catgctttgg tgggaagaag  300
tcgaggactg ctacgagcgc gaggacgtgc agaagaaaac cttcaccaaa tgggtcaacg  360
cccagttcag caagttcggc aagcagcaca tcgagaacct gttcagcgac ctgcaggatg  420
gcagaaggct gctggatctg ctggaaggcc tgacaggaca gaagctgccc aaagagaagg  480
gcagcacaag agtgcacgcc ctgaacaacg tgaacaaggc cctgagagtg ctgcagaaca  540
```

```
acaacgtgga cctggtcaac atcggcagca ccgacatcgt ggacggcaac cacaaactga  600
ccctgggcct gatctggaac atcatcctgc actggcaagt gaagaacgtg atgaagaaca  660
tcatggccgg cctgcagcag accaacagcg agaagattct gctgagctgg gtccgacaga  720
gcacccggaa ttaccctcaa gtgaacgtga tcaacttcac cacctcttgg agcgacggac  780
tggccctgaa tgccctgatc cacagccaca gacctgacct gttcgactgg aacagcgtcg  840
tgtgtcagca gagcgccaca cagaggctgg aacacgcctt caatatcgcc agataccagc  900
tgggcatcga gaaactgctg gaccccgagg atgtggacac cacctatcct gacaagaaat  960
ccatcctcat gtacatcacc agcctgttcc aggtgctgcc ccagcaggtt tccatcgagg  1020
ccattcaaga ggtcgagatg ctgcccagac ctcctaaagt gaccaaagag gaacacttcc  1080
agctgcacca ccagatgcac tactctcagc agatcaccgt gtctctggcc cagggctacg  1140
agagaacaag cagccccaag cctcggttca agagctacgc ctatacacag gccgcctacg  1200
tgaccaccag cgatcctaca agaagcccat ttcctagcca gcatctggaa gcccctgagg  1260
acaagagctt tggcagcagc ctgatggaaa gcgaagtgaa cctggaccgc taccagacag  1320
ccctggaaga ggttctgagc tggctgctgt ctgccgagga tacactgcag gctcagggcg  1380
agatcagcaa cgacgtggaa gtggtcaagg accagtttca cacccacgag ggctacatga  1440
tggacctgac agcccaccag ggcagagtgg gcaatattct gcagctgggc tccaagctga  1500
tcggcacagg caagctgagc gaggacgaag agacagaggt gcaagagcag atgaacctgc  1560
tgaacagcag atgggagtgt ctgagagtgg ccagcatgga aaagcagagc aacctgcacc  1620
gggtgctgat ggatctccag aaccagaagc tgaaagagct gaacgactgg ctgaccaaga  1680
ccgaggaacg gacccggaag atggaagagg aacctctggg acccgacctg gaagatctga  1740
aaagacaggt gcagcagcat aaggtgctgc aagaggacct cgaacaagag caagtgcgcg  1800
tgaacagcct gacacacatg gtggtggtcg tggatgagag cagcggagat catgccacag  1860
ccgctctgga agaacagctg aaggtgctgg gagacagatg ggccaatatc tgccggtgga  1920
ccgaggatag atgggtgctg ctccaggaca tcctgctgaa gtggcagcgg ctgacagagg  1980
aacagtgcct gtttagcgcc tggctgtccg agaaagagga cgccgtcaac aagatccaca  2040
ccaccggctt caaggatcag aatgagatgc tgagcagcct gcagaaactg gccgtgctga  2100
aggctgacct ggaaaagaaa aagcagtcca tgggcaagct gtactccctg aagcaggacc  2160
tgctgagcac actgaagaac aagtctgtga cccagaaaac cgaggcctgg ctggacaact  2220
tcgcccggtg ttgggataac ctggtgcaga agctggaaaa gtccaccgct cagatctctc  2280
aggccgtgac cacaacacag ccttctctga cccagaccac cgtgatggaa acagtgacca  2340
cagtgacaac ccgcgagcag atcctggtca agcacgccca agaagaactg cctcctccac  2400
ctcctcagaa gaaacggcag atcacagtgg acagcgagat ccggaagaga ctggacgtgg  2460
acatcaccga gctgcacagc tggatcacca gatccgaagc cgtgctgcag tcccctgagt  2520
tcgccatctt cagaaaagag ggcaacttct ccgacctgaa agagaaagtc aacgccatcg  2580
agagagagaa ggccgagaag ttccggaagc tgcaggacgc ctctagatct gcccaggctc  2640
tggtggaaca gatggtcaac gaaggcgtga acgccgacag catcaagcag gcctcagagc  2700
agctgaactc ccggtggatc gagttctgtc agctcctgag cgagagactg aactggctgg  2760
aataccagaa caatatcatt gccttctaca accagctcca gcagctcgaa cagatgacca  2820
ccacagccga gaattggctg aagatccagc ctaccacacc tagcgagccc accgccatta  2880
agagccagct gaaaatctgc aaggacgaag tgaatcggct gagcgatctg cagccccaga  2940
tcgaaagact gaaaatccag tctatcgccc tcaaagagaa aggacagggc cccatgttcc  3000
tggacgccga ttttgtggcc tttaccaacc acttcaaaca ggtgttctcc gacgtgcagg  3060
cccgggaaaa agagctgcag accatcttcg acaccctgcc tccaatgaga taccaagaga  3120
caatgagcgc catccggacc tgggtgcagc aaagcgagac aaagctgagc atcccacagc  3180
tgagcgtgac cgactacgag atcatggaac agagactggg cgaactgcag gccctccagt  3240
ctagcctgca agaacagcag tccggcctgt actacctgag cacaaccgtg aaagagatga  3300
gcaagaaggc ccctagcgag atctcccgga agtaccagag cgagttcgaa gagatcgaag  3360
gccggtggaa gaagctgtct agccagctgg ttgagcactg ccagaaactc gaagaacaaa  3420
tgaacaagct gcgcaagatc cagaatcaca tccagacgct gaagaaatgg atggccgagg  3480
tggacgtgtt cctgaaagaa gagtggcccg ctctgggcga ctccgagatt ctgaagaaac  3540
agctcaaaca gtgccggctg ctggtgtccg atatccagac aatccagcca agcctgaact  3600
ccgtgaatga aggcggccag aagatcaaga acgaggccga gcctgagttt gccagcagac  3660
tggaaaccga actgaaagaa ctcaacaccc agtgggacca catgtgccag caagtgtacg  3720
cccggaaaga ggccctgaaa ggcggactcg aaaagactgt gtctctgcag aaagacctgt  3780
ctgagatgca cgagtggatg acccaggccg aagaggaata cctggaacgg gacttcgagt  3840
acaagacccc tgatgagctg caaaaagccg tcgaggaaat gaagcgggcc aaagaagagg  3900
cccagcagaa agaagccaaa gtcaagctgc tgaccgagtc cgtgaatagc gttatcgctc  3960
aggcccctcc tgtggctcaa gaggctctca agaaagaact ggaaactctg accaccaact  4020
accagtggct gtgcaccaga ctgaacggca agtgcaagac actggaagaa gtgtgggcct  4080
gctggcacga actgctgtcc tatctggaaa aggccaacaa gtggctgaac gaggtggaat  4140
tcaagctgaa aaccaccgag aacatccctg gcggcgctga agagattagc gaggtgctgg  4200
acagcctgga aaacctgatg agacacagcg aggacaaccc caatcagatc agaatcctgg  4260
ctcagaccct gaccgatggc ggcgtgatgg acgagctgat caacgaggaa ctcgaaacct  4320
tcaacagccg gtggcgggaa ctgcacgagg aagctgttcg gaggcagaag ttgctggaac  4380
agtctatcca gagcgcacaa gaaaccgaga agtccctgca cctgatccaa gagagcctga  4440
ccttcatcga caagcagctg gccgcttata tcgccgacaa ggtggacgct gctcagatgc  4500
cccaagaggc acagaagatt cagagcgacc tgaccagcca cgagattagc ctggaagaaa  4560
tgaagaagca caaccagggc aaagaggccg ctcagagagt cctgagccag atcgatgtgg  4620
cacagaaaaa gctccaggat gtgtccatga agtttcggct gtttcagaag cccgccaact  4680
tcgagcagag actgcaagag tccaagatga tcctggacga agtcaaaatg catctgcccg  4740
cactggaaac aaagtccgtg gaacaagaag tggtgcagtc ccagctgaac cactgcgtga  4800
acctgtacaa gagcctgtcc gaagtgaagt ctgaggtgga aatggtcatc aagaccggca  4860
ggcagatcgt ccagaagaag cagaccgaga atcccaaaga actcgacgag agagtgaccg  4920
ctctgaagct gcactacaat gagctgggcg ccaaagtgac cgagcggaag caacagcttg  4980
agaagtgcct gaaactgtct cggaagatgc ggaaagaaat gaacgtgctg acagagtggc  5040
tggccgccac cgatatggaa ctgactaaga gaagcgccgt ggaaggcatg cccagcaacc  5100
tggatagtga agtggcctgg ggcaaagcca ctcagaaaga gattgagaag cagaaggtcc  5160
acctgaagtc catcaccgaa gtgggcgaag ccctgaaaac cgtgctggga aagaaagaga  5220
cactggtcga ggacaagctg tccctgctga attccaactg gatcgccgtg acctccagag  5280
```

```
ctgaggaatg gctgaatctg ctgcttgagt accagaaaca catggaaacg ttcgaccaga  5340
acgtcgacca catcacaaag tggatcatcc aggctgatac cctgctggac gagtccgaga  5400
agaagaaacc ccaacaaaaa gaagatgtgc tgaagcggct gaaagccgag ctgaatgaca  5460
tccggcctaa ggtggacagc accagagatc aggcagccaa cctgatggcc aacagaggcg  5520
accactgtcg gaagctcgtg gaacctcaga tcagcgagct taaccacaga tttgccgcca  5580
tcagccaccg gatcaagaca ggcaaggcca gcattcctct caaagagctt gagcagttca  5640
acagcgacat ccaaaagctg ctcgaacccc tggaagccga gatccaacag ggcgtcaacc  5700
tcaaagaaga agatttcaac aaggacatga acgaggacaa tgagggcacc gtcaaagaac  5760
tgctgcagcg gggcgataat ctgcagcagc ggattaccga tgagcgcaag cgggaagaga  5820
tcaagattaa gcagcagctg ctgcagacca agcacaacgc cctgaaggac ctgcggagcc  5880
agagaagaaa gaaggccctg gaaatcagcc accagtggta tcagtacaag cggcaggccg  5940
acgacctgct gaagtgcctg gatgacatcg agaagaagct ggcctctctg cccgagccta  6000
gggacgagag aaagatcaaa gagatcgacc gcgagctgca gaaaaagaaa gaggaactga  6060
acgccgtccg cagacaggcc gaaggacttt ctgaagatgg cgccgctatg gccgtggaac  6120
ccacacagat tcagctgagc aagcggtggc gggaaatcga gagcaagttc gcccagttcc  6180
ggcggctgaa tttcgcccag atccacaccg tgcgggaaga gacaatgatg gtcatgacag  6240
aggacatgcc ccttgagatc agctacgtgc ccagcaccta cctgaccgag atcacccatg  6300
tgtctcaggc cctgctggaa gtggaacagc tgctgaatgc ccctgacctg tgcgccaagg  6360
acttcgagga cctgttcaag caagaggaaa gcctgaagaa catcaaggac agcctgcagc  6420
agagcagcgg ccggatcgat atcatccaca gcaagaaaac cgccgcactg cagagcgcca  6480
cacctgtgga aagagtgaag ctgcaagagg ccctgagcca gctggatttc cagtgggaga  6540
aagtgaacaa gatgtacaag gaccggcagg gcagattcga ccgcagcgtt gaaaagtggc  6600
ggcggttcca ctacgacatc aagatcttca accagtggct gaccgaggcc gagcagttcc  6660
tgagaaagac acagatcccc gagaactggg agcacgccaa gtacaagtgg tatctgaaag  6720
agctgcagga cggcatcggc cagagacaga cagtcgtgcg gacactgaat gccaccggcg  6780
aggaaatcat ccagcagtcc agcaagaccg acgccagcat cctgcaagag aagctgggca  6840
gcctgaacct gcggtggcaa gaagtgtgca agcagctgag cgaccggaag aagcggctgg  6900
aagaacagaa gaatatcctg agcgagttcc agcgggacct gaacgagttc gtgctgtggc  6960
tcgaagaggc cgacaatatc gccagcattc ccctggaacc tggcaaagag cagcagctga  7020
aagaaaagct ggaacaagtg aaactgctgg tcgaggaact gcccctgaga cagggaatcc  7080
tgaaacagct gaacgagaca ggcggccctg tgctggtgtc tgcccctatt tctcccgagg  7140
aacaggacaa gctggaaaac aagctgaagc agaccaacct gcagtggatc aaggtgtcca  7200
gagcactgcc tgagaagcag ggcgagatcg aggcccagat caaggacctg ggacagctcg  7260
aaaagaagct tgaggacctc gaagaacagc tcaaccatct gctgctttgg ctgagcccca  7320
tccggaacca gctggaaatc tacaaccagc ctaatcaaga gggccccttc gacgtgaaag  7380
aaaccgagat tgccgtgcag gccaagcagc ccgatgtgga agagatcctg tctaagggcc  7440
agcacctgta caaagagaag cccgccacac agcccgtgaa gcggaaactg gaagatctga  7500
gcagcgagtg gaaggccgtg aaccggctgc tgcaagaact gagagccaaa cagcctgatc  7560
tggcccctgg cctgacaaca attggcgcct ctcctacaca gaccgtgaca ctggtcacac  7620
agcctgtggt caccaaagag acagccatca gcaaactgga aatgcccagc agtctgatgc  7680
tcgaagtgcc cgcactggcc gacttcaata gagcctggac cgagctgacc gactggctca  7740
gtctgctgga ccaagtcatc aagtcccaga gagtgatggt cggagatctt gaggacatca  7800
acgagatgat cattaagcag aaagccacca tgcaggacct tgagcagaga aggccccagc  7860
ttgaagaact gatcaccgcc gctcagaacc tgaaaaacaa gaccagcaat caagaagccc  7920
ggaccatcat caccgaccgg atcgagagaa tccagaacca gtgggacgaa gtgcaagagc  7980
atctgcagaa cagacggcag cagctcaatg agatgctgaa ggacagcaca cagtggctgg  8040
aagccaaaga agaagccgag caggttctcg gacaggccag agctaagctg gaatcttgga  8100
aagagggacc ctacaccgtc gacgccatcc agaagaagat caccgagaca aagcagctgg  8160
ccaaggatct gagacagtgg cagaccaatg tggacgtggc caacgacctg gctctgaagc  8220
tgctgagaga ctacagcgcc gacgacacca gaaaggtgca catgatcacc gaaaacatca  8280
acgcctcttg gcggagcatc cacaagcggg tgtcagagag agaagccgct ctggaagaaa  8340
cacatagact gctccagcag ttcccactcg acctggaaaa gttcctggcc tggctgacag  8400
aagccgaaac caccgctaac gtgctccagg atgccaccag aaaagagcgg ctgttggagg  8460
acagcaaggg cgtcaaagaa ctcatgaagc agtggcagga tctgcaaggg gagattgaag  8520
cccacaccga cgtgtaccac aacctggacg agaacagcca gaagatcctg cggtccctgg  8580
aaggctctga tgatgctgtg ctgcttcaga ggcggctgga caacatgaac ttcaagtgga  8640
gcgagctgcg gaagaagtcc ctgaacatca gaagccacct ggaagcctcc agcgaccagt  8700
ggaaaagact gcacctgtct ctccaagagc tgctcgtgtg gctgcagctg aaggatgacg  8760
agctgagtag acaggcccct atcggcggag attttcccgc cgtgcagaaa cagaacgacg  8820
tgcaccgggc cttcaagaga gagctgaaaa caaaagaacc cgtcatcatg agcaccctgg  8880
aaaccgtgcg gatctttctg accgagcagc ctctggaagg actggaaaag ctgtaccaag  8940
agcctagaga gctgcctcct gaagaaaggg cccagaacgt gacacggctg cttagaaagc  9000
aggccgagga agtgaacacc gaatgggaga agctgaacct ccactccgcc gactggcagc  9060
ggaagatcga tgagacactg gaacggctgc gggaactgca agaagccaca gacgagctgg  9120
acctgaaact gcggcaggct gaagtgatca aaggctcctg gcagccagtg ggcgatctgc  9180
tgatcgatag cctgcaggac catctggaaa aagtcaaggc cctgcgggga gagatcgccc  9240
ctctcaaaga aaacgtgtcc cacgtgaacg atctggccag gcagctgaca acactgggca  9300
tccagctgag cccttacaac ctgtctacct tggaggacct gaatacccgg tggaagctgc  9360
tccaagtggc cgtcgaggat agagtgcggc agctgcatga ggctcacaga gattttggac  9420
ccgccagcca gcacttcctg agcacatctg ttcaaggccc ctgggagaga gctatcagcc  9480
ctaacaaggt gccctactac atcaaccacg agacacagac cacctgttgg gatcacccca  9540
agatgaccga actgtatcag tccctggccg acctgaacaa cgtgcggttt agcgcctacc  9600
ggaccgccat gaagctgcgc agactgcaga aagctctgtg cctggacctg ctgtctctga  9660
gcgctgcttg tgatgccctg gaccagcata acctcaagca gaacgaccag cctatggaca  9720
tcctgcagat catcaactgc ctgaccacca tctacgaccg gctcgaacaa gagcacaaca  9780
acctggtcaa cgtgcccctg tgcgtggaca tgtgcctgaa ttggctgctg aacgtgtacg  9840
acaccggcag aaccggcagg atcagagtgc tgagcttcaa gaccggcatc atctccctgt  9900
gcaaggccca ccttgaggat aagtaccgct acctgtttaa gcaggtcgcc agcagcaccg  9960
gcttttgcga ccaaagaagg ctgggactgc tgctccacga cagcattcag atccctagac  10020
```

```
agctgggcga agtggcctct ttcggcggct ctaatatcga gcctagcgtg cggagctgct  10080
tccagttcgc caacaacaag cccgagattg aggccgcact gttcctggac tggatgagac  10140
tggaacccca gagcatggtc tggctgcctg tgctgcatag agtggccgca gccgaaacag  10200
ccaagcacca ggccaagtgc aacatctgca aagagtgccc catcatcggc ttccggtaca  10260
gatccctgaa gcacttcaac tacgatatct gccagtcctg cttcttcagc ggcagagtgg  10320
ccaagggcca caagatgcac taccccatgg tggaatactg cacccctacc acctctggcg  10380
aggacgtgcg ggattttgcc aaggtgctca agaacaagtt ccggaccaag cgctacttcg  10440
ctaagcaccc cagaatgggc tacctgccag tgcagacagt gcttgagggc gacaacatgg  10500
aaacccctgt gactctgatc aacttctggc ccgtggatag cgcccctgct agttctcctc  10560
agctgtctca cgacgatacc cacagcagaa tcgagcacta cgcctccaga ctggccgaga  10620
tggaaaacag caacggcagc tacctgaatg acagcatcag ccccaacgag agcatcgacg  10680
acgaacatct gctcattcag cactactgcc agagcctgaa tcaggacagc cctctgtctc  10740
agcctagaag ccctgcacag atcctgatca gcctggaaag cgaggaacgc ggcgagctgg  10800
aaagaatcct ggcagacctg gaagaggaaa accggaacct gcaggccgaa tacgacagac  10860
tcaagcagca gcacgagcac aagggactgt ctccactgcc ttctccacct gaaatgatgc  10920
ccacctctcc acagagcccc agagatgccg agctgattgc cgaagccaaa ctgctgaggc  10980
agcacaaagg cagactcgaa gccagaatgc agattctcga agatcacaac aagcagctcg  11040
aatcccagct gcacagactt aggcagctgc tggaacagcc tcaggcagag gccaaagtga  11100
atggcaccac cgtgtctagc cctagcacaa gcctgcagag atccgacagc agccagccaa  11160
tgcttctgag agtcgtgggc tcccagacca gcgattctat gggcgaagag gacctgctca  11220
gccctcctca ggatacaagc accggcctgg aagaagtgat ggaacaactg aacaacagct  11280
tccccagcag cagaggcaga aacacccctg gcaagcccat gcgcgaggac accatgtgat  11340
aactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acctagctgg cttgttgtcc acaaccatta  12180
aaccttaaaa gctttaaaag ccttatatat tcttttttttt cttataaaac ttaaaacctt  12240
agaggctatt taagttgctg atttatatta attttattgt tcaaacatga gagcttagta  12300
cgtgaaacat gagagcttag tacattagcc atgagagctt agtacattag ccatgagggt  12360
ttagttcatt aaacatgaga gcttagtaca ttaaacatga gagcttagta cattaaacat  12420
gagagcttag tacatactat caacaggttg aactgctgat ctgtacagta gaattggtaa  12480
agagagttgt gtaaaatatt gagttcgcac atcttgttgt ctgattattg atttttggcg  12540
aaaccatttg atcatatgac aagatgtgta tctaccttaa cttaatgatt ttgataaaaa  12600
tcattacgaa tgcatctaga agctgcatgt ctaagctaga cccttcagat taaaaataac  12660
tgaggtaagg gcctgggtag gggaggtggt gtgagacgct cctgtctctc ctctatctgc  12720
ccatcggccc tttggggagg aggaatgtgc ccaaggacta aaaaaaggcc atggagccag  12780
aggggcgagg gcaacagacc tttcatgggc aaaccttggg gccctgctgt ctagcatgcc  12840
ccactacggg tctaggctgc ccatgtaagg aggcaaggcc tggggacacc cgagatgcct  12900
ggttataatt aacccagaca tgtggctgcc cccccccccc caacacctgc tgcctctaaa  12960
aataaccctg tccctggtgg atcccctgca tgcgaagatc ttcgaacaag gctgtggggg  13020
actgagggca ggctgtaaca ggcttggggg ccagggctta tacgtgcctg ggactcccaa  13080
agtattactg ttccatgttc ccggcgaagg gccagctgtc ccccgccagc tagactcagc  13140
acttagttta ggaaccagtg agcaagtcag cccttggggc agcccataca aggccatggg  13200
gctgggcaag ctgcacgcct gggtccgggg tgggcacggt gcccgggcaa cgagctgaaa  13260
gctcatctgc tctcaggggc ccctccctgg ggacagcccc tcctggctag tcacaccctg  13320
taggctcctc tatataaccc aggggcacag gggctgccct cattctacca ccacctccac  13380
agcac                                                              13385
```

```
SEQ ID NO: 18           moltype = DNA  length = 868
FEATURE                 Location/Qualifiers
source                  1..868
                        mol_type = other DNA
                        note = CBA
                        organism = synthetic construct
SEQUENCE: 18
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctccccccc cctccccacc  360
cccaattttg tatttattta ttttttaatt attttgtgca gcgatggggg cggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tcgtaagtac tagcagctac aatccagcta ccattctgct tttattttat  720
ggttgggata aggctggatt attctgagtc caagctaggc ccttttgcta atcatgttca  780
tacctcttat cttcctccca cagctcctgg gcaacgtgct ggtctgtgtg ctggcccatc  840
```

```
actttggcaa agaattgcga tcgccacc                                    868

SEQ ID NO: 19          moltype = DNA  length = 11061
FEATURE                Location/Qualifiers
source                 1..11061
                       mol_type = other DNA
                       note = DMD-1
                       organism = synthetic construct
SEQUENCE: 19
atgctgtggt gggaagaggt ggaggattgc tacgagcggg aggatgtgca gaaaaagact  60
ttcaccaagt gggtaaatgc tcagttctct aagttcggga agcaacacat cgagaacttg  120
ttttccgacc tccaggatgg caggcgcctg cttgacttgc tggagggtct gactggtcag  180
aagctcccta aggagaaggg cagcaccaga gttcacgctc tgaataacgt taacaaagcc  240
ctgagggtcc tccagaataa caatgtagac ctggtgaaca tcggttctac cgacatcgtg  300
gacgggaatc ataaactgac cttggggctc atctggaaca ttatcttgca ctggcaggtg  360
aagaacgtca tgaagaatat catggccggg ctgcaacaga ccaactccga aaagattttg  420
ctcagctggg tgcgccagtc cacccgcaat tatccacaag tcaacgttat caatttcacc  480
actagttgga gtgatggcct cgccctgaac gccttgatcc acagtcaccg ccccgacctg  540
tttgactgga actctgtggt ttgccaacag agcgctaccc agcgtctcga acatgctttc  600
aatatcgcta gataccagct cggtatcgag aagctgttgg atcctgagga cgtagacacg  660
acctaccccg ataaaaagag catcctgatg tatatcactt ctctgtttca ggtgcttcct  720
caacaggtgt ccattgaagc catccaagag gtcgaaatgc tgcccaggcc ccctaaggtg  780
acaaaagaag agcatttcca gctgcatcac cagatgcatt acagtcaaca gattaccgtc  840
agcttggctc agggatatga gcgcacgtcc tctcctaagc ccagatttaa gtcctacgca  900
tatacccagg ctgcctacgt gaccacttcc gacccaacta ggagcccctt tccctcccaa  960
cacctggagg cccctgagga caaaagcttc ggatctagtc tgatggagtc cgaggtgaat  1020
ctggatcggt accaaactgc tctggaggaa gtgctgtcct ggcttctgtc cgctgaagac  1080
accctgcagg cgcaaggtga gatttctaac gacgtcgagg tcgtgaagga tcagttccac  1140
actcatgagg gctacatgat ggacttgaca gctcaccagg gaagagttgg taacatcctg  1200
cagcttggct ccaagttgat tggcacggga aagcttagcg aggacgagga aaccgaggta  1260
caggagcaga tgaacttgct gaattcccgc tgggagtgcc tgagagttgc gtccatggaa  1320
aagcagtcaa accttcacag agtgctgatg gaccttcaga accagaagct gaaggagctg  1380
aacgattggc tgacaaagac cgaggaacgc acaagaaaaa tggaagagga acctctggga  1440
cctgatctgg aggatctgaa gcgccaggtc caacagcata aggtgctgca ggaggatttg  1500
gagcaggagc aggtgcgggt caacagcctg acacatatgg tggttgtggt cgatgagtcc  1560
tctggcgatc atgctaccgc agcgctggaa gagcagctga aggtgctggg ggatcgctgg  1620
gccaacattt gcagatggac agaagaccgg tgggtcctgc ttcaagatat cctgctcaag  1680
tggcagcgcc tgactgaaga gcagtgcctg ttctcagctt ggttgagcga aaaagaggac  1740
gcagttaaca agatccatac cacaggcttc aaggatcaga atgagatgct gagctcactg  1800
cagaagctgg ctgtgctgaa ggccgacttg gagaagaaaa agcagtccat gggcaaactg  1860
tatagcctga agcaggacct gctcagcacc ctgaagaaca aaagcgttac gcagaaaact  1920
gaggcctggt tggacaactt tgctcgctgc tgggataacc ttgtgcagaa gctggaaaag  1980
tcaaccgcac agatctccca ggctgtgacc actacgcagc ctagcttgac ccagacaacc  2040
gttatggaaa ccgtgacaac cgtgacaacg agagagcaaa tcctggttaa gcatgcccag  2100
gaggaactgc cgccaccccc gcctcagaag aaacggcaga ttacggtgga cagcgagatc  2160
cgcaagaggc tggacgtcga catcactgag ctccactcat ggatcacgcg gagtgaggcc  2220
gtgctgcagt ctcccgagtt cgctattttc cgcaaggagg gaaacttctc tgacttgaaa  2280
gagaaggtga atgccatcga gcgtgaaaag gcagaaaagt tcagaaagct gcaggacgcc  2340
tctcgctctg cgcaggccct ggtggagcag atggtcaacg agggtgttaa cgctgacagc  2400
atcaaacagg caagcgaaca gctgaactcc agatggatcg aattttgcca actgctctcc  2460
gaacgcctca actggttgga gtaccagaac aatattatcg ctttttacaa ccagctgcag  2520
caactggagc agatgacaac taccgccgaa aactggctga aaattcagcc aaccacaccg  2580
tccgagccaa ctgcgatcaa gtctcagctg aagatctgca aggacgaagt gaaccgtctt  2640
agcgacttgc aaccccagat tgaacggctc aagattcagt ctattgctct gaaggagaag  2700
ggtcagggtc cgatgttcct ggatgcagat tttgtcgcat ttaccaatca cttcaaacag  2760
gtgtttagtg acgtccaggc gcgcgagaaa gagctgcaga ctatttttga caccctgcct  2820
cccatgaggt accaggagac aatgagtgcc attcgcacct gggtgcaaca gtccgagacg  2880
aaattgtcaa tcccacagct gtccgtgaca gactacgaga ttatggagca acggttgggg  2940
gagctgcagg ctcttcagag ttccctgcag gagcaacaga gcggactgta ctatctttcc  3000
actaccgtga aggaaatgag taagaaagcc ccttccgaga tcagccgcaa ataccagtct  3060
gaattcgaag agatcgaggg acgctggaaa aagctgtcaa gccagctggt cgagcactgt  3120
cagaagctgg aagagcagat gaacaagctg cgtaaaatcc agaaccatat tcagaccctc  3180
aagaaatgga tggcagaagt tgacgtgttt ctgaaggaag agtggcctgc cctcggcgat  3240
agcgaaatcc ttaagaaaca actcaagcag tgccgcctcc tggtgtccga tattcagaca  3300
atccagcctt ccctgaacag cgttaatgag ggcggacaga aaattaaaaa cgaggccgaa  3360
cccgagttcg cttctcgcct ggagactgaa ctgaaggagc tgaataccca gtgggaccat  3420
atgtgtcaac aggtctacgc acgcaaagag gcactgaagg gcggtctgga gaagactgtc  3480
tcactccaga aggacctgag cgagatgcac gagtggatga cccaggccga agaggaatac  3540
ctggagcgtg attttgagta taagacccca gacgaactcc agaaagccgt tgaagagatg  3600
aagagggcta aggaggaagc ccaacagaag gaggcgaaag tgaagctcct gacagagtcc  3660
gtgaactccg tcatcgctca agctcctccc gtggctcagg aggccctcaa gaaagagctg  3720
gaaactctga ccacaaatta ccagtggttg tgtacccgct tgaacggtaa gtgcaagacc  3780
ctggaagagg tgtgggcctg ctggcacgag ctcctgtcct atcttgagaa ggcgaacaaa  3840
tggctgaacg aagtggaatt caagttgaaa acaactgaga acattccggg aggcgctgag  3900
gaaatctctg aggtgctgga ctctctggaa aatctgatgc gtcattctga agacaatcct  3960
aaccagatca ggattctggc acagaccctc actgacggag gcgttatgga cgaacttatc  4020
aacgaggaac tggagacatt caattcccgt tggcgtgagc tgcacgaaga ggccgtgcgc  4080
cgtcagaagt tgctggaaca gtctatccag tccgcccagg agacagagaa atctctccac  4140
ctgatccagg agagtctgac gtttatcgat aagcagctgg ctgcctacat cgccgacaag  4200
```

```
gtggacgctg cccagatgcc ccaagaggct cagaagatcc agtccgacct gacgtctcat  4260
gaaatcagcc tggaagagat gaaaaagcac aaccagggca aagaggctgc ccagcgcgtc  4320
ctctcccaga ttgacgtggc tcagaaaaag ttgcaggacg tgagcatgaa gtttaggctg  4380
ttccagaaac ccgccaactt cgaacagaga ctgcaggagt ctaagatgat cctggatgag  4440
gtcaagatgc acctccctgc tctggaaaca aaatctgtgg agcaggaggt cgtgcagtca  4500
caactgaacc attgtgtgaa cctctacaag tctctcagcg aggtgaagtc cgaggtcgag  4560
atggtgatca agaccggacg ccagattgtg cagaaaaagc agacagagaa cccaaaggag  4620
ctggacgaac gggtgaccgc cctgaagctc cactacaacg agttgggtgc caaagtcact  4680
gaaagaaagc aacagctgga gaagtgtctg aagctgagcc gcaagatgcg caaagaaatg  4740
aacgtcttga ccgagtggtt ggcggccacc gacatggagc tgaccaagag atccgctgtg  4800
gagggcatgc cctccaacct tgactcagag gtggcctggg gcaaggccac acagaaggag  4860
atcgaaaaac agaaggtgca tcttaaatca atcactgagg tgggcgaagc tctgaagaca  4920
gtgctgggca agaaagagac acttgtagag gacaagctct cccttctgaa tagcaattgg  4980
atcgccgtaa ctagtcgcgc ggaggaatgg ctgaacctcc tgttggaata ccagaaacac  5040
atggaaacct tcgatcagaa cgtggaccat attaccaagt ggattatcca ggctgacact  5100
ctcctggacg agtctgagaa aaagaaaccc cagcaaaagg aagatgtgct gaagcgcctg  5160
aaggcggaat tgaacgacat ccgcccgaag gttgattcca cccgcgacca agcggccaac  5220
cttatggcta accgcgggga ccattgcaga aaactggtgg aaccgcagat ctctgagctg  5280
aaccacagat tcgccgcgat ttctcacaga attaagactg gcaaggcctc catccctctg  5340
aaagagctgg agcagttcaa ctctgatatt cagaagcttc tggagcccct ggaggcagaa  5400
atccaacagg gcgtcaacct gaaagaggaa gactttaata aggacatgaa tgaggataac  5460
gaaggtaccg tcaaggagct cctgcagagg ggcgacaatc tgcagcaaag aatcactgac  5520
gaacgtaagc gcgaagagat taagatcaag caacagctgt tgcagactaa gcacaacgcc  5580
ctgaaggatc tgaggtccca gcgcaggaaa aaggccctgg agatttccca ccagtggtac  5640
cagtacaagc gccaggccga tgaccttctg aagtgcctcg acgatatcga gaaaaagctg  5700
gcctcactgc ccgagccccg cgacgagcgc aagatcaagg agattgaccg tgagctccag  5760
aagaaaaagg aggaactgaa cgcggtgcgc agacaggccg agggcctctc cgaggacggc  5820
gctgcgatgg ctgttgagcc cactcagatc caactgagca agcggtggag agagatcgag  5880
tctaagttcg cgcaatttag gcgcctcaac ttcgcccaga ttcacacggt ccgtgaggaa  5940
acgatgatgg tgatgacaga ggatatgcca ctggaaatca gctacgtgcc cagtacatat  6000
ctcaccgaaa tcacccatgt gtcccaggct ctcctggagg tggaacagtt gctcaacgct  6060
cccgacttgt gcgctaagga cttcgaggac ctgttcaagc aggaagagag cctgaaaaac  6120
attaaggact ccctgcaaca gtcaagcggc cgcatcgata tcattcattc taagaaaacc  6180
gctgccctgc agtctgcaac ccccgtagag cgcgtcaaac tgcaggaagc tctcagccaa  6240
ctggatttcc agtgggagaa ggtgaacaag atgtataagg atcgtcaggg ccggttcgac  6300
cgctctgtgg agaagtggcg ccgtttccac tacgatatca agattttcaa tcaatggttg  6360
accgaggcag agcagttcct cagaaagaca cagatccctg aaaattggga gcatgccaag  6420
tacaagtggt atctgaagga gctgcaggac gggatcggac aacgtcagac cgtggtccgc  6480
accctgaacg caaccggcga ggaaattatc caacagtcta gcaagacaga tgctagcatc  6540
ctccaggaga agctcggaag cctcaacctt cgctggcagg aggtgtgcaa gcagctgtca  6600
gacaggaaga aacgcctgga ggaacagaag aacatccttt cagagttcca gagagatctg  6660
aacgaattcg tgctttggct tgaagaggcc gataacatcg caagcatccc actggagcct  6720
ggtaaggaac agcaattgaa ggagaagctg gagcaggtaa agctgctcgt ggaagagctg  6780
cctctgaggc agggaattct caagcagctc aacgagactg gggcccggt tttggtgagc  6840
gccccaatta gcccagaaga gcaggacaag ttggagaaca agctgaagca gaccaacctg  6900
cagtggatca aggtgtcccg cgcactgccc gaaaagcagg gagagattga ggcccagatc  6960
aaggatctgg gacagctgga gaaaaagctg gaagacctgg aggaacagct gaaccatttg  7020
ctcctgtggt tgtcccccat cagaaatcag ctggaaatct acaaccaacc gaaccaggaa  7080
ggtccgtttg atgttaagga aaccgagatc gctgtgcagg cgaagcagcc tgacgtagaa  7140
gagatcctgt caaagggaca gcacctctac aaggagaagc ccgccaccca gccagtcaag  7200
cggaagctcg aagacctgtc cagcgagtgg aaagccgtca accgcctcct gcaagagctg  7260
cgtgccaagc aaccggacct ggcgccaggt ctgactacca ttggcgcaag tcctacccag  7320
actgtcaccc tggtgaccca acccgttgtg acaaaggaaa ccgccatcag caagctggag  7380
atgcctagct ctttgatgct ggaggttccc gccctcgccg acttcaaccg tgcttggaca  7440
gaactgaccg actggctgtc cctcctggac caagtgatca agagccagcg cgtgatggtg  7500
ggtgatcttg aggatattaa cgaaatgatt atcaagcaga aggccaccat gcaggacttg  7560
gagcagaggc gcccccagtt ggaggaactg atcaccgccg cgcagaatct gaaaaacaaa  7620
acttccaatc aggaagcgag aaccatcatt acagacagaa ttgagagaat tcaaaaccag  7680
tgggacgaag tgcaagaaca cctccagaac cggcgtcaac agctgaacga gatgctgaag  7740
gattccactc aatggctgga agctaaggaa gaggccgagc aggtccttgg acaggcacgc  7800
gctaagctgg agtcctggaa agaaggcccc tatacagtgg acgcaattca aaagaaaatc  7860
accgagacga agcaactggc caaggacctg agacagtggc aaaccaacgt tgatgtggct  7920
aatgacctgg ccttgaagct cctgcgtgac tactccgcgg atgacactag aaaggtgcac  7980
atgatcaccg agaatatcaa cgctagctgg cgctccatcc ataagcgtgt gagtgagcgc  8040
gaagccgctc tggaggaaac ccatcgcctg cttcaacagt ttcctttgga cctggaaaag  8100
ttcctggcct ggctcacaga agccgagaca accgccaacg tgctgcagga cgccacccgt  8160
aaggagcgct tgctggagga tagtaagggg gtgaaggagt tgatgaagca gtggcaagat  8220
ctgcaggggg aaatcgaggc acataccgac gtctatcata acctggatga gaattcccag  8280
aaaatcctgc gcagcttgga gggcagtgat gacgcggtgc ttctgcaacg gcgcttggac  8340
aacatgaact tcaagtggtc cgagttgcgt aaaaagagtc tgaacattcg ctcccacctg  8400
gaggcttcta gtgaccagtg gaagcgcctg cacctgagcc tgcaagaact gctcgtgtgg  8460
ctgcaactga aggatgacga gttgagtcgt caggccccta tcggaggtga ctttccggct  8520
gtccagaaac agaacgacgt gcatagggca tttaagcgcg agttgaagac aaaggagcca  8580
gtcattatgt ccacgctgga aaccgtgcgc attttcctga ctgagcagcc tctggagggg  8640
ctggagaagc tgtaccagga gcctcgcgag ttgcccccctg aagagcgtgc ccagaatgtg  8700
acccgcctgt tgcgtaagca ggccgaggaa gtgaacaccg agtgggagaa gctgaacctg  8760
cattccgcgg attggcagag gaagattgac gagacgctgg agaggctccg tgagttgcag  8820
gaggcaaccg acgaactgga cctcaagctg cgtcaagcag aggtgatcaa ggggagttgg  8880
cagccggtcg gcgatttgct gatcgactcc ctgcaggatc acctggaaaa ggttaaagct  8940
```

```
ttgcgcgggg aaattgcccc gctgaaggag aacgtgagcc acgttaacga tctggccaga  9000
cagctgacca ctctgggtat ccagctgagc ccgtacaatc tgagcaccct cgaagacttg  9060
aatacgagat ggaaactcct gcaggtggca gtggaggaca gggtgcgcca attgcacgag  9120
gcccaccggg actttggacc ggccagccag catttcctca gtacctctgt tcagggcccg  9180
tgggagcggg ccatctcccc caacaaggtc ccctattaca tcaaccatga aacccagact  9240
acctgttggg accaccctaa aatgactgag ttgtatcaat ctctggccga cttgaataac  9300
gtgcgcttct cagcctacag gactgcaatg aaactcagac gcctccaaaa ggccctttgt  9360
ctggacttgc tgtcccttag cgctgcctgt gatgctctgg atcagcacaa tttgaaacaa  9420
aacgaccagc cgatggacat cctccagatt atcaactgcc tgactaccat ctacgacaga  9480
ctggaacagg agcataataa cctggtgaac gtcccccctgt gcgtggacat gtgcctgaac  9540
tggctgctca atgtgtatga cacgggtaga acaggacgga tcagggtcct gtcctttaag  9600
accggtatca tttctctgtg taaggcacat ctggaggaca agtaccgcta cctgtttaag  9660
caggtcgcca gctccactgg cttctgcgat caaaggcggc tgggtctgct cctgcacgac  9720
tccattcaga tcccgagaca gttgggtgaa gtggcgtcct tcggcggttc taatatcgag  9780
cctagcgtcc gcagctgttt ccaattcgcc aataacaagc cggagatcga agcggccctt  9840
ttcctggact ggatgcgtct ggaacctcag agcatggttt ggcttccggt gcttcatcgc  9900
gtggccgctg ccgaaaccgc taaacatcag gccaaatgta acatctgtaa ggaatgcccg  9960
attatcggtt tccggtaccg tagcctcaag catttcaact atgatatttg tcaatcttgc  10020
ttctttagcg gacgggtggc caaaggccac aaaatgcact acccgatggt cgagtattgc  10080
actcctacaa cctccggcga ggacgtgcgc gattttgcca aagtgctgaa aaacaagttt  10140
agaaccaagc gttactttgc caagcatcca cgtatgggct acctgcctgt ccagaccgtt  10200
ctggaaggtg ataacatgga gacacccgtg actttgatta acttttggcc agtagactct  10260
gctccggcaa gctcccctca gctctcccac gatgacactc acagccgtat cgagcactac  10320
gcctctcgcc tggctgagat ggagaactct aacggttcat acctgaatga cagtatctcc  10380
ccaaacgaga gtatcgatga cgaacatctg ctcattcagc attactgtca atccttgaat  10440
caggacagcc ccctgtccca gccacggtcc ccggcccaga tcctgatttc actggagtcc  10500
gaagagagag gggaactgga aaggatcctc gctgacctgg aagaggaaaa ccggaacctg  10560
caggctgaat acgaccgctt gaagcagcaa cacgagcaca agggcttgag cccgttgcca  10620
agccctccgg agatgatgcc aactagccct cagagcccac gggatgccga gctcatcgct  10680
gaagctaagt tgctgagaca gcacaaggga cgtctggagg cccgcatgca gatcctggag  10740
gatcataata aacagttgga gagccaactg cataggctgc gccagctcct ggagcagcca  10800
caggccgagg ctaaggtcaa cggaactacc gtttccagcc cgtccacatc tctgcagcgc  10860
tcagatagtt cccagcctat gttgctgaga gtggttggat ctcagacctc cgactcaatg  10920
ggcgaagagg acttgctgtc tcccccacag gacactagca caggactcga agaggtgatg  10980
gaacagctca ataactcttt tccttctagt cggggtcgca ataccccctgg aaagcccatg  11040
cgcgaagaca ccatgtaata g                                          11061
```

```
SEQ ID NO: 20          moltype = DNA  length = 11061
FEATURE                Location/Qualifiers
source                 1..11061
                       mol_type = other DNA
                       note = DMD-5
                       organism = synthetic construct
SEQUENCE: 20
atgctgtggt gggaggaagt tgaagattgt tatgagagag aagatgtcca gaaaaagacc  60
tttaccaaat gggtgaacgc acagttctcc aaatttggga aacagcatat agaaaatttg  120
ttcagcgatc ttcaggatgg gcgcaggttg cttgaccttc tggaaggact gaccgggcag  180
aagctgccca aagagaaagg gtctaccaga gttcacgctc tgaacaacgt gaataaggca  240
ctgcgagtcc tgcaaaataa caacgtcgac ctggtgaaca taggcagcac tgatattgtt  300
gatgggaacc ataaactcac actgggtctg atttggaata ttatactgca ctggcaggtc  360
aaaaatgtta tgaaaaatat tatggccggg cttcaacaga ccaattccga gaagatcctg  420
ctgtcttggg ttaggcagtc cacgaggaac taccctcaag tgaacgttat taacttcaca  480
acatcatgga gtgatggact tgccctgaac gccttgatcc actcccatag gccagacctg  540
ttcgattgga atagcgtagt ctgtcagcag agtgctacac aacgcctgga acacgccttt  600
aacatagcca ggtatcagct tggaattgag aaactcctcg accctgaaga cgtagacacc  660
acttaccccg acaaaaaatc cattcttatg tacataactt ccttgtttca ggttctcccc  720
cagcaggtgt ccatcgaggc tatacaggag gtcgaaatgc tccccagacc ccctaaggtc  780
acgaaggaag agcacttcca actgcaccat cagatgcact acagtcaaca gatcactgtg  840
agtctcgcac aggggtacga aaggaccagc tcccctaaac cccgcttcaa gtcctacgcc  900
tatactcagg cagcttacgt aaccacaagt gaccccacgc ggtcaccctt cccaagccag  960
cacctggagg ctcccgagga caaaagcttt ggatcatccc tgatggaatc tgaagtcaat  1020
ctcgataggt accaaaccgc tctggaggag gtcctcagtt ggctcccttc agctgaagat  1080
actctgcagg cacagggtga gatcagcaat gacgtggagg tagtgaaaga tcagtttcac  1140
actcacgagg gctatatgat ggacctgaca gcccatcaag gtcgcgttgg caatatcctg  1200
cagttggggt ccaaactgat tggtaccggt aagttgtccg aggacgaaga gacagaagtg  1260
caggagcaga tgaacctgct taattctaga tgggaatgcc tccgcgtggc ctctatggag  1320
aagcagtcca atctccatcg ggttctcatg gacttgcaga atcagaagct gaaggaactc  1380
aacgactggt tgaccaagac tgaggagcgc accagaaaga tggaggagga gccactcggt  1440
cctgatcttg aagatctgaa acgacaagtt cagcagcaca aggtcctgca ggaggatctc  1500
gaacaggagc aggtccgggt gaacagcctg acccatatgg ttgtcgttgt cgacgagtca  1560
agtggggacc atgctacggc tgcgcttgag gaacagctga aggtcttggg cgatagatgg  1620
gcgaatatct gccgctggac tgaagataga tgggtgctgc tgcaggatat tcttttgaag  1680
tggcagcggt tgaccgaaga acaatgcttg tttagcgcct ggctgagtga gaaagaggat  1740
gcggtgaata agatacacac tactggcttc aaagaccaga atgaaatgct tagcagcctg  1800
cagaaacttg cggttcttaa ggccgacttg gaaaagaaaa agcagtcaat gggtaagctg  1860
tactcactca agcaggacct gctgtcaact ttgaagaaca agagcgtcac gcaaaagact  1920
gaggcctggc tcgacaattt tgctaggtgc tgggataacc tggtgcagaa gttggaaaag  1980
tccactgctc agatctctca agccgtgact actacccagc ccagcctgac acagactacc  2040
gtcatggaaa ccgttaccac tgtgacgact agggagcaga tactcgttaa gcacgctcaa  2100
```

```
gaggaattgc cgccacctcc tccccaaaag aaacgccaga ttaccgtcga ctctgaaata  2160
cgcaagagac tggatgtgga catcacggaa ctgcactctt ggattaccag aagcgaggca  2220
gtcctccaga gccccgagtt tgcgatcttc aggaaggaag gcaacttttc agatctgaag  2280
gaaaaggtga acgccatcga gcgcgagaaa gccgagaagt tccgcaaact gcaggatgcg  2340
agccggtctg ctcaggcctt ggtggagcaa atggtgaatg aaggcgtaaa tgcggacagc  2400
atcaagcagg cctccgagca gctcaattca agatggatcg agttctgtca gctgctcagc  2460
gagcgattga actggctgga gtatcaaaat aacataatcg cgttttacaa ccagctgcaa  2520
cagctggaac agatgacgac tactgcagag aactggctta aatccagcc tacaactcct  2580
tctgaaccca cagcaatcaa aagccagctc aagatctgca aggacgaagt caaccgcctc  2640
tccgatttgc agcctcagat agaacgactc aagatccaaa gtatcgcact caaagaaaag  2700
gggcaaggcc ctatgtttct cgatgctgat tttgtggctt tcaccaacca ttttaagcaa  2760
gtgttttcag atgtgcaagc ccgggaaaag gaactgcaaa ccatttttga taccctgcct  2820
ccaatgcggt accaggagac tatgtctgca attcgcacct gggtgcaaca aagcgagacg  2880
aaactttcta ttccacaact gtccgtgaca gactacgaaa ttatggaaca gcgactggga  2940
gaactccaag cccttcagtc cagccttcag gagcagcagt caggattgta ctatctgtca  3000
accaccgtga aggaaatgtc aaaaaaggct ccctccgaaa tatctcgcaa gtatcagtct  3060
gagtttgaag agattgaagg gagatggaag aaactgtcct cacagctggt tgagcactgt  3120
cagaagttgg aagagcagat gaacaagttg cgcaagattc aaaatcacat acagacactc  3180
aaaaagtgga tggcggaggt tgacgtcttc cttaaagagg agtggccagc cctgggcgac  3240
tcagagatcc tgaaaaagca actgaaacag tgccgactgc tggtgtccga catccagaca  3300
atacagccaa gtttgaatag cgtgaatgag ggtggacaaa aaatcaaaaa cgaggctgag  3360
cccgagttcg cctccagatt ggaaaccgag ctgaaggaac ttaatacaca gtgggatcat  3420
atgtgtcagc aggtttatgc ccggaaggaa gcactgaaag gggggctgga gaaaaccgtg  3480
agccttcaga aggaccttag cgagatgcac gagtggatga cccaggcgga ggaagagtat  3540
ctcgaacggg attttgagta taagacacca gatgaacttc agaaggcagt cgaagagatg  3600
aaacgggcaa aggaagaggc tcagcagaag gaagcaaagg ttaaacttct gacagaatcc  3660
gttaacagcg ttatagccca agctcccccc gttgcccagg aagctcttaa aaaggaactg  3720
gaaacactga caacaaacta ccagtggctg tgcacccgct tgaacggcaa atgcaaaacc  3780
ctggaagagg tctgggcttg ttggcatgaa ctcctgtcat acctggaaaa agctaataag  3840
tggctgaatg aggtggagtt taaattgaaa acgaccgaaa acatccctgg cggtgcagag  3900
gagatatctg aggtgctcga tagcctggag aatcttatga ggcatagcga ggataacccc  3960
aaccagatta ggatactggc ccaaactctg accgacggcg gagtgatgga cgagctgata  4020
aacgaggaac tggaaacctt taattcacgc tggcgagaac ttcacgagga ggcagtcagg  4080
cgccagaaac tgctggagca gtccatccag agtgcccagg agactgagaa gtcacttcat  4140
ctgatccagg agagtttgac gtttatcgac aagcagcttg ccgcctacat tgcagacaag  4200
gtcgatgctg ctcagatgcc gcaagaggct cagaaaatcc agagcgacct gacaagccac  4260
gagattagcc tggaggaaat gaaaaagcac aaccagggta aagaggccgc ccagcgggtt  4320
ctgagccaga tcgatgtcgc acagaagaaa ctccaagatg taagcatgaa gttccgactg  4380
tttcagaaac cagcgaactt tgagcagcga ctgcaggagt ctaaaatgat cctcgatgag  4440
gtgaaaatgc atctgccagc cctggaaact aagagcgtgg agcaggaggt ggttcagagt  4500
cagctgaacc actgcgtaaa cctctataaa agtcttagtg aagtgaagag cgaggtggag  4560
atggtgatta agactggtag acagattgta cagaaaaagc agacggagaa ccccaaagag  4620
ttggatgaac gggtgacagc ccttaagctc cactataacg agctgggagc caaagtgact  4680
gagagaaagc agcaacttga aaaatgtctg aagctgagca gaaagatgcg gaaggaaatg  4740
aatgtgctga cagagtggct ggctgcgacc gacatggaac ttacaaagag gagcgccgtg  4800
gaaggcatgc cttccaatct ggatagtgag gtcgcttggg gcaaagctac acagaaggaa  4860
attgagaagc aaaaagtgca tcttaagagc attactgaag ttggcgaggc tttgaaaacc  4920
gtcctcggca agaaagagac tctggtagaa gataaactct cactgctgaa ctcaaactgg  4980
atcgcagtca ctagtcgggc cgaagagtgg ctgaatttgc tgttggagta ccaaaagcat  5040
atggagactt tcgatcagaa tgtcgaccac attacgaagt ggataatcca ggcggacaca  5100
ctgttggatg agtccgagaa aaagaaacct cagcagaagg aagacgtgct caaacgactc  5160
aaagccgaac tgaacgacat caggcccaaa gttgattcca cccgggatca agcggccaat  5220
ctcatggcca accgggggga tcactgcaga aagttggtag aacctcagat aagcgaactt  5280
aatcatagat ttgccgccat atcacatagg attaagaccg gtaaggcttc aatccccctg  5340
aaggaactcg aacagtttaa tagtgacatc cagaagctcc tggagcctct cgaagccgag  5400
attcaacagg gtgtaaacct taaggaagag gattttaata aggatatgaa tgaggacaat  5460
gaaggcacgg tcaaagagct cctccagagg ggagacaatt tgcagcagcg gatcaccgat  5520
gaacgcaaac gcgaagagat caaaattaag cagcagctcc tccaaacaaa gcacaatgcc  5580
cttaaagacc tcagaagcca gcggcggaaa aaggctctgg aaatcagcca tcaatggtat  5640
cagtacaagc ggcaagcgga cgatctcctg aaatgtctgg atgatatcga gaaaaaactg  5700
gccagtctgc cagagcccag agatgagcgc aaaatcaagg aaatcgacag ggagcttcag  5760
aagaaaaaag aggagctgaa cgccgtccga aggcaggccg aagggctgtc agaagatggg  5820
gccgccatgg cagtggaacc tacccagatt caactgtcca agcgctggag agagattgaa  5880
agtaagttcg cacaattccg gaggcttaat tttgctcaga ttcacacagt tagggaggaa  5940
accatgatgg tgatgaccga agacatgcca ctcgaaatca gctacgtccc tagcacatat  6000
ctcacggaga ttacccacgt gtcccaggca ctgctggaag tcgagcaatt gttgaacgcc  6060
cctgatctct gcgccaagga tttcgaagac ttgttcaagc aagaggaaag cctcaagaac  6120
atcaaagaca gtcttcagca gtcctcaggc agaattgata ttatccactc caagaaaaca  6180
gccgctctcc agagcgctac ccctgtcgaa cgagtgaaac tgcaagaggc cttgtctcag  6240
ttggacttcc agtgggagaa agtcaacaag atgtacaagg acaggcaggg tcggttcgac  6300
cggagcgtcg aaaaatggcg gagattccat tatgacatca agatattcaa tcagtggctt  6360
acagaggcgg agcaattttt gagaaagacg cagattcccg aaaactggga gcatgccaag  6420
tacaagtggt acctcaaaga gctccaggat ggaatcggcc agagacagac cgtagttaga  6480
acactgaacg caactggaga agagattatc cagcagtcct ccaaaactga cgcctctatc  6540
ctccaggaga agcttggcag ccttaacctg cggtggcagg aggtgtgtaa acaactgtca  6600
gataggaaaa aaagacttga ggaacagaag aacattctga gcgagttcca acgagatctc  6660
aacgagttcg tactgtggct ggaggaggcc gacaacatcg cttcaatccc cctggaaccc  6720
ggcaaggaac agcagcttaa ggaaaaattg gaacaggtaa aactgttggt agaggagctc  6780
ccattgcggc agggcattct caagcagctg aatgaaactg gaggtcccgt tctggtcagt  6840
```

```
gcgcccataa gcccggaaga gcaggacaag ttggaaaaca agctgaagca aacaaatctg  6900
cagtggatca aagtgagccg ggctcttcca gaaaagcaag gcgagattga agcccagatt  6960
aaggatcttg gccagcttga gaaaaagctg gaggatctgg aagagcagct gaaccatttg  7020
cttctgtggc tgagtcccat tagaaaccag ctggaaatct acaaccagcc aaaccaagag  7080
ggccctttcg acgtcaagga aactgagata gcagtccagg caaaacagcc cgatgtcgaa  7140
gaaatcttgt ctaaggggca gcacctctac aaagagaaac ctgccaccca gcccgtgaag  7200
agaaaactgg aagacctctc ttcagagtgg aaggctgtaa acaggttgct ccaggagctg  7260
agagctaagc aacctgacct cgcacccggc ctgactacta ttggcgccag cccgacccaa  7320
accgtcacac tggtgaccca gcctgtagtc acaaaagaaa ccgccatctc caaactggag  7380
atgccttcaa gcctgatgct ggaggtgcct gctctggccg atttcaacag agcctggaca  7440
gagctgacag actggctgtc tctgctcgac caagtgataa agtcacagcg cgtcatggtg  7500
ggtgacctgg aggacatcaa tgagatgatc ataaagcaaa aggctaccat gcaggacttg  7560
gagcagcgca ggccgcagtt ggaagaactg attacagcag cccagaacct caagaacaag  7620
acttcaaatc aggaggcaag gaccatcata acagatagaa tcgagaggat tcagaaccaa  7680
tgggatgagg tgcaggagca cctgcagaac agaaggcagc agctgaacga aatgctgaaa  7740
gactccacac agtggctgga ggccaaagag gaggcagaac aggtgctggg ccaggctagg  7800
gccaagctgg aaagttggaa ggaagggccc tacaccgtgg acgccataca gaagaaaata  7860
acggagacaa aacagctggc caaagacctc cgccaatggc agaccaacgt agacgtcgcc  7920
aatgacctgg cactcaagtt gttgagagat tattccgcag atgacacccg aaaagtacac  7980
atgatcactg agaatatcaa cgccagttgg cggagcattc acaaacgggt gagcgagaga  8040
gaagccgccc ttgaggagac gcatcgcctt ttgcagcaat ttccgcttga cctggaaaag  8100
tttctggctt ggttgacaga ggccgagaca actgctaacg tgctgcaaga tgccacccgc  8160
aaagagcggc ttcttgagga ctctaaaggg gtgaaagaat tgatgaagca gtggcaggac  8220
ctccagggcg aaatcgaggc ccatactgat gtctaccaca acctggatga aaatagtcag  8280
aaaatcctga gatccctgga agggagtgat gatgcggtgc tgctgcagcg ccgactcgat  8340
aacatgaact ttaagtggtc tgaactccgg aaaaaaagcc tgaacattcg gagccatctg  8400
gaggcttctt ctgatcagtg gaagagactt catctgtcct tgcaggagct tctggtgtgg  8460
ctgcagctga aagacgacga gctgtcaagg caggcaccaa tagggggcga cttccccgct  8520
gttcagaaac aaaatgatgt gcacagggca ttcaagcggg aactgaagac gaaagaacca  8580
gtgattatga gcactctgga gacggtacgc atctttctga ccgagcagcc acttgaaggc  8640
ctcgaaaagt tgtaccagga gccacgggaa ttgcctcccg aagaacgggc tcagaatgtt  8700
acccgactgc ttcgcaagca ggctgaggaa gtgaacactg agtgggaaaa actgaatctg  8760
cacagtgccg attggcagcg caaaattgac gagacattgg agcgcttgcg ggagctgcag  8820
gaagccacag atgaacttga tctgaaactc agacaggccg aggtcataaa gggttcttgg  8880
caacccgtag gcgacctttt gattgactca ctgcaggatc atctggagaa agtaaaggcg  8940
ctgcgggggg aaattgctcc gctgaaggaa aacgtgagcc atgtgaatga tctggctcgg  9000
caattgacta ccctgggtat ccagctgtcc ccctacaatc tgagcactct cgaagacctc  9060
aacacaagat ggaaactgct gcaggtcgcc gtggaggaca gggtgaggca gctgcatgag  9120
gcacacaggg acttcggtcc ggcaagccaa cacttcctgt ctacttctgt tcaagggcct  9180
tgggaacgcg ctatttcccc aaacaaagtg ccgtactata ttaaccatga aactcagaca  9240
acctgctggg atcatcctaa aatgactgag ctgtaccaga gcctcgccga tctgaataac  9300
gtgaggttta gcgcatacag aaccgcaatg aagctcagga gactgcagaa ggcactttgc  9360
ctggacctcc tgagcctctc cgctgcctgc gatgccctcg accagcacaa cctgaagcag  9420
aatgatcagc ctatggacat cctgcaaatc ataaattgtc tgacgacaat ctacgaccgg  9480
ctcgaacagg agcacaataa tctcgtgaac gttccacttt gtgtggatat gtgtctcaac  9540
tggctgttga acgtctatga caccgggaga actggaagga tccgcgttct gtcctttaag  9600
actggaatca tcagcttgtg taaggcgcac cttgaggaca aatatcgata cctgtttaag  9660
caggttgcaa gctccactgg attctgcgac cagaggcgcc tcgggctgct gcttcatgat  9720
agtatccaaa tcccacgcca actcggagag gtggcaagct tcggcgggag caatattgag  9780
ccaagcgtca gatcttgttt ccagtttgcc aacaataagc ctgagatcga agccgcactg  9840
tttttggatt ggatgcggtt ggagccccag agtatggtgt ggttgcccgt gctgcatagg  9900
gtcgctgccg ctgaaaccgc caaacaccag gccaagtgca atatttgcaa ggaatgtccc  9960
atcatcgggt ttagataccg gagcctgaag cacttcaatt atgatatctg ccagtcttgt  10020
tttttttccg gccgagttgc taagggacac aagatgcatt acccaatggt ggaatattgt  10080
acgccaacca ccagcggcga agatgtcaga gattttgcaa aagtactcaa gaacaagttc  10140
cgcaccaagc gatatttcgc gaagcacccc cggatgggct acctcccagt gcagacggtt  10200
ctggaaggcg ataacatgga aactccagtc accctgatca atttctggcc tgtggactct  10260
gcgcctgcct cttcacctca gctctcccac gatgacaccc attccagaat cgagcactac  10320
gcgtctcgac tggcggagat ggagaacagc aatggttctt acctcaatga cagcattagc  10380
cccaacgaaa gcatcgatga cgagcacctc ttgattcaac actactgcca gtccctgaat  10440
caggacagtc ctctgtccca acccaggagc ccagcccaga tactgatctc tctcgaatca  10500
gaagaaagag gggagttgga gcgaattttg gccgacctgg aggaggagaa tagaaatctt  10560
caggccgagt acgatagact gaagcagcag cacgagcaca agggcctttc tccactgccc  10620
tctccaccgg aaatgatgcc aacctcccct caaagtccca gggacgctga gctcattgcc  10680
gaggcaaagc tgttgcgcca gcacaaagga cgcctggagg cgagaatgca gatcctggaa  10740
gaccataaca agcagcttga gtctcagctg caccgactta gacagctgtt ggagcagcca  10800
caagcggaag caaaggtcaa tggaactacc gtgagttccc ccagtacaag tctgcagcgc  10860
tctgactcaa gccagccaat gctgctccgg gtagtcggtt ctcagactag tgattcaatg  10920
ggggaggagg atcttctttc cccaccccaa gacacctcaa cagggcttga ggaagtgatg  10980
gagcagctga acaactcctt cccctcttca cgggggagaa atactcctgg gaagcctatg  11040
agagaggata ccatgtaatg a                                            11061
```

```
SEQ ID NO: 21          moltype = DNA  length = 12706
FEATURE                Location/Qualifiers
source                 1..12706
                       mol_type = other DNA
                       note = CBA-hBGi-DMD-1-WPRE3-DTS
                       organism = synthetic construct
SEQUENCE: 21
```

```
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttaatt attttgtgca gcgatggggg cggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tcgtaagtac tagcagctac aatccagcta ccattctgct tttattttat  720
ggttgggata aggctggatt attctgagtc caagctaggc ccttttgcta atcatgttca  780
tacctcttat cttcctccca cagctcctgg gcaacgtgct ggtctgtgtg ctggcccatc  840
actttggcaa agaattgcga tcgccaccat gctgtggtgg gaagaggtgg aggattgcta  900
cgagcgggag gatgtgcaga aaaagacttt caccaagtgg gtaaatgctc agttctctaa  960
gttcgggaag caacacatcg agaacttgtt ttccgacctc caggatggca ggcgcctgct  1020
tgacttgctg gagggtctga ctggtcagaa gctccctaag gagaagggca gcaccagagt  1080
tcacgctctg aataacgtta acaaagccct gagggtcctc cagaataaca atgtagacct  1140
ggtgaacatc ggttctaccg acatcgtgga cgggaatcat aaactgacct tggggctcat  1200
ctggaacatt atcttgcact ggcaggtgaa gaacgtcatg aagaatatca tggccgggct  1260
gcaacagacc aactccgaaa agattttgct cagctgggtg cgccagtcca cccgcaatta  1320
tccacaagtc aacgttatca atttcaccac tagttggagt gatggcctcg ccctgaacgc  1380
cttgatccac agtcaccgcc ccgacctgtt tgactggaac tctgtggttt gccaacagag  1440
cgctacccag cgtctcgaac atgctttcaa tatcgctaga taccagctcg gtatcgagaa  1500
gctgttggat cctgaggacg tagacacgac ctaccccgat aaaaagagca tcctgatgta  1560
tatcacttct ctgtttcagg tgcttcctca acaggtgtcc attgaagcca tccaagaggt  1620
cgaaatgctg cccaggcccc ctaaggtgac aaaagaagag catttccagc tgcatcacca  1680
gatgcattac agtcaacaga ttaccgtcag cttggctcag ggatatgagc gcacgtcctc  1740
tcctaagccc agatttaagt cctacgcata tacccaggct gcctacgtga ccacttccga  1800
cccaactagg agcccctttc cctcccaaca cctggaggcc cctgaggaca aaagcttcgg  1860
atctagtctg atggagtccg aggtgaatct ggatcggtac caaactgctc tggaggaagt  1920
gctgtcctgg cttctgtccg ctgaagacac cctgcaggcg caaggtgaga tttctaacga  1980
cgtcgaggtc gtgaaggatc agttccacac tcatgagggc tacatgatgg acttgacagc  2040
tcaccaggga agagttggta acatcctgca gcttggctcc aagttgattg gcacgggaaa  2100
gcttagcgag gacgaggaaa ccgaggtaca ggagcagatg aacttgctga attcccgctg  2160
ggagtgcctg agagttgcgt ccatggaaaa gcagtcaaac cttcacagag tgctgatgga  2220
ccttcagaac cagaagctga aggagctgaa cgattggctg acaaagaccg aggaacgcac  2280
aagaaaaatg gaagaggaac ctctgggacc tgatctggag gatctgaagc gccaggtcca  2340
acagcataag gtgctgcagg aggatttgga gcaggagcag gtgcgggtca acagcctgac  2400
acatatggtg gttgtggtcg atgagtcctc tggcgatcat gctaccgcag cgctggaaga  2460
gcagctgaag gtgctggggg atcgctgggc caacatttgc agatggacag aagaccggtg  2520
ggtcctgctt caagatatcc tgctcaagtg gcagcgcctg actgaagagc agtgcctgtt  2580
ctcagcttgg ttgagcgaaa aagaggacgc agttaacaag atccatacca caggcttcaa  2640
ggatcagaat gagatgctga gctcactgca gaagctggct gtgctgaagg ccgacttgga  2700
gaagaaaaag cagtccatgg gcaaactgta tagcctgaag caggacctgc tcagcaccct  2760
gaagaacaaa agcgttacgc agaaaactga ggcctggttg gacaactttg ctcgctgctg  2820
ggataacctt gtgcagaagc tggaaaagtc aaccgcacag atctcccagg ctgtgaccac  2880
tacgcagcct agcttgaccc agacaaccgt tatggaaacc gtgacaaccg tgacaacgag  2940
agagcaaatc ctggttaagc atgcccagga ggaactgccg ccaccccccgc ctcagaagaa  3000
acggcagatt acggtggaca gcgagatccg caagaggctg gacgtcgaca tcactgagct  3060
ccactcatgg atcacgcgga gtgaggccgt gctgcagtct cccgagttcg ctattttccg  3120
caaggaggga aacttctctg acttgaaaga gaaggtgaat gccatcgagc gtgaaaaggc  3180
agaaaagttc agaaagctgc aggacgcctc tcgctctgcg caggccctgg tggagcagat  3240
ggtcaacgag ggtgttaacg ctgacagcat caaacaggca agcgaacagc tgaactccag  3300
atggatcgaa ttttgccaac tgctctccga acgcctcaac tggttggagt accagaacaa  3360
tattatcgct ttttacaacc agctgcagca actggagcag atgacaacta ccgccgaaaa  3420
ctggctgaaa attcagccaa ccacaccgtc cgagccaact gcgatcaagt ctcagctgaa  3480
gatctgcaag gacgaagtga accgtcttag cgacttgcaa ccccagattg aacggctcaa  3540
gattcagtct attgctctga aggagaaggg tcagggtccg atgttcctgg atgcagattt  3600
tgtcgcattt accaatcact tcaaacaggt gtttagtgac gtccaggcgc gcgagaaaga  3660
gctgcagact atttttgaca ccctgcctcc catgaggtac caggagacaa tgagtgccat  3720
tcgcacctgg gtgcaacagt ccgagacgaa attgtcaatc ccacagctgt ccgtgacaga  3780
ctacgagatt atggagcaac ggttggggga gctgcaggct cttcagagtt ccctgcagga  3840
gcaacagagc ggactgtact atctttccac taccgtgaag gaaatgagta agaaagcccc  3900
ttccgagatc agccgcaaat accagtctga attcgaagag atcgagggac gctggaaaaa  3960
gctgtcaagc cagctggtcg agcactgtca gaagctggaa gagcagatga acaagctgcg  4020
taaaatccag aaccatattc agaccctcaa gaaatggatg gcagaagttg acgtgtttct  4080
gaaggaagag tggcctgccc tcggcgatag cgaaatcctt aagaaacaac tcaagcagtg  4140
ccgcctcctg gtgtccgata ttcagacaat ccagccttcc ctgaacagcg ttaatgaggg  4200
cggacagaaa attaaaaacg aggccgaacc cgagttcgct tctcgcctgg agactgaact  4260
gaaggagctg aatacccagt gggaccatat gtgtcaacag gtctacgcac gcaaagaggc  4320
actgaagggc ggtctggaga agactgtctc actccagaag gacctgagcg agatgcacga  4380
gtggatgacc caggccgaag aggaatacct ggagcgtgat tttgagtata agaccccaga  4440
cgaactccag aaagccgttg aagagatgaa gagggctaag gaggaagccc aacagaagga  4500
ggcgaaagtg aagctcctga cagagtccgt gaactccgtc atcgctcaag ctcctcccgt  4560
ggctcaggag gccctcaaga aagagctgga aactctgacc acaaattacc agtggttgtg  4620
tacccgcttg aacggtaagt gcaagaccct ggaagaggtg tgggcctgct ggcacgagct  4680
cctgtcctat cttgagaagg cgaacaaatg gctgaacgaa gtggaattca agttgaaaac  4740
```

```
aactgagaac attccgggag gcgctgagga aatctctgag gtgctggact ctctggaaaa  4800
tctgatgcgt cattctgaag acaatcctaa ccagatcagg attctggcac agaccctcac  4860
tgacggaggc gttatggacg aacttatcaa cgaggaactg gagacattca attcccgttg  4920
gcgtgagctg cacgaagagg ccgtgcgccg tcagaagttg ctggaacagt ctatccagtc  4980
cgcccaggag acagagaaat ctctccacct gatccaggag agtctgacgt ttatcgataa  5040
gcagctggct gcctacatcg ccgacaaggt ggacgctgcc cagatgcccc aagaggctca  5100
gaagatccag tccgacctga cgtctcatga aatcagcctg gaagagatga aaaagcacaa  5160
ccagggcaaa gaggctgccc agcgcgtcct ctcccagatt gacgtggctc agaaaaagtt  5220
gcaggacgtg agcatgaagt ttaggctgtt ccagaaaccc gccaacttcg aacagagact  5280
gcaggagtct aagatgatcc tggatgaggt caagatgcac ctccctgctc tggaaacaaa  5340
atctgtggag caggaggtcg tgcagtcaca actgaaccat tgtgtgaacc tctacaagtc  5400
tctcagcgag gtgaagtccg aggtcgagat ggtgatcaag accggacgcc agattgtgca  5460
gaaaaagcag acagagaacc caaaggagct ggacgaacgg gtgaccgccc tgaagctcca  5520
ctacaacgag ttgggtgcca aagtcactga aagaaagcaa cagctggaga agtgtctgaa  5580
gctgagccgc aagatgcgca aagaaatgaa cgtcttgacc gagtggttgg cggccaccga  5640
catggagctg accaagagat ccgctgtgga gggcatgccc tccaaccttg actcagaggt  5700
ggcctggggc aaggccacac agaaggagat cgaaaaacag aaggtgcatc ttaaatcaat  5760
cactgaggtg ggcgaagctc tgaagacagt gctgggcaag aaagagacac ttgtagagga  5820
caagctctcc cttctgaata gcaattggat cgccgtaact agtcgcgcgg aggaatggct  5880
gaacctcctg ttggaatacc agaaacacat ggaaaccttc gatcagaacg tggaccatat  5940
taccaagtgg attatccagg ctgacactct cctggacgag tctgagaaaa agaaacccca  6000
gcaaaaggaa gatgtgctga agcgcctgaa ggcggaattg aacgacatcc gcccgaaggt  6060
tgattccacc cgcgaccaag cggccaacct tatggctaac cgcggggacc attgcagaaa  6120
actggtggaa ccgcagatct ctgagctgaa ccacagattc gccgcgattt ctcacagaat  6180
taagactggc aaggcctcca tccctctgaa agagctggag cagttcaact ctgatattca  6240
gaagcttctg gagcccctgg aggcagaaat ccaacagggc gtcaacctga aagaggaaga  6300
ctttaataag gacatgaatg aggataacga aggtaccgtc aaggagctcc tgcagagggg  6360
cgacaatctg cagcaaagaa tcactgacga acgtaagcgc gaagagatta agatcaagca  6420
acagctgttg cagactaagc acaacgccct gaaggatctg aggtcccagc gcaggaaaaa  6480
ggccctggag atttcccacc agtggtacca gtacaagcgc caggccgatg accttctgaa  6540
gtgcctcgac gatatcgaga aaaagctggc ctcactgccc gagccccgcg acgagcgcaa  6600
gatcaaggag attgaccgtg agctccagaa gaaaaaggag gaactgaacg cggtgcgcag  6660
acaggccgag ggcctctccg aggacggcgc tgcgatggct gttgagccca ctcagatcca  6720
actgagcaag cggtggagag agatcgagtc taagttcgcg caatttaggc gcctcaactt  6780
cgcccagatt cacacggtcc gtgaggaaac gatgatggtg atgacagagg atatgccact  6840
ggaaatcagc tacgtgccca gtacatatct caccgaaatc acccatgtgt cccaggctct  6900
cctggaggtg gaacagttgc tcaacgctcc cgacttgtgc gctaaggact tcgaggacct  6960
gttcaagcag gaagagagcc tgaaaaacat taaggactcc ctgcaacagt caagcggccg  7020
catcgatatc attcattcta agaaaaccgc tgccctgcag tctgcaaccc ccgtagagcg  7080
cgtcaaactg caggaagctc tcagccaact ggatttccag tgggagaagg tgaacaagat  7140
gtataaggat cgtcagggcc ggttcgaccg ctctgtggag aagtggcgcc gtttccacta  7200
cgatatcaag attttcaatc aatggttgac cgaggcagag cagttcctca gaaagacaca  7260
gatccctgaa aattgggagc atgccaagta caagtggtat ctgaaggagc tgcaggacgg  7320
gatcggacaa cgtcagaccg tggtccgcac cctgaacgca accggcgagg aaattatcca  7380
acagtctagc aagacagatg ctagcatcct ccaggagaag ctcggaagcc tcaaccttcg  7440
ctggcaggag gtgtgcaagc agctgtcaga caggaagaaa cgcctggagg aacagaagaa  7500
catcctttca gagttccaga gagatctgaa cgaattcgtg ctttggcttg aagaggccga  7560
taacatcgca agcatcccac tggagcctgg taaggaacag caattgaagg agaagctgga  7620
gcaggtaaag ctgctcgtgg aagagctgcc tctgaggcag ggaattctca agcagctcaa  7680
cgagactggg ggcccggttt tggtgagcgc cccaattagc ccagaagagc aggacaagtt  7740
ggagaacaag ctgaagcaga ccaacctgca gtggatcaag gtgtcccgcg cactgcccga  7800
aaagcaggga gagattgagg cccagatcaa ggatctggga cagctggaga aaaagctgga  7860
agacctggag gaacagctga accatttgct cctgtggttg tcccccatca gaaatcagct  7920
ggaaatctac aaccaaccga accaggaagg tccgtttgat gttaaggaaa ccgagatcgc  7980
tgtgcaggcg aagcagcctg acgtagaaga gatcctgtca aagggacagc acctctacaa  8040
ggagaagccc gccacccagc cagtcaagcg gaagctcgaa gacctgtcca gcgagtggaa  8100
agccgtcaac cgcctcctgc aagagctgcg tgccaagcaa ccggacctgg cgccaggtct  8160
gactaccatt ggcgcaagtc ctacccagac tgtcaccctg gtgacccaac ccgttgtgac  8220
aaaggaaacc gccatcagca agctggagat gcctagctct ttgatgctgg aggttcccgc  8280
cctcgccgac ttcaaccgtg cttggacaga actgaccgac tggctgtccc tcctggacca  8340
agtgatcaag agccagcgcg tgatggtggg tgatcttgag gatattaacg aaatgattat  8400
caagcagaag gccaccatgc aggacttgga gcagaggcgc ccccagttgg aggaactgat  8460
caccgccgcg cagaatctga aaaacaaaac ttccaatcag gaagcgagaa ccatcattac  8520
agacagaatt gagagaattc aaaaccagtg ggacgaagtg caagaacacc tccagaaccg  8580
gcgtcaacag ctgaacgaga tgctgaagga ttccactcaa tggctggaag ctaaggaaga  8640
ggccgagcag gtccttggac aggcacgcgc taagctggag tcctggaaag aaggccccta  8700
tacagtggac gcaattcaaa agaaaatcac cgagacgaag caactggcca aggacctgag  8760
acagtggcaa accaacgttg atgtggctaa tgacctggcc ttgaagctcc tgcgtgacta  8820
ctccgcggat gacactagaa aggtgcacat gatcaccgag aatatcaacg ctagctggcg  8880
ctccatccat aagcgtgtga gtgagcgcga agccgctctg gaggaaaccc atcgcctgct  8940
tcaacagttt cctttggacc tggaaaagtt cctggcctgg ctcacagaag ccgagacaac  9000
cgccaacgtg ctgcaggacg ccacccgtaa ggagcgcttg ctggaggata gtaagggggt  9060
gaaggagttg atgaagcagt ggcaagatct gcagggggaa atcgaggcac ataccgacgt  9120
ctatcataac ctggatgaga attcccagaa aatcctgcgc agcttggagg gcagtgatga  9180
cgcggtgctt ctgcaacggc gcttggacaa catgaacttc aagtggtccg agttgcgtaa  9240
aaagagtctg aacattcgct cccacctgga ggcttctagt gaccagtgga agcgcctgca  9300
cctgagcctg caagaactgc tcgtgtggct gcaactgaag gatgacgagt tgagtcgtca  9360
ggcccctatc ggaggtgact ttccggctgt ccagaaacag aacgacgtgc atagggcatt  9420
taagcgcgag ttgaagacaa aggagccagt cattatgtcc acgctggaaa ccgtgcgcat  9480
```

```
tttcctgact gagcagcctc tggaggggct ggagaagctg taccaggagc ctcgcgagtt  9540
gccccctgaa gagcgtgccc agaatgtgac ccgcctgttg cgtaagcagg ccgaggaagt  9600
gaacaccgag tgggagaagc tgaacctgca ttccgcggat tggcagagga agattgacga  9660
gacgctggag aggctccgtg agttgcagga ggcaaccgac gaactggacc tcaagctgcg  9720
tcaagcagag gtgatcaagg ggagttggca gccggtcggc gatttgctga tcgactccct  9780
gcaggatcac ctggaaaagg ttaaagcttt gcgcggggaa attgccccgc tgaaggagaa  9840
cgtgagccac gttaacgatc tggccagaca gctgaccact ctgggtatcc agctgagccc  9900
gtacaatctg agcaccctcg aagacttgaa tacgagatgg aaactcctgc aggtggcagt  9960
ggaggacagg gtgcgccaat tgcacgaggc ccaccgggac tttggaccgg ccagccagca  10020
tttcctcagt acctctgttc agggcccgtg ggagcgggcc atctccccca acaaggtccc  10080
ctattacatc aaccatgaaa cccagactac ctgttgggac caccctaaaa tgactgagtt  10140
gtatcaatct ctggccgact tgaataacgt gcgcttctca gcctacagga ctgcaatgaa  10200
actcagacgc ctccaaaagg ccctttgtct ggacttgctg tcccttagcg ctgcctgtga  10260
tgctctggat cagcacaatt tgaaacaaaa cgaccagccg atggacatcc tccagattat  10320
caactgcctg actaccatct acgacagact ggaacaggag cataataacc tggtgaacgt  10380
cccccctgtgc gtggacatgt gcctgaactg gctgctcaat gtgtatgaca cgggtagaac  10440
aggacggatc agggtcctgt cctttaagac cggtatcatt tctctgtgta aggcacatct  10500
ggaggacaag taccgctacc tgtttaagca ggtcgccagc tccactggct tctgcgatca  10560
aaggcggctg ggtctgctcc tgcacgactc cattcagatc ccgagacagt tgggtgaagt  10620
ggcgtccttc ggcggttcta atatcgagcc tagcgtccgc agctgtttcc aattcgccaa  10680
taacaagccg gagatcgaag cggccctttt cctggactgg atgcgtctgg aacctcagag  10740
catggtttgg cttccggtgc ttcatcgcgt ggccgctgcc gaaaccgcta aacatcaggc  10800
caaatgtaac atctgtaagg aatgcccgat tatcggtttc cggtaccgta gcctcaagca  10860
tttcaactat gatatttgtc aatcttgctt ctttagcgga cgggtggcca aaggccacaa  10920
aatgcactac ccgatggtcg agtattgcac tcctacaacc tccggcgagg acgtgcgcga  10980
ttttgccaaa gtgctgaaaa acaagtttag aaccaagcgt tactttgcca agcatccacg  11040
tatgggctac ctgcctgtcc agaccgttct ggaaggtgat aacatggaga cacccgtgac  11100
tttgattaac ttttggccag tagactctgc tccggcaagc tcccctcagc tctcccacga  11160
tgacactcac agccgtatcg agcactacgc ctctcgcctg gctgagatgg agaactctaa  11220
cggttcatac ctgaatgaca gtatctcccc aaacgagagt atcgatgacg aacatctgct  11280
cattcagcat tactgtcaat ccttgaatca ggacagcccc ctgtcccagc cacggtcccc  11340
ggcccagatc ctgatttcac tggagtccga agagagaggg gaactggaaa ggatcctcgc  11400
tgacctggaa gaggaaaacc ggaacctgca ggctgaatac gaccgcttga agcagcaaca  11460
cgagcacaag ggcttgagcc cgttgccaag ccctccggag atgatgccaa ctagccctca  11520
gagcccacgg gatgccgagc tcatcgctga agctaagttg ctgagacagc acaagggacg  11580
tctggaggcc cgcatgcaga tcctggagga tcataataaa cagttggaga gccaactgca  11640
taggctgcgc cagctcctgg agcagccaca ggccgaggct aaggtcaacg gaactaccgt  11700
ttccagcccg tccacatctc tgcagcgctc agatagttcc cagcctatgt tgctgagagt  11760
ggttggatct cagacctccg actcaatggg cgaagaggac ttgctgtctc ccccacagga  11820
cactagcaca ggactcgaag aggtgatgga acagctcaat aactcttttc cttctagtcg  11880
gggtcgcaat acccctggaa agcccatgcg cgaagacacc atgtaatagc tcgagaatca  11940
acctctggat tacaaaattt gtgaaagatt gactggtatt cttaactatg ttgctccttt  12000
tacgctatgt ggatacgctg ctttaatgcc tttgtatcat gctattgctt cccgtatggc  12060
tttcattttc tcctccttgt ataaatcctg gttgctgtct ctttatgagg agttgtggcc  12120
cgttgtcagg caacgtggcg tggtgtgcac tgtgtttgct gacgcaaccc ccactggttg  12180
gggcattgcc accacctgtc agctcctttc cgggactttc gctttccccc tccctattgc  12240
cacggcggaa ctcatcgccg cctgccttgc ccgctgctgg acaggggctc ggctgttggg  12300
cactgacaat tccgtggggt gtgccttcta gttgccagcc atctgttgtt tgcccctccc  12360
ccgtgccttc cttgaccctg gaaggtgcca ctcccactgt cctttcctaa taaaatgagg  12420
aaattgcatc gcattgtctg agtaggtgtc attctattct ggggggtggg gtggggcagg  12480
acagcaaggg ggaggattgg gaagacaata gcaggcatgc tggggatgcg gtgggctcta  12540
tgggaagatg tctactgagc tgtgcgatcc ctgctgggga ctttccgctg gggactttcc  12600
gctggggact ttccgccttc agctaaggaa gctaccaata tttagaggta cattttgttc  12660
tagaacaaaa tgtaccggta cattttgttc tggtacattt tgttct                12706

SEQ ID NO: 22          moltype = DNA  length = 12706
FEATURE                Location/Qualifiers
source                 1..12706
                       mol_type = other DNA
                       note = CBA-hBGi-DMD-3-WPRE3-DTS
                       organism = synthetic construct
SEQUENCE: 22
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttaatt attttgtgca gcgatggggg cggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tcgtaagtac tagcagctac aatccagcta ccattctgct tttattttat  720
ggttgggata aggctggatt attctgagtc caagctaggc ccttttgcta atcatgttca  780
tacctcttat cttcctccca cagctcctgg gcaacgtgct ggtctgtgtg ctggcccatc  840
actttggcaa agaattgcga tcgccaccat gctgtggtgg gaagaggtgg aggactgtta  900
cgagagagag gacgtgcaga agaagacatt caccaagtgg gtgaacgctc agttcagcaa  960
gttcggcaag cagcacatcg agaacctgtt tagcgatcta caagatggca gaagactgct  1020
```

```
ggacctgctg gagggcctga ccgggcagaa gctgcccaaa gaaaaggggt ctacaagagt  1080
gcacgccctg aacaacgtga acaaggccct gagagtgctg cagaacaaca acgtggacct  1140
ggtgaacatc ggcagcaccg acatcgtgga cggcaaccac aagctgaccc tgggcctgat  1200
ctggaacatc atcctgcact ggcaagtgaa gaacgtgatg aagaacatca tggccggcct  1260
gcagcagacc aacagcgaga agatcctgct gagctgggtg agacagagca caagaaacta  1320
cccccaagtg aacgtgatca acttcaccac aagctggagc gacggcctgg ccctgaacgc  1380
cctgatccac agccacagac ccgacctgtt cgactggaac agcgtggtgt gtcagcagag  1440
cgccacacag agactggagc acgccttcaa catcgctaga tatcagctgg gcatcgagaa  1500
gttactggac cccgaagatg tggacaccac ctaccccgac aagaagagca tcctgatgta  1560
catcacaagc ctgttccaag tgctgcctca gcaagtgagc atcgaggcca tccaagaagt  1620
cgagatgctg cctagacccc ccaaggtgac caaggaggag cactttcagc tgcaccatca  1680
gatgcactac tctcagcaga tcacagtcag cttggcacaa ggctacgaga gaacaagcag  1740
ccccaagcct agattcaaga gctacgccta cacccaagcc gcctacgtga ccacaagtga  1800
ccccacaaga agccccttcc cttctcagca cctggaggcc cccgaggaca agagcttcgg  1860
cagcagcctg atggagagcg aggtgaacct ggacagatat cagaccgcgt tagaagaagt  1920
gttgagctgg ctgctgagcg ccgaggacac cctgcaagcc caaggcgaga tcagcaacga  1980
tgtggaggtg gtgaaggatc agttccacac ccacgagggc tacatgatgg acctgaccgc  2040
ccaccaaggc agagtgggca acatcctgca gctgggcagc aagctgatcg gcaccggcaa  2100
gctgagcgag gacgaggaaa ccgaggttca agagcaaatg aacctgctaa acagcagatg  2160
ggagtgcctg agagtggcta gcatggaaaa gcagagtaac ctgcacagag tgctgatgga  2220
cctgcagaat cagaaattga aagaacttaa tgattggctg accaagaccg aggagagaac  2280
aagaaagatg gaggaggagc ccctgggccc cgacctggag gacctgaaga gacaagtgca  2340
gcagcacaag gtgctgcaag aggacctgga gcaagagcaa gtgagagtga actctctgac  2400
acacatggtg gtggtagtgg acgagagcag cggcgatcac gctaccgcgg cgctggaaga  2460
gcagctgaaa gtgctgggcg acagatgggc caacatctgc agatggaccg aggacagatg  2520
ggtgctgctg caagacatcc tgctgaagtg gcagagactg accgaggagc agtgcctgtt  2580
cagcgcctgg ctgagcgaga aggaagacgc tgtgaacaag atccacacca ccggcttcaa  2640
ggatcagaac gagatgctga gctccctcca aaagctcgca gtgctgaagg ccgacctgga  2700
aaagaaaaaa cagtcgatgg gcaagctgta cagcctgaag caagacctgc tgagcaccct  2760
gaagaacaag agcgtgacac agaagaccga ggcctggctg gacaacttcg ctagatgctg  2820
ggacaacctg gtacagaagt tagagaagtc taccgctcag atcagccaag ccgtaaccac  2880
cacacaacct agcctgactc agaccaccgt gatggaaacc gtgaccaccg tgacaacccg  2940
tgagcagatc ctggtgaagc acgcccaaga ggagctgccc cccccccccc ctcagaagaa  3000
gagacagatc accgtggact cagagattcg caagagactg gacgtggaca tcaccgagct  3060
gcacagctgg atcacaagaa gcgaggccgt gctgcagagc cctgagttcg cgatctttag  3120
aaaggagggc aacttcagcg acttgaagga gaaagtgaac gccatcgaga gagagaaggc  3180
cgagaagttc agaaagttgc aagacgcctc aagaagcgcc caagccctgg tggagcagat  3240
ggttaacgaa ggcgtgaatg ccgacagcat caagcaagct agcgagcagc tgaatagccg  3300
gtggattgaa ttctgtcagc tgctgagcga gagattaaac tggctggagt atcagaacaa  3360
catcatcgcc ttctacaatc agctgcagca actagaacaa atgaccacca ccgccgagaa  3420
ctggctaaag attcagccca ccacccctag cgagcccacc gccatcaaat ctcagctgaa  3480
aatttgcaag gacgaagtga acagactgtc ggacctgcag cctcaaatcg aaagactgaa  3540
aattcagagc atcgcactta aggagaaggg ccaaggaccc atgttcctgg acgccgactt  3600
cgtggccttc accaaccact tcaagcaagt gttcagcgac gtgcaagcta gagagaagga  3660
gctgcagacc atcttcgaca ccctgccccc catgagatac caagaaacca tgagcgccat  3720
cagaacctgg gtgcagcaga gcgaaaccaa gctgagcatc cctcagctga gcgtgaccga  3780
ctacgagatc atggagcaaa gactgggaga gctgcaagcc ctgcagagca gcctgcaaga  3840
gcagcagagc ggcctgtact acctgagcac caccgtgaag gagatgtcga agaaagcccc  3900
gtcggagatc agcagaaagt atcagagcga gttcgaggag atcgagggca gatggaagaa  3960
gctgagcagc caactggtgg aacactgtca gaaattagaa gaacagatga acaagctgag  4020
aaagattcag aaccacattc agaccctgaa gaagtggatg gccgaggtgg acgtgttcct  4080
gaaagaggag tggcccgccc tgggcgattc cgaaatctta aaaaagcagc tgaagcagtg  4140
cagactgctg gtgtcagata tccaaaccat tcaaccaagc ctgaacagcg tgaacgaagg  4200
cgggcagaag atcaagaacg aggccgagcc cgagttcgct agcagactgg aaaccgagct  4260
gaaggagctg aatacacagt gggaccacat gtgtcagcaa gtgtacgcta gaaaggaagc  4320
gctgaagggc gggctggaga agaccgttag cctgcaaaag gatctgagcg agatgcacga  4380
gtggatgacc caagccgagg aggagtacct ggagagagac ttcgagtaca agacccccga  4440
cgagctgcag aaggccgtcg aggaaatgaa gagagcgaag gaggaggctc agcagaagga  4500
agccaaggtg aagctgctga ctgaatctgt caacagtgtg atagctcaag cacccccgt  4560
tgcccaagag gcactaaaga aggagctgga aactctgacc accaactatc agtggctgtg  4620
cacaagactg aacggcaagt gcaagaccct ggaggaagtg tgggcctgct ggcacgagct  4680
gctgagctac ctggagaagg ccaacaagtg gctgaacgag gtggagttca agctgaagac  4740
caccgagaac atccccggcg gcgccgagga gatcagcgag gtgctggaca gcctggagaa  4800
cctgatgaga cacagcgagg acaaccccaa tcagatcaga atcctggctc agaccctgac  4860
cgacggcggc gtgatggacg agctgatcaa cgaggagctg gaaaccttta actctagatg  4920
gcgagaactg cacgaggagg ccgtgagaag acagaagctg ctggagcaaa gcattcagag  4980
cgcccaagaa accgagaaga gcctgcacct gatccaagag agcctgacct tcatcgacaa  5040
gcagctggcc gcctacatcg ccgacaaggt ggacgccgct cagatgccac aagaggctca  5100
gaagattcag tccgatctga caagccacga gatcagcctg gaggagatga aaaaacacaa  5160
ccaaggcaag gaggccgctc agagagtgct gtctcagatc gacgtggctc agaagaagct  5220
gcaagacgtg agcatgaagt tcagactgtt tcagaagccc gccaacttcg agcagcgact  5280
gcaagagagc aagatgatcc tggacgaggt gaagatgcac ctgcccgccc tggaaaccaa  5340
gagcgtggag caagaggtgg tgcagtctca gttgaaccac tgcgtgaacc tgtacaagag  5400
cctgtcggag gtcaagagtg aggtcgagat ggtgatcaaa actgggagac agatcgtgca  5460
aaaaaagcag accgagaacc ccaaggagct ggacgagcgt gttaccgccc tgaagctgca  5520
ctacaacgag ctgggcgcca aggtgaccga gagaaagcag cagctggaga agtgcctgaa  5580
gctgagcaga aagatgagaa aggagatgaa cgtgctgacc gagtggctgg ccgccaccga  5640
catggagctg accaagagaa gcgccgtgga gggcatgcct agcaacctgg acagcgaggt  5700
ggcctggggc aaggccacac agaaggagat cgagaagcag aaggtgcacc tgaagagcat  5760
```

caccgaggtg ggcgaggccc tgaagaccgt gctgggcaag aaggaaaccc tggtggagga 5820
caagctgagc ctgctgaact cgaactggat cgccgtgaca agcagagccg aggagtggct 5880
gaacctgctg ttagagtacc aaaaacacat ggaaaccttc gatcagaacg tggaccacat 5940
caccaagtgg atcatccaag ccgacaccct gctggacgaa agcgaaaaga agaagccgca 6000
acaaaaggag gatgtgctga agagactgaa ggccgaactg aacgatatca gacccaaggt 6060
ggacagcaca cgggaccaag ccgccaacct gatggccaac agaggcgacc actgcagaaa 6120
actggtggag cctcagatca gcgagctgaa ccacagattc gccgccatca gccacagaat 6180
caaaaccggc aaagcgagca tcccccttgaa ggaactggag caatttaaca gcgacatcca 6240
aaaattgctc gaaccactgg aggccgagat tcagcaaggc gtgaacctga aggaagagga 6300
cttcaacaag gacatgaacg aggacaacga gggcaccgtg aaagaactgc tgcagagagg 6360
cgacaacctg cagcagagaa tcaccgacga gagaaagaga gaggagatca agatcaagca 6420
gcagctgctg cagactaagc acaacgccct gaaggatctg agatctcaga ggagaaaaaa 6480
ggctctggaa atttcacatc agtggtatca gtacaagaga caagcagacg acctgctgaa 6540
gtgcctggac gacatcgaga agaagttagc tagcctgccc gagcctagag acgagagaaa 6600
gatcaaggag atcgacagag agttacaaaa gaagaaggag gagctgaatg cggtaagaag 6660
acaagcggaa ggcctgtccg aggacggcgc agccatggcc gtggagccca cacagattca 6720
gctcagcaag agatggagag agatcgagag caagttcgct cagttcagaa gactgaactt 6780
cgctcagatc cacaccgtga gagaggaaac catgatggtg atgaccgagg acatgcccct 6840
ggagatctca tacgttccta gcacctacct gaccgagatc acccacgtga gccaagccct 6900
gctggaggtg gagcagctgc tgaacgcccc cgacctgtgc gccaaggact tcgaggacct 6960
gttcaaacaa gaggagagcc tgaagaacat caaggacagc ctgcagcaaa gtagcggcag 7020
aatcgacatc atccacagca agaagaccgc cgccctgcag agcgccaccc ccgtggagag 7080
agtgaagctt caagaggccc tttcgcagct ggattttcag tgggagaagg tgaacaaaat 7140
gtacaaggac agacaaggca gattcgacag aagcgtggag aagtggagaa gattccacta 7200
cgacatcaag atcttcaatc agtggctgac cgaggcagag cagttcctga gaaagacaca 7260
gatccccgag aactgggagc acgccaagta caagtggtac ctgaaggagc tgcaagacgg 7320
catcgggcag agacagaccg tggtgagaac cctgaacgcc accggcgagg agatcatcca 7380
acaaagctcc aaaaccgacg ctagcatcct gcaagagaaa ctgggcagcc tgaacctgag 7440
atggcaagag gtgtgcaagc agctgagcga ccgcaaaaaa cggttagagg agcagaagaa 7500
catcctgagc gagtttcagc gggacctgaa cgagttcgtg ctgtggctgg aggaggccga 7560
taacatcgct agcatccccc tggagcccgg caaggagcag cagttaaaag aaaaacttga 7620
gcaagtgaag ctgctggtgg aggagctgcc cctgagacaa ggcatcctga agcagctgaa 7680
cgagactggc ggcccccgtgc tggtgagcgc ccccatcagc cccgaggagc aagacaagct 7740
ggagaacaag ctgaagcaga ccaacctgca gtggatcaag gtgagcagag ccctgcccga 7800
gaagcaaggc gaaatcgagg cccaaataaa ggacctgggg cagctggaga agaaactcga 7860
agacttggaa gaacaactca accacttgct gctgtggctg agccccatca gaaatcagct 7920
ggagatctac aatcagccca accaagaggg gccattcgac gtgaaggaaa ccgagatcgc 7980
cgtgcaagcc aagcagcccg atgtggagga gatcctgagc aaggggcagc acctgtacaa 8040
ggagaagccc gccacacagc ccgtcaagcg taaactagag gatctttcct ctgagtggaa 8100
ggccgtgaac cgtctgctac aagagctgcg ggctaagcaa cccgacttag cgcccggcct 8160
gaccaccatc ggtgcaagcc ccacgcagac cgtgaccctg gtgacccaac ccgtggtgac 8220
caaggaaacc gccatcagca agctggagat gcctagcagc ctgatgctgg aggtgcccgc 8280
cctggccgac ttcaacagag cctggaccga gctgaccgac tggctgagcc tgctggacca 8340
agtgatcaag tctcagagag tgatggtggg cgatctggag gacatcaatg agatgatcat 8400
caagcagaag gccaccatgc aagacctgga gcagagaaga cctcagctgg aggagctgat 8460
caccgccgct cagaacctga aaaacaagac gagcaaccaa gaggctagaa ccatcatcac 8520
cgacagaatc gagagaattc agaatcagtg ggacgaggtg caagagcacc tgcagaacag 8580
aagacagcaa ctaaacgaaa tgctcaagga cagcacacag tggctggagg ccaaggagga 8640
ggcggagcaa gtgttgggcc aagctagagc caagctggag agctggaagg agggacccta 8700
caccgtggac gccattcaga agaagatcac cgaaaccaag cagctggcca aggacctgcg 8760
acagtggcag accaacgtgg acgtggccaa cgatcttgcc ctgaagctgc tgcgcgacta 8820
tagcgccgac gacacaagaa aggtgcacat gatcaccgag aacatcaacg ctagctggcg 8880
tagcatccac aagagagtga gcgagagaga ggcggctttg gaggaaaccc atagactgct 8940
gcagcagttt ccccctggacc tggagaagtt cctggcctgg ctgaccgaag ccgaaacaac 9000
cgccaacgtg ctgcaagacg ccacaagaaa ggagagactg ctggaggaca gcaagggcgt 9060
gaaggagctg atgaagcagt ggcaagacct gcaaggcgag atcgaagcgc acaccgacgt 9120
gtaccacaac ctggacgaga actctcagaa gatcctgaga agcctggagg gcagcgacga 9180
cgccgtgctg ttacagagaa ggctggacaa catgaacttc aagtggagcg agctgagaaa 9240
gaagagcctg aacatcagaa gccacctgga ggctagcagc gatcagtgga agagactgca 9300
cctgagcctg caagagctgc tggtctggct tcagttgaag gacgatgagc tgagcagaca 9360
agcccccatc ggcggcgact tccccgccgt gcagaagcag aacgacgtgc atagagcctt 9420
caagagagag ctgaagacca aggagcccgt gatcatgagc accctggaaa cggtgagaat 9480
cttcctgacc gagcagcccc tggagggcct ggagaagctg taccaagagc ctagagagct 9540
gccccccgag gagagagctc agaacgtgac aagactgctg agaaagcaag ccgaagaggt 9600
gaacaccgag tgggagaagc tgaacctgca cagcgccgac tggcagagaa agatcgacga 9660
aaccctggag agactgagag aattgcaaga ggcgaccgac gagctggacc tgaagctgag 9720
acaagccgag gtcatcaagg gcagctggca gcccgtgggc gatctattaa ttgactctct 9780
acaagaccac ctggagaaag tgaaggccct gagaggcgag atcgcccccc tgaaggagaa 9840
cgtgagccac gtgaatgatc tggcacgtca gctgaccacc ctgggcatac aactgtcccc 9900
ctataacctg agcacactgg aggatttgaa tactagatgg aagctgctgc aagtggccgt 9960
ggaggacaga gtaagacaat tacatgaggc ccacagagac ttcggccccg cttctcagca 10020
cttcctgagc acaagcgtgc aaggcccctg ggagagagcc atttccccca acaaggtccc 10080
ctactacatc aaccacgaga cacagaccac ctgctgggac caccccaaga tgaccgagct 10140
gtatcagagc ctcgccgatc tgaacaatgt gagattcagc gcctacagaa ccgccatgaa 10200
gctgagaaga ctgcagaagg ccctgtgcct ggacttatta agcctgagcg ccgcctgcga 10260
cgccctggat cagcacaacc tgaagcaaaa cgaccaaccc atggacatcc tgcagatcat 10320
caactgcctc accaccatat acgacagact ggaacaagag cacaacaacc tggtgaacgt 10380
gcccctgtgc gtggacatgt gcctgaactg gctgctgaac gtgtacgaca ccggcagaac 10440
cggcagaatc agagtgctga gcttcaagac cggcatcatc agcctgtgca aggcccacct 10500

```
ggaggacaaa tacagatacc ttttcaaaca agtggctagc agcaccggct tctgcgacca  10560
aagaagactg ggtctgctgc tgcacgacag cattcagatc cctagacagc tgggcgaggt  10620
ggctagcttc ggcggcagca acatcgagcc tagcgtgaga agctgctttc agttcgccaa  10680
caacaagccc gagatagagg cagccctctt cttagactgg atgagactgg agcctcagag  10740
catggtatgg ctgccggtcc tgcacagagt ggccgccgcc gaaaccgcca agcaccaagc  10800
caagtgcaac atctgcaagg agtgccccat catcggcttc agatacagaa gcctgaagca  10860
cttcaactac gacatctgtc agagctgctt cttcagcggc agagtggcca agggccacaa  10920
gatgcactac cccatggtgg agtactgcac ccccaccaca agcggcgagg acgtgagaga  10980
cttcgccaag gtgttgaaga ataagtttag aaccaagaga tacttcgcca agcaccctag  11040
aatgggctac ctgcccgtgc agaccgtgct ggagggcgac aacatggaaa cccccgtgac  11100
cctgatcaac ttctggcccg tggacagcgc ccccgctagc agccctcagc tgagccacga  11160
cgacacccac agcagaatcg agcactacgc tagcagactg gccgagatgg agaacagcaa  11220
cggcagctac ctgaacgaca gcatcagccc gaatgagagc atcgacgacg agcacctgct  11280
gattcagcac tactgtcaga gcctgaacca agacagcccc ctgtctcagc ctagaagccc  11340
cgctcagatc ctgatcagcc tggagagcga ggagagaggc gagctggaga gaatcctagc  11400
agatctggag gaagagaaca gaaacctgca agccgagtat gaccgactga aacagcaaca  11460
tgagcacaaa ggcctgagcc cactgccctc ccccccgag atgatgccca caagccctca  11520
gagccctaga gacgccgagc tgatcgctga agcgaagtta cttagacaac acaagggcag  11580
actggaggct agaatgcaga tcctggagga ccacaacaag cagctggagt ctcagctgca  11640
cagactgagg cagctgctgg aacagcccca agccgaggcc aaagtgaacg gcaccaccgt  11700
gagcagtcct agcacaagcc tgcagagaag cgacagctct cagcccatgc tgctgagagt  11760
ggtgggctct cagacaagcg acagcatggg cgaggaggat ctgctgagtc cgccccaaga  11820
cacaagcacc ggcctggaag aggtgatgga gcaactgaac aatagcttcc ctagcagcag  11880
aggcagaaac accccccggca agcccatgag agaggacacc atgtgatgac tcgagaatca  11940
acctctggat tacaaaattt gtgaaagatt gactggtatt cttaactatg ttgctccttt  12000
tacgctatgt ggatacgctg ctttaatgcc tttgtatcat gctattgctt cccgtatggc  12060
tttcattttc tcctccttgt ataaatcctg gttgctgtct ctttatgagg agttgtggcc  12120
cgttgtcagg caacgtggcg tggtgtgcac tgtgtttgct gacgcaaccc ccactggttg  12180
gggcattgcc accacctgtc agctcctttc cgggactttc gctttccccc tccctattgc  12240
cacggcggaa ctcatcgccg cctgccttgc ccgctgctgg acaggggctc ggctgttggg  12300
cactgacaat tccgtggggt gtgccttcta gttgccagcc atctgttgtt tgcccctccc  12360
ccgtgccttc cttgaccctg gaaggtgcca ctcccactgt cctttcctaa taaaatgagg  12420
aaattgcatc gcattgtctg agtaggtgtc attctattct ggggggtggg gtggggcagg  12480
acagcaaggg ggaggattgg gaagacaata gcaggcatgc tggggatgcg gtgggctcta  12540
tgggaagatg tctactgagc tgtgcgatcc ctgctgggga ctttccgctg ggactttcc   12600
gctggggact ttccgccttc agctaaggaa gctaccaata tttagaggta catttttgttc  12660
tagaacaaaa tgtaccggta cattttgttc tggtacattt tgttct                 12706

SEQ ID NO: 23           moltype = DNA  length = 12706
FEATURE                 Location/Qualifiers
source                  1..12706
                        mol_type = other DNA
                        note = CBA-hBGi-DMD-4-WPRE3-DTS
                        organism = synthetic construct
SEQUENCE: 23
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta ttttttaatt attttgtgca gcgatggggg cggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tcgtaagtac tagcagctac aatccagcta ccattctgct tttattttat  720
ggttgggata aggctggatt attctgagtc caagctaggc ccttttgcta atcatgttca  780
tacctcttat cttcctccca cagctcctgg gcaacgtgct ggtctgtgtg ctggcccatc  840
actttggcaa agaattgcga tcgccaccat gctttggtgg gaagaagtcg aggactgcta  900
cgagcgcgag gacgtgcaga agaaaacctt caccaaatgg gtcaacgccc agttcagcaa  960
gttcggcaag cagcacatcg agaacctgtt cagcgacctg caggatggca gaaggctgct  1020
ggatctgctg gaaggcctga caggacagaa gctgcccaaa gagaagggca gcacaagagt  1080
gcacgccctg aacaacgtga acaaggccct gagagtgctg cagaacaaca acgtggacct  1140
ggtcaacatc ggcagcaccg acatcgtgga cggcaaccac aaactgaccc tgggcctgat  1200
ctggaacatc atcctgcact ggcaagtgaa gaacgtgatg aagaacatca tggccggcct  1260
gcagcagacc aacagcgaga agattctgct gagctgggtc cgacagagca cccggaatta  1320
ccctcaagtg aacgtgatca acttcaccac ctcttggagc gacggactgg ccctgaatgc  1380
cctgatccac agccacagac ctgacctgtt cgactggaac agcgtcgtgt gtcagcagag  1440
cgccacacag aggctggaac acgccttcaa tatcgccaga taccagctgg gcatcgagaa  1500
actgctggac cccgaggatg tggacaccac ctatcctgac aagaaatcca tcctcatgta  1560
catcaccagc ctgttccagg tgctgcccca gcaggtttcc atcgaggcca ttcaagaggt  1620
cgagatgctg cccagacctc ctaaagtgac caaagaggaa cacttccagc tgcaccacca  1680
gatgcactac tctcagcaga tcaccgtgtc tctggcccag ggctacgaga gaacaagcag  1740
ccccaagcct cggttcaaga gctacgccta tacacaggcc gcctacgtga ccaccagcga  1800
tcctacaaga agcccatttc ctagccagca tctggaagcc cctgaggaca agagctttgg  1860
cagcagcctg atggaaagcg aagtgaacct ggaccgctac cagacagccc tggaagaggt  1920
tctgagctgg ctgctgtctg ccgaggatac actgcaggct cagggcgaga tcagcaacga  1980
cgtggaagtg gtcaaggacc agtttcacac ccacgagggc tacatgatgg acctgacagc  2040
```

```
ccaccagggc agagtgggca atattctgca gctgggctcc aagctgatcg gcacaggcaa  2100
gctgagcgag gacgaagaga cagaggtgca agagcagatg aacctgctga acagcagatg  2160
ggagtgtctg agagtggcca gcatggaaaa gcagagcaac ctgcaccggg tgctgatgga  2220
tctccagaac cagaagctga aagagctgaa cgactggctg accaagaccg aggaacggac  2280
ccggaagatg gaagaggaac ctctgggacc cgacctggaa gatctgaaaa gacaggtgca  2340
gcagcataag gtgctgcaag aggacctcga acaagagcaa gtgcgcgtga acagcctgac  2400
acacatggtg gtggtcgtgg atgagagcag cggagatcat gccacagccg ctctggaaga  2460
acagctgaag gtgctgggag acagatgggc caatatctgc cggtggaccg aggatagatg  2520
ggtgctgctc caggacatcc tgctgaagtg gcagcggctg acagaggaac agtgcctgtt  2580
tagcgcctgg ctgtccgaga aagaggacgc cgtcaacaag atccacacca ccggcttcaa  2640
ggatcagaat gagatgctga gcagcctgca gaaactggcc gtgctgaagg ctgacctgga  2700
aaagaaaaag cagtccatgg gcaagctgta ctccctgaag caggacctgc tgagcacact  2760
gaagaacaag tctgtgaccc agaaaaccga ggcctggctg gacaacttcg cccggtgttg  2820
ggataacctg gtgcagaagc tggaaaagtc caccgctcag atctctcagg ccgtgaccac  2880
aacacagcct tctctgaccc agaccaccgt gatggaaaca gtgaccacag tgacaacccg  2940
cgagcagatc ctggtcaagc acgcccaaga agaactgcct cctccacctc ctcagaagaa  3000
acggcagatc acagtggaca gcgagatccg gaagagactg gacgtggaca tcaccgagct  3060
gcacagctgg atcaccagat ccgaagccgt gctgcagtcc cctgagttcg ccatcttcag  3120
aaaagagggc aacttctccg acctgaaaga gaaagtcaac gccatcgaga gagagaaggc  3180
cgagaagttc cggaagctgc aggacgcctc tagatctgcc caggctctgg tggaacagat  3240
ggtcaacgaa ggcgtgaacg ccgacagcat caagcaggcc tcagagcagc tgaactcccg  3300
gtggatcgag ttctgtcagc tcctgagcga gagactgaac tggctggaat accagaacaa  3360
tatcattgcc ttctacaacc agctccagca gctcgaacag atgaccacca cagccgagaa  3420
ttggctgaag atccagccta ccacacctag cgagcccacc gccattaaga gccagctgaa  3480
aatctgcaag gacgaagtga atcggctgag cgatctgcag ccccagatcg aaagactgaa  3540
aatccagtct atcgccctca aagagaaagg acagggcccc atgttcctgg acgccgattt  3600
tgtggccttt accaaccact tcaaacaggt gttctccgac gtgcaggccc gggaaaaaga  3660
gctgcagacc atcttcgaca ccctgcctcc aatgagatac caagagacaa tgagcgccat  3720
ccggacctgg gtgcagcaaa gcgagacaaa gctgagcatc ccacagctga gcgtgaccga  3780
ctacgagatc atggaacaga gactgggcga actgcaggcc ctccagtcta gcctgcaaga  3840
acagcagtcc ggcctgtact acctgagcac aaccgtgaaa gagatgagca agaaggcccc  3900
tagcgagatc tcccggaagt accagagcga gttcgaagag atcgaaggcc ggtggaagaa  3960
gctgtctagc cagctggttg agcactgcca gaaactcgaa gaacaaatga acaagctgcg  4020
caagatccag aatcacatcc agacgctgaa gaaatggatg gccgaggtgg acgtgttcct  4080
gaaagaagag tggcccgctc tgggcgactc cgagattctg aagaaacagc tcaaacagtg  4140
ccggctgctg gtgtccgata tccagacaat ccagccaagc ctgaactccg tgaatgaagg  4200
cggccagaag atcaagaacg aggccgagcc tgagtttgcc agcagactgg aaaccgaact  4260
gaaagaactc aacacccagt gggaccacat gtgccagcaa gtgtacgccc ggaaagaggc  4320
cctgaaaggc ggactcgaaa agactgtgtc tctgcagaaa gacctgtctg agatgcacga  4380
gtggatgacc caggccgaag aggaatacct ggaacgggac ttcgagtaca agacccctga  4440
tgagctgcaa aaagccgtcg aggaaatgaa gcgggccaaa gaagaggccc agcagaaaga  4500
agccaaagtc aagctgctga ccgagtccgt gaatagcgtt atcgctcagg cccctcctgt  4560
ggctcaagag gctctcaaga aagaactgga aactctgacc accaactacc agtggctgtg  4620
caccagactg aacggcaagt gcaagacact ggaagaagtg tgggcctgct ggcacgaact  4680
gctgtcctat ctggaaaagg ccaacaagtg gctgaacgag gtggaattca agctgaaaac  4740
caccgagaac atccctggcg gcgctgaaga gattagcgag gtgctggaca gcctggaaaa  4800
cctgatgaga cacagcgagg acaaccccaa tcagatcaga atcctggctc agaccctgac  4860
cgatggcggc gtgatggacg agctgatcaa cgaggaactc gaaaccttca acagccggtg  4920
gcgggaactg cacgaggaag ctgttcggag gcagaagttg ctggaacagt ctatccagag  4980
cgcacaagaa accgagaagt ccctgcacct gatccaagag agcctgacct tcatcgacaa  5040
gcagctggcc gcttatatcg ccgacaaggt ggacgctgct cagatgcccc aagaggcaca  5100
gaagattcag agcgacctga ccagccacga gattagcctg gaagaaatga agaagcacaa  5160
ccagggcaaa gaggccgctc agagagtcct gagccagatc gatgtggcac agaaaaagct  5220
ccaggatgtg tccatgaagt ttcggctgtt tcagaagccc gccaacttcg agcagagact  5280
gcaagagtcc aagatgatcc tggacgaagt caaaatgcat ctgcccgcac tggaaacaaa  5340
gtccgtggaa caagaagtgg tgcagtccca gctgaaccac tgcgtgaacc tgtacaagag  5400
cctgtccgaa gtgaagtctg aggtggaaat ggtcatcaag accggcaggc agatcgtcca  5460
gaagaagcag accgagaatc ccaaagaact cgacgagaga gtgaccgctc tgaagctgca  5520
ctacaatgag ctgggcgcca aagtgaccga gcggaagcaa cagcttgaga agtgcctgaa  5580
actgtctcgg aagatgcgga aagaaatgaa cgtgctgaca gagtggctgg ccgccaccga  5640
tatggaactg actaagagaa gcgccgtgga aggcatgccc agcaacctgg atagtgaagt  5700
ggcctggggc aaagccactc agaaagagat tgagaagcag aaggtccacc tgaagtccat  5760
caccgaagtg ggcgaagccc tgaaaaccgt gctgggaaag aaagagacac tggtcgagga  5820
caagctgtcc ctgctgaatt ccaactggat cgccgtgacc tccagagctg aggaatggct  5880
gaatctgctg cttgagtacc agaaacacat ggaaacgttc gaccagaacg tcgaccacat  5940
cacaaagtgg atcatccagg ctgataccct gctggacgag tccgagaaga agaaacccca  6000
acaaaaagaa gatgtgctga agcggctgaa agccgagctg aatgacatcc ggcctaaggt  6060
ggacagcacc agagatcagg cagccaacct gatggccaac agaggcgacc actgtcggaa  6120
gctcgtggaa cctcagatca gcgagcttaa ccacagattt gccgccatca gccaccggat  6180
caagacaggc aaggccagca ttcctctcaa agagcttgag cagttcaaca gcgacatcca  6240
aaagctgctc gaacccctgg aagccgagat ccaacagggc gtcaacctca aagaagaaga  6300
tttcaacaag gacatgaacg aggacaatga gggcaccgtc aaagaactgc tgcagcgggg  6360
cgataatctg cagcagcgga ttaccgatga gcgcaagcgg gaagagatca agattaagca  6420
gcagctgctg cagaccaagc acaacgccct gaaggacctg cggagccaga gaagaaagaa  6480
ggccctggaa atcagccacc agtggtatca gtacaagcgg caggccgacg acctgctgaa  6540
gtgcctggat gacatcgaga agaagctggc ctctctgccc gagcctaggg acgagagaaa  6600
gatcaaagag atcgaccgcg agctgcagaa aaagaaagag gaactgaacg ccgtccgcag  6660
acaggccgaa ggactttctg aagatggcgc cgctatggcc gtggaaccca cacagattca  6720
gctgagcaag cggtggcggg aaatcgagag caagttcgcc cagttccggc ggctgaattt  6780
```

```
cgcccagatc cacaccgtgc gggaagagac aatgatggtc atgacagagg acatgcccct  6840
tgagatcagc tacgtgccca gcacctacct gaccgagatc acccatgtgt ctcaggccct  6900
gctggaagtg gaacagctgc tgaatgcccc tgacctgtgc gccaaggact tcgaggacct  6960
gttcaagcaa gaggaaagcc tgaagaacat caaggacagc ctgcagcaga gcagcggccg  7020
gatcgatatc atccacagca agaaaaccgc cgcactgcag agcgccacac ctgtggaaag  7080
agtgaagctg caagaggccc tgagccagct ggatttccag tgggagaaag tgaacaagat  7140
gtacaaggac cggcagggca gattcgaccg cagcgttgaa aagtggcggc ggttccacta  7200
cgacatcaag atcttcaacc agtggctgac cgaggccgag cagttcctga gaaagacaca  7260
gatccccgag aactgggagc acgccaagta caagtggtat ctgaaagagc tgcaggacgg  7320
catcggccag agacagacag tcgtgcggac actgaatgcc accggcgagg aaatcatcca  7380
gcagtccagc aagaccgacg ccagcatcct gcaagagaag ctgggcagcc tgaacctgcg  7440
gtggcaagaa gtgtgcaagc agctgagcga ccggaagaag cggctggaag aacagaagaa  7500
tatcctgagc gagttccagc gggacctgaa cgagttcgtg ctgtggctcg aagaggccga  7560
caatatcgcc agcattcccc tggaacctgg caaagagcag cagctgaaag aaaagctgga  7620
acaagtgaaa ctgctggtcg aggaactgcc cctgagacag ggaatcctga aacagctgaa  7680
cgagacaggc ggccctgtgc tggtgtctgc ccctatttct cccgaggaac aggacaagct  7740
ggaaaacaag ctgaagcaga ccaacctgca gtggatcaag gtgtccagag cactgcctga  7800
gaagcagggc gagatcgagg cccagatcaa ggacctggga cagctcgaaa agaagcttga  7860
ggacctcgaa gaacagctca accatctgct gctttggctg agccccatcc ggaaccagct  7920
ggaaatctac aaccagccta atcaagaggg ccccttcgac gtgaaagaaa ccgagattgc  7980
cgtgcaggcc aagcagcccg atgtggaaga gatcctgtct aagggccagc acctgtacaa  8040
agagaagccc gccacacagc ccgtgaagcg gaaactggaa gatctgagca gcgagtggaa  8100
ggccgtgaac cggctgctgc aagaactgag agccaaacag cctgatctgg cccctggcct  8160
gacaacaatt ggcgcctctc ctacacagac cgtgacactg gtcacacagc ctgtggtcac  8220
caaagagaca gccatcagca aactggaaat gcccagcagt ctgatgctcg aagtgcccgc  8280
actggccgac ttcaatagag cctggaccga gctgaccgac tggctcagtc tgctggacca  8340
agtcatcaag tcccagagag tgatggtcgg agatcttgag gacatcaacg agatgatcat  8400
taagcagaaa gccaccatgc aggaccttga gcagagaagg ccccagcttg aagaactgat  8460
caccgccgct cagaacctga aaaacaagac cagcaatcaa gaagcccgga ccatcatcac  8520
cgaccggatc gagagaatcc agaaccagtg ggacgaagtg caagagcatc tgcagaacag  8580
acggcagcag ctcaatgaga tgctgaagga cagcacacag tggctggaag ccaaagaaga  8640
agccgagcag gttctcggac aggccagagc taagctggaa tcttggaaag agggacccta  8700
caccgtcgac gccatccaga agaagatcac cgagacaaag cagctggcca aggatctgag  8760
acagtggcag accaatgtgg acgtggccaa cgacctggct ctgaagctgc tgagagacta  8820
cagcgccgac gacaccagaa aggtgcacat gatcaccgaa aacatcaacg cctcttggcg  8880
gagcatccac aagcgggtgt cagagagaga agccgctctg gaagaaacac atagactgct  8940
ccagcagttc ccactcgacc tggaaaagtt cctggcctgg ctgacagaag ccgaaaccac  9000
cgctaacgtg ctccaggatg ccaccagaaa agagcggctg ttggaggaca gcaagggcgt  9060
caaagaactc atgaagcagt ggcaggatct gcaaggggag attgaagccc acaccgacgt  9120
gtaccacaac ctggacgaga acagccagaa gatcctgcgg tccctggaag gctctgatga  9180
tgctgtgctg cttcagaggc ggctggacaa catgaacttc aagtggagcg agctgcggaa  9240
gaagtccctg aacatcagaa gccacctgga agcctccagc gaccagtgga aaagactgca  9300
cctgtctctc caagagctgc tcgtgtggct gcagctgaag gatgacgagc tgagtagaca  9360
ggcccctatc ggcggagatt ttcccgccgt gcagaaacag aacgacgtgc accgggcctt  9420
caagagagag ctgaaaacaa aagaacccgt catcatgagc accctggaaa ccgtgcggat  9480
ctttctgacc gagcagcctc tggaaggact ggaaaagctg taccaagagc ctagagagct  9540
gcctcctgaa gaaagggccc agaacgtgac acggctgctt agaaagcagg ccgaggaagt  9600
gaacaccgaa tgggagaagc tgaacctcca ctccgccgac tggcagcgga agatcgatga  9660
gacactggaa cggctgcggg aactgcaaga agccacagac gagctggacc tgaaactgcg  9720
gcaggctgaa gtgatcaaag gctcctggca gccagtgggc gatctgctga tcgatagcct  9780
gcaggaccat ctggaaaaag tcaaggccct gcggggagag atcgcccctc tcaaagaaaa  9840
cgtgtcccac gtgaacgatc tggccaggca gctgacaaca ctgggcatcc agctgagccc  9900
ttacaacctg tctaccttgg aggacctgaa tacccggtgg aagctgctcc aagtggccgt  9960
cgaggataga gtgcggcagc tgcatgaggc tcacagagat tttggacccg ccagccagca  10020
cttcctgagc acatctgttc aaggcccctg ggagagagct atcagcccta acaaggtgcc  10080
ctactacatc aaccacgaga cacagaccac ctgttgggat caccccaaga tgaccgaact  10140
gtatcagtcc ctggccgacc tgaacaacgt gcggtttagc gcctaccgga ccgccatgaa  10200
gctgcgcaga ctgcagaaag ctctgtgcct ggacctgctg tctctgagcg ctgcttgtga  10260
tgccctggac cagcataacc tcaagcagaa cgaccagcct atggacatcc tgcagatcat  10320
caactgcctg accaccatct acgaccggct cgaacaagag cacaacaacc tggtcaacgt  10380
gcccctgtgc gtggacatgt gcctgaattg gctgctgaac gtgtacgaca ccggcagaac  10440
cggcaggatc agagtgctga gcttcaagac cggcatcatc tccctgtgca aggcccacct  10500
tgaggataag taccgctacc tgtttaagca ggtcgccagc agcaccggct tttgcgacca  10560
aagaaggctg ggactgctgc tccacgacag cattcagatc cctagacagc tgggcgaagt  10620
ggcctctttc ggcggctcta atatcgagcc tagcgtgcgg agctgcttcc agttcgccaa  10680
caacaagccc gagattgagg ccgcactgtt cctggactgg atgagactgg aaccccagag  10740
catggtctgg ctgcctgtgc tgcatagagt ggccgcagcc gaaacagcca agcaccaggc  10800
caagtgcaac atctgcaaag agtgccccat catcggcttc cggtacagat ccctgaagca  10860
cttcaactac gatatctgcc agtcctgctt cttcagcggc agagtggcca agggccacaa  10920
gatgcactac cccatggtgg aatactgcac ccctaccacc tctggcgagg acgtgcggga  10980
ttttgccaag gtgctcaaga acaagttccg gaccaagcgc tacttcgcta agcaccccag  11040
aatgggctac ctgccagtgc agacagtgct tgagggcgac aacatggaaa cccctgtgac  11100
tctgatcaac ttctggcccg tggatagcgc ccctgctagt tctcctcagc tgtctcacga  11160
cgatacccac agcagaatcg agcactacgc ctccagactg gccgagatgg aaaacagcaa  11220
cggcagctac ctgaatgaca gcatcagccc caacgagagc atcgacgacg aacatctgct  11280
cattcagcac tactgccaga gcctgaatca ggacagccct ctgtctcagc ctagaagccc  11340
tgcacagatc ctgatcagcc tggaaagcga ggaacgcggc gagctggaaa gaatcctggc  11400
agacctggaa gaggaaaacc ggaacctgca ggccgaatac gacagactca agcagcagca  11460
cgagcacaag ggactgtctc cactgccttc tccacctgaa atgatgccca cctctccaca  11520
```

```
gagccccaga gatgccgagc tgattgccga agccaaactg ctgaggcagc acaaaggcag  11580
actcgaagcc agaatgcaga ttctcgaaga tcacaacaag cagctcgaat cccagctgca  11640
cagacttagg cagctgctgg aacagcctca ggcagaggcc aaagtgaatg gcaccaccgt  11700
gtctagccct agcacaagcc tgcagagatc cgacagcagc cagccaatgc ttctgagagt  11760
cgtgggctcc cagaccagcg attctatggg cgaagaggac ctgctcagcc ctcctcagga  11820
tacaagcacc ggcctggaag aagtgatgga acaactgaac aacagcttcc ccagcagcag  11880
aggcagaaac acccctggca agcccatgcg cgaggacacc atgtgataac tcgagaatca  11940
acctctggat tacaaaattt gtgaaagatt gactggtatt cttaactatg ttgctccttt  12000
tacgctatgt ggatacgctg ctttaatgcc tttgtatcat gctattgctt cccgtatggc  12060
tttcattttc tcctccttgt ataaatcctg gttgctgtct ctttatgagg agttgtggcc  12120
cgttgtcagg caacgtggcg tggtgtgcac tgtgtttgct gacgcaaccc ccactggttg  12180
gggcattgcc accacctgtc agctcctttc cgggactttc gctttccccc tccctattgc  12240
cacggcggaa ctcatcgccg cctgccttgc ccgctgctgg acaggggctc ggctgttggg  12300
cactgacaat tccgtggggt gtgccttcta gttgccagcc atctgttgtt tgcccctccc  12360
ccgtgccttc cttgaccctg gaaggtgcca ctcccactgt cctttcctaa taaaatgagg  12420
aaattgcatc gcattgtctg agtaggtgtc attctattct ggggggtggg gtggggcagg  12480
acagcaaggg ggaggattgg gaagacaata gcaggcatgc tggggatgcg gtgggctcta  12540
tgggaagatg tctactgagc tgtgcgatcc ctgctgggga ctttccgctg gggactttcc  12600
gctggggact ttccgccttc agctaaggaa gctaccaata tttagaggta cattttgttc  12660
tagaacaaaa tgtaccggta cattttgttc tggtacattt tgttct                 12706

SEQ ID NO: 24          moltype = DNA  length = 12706
FEATURE                Location/Qualifiers
source                 1..12706
                       mol_type = other DNA
                       note = CBA-hBGi-DMD-5-WPRE3-DTS
                       organism = synthetic construct
SEQUENCE: 24
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttttaatt attttgtgca gcgatggggg cggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tcgtaagtac tagcagctac aatccagcta ccattctgct tttattttat  720
ggttgggata aggctggatt attctgagtc caagctaggc ccttttgcta atcatgttca  780
tacctcttat cttcctccca cagctcctgg gcaacgtgct ggtctgtgtg ctggcccatc  840
actttggcaa agaattgcga tcgccaccat gctgtggtgg gaggaagttg aagattgtta  900
tgagagagaa gatgtccaga aaaagacctt taccaaatgg gtgaacgcac agttctccaa  960
atttgggaaa cagcatatag aaaatttgtt cagcgatctt caggatgggc gcaggttgct  1020
tgaccttctg gaaggactga ccgggcagaa gctgcccaaa gagaaagggt ctaccagagt  1080
tcacgctctg aacaacgtga ataaggcact gcgagtcctg caaaataaca acgtcgacct  1140
ggtgaacata ggcagcactg atattgttga tgggaaccat aaactcacac tgggtctgat  1200
ttggaatatt atactgcact ggcaggtcaa aaatgttatg aaaaatatta tggccgggct  1260
tcaacagacc aattccgaga agatcctgct gtcttgggtt aggcagtcca cgaggaacta  1320
ccctcaagtg aacgttatta acttcacaac atcatggagt gatggacttg ccctgaacgc  1380
cttgatccac tcccataggc cagacctgtt cgattggaat agcgtagtct gtcagcagag  1440
tgctacacaa cgcctggaac acgcctttaa catagccagg tatcagcttg gaattgagaa  1500
actcctcgac cctgaagacg tagacaccac ttaccccgac aaaaaatcca ttcttatgta  1560
cataacttcc ttgtttcagg ttctccccca gcaggtgtcc atcgaggcta tacaggaggt  1620
cgaaatgctc cccagacccc ctaaggtcac gaaggaagag cacttccaac tgcaccatca  1680
gatgcactac agtcaacaga tcactgtgag tctcgcacag ggtacgaaa ggaccagctc   1740
ccctaaaccc cgcttcaagt cctacgccta tactcaggca gcttacgtaa ccacaagtga  1800
ccccacgcgg tcacccttcc caagccagca cctggaggct cccgaggaca aaagctttgg  1860
atcatccctg atggaatctg aagtcaatct cgataggtac caaaccgctc tggaggaggt  1920
cctcagttgg ctcctttcag ctgaagatac tctgcaggca cagggtgaga tcagcaatga  1980
cgtggaggta gtgaaagatc agtttcacac tcacgagggc tatatgatgg acctgacagc  2040
ccatcaaggt cgcgttggca atatcctgca gttggggtcc aaactgattg gtaccggtaa  2100
gttgtccgag gacgaagaga cagaagtgca ggagcagatg aacctgctta attctagatg  2160
ggaatgcctc cgcgtggcct ctatggagaa gcagtccaat ctccatcggg ttctcatgga  2220
cttgcagaat cagaagctga aggaactcaa cgactggttg accaagactg aggagcgcac  2280
cagaaagatg gaggaggagc cactcggtcc tgatcttgaa gatctgaaac gacaagttca  2340
gcagcacaag gtcctgcagg aggatctcga acaggagcag gtccgggtga acagcctgac  2400
ccatatggtt gtcgttgtcg acgagtcaag tggggaccat gctacggctg cgcttgagga  2460
acagctgaag gtcttgggcg atagatgggc gaatatctgc cgctggactg aagatagatg  2520
ggtgctgctg caggatattc ttttgaagtg gcagcggttg accgaagaac aatgcttgtt  2580
tagcgcctgg ctgagtgaga aagaggatgc ggtgaataag atacacacta ctggcttcaa  2640
agaccagaat gaaatgctta gcagcctgca gaaacttgcg gttcttaagg ccgacttgga  2700
aaagaaaaag cagtcaatgg gtaagctgta ctcactcaag caggacctgc tgtcaacttt  2760
gaagaacaag agcgtcacgc aaaagactga ggcctggctc gacaattttg ctaggtgctg  2820
ggataacctg gtgcagaagt tggaaaagtc cactgctcag atctctcaag ccgtgactac  2880
tacccagccc agcctgacac agactaccgt catggaaacc gttaccactg tgacgactag  2940
ggagcagata ctcgttaagc acgctcaaga ggaattgccg ccacctcctc cccaaaagaa  3000
acgccagatt accgtcgact ctgaaatacg caagagactg gatgtggaca tcacggaact  3060
```

```
gcactcttgg attaccagaa gcgaggcagt cctccagagc cccgagtttg cgatcttcag  3120
gaaggaaggc aacttttcag atctgaagga aaaggtgaac gccatcgagc gcgagaaagc  3180
cgagaagttc cgcaaactgc aggatgcgag ccggtctgct caggccttgg tggagcaaat  3240
ggtgaatgaa ggcgtaaatg cggacagcat caagcaggcc tccgagcagc tcaattcaag  3300
atggatcgag ttctgtcagc tgctcagcga gcgattgaac tggctggagt atcaaaataa  3360
cataatcgcg ttttacaacc agctgcaaca gctggaacag atgacgacta ctgcagagaa  3420
ctggcttaaa atccagccta caactccttc tgaacccaca gcaatcaaaa gccagctcaa  3480
gatctgcaag gacgaagtca accgcctctc cgatttgcag cctcagatag aacgactcaa  3540
gatccaaagt atcgcactca aagaaaaggg gcaaggccct atgtttctcg atgctgattt  3600
tgtggctttc accaaccatt ttaagcaagt gttttcagat gtgcaagccc gggaaaagga  3660
actgcaaacc atttttgata ccctgcctcc aatgcggtac caggagacta tgtctgcaat  3720
tcgcacctgg gtgcaacaaa gcgagacgaa actttctatt ccacaactgt ccgtgacaga  3780
ctacgaaatt atggaacagc gactgggaga actccaagcc cttcagtcca gccttcagga  3840
gcagcagtca ggattgtact atctgtcaac caccgtgaag gaaatgtcaa aaaaggctcc  3900
ctccgaaata tctcgcaagt atcagtctga gtttgaagag attgaaggga gatggaagaa  3960
actgtcctca cagctggttg agcactgtca gaagttggaa gagcagatga acaagttgcg  4020
caagattcaa aatcacatac agacactcaa aaagtggatg gcggaggttg acgtcttcct  4080
taaagaggag tggccagccc tgggcgactc agagatcctg aaaaagcaac tgaaacagtg  4140
ccgactgctg gtgtccgaca tccagacaat acagccaagt ttgaatagcg tgaatgaggg  4200
tggacaaaaa atcaaaaacg aggctgagcc cgagttcgcc tccagattgg aaaccgagct  4260
gaaggaactt aatacacagt gggatcatat gtgtcagcag gtttatgccc ggaaggaagc  4320
actgaaaggg gggctggaga aaaccgtgag ccttcagaag gaccttagcg agatgcacga  4380
gtggatgacc caggcggagg aagagtatct cgaacgggat tttgagtata agacaccaga  4440
tgaacttcag aaggcagtcg aagagatgaa acgggcaaag gaagaggctc agcagaagga  4500
agcaaaggtt aaacttctga cagaatccgt taacagcgtt atagcccaag ctccccccgt  4560
tgcccaggaa gctcttaaaa aggaactgga aacactgaca acaaactacc agtggctgtg  4620
cacccgcttg aacggcaaat gcaaaaccct ggaagaggtc tgggcttgtt ggcatgaact  4680
cctgtcatac ctggaaaaag ctaataagtg gctgaatgag gtggagttta aattgaaaac  4740
gaccgaaaac atccctggcg gtgcagagga gatatctgag gtgctcgata gcctggagaa  4800
tcttatgagg catagcgagg ataaccccaa ccagattagg atactggccc aaactctgac  4860
cgacggcgga gtgatggacg agctgataaa cgaggaactg gaaaccttta attcacgctg  4920
gcgagaactt cacgaggagg cagtcaggcg ccagaaactg ctggagcagt ccatccagag  4980
tgcccaggag actgagaagt cacttcatct gatccaggag agtttgacgt ttatcgacaa  5040
gcagcttgcc gcctacattg cagacaaggt cgatgctgct cagatgccgc aagaggctca  5100
gaaaatccag agcgacctga caagccacga gattagcctg gaggaaatga aaaagcacaa  5160
ccagggtaaa gaggccgccc agcgggttct gagccagatc gatgtcgcac agaagaaact  5220
ccaagatgta agcatgaagt tccgactgtt tcagaaacca gcgaactttg agcagcgact  5280
gcaggagtct aaaatgatcc tcgatgaggt gaaaatgcat ctgccagccc tggaaactaa  5340
gagcgtggag caggaggtgg ttcagagtca gctgaaccac tgcgtaaacc tctataaaag  5400
tcttagtgaa gtgaagagcg aggtggagat ggtgattaag actggtagac agattgtaca  5460
gaaaaagcag acggagaacc ccaaagagtt ggatgaacgg gtgacagccc ttaagctcca  5520
ctataacgag ctgggagcca aagtgactga gagaaagcag caacttgaaa aatgtctgaa  5580
gctgagcaga aagatgcgga aggaaatgaa tgtgctgaca gagtggctgg ctgcgaccga  5640
catggaactt acaaagagga gcgccgtgga aggcatgcct tccaatctgg atagtgaggt  5700
cgcttggggc aaagctacac agaaggaaat tgagaagcaa aaagtgcatc ttaagagcat  5760
tactgaagtt ggcgaggctt tgaaaaccgt cctcggcaag aaagagactc tggtagaaga  5820
taaactctca ctgctgaact caaactggat cgcagtcact agtcgggccg aagagtggct  5880
gaatttgctg ttggagtacc aaaagcatat ggagactttc gatcagaatg tcgaccacat  5940
tacgaagtgg ataatccagg cggacacact gttggatgag tccgagaaaa agaaacctca  6000
gcagaaggaa gacgtgctca aacgactcaa agccgaactg aacgacatca ggcccaaagt  6060
tgattccacc cgggatcaag cggccaatct catggccaac cggggggatc actgcagaaa  6120
gttggtagaa cctcagataa gcgaacttaa tcatagattt gccgccatat cacataggat  6180
taagaccggt aaggcttcaa tccccctgaa ggaactcgaa cagtttaata gtgacatcca  6240
gaagctcctg gagcctctcg aagccgagat tcaacagggt gtaaacctta aggaagagga  6300
ttttaataag gatatgaatg aggacaatga aggcacggtc aaagagctcc tccagagggg  6360
agacaatttg cagcagcgga tcaccgatga acgcaaacgc gaagagatca aaattaagca  6420
gcagctcctc caaacaaagc acaatgccct taaagacctc agaagccagc ggcggaaaaa  6480
ggctctggaa atcagccatc aatggtatca gtacaagcgg caagcggacg atctcctgaa  6540
atgtctggat gatatcgaga aaaaactggc cagtctgcca gagcccagag atgagcgcaa  6600
aatcaaggaa atcgacaggg agcttcagaa gaaaaaagag gagctgaacg ccgtccgaag  6660
gcaggccgaa gggctgtcag aagatggggc cgccatggca gtggaaccta cccagattca  6720
actgtccaag cgctggagag agattgaaag taagttcgca caattccgga ggcttaattt  6780
tgctcagatt cacacagtta gggaggaaac catgatggtg atgaccgaag acatgccact  6840
cgaaatcagc tacgtcccta gcacatatct cacggagatt acccacgtgt cccaggcact  6900
gctggaagtc gagcaattgt tgaacgcccc tgatctctgc gccaaggatt tcgaagactt  6960
gttcaagcaa gaggaaagcc tcaagaacat caaagacagt cttcagcagt cctcaggcag  7020
aattgatatt atccactcca agaaaacagc cgctctccag agcgctaccc ctgtcgaacg  7080
agtgaaactg caagaggcct tgtctcagtt ggacttccag tgggagaaag tcaacaagat  7140
gtacaaggac aggcagggtc ggttcgaccg gagcgtcgaa aaatggcgga gattccatta  7200
tgacatcaag atattcaatc agtggcttac agaggcggag caatttttga gaaagacgca  7260
gattcccgaa aactgggagc atgccaagta caagtggtac ctcaaagagc tccaggatgg  7320
aatcggccag agacagaccg tagttagaac actgaacgca actggagaag agattatcca  7380
gcagtcctcc aaaactgacg cctctatcct ccaggagaag cttggcagcc ttaacctgcg  7440
gtggcaggag gtgtgtaaac aactgtcaga taggaaaaaa agacttgagg aacagaagaa  7500
cattctgagc gagttccaac gagatctcaa cgagttcgta ctgtggctgg aggaggccga  7560
caacatcgct tcaatccccc tggaacccgg caaggaacag cagcttaagg aaaaattgga  7620
acaggtaaaa ctgttggtag aggagctccc attgcggcag ggcattctca agcagctgaa  7680
tgaaactgga ggtcccgttc tggtcagtgc gcccataagc ccggaagagc aggacaagtt  7740
ggaaaacaag ctgaagcaaa caaatctgca gtggatcaaa gtgagccggg ctcttccaga  7800
```

```
aaagcaaggc gagattgaag cccagattaa ggatcttggc cagcttgaga aaaagctgga  7860
ggatctggaa gagcagctga accatttgct tctgtggctg agtcccatta gaaaccagct  7920
ggaaatctac aaccagccaa accaagaggg ccctttcgac gtcaaggaaa ctgagatagc  7980
agtccaggca aaacagcccg atgtcgaaga aatcttgtct aaggggcagc acctctacaa  8040
agagaaacct gccacccagc ccgtgaagag aaaactggaa gacctctctt cagagtggaa  8100
ggctgtaaac aggttgctcc aggagctgag agctaagcaa cctgacctcg cacccggcct  8160
gactactatt ggcgccagcc cgacccaaac cgtcacactg gtgacccagc ctgtagtcac  8220
aaaagaaacc gccatctcca aactggagat gccttcaagc ctgatgctgg aggtgcctgc  8280
tctggccgat ttcaacagag cctggacaga gctgacagac tggctgtctc tgctcgacca  8340
agtgataaag tcacagcgcg tcatggtggg tgacctggag gacatcaatg agatgatcat  8400
aaagcaaaag gctaccatgc aggacttgga gcagcgcagg ccgcagttgg aagaactgat  8460
tacagcagcc cagaacctca agaacaagac ttcaaatcag gaggcaagga ccatcataac  8520
agatagaatc gagaggattc agaaccaatg ggatgaggtg caggagcacc tgcagaacag  8580
aaggcagcag ctgaacgaaa tgctgaaaga ctccacacag tggctggagg ccaaagagga  8640
ggcagaacag gtgctgggcc aggctagggc caagctggaa agttggaagg aagggcccta  8700
caccgtggac gccatacaga agaaaataac ggagacaaaa cagctggcca aagacctccg  8760
ccaatggcag accaacgtag acgtcgccaa tgacctggca ctcaagttgt tgagagatta  8820
ttccgcagat gacacccgaa aagtacacat gatcactgag aatatcaacg ccagttggcg  8880
gagcattcac aaacgggtga gcgagagaga agccgccctt gaggagacgc atcgcctttt  8940
gcagcaattt ccgcttgacc tggaaaagtt tctggcttgg ttgacagagg ccgagacaac  9000
tgctaacgtg ctgcaagatg ccacccgcaa agagcggctt cttgaggact ctaaaggggt  9060
gaaagaattg atgaagcagt ggcaggacct ccagggcgaa atcgaggccc atactgatgt  9120
ctaccacaac ctggatgaaa atagtcagaa aatcctgaga tccctggaag ggagtgatga  9180
tgcggtgctg ctgcagcgcc gactcgataa catgaacttt aagtggtctg aactccggaa  9240
aaaaagcctg aacattcgga gccatctgga ggcttcttct gatcagtgga agagacttca  9300
tctgtccttg caggagcttc tggtgtggct gcagctgaaa gacgacgagc tgtcaaggca  9360
ggcaccaata gggggcgact tccccgctgt tcagaaacaa aatgatgtgc acagggcatt  9420
caagcgggaa ctgaagacga aagaaccagt gattatgagc actctggaga cggtacgcat  9480
ctttctgacc gagcagccac ttgaaggcct cgaaaagttg taccaggagc cacgggaatt  9540
gcctcccgaa gaacgggctc agaatgttac ccgactgctt cgcaagcagg ctgaggaagt  9600
gaacactgag tgggaaaaac tgaatctgca cagtgccgat tggcagcgca aaattgacga  9660
gacattggag cgcttgcggg agctgcagga agccacagat gaacttgatc tgaaactcag  9720
acaggccgag gtcataaagg gttcttggca acccgtaggc gaccttttga ttgactcact  9780
gcaggatcat ctggagaaag taaaggcgct gcggggggaa attgctccgc tgaaggaaaa  9840
cgtgagccat gtgaatgatc tggctcggca attgactacc ctgggtatcc agctgtcccc  9900
ctacaatctg agcactctcg aagacctcaa cacaagatgg aaactgctgc aggtcgccgt  9960
ggaggacagg gtgaggcagc tgcatgaggc acacagggac ttcggtccgg caagccaaca  10020
cttcctgtct acttctgttc aagggccttg ggaacgcgct atttccccaa acaaagtgcc  10080
gtactatatt aaccatgaaa ctcagacaac ctgctgggat catcctaaaa tgactgagct  10140
gtaccagagc ctcgccgatc tgaataacgt gaggtttagc gcatacagaa ccgcaatgaa  10200
gctcaggaga ctgcagaagg cactttgcct ggacctcctg agcctctccg ctgcctgcga  10260
tgccctcgac cagcacaacc tgaagcagaa tgatcagcct atggacatcc tgcaaatcat  10320
aaattgtctg acgacaatct acgaccggct cgaacaggag cacaataatc tcgtgaacgt  10380
tccactttgt gtggatatgt gtctcaactg gctgttgaac gtctatgaca ccgggagaac  10440
tggaaggatc cgcgttctgt cctttaagac tggaatcatc agcttgtgta aggcgcacct  10500
tgaggacaaa tatcgatacc tgtttaagca ggttgcaagc tccactggat tctgcgacca  10560
gaggcgcctc gggctgctgc ttcatgatag tatccaaatc ccacgccaac tcggagaggt  10620
ggcaagcttc ggcgggagca atattgagcc aagcgtcaga tcttgtttcc agtttgccaa  10680
caataagcct gagatcgaag ccgcactgtt tttggattgg atgcggttgg agccccagag  10740
tatggtgtgg ttgcccgtgc tgcatagggt cgctgccgct gaaaccgcca aacaccaggc  10800
caagtgcaat atttgcaagg aatgtcccat catcgggttt agataccgga gcctgaagca  10860
cttcaattat gatatctgcc agtcttgttt tttttccggc cgagttgcta agggacacaa  10920
gatgcattac ccaatggtgg aatattgtac gccaaccacc agcggcgaag atgtcagaga  10980
ttttgcaaaa gtactcaaga acaagttccg caccaagcga tatttcgcga agcacccccg  11040
gatgggctac ctcccagtgc agacggttct ggaaggcgat aacatggaaa ctccagtcac  11100
cctgatcaat ttctggcctg tggactctgc gcctgcctct tcacctcagc tctcccacga  11160
tgacacccat tccagaatcg agcactacgc gtctcgactg gcggagatgg agaacagcaa  11220
tggttcttac ctcaatgaca gcattagccc caacgaaagc atcgatgacg agcacctctt  11280
gattcaacac tactgccagt ccctgaatca ggacagtcct ctgtcccaac ccaggagccc  11340
agcccagata ctgatctctc tcgaatcaga agaaagaggg gagttggagc gaattttggc  11400
cgacctggag gaggagaata gaaatcttca ggccgagtac gatagactga agcagcagca  11460
cgagcacaag ggcctttctc cactgccctc tccaccggaa atgatgccaa cctcccctca  11520
aagtcccagg gacgctgagc tcattgccga ggcaaagctg ttgcgccagc acaaaggacg  11580
cctggaggcg agaatgcaga tcctggaaga ccataacaag cagcttgagt ctcagctgca  11640
ccgacttaga cagctgttgg agcagccaca agcggaagca aaggtcaatg gaactaccgt  11700
gagttccccc agtacaagtc tgcagcgctc tgactcaagc cagccaatgc tgctccgggt  11760
agtcggttct cagactagtg attcaatggg ggaggaggat cttctttccc caccccaaga  11820
cacctcaaca gggcttgagg aagtgatgga gcagctgaac aactccttcc cctcttcacg  11880
ggggagaaat actcctggga agcctatgag agaggatacc atgtaatgac tcgagaatca  11940
acctctggat tacaaaattt gtgaaagatt gactggtatt cttaactatg ttgctccttt  12000
tacgctatgt ggatacgctg ctttaatgcc tttgtatcat gctattgctt cccgtatggc  12060
tttcattttc tcctccttgt ataaatcctg gttgctgtct ctttatgagg agttgtggcc  12120
cgttgtcagg caacgtggcg tggtgtgcac tgtgtttgct gacgcaaccc ccactggttg  12180
gggcattgcc accacctgtc agctcctttc cgggactttc gctttccccc tccctattgc  12240
cacggcggaa ctcatcgccg cctgccttgc ccgctgctgg acaggggctc ggctgttggg  12300
cactgacaat tccgtggggt gtgccttcta gttgccagcc atctgttgtt tgcccctccc  12360
ccgtgccttc cttgaccctg gaaggtgcca ctcccactgt cctttcctaa taaaatgagg  12420
aaattgcatc gcattgtctg agtaggtgtc attctattct ggggggtggg gtggggcagg  12480
acagcaaggg ggaggattgg gaagacaata gcaggcatgc tggggatgcg gtgggctcta  12540
```

```
tgggaagatg tctactgagc tgtgcgatcc ctgctgggga ctttccgctg gggactttcc  12600
gctggggact ttccgccttc agctaaggaa gctaccaata tttagaggta cattttgttc  12660
tagaacaaaa tgtaccggta cattttgttc tggtacattt tgttct                 12706

SEQ ID NO: 25          moltype = DNA  length = 12889
FEATURE                Location/Qualifiers
source                 1..12889
                       mol_type = other DNA
                       note = MHCK7-hBGi-DMD-1-WPRE3-DTS
                       organism = synthetic construct
SEQUENCE: 25
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgccccact acgggtctag  240
gctgcccatg taaggaggca aggcctgggg acacccgaga tgcctggtta taattaaccc  300
agacatgtgg ctgccccccc cccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctgtgg tgggaagagg tggaggattg  1080
ctacgagcgg gaggatgtgc agaaaaagac tttcaccaag tgggtaaatg ctcagttctc  1140
taagttcggg aagcaacaca tcgagaactt gttttccgac ctccaggatg gcaggcgcct  1200
gcttgacttg ctggagggtc tgactggtca gaagctccct aaggagaagg gcagcaccag  1260
agttcacgct ctgaataacg ttaacaaagc cctgagggtc ctccagaata acaatgtaga  1320
cctggtgaac atcggttcta ccgacatcgt ggacgggaat cataaactga ccttggggct  1380
catctggaac attatcttgc actggcaggt gaagaacgtc atgaagaata tcatggccgg  1440
gctgcaacag accaactccg aaaagatttt gctcagctgg gtgcgccagt ccacccgcaa  1500
ttatccacaa gtcaacgtta tcaatttcac cactagttgg agtgatggcc tcgccctgaa  1560
cgccttgatc cacagtcacc gccccgacct gtttgactgg aactctgtgg tttgccaaca  1620
gagcgctacc cagcgtctcg aacatgcttt caatatcgct agataccagc tcggtatcga  1680
gaagctgttg gatcctgagg acgtagacac gacctacccc gataaaaaga gcatcctgat  1740
gtatatcact tctctgtttc aggtgcttcc tcaacaggtg tccattgaag ccatccaaga  1800
ggtcgaaatg ctgcccaggc cccctaaggt gacaaaagaa gagcatttcc agctgcatca  1860
ccagatgcat tacagtcaac agattaccgt cagcttggct cagggatatg agcgcacgtc  1920
ctctcctaag cccagattta agtcctacgc atatacccag gctgcctacg tgaccacttc  1980
cgacccaact aggagcccct ttccctccca acacctggag gcccctgagg acaaaagctt  2040
cggatctagt ctgatggagt ccgaggtgaa tctggatcgg taccaaactg ctctggagga  2100
agtgctgtcc tggcttctgt ccgctgaaga caccctgcag gcgcaaggtg agatttctaa  2160
cgacgtcgag gtcgtgaagg atcagttcca cactcatgag ggctacatga tggacttgac  2220
agctcaccag ggaagagttg gtaacatcct gcagcttggc tccaagttga ttggcacggg  2280
aaagcttagc gaggacgagg aaaccgaggt acaggagcag atgaacttgc tgaattcccg  2340
ctgggagtgc ctgagagttg cgtccatgga aaagcagtca aaccttcaca gagtgctgat  2400
ggaccttcag aaccagaagc tgaaggagct gaacgattgg ctgacaaaga ccgaggaacg  2460
cacaagaaaa atggaagagg aacctctggg acctgatctg gaggatctga agcgccaggt  2520
ccaacagcat aaggtgctgc aggaggattt ggagcaggag caggtgcggg tcaacagcct  2580
gacacatatg gtggttgtgg tcgatgagtc ctctggcgat catgctaccg cagcgctgga  2640
agagcagctg aaggtgctgg gggatcgctg ggccaacatt tgcagatgga cagaagaccg  2700
gtgggtcctg cttcaagata tcctgctcaa gtggcagcgc ctgactgaag agcagtgcct  2760
gttctcagct tggttgagcg aaaaagagga cgcagttaac aagatccata ccacaggctt  2820
caaggatcag aatgagatgc tgagctcact gcagaagctg gctgtgctga aggccgactt  2880
ggagaagaaa aagcagtcca tgggcaaact gtatagcctg aagcaggacc tgctcagcac  2940
cctgaagaac aaaagcgtta cgcagaaaac tgaggcctgg ttggacaact ttgctcgctg  3000
ctgggataac cttgtgcaga agctggaaaa gtcaaccgca cagatctccc aggctgtgac  3060
cactacgcag cctagcttga cccagacaac cgttatggaa accgtgacaa ccgtgacaac  3120
gagagagcaa atcctggtta agcatgccca ggaggaactg ccgccacccc cgcctcagaa  3180
gaaacggcag attacggtgg acagcgagat ccgcaagagg ctggacgtcg acatcactga  3240
gctccactca tggatcacgc ggagtgaggc cgtgctgcag tctcccgagt tcgctatttt  3300
ccgcaaggag ggaaacttct ctgacttgaa agagaaggtg aatgccatcg agcgtgaaaa  3360
ggcagaaaag ttcagaaagc tgcaggacgc ctctcgctct gcgcaggccc tggtggagca  3420
gatggtcaac gagggtgtta acgctgacag catcaaacag gcaagcgaac agctgaactc  3480
cagatggatc gaattttgcc aactgctctc cgaacgcctc aactggttgg agtaccagaa  3540
caatattatc gctttttaca accagctgca gcaactggag cagatgacaa ctaccgccga  3600
aaactggctg aaaattcagc caaccacacc gtccgagcca actgcgatca agtctcagct  3660
gaagatctgc aaggacgaag tgaaccgtct tagcgacttg caaccccaga ttgaacggct  3720
caagattcag tctattgctc tgaaggagaa gggtcagggt ccgatgttcc tggatgcaga  3780
ttttgtcgca tttaccaatc acttcaaaca ggtgtttagt gacgtccagg cgcgcgagaa  3840
agagctgcag actatttttg acaccctgcc tcccatgagg taccaggaga caatgagtgc  3900
cattcgcacc tgggtgcaac agtccgagac gaaattgtca atcccacagc tgtccgtgac  3960
agactacgag attatggagc aacggttggg ggagctgcag gctcttcaga gttccctgca  4020
ggagcaacag agcggactgt actatctttc cactaccgtg aaggaaatga gtaagaaagc  4080
```

```
cccttccgag atcagccgca aataccagtc tgaattcgaa gagatcgagg gacgctggaa  4140
aaagctgtca agccagctgg tcgagcactg tcagaagctg gaagagcaga tgaacaagct  4200
gcgtaaaatc cagaaccata ttcagaccct caagaaatgg atggcagaag ttgacgtgtt  4260
tctgaaggaa gagtggcctg ccctcggcga tagcgaaatc cttaagaaac aactcaagca  4320
gtgccgcctc ctggtgtccg atattcagac aatccagcct tccctgaaca gcgttaatga  4380
gggcggacag aaaattaaaa acgaggccga acccgagttc gcttctcgcc tggagactga  4440
actgaaggag ctgaataccc agtgggacca tatgtgtcaa caggtctacg cacgcaaaga  4500
ggcactgaag ggcggtctgg agaagactgt ctcactccag aaggacctga gcgagatgca  4560
cgagtggatg acccaggccg aagaggaata cctggagcgt gattttgagt ataagacccc  4620
agacgaactc cagaaagccg ttgaagagat gaagagggct aaggaggaag cccaacagaa  4680
ggaggcgaaa gtgaagctcc tgacagagtc cgtgaactcc gtcatcgctc aagctcctcc  4740
cgtggctcag gaggccctca agaaagagct ggaaactctg accacaaatt accagtggtt  4800
gtgtacccgc ttgaacggta agtgcaagac cctggaagag gtgtgggcct gctggcacga  4860
gctcctgtcc tatcttgaga aggcgaacaa atggctgaac gaagtggaat tcaagttgaa  4920
aacaactgag aacattccgg gaggcgctga ggaaatctct gaggtgctgg actctctgga  4980
aaatctgatg cgtcattctg aagacaatcc taaccagatc aggattctgg cacagaccct  5040
cactgacgga ggcgttatgg acgaacttat caacgaggaa ctggagacat tcaattcccg  5100
ttggcgtgag ctgcacgaag aggccgtgcg ccgtcagaag ttgctggaac agtctatcca  5160
gtccgcccag gagacagaga aatctctcca cctgatccag gagagtctga cgtttatcga  5220
taagcagctg gctgcctaca tcgccgacaa ggtggacgct gcccagatgc cccaagaggc  5280
tcagaagatc cagtccgacc tgacgtctca tgaaatcagc ctggaagaga tgaaaaagca  5340
caaccagggc aaagaggctg cccagcgcgt cctctcccag attgacgtgg ctcagaaaaa  5400
gttgcaggac gtgagcatga agtttaggct gttccagaaa cccgccaact tcgaacagag  5460
actgcaggag tctaagatga tcctggatga ggtcaagatg cacctccctg ctctggaaac  5520
aaaatctgtg gagcaggagg tcgtgcagtc acaactgaac cattgtgtga acctctacaa  5580
gtctctcagc gaggtgaagt ccgaggtcga gatggtgatc aagaccggac gccagattgt  5640
gcagaaaaag cagacagaga acccaaagga gctggacgaa cgggtgaccg ccctgaagct  5700
ccactacaac gagttgggtg ccaaagtcac tgaaagaaag caacagctgg agaagtgtct  5760
gaagctgagc cgcaagatgc gcaaagaaat gaacgtcttg accgagtggt tggcggccac  5820
cgacatggag ctgaccaaga gatccgctgt ggagggcatg ccctccaacc ttgactcaga  5880
ggtggcctgg ggcaaggcca cacagaagga gatcgaaaaa cagaaggtgc atcttaaatc  5940
aatcactgag gtgggcgaag ctctgaagac agtgctgggc aagaaagaga cacttgtaga  6000
ggacaagctc tcccttctga atagcaattg gatcgccgta actagtcgcg cggaggaatg  6060
gctgaacctc ctgttggaat accagaaaca catggaaacc ttcgatcaga acgtggacca  6120
tattaccaag tggattatcc aggctgacac tctcctggac gagtctgaga aaaagaaacc  6180
ccagcaaaag gaagatgtgc tgaagcgcct gaaggcggaa ttgaacgaca tccgccccaa  6240
ggttgattcc acccgcgacc aagcggccaa ccttatggct aaccgcgggg accattgcag  6300
aaaactggtg gaaccgcaga tctctgagct gaaccacaga ttcgccgcga tttctcacag  6360
aattaagact ggcaaggcct ccatccctct gaaagagctg gagcagttca actctgatat  6420
tcagaagctt ctggagcccc tggaggcaga aatccaacag ggcgtcaacc tgaaagagga  6480
agactttaat aaggacatga atgaggataa cgaaggtacc gtcaaggagc tcctgcagag  6540
gggcgacaat ctgcagcaaa gaatcactga cgaacgtaag cgcgaagaga ttaagatcaa  6600
gcaacagctg ttgcagacta agcacaacgc cctgaaggat ctgaggtccc agcgcaggaa  6660
aaaggccctg gagatttccc accagtggta ccagtacaag cgccaggccg atgaccttct  6720
gaagtgcctc gacgatatcg agaaaaagct ggcctcactg cccgagcccc gcgacgagcg  6780
caagatcaag gagattgacc gtgagctcca gaagaaaaag gaggaactga acgcggtgcg  6840
cagacaggcc gagggcctct ccgaggacgg cgctgcgatg gctgttgagc ccactcagat  6900
ccaactgagc aagcggtgga gagagatcga gtctaagttc gcgcaattta ggcgcctcaa  6960
cttcgcccag attcacacgg tccgtgagga aacgatgatg gtgatgacag aggatatgcc  7020
actggaaatc agctacgtgc ccagtacata tctcaccgaa atcacccatg tgtcccaggc  7080
tctcctggag gtggaacagt tgctcaacgc tcccgacttg tgcgctaagg acttcgagga  7140
cctgttcaag caggaagaga gcctgaaaaa cattaaggac tccctgcaac agtcaagcgg  7200
ccgcatcgat atcattcatt ctaagaaaac cgctgccctg cagtctgcaa cccccgtaga  7260
gcgcgtcaaa ctgcaggaag ctctcagcca actggatttc cagtgggaga aggtgaacaa  7320
gatgtataag gatcgtcagg gccggttcga ccgctctgtg gagaagtggc gccgtttcca  7380
ctacgatatc aagattttca atcaatggtt gaccgaggca gagcagttcc tcagaaagac  7440
acagatccct gaaaattggg agcatgccaa gtacaagtgg tatctgaagg agctgcagga  7500
cgggatcgga caacgtcaga ccgtggtccg caccctgaac gcaaccggcg aggaaattat  7560
ccaacagtct agcaagacag atgctagcat cctccaggag aagctcggaa gcctcaacct  7620
tcgctggcag gaggtgtgca agcagctgtc agacaggaag aaacgcctgg aggaacagaa  7680
gaacatcctt tcagagttcc agagagatct gaacgaattc gtgctttggc ttgaagaggc  7740
cgataacatc gcaagcatcc cactggagcc tggtaaggaa cagcaattga aggagaagct  7800
ggagcaggta aagctgctcg tggaagagct gcctctgagg cagggaattc tcaagcagct  7860
caacgagact ggggggcccgg ttttggtgag cgccccaatt agcccagaag agcaggacaa  7920
gttggagaac aagctgaagc agaccaacct gcagtggatc aaggtgtccc gcgcactgcc  7980
cgaaaagcag ggagagattg aggcccagat caaggatctg ggacagctgg agaaaaagct  8040
ggaagacctg gaggaacagc tgaaccattt gctcctgtgg ttgtccccca tcagaaatca  8100
gctggaaatc tacaaccaac cgaaccagga aggtccgttt gatgttaagg aaaccgagat  8160
cgctgtgcag gcgaagcagc ctgacgtaga agagatcctg tcaaagggac agcacctcta  8220
caaggagaag cccgccaccc agccagtcaa gcggaagctc gaagacctgt ccagcgagtg  8280
gaaagccgtc aaccgcctcc tgcaagagct gcgtgccaag caaccggacc tggcgccagg  8340
tctgactacc attggcgcaa gtcctaccca gactgtcacc ctggtgaccc aacccgttgt  8400
gacaaaggaa accgccatca gcaagctgga gatgcctagc tctttgatgc tggaggttcc  8460
cgccctcgcc gacttcaacc gtgcttggac agaactgacc gactggctgt ccctcctgga  8520
ccaagtgatc aagagccagc gcgtgatggt gggtgatctt gaggatatta acgaaatgat  8580
tatcaagcag aaggccacca tgcaggactt ggagcagagg cgcccccagt tggaggaact  8640
gatcaccgcc gcgcagaatc tgaaaaacaa aacttccaat caggaagcga gaaccatcat  8700
tacagacaga attgagagaa ttcaaaacca gtgggacgaa gtgcaagaac acctccagaa  8760
ccggcgtcaa cagctgaacg agatgctgaa ggattccact caatggctgg aagctaagga  8820
```

```
agaggccgag caggtccttg gacaggcacg cgctaagctg gagtcctgga aagaaggccc  8880
ctatacagtg gacgcaattc aaaagaaaat caccgagacg aagcaactgg ccaaggacct  8940
gagacagtgg caaaccaacg ttgatgtggc taatgacctg gccttgaagc tcctgcgtga  9000
ctactccgcg gatgacacta gaaaggtgca catgatcacc gagaatatca acgctagctg  9060
gcgctccatc cataagcgtg tgagtgagcg cgaagccgct ctggaggaaa cccatcgcct  9120
gcttcaacag tttcctttgg acctggaaaa gttcctggcc tggctcacag aagccgagac  9180
aaccgccaac gtgctgcagg acgccacccg taaggagcgc ttgctggagg atagtaaggg  9240
ggtgaaggag ttgatgaagc agtggcaaga tctgcagggg gaaatcgagg cacataccga  9300
cgtctatcat aacctggatg agaattccca gaaaatcctg cgcagcttgg agggcagtga  9360
tgacgcggtg cttctgcaac ggcgcttgga caacatgaac ttcaagtggt ccgagttgcg  9420
taaaaagagt ctgaacattc gctcccacct ggaggcttct agtgaccagt ggaagcgcct  9480
gcacctgagc ctgcaagaac tgctcgtgtg gctgcaactg aaggatgacg agttgagtcg  9540
tcaggcccct atcggaggtg actttccggc tgtccagaaa cagaacgacg tgcatagggc  9600
atttaagcgc gagttgaaga caaaggagcc agtcattatg tccacgctgg aaaccgtgcg  9660
cattttcctg actgagcagc ctctggaggg gctggagaag ctgtaccagg agcctcgcga  9720
gttgcccccct gaagagcgtg cccagaatgt gacccgcctg ttgcgtaagc aggccgagga  9780
agtgaacacc gagtgggaga agctgaacct gcattccgcg gattggcaga ggaagattga  9840
cgagacgctg gagaggctcc gtgagttgca ggaggcaacc gacgaactgg acctcaagct  9900
gcgtcaagca gaggtgatca aggggagttg gcagccggtc ggcgatttgc tgatcgactc  9960
cctgcaggat cacctggaaa aggttaaagc tttgcgcggg gaaattgccc cgctgaagga  10020
gaacgtgagc cacgttaacg atctggccag acagctgacc actctgggta tccagctgag  10080
cccgtacaat ctgagcaccc tcgaagactt gaatacgaga tggaaactcc tgcaggtggc  10140
agtggaggac agggtgcgcc aattgcacga ggcccaccgg gactttggac cggccagcca  10200
gcatttcctc agtacctctg ttcagggccc gtgggagcgg gccatctccc ccaacaaggt  10260
cccctattac atcaaccatg aaacccagac tacctgttgg gaccacccta aaatgactga  10320
gttgtatcaa tctctggccg acttgaataa cgtgcgcttc tcagcctaca ggactgcaat  10380
gaaactcaga cgcctccaaa aggccctttg tctggacttg ctgtccctta gcgctgcctg  10440
tgatgctctg gatcagcaca atttgaaaca aaacgaccag ccgatggaca tcctccagat  10500
tatcaactgc ctgactacca tctacgacag actggaacag gagcataata acctggtgaa  10560
cgtcccccctg tgcgtggaca tgtgcctgaa ctggctgctc aatgtgtatg acacgggtag  10620
aacaggacgg atcagggtcc tgtcctttaa gaccggtatc atttctctgt gtaaggcaca  10680
tctggaggac aagtaccgct acctgtttaa gcaggtcgcc agctccactg gcttctgcga  10740
tcaaaggcgg ctgggtctgc tcctgcacga ctccattcag atcccgagac agttgggtga  10800
agtggcgtcc ttcggcggtt ctaatatcga gcctagcgtc cgcagctgtt tccaattcgc  10860
caataacaag ccggagatcg aagcggccct tttcctggac tggatgcgtc tggaacctca  10920
gagcatggtt tggcttccgg tgcttcatcg cgtggccgct gccgaaaccg ctaaacatca  10980
ggccaaatgt aacatctgta aggaatgccc gattatcggt ttccggtacc gtagcctcaa  11040
gcatttcaac tatgatattt gtcaatcttg cttctttagc ggacgggtgg ccaaaggcca  11100
caaaatgcac tacccgatgg tcgagtattg cactcctaca acctccggcg aggacgtgcg  11160
cgattttgcc aaagtgctga aaaacaagtt tagaaccaag cgttactttg ccaagcatcc  11220
acgtatgggc tacctgcctg tccagaccgt tctggaaggt gataacatgg agacacccgt  11280
gactttgatt aacttttggc cagtagactc tgctccggca agctcccctc agctctccca  11340
cgatgacact cacagccgta tcgagcacta cgcctctcgc ctggctgaga tggagaactc  11400
taacggttca tacctgaatg acagtatctc cccaaacgag agtatcgatg acgaacatct  11460
gctcattcag cattactgtc aatccttgaa tcaggacagc cccctgtccc agccacggtc  11520
cccggcccag atcctgattt cactggagtc cgaagagaga ggggaactgg aaaggatcct  11580
cgctgacctg gaagaggaaa accggaacct gcaggctgaa tacgaccgct tgaagcagca  11640
acacgagcac aagggcttga gcccgttgcc aagccctccg gagatgatgc caactagccc  11700
tcagagccca cgggatgccg agctcatcgc tgaagctaag ttgctgagac agcacaaggg  11760
acgtctggag gcccgcatgc agatcctgga ggatcataat aaacagttgg agagccaact  11820
gcataggctg cgccagctcc tggagcagcc acaggccgag gctaaggtca acggaactac  11880
cgtttccagc ccgtccacat ctctgcagcg ctcagatagt tcccagccta tgttgctgag  11940
agtggttgga tctcagacct ccgactcaat gggcgaagag gacttgctgt ctcccccaca  12000
ggacactagc acaggactcg aagaggtgat ggaacagctc aataactctt ttccttctag  12060
tcggggtcgc aataccccctg gaaagcccat gcgcgaagac accatgtaat agctcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg ggtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgggaag atgtctactg agctgtgcga tccctgctgg ggactttccg ctggggactt  12780
tccgctgggg actttccgcc ttcagctaag gaagctacca atatttagag gtacattttg  12840
ttctagaaca aaatgtaccg gtacattttg ttctggtaca ttttgttct             12889
```

```
SEQ ID NO: 26          moltype = DNA  length = 12889
FEATURE                Location/Qualifiers
source                 1..12889
                       mol_type = other DNA
                       note = MHCK7-hBGi-DMD-3-WPRE3-DTS
                       organism = synthetic construct
SEQUENCE: 26
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
```

```
agacctttca tgggcaaacc ttggggccct gctgtctagc atgccccact acgggtctag  240
gctgcccatg taaggaggca aggcctgggg acacccgaga tgcctggtta taattaaccc  300
agacatgtgg ctgccccccc ccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtccccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggccctttttg ctaatcatgt  960
tcatacctct tatcttcctc ccacagctcc tgggcaacgt gctggtctgt gtgctggccc  1020
atcactttgg caaagaattg cgatcgccac catgctgtgg tgggaagagg tggaggactg  1080
ttacgagaga gaggacgtgc agaagaagac attcaccaag tgggtgaacg ctcagttcag  1140
caagttcggc aagcagcaca tcgagaacct gtttagcgat ctacaagatg gcagaagact  1200
gctggacctg ctggagggcc tgaccgggca gaagctgccc aaagaaaagg ggtctacaag  1260
agtgcacgcc ctgaacaacg tgaacaaggc cctgagagtg ctgcagaaca acaacgtgga  1320
cctggtgaac atcggcagca ccgacatcgt ggacggcaac cacaagctga ccctgggcct  1380
gatctggaac atcatcctgc actggcaagt gaagaacgtg atgaagaaca tcatggccgg  1440
cctgcagcag accaacagcg agaagatcct gctgagctgg gtgagacaga gcacaagaaa  1500
ctacccccaa gtgaacgtga tcaacttcac cacaagctgg agcgacggcc tggccctgaa  1560
cgccctgatc cacagccaca gacccgacct gttcgactgg aacagcgtgg tgtgtcagca  1620
gagcgccaca cagagactgg agcacgcctt caacatcgct agatatcagc tgggcatcga  1680
gaagttactg gaccccgaag atgtggacac cacctacccc gacaagaaga gcatcctgat  1740
gtacatcaca agcctgttcc aagtgctgcc tcagcaagtg agcatcgagg ccatccaaga  1800
agtcgagatg ctgcctagac cccccaaggt gaccaaggag gagcactttc agctgcacca  1860
tcagatgcac tactctcagc agatcacagt cagcttggca caaggctacg agagaacaag  1920
cagccccaag cctagattca agagctacgc ctacacccaa gccgcctacg tgaccacaag  1980
tgaccccaca agaagcccct tcccttctca gcacctggag gcccccgagg acaagagctt  2040
cggcagcagc ctgatggaga gcgaggtgaa cctggacaga tatcagaccg cgttagaaga  2100
agtgttgagc tggctgctga gcgccgagga caccctgcaa gcccaaggcg agatcagcaa  2160
cgatgtggag gtggtgaagg atcagttcca cacccacgag ggctacatga tggacctgac  2220
cgcccaccaa ggcagagtgg gcaacatcct gcagctgggc agcaagctga tcggcaccgg  2280
caagctgagc gaggacgagg aaaccgaggt tcaagagcaa atgaacctgc taaacagcag  2340
atgggagtgc ctgagagtgg ctagcatgga aaagcagagt aacctgcaca gagtgctgat  2400
ggacctgcag aatcagaaat tgaaagaact taatgattgg ctgaccaaga ccgaggagag  2460
aacaagaaag atggaggagg agcccctggg ccccgacctg gaggacctga agagacaagt  2520
gcagcagcac aaggtgctgc aagaggacct ggagcaagag caagtgagag tgaactctct  2580
gacacacatg gtggtggtag tggacgagag cagcggcgat cacgctaccg cggcgctgga  2640
agagcagctg aaagtgctgg gcgacagatg ggccaacatc tgcagatgga ccgaggacag  2700
atgggtgctg ctgcaagaca tcctgctgaa gtggcagaga ctgaccgagg agcagtgcct  2760
gttcagcgcc tggctgagcg agaaggaaga cgctgtgaac aagatccaca ccaccggctt  2820
caaggatcag aacgagatgc tgagctccct ccaaaagctc gcagtgctga aggccgacct  2880
ggaaaagaaa aaacagtcga tgggcaagct gtacagcctg aagcaagacc tgctgagcac  2940
cctgaagaac aagagcgtga cacagaagac cgaggcctgg ctggacaact tcgctagatg  3000
ctgggacaac ctggtacaga agttagagaa gtctaccgct cagatcagcc aagccgtaac  3060
caccacacaa cctagcctga ctcagaccac cgtgatggaa accgtgacca ccgtgacaac  3120
ccgtgagcag atcctggtga agcacgccca agaggagctg cccccccccc cccctcagaa  3180
gaagagacag atcaccgtgg actcagagat tcgcaagaga ctggacgtgg acatcaccga  3240
gctgcacagc tggatcacaa gaagcgaggc cgtgctgcag agccctgagt tcgcgatctt  3300
tagaaaggag ggcaacttca gcgacttgaa ggagaaagtg aacgccatcg agagagagaa  3360
ggccgagaag ttcagaaagt tgcaagacgc ctcaagaagc gcccaagccc tggtggagca  3420
gatggttaac gaaggcgtga atgccgacag catcaagcaa gctagcgagc agctgaatag  3480
ccggtggatt gaattctgtc agctgctgag cgagagatta aactggctgg agtatcagaa  3540
caacatcatc gccttctaca atcagctgca gcaactagaa caaatgacca ccaccgccga  3600
gaactggcta aagattcagc ccaccacccc tagcgagccc accgccatca aatctcagct  3660
gaaaatttgc aaggacgaag tgaacagact gtcggacctg cagcctcaaa tcgaaagact  3720
gaaaattcag agcatcgcac ttaaggagaa gggccaagga cccatgttcc tggacgccga  3780
cttcgtggcc ttcaccaacc acttcaagca agtgttcagc gacgtgcaag ctagagagaa  3840
ggagctgcag accatcttcg acaccctgcc ccccatgaga taccaagaaa ccatgagcgc  3900
catcagaacc tgggtgcagc agagcgaaac caagctgagc atccctcagc tgagcgtgac  3960
cgactacgag atcatggagc aaagactggg agagctgcaa gccctgcaga gcagcctgca  4020
agagcagcag agcggcctgt actacctgag caccaccgtg aaggagatgt cgaagaaagc  4080
cccgtcggag atcagcagaa agtatcagag cgagttcgag gagatcgagg gcagatggaa  4140
gaagctgagc agccaactgg tggaacactg tcagaaatta gaagaacaga tgaacaagct  4200
gagaaagatt cagaaccaca ttcagaccct gaagaagtgg atggccgagg tggacgtgtt  4260
cctgaaagag gagtggcccg ccctgggcga ttccgaaatc ttaaaaaagc agctgaagca  4320
gtgcagactg ctggtgtcag atatccaaac cattcaacca agcctgaaca gcgtgaacga  4380
aggcgggcag aagatcaaga acgaggccga gcccgagttc gctagcagac tggaaaccga  4440
gctgaaggag ctgaatacac agtgggacca catgtgtcag caagtgtacg ctagaaagga  4500
agcgctgaag ggcgggctgg agaagaccgt tagcctgcaa aaggatctga gcgagatgca  4560
cgagtggatg acccaagccg aggaggagta cctggagaga gacttcgagt acaagacccc  4620
cgacgagctg cagaaggccg tcgaggaaat gaagagagcg aaggaggagg ctcagcagaa  4680
ggaagccaag gtgaagctgc tgactgaatc tgtcaacagt gtgatagctc aagcaccccc  4740
cgttgcccaa gaggcactaa agaaggagct ggaaactctg accaccaact atcagtggct  4800
gtgcacaaga ctgaacggca agtgcaagac cctggaggaa gtgtgggcct gctggcacga  4860
gctgctgagc tacctggaga aggccaacaa gtggctgaac gaggtggagt tcaagctgaa  4920
```

gaccaccgag aacatccccg gcggcgccga ggagatcagc gaggtgctgg acagcctgga 4980
gaacctgatg agacacagcg aggacaaccc caatcagatc agaatcctgg ctcagaccct 5040
gaccgacggc ggcgtgatgg acgagctgat caacgaggag ctggaaacct ttaactctag 5100
atggcgagaa ctgcacgagg aggccgtgag aagacagaag ctgctggagc aaagcattca 5160
gagcgcccaa gaaaccgaga agagcctgca cctgatccaa gagagcctga ccttcatcga 5220
caagcagctg gccgcctaca tcgccgacaa ggtggacgcc gctcagatgc cacaagaggc 5280
tcagaagatt cagtccgatc tgacaagcca cgagatcagc ctggaggaga tgaaaaaaca 5340
caaccaaggc aaggaggccg ctcagagagt gctgtctcag atcgacgtgg ctcagaagaa 5400
gctgcaagac gtgagcatga agttcagact gtttcagaag cccgccaact tcgagcagcg 5460
actgcaagag agcaagatga tcctggacga ggtgaagatg cacctgcccg ccctggaaac 5520
caagagcgtg gagcaagagg tggtgcagtc tcagttgaac cactgcgtga acctgtacaa 5580
gagcctgtcg gaggtcaaga gtgaggtcga gatggtgatc aaaactggga gacagatcgt 5640
gcaaaaaaag cagaccgaga accccaagga gctggacgag cgtgttaccg ccctgaagct 5700
gcactacaac gagctgggcg ccaaggtgac cgagagaaag cagcagctgg agaagtgcct 5760
gaagctgagc agaaagatga gaaaggagat gaacgtgctg accgagtggc tggccgccac 5820
cgacatggag ctgaccaaga gaagcgccgt ggagggcatg cctagcaacc tggacagcga 5880
ggtggcctgg ggcaaggcca cacagaagga gatcgagaag cagaaggtgc acctgaagag 5940
catcaccgag gtgggcgagg ccctgaagac cgtgctgggc aagaaggaaa ccctggtgga 6000
ggacaagctg agcctgctga actcgaactg gatcgccgtg acaagcagag ccgaggagtg 6060
gctgaacctg ctgttagagt accaaaaaca catggaaacc ttcgatcaga acgtggacca 6120
catcaccaag tggatcatcc aagccgacac cctgctggac gaaagcgaaa agaagaagcc 6180
gcaacaaaag gaggatgtgc tgaagagact gaaggccgaa ctgaacgata tcagacccaa 6240
ggtggacagc acacgggacc aagccgccaa cctgatggcc aacagaggcg accactgcag 6300
aaaactggtg gagcctcaga tcagcgagct gaaccacaga ttcgccgcca tcagccacag 6360
aatcaaaacc ggcaaagcga gcatcccctt gaaggaactg gagcaattta acagcgacat 6420
ccaaaaattg ctcgaaccac tggaggccga gattcagcaa ggcgtgaacc tgaaggaaga 6480
ggacttcaac aaggacatga acgaggacaa cgagggcacc gtgaaagaac tgctgcagag 6540
aggcgacaac ctgcagcaga gaatcaccga cgagagaaag agagaggaga tcaagatcaa 6600
gcagcagctg ctgcagacta agcacaacgc cctgaaggat ctgagatctc agaggagaaa 6660
aaaggctctg gaaatttcac atcagtggta tcagtacaag agacaagcag acgacctgct 6720
gaagtgcctg gacgacatcg agaagaagtt agctagcctg cccgagccta gagacgagag 6780
aaagatcaag gagatcgaca gagagttaca aaagaagaag gaggagctga atgcggtaag 6840
aagacaagcg gaaggcctgt ccgaggacgg cgcagccatg gccgtggagc ccacacagat 6900
tcagctcagc aagagatgga gagagatcga gagcaagttc gctcagttca gaagactgaa 6960
cttcgctcag atccacaccg tgagagagga aaccatgatg gtgatgaccg aggacatgcc 7020
cctggagatc tcatacgttc ctagcaccta cctgaccgag atcacccacg tgagccaagc 7080
cctgctggag gtggagcagc tgctgaacgc ccccgacctg tgcgccaagg acttcgagga 7140
cctgttcaaa caagaggaga gcctgaagaa catcaaggac agcctgcagc aaagtagcgg 7200
cagaatcgac atcatccaca gcaagaagac cgccgccctg cagagcgcca cccccgtgga 7260
gagagtgaag cttcaagagg ccctttcgca gctggatttt cagtgggaga aggtgaacaa 7320
aatgtacaag gacagacaag gcagattcga cagaagcgtg gagaagtgga gaagattcca 7380
ctacgacatc aagatcttca atcagtggct gaccgaggca gagcagttcc tgagaaagac 7440
acagatcccc gagaactggg agcacgccaa gtacaagtgg tacctgaagg agctgcaaga 7500
cggcatcggg cagagacaga ccgtggtgag aaccctgaac gccaccggcg aggagatcat 7560
ccaacaaagc tccaaaaccg acgctagcat cctgcaagag aaactgggca gcctgaacct 7620
gagatggcaa gaggtgtgca agcagctgag cgaccgcaaa aaacggttag aggagcagaa 7680
gaacatcctg agcgagtttc agcgggacct gaacgagttc gtgctgtggc tggaggaggc 7740
cgataacatc gctagcatcc ccctggagcc cggcaaggag cagcagttaa aagaaaaact 7800
tgagcaagtg aagctgctgg tggaggagct gcccctgaga caaggcatcc tgaagcagct 7860
gaacgagact ggcggccccg tgctggtgag cgcccccatc agccccgagg agcaagacaa 7920
gctggagaac aagctgaagc agaccaacct gcagtggatc aaggtgagca gagccctgcc 7980
cgagaagcaa ggcgaaatcg aggcccaaat aaaggacctg ggccagctgg agaagaaact 8040
cgaagacttg gaagaacaac tcaaccactt gctgctgtgg ctgagcccca tcagaaatca 8100
gctggagatc tacaatcagc ccaaccaaga ggggccattc gacgtgaagg aaaccgagat 8160
cgccgtgcaa gccaagcagc ccgatgtgga ggagatcctg agcaaggggc agcacctgta 8220
caaggagaag cccgccacac agcccgtcaa gcgtaaacta gaggatcttt cctctgagtg 8280
gaaggccgtg aaccgtctgc tacaagagct gcgggctaag caacccgact tagcgcccgg 8340
cctgaccacc atcggtgcaa gccccacgca gaccgtgacc ctggtgaccc aacccgtggt 8400
gaccaaggaa accgccatca gcaagctgga gatgcctagc agcctgatgc tggaggtgcc 8460
cgccctggcc gacttcaaca gagcctggac cgagctgacc gactggctga gcctgctgga 8520
ccaagtgatc aagtctcaga gagtgatggt gggcgatctg gaggacatca atgagatgat 8580
catcaagcag aaggccacca tgcaagacct ggagcagaga agacctcagc tggaggagct 8640
gatcaccgcc gctcagaacc tgaaaaacaa gacgagcaac caagaggcta gaaccatcat 8700
caccgacaga atcgagagaa ttcagaatca gtgggacgag gtgcaagagc acctgcagaa 8760
cagaagacag caactaaacg aaatgctcaa ggacagcaca cagtggctgg aggccaagga 8820
ggaggcggag caagtgttgg gccaagctag agccaagctg gagagctgga aggagggacc 8880
ctacaccgtg gacgccattc agaagaagat caccgaaacc aagcagctgg ccaaggacct 8940
gcgacagtgg cagaccaacg tggacgtggc caacgatctt gccctgaagc tgctgcgcga 9000
ctatagcgcc gacgacacaa gaaaggtgca catgatcacc gagaacatca acgctagctg 9060
gcgtagcatc cacaagagag tgagcgagag agaggcggct ttggaggaaa cccatagact 9120
gctgcagcag tttcccctgg acctggagaa gttcctggcc tggctgaccg aagccgaaac 9180
aaccgccaac gtgctgcaag acgccacaag aaaggagaga ctgctggagg acagcaaggg 9240
cgtgaaggag ctgatgaagc agtggcaaga cctgcaaggc gagatcgaag cgcacaccga 9300
cgtgtaccac aacctggacg agaactctca gaagatcctg agaagcctgg agggcagcga 9360
cgacgccgtg ctgttacaga gaaggctgga caacatgaac ttcaagtgga gcgagctgag 9420
aaagaagagc ctgaacatca gaagccacct ggaggctagc agcgatcagt ggaagagact 9480
gcacctgagc ctgcaagagc tgctggtctg gcttcagttg aaggacgatg agctgagcag 9540
acaagccccc atcggcggcg acttccccgc cgtgcagaag cagaacgacg tgcatagagc 9600
cttcaagaga gagctgaaga ccaaggagcc cgtgatcatg agcaccctgg aaacggtgag 9660

```
aatcttcctg accgagcagc ccctggaggg cctggagaag ctgtaccaag agcctagaga  9720
gctgcccccc gaggagagag ctcagaacgt gacaagactg ctgagaaagc aagccgaaga  9780
ggtgaacacc gagtgggaga agctgaacct gcacagcgcc gactggcaga gaaagatcga  9840
cgaaaccctg gagagactga gagaattgca agaggcgacc gacgagctgg acctgaagct  9900
gagacaagcc gaggtcatca agggcagctg gcagcccgtg ggcgatctat taattgactc  9960
tctacaagac cacctggaga aagtgaaggc cctgagaggc gagatcgccc ccctgaagga  10020
gaacgtgagc cacgtgaatg atctggcacg tcagctgacc accctgggca tacaactgtc  10080
cccctataac ctgagcacac tggaggattt gaatactaga tggaagctgc tgcaagtggc  10140
cgtggaggac agagtaagac aattacatga ggcccacaga gacttcggcc ccgcttctca  10200
gcacttcctg agcacaagcg tgcaaggccc ctgggagaga gccatttccc ccaacaaggt  10260
cccctactac atcaaccacg agacacagac cacctgctgg gaccacccca agatgaccga  10320
gctgtatcag agcctcgccg atctgaacaa tgtgagattc agcgcctaca gaaccgccat  10380
gaagctgaga agactgcaga aggccctgtg cctggactta ttaagcctga gcgccgcctg  10440
cgacgccctg gatcagcaca acctgaagca aaacgaccaa cccatggaca tcctgcagat  10500
catcaactgc ctcaccacca tatacgacag actggaacaa gagcacaaca acctggtgaa  10560
cgtgcccctg tgcgtggaca tgtgcctgaa ctggctgctg aacgtgtacg acaccggcag  10620
aaccggcaga atcagagtgc tgagcttcaa gaccggcatc atcagcctgt gcaaggccca  10680
cctggaggac aaatacagat accttttcaa acaagtggct agcagcaccg gcttctgcga  10740
ccaaagaaga ctgggtctgc tgctgcacga cagcattcag atccctagac agctgggcga  10800
ggtggctagc ttcggcggca gcaacatcga gcctagcgtg agaagctgct ttcagttcgc  10860
caacaacaag cccgagatag aggcagccct cttcttagac tggatgagac tggagcctca  10920
gagcatggta tggctgccgg tcctgcacag agtggccgcc gccgaaaccg ccaagcacca  10980
agccaagtgc aacatctgca aggagtgccc catcatcggc ttcagataca gaagcctgaa  11040
gcacttcaac tacgacatct gtcagagctg cttcttcagc ggcagagtgg ccaagggcca  11100
caagatgcac taccccatgg tggagtactg cacccccacc acaagcggcg aggacgtgag  11160
agacttcgcc aaggtgttga agaataagtt tagaaccaag agatacttcg ccaagcaccc  11220
tagaatgggc tacctgcccg tgcagaccgt gctggagggc gacaacatgg aaacccccgt  11280
gaccctgatc aacttctggc ccgtggacag cgcccccgct agcagccctc agctgagcca  11340
cgacgacacc cacagcagaa tcgagcacta cgctagcaga ctggccgaga tggagaacag  11400
caacggcagc tacctgaacg acagcatcag cccgaatgag agcatcgacg acgagcacct  11460
gctgattcag cactactgtc agagcctgaa ccaagacagc cccctgtctc agcctagaag  11520
ccccgctcag atcctgatca gcctggagag cgaggagaga ggcgagctgg agagaatcct  11580
agcagatctg gaggaagaga acagaaacct gcaagccgag tatgaccgac tgaaacagca  11640
acatgagcac aaaggcctga gcccactgcc ctccccccccc gagatgatgc ccacaagccc  11700
tcagagccct agagacgccg agctgatcgc tgaagcgaag ttacttagac aacacaaggg  11760
cagactggag gctagaatgc agatcctgga ggaccacaac aagcagctgg agtctcagct  11820
gcacagactg aggcagctgc tggaacagcc ccaagccgag gccaaagtga acggcaccac  11880
cgtgagcagt cctagcacaa gcctgcagag aagcgacagc tctcagccca tgctgctgag  11940
agtggtgggc tctcagacaa gcgacagcat gggcgaggag gatctgctga gtccgcccca  12000
agacacaagc accggcctgg aagaggtgat ggagcaactg aacaatagct tccctagcag  12060
cagaggcaga aacacccccg gcaagcccat gagagaggac accatgtgat gactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg ggtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgggaag atgtctactg agctgtgcga tccctgctgg ggactttccg ctggggactt  12780
tccgctgggg actttccgcc ttcagctaag gaagctacca atatttagag gtacattttg  12840
ttctagaaca aaatgtaccg gtacattttg ttctggtaca ttttgttct              12889
```

```
SEQ ID NO: 27          moltype = DNA  length = 12889
FEATURE                Location/Qualifiers
source                 1..12889
                       mol_type = other DNA
                       note = MHCK7-hBGi-DMD-4-WPRE3-DTS
                       organism = synthetic construct
SEQUENCE: 27
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgccccact acgggtctag  240
gctgcccatg taaggaggca aggcctgggg acacccgaga tgcctggtta taattaaccc  300
agacatgtgg ctgccccccc ccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtccccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggccctttg ctaatcatgt  960
tcatacctct tatcttcctc ccacagctcc tgggcaacgt gctggtctgt gtgctggccc  1020
```

-continued

```
atcactttgg caaagaattg cgatcgccac catgctttgg tgggaagaag tcgaggactg  1080
ctacgagcgc gaggacgtgc agaagaaaac cttcaccaaa tgggtcaacg cccagttcag  1140
caagttcggc aagcagcaca tcgagaacct gttcagcgac ctgcaggatg gcagaaggct  1200
gctggatctg ctggaaggcc tgacaggaca gaagctgccc aaagagaagg gcagcacaag  1260
agtgcacgcc ctgaacaacg tgaacaaggc cctgagagtg ctgcagaaca acaacgtgga  1320
cctggtcaac atcggcagca ccgacatcgt ggacggcaac cacaaactga ccctgggcct  1380
gatctggaac atcatcctgc actggcaagt gaagaacgtg atgaagaaca tcatggccgg  1440
cctgcagcag accaacagcg agaagattct gctgagctgg gtccgacaga gcacccggaa  1500
ttaccctcaa gtgaacgtga tcaacttcac cacctcttgg agcgacggac tggccctgaa  1560
tgccctgatc cacagccaca gacctgacct gttcgactgg aacagcgtcg tgtgtcagca  1620
gagcgccaca cagaggctgg aacacgcctt caatatcgcc agataccagc tgggcatcga  1680
gaaactgctg gaccccgagg atgtggacac cacctatcct gacaagaaat ccatcctcat  1740
gtacatcacc agcctgttcc aggtgctgcc ccagcaggtt tccatcgagg ccattcaaga  1800
ggtcgagatg ctgcccagac ctcctaaagt gaccaaagag gaacacttcc agctgcacca  1860
ccagatgcac tactctcagc agatcaccgt gtctctggcc cagggctacg agagaacaag  1920
cagccccaag cctcggttca agagctacgc ctatacacag gccgcctacg tgaccaccag  1980
cgatcctaca agaagcccat ttcctagcca gcatctggaa gcccctgagg acaagagctt  2040
tggcagcagc ctgatggaaa gcgaagtgaa cctggaccgc taccagacag ccctggaaga  2100
ggttctgagc tggctgctgt ctgccgagga tacactgcag gctcagggcg agatcagcaa  2160
cgacgtggaa gtggtcaagg accagtttca cacccacgag ggctacatga tggacctgac  2220
agcccaccag ggcagagtgg gcaatattct gcagctgggc tccaagctga tcggcacagg  2280
caagctgagc gaggacgaag agacagaggt gcaagagcag atgaacctgc tgaacagcag  2340
atgggagtgt ctgagagtgg ccagcatgga aaagcagagc aacctgcacc gggtgctgat  2400
ggatctccag aaccagaagc tgaaagagct gaacgactgg ctgaccaaga ccgaggaacg  2460
gacccggaag atggaagagg aacctctggg acccgacctg gaagatctga aaagacaggt  2520
gcagcagcat aaggtgctgc aagaggacct cgaacaagag caagtgcgcg tgaacagcct  2580
gacacacatg gtggtggtcg tggatgagag cagcggagat catgccacag ccgctctgga  2640
agaacagctg aaggtgctgg gagacagatg ggccaatatc tgccggtgga ccgaggatag  2700
atgggtgctg ctccaggaca tcctgctgaa gtggcagcgg ctgacagagg aacagtgcct  2760
gtttagcgcc tggctgtccg agaaagagga cgccgtcaac aagatccaca ccaccggctt  2820
caaggatcag aatgagatgc tgagcagcct gcagaaactg gccgtgctga aggctgacct  2880
ggaaaagaaa aagcagtcca tgggcaagct gtactccctg aagcaggacc tgctgagcac  2940
actgaagaac aagtctgtga cccagaaaac cgaggcctgg ctggacaact tcgcccggtg  3000
ttgggataac ctggtgcaga agctggaaaa gtccaccgct cagatctctc aggccgtgac  3060
cacaacacag ccttctctga cccagaccac cgtgatggaa acagtgacca cagtgacaac  3120
ccgcgagcag atcctggtca agcacgccca agaagaactg cctcctccac ctcctcagaa  3180
gaaacggcag atcacagtgg acagcgagat ccggaagaga ctggacgtgg acatcaccga  3240
gctgcacagc tggatcacca gatccgaagc cgtgctgcag tcccctgagt tcgccatctt  3300
cagaaaagag ggcaacttct ccgacctgaa agagaaagtc aacgccatcg agagagagaa  3360
ggccgagaag ttccggaagc tgcaggacgc ctctagatct gcccaggctc tggtggaaca  3420
gatggtcaac gaaggcgtga acgccgacag catcaagcag gcctcagagc agctgaactc  3480
ccggtggatc gagttctgtc agctcctgag cgagagactg aactggctgg aataccagaa  3540
caatatcatt gccttctaca accagctcca gcagctcgaa cagatgacca ccacagccga  3600
gaattggctg aagatccagc ctaccacacc tagcgagccc accgccatta agagccagct  3660
gaaaatctgc aaggacgaag tgaatcggct gagcgatctg cagccccaga tcgaaagact  3720
gaaaatccag tctatcgccc tcaaagagaa aggacagggc cccatgttcc tggacgccga  3780
ttttgtggcc tttaccaacc acttcaaaca ggtgttctcc gacgtgcagg cccgggaaaa  3840
agagctgcag accatcttcg acaccctgcc tccaatgaga taccaagaga caatgagcgc  3900
catccggacc tgggtgcagc aaagcgagac aaagctgagc atcccacagc tgagcgtgac  3960
cgactacgag atcatggaac agagactggg cgaactgcag gccctccagt ctagcctgca  4020
agaacagcag tccggcctgt actacctgag cacaaccgtg aaagagatga gcaagaaggc  4080
ccctagcgag atctcccgga agtaccagag cgagttcgaa gagatcgaag gccggtggaa  4140
gaagctgtct agccagctgg ttgagcactg ccagaaactc gaagaacaaa tgaacaagct  4200
gcgcaagatc cagaatcaca tccagacgct gaagaaatgg atggccgagg tggacgtgtt  4260
cctgaaagaa gagtggcccg ctctgggcga ctccgagatt ctgaagaaac agctcaaaca  4320
gtgccggctg ctggtgtccg atatccagac aatccagcca agcctgaact ccgtgaatga  4380
aggcggccag aagatcaaga acgaggccga gcctgagttt gccagcagac tggaaaccga  4440
actgaaagaa ctcaacaccc agtgggacca catgtgccag caagtgtacg cccggaaaga  4500
ggccctgaaa ggcggactcg aaaagactgt gtctctgcag aaagacctgt ctgagatgca  4560
cgagtggatg acccaggccg aagaggaata cctggaacgg gacttcgagt acaagacccc  4620
tgatgagctg caaaaagccg tcgaggaaat gaagcgggcc aaagaagagg cccagcagaa  4680
agaagccaaa gtcaagctgc tgaccgagtc cgtgaatagc gttatcgctc aggcccctcc  4740
tgtggctcaa gaggctctca agaaagaact ggaaactctg accaccaact accagtggct  4800
gtgcaccaga ctgaacggca agtgcaagac actggaagaa gtgtgggcct gctggcacga  4860
actgctgtcc tatctggaaa aggccaacaa gtggctgaac gaggtggaat tcaagctgaa  4920
aaccaccgag aacatccctg gcggcgctga agagattagc gaggtgctgg acagcctgga  4980
aaacctgatg agacacagcg aggacaaccc caatcagatc agaatcctgg ctcagaccct  5040
gaccgatggc ggcgtgatgg acgagctgat caacgaggaa ctcgaaacct tcaacagccg  5100
gtggcgggaa ctgcacgagg aagctgttcg gaggcagaag ttgctggaac agtctatcca  5160
gagcgcacaa gaaaccgaga agtccctgca cctgatccaa gagagcctga ccttcatcga  5220
caagcagctg gccgcttata tcgccgacaa ggtggacgct gctcagatgc cccaagaggc  5280
acagaagatt cagagcgacc tgaccagcca cgagattagc ctggaagaaa tgaagaagca  5340
caaccagggc aaagaggccg ctcagagagt cctgagccag atcgatgtgg cacagaaaaa  5400
gctccaggat gtgtccatga agtttcggct gtttcagaag cccgccaact tcgagcagag  5460
actgcaagag tccaagatga tcctggacga agtcaaaatg catctgcccg cactggaaac  5520
aaagtccgtg gaacaagaag tggtgcagtc ccagctgaac cactgcgtga acctgtacaa  5580
gagcctgtcc gaagtgaagt ctgaggtgga aatggtcatc aagaccggca ggcagatcgt  5640
ccagaagaag cagaccgaga atcccaaaga actcgacgag agagtgaccg ctctgaagct  5700
gcactacaat gagctgggcg ccaaagtgac cgagcggaag caacagcttg agaagtgcct  5760
```

```
gaaactgtct cggaagatgc ggaaagaaat gaacgtgctg acagagtggc tggccgccac  5820
cgatatggaa ctgactaaga gaagcgccgt ggaaggcatg cccagcaacc tggatagtga  5880
agtggcctgg ggcaaagcca ctcagaaaga gattgagaag cagaaggtcc acctgaagtc  5940
catcaccgaa gtgggcgaag ccctgaaaac cgtgctggga aagaaagaga cactggtcga  6000
ggacaagctg tccctgctga attccaactg gatcgccgtg acctccagag ctgaggaatg  6060
gctgaatctg ctgcttgagt accagaaaca catggaaacg ttcgaccaga acgtcgacca  6120
catcacaaag tggatcatcc aggctgatac cctgctggac gagtccgaga agaagaaacc  6180
ccaacaaaaa gaagatgtgc tgaagcggct gaaagccgag ctgaatgaca tccggcctaa  6240
ggtggacagc accagagatc aggcagccaa cctgatggcc aacagaggcg accactgtcg  6300
gaagctcgtg gaacctcaga tcagcgagct taaccacaga tttgccgcca tcagccaccg  6360
gatcaagaca ggcaaggcca gcattcctct caaagagctt gagcagttca acagcgacat  6420
ccaaaagctg ctcgaacccc tggaagccga gatccaacag ggcgtcaacc tcaaagaaga  6480
agatttcaac aaggacatga acgaggacaa tgagggcacc gtcaaagaac tgctgcagcg  6540
gggcgataat ctgcagcagc ggattaccga tgagcgcaag cgggaagaga tcaagattaa  6600
gcagcagctg ctgcagacca agcacaacgc cctgaaggac ctgcggagcc agagaagaaa  6660
gaaggccctg gaaatcagcc accagtggta tcagtacaag cggcaggccg acgacctgct  6720
gaagtgcctg gatgacatcg agaagaagct ggcctctctg cccgagccta gggacgagag  6780
aaagatcaaa gagatcgacc gcgagctgca gaaaaagaaa gaggaactga acgccgtccg  6840
cagacaggcc gaaggacttt ctgaagatgg cgccgctatg gccgtggaac ccacacagat  6900
tcagctgagc aagcggtggc gggaaatcga gagcaagttc gcccagttcc ggcggctgaa  6960
tttcgcccag atccacaccg tgcgggaaga gacaatgatg gtcatgacag aggacatgcc  7020
ccttgagatc agctacgtgc ccagcaccta cctgaccgag atcacccatg tgtctcaggc  7080
cctgctggaa gtggaacagc tgctgaatgc ccctgacctg tgcgccaagg acttcgagga  7140
cctgttcaag caagaggaaa gcctgaagaa catcaaggac agcctgcagc agagcagcgg  7200
ccggatcgat atcatccaca gcaagaaaac cgccgcactg cagagcgcca cacctgtgga  7260
aagagtgaag ctgcaagagg ccctgagcca gctggatttc cagtgggaga aagtgaacaa  7320
gatgtacaag gaccggcagg gcagattcga ccgcagcgtt gaaaagtggc ggcggttcca  7380
ctacgacatc aagatcttca accagtggct gaccgaggcc gagcagttcc tgagaaagac  7440
acagatcccc gagaactggg agcacgccaa gtacaagtgg tatctgaaag agctgcagga  7500
cggcatcggc cagagacaga cagtcgtgcg gacactgaat gccaccggcg aggaaatcat  7560
ccagcagtcc agcaagaccg acgccagcat cctgcaagag aagctgggca gcctgaacct  7620
gcggtggcaa gaagtgtgca agcagctgag cgaccggaag aagcggctgg aagaacagaa  7680
gaatatcctg agcgagttcc agcgggacct gaacgagttc gtgctgtggc tcgaagaggc  7740
cgacaatatc gccagcattc ccctggaacc tggcaaagag cagcagctga aagaaaagct  7800
ggaacaagtg aaactgctgg tcgaggaact gcccctgaga cagggaatcc tgaaacagct  7860
gaacgagaca ggcggccctg tgctggtgtc tgcccctatt tctcccgagg aacaggacaa  7920
gctggaaaac aagctgaagc agaccaacct gcagtggatc aaggtgtcca gagcactgcc  7980
tgagaagcag ggcgagatcg aggcccagat caaggacctg ggacagctcg aaaagaagct  8040
tgaggacctc gaagaacagc tcaaccatct gctgctttgg ctgagcccca tccggaacca  8100
gctggaaatc tacaaccagc ctaatcaaga gggccccttc gacgtgaaag aaaccgagat  8160
tgccgtgcag gccaagcagc ccgatgtgga agagatcctg tctaagggcc agcacctgta  8220
caaagagaag cccgccacac agcccgtgaa gcggaaactg gaagatctga gcagcgagtg  8280
gaaggccgtg aaccggctgc tgcaagaact gagagccaaa cagcctgatc tggcccctgg  8340
cctgacaaca attggcgcct ctcctacaca gaccgtgaca ctggtcacac agcctgtggt  8400
caccaaagag acagccatca gcaaactgga aatgcccagc agtctgatgc tcgaagtgcc  8460
cgcactggcc gacttcaata gagcctggac cgagctgacc gactggctca gtctgctgga  8520
ccaagtcatc aagtcccaga gagtgatggt cggagatctt gaggacatca acgagatgat  8580
cattaagcag aaagccacca tgcaggacct tgagcagaga aggccccagc ttgaagaact  8640
gatcaccgcc gctcagaacc tgaaaaacaa gaccagcaat caagaagccc ggaccatcat  8700
caccgaccgg atcgagagaa tccagaacca gtgggacgaa gtgcaagagc atctgcagaa  8760
cagacggcag cagctcaatg agatgctgaa ggacagcaca cagtggctgg aagccaaaga  8820
agaagccgag caggttctcg gacaggccag agctaagctg gaatcttgga aagagggacc  8880
ctacaccgtc gacgccatcc agaagaagat caccgagaca aagcagctgg ccaaggatct  8940
gagacagtgg cagaccaatg tggacgtggc caacgacctg gctctgaagc tgctgagaga  9000
ctacagcgcc gacgacacca gaaaggtgca catgatcacc gaaaacatca acgcctcttg  9060
gcggagcatc cacaagcggg tgtcagagag agaagccgct ctggaagaaa cacatagact  9120
gctccagcag ttcccactcg acctggaaaa gttcctggcc tggctgacag aagccgaaac  9180
caccgctaac gtgctccagg atgccaccag aaaagagcgg ctgttggagg acagcaaggg  9240
cgtcaaagaa ctcatgaagc agtggcagga tctgcaaggg gagattgaag cccacaccga  9300
cgtgtaccac aacctggacg agaacagcca gaagatcctg cggtccctgg aaggctctga  9360
tgatgctgtg ctgcttcaga ggcggctgga caacatgaac ttcaagtgga gcgagctgcg  9420
gaagaagtcc ctgaacatca gaagccacct ggaagcctcc agcgaccagt ggaaaagact  9480
gcacctgtct ctccaagagc tgctcgtgtg gctgcagctg aaggatgacg agctgagtag  9540
acaggcccct atcggcggag attttcccgc cgtgcagaaa cagaacgacg tgcaccgggc  9600
cttcaagaga gagctgaaaa caaaagaacc cgtcatcatg agcaccctgg aaaccgtgcg  9660
gatctttctg accgagcagc ctctggaagg actggaaaag ctgtaccaag agcctagaga  9720
gctgcctcct gaagaaaggg cccagaacgt gacacggctg cttagaaagc aggccgagga  9780
agtgaacacc gaatgggaga agctgaacct ccactccgcc gactggcagc ggaagatcga  9840
tgagacactg gaacggctgc gggaactgca agaagccaca gacgagctgg acctgaaact  9900
gcggcaggct gaagtgatca aaggctcctg gcagccagtg ggcgatctgc tgatcgatag  9960
cctgcaggac catctggaaa aagtcaaggc cctgcgggga gagatcgccc ctctcaaaga  10020
aaacgtgtcc cacgtgaacg atctggccag gcagctgaca acactgggca tccagctgag  10080
cccttacaac ctgtctacct tggaggacct gaatacccgg tggaagctgc tccaagtggc  10140
cgtcgaggat agagtgcggc agctgcatga ggctcacaga gattttggac ccgccagcca  10200
gcacttcctg agcacatctg ttcaaggccc ctgggagaga gctatcagcc ctaacaaggt  10260
gccctactac atcaaccacg agacacagac cacctgttgg gatcacccca agatgaccga  10320
actgtatcag tccctggccg acctgaacaa cgtgcggttt agcgcctacc ggaccgccat  10380
gaagctgcgc agactgcaga aagctctgtg cctggacctg ctgtctctga gcgctgcttg  10440
tgatgccctg gaccagcata acctcaagca gaacgaccag cctatggaca tcctgcagat  10500
```

```
catcaactgc ctgaccacca tctacgaccg gctcgaacaa gagcacaaca acctggtcaa  10560
cgtgcccctg tgcgtggaca tgtgcctgaa ttggctgctg aacgtgtacg acaccggcag  10620
aaccggcagg atcagagtgc tgagcttcaa gaccggcatc atctccctgt gcaaggccca  10680
ccttgaggat aagtaccgct acctgtttaa gcaggtcgcc agcagcaccg gcttttgcga  10740
ccaaagaagg ctgggactgc tgctccacga cagcattcag atccctagac agctgggcga  10800
agtggcctct ttcggcggct ctaatatcga gcctagcgtg cggagctgct tccagttcgc  10860
caacaacaag cccgagattg aggccgcact gttcctggac tggatgagac tggaacccca  10920
gagcatggtc tggctgcctg tgctgcatag agtggccgca gccgaaacag ccaagcacca  10980
ggccaagtgc aacatctgca aagagtgccc catcatcggc ttccggtaca gatccctgaa  11040
gcacttcaac tacgatatct gccagtcctg cttcttcagc ggcagagtgg ccaagggcca  11100
caagatgcac taccccatgg tggaatactg cacccctacc acctctggcg aggacgtgcg  11160
ggattttgcc aaggtgctca agaacaagtt ccggaccaag cgctacttcg ctaagcaccc  11220
cagaatgggc tacctgccag tgcagacagt gcttgagggc gacaacatgg aaacccctgt  11280
gactctgatc aacttctggc ccgtggatag cgcccctgct agttctcctc agctgtctca  11340
cgacgatacc cacagcagaa tcgagcacta cgcctccaga ctggccgaga tggaaaacag  11400
caacggcagc tacctgaatg acagcatcag ccccaacgag agcatcgacg acgaacatct  11460
gctcattcag cactactgcc agagcctgaa tcaggacagc cctctgtctc agcctagaag  11520
ccctgcacag atcctgatca gcctggaaag cgaggaacgc ggcgagctgg aaagaatcct  11580
ggcagacctg gaagaggaaa accggaacct gcaggccgaa tacgacagac tcaagcagca  11640
gcacgagcac aagggactgt ctccactgcc ttctccacct gaaatgatgc ccacctctcc  11700
acagagcccc agagatgccg agctgattgc cgaagccaaa ctgctgaggc agcacaaagg  11760
cagactcgaa gccagaatgc agattctcga agatcacaac aagcagctcg aatcccagct  11820
gcacagactt aggcagctgc tggaacagcc tcaggcagag gccaaagtga atggcaccac  11880
cgtgtctagc cctagcacaa gcctgcagag atccgacagc agccagccaa tgcttctgag  11940
agtcgtgggc tcccagacca gcgattctat gggcgaagag gacctgctca gccctcctca  12000
ggatacaagc accggcctgg aagaagtgat ggaacaactg aacaacagct tccccagcag  12060
cagaggcaga aacacccctg gcaagcccat gcgcgaggac accatgtgat aactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg ggtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgggaag atgtctactg agctgtgcga tccctgctgg ggactttccg ctggggactt  12780
tccgctgggg actttccgcc ttcagctaag gaagctacca atatttagag gtacattttg  12840
ttctagaaca aaatgtaccg gtacattttg ttctggtaca ttttgttct              12889
```

```
SEQ ID NO: 28           moltype = DNA  length = 12889
FEATURE                 Location/Qualifiers
source                  1..12889
                        mol_type = other DNA
                        note = MHCK7-hBGi-DMD-5-WPRE3-DTS
                        organism = synthetic construct
SEQUENCE: 28
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgccccact acgggtctag  240
gctgcccatg taaggaggca aggcctgggg acacccgaga tgcctggtta taattaaccc  300
agacatgtgg ctgccccccc ccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctgtgg tgggaggaag ttgaagattg  1080
ttatgagaga gaagatgtcc agaaaaagac ctttaccaaa tgggtgaacg cacagttctc  1140
caaatttggg aaacagcata tagaaaattt gttcagcgat cttcaggatg ggcgcaggtt  1200
gcttgacctt ctggaaggac tgaccgggca gaagctgccc aaagagaaag ggtctaccag  1260
agttcacgct ctgaacaacg tgaataaggc actgcgagtc ctgcaaaata acaacgtcga  1320
cctggtgaac ataggcagca ctgatattgt tgatgggaac cataaactca cactgggtct  1380
gatttggaat attatactgc actggcaggt caaaaatgtt atgaaaaata ttatggccgg  1440
gcttcaacag accaattccg agaagatcct gctgtcttgg gttaggcagt ccacgaggaa  1500
ctaccctcaa gtgaacgtta ttaacttcac aacatcatgg agtgatggac ttgccctgaa  1560
cgccttgatc cactcccata ggccagacct gttcgattgg aatagcgtag tctgtcagca  1620
gagtgctaca caacgcctgg aacacgcctt taacatagcc aggtatcagc ttggaattga  1680
gaaactcctc gaccctgaag acgtagacac cacttacccc gacaaaaaat ccattcttat  1740
gtacataact tccttgtttc aggttctccc ccagcaggtg tccatcgagg ctatacagga  1800
ggtcgaaatg ctccccagac cccctaaggt cacgaaggaa gagcacttcc aactgcacca  1860
```

-continued

```
tcagatgcac tacagtcaac agatcactgt gagtctcgca caggggtacg aaaggaccag  1920
ctcccctaaa ccccgcttca agtcctacgc ctatactcag gcagcttacg taaccacaag  1980
tgaccccacg cggtcaccct tcccaagcca gcacctggag gctcccgagg acaaaagctt  2040
tggatcatcc ctgatggaat ctgaagtcaa tctcgatagg taccaaaccg ctctggagga  2100
ggtcctcagt tggctccttt cagctgaaga tactctgcag gcacagggtg agatcagcaa  2160
tgacgtggag gtagtgaaag atcagtttca cactcacgag ggctatatga tggacctgac  2220
agcccatcaa ggtcgcgttg gcaatatcct gcagttgggg tccaaactga ttggtaccgg  2280
taagttgtcc gaggacgaag agacagaagt gcaggagcag atgaacctgc ttaattctag  2340
atgggaatgc ctccgcgtgg cctctatgga gaagcagtcc aatctccatc gggttctcat  2400
ggacttgcag aatcagaagc tgaaggaact caacgactgg ttgaccaaga ctgaggagcg  2460
caccagaaag atggaggagg agccactcgg tcctgatctt gaagatctga aacgacaagt  2520
tcagcagcac aaggtcctgc aggaggatct cgaacaggag caggtccggg tgaacagcct  2580
gacccatatg gttgtcgttg tcgacgagtc aagtggggac catgctacgg ctgcgcttga  2640
ggaacagctg aaggtcttgg gcgatagatg ggcgaatatc tgccgctgga ctgaagatag  2700
atgggtgctg ctgcaggata ttcttttgaa gtggcagcgg ttgaccgaag aacaatgctt  2760
gtttagcgcc tggctgagtg agaaagagga tgcggtgaat aagatacaca ctactggctt  2820
caaagaccag aatgaaatgc ttagcagcct gcagaaactt gcggttctta aggccgactt  2880
ggaaaagaaa aagcagtcaa tgggtaagct gtactcactc aagcaggacc tgctgtcaac  2940
tttgaagaac aagagcgtca cgcaaaagac tgaggcctgg ctcgacaatt ttgctaggtg  3000
ctgggataac ctggtgcaga agttggaaaa gtccactgct cagatctctc aagccgtgac  3060
tactacccag cccagcctga cacagactac cgtcatggaa accgttacca ctgtgacgac  3120
tagggagcag atactcgtta agcacgctca agaggaattg ccgccacctc ctccccaaaa  3180
gaaacgccag attaccgtcg actctgaaat acgcaagaga ctggatgtgg acatcacgga  3240
actgcactct tggattacca gaagcgaggc agtcctccag agccccgagt ttgcgatctt  3300
caggaaggaa ggcaactttt cagatctgaa ggaaaaggtg aacgccatcg agcgcgagaa  3360
agccgagaag ttccgcaaac tgcaggatgc gagccggtct gctcaggcct tggtggagca  3420
aatggtgaat gaaggcgtaa atgcggacag catcaagcag gcctccgagc agctcaattc  3480
aagatggatc gagttctgtc agctgctcag cgagcgattg aactggctgg agtatcaaaa  3540
taacataatc gcgttttaca accagctgca acagctggaa cagatgacga ctactgcaga  3600
gaactggctt aaaatccagc ctacaactcc ttctgaaccc acagcaatca aaagccagct  3660
caagatctgc aaggacgaag tcaaccgcct ctccgatttg cagcctcaga tagaacgact  3720
caagatccaa agtatcgcac tcaaagaaaa ggggcaaggc cctatgtttc tcgatgctga  3780
ttttgtggct ttcaccaacc attttaagca agtgttttca gatgtgcaag cccgggaaaa  3840
ggaactgcaa accatttttg ataccctgcc tccaatgcgg taccaggaga ctatgtctgc  3900
aattcgcacc tgggtgcaac aaagcgagac gaaactttct attccacaac tgtccgtgac  3960
agactacgaa attatggaac agcgactggg agaactccaa gcccttcagt ccagccttca  4020
ggagcagcag tcaggattgt actatctgtc aaccaccgtg aaggaaatgt caaaaaaggc  4080
tccctccgaa atatctcgca agtatcagtc tgagtttgaa gagattgaag ggagatggaa  4140
gaaactgtcc tcacagctgg ttgagcactg tcagaagttg gaagagcaga tgaacaagtt  4200
gcgcaagatt caaaatcaca tacagacact caaaaagtgg atggcggagg ttgacgtctt  4260
ccttaaagag gagtggccag ccctgggcga ctcagagatc ctgaaaaagc aactgaaaca  4320
gtgccgactg ctggtgtccg acatccagac aatacagcca agtttgaata gcgtgaatga  4380
gggtggacaa aaaatcaaaa acgaggctga gcccgagttc gcctccagat tggaaaccga  4440
gctgaaggaa cttaatacac agtgggatca tatgtgtcag caggtttatg cccggaagga  4500
agcactgaaa gggggctgg agaaaaccgt gagccttcag aaggacctta gcgagatgca  4560
cgagtggatg acccaggcgg aggaagagta tctcgaacgg gattttgagt ataagacacc  4620
agatgaactt cagaaggcag tcgaagagat gaaacgggca aaggaagagg ctcagcagaa  4680
ggaagcaaag gttaaacttc tgacagaatc cgttaacagc gttatagccc aagctccccc  4740
cgttgcccag gaagctctta aaaaggaact ggaaacactg acaacaaact accagtggct  4800
gtgcacccgc ttgaacggca aatgcaaaac cctggaagag gtctgggctt gttggcatga  4860
actcctgtca tacctggaaa aagctaataa gtggctgaat gaggtggagt ttaaattgaa  4920
aacgaccgaa aacatccctg gcggtgcaga ggagatatct gaggtgctcg atagcctgga  4980
gaatcttatg aggcatagcg aggataaccc caaccagatt aggatactgg cccaaactct  5040
gaccgacggc ggagtgatgg acgagctgat aaacgaggaa ctggaaacct ttaattcacg  5100
ctggcgagaa cttcacgagg aggcagtcag gcgccagaaa ctgctggagc agtccatcca  5160
gagtgcccag gagactgaga agtcacttca tctgatccag gagagtttga cgtttatcga  5220
caagcagctt gccgcctaca ttgcagacaa ggtcgatgct gctcagatgc cgcaagaggc  5280
tcagaaaatc cagagcgacc tgacaagcca cgagattagc ctggaggaaa tgaaaaagca  5340
caaccagggt aaagaggccg cccagcgggt tctgagccag atcgatgtcg cacagaagaa  5400
actccaagat gtaagcatga agttccgact gtttcagaaa ccagcgaact ttgagcagcg  5460
actgcaggag tctaaaatga tcctcgatga ggtgaaaatg catctgccag ccctggaaac  5520
taagagcgtg gagcaggagg tggttcagag tcagctgaac cactgcgtaa acctctataa  5580
aagtcttagt gaagtgaaga gcgaggtgga gatggtgatt aagactggta gacagattgt  5640
acagaaaaag cagacggaga accccaaaga gttggatgaa cgggtgacag cccttaagct  5700
ccactataac gagctgggag ccaaagtgac tgagagaaag cagcaacttg aaaaatgtct  5760
gaagctgagc agaaagatgc ggaaggaaat gaatgtgctg acagagtggc tggctgcgac  5820
cgacatggaa cttacaaaga ggagcgccgt ggaaggcatg ccttccaatc tggatagtga  5880
ggtcgcttgg ggcaaagcta cacagaagga aattgagaag caaaaagtgc atcttaagag  5940
cattactgaa gttggcgagg ctttgaaaac cgtcctcggc aagaaagaga ctctggtaga  6000
agataaactc tcactgctga actcaaactg gatcgcagtc actagtcggg ccgaagagtg  6060
gctgaatttg ctgttggagt accaaaagca tatggagact ttcgatcaga atgtcgacca  6120
cattacgaag tggataatcc aggcggacac actgttggat gagtccgaga aaaagaaacc  6180
tcagcagaag gaagacgtgc tcaaacgact caaagccgaa ctgaacgaca tcaggcccaa  6240
agttgattcc acccgggatc aagcggccaa tctcatggcc aaccgggggg atcactgcag  6300
aaagttggta gaacctcaga taagcgaact taatcataga tttgccgcca tatcacatag  6360
gattaagacc ggtaaggctt caatccccct gaaggaactc gaacagttta atagtgacat  6420
ccagaagctc ctggagcctc tcgaagccga gattcaacag ggtgtaaacc ttaaggaaga  6480
ggattttaat aaggatatga atgaggacaa tgaaggcacg gtcaaagagc tcctccagag  6540
gggagacaat ttgcagcagc ggatcaccga tgaacgcaaa cgcgaagaga tcaaaattaa  6600
```

```
gcagcagctc ctccaaacaa agcacaatgc ccttaaagac ctcagaagcc agcggcggaa  6660
aaaggctctg gaaatcagcc atcaatggta tcagtacaag cggcaagcgg acgatctcct  6720
gaaatgtctg gatgatatcg agaaaaaact ggccagtctg ccagagccca gagatgagcg  6780
caaaatcaag gaaatcgaca gggagcttca gaagaaaaaa gaggagctga acgccgtccg  6840
aaggcaggcc gaagggctgt cagaagatgg ggccgccatg gcagtggaac ctacccagat  6900
tcaactgtcc aagcgctgga gagagattga aagtaagttc gcacaattcc ggaggcttaa  6960
ttttgctcag attcacacag ttagggagga aaccatgatg gtgatgaccg aagacatgcc  7020
actcgaaatc agctacgtcc ctagcacata tctcacggag attacccacg tgtcccaggc  7080
actgctggaa gtcgagcaat tgttgaacgc ccctgatctc tgcgccaagg atttcgaaga  7140
cttgttcaag caagaggaaa gcctcaagaa catcaaagac agtcttcagc agtcctcagg  7200
cagaattgat attatccact ccaagaaaac agccgctctc cagagcgcta cccctgtcga  7260
acgagtgaaa ctgcaagagg ccttgtctca gttggacttc cagtgggaga aagtcaacaa  7320
gatgtacaag gacaggcagg gtcggttcga ccggagcgtc gaaaaatggc ggagattcca  7380
ttatgacatc aagatattca atcagtggct tacagaggcg gagcaatttt tgagaaagac  7440
gcagattccc gaaaactggg agcatgccaa gtacaagtgg tacctcaaag agctccagga  7500
tggaatcggc cagagacaga ccgtagttag aacactgaac gcaactggag aagagattat  7560
ccagcagtcc tccaaaactg acgcctctat cctccaggag aagcttggca gccttaacct  7620
gcggtggcag gaggtgtgta aacaactgtc agataggaaa aaaagacttg aggaacagaa  7680
gaacattctg agcgagttcc aacgagatct caacgagttc gtactgtggc tggaggaggc  7740
cgacaacatc gcttcaatcc ccctggaacc cggcaaggaa cagcagctta aggaaaaatt  7800
ggaacaggta aaactgttgg tagaggagct cccattgcgg cagggcattc tcaagcagct  7860
gaatgaaact ggaggtcccg ttctggtcag tgcgcccata agcccggaag agcaggacaa  7920
gttggaaaac aagctgaagc aaacaaatct gcagtggatc aaagtgagcc gggctcttcc  7980
agaaaagcaa ggcgagattg aagcccagat taaggatctt ggccagcttg agaaaaagct  8040
ggaggatctg gaagagcagc tgaaccattt gcttctgtgg ctgagtccca ttagaaacca  8100
gctggaaatc tacaaccagc caaaccaaga gggccccttc gacgtcaagg aaactgagat  8160
agcagtccag gcaaaacagc ccgatgtcga agaaatcttg tctaaggggc agcacctcta  8220
caaagagaaa cctgccaccc agcccgtgaa gagaaaactg gaagacctct cttcagagtg  8280
gaaggctgta aacaggttgc tccaggagct gagagctaag caacctgacc tcgcacccgg  8340
cctgactact attggcgcca gcccgaccca aaccgtcaca ctggtgaccc agcctgtagt  8400
cacaaaagaa accgccatct ccaaactgga gatgccttca agcctgatgc tggaggtgcc  8460
tgctctggcc gatttcaaca gagcctggac agagctgaca gactggctgt ctctgctcga  8520
ccaagtgata aagtcacagc gcgtcatggt gggtgacctg gaggacatca atgagatgat  8580
cataaagcaa aaggctacca tgcaggactt ggagcagcgc aggccgcagt tggaagaact  8640
gattacagca gcccagaacc tcaagaacaa gacttcaaat caggaggcaa ggaccatcat  8700
aacagataga atcgagagga ttcagaacca atgggatgag gtgcaggagc acctgcagaa  8760
cagaaggcag cagctgaacg aaatgctgaa agactccaca cagtggctgg aggccaaaga  8820
ggaggcagaa caggtgctgg gccaggctag ggccaagctg gaaagttgga aggaagggcc  8880
ctacaccgtg gacgccatac agaagaaaat aacggagaca aaacagctgg ccaaagacct  8940
ccgccaatgg cagaccaacg tagacgtcgc caatgacctg gcactcaagt tgttgagaga  9000
ttattccgca gatgacaccc gaaaagtaca catgatcact gagaatatca acgccagttg  9060
gcggagcatt cacaaacggg tgagcgagag agaagccgcc cttgaggaga cgcatcgcct  9120
tttgcagcaa tttccgcttg acctggaaaa gtttctggct tggttgacag aggccgagac  9180
aactgctaac gtgctgcaag atgccacccg caaagagcgg cttcttgagg actctaaagg  9240
ggtgaaagaa ttgatgaagc agtggcagga cctccagggc gaaatcgagg cccatactga  9300
tgtctaccac aacctggatg aaaatagtca gaaaatcctg agatccctgg aagggagtga  9360
tgatgcggtg ctgctgcagc gccgactcga taacatgaac tttaagtggt ctgaactccg  9420
gaaaaaaagc ctgaacattc ggagccatct ggaggcttct tctgatcagt ggaagagact  9480
tcatctgtcc ttgcaggagc ttctggtgtg gctgcagctg aaagacgacg agctgtcaag  9540
gcaggcacca ataggggggcg acttccccgc tgttcagaaa caaaatgatg tgcacagggc  9600
attcaagcgg gaactgaaga cgaaagaacc agtgattatg agcactctgg agacggtacg  9660
catctttctg accgagcagc cacttgaagg cctcgaaaag ttgtaccagg agccacggga  9720
attgcctccc gaagaacggg ctcagaatgt tacccgactg cttcgcaagc aggctgagga  9780
agtgaacact gagtgggaaa aactgaatct gcacagtgcc gattggcagc gcaaaattga  9840
cgagacattg gagcgcttgc gggagctgca ggaagccaca gatgaacttg atctgaaact  9900
cagacaggcc gaggtcataa agggttcttg gcaacccgta ggcgaccttt tgattgactc  9960
actgcaggat catctggaga aagtaaaggc gctgcggggg gaaattgctc cgctgaagga  10020
aaacgtgagc catgtgaatg atctggctcg gcaattgact accctgggta tccagctgtc  10080
cccctacaat ctgagcactc tcgaagacct caacacaaga tggaaactgc tgcaggtcgc  10140
cgtggaggac agggtgaggc agctgcatga ggcacacagg gacttcggtc cggcaagcca  10200
acacttcctg tctacttctg ttcaagggcc ttgggaacgc gctatttccc caaacaaagt  10260
gccgtactat attaaccatg aaactcagac aacctgctgg gatcatccta aaatgactga  10320
gctgtaccag agcctcgccg atctgaataa cgtgaggttt agcgcataca gaaccgcaat  10380
gaagctcagg agactgcaga aggcactttg cctggacctc ctgagcctct ccgctgcctg  10440
cgatgccctc gaccagcaca acctgaagca gaatgatcag cctatggaca tcctgcaaat  10500
cataaattgt ctgacgacaa tctacgaccg gctcgaacag gagcacaata atctcgtgaa  10560
cgttccactt tgtgtggata tgtgtctcaa ctggctgttg aacgtctatg acaccgggag  10620
aactggaagg atccgcgttc tgtcctttaa gactggaatc atcagcttgt gtaaggcgca  10680
ccttgaggac aaatatcgat acctgtttaa gcaggttgca agctccactg gattctgcga  10740
ccagaggcgc ctcgggctgc tgcttcatga tagtatccaa atcccacgcc aactcggaga  10800
ggtggcaagc ttcggcggga gcaatattga gccaagcgtc agatcttgtt tccagtttgc  10860
caacaataag cctgagatcg aagccgcact gtttttggat tggatgcggt tggagcccca  10920
gagtatggtg tggttgcccg tgctgcatag ggtcgctgcc gctgaaaccg ccaaacacca  10980
ggccaagtgc aatatttgca aggaatgtcc catcatcggg tttagatacc ggagcctgaa  11040
gcacttcaat tatgatatct gccagtcttg tttttttttcc ggccgagttg ctaagggaca  11100
caagatgcat tacccaatgg tggaatattg tacgccaacc accagcggcg aagatgtcag  11160
agattttgca aaagtactca agaacaagtt ccgcaccaag cgatatttcg cgaagcaccc  11220
ccggatgggc tacctcccag tgcagacggt tctggaaggc gataacatgg aaactccagt  11280
caccctgatc aatttctggc ctgtggactc tgcgcctgcc tcttcacctc agctctccca  11340
```

```
cgatgacacc cattccagaa tcgagcacta cgcgtctcga ctggcggaga tggagaacag  11400
caatggttct tacctcaatg acagcattag ccccaacgaa agcatcgatg acgagcacct  11460
cttgattcaa cactactgcc agtccctgaa tcaggacagt cctctgtccc aacccaggag  11520
cccagcccag atactgatct ctctcgaatc agaagaaaga ggggagttgg agcgaatttt  11580
ggccgacctg gaggaggaga atagaaatct tcaggccgag tacgatagac tgaagcagca  11640
gcacgagcac aagggccttt ctccactgcc ctctccaccg gaaatgatgc caacctcccc  11700
tcaaagtccc agggacgctg agctcattgc cgaggcaaag ctgttgcgcc agcacaaagg  11760
acgcctggag gcgagaatgc agatcctgga agaccataac aagcagcttg agtctcagct  11820
gcaccgactt agacagctgt tggagcagcc acaagcggaa gcaaaggtca atggaactac  11880
cgtgagttcc cccagtacaa gtctgcagcg ctctgactca agccagccaa tgctgctccg  11940
ggtagtcggt tctcagacta gtgattcaat gggggaggag gatcttcttt ccccacccca  12000
agacacctca acagggcttg aggaagtgat ggagcagctg aacaactcct tcccctcttc  12060
acgggggaga aatactcctg ggaagcctat gagagaggat accatgtaat gactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg ggtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgggaag atgtctactg agctgtgcga tccctgctgg ggactttccg ctggggactt  12780
tccgctgggg actttccgcc ttcagctaag gaagctacca atatttagag gtacattttg  12840
ttctagaaca aaatgtaccg gtacattttg ttctggtaca ttttgttct             12889

SEQ ID NO: 29           moltype = DNA  length = 4594
FEATURE                 Location/Qualifiers
source                  1..4594
                        mol_type = other DNA
                        note = NP-CBA-hBGi-EGFP-P2A-Fluc-WPRE3-DTS
                        organism = synthetic construct
SEQUENCE: 29
tgcatgcggc cgccgttaca taacttacgg taaatggccc gcctggctga ccgcccaacg  60
accccccgccc attgacgtca ataatgacgt atgttcccat agtaacgcca atagggactt  120
tccattgacg tcaatgggtg gagtatttac ggtaaactgc ccacttggca gtacatcaag  180
tgtatcatat gccaagtacg ccccctattg acgtcaatga cggtaaatgg cccgcctggc  240
attatgccca gtacatgacc ttatgggact ttcctacttg gcagtacatc tacgtattag  300
tcatcgctat taccatggtc gaggtgagcc ccacgttctg cttcactctc cccatctccc  360
ccccctcccc acccccaatt ttgtatttat ttatttttta attattttgt gcagcgatgg  420
gggcgggggg gggggggggcg cgcgccaggc ggggcggggc ggggcgaggg gcggggcggg  480
gcgaggcgga gaggtgcggc ggcagccaat cagagcggcg cgctccgaaa gtttcctttt  540
atggcgaggc ggcggcggcg gcggccctat aaaaagcgaa gcgcgcggcg ggcgggagtc  600
tctggatcca ctgcttaaat acggacgagg acagggccct gtctcctcag cttcaggcac  660
caccactgac ctgggacagt gaatcgtaag tactagcagc tacaatccag ctaccattct  720
gcttttattt tatggttggg ataaggctgg attattctga gtccaagcta ggcccttttg  780
ctaatcatgt tcatacctct tatcttcctc ccacagctcc tgggcaacgt gctggtctgt  840
gtgctggccc atcactttgg caaagaattg cgatcgccac catggtgagc aagggcgagg  900
agctgttcac cggggtggtg cccatcctgg tcgagctgga cggcgacgta aacggccaca  960
agttcagcgt gtccggcgag ggcgagggcg atgccaccta cggcaagctg accctgaagt  1020
tcatctgcac caccggcaag ctgcccgtgc cctggcccac cctcgtgacc accctgacct  1080
acggcgtgca gtgcttcagc cgctaccccg accacatgaa gcagcacgac ttcttcaagt  1140
ccgccatgcc cgaaggctac gtccaggagc gcaccatctt cttcaaggac gacggcaact  1200
acaagacccg cgccgaggtg aagttcgagg gcgacaccct ggtgaaccgc atcgagctga  1260
agggcatcga cttcaaggag gacggcaaca tcctggggca caagctggag tacaactaca  1320
acagccacaa cgtctatatc atggccgaca agcagaagaa cggcatcaag gtgaacttca  1380
agatccgcca caacatcgag gacggcagcg tgcagctcgc cgaccactac cagcagaaca  1440
cccccatcgg cgacggcccc gtgctgctgc ccgacaacca ctacctgagc acccagtccg  1500
ccctgagcaa agaccccaac gagaagcgcg atcacatggt cctgctggag ttcgtgaccg  1560
ccgccgggat cactctcggc atggacgagc tgtacaagaa tcgcgctact aacttcagcc  1620
tgctgaagca ggctggagac gtggaggaga accctggacc tatggaagac gccaaaaaca  1680
taaagaaagg cccggcgcca ttctatccgc tggaagatgg aaccgctgga gagcaactgc  1740
ataaggctat gaagagatac gccctggttc ctggaacaat tgcttttaca gatgcacata  1800
tcgaggtgga catcacttac gctgagtact tcgaaatgtc cgttcggttg gcagaagcta  1860
tgaaacgata tgggctgaat acaaatcaca gaatcgtcgt atgcagtgaa aactctcttc  1920
aattctttat gccggtgttg ggcgcgttat ttatcggagt tgcagttgcg cccgcgaacg  1980
acatttataa tgaacgtgaa ttgctcaaca gtatgggcat ttcgcagcct accgtggtgt  2040
tcgtttccaa aaaggggttg caaaaaattt tgaacgtgca aaaaaagctc ccaatcatcc  2100
aaaaaattat tatcatggat tctaaaacgg attaccaggg atttcagtcg atgtacacgt  2160
tcgtcacatc tcatctacct cccggtttta atgaatacga ttttgtgcca gagtccttcg  2220
atagggacaa gacaattgca ctgatcatga actcctctgg atctactggt ctgcctaaag  2280
gtgtcgctct gcctcataga actgcctgcg tgagattctc gcatgccaga gatcctattt  2340
ttggcaatca aatcattccg gatactgcga ttttaagtgt tgttccattc catcacggtt  2400
ttggaatgtt tactacactc ggatatttga tatgtggatt tcgagtcgtc ttaatgtata  2460
gatttgaaga agagctgttt ctgaggagcc ttcaggatta caagattcaa agtgcgctgc  2520
tggtgccaac cctattctcc ttcttcgcca aaagcactct gattgacaaa tacgatttat  2580
ctaatttaca cgaaattgct tctggtggcg ctcccctctc taaggaagtc ggggaagcgg  2640
ttgccaagag gttccatctg ccaggtatca ggcaaggata tgggctcact gagactacat  2700
```

```
cagctattct gattacaccc gagggggatg ataaaccggg cgcggtcggt aaagttgttc  2760
catttttgga agcgaaggtt gtggatctgg ataccgggaa aacgctgggc gttaatcaaa  2820
gaggcgaact gtgtgtgaga ggtcctatga ttatgtccgg ttatgtaaac aatccggaag  2880
cgaccaacgc cttgattgac aaggatggat ggctacattc tggagacata gcttactggg  2940
acgaagacga acacttcttc atcgttgacc gcctgaagtc tctgattaag tacaaaggct  3000
atcaggtggc tcccgctgaa ttggaatcca tcttgctcca acaccccaac atcttcgacg  3060
caggtgtcgc aggtcttccc gacgatgacg ccggtgaact tcccgccgcc gttgttgttt  3120
tggagcacgg aaagacgatg acggaaaaag agatcgtgga ttacgtcgcc agtcaagtaa  3180
caaccgcgaa aaagttgcgc ggaggagttg tgtttgtgga cgaagtaccg aaaggtctta  3240
ccggaaaact cgacgcaaga aaaatcagag agatcctcat aaaggccaag aagggcggaa  3300
agatcgccgt gtaactcgag aatcaacctc tggattacaa aatttgtgaa agattgactg  3360
gtattcttaa ctatgttgct ccttttacgc tatgtggata cgctgcttta atgcctttgt  3420
atcatgctat tgcttcccgt atggctttca ttttctcctc cttgtataaa tcctggttgc  3480
tgtctcttta tgaggagttg tggcccgttg tcaggcaacg tggcgtggtg tgcactgtgt  3540
ttgctgacgc aacccccact ggttggggca ttgccaccac ctgtcagctc ctttccggga  3600
ctttcgcttt ccccctccct attgccacgg cggaactcat cgccgcctgc cttgcccgct  3660
gctggacagg ggctcggctg ttgggcactg acaattccgt ggggtgtgcc ttctagttgc  3720
cagccatctg ttgtttgccc ctcccccgtg ccttccttga ccctggaagg tgccactccc  3780
actgtccttt cctaataaaa tgaggaaatt gcatcgcatt gtctgagtag gtgtcattct  3840
attctggggg gtggggtggg gcaggacagc aagggggagg attgggaaga caatagcagg  3900
catgctgggg atgcggtggg ctctatggga agatgtctac tgagctgtgc gatccctgct  3960
ggggactttc cgctggggac tttccgctgg ggactttccg ccttcagcta aggaagctac  4020
caatatttag aggtacattt tgttctagaa caaaatgtac cggtacattt tgttctggta  4080
cattttgttc tattaaggac aacgtaagta tagcgcatag acacgtggcg ccatcggatc  4140
ccgggtggct tgttgtccac aaccattaaa ccttaaaagc tttaaaagcc ttatatattc  4200
tttttttct tataaaactt aaaaccttag aggctattta agttgctgat ttatattaat  4260
tttattgttc aaacatgaga gcttagtacg tgaaacatga gagcttagta cattagccat  4320
gagagcttag tacattagcc atgagggttt agttcattaa acatgagagc ttagtacatt  4380
aaacatgaga gcttagtaca ttaaacatga gagcttagta catactatca acaggttgaa  4440
ctgctgatct gtacagtaga attggtaaag agagttgtgt aaaatattga gttcgcacat  4500
cttgttgtct gattattgat ttttggcgaa accatttgat catatgacaa gatgtgtatc  4560
taccttaact taatgatttt gataaaaatc atta                             4594

SEQ ID NO: 30          moltype = DNA  length = 4786
FEATURE                Location/Qualifiers
source                 1..4786
                       mol_type = other DNA
                       note = NP-MHCK7-hBGi-EGFP-P2A-Fluc-WPRE3-DTS
                       organism = synthetic construct
SEQUENCE: 30
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccccact acgggtctag  240
gctgcccatg taaggaggca aggcctgggg acacccgaga tgcctggtta taattaaccc  300
agacatgtgg ctgccccccc ccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catggtgagc aagggcgagg agctgttcac  1080
cggggtggtg cccatcctgg tcgagctgga cggcgacgta aacggccaca agttcagcgt  1140
gtccggcgag ggcgagggcg atgccaccta cggcaagctg accctgaagt tcatctgcac  1200
caccggcaag ctgcccgtgc cctggcccac cctcgtgacc accctgacct acggcgtgca  1260
gtgcttcagc cgctaccccg accacatgaa gcagcacgac ttcttcaagt ccgccatgcc  1320
cgaaggctac gtccaggagc gcaccatctt cttcaaggac gacggcaact acaagacccg  1380
cgccgaggtg aagttcgagg gcgacaccct ggtgaaccgc atcgagctga agggcatcga  1440
cttcaaggag gacggcaaca tcctggggca caagctggag tacaactaca acagccacaa  1500
cgtctatatc atggccgaca agcagaagaa cggcatcaag gtgaacttca agatccgcca  1560
caacatcgag gacggcagcg tgcagctcgc cgaccactac cagcagaaca cccccatcgg  1620
cgacggcccc gtgctgctgc ccgacaacca ctacctgagc acccagtccg ccctgagcaa  1680
agaccccaac gagaagcgcg atcacatggt cctgctggag ttcgtgaccg ccgccgggat  1740
cactctcggc atggacgagc tgtacaagaa tcgcgctact aacttcagcc tgctgaagca  1800
ggctggagac gtggaggaga accctggacc tatggaagac gccaaaaaca taaagaaagg  1860
cccggcgcca ttctatccgc tggaagatgg aaccgctgga gagcaactgc ataaggctat  1920
gaagagatac gccctggttc ctggaacaat tgcttttaca gatgcacata tcgaggtgga  1980
catcacttac gctgagtact tcgaaatgtc cgttcggttg gcagaagcta tgaaacgata  2040
tgggctgaat acaaatcaca gaatcgtcgt atgcagtgaa aactctcttc aattctttat  2100
gccggtgttg ggcgcgttat ttatcggagt tgcagttgcg cccgcgaacg acatttataa  2160
tgaacgtgaa ttgctcaaca gtatgggcat ttcgcagcct accgtggtgt tcgtttccaa  2220
aaaggggttg caaaaaattt tgaacgtgca aaaaaagctc ccaatcatcc aaaaaattat  2280
tatcatggat tctaaaacgg attaccaggg atttcagtcg atgtacacgt tcgtcacatc  2340
```

```
tcatctacct cccggtttta atgaatacga ttttgtgcca gagtccttcg atagggacaa  2400
gacaattgca ctgatcatga actcctctgg atctactggt ctgcctaaag gtgtcgctct  2460
gcctcataga actgcctgcg tgagattctc gcatgccaga gatcctattt ttggcaatca  2520
aatcattccg gatactgcga ttttaagtgt tgttccattc catcacggtt ttggaatgtt  2580
tactacactc ggatatttga tatgtggatt tcgagtcgtc ttaatgtata gatttgaaga  2640
agagctgttt ctgaggagcc ttcaggatta caagattcaa agtgcgctgc tggtgccaac  2700
cctattctcc ttcttcgcca aaagcactct gattgacaaa tacgatttat ctaatttaca  2760
cgaaattgct tctggtggcg ctcccctctc taaggaagtc ggggaagcgg ttgccaagag  2820
gttccatctg ccaggtatca ggcaaggata tgggctcact gagactacat cagctattct  2880
gattacaccc gagggggatg ataaaccggg cgcggtcggt aaagttgttc cattttttga  2940
agcgaaggtt gtggatctgg ataccgggaa aacgctgggc gttaatcaaa gaggcgaact  3000
gtgtgtgaga ggtcctatga ttatgtccgg ttatgtaaac aatccggaag cgaccaacgc  3060
cttgattgac aaggatggat ggctacattc tggagacata gcttactggg acgaagacga  3120
acacttcttc atcgttgacc gcctgaagtc tctgattaag tacaaaggct atcaggtggc  3180
tcccgctgaa ttggaatcca tcttgctcca acaccccaac atcttcgacg caggtgtcgc  3240
aggtcttccc gacgatgacg ccggtgaact tcccgccgcc gttgttgttt tggagcacgg  3300
aaagacgatg acggaaaaag agatcgtgga ttacgtcgcc agtcaagtaa caaccgcgaa  3360
aaagttgcgc ggaggagttg tgtttgtgga cgaagtaccg aaaggtctta ccggaaaact  3420
cgacgcaaga aaaatcagag agatcctcat aaaggccaag aagggcggaa agatcgccgt  3480
gtaactcgag aatcaacctc tggattacaa aatttgtgaa agattgactg gtattcttaa  3540
ctatgttgct ccttttacgc tatgtggata cgctgcttta atgcctttgt atcatgctat  3600
tgcttcccgt atggctttca ttttctcctc cttgtataaa tcctggttgc tgtctcttta  3660
tgaggagttg tggcccgttg tcaggcaacg tggcgtggtg tgcactgtgt ttgctgacgc  3720
aacccccact ggttggggca ttgccaccac ctgtcagctc ctttccggga ctttcgcttt  3780
ccccctccct attgccacgg cggaactcat cgccgcctgc cttgcccgct gctggacagg  3840
ggctcggctg ttgggcactg acaattccgt ggggtgtgcc ttctagttgc cagccatctg  3900
ttgtttgccc ctcccccgtg ccttccttga ccctggaagg tgccactccc actgtccttt  3960
cctaataaaa tgaggaaatt gcatcgcatt gtctgagtag gtgtcattct attctggggg  4020
gtggggtggg gcaggacagc aagggggagg attgggaaga caatagcagg catgctgggg  4080
atgcggtggg ctctatggga agatgtctac tgagctgtgc gatccctgct ggggactttc  4140
cgctggggac tttccgctgg ggactttccg ccttcagcta aggaagctac caatatttag  4200
aggtacattt tgttctagaa caaaatgtac cggtacattt tgttctggta cattttgttc  4260
tattaaggac aacgtaagta tagcgcatag acacgtggcg ccatcggatc ccgggcccgt  4320
cgacttaagt ggcttgttgt ccacaaccat taaaccttaa aagctttaaa agccttatat  4380
attctttttt ttcttataaa acttaaaacc ttagaggcta tttaagttgc tgatttatat  4440
taattttatt gttcaaacat gagagcttag tacgtgaaac atgagagctt agtacattag  4500
ccatgagagc ttagtacatt agccatgagg gtttagttca ttaaacatga gagcttagta  4560
cattaaacat gagagcttag tacattaaac atgagagctt agtacatact atcaacaggt  4620
tgaactgctg atctgtacag tagaattggt aaagagagtt gtgtaaaata ttgagttcgc  4680
acatcttgtt gtctgattat tgatttttgg cgaaaccatt tgatcatatg acaagatgtg  4740
tatctacctt aacttaatga ttttgataaa aatcattagc ggccgc                4786

SEQ ID NO: 31          moltype = DNA  length = 15459
FEATURE                Location/Qualifiers
source                 1..15459
                       mol_type = other DNA
                       note = pUC57-CBA-hBGi-DMD-4-WPRE3-DTS
                       organism = synthetic construct
SEQUENCE: 31
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac catgctttgg tgggaagaag  300
tcgaggactg ctacgagcgc gaggacgtgc agaagaaaac cttcaccaaa tgggtcaacg  360
cccagttcag caagttcggc aagcagcaca tcgagaacct gttcagcgac ctgcaggatg  420
gcagaaggct gctggatctg ctggaaggcc tgacaggaca gaagctgccc aaagagaagg  480
gcagcacaag agtgcacgcc ctgaacaacg tgaacaaggc cctgagagtg ctgcagaaca  540
acaacgtgga cctggtcaac atcggcagca ccgacatcgt ggacggcaac cacaaactga  600
ccctgggcct gatctggaac atcatcctgc actggcaagt gaagaacgtg atgaagaaca  660
tcatggccgg cctgcagcag accaacagcg agaagattct gctgagctgg gtccgacaga  720
gcacccggaa ttaccctcaa gtgaacgtga tcaacttcac cacctcttgg agcgacggac  780
tggccctgaa tgccctgatc cacagccaca gacctgacct gttcgactgg aacagcgtcg  840
tgtgtcagca gagcgccaca cagaggctgg aacacgcctt caatatcgcc agataccagc  900
tgggcatcga gaaactgctg gaccccgagg atgtggacac cacctatcct gacaagaaat  960
ccatcctcat gtacatcacc agcctgttcc aggtgctgcc ccagcaggtt tccatcgagg  1020
ccattcaaga ggtcgagatg ctgcccagac ctcctaaagt gaccaaagag gaacacttcc  1080
agctgcacca ccagatgcac tactctcagc agatcaccgt gtctctggcc cagggctacg  1140
agagaacaag cagccccaag cctcggttca agagctacgc ctatacacag gccgcctacg  1200
tgaccaccag cgatcctaca agaagcccat ttcctagcca gcatctggaa gcccctgagg  1260
acaagagctt tggcagcagc ctgatggaaa gcgaagtgaa cctggaccgc taccagacag  1320
ccctggaaga ggttctgagc tggctgctgt ctgccgagga tacactgcag gctcagggcg  1380
agatcagcaa cgacgtggaa gtggtcaagg accagtttca cacccacgag ggctacatga  1440
tggacctgac agcccaccag ggcagagtgg gcaatattct gcagctgggc tccaagctga  1500
tcggcacagg caagctgagc gaggacgaag agacagaggt gcaagagcag atgaacctgc  1560
tgaacagcag atgggagtgt ctgagagtgg ccagcatgga aaagcagagc aacctgcacc  1620
gggtgctgat ggatctccag aaccagaagc tgaaagagct gaacgactgg ctgaccaaga  1680
ccgaggaacg gacccggaag atggaagagg aacctctggg acccgacctg gaagatctga  1740
aaagacaggt gcagcagcat aaggtgctgc aagaggacct cgaacaagag caagtgcgcg  1800
```

```
tgaacagcct gacacacatg gtggtggtcg tggatgagag cagcggagat catgccacag  1860
ccgctctgga agaacagctg aaggtgctgg gagacagatg ggccaatatc tgccggtgga  1920
ccgaggatag atgggtgctg ctccaggaca tcctgctgaa gtggcagcgg ctgacagagg  1980
aacagtgcct gtttagcgcc tggctgtccg agaaagagga cgccgtcaac aagatccaca  2040
ccaccggctt caaggatcag aatgagatgc tgagcagcct gcagaaactg gccgtgctga  2100
aggctgacct ggaaaagaaa aagcagtcca tgggcaagct gtactccctg aagcaggacc  2160
tgctgagcac actgaagaac aagtctgtga cccagaaaac cgaggcctgg ctggacaact  2220
tcgcccggtg ttgggataac ctggtgcaga agctggaaaa gtccaccgct cagatctctc  2280
aggccgtgac cacaacacag ccttctctga cccagaccac cgtgatggaa acagtgacca  2340
cagtgacaac ccgcgagcag atcctggtca agcacgccca agaagaactg cctcctccac  2400
ctcctcagaa gaaacggcag atcacagtgg acagcgagat ccggaagaga ctggacgtgg  2460
acatcaccga gctgcacagc tggatcacca gatccgaagc cgtgctgcag tcccctgagt  2520
tcgccatctt cagaaaagag ggcaacttct ccgacctgaa agagaaagtc aacgccatcg  2580
agagagagaa ggccgagaag ttccggaagc tgcaggacgc ctctagatct gcccaggctc  2640
tggtggaaca gatggtcaac gaaggcgtga acgccgacag catcaagcag gcctcagagc  2700
agctgaactc ccggtggatc gagttctgtc agctcctgag cgagagactg aactggctgg  2760
aataccagaa caatatcatt gccttctaca accagctcca gcagctcgaa cagatgacca  2820
ccacagccga gaattggctg aagatccagc ctaccacacc tagcgagccc accgccatta  2880
agagccagct gaaaatctgc aaggacgaag tgaatcggct gagcgatctg cagccccaga  2940
tcgaaagact gaaaatccag tctatcgccc tcaaagagaa aggacagggc cccatgttcc  3000
tggacgccga ttttgtggcc tttaccaacc acttcaaaca ggtgttctcc gacgtgcagg  3060
cccgggaaaa agagctgcag accatcttcg acaccctgcc tccaatgaga taccaagaga  3120
caatgagcgc catccggacc tgggtgcagc aaagcgagac aaagctgagc atcccacagc  3180
tgagcgtgac cgactacgag atcatggaac agagactggg cgaactgcag gccctccagt  3240
ctagcctgca agaacagcag tccggcctgt actacctgag cacaaccgtg aaagagatga  3300
gcaagaaggc ccctagcgag atctcccgga agtaccagag cgagttcgaa gagatcgaag  3360
gccggtggaa gaagctgtct agccagctgg ttgagcactg ccagaaactc gaagaacaaa  3420
tgaacaagct gcgcaagatc cagaatcaca tccagacgct gaagaaatgg atggccgagg  3480
tggacgtgtt cctgaaagaa gagtggcccg ctctgggcga ctccgagatt ctgaagaaac  3540
agctcaaaca gtgccggctg ctggtgtccg atatccagac aatccagcca agcctgaact  3600
ccgtgaatga aggcggccag aagatcaaga acgaggccga gcctgagttt gccagcagac  3660
tggaaaccga actgaaagaa ctcaacaccc agtgggacca catgtgccag caagtgtacg  3720
cccggaaaga ggccctgaaa ggcggactcg aaaagactgt gtctctgcag aaagacctgt  3780
ctgagatgca cgagtggatg acccaggccg aagaggaata cctggaacgg gacttcgagt  3840
acaagacccc tgatgagctg caaaaagccg tcgaggaaat gaagcgggcc aaagaagagg  3900
cccagcagaa agaagccaaa gtcaagctgc tgaccgagtc cgtgaatagc gttatcgctc  3960
aggcccctcc tgtggctcaa gaggctctca agaaagaact ggaaactctg accaccaact  4020
accagtggct gtgcaccaga ctgaacggca agtgcaagac actggaagaa gtgtgggcct  4080
gctggcacga actgctgtcc tatctggaaa aggccaacaa gtggctgaac gaggtggaat  4140
tcaagctgaa aaccaccgag aacatccctg gcggcgctga agagattagc gaggtgctgg  4200
acagcctgga aaacctgatg agacacagcg aggacaaccc caatcagatc agaatcctgg  4260
ctcagaccct gaccgatggc ggcgtgatgg acgagctgat caacgaggaa ctcgaaacct  4320
tcaacagccg gtggcgggaa ctgcacgagg aagctgttcg gaggcagaag ttgctggaac  4380
agtctatcca gagcgcacaa gaaaccgaga agtccctgca cctgatccaa gagagcctga  4440
ccttcatcga caagcagctg gccgcttata tcgccgacaa ggtggacgct gctcagatgc  4500
cccaagaggc acagaagatt cagagcgacc tgaccagcca cgagattagc ctggaagaaa  4560
tgaagaagca caaccagggc aaagaggccg ctcagagagt cctgagccag atcgatgtgg  4620
cacagaaaaa gctccaggat gtgtccatga agtttcggct gtttcagaag cccgccaact  4680
tcgagcagag actgcaagag tccaagatga tcctggacga agtcaaaatg catctgcccg  4740
cactggaaac aaagtccgtg gaacaagaag tggtgcagtc ccagctgaac cactgcgtga  4800
acctgtacaa gagcctgtcc gaagtgaagt ctgaggtgga aatggtcatc aagaccggca  4860
ggcagatcgt ccagaagaag cagaccgaga atcccaaaga actcgacgag agagtgaccg  4920
ctctgaagct gcactacaat gagctgggcg ccaaagtgac cgagcggaag caacagcttg  4980
agaagtgcct gaaactgtct cggaagatgc ggaaagaaat gaacgtgctg acagagtggc  5040
tggccgccac cgatatggaa ctgactaaga gaagcgccgt ggaaggcatg cccagcaacc  5100
tggatagtga agtggcctgg ggcaaagcca ctcagaaaga gattgagaag cagaaggtcc  5160
acctgaagtc catcaccgaa gtgggcgaag ccctgaaaac cgtgctggga aagaaagaga  5220
cactggtcga ggacaagctg tccctgctga attccaactg gatcgccgtg acctccagag  5280
ctgaggaatg gctgaatctg ctgcttgagt accagaaaca catggaaacg ttcgaccaga  5340
acgtcgacca catcacaaag tggatcatcc aggctgatac cctgctggac gagtccgaga  5400
agaagaaacc ccaacaaaaa gaagatgtgc tgaagcggct gaaagccgag ctgaatgaca  5460
tccggcctaa ggtggacagc accagagatc aggcagccaa cctgatggcc aacagaggcg  5520
accactgtcg gaagctcgtg gaacctcaga tcagcgagct taaccacaga tttgccgcca  5580
tcagccaccg gatcaagaca ggcaaggcca gcattcctct caaagagctt gagcagttca  5640
acagcgacat ccaaaagctg ctcgaacccc tggaagccga gatccaacag ggcgtcaacc  5700
tcaaagaaga agatttcaac aaggacatga acgaggacaa tgagggcacc gtcaaagaac  5760
tgctgcagcg gggcgataat ctgcagcagc ggattaccga tgagcgcaag cgggaagaga  5820
tcaagattaa gcagcagctg ctgcagacca agcacaacgc cctgaaggac ctgcggagcc  5880
agagaagaaa gaaggccctg gaaatcagcc accagtggta tcagtacaag cggcaggccg  5940
acgacctgct gaagtgcctg gatgacatcg agaagaagct ggcctctctg cccgagccta  6000
gggacgagag aaagatcaaa gagatcgacc gcgagctgca gaaaaagaaa gaggaactga  6060
acgccgtccg cagacaggcc gaaggacttt ctgaagatgg cgccgctatg gccgtggaac  6120
ccacacagat tcagctgagc aagcggtggc gggaaatcga gagcaagttc gcccagttcc  6180
ggcggctgaa tttcgcccag atccacaccg tgcgggaaga gacaatgatg gtcatgacag  6240
aggacatgcc ccttgagatc agctacgtgc ccagcaccta cctgaccgag atcacccatg  6300
tgtctcaggc cctgctggaa gtggaacagc tgctgaatgc ccctgacctg tgcgccaagg  6360
acttcgagga cctgttcaag caagaggaaa gcctgaagaa catcaaggac agcctgcagc  6420
agagcagcgg ccggatcgat atcatccaca gcaagaaaac cgccgcactg cagagcgcca  6480
cacctgtgga aagagtgaag ctgcaagagg ccctgagcca gctggatttc cagtgggaga  6540
```

```
aagtgaacaa gatgtacaag gaccggcagg gcagattcga ccgcagcgtt gaaaagtggc  6600
ggcggttcca ctacgacatc aagatcttca accagtggct gaccgaggcc gagcagttcc  6660
tgagaaagac acagatcccc gagaactggg agcacgccaa gtacaagtgg tatctgaaag  6720
agctgcagga cggcatcggc cagagacaga cagtcgtgcg gacactgaat gccaccggcg  6780
aggaaatcat ccagcagtcc agcaagaccg acgccagcat cctgcaagag aagctgggca  6840
gcctgaacct gcggtggcaa gaagtgtgca agcagctgag cgaccggaag aagcggctgg  6900
aagaacagaa gaatatcctg agcgagttcc agcgggacct gaacgagttc gtgctgtggc  6960
tcgaagaggc cgacaatatc gccagcattc ccctggaacc tggcaaagag cagcagctga  7020
aagaaaagct ggaacaagtg aaactgctgg tcgaggaact gcccctgaga cagggaatcc  7080
tgaaacagct gaacgagaca ggcggccctg tgctggtgtc tgcccctatt tctcccgagg  7140
aacaggacaa gctggaaaac aagctgaagc agaccaacct gcagtggatc aaggtgtcca  7200
gagcactgcc tgagaagcag ggcgagatcg aggcccagat caaggacctg ggacagctcg  7260
aaaagaagct tgaggacctc gaagaacagc tcaaccatct gctgctttgg ctgagcccca  7320
tccggaacca gctggaaatc tacaaccagc ctaatcaaga gggcccctc gacgtgaaag  7380
aaaccgagat tgccgtgcag gccaagcagc ccgatgtgga agagatcctg tctaagggcc  7440
agcacctgta caaagagaag cccgccacac agcccgtgaa gcggaaactg gaagatctga  7500
gcagcgagtg gaaggccgtg aaccggctgc tgcaagaact gagagccaaa cagcctgatc  7560
tggcccctgg cctgacaaca attggcgcct ctcctacaca gaccgtgaca ctggtcacac  7620
agcctgtggt caccaaagag acagccatca gcaaactgga aatgcccagc agtctgatgc  7680
tcgaagtgcc cgcactggcc gacttcaata gagcctggac cgagctgacc gactggctca  7740
gtctgctgga ccaagtcatc aagtcccaga gagtgatggt cggagatctt gaggacatca  7800
acgagatgat cattaagcag aaagccacca tgcaggacct tgagcagaga aggccccagc  7860
ttgaagaact gatcaccgcc gctcagaacc tgaaaaacaa gaccagcaat caagaagccc  7920
ggaccatcat caccgaccgg atcgagagaa tccagaacca gtgggacgaa gtgcaagagc  7980
atctgcagaa cagacggcag cagctcaatg agatgctgaa ggacagcaca cagtggctgg  8040
aagccaaaga agaagccgag caggttctcg gacaggccag agctaagctg gaatcttgga  8100
aagagggacc ctacaccgtc gacgccatcc agaagaagat caccgagaca aagcagctgg  8160
ccaaggatct gagacagtgg cagaccaatg tggacgtggc caacgacctg gctctgaagc  8220
tgctgagaga ctacagcgcc gacgacacca gaaaggtgca catgatcacc gaaaacatca  8280
acgcctcttg gcggagcatc cacaagcggg tgtcagagag agaagccgct ctggaagaaa  8340
cacatagact gctccagcag ttcccactcg acctggaaaa gttcctggcc tggctgacag  8400
aagccgaaac caccgctaac gtgctccagg atgccaccag aaaagagcgg ctgttggagg  8460
acagcaaggg cgtcaaagaa ctcatgaagc agtggcagga tctgcaaggg gagattgaag  8520
cccacaccga cgtgtaccac aacctggacg agaacagcca gaagatcctg cggtccctgg  8580
aaggctctga tgatgctgtg ctgcttcaga ggcggctgga caacatgaac ttcaagtgga  8640
gcgagctgcg gaagaagtcc ctgaacatca gaagccacct ggaagcctcc agcgaccagt  8700
ggaaaagact gcacctgtct ctccaagagc tgctcgtgtg gctgcagctg aaggatgacg  8760
agctgagtag acaggcccct atcggcggag attttcccgc cgtgcagaaa cagaacgacg  8820
tgcaccgggc cttcaagaga gagctgaaaa caaaagaacc cgtcatcatg agcaccctgg  8880
aaaccgtgcg gatctttctg accgagcagc ctctggaagg actggaaaag ctgtaccaag  8940
agcctagaga gctgcctcct gaagaaaggg cccagaacgt gacacggctg cttagaaagc  9000
aggccgagga agtgaacacc gaatgggaga agctgaacct ccactccgcc gactggcagc  9060
ggaagatcga tgagacactg gaacggctgc gggaactgca agaagccaca gacgagctgg  9120
acctgaaact gcggcaggct gaagtgatca aaggctcctg gcagccagtg ggcgatctgc  9180
tgatcgatag cctgcaggac catctggaaa aagtcaaggc cctgcgggga gagatcgccc  9240
ctctcaaaga aaacgtgtcc cacgtgaacg atctggccag gcagctgaca acactgggca  9300
tccagctgag cccttacaac ctgtctacct tggaggacct gaatacccgg tggaagctgc  9360
tccaagtggc cgtcgaggat agagtgcggc agctgcatga ggctcacaga gattttggac  9420
ccgccagcca gcacttcctg agcacatctg ttcaaggccc ctgggagaga gctatcagcc  9480
ctaacaaggt gccctactac atcaaccacg agacacagac cacctgttgg gatcacccca  9540
agatgaccga actgtatcag tccctggccg acctgaacaa cgtgcggttt agcgcctacc  9600
ggaccgccat gaagctgcgc agactgcaga aagctctgtg cctggacctg ctgtctctga  9660
gcgctgcttg tgatgccctg gaccagcata acctcaagca gaacgaccag cctatggaca  9720
tcctgcagat catcaactgc ctgaccacca tctacgaccg gctcgaacaa gagcacaaca  9780
acctggtcaa cgtgcccctg tgcgtggaca tgtgcctgaa ttggctgctg aacgtgtacg  9840
acaccggcag aaccggcagg atcagagtgc tgagcttcaa gaccggcatc atctccctgt  9900
gcaaggccca ccttgaggat aagtaccgct acctgtttaa gcaggtcgcc agcagcaccg  9960
gcttttgcga ccaaagaagg ctgggactgc tgctccacga cagcattcag atccctagac  10020
agctgggcga agtggcctct ttcggcggct ctaatatcga gcctagcgtg cggagctgct  10080
tccagttcgc caacaacaag cccgagattg aggccgcact gttcctggac tggatgagac  10140
tggaacccca gagcatggtc tggctgcctg tgctgcatag agtggccgca gccgaaacag  10200
ccaagcacca ggccaagtgc aacatctgca aagagtgccc catcatcggc ttccggtaca  10260
gatccctgaa gcacttcaac tacgatatct gccagtcctg cttcttcagc ggcagagtgg  10320
ccaagggcca caagatgcac taccccatgg tggaatactg cacccctacc acctctggcg  10380
aggacgtgcg ggattttgcc aaggtgctca agaacaagtt ccggaccaag cgctacttcg  10440
ctaagcaccc cagaatgggc tacctgccag tgcagacagt gcttgagggc gacaacatgg  10500
aaacccctgt gactctgatc aacttctggc ccgtggatag cgcccctgct agttctcctc  10560
agctgtctca cgacgatacc cacagcagaa tcgagcacta cgcctccaga ctggccgaga  10620
tggaaaacag caacggcagc tacctgaatg acagcatcag ccccaacgag agcatcgacg  10680
acgaacatct gctcattcag cactactgcc agagcctgaa tcaggacagc cctctgtctc  10740
agcctagaag ccctgcacag atcctgatca gcctggaaag cgaggaacgc ggcgagctgg  10800
aaagaatcct ggcagacctg gaagaggaaa accggaacct gcaggccgaa tacgacagac  10860
tcaagcagca gcacgagcac aagggactgt ctccactgcc ttctccacct gaaatgatgc  10920
ccacctctcc acagagcccc agagatgccg agctgattgc cgaagccaaa ctgctgaggc  10980
agcacaaagg cagactcgaa gccagaatgc agattctcga agatcacaac aagcagctcg  11040
aatcccagct gcacagactt aggcagctgc tggaacagcc tcaggcagag gccaaagtga  11100
atggcaccac cgtgtctagc cctagcacaa gcctgcagag atccgacagc agccagccaa  11160
tgcttctgag agtcgtgggc tcccagacca gcgattctat gggcgaagag gacctgctca  11220
gccctcctca ggatacaagc accggcctgg aagaagtgat ggaacaactg aacaacagct  11280
```

```
tccccagcag cagaggcaga aacacccctg gcaagcccat gcgcgaggac accatgtgat  11340
aactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg tgttgtcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acgtggcgcc atcggatccc gggcccgtcg  12180
actgcagagg cctgcatgca agcttggcgt aatcatggtc atagctgttt cctgtgtgaa  12240
attgttatcc gctcacaatt ccacacaaca tacgagccgg aagcataaag tgtaaagcct  12300
ggggtgccta atgagtgagc taactcacat taattgcgtt gcgctcactg cccgctttcc  12360
agtcgggaaa cctgtcgtgc cagctgcatt aatgaatcgg ccaacgcgcg gggagaggcg  12420
gtttgcgtat tgggcgctct tccgcttcct cgctcactga ctcgctgcgc tcggtcgttc  12480
ggctgcggcg agcggtatca gctcactcaa aggcggtaat acggttatcc acagaatcag  12540
gggataacgc aggaaagaac atgtgagcaa aaggccagca aaaggccagg aaccgtaaaa  12600
aggccgcgtt gctggcgttt ttccataggc tccgcccccc tgacgagcat cacaaaaatc  12660
gacgctcaag tcagaggtgg cgaaacccga caggactata aagataccag gcgtttcccc  12720
ctggaagctc cctcgtgcgc tctcctgttc cgaccctgcc gcttaccgga tacctgtccg  12780
cctttctccc ttcgggaagc gtggcgcttt ctcatagctc acgctgtagg tatctcagtt  12840
cggtgtaggt cgttcgctcc aagctgggct gtgtgcacga accccccgtt cagcccgacc  12900
gctgcgcctt atccggtaac tatcgtcttg agtccaaccc ggtaagacac gacttatcgc  12960
cactggcagc agccactggt aacaggatta gcagagcgag gtatgtaggc ggtgctacag  13020
agttcttgaa gtggtggcct aactacggct acactagaag aacagtattt ggtatctgcg  13080
ctctgctgaa gccagttacc ttcggaaaaa gagttggtag ctcttgatcc ggcaaacaaa  13140
ccaccgctgg tagcggtggt ttttttgttt gcaagcagca gattacgcgc agaaaaaaag  13200
gatctcaaga agatcctttg atcttttcta cggggtctga cgctcagtgg aacgaaaact  13260
cacgttaagg gattttggtc atgagattat caaaaaggat cttcacctag atccttttaa  13320
attaaaaatg aagttttaaa tcaatctaaa gtatatatga gtaaacttgg tctgacagtt  13380
accaatgctt aatcagtgag gcacctatct cagcgatctg tctatttcgt tcatccatag  13440
ttgcctgact ccccgtcgtg tagataacta cgatacggga gggcttacca tctggcccca  13500
gtgctgcaat gataccgcga gacccacgct caccggctcc agatttatca gcaataaacc  13560
agccagccgg aagggccgag cgcagaagtg gtcctgcaac tttatccgcc tccatccagt  13620
ctattaattg ttgccgggaa gctagagtaa gtagttcgcc agttaatagt ttgcgcaacg  13680
ttgttgccat tgctacaggc atcgtggtgt cacgctcgtc gtttggtatg gcttcattca  13740
gctccggttc ccaacgatca aggcgagtta catgatcccc catgttgtgc aaaaaagcgg  13800
ttagctcctt cggtcctccg atcgttgtca gaagtaagtt ggccgcagtg ttatcactca  13860
tggttatggc agcactgcat aattctctta ctgtcatgcc atccgtaaga tgcttttctg  13920
tgactggtga gtactcaacc aagtcattct gagaatagtg tatgcggcga ccgagttgct  13980
cttgcccggc gtcaatacgg gataataccg cgccacatag cagaacttta aaagtgctca  14040
tcattggaaa acgttcttcg gggcgaaaac tctcaaggat cttaccgctg ttgagatcca  14100
gttcgatgta acccactcgt gcacccaact gatcttcagc atcttttact ttcaccagcg  14160
tttctgggtg agcaaaaaca ggaaggcaaa atgccgcaaa aaagggaata agggcgacac  14220
ggaaatgttg aatactcata ctcttccttt ttcaatatta ttgaagcatt tatcagggtt  14280
attgtctcat gagcggatac atatttgaat gtatttagaa aaataaacaa ataggggttc  14340
cgcgcacatt tccccgaaaa gtgccacctg acgtctaaga aaccattatt atcatgacat  14400
taacctataa aaataggcgt atcacgaggc cctttcgtct cgcgcgtttc ggtgatgacg  14460
gtgaaaacct ctgacacatg cagctcccgg agacggtcac agcttgtctg taagcggatg  14520
ccgggagcag acaagcccgt cagggcgcgt cagcgggtgt tggcgggtgt cggggctggc  14580
ttaactatgc ggcatcagag cagattgtac tgagagtgca ccatatgcgg tgtgaaatac  14640
cgcacagatg cgtaaggaga aaataccgca tcaggcgcca ttcgccattc aggctgcgca  14700
actgttggga agggcgatcg gtgcgggcct cttcgctatt acgccagctg gcgaaagggg  14760
gatgtgctgc aaggcgatta agttgggtaa cgccagggtt ttcccagtca cgacgttgta  14820
aaacgacggc cagtgaattc gagctcggta cctcgcgaat gcatgcggcc gccgttacat  14880
aacttacggt aaatggcccg cctggctgac cgcccaacga cccccgccca ttgacgtcaa  14940
taatgacgta tgttcccata gtaacgccaa tagggacttt ccattgacgt caatgggtgg  15000
agtatttacg gtaaactgcc cacttggcag tacatcaagt gtatcatatg ccaagtacgc  15060
cccctattga cgtcaatgac ggtaaatggc ccgcctggca ttatgcccag tacatgacct  15120
tatgggactt tcctacttgg cagtacatct acgtattagt catcgctatt accatggtcg  15180
aggtgagccc cacgttctgc ttcactctcc ccatctcccc cccctcccca cccccaattt  15240
tgtatttatt tattttttaa ttattttgtg cagcgatggg ggcggggggg gggggggcgc  15300
gcgccaggcg gggcggggcg gggcgagggg cggggcgggg cgaggcggag aggtgcggcg  15360
gcagccaatc agagcggcgc gctccgaaag tttcctttta tggcgaggcg gcggcggcgg  15420
cggccctata aaaagcgaag cgcgcggcgg gcgggagtc                        15459
```

```
SEQ ID NO: 32          moltype = DNA  length = 15634
FEATURE                Location/Qualifiers
source                 1..15634
                       mol_type = other DNA
                       note = pUC57-MHCK7-hBGi-DMD-4-WPRE3-DTS
                       organism = synthetic construct
SEQUENCE: 32
tctggatcca ctgcttaaat acggacgagg acagggccct gtctcctcag cttcaggcac  60
```

-continued caccactgac ctgggacagt gaatcgtaag tactagcagc tacaatccag ctaccattct 120
gcttttattt tatggttggg ataaggctgg attattctga gtccaagcta ggcccttttg 180
ctaatcatgt tcatacctct tatcttcctc ccacagctcc tgggcaacgt gctggtctgt 240
gtgctggccc atcactttgg caaagaattg cgatcgccac catgctttgg tgggaagaag 300
tcgaggactg ctacgagcgc gaggacgtgc agaagaaaac cttcaccaaa tgggtcaacg 360
cccagttcag caagttcggc aagcagcaca tcgagaacct gttcagcgac ctgcaggatg 420
gcagaaggct gctggatctg ctggaaggcc tgacaggaca gaagctgccc aaagagaagg 480
gcagcacaag agtgcacgcc ctgaacaacg tgaacaaggc cctgagagtg ctgcagaaca 540
acaacgtgga cctggtcaac atcggcagca ccgacatcgt ggacggcaac cacaaactga 600
ccctgggcct gatctggaac atcatcctgc actggcaagt gaagaacgtg atgaagaaca 660
tcatggccgg cctgcagcag accaacagcg agaagattct gctgagctgg gtccgacaga 720
gcacccggaa ttaccctcaa gtgaacgtga tcaacttcac cacctcttgg agcgacggac 780
tggccctgaa tgccctgatc cacagccaca gacctgacct gttcgactgg aacagcgtcg 840
tgtgtcagca gagcgccaca cagaggctgg aacacgcctt caatatcgcc agataccagc 900
tgggcatcga gaaactgctg gaccccgagg atgtggacac cacctatcct gacaagaaat 960
ccatcctcat gtacatcacc agcctgttcc aggtgctgcc ccagcaggtt tccatcgagg 1020
ccattcaaga ggtcgagatg ctgcccagac ctcctaaagt gaccaaagag gaacacttcc 1080
agctgcacca ccagatgcac tactctcagc agatcaccgt gtctctggcc cagggctacg 1140
agagaacaag cagccccaag cctcggttca agagctacgc ctatacacag gccgcctacg 1200
tgaccaccag cgatcctaca agaagcccat ttcctagcca gcatctggaa gcccctgagg 1260
acaagagctt tggcagcagc ctgatggaaa gcgaagtgaa cctggaccgc taccagacag 1320
ccctggaaga ggttctgagc tggctgctgt ctgccgagga tacactgcag gctcagggcg 1380
agatcagcaa cgacgtggaa gtggtcaagg accagtttca cacccacgag ggctacatga 1440
tggacctgac agcccaccag ggcagagtgg gcaatattct gcagctgggc tccaagctga 1500
tcggcacagg caagctgagc gaggacgaag agacagaggt gcaagagcag atgaacctgc 1560
tgaacagcag atgggagtgt ctgagagtgg ccagcatgga aaagcagagc aacctgcacc 1620
gggtgctgat ggatctccag aaccagaagc tgaaagagct gaacgactgg ctgaccaaga 1680
ccgaggaacg gacccggaag atggaagagg aacctctggg acccgacctg gaagatctga 1740
aaagacaggt gcagcagcat aaggtgctgc aagaggacct cgaacaagag caagtgcgcg 1800
tgaacagcct gacacacatg gtggtggtcg tggatgagag cagcggagat catgccacag 1860
ccgctctgga agaacagctg aaggtgctgg gagacagatg ggccaatatc tgccggtgga 1920
ccgaggatag atgggtgctg ctccaggaca tcctgctgaa gtggcagcgg ctgacagagg 1980
aacagtgcct gtttagcgcc tggctgtccg agaaagagga cgccgtcaac aagatccaca 2040
ccaccggctt caaggatcag aatgagatgc tgagcagcct gcagaaactg gccgtgctga 2100
aggctgacct ggaaaagaaa aagcagtcca tgggcaagct gtactccctg aagcaggacc 2160
tgctgagcac actgaagaac aagtctgtga cccagaaaac cgaggcctgg ctggacaact 2220
tcgcccggtg ttgggataac ctggtgcaga agctggaaaa gtccaccgct cagatctctc 2280
aggccgtgac cacaacacag ccttctctga cccagaccac cgtgatggaa acagtgacca 2340
cagtgacaac ccgcgagcag atcctggtca agcacgccca agaagaactg cctcctccac 2400
ctcctcagaa gaaacggcag atcacagtgg acagcgagat ccggaagaga ctggacgtgg 2460
acatcaccga gctgcacagc tggatcacca gatccgaagc cgtgctgcag tcccctgagt 2520
tcgccatctt cagaaaagag ggcaacttct ccgacctgaa agagaaagtc aacgccatcg 2580
agagagagaa ggccgagaag ttccggaagc tgcaggacgc ctctagatct gcccaggctc 2640
tggtggaaca gatggtcaac gaaggcgtga acgccgacag catcaagcag gcctcagagc 2700
agctgaactc ccggtggatc gagttctgtc agctcctgag cgagagactg aactggctgg 2760
aataccagaa caatatcatt gccttctaca accagctcca gcagctcgaa cagatgacca 2820
ccacagccga gaattggctg aagatccagc ctaccacacc tagcgagccc accgccatta 2880
agagccagct gaaaatctgc aaggacgaag tgaatcggct gagcgatctg cagccccaga 2940
tcgaaagact gaaaatccag tctatcgccc tcaaagagaa aggacagggc cccatgttcc 3000
tggacgccga ttttgtggcc tttaccaacc acttcaaaca ggtgttctcc gacgtgcagg 3060
cccgggaaaa agagctgcag accatcttcg acaccctgcc tccaatgaga taccaagaga 3120
caatgagcgc catccggacc tgggtgcagc aaagcgagac aaagctgagc atcccacagc 3180
tgagcgtgac cgactacgag atcatggaac agagactggg cgaactgcag gccctccagt 3240
ctagcctgca agaacagcag tccggcctgt actacctgag cacaaccgtg aaagagatga 3300
gcaagaaggc ccctagcgag atctcccgga agtaccagag cgagttcgaa gagatcgaag 3360
gccggtggaa gaagctgtct agccagctgg ttgagcactg ccagaaactc gaagaacaaa 3420
tgaacaagct gcgcaagatc cagaatcaca tccagacgct gaagaaatgg atggccgagg 3480
tggacgtgtt cctgaaagaa gagtggcccg ctctgggcga ctccgagatt ctgaagaaac 3540
agctcaaaca gtgccggctg ctggtgtccg atatccagac aatccagcca agcctgaact 3600
ccgtgaatga aggcggccag aagatcaaga acgaggccga gcctgagttt gccagcagac 3660
tggaaaccga actgaaagaa ctcaacaccc agtgggacca catgtgccag caagtgtacg 3720
cccggaaaga ggccctgaaa ggcggactcg aaaagactgt gtctctgcag aaagacctgt 3780
ctgagatgca cgagtggatg acccaggccg aagaggaata cctggaacgg gacttcgagt 3840
acaagacccc tgatgagctg caaaaagccg tcgaggaaat gaagcgggcc aaagaagagg 3900
cccagcagaa agaagccaaa gtcaagctgc tgaccgagtc cgtgaatagc gttatcgctc 3960
aggcccctcc tgtggctcaa gaggctctca agaaagaact ggaaactctg accaccaact 4020
accagtggct gtgcaccaga ctgaacggca agtgcaagac actggaagaa gtgtgggcct 4080
gctggcacga actgctgtcc tatctggaaa aggccaacaa gtggctgaac gaggtggaat 4140
tcaagctgaa aaccaccgag aacatccctg gcggcgctga agagattagc gaggtgctgg 4200
acagcctgga aaacctgatg agacacagcg aggacaaccc caatcagatc agaatcctgg 4260
ctcagaccct gaccgatggc ggcgtgatgg acgagctgat caacgaggaa ctcgaaacct 4320
tcaacagccg gtggcgggaa ctgcacgagg aagctgttcg gaggcagaag ttgctggaac 4380
agtctatcca gagcgcacaa gaaaccgaga agtccctgca cctgatccaa gagagcctga 4440
ccttcatcga caagcagctg gccgcttata tcgccgacaa ggtggacgct gctcagatgc 4500
cccaagaggc acagaagatt cagagcgacc tgaccagcca cgagattagc ctggaagaaa 4560
tgaagaagca caaccagggc aaagaggccg ctcagagagt cctgagccag atcgatgtgg 4620
cacagaaaaa gctccaggat gtgtccatga agtttcggct gtttcagaag cccgccaact 4680
tcgagcagag actgcaagag tccaagatga tcctggacga agtcaaaatg catctgcccg 4740
cactggaaac aaagtccgtg gaacaagaag tggtgcagtc ccagctgaac cactgcgtga 4800

```
acctgtacaa gagcctgtcc gaagtgaagt ctgaggtgga aatggtcatc aagaccggca  4860
ggcagatcgt ccagaagaag cagaccgaga atcccaaaga actcgacgag agagtgaccg  4920
ctctgaagct gcactacaat gagctgggcg ccaaagtgac cgagcggaag caacagcttg  4980
agaagtgcct gaaactgtct cggaagatgc ggaaagaaat gaacgtgctg acagagtggc  5040
tggccgccac cgatatggaa ctgactaaga gaagcgccgt ggaaggcatg cccagcaacc  5100
tggatagtga agtggcctgg ggcaaagcca ctcagaaaga gattgagaag cagaaggtcc  5160
acctgaagtc catcaccgaa gtgggcgaag ccctgaaaac cgtgctggga aagaaagaga  5220
cactggtcga ggacaagctg tccctgctga attccaactg gatcgccgtg acctccagag  5280
ctgaggaatg gctgaatctg ctgcttgagt accagaaaca catggaaacg ttcgaccaga  5340
acgtcgacca catcacaaag tggatcatcc aggctgatac cctgctggac gagtccgaga  5400
agaagaaacc ccaacaaaaa gaagatgtgc tgaagcggct gaaagccgag ctgaatgaca  5460
tccggcctaa ggtggacagc accagagatc aggcagccaa cctgatggcc aacagaggcg  5520
accactgtcg gaagctcgtg gaacctcaga tcagcgagct taaccacaga tttgccgcca  5580
tcagccaccg gatcaagaca ggcaaggcca gcattcctct caaagagctt gagcagttca  5640
acagcgacat ccaaaagctg ctcgaacccc tggaagccga gatccaacag ggcgtcaacc  5700
tcaaagaaga agatttcaac aaggacatga acgaggacaa tgagggcacc gtcaaagaac  5760
tgctgcagcg gggcgataat ctgcagcagc ggattaccga tgagcgcaag cgggaagaga  5820
tcaagattaa gcagcagctg ctgcagacca agcacaacgc cctgaaggac ctgcggagcc  5880
agagaagaaa gaaggccctg gaaatcagcc accagtggta tcagtacaag cggcaggccg  5940
acgacctgct gaagtgcctg gatgacatcg agaagaagct ggcctctctg cccgagccta  6000
gggacgagag aaagatcaaa gagatcgacc gcgagctgca gaaaaagaaa gaggaactga  6060
acgccgtccg cagacaggcc gaaggacttt ctgaagatgg cgccgctatg gccgtggaac  6120
ccacacagat tcagctgagc aagcggtggc gggaaatcga gagcaagttc gcccagttcc  6180
ggcggctgaa tttcgcccag atccacaccg tgcgggaaga gacaatgatg gtcatgacag  6240
aggacatgcc ccttgagatc agctacgtgc ccagcaccta cctgaccgag atcacccatg  6300
tgtctcaggc cctgctggaa gtggaacagc tgctgaatgc ccctgacctg tgcgccaagg  6360
acttcgagga cctgttcaag caagaggaaa gcctgaagaa catcaaggac agcctgcagc  6420
agagcagcgg ccggatcgat atcatccaca gcaagaaaac cgccgcactg cagagcgcca  6480
cacctgtgga aagagtgaag ctgcaagagg ccctgagcca gctggatttc cagtgggaga  6540
aagtgaacaa gatgtacaag gaccggcagg gcagattcga ccgcagcgtt gaaaagtggc  6600
ggcggttcca ctacgacatc aagatcttca accagtggct gaccgaggcc gagcagttcc  6660
tgagaaagac acagatcccc gagaactggg agcacgccaa gtacaagtgg tatctgaaag  6720
agctgcagga cggcatcggc cagagacaga cagtcgtgcg gacactgaat gccaccggcg  6780
aggaaatcat ccagcagtcc agcaagaccg acgccagcat cctgcaagag aagctgggca  6840
gcctgaacct gcggtggcaa gaagtgtgca agcagctgag cgaccggaag aagcggctgg  6900
aagaacagaa gaatatcctg agcgagttcc agcgggacct gaacgagttc gtgctgtggc  6960
tcgaagaggc cgacaatatc gccagcattc ccctggaacc tggcaaagag cagcagctga  7020
aagaaaagct ggaacaagtg aaactgctgg tcgaggaact gcccctgaga cagggaatcc  7080
tgaaacagct gaacgagaca ggcggccctg tgctggtgtc tgcccctatt tctcccgagg  7140
aacaggacaa gctggaaaac aagctgaagc agaccaacct gcagtggatc aaggtgtcca  7200
gagcactgcc tgagaagcag ggcgagatcg aggcccagat caaggacctg ggacagctcg  7260
aaaagaagct tgaggacctc gaagaacagc tcaaccatct gctgctttgg ctgagcccca  7320
tccggaacca gctggaaatc tacaaccagc ctaatcaaga gggccccttc gacgtgaaag  7380
aaaccgagat tgccgtgcag gccaagcagc ccgatgtgga agagatcctg tctaagggcc  7440
agcacctgta caaagagaag cccgccacac agcccgtgaa gcggaaactg gaagatctga  7500
gcagcgagtg gaaggccgtg aaccggctgc tgcaagaact gagagccaaa cagcctgatc  7560
tggcccctgg cctgacaaca attggcgcct ctcctacaca gaccgtgaca ctggtcacac  7620
agcctgtggt caccaaagag acagccatca gcaaactgga aatgcccagc agtctgatgc  7680
tcgaagtgcc cgcactggcc gacttcaata gagcctggac cgagctgacc gactggctca  7740
gtctgctgga ccaagtcatc aagtcccaga gagtgatggt cggagatctt gaggacatca  7800
acgagatgat cattaagcag aaagccacca tgcaggacct tgagcagaga aggccccagc  7860
ttgaagaact gatcaccgcc gctcagaacc tgaaaaacaa gaccagcaat caagaagccc  7920
ggaccatcat caccgaccgg atcgagagaa tccagaacca gtgggacgaa gtgcaagagc  7980
atctgcagaa cagacggcag cagctcaatg agatgctgaa ggacagcaca cagtggctgg  8040
aagccaaaga agaagccgag caggttctcg gacaggccag agctaagctg gaatcttgga  8100
aagagggacc ctacaccgtc gacgccatcc agaagaagat caccgagaca aagcagctgg  8160
ccaaggatct gagacagtgg cagaccaatg tggacgtggc caacgacctg gctctgaagc  8220
tgctgagaga ctacagcgcc gacgacacca gaaaggtgca catgatcacc gaaaacatca  8280
acgcctcttg gcggagcatc cacaagcggg tgtcagagag agaagccgct ctggaagaaa  8340
cacatagact gctccagcag ttcccactcg acctggaaaa gttcctggcc tggctgacag  8400
aagccgaaac caccgctaac gtgctccagg atgccaccag aaaagagcgg ctgttggagg  8460
acagcaaggg cgtcaaagaa ctcatgaagc agtggcagga tctgcaaggg gagattgaag  8520
cccacaccga cgtgtaccac aacctggacg agaacagcca gaagatcctg cggtccctgg  8580
aaggctctga tgatgctgtg ctgcttcaga ggcggctgga caacatgaac ttcaagtgga  8640
gcgagctgcg gaagaagtcc ctgaacatca gaagccacct ggaagcctcc agcgaccagt  8700
ggaaaagact gcacctgtct ctccaagagc tgctcgtgtg gctgcagctg aaggatgacg  8760
agctgagtag acaggcccct atcggcggag attttcccgc cgtgcagaaa cagaacgacg  8820
tgcaccgggc cttcaagaga gagctgaaaa caaaagaacc cgtcatcatg agcaccctgg  8880
aaaccgtgcg gatctttctg accgagcagc ctctggaagg actggaaaag ctgtaccaag  8940
agcctagaga gctgcctcct gaagaaaggg cccagaacgt gacacggctg cttagaaagc  9000
aggccgagga agtgaacacc gaatgggaga agctgaacct ccactccgcc gactggcagc  9060
ggaagatcga tgagacactg gaacggctgc gggaactgca agaagccaca gacgagctgg  9120
acctgaaact gcggcaggct gaagtgatca aaggctcctg gcagccagtg ggcgatctgc  9180
tgatcgatag cctgcaggac catctggaaa aagtcaaggc cctgcgggga gagatcgccc  9240
ctctcaaaga aaacgtgtcc cacgtgaacg atctggccag gcagctgaca acactgggca  9300
tccagctgag cccttacaac ctgtctacct tggaggacct gaatacccgg tggaagctgc  9360
tccaagtggc cgtcgaggat agagtgcggc agctgcatga ggctcacaga gattttggac  9420
ccgccagcca gcacttcctg agcacatctg ttcaaggccc ctgggagaga gctatcagcc  9480
ctaacaaggt gccctactac atcaaccacg agacacagac cacctgttgg gatcacccca  9540
```

```
agatgaccga actgtatcag tccctggccg acctgaacaa cgtgcggttt agcgcctacc  9600
ggaccgccat gaagctgcgc agactgcaga aagctctgtg cctggacctg ctgtctctga  9660
gcgctgcttg tgatgccctg gaccagcata acctcaagca gaacgaccag cctatggaca  9720
tcctgcagat catcaactgc ctgaccacca tctacgaccg gctcgaacaa gagcacaaca  9780
acctggtcaa cgtgcccctg tgcgtggaca tgtgcctgaa ttggctgctg aacgtgtacg  9840
acaccggcag aaccggcagg atcagagtgc tgagcttcaa gaccggcatc atctccctgt  9900
gcaaggccca ccttgaggat aagtaccgct acctgtttaa gcaggtcgcc agcagcaccg  9960
gcttttgcga ccaaagaagg ctgggactgc tgctccacga cagcattcag atccctagac  10020
agctgggcga agtggcctct ttcggcggct ctaatatcga gcctagcgtg cggagctgct  10080
tccagttcgc caacaacaag cccgagattg aggccgcact gttcctggac tggatgagac  10140
tggaacccca gagcatggtc tggctgcctg tgctgcatag agtggccgca gccgaaacag  10200
ccaagcacca ggccaagtgc aacatctgca aagagtgccc catcatcggc ttccggtaca  10260
gatccctgaa gcacttcaac tacgatatct gccagtcctg cttcttcagc ggcagagtgg  10320
ccaagggcca caagatgcac taccccatgg tggaatactg caccccctacc acctctggcg  10380
aggacgtgcg ggattttgcc aaggtgctca agaacaagtt ccggaccaag cgctacttcg  10440
ctaagcaccc cagaatgggc tacctgccag tgcagacagt gcttgagggc gacaacatgg  10500
aaacccctgt gactctgatc aacttctggc ccgtggatag cgcccctgct agttctcctc  10560
agctgtctca cgacgatacc cacagcagaa tcgagcacta cgcctccaga ctggccgaga  10620
tggaaaacag caacggcagc tacctgaatg acagcatcag ccccaacgag agcatcgacg  10680
acgaacatct gctcattcag cactactgcc agagcctgaa tcaggacagc cctctgtctc  10740
agcctagaag ccctgcacag atcctgatca gcctggaaag cgaggaacgc ggcgagctgg  10800
aaagaatcct ggcagacctg gaagaggaaa accggaacct gcaggccgaa tacgacagac  10860
tcaagcagca gcacgagcac aagggactgt ctccactgcc ttctccacct gaaatgatgc  10920
ccacctctcc acagagcccc agagatgccg agctgattgc cgaagccaaa ctgctgaggc  10980
agcacaaagg cagactcgaa gccagaatgc agattctcga agatcacaac aagcagctcg  11040
aatcccagct gcacagactt aggcagctgc tggaacagcc tcaggcagag gccaaagtga  11100
atggcaccac cgtgtctagc cctagcacaa gcctgcagag atccgacagc agccagccaa  11160
tgcttctgag agtcgtgggc tcccagacca gcgattctat gggcgaagag gacctgctca  11220
gccctcctca ggatacaagc accggcctgg aagaagtgat ggaacaactg aacaacagct  11280
tccccagcag cagaggcaga aacacccctg gcaagcccat gcgcgaggac accatgtgat  11340
aactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acgtggcgcc atcggatccc gggcccgtcg  12180
actgcagagg cctgcatgca agcttggcgt aatcatggtc atagctgttt cctgtgtgaa  12240
attgttatcc gctcacaatt ccacacaaca tacgagccgg aagcataaag tgtaaagcct  12300
ggggtgccta atgagtgagc taactcacat taattgcgtt gcgctcactg cccgctttcc  12360
agtcgggaaa cctgtcgtgc cagctgcatt aatgaatcgg ccaacgcgcg gggagaggcg  12420
gtttgcgtat tgggcgctct tccgcttcct cgctcactga ctcgctgcgc tcggtcgttc  12480
ggctgcggcg agcggtatca gctcactcaa aggcggtaat acggttatcc acagaatcag  12540
gggataacgc aggaaagaac atgtgagcaa aaggccagca aaaggccagg aaccgtaaaa  12600
aggccgcgtt gctggcgttt ttccataggc tccgcccccc tgacgagcat cacaaaaatc  12660
gacgctcaag tcagaggtgg cgaaacccga caggactata aagataccag gcgtttcccc  12720
ctggaagctc cctcgtgcgc tctcctgttc cgaccctgcc gcttaccgga tacctgtccg  12780
cctttctccc ttcgggaagc gtggcgcttt ctcatagctc acgctgtagg tatctcagtt  12840
cggtgtaggt cgttcgctcc aagctgggct gtgtgcacga accccccgtt cagcccgacc  12900
gctgcgcctt atccggtaac tatcgtcttg agtccaaccc ggtaagacac gacttatcgc  12960
cactggcagc agccactggt aacaggatta gcagagcgag gtatgtaggc ggtgctacag  13020
agttcttgaa gtggtggcct aactacggct acactagaag aacagtattt ggtatctgcg  13080
ctctgctgaa gccagttacc ttcggaaaaa gagttggtag ctcttgatcc ggcaaacaaa  13140
ccaccgctgg tagcggtggt ttttttgttt gcaagcagca gattacgcgc agaaaaaaag  13200
gatctcaaga agatcctttg atcttttcta cggggtctga cgctcagtgg aacgaaaact  13260
cacgttaagg gattttggtc atgagattat caaaaaggat cttcacctag atccttttaa  13320
attaaaaatg aagttttaaa tcaatctaaa gtatatatga gtaaacttgg tctgacagtt  13380
accaatgctt aatcagtgag gcacctatct cagcgatctg tctatttcgt tcatccatag  13440
ttgcctgact ccccgtcgtg tagataacta cgatacggga gggcttacca tctggcccca  13500
gtgctgcaat gataccgcga gacccacgct caccggctcc agatttatca gcaataaacc  13560
agccagccgg aagggccgag cgcagaagtg gtcctgcaac tttatccgcc tccatccagt  13620
ctattaattg ttgccgggaa gctagagtaa gtagttcgcc agttaatagt ttgcgcaacg  13680
ttgttgccat tgctacaggc atcgtggtgt cacgctcgtc gtttggtatg gcttcattca  13740
gctccggttc ccaacgatca aggcgagtta catgatcccc catgttgtgc aaaaaagcgg  13800
ttagctcctt cggtcctccg atcgttgtca gaagtaagtt ggccgcagtg ttatcactca  13860
tggttatggc agcactgcat aattctctta ctgtcatgcc atccgtaaga tgcttttctg  13920
tgactggtga gtactcaacc aagtcattct gagaatagtg tatgcggcga ccgagttgct  13980
cttgcccggc gtcaatacgg gataataccg cgccacatag cagaacttta aaagtgctca  14040
tcattggaaa acgttcttcg gggcgaaaac tctcaaggat cttaccgctg ttgagatcca  14100
gttcgatgta acccactcgt gcacccaact gatcttcagc atcttttact ttcaccagcg  14160
tttctgggtg agcaaaaaca ggaaggcaaa atgccgcaaa aaagggaata agggcgacac  14220
ggaaatgttg aatactcata ctcttccttt ttcaatatta ttgaagcatt tatcagggtt  14280
```

```
attgtctcat gagcggatac atatttgaat gtatttagaa aaataaacaa ataggggttc  14340
cgcgcacatt tccccgaaaa gtgccacctg acgtctaaga aaccattatt atcatgacat  14400
taacctataa aaataggcgt atcacgaggc cctttcgtct cgcgcgtttc ggtgatgacg  14460
gtgaaaacct ctgacacatg cagctcccgg agacggtcac agcttgtctg taagcggatg  14520
ccgggagcag acaagcccgt cagggcgcgt cagcgggtgt tggcgggtgt cggggctggc  14580
ttaactatgc ggcatcagag cagattgtac tgagagtgca ccatatgcgg tgtgaaatac  14640
cgcacagatg cgtaaggaga aaataccgca tcaggcgcca ttcgccattc aggctgcgca  14700
actgttggga agggcgatcg gtgcgggcct cttcgctatt acgccagctg gcgaaagggg  14760
gatgtgctgc aaggcgatta agttgggtaa cgccagggtt ttcccagtca cgacgttgta  14820
aaacgacggc cagtgaattc gagctcggta cctcgcgaat gcatctagaa gctgcatgtc  14880
taagctagac ccttcagatt aaaaataact gaggtaaggg cctgggtagg ggaggtggtg  14940
tgagacgctc ctgtctctcc tctatctgcc catcggccct tggggaggag ggaatgtgcc  15000
caaggactaa aaaaaggcca tggagccaga ggggcgaggg caacagacct ttcatgggca  15060
aaccttgggg ccctgctgtc tagcatgccc cactacgggt ctaggctgcc catgtaagga  15120
ggcaaggcct ggggacaccc gagatgcctg gttataatta acccagacat gtggctgccc  15180
cccccccccc aacacctgct gcctctaaaa ataaccctgt ccctggtgga tcccctgcat  15240
gcgaagatct tcgaacaagg ctgtggggga ctgagggcag gctgtaacag gcttgggggc  15300
cagggcttat acgtgcctgg gactcccaaa gtattactgt tccatgttcc cggcgaaggg  15360
ccagctgtcc cccgccagct agactcagca cttagtttag gaaccagtga gcaagtcagc  15420
ccttggggca gcccatacaa ggccatgggg ctgggcaagc tgcacgcctg ggtccggggt  15480
gggcacggtg cccgggcaac gagctgaaag ctcatctgct ctcaggggcc cctccctggg  15540
gacagcccct cctggctagt cacaccctgt aggctcctct atataaccca ggggcacagg  15600
ggctgccctc attctaccac cacctccaca gcac                              15634

SEQ ID NO: 33           moltype = DNA  length = 13428
FEATURE                 Location/Qualifiers
source                  1..13428
                        mol_type = other DNA
                        note = NP-MHCK7-hBGi-mafaDMD
                        organism = synthetic construct
SEQUENCE: 33
agctcggtac ctcgcgaatg catctagaag ctgcatgtct aagctagacc cttcagatta  60
aaaataactg aggtaagggc ctgggtaggg gaggtggtgt gagacgctcc tgtctctcct  120
ctatctgccc atcggccctt tggggaggag gaatgtgccc aaggactaaa aaaaggccat  180
ggagccagag gggcgagggc aacagacctt tcatgggcaa accttggggc cctgctgtct  240
agcatgcccc actacgggtc taggctgccc atgtaaggag gcaaggcctg gggacacccg  300
agatgcctgg ttataattaa cccagacatg tggctgcccc cccccccca acacctgctg  360
cctctaaaaa taaccctgtc cctggtggat cccctgcatg cgaagatctt cgaacaaggc  420
tgtgggggac tgagggcagg ctgtaacagg cttgggggcc agggcttata cgtgcctggg  480
actcccaaag tattactgtt ccatgttccc ggcgaagggc cagctgtccc ccgccagcta  540
gactcagcac ttagtttagg aaccagtgag caagtcagcc cttggggcag cccatacaag  600
gccatggggc tgggcaagct gcacgcctgg gtccggggtg ggcacggtgc ccgggcaacg  660
agctgaaagc tcatctgctc tcaggggccc ctccctgggg acagcccctc ctggctagtc  720
acaccctgta ggctcctcta tataacccag gggcacaggg gctgccctca ttctaccacc  780
acctccacag cactctggat ccactgctta aatacggacg aggacagggc cctgtctcct  840
cagcttcagg caccaccact gacctgggac agtgaatcgt aagtactagc agctacaatc  900
cagctaccat tctgctttta ttttatggtt gggataaggc tggattattc tgagtccaag  960
ctaggccctt ttgctaatca tgttcatacc tcttatcttc ctcccacagc tcctgggcaa  1020
cgtgctggtc tgtgtgctgg cccatcactt tggcaaagaa ttgcgatcgc caccatgctg  1080
tggtgggagg aggtggagga ttgctacgag agggaagatg tccagaagaa aaccttcacc  1140
aagtgggtga acgcccagtt tagcaagttc ggcaagcagc acatcgagaa cctgtttagc  1200
gacctgcagg acggcagaag gctgctggac ctcctggagg ggctgaccgg ccagaagctg  1260
cccaaggaaa agggcagcac cagggtgcac gccctgaata acgtgaacaa ggccctgaga  1320
gtgctgcaga acaacaacgt ggacctggtg aacatcggca gcaccgacat cgtggacggc  1380
aaccacaagc tgaccctggg cctgatctgg aatatcatcc tgcactggca ggtgaagaac  1440
gtgatgaaga acatcatggc cggcctgcag cagaccaaca gcgagaagat cctgctgagc  1500
tgggtgagac agagcaccag gaactacccc caggtgaacg tgatcaactt caccaccagc  1560
tggagcgacg ggctggccct gaacgccctg atccacagcc acaggcccga cctgttcgac  1620
tggaacagcg tggtgtgcca acagagcgcc acgcagaggc tggagcacgc cttcaacatc  1680
gccagatacc agctgggcat cgagaagctg ttggaccccg aggacgtggc caccacctac  1740
cccgacaaga agagcatcct gatgtacatc accagcctgt tccaggtgct gccccagcag  1800
gtgagcatcg aggccatcca ggaggtggag atgctgccca ggccccccaa ggtgacaaag  1860
gaggagcact tccagctgca ccaccagatg cactacagcc agcagatcac ggtgtcactg  1920
gcccagggct acgagaggac cagcagcccc aagcccagat tcaagagcta cgcctacacc  1980
caggccgcct acgtgaccac cagcgacccc accaggtccc ccttccccag ccagcacctg  2040
gaggcccccg aggataagag tttcggcagc agcctcatgg agagcgaagt gaacctggac  2100
agataccaga ccgccctcga agaggtgctg agctggctgc tgagcgccga ggataccctg  2160
caggcccagg gcgagatcag caacgacgtg gaggtggtga aggagcagtt ccacgcccac  2220
gagggctaca tgatggacct gaccgcccac cagggcaggg tgggcaacat cctccaactg  2280
ggcagccagc tgatcggcac cggcaagctg agcgaggacg aggagactga ggtgcaggag  2340
cagatgaacc tgctgaacag caggtgggag tgcctgaggg tggccagcat ggagaaacag  2400
tccaacctgc acagggtcct gatggacctg cagaaccaga agctcaagga actcaacgac  2460
tggctgacca agaccgagga gagaaccagg aagatggagg aggagcccct gggccccgac  2520
ctggaggacc tgaagaggca ggtgcagcag cacaaggtgc tgcaggagga tctggagcag  2580
gaacaggtga gggtgaacag cctgacccac atggtggtgg tcgtggacga gagcagcggc  2640
gaccatgcca ccgccgctct ggaggagcaa ctgaaggtgc tgggcgacag atgggccaac  2700
atctgcagat ggaccgagga caggtgggtg ctgctccagg acatcctcct gaagtggcag  2760
aggctgacag aggagcagtg cctgttcagc gcctggctga gcgagaagga ggacgtggtg  2820
aacaggatcc acaccaccgg cttcaaggac cagaacgaga tgctcagcag cctgcaaaag  2880
```

-continued

```
ctggccgtcc tgaaggccga cttggagaaa aagaagcaga gcatggacaa gctgtacagc  2940
ctgaagcagg acctcctgag caccctgaag aacaagagtg tgacccagaa gatggaggcg  3000
tggctggaga acttcgccag gtgctgggac aacctggtgc agaagctgga gaagagcacc  3060
gcccagatta gccaggccgt gaccaccacc cagcctagcc tgacccagac cacggtgatg  3120
gagactgtga ccatggtgac caccagggag cagatcctgg tgaagcacgc ccaggaggaa  3180
ctcccccccc ccccgcccca gaagaagaga cagatcaccg tggactccga gatcaggaag  3240
aggctcgacg tggacatcac cgaactgcat agctggatca ccagaagcga ggccgtgctg  3300
cagagccccg agttcgcgat ctacaggaag gagggcaact tcagcgacct gaaggaaaag  3360
gtgaacgcca tcgagaggga gaaggccgag aagttcagga agctccagga cgccagcagg  3420
agcgcccagg tgctggtgga gcagatggtg aacgaggggg tgaacgccga cagcattagg  3480
caggccagtg agcagctgaa tagcaggtgg atcgagttct gccagctgct cagcgagagg  3540
ctcaactggc tggagtacca gaacaacatt atcaccttct acaaccagct gcagcagctg  3600
gagcagatga ccaccaccgc cgagaactgg ctgaagatcc agcccaccac ccccagcgag  3660
cccaccgcca tcaagagtca gctgaagatc tgcaaggacg aggtgaacag actgagcgcc  3720
ctgcagcccc agatcgagag actcaagatc cagtccatca ccctgaagga gaagggccag  3780
ggccccatgt tcctggacgc cgacttcgtg gccttcacca accacttcag ccaggtgttc  3840
agcgacatgc aggccaggga gaaggagctg cagaccatct tcgacaccct gcccccccatg  3900
aggtaccaag aaaccatgag cgccatcagg acctgggtgc agcagagcga gactaagctg  3960
agcatccccc agctgagcgt gaccgactac gagatcatgg agcagagact gggcgagctg  4020
caggtgctgc aaagcagcct gcaggagcaa cagagcggcc tgaactacct gagcaccacc  4080
gttaaggaga tgagcaagaa ggcccccagc gaaatcagca ggaagtacca gctggagttc  4140
gaggaaatcg agacaaggtg gaagaagctc tccagccagc tggccgagca ctgccagaag  4200
ttggaggagc aaatgaacaa gctgagaaaa atccagaacc acatccagac cctgaagaag  4260
tggatggccg aggtggacgt gttcctcaag gaggagtggc ccgccctggg cgactccgag  4320
attctcaaaa agcagctgaa gcagtgtagg ctgctggtga acgacatcca gaccatccag  4380
cccagcctga acagcgtgaa cgagggcggc cagaagatca agaacgaggc cgagcccgag  4440
ttcgccctga ggctggagat cgagctgaag gagctgaaca cccagtggga ccacatgtgc  4500
cagcaggtgt acgccaggaa ggaggccctg aagggcggcc tggaaaagac cgtgagcctg  4560
cagaaggacc tcagcgagat gcacgagtgg atgacccagg ccgaggagga gtacctggag  4620
agggacttcg agtacaagac ccccgacgaa ctgcagaagg ccgtggaaga gatgaagagg  4680
gccaaggagg aggcccaaca aaaggaggcc aaggtgaagc tgctgacaga gagcgtgaat  4740
agcgtgatcg cccaggcccc tcccgtggcc caggaggcgc tgaagaagga actggaaacc  4800
ctgaccacca actaccagtg gctgtgcacc aggctgaacg gcaagtgcaa gaccctggag  4860
gaggtgtggg cctgctggca cgagctgctg agctacctgg aaaaggccaa caagtggctg  4920
aacgaggtgg agttcaagct gaaaacgacc gagaacatcc ccggcggcgc cgaggagatc  4980
agcgaggtgc tgcacagcct ggagaacctg atgcagcaca gcgaggataa ccccaaccag  5040
atcaggatcc tggcccagac cctgaccgac ggcggcgtga tggacgaact catcaacgag  5100
gagctggaaa ccttcaactc cagatggagg gagctgcacg aggaggccgt gaggagacag  5160
aagctgctcg aacagagcat ccagagcgcc caggagatcg aaaagagcct gcacctgatc  5220
caggagagcc tgaccttcat cgacaagcag ctgaccgcct acatcgccga caaggtggac  5280
gccgcccaga tgccccagga ggcccagaag atccagagcg acctgaccag ccacgagatc  5340
agcctggagg agatgaagaa gcacaaccag ggcaaggagg ccgcccagag ggtgctgtcc  5400
cagatcgacg tggcccagaa gaagctgcag gacgtgagca tgaagttccg gctgttccaa  5460
aagcccgcga acttcgaaca gaggctgcag gagagcaaga tgatcctgga cgaggtcaag  5520
atgcacctgc ccgccctgga aaccaagagt gtggagcagg aggtggtgca gagccagctc  5580
aaccactgcg tgaacctgta caagagcctg agcgaggtga agagtgaggt cgagatggtg  5640
attaagaccg ggaggcagat cgtgcagaaa aagcagaccg agaaccccaa agagctggac  5700
gagagggtga ccgccctgaa actgcactac aacgagctgg gcgccaaggt gaccgagagg  5760
aagcagcagc ttgagaagtg cctgaagctg tccaggaaga tgaggaagga gatgaacgtg  5820
ctgaccgagt ggctggccgc caccgacatg gagctgacca agaggagcgc cgtggagggg  5880
atgcccagca acctggacag cgaggtggcc tggggcaagg ccacccagaa ggagatcgag  5940
aagcagaagg tgcacctgaa gagtatcacc gaggtggggg aggccctcaa gaccgtgctg  6000
ggcaagaagg agacactggt ggaggataag ctgagcctcc tgaacagcaa ctggatcgcc  6060
gtgaccagca gggccgagga gtggctgaac ctgctgctgg agtatcaaaa gcacatggag  6120
acattcgacc agaacgtgga ccacatcacc aagtggatca tccaggccga caccctgctc  6180
gacgagagcg aaaagaagaa gagccagcag aaggaggatg tgttgaagag gctgaaggcc  6240
gagctgaacg acatcaggcc caaggtggac agcaccaggg accaggccgc caacctgatg  6300
gccaacaggg gcgaccactg caggaagctg gtggagcccc agatcagcga gctgaaccac  6360
aggttcgccg ccatcagcca caggatcaag accggcaagg ccagtatccc cctcaaggag  6420
ctggagcagt tcaacagcga catccagaag ctgctggagc ctctggaggc cgagatccag  6480
cagggcgtga acctgaagga ggaggatttc aacaaggaca tgaacgagga taacgagggc  6540
accgtgaagg agttgctcca gaggggcgac aacctgcagc agaggatcac cgatgagaga  6600
aagagggagg agatcaagat caagcagcaa ctgctccaga ccaagcacaa cgccctgaag  6660
gacctgagat cccagaggag gaagaaggcc ctggagatca gccaccagtg gtaccagtac  6720
aagcggcagg ccgacgacct gctgaagtgc ctggacgaca tcgagaagaa gctggccagc  6780
ctgcccgagc ccagggacga gagaaagatt aaggagatcg acagggagct gcagaagaag  6840
aaggaggagc tgaacgccgt gaggaggcag gccgagggcc tgagcgaaga tggcgccgcc  6900
atggccgtgg agcccaccca gatccagctg tccaagaggt ggagggagat cgagagcaag  6960
ttcgcccaat tcaggaggct gaacttcgcc cagatccaca ccgtgaggga ggaaaccatg  7020
atggtgatga ccgaggatat gccccctggaa atcagctacg tgcccagcac ctacctgacc  7080
gagatcaccc acgtgagcca ggccctgagc gaagtggagc agctgctgaa cgcccccgac  7140
ctgtgcgcca aggacttcga ggatctgttt aagcaggagg agagcctcaa gaacatcaag  7200
gacatcctgc agcaaagctc cggcaggatc gacatcatcc acagcaagaa aaccgccgcc  7260
ctgcagagcg ccacccccgt ggagagagtc aagctgcagg aagccctgag ccagatcgac  7320
ttccagtggg agaaggtcaa caagatgtac aaggacagac agggcaggtt cgacagaagc  7380
gtggagaagt ggaggaggtt ccactacgac atcaagatct tcaaccagtg gctgaccgaa  7440
gccgagcagt tcctgaggaa aacccagatc cccgagaact gggagcacgc caagtacaag  7500
tggtacctga aggaactcca ggatggcatc ggccagaggc agaccgtggt gaggaccctg  7560
aatgccaccg gcgaggagat catccagcaa agcagcaaga ccgacgccag catcctgcag  7620
```

```
gagaaactcg gcagcctgaa cctgaggtgg caggaggtgt gcaagcagct gagcgagagg  7680
aagaagaggc tggaggagca gaagaacatc ctgagcgagt tccagaggga cctgaacgag  7740
ttcgtgctgt ggctggagga ggccgacaac atcgcctcca tccccctgga gcccggcaac  7800
gagcaacagc tgaaagagaa gctggagcag gtcaagctgc tggtggagga gctgcccctg  7860
aggcagggca tcctgaagca gctgaacgaa accggcggcc ccgtgctggt gagcgccccc  7920
atcagccccg aggagcagga caagctggag aacaagctga agagaaccaa cctgcagtgg  7980
atcaaggtga gcagggccct gcccgagaag caaggcgaga tagaggccca gatcaaggac  8040
ctgggccaac tggaaaagaa gctggaggat ctcgaagaac agctgaacca cctgctgctg  8100
tggctgagcc ccatcaggaa ccagctggag atctataacc agcccaacca ggagggcccc  8160
ttcgacatca aggagacaga gatcgccgtg caggccaagc agcccgacgt ggagggcatc  8220
ctgtccaagg gccagaggct gtacaaggag aagcccgcca cacagcccgt gaagagaaag  8280
ctggaagatc tcagcagcga gtggaaaacc gtgaaccatc tgctgcagga gctgagggcc  8340
aagcaacccg acctggcccc cggcctgacc accgtgggcg ctagccccag ccagaccgtg  8400
accctggtga cccagcccgt ggtgaccaag gaaaccgcca tcagcaagct ggagatgccc  8460
agcagcctga tgctggaggt gcctgccctg gccgacttca acagggcctg gaccgagctg  8520
acagagtggc tgagcctgct gggcagggtg atcaagagcc agagggtgat ggtgggcgac  8580
ctggaagata tcaacgagat gatcatcaag cagaaggcca ccgtgcagga cctggagcag  8640
agaaggcccc agctggagga gctgatcacc gccgcccaga acctgaagaa taagaccagc  8700
aaccaggagg ccaggacaat catcaccgac agaatcgaga ggatccagaa ccagtgggac  8760
gaagtgcagg agcacctgca gaacaggagg cagcagctca acgagatgct gaaggacagc  8820
acccagtggc tggaagccaa ggaggaagct gagcaggtgc tgggccaggc cagggccaag  8880
ctggagagct ggaaggaagg cccctacacc atcgacgcca tccagaagaa gatcaccgaa  8940
accaagcagc tggccaagga cctgaggcag tggcagatca acgtggacgt ggccaacgac  9000
ctggccctga agctgctgcg ggactacagc gccgacgaca ccaggaaggt gcacatgatc  9060
accgaaaaca tcaacgccag ctgggggagc atccacaaga gggtgagcga gcaggaggcc  9120
gcgctggagg aaacccacag gctgctgcag cagttccccc tggacctcga aaagttcctg  9180
gcctggctga ccgaggccga gacaaccgcc aacgtgctgc aggacgctac caggaaggag  9240
aggctgctgg aggatagcaa gggcgtgaag gaactcatga agcagtggca ggacctgcag  9300
ggcgagattg aggcccacac cgacgtgtac cacaacctgg acgagaacag ccagaaggtc  9360
ctgaggagct tggagggcag cgacgacgcc gtgctgctgc agagaaggct ggacaacatg  9420
aacttcaagt ggagcgagct gaggaagaag tccctgaaca ttagaagcca cctggaggct  9480
agtagcgacc agtggaaaag gctgcacctg agcctccagg agctgctcgt gtggctgcag  9540
ctgaaggacg acgagctgag cagacagacc cccatcggcg gcgacttccc cgccgtgcag  9600
aagcagaacg acgtgcacag ggctttcaag agggagctga aaaccaagga gcccgtgatc  9660
atgagcaccc tggagacagt gaggatcttc ctcaccgagc agcccctgga gggcctggag  9720
aagctgtacc aggagcccag ggagctgccc cccgaggaga gagcgcagaa cgtgaccaga  9780
ctgctgagga agcaggccga ggaagtgaac accgagtggg agaagctgaa cctgcacagc  9840
accgactggc agaggaagat cgacgaaacc ctggagaggc tgcaagagct gcaggaggcc  9900
atggacgagc tggacctgaa actgagacag gccgaggtga tcaagggcag ctggcagccc  9960
gtcggcgacc tgctgatcga cagcctccag gaccacctgg aaaaagtgaa ggccctgagg  10020
ggcgagatcg cccctctgaa ggagaacgtg agccacgtga acgacctcgc cagacagctg  10080
accaccctgg gcatccagct gagcccctac aacctcagca ccctggaaga tctgaacacc  10140
aggtggaagc tgctgcaggt ggccgtcgag gacagggtga ggcagctcca cgaggcccac  10200
agggacttcg gccccgccag ccagcacttc ctgagcacca gcgtgcaggg cccctgggag  10260
agagccatca gccgaacaa ggtgccctac tacatcaacc acgaaaccca gaccacctgc  10320
tgggaccacc ccaagatgac cgagctgtac cagagcctgg ccgacctgaa caatgtgaga  10380
ttctccgcct acagaaccgc catgaagctg aggaggctcc agaaggccct gtgcctggac  10440
ctgctgagcc tgagcgccgc ctgcgacgcc ctggaccagc acaacctgaa gcaaaacgac  10500
cagcccatgg acatcctcca gatcatcaac tgcctgacca ccatctacga cagactggag  10560
caggagcaca acaacctggt gaacgtgccc ctgtgcgtgg acatgtgcct gaactggctg  10620
ctgaacgtgt acgacaccgg caggaccggc agaatcagag tgctgagctt caagaccggg  10680
atcatcagcc tgtgcaaggc ccacctggag gacaagtaca ggtacctgtt caagcaggtc  10740
agcagcagca ccggcttctg cgaccagaga cggctgggcc tgctgctgca cgacagcatc  10800
cagatcccca gacagctggg cgaggtggcc agcttcggcg gcagcaacat cgagcccagc  10860
gtgagaagct gcttccagtt cgccaacaac aagcccgaga tcgaggccgc cctgttcctg  10920
gactggatga ggctggagcc ccaaagcatg gtgtggctgc ccgtgctgca cagggtggcc  10980
gccgccgaga cagccaagca ccaggccaag tgcaacatct gcaaggagtg ccccatcatc  11040
ggcttcaggt acaggagcct gaagcacttc aactacgaca tctgccagag ctgcttcttc  11100
agcggcaggg tggccaaggg ccacaagatg cactacccca tggtggagta ctgcaccccc  11160
accaccagcg gcgaggatgt gagagacttc gccaaggtgc tgaaaaacaa gttcaggacc  11220
aagaggtact tcgccaagca ccccagaatg ggctacctgc ccgtgcagac cgtcctggag  11280
ggcgacaaca tggagacacc cgtgaccctg atcaacttct ggcccgtgga cagcgccccc  11340
gccagcagcc ctcagctgag ccacgacgac acccacagca ggatcgagca ctacgccagc  11400
aggctggccg agatggagaa cagcaacggc agctacctga acgacagcat cagccccaac  11460
gagagcatcg acgacgagca cctgctgatc cagcactact gccagagcct gaaccaggac  11520
agcccccctga gccagcccag gtcccccgcc cagatcctga tcagcctcga aagcgaggag  11580
aggggcgagc tggagagaat cctggccgat ctggaggagg agaacaggaa cctgcaggcc  11640
gagtacgaca ggctgaagca gcagcacgag cacaagggcc tgagccccct gcccagcccc  11700
cccgagatga tgcccaccag cccccagagc cccagggacg ccgagctgat cgccgaggcg  11760
aagctgctga ggcagcacaa gggcaggctg gaggccagga tgcagatcct ggaggaccac  11820
aacaagcagc tggagagcca gctgcacaga ctgaggcagc tgcttgagca gccccaggcc  11880
gaagccaagg tgaacggcac caccgtcagc agccccagca ccagcctgca gaggagcgac  11940
agcagccagc ccatgctgct gagggtggtg ggcagccaga ccagcgacag catgggcgag  12000
gaggatgtgc tgagcccccc ccaggacacc agcaccggcc tggaggaagt gatggagcag  12060
ctgaacaaca gcttccccag cagcaggggc aggaacaccc ccggcaagcc catgagggag  12120
gacaccatgg attacaagga tgacgatgac aagtgataac tcgagaatca acctctggat  12180
tacaaaattt gtgaaagatt gactggtatt cttaactatg ttgctccttt tacgctatgt  12240
ggatacgctg ctttaatgcc tttgtatcat gctattgctt cccgtatggc tttcattttc  12300
tcctccttgt ataaatcctg gttgctgtct ctttatgagg agttgtggcc cgttgtcagg  12360
```

```
caacgtggcg tggtgtgcac tgtgtttgct gacgcaaccc ccactggttg gggcattgcc  12420
accacctgtc agctcctttc cgggactttc gctttccccc tccctattgc cacggcggaa  12480
ctcatcgccg cctgccttgc ccgctgctgg acaggggctc ggctgttggg cactgacaat  12540
tccgtggggt gtgccttcta gttgccagcc atctgttgtt tgcccctccc ccgtgccttc  12600
cttgaccctg gaaggtgcca ctcccactgt cctttcctaa taaaatgagg aaattgcatc  12660
gcattgtctg agtaggtgtc attctattct ggggggtggg gtggggcagg acagcaaggg  12720
ggaggattgg gaagacaata gcaggcatgc tggggatgcg gtgggctcta tgggaagatg  12780
tctactgagc tgtgcgatcc ctgctgggga ctttccgctg gggactttcc gctggggact  12840
ttccgccttc agctaaggaa gctaccaata tttagaggta cattttgttc tagaacaaaa  12900
tgtaccggta cattttgttc tggtacattt tgttctatta aggaccgggc gcgccgttta  12960
aactggcttg ttgtccacaa ccattaaacc ttaaaagctt taaaagcctt atatattctt  13020
ttttttctta taaaacttaa aaccttagag gctatttaag ttgctgattt atattaattt  13080
tattgttcaa acatgagagc ttagtacgtg aaacatgaga gcttagtaca ttagccatga  13140
gagcttagta cattagccat gagggtttag ttcattaaac atgagagctt agtacattaa  13200
acatgagagc ttagtacatt aaacatgaga gcttagtaca tactatcaac aggttgaact  13260
gctgatctgt acagtagaat tggtaaagag agttgtgtaa aatattgagt tcgcacatct  13320
tgttgtctga ttattgattt ttggcgaaac catttgatca tatgacaaga tgtgtatcta  13380
ccttaactta atgattttga taaaaatcat taggcgcgcc gaagagcg               13428

SEQ ID NO: 34          moltype = DNA  length = 12112
FEATURE                Location/Qualifiers
source                 1..12112
                       mol_type = other DNA
                       note = MHCK7-hBGi-DMD-4--
                       organism = synthetic construct
SEQUENCE: 34
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccact acgggtctag  240
gctgcccatg taaggaggca aggcctgggg acacccgaga tgcctggtta taattaaccc  300
agacatgtgg ctgccccccc cccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctttgg tgggaagaag tcgaggactg  1080
ctacgagcgc gaggacgtgc agaagaaaac cttcaccaaa tgggtcaacg cccagttcag  1140
caagttcggc aagcagcaca tcgagaacct gttcagcgac ctgcaggatg gcagaaggct  1200
gctggatctg ctggaaggcc tgacaggaca gaagctgccc aaagagaagg gcagcacaag  1260
agtgcacgcc ctgaacaacg tgaacaaggc cctgagagtg ctgcagaaca acaacgtgga  1320
cctggtcaac atcggcagca ccgacatcgt ggacggcaac cacaaactga ccctgggcct  1380
gatctggaac atcatcctgc actggcaagt gaagaacgtg atgaagaaca tcatggccgg  1440
cctgcagcag accaacagcg agaagattct gctgagctgg gtccgacaga gcacccggaa  1500
ttaccctcaa gtgaacgtga tcaacttcac cacctcttgg agcgacggac tggccctgaa  1560
tgccctgatc cacagccaca gacctgacct gttcgactgg aacagcgtcg tgtgtcagca  1620
gagcgccaca cagaggctgg aacacgcctt caatatcgcc agataccagc tgggcatcga  1680
gaaactgctg gaccccgagg atgtggacac cacctatcct gacaagaaat ccatcctcat  1740
gtacatcacc agcctgttcc aggtgctgcc ccagcaggtt tccatcgagg ccattcaaga  1800
ggtcgagatg ctgcccagac ctcctaaagt gaccaaagag gaacacttcc agctgcacca  1860
ccagatgcac tactctcagc agatcaccgt gtctctggcc cagggctacg agagaacaag  1920
cagccccaag cctcggttca agagctacgc ctatacacag gccgcctacg tgaccaccag  1980
cgatcctaca agaagcccat ttcctagcca gcatctggaa gcccctgagg acaagagctt  2040
tggcagcagc ctgatggaaa gcgaagtgaa cctggaccgc taccagacag ccctggaaga  2100
ggttctgagc tggctgctgt ctgccgagga tacactgcag gctcagggcg agatcagcaa  2160
cgacgtggaa gtggtcaagg accagtttca cacccacgag ggctacatga tggacctgac  2220
agcccaccag ggcagagtgg gcaatattct gcagctgggc tccaagctga tcggcacagg  2280
caagctgagc gaggacgaag agacagaggt gcaagagcag atgaacctgc tgaacagcag  2340
atgggagtgt ctgagagtgg ccagcatgga aaagcagagc aacctgcacc gggtgctgat  2400
ggatctccag aaccagaagc tgaaagagct gaacgactgg ctgaccaaga ccgaggaacg  2460
gacccggaag atggaagagg aacctctggg acccgacctg gaagatctga aaagacaggt  2520
gcagcagcat aaggtgctgc aagaggacct cgaacaagag caagtgcgcg tgaacagcct  2580
gacacacatg gtggtggtcg tggatgagag cagcggagat catgccacag ccgctctgga  2640
agaacagctg aaggtgctgg gagacagatg ggccaatatc tgccggtgga ccgaggatag  2700
atgggtgctg ctccaggaca tcctgctgaa gtggcagcgg ctgacagagg aacagtgcct  2760
gtttagcgcc tggctgtccg agaaagagga cgccgtcaac aagatccaca ccaccggctt  2820
caaggatcag aatgagatgc tgagcagcct gcagaaactg gccgtgctga aggctgacct  2880
ggaaaagaaa aagcagtcca tgggcaagct gtactccctg aagcaggacc tgctgagcac  2940
actgaagaac aagtctgtga cccagaaaac cgaggcctgg ctggacaact tcgcccggtg  3000
ttgggataac ctggtgcaga agctggaaaa gtccaccgct cagatctctc aggccgtgac  3060
cacaacacag ccttctctga cccagaccac cgtgatggaa acagtgacca cagtgacaac  3120
ccgcgagcag atcctggtca agcacgccca agaagaactg cctcctccac ctcctcagaa  3180
```

```
gaaacggcag atcacagtgg acagcgagat ccggaagaga ctggacgtgg acatcaccga 3240
gctgcacagc tggatcacca gatccgaagc cgtgctgcag tcccctgagt tcgccatctt 3300
cagaaaagag ggcaacttct ccgacctgaa agagaaagtc aacgccatcg agagagagaa 3360
ggccgagaag ttccggaagc tgcaggacgc ctctagatct gcccaggctc tggtggaaca 3420
gatggtcaac gaaggcgtga acgccgacag catcaagcag gcctcagagc agctgaactc 3480
ccggtggatc gagttctgtc agctcctgag cgagagactg aactggctgg aataccagaa 3540
caatatcatt gccttctaca accagctcca gcagctcgaa cagatgacca ccacagccga 3600
gaattggctg aagatccagc ctaccacacc tagcgagccc accgccatta agagccagct 3660
gaaaatctgc aaggacgaag tgaatcggct gagcgatctg cagccccaga tcgaaagact 3720
gaaaatccag tctatcgccc tcaaagagaa aggacagggc cccatgttcc tggacgccga 3780
ttttgtggcc tttaccaacc acttcaaaca ggtgttctcc gacgtgcagg cccgggaaaa 3840
agagctgcag accatcttcg acaccctgcc tccaatgaga taccaagaga caatgagcgc 3900
catccggacc tgggtgcagc aaagcgagac aaagctgagc atcccacagc tgagcgtgac 3960
cgactacgag atcatggaac agagactggg cgaactgcag gccctccagt ctagcctgca 4020
agaacagcag tccggcctgt actacctgag cacaaccgtg aaagagatga gcaagaaggc 4080
ccctagcgag atctcccgga agtaccagag cgagttcgaa gagatcgaag gccggtggaa 4140
gaagctgtct agccagctgg ttgagcactg ccagaaactc gaagaacaaa tgaacaagct 4200
gcgcaagatc cagaatcaca tccagacgct gaagaaatgg atggccgagg tggacgtgtt 4260
cctgaaagaa gagtggcccg ctctgggcga ctccgagatt ctgaagaaac agctcaaaca 4320
gtgccggctg ctggtgtccg atatccagac aatccagcca agcctgaact ccgtgaatga 4380
aggcggccag aagatcaaga acgaggccga gcctgagttt gccagcagac tggaaaccga 4440
actgaaagaa ctcaacaccc agtgggacca catgtgccag caagtgtacg cccggaaaga 4500
ggccctgaaa ggcggactcg aaaagactgt gtctctgcag aaagacctgt ctgagatgca 4560
cgagtggatg acccaggccg aagaggaata cctggaacgg gacttcgagt acaagacccc 4620
tgatgagctg caaaaagccg tcgaggaaat gaagcgggcc aaagaagagg cccagcagaa 4680
agaagccaaa gtcaagctgc tgaccgagtc cgtgaatagc gttatcgctc aggcccctcc 4740
tgtggctcaa gaggctctca agaaagaact ggaaactctg accaccaact accagtggct 4800
gtgcaccaga ctgaacggca agtgcaagac actggaagaa gtgtgggcct gctggcacga 4860
actgctgtcc tatctggaaa aggccaacaa gtggctgaac gaggtggaat tcaagctgaa 4920
aaccaccgag aacatccctg gcggcgctga agagattagc gaggtgctgg acagcctgga 4980
aaacctgatg agacacagcg aggacaaccc caatcagatc agaatcctgg ctcagaccct 5040
gaccgatggc ggcgtgatgg acgagctgat caacgaggaa ctcgaaacct tcaacagccg 5100
gtggcgggaa ctgcacgagg aagctgttcg gaggcagaag ttgctggaac agtctatcca 5160
gagcgcacaa gaaaccgaga agtccctgca cctgatccaa gagagcctga ccttcatcga 5220
caagcagctg gccgcttata tcgccgacaa ggtggacgct gctcagatgc cccaagaggc 5280
acagaagatt cagagcgacc tgaccagcca cgagattagc ctggaagaaa tgaagaagca 5340
caaccagggc aaagaggccg ctcagagagt cctgagccag atcgatgtgg cacagaaaaa 5400
gctccaggat gtgtccatga agtttcggct gtttcagaag cccgccaact tcgagcagag 5460
actgcaagag tccaagatga tcctggacga agtcaaaatg catctgcccg cactggaaac 5520
aaagtccgtg gaacaagaag tggtgcagtc ccagctgaac cactgcgtga acctgtacaa 5580
gagcctgtcc gaagtgaagt ctgaggtgga aatggtcatc aagaccggca ggcagatcgt 5640
ccagaagaag cagaccgaga atcccaaaga actcgacgag agagtgaccg ctctgaagct 5700
gcactacaat gagctgggcg ccaaagtgac cgagcggaag caacagcttg agaagtgcct 5760
gaaactgtct cggaagatgc ggaaagaaat gaacgtgctg acagagtggc tggccgccac 5820
cgatatggaa ctgactaaga gaagcgccgt ggaaggcatg cccagcaacc tggatagtga 5880
agtggcctgg ggcaaagcca ctcagaaaga gattgagaag cagaaggtcc acctgaagtc 5940
catcaccgaa gtgggcgaag ccctgaaaac cgtgctggga aagaaagaga cactggtcga 6000
ggacaagctg tccctgctga attccaactg gatcgccgtg acctccagag ctgaggaatg 6060
gctgaatctg ctgcttgagt accagaaaca catggaaacg ttcgaccaga acgtcgacca 6120
catcacaaag tggatcatcc aggctgatac cctgctggac gagtccgaga agaagaaacc 6180
ccaacaaaaa gaagatgtgc tgaagcggct gaaagccgag ctgaatgaca tccggcctaa 6240
ggtggacagc accagagatc aggcagccaa cctgatggcc aacagaggcg accactgtcg 6300
gaagctcgtg gaacctcaga tcagcgagct taaccacaga tttgccgcca tcagccaccg 6360
gatcaagaca ggcaaggcca gcattcctct caaagagctt gagcagttca acagcgacat 6420
ccaaaagctg ctcgaacccc tggaagccga gatccaacag ggcgtcaacc tcaaagaaga 6480
agatttcaac aaggacatga acgaggacaa tgagggcacc gtcaaagaac tgctgcagcg 6540
gggcgataat ctgcagcagc ggattaccga tgagcgcaag cgggaagaga tcaagattaa 6600
gcagcagctg ctgcagacca agcacaacgc cctgaaggac ctgcggagcc agagaagaaa 6660
gaaggccctg gaaatcagcc accagtggta tcagtacaag cggcaggccg acgacctgct 6720
gaagtgcctg gatgacatcg agaagaagct ggcctctctg cccgagccta gggacgagag 6780
aaagatcaaa gagatcgacc gcgagctgca gaaaaagaaa gaggaactga acgccgtccg 6840
cagacaggcc gaaggacttt ctgaagatgg cgccgctatg gccgtggaac ccacacagat 6900
tcagctgagc aagcggtggc gggaaatcga gagcaagttc gcccagttcc ggcggctgaa 6960
tttcgcccag atccacaccg tgcgggaaga gacaatgatg gtcatgacag aggacatgcc 7020
ccttgagatc agctacgtgc ccagcaccta cctgaccgag atcacccatg tgtctcaggc 7080
cctgctggaa gtggaacagc tgctgaatgc ccctgacctg tgcgccaagg acttcgagga 7140
cctgttcaag caagaggaaa gcctgaagaa catcaaggac agcctgcagc agagcagcgg 7200
ccggatcgat atcatccaca gcaagaaaac cgccgcactg cagagcgcca cacctgtgga 7260
aagagtgaag ctgcaagagg ccctgagcca gctggatttc cagtgggaga aagtgaacaa 7320
gatgtacaag gaccggcagg gcagattcga ccgcagcgtt gaaaagtggc ggcggttcca 7380
ctacgacatc aagatcttca accagtggct gaccgaggcc gagcagttcc tgagaaagac 7440
acagatcccc gagaactggg agcacgccaa gtacaagtgg tatctgaaag agctgcagga 7500
cggcatcggc cagagacaga cagtcgtgcg gacactgaat gccaccggcg aggaaatcat 7560
ccagcagtcc agcaagaccg acgccagcat cctgcaagag aagctgggca gcctgaacct 7620
gcggtggcaa gaagtgtgca agcagctgag cgaccggaag aagcggctgg aagaacagaa 7680
gaatatcctg agcgagttcc agcgggacct gaacgagttc gtgctgtggc tcgaagaggc 7740
cgacaatatc gccagcattc ccctggaacc tggcaaagag cagcagctga aagaaaagct 7800
ggaacaagtg aaactgctgg tcgaggaact gcccctgaga cagggaatcc tgaaacagct 7860
gaacgagaca ggcggccctg tgctggtgtc tgcccctatt tctcccgagg aacaggacaa 7920
```

```
gctggaaaac aagctgaagc agaccaacct gcagtggatc aaggtgtcca gagcactgcc  7980
tgagaagcag ggcgagatcg aggcccagat caaggacctg ggacagctcg aaaagaagct  8040
tgaggacctc gaagaacagc tcaaccatct gctgctttgg ctgagcccca tccggaacca  8100
gctggaaatc tacaaccagc ctaatcaaga gggccccttc gacgtgaaag aaaccgagat  8160
tgccgtgcag gccaagcagc ccgatgtgga agagatcctg tctaagggcc agcacctgta  8220
caaagagaag cccgccacac agcccgtgaa gcggaaactg gaagatctga gcagcgagtg  8280
gaaggccgtg aaccggctgc tgcaagaact gagagccaaa cagcctgatc tggcccctgg  8340
cctgacaaca attggcgcct ctcctacaca gaccgtgaca ctggtcacac agcctgtggt  8400
caccaaagag acagccatca gcaaactgga aatgcccagc agtctgatgc tcgaagtgcc  8460
cgcactggcc gacttcaata gagcctggac cgagctgacc gactggctca gtctgctgga  8520
ccaagtcatc aagtcccaga gagtgatggt cggagatctt gaggacatca acgagatgat  8580
cattaagcag aaagccacca tgcaggacct tgagcagaga aggccccagc ttgaagaact  8640
gatcaccgcc gctcagaacc tgaaaaacaa gaccagcaat caagaagccc ggaccatcat  8700
caccgaccgg atcgagagaa tccagaacca gtgggacgaa gtgcaagagc atctgcagaa  8760
cagacggcag cagctcaatg agatgctgaa ggacagcaca cagtggctgg aagccaaaga  8820
agaagccgag caggttctcg gacaggccag agctaagctg gaatcttgga aagagggacc  8880
ctacaccgtc gacgccatcc agaagaagat caccgagaca aagcagctgg ccaaggatct  8940
gagacagtgg cagaccaatg tggacgtggc caacgacctg gctctgaagc tgctgagaga  9000
ctacagcgcc gacgacacca gaaaggtgca catgatcacc gaaaacatca acgcctcttg  9060
gcggagcatc cacaagcggg tgtcagagag agaagccgct ctggaagaaa cacatagact  9120
gctccagcag ttcccactcg acctggaaaa gttcctggcc tggctgacag aagccgaaac  9180
caccgctaac gtgctccagg atgccaccag aaaagagcgg ctgttggagg acagcaaggg  9240
cgtcaaagaa ctcatgaagc agtggcagga tctgcaaggg gagattgaag cccacaccga  9300
cgtgtaccac aacctggacg agaacagcca gaagatcctg cggtccctgg aaggctctga  9360
tgatgctgtg ctgcttcaga ggcggctgga caacatgaac ttcaagtgga gcgagctgcg  9420
gaagaagtcc ctgaacatca gaagccacct ggaagcctcc agcgaccagt ggaaaagact  9480
gcacctgtct ctccaagagc tgctcgtgtg gctgcagctg aaggatgacg agctgagtag  9540
acaggcccct atcggcggag attttcccgc cgtgcagaaa cagaacgacg tgcaccgggc  9600
cttcaagaga gagctgaaaa caaaagaacc cgtcatcatg agcaccctgg aaaccgtgcg  9660
gatctttctg accgagcagc ctctggaagg actggaaaag ctgtaccaag agcctagaga  9720
gctgcctcct gaagaaaggg cccagaacgt gacacggctg cttagaaagc aggccgagga  9780
agtgaacacc gaatgggaga agctgaacct ccactccgcc gactggcagc ggaagatcga  9840
tgagacactg gaacggctgc gggaactgca agaagccaca gacgagctgg acctgaaact  9900
gcggcaggct gaagtgatca aaggctcctg gcagccagtg ggcgatctgc tgatcgatag  9960
cctgcaggac catctggaaa aagtcaaggc cctgcgggga gagatcgccc ctctcaaaga  10020
aaacgtgtcc cacgtgaacg atctggccag gcagctgaca acactgggca tccagctgag  10080
cccttacaac ctgtctacct tggaggacct gaatacccgg tggaagctgc tccaagtggc  10140
cgtcgaggat agagtgcggc agctgcatga ggctcacaga gattttggac ccgccagcca  10200
gcacttcctg agcacatctg ttcaaggccc ctgggagaga gctatcagcc ctaacaaggt  10260
gccctactac atcaaccacg agacacagac cacctgttgg gatcacccca agatgaccga  10320
actgtatcag tccctggccg acctgaacaa cgtgcggttt agcgcctacc ggaccgccat  10380
gaagctgcgc agactgcaga aagctctgtg cctggacctg ctgtctctga gcgctgcttg  10440
tgatgccctg gaccagcata acctcaagca gaacgaccag cctatggaca tcctgcagat  10500
catcaactgc ctgaccacca tctacgaccg gctcgaacaa gagcacaaca acctggtcaa  10560
cgtgcccctg tgcgtggaca tgtgcctgaa ttggctgctg aacgtgtacg acaccggcag  10620
aaccggcagg atcagagtgc tgagcttcaa gaccggcatc atctccctgt gcaaggccca  10680
ccttgaggat aagtaccgct acctgtttaa gcaggtcgcc agcagcaccg gcttttgcga  10740
ccaaagaagg ctgggactgc tgctccacga cagcattcag atccctagac agctgggcga  10800
agtggcctct ttcggcggct ctaatatcga gcctagcgtg cggagctgct tccagttcgc  10860
caacaacaag cccgagattg aggccgcact gttcctggac tggatgagac tggaacccca  10920
gagcatggtc tggctgcctg tgctgcatag agtggccgca gccgaaacag ccaagcacca  10980
ggccaagtgc aacatctgca aagagtgccc catcatcggc ttccggtaca gatccctgaa  11040
gcacttcaac tacgatatct gccagtcctg cttcttcagc ggcagagtgg ccaagggcca  11100
caagatgcac taccccatgg tggaatactg cacccctacc acctctggcg aggacgtgcg  11160
ggattttgcc aaggtgctca agaacaagtt ccggaccaag cgctacttcg ctaagcaccc  11220
cagaatgggc tacctgccag tgcagacagt gcttgagggc gacaacatgg aaaccccctgt  11280
gactctgatc aacttctggc ccgtggatag cgcccctgct agttctcctc agctgtctca  11340
cgacgatacc cacagcagaa tcgagcacta cgcctccaga ctggccgaga tggaaaacag  11400
caacggcagc tacctgaatg acagcatcag ccccaacgag agcatcgacg acgaacatct  11460
gctcattcag cactactgcc agagcctgaa tcaggacagc cctctgtctc agcctagaag  11520
ccctgcacag atcctgatca gcctggaaag cgaggaacgc ggcgagctgg aaagaatcct  11580
ggcagacctg gaagaggaaa accggaacct gcaggccgaa tacgacagac tcaagcagca  11640
gcacgagcac aagggactgt ctccactgcc ttctccacct gaaatgatgc ccacctctcc  11700
acagagcccc agagatgccg agctgattgc cgaagccaaa ctgctgaggc agcacaaagg  11760
cagactcgaa gccagaatgc agattctcga agatcacaac aagcagctcg aatcccagct  11820
gcacagactt aggcagctgc tggaacagcc tcaggcagag gccaaagtga atggcaccac  11880
cgtgtctagc cctagcacaa gcctgcagag atccgacagc agccagccaa tgcttctgag  11940
agtcgtgggc tcccagacca gcgattctat gggcgaagag gacctgctca gccctcctca  12000
ggatacaagc accggcctgg aagaagtgat ggaacaactg aacaacagct tccccagcag  12060
cagaggcaga aacacccctg gcaagcccat gcgcgaggac accatgtgat aa          12112
```

```
SEQ ID NO: 35          moltype = DNA  length = 12500
FEATURE                Location/Qualifiers
source                 1..12500
                       mol_type = other DNA
                       note = MHCK7-hBGi-DMD-4-WPRE3-
                       organism = synthetic construct
SEQUENCE: 35
ctagaagctg catgtctaag ctagaccctt cagattaaaa ataactgagg taagggcctg  60
```

```
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccccact acgggtctag  240
gctgcccatg taaggaggca aggcctgggg acacccgaga tgcctggtta taattaaccc  300
agacatgtgg ctgcccccccc cccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctttgg tgggaagaag tcgaggactg  1080
ctacgagcgc gaggacgtgc agaagaaaac cttcaccaaa tgggtcaacg cccagttcag  1140
caagttcggc aagcagcaca tcgagaacct gttcagcgac ctgcaggatg gcagaaggct  1200
gctggatctg ctggaaggcc tgacaggaca gaagctgccc aaagagaagg gcagcacaag  1260
agtgcacgcc ctgaacaacg tgaacaaggc cctgagagtg ctgcagaaca acaacgtgga  1320
cctggtcaac atcggcagca ccgacatcgt ggacggcaac cacaaactga ccctgggcct  1380
gatctggaac atcatcctgc actggcaagt gaagaacgtg atgaagaaca tcatggccgg  1440
cctgcagcag accaacagcg agaagattct gctgagctgg gtccgacaga gcacccggaa  1500
ttaccctcaa gtgaacgtga tcaacttcac cacctcttgg agcgacggac tggccctgaa  1560
tgccctgatc cacagccaca gacctgacct gttcgactgg aacagcgtcg tgtgtcagca  1620
gagcgccaca cagaggctgg aacacgcctt caatatcgcc agataccagc tgggcatcga  1680
gaaactgctg gaccccgagg atgtggacac cacctatcct gacaagaaat ccatcctcat  1740
gtacatcacc agcctgttcc aggtgctgcc ccagcaggtt tccatcgagg ccattcaaga  1800
ggtcgagatg ctgcccagac ctcctaaagt gaccaaagag gaacacttcc agctgcacca  1860
ccagatgcac tactctcagc agatcaccgt gtctctggcc cagggctacg agagaacaag  1920
cagccccaag cctcggttca agagctacgc ctatacacag gccgcctacg tgaccaccag  1980
cgatcctaca agaagcccat ttcctagcca gcatctggaa gcccctgagg acaagagctt  2040
tggcagcagc ctgatggaaa gcgaagtgaa cctggaccgc taccagacag ccctggaaga  2100
ggttctgagc tggctgctgt ctgccgagga tacactgcag gctcagggcg agatcagcaa  2160
cgacgtggaa gtggtcaagg accagtttca cacccacgag ggctacatga tggacctgac  2220
agcccaccag ggcagagtgg gcaatattct gcagctgggc tccaagctga tcggcacagg  2280
caagctgagc gaggacgaag agacagaggt gcaagagcag atgaacctgc tgaacagcag  2340
atgggagtgt ctgagagtgg ccagcatgga aaagcagagc aacctgcacc gggtgctgat  2400
ggatctccag aaccagaagc tgaaagagct gaacgactgg ctgaccaaga ccgaggaacg  2460
gacccggaag atggaagagg aacctctggg acccgacctg gaagatctga aaagacaggt  2520
gcagcagcat aaggtgctgc aagaggacct cgaacaagag caagtgcgcg tgaacagcct  2580
gacacacatg gtggtggtcg tggatgagag cagcggagat catgccacag ccgctctgga  2640
agaacagctg aaggtgctgg gagacagatg ggccaatatc tgccggtgga ccgaggatag  2700
atgggtgctg ctccaggaca tcctgctgaa gtggcagcgg ctgacagagg aacagtgcct  2760
gtttagcgcc tggctgtccg agaaagagga cgccgtcaac aagatccaca ccaccggctt  2820
caaggatcag aatgagatgc tgagcagcct gcagaaactg gccgtgctga aggctgacct  2880
ggaaaagaaa aagcagtcca tgggcaagct gtactccctg aagcaggacc tgctgagcac  2940
actgaagaac aagtctgtga cccagaaaac cgaggcctgg ctggacaact tcgcccggtg  3000
ttgggataac ctggtgcaga agctggaaaa gtccaccgct cagatctctc aggccgtgac  3060
cacaacacag ccttctctga cccagaccac cgtgatggaa acagtgacca cagtgacaac  3120
ccgcgagcag atcctggtca agcacgccca agaagaactg cctcctccac ctcctcagaa  3180
gaaacggcag atcacagtgg acagcgagat ccggaagaga ctggacgtgg acatcaccga  3240
gctgcacagc tggatcacca gatccgaagc cgtgctgcag tcccctgagt tcgccatctt  3300
cagaaaagag ggcaacttct ccgacctgaa agagaaagtc aacgccatcg agagagagaa  3360
ggccgagaag ttccggaagc tgcaggacgc ctctagatct gcccaggctc tggtggaaca  3420
gatggtcaac gaaggcgtga acgccgacag catcaagcag gcctcagagc agctgaactc  3480
ccggtggatc gagttctgtc agctcctgag cgagagactg aactggctgg aataccagaa  3540
caatatcatt gccttctaca accagctcca gcagctcgaa cagatgacca ccacagccga  3600
gaattggctg aagatccagc ctaccacacc tagcgagccc accgccatta agagccagct  3660
gaaaatctgc aaggacgaag tgaatcggct gagcgatctg cagccccaga tcgaaagact  3720
gaaaatccag tctatcgccc tcaaagagaa aggacagggc cccatgttcc tggacgccga  3780
ttttgtggcc tttaccaacc acttcaaaca ggtgttctcc gacgtgcagg cccgggaaaa  3840
agagctgcag accatcttcg acaccctgcc tccaatgaga taccaagaga caatgagcgc  3900
catccggacc tgggtgcagc aaagcgagac aaagctgagc atcccacagc tgagcgtgac  3960
cgactacgag atcatggaac agagactggg cgaactgcag gccctccagt ctagcctgca  4020
agaacagcag tccggcctgt actacctgag cacaaccgtg aaagagatga gcaagaaggc  4080
ccctagcgag atctcccgga agtaccagag cgagttcgaa gagatcgaag gccggtggaa  4140
gaagctgtct agccagctgg ttgagcactg ccagaaactc gaagaacaaa tgaacaagct  4200
gcgcaagatc cagaatcaca tccagacgct gaagaaatgg atggccgagg tggacgtgtt  4260
cctgaaagaa gagtggcccg ctctgggcga ctccgagatt ctgaagaaac agctcaaaca  4320
gtgccggctg ctggtgtccg atatccagac aatccagcca agcctgaact ccgtgaatga  4380
aggcggccag aagatcaaga acgaggccga gcctgagttt gccagcagac tggaaaccga  4440
actgaaagaa ctcaacaccc agtgggacca catgtgccag caagtgtacg cccggaaaga  4500
ggccctgaaa ggcggactcg aaaagactgt gtctctgcag aaagacctgt ctgagatgca  4560
cgagtggatg acccaggccg aagaggaata cctggaacgg gacttcgagt acaagacccc  4620
tgatgagctg caaaaagccg tcgaggaaat gaagcgggcc aaagaagagg cccagcagaa  4680
agaagccaaa gtcaagctgc tgaccgagtc cgtgaatagc gttatcgctc aggcccctcc  4740
tgtggctcaa gaggctctca agaaagaact ggaaactctg accaccaact accagtggct  4800
```

```
gtgcaccaga ctgaacggca agtgcaagac actggaagaa gtgtgggcct gctggcacga  4860
actgctgtcc tatctggaaa aggccaacaa gtggctgaac gaggtggaat tcaagctgaa  4920
aaccaccgag aacatccctg gcggcgctga agagattagc gaggtgctgg acagcctgga  4980
aaacctgatg agacacagcg aggacaaccc caatcagatc agaatcctgg ctcagaccct  5040
gaccgatggc ggcgtgatgg acgagctgat caacgaggaa ctcgaaacct tcaacagccg  5100
gtggcgggaa ctgcacgagg aagctgttcg gaggcagaag ttgctggaac agtctatcca  5160
gagcgcacaa gaaaccgaga agtccctgca cctgatccaa gagagcctga ccttcatcga  5220
caagcagctg gccgcttata tcgccgacaa ggtggacgct gctcagatgc cccaagaggc  5280
acagaagatt cagagcgacc tgaccagcca cgagattagc ctggaagaaa tgaagaagca  5340
caaccagggc aaagaggccg ctcagagagt cctgagccag atcgatgtgg cacagaaaaa  5400
gctccaggat gtgtccatga agtttcggct gtttcagaag cccgccaact tcgagcagag  5460
actgcaagag tccaagatga tcctggacga agtcaaaatg catctgcccg cactggaaac  5520
aaagtccgtg gaacaagaag tggtgcagtc ccagctgaac cactgcgtga acctgtacaa  5580
gagcctgtcc gaagtgaagt ctgaggtgga aatggtcatc aagaccggca ggcagatcgt  5640
ccagaagaag cagaccgaga atcccaaaga actcgacgag agagtgaccg ctctgaagct  5700
gcactacaat gagctgggcg ccaaagtgac cgagcggaag caacagcttg agaagtgcct  5760
gaaactgtct cggaagatgc ggaaagaaat gaacgtgctg acagagtggc tggccgccac  5820
cgatatggaa ctgactaaga gaagcgccgt ggaaggcatg cccagcaacc tggatagtga  5880
agtggcctgg ggcaaagcca ctcagaaaga gattgagaag cagaaggtcc acctgaagtc  5940
catcaccgaa gtgggcgaag ccctgaaaac cgtgctggga aagaaagaga cactggtcga  6000
ggacaagctg tccctgctga attccaactg gatcgccgtg acctccagag ctgaggaatg  6060
gctgaatctg ctgcttgagt accagaaaca catggaaacg ttcgaccaga acgtcgacca  6120
catcacaaag tggatcatcc aggctgatac cctgctggac gagtccgaga agaagaaacc  6180
ccaacaaaaa gaagatgtgc tgaagcggct gaaagccgag ctgaatgaca tccggcctaa  6240
ggtggacagc accagagatc aggcagccaa cctgatggcc aacagaggcg accactgtcg  6300
gaagctcgtg gaacctcaga tcagcgagct taaccacaga tttgccgcca tcagccaccg  6360
gatcaagaca ggcaaggcca gcattcctct caaagagctt gagcagttca acagcgacat  6420
ccaaaagctg ctcgaacccc tggaagccga gatccaacag ggcgtcaacc tcaaagaaga  6480
agatttcaac aaggacatga acgaggacaa tgagggcacc gtcaaagaac tgctgcagcg  6540
gggcgataat ctgcagcagc ggattaccga tgagcgcaag cgggaagaga tcaagattaa  6600
gcagcagctg ctgcagacca agcacaacgc cctgaaggac ctgcggagcc agagaagaaa  6660
gaaggccctg gaaatcagcc accagtggta tcagtacaag cggcaggccg acgacctgct  6720
gaagtgcctg gatgacatcg agaagaagct ggcctctctg cccgagccta gggacgagag  6780
aaagatcaaa gagatcgacc gcgagctgca gaaaaagaaa gaggaactga acgccgtccg  6840
cagacaggcc gaaggacttt ctgaagatgg cgccgctatg gccgtggaac ccacacagat  6900
tcagctgagc aagcggtggc gggaaatcga gagcaagttc gcccagttcc ggcggctgaa  6960
tttcgcccag atccacaccg tgcgggaaga gacaatgatg gtcatgacag aggacatgcc  7020
ccttgagatc agctacgtgc ccagcaccta cctgaccgag atcacccatg tgtctcaggc  7080
cctgctggaa gtggaacagc tgctgaatgc ccctgacctg tgcgccaagg acttcgagga  7140
cctgttcaag caagaggaaa gcctgaagaa catcaaggac agcctgcagc agagcagcgg  7200
ccggatcgat atcatccaca gcaagaaaac cgccgcactg cagagcgcca cacctgtgga  7260
aagagtgaag ctgcaagagg ccctgagcca gctggatttc cagtgggaga aagtgaacaa  7320
gatgtacaag gaccggcagg gcagattcga ccgcagcgtt gaaaagtggc ggcggttcca  7380
ctacgacatc aagatcttca accagtggct gaccgaggcc gagcagttcc tgagaaagac  7440
acagatcccc gagaactggg agcacgccaa gtacaagtgg tatctgaaag agctgcagga  7500
cggcatcggc cagagacaga cagtcgtgcg gacactgaat gccaccggcg aggaaatcat  7560
ccagcagtcc agcaagaccg acgccagcat cctgcaagag aagctgggca gcctgaacct  7620
gcggtggcaa gaagtgtgca agcagctgag cgaccggaag aagcggctgg aagaacagaa  7680
gaatatcctg agcgagttcc agcgggacct gaacgagttc gtgctgtggc tcgaagaggc  7740
cgacaatatc gccagcattc ccctggaacc tggcaaagag cagcagctga aagaaaagct  7800
ggaacaagtg aaactgctgg tcgaggaact gcccctgaga cagggaatcc tgaaacagct  7860
gaacgagaca ggcggccctg tgctggtgtc tgcccctatt tctcccgagg aacaggacaa  7920
gctggaaaac aagctgaagc agaccaacct gcagtggatc aaggtgtcca gagcactgcc  7980
tgagaagcag ggcgagatcg aggcccagat caaggacctg ggacagctcg aaaagaagct  8040
tgaggacctc gaagaacagc tcaaccatct gctgctttgg ctgagcccca tccggaacca  8100
gctggaaatc tacaaccagc ctaatcaaga gggccccttc gacgtgaaag aaaccgagat  8160
tgccgtgcag gccaagcagc ccgatgtgga agagatcctg tctaagggcc agcacctgta  8220
caaagagaag cccgccacac agcccgtgaa gcggaaactg gaagatctga gcagcgagtg  8280
gaaggccgtg aaccggctgc tgcaagaact gagagccaaa cagcctgatc tggcccctgg  8340
cctgacaaca attggcgcct ctcctacaca gaccgtgaca ctggtcacac agcctgtggt  8400
caccaaagag acagccatca gcaaactgga aatgcccagc agtctgatgc tcgaagtgcc  8460
cgcactggcc gacttcaata gagcctggac cgagctgacc gactggctca gtctgctgga  8520
ccaagtcatc aagtcccaga gagtgatggt cggagatctt gaggacatca acgagatgat  8580
cattaagcag aaagccacca tgcaggacct tgagcagaga aggccccagc ttgaagaact  8640
gatcaccgcc gctcagaacc tgaaaaacaa gaccagcaat caagaagccc ggaccatcat  8700
caccgaccgg atcgagagaa tccagaacca gtgggacgaa gtgcaagagc atctgcagaa  8760
cagacggcag cagctcaatg agatgctgaa ggacagcaca cagtggctgg aagccaaaga  8820
agaagccgag caggttctcg gacaggccag agctaagctg gaatcttgga aagagggacc  8880
ctacaccgtc gacgccatcc agaagaagat caccgagaca aagcagctgg ccaaggatct  8940
gagacagtgg cagaccaatg tggacgtggc caacgacctg gctctgaagc tgctgagaga  9000
ctacagcgcc gacgacacca gaaaggtgca catgatcacc gaaaacatca acgcctcttg  9060
gcggagcatc cacaagcggg tgtcagagag agaagccgct ctggaagaaa cacatagact  9120
gctccagcag ttcccactcg acctggaaaa gttcctggcc tggctgacag aagccgaaac  9180
caccgctaac gtgctccagg atgccaccag aaaagagcgg ctgttggagg acagcaaggg  9240
cgtcaaagaa ctcatgaagc agtggcagga tctgcaaggg gagattgaag cccacaccga  9300
cgtgtaccac aacctggacg agaacagcca gaagatcctg cggtccctgg aaggctctga  9360
tgatgctgtg ctgcttcaga ggcggctgga caacatgaac ttcaagtgga gcgagctgcg  9420
gaagaagtcc ctgaacatca gaagccacct ggaagcctcc agcgaccagt ggaaaagact  9480
gcacctgtct ctccaagagc tgctcgtgtg gctgcagctg aaggatgacg agctgagtag  9540
```

```
acaggcccct atcggcggag attttcccgc cgtgcagaaa cagaacgacg tgcaccgggc  9600
cttcaagaga gagctgaaaa caaaagaacc cgtcatcatg agcaccctgg aaaccgtgcg  9660
gatctttctg accgagcagc ctctggaagg actggaaaag ctgtaccaag agcctagaga  9720
gctgcctcct gaagaaaggg cccagaacgt gacacggctg cttagaaagc aggccgagga  9780
agtgaacacc gaatgggaga agctgaacct ccactccgcc gactggcagc ggaagatcga  9840
tgagacactg gaacggctgc gggaactgca agaagccaca gacgagctgg acctgaaact  9900
gcggcaggct gaagtgatca aaggctcctg gcagccagtg ggcgatctgc tgatcgatag  9960
cctgcaggac catctggaaa aagtcaaggc cctgcgggga gagatcgccc ctctcaaaga  10020
aaacgtgtcc cacgtgaacg atctggccag gcagctgaca acactgggca tccagctgag  10080
cccttacaac ctgtctacct tggaggacct gaatacccgg tggaagctgc tccaagtggc  10140
cgtcgaggat agagtgcggc agctgcatga ggctcacaga gattttggac ccgccagcca  10200
gcacttcctg agcacatctg ttcaaggccc ctgggagaga gctatcagcc ctaacaaggt  10260
gccctactac atcaaccacg agacacagac cacctgttgg gatcacccca agatgaccga  10320
actgtatcag tccctggccg acctgaacaa cgtgcggttt agcgcctacc ggaccgccat  10380
gaagctgcgc agactgcaga aagctctgtg cctggacctg ctgtctctga gcgctgcttg  10440
tgatgccctg gaccagcata acctcaagca gaacgaccag cctatggaca tcctgcagat  10500
catcaactgc ctgaccacca tctacgaccg gctcgaacaa gagcacaaca acctggtcaa  10560
cgtgcccctg tgcgtggaca tgtgcctgaa ttggctgctg aacgtgtacg acaccggcag  10620
aaccggcagg atcagagtgc tgagcttcaa gaccggcatc atctccctgt gcaaggccca  10680
ccttgaggat aagtaccgct acctgtttaa gcaggtcgcc agcagcaccg gcttttgcga  10740
ccaaagaagg ctgggactgc tgctccacga cagcattcag atccctagac agctgggcga  10800
agtggcctct ttcggcggct ctaatatcga gcctagcgtg cggagctgct tccagttcgc  10860
caacaacaag cccgagattg aggccgcact gttcctggac tggatgagac tggaacccca  10920
gagcatggtc tggctgcctg tgctgcatag agtggccgca gccgaaacag ccaagcacca  10980
ggccaagtgc aacatctgca aagagtgccc catcatcggc ttccggtaca gatccctgaa  11040
gcacttcaac tacgatatct gccagtcctg cttcttcagc ggcagagtgg ccaagggcca  11100
caagatgcac taccccatgg tggaatactg cacccctacc acctctggcg aggacgtgcg  11160
ggattttgcc aaggtgctca agaacaagtt ccggaccaag cgctacttcg ctaagcaccc  11220
cagaatgggc tacctgccag tgcagacagt gcttgagggc gacaacatgg aaacccctgt  11280
gactctgatc aacttctggc ccgtggatag cgcccctgct agttctcctc agctgtctca  11340
cgacgatacc cacagcagaa tcgagcacta cgcctccaga ctggccgaga tggaaaacag  11400
caacggcagc tacctgaatg acagcatcag ccccaacgag agcatcgacg acgaacatct  11460
gctcattcag cactactgcc agagcctgaa tcaggacagc cctctgtctc agcctagaag  11520
ccctgcacag atcctgatca gcctggaaag cgaggaacgc ggcgagctgg aaagaatcct  11580
ggcagacctg gaagaggaaa accggaacct gcaggccgaa tacgacagac tcaagcagca  11640
gcacgagcac aagggactgt ctccactgcc ttctccacct gaaatgatgc ccacctctcc  11700
acagagcccc agagatgccg agctgattgc cgaagccaaa ctgctgaggc agcacaaagg  11760
cagactcgaa gccagaatgc agattctcga agatcacaac aagcagctcg aatcccagct  11820
gcacagactt aggcagctgc tggaacagcc tcaggcagag gccaaagtga atggcaccac  11880
cgtgtctagc cctagcacaa gcctgcagag atccgacagc agccagccaa tgcttctgag  11940
agtcgtgggc tcccagacca gcgattctat gggcgaagag gacctgctca gccctcctca  12000
ggatacaagc accggcctgg aagaagtgat ggaacaactg aacaacagct tccccagcag  12060
cagaggcaga aacacccctg gcaagcccat gcgcgaggac accatgtgat aactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg                                              12500
```

```
SEQ ID NO: 36           moltype = DNA  length = 12726
FEATURE                 Location/Qualifiers
source                  1..12726
                        mol_type = other DNA
                        note = MHCK7-hBGi-DMD-4-WPRE3-PolyA
                        organism = synthetic construct
SEQUENCE: 36
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgccccact acgggtctag  240
gctgcccatg taaggaggca aggcctgggg acacccgaga tgcctggtta taattaaccc  300
agacatgtgg ctgccccccc cccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac catgctttgg tgggaagaag tcgaggactg  1080
ctacgagcgc gaggacgtgc agaagaaaac cttcaccaaa tgggtcaacg cccagttcag  1140
caagttcggc aagcagcaca tcgagaacct gttcagcgac ctgcaggatg gcagaaggct  1200
gctggatctg ctggaaggcc tgacaggaca gaagctgccc aaagagaagg gcagcacaag  1260
```

```
agtgcacgcc ctgaacaacg tgaacaaggc cctgagagtg ctgcagaaca acaacgtgga  1320
cctggtcaac atcggcagca ccgacatcgt ggacggcaac cacaaactga ccctgggcct  1380
gatctggaac atcatcctgc actggcaagt gaagaacgtg atgaagaaca tcatggccgg  1440
cctgcagcag accaacagcg agaagattct gctgagctgg gtccgacaga gcacccggaa  1500
ttaccctcaa gtgaacgtga tcaacttcac cacctcttgg agcgacggac tggccctgaa  1560
tgccctgatc cacagccaca gacctgacct gttcgactgg aacagcgtcg tgtgtcagca  1620
gagcgccaca cagaggctgg aacacgcctt caatatcgcc agataccagc tgggcatcga  1680
gaaactgctg gaccccgagg atgtggacac cacctatcct gacaagaaat ccatcctcat  1740
gtacatcacc agcctgttcc aggtgctgcc ccagcaggtt tccatcgagg ccattcaaga  1800
ggtcgagatg ctgcccagac ctcctaaagt gaccaaagag gaacacttcc agctgcacca  1860
ccagatgcac tactctcagc agatcaccgt gtctctggcc cagggctacg agagaacaag  1920
cagccccaag cctcggttca agagctacgc ctatacacag gccgcctacg tgaccaccag  1980
cgatcctaca agaagcccat ttcctagcca gcatctggaa gcccctgagg acaagagctt  2040
tggcagcagc ctgatggaaa gcgaagtgaa cctggaccgc taccagacag ccctggaaga  2100
ggttctgagc tggctgctgt ctgccgagga tacactgcag gctcagggcg agatcagcaa  2160
cgacgtggaa gtggtcaagg accagtttca cacccacgag ggctacatga tggacctgac  2220
agcccaccag ggcagagtgg gcaatattct gcagctgggc tccaagctga tcggcacagg  2280
caagctgagc gaggacgaag agacagaggt gcaagagcag atgaacctgc tgaacagcag  2340
atgggagtgt ctgagagtgg ccagcatgga aaagcagagc aacctgcacc gggtgctgat  2400
ggatctccag aaccagaagc tgaaagagct gaacgactgg ctgaccaaga ccgaggaacg  2460
gacccggaag atggaagagg aacctctggg acccgacctg gaagatctga aaagacaggt  2520
gcagcagcat aaggtgctgc aagaggacct cgaacaagag caagtgcgcg tgaacagcct  2580
gacacacatg gtggtggtcg tggatgagag cagcggagat catgccacag ccgctctgga  2640
agaacagctg aaggtgctgg gagacagatg ggccaatatc tgccggtgga ccgaggatag  2700
atgggtgctg ctccaggaca tcctgctgaa gtggcagcgg ctgacagagg aacagtgcct  2760
gtttagcgcc tggctgtccg agaaagagga cgccgtcaac aagatccaca ccaccggctt  2820
caaggatcag aatgagatgc tgagcagcct gcagaaactg gccgtgctga aggctgacct  2880
ggaaaagaaa aagcagtcca tggcaagct gtactccctg aagcaggacc tgctgagcac  2940
actgaagaac aagtctgtga cccagaaaac cgaggcctgg ctggacaact tcgcccggtg  3000
ttgggataac ctggtgcaga agctggaaaa gtccaccgct cagatctctc aggccgtgac  3060
cacaacacag ccttctctga cccagaccac cgtgatggaa acagtgacca cagtgacaac  3120
ccgcgagcag atcctggtca agcacgccca agaagaactg cctcctccac ctcctcagaa  3180
gaaacggcag atcacagtgg acagcgagat ccggaagaga ctggacgtgg acatcaccga  3240
gctgcacagc tggatcacca gatccgaagc cgtgctgcag tcccctgagt tcgccatctt  3300
cagaaaagag ggcaacttct ccgacctgaa agagaaagtc aacgccatcg agagagagaa  3360
ggccgagaag ttccggaagc tgcaggacgc ctctagatct gcccaggctc tggtggaaca  3420
gatggtcaac gaaggcgtga acgccgacag catcaagcag gcctcagagc agctgaactc  3480
ccggtggatc gagttctgtc agctcctgag cgagagactg aactggctgg aataccagaa  3540
caatatcatt gccttctaca accagctcca gcagctcgaa cagatgacca ccacagccga  3600
gaattggctg aagatccagc ctaccacacc tagcgagccc accgccatta agagccagct  3660
gaaaatctgc aaggacgaag tgaatcggct gagcgatctg cagccccaga tcgaaagact  3720
gaaaatccag tctatcgccc tcaaagagaa aggacagggc cccatgttcc tggacgccga  3780
ttttgtggcc tttaccaacc acttcaaaca ggtgttctcc gacgtgcagg cccgggaaaa  3840
agagctgcag accatcttcg acaccctgcc tccaatgaga taccaagaga caatgagcgc  3900
catccggacc tgggtgcagc aaagcgagac aaagctgagc atcccacagc tgagcgtgac  3960
cgactacgag atcatggaac agagactggg cgaactgcag gccctccagt ctagcctgca  4020
agaacagcag tccggcctgt actacctgag cacaaccgtg aaagagatga gcaagaaggc  4080
ccctagcgag atctcccgga agtaccagag cgagttcgaa gagatcgaag gccggtggaa  4140
gaagctgtct agccagctgg ttgagcactg ccagaaactc gaagaacaaa tgaacaagct  4200
gcgcaagatc cagaatcaca tccagacgct gaagaaatgg atggccgagg tggacgtgtt  4260
cctgaaagaa gagtggcccg ctctgggcga ctccgagatt ctgaagaaac agctcaaaca  4320
gtgccggctg ctggtgtccg atatccagac aatccagcca agcctgaact ccgtgaatga  4380
aggcggccag aagatcaaga acgaggccga gcctgagttt gccagcagac tggaaaccga  4440
actgaaagaa ctcaacaccc agtgggacca catgtgccag caagtgtacg cccggaaaga  4500
ggccctgaaa ggcggactcg aaaagactgt gtctctgcag aaagacctgt ctgagatgca  4560
cgagtggatg acccaggccg aagaggaata cctggaacgg gacttcgagt acaagacccc  4620
tgatgagctg caaaaagccg tcgaggaaat gaagcgggcc aaagaagagg cccagcagaa  4680
agaagccaaa gtcaagctgc tgaccgagtc cgtgaatagc gttatcgctc aggcccctcc  4740
tgtggctcaa gaggctctca agaaagaact ggaaactctg accaccaact accagtggct  4800
gtgcaccaga ctgaacggca agtgcaagac actggaagaa gtgtgggcct gctggcacga  4860
actgctgtcc tatctggaaa aggccaacaa gtggctgaac gaggtggaat tcaagctgaa  4920
aaccaccgag aacatccctg gcggcgctga agagattagc gaggtgctgg acagcctgga  4980
aaacctgatg agacacagcg aggacaaccc caatcagatc agaatcctgg ctcagaccct  5040
gaccgatggc ggcgtgatgg acgagctgat caacgaggaa ctcgaaacct tcaacagccg  5100
gtggcgggaa ctgcacgagg aagctgttcg gaggcagaag ttgctggaac agtctatcca  5160
gagcgcacaa gaaaccgaga agtccctgca cctgatccaa gagagcctga ccttcatcga  5220
caagcagctg gccgcttata tcgccgacaa ggtggacgct gctcagatgc cccaagaggc  5280
acagaagatt cagagcgacc tgaccagcca cgagattagc ctggaagaaa tgaagaagca  5340
caaccagggc aaagaggccg ctcagagagt cctgagccag atcgatgtgg cacagaaaaa  5400
gctccaggat gtgtccatga agtttcggct gtttcagaag cccgccaact tcgagcagag  5460
actgcaagag tccaagatga tcctggacga agtcaaaatg catctgcccg cactggaaac  5520
aaagtccgtg gaacaagaag tggtgcagtc ccagctgaac cactgcgtga acctgtacaa  5580
gagcctgtcc gaagtgaagt ctgaggtgga aatggtcatc aagaccggca ggcagatcgt  5640
ccagaagaag cagaccgaga atcccaaaga actcgacgag agagtgaccg ctctgaagct  5700
gcactacaat gagctgggcg ccaaagtgac cgagcggaag caacagcttg agaagtgcct  5760
gaaactgtct cggaagatgc ggaaagaaat gaacgtgctg acagagtggc tggccgccac  5820
cgatatggaa ctgactaaga gaagcgccgt ggaaggcatg cccagcaacc tggatagtga  5880
agtggcctgg ggcaaagcca ctcagaaaga gattgagaag cagaaggtcc acctgaagtc  5940
catcaccgaa gtgggcgaag ccctgaaaac cgtgctggga aagaaagaga cactggtcga  6000
```

```
ggacaagctg tccctgctga attccaactg gatcgccgtg acctccagag ctgaggaatg  6060
gctgaatctg ctgcttgagt accagaaaca catggaaacg ttcgaccaga acgtcgacca  6120
catcacaaag tggatcatcc aggctgatac cctgctggac gagtccgaga agaagaaacc  6180
ccaacaaaaa gaagatgtgc tgaagcggct gaaagccgag ctgaatgaca tccggcctaa  6240
ggtggacagc accagagatc aggcagccaa cctgatggcc aacagaggcg accactgtcg  6300
gaagctcgtg gaacctcaga tcagcgagct taaccacaga tttgccgcca tcagccaccg  6360
gatcaagaca ggcaaggcca gcattcctct caaagagctt gagcagttca acagcgacat  6420
ccaaaagctg ctcgaacccc tggaagccga gatccaacag ggcgtcaacc tcaaagaaga  6480
agatttcaac aaggacatga acgaggacaa tgagggcacc gtcaaagaac tgctgcagcg  6540
gggcgataat ctgcagcagc ggattaccga tgagcgcaag cgggaagaga tcaagattaa  6600
gcagcagctg ctgcagacca agcacaacgc cctgaaggac ctgcggagcc agagaagaaa  6660
gaaggccctg gaaatcagcc accagtggta tcagtacaag cggcaggccg acgacctgct  6720
gaagtgcctg gatgacatcg agaagaagct ggcctctctg cccgagccta gggacgagag  6780
aaagatcaaa gagatcgacc gcgagctgca gaaaaagaaa gaggaactga acgccgtccg  6840
cagacaggcc gaaggacttt ctgaagatgg cgccgctatg gccgtggaac ccacacagat  6900
tcagctgagc aagcggtggc gggaaatcga gagcaagttc gcccagttcc ggcggctgaa  6960
tttcgcccag atccacaccg tgcgggaaga gacaatgatg gtcatgacag aggacatgcc  7020
ccttgagatc agctacgtgc ccagcaccta cctgaccgag atcacccatg tgtctcaggc  7080
cctgctggaa gtggaacagc tgctgaatgc ccctgacctg tgcgccaagg acttcgagga  7140
cctgttcaag caagaggaaa gcctgaagaa catcaaggac agcctgcagc agagcagcgg  7200
ccggatcgat atcatccaca gcaagaaaac cgccgcactg cagagcgcca cacctgtgga  7260
aagagtgaag ctgcaagagg ccctgagcca gctggatttc cagtgggaga aagtgaacaa  7320
gatgtacaag gaccggcagg gcagattcga ccgcagcgtt gaaaagtggc ggcggttcca  7380
ctacgacatc aagatcttca accagtggct gaccgaggcc gagcagttcc tgagaaagac  7440
acagatcccc gagaactggg agcacgccaa gtacaagtgg tatctgaaag agctgcagga  7500
cggcatcggc cagagacaga cagtcgtgcg gacactgaat gccaccggcg aggaaatcat  7560
ccagcagtcc agcaagaccg acgccagcat cctgcaagag aagctgggca gcctgaacct  7620
gcggtggcaa gaagtgtgca agcagctgag cgaccggaag aagcggctgg aagaacagaa  7680
gaatatcctg agcgagttcc agcgggacct gaacgagttc gtgctgtggc tcgaagaggc  7740
cgacaatatc gccagcattc ccctggaacc tggcaaagag cagcagctga aagaaaagct  7800
ggaacaagtg aaactgctgg tcgaggaact gcccctgaga cagggaatcc tgaaacagct  7860
gaacgagaca ggcggccctg tgctggtgtc tgcccctatt tctcccgagg aacaggacaa  7920
gctggaaaac aagctgaagc agaccaacct gcagtggatc aaggtgtcca gagcactgcc  7980
tgagaagcag ggcgagatcg aggcccagat caaggacctg ggacagctcg aaaagaagct  8040
tgaggacctc gaagaacagc tcaaccatct gctgctttgg ctgagcccca tccggaacca  8100
gctggaaatc tacaaccagc ctaatcaaga gggccccttc gacgtgaaag aaaccgagat  8160
tgccgtgcag gccaagcagc ccgatgtgga agagatcctg tctaagggcc agcacctgta  8220
caaagagaag cccgccacac agcccgtgaa gcggaaactg gaagatctga gcagcgagtg  8280
gaaggccgtg aaccggctgc tgcaagaact gagagccaaa cagcctgatc tggcccctgg  8340
cctgacaaca attggcgcct ctcctacaca gaccgtgaca ctggtcacac agcctgtggt  8400
caccaaagag acagccatca gcaaactgga aatgcccagc agtctgatgc tcgaagtgcc  8460
cgcactggcc gacttcaata gagcctggac cgagctgacc gactggctca gtctgctgga  8520
ccaagtcatc aagtcccaga gagtgatggt cggagatctt gaggacatca acgagatgat  8580
cattaagcag aaagccacca tgcaggacct tgagcagaga aggccccagc ttgaagaact  8640
gatcaccgcc gctcagaacc tgaaaaacaa gaccagcaat caagaagccc ggaccatcat  8700
caccgaccgg atcgagagaa tccagaacca gtgggacgaa gtgcaagagc atctgcagaa  8760
cagacggcag cagctcaatg agatgctgaa ggacagcaca cagtggctgg aagccaaaga  8820
agaagccgag caggttctcg gacaggccag agctaagctg gaatcttgga aagagggacc  8880
ctacaccgtc gacgccatcc agaagaagat caccgagaca aagcagctgg ccaaggatct  8940
gagacagtgg cagaccaatg tggacgtggc caacgacctg gctctgaagc tgctgagaga  9000
ctacagcgcc gacgacacca gaaaggtgca catgatcacc gaaaacatca acgcctcttg  9060
gcggagcatc cacaagcggg tgtcagagag agaagccgct ctggaagaaa cacatagact  9120
gctccagcag ttcccactcg acctggaaaa gttcctggcc tggctgacag aagccgaaac  9180
caccgctaac gtgctccagg atgccaccag aaaagagcgg ctgttggagg acagcaaggg  9240
cgtcaaagaa ctcatgaagc agtggcagga tctgcaaggg gagattgaag cccacaccga  9300
cgtgtaccac aacctggacg agaacagcca gaagatcctg cggtccctgg aaggctctga  9360
tgatgctgtg ctgcttcaga ggcggctgga caacatgaac ttcaagtgga gcgagctgcg  9420
gaagaagtcc ctgaacatca gaagccacct ggaagcctcc agcgaccagt ggaaaagact  9480
gcacctgtct ctccaagagc tgctcgtgtg gctgcagctg aaggatgacg agctgagtag  9540
acaggcccct atcggcggag attttcccgc cgtgcagaaa cagaacgacg tgcaccgggc  9600
cttcaagaga gagctgaaaa caaaagaacc cgtcatcatg agcaccctgg aaaccgtgcg  9660
gatctttctg accgagcagc ctctggaagg actggaaaag ctgtaccaag agcctagaga  9720
gctgcctcct gaagaaaggg cccagaacgt gacacggctg cttagaaagc aggccgagga  9780
agtgaacacc gaatgggaga agctgaacct ccactccgcc gactggcagc ggaagatcga  9840
tgagacactg gaacggctgc gggaactgca agaagccaca gacgagctgg acctgaaact  9900
gcggcaggct gaagtgatca aaggctcctg gcagccagtg ggcgatctgc tgatcgatag  9960
cctgcaggac catctggaaa aagtcaaggc cctgcgggga gagatcgccc ctctcaaaga  10020
aaacgtgtcc cacgtgaacg atctggccag gcagctgaca acactgggca tccagctgag  10080
cccttacaac ctgtctacct tggaggacct gaatacccgg tggaagctgc tccaagtggc  10140
cgtcgaggat agagtgcggc agctgcatga ggctcacaga gattttggac ccgccagcca  10200
gcacttcctg agcacatctg ttcaaggccc ctgggagaga gctatcagcc ctaacaaggt  10260
gccctactac atcaaccacg agacacagac cacctgttgg gatcacccca agatgaccga  10320
actgtatcag tccctggccg acctgaacaa cgtgcggttt agcgcctacc ggaccgccat  10380
gaagctgcgc agactgcaga aagctctgtg cctggacctg ctgtctctga gcgctgcttg  10440
tgatgccctg gaccagcata acctcaagca gaacgaccag cctatggaca tcctgcagat  10500
catcaactgc ctgaccacca tctacgaccg gctcgaacaa gagcacaaca acctggtcaa  10560
cgtgcccctg tgcgtggaca tgtgcctgaa ttggctgctg aacgtgtacg acaccggcag  10620
aaccggcagg atcagagtgc tgagcttcaa gaccggcatc atctccctgt gcaaggccca  10680
ccttgaggat aagtaccgct acctgtttaa gcaggtcgcc agcagcaccg gcttttgcga  10740
```

```
ccaaagaagg ctgggactgc tgctccacga cagcattcag atccctagac agctgggcga  10800
agtggcctct ttcggcggct ctaatatcga gcctagcgtg cggagctgct tccagttcgc  10860
caacaacaag cccgagattg aggccgcact gttcctggac tggatgagac tggaacccca  10920
gagcatggtc tggctgcctg tgctgcatag agtggccgca gccgaaacag ccaagcacca  10980
ggccaagtgc aacatctgca aagagtgccc catcatcggc ttccggtaca gatccctgaa  11040
gcacttcaac tacgatatct gccagtcctg cttcttcagc ggcagagtgg ccaagggcca  11100
caagatgcac taccccatgg tggaatactg cacccctacc acctctggcg aggacgtgcg  11160
ggattttgcc aaggtgctca agaacaagtt ccggaccaag cgctacttcg ctaagcaccc  11220
cagaatgggc tacctgccag tgcagacagt gcttgagggc gacaacatgg aaacccctgt  11280
gactctgatc aacttctggc ccgtggatag cgcccctgct agttctcctc agctgtctca  11340
cgacgatacc cacagcagaa tcgagcacta cgcctccaga ctggccgaga tggaaaacag  11400
caacggcagc tacctgaatg acagcatcag ccccaacgag agcatcgacg acgaacatct  11460
gctcattcag cactactgcc agagcctgaa tcaggacagc cctctgtctc agcctagaag  11520
ccctgcacag atcctgatca gcctggaaag cgaggaacgc ggcgagctgg aaagaatcct  11580
ggcagacctg gaagaggaaa accggaacct gcaggccgaa tacgacagac tcaagcagca  11640
gcacgagcac aagggactgt ctccactgcc ttctccacct gaaatgatgc ccacctctcc  11700
acagagcccc agagatgccg agctgattgc cgaagccaaa ctgctgaggc agcacaaagg  11760
cagactcgaa gccagaatgc agattctcga agatcacaac aagcagctcg aatcccagct  11820
gcacagactt aggcagctgc tggaacagcc tcaggcagag gccaaagtga atggcaccac  11880
cgtgtctagc cctagcacaa gcctgcagag atccgacagc agccagccaa tgcttctgag  11940
agtcgtgggc tcccagacca gcgattctat gggcgaagag gacctgctca gccctcctca  12000
ggatacaagc accggcctgg aagaagtgat ggaacaactg aacaacagct tccccagcag  12060
cagaggcaga aacacccctg gcaagcccat gcgcgaggac accatgtgat aactcgagaa  12120
tcaacctctg gattacaaaa tttgtgaaag attgactggt attcttaact atgttgctcc  12180
ttttacgcta tgtggatacg ctgctttaat gcctttgtat catgctattg cttcccgtat  12240
ggctttcatt ttctcctcct tgtataaatc ctggttgctg tctctttatg aggagttgtg  12300
gcccgttgtc aggcaacgtg gcgtggtgtg cactgtgttt gctgacgcaa cccccactgg  12360
ttggggcatt gccaccacct gtcagctcct ttccgggact ttcgctttcc ccctccctat  12420
tgccacggcg gaactcatcg ccgcctgcct tgcccgctgc tggacagggg ctcggctgtt  12480
gggcactgac aattccgtgg ggtgtgcctt ctagttgcca gccatctgtt gtttgcccct  12540
cccccgtgcc ttccttgacc ctggaaggtg ccactcccac tgtcctttcc taataaaatg  12600
aggaaattgc atcgcattgt ctgagtaggt gtcattctat tctggggggt ggggtggggc  12660
aggacagcaa gggggaggat tgggaagaca atagcaggca tgctggggat gcggtgggct  12720
ctatgg                                                             12726
```

```
SEQ ID NO: 37          moltype = DNA  length = 868
FEATURE                Location/Qualifiers
source                 1..868
                       mol_type = other DNA
                       note = CMV enhancer-CBA Promoter-AAT Exon-hBGI-hBG Exon
                       organism = synthetic construct
SEQUENCE: 37
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttttaatt attttgtgca gcgatggggg cgggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tcgtaagtac tagcagctac aatccagcta ccattctgct tttattttat  720
ggttgggata aggctggatt attctgagtc caagctaggc ccttttgcta atcatgttca  780
tacctcttat cttcctccca cagctcctgg gcaacgtgct ggtctgtgtg ctggcccatc  840
actttggcaa agaattgcga tcgccacc                                    868
```

```
SEQ ID NO: 38          moltype = DNA  length = 672
FEATURE                Location/Qualifiers
source                 1..672
                       mol_type = other DNA
                       note = CMV enhancer-CBA Promoter-AAT Exon
                       organism = synthetic construct
SEQUENCE: 38
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttttaatt attttgtgca gcgatggggg cgggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtctct ggatccactg  600
cttaaatacg gacgaggaca gggccctgtc tcctcagctt caggcaccac cactgacctg  660
ggacagtgaa tc                                                      672
```

```
SEQ ID NO: 39          moltype = DNA  length = 370
```

```
FEATURE                 Location/Qualifiers
source                  1..370
                        mol_type = other DNA
                        note = CBA Promoter-AAT Exon
                        organism = synthetic construct
SEQUENCE: 39
tggtcgaggt gagccccacg ttctgcttca ctctccccat ctcccccccc tccccacccc  60
caattttgta tttatttatt ttttaattat tttgtgcagc gatgggggcg gggggggggg  120
gggcgcgcgc caggcggggc ggggcggggc gaggggcggg gcggggcgag gcggagaggt  180
gcggcggcag ccaatcagag cggcgcgctc cgaaagtttc cttttatggc gaggcggcgg  240
cggcggcggc cctataaaaa gcgaagcgcg cggcgggcgg gagtctctgg atccactgct  300
taaatacgga cgaggacagg gccctgtctc ctcagcttca ggcaccacca ctgacctggg  360
acagtgaatc                                                         370

SEQ ID NO: 40           moltype = DNA  length = 566
FEATURE                 Location/Qualifiers
source                  1..566
                        mol_type = other DNA
                        note = CBA Promoter-AAT Exon-hBGI-hBG Exon
                        organism = synthetic construct
SEQUENCE: 40
tggtcgaggt gagccccacg ttctgcttca ctctccccat ctcccccccc tccccacccc  60
caattttgta tttatttatt ttttaattat tttgtgcagc gatgggggcg gggggggggg  120
gggcgcgcgc caggcggggc ggggcggggc gaggggcggg gcggggcgag gcggagaggt  180
gcggcggcag ccaatcagag cggcgcgctc cgaaagtttc cttttatggc gaggcggcgg  240
cggcggcggc cctataaaaa gcgaagcgcg cggcgggcgg gagtctctgg atccactgct  300
taaatacgga cgaggacagg gccctgtctc ctcagcttca ggcaccacca ctgacctggg  360
acagtgaatc gtaagtacta gcagctacaa tccagctacc attctgcttt tattttatgg  420
ttgggataag gctggattat tctgagtcca agctaggccc ttttgctaat catgttcata  480
cctcttatct tcctcccaca gctcctgggc aacgtgctgg tctgtgtgct ggcccatcac  540
tttggcaaag aattgcgatc gccacc                                       566

SEQ ID NO: 41           moltype = DNA  length = 1652
FEATURE                 Location/Qualifiers
source                  1..1652
                        mol_type = other DNA
                        note = CAG
                        organism = synthetic construct
SEQUENCE: 41
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta ttttttaatt attttgtgca gcgatggggg cggggggggg  420
gggggcgcgc gccaggcggg gcggggcggg gcgaggggcg gggcggggcg aggcggagag  480
gtgcggcggc agccaatcag agcggcgcgc tccgaaagtt tccttttatg gcgaggcggc  540
ggcggcggcg gccctataaa aagcgaagcg cgcggcgggc gggagtcgct gcgcgctgcc  600
ttcgccccgt gccccgctcc gccgccgcct cgcgccgccc gccccggctc tgactgaccg  660
cgttactccc acaggtgagc gggcgggacg gcccttctcc tccgggctgt aattagcgct  720
tggtttaatg acggcttgtt tcttttctgt ggctgcgtga aagccttgag gggctccggg  780
agggcccttt gtgcgggggg agcggctcgg ggggtgcgtg cgtgtgtgtg tgcgtgggga  840
gcgccgcgtg cggctccgcg ctgcccggcg gctgtgagcg ctgcgggcgc ggcgcggggc  900
tttgtgcgct ccgcagtgtg cgcgagggga gcgcggccgg gggcggtgcc ccgcggtgcg  960
gggggggctg cgaggggaac aaaggctgcg tgcggggtgt gtgcgtgggg gggtgagcag  1020
ggggtgtggg cgcgtcggtc gggctgcaac cccccctgca cccccctccc cgagttgctg  1080
agcacggccc ggcttcgggt gcggggctcc gtacggggcg tggcgcgggg ctcgccgtgc  1140
cgggcggggg gtggcggcag gtgggggtgc cgggcggggc ggggccgcct cgggccgggg  1200
agggctcggg ggaggggcgc ggcggccccc ggagcgccgg cggctgtcga ggcgcggcga  1260
gccgcagcca ttgcctttta tggtaatcgt gcgagagggc gcagggactt cctttgtccc  1320
aaatctgtgc ggagccgaaa tctgggaggc gccgccgcac cccctctagc gggcgcgggg  1380
cgaagcggtg cggcgccggc aggaaggaaa tgggcgggga gggccttcgt gcgtcgccgc  1440
gccgccgtcc ccttctccct ctccagcctc ggggctgtcc gcggggggac ggctgccttc  1500
ggggggggacg gggcagggcg gggttcggct tctggcgtgt gaccggcggc tctagagcct  1560
ctgctaacca tgttcatgcc ttcttctttt tcctacagct cctgggcaac gtgctggtta  1620
ttgtgctgtc tcatcatttt ggcaaagaac gc                                1652

SEQ ID NO: 42           moltype = DNA  length = 5405
FEATURE                 Location/Qualifiers
source                  1..5405
                        mol_type = other DNA
                        note = NP-CAG-EGFP-P2A-Fluc-WPRE3-DTS
                        organism = synthetic construct
SEQUENCE: 42
gtacagtaga attggtaaag agagttgtgt aaaatattga gttcgcacat cttgttgtct  60
gattattgat ttttggcgaa accatttgat catatgacaa gatgtgtatc taccttaact  120
taatgatttt gataaaaatc attaggtacc tcgcgaatgc atctagatcc gacgttacat  180
aacttacggt aaatggcccg cctggctgac cgcccaacga cccccgccca ttgacgtcaa  240
```

```
taatgacgta tgttcccata gtaacgccaa tagggacttt ccattgacgt caatgggtgg  300
agtatttacg gtaaactgcc cacttggcag tacatcaagt gtatcatatg ccaagtacgc  360
cccctattga cgtcaatgac ggtaaatggc ccgcctggca ttatgcccag tacatgacct  420
tatgggactt tcctacttgg cagtacatct acgtattagt catcgctatt accatggtcg  480
aggtgagccc cacgttctgc ttcactctcc ccatctcccc cccctcccca cccccaattt  540
tgtatttatt tattttttaa ttattttgtg cagcgatggg ggcggggggg gggggggcgc  600
gcgccaggcg gggcggggcg gggcgagggg cggggcgggg cgaggcggag aggtgcggcg  660
gcagccaatc agagcggcgc gctccgaaag tttcctttta tggcgaggcg gcggcggcgg  720
cggccctata aaaagcgaag cgcgcggcgg gcgggagtcg ctgcgcgctg ccttcgcccc  780
gtgccccgct ccgccgccgc ctcgcgccgc ccgccccggc tctgactgac cgcgttactc  840
ccacaggtga gcgggcggga cggcccttct cctccgggct gtaattagcg cttggtttaa  900
tgacggcttg tttcttttct gtggctgcgt gaaagccttg aggggctccg ggagggccct  960
ttgtgcgggg ggagcggctc ggggggtgcg tgcgtgtgtg tgtgcgtggg gagcgccgcg  1020
tgcggctccg cgctgcccgg cggctgtgag cgctgcgggc gcggcgcggg gctttgtgcg  1080
ctccgcagtg tgcgcgaggg gagcgcggcc gggggcggtg ccccgcggtg cggggggggc  1140
tgcgagggga acaaaggctg cgtgcggggt gtgtgcgtgg gggggtgagc agggggtgtg  1200
ggcgcgtcgg tcgggctgca acccccccctg caccccccctc cccgagttgc tgagcacggc  1260
ccggcttcgg gtgcggggct ccgtacgggg cgtggcgcgg ggctcgccgt gccgggcggg  1320
gggtggcggc aggtgggggt gccgggcggg gcggggccgc ctcgggccgg ggagggctcg  1380
ggggagggc gcggcggccc ccggagcgcc ggcggctgtc gaggcgcggc gagccgcagc  1440
cattgccttt tatggtaatc gtgcgagagg gcgcagggac ttcctttgtc ccaaatctgt  1500
gcggagccga aatctgggag gcgccgccgc accccctcta gcgggcgcgg ggcgaagcgg  1560
tgcggcgccg gcaggaagga aatgggcggg gagggccttc gtgcgtcgcc gcgccgccgt  1620
ccccttctcc ctctccagcc tcggggctgt ccgcgggggg acggctgcct tcggggggga  1680
cggggcaggg cggggttcgg cttctggcgt gtgaccggcg gctctagagc ctctgctaac  1740
catgttcatg ccttcttctt tttcctacag ctcctgggca acgtgctggt tattgtgctg  1800
tctcatcatt ttggcaaaga acgcgcgatc gccaccatgg tgagcaaggg cgaggagctg  1860
ttcaccgggg tggtgcccat cctggtcgag ctggacggcg acgtaaacgg ccacaagttc  1920
agcgtgtccg gcgagggcga gggcgatgcc acctacggca agctgaccct gaagttcatc  1980
tgcaccaccg gcaagctgcc cgtgccctgg cccaccctcg tgaccaccct gacctacggc  2040
gtgcagtgct tcagccgcta ccccgaccac atgaagcagc acgacttctt caagtccgcc  2100
atgcccgaag gctacgtcca ggagcgcacc atcttcttca aggacgacgg caactacaag  2160
acccgcgccg aggtgaagtt cgagggcgac accctggtga accgcatcga gctgaagggc  2220
atcgacttca aggaggacgg caacatcctg gggcacaagc tggagtacaa ctacaacagc  2280
cacaacgtct atatcatggc cgacaagcag aagaacggca tcaaggtgaa cttcaagatc  2340
cgccacaaca tcgaggacgg cagcgtgcag ctcgccgacc actaccagca gaacaccccc  2400
atcggcgacg gccccgtgct gctgcccgac aaccactacc tgagcaccca gtccgccctg  2460
agcaaagacc ccaacgagaa gcgcgatcac atggtcctgc tggagttcgt gaccgccgcc  2520
gggatcactc tcggcatgga cgagctgtac aagaatcgcg ctactaactt cagcctgctg  2580
aagcaggctg gagacgtgga ggagaaccct ggacctatgg aagacgccaa aaacataaag  2640
aaaggcccgg cgccattcta tccgctggaa gatggaaccg ctggagagca actgcataag  2700
gctatgaaga gatacgccct ggttcctgga acaattgctt ttacagatgc acatatcgag  2760
gtggacatca cttacgctga gtacttcgaa atgtccgttc ggttggcaga agctatgaaa  2820
cgatatgggc tgaatacaaa tcacagaatc gtcgtatgca gtgaaaactc tcttcaattc  2880
tttatgccgg tgttgggcgc gttatttatc ggagttgcag ttgcgcccgc gaacgacatt  2940
tataatgaac gtgaattgct caacagtatg ggcatttcgc agcctaccgt ggtgttcgtt  3000
tccaaaaagg ggttgcaaaa aattttgaac gtgcaaaaaa agctcccaat catccaaaaa  3060
attattatca tggattctaa aacggattac cagggatttc agtcgatgta cacgttcgtc  3120
acatctcatc tacctcccgg ttttaatgaa tacgattttg tgccagagtc cttcgatagg  3180
gacaagacaa ttgcactgat catgaactcc tctggatcta ctggtctgcc taaaggtgtc  3240
gctctgcctc atagaactgc ctgcgtgaga ttctcgcatg ccagagatcc tatttttggc  3300
aatcaaatca ttccggatac tgcgatttta agtgttgttc cattccatca cggttttgga  3360
atgtttacta cactcggata tttgatatgt ggatttcgag tcgtcttaat gtatagattt  3420
gaagaagagc tgtttctgag gagccttcag gattacaaga ttcaaagtgc gctgctggtg  3480
ccaaccctat tctccttctt cgccaaaagc actctgattg acaaatacga tttatctaat  3540
ttacacgaaa ttgcttctgg tggcgctccc ctctctaagg aagtcgggga agcggttgcc  3600
aagaggttcc atctgccagg tatcaggcaa ggatatgggc tcactgagac tacatcagct  3660
attctgatta cacccgaggg ggatgataaa ccgggcgcgg tcggtaaagt tgttccattt  3720
tttgaagcga aggttgtgga tctggatacc gggaaaacgc tgggcgttaa tcaaagaggc  3780
gaactgtgtg tgagaggtcc tatgattatg tccggttatg taaacaatcc ggaagcgacc  3840
aacgccttga ttgacaagga tggatggcta cattctggag acatagctta ctgggacgaa  3900
gacgaacact tcttcatcgt tgaccgcctg aagtctctga ttaagtacaa aggctatcag  3960
gtggctcccg ctgaattgga atccatcttg ctccaacacc ccaacatctt cgacgcaggt  4020
gtcgcaggtc ttcccgacga tgacgccggt gaacttcccg ccgccgttgt tgttttggag  4080
cacggaaaga cgatgacgga aaaagagatc gtggattacg tcgccagtca agtaacaacc  4140
gcgaaaaagt tgcgcggagg agttgtgttt gtggacgaag taccgaaagg tcttaccgga  4200
aaactcgacg caagaaaaat cagagagatc ctcataaagg ccaagaaggg cggaaagatc  4260
gccgtgtaac tcgagaatca acctctggat tacaaaattt gtgaaagatt gactggtatt  4320
cttaactatg ttgctccttt tacgctatgt ggatacgctg ctttaatgcc tttgtatcat  4380
gctattgctt cccgtatggc tttcattttc tcctccttgt ataaatcctg gttgctgtct  4440
ctttatgagg agttgtggcc cgttgtcagg caacgtggcg tggtgtgcac tgtgtttgct  4500
gacgcaaccc ccactggttg gggcattgcc accacctgtc agctcctttc cgggactttc  4560
gctttccccc tccctattgc cacggcggaa ctcatcgccg cctgccttgc ccgctgctgg  4620
acaggggctc ggctgttggg cactgacaat tccgtggggt gtgccttcta gttgccagcc  4680
atctgttgtt tgcccctccc ccgtgccttc cttgaccctg gaaggtgcca ctcccactgt  4740
cctttcctaa taaaatgagg aaattgcatc gcattgtctg agtaggtgtc attctattct  4800
ggggggtggg gtggggcagg acagcaaggg ggaggattgg gaagacaata gcaggcatgc  4860
tggggatgcg gtgggctcta tggaagatg tctactgagc tgtgcgatcc ctgctgggga  4920
ctttccgctg ggactttcc gctggggact ttccgccttc agctaaggaa gctaccaata  4980
```

```
tttagaggta cattttgttc tagaacaaaa tgtaccggta cattttgttc tggtacattt  5040
tgttctatta aggacaacgt aagtatagcg catagacacg tggcgccatc ggatcccggg  5100
tggcttgttg tccacaacca ttaaacctta aaagctttaa aagccttata tattcttttt  5160
tttcttataa aacttaaaac cttagaggct atttaagttg ctgatttata ttaattttat  5220
tgttcaaaca tgagagctta gtacgtgaaa catgagagct tagtacatta gccatgagag  5280
cttagtacat tagccatgag ggtttagttc attaaacatg agagcttagt acattaaaca  5340
tgagagctta gtacattaaa catgagagct tagtacatac tatcaacagg ttgaactgct  5400
gatct                                                              5405

SEQ ID NO: 43           moltype = DNA  length = 4594
FEATURE                 Location/Qualifiers
source                  1..4594
                        mol_type = other DNA
                        note = NP-CBA-hBGi-EGFP-P2A-Fluc-WPRE3-DTS
                        organism = synthetic construct
SEQUENCE: 43
tgcatgcggc cgccgttaca taacttacgg taaatggccc gcctggctga ccgcccaacg  60
acccccgccc attgacgtca ataatgacgt atgttcccat agtaacgcca atagggactt  120
tccattgacg tcaatgggtg gagtatttac ggtaaactgc ccacttggca gtacatcaag  180
tgtatcatat gccaagtacg ccccctattg acgtcaatga cggtaaatgg cccgcctggc  240
attatgccca gtacatgacc ttatgggact ttcctacttg gcagtacatc tacgtattag  300
tcatcgctat taccatggtc gaggtgagcc ccacgttctg cttcactctc cccatctccc  360
ccccctcccc acccccaatt ttgtatttat ttatttttta attattttgt gcagcgatgg  420
gggcgggggg gggggggggcg cgcgccaggc ggggcggggc ggggcgaggg gcggggcggg  480
gcgaggcgga gaggtgcggc ggcagccaat cagagcggcg cgctccgaaa gtttcctttt  540
atggcgaggc ggcggcggcg gcggccctat aaaaagcgaa gcgcgcggcg ggcgggagtc  600
tctggatcca ctgcttaaat acggacgagg acagggccct gtctcctcag cttcaggcac  660
caccactgac ctgggacagt gaatcgtaag tactagcagc tacaatccag ctaccattct  720
gcttttattt tatggttggg ataaggctgg attattctga gtccaagcta ggcccttttg  780
ctaatcatgt tcatacctct tatcttcctc ccacagctcc tgggcaacgt gctggtctgt  840
gtgctggccc atcactttgg caaagaattg cgatcgccac catggtgagc aagggcgagg  900
agctgttcac cggggtggtg cccatcctgg tcgagctgga cggcgacgta aacggccaca  960
agttcagcgt gtccggcgag ggcgagggcg atgccaccta cggcaagctg accctgaagt  1020
tcatctgcac caccggcaag ctgcccgtgc cctggcccac cctcgtgacc accctgacct  1080
acggcgtgca gtgcttcagc cgctaccccg accacatgaa gcagcacgac ttcttcaagt  1140
ccgccatgcc cgaaggctac gtccaggagc gcaccatctt cttcaaggac gacggcaact  1200
acaagacccg cgccgaggtg aagttcgagg gcgacaccct ggtgaaccgc atcgagctga  1260
agggcatcga cttcaaggag gacggcaaca tcctggggca caagctggag tacaactaca  1320
acagccacaa cgtctatatc atggccgaca agcagaagaa cggcatcaag gtgaacttca  1380
agatccgcca caacatcgag gacggcagcg tgcagctcgc cgaccactac cagcagaaca  1440
cccccatcgg cgacggcccc gtgctgctgc ccgacaacca ctacctgagc acccagtccg  1500
ccctgagcaa agaccccaac gagaagcgcg atcacatggt cctgctggag ttcgtgaccg  1560
ccgccgggat cactctcggc atggacgagc tgtacaagaa tcgcgctact aacttcagcc  1620
tgctgaagca ggctggagac gtggaggaga accctggacc tatggaagac gccaaaaaca  1680
taaagaaagg cccggcgcca ttctatccgc tggaagatgg aaccgctgga gagcaactgc  1740
ataaggctat gaagagatac gccctggttc ctggaacaat tgcttttaca gatgcacata  1800
tcgaggtgga catcacttac gctgagtact tcgaaatgtc cgttcggttg gcagaagcta  1860
tgaaacgata tgggctgaat acaaatcaca gaatcgtcgt atgcagtgaa aactctcttc  1920
aattctttat gccggtgttg ggcgcgttat ttatcggagt tgcagttgcg cccgcgaacg  1980
acatttataa tgaacgtgaa ttgctcaaca gtatgggcat ttcgcagcct accgtggtgt  2040
tcgtttccaa aaaggggttg caaaaaattt tgaacgtgca aaaaaagctc ccaatcatcc  2100
aaaaaattat tatcatggat tctaaaacgg attaccaggg atttcagtcg atgtacacgt  2160
tcgtcacatc tcatctacct cccggtttta atgaatacga ttttgtgcca gagtccttcg  2220
atagggacaa gacaattgca ctgatcatga actcctctgg atctactggt ctgcctaaag  2280
gtgtcgctct gcctcataga actgcctgcg tgagattctc gcatgccaga gatcctattt  2340
ttggcaatca aatcattccg gatactgcga ttttaagtgt tgttccattc catcacggtt  2400
ttggaatgtt tactacactc ggatatttga tatgtggatt tcgagtcgtc ttaatgtata  2460
gatttgaaga agagctgttt ctgaggagcc ttcaggatta caagattcaa agtgcgctgc  2520
tggtgccaac cctattctcc ttcttcgcca aaagcactct gattgacaaa tacgatttat  2580
ctaatttaca cgaaattgct tctggtggcg ctcccctctc taaggaagtc ggggaagcgg  2640
ttgccaagag gttccatctg ccaggtatca ggcaaggata tgggctcact gagactacat  2700
cagctattct gattacaccc gagggggatg ataaaccggg cgcggtcggt aaagttgttc  2760
cattttttga agcgaaggtt gtggatctgg ataccgggaa aacgctgggc gttaatcaaa  2820
gaggcgaact gtgtgtgaga ggtcctatga ttatgtccgg ttatgtaaac aatccggaag  2880
cgaccaacgc cttgattgac aaggatggat ggctacattc tggagacata gcttactggg  2940
acgaagacga acacttcttc atcgttgacc gcctgaagtc tctgattaag tacaaaggct  3000
atcaggtggc tcccgctgaa ttggaatcca tcttgctcca acaccccaac atcttcgacg  3060
caggtgtcgc aggtcttccc gacgatgacg ccggtgaact tcccgccgcc gttgttgttt  3120
tggagcacgg aaagacgatg acggaaaaag agatcgtgga ttacgtcgcc agtcaagtaa  3180
caaccgcgaa aaagttgcgc ggaggagttg tgtttgtgga cgaagtaccg aaaggtctta  3240
ccggaaaact cgacgcaaga aaaatcagag agatcctcat aaaggccaag aagggcggaa  3300
agatcgccgt gtaactcgag aatcaacctc tggattacaa aatttgtgaa agattgactg  3360
gtattcttaa ctatgttgct ccttttacgc tatgtggata cgctgcttta atgcctttgt  3420
atcatgctat tgcttcccgt atggctttca ttttctcctc cttgtataaa tcctggttgc  3480
tgtctcttta tgaggagttg tggcccgttg tcaggcaacg tggcgtggtg tgcactgtgt  3540
ttgctgacgc aacccccact ggttggggca ttgccaccac ctgtcagctc ctttccggga  3600
ctttcgcttt ccccctccct attgccacgg cggaactcat cgccgcctgc cttgcccgct  3660
gctggacagg ggctcggctg ttgggcactg acaattccgt ggggtgtgcc ttctagttgc  3720
cagccatctg ttgtttgccc ctcccccgtg ccttccttga ccctggaagg tgccactccc  3780
```

```
actgtccttt cctaataaaa tgaggaaatt gcatcgcatt gtctgagtag gtgtcattct  3840
attctggggg gtggggtggg gcaggacagc aagggggagg attgggaaga caatagcagg  3900
catgctgggg atgcggtggg ctctatggga agatgtctac tgagctgtgc gatccctgct  3960
ggggactttc cgctggggac tttccgctgg ggactttccg ccttcagcta aggaagctac  4020
caatatttag aggtacattt tgttctagaa caaaatgtac cggtacattt tgttctggta  4080
cattttgttc tattaaggac aacgtaagta tagcgcatag acacgtggcg ccatcggatc  4140
ccgggtggct tgttgtccac aaccattaaa ccttaaaagc tttaaaagcc ttatatattc  4200
tttttttct tataaaactt aaaaccttag aggctattta agttgctgat ttatattaat  4260
tttattgttc aaacatgaga gcttagtacg tgaaacatga gagcttagta cattagccat  4320
gagagcttag tacattagcc atgagggttt agttcattaa acatgagagc ttagtacatt  4380
aaacatgaga gcttagtaca ttaaacatga gagcttagta catactatca acaggttgaa  4440
ctgctgatct gtacagtaga attggtaaag agagttgtgt aaaatattga gttcgcacat  4500
cttgttgtct gattattgat ttttggcgaa accatttgat catatgacaa gatgtgtatc  4560
taccttaact taatgatttt gataaaaatc atta                               4594
```

```
SEQ ID NO: 44          moltype = DNA  length = 1477
FEATURE                Location/Qualifiers
source                 1..1477
                       mol_type = other DNA
                       note = hNPHS1-hBGi
                       organism = synthetic construct
SEQUENCE: 44
cacctgaggt caggagttcg agaccagcgt ggccaacatg atgaaacccc gtctctagta  60
aaaatacaaa aattagccag gcatggtgct atatacctgt agcaccagct acttgggaga  120
cagaggtggg agaattactt gaacctggga ggttcaagcc atgggaggtg gaagttgcag  180
tgagccgaga tgccactgca ctccagcctg agcaacagag caagactatc tcaagaaaag  240
aaagaaagaa agaaagagac ttgccaaggt catgtatcag ggcaaggaag agctgggggc  300
ccagctggct gctcccctgc tgagctggga gaccaccttg atctgacttc tcccatcttc  360
ccagcctaag ccaggccctg gggtcacgga ggctggggag gcaccgagga acgcgcctgg  420
catgtgctga caggggattt tatgctccag ctgggccagc tgggaggagc ctgctgggca  480
gaggccagag ctgggggctc tggaaggtac ctgggggagg ttgcactgtg agaatgagct  540
caagctgggt cagagagcag ggctgactct gccagtgcct gcatcagcct catcgctctc  600
ctaggctcct ggcctgctgg actctgggct gcaggtcctt cttgaaaggc tgtgagtagt  660
gagacaagga gcaggagtga ggggtggcag gagagaagat agagattgag agagagagag  720
agagagagac agagagagag gaagagacag agacaaaagg agagagaacg gcttagacaa  780
ggagagaaag atggaaagat aaagagactg ggcgcagtgg ctcacgcctg taatcccaac  840
acttggggag gccaaggtgg gaggatggct tgaaggaaag agtctgagat caacctggcc  900
aacatagtga gaccctgtct ctaaaaaaaa aaaaaagaaa aaaaaaagaa aaaagaaaaa  960
aaagtttttt taaagagaca gagaaagaga ctcagagatt gagactgaga gcaagacaga  1020
gagagatact cacagggaag agggaagag gaaaacgaga aagggaggag agtaacggaa  1080
agagataaaa aagaaaagca ggtggcagag acacacagag agggacccag agaaagccag  1140
acagacgcag gtggctggca gcgggcgctg tgggggtcac agtaggggga cctgtgtctg  1200
gatccactgc ttaaatacgg acgaggacag ggccctgtct cctcagcttc aggcaccacc  1260
actgacctgg gacagtgaat cgtaagtact agcagctaca atccagctac cattctgctt  1320
ttattttatg gttgggataa ggctggatta ttctgagtcc aagctaggcc cttttgctaa  1380
tcatgttcat acctcttatc ttcctcccac agctcctggg caacgtgctg gtctgtgtgc  1440
tggcccatca ctttggcaaa gaattgcgat cgccacc                              1477
```

```
SEQ ID NO: 45          moltype = DNA  length = 5171
FEATURE                Location/Qualifiers
source                 1..5171
                       mol_type = other DNA
                       note = NP-hNPHS1-hBGi-EGFP-P2A-Fluc-WPRE3-DTS
                       organism = synthetic construct
SEQUENCE: 45
gccacctgag gtcaggagtt cgagaccagc gtggccaaca tgatgaaacc ccgtctctag  60
taaaaataca aaaattagcc aggcatggtg ctatatacct gtagcaccag ctacttggga  120
gacagaggtg ggagaattac ttgaacctgg gaggttcaag ccatgggagg tggaagttgc  180
agtgagccga gatgccactg cactccagcc tgagcaacag agcaagacta tctcaagaaa  240
agaaagaaag aaagaaagag acttgccaag gtcatgtatc agggcaagga agagctgggg  300
gcccagctgg ctgctcccct gctgagctgg gagaccacct tgatctgact tctcccatct  360
tcccagccta agccaggccc tggggtcacg gaggctgggg aggcaccgag gaacgcgcct  420
ggcatgtgct gacaggggat tttatgctcc agctgggcca gctgggagga gcctgctggg  480
cagaggccag agctgggggc tctggaaggt acctggggga ggttgcactg tgagaatgag  540
ctcaagctgg gtcagagagc agggctgact ctgccagtgc ctgcatcagc ctcatcgctc  600
tcctaggctc ctggcctgct ggactctggg ctgcaggtcc ttcttgaaag gctgtgagta  660
gtgagacaag gagcaggagt gaggggtggc aggagagaag atagagattg agagagagag  720
agagagagag acagagagag aggaagagac agagacaaaa ggagagagaa cggcttagac  780
aaggagagaa agatggaaag ataaagagac tgggcgcagt ggctcacgcc tgtaatccca  840
acacttgggg aggccaaggt gggaggatgg cttgaaggaa agagtctgag atcaacctgg  900
ccaacatagt gagaccctgt ctctaaaaaa aaaaaaaaga aaaaaaaaag aaaaaagaaa  960
aaaaagtttt tttaaagaga cagagaaaga gactcagaga ttgagactga gagcaagaca  1020
gagagagata ctcacaggga agaggggaag aggaaaacga gaaagggagg agagtaacgg  1080
aaagagataa aaaagaaaag caggtggcag agacacacag agagggaccc agagaaagcc  1140
agacagacgc aggtggctgg cagcgggcgc tgtgggggtc acagtagggg gacctgtgtc  1200
tggatccact gcttaaatac ggacgaggac agggccctgt ctcctcagct tcaggcacca  1260
ccactgacct gggacagtga atcgtaagta ctagcagcta caatccagct accattctgc  1320
ttttatttta tggttgggat aaggctggat tattctgagt ccaagctagg cccttttgct  1380
aatcatgttc atacctctta tcttcctccc acagctcctg ggcaacgtgc tggtctgtgt  1440
```

```
gctggcccat cactttggca aagaattgcg atcgccacca tggtgagcaa gggcgaggag  1500
ctgttcaccg gggtggtgcc catcctggtc gagctggacg gcgacgtaaa cggccacaag  1560
ttcagcgtgt ccggcgaggg cgagggcgat gccacctacg gcaagctgac cctgaagttc  1620
atctgcacca ccggcaagct gcccgtgccc tggcccaccc tcgtgaccac cctgacctac  1680
ggcgtgcagt gcttcagccg ctaccccgac cacatgaagc agcacgactt cttcaagtcc  1740
gccatgcccg aaggctacgt ccaggagcgc accatcttct tcaaggacga cggcaactac  1800
aagacccgcg ccgaggtgaa gttcgagggc gacaccctgg tgaaccgcat cgagctgaag  1860
ggcatcgact tcaaggagga cggcaacatc ctggggcaca agctggagta caactacaac  1920
agccacaacg tctatatcat ggccgacaag cagaagaacg gcatcaaggt gaacttcaag  1980
atccgccaca acatcgagga cggcagcgtg cagctcgccg accactacca gcagaacacc  2040
cccatcggcg acggccccgt gctgctgccc gacaaccact acctgagcac ccagtccgcc  2100
ctgagcaaag accccaacga gaagcgcgat cacatggtcc tgctggagtt cgtgaccgcc  2160
gccgggatca ctctcggcat ggacgagctg tacaagaatc gcgctactaa cttcagcctg  2220
ctgaagcagg ctggagacgt ggaggagaac cctggaccta tggaagacgc caaaaacata  2280
aagaaaggcc cggcgccatt ctatccgctg gaagatggaa ccgctggaga gcaactgcat  2340
aaggctatga agagatacgc cctggttcct ggaacaattg cttttacaga tgcacatatc  2400
gaggtggaca tcacttacgc tgagtacttc gaaatgtccg ttcggttggc agaagctatg  2460
aaacgatatg ggctgaatac aaatcacaga atcgtcgtat gcagtgaaaa ctctcttcaa  2520
ttctttatgc cggtgttggg cgcgttattt atcggagttg cagttgcgcc cgcgaacgac  2580
atttataatg aacgtgaatt gctcaacagt atgggcattt cgcagcctac cgtggtgttc  2640
gtttccaaaa aggggttgca aaaaattttg aacgtgcaaa aaaagctccc aatcatccaa  2700
aaaattatta tcatggattc taaaacggat taccagggat ttcagtcgat gtacacgttc  2760
gtcacatctc atctacctcc cggttttaat gaatacgatt ttgtgccaga gtccttcgat  2820
agggacaaga caattgcact gatcatgaac tcctctggat ctactggtct gcctaaaggt  2880
gtcgctctgc ctcatagaac tgcctgcgtg agattctcgc atgccagaga tcctattttt  2940
ggcaatcaaa tcattccgga tactgcgatt ttaagtgttg ttccattcca tcacggtttt  3000
ggaatgttta ctacactcgg atatttgata tgtggatttc gagtcgtctt aatgtataga  3060
tttgaagaag agctgtttct gaggagcctt caggattaca agattcaaag tgcgctgctg  3120
gtgccaaccc tattctcctt cttcgccaaa agcactctga ttgacaaata cgatttatct  3180
aatttacacg aaattgcttc tggtggcgct cccctctcta aggaagtcgg ggaagcggtt  3240
gccaagaggt tccatctgcc aggtatcagg caaggatatg ggctcactga gactacatca  3300
gctattctga ttacacccga gggggatgat aaaccgggcg cggtcggtaa agttgttcca  3360
ttttttgaag cgaaggttgt ggatctggat accgggaaaa cgctgggcgt taatcaaaga  3420
ggcgaactgt gtgtgagagg tcctatgatt atgtccggtt atgtaaacaa tccggaagcg  3480
accaacgcct tgattgacaa ggatggatgg ctacattctg gagacatagc ttactgggac  3540
gaagacgaac acttcttcat cgttgaccgc ctgaagtctc tgattaagta caaaggctat  3600
caggtggctc ccgctgaatt ggaatccatc ttgctccaac accccaacat cttcgacgca  3660
ggtgtcgcag gtcttcccga cgatgacgcc ggtgaacttc ccgccgccgt tgttgttttg  3720
gagcacggaa agacgatgac ggaaaaagag atcgtggatt acgtcgccag tcaagtaaca  3780
accgcgaaaa agttgcgcgg aggagttgtg tttgtggacg aagtaccgaa aggtcttacc  3840
ggaaaactcg acgcaagaaa aatcagagag atcctcataa aggccaagaa gggcggaaag  3900
atcgccgtgt aactcgagaa tcaacctctg gattacaaaa tttgtgaaag attgactggt  3960
attcttaact atgttgctcc ttttacgcta tgtggatacg ctgctttaat gcctttgtat  4020
catgctattg cttcccgtat ggctttcatt ttctcctcct tgtataaatc ctggttgctg  4080
tctctttatg aggagttgtg gcccgttgtc aggcaacgtg gcgtggtgtg cactgtgttt  4140
gctgacgcaa cccccactgg ttggggcatt gccaccacct gtcagctcct ttccgggact  4200
ttcgctttcc ccctccctat tgccacggcg gaactcatcg ccgcctgcct tgcccgctgc  4260
tggacagggg ctcggctgtt gggcactgac aattccgtgg ggtgtgcctt ctagttgcca  4320
gccatctgtt gtttgcccct cccccgtgcc ttccttgacc ctggaaggtg ccactcccac  4380
tgtcctttcc taataaaatg aggaaattgc atcgcattgt ctgagtaggt gtcattctat  4440
tctggggggt ggggtggggc aggacagcaa gggggaggat tgggaagaca atagcaggca  4500
tgctggggat gcggtgggct ctatggaagg atgtctactg agctgtgcga tccctgctgg  4560
ggactttccg ctggggactt tccgctgggg actttccgcc ttcagctaag gaagctacca  4620
atatttagag gtacattttg ttctagaaca aaatgtaccg gtacattttg ttctggtaca  4680
ttttgttcta ttaaggacaa cgtaagtata gcgcatagac actggcttgt tgtccacaac  4740
cattaaacct taaaagcttt aaaagcctta tatattcttt tttttcttat aaaacttaaa  4800
accttagagg ctatttaagt tgctgattta tattaatttt attgttcaaa catgagagct  4860
tagtacgtga aacatgagag cttagtacat tagccatgag agcttagtac attagccatg  4920
agggtttagt tcattaaaca tgagagctta gtacattaaa catgagagct tagtacatta  4980
aacatgagag cttagtacat actatcaaca ggttgaactg ctgatctgta cagtagaatt  5040
ggtaaagaga gttgtgtaaa atattgagtt cgcacatctt gttgtctgat tattgatttt  5100
tggcgaaacc atttgatcat atgacaagat gtgtatctac cttaacttaa tgattttgat  5160
aaaaatcatt a                                                        5171
```

```
SEQ ID NO: 46           moltype = DNA  length = 1051
FEATURE                 Location/Qualifiers
source                  1..1051
                        mol_type = other DNA
                        note = MHCK Promoter
                        organism = synthetic construct
SEQUENCE: 46
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgcccact acgggtctag  240
gctgcccatg taaggaggca aggcctgggg acacccgaga tgcctggtta taattaaccc  300
agacatgtgg ctgccccccc cccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
```

```
tgttcccggc gaagggccag ctgtccccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggcccttttg ctaatcatgt  960
tcatacctct tatcttcctc ccacagctcc tgggcaacgt gctggtctgt gtgctggccc  1020
atcactttgg caaagaattg cgatcgccac c                                 1051

SEQ ID NO: 47           moltype = DNA  length = 4594
FEATURE                 Location/Qualifiers
source                  1..4594
                        mol_type = other DNA
                        note = NP-CBA-hBGi-EGFP-P2A-Fluc-WPRE3-DTS
                        organism = synthetic construct
SEQUENCE: 47
tgcatgcggc cgccgttaca taacttacgg taaatggccc gcctggctga ccgcccaacg  60
acccccgccc attgacgtca ataatgacgt atgttcccat agtaacgcca atagggactt  120
tccattgacg tcaatgggtg gagtatttac ggtaaactgc ccacttggca gtacatcaag  180
tgtatcatat gccaagtacg ccccctattg acgtcaatga cggtaaatgg cccgcctggc  240
attatgccca gtacatgacc ttatgggact ttcctacttg gcagtacatc tacgtattag  300
tcatcgctat taccatggtc gaggtgagcc ccacgttctg cttcactctc cccatctccc  360
ccccctcccc acccccaatt ttgtatttat ttatttttta attattttgt gcagcgatgg  420
gggcgggggg gggggggggcg cgcgccaggc ggggcggggc ggggcgaggg gcggggcggg  480
gcgaggcgga gaggtgcggc ggcagccaat cagagcggcg cgctccgaaa gtttcctttt  540
atggcgaggc ggcggcggcg gcggccctat aaaaagcgaa gcgcgcggcg ggcgggagtc  600
tctggatcca ctgcttaaat acggacgagg acagggccct gtctcctcag cttcaggcac  660
caccactgac ctgggacagt gaatcgtaag tactagcagc tacaatccag ctaccattct  720
gcttttattt tatggttggg ataaggctgg attattctga gtccaagcta ggcccttttg  780
ctaatcatgt tcatacctct tatcttcctc ccacagctcc tgggcaacgt gctggtctgt  840
gtgctggccc atcactttgg caaagaattg cgatcgccac catggtgagc aagggcgagg  900
agctgttcac cggggtggtg cccatcctgg tcgagctgga cggcgacgta aacggccaca  960
agttcagcgt gtccggcgag ggcgagggcg atgccaccta cggcaagctg accctgaagt  1020
tcatctgcac caccggcaag ctgcccgtgc cctggcccac cctcgtgacc accctgacct  1080
acggcgtgca gtgcttcagc cgctaccccg accacatgaa gcagcacgac ttcttcaagt  1140
ccgccatgcc cgaaggctac gtccaggagc gcaccatctt cttcaaggac gacggcaact  1200
acaagacccg cgccgaggtg aagttcgagg gcgacaccct ggtgaaccgc atcgagctga  1260
agggcatcga cttcaaggag gacggcaaca tcctggggca caagctggag tacaactaca  1320
acagccacaa cgtctatatc atggccgaca agcagaagaa cggcatcaag gtgaacttca  1380
agatccgcca caacatcgag gacggcagcg tgcagctcgc cgaccactac cagcagaaca  1440
cccccatcgg cgacggcccc gtgctgctgc ccgacaacca ctacctgagc acccagtccg  1500
ccctgagcaa agaccccaac gagaagcgcg atcacatggt cctgctggag ttcgtgaccg  1560
ccgccgggat cactctcggc atggacgagc tgtacaagaa tcgcgctact aacttcagcc  1620
tgctgaagca ggctggagac gtggaggaga accctggacc tatggaagac gccaaaaaca  1680
taaagaaagg cccggcgcca ttctatccgc tggaagatgg aaccgctgga gagcaactgc  1740
ataaggctat gaagagatac gccctggttc ctggaacaat tgcttttaca gatgcacata  1800
tcgaggtgga catcacttac gctgagtact tcgaaatgtc cgttcggttg gcagaagcta  1860
tgaaacgata tgggctgaat acaaatcaca gaatcgtcgt atgcagtgaa aactctcttc  1920
aattctttat gccggtgttg ggcgcgttat ttatcggagt tgcagttgcg cccgcgaacg  1980
acatttataa tgaacgtgaa ttgctcaaca gtatgggcat ttcgcagcct accgtggtgt  2040
tcgtttccaa aaaggggttg caaaaaattt tgaacgtgca aaaaaagctc ccaatcatcc  2100
aaaaaattat tatcatggat tctaaaacgg attaccaggg atttcagtcg atgtacacgt  2160
tcgtcacatc tcatctacct cccggtttta atgaatacga ttttgtgcca gagtccttcg  2220
atagggacaa gacaattgca ctgatcatga actcctctgg atctactggt ctgcctaaag  2280
gtgtcgctct gcctcataga actgcctgcg tgagattctc gcatgccaga gatcctattt  2340
ttggcaatca aatcattccg gatactgcga ttttaagtgt tgttccattc catcacggtt  2400
ttggaatgtt tactacactc ggatatttga tatgtggatt tcgagtcgtc ttaatgtata  2460
gatttgaaga agagctgttt ctgaggagcc ttcaggatta caagattcaa agtgcgctgc  2520
tggtgccaac cctattctcc ttcttcgcca aaagcactct gattgacaaa tacgatttat  2580
ctaatttaca cgaaattgct tctggtggcg ctcccctctc taaggaagtc ggggaagcgg  2640
ttgccaagag gttccatctg ccaggtatca ggcaaggata tgggctcact gagactacat  2700
cagctattct gattacaccc gagggggatg ataaaccggg cgcggtcggt aaagttgttc  2760
catttttga agcgaaggtt gtggatctgg ataccgggaa aacgctgggc gttaatcaaa  2820
gaggcgaact gtgtgtgaga ggtcctatga ttatgtccgg ttatgtaaac aatccggaag  2880
cgaccaacgc cttgattgac aaggatggat ggctacattc tggagacata gcttactggg  2940
acgaagacga acacttcttc atcgttgacc gcctgaagtc tctgattaag tacaaaggct  3000
atcaggtggc tcccgctgaa ttggaatcca tcttgctcca acaccccaac atcttcgacg  3060
caggtgtcgc aggtcttccc gacgatgacg ccggtgaact tcccgccgcc gttgttgttt  3120
tggagcacgg aaagacgatg acggaaaaag agatcgtgga ttacgtcgcc agtcaagtaa  3180
caaccgcgaa aaagttgcgc ggaggagttg tgtttgtgga cgaagtaccg aaaggtctta  3240
ccggaaaact cgacgcaaga aaaatcagag agatcctcat aaaggccaag aagggcggaa  3300
agatcgccgt gtaactcgag aatcaacctc tggattacaa aatttgtgaa agattgactg  3360
gtattcttaa ctatgttgct ccttttacgc tatgtggata cgctgcttta atgcctttgt  3420
atcatgctat tgcttcccgt atggctttca ttttctcctc cttgtataaa tcctggttgc  3480
tgtctcttta tgaggagttg tggcccgttg tcaggcaacg tggcgtggtg tgcactgtgt  3540
ttgctgacgc aacccccact ggttggggca ttgccaccac ctgtcagctc ctttccggga  3600
ctttcgcttt ccccctccct attgccacgg cggaactcat cgccgcctgc cttgcccgct  3660
```

```
gctggacagg ggctcggctg ttgggcactg acaattccgt ggggtgtgcc ttctagttgc  3720
cagccatctg ttgtttgccc ctcccccgtg ccttccttga ccctggaagg tgccactccc  3780
actgtccttt cctaataaaa tgaggaaatt gcatcgcatt gtctgagtag gtgtcattct  3840
attctggggg gtggggtggg gcaggacagc aaggggggagg attgggaaga caatagcagg  3900
catgctgggg atgcggtggg ctctatggga agatgtctac tgagctgtgc gatccctgct  3960
ggggactttc cgctggggac tttccgctgg ggactttccg ccttcagcta aggaagctac  4020
caatatttag aggtacattt tgttctagaa caaaatgtac cggtacattt tgttctggta  4080
cattttgttc tattaaggac aacgtaagta tagcgcatag acacgtggcg ccatcggatc  4140
ccgggtggct tgttgtccac aaccattaaa ccttaaaagc tttaaaagcc ttatatattc  4200
ttttttttct tataaaactt aaaaccttag aggctattta agttgctgat ttatattaat  4260
tttattgttc aaacatgaga gcttagtacg tgaaacatga gagcttagta cattagccat  4320
gagagcttag tacattagcc atgagggttt agttcattaa acatgagagc ttagtacatt  4380
aaacatgaga gcttagtaca ttaaacatga gagcttagta catactatca acaggttgaa  4440
ctgctgatct gtacagtaga attggtaaag agagttgtgt aaaatattga gttcgcacat  4500
cttgttgtct gattattgat tttggcgaa accatttgat catatgacaa gatgtgtatc  4560
taccttaact taatgatttt gataaaaatc atta                             4594
```

```
SEQ ID NO: 48          moltype = DNA  length = 4786
FEATURE                Location/Qualifiers
source                 1..4786
                       mol_type = other DNA
                       note = NP-MHCK7-hBGi-EGFP-P2A-Fluc-WPRE3-DTS
                       organism = synthetic construct
SEQUENCE: 48
ctagaagctg catgtctaag ctagaccctt cagattaaaa ataactgagg taagggcctg  60
ggtaggggag gtggtgtgag acgctcctgt ctctcctcta tctgcccatc ggccctttgg  120
ggaggaggaa tgtgcccaag gactaaaaaa aggccatgga gccagagggg cgagggcaac  180
agacctttca tgggcaaacc ttggggccct gctgtctagc atgccccact acgggtctag  240
gctgcccatg taaggaggca aggcctgggg acacccgaga tgcctggtta taattaaccc  300
agacatgtgg ctgccccccc ccccccaaca cctgctgcct ctaaaaataa ccctgtccct  360
ggtggatccc ctgcatgcga agatcttcga acaaggctgt gggggactga gggcaggctg  420
taacaggctt gggggccagg gcttatacgt gcctgggact cccaaagtat tactgttcca  480
tgttcccggc gaagggccag ctgtcccccg ccagctagac tcagcactta gtttaggaac  540
cagtgagcaa gtcagccctt ggggcagccc atacaaggcc atggggctgg gcaagctgca  600
cgcctgggtc cggggtgggc acggtgcccg ggcaacgagc tgaaagctca tctgctctca  660
ggggcccctc cctggggaca gcccctcctg gctagtcaca ccctgtaggc tcctctatat  720
aacccagggg cacaggggct gccctcattc taccaccacc tccacagcac tctggatcca  780
ctgcttaaat acggacgagg acagggccct gtctcctcag cttcaggcac caccactgac  840
ctgggacagt gaatcgtaag tactagcagc tacaatccag ctaccattct gcttttattt  900
tatggttggg ataaggctgg attattctga gtccaagcta ggccctttg ctaatcatgt  960
tcatacctct tatcttcctc ccacagctcc tgggcaacgt gctggtctgt gtgctggccc  1020
atcactttgg caaagaattg cgatcgccac catggtgagc aagggcgagg agctgttcac  1080
cggggtggtg cccatcctgg tcgagctgga cggcgacgta aacggccaca agttcagcgt  1140
gtccggcgag ggcgagggcg atgccaccta cggcaagctg accctgaagt tcatctgcac  1200
caccggcaag ctgcccgtgc cctggcccac cctcgtgacc accctgacct acggcgtgca  1260
gtgcttcagc cgctaccccg accacatgaa gcagcacgac ttcttcaagt ccgccatgcc  1320
cgaaggctac gtccaggagc gcaccatctt cttcaaggac gacggcaact acaagacccg  1380
cgccgaggtg aagttcgagg gcgacaccct ggtgaaccgc atcgagctga agggcatcga  1440
cttcaaggag gacggcaaca tcctggggca caagctggag tacaactaca acagccacaa  1500
cgtctatatc atggccgaca agcagaagaa cggcatcaag gtgaacttca agatccgcca  1560
caacatcgag gacggcagcg tgcagctcgc cgaccactac cagcagaaca cccccatcgg  1620
cgacggcccc gtgctgctgc ccgacaacca ctacctgagc acccagtccg ccctgagcaa  1680
agaccccaac gagaagcgcg atcacatggt cctgctggag ttcgtgaccg ccgccgggat  1740
cactctcggc atggacgagc tgtacaagaa tcgcgctact aacttcagcc tgctgaagca  1800
ggctggagac gtggaggaga accctggacc tatggaagac gccaaaaaca taaagaaagg  1860
cccggcgcca ttctatccgc tggaagatgg aaccgctgga gagcaactgc ataaggctat  1920
gaagagatac gccctggttc ctggaacaat tgcttttaca gatgcacata tcgaggtgga  1980
catcacttac gctgagtact tcgaaatgtc cgttcggttg gcagaagcta tgaaacgata  2040
tgggctgaat acaaatcaca gaatcgtcgt atgcagtgaa aactctcttc aattctttat  2100
gccggtgttg ggcgcgttat ttatcggagt tgcagttgcg cccgcgaacg acatttataa  2160
tgaacgtgaa ttgctcaaca gtatgggcat ttcgcagcct accgtggtgt tcgtttccaa  2220
aaaggggttg caaaaaattt tgaacgtgca aaaaaagctc ccaatcatcc aaaaaattat  2280
tatcatggat tctaaaacgg attaccaggg atttcagtcg atgtacacgt tcgtcacatc  2340
tcatctacct cccggtttta atgaatacga ttttgtgcca gagtccttcg atagggacaa  2400
gacaattgca ctgatcatga actcctctgg atctactggt ctgcctaaag gtgtcgctct  2460
gcctcataga actgcctgcg tgagattctc gcatgccaga gatcctattt ttggcaatca  2520
aatcattccg gatactgcga ttttaagtgt tgttccattc catcacggtt ttggaatgtt  2580
tactacactc ggatatttga tatgtggatt tcgagtcgtc ttaatgtata gatttgaaga  2640
agagctgttt ctgaggagcc ttcaggatta caagattcaa agtgcgctgc tggtgccaac  2700
cctattctcc ttcttcgcca aaagcactct gattgacaaa tacgatttat ctaatttaca  2760
cgaaattgct tctggtggcg ctcccctctc taaggaagtc ggggaagcgg ttgccaagag  2820
gttccatctg ccaggtatca ggcaaggata tgggctcact gagactacat cagctattct  2880
gattacaccc gagggggatg ataaaccggg cgcggtcggt aaagttgttc cattttttga  2940
agcgaaggtt gtggatctgg ataccgggaa aacgctgggc gttaatcaaa gaggcgaact  3000
gtgtgtgaga ggtcctatga ttatgtccgg ttatgtaaac aatccggaag cgaccaacgc  3060
cttgattgac aaggatggat ggctacattc tggagacata gcttactggg acgaagacga  3120
acacttcttc atcgttgacc gcctgaagtc tctgattaag tacaaaggct atcaggtggc  3180
tcccgctgaa ttggaatcca tcttgctcca acaccccaac atcttcgacg caggtgtcgc  3240
aggtcttccc gacgatgacg ccggtgaact tcccgccgcc gttgttgttt tggagcacgg  3300
```

```
aaagacgatg acggaaaaag agatcgtgga ttacgtcgcc agtcaagtaa caaccgcgaa  3360
aaagttgcgc ggaggagttg tgtttgtgga cgaagtaccg aaaggtctta ccggaaaact  3420
cgacgcaaga aaaatcagag agatcctcat aaaggccaag aagggcggaa agatcgccgt  3480
gtaactcgag aatcaacctc tggattacaa aatttgtgaa agattgactg gtattcttaa  3540
ctatgttgct ccttttacgc tatgtggata cgctgcttta atgcctttgt atcatgctat  3600
tgcttcccgt atggctttca ttttctcctc cttgtataaa tcctggttgc tgtctcttta  3660
tgaggagttg tggcccgttg tcaggcaacg tggcgtggtg tgcactgtgt ttgctgacgc  3720
aacccccact ggttggggca ttgccaccac ctgtcagctc ctttccggga ctttcgcttt  3780
ccccctccct attgccacgg cggaactcat cgccgcctgc cttgcccgct gctggacagg  3840
ggctcggctg ttgggcactg acaattccgt ggggtgtgcc ttctagttgc cagccatctg  3900
ttgtttgccc ctcccccgtg ccttccttga ccctggaagg tgccactccc actgtccttt  3960
cctaataaaa tgaggaaatt gcatcgcatt gtctgagtag gtgtcattct attctggggg  4020
gtggggtggg gcaggacagc aagggggagg attgggaaga caatagcagg catgctgggg  4080
atgcggtggg ctctatggga agatgtctac tgagctgtgc gatccctgct ggggactttc  4140
cgctggggac tttccgctgg ggactttccg ccttcagcta aggaagctac caatatttag  4200
aggtacattt tgttctagaa caaaatgtac cggtacattt tgttctggta cattttgttc  4260
tattaaggac aacgtaagta tagcgcatag acacgtggcg ccatcggatc ccgggcccgt  4320
cgacttaagt ggcttgttgt ccacaaccat taaaccttaa aagctttaaa agccttatat  4380
attctttttt ttcttataaa acttaaaacc ttagaggcta tttaagttgc tgatttatat  4440
taattttatt gttcaaacat gagagcttag tacgtgaaac atgagagctt agtacattag  4500
ccatgagagc ttagtacatt agccatgagg gtttagttca ttaaacatga gagcttagta  4560
cattaaacat gagagcttag tacattaaac atgagagctt agtacatact atcaacaggt  4620
tgaactgctg atctgtacag tagaattggt aaagagagtt gtgtaaaata ttgagttcgc  4680
acatcttgtt gtctgattat tgatttttgg cgaaaccatt tgatcatatg acaagatgtg  4740
tatctacctt aacttaatga ttttgataaa aatcattagc ggccgc                4786
```

```
SEQ ID NO: 49          moltype = DNA  length = 15459
FEATURE                Location/Qualifiers
source                 1..15459
                       mol_type = other DNA
                       note = pUC57-CBA-hBGi-DMD-4-WPRE3-DTS
                       organism = synthetic construct
SEQUENCE: 49
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac catgctttgg tgggaagaag  300
tcgaggactg ctacgagcgc gaggacgtgc agaagaaaac cttcaccaaa tgggtcaacg  360
cccagttcag caagttcggc aagcagcaca tcgagaacct gttcagcgac ctgcaggatg  420
gcagaaggct gctggatctg ctggaaggcc tgacaggaca gaagctgccc aaagagaagg  480
gcagcacaag agtgcacgcc ctgaacaacg tgaacaaggc cctgagagtg ctgcagaaca  540
acaacgtgga cctggtcaac atcggcagca ccgacatcgt ggacggcaac cacaaactga  600
ccctgggcct gatctggaac atcatcctgc actggcaagt gaagaacgtg atgaagaaca  660
tcatggccgg cctgcagcag accaacagcg agaagattct gctgagctgg gtccgacaga  720
gcacccggaa ttaccctcaa gtgaacgtga tcaacttcac cacctcttgg agcgacggac  780
tggccctgaa tgccctgatc cacagccaca gacctgacct gttcgactgg aacagcgtcg  840
tgtgtcagca gagcgccaca cagaggctgg aacacgcctt caatatcgcc agataccagc  900
tgggcatcga gaaactgctg gaccccgagg atgtggacac cacctatcct gacaagaaat  960
ccatcctcat gtacatcacc agcctgttcc aggtgctgcc ccagcaggtt tccatcgagg  1020
ccattcaaga ggtcgagatg ctgcccagac ctcctaaagt gaccaaagag gaacacttcc  1080
agctgcacca ccagatgcac tactctcagc agatcaccgt gtctctggcc cagggctacg  1140
agagaacaag cagccccaag cctcggttca agagctacgc ctatacacag gccgcctacg  1200
tgaccaccag cgatcctaca agaagcccat ttcctagcca gcatctggaa gcccctgagg  1260
acaagagctt tggcagcagc ctgatggaaa gcgaagtgaa cctggaccgc taccagacag  1320
ccctggaaga ggttctgagc tggctgctgt ctgccgagga tacactgcag gctcagggcg  1380
agatcagcaa cgacgtggaa gtggtcaagg accagtttca cacccacgag ggctacatga  1440
tggacctgac agcccaccag ggcagagtgg gcaatattct gcagctgggc tccaagctga  1500
tcggcacagg caagctgagc gaggacgaag agacagaggt gcaagagcag atgaacctgc  1560
tgaacagcag atgggagtgt ctgagagtgg ccagcatgga aaagcagagc aacctgcacc  1620
gggtgctgat ggatctccag aaccagaagc tgaaagagct gaacgactgg ctgaccaaga  1680
ccgaggaacg gacccggaag atggaagagg aacctctggg acccgacctg gaagatctga  1740
aaagacaggt gcagcagcat aaggtgctgc aagaggacct cgaacaagag caagtgcgcg  1800
tgaacagcct gacacacatg gtggtggtcg tggatgagag cagcggagat catgccacag  1860
ccgctctgga agaacagctg aaggtgctgg gagacagatg ggccaatatc tgccggtgga  1920
ccgaggatag atgggtgctg ctccaggaca tcctgctgaa gtggcagcgg ctgacagagg  1980
aacagtgcct gtttagcgcc tggctgtccg agaaagagga cgccgtcaac aagatccaca  2040
ccaccggctt caaggatcag aatgagatgc tgagcagcct gcagaaactg gccgtgctga  2100
aggctgacct ggaaaagaaa aagcagtcca tgggcaagct gtactccctg aagcaggacc  2160
tgctgagcac actgaagaac aagtctgtga cccagaaaac cgaggcctgg ctggacaact  2220
tcgcccggtg ttgggataac ctggtgcaga agctggaaaa gtccaccgct cagatctctc  2280
aggccgtgac cacaacacag ccttctctga cccagaccac cgtgatggaa acagtgacca  2340
cagtgacaac ccgcgagcag atcctggtca agcacgccca agaagaactg cctcctccac  2400
ctcctcagaa gaaacggcag atcacagtgg acagcgagat ccggaagaga ctggacgtgg  2460
acatcaccga gctgcacagc tggatcacca gatccgaagc cgtgctgcag tcccctgagt  2520
tcgccatctt cagaaaagag ggcaacttct ccgacctgaa agagaaagtc aacgccatcg  2580
agagagagaa ggccgagaag ttccggaagc tgcaggacgc ctctagatct gcccaggctc  2640
tggtggaaca gatggtcaac gaaggcgtga acgccgacag catcaagcag gcctcagagc  2700
agctgaactc ccggtggatc gagttctgtc agctcctgag cgagagactg aactggctgg  2760
```

-continued aataccagaa caatatcatt gccttctaca accagctcca gcagctcgaa cagatgacca 2820
ccacagccga gaattggctg aagatccagc ctaccacacc tagcgagccc accgccatta 2880
agagccagct gaaaatctgc aaggacgaag tgaatcggct gagcgatctg cagccccaga 2940
tcgaaagact gaaaatccag tctatcgccc tcaaagagaa aggacagggc cccatgttcc 3000
tggacgccga ttttgtggcc tttaccaacc acttcaaaca ggtgttctcc gacgtgcagg 3060
cccgggaaaa agagctgcag accatcttcg acaccctgcc tccaatgaga taccaagaga 3120
caatgagcgc catccggacc tgggtgcagc aaagcgagac aaagctgagc atcccacagc 3180
tgagcgtgac cgactacgag atcatggaac agagactggg cgaactgcag gccctccagt 3240
ctagcctgca agaacagcag tccggcctgt actacctgag cacaaccgtg aaagagatga 3300
gcaagaaggc ccctagcgag atctcccgga agtaccagag cgagttcgaa gagatcgaag 3360
gccggtggaa gaagctgtct agccagctgg ttgagcactg ccagaaactc gaagaacaaa 3420
tgaacaagct gcgcaagatc cagaatcaca tccagacgct gaagaaatgg atggccgagg 3480
tggacgtgtt cctgaaagaa gagtggcccg ctctgggcga ctccgagatt ctgaagaaac 3540
agctcaaaca gtgccggctg ctggtgtccg atatccagac aatccagcca agcctgaact 3600
ccgtgaatga aggcggccag aagatcaaga acgaggccga gcctgagttt gccagcagac 3660
tggaaaccga actgaaagaa ctcaacaccc agtgggacca catgtgccag caagtgtacg 3720
cccggaaaga ggccctgaaa ggcggactcg aaaagactgt gtctctgcag aaagacctgt 3780
ctgagatgca cgagtggatg acccaggccg aagaggaata cctggaacgg gacttcgagt 3840
acaagacccc tgatgagctg caaaaagccg tcgaggaaat gaagcgggcc aaagaagagg 3900
cccagcagaa agaagccaaa gtcaagctgc tgaccgagtc cgtgaatagc gttatcgctc 3960
aggcccctcc tgtggctcaa gaggctctca agaaagaact ggaaactctg accaccaact 4020
accagtggct gtgcaccaga ctgaacggca agtgcaagac actggaagaa gtgtgggcct 4080
gctggcacga actgctgtcc tatctggaaa aggccaacaa gtggctgaac gaggtggaat 4140
tcaagctgaa aaccaccgag aacatccctg gcggcgctga agagattagc gaggtgctgg 4200
acagcctgga aaacctgatg agacacagcg aggacaaccc caatcagatc agaatcctgg 4260
ctcagaccct gaccgatggc ggcgtgatgg acgagctgat caacgaggaa ctcgaaacct 4320
tcaacagccg gtggcgggaa ctgcacgagg aagctgttcg gaggcagaag ttgctggaac 4380
agtctatcca gagcgcacaa gaaaccgaga agtccctgca cctgatccaa gagagcctga 4440
ccttcatcga caagcagctg gccgcttata tcgccgacaa ggtggacgct gctcagatgc 4500
cccaagaggc acagaagatt cagagcgacc tgaccagcca cgagattagc ctggaagaaa 4560
tgaagaagca caaccagggc aaagaggccg ctcagagagt cctgagccag atcgatgtgg 4620
cacagaaaaa gctccaggat gtgtccatga agtttcggct gtttcagaag cccgccaact 4680
tcgagcagag actgcaagag tccaagatga tcctggacga agtcaaaatg catctgcccg 4740
cactggaaac aaagtccgtg gaacaagaag tggtgcagtc ccagctgaac cactgcgtga 4800
acctgtacaa gagcctgtcc gaagtgaagt ctgaggtgga aatggtcatc aagaccggca 4860
ggcagatcgt ccagaagaag cagaccgaga atcccaaaga actcgacgag agagtgaccg 4920
ctctgaagct gcactacaat gagctgggcg ccaaagtgac cgagcggaag caacagcttg 4980
agaagtgcct gaaactgtct cggaagatgc ggaaagaaat gaacgtgctg acagagtggc 5040
tggccgccac cgatatggaa ctgactaaga gaagcgccgt ggaaggcatg cccagcaacc 5100
tggatagtga agtggcctgg ggcaaagcca ctcagaaaga gattgagaag cagaaggtcc 5160
acctgaagtc catcaccgaa gtgggcgaag ccctgaaaac cgtgctggga aagaaagaga 5220
cactggtcga ggacaagctg tccctgctga attccaactg gatcgccgtg acctccagag 5280
ctgaggaatg gctgaatctg ctgcttgagt accagaaaca catggaaacg ttcgaccaga 5340
acgtcgacca catcacaaag tggatcatcc aggctgatac cctgctggac gagtccgaga 5400
agaagaaacc ccaacaaaaa gaagatgtgc tgaagcggct gaaagccgag ctgaatgaca 5460
tccggcctaa ggtggacagc accagagatc aggcagccaa cctgatggcc aacagaggcg 5520
accactgtcg gaagctcgtg gaacctcaga tcagcgagct taaccacaga tttgccgcca 5580
tcagccaccg gatcaagaca ggcaaggcca gcattcctct caaagagctt gagcagttca 5640
acagcgacat ccaaaagctg ctcgaacccc tggaagccga gatccaacag ggcgtcaacc 5700
tcaaagaaga agatttcaac aaggacatga acgaggacaa tgagggcacc gtcaaagaac 5760
tgctgcagcg gggcgataat ctgcagcagc ggattaccga tgagcgcaag cgggaagaga 5820
tcaagattaa gcagcagctg ctgcagacca agcacaacgc cctgaaggac ctgcggagcc 5880
agagaagaaa gaaggccctg gaaatcagcc accagtggta tcagtacaag cggcaggccg 5940
acgacctgct gaagtgcctg gatgacatcg agaagaagct ggcctctctg cccgagccta 6000
gggacgagag aaagatcaaa gagatcgacc gcgagctgca gaaaaagaaa gaggaactga 6060
acgccgtccg cagacaggcc gaaggacttt ctgaagatgg cgccgctatg gccgtggaac 6120
ccacacagat tcagctgagc aagcggtggc gggaaatcga gagcaagttc gcccagttcc 6180
ggcggctgaa tttcgcccag atccacaccg tgcgggaaga gacaatgatg gtcatgacag 6240
aggacatgcc ccttgagatc agctacgtgc ccagcaccta cctgaccgag atcacccatg 6300
tgtctcaggc cctgctggaa gtggaacagc tgctgaatgc ccctgacctg tgcgccaagg 6360
acttcgagga cctgttcaag caagaggaaa gcctgaagaa catcaaggac agcctgcagc 6420
agagcagcgg ccggatcgat atcatccaca gcaagaaaac cgccgcactg cagagcgcca 6480
cacctgtgga aagagtgaag ctgcaagagg ccctgagcca gctggatttc cagtgggaga 6540
aagtgaacaa gatgtacaag gaccggcagg gcagattcga ccgcagcgtt gaaaagtggc 6600
ggcggttcca ctacgacatc aagatcttca accagtggct gaccgaggcc gagcagttcc 6660
tgagaaagac acagatcccc gagaactggg agcacgccaa gtacaagtgg tatctgaaag 6720
agctgcagga cggcatcggc cagagacaga cagtcgtgcg gacactgaat gccaccggcg 6780
aggaaatcat ccagcagtcc agcaagaccg acgccagcat cctgcaagag aagctgggca 6840
gcctgaacct gcggtggcaa gaagtgtgca agcagctgag cgaccggaag aagcggctgg 6900
aagaacagaa gaatatcctg agcgagttcc agcgggacct gaacgagttc gtgctgtggc 6960
tcgaagaggc cgacaatatc gccagcattc ccctggaacc tggcaaagag cagcagctga 7020
aagaaaagct ggaacaagtg aaactgctgg tcgaggaact gcccctgaga cagggaatcc 7080
tgaaacagct gaacgagaca ggcggccctg tgctggtgtc tgcccctatt tctcccgagg 7140
aacaggacaa gctggaaaac aagctgaagc agaccaacct gcagtggatc aaggtgtcca 7200
gagcactgcc tgagaagcag ggcgagatcg aggcccagat caaggacctg ggacagctcg 7260
aaaagaagct tgaggacctc gaagaacagc tcaaccatct gctgctttgg ctgagcccca 7320
tccggaacca gctggaaatc tacaaccagc ctaatcaaga gggccccttc gacgtgaaag 7380
aaaccgagat tgccgtgcag gccaagcagc ccgatgtgga agagatcctg tctaagggcc 7440
agcacctgta caaagagaag cccgccacac agcccgtgaa gcggaaactg gaagatctga 7500

```
gcagcgagtg gaaggccgtg aaccggctgc tgcaagaact gagagccaaa cagcctgatc  7560
tggcccctgg cctgacaaca attggcgcct ctcctacaca gaccgtgaca ctggtcacac  7620
agcctgtggt caccaaagag acagccatca gcaaactgga aatgcccagc agtctgatgc  7680
tcgaagtgcc cgcactggcc gacttcaata gagcctggac cgagctgacc gactggctca  7740
gtctgctgga ccaagtcatc aagtcccaga gagtgatggt cggagatctt gaggacatca  7800
acgagatgat cattaagcag aaagccacca tgcaggacct tgagcagaga aggccccagc  7860
ttgaagaact gatcaccgcc gctcagaacc tgaaaaacaa gaccagcaat caagaagccc  7920
ggaccatcat caccgaccgg atcgagagaa tccagaacca gtgggacgaa gtgcaagagc  7980
atctgcagaa cagacggcag cagctcaatg agatgctgaa ggacagcaca cagtggctgg  8040
aagccaaaga agaagccgag caggttctcg gacaggccag agctaagctg gaatcttgga  8100
aagagggacc ctacaccgtc gacgccatcc agaagaagat caccgagaca aagcagctgg  8160
ccaaggatct gagacagtgg cagaccaatg tggacgtggc caacgacctg gctctgaagc  8220
tgctgagaga ctacagcgcc gacgacacca gaaaggtgca catgatcacc gaaaacatca  8280
acgcctcttg gcggagcatc cacaagcggg tgtcagagag agaagccgct ctggaagaaa  8340
cacatagact gctccagcag ttcccactcg acctggaaaa gttcctggcc tggctgacag  8400
aagccgaaac caccgctaac gtgctccagg atgccaccag aaaagagcgg ctgttggagg  8460
acagcaaggg cgtcaaagaa ctcatgaagc agtggcagga tctgcaaggg gagattgaag  8520
cccacaccga cgtgtaccac aacctggacg agaacagcca gaagatcctg cggtccctgg  8580
aaggctctga tgatgctgtg ctgcttcaga ggcggctgga caacatgaac ttcaagtgga  8640
gcgagctgcg gaagaagtcc ctgaacatca gaagccacct ggaagcctcc agcgaccagt  8700
ggaaaagact gcacctgtct ctccaagagc tgctcgtgtg gctgcagctg aaggatgacg  8760
agctgagtag acaggcccct atcggcggag attttcccgc cgtgcagaaa cagaacgacg  8820
tgcaccgggc cttcaagaga gagctgaaaa caaaagaacc cgtcatcatg agcaccctgg  8880
aaaccgtgcg gatctttctg accgagcagc ctctggaagg actggaaaag ctgtaccaag  8940
agcctagaga gctgcctcct gaagaaaggg cccagaacgt gacacggctg cttagaaagc  9000
aggccgagga agtgaacacc gaatgggaga agctgaacct ccactccgcc gactggcagc  9060
ggaagatcga tgagacactg gaacggctgc gggaactgca agaagccaca gacgagctgg  9120
acctgaaact gcggcaggct gaagtgatca aaggctcctg gcagccagtg ggcgatctgc  9180
tgatcgatag cctgcaggac catctggaaa aagtcaaggc cctgcgggga gagatcgccc  9240
ctctcaaaga aaacgtgtcc cacgtgaacg atctggccag gcagctgaca acactgggca  9300
tccagctgag cccttacaac ctgtctacct tggaggacct gaatacccgg tggaagctgc  9360
tccaagtggc cgtcgaggat agagtgcggc agctgcatga ggctcacaga gattttggac  9420
ccgccagcca gcacttcctg agcacatctg ttcaaggccc ctgggagaga gctatcagcc  9480
ctaacaaggt gccctactac atcaaccacg agacacagac cacctgttgg gatcacccca  9540
agatgaccga actgtatcag tccctggccg acctgaacaa cgtgcggttt agcgcctacc  9600
ggaccgccat gaagctgcgc agactgcaga aagctctgtg cctggacctg ctgtctctga  9660
gcgctgcttg tgatgccctg gaccagcata acctcaagca gaacgaccag cctatggaca  9720
tcctgcagat catcaactgc ctgaccacca tctacgaccg gctcgaacaa gagcacaaca  9780
acctggtcaa cgtgcccctg tgcgtggaca tgtgcctgaa ttggctgctg aacgtgtacg  9840
acaccggcag aaccggcagg atcagagtgc tgagcttcaa gaccggcatc atctccctgt  9900
gcaaggccca ccttgaggat aagtaccgct acctgtttaa gcaggtcgcc agcagcaccg  9960
gcttttgcga ccaaagaagg ctgggactgc tgctccacga cagcattcag atccctagac  10020
agctgggcga agtggcctct ttcggcggct ctaatatcga gcctagcgtg cggagctgct  10080
tccagttcgc caacaacaag cccgagattg aggccgcact gttcctggac tggatgagac  10140
tggaacccca gagcatggtc tggctgcctg tgctgcatag agtggccgca gccgaaacag  10200
ccaagcacca ggccaagtgc aacatctgca aagagtgccc catcatcggc ttccggtaca  10260
gatccctgaa gcacttcaac tacgatatct gccagtcctg cttcttcagc ggcagagtgg  10320
ccaagggcca caagatgcac taccccatgg tggaatactg cacccctacc acctctggcg  10380
aggacgtgcg ggattttgcc aaggtgctca agaacaagtt ccggaccaag cgctacttcg  10440
ctaagcaccc cagaatgggc tacctgccag tgcagacagt gcttgagggc gacaacatgg  10500
aaacccctgt gactctgatc aacttctggc ccgtggatag cgcccctgct agttctcctc  10560
agctgtctca cgacgatacc cacagcagaa tcgagcacta cgcctccaga ctggccgaga  10620
tggaaaacag caacggcagc tacctgaatg acagcatcag ccccaacgag agcatcgacg  10680
acgaacatct gctcattcag cactactgcc agagcctgaa tcaggacagc cctctgtctc  10740
agcctagaag ccctgcacag atcctgatca gcctggaaag cgaggaacgc ggcgagctgg  10800
aaagaatcct ggcagacctg gaagaggaaa accggaacct gcaggccgaa tacgacagac  10860
tcaagcagca gcacgagcac aagggactgt ctccactgcc ttctccacct gaaatgatgc  10920
ccacctctcc acagagcccc agagatgccg agctgattgc cgaagccaaa ctgctgaggc  10980
agcacaaagg cagactcgaa gccagaatgc agattctcga agatcacaac aagcagctcg  11040
aatcccagct gcacagactt aggcagctgc tggaacagcc tcaggcagag gccaaagtga  11100
atggcaccac cgtgtctagc cctagcacaa gcctgcagag atccgacagc agccagccaa  11160
tgcttctgag agtcgtgggc tcccagacca gcgattctat gggcgaagag gacctgctca  11220
gccctcctca ggatacaagc accggcctgg aagaagtgat ggaacaactg aacaacagct  11280
tccccagcag cagaggcaga aacacccctg gcaagcccat gcgcgaggac accatgtgat  11340
aactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acgtggcgcc atcggatccc gggcccgtcg  12180
actgcagagg cctgcatgca agcttggcgt aatcatggtc atagctgttt cctgtgtgaa  12240
```

```
attgttatcc gctcacaatt ccacacaaca tacgagccgg aagcataaag tgtaaagcct  12300
ggggtgccta atgagtgagc taactcacat taattgcgtt gcgctcactg cccgctttcc  12360
agtcgggaaa cctgtcgtgc cagctgcatt aatgaatcgg ccaacgcgcg gggagaggcg  12420
gtttgcgtat tgggcgctct tccgcttcct cgctcactga ctcgctgcgc tcggtcgttc  12480
ggctgcggcg agcggtatca gctcactcaa aggcggtaat acggttatcc acagaatcag  12540
gggataacgc aggaaagaac atgtgagcaa aaggccagca aaaggccagg aaccgtaaaa  12600
aggccgcgtt gctggcgttt ttccataggc tccgcccccc tgacgagcat cacaaaaatc  12660
gacgctcaag tcagaggtgg cgaaacccga caggactata aagataccag gcgtttcccc  12720
ctggaagctc cctcgtgcgc tctcctgttc cgaccctgcc gcttaccgga tacctgtccg  12780
cctttctccc ttcgggaagc gtggcgcttt ctcatagctc acgctgtagg tatctcagtt  12840
cggtgtaggt cgttcgctcc aagctgggct gtgtgcacga accccccgtt cagcccgacc  12900
gctgcgcctt atccggtaac tatcgtcttg agtccaaccc ggtaagacac gacttatcgc  12960
cactggcagc agccactggt aacaggatta gcagagcgag gtatgtaggc ggtgctacag  13020
agttcttgaa gtggtggcct aactacggct acactagaag aacagtattt ggtatctgcg  13080
ctctgctgaa gccagttacc ttcggaaaaa gagttggtag ctcttgatcc ggcaaacaaa  13140
ccaccgctgg tagcggtggt ttttttgttt gcaagcagca gattacgcgc agaaaaaaag  13200
gatctcaaga agatcctttg atcttttcta cggggtctga cgctcagtgg aacgaaaact  13260
cacgttaagg gattttggtc atgagattat caaaaaggat cttcacctag atccttttaa  13320
attaaaaatg aagttttaaa tcaatctaaa gtatatatga gtaaacttgg tctgacagtt  13380
accaatgctt aatcagtgag gcacctatct cagcgatctg tctatttcgt tcatccatag  13440
ttgcctgact ccccgtcgtg tagataacta cgatacggga gggcttacca tctggcccca  13500
gtgctgcaat gataccgcga gacccacgct caccggctcc agatttatca gcaataaacc  13560
agccagccgg aagggccgag cgcagaagtg gtcctgcaac tttatccgcc tccatccagt  13620
ctattaattg ttgccgggaa gctagagtaa gtagttcgcc agttaatagt ttgcgcaacg  13680
ttgttgccat tgctacaggc atcgtggtgt cacgctcgtc gtttggtatg gcttcattca  13740
gctccggttc ccaacgatca aggcgagtta catgatcccc catgttgtgc aaaaaagcgg  13800
ttagctcctt cggtcctccg atcgttgtca gaagtaagtt ggccgcagtg ttatcactca  13860
tggttatggc agcactgcat aattctctta ctgtcatgcc atccgtaaga tgcttttctg  13920
tgactggtga gtactcaacc aagtcattct gagaatagtg tatgcggcga ccgagttgct  13980
cttgcccggc gtcaatacgg gataataccg cgccacatag cagaacttta aaagtgctca  14040
tcattggaaa acgttcttcg gggcgaaaac tctcaaggat cttaccgctg ttgagatcca  14100
gttcgatgta acccactcgt gcacccaact gatcttcagc atcttttact ttcaccagcg  14160
tttctgggtg agcaaaaaca ggaaggcaaa atgccgcaaa aaagggaata agggcgacac  14220
ggaaatgttg aatactcata ctcttccttt ttcaatatta ttgaagcatt tatcagggtt  14280
attgtctcat gagcggatac atatttgaat gtatttagaa aaataaacaa ataggggttc  14340
cgcgcacatt tccccgaaaa gtgccacctg acgtctaaga aaccattatt atcatgacat  14400
taacctataa aaataggcgt atcacgaggc cctttcgtct cgcgcgtttc ggtgatgacg  14460
gtgaaaacct ctgacacatg cagctcccgg agacggtcac agcttgtctg taagcggatg  14520
ccgggagcag acaagcccgt cagggcgcgt cagcgggtgt tggcgggtgt cggggctggc  14580
ttaactatgc ggcatcagag cagattgtac tgagagtgca ccatatgcgg tgtgaaatac  14640
cgcacagatg cgtaaggaga aaataccgca tcaggcgcca ttcgccattc aggctgcgca  14700
actgttggga agggcgatcg gtgcgggcct cttcgctatt acgccagctg gcgaaagggg  14760
gatgtgctgc aaggcgatta agttgggtaa cgccagggtt ttcccagtca cgacgttgta  14820
aaacgacggc cagtgaattc gagctcggta cctcgcgaat gcatgcggcc gccgttacat  14880
aacttacggt aaatggcccg cctggctgac cgcccaacga cccccgccca ttgacgtcaa  14940
taatgacgta tgttcccata gtaacgccaa tagggacttt ccattgacgt caatgggtgg  15000
agtatttacg gtaaactgcc cacttggcag tacatcaagt gtatcatatg ccaagtacgc  15060
cccctattga cgtcaatgac ggtaaatggc ccgcctggca ttatgcccag tacatgacct  15120
tatgggactt tcctacttgg cagtacatct acgtattagt catcgctatt accatggtcg  15180
aggtgagccc cacgttctgc ttcactctcc ccatctcccc cccctcccca cccccaattt  15240
tgtatttatt tatttttaa ttattttgtg cagcgatggg ggcggggggg gggggggcgc  15300
gcgccaggcg gggcggggcg gggcgagggg cggggcgggg cgaggcggag aggtgcggcg  15360
gcagccaatc agagcggcgc gctccgaaag tttcctttta tggcgaggcg gcggcggcgg  15420
cggccctata aaaagcgaag cgcgcggcgg gcgggagtc                        15459

SEQ ID NO: 50           moltype = DNA  length = 15634
FEATURE                 Location/Qualifiers
source                  1..15634
                        mol_type = other DNA
                        note = pUC57-MHCK7-hBGi-DMD-4-WPRE3-DTS
                        organism = synthetic construct
SEQUENCE: 50
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac catgctttgg tgggaagaag  300
tcgaggactg ctacgagcgc gaggacgtgc agaagaaaac cttcaccaaa tgggtcaacg  360
cccagttcag caagttcggc aagcagcaca tcgagaacct gttcagcgac ctgcaggatg  420
gcagaaggct gctggatctg ctggaaggcc tgacaggaca gaagctgccc aaagagaagg  480
gcagcacaag agtgcacgcc ctgaacaacg tgaacaaggc cctgagagtg ctgcagaaca  540
acaacgtgga cctggtcaac atcggcagca ccgacatcgt ggacggcaac cacaaactga  600
ccctgggcct gatctggaac atcatcctgc actggcaagt gaagaacgtg atgaagaaca  660
tcatggccgg cctgcagcag accaacagcg agaagattct gctgagctgg gtccgacaga  720
gcacccggaa ttaccctcaa gtgaacgtga tcaacttcac cacctcttgg agcgacggac  780
tggccctgaa tgccctgatc cacagccaca gacctgacct gttcgactgg aacagcgtcg  840
tgtgtcagca gagcgccaca cagaggctgg aacacgcctt caatatcgcc agataccagc  900
tgggcatcga gaaactgctg gaccccgagg atgtggacac cacctatcct gacaagaaat  960
ccatcctcat gtacatcacc agcctgttcc aggtgctgcc ccagcaggtt tccatcgagg  1020
```

```
ccattcaaga ggtcgagatg ctgcccagac ctcctaaagt gaccaaagag gaacacttcc  1080
agctgcacca ccagatgcac tactctcagc agatcaccgt gtctctggcc cagggctacg  1140
agagaacaag cagccccaag cctcggttca agagctacgc ctatacacag gccgcctacg  1200
tgaccaccag cgatcctaca agaagcccat ttcctagcca gcatctggaa gcccctgagg  1260
acaagagctt tggcagcagc ctgatggaaa gcgaagtgaa cctggaccgc taccagacag  1320
ccctggaaga ggttctgagc tggctgctgt ctgccgagga tacactgcag gctcagggcg  1380
agatcagcaa cgacgtggaa gtggtcaagg accagtttca cacccacgag ggctacatga  1440
tggacctgac agcccaccag ggcagagtgg gcaatattct gcagctgggc tccaagctga  1500
tcggcacagg caagctgagc gaggacgaag agacagaggt gcaagagcag atgaacctgc  1560
tgaacagcag atgggagtgt ctgagagtgg ccagcatgga aaagcagagc aacctgcacc  1620
gggtgctgat ggatctccag aaccagaagc tgaaagagct gaacgactgg ctgaccaaga  1680
ccgaggaacg gacccggaag atggaagagg aacctctggg acccgacctg gaagatctga  1740
aaagacaggt gcagcagcat aaggtgctgc aagaggacct cgaacaagag caagtgcgcg  1800
tgaacagcct gacacacatg gtggtggtcg tggatgagag cagcggagat catgccacag  1860
ccgctctgga agaacagctg aaggtgctgg gagacagatg ggccaatatc tgccggtgga  1920
ccgaggatag atgggtgctg ctccaggaca tcctgctgaa gtggcagcgg ctgacagagg  1980
aacagtgcct gtttagcgcc tggctgtccg agaaagagga cgccgtcaac aagatccaca  2040
ccaccggctt caaggatcag aatgagatgc tgagcagcct gcagaaactg gccgtgctga  2100
aggctgacct ggaaaagaaa aagcagtcca tgggcaagct gtactccctg aagcaggacc  2160
tgctgagcac actgaagaac aagtctgtga cccagaaaac cgaggcctgg ctggacaact  2220
tcgcccggtg ttgggataac ctggtgcaga agctggaaaa gtccaccgct cagatctctc  2280
aggccgtgac cacaacacag ccttctctga cccagaccac cgtgatggaa acagtgacca  2340
cagtgacaac ccgcgagcag atcctggtca agcacgccca agaagaactg cctcctccac  2400
ctcctcagaa gaaacggcag atcacagtgg acagcgagat ccggaagaga ctggacgtgg  2460
acatcaccga gctgcacagc tggatcacca gatccgaagc cgtgctgcag tcccctgagt  2520
tcgccatctt cagaaaagag ggcaacttct ccgacctgaa agagaaagtc aacgccatcg  2580
agagagagaa ggccgagaag ttccggaagc tgcaggacgc ctctagatct gcccaggctc  2640
tggtggaaca gatggtcaac gaaggcgtga acgccgacag catcaagcag gcctcagagc  2700
agctgaactc ccggtggatc gagttctgtc agctcctgag cgagagactg aactggctgg  2760
aataccagaa caatatcatt gccttctaca accagctcca gcagctcgaa cagatgacca  2820
ccacagccga gaattggctg aagatccagc ctaccacacc tagcgagccc accgccatta  2880
agagccagct gaaaatctgc aaggacgaag tgaatcggct gagcgatctg cagccccaga  2940
tcgaaagact gaaaatccag tctatcgccc tcaaagagaa aggacagggc cccatgttcc  3000
tggacgccga ttttgtggcc tttaccaacc acttcaaaca ggtgttctcc gacgtgcagg  3060
cccgggaaaa agagctgcag accatcttcg acaccctgcc tccaatgaga taccaagaga  3120
caatgagcgc catccggacc tgggtgcagc aaagcgagac aaagctgagc atcccacagc  3180
tgagcgtgac cgactacgag atcatggaac agagactggg cgaactgcag gccctccagt  3240
ctagcctgca agaacagcag tccggcctgt actacctgag cacaaccgtg aaagagatga  3300
gcaagaaggc ccctagcgag atctcccgga agtaccagag cgagttcgaa gagatcgaag  3360
gccggtggaa gaagctgtct agccagctgg ttgagcactg ccagaaactc gaagaacaaa  3420
tgaacaagct gcgcaagatc cagaatcaca tccagacgct gaagaaatgg atggccgagg  3480
tggacgtgtt cctgaaagaa gagtggcccg ctctgggcga ctccgagatt ctgaagaaac  3540
agctcaaaca gtgccggctg ctggtgtccg atatccagac aatccagcca agcctgaact  3600
ccgtgaatga aggcggccag aagatcaaga acgaggccga gcctgagttt gccagcagac  3660
tggaaaccga actgaaagaa ctcaacaccc agtgggacca catgtgccag caagtgtacg  3720
cccggaaaga ggccctgaaa ggcggactcg aaaagactgt gtctctgcag aaagacctgt  3780
ctgagatgca cgagtggatg acccaggccg aagaggaata cctggaacgg gacttcgagt  3840
acaagacccc tgatgagctg caaaaagccg tcgaggaaat gaagcgggcc aaagaagagg  3900
cccagcagaa agaagccaaa gtcaagctgc tgaccgagtc cgtgaatagc gttatcgctc  3960
aggcccctcc tgtggctcaa gaggctctca agaaagaact ggaaactctg accaccaact  4020
accagtggct gtgcaccaga ctgaacggca agtgcaagac actggaagaa gtgtgggcct  4080
gctggcacga actgctgtcc tatctggaaa aggccaacaa gtggctgaac gaggtggaat  4140
tcaagctgaa aaccaccgag aacatccctg gcggcgctga agagattagc gaggtgctgg  4200
acagcctgga aaacctgatg agacacagcg aggacaaccc caatcagatc agaatcctgg  4260
ctcagaccct gaccgatggc ggcgtgatgg acgagctgat caacgaggaa ctcgaaacct  4320
tcaacagccg gtggcgggaa ctgcacgagg aagctgttcg gaggcagaag ttgctggaac  4380
agtctatcca gagcgcacaa gaaaccgaga agtccctgca cctgatccaa gagagcctga  4440
ccttcatcga caagcagctg gccgcttata tcgccgacaa ggtggacgct gctcagatgc  4500
cccaagaggc acagaagatt cagagcgacc tgaccagcca cgagattagc ctggaagaaa  4560
tgaagaagca caaccagggc aaagaggccg ctcagagagt cctgagccag atcgatgtgg  4620
cacagaaaaa gctccaggat gtgtccatga agtttcggct gtttcagaag cccgccaact  4680
tcgagcagag actgcaagag tccaagatga tcctggacga agtcaaaatg catctgcccg  4740
cactggaaac aaagtccgtg gaacaagaag tggtgcagtc ccagctgaac cactgcgtga  4800
acctgtacaa gagcctgtcc gaagtgaagt ctgaggtgga aatggtcatc aagaccggca  4860
ggcagatcgt ccagaagaag cagaccgaga atcccaaaga actcgacgag agagtgaccg  4920
ctctgaagct gcactacaat gagctgggcg ccaaagtgac cgagcggaag caacagcttg  4980
agaagtgcct gaaactgtct cggaagatgc ggaaagaaat gaacgtgctg acagagtggc  5040
tggccgccac cgatatggaa ctgactaaga gaagcgccgt ggaaggcatg cccagcaacc  5100
tggatagtga agtggcctgg ggcaaagcca ctcagaaaga gattgagaag cagaaggtcc  5160
acctgaagtc catcaccgaa gtgggcgaag ccctgaaaac cgtgctggga aagaaagaga  5220
cactggtcga ggacaagctg tccctgctga attccaactg gatcgccgtg acctccagag  5280
ctgaggaatg gctgaatctg ctgcttgagt accagaaaca catggaaacg ttcgaccaga  5340
acgtcgacca catcacaaag tggatcatcc aggctgatac cctgctggac gagtccgaga  5400
agaagaaacc ccaacaaaaa gaagatgtgc tgaagcggct gaaagccgag ctgaatgaca  5460
tccggcctaa ggtggacagc accagagatc aggcagccaa cctgatggcc aacagaggcg  5520
accactgtcg gaagctcgtg gaacctcaga tcagcgagct taaccacaga tttgccgcca  5580
tcagccaccg gatcaagaca ggcaaggcca gcattcctct caaagagctt gagcagttca  5640
acagcgacat ccaaaagctg ctcgaacccc tggaagccga gatccaacag ggcgtcaacc  5700
tcaaagaaga agatttcaac aaggacatga acgaggacaa tgagggcacc gtcaaagaac  5760
```

```
tgctgcagcg gggcgataat ctgcagcagc ggattaccga tgagcgcaag cgggaagaga  5820
tcaagattaa gcagcagctg ctgcagacca agcacaacgc cctgaaggac ctgcggagcc  5880
agagaagaaa gaaggccctg gaaatcagcc accagtggta tcagtacaag cggcaggccg  5940
acgacctgct gaagtgcctg gatgacatcg agaagaagct ggcctctctg cccgagccta  6000
gggacgagag aaagatcaaa gagatcgacc gcgagctgca gaaaaagaaa gaggaactga  6060
acgccgtccg cagacaggcc gaaggacttt ctgaagatgg cgccgctatg gccgtggaac  6120
ccacacagat tcagctgagc aagcggtggc gggaaatcga gagcaagttc gcccagttcc  6180
ggcggctgaa tttcgcccag atccacaccg tgcgggaaga gacaatgatg gtcatgacag  6240
aggacatgcc ccttgagatc agctacgtgc ccagcaccta cctgaccgag atcacccatg  6300
tgtctcaggc cctgctggaa gtggaacagc tgctgaatgc ccctgacctg tgcgccaagg  6360
acttcgagga cctgttcaag caagaggaaa gcctgaagaa catcaaggac agcctgcagc  6420
agagcagcgg ccggatcgat atcatccaca gcaagaaaac cgccgcactg cagagcgcca  6480
cacctgtgga aagagtgaag ctgcaagagg ccctgagcca gctggatttc cagtgggaga  6540
aagtgaacaa gatgtacaag gaccggcagg gcagattcga ccgcagcgtt gaaaagtggc  6600
ggcggttcca ctacgacatc aagatcttca accagtggct gaccgaggcc gagcagttcc  6660
tgagaaagac acagatcccc gagaactggg agcacgccaa gtacaagtgg tatctgaaag  6720
agctgcagga cggcatcggc cagagacaga cagtcgtgcg gacactgaat gccaccggcg  6780
aggaaatcat ccagcagtcc agcaagaccg acgccagcat cctgcaagag aagctgggca  6840
gcctgaacct gcggtggcaa gaagtgtgca agcagctgag cgaccggaag aagcggctgg  6900
aagaacagaa gaatatcctg agcgagttcc agcgggacct gaacgagttc gtgctgtggc  6960
tcgaagaggc cgacaatatc gccagcattc ccctggaacc tggcaaagag cagcagctga  7020
aagaaaagct ggaacaagtg aaactgctgg tcgaggaact gcccctgaga cagggaatcc  7080
tgaaacagct gaacgagaca ggcggccctg tgctggtgtc tgcccctatt tctcccgagg  7140
aacaggacaa gctggaaaac aagctgaagc agaccaacct gcagtggatc aaggtgtcca  7200
gagcactgcc tgagaagcag ggcgagatcg aggcccagat caaggacctg ggacagctcg  7260
aaaagaagct tgaggacctc gaagaacagc tcaaccatct gctgctttgg ctgagcccca  7320
tccggaacca gctggaaatc tacaaccagc ctaatcaaga gggccccttc gacgtgaaag  7380
aaaccgagat tgccgtgcag gccaagcagc ccgatgtgga agagatcctg tctaagggcc  7440
agcacctgta caaagagaag cccgccacac agcccgtgaa gcggaaactg gaagatctga  7500
gcagcgagtg gaaggccgtg aaccggctgc tgcaagaact gagagccaaa cagcctgatc  7560
tggcccctgg cctgacaaca attggcgcct ctcctacaca gaccgtgaca ctggtcacac  7620
agcctgtggt caccaaagag acagccatca gcaaactgga aatgcccagc agtctgatgc  7680
tcgaagtgcc cgcactggcc gacttcaata gagcctggac cgagctgacc gactggctca  7740
gtctgctgga ccaagtcatc aagtcccaga gagtgatggt cggagatctt gaggacatca  7800
acgagatgat cattaagcag aaagccacca tgcaggacct tgagcagaga aggccccagc  7860
ttgaagaact gatcaccgcc gctcagaacc tgaaaaacaa gaccagcaat caagaagccc  7920
ggaccatcat caccgaccgg atcgagagaa tccagaacca gtgggacgaa gtgcaagagc  7980
atctgcagaa cagacggcag cagctcaatg agatgctgaa ggacagcaca cagtggctgg  8040
aagccaaaga agaagccgag caggttctcg gacaggccag agctaagctg gaatcttgga  8100
aagagggacc ctacaccgtc gacgccatcc agaagaagat caccgagaca aagcagctgg  8160
ccaaggatct gagacagtgg cagaccaatg tggacgtggc caacgacctg gctctgaagc  8220
tgctgagaga ctacagcgcc gacgacacca gaaaggtgca catgatcacc gaaaacatca  8280
acgcctcttg gcggagcatc cacaagcggg tgtcagagag agaagccgct ctggaagaaa  8340
cacatagact gctccagcag ttcccactcg acctggaaaa gttcctggcc tggctgacag  8400
aagccgaaac caccgctaac gtgctccagg atgccaccag aaaagagcgg ctgttggagg  8460
acagcaaggg cgtcaaagaa ctcatgaagc agtggcagga tctgcaaggg gagattgaag  8520
cccacaccga cgtgtaccac aacctggacg agaacagcca gaagatcctg cggtccctgg  8580
aaggctctga tgatgctgtg ctgcttcaga ggcggctgga caacatgaac ttcaagtgga  8640
gcgagctgcg gaagaagtcc ctgaacatca gaagccacct ggaagcctcc agcgaccagt  8700
ggaaaagact gcacctgtct ctccaagagc tgctcgtgtg gctgcagctg aaggatgacg  8760
agctgagtag acaggcccct atcggcggag attttcccgc cgtgcagaaa cagaacgacg  8820
tgcaccgggc cttcaagaga gagctgaaaa caaaagaacc cgtcatcatg agcaccctgg  8880
aaaccgtgcg gatctttctg accgagcagc ctctggaagg actggaaaag ctgtaccaag  8940
agcctagaga gctgcctcct gaagaaaggg cccagaacgt gacacggctg cttagaaagc  9000
aggccgagga agtgaacacc gaatgggaga agctgaacct ccactccgcc gactggcagc  9060
ggaagatcga tgagacactg gaacggctgc gggaactgca agaagccaca gacgagctgg  9120
acctgaaact gcggcaggct gaagtgatca aaggctcctg gcagccagtg ggcgatctgc  9180
tgatcgatag cctgcaggac catctggaaa aagtcaaggc cctgcgggga gagatcgccc  9240
ctctcaaaga aaacgtgtcc cacgtgaacg atctggccag gcagctgaca acactgggca  9300
tccagctgag cccttacaac ctgtctacct tggaggacct gaatacccgg tggaagctgc  9360
tccaagtggc cgtcgaggat agagtgcggc agctgcatga ggctcacaga gatttggac  9420
ccgccagcca gcacttcctg agcacatctg ttcaaggccc ctgggagaga gctatcagcc  9480
ctaacaaggt gccctactac atcaaccacg agacacagac cacctgttgg gatcacccca  9540
agatgaccga actgtatcag tccctggccg acctgaacaa cgtgcggttt agcgcctacc  9600
ggaccgccat gaagctgcgc agactgcaga aagctctgtg cctggacctg ctgtctctga  9660
gcgctgcttg tgatgccctg gaccagcata acctcaagca gaacgaccag cctatggaca  9720
tcctgcagat catcaactgc ctgaccacca tctacgaccg gctcgaacaa gagcacaaca  9780
acctggtcaa cgtgcccctg tgcgtggaca tgtgcctgaa ttggctgctg aacgtgtacg  9840
acaccggcag aaccggcagg atcagagtgc tgagcttcaa gaccggcatc atctccctgt  9900
gcaaggccca ccttgaggat aagtaccgct acctgtttaa gcaggtcgcc agcagcaccg  9960
gcttttgcga ccaaagaagg ctgggactgc tgctccacga cagcattcag atccctagac  10020
agctgggcga agtggcctct ttcggcggct ctaatatcga gcctagcgtg cggagctgct  10080
tccagttcgc caacaacaag cccgagattg aggccgcact gttcctggac tggatgagac  10140
tggaacccca gagcatggtc tggctgcctg tgctgcatag agtggccgca gccgaaacag  10200
ccaagcacca ggccaagtgc aacatctgca aagagtgccc catcatcggc ttccggtaca  10260
gatccctgaa gcacttcaac tacgatatct gccagtcctg cttcttcagc ggcagagtgg  10320
ccaagggcca caagatgcac taccccatgg tggaatactg caccccctacc acctctggcg  10380
aggacgtgcg ggattttgcc aaggtgctca agaacaagtt ccggaccaag cgctacttcg  10440
ctaagcaccc cagaatgggc tacctgccag tgcagacagt gcttgagggc gacaacatgg  10500
```

```
aaacccctgt gactctgatc aacttctggc ccgtggatag cgcccctgct agttctcctc  10560
agctgtctca cgacgatacc cacagcagaa tcgagcacta cgcctccaga ctggccgaga  10620
tggaaaacag caacggcagc tacctgaatg acagcatcag ccccaacgag agcatcgacg  10680
acgaacatct gctcattcag cactactgcc agagcctgaa tcaggacagc cctctgtctc  10740
agcctagaag ccctgcacag atcctgatca gcctggaaag cgaggaacgc ggcgagctgg  10800
aaagaatcct ggcagacctg gaagaggaaa accggaacct gcaggccgaa tacgacagac  10860
tcaagcagca gcacgagcac aagggactgt ctccactgcc ttctccacct gaaatgatgc  10920
ccacctctcc acagagcccc agagatgccg agctgattgc cgaagccaaa ctgctgaggc  10980
agcacaaagg cagactcgaa gccagaatgc agattctcga agatcacaac aagcagctcg  11040
aatcccagct gcacagactt aggcagctgc tggaacagcc tcaggcagag gccaaagtga  11100
atggcaccac cgtgtctagc cctagcacaa gcctgcagag atccgacagc agccagccaa  11160
tgcttctgag agtcgtgggc tcccagacca gcgattctat gggcgaagag gacctgctca  11220
gccctcctca ggatacaagc accggcctgg aagaagtgat ggaacaactg aacaacagct  11280
tccccagcag cagaggcaga aacacccctg gcaagcccat gcgcgaggac accatgtgat  11340
aactcgagaa tcaacctctg gattacaaaa tttgtgaaag attgactggt attcttaact  11400
atgttgctcc ttttacgcta tgtggatacg ctgctttaat gcctttgtat catgctattg  11460
cttcccgtat ggctttcatt ttctcctcct tgtataaatc ctggttgctg tctctttatg  11520
aggagttgtg gcccgttgtc aggcaacgtg gcgtggtgtg cactgtgttt gctgacgcaa  11580
cccccactgg ttggggcatt gccaccacct gtcagctcct ttccgggact ttcgctttcc  11640
ccctccctat tgccacggcg gaactcatcg ccgcctgcct tgcccgctgc tggacagggg  11700
ctcggctgtt gggcactgac aattccgtgg ggtgtgcctt ctagttgcca gccatctgtt  11760
gtttgcccct cccccgtgcc ttccttgacc ctggaaggtg ccactcccac tgtcctttcc  11820
taataaaatg aggaaattgc atcgcattgt ctgagtaggt gtcattctat tctggggggt  11880
ggggtggggc aggacagcaa gggggaggat tgggaagaca atagcaggca tgctggggat  11940
gcggtgggct ctatgggaag atgtctactg agctgtgcga tccctgctgg ggactttccg  12000
ctggggactt tccgctgggg actttccgcc ttcagctaag gaagctacca atatttagag  12060
gtacattttg ttctagaaca aaatgtaccg gtacattttg ttctggtaca ttttgttcta  12120
ttaaggacaa cgtaagtata gcgcatagac acgtggcgcc atcggatccc gggcccgtcg  12180
actgcagagg cctgcatgca agcttggcgt aatcatggtc atagctgttt cctgtgtgaa  12240
attgttatcc gctcacaatt ccacacaaca tacgagccgg aagcataaag tgtaaagcct  12300
ggggtgccta atgagtgagc taactcacat taattgcgtt gcgctcactg cccgctttcc  12360
agtcgggaaa cctgtcgtgc cagctgcatt aatgaatcgg ccaacgcgcg gggagaggcg  12420
gtttgcgtat tgggcgctct tccgcttcct cgctcactga ctcgctgcgc tcggtcgttc  12480
ggctgcggcg agcggtatca gctcactcaa aggcggtaat acggttatcc acagaatcag  12540
gggataacgc aggaaagaac atgtgagcaa aaggccagca aaaggccagg aaccgtaaaa  12600
aggccgcgtt gctggcgttt ttccataggc tccgcccccc tgacgagcat cacaaaaatc  12660
gacgctcaag tcagaggtgg cgaaacccga caggactata aagataccag gcgtttcccc  12720
ctggaagctc cctcgtgcgc tctcctgttc cgaccctgcc gcttaccgga tacctgtccg  12780
cctttctccc ttcgggaagc gtggcgcttt ctcatagctc acgctgtagg tatctcagtt  12840
cggtgtaggt cgttcgctcc aagctgggct gtgtgcacga accccccgtt cagcccgacc  12900
gctgcgcctt atccggtaac tatcgtcttg agtccaaccc ggtaagacac gacttatcgc  12960
cactggcagc agccactggt aacaggatta gcagagcgag gtatgtaggc ggtgctacag  13020
agttcttgaa gtggtggcct aactacggct acactagaag aacagtattt ggtatctgcg  13080
ctctgctgaa gccagttacc ttcggaaaaa gagttggtag ctcttgatcc ggcaaacaaa  13140
ccaccgctgg tagcggtggt ttttttgttt gcaagcagca gattacgcgc agaaaaaaag  13200
gatctcaaga agatcctttg atcttttcta cggggtctga cgctcagtgg aacgaaaact  13260
cacgttaagg gattttggtc atgagattat caaaaaggat cttcacctag atccttttaa  13320
attaaaaatg aagttttaaa tcaatctaaa gtatatatga gtaaacttgg tctgacagtt  13380
accaatgctt aatcagtgag gcacctatct cagcgatctg tctatttcgt tcatccatag  13440
ttgcctgact ccccgtcgtg tagataacta cgatacggga gggcttacca tctggcccca  13500
gtgctgcaat gataccgcga gacccacgct caccggctcc agatttatca gcaataaacc  13560
agccagccgg aagggccgag cgcagaagtg gtcctgcaac tttatccgcc tccatccagt  13620
ctattaattg ttgccgggaa gctagagtaa gtagttcgcc agttaatagt ttgcgcaacg  13680
ttgttgccat tgctacaggc atcgtggtgt cacgctcgtc gtttggtatg gcttcattca  13740
gctccggttc ccaacgatca aggcgagtta catgatcccc catgttgtgc aaaaaagcgg  13800
ttagctcctt cggtcctccg atcgttgtca gaagtaagtt ggccgcagtg ttatcactca  13860
tggttatggc agcactgcat aattctctta ctgtcatgcc atccgtaaga tgcttttctg  13920
tgactggtga gtactcaacc aagtcattct gagaatagtg tatgcggcga ccgagttgct  13980
cttgcccggc gtcaatacgg gataataccg cgccacatag cagaacttta aaagtgctca  14040
tcattggaaa acgttcttcg gggcgaaaac tctcaaggat cttaccgctg ttgagatcca  14100
gttcgatgta acccactcgt gcacccaact gatcttcagc atcttttact ttcaccagcg  14160
tttctgggtg agcaaaaaca ggaaggcaaa atgccgcaaa aaagggaata agggcgacac  14220
ggaaatgttg aatactcata ctcttccttt ttcaatatta ttgaagcatt tatcagggtt  14280
attgtctcat gagcggatac atatttgaat gtatttagaa aaataaacaa ataggggttc  14340
cgcgcacatt tccccgaaaa gtgccacctg acgtctaaga aaccattatt atcatgacat  14400
taacctataa aaataggcgt atcacgaggc cctttcgtct cgcgcgtttc ggtgatgacg  14460
gtgaaaacct ctgacacatg cagctcccgg agacggtcac agcttgtctg taagcggatg  14520
ccgggagcag acaagcccgt cagggcgcgt cagcgggtgt tggcgggtgt cggggctggc  14580
ttaactatgc ggcatcagag cagattgtac tgagagtgca ccatatgcgg tgtgaaatac  14640
cgcacagatg cgtaaggaga aaataccgca tcaggcgcca ttcgccattc aggctgcgca  14700
actgttggga agggcgatcg gtgcgggcct cttcgctatt acgccagctg gcgaaagggg  14760
gatgtgctgc aaggcgatta agttgggtaa cgccagggtt ttcccagtca cgacgttgta  14820
aaacgacggc cagtgaattc gagctcggta cctcgcgaat gcatctagaa gctgcatgtc  14880
taagctagac ccttcagatt aaaaataact gaggtaaggg cctgggtagg ggaggtggtg  14940
tgagacgctc ctgtctctcc tctatctgcc catcggccct ttggggagga ggaatgtgcc  15000
caaggactaa aaaaaggcca tggagccaga ggggcgaggg caacagacct ttcatgggca  15060
aaccttgggg ccctgctgtc tagcatgccc cactacgggt ctaggctgcc catgtaagga  15120
ggcaaggcct ggggacaccc gagatgcctg gttataatta acccagacat gtggctgccc  15180
cccccccccc aacacctgct gcctctaaaa ataaccctgt ccctggtgga tcccctgcat  15240
```

-continued

```
gcgaagatct tcgaacaagg ctgtggggga ctgagggcag gctgtaacag gcttgggggc  15300
cagggcttat acgtgcctgg gactcccaaa gtattactgt tccatgttcc cggcgaaggg  15360
ccagctgtcc cccgccagct agactcagca cttagtttag gaaccagtga gcaagtcagc  15420
ccttggggca gcccatacaa ggccatgggg ctgggcaagc tgcacgcctg ggtccggggt  15480
gggcacggtg cccgggcaac gagctgaaag ctcatctgct ctcaggggcc cctccctggg  15540
gacagcccct cctggctagt cacaccctgt aggctcctct atataaccca ggggcacagg  15600
ggctgccctc attctaccac cacctccaca gcac                              15634

SEQ ID NO: 51          moltype = DNA  length = 281
FEATURE                Location/Qualifiers
source                 1..281
                       mol_type = other DNA
                       organism = synthetic construct
SEQUENCE: 51
tctggatcca ctgcttaaat acggacgagg acagggccct gtctcctcag cttcaggcac  60
caccactgac ctgggacagt gaatcgtaag tactagcagc tacaatccag ctaccattct  120
gcttttattt tatggttggg ataaggctgg attattctga gtccaagcta ggcccttttg  180
ctaatcatgt tcatacctct tatcttcctc ccacagctcc tgggcaacgt gctggtctgt  240
gtgctggccc atcactttgg caaagaattg cgatcgccac c                     281
```

METHODS AND COMPOSITIONS FOR IMPROVED DELIVERY VIA ULTRASOUND

CROSS REFERENCE TO RELATED APPLICATIONS

This application is a continuation of PCT/US2025/055812 filed 17 Nov. 2025 which claims priority to and the benefit of U.S. Provisional Patent Application No. 63/722,045 filed 18 Nov. 2024, and U.S. Provisional Patent Application No. 63/774,082 filed 18 Mar. 2025, U.S. Provisional Patent Application No. 63/805,758 filed 14 May 2025, and U.S. Provisional Patent Application No. 63/894,540 filed 6 Oct. 2025, each of which is incorporated herein by reference in its entirety and for all purposes.

INCORPORATION BY REFERENCE OF SEQUENCE LISTING

The present application is being filed along with a Sequence Listing in electronic format. The Sequence Listing is provided as a file entitled 62668-742601.XML, created Nov. 14, 2025, which is 453,268 bytes in size. The information in the electronic format of the Sequence Listing is incorporated by reference in its entirety.

BACKGROUND

Gene therapy, in which a functional copy of a gene is transfected into a cell, has been proposed as a possible method of treating genetic diseases. One proposed method of delivering a gene therapy to a subject is delivery of therapeutic agents using ultrasound and microbubbles, also referred to as sonoporation. However, prior art methods of gene therapy using ultrasound or sonoporation suffer from significant shortcomings such as low transfection rates, and insufficient gene expression, which have prevented the clinical development and commercialization of these methodologies. There remains a need in the art for more effective gene therapy techniques that can transfect a gene to a cell in an organ or a tissue in a subject in a safe, effective, and durable manner.

SUMMARY

Dystrophinopathy disorders such as Duchenne muscular dystrophy (DMD), Becker muscular dystrophy (BMD), and DMD-associated dilated cardiomyopathy (DCM) are genetic disorders associated with disfunction of the dystrophin gene in mammalian subjects, and are among the most devastating genetic disorders of our time. Lacking a safe and effective treatment, affected subjects generally begin to experience symptoms of progressive muscle fiber degeneration and weakness in mid-childhood to teenage years, with most DMD patients having a life expectancy of only 18 to 25 years. While various gene therapy approaches attempt to a treat dystrophinopathy disorders within the limitations of current technology, such as with delivery of dystrophin truncates or dystrophin fusion proteins, there are no therapies which improve the functional outcome of affected patients by delivering a gene therapy which results in the production of a functional copy of the dystrophin protein.

Aspects disclosed herein provide a method of expressing a nucleic acid encoding a dystrophin protein in a cell of a subject, comprising: administering the nucleic acid encoding the dystrophin protein to the subject, administering a sonoactive agent to the subject, and applying ultrasound energy the cell. Aspects disclosed herein provide a method of treating a dystrophinopathy disorder in a subject in need thereof comprising administering to the subject a nucleic acid encoding a functional dystrophin protein, delivering the nucleic acid to a myocyte in a muscle tissue of the subject along a length of a muscle fiber in the muscle tissue and/or about the sarcolemma of a muscle fiber in the muscle tissue, thereby treating the dystrophinopathy disorder. Aspects disclosed herein provide a method of expressing dystrophin in a subject comprising: inducing uptake by a cell of an expression vector encoding a functional dystrophin protein or a functional fragment thereof. Aspects disclosed herein provide a method of expressing dystrophin in a subject comprising: inducing uptake by a cell in a population of cells of an expression vector encoding a functional dystrophin protein or a functional fragment thereof, in which at least 0.25% of cells in the population of cells uptake the expression vector. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject in an amount exceeding 0.5% of a dystrophin level in a wild type subject not having the dystrophinopathy disorder, thereby treating the dystrophinopathy disorder. Aspects disclosed herein provide a use of a nucleic acid encoding a functional dystrophin protein and a sonoactive agent in a method of treating a subject having a dystrophinopathy disorder requiring a dystrophin gene therapy or a dystrophin protein replacement therapy. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject about the cellular membrane of the myocyte, throughout the cytoplasm of the myocyte, or both about the about the cellular membrane and throughout the cytoplasm of the myocyte, thereby treating the dystrophinopathy disorder. Aspects disclosed herein provide a method of expressing dystrophin in a subject comprising: inducing uptake by a cell in a diaphragm of a subject of an expression vector encoding a functional dystrophin protein or a functional fragment thereof. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject, thereby treating the dystrophinopathy disorder, wherein the nucleic acid encoding the functional dystrophin protein is not conjugated to an antibody. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject, thereby treating the dystrophinopathy disorder, wherein the nucleic acid encoding the functional dystrophin protein is not associated with cationic peptide moieties. Aspects disclosed herein provide a method of treating a dystrophinopathy disorder in a subject in need thereof comprising administering to the subject a nucleic acid encoding a functional dystrophin protein, transfecting the nucleic acid to a muscle tissue of the subject, wherein at least 5% of muscle fibers in the muscle tissue of the subject contain the nucleic acid encoding the functional dystrophin protein. Aspects disclosed herein provide a method of delivering a nucleic acid encoding a functional dystrophin protein in a muscle cell in a muscle tissue of a subject, comprising: administering the nucleic acid encoding the dystrophin protein to the subject wherein a coding sequence of the nucleic acid encoding the dystrophin protein is at least 10000 nucleotides; administering a sonoactive agent to the subject; and applying ultrasound energy having an ultrasound intensity (Ispta) of at least 100 mW/cm2, a pulse length of at least 20 μs, and a duty cycle of less than 5% in which the ultrasound energy applies an acoustic radiation force to the muscle tissue and displaces the muscle tissue by at least 0.1 mm and displaces a volume of blood in the capillaries of the muscle tissue and transmits a pressure wave throughout a vascular system of the muscle tissue thereby disrupting the sonoactive agent and delivering the nucleic acid encoding the dystrophin protein to at least 5% of muscle fibers in the muscle tissue.

In some embodiments, the cells comprise a myocyte, and wherein the functional dystrophin protein or a functional fragment thereof is expressed in the myocyte in an amount exceeding 0.5% of a dystrophin level in a wild type subject. In some embodiments, the cells comprise a myocyte, and wherein the functional dystrophin protein or a functional fragment thereof is expressed (i) about the cellular membrane of the myocyte, (ii) throughout the cytoplasm of the myocyte, or (iii) both about the cellular membrane and throughout the cytoplasm of the myocyte. In some embodiments, the functional dystrophin protein positioned about the sarcolemma is located along a surface of the sarcolemma along a length of the sarcolemma in a direction parallel to the muscle fiber encapsulated within the sarcolemma. In some embodiments, the functional dystrophin protein is expressed in the myocyte in the muscle tissue. In some embodiments, the functional dystrophin protein is expressed along the length of the muscle fiber in the muscle tissue. In some embodiments, the functional dystrophin protein is about the sarcolemma of the muscle fiber in the muscle tissue. In some embodiments, the functional dystrophin protein transfers tension along the length of the muscle fiber or improves a maximum tension loading capacity of the muscle tissue. In some embodiments, at least 1, 3, 5, 10, 15, 20, 25, or 28% of the muscle fibers in the treated muscle tissue comprise the nucleic acid encoding the functional dystrophin protein. In some embodiments, the cell is a myocyte, wherein the dystrophin protein or a functional fragment thereof is expressed in the myocyte in an amount exceeding 0.5% of a dystrophin level in a wild type subject. In some embodiments, the method induces uptake of the nucleic acid into at least 0.25% of a population of cells comprising the cell. In some embodiments, the population of cells is in a cardiac tissue or a heart of the subject, a skeletal muscle tissue or a skeletal muscle of the subject, or a diaphragm tissue or a diaphragm of the subject. In some embodiments, the cell is a multinucleated cell, a myocyte or a muscle cell. In some embodiments, the myocyte or the muscle cell comprises a skeletal muscle myocyte, a cardiomyocyte, or a smooth muscle cell. In some embodiments, the myocyte or the muscle cell is located in a cardiac tissue or a heart of the subject. In some embodiments, dystrophin is expressed in the cardiac tissue or the heart in an amount of at least 0.3, 0.5, 0.75, 1, 2, 3, 4, 5, 6, 7, 8, 9, or 10% of a dystrophin level in human heart whole tissue lysate as measured by western blot assay. In some embodiments, the myocyte or the muscle cell is located in a skeletal muscle tissue or a skeletal muscle of the subject. In some embodiments, the dystrophin is expressed in the muscle tissue or the skeletal muscle in an amount of at least 0.3, 0.5, 0.75, 1, 2, 3, 4, 5% of a dystrophin level in human skeletal muscle whole tissue lysate when measured by western blot assay. In some embodiments, the myocyte or the muscle cell is located in a diaphragm tissue or a diaphragm of the subject. In some embodiments, the dystrophin is expressed in the diaphragm tissue or the diaphragm in an amount of at least 0.3, 0.5, 0.75, 1, 2, 3, 4, 5, 6, 7, 8, 9, or 10% of a dystrophin level in human diaphragm whole tissue lysate when measured by western blot assay. In some embodiments, the dystrophin is expressed in the cardiac tissue, the muscle tissue, or the diaphragm tissue, throughout a treated organ comprising the cardiac tissue, the muscle tissue, or the diaphragm tissue. In some embodiments, the dystrophin is expressed at detectable levels throughout the treated organ in two or more samples taken from opposite ends of the treated organ. In some embodiments, the nucleic acid or the expression vector is an unencapsulated nucleic acid. In some embodiments, the nucleic acid encodes a full length dystrophin protein. In some embodiments, a coding sequence of the nucleic acid encoding the full length dystrophin protein is at least 5000, 6000, 7000, 8000, 9000, 10000, or 11000 nucleotides. In some embodiments, a length the functional dystrophin protein is at least 1750, 2000, 2250, 2500, 2750, 3000, or 3250 amino acids. In some embodiments, the myocyte is a skeletal muscle myocyte and wherein dystrophin is expressed in the myocyte at a level of at least 1, 2, 3, 4, 5, 10, 20, 30, 40, 50, 60, 70, 80, 90, 100, 110, or 120% of a normal dystrophin level in a subject not having a dystrophinopathy disorder. A normal dystrophin level in skeletal muscle tissue generally refers to a dystrophin level in human skeletal muscle whole tissue lysate. In some embodiments, a coding sequence of the functional dystrophin protein is at least 5000, 6000, 7000, 8000, 9000, 10000, or 11000 nucleotides. In some embodiments, the method further includes administering a sonoactive agent to the subject, and applying ultrasound energy a cell of the subject. In some embodiments, a length the functional dystrophin protein is at least 1750, 2000, 2250, 2500, 2750, 3000, or 3250 amino acids. In some embodiments, a coding sequence of the functional dystrophin protein is at least 5000 nucleotides. In some embodiments, the nucleic acid encoding the functional dystrophin protein and the sonoactive agent are configured to induce expression of the functional dystrophin protein in a cell of the subject upon administration of ultrasound energy to the cell. In some embodiments, a coding sequence of the dystrophin protein is at least 6000, 7000, 8000, 9000, 10000, or 11000 nucleotides. In some embodiments, the coding sequence of the dystrophin protein encodes a functional dystrophin protein. In some embodiments, the dystrophin protein is at least 1750, 2000, 2250, 2500, 2750, 3000, or 3250 amino acids in length. In some embodiments, the coding sequence of the functional dystrophin protein encodes a full length dystrophin protein. In some embodiments, the functional dystrophin protein is at least 1750, 2000, 2250, 2500, 2750, 3000, or 3250 amino acids in length. In some embodiments, the nucleic acid encoding the dystrophin protein further comprises a promoter sequence. In some embodiments, the promoter sequence comprises a sequence of any one of SEQ ID NO: 4-5, or 18. In some embodiments, the nucleic acid encoding the dystrophin protein further comprises a post transcriptional regulatory element. In some embodiments, the post transcriptional regulatory element comprises the sequence of any one of SEQ ID NO: 8-10. In some embodiments, the nucleic acid encoding the dystrophin protein further comprises a nuclear targeting sequence. In some embodiments, the nuclear targeting sequence comprise a sequence of SEQ ID NO: 11. In some embodiments, the nucleic acid encoding the dystrophin protein further comprises a post transcriptional regulatory element and a nuclear targeting sequence. In some embodiments, the post transcriptional regulatory element and the nuclear targeting sequence comprise a sequence of SEQ ID NO: 12. In some embodiments, the nucleic acid encoding the dystrophin protein comprises the sequence of any one of SEQ ID NO: 2-3. In some embodiments, the nucleic acid encoding the dystrophin protein comprises the sequence of any one of SEQ ID NO: 6-7. In some embodiments, the cell is a myocyte. In some embodiments, the muscle cell comprises a skeletal muscle myocyte, a cardiomyocyte, or a smooth muscle cell. In some embodiments, the muscle cell is located within a muscle tissue of the subject, the method further comprising one or more of: applying heat to the muscle tissue, or increasing a blood flow rate in the muscle tissue. In some embodiments, heat is applied to the muscle tissue using a transcutaneous compress at a temperature of at least 37 C. In some embodiments, heat is applied to the muscle tissue using ultrasound energy. In some embodiments, a coding sequence of the nucleic acid encoding the full length dystrophin protein is contiguous. In some embodiments, the nucleic acid coding sequence of the functional dystrophin protein is contiguous. In some embodiments, at least 6, 7, 8, 9. 10, 11, 12, 13, 14, 15, 16, 17, 18, 19, 20, 21, 22, 23, 24, 25, 26, 27, 28, 29, 30, 35, 40, 45, 50, 55, 60, or 65% of muscle fibers in the muscle tissue of the subject contain the nucleic acid encoding the functional dystrophin protein. In some embodiments, at least 1% of muscle fibers in the muscle tissue of the subject express the dystrophin protein. In some embodiments, the cell or the myocyte is in a muscle tissue of the subject, wherein administering the sonoactive agent to the subject comprises distributing the sonoactive agent throughout the capillaries of the muscle tissue. In some embodiments, applying the ultrasound energy comprises applying an acoustic radiation force to the muscle tissue In some embodiments, applying the acoustic radiation force comprises displacing the muscle tissue In some embodiments, applying the acoustic radiation force comprises displacing a volume of blood in the capillaries of the muscle tissue In some embodiments, displacing the volume of blood in the capillaries of the muscle tissue transmits a pressure wave throughout a vascular system of the muscle tissue, thereby disrupting the sonoactive agent. In some embodiments, the pressure wave does and/or the ultrasound energy applying the acoustic radiation force does not induce vibrational cavitation of the sonoactive agent. In some embodiments, the muscle tissue is located in a heart or a diaphragm of the subject. In some embodiments, administering the ultrasound acoustic energy comprises applying a first ultrasound energy at a MI of up to 0.4, and a first second ultrasound energy at a MI of greater than 0.4 and up to 3.0. In some embodiments, administering the ultrasound acoustic energy comprises applying a first ultrasound energy at a MI of up to 0.4, and a first second ultrasound energy at a MI of 0.8-1.9. In some embodiments, administering the ultrasound acoustic energy comprises applying an acoustic radiation force to the subject. In some embodiments, the ultrasound energy is applied at an intensity (ISPTA) of at least 200 mW/cm2. In some embodiments, the ultrasound energy displaces a muscle tissue of the subject by at least 0.1 mm. In some embodiments, the ultrasound energy is applied at a pulse length of at least 20 microseconds. In some embodiments, the sonoactive agent comprises a shell filled with a gas. In some embodiments, the shell comprises a protein stabilized shell or a lipid stabilized shell. In some embodiments, the gas comprises a perfluorinated case. In some embodiments, the sonoactive agent comprises microbubbles. In some embodiments, the sonoactive agent comprises nanobubbles. In some embodiments, the subject has a mutation in a gene encoding a dystrophin protein in a genome of the subject. In some embodiments, the subject has a dystrophinopathy disorder. In some embodiments, the dystrophinopathy disorder comprises Duchenne muscular dystrophy (DIMD), Becker muscular dystrophy (BMD), or DMD-associated dilated cardiomyopathy. In some embodiments, the dystrophinopathy disorder comprises Duchenne muscular dystrophy (DMD), and wherein the cell is a skeletal muscle myocyte. In some embodiments, the dystrophinopathy disorder comprises Becker muscular dystrophy (BMD), and wherein the cell is a skeletal muscle myocyte. In some embodiments, the dystrophinopathy disorder comprises DMD-associated dilated cardiomyopathy, and wherein the cell is a cardiac myocyte. In some embodiments, administering the nucleic acid, administering the sonoactive agent, and applying the ultrasound energy induces expression of the dystrophin protein thereby treating the subject having the dystrophinopathy disorder. In some embodiments, the method reduces or ameliorates a symptom of the dystrophinopathy disorder in the subject. In some embodiments, the method further includes administering a second dose of the nucleic acid encoding the dystrophin protein, the sonoactive agent, and the ultrasound energy to the subject. In some embodiments, the subject is a mammalian subject. In some embodiments, the subject is a human subject. In some embodiments, the nucleic acid encoding the dystrophin protein is not comprised within a viral vector. In some embodiments, the subject is non-embryonic. In some embodiments, the subject weighs at least 5 kg Aspects disclosed herein provide a nucleic acid comprising a nucleic acid sequence having at least 90% sequence identity to SEQ ID NO: 4. In some embodiments, the nucleic acid sequence has at least 91% sequence identity to SEQ ID NO: 4. In some embodiments, the nucleic acid sequence has at least 92% sequence identity to SEQ ID NO: 4. In some embodiments, the nucleic acid sequence has at least 93% sequence identity to SEQ ID NO: 4. In some embodiments, the nucleic acid sequence has at least 94% sequence identity to SEQ ID NO: 4. In some embodiments, the nucleic acid sequence has at least 95% sequence identity to SEQ ID NO: 4. In some embodiments, the nucleic acid sequence has at least 96% sequence identity to SEQ ID NO: 4. In some embodiments, the nucleic acid sequence has at least 97% sequence identity to SEQ ID NO: 4. In some embodiments, the nucleic acid sequence has at least 98% sequence identity to SEQ ID NO: 4. In some embodiments, the nucleic acid sequence has at least 99% sequence identity to SEQ ID NO: 4. In some embodiments, the nucleic acid sequence is a muscle tissue specific promoter sequence. In some embodiments, the nucleic acid sequence enhances expression of a therapeutic transgene in a muscle cell. In some embodiments, the muscle cell comprises a myocyte, a cardiomyocyte, or a smooth muscle cell. In some embodiments, the nucleic acid sequence facilitates expression of a transgene coupled to the promoter for at least 30, 60, 90, 120, 150, 180, 210, 240, 270, or 275 days. In some embodiments, the nucleic acid sequence is comprised within a nucleic acid delivery vector and coupled to a nucleic acid coding sequence encoding a therapeutic transgene, wherein the therapeutic transgene encodes a protein having at least 90% sequence identity to SEQ ID NO: 13. Aspects disclosed herein provide a nucleic acid delivery vector comprising the nucleic acid which is a muscle tissue specific promoter sequence having at least 90% sequence identity to SEQ ID NO: 4. Aspects disclosed herein provide a pharmaceutical composition comprising the nucleic acid which is a muscle tissue specific promoter sequence having at least 90% sequence identity to SEQ ID NO: 4. Aspects disclosed herein provide a cell comprising the nucleic acid which is a muscle tissue specific promoter sequence having at least 90% sequence identity to SEQ ID NO: 4. Aspects disclosed herein provide a kit comprising: 1) a sonoactive agent; and 2) means for expressing a therapeutic transgene in a subject. Aspects disclosed herein provide a kit comprising: 1) a sonoactive agent; and 2) the nucleic acid which is a muscle tissue specific promoter sequence having at least 90% sequence identity to SEQ ID NO: 4.

Aspects disclosed herein provide a nucleic acid comprising a nucleic acid sequence having at least 90% sequence identity to SEQ ID NO: 34. In some embodiments, the nucleic acid sequence has at least 91% sequence identity to SEQ ID NO: 34. In some embodiments, the nucleic acid sequence has at least 92% sequence identity to SEQ ID NO: 34. In some embodiments, the nucleic acid sequence has at least 93% sequence identity to SEQ ID NO: 34. In some embodiments, the nucleic acid sequence has at least 95% sequence identity to SEQ ID NO: 34. In some embodiments, the nucleic acid sequence has at least 97% sequence identity to SEQ ID NO: 34. In some embodiments, the nucleic acid sequence has at least 99% sequence identity to SEQ ID NO: 34. In some embodiments, the nucleic acid sequence is SEQ ID NO: 34. In some embodiments, the nucleic acid sequence encodes a dystrophin protein. In some embodiments, the nucleic acid sequence encodes a full length dystrophin protein. In some embodiments, the nucleic acid sequence encodes a dystrophin protein at least 3500 amino acids in length. In some embodiments, the nucleic acid sequence encodes a protein having at least 90% sequence identity to SEQ ID NO: 13. In some embodiments, the nucleic acid sequence comprises a muscle tissue specific promoter sequence. In some embodiments, the muscle tissue specific promoter sequence enhances expression of a dystrophin protein in a muscle cell. In some embodiments, the muscle cell comprises a myocyte, a cardiomyocyte, or a smooth muscle cell. In some embodiments, the nucleic acid sequence is an expression cassette for a dystrophin protein. In some embodiments, the nucleic acid sequence is an expression cassette for a dystrophin protein optimized for expression of the dystrophin protein in mammalian cells. In some embodiments, the nucleic acid sequence is an expression cassette for a dystrophin protein optimized for expression of the dystrophin protein in myocytes. In some embodiments, the nucleic acid sequence is comprised within a nucleic acid delivery vector having a sequence of SEQ ID NO: 17.

Aspects disclosed herein provide a nucleic acid sequence comprising a sequence having at least 80% sequence identity to any one of SEQ ID NO: 2-3. In some embodiments, the nucleic acid sequence has at least 81, 82, 83, 84, 85, 86, 87, 88, 89, 90, 91, 92, 93, 94, 95, 96, 97, 98, or 99% sequence identity to any one of SEQ ID NO: 2-3. In some embodiments, the nucleic acid sequence is any one of SEQ ID NO: 2-3. In some embodiments, the nucleic acid sequence encodes a dystrophin protein. In some embodiments, the nucleic acid sequence encodes a full length dystrophin protein. In some embodiments, the nucleic acid sequence encodes a dystrophin protein at least 3500 amino acids in length. Aspects disclosed herein provide a nucleic acid delivery vector comprising the nucleic acid of embodiments disclosed herein. Aspects disclosed herein provide a use of the nucleic acids of any one of embodiments disclosed herein in a method of treating a subject having a dystrophinopathy disorder requiring a dystrophin gene therapy or a dystrophin protein replacement therapy. Aspects disclosed herein provide a pharmaceutical composition comprising the nucleic acid of embodiments disclosed herein. Aspects disclosed herein provide a use of the pharmaceutical composition of embodiments disclosed herein in a method of treating a subject having a dystrophinopathy disorder requiring a dystrophin gene therapy or a dystrophin protein replacement therapy. In some embodiments, the dystrophinopathy disorder comprises Duchenne muscular dystrophy (DMD), Becker muscular dystrophy (BMD), or DMD-associated dilated cardiomyopathy. In some embodiments, the dystrophinopathy disorder comprises Duchenne muscular dystrophy (DMD), and wherein the cell is a skeletal muscle myocyte. In some embodiments, the dystrophinopathy disorder comprises Becker muscular dystrophy (BMD), and wherein the cell is a skeletal muscle myocyte. In some embodiments, the dystrophinopathy disorder comprises DMD-associated dilated cardiomyopathy, and wherein the cell is a cardiac myocyte. Aspects disclosed herein provide a cell comprising the nucleic acid of embodiments disclosed herein.

Aspects disclosed herein provide a nucleic acid comprising a nucleic acid sequence having at least 80% sequence identity to any one of SEQ ID NO: 4-5. In some embodiments, the nucleic acid has at least 81, 82, 83, 84, 85, 86, 87, 88, 89, 90, 91, 92, 93, 94, 95, 96, 97, 98, or 99% sequence identity to any one of SEQ ID NO: 4-5. In some embodiments, the nucleic acid is a muscle tissue specific promoter sequence. In some embodiments, the nucleic acid which comprises the muscle specific promoter sequence facilitates expression of a transgene coupled to the promoter for at least 30, 60, 90, 120, 150, 180, 210, 240, 270, or 275 days. In some embodiments, a nucleic acid delivery vector comprises the muscle specific promoter sequence facilitates expression of a transgene coupled to the promoter for at least 30, 60, 90, 120, 150, 180, 210, 240, 270, or 275 days. In some embodiments, the nucleic acid enhances expression of a therapeutic transgene in a muscle cell. In some embodiments, the muscle cell comprises a myocyte, a cardiomyocyte, or a smooth muscle cell. Aspects disclosed herein provide a nucleic acid delivery vector comprising the nucleic acid of any one of embodiments disclosed. Aspects disclosed herein provide a use of the nucleic acid of any one of embodiments disclosed in a method of treating a subject having a dystrophinopathy disorder requiring a dystrophin gene therapy or a dystrophin protein replacement therapy. Aspects disclosed herein provide a pharmaceutical composition comprising the nucleic acid of any one of embodiments disclosed. Aspects disclosed herein provide a use of the pharmaceutical composition of embodiments disclosed in a method of treating a subject having a dystrophinopathy disorder requiring a dystrophin gene therapy or a dystrophin protein replacement therapy. Aspects disclosed herein provide a cell comprising the nucleic acid of any one of embodiments disclosed. In some embodiments, the dystrophinopathy disorder comprises Duchenne muscular dystrophy (DMD), Becker muscular dystrophy (BMD), or DMD-associated dilated cardiomyopathy. In some embodiments, the dystrophinopathy disorder comprises Duchenne muscular dystrophy (DMD), and wherein the cell is a skeletal muscle myocyte. In some embodiments, the dystrophinopathy disorder comprises Becker muscular dystrophy (BMD), and wherein the cell is a skeletal muscle myocyte. In some embodiments, the dystrophinopathy disorder comprises DMD-associated dilated cardiomyopathy, and wherein the cell is a cardiac myocyte.

Aspects disclosed herein provide a nucleic acid comprising a promoter sequence having at least 90% sequence identity to SEQ ID NO: 18. In some embodiments, the promoter sequence has at least 91, 92, 93, 94, 95, 96, 97, 98, or 99% sequence identity to SEQ ID NO: 18. In some embodiments, the promoter sequence is SEQ ID NO: 18.

Aspects disclosed herein provide a nucleic acid comprising a sequence which has at least 80% sequence identity to any one of SEQ ID NO: 16-17. Aspects disclosed herein provide a nucleic acid comprising a sequence of SEQ ID NO: 16-17.

In some embodiments, a coding sequence of the nucleic acid encoding the full length dystrophin protein is contiguous. In some embodiments, the nucleic acid coding sequence of the functional dystrophin protein is contiguous. In some embodiments, at least 6, 7, 8, 9. 10, 11, 12, 13, 14, 15, 16, 17, 18, 19, 20, 21, 22, 23, 24, 25, 26, 27, 28, 29, 30, 35, 40, 45, 50, 55, 60, or 65% of muscle fibers in the muscle tissue of the subject contain the nucleic acid encoding the functional dystrophin protein. In some embodiments, at least 1% of muscle fibers in the muscle tissue of the subject express the dystrophin protein. In some embodiments, the cell or the myocyte is in a muscle tissue of the subject, wherein administering the sonoactive agent to the subject comprises distributing the sonoactive agent throughout the capillaries of the muscle tissue. In some embodiments, applying the ultrasound energy comprises applying an acoustic radiation force to the muscle tissue In some embodiments, applying the acoustic radiation force comprises displacing the muscle tissue In some embodiments, applying the acoustic radiation force comprises displacing a volume of blood in the capillaries of the muscle tissue In some embodiments, displacing the volume of blood in the capillaries of the muscle tissue transmits a pressure wave throughout a vascular system of the muscle tissue, thereby disrupting the sonoactive agent. In some embodiments, the pressure wave does and/or the ultrasound energy applying the acoustic radiation force does not induce vibrational cavitation of the sonoactive agent.

Aspects disclosed herein provide a kit comprising: 1) a sonoactive agent; and 2) means for expressing a functional dystrophin protein in a subject. Aspects disclosed herein provide a kit comprising: 1) a sonoactive agent; and 2) a nucleic acid of any one of SEQ ID NO: 1-12 and 14-50. Aspects disclosed herein provide a kit comprising: 1) a sonoactive agent; and 2) the nucleic acid of SEQ ID NOS: 2-7, 34-36, or 37-40. In some embodiments, the kit further comprises instructions for administering ultrasound acoustic energy to a subject to facilitate expression of the functional dystrophin protein in a subject. In some embodiments, the kit further comprises instructions for administering ultrasound acoustic energy to a subject to facilitate expression of the nucleic acid in a subject. In some embodiments, the sonoactive agent comprises lipid-stabilized microstructures. In some embodiments, wherein the lipid-stabilized microstructures comprise a lipid stabilized shell surrounding a perfluorinated gas core. In some embodiments, the lipid stabilized shell comprises a monomolecular membrane of hydrogenated egg yolk phosphatidyl serine, wherein the perfluorinated gas core comprises perfluorobutane gas. In some embodiments, the sonoactive agent is a Sonazoid microbubble. In some embodiments, the sonoactive agent comprises protein stabilized microstructures. In some embodiments, the protein stabilized microstructures comprise an albumin stabilized shell surrounding a perfluorinated gas core. In some embodiments, the protein stabilized microstructures are Optison microbubbles.

Aspects disclosed herein provide a nucleic acid comprising a sequence which has at least 80% sequence identity to any one of SEQ ID NO: 1-12 and 14-50. Aspects disclosed herein provide a nucleic acid comprising a sequence of SEQ ID NO: 1-12 and 14-50.

Aspects disclosed herein provide a nucleic acid comprising a promoter sequence having at least 90% sequence identity to any one of SEQ ID NOS: 37-40. In some embodiments, the promoter sequence comprises at least 91, 92, 93, 94, 95, 96, 97, 98, or 99% sequence identity to any one of SEQ ID NOS: 37-40. In some embodiments, the promoter sequence comprises any one of SEQ ID NOS: 37-40. In some embodiments, the promoter sequence is configured to increase expression of a nucleic acid encoding a therapeutic protein operably coupled to the promoter sequence. In some embodiments, the promoter sequence is configured to increase expression of a nucleic acid encoding a therapeutic protein operably coupled to the promoter sequence in multiple cell types. In some embodiments, the promoter sequence is configured to increase expression of the nucleic acid encoding the therapeutic protein in a muscle cell. In some embodiments, the promoter sequence is configured to increase expression of the nucleic acid encoding the therapeutic protein in a kidney cell. In some embodiments, the promoter sequence is configured to increase expression of the nucleic acid encoding the therapeutic protein in a liver cell. In some embodiments, the liver cell is a hepatocyte, or a LSEC. In some embodiments, the promoter sequence is configured to increase expression of the nucleic acid encoding the therapeutic protein in a myocyte. Aspects disclosed herein provide nucleic acid delivery vector comprising the nucleic acid of any one of the present embodiments disclosed herein. Aspects disclosed herein provide pharmaceutical composition comprising the nucleic acid of any one of the present embodiments disclosed herein Aspects disclosed herein provide cell comprising the nucleic acid of any one of the present embodiments disclosed herein. Aspects disclosed herein provide method of treating a subject comprising administering the nucleic acid of any one of the present embodiments disclosed herein. In some embodiments, the method further includes administering ultrasound to the subject. In some embodiments, the method further includes administering a sonoactive agent to the subject. In some embodiments, the method further includes administering a lipid nanoparticle or a polymer nanoparticle to the subject. In some embodiments, the nucleic acid is contained within a viral vector.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
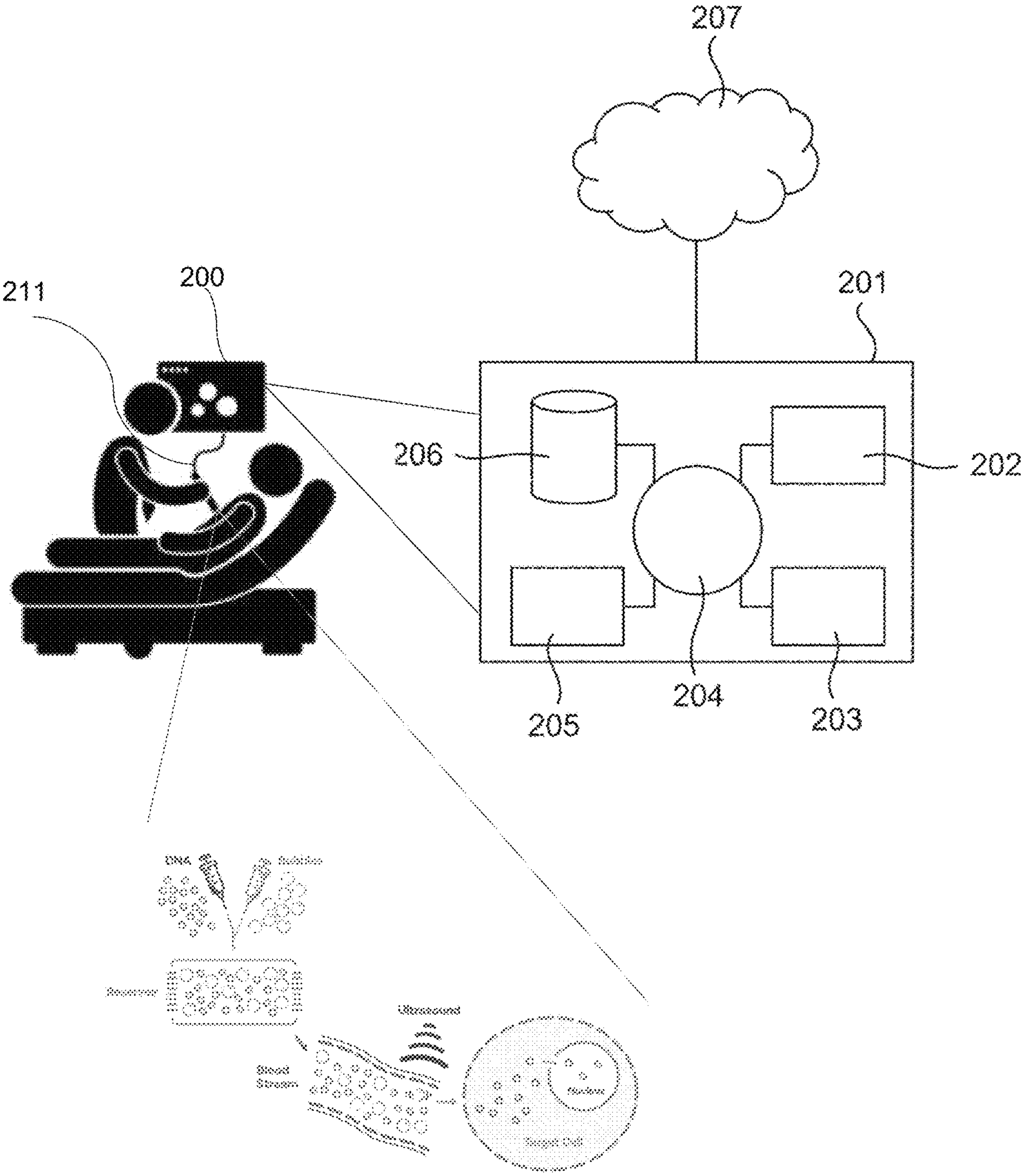
FIG. 1 illustrates an exemplary ultrasound transducer system having computer processors with a computer readable medium storing instructions for implementing the methods of the present disclosure.

Dystrophinopathy disorders such as Duchenne muscular dystrophy (DMD), Becker muscular dystrophy (BMD), and DMD-associated dilated cardiomyopathy (DCM) are genetic disorders associated with disfunction of the dystrophin gene in mammalian subjects, and are among the most devastating genetic disorders of our time. Lacking a safe and effective treatment, affected subjects generally begin to experience symptoms of progressive muscle fiber degeneration and weakness in mid-childhood to teenage years, with most DMD patients having a life expectancy of only 18 to 25 years. While various gene therapy approaches attempt to a treat dystrophinopathy disorders within the limitations of current technology, such as with delivery of dystrophin truncates or dystrophin fusion proteins, there are no therapies which improve the functional outcome of affected patients by delivering a gene therapy which results in the production of a functional copy of the dystrophin protein.

Dystrophinopathy disorders are exceptionally difficult genetic disorders to treat due to the many challenges associated with attempting to deliver and express a functional copy of the dystrophin protein in affected subjects. Extensive muscle mass in skeletal muscles and heart are difficult to target with viral vectors, with most viral vectors poorly penetrating through vascular tissue to reach myocytes, and significant immune response to viral vectors in the skeletal muscles and heart further reducing their ability target these tissues. In addition, dystrophin is among the largest genes in the human genome at over 3500 amino acids, and far exceeds the carrying capacity of viral vectors for gene replacement therapies. Other gene therapy approaches such as gene editing with CRISPR or exon skipping are disfavored modalities for correction of the dystrophin gene because they would need to be tailored for specific mutations in view of the large length of the dystrophin gene, limiting the broad applicability of any such therapy. Further, the early on-set of most dystrophinopathy disorders also requires effective treatments to start in childhood, which significantly limits the options for readministering the gene therapy, and complicating development efforts. Proposed herein are methods of expressing a functional dystrophin protein in a cell of a subject using an ultrasound based delivery modality which is highly effective at inducing expression of the dystrophin protein, while also avoiding many of the problems associated with prior approaches such as the lack of general applicability, the inability to transfect a large or full length dystrophin protein, inability to repeatedly dose subjects, and safety/toxicity concerns.

Aspects disclosed herein provide a method of expressing a nucleic acid encoding a dystrophin protein in a cell of a subject, comprising: administering the nucleic acid encoding the dystrophin protein to the subject, administering a sonoactive agent to the subject, and applying ultrasound energy the cell. Aspects disclosed herein provide a method of treating a dystrophinopathy disorder in a subject in need thereof comprising administering to the subject a nucleic acid encoding a functional dystrophin protein, delivering the nucleic acid to a myocyte in a muscle tissue of the subject along a length of a muscle fiber in the muscle tissue and/or about the sarcolemma of a muscle fiber in the muscle tissue, thereby treating the dystrophinopathy disorder. Aspects disclosed herein provide a method of expressing dystrophin in a subject comprising: inducing uptake by a cell in a population of cells of an expression vector encoding a functional dystrophin protein or a functional fragment thereof, in which at least 0.25% of cells in the population of cells uptake the expression vector. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject in an amount exceeding 0.5% of a dystrophin level in a wild type subject not having the dystrophinopathy disorder, thereby treating the dystrophinopathy disorder. Aspects disclosed herein provide a use of a nucleic acid encoding a functional dystrophin protein and a sonoactive agent in a method of treating a subject having a dystrophinopathy disorder requiring a dystrophin gene therapy or a dystrophin protein replacement therapy. Aspects disclosed herein provide a method of delivering a nucleic acid encoding a functional dystrophin protein in a muscle cell in a muscle tissue of a subject, comprising: administering the nucleic acid encoding the dystrophin protein to the subject wherein a coding sequence of the nucleic acid encoding the dystrophin protein is at least 10000 nucleotides; administering a sonoactive agent to the subject; and applying ultrasound energy having an ultrasound intensity (Ispta) of at least 100 mW/cm2, a pulse length of at least 20 μs, and a duty cycle of less than 5% in which the ultrasound energy applies an acoustic radiation force to the muscle tissue and displaces the muscle tissue by at least 0.1 mm and displaces a volume of blood in the capillaries of the muscle tissue and transmits a pressure wave throughout a vascular system of the muscle tissue thereby disrupting the sonoactive agent and delivering the nucleic acid encoding the dystrophin protein to at least 5% of muscle fibers in the muscle tissue.

In some embodiments, the cells comprise a myocyte, and wherein the functional dystrophin protein or a functional fragment thereof is expressed in the myocyte in an amount exceeding 0.5% of a dystrophin level in a wild type subject. In some embodiments, the cells comprise a myocyte, and wherein the functional dystrophin protein or a functional fragment thereof is expressed (i) about the cellular membrane of the myocyte, (ii) throughout the cytoplasm of the myocyte, or (iii) both about the cellular membrane and throughout the cytoplasm of the myocyte. In some embodiments, the functional dystrophin protein positioned about the sarcolemma is located along a surface of the sarcolemma along a length of the sarcolemma in a direction parallel to the muscle fiber encapsulated within the sarcolemma. In some embodiments, the cell is a myocyte, wherein the dystrophin protein or a functional fragment thereof is expressed in the myocyte in an amount exceeding 0.5% of a dystrophin level in a wild type subject. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject about the cellular membrane of the myocyte, throughout the cytoplasm of the myocyte, or both about the about the cellular membrane and throughout the cytoplasm of the myocyte, thereby treating the dystrophinopathy disorder. Aspects disclosed herein provide a method of expressing dystrophin in a subject comprising: inducing uptake by a cell in a diaphragm of a subject of an expression vector encoding a functional dystrophin protein or a functional fragment thereof. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject, thereby treating the dystrophinopathy disorder, wherein the nucleic acid encoding the functional dystrophin protein is not conjugated to an antibody. Aspects disclosed herein provide a method of treating a dystrophinopathy disorder in a subject in need thereof comprising administering to the subject a nucleic acid encoding a functional dystrophin protein, expressing the functional dystrophin protein or a functional fragment thereof in a myocyte of the subject, thereby treating the dystrophinopathy disorder, wherein the nucleic acid encoding the functional dystrophin protein is not associated with cationic peptide moieties. Aspects disclosed herein provide a method of treating a dystrophinopathy disorder in a subject in need thereof comprising administering to the subject a nucleic acid encoding a functional dystrophin protein, transfecting the nucleic acid to a muscle tissue of the subject, wherein at least 5% of muscle fibers in the muscle tissue of the subject contain the nucleic acid encoding the functional dystrophin protein.

Dystrophin is a critical structural protein essential for maintaining the integrity and functionality of muscle cells. Encoded by a gene located on the X chromosome, dystrophin's absence or dysfunction leads to severe muscle disorders like Duchenne muscular dystrophy (DMD) and Becker muscular dystrophy (BMD). Structurally, dystrophin is a large rod-shaped protein with a molecular weight of approximately 427 kDa. It consists of several domains: the N-terminal actin-binding domain (ABD), which anchors dystrophin to the intracellular actin cytoskeleton and provides mechanical support; the central rod domain, made up of 24 spectrin-like repeats and hinge regions, giving the protein its flexibility and elasticity; the cysteine-rich domain, which connects dystrophin to 0-dystroglycan in the sarcolemma via the dystroglycan complex; and the C-terminal domain, which interacts with syntrophins and dystrobrevin to form and stabilize the dystrophin-associated protein complex (DAPC). Functionally, dystrophin serves as a mechanical stabilizer and a signaling hub within muscle cells. It links the internal actin cytoskeleton to the extracellular matrix (ECM) via the DAPC, distributing mechanical forces generated during muscle contraction and protecting the sarcolemma from damage. This connection maintains sarcolemma integrity, preventing ruptures and excessive permeability. Additionally, dystrophin facilitates signal transduction by interacting with various proteins in the DAPC, modulating cellular pathways critical for muscle repair, regeneration, and stress response. The protein also contributes to calcium homeostasis by stabilizing membrane channels that control calcium influx, thereby protecting muscle cells from calcium-mediated damage. Furthermore, dystrophin helps mitigate fibrosis and inflammation, which are consequences of sarcolemma instability in its absence.

It is proposed that one possible reason for the failure of prior gene therapies to produce a functional copy of a dystrophin protein is due to the inability to deliver a full length dystrophin protein, or a fragment thereof which approaches a full length dystrophin protein. Most AAV vectors seeking to delivery dystrophin truncates only result in expression of dystrophin truncates of less than 1500 amino acids, far fewer than the 3500 amino acids of the native protein. Similarly, other AAV and viral vectors seeking to delivery dystrophin fragments for formation of a fusion protein also fail to form functional dystrophin protein in the subject. As is disclosed herein, the methods disclosed herein provide a beneficial technical effect of allowing for the delivery of gene therapies encoding large and, in some cases, full length dystrophin protein. In some cases, the expression of such large and/or full length dystrophin proteins in subjects can provide beneficial technical effect of treating or ameliorating a symptom of a dystrophinopathy disorders where prior gene therapies have failed to do so.

In some embodiments, the method induces uptake of the nucleic acid into at least 0.25% of a population of cells comprising the cell. In some embodiments, the population of cells is in a cardiac tissue or a heart of the subject, a skeletal muscle tissue or a skeletal muscle of the subject, or a diaphragm tissue or a diaphragm of the subject. In some embodiments, the cell is a multinucleated cell, a myocyte or a muscle cell. In sone embodiments, the functional dystrophin protein or a functional fragment thereof is expressed about the cellular membrane of the myocyte, throughout the cytoplasm of the myocyte, or both about the about the cellular membrane and throughout the cytoplasm of the myocyte. In some embodiments, the myocyte or the muscle cell comprises a skeletal muscle myocyte, a cardiomyocyte, or a smooth muscle cell. In some embodiments, the myocyte or the muscle cell is located in a cardiac tissue or a heart of the subject. In some embodiments, dystrophin is expressed in the cardiac tissue or the heart in an amount of at least 0.3, 0.5, 0.75, 1, 2, 3, 4, 5, 6, 7, 8, 9, or 10% of a dystrophin level in human heart whole tissue lysate as measured by western blot assay. In some embodiments, the myocyte or the muscle cell is located in a skeletal muscle tissue or a skeletal muscle of the subject. In some embodiments, the dystrophin is expressed in the muscle tissue or the skeletal muscle in an amount of at least 0.3, 0.5, 0.75, 1, 2, 3, 4, 5% of a dystrophin level in human skeletal muscle whole tissue lysate when measured by western blot assay. In some embodiments, the myocyte or the muscle cell is located in a diaphragm tissue or a diaphragm of the subject. In some embodiments, the dystrophin is expressed in the diaphragm tissue or the diaphragm in an amount of at least 0.3, 0.5, 0.75, 1, 2, 3, 4, 5, 6, 7, 8, 9, or 10% of a dystrophin level in human diaphragm whole tissue lysate when measured by western blot assay. In some embodiments, the dystrophin is expressed in the cardiac tissue, the muscle tissue, or the diaphragm tissue, throughout a treated organ comprising the cardiac tissue, the muscle tissue, or the diaphragm tissue. In some embodiments, the dystrophin is expressed at detectable levels throughout the treated organ in two or more samples taken from opposite ends of the treated organ. In some embodiments, the nucleic acid or the expression vector is an unencapsulated nucleic acid. In some embodiments, a coding sequence of the nucleic acid encoding the full length dystrophin protein is contiguous. In some embodiments, the nucleic acid coding sequence of the functional dystrophin protein is contiguous. In some embodiments, at least 6, 7, 8, 9. 10, 11, 12, 13, 14, 15, 16, 17, 18, 19, 20, 21, 22, 23, 24, 25, 26, 27, 28, 29, 30, 35, 40, 45, 50, 55, 60, or 65% of muscle fibers in the muscle tissue of the subject contain the nucleic acid encoding the functional dystrophin protein. In some embodiments, at least 1% of muscle fibers in the muscle tissue of the subject express the dystrophin protein.

Aspects disclosed herein provide a method of delivering a nucleic acid encoding a functional dystrophin protein in a muscle cell in a muscle tissue of a subject, comprising: administering the nucleic acid encoding the dystrophin protein to the subject wherein a coding sequence of the nucleic acid encoding the dystrophin protein is at least 10000 nucleotides; administering a sonoactive agent to the subject; and applying ultrasound energy having an ultrasound intensity (Ispta) of at least 100 mW/cm2, a pulse length of at least 20 μs, and a duty cycle of less than 5% in which the ultrasound energy applies an acoustic radiation force to the muscle tissue and displaces the muscle tissue by at least 0.1 mm and displaces a volume of blood in the capillaries of the muscle tissue and transmits a pressure wave throughout a vascular system of the muscle tissue thereby disrupting the sonoactive agent and delivering the nucleic acid encoding the dystrophin protein to at least 5% of muscle fibers in the muscle tissue. In some embodiments, the method includes applying heat to the muscle tissue and increasing a perfusion of the nucleic acid and the sonoactive agent in the muscle tissue before administering the ultrasound. In some cases, the methods of administration and the ultrasound mediated delivery described herein which includes perfusing the muscle tissue with the sonoactive agent and the nucleic acid and then applying ultrasound energy having an ultrasound intensity (Ispta) of at least 100 mW/cm2, a pulse length of at least 20 μs, and a duty cycle of less than 5% in which the ultrasound energy applies an acoustic radiation force to the muscle tissue and displaces the muscle tissue by at least 0.1 mm and displaces a volume of blood in the capillaries of the muscle tissue and transmits a pressure wave throughout a vascular system of the muscle tissue provides a beneficial technical effect in disrupting the sonoactive agent throughout the muscle tissue and delivering the nucleic acid encoding the dystrophin protein to at least 5% of muscle fibers in the muscle tissue. In some cases, the method further provides a technical benefit of properly localizing the functional dystrophin protein positioned about the sarcolemma along a surface of the sarcolemma along a length of the sarcolemma in a direction parallel to the muscle fiber encapsulated within the sarcolemma.

In some embodiments, a coding sequence of the functional dystrophin protein is at least 5000, 6000, 7000, 8000, 9000, 10000, or 11000 nucleotides. In some embodiments, the method further includes administering a s agent to the subject, and applying ultrasound energy a cell of the subject. In some embodiments, a length the functional dystrophin protein is at least 1750, 2000, 2250, 2500, 2750, 3000, or 3250 amino acids. In some embodiments, a coding sequence of the functional dystrophin protein is at least 5000 nucleotides. In some embodiments, the nucleic acid encoding the functional dystrophin protein and the sonoactive agent are configured to induce expression of the functional dystrophin protein in a cell of the subject upon administration of ultrasound energy to the cell. In some embodiments, the nucleic acid encodes a full length dystrophin protein. In some embodiments, a coding sequence of the nucleic acid encoding the full length dystrophin protein is at least 5000, 6000, 7000, 8000, 9000, 10000, or 11000 nucleotides. In some embodiments, a length the functional dystrophin protein is at least 1750, 2000, 2250, 2500, 2750, 3000, or 3250 amino acids. In some embodiments, the myocyte is a skeletal muscle myocyte and wherein dystrophin is expressed in the myocyte at a level of at least 1, 2, 3, 4, 5, 10, 20, 30, 40, 50, 60, 70, 80, 90, 100, 110, or 120% of a normal dystrophin level in a subject not having a dystrophinopathy disorder. A normal dystrophin level in skeletal muscle tissue generally refers to a dystrophin level in human skeletal muscle whole tissue lysate. In some embodiments, a coding sequence of the dystrophin protein in the nucleic acid encoding the dystrophin protein is at least 6000, 7000, 8000, 9000, 10000, or 11000 nucleotides. In some embodiments, the coding sequence of the dystrophin protein encodes a functional dystrophin protein. In some embodiments, the dystrophin protein is at least 1750, 2000, 2250, 2500, 2750, 3000, or 3250 amino acids in length. In some embodiments, the coding sequence of the functional dystrophin protein encodes a full length dystrophin protein. In some embodiments, the functional dystrophin protein is at least 1750, 2000, 2250, 2500, 2750, 3000, or 3250 amino acids in length. In some embodiments, the nucleic acid encoding the dystrophin protein is not comprised within a viral vector. In some embodiments, a coding sequence of the nucleic acid encoding the full length dystrophin protein is contiguous. In some embodiments, the nucleic acid coding sequence of the functional dystrophin protein is contiguous. In some embodiments, at least 6, 7, 8, 9. 10, 11, 12, 13, 14, 15, 16, 17, 18, 19, 20, 21, 22, 23, 24, 25, 26, 27, 28, 29, 30, 35, 40, 45, 50, 55, 60, or 65% of muscle fibers in the muscle tissue of the subject contain the nucleic acid encoding the functional dystrophin protein. In some embodiments, at least 1% of muscle fibers in the muscle tissue of the subject express the dystrophin protein. In some embodiments, a functional dystrophin protein is a dystrophin protein which is effective at reducing or ameliorating a symptom of the dystrophinopathy disorder in a subject.

It is further proposed that an additional reason for the failure of prior gene therapies to produce a functional copy of a dystrophin protein is due to the inability to correct disease phenotypes associated with dystrophinopathy disorder is the failure of micro-dystrophin transgene products to properly be delivered or localize within treated myocytes in a manner which fulfills the mechanical function of an endogenously produced dystrophin protein in healthy subjects, for example, due to failure to localize to the inner (cytoplasmic) surface of the sarcolemma and link the internal actin cytoskeleton to the extracellular matrix (ECM) and distributing mechanical forces generated during muscle contraction. Aspects disclosed herein provide a method of treating a dystrophinopathy disorder in a subject in need thereof comprising administering to the subject a nucleic acid encoding a functional dystrophin protein, delivering the nucleic acid to a myocyte in a muscle tissue of the subject along a length of a muscle fiber in the muscle tissue and/or about the sarcolemma of a muscle fiber in the muscle tissue, thereby treating the dystrophinopathy disorder. In some embodiments, the functional dystrophin protein is expressed in the myocyte in the muscle tissue. In some embodiments, the functional dystrophin protein is expressed along the length of the muscle fiber in the muscle tissue. In some embodiments, the functional dystrophin protein is about the sarcolemma of the muscle fiber in the muscle tissue. In some embodiments, the functional dystrophin protein transfers tension along the length of the muscle fiber or improves a maximum tension loading capacity of the muscle tissue. In some embodiments, at least 1, 3, 5, 10, 15, 20, 25, or 28% of the muscle fibers in the treated muscle tissue are contain the nucleic acid encoding the functional dystrophin protein. In some cases, the methods of ultrasound mediated delivery described herein provide a beneficial technical effect in delivering the nucleic acid to a myocyte in a muscle tissue of the subject along a length of a muscle fiber in the muscle tissue and/or about the sarcolemma of a muscle fiber in the muscle tissue. In some embodiments, along the length of a muscle fiber refers to positioning along the longitudinal (axial) of the muscle fiber sarcolemma, running parallel to the axial direction of the muscle fibers. In some cases, the methods of ultrasound mediated delivery described herein provide a beneficial technical effect in expressing the functional dystrophin protein in a myocyte in a muscle tissue of the subject along a length of a muscle fiber in the muscle tissue and/or about the sarcolemma of a muscle fiber in the muscle tissue.

Disclosed herein are optimized vectors for promoting expression of a dystrophin in a myocyte of a subject. In some embodiments, the nucleic acid encoding the dystrophin protein further comprises a promoter sequence. In some cases, the promoter sequence provides a beneficial technical effect of enhancing expression of the dystrophin in a myocyte of a subject. In some cases, the promoter sequence provides a beneficial technical effect of reducing off-target expression of the dystrophin in cells other than myocytes in the subject. In some embodiments, the promoter sequence comprises a sequence of any one of SEQ ID NO: 4-5, or 18.

In some embodiments, the nucleic acid delivery vectors disclosed herein comprise a Woodchuck Hepatitis Virus Posttranscriptional Regulatory Element 3 (WPRE3). In some cases, the WPRE3 element improves ribosomal recruitment to a transcribed mRNA, enhances translation initiation of a transcribed mRNA, and promotes the expression of the therapeutic nucleic acid sequence. In some cases, the WPRE3 element contains sequences which interacts with cellular translation initiation factors, such as eIF4E (eukaryotic translation initiation factor 4E) and eIF4G (eukaryotic translation initiation factor 4G) and enhances the assembly of the translation initiation complex, facilitating the recruitment of ribosomes to the mRNA. In some cases, the WPRE3 element promotes efficient scanning of ribosomes along the mRNA, increasing initiation of translation at the correct site, and promoting the expression of the therapeutic nucleic acid sequence in the cell. In some cases, the translated WPRE3 element contains sequences that are recognized by ribosomal RNA or elements that stabilize the interaction between ribosomal subunits and the mRNA. In some cases, the translated WPRE3 element can reduce secondary mRNA structures such as hairpins and stem-loops, which can hinder ribosomal recruitment and reduce the efficiency of translation. In some cases, the translated WPRE3 element interacts with ribosomal proteins, promoting their binding to the mRNA, and increasing the stability of association between ribosomes and the mRNA. In some cases, the nucleic acid delivery vectors of the present disclosure may comprise one or more genetic regulatory elements including promoters, enhancers, polyadenylation signals, terminator sequences, transcriptional regulatory elements, nuclear targeting sequences, and viral sequences. In some cases, the nucleic acid delivery vectors or the present disclosure may comprise a promoter sequence operatively linked to a therapeutic nucleic acid sequence. In some cases, the nucleic acid delivery vectors or the present disclosure may comprise a polyadenylation sequence operatively linked to a therapeutic nucleic acid sequence. In some cases, the nucleic acid delivery vectors of the present disclosure may comprise an intron sequence operatively linked to a therapeutic nucleic acid sequence. In some cases, the nucleic acid delivery vectors of the present disclosure may comprise a nuclear targeting sequence positioned downstream of the therapeutic nucleic acid sequence. In some cases, the nucleic acid delivery vectors of the present disclosure may comprise a nuclear targeting sequence positioned downstream of the transgene and other regulatory elements, for example, a post transcriptional regulatory element, a polyadenylation signal, and/or other regulatory element. In some cases, the nucleic acid delivery vectors may comprise promoter sequences positioned upstream of the therapeutic nucleic acid sequence. In some embodiments, the nucleic acid delivery vectors may comprise an intron sequence positioned in between a promoter sequence and a therapeutic nucleic acid sequence. In some cases, the nucleic acid delivery vectors may comprise a post transcriptional regulatory element positioned downstream of a therapeutic nucleic acid sequence. In some cases, the nucleic acid delivery vectors may comprise polyadenylation sequence positioned downstream of a therapeutic nucleic acid sequence. In some cases, the nucleic acid delivery vectors may comprise a nuclear targeting sequence positioned downstream of a therapeutic nucleic acid sequence. In some cases, the nucleic acid delivery vectors comprise a WPRE3 element positioned downstream of the transgene. In some cases, the nucleic acid delivery vector comprises a bGH-polyA element position downstream of the WPRE3 element. In some cases, the WPRE3 element is positioned in between the therapeutic nucleic acid sequence and the bGH-polyA element. In some cases, the WPRE3 element is operably linked to the WPRE3 element and the bGH-polyA element. In some cases, the nuclear targeting sequence is positioned downstream of the bGH-polyA element. In some cases, the nuclear targeting sequence is operatively linked to the bGH-polyA element. In some cases, the nucleic acid delivery of vectors of the present disclosure may comprise a post transcriptional regulatory element operatively linked to the therapeutic nucleic acid sequence. In some cases, the nucleic acid delivery vectors of the present disclosure may comprise a nuclear targeting sequence operatively linked to a therapeutic nucleic acid sequence. In some cases, the nucleic acid delivery vectors of the present disclosure may comprise one or more viral sequences operatively linked to a therapeutic nucleic acid sequence. In some embodiments, the nucleic acid encoding the dystrophin protein further comprises a post transcriptional regulatory element. In some embodiments, the post transcriptional regulatory element comprises the sequence of any one of SEQ ID NO: 8-10. In some embodiments, the post transcriptional regulatory element and the nuclear targeting sequence comprise a sequence of SEQ ID NO: 12. Aspects disclosed herein provide a nucleic acid delivery vector comprising: a therapeutic nucleic acid sequence encoding a peptide having an amino acid sequence of SEQ ID NO:1; a first regulatory element comprising a sequence of SEQ ID NO: 51 positioned upstream of the therapeutic nucleic acid sequence; and a second regulatory element comprising a sequence of SEQ ID NO: 8 positioned downstream of the therapeutic nucleic acid sequence. In some embodiments, the second regulatory element comprises a sequence of SEQ ID NO: 8 upstream of SEQ ID NO: 9. In some embodiments, the nucleic acid delivery vector further comprises a nuclear targeting sequence having a sequence of SEQ ID NO: 11. In some embodiments, the nuclear targeting sequence is positioned downstream of the second regulatory element.

In some embodiments, the nucleic acid encoding the dystrophin protein further comprises a nuclear targeting sequence. The delivery vectors disclosed herein may comprise DNA nuclear targeting sequences (DTS) that enhance delivery of the nucleic acid composition and/or the therapeutic nucleic acid sequence to a cell. In some cases, the DTS sequences may comprise recognition sequences for endogenous DNA-binding proteins which lead to increased transfection efficiency of non-viral gene delivery by virtue of enhanced nuclear import of the nucleic acid composition, which can lead to enhanced transgene expression. In some cases, the DTS sequences are recognized by nuclear transport proteins, such as importins, bind the DTS sequences and form an import complex which shields the delivery vector from cytoplasmic nucleases during movement toward the nuclear envelope, and facilitate translocation of the delivery vector through the nuclear pore complex. In some cases, the enhanced nuclear import of the nucleic acid composition avoids degradation of the nucleic acid composition in the cytoplasm, brings nucleic acid composition closer in proximity to the transcriptional machinery, thereby promoting efficient transcription of the delivered transgene. In some cases, the DTS sequence minimizes the loss of transgene during cell division, and increases the likelihood of stable inheritance of the transgene by one or more daughter cells. Various DNA nuclear targeting sequences can be operably linked with nucleic acid sequences comprising the transgene of interest in the delivery vectors disclosed herein. In some embodiments, the nuclear targeting sequence comprise a sequence of SEQ ID NO: 11. In some embodiments, the nucleic acid encoding the dystrophin protein further comprises a post transcriptional regulatory element and a nuclear targeting sequence. In some embodiments, the post transcriptional regulatory element and the nuclear targeting sequence comprise a sequence of SEQ ID NO: 12.

Aspects disclosed herein provide a nucleic acid comprising a nucleic acid sequence having at least 80% sequence identity to any one of SEQ ID NO: 4-5. In some embodiments, the nucleic acid has at least 81, 82, 83, 84, 85, 86, 87, 88, 89, 90, 91, 92, 93, 94, 95, 96, 97, 98, or 99% sequence identity to any one of SEQ ID NO: 4-5. In some embodiments, the nucleic acid which comprises the muscle specific promoter sequence facilitates expression of a transgene coupled to the promoter for at least 30, 60, 90, 120, 150, 180, 210, 240, 270, or 275 days. In some embodiments, a nucleic acid delivery vector comprises the muscle specific promoter sequence facilitates expression of a transgene coupled to the promoter for at least 30, 60, 90, 120, 150, 180, 210, 240, 270, or 275 days. In some embodiments, the nucleic acid is a muscle tissue specific promoter sequence. In some embodiments, the nucleic acid enhances expression of a therapeutic transgene in a muscle cell. In some embodiments, the muscle cell comprises a myocyte, a cardiomyocyte, or a smooth muscle cell. Aspects disclosed herein provide a nucleic acid delivery vector comprising the nucleic acid of any one of embodiments disclosed. Aspects disclosed herein provide a use of the nucleic acid of any one of embodiments disclosed in a method of treating a subject having a dystrophinopathy disorder requiring a dystrophin gene therapy or a dystrophin protein replacement therapy. Aspects disclosed herein provide a pharmaceutical composition comprising the nucleic acid of any one of embodiments disclosed. Aspects disclosed herein provide a use of the pharmaceutical composition of embodiments disclosed in a method of treating a subject having a dystrophinopathy disorder requiring a dystrophin gene therapy or a dystrophin protein replacement therapy. Aspects disclosed herein provide a cell comprising the nucleic acid of any one of embodiments disclosed. In some embodiments, the dystrophinopathy disorder comprises Duchenne muscular dystrophy (DMD), Becker muscular dystrophy (BMD), or DMD-associated dilated cardiomyopathy. In some embodiments, the dystrophinopathy disorder comprises Duchenne muscular dystrophy (DMD), and wherein the cell is a skeletal muscle myocyte. In some embodiments, the dystrophinopathy disorder comprises Becker muscular dystrophy (BMD), and wherein the cell is a skeletal muscle myocyte. In some embodiments, the dystrophinopathy disorder comprises DMD-associated dilated cardiomyopathy, and wherein the cell is a cardiac myocyte.

Aspects disclosed herein provide a nucleic acid comprising a sequence which has at least 80% sequence identity to any one of SEQ ID NO: 16-17. Aspects disclosed herein provide a nucleic acid comprising a sequence of SEQ ID NO: 16-17.

In addition to challenges associated with aspects of nucleic acid vector design outside of the transgene coding sequence, modifying the nucleic acid coding sequence of therapeutic transgenes can improve transgene expression even without modifying the amino acids coded by the nucleic acid coding sequence. Certain nucleic acid coding sequence, even those which are native to the human genome, can present challenges with inducing proper gene expression and protein synthesis in human gene therapies. For example, different organisms may prefer specific codons for the same amino acid, and non-preferred codons may result in inefficient protein production in certain organisms (e.g., mammalian organisms). In some cases, codon optimization can adjust codons to match the preferences of the host organism, improving translation efficiency. In other cases, mRNA can form secondary structures such hairpins or loops, which can block ribosomal translation of the mRNA into protein. Even in the absence of the formation of secondary structures, the sequence of the mRNA itself with too many repetitive sequences can trigger immune response to the transcribed mRNA. In other cases, the lack of optimized codons around the ribosomal binding site can reduce the initiation of translation by the ribosome.

Disclosed herein are optimized coding sequences of human dystrophin protein s which provide a beneficial technical effect of increasing expression of the dystrophin in the subject. In some embodiments, the nucleic acid encoding the dystrophin protein comprises the sequence of any one of SEQ ID NO: 2-3. In some embodiments, the nucleic acid encoding the dystrophin protein comprises the sequence of any one of SEQ ID NO: 6-7. In some embodiments, the cell is a myocyte. In some embodiments, the muscle cell comprises a skeletal muscle myocyte, a cardiomyocyte, or a smooth muscle cell.

Aspects disclosed herein provide a nucleic acid sequence comprising a sequence having at least 80% sequence identity to any one of SEQ ID NO: 2-3. In some embodiments, the nucleic acid sequence has at least 81, 82, 83, 84, 85, 86, 87, 88, 89, 90, 91, 92, 93, 94, 95, 96, 97, 98, or 99% sequence identity to any one of SEQ ID NO: 2-3. In some embodiments, the nucleic acid sequence is any one of SEQ ID NO: 2-3. In some embodiments, the nucleic acid sequence encodes a dystrophin protein. In some embodiments, the nucleic acid sequence encodes a full length dystrophin protein. In some embodiments, the nucleic acid sequence encodes a dystrophin protein at least 3500 amino acids in length. Aspects disclosed herein provide a nucleic acid delivery vector comprising the nucleic acid of embodiments disclosed herein. Aspects disclosed herein provide a use of the nucleic acids of any one of embodiments disclosed herein in a method of treating a subject having a dystrophinopathy disorder requiring a dystrophin gene therapy or a dystrophin protein replacement therapy. Aspects disclosed herein provide a pharmaceutical composition comprising the nucleic acid of embodiments disclosed herein. Aspects disclosed herein provide a use of the pharmaceutical composition of embodiments disclosed herein in a method of treating a subject having a dystrophinopathy disorder requiring a dystrophin gene therapy or a dystrophin protein replacement therapy. In some embodiments, the dystrophinopathy disorder comprises Duchenne muscular dystrophy (DMD), Becker muscular dystrophy (BMD), or DMD-associated dilated cardiomyopathy. In some embodiments, the dystrophinopathy disorder comprises Duchenne muscular dystrophy (DMD), and wherein the cell is a skeletal muscle myocyte. In some embodiments, the dystrophinopathy disorder comprises Becker muscular dystrophy (BMD), and wherein the cell is a skeletal muscle myocyte. In some embodiments, the dystrophinopathy disorder comprises DMD-associated dilated cardiomyopathy, and wherein the cell is a cardiac myocyte. Aspects disclosed herein provide a cell comprising the nucleic acid of embodiments disclosed herein.

In some embodiments, the muscle cell is located within a muscle tissue of the subject, the method further comprising one or more of: applying heat to the muscle tissue, or increasing a blood flow rate in the muscle tissue. In some embodiments, heat is applied to the muscle tissue using a transcutaneous compress at a temperature of at least 37 C. In some embodiments, heat is applied to the muscle tissue using ultrasound energy. In some embodiments, the muscle tissue is located in a heart or a diaphragm of the subject. In some cases, applying heat to the muscle tissue and/or increasing a blood flow rate provides a beneficial technical effect of increasing delivery of the nucleic acid encoding the functional dystrophin protein to the cell, and resulting expression of the functional dystrophin protein.

Aspects disclosed herein provide a nucleic acid comprising a promoter sequence having at least 90% sequence identity to any one of SEQ ID NOS: 37-40. In some embodiments, the promoter sequence comprises at least 91, 92, 93, 94, 95, 96, 97, 98, or 99% sequence identity to any one of SEQ ID NOS: 37-40. In some embodiments, the promoter sequence comprises any one of SEQ ID NOS: 37-40. In some embodiments, the promoter sequence is configured to increase expression of a nucleic acid encoding a therapeutic protein operably coupled to the promoter sequence. In some embodiments, the promoter sequence is configured to increase expression of a nucleic acid encoding a therapeutic protein operably coupled to the promoter sequence in multiple cell types. In some embodiments, the promoter sequence is configured to increase expression of the nucleic acid encoding the therapeutic protein in a muscle cell. In some embodiments, the promoter sequence is configured to increase expression of the nucleic acid encoding the therapeutic protein in a kidney cell. In some embodiments, the promoter sequence is configured to increase expression of the nucleic acid encoding the therapeutic protein in a liver cell. In some embodiments, the liver cell is a hepatocyte, or a LSEC. In some embodiments, the promoter sequence is configured to increase expression of the nucleic acid encoding the therapeutic protein in a myocyte. Aspects disclosed herein provide nucleic acid delivery vector comprising the nucleic acid of any one of the present embodiments disclosed herein. Aspects disclosed herein provide pharmaceutical composition comprising the nucleic acid of any one of the present embodiments disclosed herein Aspects disclosed herein provide cell comprising the nucleic acid of any one of the present embodiments disclosed herein. Aspects disclosed herein provide method of treating a subject comprising administering the nucleic acid of any one of the present embodiments disclosed herein. In some embodiments, the method further includes administering ultrasound to the subject. In some embodiments, the method further includes administering a sonoactive agent to the subject. In some embodiments, the method further includes administering a lipid nanoparticle or a polymer nanoparticle to the subject. In some embodiments, the nucleic acid is contained within a viral vector.

Aspects disclosed herein provide a nucleic acid comprising a nucleic acid sequence having at least 90% sequence identity to SEQ ID NO: 34. In some embodiments, the nucleic acid sequence has at least 91% sequence identity to SEQ ID NO: 34. In some embodiments, the nucleic acid sequence has at least 92% sequence identity to SEQ ID NO: 34. In some embodiments, the nucleic acid sequence has at least 93% sequence identity to SEQ ID NO: 34. In some embodiments, the nucleic acid sequence has at least 95% sequence identity to SEQ ID NO: 34. In some embodiments, the nucleic acid sequence has at least 97% sequence identity to SEQ ID NO: 34. In some embodiments, the nucleic acid sequence has at least 99% sequence identity to SEQ ID NO: 34. In some embodiments, the nucleic acid sequence is SEQ ID NO: 34. In some embodiments, the nucleic acid sequence encodes a dystrophin protein. In some embodiments, the nucleic acid sequence encodes a full length dystrophin protein. In some embodiments, the nucleic acid sequence encodes a dystrophin protein at least 3500 amino acids in length. In some embodiments, the nucleic acid sequence encodes a protein having at least 90% sequence identity to SEQ ID NO: 13. In some embodiments, the nucleic acid sequence comprises a muscle tissue specific promoter sequence. In some embodiments, the muscle tissue specific promoter sequence enhances expression of a dystrophin protein in a muscle cell. In some embodiments, the muscle cell comprises a myocyte, a cardiomyocyte, or a smooth muscle cell. In some embodiments, the nucleic acid sequence is an expression cassette for a dystrophin protein. In some embodiments, the nucleic acid sequence is an expression cassette for a dystrophin protein optimized for expression of the dystrophin protein in mammalian cells. In some embodiments, the nucleic acid sequence is an expression cassette for a dystrophin protein optimized for expression of the dystrophin protein in myocytes. In some embodiments, the nucleic acid sequence is comprised within a nucleic acid delivery vector having a sequence of SEQ ID NO: 17. In some cases, the expression cassette of SEQ ID NO: 34 provides a beneficial technical effect of improving delivery and expression of a dystrophin transgene encoded by the nucleic acid delivery vector in muscle cells of a subject.

Aspects disclosed herein provide a nucleic acid comprising a nucleic acid sequence having at least 90% sequence identity to SEQ ID NO: 4. In some embodiments, the nucleic acid sequence has at least 91% sequence identity to SEQ ID NO: 4. In some embodiments, the nucleic acid sequence has at least 92% sequence identity to SEQ ID NO: 4. In some embodiments, the nucleic acid sequence has at least 93% sequence identity to SEQ ID NO: 4. In some embodiments, the nucleic acid sequence has at least 94% sequence identity to SEQ ID NO: 4. In some embodiments, the nucleic acid sequence has at least 95% sequence identity to SEQ ID NO: 4. In some embodiments, the nucleic acid sequence has at least 96% sequence identity to SEQ ID NO: 4. In some embodiments, the nucleic acid sequence has at least 97% sequence identity to SEQ ID NO: 4. In some embodiments, the nucleic acid sequence has at least 98% sequence identity to SEQ ID NO: 4. In some embodiments, the nucleic acid sequence has at least 99% sequence identity to SEQ ID NO: 4. In some embodiments, the nucleic acid sequence is a muscle tissue specific promoter sequence. In some embodiments, the nucleic acid sequence enhances expression of a therapeutic transgene in a muscle cell. In some embodiments, the muscle cell comprises a myocyte, a cardiomyocyte, or a smooth muscle cell. In some embodiments, the nucleic acid sequence facilitates expression of a transgene coupled to the promoter for at least 30, 60, 90, 120, 150, 180, 210, 240, 270, or 275 days. In some embodiments, the nucleic acid sequence is comprised within a nucleic acid delivery vector and coupled to a nucleic acid coding sequence encoding a therapeutic transgene, wherein the therapeutic transgene encodes a protein having at least 90% sequence identity to SEQ ID NO: 13. Aspects disclosed herein provide a nucleic acid delivery vector comprising the nucleic acid which is a muscle tissue specific promoter sequence having at least 90% sequence identity to SEQ ID NO: 4. Aspects disclosed herein provide a pharmaceutical composition comprising the nucleic acid which is a muscle tissue specific promoter sequence having at least 90% sequence identity to SEQ ID NO: 4. Aspects disclosed herein provide a cell comprising the nucleic acid which is a muscle tissue specific promoter sequence having at least 90% sequence identity to SEQ ID NO: 4. Aspects disclosed herein provide a kit comprising: 1) a sonoactive agent; and 2) means for expressing a therapeutic transgene in a subject. Aspects disclosed herein provide a kit comprising: 1) a sonoactive agent; and 2) the nucleic acid which is a muscle tissue specific promoter sequence having at least 90% sequence identity to SEQ ID NO: 4. In some cases, the muscle specific promoter sequence of SEQ ID NO: 4 provides a beneficial technical effect of improving delivery and expression of a therapeutic transgene coupled to the muscle specific promoter sequence in muscle cells of a subject.

In some embodiments, administering the ultrasound acoustic energy comprises applying a first ultrasound energy at a MI of up to 0.4, and a first second ultrasound energy at a MI of greater than 0.4 and up to 3.0. In some embodiments, administering the ultrasound acoustic energy comprises applying a first ultrasound energy at a MI of up to 0.4, and a first second ultrasound energy at a MI of 0.8-1.9. In some embodiments, administering the ultrasound acoustic energy comprises applying an acoustic radiation force to the subject. In some embodiments, the ultrasound energy is applied at an intensity (ISPTA) of at least 200 mW/cm2. In some embodiments, the ultrasound energy displaces a muscle tissue of the subject by at least 0.1 mm. In some embodiments, the muscle tissue is displaced by at least 0.1, 0.2, 0.3, 0.4, 0.5, 0.6, 0.7, 0.8, 0.9, or 1 mm. In some embodiments, the ultrasound energy is applied at a pulse length of at least 20 microseconds. In some embodiments, the cell or the myocyte is in a muscle tissue of the subject, wherein administering the sonoactive agent to the subject comprises distributing the sonoactive agent throughout the capillaries of the muscle tissue. In some embodiments, applying the ultrasound energy comprises applying an acoustic radiation force to the muscle tissue In some embodiments, applying the acoustic radiation force comprises displacing the muscle tissue In some embodiments, applying the acoustic radiation force comprises displacing a volume of blood in the capillaries of the muscle tissue In some embodiments, displacing the volume of blood in the capillaries of the muscle tissue transmits a pressure wave throughout a vascular system of the muscle tissue, thereby disrupting the sonoactive agent. In some embodiments, the pressure wave does and/or the ultrasound energy applying the acoustic radiation force does not induce vibrational cavitation of the sonoactive agent. In some embodiments, the sonoactive agent comprises a shell filled with a gas. In some embodiments, the shell comprises a protein stabilized shell or a lipid stabilized shell. In some embodiments, the gas comprises a perfluorinated case. In some embodiments, the sonoactive agent comprises microbubbles. In some embodiments, the sonoactive agent comprises nanobubbles. In some embodiments, the subject has a mutation in a gene encoding a dystrophin protein in a genome of the subject. In some embodiments, the subject has a dystrophinopathy disorder. In some embodiments, the dystrophinopathy disorder comprises Duchenne muscular dystrophy (DMD), Becker muscular dystrophy (BMD), or DMD-associated dilated cardiomyopathy. In some embodiments, the dystrophinopathy disorder comprises Duchenne muscular dystrophy (DMD), and wherein the cell is a skeletal muscle myocyte. In some embodiments, the dystrophinopathy disorder comprises Becker muscular dystrophy (BMD), and wherein the cell is a skeletal muscle myocyte. In some embodiments, the dystrophinopathy disorder comprises DMD-associated dilated cardiomyopathy, and wherein the cell is a cardiac myocyte. In some embodiments, administering the nucleic acid, administering the sonoactive agent, and applying the ultrasound energy induces expression of the dystrophin protein thereby treating the subject having the dystrophinopathy disorder. In some embodiments, the method reduces or ameliorates a symptom of the dystrophinopathy disorder in the subject. In some embodiments, the method further includes administering a second dose of the nucleic acid encoding the dystrophin protein, the sonoactive agent, and the ultrasound energy to the subject. In some embodiments, the subject is a mammalian subject. In some embodiments, the subject is a human subject.

Aspects disclosed herein provide a nucleic acid comprising a promoter sequence having at least 90% sequence identity to SEQ ID NO: 18. In some embodiments, the promoter sequence has at least 91, 92, 93, 94, 95, 96, 97, 98, or 99% sequence identity to SEQ ID NO: 18. In some embodiments, the promoter sequence is SEQ ID NO: 18.

Ultrasound refers to the application of electromagnetic energy in the range of greater than 20 kHz up to several gigahertz. Ultrasound is used in many different fields, most commonly in the field of diagnostics and medical imaging for producing images of tissue within the human body. Ultrasound energy can be generated at various frequencies within the 20 kHz up to several gigahertz range, most commonly within the range of about 1 to 10 megahertz when used for diagnostic imaging purposes. Ultrasound is commonly applied using ultrasonic transducers comprising one or more piezoelectric crystals which convert electrical energy into acoustic energy. In addition to imaging applications, ultrasound can also be used for a variety of other diagnostic and therapeutic applications, including determination of tissue elasticity and fibrosis, focused destruction of tissue using ultrasound ablation, and for the delivery of exogenous payloads (e.g., nucleic acids and therapeutic agents) to a cell. Sonoporation refers to the delivery of therapeutic agents, for example nucleic acids, using ultrasound and/or sonoactive microstructures to a cell. Provided in certain embodiments herein are methods of delivering a nucleic acid construct into a target cell or tissue (e.g., of a subject) by applying ultrasound energy to a cell, tissue, or organ (e.g., with sonoporation).

B mode ultrasound imaging refers to brightness mode imaging, in which ultrasonic waves are reflected from the tissue of a subject back to the ultrasound probe, and displayed on a 2 dimensional objects that are closer to the ultrasound transducer appear brighter, and objects which are farther away from the ultrasound transducer appear darker. B mode ultrasound imaging generally will focus ultrasound energy emitted from a plurality of ultrasound arrays comprising piezoelectric crystals into a focused ultrasound beam which penetrates into the tissue about a vertical axis which is perpendicular to the surface of the ultrasound probe. The focused ultrasound beam reflects off the tissue and back towards the ultrasound transducer, forming a scan line in an ultrasound image. By moving the ultrasound transducer about a surface of tissue, an image of the underlying tissue can be generated using a B mode ultrasound image. B mode ultrasound imaging is the most common form of ultrasound used in the United States for medical imaging, and is what is commonly referred to as diagnostic or imaging ultrasound.

Plane wave imaging refers to an ultrasound imaging technique in which a plurality of ultrasound arrays comprising piezoelectric crystals in an ultrasound transducer are simultaneously fired without directing ultrasound energy into a focused ultrasound beam, and which instead direct a large unfocused sheet or wave of ultrasound energy into a medium or tissue underlying an ultrasound probe. The primary difference between plane wave ultrasound imaging and B mode ultrasound imaging is the number of transducer arrays which are fired. Plain wave imaging typically will fire all arrays within an ultrasound transducer Producing a much larger and less focused wave of ultrasonic energy, while B mode imaging will typically only fire a subset of arrays which focused the ultrasound into a beam producing what is commonly referred to as a scan line. In plane wave imaging, the acoustic radiation pressure is almost uniform over the entire field of view, and lower peak and negative pressures are typically experienced as compared to traditional beam mode focused ultrasound beam imaging.

Acoustic radiation force refers to a static or transient force applied by an acoustic wave on the propagation medium or to an object in the path of the acoustic wave. Acoustic radiation forces can be applied using an ultrasound transducer when applying ultrasound energy to a surface of a tissue or a propagation medium with sufficient ultrasound intensity. When applying a sufficient acoustic radiation force to a propagation medium or a tissue, the propagation medium or tissue under lying the ultrasound probe applying the acoustic radiation force may be displaced.

Shear waves, or secondary waves refer to transversely oriented waves which occur in elastic medium that is subjected to a periodic shear. Shear refers to a change in shape without a change of volume of a layer of a propagation medium or tissue produced by a pair of equal forces acting in opposite directions about two faces of the layer or the propagation medium. Shear waves are a type of elastic wave which move through the body of an object or a propagation medium. In an elastic medium, the layer or the tissue will resume its original shape following application of the shear force, adjacent layers will undergo subsequent shear, and the movement of particles within the medium or tissue will be propagated as a shear wave throughout the propagation medium or tissue. In an elastic medium, shear waves can be produced as a secondary wave following a compressional wave which is transmitted in the propagation medium or tissue. Ultrasound applying an acoustic radiation force can apply a compressional wave to a tissue, which can result in application of shear waves to a tissue when applied with sufficient intensity, at regular intervals, for sufficient periods of time to induce a regular shear in layers of a tissue. A compressional wave displaces tissue in a direction parallel to the propagation of the compressional waves. An ultrasound transducer can induce a compressional wave in a tissue which propagates from the ultrasound transducer about a vector normal to a surface of the ultrasound transducer. In some embodiments, applying the focused acoustic radiation force to the tissue comprises generating a compressional wave in the tissue. As an elastic tissue recovers from displacement due to a compressional wave, shear waves or secondary waves can be generated. In a shear wave, the direction of particle motion is parallel to the direction of propagation of the compressional wave, and the direction of propagation of the shear wave is normal to the direction of propagation of the compressional wave. The direction of particle motion in a shear wave is also normal to the direction of shear wave propagation in an elastic medium. Further, a compressional wave may be followed by a rarefaction wave which is a negative acoustic force in the tissue.

Shear wave elastography refers to a diagnostic technique using ultrasound to determine the elastic modulus of tissue, which is indicative of its fibrotic quality. Diseased tissue with certain fibrotic conditions will result in a significantly reduced elastic modulus of the tissue, as compared to a healthy tissue which is reasonably elastic as compared to diseased tissue in a fibrotic state. Shear wave elastography is a diagnostic imaging technique which uses a combination of acoustic radiation force, plane wave imaging, and B mode imaging to provide a clinician with information as to the fibrotic quality of a tissue. Shear wave elastography applies an acoustic radiation force to displace the tissue underlying an ultrasound probe with a compressional wave, thereby generating shear waves in the tissue, applies a plane wave ultrasound to the tissue to monitor the propagation of the shear waves throughout the tissue thereby calculating the elastic modulus, and overlays this data atop a standard B mode ultrasound image in order to provide a visual representation of tissue stiffness. Using ultrasound machines configured to perform shear wave elastography, an acoustic radiation force to displace the tissue underlying an ultrasound probe with a compressional wave, thereby generating shear waves in the tissue, can be applied. In some cases, a standard B mode ultrasound image and/or plane wave in order to calculate or provide a visual representation of tissue stiffness may not be performed.

Provided in certain embodiments herein are methods of delivering a nucleic acid construct into a target cell or tissue (e.g., of a subject) by applying ultrasound energy to a cell, tissue, or organ. Provided in certain embodiments herein are methods of delivering a nucleic acid construct into a target cell or tissue (e.g., of a subject) by delivering an exogenous payload to the subject; and applying a focused acoustic radiation force (ARF) to the subject, thereby generating shear waves in the tissue of the subject, wherein the focused acoustic radiation force enhances delivery of the exogenous payload to the cell in the tissue of an organ of the subject. Disclosed herein are methods of sonoporation in which an exogenous payload is delivered to a cell in a tissue of a subject using a focused acoustic radiation force applied using ultrasound. Aspects of the sonoporation methods disclosed herein may also include inducing displacing the tissue of the subject with the acoustic radiation force to induce propagation of shear waves throughout the tissue of the subject thereby enhancing delivery of a nucleic acid payload to a cell. Disclosed herein are methods of sonoporation in which an exogenous payload is delivered to a cell in a tissue of a subject using a focused acoustic radiation force applied using ultrasound. Aspects of the sonoporation methods disclosed herein may also include inducing displacing the tissue of the subject with the acoustic radiation force to induce propagation of shear waves throughout the tissue of the subject thereby enhancing delivery of a nucleic acid payload to a cell. The method may further include applying the acoustic radiation force to induce propagation of shear waves throughout the tissue in combination with other secondary ultrasound energies such as plane wave ultrasound or focused beam ultrasound in which the secondary ultrasound energy moves sonoactive microstructures toward an endothelial border of a tissue comprising the cell, while applying the focused acoustic radiation force during shear wave propagation induces inertial cavitation of sonoactive microstructures at the endothelial border of the tissue comprising the cell, thereby enhancing delivery of the therapeutic payload to a cell, and, in cases of a nucleic acid payload, resulting gene expression.

In some embodiments, the focused acoustic radiation force is applied using an ultrasound probe applying ultrasound energy to the tissue. In some embodiments, the ARF displaces the tissue of the subject. In some embodiments, the shear waves displace the tissue of the subject. In some embodiments, a tissue displacement is at least 0.001 mm. In some embodiments, a tissue displacement ranges from at least 0.001 mm to about 5 mm. In some embodiments, a tissue displacement ranges from 0.01 mm to about 1 mm.

In some embodiments, the focused acoustic radiation force is applied using an ultrasound probe applying ultrasound energy to the tissue. In some embodiments, the ultrasound energy is applied at a mechanical index greater than 0.4. In some embodiments, the ultrasound energy is applied at a mechanical index of about 1.4. In some embodiments, the ultrasound energy is applied at a mechanical index of at least 1.3. In some embodiments, the ultrasound energy is applied at a mechanical index of greater than 0.4 up to about 3.0. In some embodiments, the ultrasound energy is applied at a frequency of about 0.1 MHz to about 10 MHz. In some embodiments, the ultrasound energy is applied at a frequency of about 2.5 MHz. In some embodiments, the applying ultrasound energy to the tissue comprises applying the ultrasound energy at an ultrasound intensity of at least 100 $mW/cm^2$. In some embodiments, the applying ultrasound energy to the tissue comprises applying the ultrasound energy at an ultrasound intensity of about 100 $mW/cm^2$ to about 10,000 $mW/cm^2$. In some embodiments, the applying ultrasound energy to the tissue comprises applying the ultrasound energy at an ultrasound intensity of about 100 $mW/cm^2$ to about 5,000 $mW/cm^2$. In some embodiments, the applying ultrasound energy to the tissue comprises applying the ultrasound energy at an ultrasound intensity of about 100 $mW/cm^2$ to about 500 $mW/cm^2$. In some embodiments, the applying ultrasound energy to the tissue comprises applying the ultrasound energy at an ultrasound intensity of about 110 $mW/cm^2$ to about 200 $mW/cm^2$. In some embodiments, the applying ultrasound energy to the tissue comprises applying the ultrasound energy at an ultrasound intensity of about 188 $mW/cm^2$. In some embodiments, the ultrasound intensity is a spatial-peak temporal average intensity. In some embodiments, the spatial-peak temporal average intensity is calculated in a focal region of the tissue. In some embodiments, the focused acoustic radiation force is applied in two or more pulses, with an interval between each of the two or more pulses. In some embodiments, a plane wave ultrasound is applied to the tissue during the interval. In some embodiments, the one or more pulses are up to 500 microseconds. In some embodiments, the one or more pulses are at least 100 microseconds. In some embodiments, the one or more pulses are about 100 microseconds to about 500 microseconds. In some embodiments, the interval is up to 500 milliseconds. In some embodiments, the interval is up to 100, 500, 1000, 1500, 2000, 2500, 3000, 4000, or 5000 milliseconds. In some embodiments, the interval is from about 100 milliseconds to about 5000 milliseconds. In some embodiments, the applying the focused acoustic radiation force is performed in one or more sequences, wherein a sequence comprises two or more pulses and interval(s) therebetween. In some embodiments, a time between application of the one or more sequences is at least 5, 10, 20, 30, 60, 120, 180, 240, 300, 360, 420, 480, 540, or 600 seconds. In some embodiments, a time between application of the one or more sequences ranges from about 5 to about 300 seconds. In some embodiments, a time between application of the one or more sequences ranges from about 10 to about 60 seconds. In some embodiments, the focused acoustic radiation force is applied for at least 10, 20, 30, 60, 120, 180, 240, 300, 360, 420, 480, 540, or 600 seconds. In some embodiments, applying ultrasound energy to the tissue comprises applying the ultrasound energy at a focal depth of up to 10, 8, 6, or 4 cm from the ultrasound transducer. In some embodiments, applying ultrasound energy to the tissue comprises applying the ultrasound energy at a focal depth of about 1 to about 10 cm from the ultrasound transducer. In some embodiments, applying ultrasound energy to the tissue comprises applying the ultrasound energy at a focal depth of about 4 to about 10 cm from the ultrasound transducer. In some embodiments, applying ultrasound energy to the tissue comprises applying the ultrasound energy at a focal depth of about 4 cm from the ultrasound transducer. In some embodiments, applying ultrasound energy to the tissue comprises applying the ultrasound energy at a focal depth of about 6 cm from the ultrasound transducer.

In some embodiments, applying the focused wave ultrasound results in moving the sonoactive microstructures towards an endothelial border of the tissue comprising the cell. In some embodiments, the shear waves induce inertial cavitation the sonoactive microstructures at an endothelial border of the tissue comprising the cell, thereby enhancing delivery of the nucleic acid to the cell. In some embodiments, the focused acoustic radiation force increases internalization of the exogenous payload in the cell. In some embodiments, the shear waves increase internalization of the exogenous payload in the cell. In some embodiments, inducing inertial cavitation the sonoactive microstructures increases internalization of the exogenous payload in the cell.

In some embodiments, a process provided herein provides sonoporation at two or more different ultrasonic acoustic energies (e.g., a first and second ultrasound energy having a first and second MI, respectively). In certain embodiments, a process provided herein provides a process wherein an ultrasound energy is continuously applied (e.g., ultrasound energy transitions from the first ultrasound energy to the second ultrasound energy, without a period of no ultrasound energy being applied). In certain embodiments, a transitory (e.g., third, fourth, etc.) ultrasound energy is applied between application of the first and second ultrasonic acoustic energies. Provided in certain embodiments herein are methods of delivering a nucleic acid construct into a target cell or tissue (e.g., of a subject) by applying a first ultrasound energy to a cell, tissue, or organ, and applying a second ultrasound energy to the cell, tissue, or organ. In some embodiments herein are methods for transfecting a nucleic acid construct into a target cell or tissue by applying a first ultrasound energy having a first mechanical index (MI) and applying a second ultrasound energy having a second mechanical index (MI). The present disclosure provides methods for enhancing transfection of a nucleic acid construct into the target cell or tissue by applying alternating ultrasound energy, the alternating acoustic energy alternating between a first mechanical index (MI) and a second MI. Application of ultrasound energy can be repeated several times during sonoporation, such as to increase the efficiency of nucleic acid construct transfection and/or delivery.

In some embodiments, the sonoporation treatment comprises applying an ultrasound energy to the target cell (e.g., of a tissue or organ of the subject) (e.g., the ultrasound energy having a mechanical index (MI)). In some embodiments, applying an ultrasound energy to the target cell comprises applying a first ultrasound energy to the target cell and applying a second ultrasound energy to the target cell. In some embodiments, the (e.g., first or second) ultrasound energy has a first mechanical index (MI). In certain embodiments, (e.g., the other of the first or second) ultrasonic energy has a second mechanical index (MI). In some embodiments, the (e.g., first or second) MI is less than 0.4. In certain embodiments, the (e.g., the other of the first or second) MI is greater than 0.4 (e.g., and less than 2.0). In some embodiments, a first ultrasound energy and a second ultrasound energy are applied sequentially in a repeated manner. In some embodiments, a first MI is a Low MI (e.g., less than 0.4). In certain embodiments, a second MI is a High MI (e.g., 0.4 or greater). In some embodiments, a first MI is a Low MI (e.g., less than 0.4) and a second MI is a High MI (e.g., 0.4 or greater). In some embodiments, a second MI is a Low MI (e.g., less than 0.4). In certain embodiments, a first MI is a High MI (e.g., 0.4 or greater). In given embodiments, a second MI is a Low MI (e.g., less than 0.4) and a first MI is a High MI (e.g., 0.4 or greater). In some embodiments, a Low MI is less than 0.3. In given embodiments, a Low MI is less than 0.2. In more given embodiments, a Low MI is less than 0.1. In still more given embodiments, a Low MI is about 0.09. In still more given embodiments, a Low MI is about 0.04. In still more given embodiments, a Low MI is about 0.03. In some embodiments, a High MI is greater than 0.5. In given embodiments, a High MI is 0.5 to 2.0 or is between 0.5 and 2.0. In more given embodiments, a High MI is 0.5 to 1 or is between 0.5 and 2.0. In some embodiments, a High MI is 1.5. In some embodiments, a High MI is 1.8. In some embodiments, a High MI is 2.0. In some embodiments, a High MI is greater than 0.4. In some embodiments, a High MI is greater than 0.5. In more given embodiments, a High MI is 0.5 to 1 or is between 0.5 and 2.0. In some embodiments, a High MI is 1.5. In some embodiments, a High MI is 1.8. In some embodiments, a High MI is 2.0. In some embodiments, a High MI is 2.2. In some embodiments, a High MI is 2.5. In some embodiments, a High MI is 2.8. In some embodiments, a High MI is 3.0. In certain embodiments, any process provided herein (e.g., a sonoporation treatment) comprises administering of a continuous ultrasound energy (which may have varying energy level) that alternates (e.g., in identical, similar, or variable periods) between Low MI and High MI. In some embodiments, a low MI (e.g., less than 0.1) (e.g., first) ultrasound energy (also referred to herein as a Low MI) is administered to the subject, and a set number pulses (e.g., of less than 30 seconds) of High MI (e.g., second) ultrasound energy (also referred to herein as a High MI) is administered to the subject. In some embodiments, a process provided herein comprises administration of a plurality of pulses of high MI (e.g., second) ultrasound energy, e.g., during an otherwise continuous administration of a low MI (e.g., first) ultrasound energy. In given embodiments, the number of High MI pulses is about 4 or more, 8 or more, 12, or more, 16 or more, 18 or more, 25 or more, such as up to about 30, or an unlimited number of pulses. In given embodiments, the number of High MI pulses is 6-30. In still more given embodiments, the number of High MI pulses is between 8, 9, 12, 15, 18, 27, 36, 45, or any number therebetween. In some embodiments, at least 8, 9, 12, 15, or 18 high MI pulses are administered to the subject in between applications of low MI ultrasound energy. In still more given embodiments, the number of High MI pulses applied is at least 8, 9, 12, 15, 18, 27, 36, or 45. In still more given embodiments, the number of High MI pulses applied in a given sequence of high MI ultrasound energy is at least 8, 9, 12, 15, 18, 27, 36, or 45.

In certain embodiments, the first (either High MI or Low MI) ultrasound energy is applied before or after administration of any other agent, such as the nucleic acid and/or sonoactive structure. In some embodiments, the first ultrasound energy is applied after administration of the sonoactive structure to the subject. In certain embodiments, the first ultrasound energy is applied after administration of the nucleic acid to the subject. In some embodiments, the first ultrasound energy is applied after administration of both the nucleic acid and the sonoactive structure(s).

In some embodiments, high MI ultrasound energy is administered in a pulse. In given embodiments, a pulse length is any suitable length, such as less than 30 seconds. In more given embodiments, a pulse length is less than 15 seconds. In still more given embodiments, a pulse length is less than 10 seconds. In yet more given embodiments, a pulse length is less than 5 seconds. In more given embodiments, a pulse length is less than 2 seconds. In still more given embodiments, a pulse length is less than 1 second and/or may be greater than or equal to 1 microsecond. In some embodiments, a pulse length ranges from 100 to 300 microseconds. In some embodiments, a pulse length is up to about 200 microseconds. In some embodiments, a pulse length is up to about 500 microseconds. In some embodiments, a pulse length ranges from 1 to 500 microseconds.

In various embodiments, a High MI ultrasound energy is provided first temporally (e.g., first in order). In other embodiments, a Low MI ultrasound energy is provided second temporally (e.g., second in order).

In some embodiments, any process provided herein further comprises administering (e.g., systemically administering, such as via infusion) a nucleic acid (e.g., any nucleic acid provided herein) to a subject (e.g., to whom the ultrasonic acoustic energies are applied).

In some embodiments, any process provided herein further comprises administering (e.g., systemically administering, such as via infusion) a sonoactive structure (e.g., any sonoactive structure or microbubble described herein) to a subject (e.g., to whom the ultrasonic acoustic energies are applied).

In certain embodiments, provided herein is a method of delivering a nucleic acid payload in a target cell (e.g., of a tissue or organ) of a subject, the method comprising: (a) administering to the subject a nucleic acid construct comprising the nucleic acid payload; (b) administering to the subject a plurality of sonoactive microstructures; and (c) administering an ultrasound energy, thereby delivering a sonoporation treatment.

In some embodiments, a sonoporation treatment (e.g., application of a first ultrasound energy, a second ultrasound energy, a single cycle of a first ultrasound energy and a second ultrasound energy, or series of cycles comprising a plurality of applications of a first ultrasound energy and a plurality of applications of a second acoustic energy) can last for a few seconds (e.g., 1-100 seconds) or more, such as up to a few minutes (e.g., 1-3 minutes). In given embodiments, a sonoporation treatment lasts for 1-30 seconds. In some given embodiments, a sonoporation treatment lasts for 5-100 seconds. In certain embodiments, a sonoporation treatment lasts for at least 1 minute (e.g., 1-30 minutes).

In some embodiments, the first ultrasound energy is administered within 60 minutes of administration of the nucleic acid and/or sonoactive structure(s). In given embodiments, the first ultrasound energy is administered within 30 minutes of administration of the nucleic acid and/or sonoactive structure(s). In more given embodiments, the first ultrasound energy is administered within 5 minutes of administration of the nucleic acid and/or sonoactive structure(s). In still more given embodiments, the first ultrasound energy is administered within 2 minutes of administration of the nucleic acid and/or sonoactive structure(s). In still more given embodiments, the first ultrasound energy may be applied simultaneously with administration of the nucleic acid and/or sonoactive structure(s).

In given embodiments, the first (e.g., High MI) ultrasound energy is applied immediately upon administration (e.g., infusion) or a period of time after administration (e.g., infusion) of the sonoactive structure(s) and/or nucleic acid.

In some embodiments, either the first or second ultrasound energy is an ultrasound energy (e.g., Low MI) that when applied to a cell, tissue, or organ of a subject results in stable cavitation (or stable vibrational cavitation) of the sonoactive structure and/or a change in the average diameter of the sonoactive structure(s), for example, due to inherent resonance properties of the microbubbles.

In certain embodiments, the first or second ultrasound energy is an ultrasound energy (e.g., High MI) that when applied to a cell, tissue, or organ of a subject results in inertial cavitation or the collapse of the sonoactive structures and/or disruption of cell membrane and/or vascular endothelial integrity.

In certain embodiments, either the first or second ultrasound energy is an ultrasound energy (e.g., Low MI) that when applied to a cell, tissue, or organ of a subject results in stable cavitation (or stable vibrational cavitation) and/or a change in the average diameter of the sonoactive structure(s), and the other of the first or second ultrasound energy is an ultrasound energy (e.g., High MI) that when applied to a cell, tissue, or organ of a subject results in inertial cavitation or the collapse of the sonoactive structures and/or disruption of cell membrane and/or vascular endothelial integrity.

In some instances, disruption of cell membrane allows target cells to become permeable to circulating agents such as nucleic acid constructs. In certain instances, such circulating agents can then enter the target cells, tissues or organs, such as in a more rapid manner (e.g., relative to either Low MI or High MI ultrasound energy application alone, or in the absence of ultrasound energy application).

In some embodiments, the methods herein comprise alternating the ultrasound energy applied between a first ultrasound energy having a first MI and a second ultrasound energy having a second MI. In some embodiments, applying alternating ultrasound energy administered to a subject between a first MI and a second MI is performed repeatedly over a number of times, such as to enhance gene transfection into the target cells, tissue or organ (e.g., relative to a similar process wherein a first and second ultrasound energy are not used and/or are not alternately applied and/or are not alternately applied repeatedly).

In some embodiments, the first MI ranges from about 0.05 to less than 0.4. In some embodiments, the first MI ranges from about 0.05 to about 0.3. In some embodiments, the first MI ranges from about 0.05 to less than 0.4. In some embodiments, the first MI ranges from about 0.09 to about 0.3.

In some embodiments, the second MI ranges from about 0.4 to about 3.0. In some embodiments, the second MI ranges from about 0.5 to about 3.0. In some embodiments, the second MI ranges from greater than 1.4 to about 3.0. In some embodiments, the second MI ranges from greater than 1.4 to about 3.0. In some embodiments, the second MI ranges from about 1.5 to about 3.0.

In some instances, the ultrasound energy applied at the second MI (e.g., high MI) is applied using a pulse. In some instances, a pulse comprises applying the ultrasound energy in a short pulse (e.g., microsecond length pulse). In some cases, the high MI is applied with the pulse, results in induces inertial cavitation and destruction of the sonoactive microstructure, resulting in the disruption of cell membrane and vascular endothelial integrity, transducing the nucleic acid payload to the cell. In some instances, the pulse is applied with a duration of about 1 μs to about 200 μs. In some instances, the pulse is applied with a duration of about 1 μs to about 200 μs or greater.

In some embodiments, applying the ultrasound energy at the second MI comprises applying the ultrasound energy at the second MI using a pulse. In some instances, the duration of the second MI applied ranges from 0.1 μs to about 200 μs. In some instances, the duration of the second MI applied ranges from 1 μs to about 200 μs or greater. In some embodiments, applying the ultrasound energy at the second MI comprises applying the ultrasound energy at the second MI using a pulse with a duration of about 1 μs to about 200 μs. In some embodiments, applying the ultrasound energy at the second MI comprises applying the ultrasound energy at the second MI using a pulse with a duration of up to 200 μs. In some embodiments, applying the ultrasound energy at the second MI comprises applying the ultrasound energy at the second MI using a pulse with a duration of about 1 μs to about 500 μs. In some embodiments, applying the ultrasound energy at the second MI comprises applying the ultrasound energy at the second MI using a pulse with a duration of up to 500 μs. In some embodiments, applying the ultrasound energy at the second MI comprises applying the ultrasound energy at the second MI using a pulse with a duration of about 2.3 μs. In some embodiments, applying the ultrasound energy at the second MI comprises applying the ultrasound energy at the second MI using a pulse with a duration of at least 2.3 μs. In some embodiments, applying the ultrasound energy at the second MI comprises applying the ultrasound energy at the second MI using a pulse with a duration ranging from 1-500 μs. In some embodiments, applying the ultrasound energy at the second MI comprises applying the ultrasound energy at the second MI using a pulse with a duration ranging from 0.1-500 μs.

In some embodiments, the ultrasound energy is applied using an ultrasound probe applying ultrasound energy to the tissue. In some embodiments, the acoustic radiation force is applied using an ultrasound probe applying ultrasound energy to the tissue. In some embodiments, the ultrasound probe comprises a plurality of piezoelectric elements configured to emit ultrasound energy. In some embodiments, portions of the plurality of piezoelectric elements are arranged in one or more arrays. In some embodiments, the ultrasound probe is a phased array transducer comprising a plurality of piezoelectric elements configured to emit ultrasound energy. In some embodiments, the ultrasound probe is a phased array ultrasound probe, a linear ultrasound probe, a curvilinear ultrasound probe, a convex array ultrasound probe, an endocavitary ultrasound probe, a 3D ultrasound probe, a 4D ultrasound probe, a Doppler ultrasound probe, or a color doppler ultrasound probe.

Sonoactive agent (also referred to as sonoactive microstructures acoustic microspheres or "microbubbles") contemplated herein include, but are not limited to, those used as ultrasonic imaging contrast agents. In some embodiments, the sonoactive agent comprise a phospholipid stabilized microstructure. In some embodiments, the phospholipid stabilized microstructure comprises a high molecular wight gas core, or a perflutran core. Examples of sonoactive agent include, but are not limited to, OPTISON (GE Healthcare), Sonazoid (GE Healthcare), or DEFINITY and Definity RT (Lantheus Medical Imaging, Inc). In some embodiments, the sonoactive agent are LUMASON (Bracco) (sulfur hexafluoride lipid-type A microspheres). In some embodiments, the sonoactive agent are SonoVue (sulfur hexafluoride microbubbles). In some embodiments, the sonoactive agent comprise a protein stabilized microstructure. In some embodiments, the sonoactive agent are Optison microbubbles.

The sonoactive agent can be administered prior to, after, or simultaneous (e.g., co-administered) with the administration of the nucleic acid (or cargo polynucleotide). In some embodiments, the nucleic acid and the sonoactive agent are coadministered. In some embodiments, the administering of the nucleic acid and the sonoactive agent occurs serially, concurrently, sequentially, or continuously. In some embodiments, the administering of the nucleic acid and the sonoactive agent occurs serially. In some embodiments, the administering of the nucleic acid and the sonoactive agent occurs concurrently. In some embodiments, the administering of the nucleic acid and the sonoactive agent occurs sequentially. In some embodiments, the administering of the nucleic acid and the sonoactive agent occurs continuously.

In some embodiments, the nucleic acid is administered at a dosage of about 0.5 mg/kg to about 500 mg/kg. In some embodiments, about 2×10^13 to about 3×10^13 copies of the nucleic acid are administered to the subject.

In some embodiments, the sonoactive microstructures are administered at a dosage of about 1-50 mL, for example 1 mL of Optison. The sonoactive microstructures may be administered at a concentration of about 5M to about 8M microstructures per mL. In some embodiments, the sonoactive microstructures are administered at a concentration of about 5×10^8 to about 1.2×10^9 microstructures/mL, for example 1×10^9 of Definity RT. In some embodiments, the sonoactive microstructures are administered at a concentration of about 0.1 to about 0.8 mg/kg. In some embodiments, the sonoactive microstructures are administered at a concentration of about 0.1 to about 1.0 mL/kg. In some embodiments, the sonoactive microstructures are administered at a concentration of about 10^9 microstructures/mL. In some embodiments, the sonoactive microstructures are administered at a concentration of about 5×10^8 to about 8×10^8 microstructures/mL.

In some embodiments, the nucleic acid and the sonoactive microstructures are mixed prior to being coadministered. In some instances, the sonoactive microstructures are mixed with the nucleic acids before administering to the subject. In some instances, the sonoactive microstructures are mixed with the nucleic acids along with additional buffers or agents such as saline or other biocompatible solutions with varying electrostatic charges and surface chemistries and ligands before administering to the subject. For example, Optison sonoactive microstructures can be mixed with a miniplasmid construct, e.g., a Nanoplasmid, comprising a promoter coupled to a transgene, e.g., APOE-Fluc, and saline, and administered together.

In some embodiments, the administering of the nucleic acid and the sonoactive agent is by intravenous administration or subcutaneous or intramuscular or intra-arterial or inter-osseus or direct organ puncture.

In some embodiments, after administering of the nucleic acid and sonoactive agent, the ultrasound acoustic energy is applied at the target cell, tissue, or organ.

Once the nucleic acids are inside the target cell, expression of the cargo polynucleotide is induced. In some embodiments, the cargo polynucleotide comprises luciferase.

In some embodiments, inducing expression of the cargo polynucleotide comprises inducing expressing within about 3 to about 12 hours of administering the pay load. In some embodiments, inducing expression of the cargo polynucleotide comprises inducing expressing within about 3 hours of administration. In some embodiments, inducing expression of the cargo polynucleotide comprises inducing expressing within about 6 hours of administration. In some embodiments, inducing expression of the cargo polynucleotide comprises inducing expressing within about 12 hours of administration.

Undesirable effects on living cells or tissues can occur due to ultrasound applications. In some embodiments, the present disclosure provides methods for improvement of gene transfection and not result in substantial DNA or cell damage in the target cells, tissues, or organs, using sonoporation by alternating ultrasonic acoustic energy between the first MI and the second MI. In some embodiments, the method does not result in substantial cellular damage to the target cell. In some embodiments, the method results in less than 1%, 5%, or 10% of target cells undergoing apoptosis.

Aspects disclosed herein provide a kit comprising: 1) a sonoactive agent; and 2) means for expressing a functional dystrophin protein in a subject. Aspects disclosed herein provide a kit comprising: 1) a sonoactive agent; and 2) a nucleic acid of any one of SEQ ID NO: 1-12 and 14-50. Aspects disclosed herein provide a kit comprising: 1) a sonoactive agent; and 2) the nucleic acid as described herein. In some embodiments, the kit further comprises instructions for administering ultrasound acoustic energy to a subject to facilitate expression of the functional dystrophin protein in a subject. In some embodiments, the kit further comprises instructions for administering ultrasound acoustic energy to a subject to facilitate expression of the nucleic acid in a subject. In some embodiments, the sonoactive agent comprises lipid-stabilized microstructures. In some embodiments, wherein the lipid-stabilized microstructures comprise a lipid stabilized shell surrounding a perfluorinated gas core. In some embodiments, the lipid stabilized shell comprises a monomolecular membrane of hydrogenated egg yolk phosphatidyl serine, wherein the perfluorinated gas core comprises perfluorobutane gas. In some embodiments, the sonoactive agent is a Sonazoid microbubble. In some embodiments, the sonoactive agent comprises protein stabilized microstructures. In some embodiments, the protein stabilized microstructures comprise an albumin stabilized shell surrounding a perfluorinated gas core. In some embodiments, the protein stabilized microstructures are Optison microbubbles.

I. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used in the specification and claims, the singular forms "a", "an" and "the" include plural references unless the context clearly dictates otherwise. For example, the term "a sample" includes a plurality of samples, including mixtures thereof.

As used herein, the term "about" a number refers to that number plus or minus 10% of that number. The term "about" a range refers to that range minus 10% of its lowest value and plus 10% of its greatest value.

As used herein the term "sequence identity" refers to the percentage identity calculated as the matching residues divided by the total number of residues in the total alignment when performing a consensus alignment of two sequences which considers all residues in the query sequence under evaluation with gaps in the alignment scored as a mismatching residue, with the alignment determined by aligning the sequences using the Needleman-Wunsch alignment algorithm as implemented using the "Global Align" BLAST program available at blast.ncbi.nlm.nih.gov/Blast.cgi (with match/mismatch scores of 2, −3, a gap existence penalty of 5, and a gap extension penalty of 2) and comparing the aligned sequences. The number of exact matches divided by the total number of resides in the alignment (which corresponds with the number of nucleotides in the reference sequence plus any gaps in the reference sequence when aligned with the query sequence, including gaps or mismatches introduced at the beginning or the end of the sequence) is determined and expressed as a percentage. This is the percent sequence identity between the query sequence and the reference sequence (i.e., percent sequence identity=(# of exact matches)/(total # of residues in the query sequence)*100).

The terms "subject," "individual," or "patient" are often used interchangeably herein. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

II. Exemplary Embodiments

Among the exemplary embodiments are:

1. A method of expressing a nucleic acid encoding a dystrophin protein in a cell of a subject, comprising: administering the nucleic acid encoding the dystrophin protein to the subject, administering a sonoactive agent to the subject, and applying ultrasound energy to the cell.
2. A method of expressing a functional dystrophin protein in a subject, comprising: administering an expression vector encoding the functional dystrophin protein or a functional fragment thereof to the subject such that at least 0.25% of cells in a population of cells of the subject uptake the expression vector.
3. A method of expressing a functional dystrophin protein in a subject, comprising: administering an expression vector encoding a functional dystrophin protein or a functional fragment thereof to the subject, thereby inducing uptake of the expression vector in a cell of a diaphragm of the subject.
4. A method of treating a dystrophinopathy disorder in a subject in need thereof, comprising: administering to the subject a nucleic acid encoding a functional dystrophin protein such that the functional dystrophin protein or a functional fragment thereof is expressed in a myocyte of the subject in an amount exceeding 0.5% of a dystrophin level in a wild type subject not having the dystrophinopathy disorder, thereby treating the dystrophinopathy disorder.
5. A method of treating a dystrophinopathy disorder in a subject in need thereof, comprising: administering to the subject a nucleic acid encoding a functional dystrophin protein, expressing the functional dystrophin protein or a functional fragment thereof in a myocyte of the subject about the cellular membrane of the myocyte, throughout the cytoplasm of the myocyte, or both about the about the cellular membrane and throughout the cytoplasm of the myocyte, thereby treating the dystrophinopathy disorder.
6. Use of (i) a nucleic acid encoding a functional dystrophin protein or a functional fragment thereof and (ii) a sonoactive agent in a method of treating a subject having a dystrophinopathy disorder requiring a dystrophin gene therapy or a dystrophin protein replacement therapy.
7. A method of treating a dystrophinopathy disorder in a subject in need thereof, comprising: administering to the subject a nucleic acid encoding a functional dystrophin protein, thereby delivering the nucleic acid to a myocyte in a muscle tissue of the subject (i) along a length of a muscle fiber in the muscle tissue and/or (ii) about the sarcolemma of a muscle fiber in the muscle tissue, thereby treating the dystrophinopathy disorder.
8. A method of delivering a nucleic acid encoding a functional dystrophin protein in a subject, comprising, comprising: administering to the subject the nucleic acid encoding the functional dystrophin protein, and transfecting the nucleic acid to a muscle tissue of the subject, wherein at least 5% of muscle fibers in the muscle tissue of the subject contain the nucleic acid.

9. A method of delivering a nucleic acid encoding a functional dystrophin protein in a muscle cell in a muscle tissue of a subject, comprising: administering the nucleic acid encoding the dystrophin protein to the subject wherein a coding sequence of the nucleic acid encoding the dystrophin protein is at least 10000 nucleotides; administering a sonoactive agent to the subject; and applying ultrasound energy having an ultrasound intensity (Ispta) of at least 100 mW/cm2, a pulse length of at least 20 μs, and a duty cycle of less than 5% in which the ultrasound energy applies an acoustic radiation force to the muscle tissue and displaces the muscle tissue by at least 0.1 mm and displaces a volume of blood in the capillaries of the muscle tissue and transmits a pressure wave throughout a vascular system of the muscle tissue thereby disrupting the sonoactive agent and delivering the nucleic acid encoding the dystrophin protein to at least 5% of muscle fibers in the muscle tissue.

10. The method of any one of embodiments 1-8, wherein the nucleic acid encodes a full length dystrophin protein.

11. The method of embodiment 10, wherein a coding sequence of the nucleic acid encoding the full length dystrophin protein is at least 5000, 6000, 7000, 8000, 9000, 10000, or 11000 nucleotides.

12. The method of embodiment 10, wherein a length the functional dystrophin protein is at least 1750, 2000, 2250, 2500, 2750, 3000, or 3250 amino acids.

13. The method of any one of embodiments 9-12, wherein the coding sequence of the nucleic acid encoding the full length dystrophin protein is contiguous.

14. The method of embodiment 1, wherein the cell is a myocyte, and wherein the dystrophin protein or a functional fragment thereof is expressed in the myocyte in an amount exceeding 0.5% of a dystrophin level in a wild type subject.

15. The method of embodiment 2, wherein the cells comprise a myocyte, and wherein the functional dystrophin protein or a functional fragment thereof is expressed in the myocyte in an amount exceeding 0.5% of a dystrophin level in a wild type subject.

16. The method of embodiment 1, wherein the cell is a myocyte, and wherein the dystrophin protein or a functional fragment thereof is expressed (i) about the cellular membrane of the myocyte, (ii) throughout the cytoplasm of the myocyte, or (iii) both about the cellular membrane and throughout the cytoplasm of the myocyte.

17. The method of embodiment 2, wherein the cells comprise a myocyte, and wherein the functional dystrophin protein or a functional fragment thereof is expressed (i) about the cellular membrane of the myocyte, (ii) throughout the cytoplasm of the myocyte, or (iii) both about the cellular membrane and throughout the cytoplasm of the myocyte.

18. The method of any one of embodiments 4 or 5, wherein the functional dystrophin protein or the functional fragment thereof is expressed in a cell of the subject, wherein the cell is a myocyte.

19. The method of embodiment 7, wherein the functional dystrophin protein or a functional fragment thereof is expressed (i) about the cellular membrane of the myocyte, (ii) throughout the cytoplasm of the myocyte, or (iii) both about the about the cellular membrane and throughout the cytoplasm of the myocyte.

20. The method of any one of embodiments 1 or 3, wherein the method induces uptake of the nucleic acid into at least 0.25% of a population of cells comprising the cell.

21. The method of any one of embodiments 2 or 17, wherein the population of cells is in a cardiac tissue or a heart of the subject, a skeletal muscle tissue or a skeletal muscle of the subject, or a diaphragm tissue or a diaphragm of the subject.

22. The method of embodiment 7, wherein the functional dystrophin protein is expressed in the myocyte in the muscle tissue.

23. The method of embodiment 22, wherein the functional dystrophin protein is expressed along the length of the muscle fiber in the muscle tissue.

24. The method of embodiment 22, wherein the functional dystrophin protein is positioned about the sarcolemma of the muscle fiber in the muscle tissue.

25. The method of any one of embodiments 24, wherein the functional dystrophin protein positioned about the sarcolemma is located along a surface of the sarcolemma along a length of the sarcolemma in a direction parallel to the muscle fiber encapsulated within the sarcolemma.

26. The method of any one of embodiments 22-24, wherein the functional dystrophin protein transfers tension along the length of the muscle fiber or improves a maximum tension loading capacity of the muscle tissue.

27. The method of any one of embodiments 7 or 22-26, wherein at least 1, 3, 5, 10, 15, 20, 25, or 28% of muscle fibers in the treated muscle tissue comprise the nucleic acid encoding the functional dystrophin protein.

28. The method of embodiment 8, wherein at least 6, 7, 8, 9. 10, 11, 12, 13, 14, 15, 16, 17, 18, 19, 20, 21, 22, 23, 24, 25, 26, 27, 28, 29, 30, 35, 40, 45, 50, 55, 60, or 65% of muscle fibers in the muscle tissue of the subject contain the nucleic acid encoding the functional dystrophin protein.

29. The method of embodiment 8 or 28, wherein at least 1% of muscle fibers in the muscle tissue of the subject express the full length dystrophin protein.

30. The method of any one of embodiments 2-8, wherein the cell is a multinucleated cell, a myocyte, or a muscle cell.

31. The method of embodiment 30, wherein the myocyte or the muscle cell comprises a skeletal muscle myocyte, a cardiomyocyte, or a smooth muscle cell.

32. The method of embodiment 31, wherein the myocyte is a skeletal muscle myocyte, and wherein the functional dystrophin protein or fragment thereof is expressed in the myocyte at a level of at least 1, 2, 3, 4, 5, 10, 20, 30, 40, 50, 60, 70, 80, 90, 100, 110, or 120% of normal dystrophin level in a subject not having a dystrophinopathy disorder.

33. The method of embodiment 28, wherein the myocyte or the muscle cell is located in a cardiac tissue or a heart of the subject.

34. The method of embodiment 33, wherein the functional dystrophin protein or fragment thereof is expressed in the cardiac tissue or the heart in an amount of at least 0.3, 0.5, 0.75, 1, 2, 3, 4, 5, 6, 7, 8, 9, or 10% of a dystrophin level in human heart whole tissue lysate as measured by western blot assay.

35. The method of embodiment 30, wherein the myocyte or the muscle cell is located in a skeletal muscle tissue or a skeletal muscle of the subject.
36. The method of embodiment 35, wherein the functional dystrophin protein or fragment thereof is expressed in the muscle tissue or the skeletal muscle in an amount of at least 0.3, 0.5, 0.75, 1, 2, 3, 4, 5% of a dystrophin level in human skeletal muscle whole tissue lysate when measured by western blot assay.
37. The method of embodiment 30, wherein the myocyte or the muscle cell is located in a diaphragm tissue or a diaphragm of the subject.
38. The method of embodiment 37, wherein the functional dystrophin protein or fragment thereof is expressed in the diaphragm tissue or the diaphragm in an amount of at least 0.3, 0.5, 0.75, 1, 2, 3, 4, 5, 6, 7, 8, 9, or 10% of a dystrophin level in human diaphragm whole tissue lysate when measured by western blot assay.
39. The method of any one of embodiments 33, 35, or 37, wherein the functional dystrophin protein or fragment thereof is expressed in the cardiac tissue, the muscle tissue, or the diaphragm tissue, throughout a treated organ comprising the cardiac tissue, throughout a treated organ comprising the muscle tissue, or throughout a treated organ comprising the diaphragm tissue.
40. The method of embodiment 39, wherein the functional dystrophin protein is expressed at detectable levels throughout the treated organ in two or more samples taken from opposite ends of the treated organ.
41. The method of any one of the preceding claims, wherein the nucleic acid or the expression vector is an unencapsulated nucleic acid.
42. The method of any one of embodiments 1, 4, 5, or 7, wherein a coding sequence of the nucleic acid encoding the functional dystrophin protein is at least 5000, 6000, 7000, 8000, 9000, 10000, or 11000 nucleotides.
43. The method of any one of embodiments 2-5, 7, or 8, further comprising administering a sonoactive agent to the subject, and applying ultrasound energy a cell of the subject.
44. The method of any one of embodiments 2-8, wherein a length the functional dystrophin protein is at least 1750, 2000, 2250, 2500, 2750, 3000, or 3250 amino acids.
45. The use of embodiment 6, wherein a coding sequence of the functional dystrophin protein is at least 5000 nucleotides.
46. The use of embodiment 6, wherein the nucleic acid encoding the functional dystrophin protein and the sonoactive agent are configured to induce expression of the functional dystrophin protein in a cell of the subject upon administration of ultrasound energy to the cell.
47. The method of any one of the preceding claims, wherein a coding sequence of the dystrophin protein or the functional dystrophin protein is at least 6000, 7000, 8000, 9000, 10000, or 11000 nucleotides.
48. The method of embodiment 1, wherein a coding sequence of the nucleic acid encoding the dystrophin protein encodes a functional dystrophin protein.
49. The method of embodiment 48, wherein the dystrophin protein is at least 1750, 2000, 2250, 2500, 2750, 3000, or 3250 amino acids in length.
50. The method of any one of the preceding claims, wherein the functional dystrophin protein comprises a full length dystrophin protein.
51. The method of any one of the preceding claims, wherein the functional dystrophin protein is at least 1750, 2000, 2250, 2500, 2750, 3000, or 3250 amino acids in length.
52. The method of any one of the preceding claims, wherein a coding sequence of the nucleic acid encoding the functional dystrophin protein is contiguous.
53. The method of any one of the preceding claims, wherein the nucleic acid encoding (i) the dystrophin protein or (ii) the functional dystrophin protein further comprises a promoter sequence.
54. The method of embodiment 53, wherein the promoter sequence comprises a sequence of any one of SEQ ID NO: 4-5, or 18.
55. The method of any one of the preceding claims, wherein the nucleic acid encoding the (i) dystrophin protein or (ii) the functional dystrophin protein further comprises a post transcriptional regulatory element.
56. The method of embodiment 55, wherein the post transcriptional regulatory element comprises the sequence of any one of SEQ ID NO: 8-10.
57. The method of any one of the preceding claims, wherein the nucleic acid encoding (i) the dystrophin protein or (ii) the functional dystrophin protein further comprises a nuclear targeting sequence.
58. The method of embodiment 57, wherein the nuclear targeting sequence comprises a sequence of SEQ ID NO: 11.
59. The method of any one of the preceding claims, wherein the (i) nucleic acid encoding the dystrophin protein or (ii) the functional dystrophin protein further comprises a post transcriptional regulatory element and a nuclear targeting sequence.
60. The method of embodiment 59, wherein the post transcriptional regulatory element and the nuclear targeting sequence comprise a sequence of SEQ ID NO: 12.
61. The method of any one of the preceding claims, wherein the nucleic acid encoding (i) the dystrophin protein or (ii) the functional dystrophin protein comprises a sequence of any one of SEQ ID NO: 2-3.
62. The method of any one of the preceding claims, wherein the nucleic acid encoding (i) the dystrophin protein or (ii) the functional dystrophin protein comprises a sequence of any one of SEQ ID NO: 6-7.
63. The method of any one of embodiments 30-31, wherein the muscle cell is located within a muscle tissue of the subject, and wherein the method further comprises one or more of: applying heat to the muscle tissue or increasing a blood flow rate in the muscle tissue.
64. The method of embodiment 63, wherein the heat is applied to the muscle tissue using a transcutaneous compress at a temperature of at least 37° C.
65. The method of embodiment 63, wherein the heat is applied to the muscle tissue using ultrasound energy.
66. The method of embodiment 65, the muscle tissue is located in a heart or a diaphragm of the subject.
67. The method of any one of the preceding claims, wherein the cell or the myocyte is in a muscle tissue of the subject, wherein the method further comprises administering a sonoactive agent to the subject, and wherein the administering the sonoactive agent to the subject comprises distributing the sonoactive agent throughout the capillaries of the muscle tissue.
68. The method of any one of the preceding claims, wherein the cell or the myocyte is in a muscle tissue of the subject, wherein the method further comprises applying ultrasound energy to the subject, and wherein the applying the ultrasound energy comprises applying an acoustic radiation force to the muscle tissue.

69. The method of embodiment 68, wherein the applying the acoustic radiation force comprises displacing the muscle tissue.

70. The method of embodiment 69, wherein the muscle tissue is displaced by at least 0.1, 0.2, 0.3, 0.4, 0.5, 0.6, 0.7, 0.8, 0.9, or 1 mm.

71. The method of embodiment 68-69, wherein the applying the acoustic radiation force comprises displacing a volume of blood in capillaries of the muscle tissue.

72. The method of embodiment 71, wherein the method further comprises administering a sonoactive agent to the subject, wherein the displacing the volume of blood in the capillaries of the muscle tissue transmits a pressure wave throughout a vascular system of the muscle tissue, thereby disrupting the sonoactive agent.

73. The method of embodiment 72, wherein the pressure wave does and/or the ultrasound energy applying the acoustic radiation force does not induce vibrational cavitation of the sonoactive agent.

74. The method of any one of embodiments 1 or 41, wherein the applying the ultrasound acoustic energy comprises applying (i) a first ultrasound energy at a MI of up to 0.4 and (ii) a second ultrasound energy at a MI of greater than 0.4 and up to 3.0.

75. The method of any one of embodiments 1 or 41, wherein the applying the ultrasound acoustic energy comprises applying (i) a first ultrasound energy at a MI of up to 0.4 and (ii) a second ultrasound energy at a MI from about 0.8 to about 1.9.

76. The method of any one of embodiments 1 or 41, wherein the applying the ultrasound acoustic energy comprises applying an acoustic radiation force to the subject.

77. The method of embodiment 76, wherein the ultrasound energy is applied at an intensity (ISPTA) of at least 200 mW/cm2.

78. The method any one of embodiments 76-77, wherein the ultrasound energy displaces a muscle tissue of the subject by at least 0.1 mm.

79. The method of any one of embodiments 76-78, wherein the ultrasound energy is applied at a pulse length of at least 20 microseconds.

80. The method of any one of embodiments 1 or 41, wherein the sonoactive agent comprises a shell filled with a gas.

81. The method of embodiment 80, wherein the shell comprises a protein stabilized shell or a lipid stabilized shell.

82. The method of embodiment 80, wherein the gas comprises a perfluorinated case.

83. The method of any one of embodiments 1 or 41, wherein the sonoactive agent comprises microbubbles.

84. The method of any one of embodiments 1 or 41, wherein the sonoactive agent comprises nanobubbles.

85. The method of any one of the preceding claims, wherein the subject has a mutation in a gene encoding a dystrophin protein in a genome of the subject.

86. The method of any one of the preceding claims, wherein the subject has a dystrophinopathy disorder.

87. The method of embodiment 86, wherein the dystrophinopathy disorder comprises Duchenne muscular dystrophy (DMD), Becker muscular dystrophy (BMD), or DMD-associated dilated cardiomyopathy.

88. The method of embodiment 87, wherein the dystrophinopathy disorder comprises Duchenne muscular dystrophy (DMD), and wherein the cell is a skeletal muscle myocyte.

89. The method of embodiment 87, wherein the dystrophinopathy disorder comprises Becker muscular dystrophy (BMD), and wherein the cell is a skeletal muscle myocyte.

90. The method of embodiment 87, wherein the dystrophinopathy disorder comprises DMD-associated dilated cardiomyopathy, and wherein the cell is a cardiac myocyte.

91. The method of embodiment 86, wherein administering the nucleic acid, administering the sonoactive agent, and applying the ultrasound energy induces expression of the dystrophin protein or the functional dystrophin protein, thereby treating the subject having the dystrophinopathy disorder.

92. The method of any one of the preceding claims, wherein the method reduces or ameliorates a symptom of the dystrophinopathy disorder in the subject.

93. The method of any one of the preceding claims, wherein the nucleic acid encoding the dystrophin protein or the functional dystrophin protein is not comprised within a viral vector.

94. The method of any one of the preceding claims, further comprising administering a second dose of the nucleic acid encoding the dystrophin protein or the functional dystrophin protein, the sonoactive agent, and the ultrasound energy to the subject.

95. The method of embodiment 94, further comprising administering a third dose of the nucleic acid encoding the dystrophin protein or the functional dystrophin protein, the sonoactive agent, and the ultrasound energy to the subject, wherein the first through third dose of the nucleic acid encoding the dystrophin protein or the functional dystrophin protein, the sonoactive agent, and the ultrasound energy constitutes a triplicate treatment session.

96. The method of embodiment 95, further comprising administering a second triplicate treatment session to the subject.

97. The method of embodiment 96, further comprising administering a third triplicate treatment session to the subject.

98. The method of any one of the preceding claims, wherein the subject is non-embryonic.

99. The method of any one of the preceding claims, wherein the subject is a mammalian subject.

100. The method of any one of the preceding claims, wherein the subject is a primate subject.

101. The method of any one of the preceding claims, wherein the subject is a human subject.

102. The method of any one of the preceding claims, wherein the subject weighs at least 5 kg.

103. A nucleic acid comprising a nucleic acid sequence having at least 80% sequence identity to any one of SEQ ID NO: 2-3.

104. The nucleic acid of embodiment 103, wherein the nucleic acid sequence has at least 81, 82, 83, 84, 85, 86, 87, 88, 89, 90, 91, 92, 93, 94, 95, 96, 97, 98, or 99% sequence identity to any one of SEQ ID NO: 2-3.

105. The nucleic acid of embodiment 103, wherein the nucleic acid sequence is any one of SEQ ID NO: 2-3.

106. The nucleic acid of any one of embodiments 103-105, wherein the nucleic acid sequence comprises at least 80% sequence identity to any one of SEQ ID NO: 16-17.
107. The nucleic acid of any one of embodiments 103-106, wherein the nucleic acid sequence comprises at least 80% sequence identity to any one of SEQ ID NO: 34-36.
108. The nucleic acid of any one of embodiments 103-107, wherein the nucleic acid sequence encodes a dystrophin protein.
109. The nucleic acid of any one of embodiments 103-107, wherein the nucleic acid sequence encodes a full length dystrophin protein.
110. The nucleic acid of any one of embodiments 103-107, wherein the nucleic acid sequence encodes a dystrophin protein at least 3500 amino acids in length.
111. A nucleic acid delivery vector comprising the nucleic acid of any one of embodiments 103-110.
112. Use of the nucleic acid of any one of embodiments 103-111 in a method of treating a subject having a dystrophinopathy disorder requiring a dystrophin gene therapy or a dystrophin protein replacement therapy.
113. A pharmaceutical composition comprising the nucleic acid of any one of embodiments 103-111.
114. Use of the pharmaceutical composition of embodiment 113 in a method of treating a subject having a dystrophinopathy disorder requiring a dystrophin gene therapy or a dystrophin protein replacement therapy.
115. A cell comprising the nucleic acid of any one of embodiments 103-111.
116. A nucleic acid comprising a nucleic acid sequence having at least 80% sequence identity to any one of SEQ ID NO: 4-5.
117. The nucleic acid of embodiment 116, wherein the nucleic acid sequence has at least 81, 82, 83, 84, 85, 86, 87, 88, 89, 90, 91, 92, 93, 94, 95, 96, 97, 98, or 99% sequence identity to any one of SEQ ID NOS: 4-5.
118. The nucleic acid of embodiment 116, wherein the nucleic acid sequence is a muscle tissue specific promoter sequence.
119. The nucleic acid of embodiment 116, wherein the nucleic acid sequence enhances expression of a therapeutic transgene in a muscle cell.
120. The nucleic acid of embodiment 119, wherein the muscle cell comprises a myocyte, a cardiomyocyte, or a smooth muscle cell.
121. The nucleic acid of embodiment 119, wherein the nucleic acid sequence facilitates expression of a transgene coupled to the promoter for at least 30, 60, 90, 120, 150, 180, 210, 240, 270, or 275 days.
122. The nucleic acid of embodiment 119, wherein the nucleic acid sequence is comprised within a nucleic acid delivery vector and coupled to a nucleic acid coding sequence encoding a protein having at least 90% sequence identity to SEQ ID NO: 13.
123. The nucleic acid of embodiment 119, wherein the nucleic acid sequence is comprised within a nucleic acid delivery vector having a sequence of SEQ ID NO: 7.
124. A nucleic acid delivery vector comprising the nucleic acid of any one of embodiments 116-123.
125. Use of the nucleic acid of any one of embodiments 116-124 in a method of treating a subject having a dystrophinopathy disorder requiring a dystrophin gene therapy or a dystrophin protein replacement therapy, comprising administering the nucleic acid to the subject.
126. A pharmaceutical composition comprising the nucleic acid of any one of embodiments 116-124.
127. Use of the pharmaceutical composition of embodiment 126 in a method of treating a subject having a dystrophinopathy disorder requiring a dystrophin gene therapy or a dystrophin protein replacement therapy.
128. A cell comprising the nucleic acid of any one of embodiments 116-124.
129. A kit comprising: 1) a sonoactive agent; and 2) means for expressing a functional dystrophin protein in a subject.
130. A kit comprising: 1) a sonoactive agent; and 2) a nucleic acid of any one of SEQ ID NO: 1-12 and 14-50.
131. A kit comprising: 1) a sonoactive agent; and 2) the nucleic acid of any one of embodiments 103-111, or 116-121.
132. The kit of embodiment 129, further comprising instructions for administering ultrasound acoustic energy to a subject to facilitate expression of the functional dystrophin protein in a subject.
133. The kit of embodiment 131, further comprising instructions for administering ultrasound acoustic energy to a subject to facilitate expression of the nucleic acid in a subject.
134. The kit of any one of embodiments 129-133, wherein the sonoactive agent comprises lipid-stabilized microstructures.
135. The kit of embodiment 134, wherein the lipid-stabilized microstructures comprise a lipid stabilized shell surrounding a perfluorinated gas core.
136. The kit of embodiment 130, wherein the lipid stabilized shell comprises a monomolecular membrane of hydrogenated egg yolk phosphatidyl serine, wherein the perfluorinated gas core comprises perfluorobutane gas.
137. The kit of embodiment 134, wherein the sonoactive agent is a Sonazoid microbubble.
138. The kit of any one of embodiments 129-133, wherein the sonoactive agent comprises protein stabilized microstructures.
139. The kit of embodiment 138, wherein the protein stabilized microstructures comprise an albumin stabilized shell surrounding a perfluorinated gas core.
140. The kit of embodiment 138, wherein the protein stabilized microstructures are Optison microbubbles.
141. The use of embodiments 114 or 127, wherein the dystrophinopathy disorder comprises Duchenne muscular dystrophy (DMD), Becker muscular dystrophy (BMD), or DMD-associated dilated cardiomyopathy.
142. The use of embodiment 141, wherein the dystrophinopathy disorder comprises Duchenne muscular dystrophy (DMD).
143. The use of embodiment 141, wherein the dystrophinopathy disorder comprises Becker muscular dystrophy (BMD).
144. The use of embodiment 141, wherein the dystrophinopathy disorder comprises DMD-associated dilated cardiomyopathy.
145. A method of treating a dystrophinopathy disorder in a subject in need thereof comprising administering to the subject a nucleic acid encoding a functional dystrophin protein, expressing the functional dystrophin protein or a functional fragment thereof in a myocyte of the subject, thereby treating the dystrophinopathy disorder, wherein the nucleic acid encoding the functional dystrophin protein is not conjugated to an antibody.

146. A method of treating a dystrophinopathy disorder in a subject in need thereof comprising administering to the subject a nucleic acid encoding a functional dystrophin protein, expressing the functional dystrophin protein or a functional fragment thereof in a myocyte of the subject, thereby treating the dystrophinopathy disorder, wherein the nucleic acid encoding the functional dystrophin protein is not associated with cationic peptide moieties.

147. Aspects disclosed herein provide a nucleic acid having a sequence of any one of SEQ ID NO: 1-12 and 14-50.

148. A nucleic acid comprising a promoter sequence having at least 90% sequence identity to any one of SEQ ID NOS: 37-40.

149. The nucleic acid of embodiment 143, wherein the promoter sequence comprises at least 91, 92, 93, 94, 95, 96, 97, 98, or 99% sequence identity to any one of SEQ ID NOS: 37-40.

150. The nucleic acid of embodiment 143, wherein the promoter sequence comprises any one of SEQ ID NOS: 37-40.

151. The nucleic acid of embodiment 143, wherein the promoter sequence is configured to increase expression of a nucleic acid encoding a therapeutic protein operably coupled to the promoter sequence.

152. The nucleic acid of embodiment 143, wherein the promoter sequence is configured to increase expression of a nucleic acid encoding a therapeutic protein operably coupled to the promoter sequence in multiple cell types.

153. The nucleic acid of embodiment 151, wherein the promoter sequence is configured to increase expression of the nucleic acid encoding the therapeutic protein in a muscle cell.

154. The nucleic acid of embodiment 151, wherein the promoter sequence is configured to increase expression of the nucleic acid encoding the therapeutic protein in a kidney cell.

155. The nucleic acid of embodiment 151, wherein the promoter sequence is configured to increase expression of the nucleic acid encoding the therapeutic protein in a liver cell.

156. The nucleic acid of embodiment 150, wherein the liver cell is a hepatocyte, or a LSEC.

157. The nucleic acid of embodiment 151, wherein the promoter sequence is configured to increase expression of the nucleic acid encoding the therapeutic protein in a myocyte.

158. A nucleic acid delivery vector comprising the nucleic acid of any one of embodiments 143-156.

159. A pharmaceutical composition comprising the nucleic acid of any one of embodiments 143-156.

160. A cell comprising the nucleic acid of any one of embodiments 143-156.

161. A method of treating a subject comprising administering the nucleic acid of any one of embodiments 143-156 to a subject.

162. The method of embodiment 161, further comprising administering ultrasound to the subject.

163. The method of embodiment 162, further comprising administering a sonoactive agent to the subject.

164. The method of embodiment 161, further comprising administering a lipid nanoparticle or a polymer nanoparticle to the subject.

165. The method of embodiment 161, wherein the nucleic acid is contained within a viral vector.

166. A kit comprising a sonoactive agent and a nucleic acid of any one of SEQ ID NO: 37-40.

167. Use of a nucleic acid encoding a functional dystrophin protein in a method of treating a dystrophinopathy disorder in a subject in need thereof the method comprising delivering a nucleic acid encoding a functional dystrophin protein in a muscle cell in a muscle tissue of a subject, comprising: administering the nucleic acid encoding the dystrophin protein to the subject wherein a coding sequence of the nucleic acid encoding the dystrophin protein is at least 10000 nucleotides; administering a sonoactive agent to the subject; and applying ultrasound energy having an ultrasound intensity (Ispta) of at least 100 mW/cm2, a pulse length of at least 20 μs, and a duty cycle of less than 5% in which the ultrasound energy applies an acoustic radiation force to the muscle tissue and displaces the muscle tissue by at least 0.1 mm and displaces a volume of blood in the capillaries of the muscle tissue and transmits a pressure wave throughout a vascular system of the muscle tissue thereby disrupting the sonoactive agent and delivering the nucleic acid encoding the dystrophin protein to at least 5% of muscle fibers in the muscle tissue.

III. Examples

The following examples are included for illustrative purposes only and are not intended to limit the scope of the invention.

Example 1: In-Vitro Evaluation of Varying Dystrophin Nucleic Acid Sequences in Transfection of C2C12 Cells The following experiment evaluates expression of nucleic acid delivery vectors comprising codon optimized sequences of human dystrophin.

A plurality of variations of codon optimized sequences of human dystrophin were prepared (SEQ ID NO: 2-3, 19-20) and were compared against one another for expression level of the human dystrophin protein. The codon optimized sequences of human dystrophin were placed in a nucleic acid delivery vector under the influence of either a ubiquitous promoter sequence (SEQ ID NO: 18) or a muscle tissue specific promoter sequence (SEQ ID NO: 4). The double stranded circular DNA vectors were produced in an *E. coli* based method known within the art, and the sequences of the final vectors evaluated are shown in SEQ ID NOS: 21-28.

Transfection began by preparing the media for C2C12 cells. First, a P3000-DNA master mix was prepared by combining 1000 ng of the DNA plasmids (SEQ ID NOS: 21-28) with the P3000 reagent according to the manufacturer's instructions. Concurrently, a Lipofectamine mix was prepared by diluting Lipofectamine reagent in Opti-MEM medium. Following preparation, equal volumes of the P3000-DNA and Lipofectamine mixes were combined to form the DNA-Lipofectamine-P3000 complexes. This mixture was allowed to incubate at room temperature for 5 minutes to ensure complex formation.

Next, 100 μL of the prepared DNA-Lipofectamine-P3000 complex was added to each well of the 12-well plate according to the final plate layout. The cells were incubated under standard culture conditions, and transfection efficiency was assessed by monitoring reporter expression in positive control wells. The expression of the reporter was visualized using a Revolve microscope, and images were captured for analysis.

Cells were then harvested by collecting the cell pellet for further analysis, including protein expression verification via western blotting.

Figure 2:
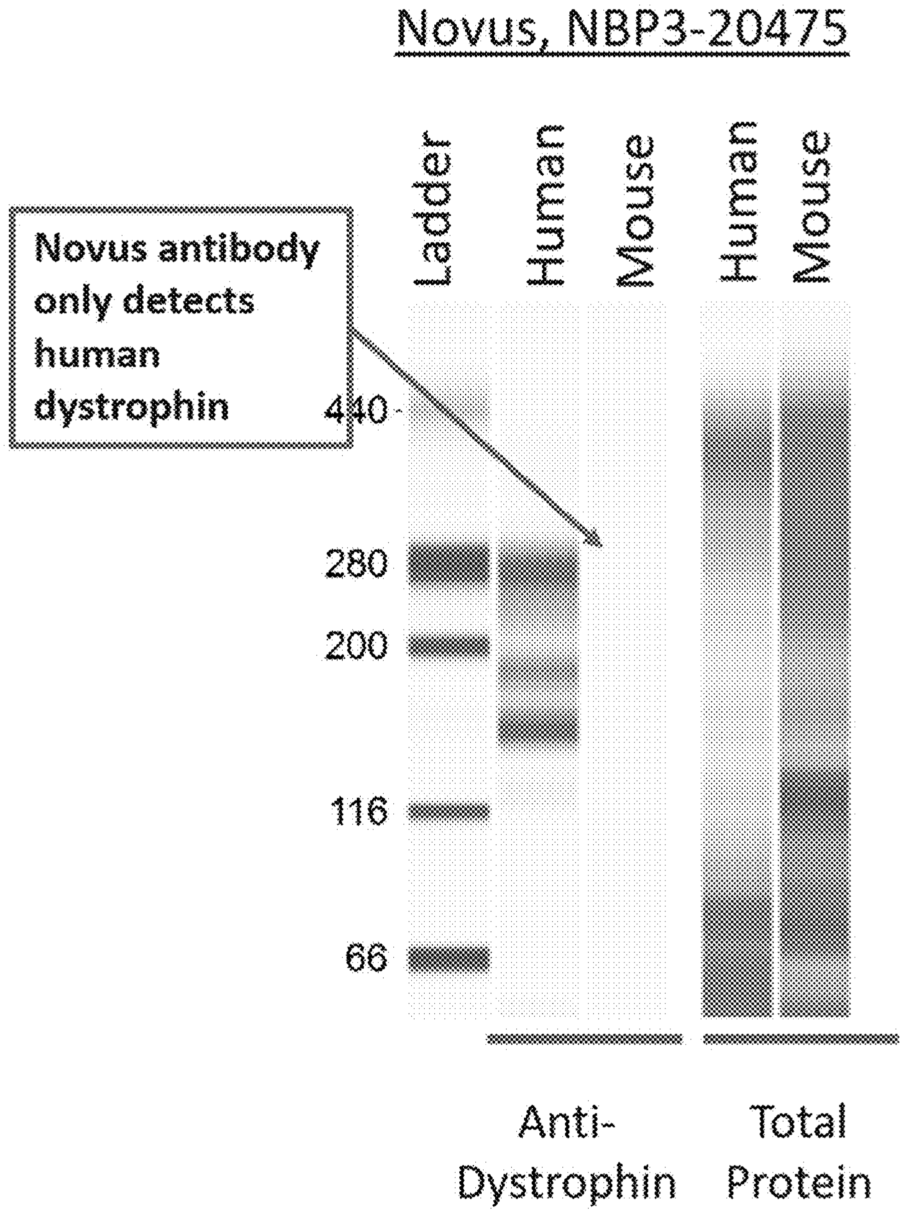
FIG. 2 shows results of a western blot assay illustrating an antibody highly specific to human dystrophin with no cross reactivity to murine dystrophin.
Figure 7:
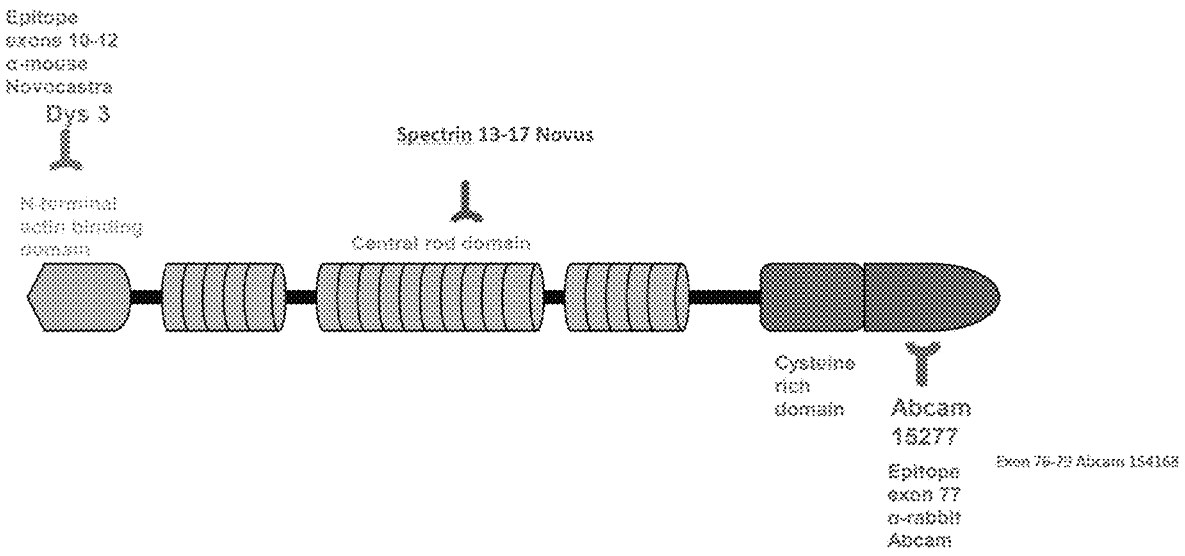
FIG. 7 illustrates a human dystrophin protein and the epitopes targeted by various antibodies used to detect human dystrophin.

Capillary Western blot evaluation of DMD transfected cells was performed to assess the expression of proteins of interest relative to reference proteins. Capillary Western blot evaluation of DMD ORFs was performed using a Novus Primary antibody, #NBP3-20475 which detects human dystrophin, and does not cross-react with mouse dystrophin. A capillary western blow was performed using Novus Primary antibody, #NBP3-20475 to determine lack of cross reactivity by measuring binding with mouse skeletal lysate and human skeletal muscle tissue lysate, the results of which are show in FIG. 2. Dystrophin is a long, rod-like protein (see FIG. 7) which maintains substantial residual secondary structure due to its elongated spectrin-repeat rod domain, even under boiling, reducing, and SDS conditions, which prevented complete unfolding and thus reduces its apparent molecular weight Western or capillary-based immunoassays because dystrophin migrated anomalously on the SDS-PAGE and Simple Western (Wes) ladders due to dystrophin's rod-like architecture and high proline/coil-content which limited SDS binding, altered its charge-to-mass ratio, and produced migration in the 280-300 kDa range despite the protein's true size. See Beekman et al., *Use of capillary Western immunoassay* (*Wes*) *for quantification of dystrophin levels in skeletal muscle of healthy controls and individuals with Becker and Duchenne muscular dystrophy*, PLOS|ONE (2018) at S1 FIG ("The ladders do not completely line up in the high molecular weight region. The 440 band of Wes ladder migrated slower than 460 band of HiMark ladder, which can lead to underestimation of high molecular weights>280 kDa on the Wes."); see also id. at FIG. 2D ("The specificity of dystrophin detection by Wes was however confirmed by the fact that 4 different antibodies against dystrophin which recognise different dystrophin epitopes, Mandys106, ab154168, Manex59B and Dys1, all resulted in a signal at 300 kDa in a healthy control sample (FIG. 2D)."); see also Goossens et al., *DMD antisense oligonucleotide mediated exon skipping efficiency correlates with flanking intron retention time and target position within the exon,* 20:1 RNA Biology 693-702 (2023) (detecting dystrophin protein by Wes capillary immunoassay after treatment of DMD patient with exon skipper 48-50 to produce a long-length but still partially truncated dystrophin protein detected at 280 kDa) and Morisaka et al., *CRISPR-Cas*3 *induces broad and unidirectional genome editing in human cells,* 10:5302 Nature Communications (2019) (detecting dystrophin protein by Wes capillary immunoassay after treatment of DMD patient with exon skipper 44 to produce a long-length but still partially truncated dystrophin protein detected at 280 kDa).

Three µl of lysate was diluted to 2 ug/ul. The protocol began with confirming that the centrifuge was at room temperature. Reagents from the EZ Standard pack of the Separation Module were prepared by placing the 5× Mastermix, Ladder, and dithiothreitol (DTT) on ice. To prepare a 400 mM DTT solution, 40 µl of double-distilled water (ddH2O) was added to the DTT tube, the foil seal was pierced with a pipette tip, and the contents were mixed thoroughly. A 10× Sample Buffer was prepared by adding 20 µl to the 5×Mastermix tube along with 20 µl of the DTT solution, and the mixture was pipetted to ensure homogeneity. Additionally, 20 µl of ddH2O was added to the Ladder tube, mixed and stored on ice.

Samples were diluted to the desired concentrations in 0.1% Sample Buffer, with protein lysates from co-immunoprecipitation (Co-IP) experiments diluted at ratios of 50× and 100× using specified volumes. Master mix was added to the diluted samples at a ratio of 1:4 in PCR strip tubes, which were thoroughly mixed and briefly centrifuged. Samples were denatured by incubating at 95° C. for 5 minutes in a thermal cycler, after which they were spun down and placed on ice to minimize evaporation. Reconstitution agents were prepared by sequentially adding 150 µl of Reconstitution Agent 1 and 150 µl of Reconstitution Agent 2 to the designated tube, with gentle pipetting for mixing. Reconstitution Reagents 1 and 2 were combined in a conical tube at a ratio of 1.4 mL to 0.35 mL and vortexed briefly. A detection reagent mixture of 450 µl Luminol-S and 450 µl peroxide was prepared and kept on ice.

The primary antibody was diluted at either 1:50 or 1:100 in Antibody Diluent 2, depending on the requirements. Reagents were dispensed into a plate as per predefined maps, with the foil cover's top portion removed for access. The plate was covered with a lid, balanced carefully in the centrifuge, and centrifuged at 2500 rpm for 5 minutes at room temperature, and. Using the ProteinSimple software, a new assay was created with parameters suitable for the specific experimental setup. The instrument door of a Jess Automated Western Blot System (Jess) door was opened by activating the top silver button, and the capillary cartridge was inserted into the holder, with the internal light shifting from orange to blue.

Following centrifugation, the plate lid was removed, and the evaporative seal on the foil's bottom portion was peeled off. Bubbles in the Separation matrix wells were eliminated using a pipette tip before the plate was placed in the holder within the Jess instrument. The door was closed, and the assay was initiated via the software's Start button, with continuous monitoring to prevent errors. Upon completion of the assay, the plate was disposed of in biosafety level (BSL) waste, and the cartridge was discarded in sharps waste.

Figure 3:
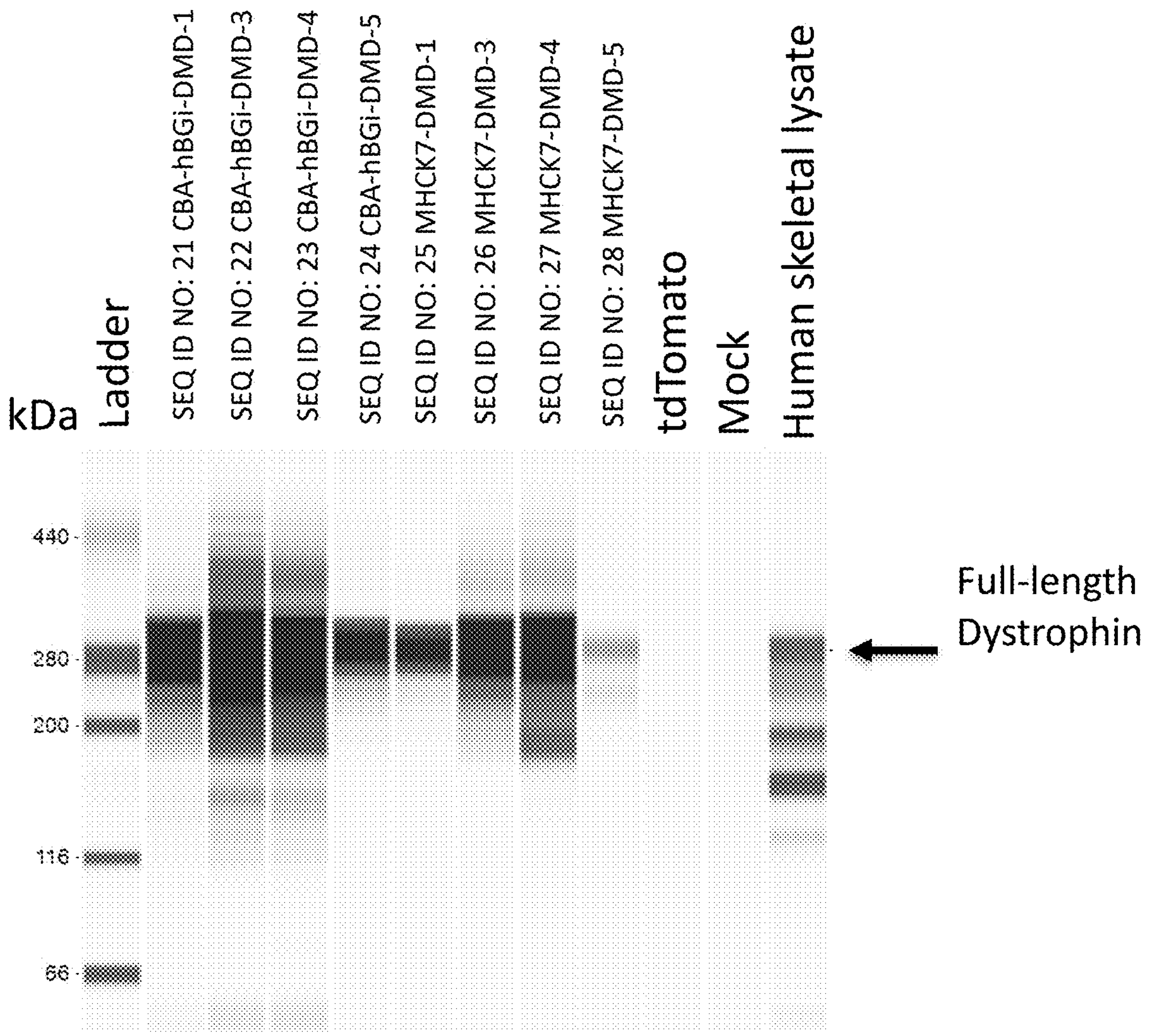
FIG. 3 shows results of a western blot assay illustrating in-vitro expression data of expression of various codon optimized human dystrophin sequences.

Band results of the capillary western blot are shown in FIG. 3, in which it is observed that some codon optimized sequences of human dystrophin SEQ ID NO: 2-3 were highly expressed under the influence of both the ubiquitous promoter sequence (hBGi; SEQ ID NO: 18) or a muscle tissue specific promoter sequence (MHCK7; SEQ ID NO: 4), while some codon optimized sequences of human dystrophin SEQ ID NO: 19-20 exhibited only modest expression under the influence of both the ubiquitous promoter sequence (SEQ ID NO: 18) or a muscle tissue specific-promoter sequence (SEQ ID NO: 4).

Figure 4:
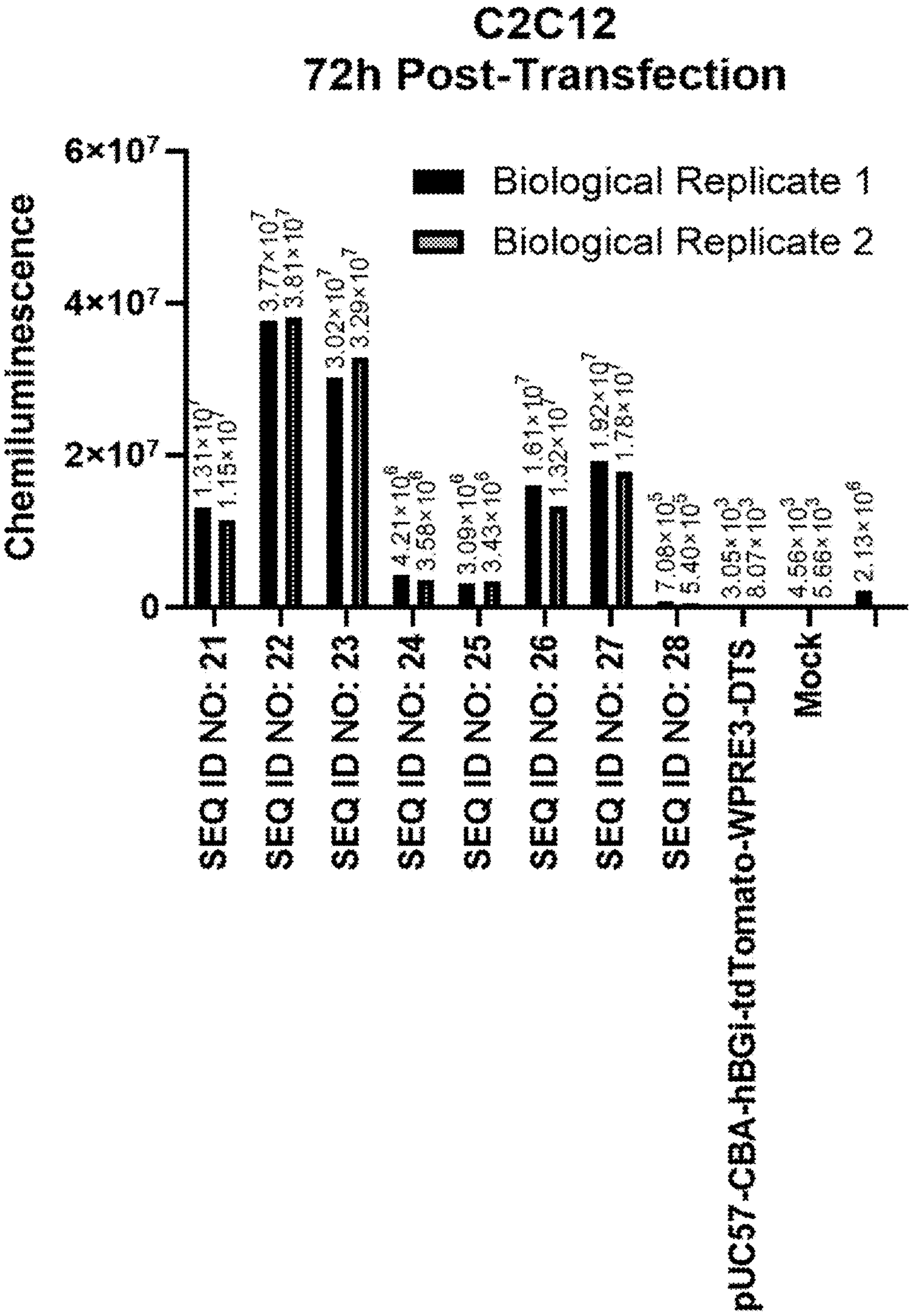
FIG. 4 shows results of a chemiluminescence immunoassay illustrating in-vitro expression data of expression of various codon optimized human dystrophin sequences.

Chemiluminescence was utilized to produce a quantitative readout of expression levels using a secondary antibody configured to bind Novus Primary antibody, #NBP3-20475. Results are shown in FIG. 4 in which it is observed that codon optimized sequences of human dystrophin SEQ ID NO: 2-3 under the influence of a ubiquitous promoter sequence (SEQ ID NO: 18) contained within vectors SEQ ID NO: 22 and 33, respectively, were highly expressed, exhibiting chemiluminescence values of about 3.8 E7 and about 3.2 E7, respectively; and codon optimized sequences of human dystrophin SEQ ID NO: 2-3 under the influence of a muscle specific promoter SEQ ID NO: 4 contained within vectors SEQ ID NO: 26 and 27, respectively, were highly expressed exhibiting chemiluminescence values of about 1.4 E7 and about 1.8 E7 respectively. In both cases, the codon optimized sequences of human dystrophin SEQ ID NO: 2-3 exhibited 3-10 fold greater expression then other codon optimized sequences of human dystrophin SEQ ID NO: 19 contained within vector sequences SEQ ID NO: 21 and 25, and codon optimized sequences of human dystrophin SEQ ID NO: 20 contained within vector sequences SEQ ID NO 24 and 28.

Example 2: In-Vivo Evaluation of Muscle Tissue Specific Vector and Expression of Full-Length Dystrophin Protein in a Murine Model of Sonoporation to the Skeletal Muscle In this example, nucleic acid delivery vectors with expression cassettes comprising promoter sequences which are optimized for expression in skeletal myocytes are evaluated in a murine model of ultrasound mediated nucleic acid delivery to the skeletal muscle (quadriceps).

Experimental Animals and Protocol

Five groups of RAG2 mice were evaluated. Prior to the experiment, mice were implanted with a jugular vein catheter though which the sonoactive agent and the DNA solution was administered. The experimental groups were set forth below. In brief, Group 1 was a no-ultrasound control administered only the vector and the sonoactive agent, Groups 2-3 were administered vectors comprising a gene encoding a fluorescent reporter protein (FLUC) under either a ubiquitous or a muscle tissue specific promoter with administration of a sonoactive agent and ultrasound, and Groups 4-5 were administered vectors comprising codon optimized sequences of human dystrophin, SEQ ID NO: 3, under either a ubiquitous or a muscle tissue specific promoter with administration of a sonoactive agent and ultrasound. Optison (human serum albumin stabilized perflutran core microbubbles) was used as the ultrasound contrast agent in this experiment.

applied at 24 hours after the first treatment session administering the second one third of the DNA payload, and a third identical treatment session was applied at 24 hours after the second treatment session administering the last one third of the DNA payload.

For Groups 1-3, the mice were injected with D-Luciferin, potassium salt and imaged using IVIS: 1 day following the first treatment session; 1 day following the second treatment session; and 1, 2 and 6 days following the third treatment session.

For Groups 4-5, necropsy was performed 4 days following the third treatment session. Tissue samples were collected, placed into a sterile tube, and snap frozen using liquid nitrogen ($N_2$). Tissue samples were directly transferred to −80° C. storage.

Capillary Western blot evaluation of DIMD transfected samples was performed to assess the expression of DMD. Capillary western blot analysis was performed as described in Example 1 but using Abcam antibody for dystrophin (ab154168) which is specific to human dystrophin, with the addition of human skeletal muscle lysate which was normalized to 2 ug/ul, then diluted to create standards at 100, 50, 25, 5, 2, and 1%. A 2 ug/uL was the selected concentration for the western blot analysis. Samples were then diluted to 2 ug/uL and compared with human skeletal muscle lysate standards. Dystrophin is a long, rod-like protein (see FIG. 7) which maintains substantial residual secondary structure due to its elongated spectrin-repeat rod domain, even under boiling, reducing, and SDS conditions, which prevented complete unfolding and thus reduces its apparent molecular weight Western or capillary-based immunoassays because dystrophin migrated anomalously on the SDS-PAGE and Simple Western (Wes) ladders due to dystrophin's rod-like architecture and high proline/coil-content which limited SDS binding, altered its charge-to-mass ratio,

| Group (n = 3) | Strain | DNA Dose (ug) | Sonoactive agent | # of doses | Ultrasound | Vector |
|---|---|---|---|---|---|---|
| 1 | Rag2 | 250 | Optison | 3 | None | SEQ ID NO: 29 (ubiquitous promoter + FLUC reporter) |
| 2 | Rag2 | 250 | Optison | 3 | L8-18, MI 1.4, 10 sec on, 20 sec off, 60 sec total on | SEQ ID NO: 29 (ubiquitous promoter + FLUC reporter) |
| 3 | Rag2 | 250 | Optison | 3 | L8-18, MI 1.4, 10 sec on, 20 sec off, 60 sec total on | SEQ ID NO: 30 (muscle tissue specific promoter + FLUC reporter) |
| 4 | Rag2 | 250 | Optison | 3 | L8-18, MI 1.4, 10 sec on, 20 sec off, 60 sec total on | SEQ ID NO: 31 (ubiquitous promoter + DMD Codon Optimized SEQ ID NO: 3) |
| 5 | Rag2 | 250 | Optison | 3 | L8-18, MI 1.4, 10 sec on, 20 sec off, 60 sec total on | SEQ ID NO: 32 (muscle tissue specific promoter + DMD Codon Optimized SEQ ID NO: 3) |

The mice received application of ultrasound energy following administration of 50 μL of the sonoactive agent and one third of the DNA payload in each treatment session. In a treatment session, the left leg of each animal was placed in a heated water bath at 38° C. for 2 minutes prior to applying ultrasound using a L8-18 probe on a General Electric LOGIQ E9 system in Elasto mode, the probe applying an acoustic radiation force at a frequency of about 2.5 MHz at a mechanical index of 1.4 at a 100% push output at an ultrasound intensity of at least 200 mW/cm2 (ISPTA) for about 10 sec on, 20 sec off, for a total of 60 sec (2 cycles) of ultrasound application over the left quadriceps region of each mouse. A second identical treatment session was and produced migration in the 280-300 kDa range despite the protein's true size. See Beekman et al., *Use of capillary Western immunoassay (Wes) for quantification of dystrophin levels in skeletal muscle of healthy controls and individuals with Becker and Duchenne muscular dystrophy*, PLOS|ONE (2018) at S1 FIG ("The ladders do not completely line up in the high molecular weight region. The 440 band of Wes ladder migrated slower than 460 band of HiMark ladder, which can lead to underestimation of high molecular weights>280 kDa on the Wes."); see also id. at FIG. 2D ("The specificity of dystrophin detection by Wes was however confirmed by the fact that 4 different antibodies against dystrophin which recognise different dystrophin epitopes, Mandys106, ab154168, Manex59B and Dys1, all resulted in a signal at 300 kDa in a healthy control sample (FIG. 2D).”); see also Goossens et al., *DMD antisense oligonucleotide mediated exon skipping efficiency correlates with flanking intron retention time and target position within the exon,* 20:1 RNA Biology 693-702 (2023) (detecting dystrophin protein by Wes capillary immunoassay after treatment of DMD patient with exon skipper 48-50 to produce a long-length but still partially truncated dystrophin protein detected at 280 kDa) and Morisaka et al., *CRISPR-Cas3 induces broad and unidirectional genome editing in human cells,* 10:5302 Nature Communications (2019) (detecting dystrophin protein by Wes capillary immunoassay after treatment of DMD patient with exon skipper 44 to produce a long-length but still partially truncated dystrophin protein detected at 280 kDa).

Results

Figure 5:
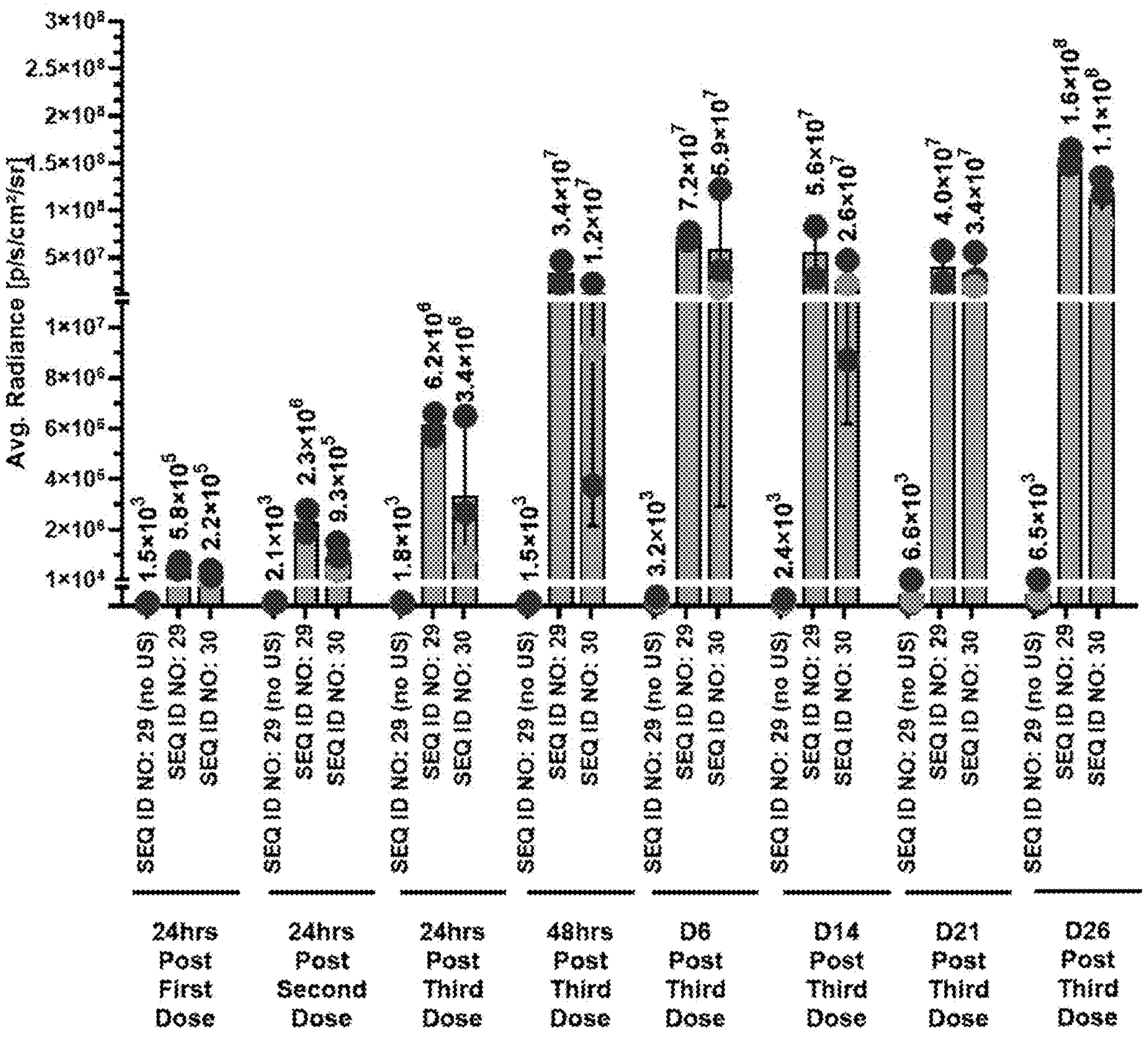
FIG. 5 shows in-vivo data fluorescence data illustrating expression of a gene encoding a reporter protein downstream of a promoter sequence of the present disclosure.
Figure 6:
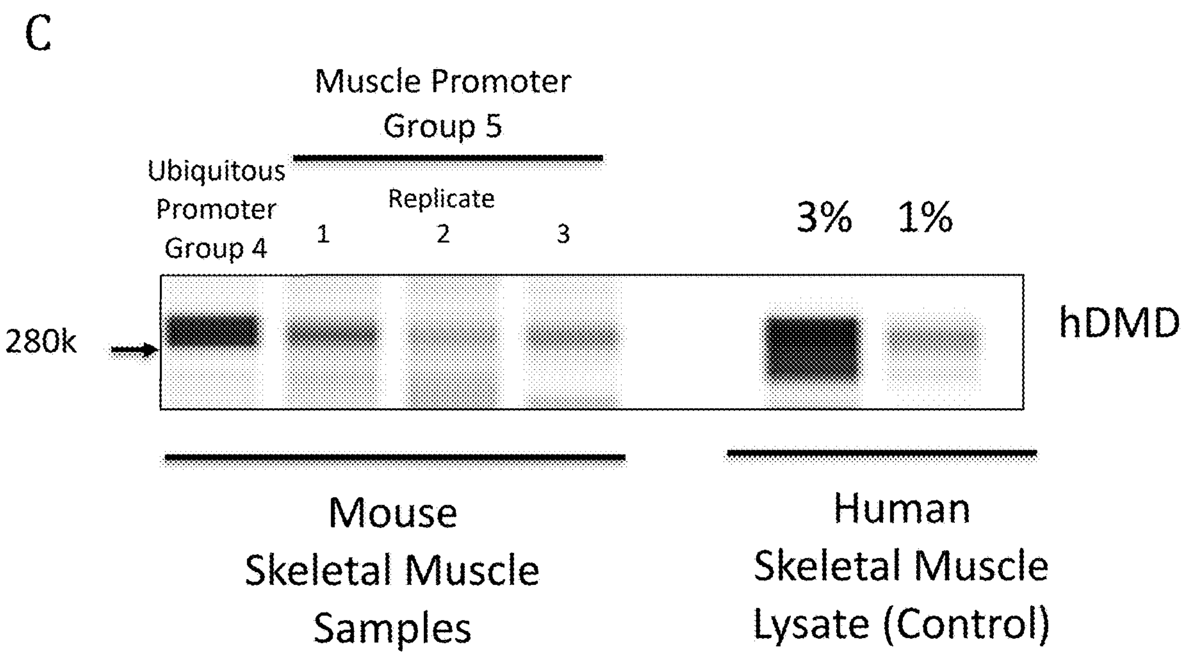
FIG. 6 shows results of a western blot assay illustrating expression of full length human dystrophin protein in-vivo.

Results for Groups 1-3 are shown in FIG. 5, in which it is shown that the negative control group 1 exhibits only background levels of average radiance at all time points; Group 2 administered the vector of SEQ ID NO: 29 (ubiquitous promoter+FLUC reporter) exhibited average radiance levels of about 2.3 E6 p/s/cm2/sr at 24 hours following the second treatment, average radiance levels of about 6.2 E6 p/s/cm2/sr at 24 hours following the third treatment, average radiance levels of about 3.44 E7 p/s/cm2/sr at 48 hours following the third treatment, and average radiance levels of about 7.2 E7 p/s/cm2/sr at 72 hours following the third treatment; and Group 3 administered the vector of SEQ ID NO: 30 (muscle tissue specific promoter+FLUC reporter) exhibited average radiance levels of about 9.3 E5 p/s/cm2/sr at 24 hours following the second treatment, average radiance levels of about 3.4 E6 p/s/cm2/sr at 24 hours following the third treatment, average radiance levels of about 1.2 E7 p/s/cm2/sr at 48 hours following the third treatment, and average radiance levels of about 5.9 E7 p/s/cm2/sr at 72 hours following the third treatment. The mice were followed for up to 26 days following the third treatment, at which point Group 2 administered the vector of SEQ ID NO: 29 (ubiquitous promoter+FLUC reporter) exhibited average radiance levels of about 1.6 E8 p/s/cm2/sr; and Group 3 administered the vector of SEQ ID NO: 30 (muscle tissue specific promoter+FLUC reporter) exhibited average radiance levels of about 1.1 E8 p/s/cm2/sr. Results of the capillary western blot are shown in FIG. 6, in which samples were diluted to 2 ug/uL and compared with human skeletal muscle lysate standards. In FIG. 6, it is observed that Group 4 (administered the vector of SEQ ID NO: 31 comprising a ubiquitous promoter coupled to DMD Codon Optimized SEQ ID NO: 3) exhibited strong expression of the full length dystrophin protein consistent with the 3% human skeletal muscle lysate standard, while Group 5 (administered the vector of SEQ ID NO: 32 comprising a muscle tissue specific promoter coupled to DMD Codon Optimized SEQ ID NO: 3) exhibited expression of the full length dystrophin protein consistent with the 1% human skeletal muscle lysate standard.

Example 3: In-Vivo Evaluation of Muscle Tissue Specific Vector and Expression of Full-Length Dystrophin Protein in a Murine Model of Sonoporation to the Diaphragm In this example, nucleic acid delivery vectors with expression cassettes comprising promoter sequences which were optimized for expression in skeletal myocytes cells were evaluated in a murine model of ultrasound mediated nucleic acid delivery to the diaphragm muscle tissue.

Experimental Animals and Protocol

Three groups of MDX mice (a mouse model which carries a point mutation in the mouse dystrophin gene (DMD) leading to a lack of functional dystrophin protein) were evaluated. Prior to the experiment, mice were implanted with a jugular vein catheter though which the sonoactive agent and the DNA solution were administered. The experimental groups used are set forth below. In brief, Group 1 was a no-ultrasound control group administered only the vector dose and the sonoactive agent, Group 2 was administered vectors comprising codon optimized sequences of human dystrophin SEQ ID NO: 3 under a muscle tissue specific promoter of SEQ ID NO: 4 (the combination of which being comprised within the expression cassette of SEQ ID NO: 34) with administration of a sonoactive agent and ultrasound and were evaluated for expression effect resulting from repeated dosing increases among the groups, and Group 3 was administered vectors comprising a gene encoding a fluorescent reporter protein under a muscle tissue specific promoter with administration of a sonoactive agent and ultrasound. Sonazoid (phospholipid stabilized perfluorobutane core microbubbles) was used as the sonoactive agent in this experiment.

| Group (n = 3) | Strain | DNA Dose (ug) | Sonoactive agent | # of doses | Ultrasound | Vector/Expression Cassette/Promoter Transgene |
|---|---|---|---|---|---|---|
| 1 (n = 1) | MDX | 250 | Sonazoid | 3 | None | SEQ ID NO: 27 (expression cassette of SEQ ID NO: 34 with muscle tissue specific promoter of SEQ ID NO: 4+ DMD Codon Optimized SEQ ID NO: 3) |
| 2 | MDX | 250 | Sonazoid | 3 | L8-18, MI 1.4, 2 sec on/2 sec off, 60 sec total on | SEQ ID NO: 27 (expression cassette of SEQ ID NO: 34 with muscle tissue specific promoter of SEQ ID NO: 4+ DMD Codon Optimized SEQ ID NO: 3) |
| 3 | MDX | 250 | Sonazoid | 3 + 3 + 3 | L8-18, MI 1.4, 2 sec on/2 sec off, 60 sec total on | SEQ ID NO: 30 (muscle tissue specific promoter of SEQ ID NO: 4+ FLUC reporter) |

The mice received application of ultrasound energy following administration of 50 μL of the sonoactive agent and one third of the DNA payload in each treatment session. In a treatment session, the middle abdomen region was targeted with ultrasound using a L8-18 probe on a General Electric LOGIQ E9 system in Elasto mode applying an acoustic radiation force at a frequency of about 6.25 MHz at a mechanical index of 1.4 at a 100% push output at an ultrasound intensity of at least 200 mW/cm2 (ISPTA) alternating between 2 seconds on of ultrasound application and 2 seconds off of ultrasound application, for a total of 60 sec of on ultrasound application (30 cycles) over the diaphragm region of each mouse. A second identical treatment session was applied at 3 days following the first treatment session, and a third identical treatment session was applied at 3-4 days after the second treatment session. Each set of three identical treatment sessions is referred to herein as a triplicate treatment session. Group 3 was administered three triplicate treatment sessions.

For Group 3, mice were injected with D-Luciferin, potassium salt and imaged using IVIS weekly following each triplicate treatment session.

For Groups 1-2, 14 days following the first triplicate treatment session, subjects were sacrificed and tissue samples were collected for further analysis.

For Groups 1-2, necropsy was performed at the stated time points, and tissue samples were collected, placed into a sterile tube, and snap frozen using liquid $N_2$. Tissue samples were directly transferred to −80° C. storage.

Capillary Western blot evaluation of DMID transfected samples was performed to assess the expression of DMD. Capillary western blot analysis was performed as described in Example 1, but using Abcam antibody for dystrophin (ab154168) which is specific to human dystrophin, with the addition of human diaphragm whole tissue lysate (Novus Bio) normalized to 1 mg/mL, then diluted to create standards at 5%, 2%, and 1%. A 1 mg/mL concentration was the selected concentration for the western blot analysis (ab154168 (1:150)). Samples were then diluted to 1 mg/mL and compared with human diaphragm whole tissue lysate standards.

Transgenic tissue samples were stained and imaged using Dystrophin DAB (3,3'-diaminobenzidine) chromogen staining, and hematoxylin nuclei staining. Slides were pre-baked at 60° C. for at least 15 minutes and positioned on a black slide tray. Labels were generated and affixed onto the slides, which were then transferred into the Slide Staining Assemblies (SSA). The Polymer Refine Detection Kit was registered on the Leica controller, and all required reagents were verified. The Refine reagent kit was loaded onto the reagent platform for dip testing. Antibodies specific to the target protein (human dystrophin) were prepared and dispensed into titration tubes. Up to 5 mL of antibody was used for a maximum 30-slide run. The necessary antibodies were loaded onto the reagent platform, and dip testing proceeded. Bulk reagents were replenished as needed, and waste containers were emptied. After dip testing, the SSA buttons were pressed to lower and lock the slide trays. The Leica Bond RX Fully Automated Research Stainer was used for the staining procedure. Once staining concluded, the SSA buttons were pressed again to release the slide trays. Cover tiles were removed, and slides were placed in a staining rack. Slides were washed in deionized water for three minutes and allowed to dry at 60° C. for a minimum of 30 minutes. Coverslipping was performed using mounting media, and slides were left to dry overnight for optimal imaging quality. The stained slides were scanned using an Olympus VS200 Slide Scanner to assess dystrophin protein presence in the transgenic tissue samples.

Results

Figure 8:
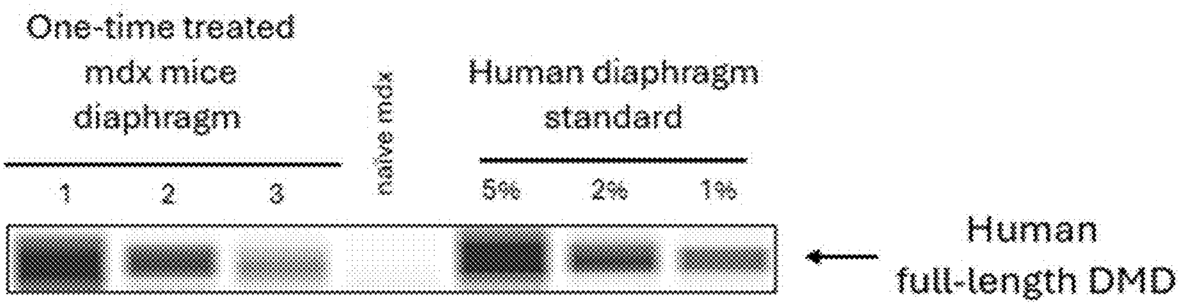
FIG. 8 shows results of a western blot assay illustrating expression of full length human dystrophin protein in-vivo.

Results of the capillary western blot for Group 2 are shown in FIG. 8 (each lane showing samples collected from a different subject MDX mouse in Group 2), in which samples are diluted to 1 mg/mL and compared with human diaphragm whole tissue lysate (Novus Bio) normalized to 1 mg/mL and diluted to 5, 2, and 1% standards.

Lanes 1, 2 and 3, labeled "one-time treated MDX diaphragm" in FIG. 8, correspond to different subjects from Group 2, and exhibit expression levels of full length human dystrophin, which are comparable to the human diaphragm whole tissue lysate 5, 2, and 1% standards respectively. A sample from a naive MDX mouse diaphragm is also shown as a negative control, and the assay indicates no detectable human dystrophin in the naïve MDX sample, validating the specificity of the antibody and the sensitivity assay for human dystrophin.

Figure 9:
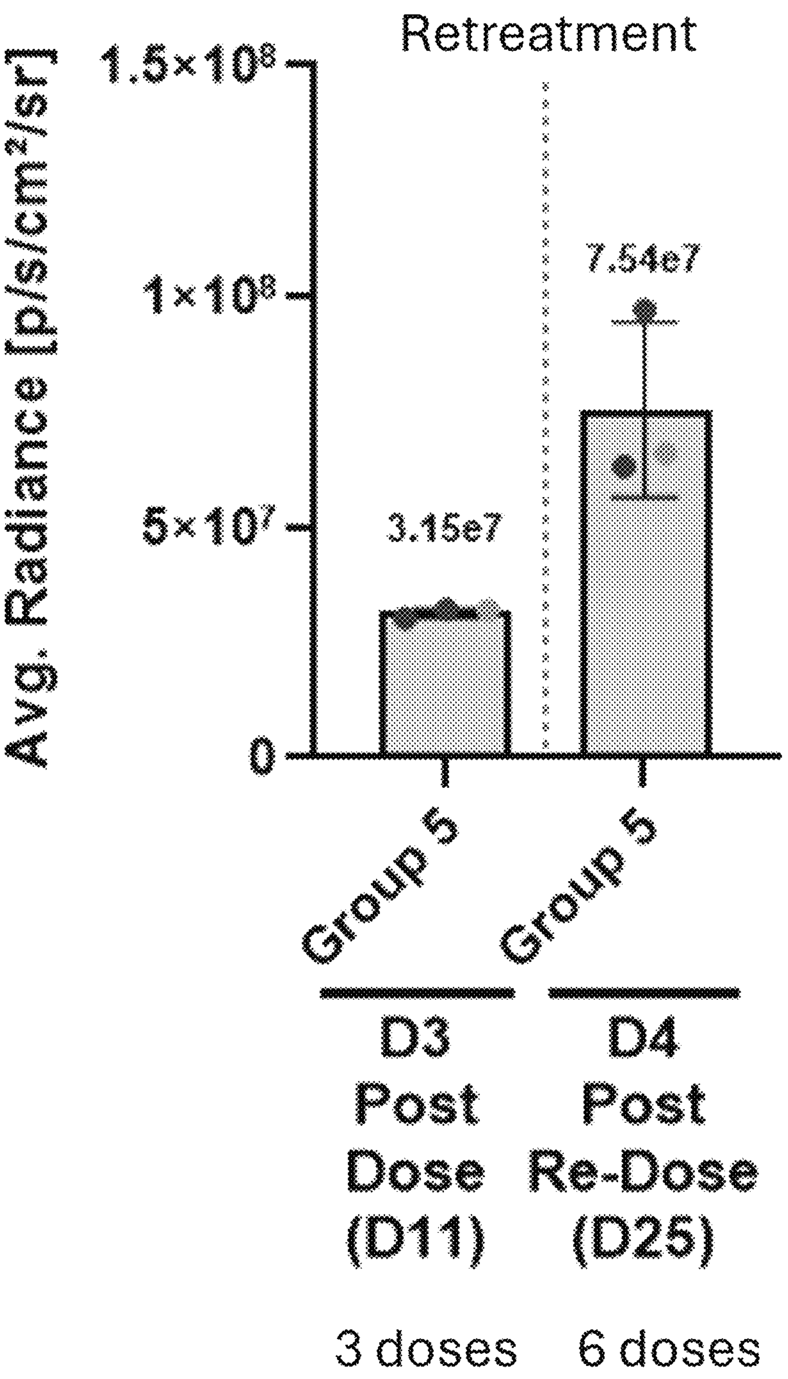
FIG. 9 shows in-vivo fluorescence data illustrating expression of a gene encoding a reporter protein downstream of a promoter sequence of the present disclosure.

IVIS results for Groups 3 are shown in FIG. 9, in which it is shown that Group 3, administered the vector of SEQ ID NO: 30 (muscle tissue specific promoter+FLUC reporter), exhibited average radiance levels of about 3.15 E7 p/s/cm2/sr at 3 days following the final dose of the first triplicate treatment session (day 11 of the study), and average radiance levels of about 7.54 E7 p/s/cm2/sr at 3 days following the final dose of the second triplicate treatment session (day 25 of the study).

Figure 12:
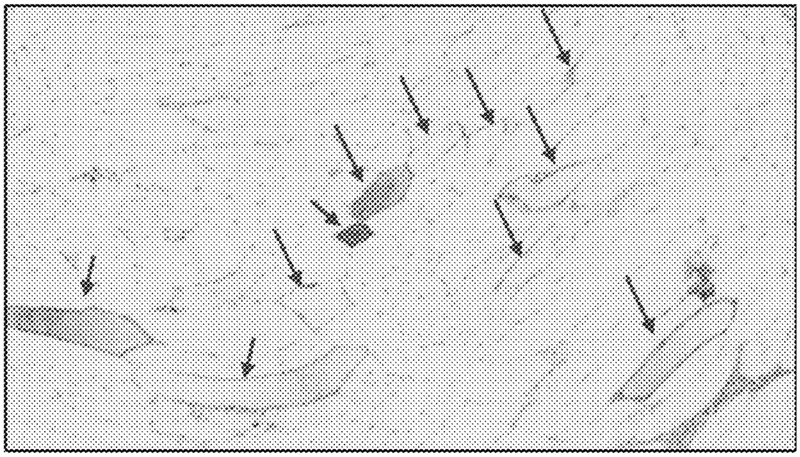
FIG. 12 shows immunohistochemistry stain images illustrating expression of full length human dystrophin protein in-vivo in transfected cells, arrows indicate cells expressing human dystrophin protein.
Figure 12:

Results of the Dystrophin DAB chromogen staining, and hematoxylin nuclei staining of samples taken from the top performing mouse in Group 2 are shown in FIG. 12 in which expression of the full length dystrophin protein can be observed in transfected myocytes of the subject in both the cellular membrane of the myocyte and throughout the cytoplasm of the myocyte, as shown by the orange and dark orange DAB staining in FIG. 12. Blue dots represent individual nuclei within the tissue samples, as stained with hematoxylin.

Example 4: In-Vivo Evaluation of Muscle Tissue Specific Vector and Expression of Full-Length Dystrophin Protein in a Murine Model of Sonoporation to the Heart In this example, nucleic acid delivery vectors with expression cassettes comprising promoter sequences which were optimized for expression in skeletal myocytes were evaluated in a murine model of ultrasound mediated nucleic acid delivery to cardiac tissue.

Experimental Animals and Protocol

Two groups of MDX mice (a mouse model which carries a point mutation in the mouse dystrophin gene (DMD) leading to a lack of functional dystrophin protein) were evaluated. Prior to the experiment, mice were implanted with a jugular vein catheter though which the sonoactive agent and the DNA solution were administered. The experimental groups used are set forth below. In brief, Group 1 was a no-ultrasound control group administered only the vector dose and the sonoactive agent, Group 2 was administered codon optimized sequences of human dystrophin SEQ ID NO: 3 under a muscle tissue specific promoter of SEQ ID NO: 4 (the combination of which being comprised within the expression cassette of SEQ ID NO: 34) with administration of a sonoactive agent and ultrasound and was evaluated for the expression effect resulting from repeated dosing increases among the groups. Sonazoid (phospholipid stabilized perfluorobutane core microbubbles) was used as the sonoactive agent in this experiment.

| Group (n = 5) | Strain | DNA Dose (ug) | Sonoactive agent | # of doses | Ultrasound | Vector/Expression Cassette/Promoter/Transgene |
|---|---|---|---|---|---|---|
| 1 (n = 1) | MDX | 80 | Sonazoid | 3 | None | SEQ ID NO: 27 (expression cassette of SEQ ID NO: 34 with muscle tissue specific promoter of SEQ ID NO: 4+ DMD Codon Optimized SEQ ID NO: 3) |
| 2 | MDX | 80 | Sonazoid | 3 | L8-18, MI 0.46, PO 30%, 40 sec on | SEQ ID NO: 27 (expression cassette of SEQ ID NO: 34 with muscle tissue specific promoter of SEQ ID NO: 4+ DMD Codon Optimized SEQ ID NO: 3) |

The mice received application of ultrasound energy following administration of 50 uL of the sonoactive agent and one third of the DNA payload in each treatment session. In a treatment session, the upper abdomen region was targeted with ultrasound using a L8-18 probe on a General Electric LOGIQ E9 system in Elasto mode applying an acoustic radiation force at a frequency of about 6.25 MHz at a mechanical index of 0.46 at a 30% push output at an ultrasound intensity of at least 200 mW/cm2 (ISPTA) applying ultrasound for 40 seconds over the cardiac region of each mouse. A second identical treatment session was applied at 3 days following the first treatment session, and a third identical treatment session was applied at 3-4 days after the second treatment session. Each set of three identical treatment sessions is referred to herein as a triplicate treatment session.

For Groups 1-2, 14 day following the first triplicate treatment session, subjects were sacrificed and tissue samples were collected for further analysis.

For Groups 1-2, necropsy was performed at the stated time points, and tissue samples were collected, placed into a sterile tube, and snap frozen using liquid $N_2$. Tissue samples were directly transferred to −80° C. storage. Capillary western blot analysis was performed as described in Example 1, with the addition of human heart whole tissue lysate (Novus Bio) normalized to 1 mg/mL, then diluted to create standards at 10, 5 and 2%. A 1 mg/mL concentration was the selected concentration for the western blot analysis (ab154168 (1:150)). Samples were then diluted to 1 mg/mL and compared with human heart whole tissue lysate.

Results

Figure 10:
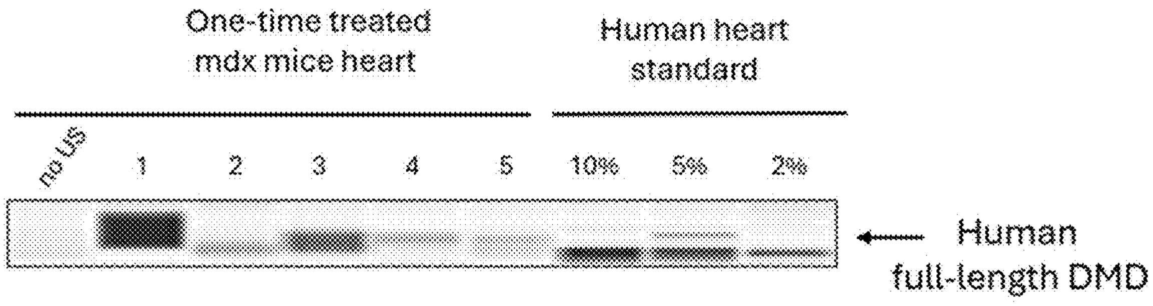
FIG. 10 shows results of a western blot assay illustrating expression of full length human dystrophin protein in-vivo.

Results of the capillary western blot are shown for Group 2 in FIG. 10 (each lane showing samples collected from a different subject MDX mouse in Group 2), in which samples are diluted to 1 mg/mL and compared with human diaphragm whole tissue lysate (Novus Bio) normalized to 1 mg/mL and diluted to 10, 5 and 2% standards.

Lanes 1-5, labeled “one-time treated MDX heart” in FIG. 10, correspond to different subjects from Group 2, and exhibit expression levels of full length human dystrophin which are comparable to the human diaphragm whole tissue lysate 10, 5 and 2% standard, with the Lane 1 subject exhibiting an expression level most similar to the 10% standard. A sample from Group 1 not administered any ultrasound is also shown as a negative control, and the assay indicates no detectable human dystrophin in this sample.

Figure 13:
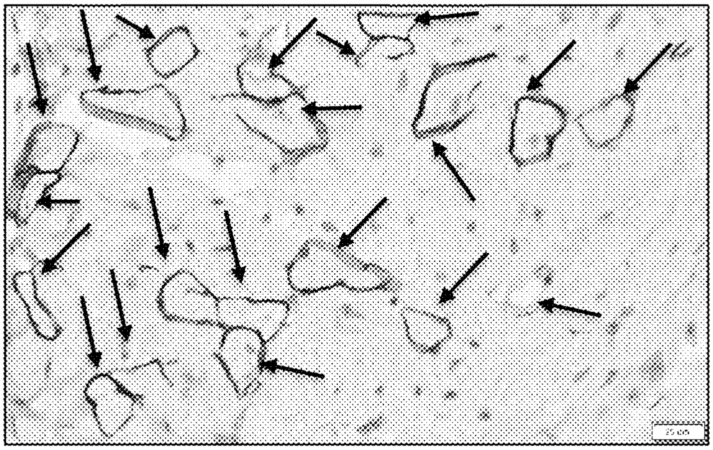
FIG. 13 shows immunohistochemistry stain images illustrating expression of full length human dystrophin protein in-vivo in transfected cells, arrows indicate cells expressing human dystrophin protein.
Figure 13:
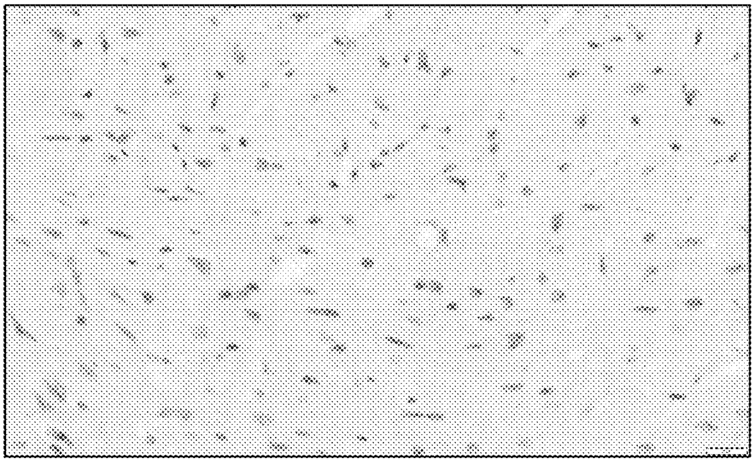

Staining was performed as described in Example 3. Results of the DAB staining are shown in FIG. 13 for the top performing mice in Group 2 in which expression of the full length dystrophin protein can be observed in transfected myocytes of the subject about the cellular membrane of the myocyte and throughout the cytoplasm of the myocyte, as shown by the orange and dark orange DAB staining in FIG. 13. Blue dots represent individual nuclei within the tissue samples stained with hematoxylin.

Example 5: In-Vivo Evaluation of Muscle Tissue Specific Vector and Expression of Full-Length Dystrophin Protein in a Murine Model of Sonoporation to the Skeletal Muscle In this example, nucleic acid delivery vectors with expression cassettes comprising promoter sequences which were optimized for expression in skeletal myocytes were evaluated in a murine model of ultrasound mediated nucleic acid delivery to the skeletal muscle (quadriceps).

Experimental Animals and Protocol

Two groups of MDX mice (a mouse model which carries a point mutation in the mouse dystrophin gene (DMD) leading to a lack of functional dystrophin protein) were evaluated. Prior to the experiment, mice were implanted with a jugular vein catheter though which the sonoactive agent and the DNA solution were administered. The experimental groups used are set forth below. In brief, Group 1 was a no-ultrasound control group administered only the vector dose and the sonoactive agent, Group 2 was administered vectors comprising codon optimized sequences of human dystrophin SEQ ID NO: 3 under a muscle tissue specific promoter of SEQ ID NO: 4 (the combination of which being comprised within the expression cassette of SEQ ID NO: 34) with administration of a sonoactive agent and ultrasound and were evaluated for expression effects resulting from repeated dosing increases among the groups. Optison (human serum albumin stabilized perflutran core microbubbles) was used as the ultrasound contrast agent in this experiment.

| Group (n = 3) | Strain | DNA Dose (ug) | Sonoactive agent | # of doses | Ultrasound | Vector/Expression Cassette/Promoter/Transgene |
|---|---|---|---|---|---|---|
| 1 (n = 1) | MDX | 250 | Optison | 3 | None | SEQ ID NO: 27 (expression cassette of SEQ ID NO: 34 with muscle tissue specific promoter of SEQ ID NO: 4+ DMD Codon Optimized SEQ ID NO: 3) |

-continued

| Group (n = 3) | Strain | DNA Dose (ug) | Sonoactive agent | # of doses | Ultrasound | Vector/Expression Cassette/Promoter/ Transgene |
|---|---|---|---|---|---|---|
| 2 | MDX | 250 | Optison | 3 | L8-18, MI 1.4, 2 sec on/2 sec off, 60 sec total on | SEQ ID NO: 27 (expression cassette of SEQ ID NO: 34 with muscle tissue specific promoter of SEQ ID NO: 4+ DMD Codon Optimized SEQ ID NO: 3) |

The mice received application of ultrasound energy following administration of 50 µL of the sonoactive agent and one third of the DNA payload in each treatment session. In a treatment session, the middle thigh region was targeted ultrasound using a L8-18 probe on a General Electric LOGIQ E9 system in Elasto mode applying an acoustic radiation force at a frequency of about 6.25 MHz at a mechanical index of 1.4 at a 100% push output at an ultrasound intensity of at least 200 mW/cm2 (ISPTA) alternating between 2 seconds on of ultrasound application and 2 seconds off of ultrasound application, for a total of 60 sec of on ultrasound application over the quadriceps region of each mouse. A second identical treatment session was applied at 3 days following the first treatment session, and a third identical treatment session was applied at 3-4 days after the second treatment session, thereby applying a triplicate treatment session to the subjects.

For Groups 1-2, 14 day following the triplicate treatment session subjects were sacrificed and tissue samples were collected for further analysis.

Necropsy was performed at the stated time points, and tissue samples were collected, placed into a sterile tube, and snap frozen using liquid $N_2$. Tissue samples were directly transferred to −80 C storage. Capillary western blot analysis was performed as described in Example 1, with the addition of human heart whole tissue lysate (Novus Bio) normalized to 1 mg/mL, then diluted to create standards at 10, 5 and 2%. A 1 mg/mL concentration was the selected concentration for the western blot analysis (ab154168 (1:150)). Samples were then diluted to 1 mg/mL and compared with human heart whole tissue lysate.

Results

Figure 11:
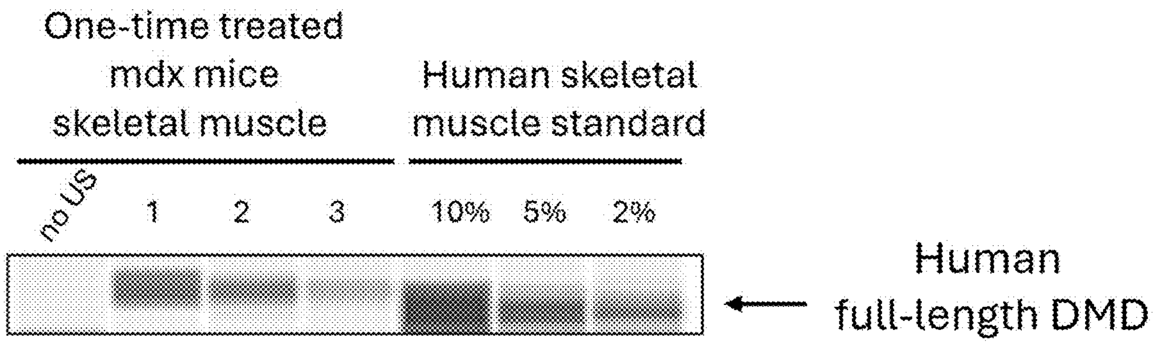
FIG. 11 shows results of a western blot assay illustrating expression of full length human dystrophin protein in-vivo.

Results of the capillary western blot for Group 2 are shown in FIG. 11 (each showing samples collected from a different subject MDX mouse in Group 2), in which samples are diluted to 1 mg/mL and compared with human diaphragm whole tissue lysate (Novus Bio) normalized to 1 mg/mL and diluted to 10, 5 and 2% standards.

Lanes 1-3 labeled "one-time treated MDX skeletal muscle" in FIG. 11 correspond to different subjects from Group 2, and exhibit expression levels of full length human dystrophin which are comparable to the human diaphragm whole tissue lysate 5 and 2% standard, with the Lane 1 subject exhibiting an expression level most similar to the 5% standard. A sample from Group 1 not administered any ultrasound is also shown as a negative control, and the assay indicates no detectable human dystrophin in this sample.

Figure 14:
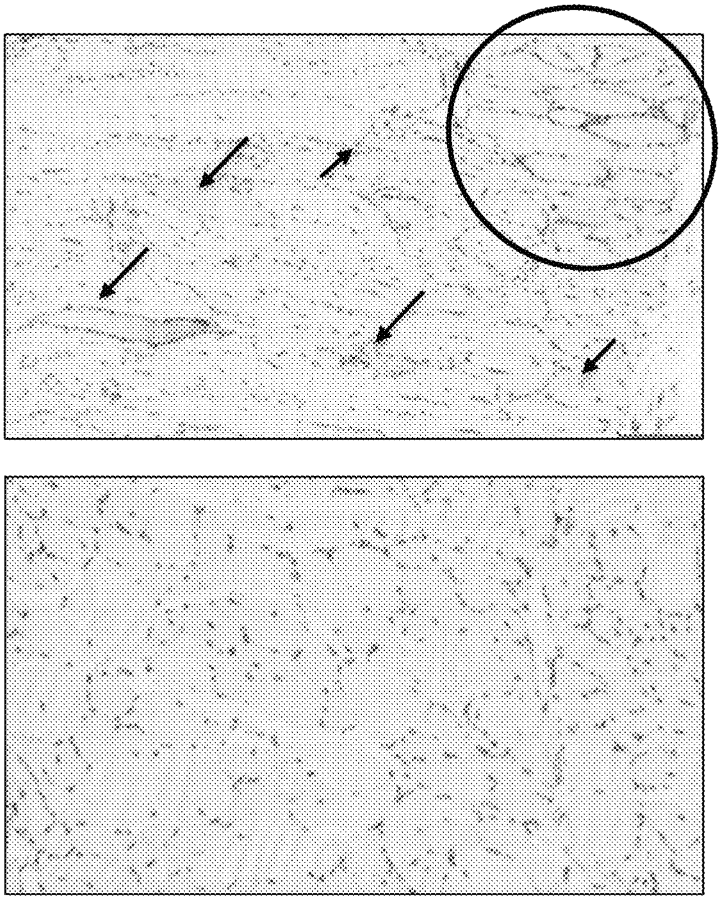
FIG. 14 shows immunohistochemistry stain images illustrating expression of full length human dystrophin protein in-vivo in transfected cells, arrows indicate cells expressing human dystrophin protein.

Staining was performed as described in Example 3. Results of the DAB staining is shown in FIG. 14 in which expression of the full length dystrophin protein can be observed in transfected myocytes of the subject both in the cellular membrane of the myocyte and throughout the cytoplasm of the myocyte, as shown by the orange and dark orange DAB staining in FIG. 14 Blue dots represent individual nuclei within the tissue samples stained with hematoxylin.

Example 6: In-Vivo Evaluation of Muscle Tissue Specific Vector and Expression of Full-Length Dystrophin Protein in a NHP Model of Sonoporation to the Skeletal Muscle In this example, nucleic acid delivery vectors with expression cassettes comprising promoter sequences which are optimized for expression in skeletal myocytes cells are evaluated in a non-human primate model of ultrasound mediated nucleic acid delivery to the skeletal muscle (quadriceps).

Experimental Animals and Protocol

The subject was one male cynomolgus macaque (cyno). and was infused with phospholipid stabilized sonoactive microstructures (Sonazoid) and nucleic acids encoding a full length dystrophin protein coupled to a muscle tissue specific promoter sequence. The nucleic acid delivery vector administered comprised codon optimized sequences of human dystrophin SEQ ID NO: 3 under a muscle tissue specific promoter of SEQ ID NO: 4 (the combination of which being comprised within the expression cassette of SEQ ID NO: 34). The subject was injected with the phospholipid stabilized sonoactive microstructures (Sonazoid) and nucleic acids via an intravenous infusion into the saphenous vein. Ultrasound energy was applied using a C-16 probe on a GE LOGIQ E10 system in research mode for the acoustic radiation force ultrasound application. An acoustic radiation force ultrasound was applied to the quadriceps of the cyno with the same GE LOGIQ e10 ultrasound system equipped with a C1-6 probe. First, contrast enhanced ultrasound energy was applied to generate an ultrasound image at a mechanical index of 0.4, and a frequency of about 2.5 MHz to confirm the presence of the sonoactive agent in the target muscle tissue. Next, the acoustic radiation force protocol was applied using ultrasound acoustic energy at an ultrasound intensity of about 500 mW/cm2 (ISPTA) (spatial-peak temporal average intensity) at frequency of about 2.3 MHz at a pulse length of 600 us to disrupt the sonoactive microstructures. Serial bolus injections of approximately 1.0-2.0 mL of sonoactive microstructure and DNA solution were re-administered to the subject and the acoustic radiation force ultrasound was applied until the full dose of nucleic acids were administered, over a treatment duration of about 10 minutes. A rapid loss of ultrasound contrast (due to inertial cavitation of the sonoactive agent) was confirmed following the application of the acoustic radiation force by intermittently switching to contrast enhanced ultrasound mode for imaging.

| Group (n = 1) | Strain | DNA Dose (ug) | Sonoactive agent | # of doses | Ultrasound | Vector/Expression Cassette/Promoter/ Transgene |
|---|---|---|---|---|---|---|
| 1 | Cyno | 50 | Sonazoid | 1 | Cl-6, ~500 mW/cm2 Ispta, 2.3 MHz, 600 us | SEQ ID NO: 27 (expression cassette of SEQ ID NO: 34 with muscle tissue specific promoter of SEQ ID NO: 4+ DMD Codon Optimized SEQ ID NO: 3) |

2 days following the sonoporation treatment, a biopsy was taken from the treated quadriceps for analysis using RNA-scope to confirm presence of the transgenic DNA and transgenic mRNA in the target tissue. A control sample biopsy was also taken from the untreated quadriceps for consideration in the analysis. Transverse cryosections (~10 μm thickness) of quadricep muscle that had been collected from non-human primates administered the nucleic acid vector encoding a human transgene delivered via ultrasound mediated nucleic acid deliver were thaw-mounted onto positively charged glass slides and air-dried for 30 minutes at room temperature. Each slide was then secured in a black slide carrier of a motorized auto staining platform and covered with fluorophore-compatible cover-tiles to minimize tissue detachment during processing. Slide records were created in the instrument software by adding a new study and assigning individual slide identifiers. The run method specified a heat-mediated antigen-retrieval step (95° C., 15 min), an endogenous peroxidase block (10 min), and a protease digestion (40° C., 10 min). Probe channel 1 was reserved for a proprietary RNAscope probe targeting the codon-optimized transgene mRNA and transgenic DNA, while channel 2 was allocated to a probe recognizing a housekeeping transcript to verify DNA integrity. All kit reagents supplied with a commercial multiplex fluorescent RNAscope reagent set were registered on the instrument; reagent wands were loaded onto the platform and validated by an automated dip-test. Fluorophores were freshly diluted in tyramide-signal-amplification (TSA) buffer according to manufacturer instructions (typical dilutions: vivid dyes, 1:3 000; near-infra-red dye, 1:125). Target probes were transferred to open reagent tubes placed on an auxiliary wand that was integrated into the reagent platform without interrupting the dip-test cycle. Bulk wash solutions were replenished and waste containers emptied before initiating the staining run. After the slide racks had been lowered and locked, the auto stainer executed the programmed protocol, which included: hybridization of target probes at 42° C. for 2 h; six proprietary amplification steps; and sequential TSA-mediated deposition of distinct fluorophores for channels 1 and 2. A final bake at 60° C. for 30 min ensured covalent coupling of fluorophores to the amplification scaffold. Upon run completion, slide racks were released, cover-tiles were removed, and the sections were washed three times in running tap water, immersed for 2 min in 0.01% ammonium hydroxide to suppress non-specific background, rinsed twice again, and dipped in deionized water. Slides were dried in a 60° C. oven for 10 min and permanently mounted in an antifade medium containing DAPI to stain nuclei. Fluorescence microscopy (20× objective) revealed discrete cytoplasmic puncta corresponding to the transgene-specific transcript in a subset of myofibers, whereas the housekeeping-gene probe produced uniform staining, confirming assay integrity. Negative-control sections treated with a bacterial dapB probe displayed≤1 punctum per field, establishing specificity. The RNAscope protocol enabled robust in-situ detection of the target transgenic DNA and mRNA within non-human-primate quadriceps muscle.

Biopsy samples were further analyzed for DMD DNA and mRNA in the NHP muscle tissue samples to quantify percentage of positive muscle fibers in treated tissue using HALO (Indica Labs) by staining quadriceps samples from subjects with a probe which binds hDMD DNA and mRNA. Using HALO and HALO AI v4.0.5107.407 muscle tissue images were uploaded and opened for analysis. Tissue boundaries were annotated using the Flood-fill tool, with refinements made via the Pen and Brush tools. Debris and unwanted regions were excluded. Nuclear segmentation was performed using Indica Labs' pre-trained "Nuc Seg BF" classifier, with real-time tuning for optimization. HALO AI classifiers (RandomForest, MiniNet, or DenseNet) were applied based on the complexity of the regions of interest (ROIs). For analysis, the "Indica Labs—ISH v4.2.3" module was selected, and stain settings were configured for a single probe. Nuclear and probe stains were calibrated by selecting representative nuclei and puncta, while debris exclusion settings were applied. Since singleplex staining was used, phenotype and AI phenotyper settings were left blank. Real-time tuning validated puncta and nuclear recognition, with adjustments were made to segmentation aggressiveness, probe size, and optical density thresholds as needed. Cell-based analysis was performed by enabling "Detect Cells" and applying the nuclear segmentation classifier. Base scope criteria were set for expression quantification. The ROI classifier and relevant classes were selected, and analysis was executed on the designated tissue regions. Greater than 50% fiber membrane had to contain hDMD puncta to be counted as positive using this analysis.

Results

Figure 15:
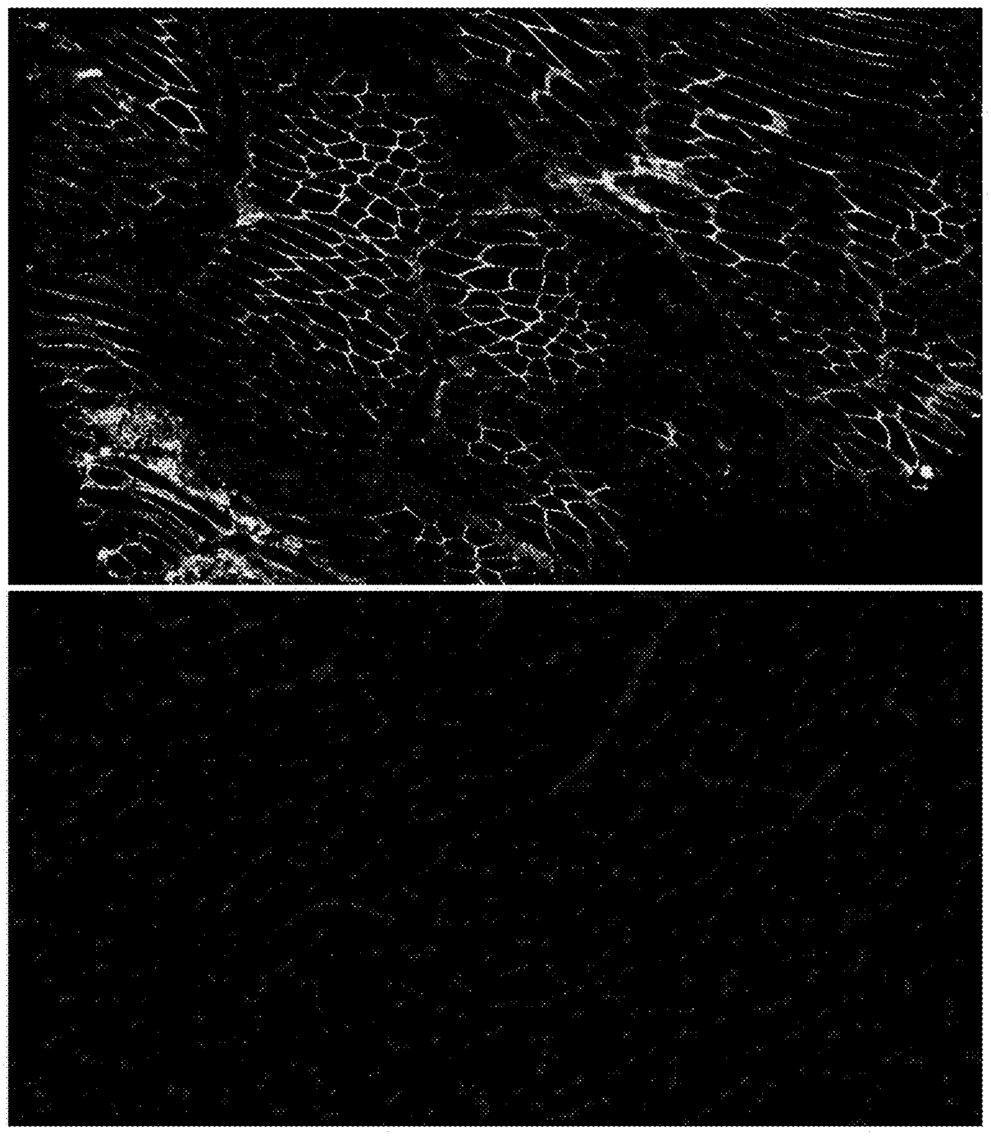
FIG. 15 shows immunohistochemistry stain images illustrating delivery of nucleic acids encoding length human dystrophin protein in-vivo in transfected tissue.

Results of the RNAscope analysis is shown in FIG. 15, in which it is observed that the naïve tissue sample shows DAPI stained nuclei throughout the sample but no yellow staining indicating a lack of presence of the dystrophin transgenic DMD nucleic acids; while the treated tissue sample treated with the ultrasound mediated nucleic acid (gene) delivery showed DAPI stained nuclei throughout the sample and extensive yellow staining along the length of a muscle fibers in the muscle tissue about the sarcolemma of a muscle fibers on the periphery of the cellular membrane of the myocytes, indicating extensive presence of the dystrophin transgenic DMD nucleic acids throughout the treated tissue.

Figure 16:
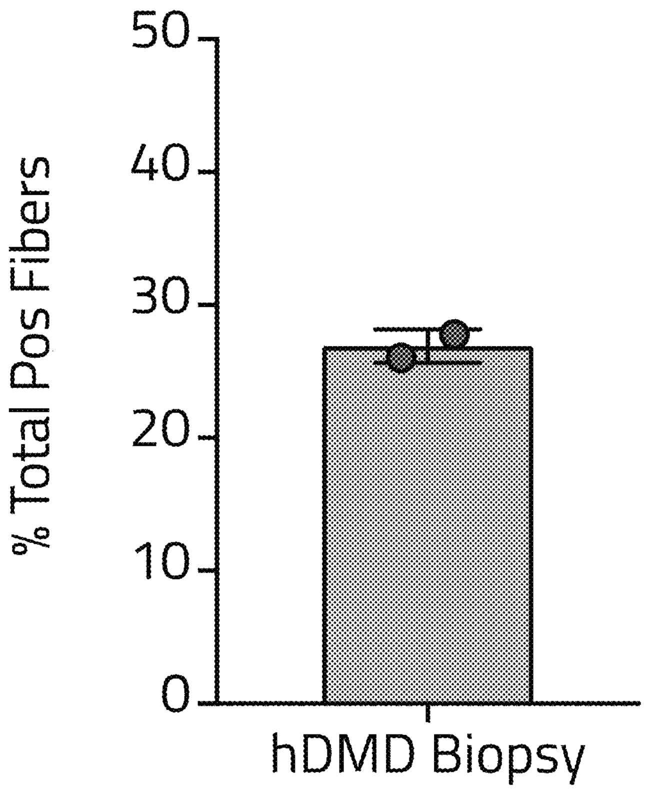
FIG. 16 shows results of a digital pathology analysis quantifying delivery of a nucleic acid of the present disclosure in a population of muscle fibers from treated muscle tissue.

Results of the HALO analysis shown in FIG. 16, in which it is observed that the treated tissue sample exhibited approximately 28% of muscle fibers which were positive for transgenic DMD nucleic acids, with each positive fiber having greater than 50% fiber membrane positive for hDMD puncta.

Example 7: In-Vivo Evaluation of Muscle Tissue Specific Vector and Expression in a Murine Model of Sonoporation to the Skeletal Muscle In this example, nucleic acid delivery vectors with expression cassettes comprising promoter sequences which were optimized for expression in skeletal myocytes were evaluated in a murine model of ultrasound mediated nucleic acid delivery to the skeletal muscle (quadriceps).

Experimental Animals and Protocol

One group of three RAG 2 mice are evaluated for long term expression of a FLUC reporter over 275 days. Prior to the experiment, mice were implanted with a jugular vein catheter though which the sonoactive agent and the DNA solution was administered. Optison (human serum albumin stabilized perflutran core microbubbles) was used as the ultrasound contrast agent in this experiment. Mice were administered three sonoporation treatments, with the second and third treatments given 24 hours after the preceding treatment. Mice were administered 250 μg of nucleic acids comprising pDNA comprising a sequence of SEQ ID NO: 30 (muscle tissue specific promoter (SEQ ID NO: 4)+FLUC reporter).

The mice received application of ultrasound energy following administration of 50 μL of the sonoactive agent and one third of the DNA payload in each treatment session. In a treatment session, the left leg of each animal was placed in a heated water bath at 38° C. for 2 minutes prior to applying ultrasound using a L8-18 probe on a General Electric LOGIQ E9 system in Elasto mode applying an acoustic radiation force at a frequency of about 2.5 MHz at a mechanical index of 1.4 at a 100% push output at an ultrasound intensity of at least 200 mW/cm2 (ISPTA) for about 10 sec on, 20 sec off, for a total of 60 sec (2 cycles) of ultrasound application over the left quadriceps region of each mouse. A second identical treatment session was applied at 24 hours following the first treatment session, and a third identical treatment session was applied at 24 hours after the second treatment session. IVIS measurements were taken approximately weekly to monitor ongoing expression of the FLUC reporter protein.

Results

Figure 17:
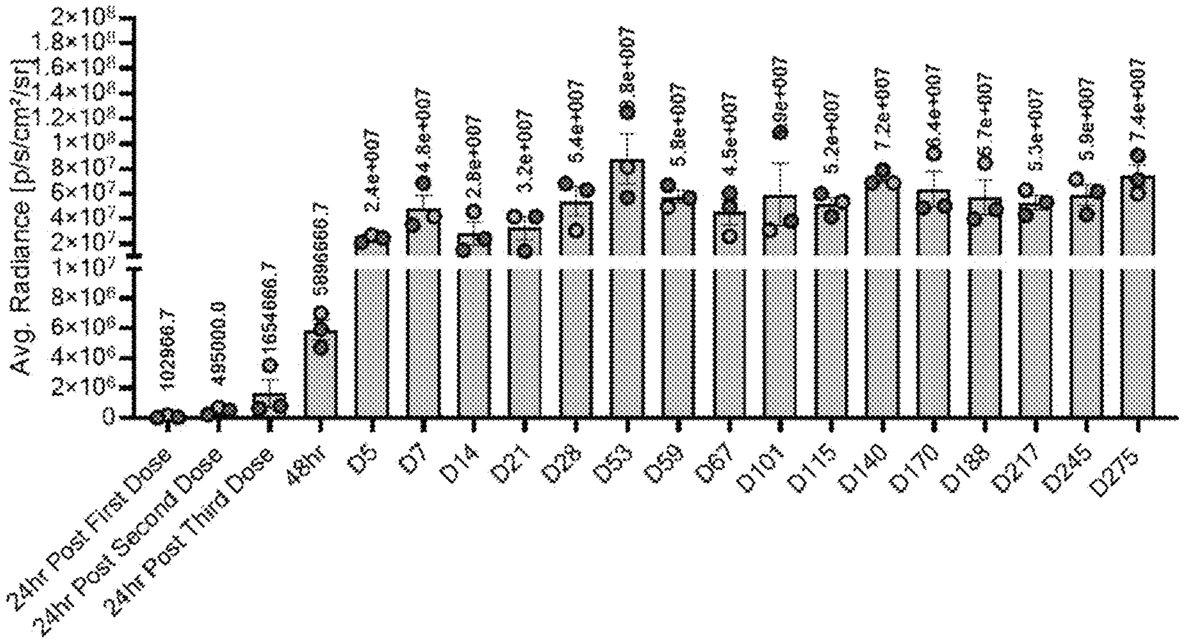
FIG. 17 shows in-vivo data fluorescence data illustrating expression of a gene encoding a reporter protein downstream of a promoter sequence of the present disclosure.

Results are shown in FIG. 17, in which it is observed that expression in the treated muscle tissue was maintained with IVIS measurements exceeding 2.4 E7 for the duration of the study, with a level of 7.4 E7 observed at day 275 of the study.

Example 8: In-Vivo Evaluation of Muscle Tissue Specific Vector and Expression in a NHP Model of Sonoporation to the Heart and Diaphragm In this example, nucleic acid delivery vectors with expression cassettes comprising promoter sequences which were optimized for expression in skeletal myocytes cells were evaluated in a non-human primate model of ultrasound mediated nucleic acid delivery to the heart and diaphragm.

Experimental Animals and Protocol

A first subject was one male cynomolgus macaque (cyno), which was evaluated for nucleic acid delivery in the heart. The subject was infused with phospholipid stabilized sonoactive microstructures (Sonazoid), and nucleic acids encoding a EGFP reporter protein. The second subject was one male cynomolgus macaque (cyno), which was evaluated for nucleic acid delivery in the diaphragm. The second subject was infused with phospholipid stabilized sonoactive microstructures (Sonazoid), and nucleic acids encoding a EGFP reporter protein. Identical ultrasound procedures and nucleic acid administration techniques were applied to each subject.

The subjects were injected with the phospholipid stabilized sonoactive microstructures (Sonazoid), and nucleic acids via an intravenous infusion into the saphenous vein. Ultrasound energy was applied using a C-16 probe on a GE LOGIQ E10 system in research mode for the acoustic radiation force ultrasound application. An acoustic radiation force ultrasound was applied to the heart or diaphragm of the cyno with the same GE LOGIQ e10 ultrasound system equipped with a C1-6 probe. First, contrast enhanced ultrasound energy was applied to generate an ultrasound image at a mechanical index of 0.4, and a frequency of about 2.5 MHz to confirm the presence of the sonoactive agent in the target muscle tissue. Next, the acoustic radiation force protocol was applied using ultrasound acoustic energy at an ultrasound intensity of about 500 mW/cm2 (ISPTA) (spatial-peak temporal average intensity) at frequency of about 2.3 MHz at a pulse length of 600 us to disrupt the sonoactive microstructures. Serial bolus injections of approximately 1.0-2.0 mL of sonoactive microstructure and DNA solution were re-administered to the subject and the acoustic radiation force ultrasound was applied until the full dose of nucleic acids were administered, over a treatment duration of about 10 minutes. A rapid loss of ultrasound contrast (due to inertial cavitation of the sonoactive agent) was confirmed following the application of the acoustic radiation force by intermittently switching to contrast enhanced ultrasound mode for imaging.

| Group (n = 1) | Strain (organ) | DNA Dose (ug) | Sonoactive agent | # of doses | Ultrasound | Vector/Promoter |
|---|---|---|---|---|---|---|
| 1 | Cyno (heart) | 50 | Sonazoid | 1 | Cl-6, ~500 mW/cm2 Ispta, 2.3 MHz, 600 us | SEQ ID NO: 30(NP-MHCK7-hBGi-EGFP-P2A-Fluc-WPRE3-DTS) comprising the promoter MHCK7 sequence of SEQ ID NO: 4 |
| 1 | Cyno (diaphragm) | 50 | Sonazoid | 1 | Cl-6, ~500 mW/cm2 Ispta, 2.3 MHz, 600 us | SEQ ID NO: 30(NP-MHCK7-hBGi-EGFP-P2A-Fluc-WPRE3-DTS) comprising the promoter MHCK7 sequence of SEQ ID NO: 4 |

Necropsy was performed 7 hours following administration of the sonoporation treatment. Samples were collected from the treated heart and diaphragm. Tissue that had been collected from non-human primates administered the nucleic acid vector encoding a human transgene delivered via ultrasound mediated nucleic acid deliver were thaw-mounted onto positively charged glass slides and air-dried for 30 minutes at room temperature. Each slide was then secured in a black slide carrier of a motorized auto staining platform and covered with fluorophore-compatible cover-tiles to minimize tissue detachment during processing. Slide records were created in the instrument software by adding a new study and assigning individual slide identifiers. The run method specified a heat-mediated antigen-retrieval step (95° C., 15 min), an endogenous peroxidase block (10 min), and a protease digestion (40° C., 10 min). Probe channel 1 was reserved for a proprietary RNAscope probe targeting the codon-optimized transgene DNA and mRNA, while channel 2 was allocated to a probe recognizing a housekeeping transcript to verify DNA integrity. All kit reagents supplied with a commercial multiplex fluorescent RNAscope reagent set were registered on the instrument; reagent wands were loaded onto the platform and validated by an automated dip-test. Fluorophores were freshly diluted in tyramide-signal-amplification (TSA) buffer according to manufacturer instructions (typical dilutions:vivid dyes, 1:3 000; near-infra-red dye, 1:125). Target probes were transferred to open reagent tubes placed on an auxiliary wand that was integrated into the reagent platform without interrupting the dip-test cycle. Bulk wash solutions were replenished and waste containers emptied before initiating the staining run. After the slide racks had been lowered and locked, the auto stainer executed the programmed protocol, which included: hybridization of target probes at 42° C. for 2 h; six proprietary amplification steps; and sequential TSA-mediated deposition of distinct fluorophores for channels 1 and 2. A final bake at 60° C. for 30 min ensured covalent coupling of fluorophores to the amplification scaffold. Upon run completion, slide racks were released, cover-tiles were removed, and the sections were washed three times in running tap water, immersed for 2 min in 0.01% ammonium hydroxide to suppress non-specific background, rinsed twice again, and dipped in deionized water. Slides were dried in a 60° C. oven for 10 min and permanently mounted in an antifade medium containing DAPI to stain nuclei. Fluorescence microscopy (20× objective) revealed discrete cytoplasmic puncta corresponding to the transgene-specific transcript in a subset of myofibers, whereas the housekeeping-gene probe produced uniform staining, confirming assay integrity. Negative-control sections treated with a bacterial dapB probe displayed≤1 punctum per field, establishing specificity. The RNAscope protocol enabled robust in-situ detection of the target transgenic nucleic acid within non-human-primate tissues.

Biopsy samples were further analyzed for transgene DNA and mRNA in the NHP tissue samples to quantify percentage of positive muscle fibers in treated tissue using HALO (Indica Labs) by staining quadriceps samples from subjects with a probe which binds hDMD DNA and mRNA. Using HALO and HALO AI v4.0.5107.407 muscle tissue images were uploaded and opened for analysis. Tissue boundaries were annotated using the Flood-fill tool, with refinements made via the Pen and Brush tools. Debris and unwanted regions were excluded. Nuclear segmentation was performed using Indica Labs' pre-trained "Nuc Seg BF" classifier, with real-time tuning for optimization. HALO AI classifiers (RandomForest, MiniNet, or DenseNet) were applied based on the complexity of the regions of interest (ROIs). For analysis, the "Indica Labs—ISH v4.2.3" module was selected, and stain settings were configured for a single probe. Nuclear and probe stains were calibrated by selecting representative nuclei and puncta, while debris exclusion settings were applied. Since singleplex staining was used, phenotype and AI phenotyper settings were left blank. Real-time tuning validated puncta and nuclear recognition, with adjustments made to segmentation aggressiveness, probe size, and optical density thresholds as needed. Cell-based analysis was performed by enabling "Detect Cells" and applying the nuclear segmentation classifier. Basescope criteria were set for expression quantification. The ROI classifier and relevant classes were selected, and analysis was executed on the designated tissue regions. Greater than 50% fiber membrane must contain hDMD puncta to be counted as positive using this analysis.

Samples were evaluated using digital droplet polymer chain reaction (ddPCR) to assess copy number per diploid genome (CN/DG) levels of DNA payload delivered to the cells, quantified with respect to a reference gene. The procedure began by preparing the Master Mix (MM) for each reaction. First, the ddPCR Supermix for probes (no dUTP) was thawed and vortexed for at least 30 seconds. For each primer/probe set, 11 μL ddPCR Supermix, 1.1 μL primer/probe mix, 0.275 μL HindIII enzyme, and water were combined to bring the final reaction volume to 18 μL. For single-plex reactions, 5.626 μL of water was added, while for duplex reactions, 4.525 μL was added. The Master Mix was calculated with a correction factor of 1.1 to account for pipetting error. After preparation, 18 μL of the Master Mix was dispensed into individual wells of a 96-well PCR plate, which was then set aside at room temperature. DNA was extracted in duplicates from 15-30 mg adipose tissue samples using QIAGEN DNeasy kit. DNA were diluted to 0.025, 0.075, and 0.25 ng/uL using nuclease-free water, and 4 μL of the diluted genomic DNA (gDNA) or $ddH_2O$ (for negative controls) was added to each well according to the plate map. The plate was then sealed with a pierceable foil seal, ensuring the red stripe faced up at the top, and vortexed for 2 minutes at room temperature. Following this, the plate was spun down at 100-300 rcf for 1 minute to remove bubbles. The sealed plate was placed in the Automated Droplet Generator (ADG), ensuring that the destination plate was on a cooling block, DG32 cartridges, ddPCR tips (with lids removed), and an empty waste container were properly positioned. The droplet generation process was initiated, and the corresponding ddPCR program was selected on the thermal cycler, which was paused while waiting for the droplet generation to finish. Once the droplet generation was completed, the 96-well plate was removed from the cooling block, resealed with a pierceable foil seal, and transferred to the thermal cycler, where the cycling process was resumed. The cooling block was returned to −20° C. in an upside-down position for future use. Thermal cycling was performed based on the ddPCR program, which typically included steps such as denaturation, annealing, and extension, although specific conditions depended on the primer/probe set used. After thermal cycling, the plate was transferred to the Droplet Reader. In the ddPCR software, the appropriate Supermix and fluorophores (e.g., FAM, VIC, HEX) were selected before initiating the droplet reading process. Once the droplet reading was completed, the results provided the quantification of plasmid DNA copy number per diploid genome, as well as its relative abundance to the reference gene. The software generated data based on the fluorescence signals detected in the droplets, enabling accurate measurement of the target gene copy numbers.

Results

Figure 18:
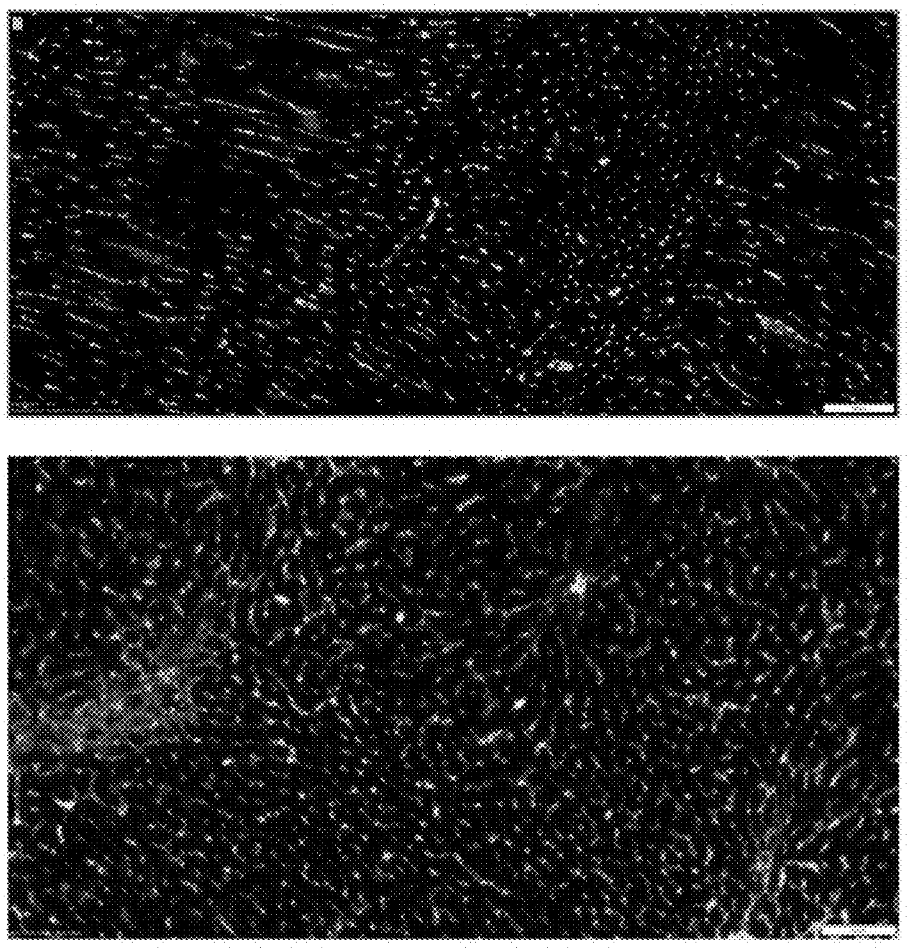
FIG. 18 shows immunohistochemistry stain images illustrating delivery of nucleic acids encoding length human dystrophin protein in-vivo throughout transfected tissue.

Results of the RNAscope analysis are shown in FIG. 18, in which the treated NHP heart tissues (top panel) are observed to exhibit delivery of transgenic DNA expression of transgene RNA (yellow staining) and treated diaphragm tissues (bottom panel) are observed to exhibit expression of transgene DNA and RNA (yellow staining) throughout the treated tissue.

Figure 19:
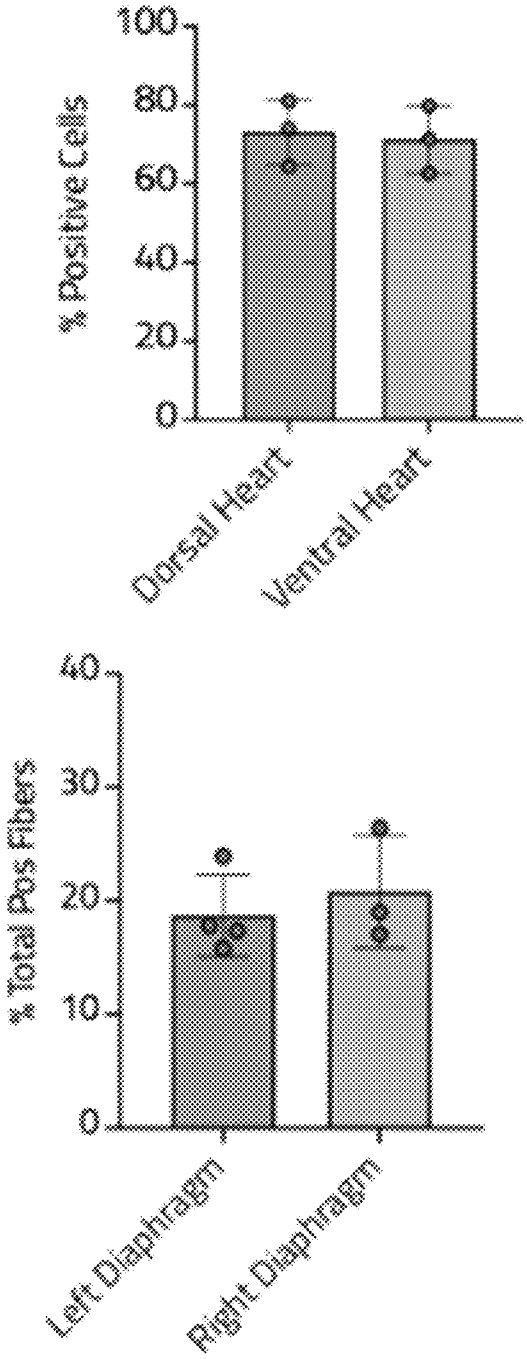
FIG. 19 shows results of a digital pathology analysis quantifying delivery of a nucleic acid of the present disclosure in a population of muscle fibers from treated muscle tissue.

Results of the HALO analysis are shown in FIG. 19, in which it is observed that the treated cardiac tissue sample (top graph) exhibited approximately 70% of muscle fibers which were positive for the transgene in both the dorsal and ventral regions of the heart, and treated diaphragm samples (lower graph) exhibited approximately 20% of muscle fibers which were positive for the transgene in both the left and right regions of the diaphragm.

Figure 20:
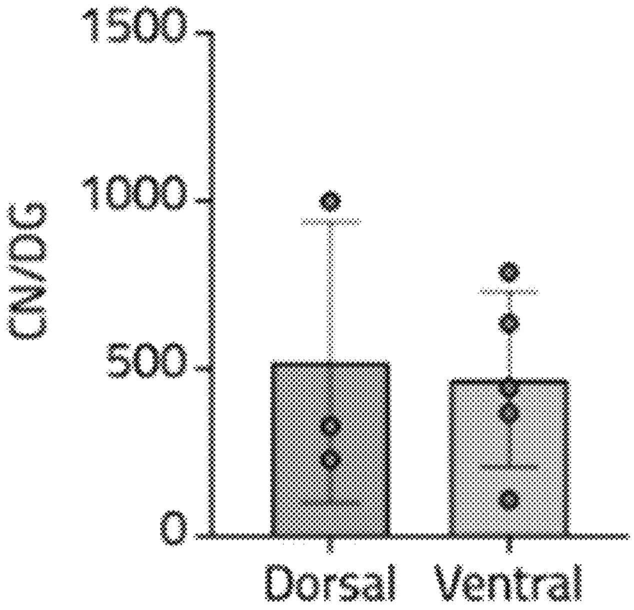
FIG. 20 shows results of a copy number analysis quantifying delivery of a nucleic acid of the present disclosure in a population of muscle cells from treated muscle tissue.

Results of the copy number analysis are shown in FIG. 20, in which it is observed that an average of 500 copies per diploid genome (CN/DG) of transgenic DNA are delivered to each cell in treated cardiac tissue samples, in both the dorsal and ventral regions of the heart.

Example 9: In-Vivo Evaluation of Muscle Tissue Specific Vector and Expression of Full-Length Dystrophin Protein in a NHP Model of Sonoporation to the Skeletal Muscle In this example, nucleic acid delivery vectors with expression cassettes comprising promoter sequences which are optimized for expression in skeletal myocytes cells were evaluated in a non-human primate model of ultrasound mediated nucleic acid delivery to the skeletal muscle (quadriceps).

Experimental Animals and Protocol

The subject was one male cynomolgus macaque (cyno). the subject was infused with phospholipid stabilized sonoactive microstructures (Sonazoid), and nucleic acids encoding a full length monkey dystrophin protein coupled to a muscle tissue specific promoter sequence. The subject was injected with the phospholipid stabilized sonoactive microstructures (Sonazoid), and nucleic acids via an intravenous infusion into the saphenous vein. Ultrasound energy was applied using a C-16 probe on a GE LOGIQ E10 system in research mode for the acoustic radiation force ultrasound application. An acoustic radiation force ultrasound was applied to the quadriceps of the cyno with the same GE LOGIQ e10 ultrasound system equipped with a C1-6 probe. First, contrast enhanced ultrasound energy was applied to generate an ultrasound image at a mechanical index of 0.4, and a frequency of about 2.5 MHz to confirm the presence of the sonoactive agent in the target muscle tissue. Next, the acoustic radiation force protocol was applied using ultrasound acoustic energy at an ultrasound intensity of about 500 mW/cm2 (ISPTA) (spatial-peak temporal average intensity) at frequency of about 2.3 MHz at a pulse length of 600 us to disrupt the sonoactive microstructures. Serial bolus injections of approximately 1.0-2.0 mL of sonoactive microstructure and DNA solution were re-administered to the subject and the acoustic radiation force ultrasound was applied until the full dose of nucleic acids were administered, over a treatment duration of about 10 minutes. A rapid loss of ultrasound contrast (due to inertial cavitation of the sonoactive agent) was confirmed following the application of the acoustic radiation force by intermittently switching to contrast enhanced ultrasound mode for imaging.

| Group (n = 1) | Strain | DNA Dose (ug) | Sonoactive agent | # of doses | Ultrasound | Vector/Promoter |
|---|---|---|---|---|---|---|
| 1 | Cyno | 5 | Sonazoid | 1 | Cl-6, ~500 mW/cm2 Ispta, 2.3 MHz, 600 us | SEQ ID NO: 33 (vector with muscle tissue specific promoter (SEQ ID NO 4)+ monkey DMD) |

5 days following treatment, a biopsy was taken from the treated quadriceps for analysis. Treated muscle tissue was evaluated for DMD expression using western blot analysis. Western blot analysis was performed as described in Example 1. Samples were further analyzed for total dystrophin expression normalized to total protein expression and were compared to a control which was a quadriceps biopsy taken from an untreated naive control animal.

Results

Figure 22:
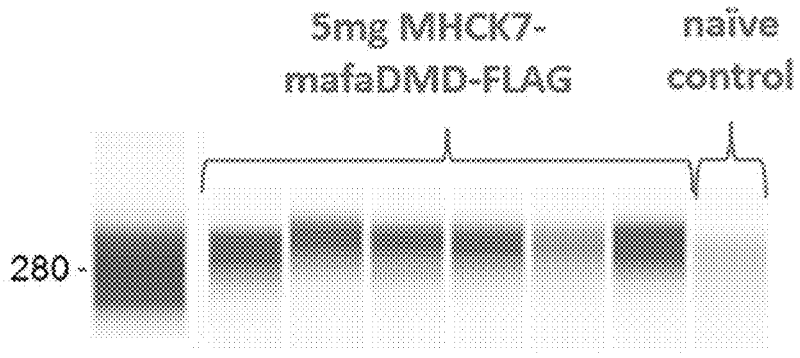
FIG. 22 shows results of a western blot assay illustrating expression of full length dystrophin protein in-vivo.

Results of the western blot assay are shown in FIG. 22, where binding of the antibody at a level which exceeds the negative (naïve) control is observed in all treated samples.

Figure 21:
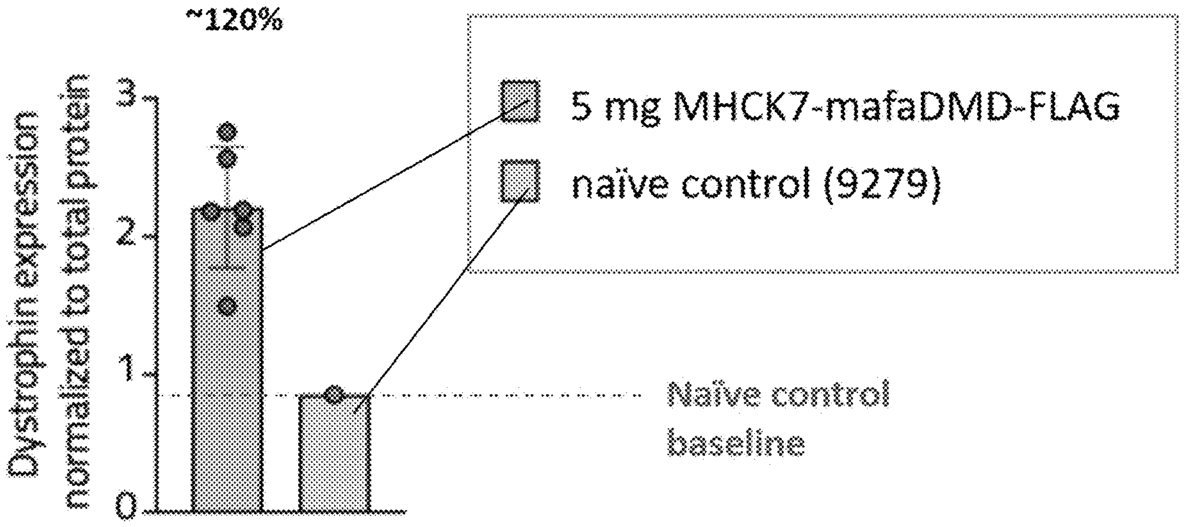
FIG. 21 shows results of a western blot assay assessing expression of full length dystrophin and normalized for total protein expression compared to an untreated control.

Results of the protein normalization assay are shown in FIG. 21, in which the treated muscle tissue exhibited approximately 220% of normal dystrophin levels, representing a 120% increase over the baseline dystrophin expression expected in a naive animal.

Example 10: In-Vivo Evaluation of Muscle Tissue Specific Vector and Expression of Full-Length Dystrophin Protein in a NHP Model of Sonoporation to the Skeletal Muscle In this example, nucleic acid delivery vectors with expression cassettes comprising promoter sequences which were optimized for expression in skeletal myocytes cells, and an expression cassette combining said promoter sequences with codon optimized DMD sequences were evaluated in a non-human primate model of ultrasound mediated nucleic acid delivery to the skeletal muscle (quadriceps). The vector further encoded an HA tag to enhance detection of the expressed protein product.

Experimental Animals and Protocol

One male cynomolgus macaque (cyno), the subject, was infused with phospholipid stabilized sonoactive microstructures (Sonazoid) and nucleic acids encoding a full length monkey dystrophin protein coupled to a muscle tissue specific promoter sequence. The subject was injected with the phospholipid stabilized sonoactive microstructures (Sonazoid), and nucleic acids via an intravenous infusion into the saphenous vein. Prior to the infusion and administration of ultrasound, a heating pad was applied to the quadricep to be treated for 2-minutes immediately preceding the infusion. Ultrasound energy was applied using a C-16 probe on a GE LOGIQ E10 system in research mode for the acoustic radiation force ultrasound application. An acoustic radiation force ultrasound was applied to the quadricep of the cyno with the same GE LOGIQ e10 ultrasound system equipped with a C1-6 probe. First, contrast enhanced ultrasound energy was applied to generate an ultrasound image at a mechanical index of 0.09, and a frequency of about 2.5 MHz to confirm the presence of the sonoactive agent in the target muscle tissue. Next, the acoustic radiation force protocol was applied using ultrasound acoustic energy at an ultrasound intensity of about 500 mW/cm2 (ISPTA) (spatial-peak temporal average intensity) at frequency of about 2.5 MHz at a pulse length of 600 us to disrupt the sonoactive microstructures. Serial bolus injections of approximately 1.0-2.0 mL of sonoactive microstructure and DNA solution were re-administered to the subject and the acoustic radiation force ultrasound was applied until the full dose of nucleic acids were administered, over a treatment duration of about 10 minutes. A rapid loss of ultrasound contrast (due to inertial cavitation of the sonoactive agent) was confirmed following the application of the acoustic radiation force by intermittently switching to contrast enhanced ultrasound mode for imaging.

| Strain DNA Sonoactive | | | | | | |
|---|---|---|---|---|---|---|
| Group (n = 1) | Strain | DNA Dose (ug) | Sonoactive agent | # of doses | Ultrasound | Expression Cassette/Promoter/Transgene |
| 1 | Cyno | 5 | Sonazoid | 1 | Cl-6, ~500 mW/cm2 Ispta, 2.3 MHz, 600 us | SEQ ID NO: 34 (vector with muscle tissue specific promoter (SEQ ID NO 4) + DMD Codon Optimized SEQ ID NO: 3) |

7 hours following treatment, necropsy was performed and a sample was taken from the treated quadriceps for analysis. Samples were analyzed using RNAscope to confirm presence of the transgenic DNA in the target tissue, and were further analyzed for DMD DNA and mRNA in the NHP muscle tissue samples to quantify percentage of positive muscle fibers in treated tissue using HALO (Indica Labs) by staining quadriceps samples from subjects with a probe that binds hDMD, as described in Example 6. Samples were also evaluated using digital droplet polymer chain reaction (ddPCR) to assess copy number per diploid genome (CN/DG) levels of DNA payload delivered to the cells, quantified with respect to a reference gene, as described in Example 8.

Results

Figure 23:
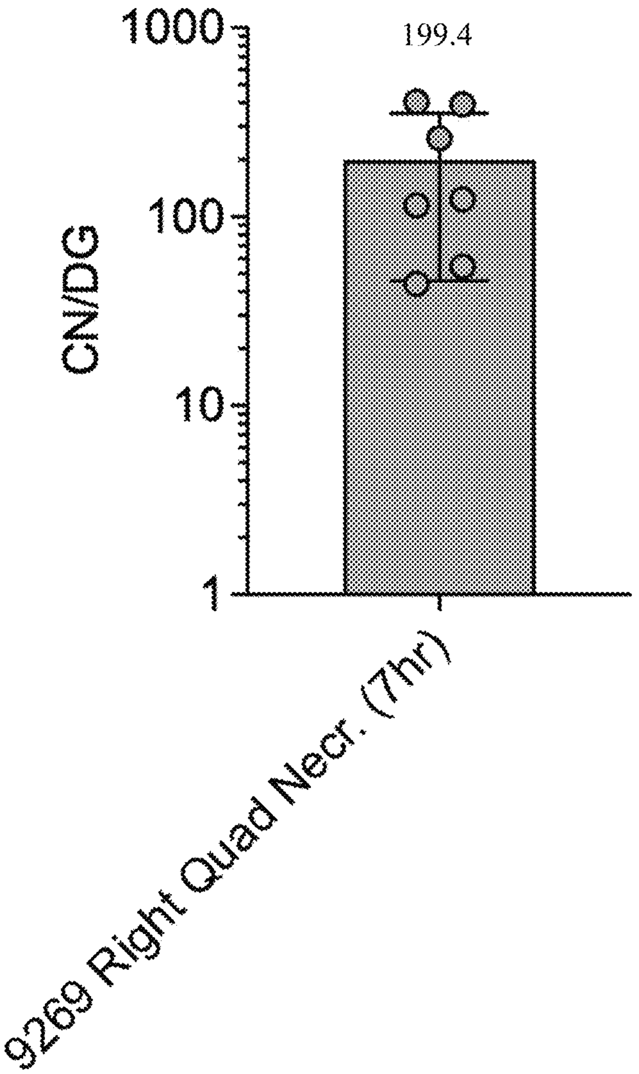
FIG. 23 results of a copy number analysis quantifying delivery of a nucleic acid of the present disclosure in a population of muscle cells from treated muscle tissue.

Results of the copy number analysis are shown in FIG. 23, in which it is observed that an average of 199.4 copies per diploid genome (CN/DG) of transgenic DNA are delivered to each cell in treated muscle tissue.

Figure 24:
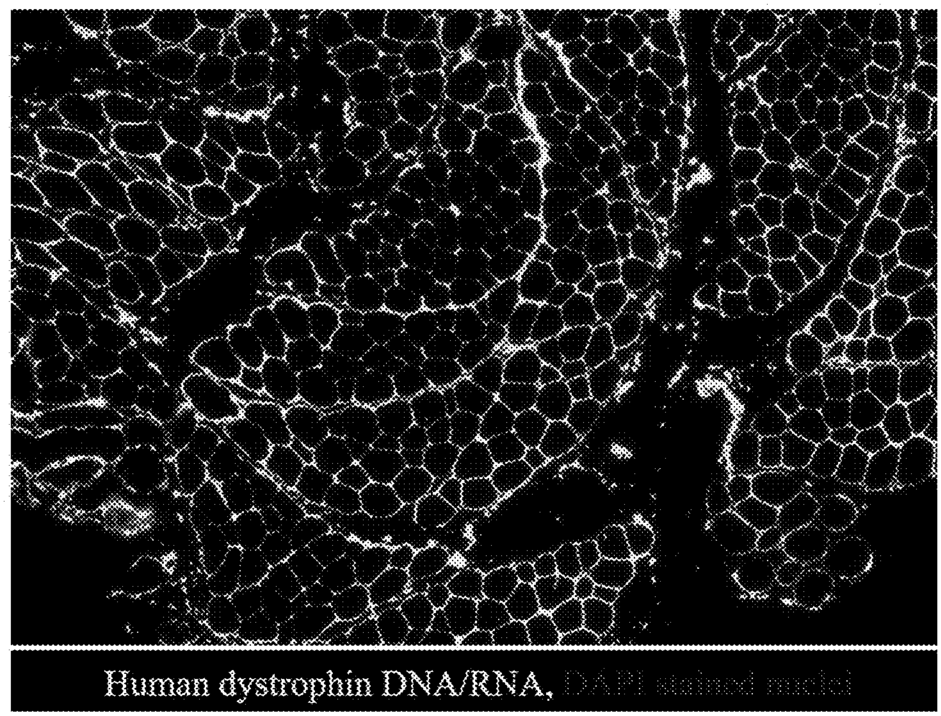
FIG. 24 shows immunohistochemistry stain images illustrating delivery of nucleic acids encoding length human dystrophin protein in-vivo throughout transfected tissue.

Results of the RNAscope analysis is shown in FIG. 24, in which it is observed that the treated tissue sample had DAPI stained nuclei throughout the sample and extensive yellow staining along the length of muscle fibers in the muscle tissue, specifically about the sarcolemma of the muscle fibers, and on the periphery of the cellular membrane of the myocytes, indicating extensive presence of the dystrophin transgenic DMD nucleic acids throughout the treated tissue.

Figure 25:
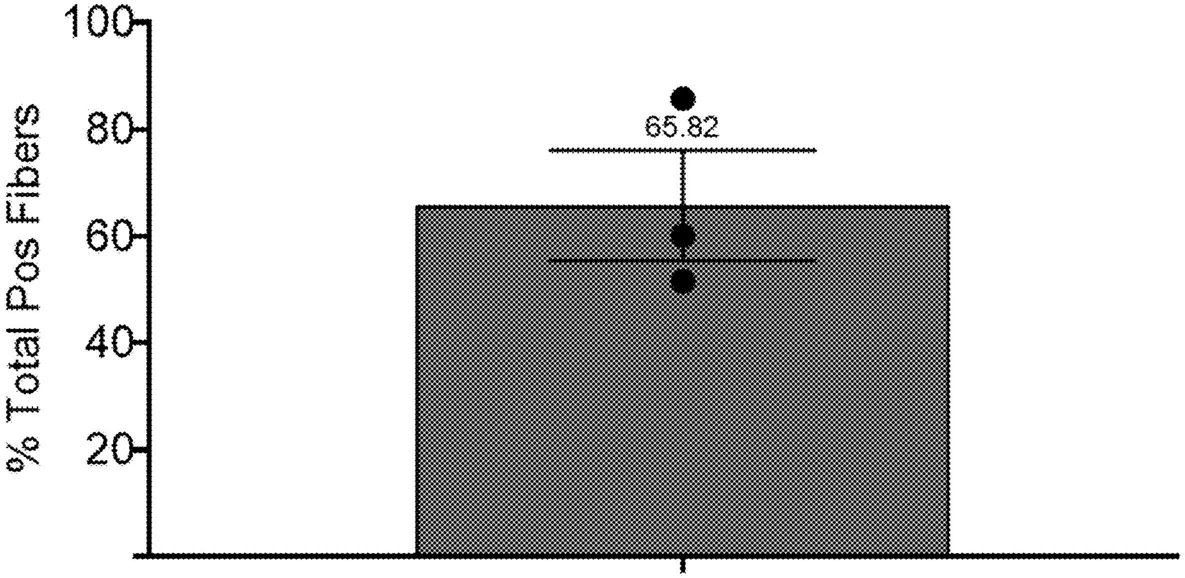
FIG. 25 shows results of a digital pathology analysis quantifying delivery of a nucleic acid of the present disclosure in a population of muscle fibers from treated muscle tissue.

Results of the HALO analysis shown in FIG. 25, in which it is observed that the treated tissue sample exhibits approximately 65% of muscle fibers which are positive for transgenic DMD nucleic acids, with each positive fiber having greater than 50% fiber membrane positive for hDMD puncta.

Example 11: Evaluation of Nucleic Acid Delivery Vectors in a Murine Model of Ultrasound Mediated Nucleic Acid Transfection to the Kidney Evaluating a Ubiquitous Promoter Sequence in the Kidney In this example, nucleic acid delivery vectors with expression cassettes comprising promoter sequences which were optimized for expression in multiple cell types were evaluated in a murine model of ultrasound mediated nucleic acid delivery to the kidney to evaluate the efficacy of a ubiquitous promoter sequence disclosed herein in the kidney.

Experimental Animals and Protocol

There are a total of 3 experimental groups of six RAG2 mice each of which varies the dosage of the promoter sequence operably coupled to the gene encoding the reporter protein were utilized in the experiment. Each group of mice received an intravenous infusion through an implanted jugular vein catheter of a composition comprising the sonoactive agent and the DNA payload. Definity RT was used as the sonoactive agent in this experiment. Each group received a dose of the nucleic acid delivery vector followed by application of ultrasound in a treatment session, and was administered a total of three treatment session each treatment session, 48 hours apart. The experimental groups are summarized below.

| Group (n = 6) | Strain | DNA Dose (ug) | MB | # of doses | Vector |
|---|---|---|---|---|---|
| 1 | Rag2 | 100 | Definity RT | 3 | SEQ ID NO: 42 (comprising CAG promoter of SEQ ID NO: 5) |
| 2 | Rag2 | 100 | Definity RT | 3 | SEQ ID NO: 43 (comprising CBA promoter of SEQ ID NO: 37) |
| 3 | Rag2 | 100 | Definity RT | 3 | SEQ ID NO: 45 (comprising NPHS1 promoter of SEQ ID NO: 44) |

Each experimental group received identical application of ultrasound energy following administration of the sonoactive agent and DNA payload. Using a L8-18 probe on a General Electric LOGIQ E9 system in Elasto mode, ultrasound was applied at a frequency of about 2.5 MHz at a mechanical index of 1.7 at a 100% push output applying a 300 us push pulse with a pulse repetition frequency of 0.5 Hz at an ultrasound intensity of at least 200 mW/cm2 (ISPTA) for about 40 seconds of ultrasound application over the left kidney region of each mouse.

3 days following the final sonoporation treatment, the mice were injected with D-Luciferin, potassium salt and imaged using IVIS.

Results

Figure 26:
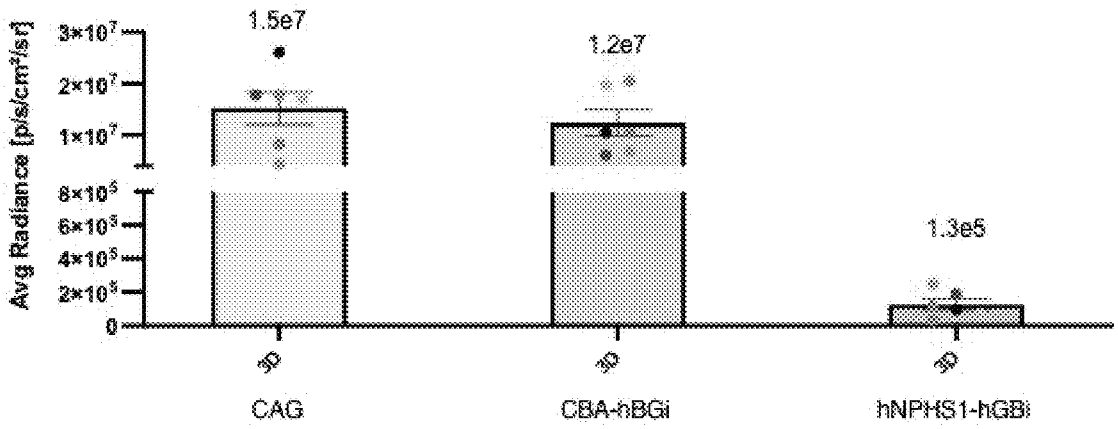
FIG. 26 shows in-vivo fluorescence data illustrating expression of a gene encoding a reporter protein downstream of a promoter sequence of the present disclosure.

The results of this experiment are illustrated in FIG. 26. In FIG. 26, it is shown that mice treated with the vector of SEQ ID NO: 43 (comprising CBA promoter of SEQ ID NO: 37) exhibited average radiance of about 1.2 E7 p/s/cm2/sr, mice treated with the vector of SEQ ID NO: 42 (comprising CBA promoter of SEQ ID NO: 5) exhibited average radiance of about 1.5 E7 p/s/cm2/sr, and mice treated with the vector of SEQ ID NO: 45 (comprising NPHS1 promoter of SEQ ID NO: 37) exhibited average radiance of about 1.3 E5 p/s/cm2/sr. Of note is that mice treated with the vector of SEQ ID NO: 43 (comprising the ubiquitous CBA promoter of SEQ ID NO: 37) exhibited gene expression consistent with mice treated with the vector of SEQ ID NO: 42 comprising the well-known and highly effective ubiquitous CAG promoter, and exhibited gene expression which significantly out-performed mice treated with the vector of SEQ ID NO: 45 comprising the kidney tissue specific NPHS1 promoter.

Example 12: Evaluation of Nucleic Acid Delivery Vectors in a Murine Model of Ultrasound Mediated Nucleic Acid Transfection to the Muscle Evaluating a Ubiquitous Promoter Sequence in the Muscle In this example, nucleic acid delivery vectors with expression cassettes comprising the ubiquitous CBA promoter sequences disclosed herein were evaluated in a murine model of ultrasound mediated nucleic acid delivery to the skeletal muscle (quadriceps).

Experimental Animals and Protocol

Five groups of RAG2 mice were evaluated. Prior to the experiment, mice were implanted with a jugular vein catheter though which the sonoactive agent and the DNA solution was administered. The experimental groups were set forth below. In brief, Group 1 was a no-ultrasound control administered only the vector and the sonoactive agent, Group 2-3 were administered vectors comprising a gene encoding a fluorescent reporter protein (FLUC) under either a ubiquitous promoter of the present disclosure (SEQ ID NO: 37) or a muscle tissue specific promoter (SEQ ID NO: 10) with administration of a sonoactive agent and ultrasound, and Groups 4-5 were administered human dystrophin under either a ubiquitous or a muscle tissue specific promoter (SEQ ID NO: 10) with administration of a sonoactive agent and ultrasound. Optison (human serum albumin stabilized perflutran core microbubbles) was used as the ultrasound contrast agent in this experiment.

| Group (n = 3) | Strain | DNA Dose (ug) | Sonoactive agent | # of doses | Ultrasound | Vector |
|---|---|---|---|---|---|---|
| 1 | Rag2 | 250 | Optison | 3 | None | SEQ ID NO: 47 (SEQ ID NO: 37 ubiquitous promoter + FLUC reporter) |
| 2 | Rag2 | 250 | Optison | 3 | L8-18, MI 1.4, 10 sec on, 20 sec off, 60 sec total on | SEQ ID NO: 47 (SEQ ID NO: 37 ubiquitous promoter + FLUC reporter) |
| 3 | Rag2 | 250 | Optison | 3 | L8-18, MI 1.4, 10 sec on, 20 sec off, 60 sec total on | SEQ ID NO: 48 (muscle tissue specific promoter + FLUC reporter) |
| 4 | Rag2 | 250 | Optison | 3 | L8-18, MI 1.4, 10 sec on, 20 sec off, 60 sec total on | SEQ ID NO: 49 (SEQ ID NO: 37 ubiquitous promoter + DMD) |
| 5 | Rag2 | 250 | Optison | 3 | L8-18, MI 1.4, 10 sec on, 20 sec off, 60 sec total on | SEQ ID NO: 50 (muscle tissue specific promoter + DMD) |

The mice received application of ultrasound energy following administration of 50 uL of the sonoactive agent and one third of the DNA payload in each treatment session. In a treatment session, the left leg of each animal was placed in a heated water bath at 38° C. for 2 minutes prior to applying ultrasound using a L8-18 probe on a General Electric LOGIQ E9 system in Elasto mode applying an acoustic radiation force at a frequency of about 2.5 MHz at a mechanical index of 1.4 at a 100% push output at an ultrasound intensity of at least 200 mW/cm2 (ISPTA) for about 10 sec on, 20 sec off, for a total of 60 sec of ultrasound application over the left quadriceps region of each mouse. A second identical treatment session was applied at 24 hours after the first treatment session, and a third identical treatment session was applied at 24 hours after the second treatment session.

For Groups 1-3, the mice were injected with D-Luciferin, potassium salt and imaged using IVIS 1 day following the first treatment session; 1 day following the second treatment session; and 1, 2 and 6 days following the third treatment session, and For Groups 4-5, mice were sacrificed 4 days following the third treatment session. Tissue samples were collected, placed into a sterile tube, and snap frozen using liquid $N_2$. Tissue samples were directly transferred to −80 C storage. Capillary western blot analysis was performed as described in Example 1, with the addition of human skeletal muscle lysate was normalized to 2 ug/ul, then diluted to create standards at 100, 50, 25, 5, 2, and 1%. A 2 ug/uL concentration was the selected concentration for the western blot analysis. Samples were then diluted to 2 ug/uL and compared with human skeletal muscle lysate standards.

Results

Figure 27:
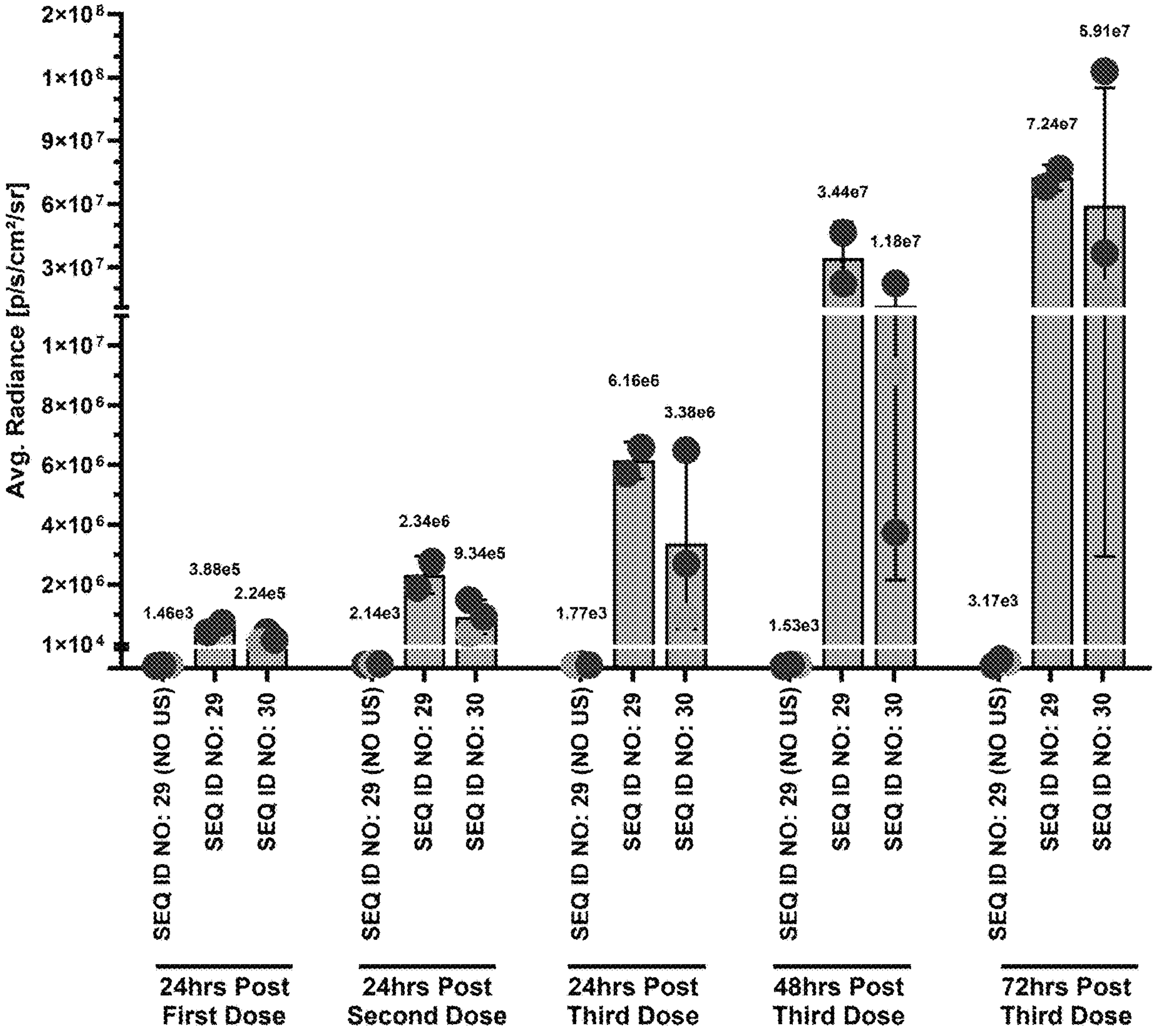
FIG. 27 shows in-vivo data fluorescence data illustrating expression of a gene encoding a reporter protein downstream of a promoter sequence of the present disclosure.

Results for Groups 1-3 are shown in FIG. 27, in which it is shown that the negative control, group 1, exhibited only background levels of average radiance at all time points; Group 2, administered the vector of SEQ ID NO: 47 (ubiquitous promoter+FLUC reporter), exhibited average radiance levels of about 2.3 E6 p/s/cm2/sr at 24 hours following the second treatment, average radiance levels of about 6.2 E6 p/s/cm2/sr at 24 hours following the third treatment, average radiance levels of about 3.44 E7 p/s/cm2/sr at 48 hours following the third treatment, and average radiance levels of about 7.2 E7 p/s/cm2/sr at 72 hours following the third treatment; and Group 3, administered the vector of SEQ ID NO: 48 (muscle tissue specific promoter+FLUC reporter), exhibited average radiance levels of about 9.3 E5 p/s/cm2/sr at 24 hours following the second treatment, average radiance levels of about 3.4 E6 p/s/cm2/sr at 24 hours following the third treatment, average radiance levels of about 1.2 E7 p/s/cm2/sr at 48 hours following the third treatment, and average radiance levels of about 5.9 E7 p/s/cm2/sr at 72 hours following the third treatment. Of note is that mice treated with the vectors comprising the SEQ ID NO: 37 ubiquitous promoter exhibited significantly increased gene expression as compared to groups treated with muscle tissue specific promoters.

Figure 28:
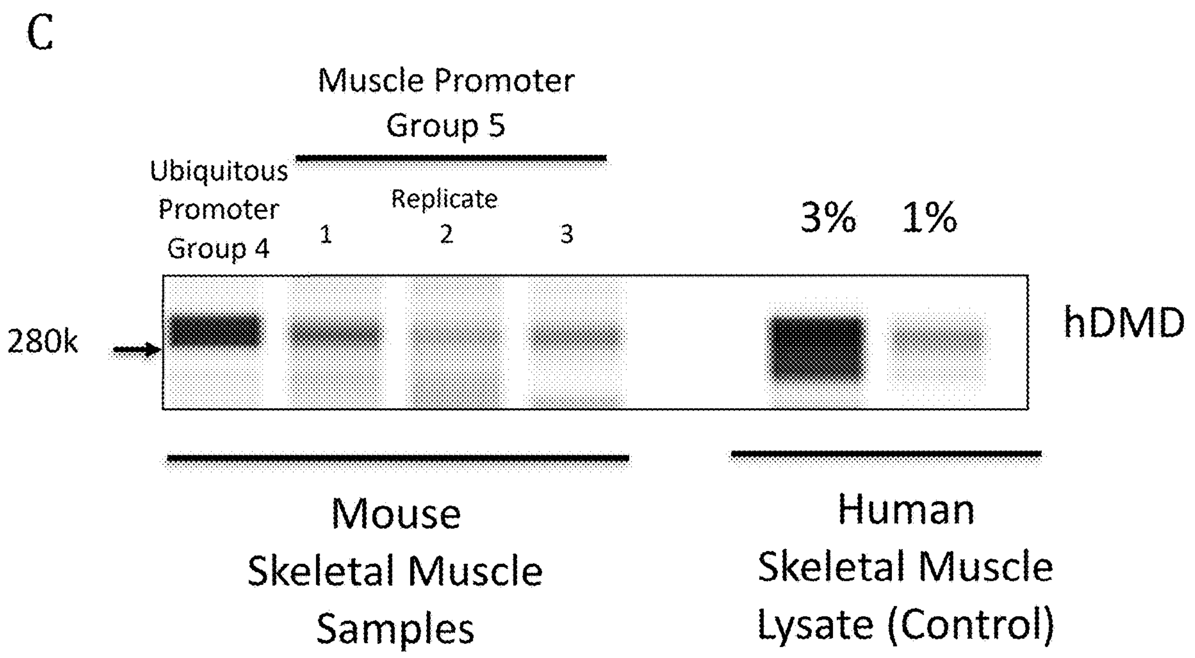
FIG. 28 shows results of a western blot assay illustrating expression of full length human dystrophin protein in-vivo with a promoter sequence of the present disclosure.

Results of the capillary western blot are shown in FIG. 28, in which samples are diluted to 2 ug/uL and compared with human skeletal muscle lysate standards. In FIG. 28, it is observed that Group 4, administered the vector of SEQ ID NO: 49 comprising a ubiquitous promoter coupled to a dystrophin transgene, exhibited strong expression of the full length dystrophin protein consistent with the 3% human skeletal muscle lysate standard, while Group 5, administered the vector of SEQ ID NO: 50 comprising a muscle tissue specific promoter coupled to a dystrophin transgene, exhibited expression of the full length dystrophin protein consistent with the 1% human skeletal muscle lysate standard. Of note is that mice treated with the vectors comprising the SEQ ID NO: 37 ubiquitous promoter exhibited significantly increased gene expression as compared to groups treated with muscle tissue specific promoters.

Example 13: Evaluation of Nucleic Acid Delivery Vectors in a Murine Model of Ultrasound Mediated Nucleic Acid Transfection to the Liver Evaluating a Ubiquitous Promoter Sequence in the Liver In this example, nucleic acid delivery vectors with expression cassettes comprising the ubiquitous CBA promoter sequences disclosed herein were evaluated in a murine model of ultrasound mediated nucleic acid delivery to the liver.

Experimental Animals and Protocol

Two groups of three RAG2 mice were evaluated. Prior to the experiment, mice were implanted with a jugular vein catheter though which the sonoactive agent and the DNA solution was administered. The experimental groups were set forth below. In brief, Group 1 was administered a vector comprising a gene encoding a fluorescent reporter protein (FLUC) under a well-known CAG promoter which is known to have strong promoter activity in a variety of cell types, and Groups 2 was administered a vector comprising a fluorescent reporter protein (FLUC) coupled to a ubiquitous promoter of the present disclosure (SEQ ID NO: 37), with each group receiving administration of a sonoactive agent and ultrasound. Sonazoid was used as the ultrasound contrast agent in this experiment.

| Group (n = 3) | Strain | DNA Dose (ug) | Sonoactive agent | # of doses | Ultrasound | Vector |
|---|---|---|---|---|---|---|
| 1 | Rag2 | 250 | Sonazoid | 1 | Cl-6, MI 1.4, 10 sec on, 20 sec off, 40 sec total on | SEQ ID NO: 42 (SEQ ID NO: 41 CAG promoter + FLUC reporter) |
| 2 | Rag2 | 250 | Sonazoid | 1 | Cl-6, MI 1.4, 10 sec on, 20 sec off, 40 sec total on | SEQ ID NO: 43 (SEQ ID NO: 37 ubiquitous promoter + FLUC reporter) |

The mice received application of ultrasound energy following administration of 50 μL of the sonoactive agent and one third of the DNA payload in each treatment session. In a treatment session, ultrasound was applied using a C1-6 probe on a General Electric LOGIQ E9 system in Elasto mode applying an acoustic radiation force at a frequency of about 2.5 MHz at a mechanical index of 1.4 at a 100% push output at an ultrasound intensity of at least 200 mW/cm2 (ISPTA) for about 10 sec on, 20 sec off, for a total of 40 sec of ultrasound application over the liver region of each mouse.

Groups 1-2 mice were injected with D-Luciferin, potassium salt and imaged using IVIS 96 hours following the treatment session; and 2 weeks following the treatment session.

Results

Figure 29:
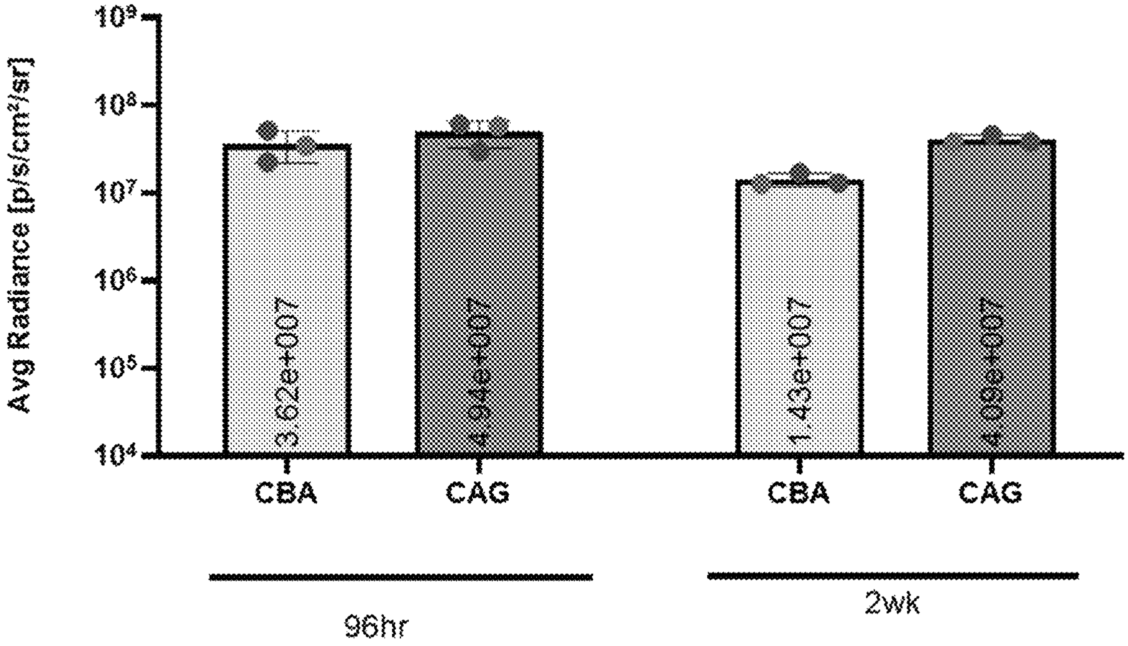
FIG. 29 shows in-vivo data fluorescence data illustrating expression of a gene encoding a reporter protein downstream of a promoter sequence of the present disclosure.

Results for Groups 1-2 are shown in FIG. 29, in which it is shown that Group 1 (CAG) mice exhibited average radiance levels of about 4.94 E7 p/s/cm2/sr at 96 hours following treatment, and exhibited average radiance levels of about 4.909 E7 p/s/cm2/sr at 2 weeks following treatment. Group 2 (CBA ubiquitous promoter sequence) exhibited average radiance levels of about 3.62 E7 p/s/cm2/sr at 96 hours following treatment, and exhibited average radiance levels of about 1.43 E7 p/s/cm2/sr at 2 weeks following treatment. The results of this experiment establish that the activity of the CBA promoter of SEQ ID NO 37 exhibits strong activity it the liver, comparable to that of the well-known CAG promoter.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

IV. Sequence Listing

| SEQ ID NO | Description | SEQ |
|---|---|---|
| 1. | DMD-WT | ATGCTTTGGTGGGAAGAAGTAGAGGACTGTTATGAAAGAGAAGATGTTCA<br>AAAGAAAACATTCACAAAATGGGTAAATGCACAATTTTCTAAGTTTGGGA<br>AGCAGCATATTGAGAACCTCTTCAGTGACCTACAGGATGGGAGGCGCCTC |

-continued

| SEQ ID NO | Description | SEQ |
|---|---|---|
| | | CTAGACCTCCTCGAAGGCCTGACAGGGCAAAAACTGCCAAAAGAAAAAGG |
| | | ATCCACAAGAGTTCATGCCCTGAACAATGTCAACAAGGCACTGCGGGTTT |
| | | TGCAGAACAATAATGTTGATTTAGTGAATATTGGAAGTACTGACATCGTA |
| | | GATGGAAATCATAAACTGACTCTTGGTTTGATTTGGAATATAATCCTCCA |
| | | CTGGCAGGTCAAAAATGTAATGAAAAATATCATGGCTGGATTGCAACAAA |
| | | CCAACAGTGAAAAGATTCTCCTGAGCTGGGTCCGACAATCAACTCGTAAT |
| | | TATCCACAGGTTAATGTAATCAACTTCACCACCAGCTGGTCTGATGGCCT |
| | | GGCTTTGAATGCTCTCATCCATAGTCATAGGCCAGACCTATTTGACTGGA |
| | | ATAGTGTGGTTTGCCAGCAGTCAGCCACACAACGACTGGAACATGCATTC |
| | | AACATCGCCAGATATCAATTAGGCATAGAGAAACTACTCGATCCTGAAGA |
| | | TGTTGATACCACCTATCCAGATAAGAAGTCCATCTTAATGTACATCACAT |
| | | CACTCTTCCAAGTTTTGCCTCAACAAGTGAGCATTGAAGCCATCCAGGAA |
| | | GTGGAAATGTTGCCAAGGCCACCTAAAGTGACTAAAGAAGAACATTTTCA |
| | | GTTACATCATCAAATGCACTATTCTCAACAGATCACGGTCAGTCTAGCAC |
| | | AGGGATATGAGAGAACTTCTTCCCCTAAGCCTCGATTCAAGAGCTATGCC |
| | | TACACACAGGCTGCTTATGTCACCACCTCTGACCCTACACGGAGCCCATT |
| | | TCCTTCACAGCATTTGGAAGCTCCTGAAGACAAGTCATTTGGCAGTTCAT |
| | | TGATGGAGAGTGAAGTAAACCTGGACCGTTATCAAACAGCTTTAGAAGAA |
| | | GTATTATCGTGGCTTCTTTCTGCTGAGGACACATTGCAAGCACAAGGAGA |
| | | GATTTCTAATGATGTGGAAGTGGTGAAAGACCAGTTTCATACTCATGAGG |
| | | GGTACATGATGGATTTGACAGCCCATCAGGGCCGGGTTGGTAATATTCTA |
| | | CAATTGGGAAGTAAGCTGATTGGAACAGGAAAATTATCAGAAGATGAAGA |
| | | AACTGAAGTACAAGAGCAGATGAATCTCCTAAATTCAAGATGGGAATGCC |
| | | TCAGGGTAGCTAGCATGGAAAAACAAAGCAATTTACATAGAGTTTTAATG |
| | | GATCTCCAGAATCAGAAACTGAAAGAGTTGAATGACTGGCTAACAAAAAC |
| | | AGAAGAAAGAACAAGGAAAATGGAGGAAGAGCCTCTTGGACCTGATCTTG |
| | | AAGACCTAAAACGCCAAGTACAACAACATAAGGTGCTTCAAGAAGATCTA |
| | | GAACAAGAACAAGTCAGGGTCAATTCTCTCACTCACATGGTGGTGGTAGT |
| | | TGATGAATCTAGTGGAGATCACGCAACTGCTGCTTTGGAAGAACAACTTA |
| | | AGGTATTGGGAGATCGATGGGCAAACATCTGTAGATGGACAGAAGACCGC |
| | | TGGGTTCTTTTACAAGACATCCTTCTCAAATGGCAACGTCTTACTGAAGA |
| | | ACAGTGCCTTTTTAGTGCATGGCTTTCAGAAAAAGAAGATGCAGTGAACA |
| | | AGATTCACACAACTGGCTTTAAAGATCAAAATGAAATGTTATCAAGTCTT |
| | | CAAAAACTGGCCGTTTTAAAAGCGGATCTAGAAAAGAAAAAGCAATCCAT |
| | | GGGCAAACTGTATTCACTCAAACAAGATCTTCTTTCAACACTGAAGAATA |
| | | AGTCAGTGACCCAGAAGACGGAAGCATGGCTGGATAACTTTGCCCGGTGT |
| | | TGGGATAATTTAGTCCAAAAACTTGAAAAGAGTACAGCACAGATTTCACA |
| | | GGCTGTCACCACCACTCAGCCATCACTAACACAGACAACTGTAATGGAAA |
| | | CAGTAACTACGGTGACCACAAGGGAACAGATCCTGGTAAAGCATGCTCAA |
| | | GAGGAACTTCCACCACCACCTCCCCAAAAGAAGAGGCAGATTACTGTGGA |
| | | TTCTGAAATTAGGAAAAGGTTGGATGTTGATATAACTGAACTTCACAGCT |
| | | GGATTACTCGCTCAGAAGCTGTGTTGCAGAGTCCTGAATTTGCAATCTTT |
| | | CGGAAGGAAGGCAACTTCTCAGACTTAAAAGAAAAAGTCAATGCCATAGA |
| | | GCGAGAAAAAGCTGAGAAGTTCAGAAAACTGCAAGATGCCAGCAGATCAG |
| | | CTCAGGCCCTGGTGGAACAGATGGTGAATGAGGGTGTTAATGCAGATAGC |
| | | ATCAAACAAGCCTCAGAACAACTGAACAGCCGGTGGATCGAATTCTGCCA |
| | | GTTGCTAAGTGAGAGACTTAACTGGCTGGAGTATCAGAACAACATCATCG |
| | | CTTTCTATAATCAGCTACAACAATTGGAGCAGATGACAACTACTGCTGAA |
| | | AACTGGTTGAAAATCCAACCCACCACCCCATCAGAGCCAACAGCAATTAA |
| | | AAGTCAGTTAAAAATTTGTAAGGATGAAGTCAACCGGCTATCAGATCTTC |
| | | AACCTCAAATTGAACGATTAAAAATTCAAAGCATAGCCCTGAAAGAGAAA |
| | | GGACAAGGACCCATGTTCCTGGATGCAGACTTTGTGGCCTTTACAAATCA |
| | | TTTTAAGCAAGTCTTTTCTGATGTGCAGGCCAGAGAGAAAGAGCTACAGA |
| | | CAATTTTTGACACTTTGCCACCAATGCGCTATCAGGAAACCATGAGTGCC |
| | | ATCAGGACATGGGTCCAGCAGTCAGAAACCAAACTCTCCATACCTCAACT |
| | | TAGTGTCACCGACTATGAAATCATGGAGCAGAGACTCGGGGAATTGCAGG |
| | | CTTTACAAAGTTCTCTGCAAGAGCAACAAAGTGGCCTATACTATCTCAGC |
| | | ACCACTGTGAAAGAGATGTCGAAGAAAGCGCCCTCTGAAATTAGCCGGAA |
| | | ATATCAATCAGAATTTGAAGAAATTGAGGGACGCTGGAAGAAGCTCTCCT |
| | | CCCAGCTGGTTGAGCATTGTCAAAAGCTAGAGGAGCAAATGAATAAACTC |
| | | CGAAAAATTCAGAATCACATACAAACCCTGAAGAAATGGATGGCTGAAGT |
| | | TGATGTTTTTCTGAAGGAGGAATGGCCTGCCCTTGGGGATTCAGAAATTC |
| | | TAAAAAAGCAGCTGAAACAGTGCAGACTTTTAGTCAGTGATATTCAGACA |
| | | ATTCAGCCCAGTCTAAACAGTGTCAATGAAGGTGGGCAGAAGATAAAGAA |
| | | TGAAGCAGAGCCAGAGTTTGCTTCGAGACTTGAGACAGAACTCAAAGAAC |
| | | TTAACACTCAGTGGGATCACATGTGCCAACAGGTCTATGCCAGAAAGGAG |
| | | GCCTTGAAGGGAGGTTTGGAGAAAACTGTAAGCCTCCAGAAAGATCTATC |
| | | AGAGATGCACGAATGGATGACACAAGCTGAAGAAGAGTATCTTGAGAGAG |
| | | ATTTTGAATATAAAACTCCAGATGAATTACAGAAAGCAGTTGAAGAGATG |
| | | AAGAGAGCTAAAGAAGAGGCCCAACAAAAAGAAGCGAAAGTGAAACTCCT |
| | | TACTGAGTCTGTAAATAGTGTCATAGCTCAAGCTCCACCTGTAGCACAAG |
| | | AGGCCTTAAAAAAGGAACTTGAAACTCTAACCACCAACTACCAGTGGCTC |
| | | TGCACTAGGCTGAATGGGAAATGCAAGACTTTGGAAGAAGTTTGGGCATG |
| | | TTGGCATGAGTTATTGTCATACTTGGAGAAAGCAAACAAGTGGCTAAATG |
| | | AAGTAGAATTTAAACTTAAAACCACTGAAAACATTCCTGGCGGAGCTGAG |

-continued

| SEQ ID NO | Description | SEQ |
|---|---|---|
| | | GAAATCTCTGAGGTGCTAGATTCACTTGAAAATTTGATGCGACATTCAGA<br>GGATAACCCAAATCAGATTCGCATATTGGCACAGACCCTAACAGATGGCG<br>GAGTCATGGATGAGCTAATCAATGAGGAACTTGAGACATTTAATTCTCGT<br>TGGAGGGAACTACATGAAGAGGCTGTAAGGAGGCAAAAGTTGCTTGAACA<br>GAGCATCCAGTCTGCCCAGGAGACTGAAAAATCCTTACACTTAATCCAGG<br>AGTCCCTCACATTCATTGACAAGCAGTTGGCAGCTTATATTGCAGACAAG<br>GTGGACGCAGCTCAAATGCCTCAGGAAGCCCAGAAAATCCAATCTGATTT<br>GACAAGTCATGAGATCAGTTTAGAAGAAATGAAGAAACATAATCAGGGGA<br>AGGAGGCTGCCCAAAGAGTCCTGTCTCAGATTGATGTTGCACAGAAAAAA<br>TTACAAGATGTCTCCATGAAGTTTCGATTATTCCAGAAACCAGCCAATTT<br>TGAGCAGCGTCTACAAGAAAGTAAGATGATTTTAGATGAAGTGAAGATGC<br>ACTTGCCTGCATTGGAAACAAAGAGTGTGGAACAGGAAGTAGTACAGTCA<br>CAGCTAAATCATTGTGTGAACTTGTATAAAAGTCTGAGTGAAGTGAAGTC<br>TGAAGTGGAAATGGTGATAAAGACTGGACGTCAGATTGTACAGAAAAAGC<br>AGACGGAAAATCCCAAAGAACTTGATGAAAGAGTAACAGCTTTGAAATTG<br>CATTATAATGAGCTGGGAGCAAAGGTAACAGAAAGAAAGCAACAGTTGGA<br>GAAATGCTTGAAATTGTCCCGTAAGATGCGAAAGGAAATGAATGTCTTGA<br>CAGAATGGCTGGCAGCTACAGATATGGAATTGACAAAGAGATCAGCAGTT<br>GAAGGAATGCCTAGTAATTTGGATTCTGAAGTTGCCTGGGGAAAGGCTAC<br>TCAAAAAGAGATTGAGAAACAGAAGGTGCACCTGAAGAGTATCACAGAGG<br>TAGGAGAGGCCTTGAAAACAGTTTTGGGCAAGAAGGAGACGTTGGTGGAA<br>GATAAACTCAGTCTTCTGAATAGTAACTGGATAGCTGTCACCTCCCGAGC<br>AGAAGAGTGGTTAAATCTTTTGTTGGAATACCAGAAACACATGGAAACTT<br>TTGACCAGAATGTGGACCACATCACAAAGTGGATCATTCAGGCTGACACA<br>CTTTTGGATGAATCAGAGAAAAAGAAACCCCAGCAAAAAGAAGACGTGCT<br>TAAGCGTTTAAAGGCAGAACTGAATGACATACGCCCAAAGGTGGACTCTA<br>CACGTGACCAAGCAGCAAACTTGATGGCAAACCGCGGTGACCACTGCAGG<br>AAATTAGTAGAGCCCCAAATCTCAGAGCTCAACCATCGATTTGCAGCCAT<br>TTCACACAGAATTAAGACTGGAAAGGCCTCCATTCCTTTGAAGGAATTGG<br>AGCAGTTTAACTCAGATATACAAAAATTGCTTGAACCACTGGAGGCTGAA<br>ATTCAGCAGGGGGTGAATCTGAAAGAGGAAGACTTCAATAAAGATATGAA<br>TGAAGACAATGAGGGTACTGTAAAAGAATTGTTGCAAAGAGGAGACAACT<br>TACAACAAAGAATCACAGATGAGAGAAAGCGAGAGGAAATAAAGATAAAA<br>CAGCAGCTGTTACAGACAAAACATAATGCTCTCAAGGATTTGAGGAGCCA<br>AAGAAGAAAAAAGGCTCTAGAAATTTCTCATCAGTGGTATCAGTACAAGA<br>GGCAGGCTGATGATCTCCTGAAATGCTTGGATGACATTGAAAAAAAATTA<br>GCCAGCCTACCTGAGCCCAGAGATGAAAGGAAAATAAAGGAAATTGATCG<br>GGAATTGCAGAAGAAGAAAGAGGAGCTGAATGCAGTGCGTAGGCAAGCTG<br>AGGGCTTGTCTGAGGATGGGGCCGCAATGGCAGTGGAGCCAACTCAGATC<br>CAGCTCAGCAAGCGCTGGCGGGAAATTGAGAGCAAATTTGCTCAGTTTCG<br>AAGACTCAACTTTGCACAAATTCACACTGTCCGTGAAGAAACGATGATGG<br>TGATGACTGAAGACATGCCTTTGGAAATTTCTTATGTGCCTTCTACTTAT<br>TTGACTGAAATCACTCATGTCTCACAAGCCCTATTAGAAGTGGAACAACT<br>TCTCAATGCTCCTGACCTCTGTGCTAAGGACTTTGAAGATCTCTTTAAGC<br>AAGAGGAGTCTCTGAAGAATATAAAAGATAGTCTACAACAAAGCTCAGGT<br>CGGATTGACATTATTCATAGCAAGAAGACAGCAGCATTGCAAAGTGCAAC<br>GCCTGTGGAAAGGGTGAAGCTACAGGAAGCTCTCTCCCAGCTTGATTTCC<br>AATGGGAAAAAGTTAACAAAATGTACAAGGACCGACAAGGGCGATTTGAC<br>AGATCTGTTGAGAAATGGCGGCGTTTTCATTATGATATAAAGATATTTAA<br>TCAGTGGCTAACAGAAGCTGAACAGTTTCTCAGAAAGACACAAATTCCTG<br>AGAATTGGGAACATGCTAAATACAAATGGTATCTTAAGGAACTCCAGGAT<br>GGCATTGGGCAGCGGCAAACTGTTGTCAGAACATTGAATGCAACTGGGGA<br>AGAAATAATTCAGCAATCCTCAAAAACAGATGCCAGTATTCTACAGGAAA<br>AATTGGGAAGCCTGAATCTGCGGTGGCAGGAGGTCTGCAAACAGCTGTCA<br>GACAGAAAAAAGAGGCTAGAAGAACAAAAGAATATCTTGTCAGAATTTCA<br>AAGAGATTTAAATGAATTTGTTTTATGGTTGGAGGAAGCAGATAACATTG<br>CTAGTATCCCACTTGAACCTGGAAAAGAGCAGCAACTAAAAGAAAAGCTT<br>GAGCAAGTCAAGTTACTGGTGGAAGAGTTGCCCCTGCGCCAGGGAATTCT<br>CAAACAATTAAATGAAACTGGAGGACCCGTGCTTGTAAGTGCTCCCATAA<br>GCCCAGAAGAGCAAGATAAACTTGAAAATAAGCTCAAGCAGACAAATCTC<br>CAGTGGATAAAGGTTTCCAGAGCTTTACCTGAGAAACAAGGAGAAATTGA<br>AGCTCAAATAAAAGACCTTGGGCAGCTTGAAAAAAAGCTTGAAGACCTTG<br>AAGAGCAGTTAAATCATCTGCTGCTGTGGTTATCTCCTATTAGGAATCAG<br>TTGGAAATTTATAACCAACCAAACCAAGAAGGACCATTTGACGTTAAGGA<br>AACTGAAATAGCAGTTCAAGCTAAACAACCGGATGTGGAAGAGATTTTGT<br>CTAAAGGGCAGCATTTGTACAAGGAAAAACCAGCCACTCAGCCAGTGAAG<br>AGGAAGTTAGAAGATCTGAGCTCTGAGTGGAAGGCGGTAAACCGTTTACT<br>TCAAGAGCTGAGGGCAAAGCAGCCTGACCTAGCTCCTGGACTGACCACTA<br>TTGGAGCCTCTCCTACTCAGACTGTTACTCTGGTGACACAACCTGTGGTT<br>ACTAAGGAAACTGCCATCTCCAAACTAGAAATGCCATCTTCCTTGATGTT<br>GGAGGTACCTGCTCTGGCAGATTTCAACCGGGCTTGGACAGAACTTACCG<br>ACTGGCTTTCTCTGCTTGATCAAGTTATAAAATCACAGAGGGTGATGGTG<br>GGTGACCTTGAGGATATCAACGAGATGATCATCAAGCAGAAGGCAACAAT<br>GCAGGATTTGGAACAGAGGCGTCCCCAGTTGGAAGAACTCATTACCGCTG<br>CCCAAAATTTGAAAAACAAGACCAGCAATCAAGAGGCTAGAACAATCATT |

-continued

| SEQ ID NO | Description | SEQ |
|---|---|---|
| | | ACGGATCGAATTGAAAGAATTCAGAATCAGTGGGATGAAGTACAAGAACA<br>CCTTCAGAACCGGAGGCAACAGTTGAATGAAATGTTAAAGGATTCAACAC<br>AATGGCTGGAAGCTAAGGAAGAAGCTGAGCAGGTCTTAGGACAGGCCAGA<br>GCCAAGCTTGAGTCATGGAAGGAGGGTCCCTATACAGTAGATGCAATCCA<br>AAAGAAAATCACAGAAACCAAGCAGTTGGCCAAAGACCTCCGCCAGTGGC<br>AGACAAATGTAGATGTGGCAAATGACTTGGCCCTGAAACTTCTCCGGGAT<br>TATTCTGCAGATGATACCAGAAAAGTCCACATGATAACAGAGAATATCAA<br>TGCCTCTTGGAGAAGCATTCATAAAAGGGTGAGTGAGCGAGAGGCTGCTT<br>TGGAAGAAACTCATAGATTACTGCAACAGTTCCCCCTGGACCTGGAAAAG<br>TTTCTTGCCTGGCTTACAGAAGCTGAAACAACTGCCAATGTCCTACAGGA<br>TGCTACCCGTAAGGAAAGGCTCCTAGAAGACTCCAAGGGAGTAAAAGAGC<br>TGATGAAACAATGGCAAGACCTCCAAGGTGAAATTGAAGCTCACACAGAT<br>GTTTATCACAACCTGGATGAAAACAGCCAAAAAATCCTGAGATCCCTGGA<br>AGGTTCCGATGATGCAGTCCTGTTACAAAGACGTTTGGATAACATGAACT<br>TCAAGTGGAGTGAACTTCGGAAAAAGTCTCTCAACATTAGGTCCCATTTG<br>GAAGCCAGTTCTGACCAGTGGAAGCGTCTGCACCTTTCTCTGCAGGAACT<br>TCTGGTGTGGCTACAGCTGAAAGATGATGAATTAAGCCGGCAGGCACCTA<br>TTGGAGGCGACTTTCCAGCAGTTCAGAAGCAGAACGATGTACATAGGGCC<br>TTCAAGAGGGAATTGAAAACTAAAGAACCTGTAATCATGAGTACTCTTGA<br>GACTGTACGAATATTTCTGACAGAGCAGCCTTTGGAAGGACTAGAGAAAC<br>TCTACCAGGAGCCCAGAGAGCTGCCTCCTGAGGAGAGAGCCCAGAATGTC<br>ACTCGGCTTCTACGAAAGCAGGCTGAGGAGGTCAATACTGAGTGGGAAAA<br>ATTGAACCTGCACTCCGCTGACTGGCAGAGAAAAATAGATGAAACCCTTG<br>AAAGACTCCGGGAACTTCAAGAGGCCACGGATGAGCTGGACCTCAAGCTG<br>CGCCAAGCTGAGGTGATCAAGGGATCCTGGCAGCCCGTGGGCGATCTCCT<br>CATTGACTCTCTCCAAGATCACCTGGAGAAAGTCAAGGCACTTCGAGGAG<br>AAATTGCGCCTCTGAAAGAGAACGTGAGCCACGTCAATGACCTTGCTCGC<br>CAGCTTACCACTTTGGGCATTCAGCTCTCACCGTATAACCTCAGCACTCT<br>GGAAGACCTGAACACCAGATGGAAGCTTCTGCAGGTGGCCGTCGAGGACC<br>GAGTCAGGCAGCTGCATGAAGCCCACAGGGACTTTGGTCCAGCATCTCAG<br>CACTTTCTTTCCACGTCTGTCCAGGGTCCCTGGGAGAGAGCCATCTCGCC<br>AAACAAAGTGCCCTACTATATCAACCACGAGACTCAAACAACTTGCTGGG<br>ACCATCCCAAAATGACAGAGCTCTACCAGTCTTTAGCTGACCTGAATAAT<br>GTCAGATTCTCAGCTTATAGGACTGCCATGAAACTCCGAAGACTGCAGAA<br>GGCCCTTTGCTTGGATCTCTTGAGCCTGTCAGCTGCATGTGATGCCTTGG<br>ACCAGCACAACCTCAAGCAAAATGACCAGCCCATGGATATCCTGCAGATT<br>ATTAATTGTTTGACCACTATTTATGACCGCCTGGAGCAAGAGCACAACAA<br>TTTGGTCAACGTCCCTCTCTGCGTGGATATGTGTCTGAACTGGCTGCTGA<br>ATGTTTATGATACGGGACGAACAGGGAGGATCCGTGTCCTGTCTTTTAAA<br>ACTGGCATCATTTCCCTGTGTAAAGCACATTTGGAAGACAAGTACAGATA<br>CCTTTTCAAGCAAGTGGCAAGTTCAACAGGATTTTGTGACCAGCGCAGGC<br>TGGGCCTCCTTCTGCATGATTCTATCCAAATTCCAAGACAGTTGGGTGAA<br>GTTGCATCCTTTGGGGGCAGTAACATTGAGCCAAGTGTCCGGAGCTGCTT<br>CCAATTTGCTAATAATAAGCCAGAGATCGAAGCGGCCCTCTTCCTAGACT<br>GGATGAGACTGGAACCCCAGTCCATGGTGTGGCTGCCCGTCCTGCACAGA<br>GTGGCTGCTGCAGAAACTGCCAAGCATCAGGCCAAATGTAACATCTGCAA<br>AGAGTGTCCAATCATTGGATTCAGGTACAGGAGTCTAAAGCACTTTAATT<br>ATGACATCTGCCAAAGCTGCTTTTTTTCTGGTCGAGTTGCAAAAGGCCAT<br>AAAATGCACTATCCCATGGTGGAATATTGCACTCCGACTACATCAGGAGA<br>AGATGTTCGAGACTTTGCCAAGGTACTAAAAAACAAATTTCGAACCAAAA<br>GGTATTTTGCGAAGCATCCCCGAATGGGCTACCTGCCAGTGCAGACTGTC<br>TTAGAGGGGGACAACATGGAAACTCCCGTTACTCTGATCAACTTCTGGCC<br>AGTAGATTCTGCGCCTGCCTCGTCCCCTCAGCTTTCACACGATGATACTC<br>ATTCACGCATTGAACATTATGCTAGCAGGCTAGCAGAAATGGAAAACAGC<br>AATGGATCTTATCTAAATGATAGCATCTCTCCTAATGAGAGCATAGATGA<br>TGAACATTTGTTAATCCAGCATTACTGCCAAAGTTTGAACCAGGACTCCC<br>CCCTGAGCCAGCCTCGTAGTCCTGCCCAGATCTTGATTTCCTTAGAGAGT<br>GAGGAAAGAGGGGAGCTAGAGAGAATCCTAGCAGATCTTGAGGAAGAAAA<br>CAGGAATCTGCAAGCAGAATATGACCGTCTAAAGCAGCAGCACGAACATA<br>AAGGCCTGTCCCCACTGCCGTCCCCTCCTGAAATGATGCCCACCTCTCCC<br>CAGAGTCCCCGGGATGCTGAGCTCATTGCTGAGGCCAAGCTACTGCGTCA<br>ACACAAAGGCCGCCTGGAAGCCAGGATGCAAATCCTGGAAGACCACAATA<br>AACAGCTGGAGTCACAGTTACACAGGCTAAGGCAGCTGCTGGAGCAACCC<br>CAGGCAGAGGCCAAAGTGAATGGCACAACGGTGTCCTCTCCTTCTACCTC<br>TCTACAGAGGTCCGACAGCAGTCAGCCTATGCTGCTCCGAGTGGTTGGCA<br>GTCAAACTTCGGACTCCATGGGTGAGGAAGATCTTCTCAGTCCTCCCCAG<br>GACACAAGCACAGGGTTAGAGGAGGTGATGGAGCAACTCAACAACTCCTT<br>CCCTAGTTCAAGAGGAAGAAATACCCCTGGAAAGCCAATGAGAGAGGACA<br>CAATGTAGTAA |
| 2. | DMD-3 | ATGCTGTGGTGGGAAGAGGTGGAGGACTGTTACGAGAGAGAGGACGTGCA<br>GAAGAAGACATTCACCAAGTGGGTGAACGCTCAGTTCAGCAAGTTCGGCA<br>AGCAGCACATCGAGAACCTGTTTAGCGATCTACAAGATGGCAGAAGACTG<br>CTGGACCTGCTGGAGGGCCTGACCGGGCAGAAGCTGCCCAAAGAAAAGGG<br>GTCTACAAGAGTGCACGCCCTGAACAACGTGAACAAGGCCCTGAGAGTGC |

-continued

| SEQ ID NO | Description | SEQ |
|---|---|---|
| | | TGCAGAACAACAACGTGGACCTGGTGAACATCGGCAGCACCGACATCGTG<br>GACGGCAACCACAAGCTGACCCTGGGCCTGATCTGGAACATCATCCTGCA<br>CTGGCAAGTGAAGAACGTGATGAAGAACATCATGGCCGGCCTGCAGCAGA<br>CCAACAGCGAGAAGATCCTGCTGAGCTGGGTGAGACAGAGCACAAGAAAC<br>TACCCCCAAGTGAACGTGATCAACTTCACCACAAGCTGGAGCGACGGCCT<br>GGCCCTGAACGCCCTGATCCACAGCCACAGACCCGACCTGTTCGACTGGA<br>ACAGCGTGGTGTGTCAGCAGAGCGCCACACAGAGACTGGAGCACGCCTTC<br>AACATCGCTAGATATCAGCTGGGCATCGAGAAGTTACTGGACCCCGAAGA<br>TGTGGACACCACCTACCCCGACAAGAAGAGCATCCTGATGTACATCACAA<br>GCCTGTTCCAAGTGCTGCCTCAGCAAGTGAGCATCGAGGCCATCCAAGAA<br>GTCGAGATGCTGCCTAGACCCCCCAAGGTGACCAAGGAGGAGCACTTTCA<br>GCTGCACCATCAGATGCACTACTCTCAGCAGATCACAGTCAGCTTGGCAC<br>AAGGCTACGAGAGAACAAGCAGCCCCAAGCCTAGATTCAAGAGCTACGCC<br>TACACCCAAGCCGCCTACGTGACCACAAGTGACCCCACAAGAAGCCCCTT<br>CCCTTCTCAGCACCTGGAGGCCCCCGAGGACAAGAGCTTCGGCAGCAGCC<br>TGATGGAGAGCGAGGTGAACCTGGACAGATATCAGACCGCGTTAGAAGAA<br>GTGTTGAGCTGGCTGCTGAGCGCCGAGGACACCCTGCAAGCCCAAGGCGA<br>GATCAGCAACGATGTGGAGGTGGTGAAGGATCAGTTCCACACCCACGAGG<br>GCTACATGATGGACCTGACCGCCCACCAAGGCAGAGTGGGCAACATCCTG<br>CAGCTGGGCAGCAAGCTGATCGGCACCGGCAAGCTGAGCGAGGACGAGGA<br>AACCGAGGTTCAAGAGCAAATGAACCTGCTAAACAGCAGATGGGAGTGCC<br>TGAGAGTGGCTAGCATGGAAAAGCAGAGTAACCTGCACAGAGTGCTGATG<br>GACCTGCAGAATCAGAAATTGAAAGAACTTAATGATTGGCTGACCAAGAC<br>CGAGGAGAGAACAAGAAAGATGGAGGAGGAGCCCCTGGGCCCCGACCTGG<br>AGGACCTGAAGAGACAAGTGCAGCAGCACAAGGTGCTGCAAGAGGACCTG<br>GAGCAAGAGCAAGTGAGAGTGAACTCTCTGACACACATGGTGGTGGTAGT<br>GGACGAGAGCAGCGGCGATCACGCTACCGCGGCGCTGGAAGAGCAGCTGA<br>AAGTGCTGGGCGACAGATGGGCCAACATCTGCAGATGGACCGAGGACAGA<br>TGGGTGCTGCTGCAAGACATCCTGCTGAAGTGGCAGAGACTGACCGAGGA<br>GCAGTGCCTGTTCAGCGCCTGGCTGAGCGAGAAGGAAGACGCTGTGAACA<br>AGATCCACACCACCGGCTTCAAGGATCAGAACGAGATGCTGAGCTCCCTC<br>CAAAAGCTCGCAGTGCTGAAGGCCGACCTGGAAAAGAAAAAACAGTCGAT<br>GGGCAAGCTGTACAGCCTGAAGCAAGACCTGCTGAGCACCCTGAAGAACA<br>AGAGCGTGACACAGAAGACCGAGGCCTGGCTGGACAACTTCGCTAGATGC<br>TGGGACAACCTGGTACAGAAGTTAGAGAAGTCTACCGCTCAGATCAGCCA<br>AGCCGTAACCACCACACAACCTAGCCTGACTCAGACCACCGTGATGGAAA<br>CCGTGACCACCGTGACAACCCGTGAGCAGATCCTGGTGAAGCACGCCCAA<br>GAGGAGCTGCCCCCCCCCCCCCCTCAGAAGAAGAGACAGATCACCGTGGA<br>CTCAGAGATTCGCAAGAGACTGGACGTGGACATCACCGAGCTGCACAGCT<br>GGATCACAAGAAGCGAGGCCGTGCTGCAGAGCCCTGAGTTCGCGATCTTT<br>AGAAAGGAGGGCGGAGCTGCCCCTGAGACAAGGCATCCTGAAGCAGCTGA<br>ACGAGACTGGCGGCCCCGTGCTGGTGAGCGCCCCCATCAGCCCCGAGGAG<br>CAAGACAAGCTGGAGAACAAGCTGAAGCAGACCAACCTGCAGTGGATCAA<br>GGTGAGCAGAGCCCTGCCCGAGAAGCAAGGCGAAATCGAGGCCCAAATAA<br>AGGACCTGGGGCAGCTGGAGAAGAAACTCGAAGACTTGGAAGAACAACTC<br>AACCACTTGCTGCTGTGGCTGAGCCCCATCAGAAATCAGCTGGAGATCTA<br>CAATCAGCCCAACCAAGAGGGGCCATTCGACGTGAAGGAAACCGAGATCG<br>CCGTGCAAGCCAAGCAGCCCGATGTGGAGGAGATCCTGAGCAAGGGGCAG<br>CACCTGTACAAGGAGAAGCCCGCCACACAGCCCGTCAAGCGTAAACTAGA<br>GGATCTTTCCTCTGAGTGGAAGGCCGTGAACCGTCTGCTACAAGAGCTGC<br>GGGCTAAGCAACCCGACTTAGCGCCCGGCCTGACCACCATCGGTGCAAGC<br>CCCACGCAGACCGTGACCCTGGTGACCCAACCCGTGGTGACCAAGGAAAC<br>CGCCATCAGCAAGCTGGAGATGCCTAGCAGCCTGATGCTGGAGGTGCCCG<br>CCCTGGCCGACTTCAACAGAGCCTGGACCGAGCTGACCGACTGGCTGAGC<br>CTGCTGGACCAAGTGATCAAGTCTCAGAGAGTGATGGTGGGCGATCTGGA<br>GGACATCAATGAGATGATCATCAAGCAGAAGGCCACCATGCAAGACCTGG<br>AGCAGAGAAGACCTCAGCTGGAGGAGCTGATCACCGCCGCTCAGAACCTG<br>AAAAACAAGACGAGCAACCAAGAGGCTAGAACCATCATCACCGACAGAAT<br>CGAGAGAATTCAGAATCAGTGGGACGAGGTGCAAGAGCACCTGCAGAACA<br>GAAGACAGCAACTAAACGAAATGCTCAAGGACAGCACACAGTGGCTGGAG<br>GCCAAGGAGGAGGCGGAGCAAGTGTTGGGCCAAGCTAGAGCCAAGCTGGA<br>GAGCTGGAAGGAGGGACCCTACACCGTGGACGCCATTCAGAAGAAGATCA<br>CCGAAACCAAGCAGCTGGCCAAGGACCTGCGACAGTGGCAGACCAACGTG<br>GACGTGGCCAACGATCTTGCCCTGAAGCTGCTGCGCGACTATAGCGCCGA<br>CGACACAAGAAAGGTGCACATGATCACCGAGAACATCAACGCTAGCTGGC<br>GTAGCATCCACAAGAGAGTGAGCGAGAGAGAGGCGGCTTTGGAGGAAACC<br>CATAGACTGCTGCAGCAGTTTCCCCTGGACCTGGAGAAGTTCCTGGCCTG<br>GCTGACCGAAGCCGAAACAACCGCCAACGTGCTGCAAGACGCCACAAGAA<br>AGGAGAGACTGCTGGAGGACAGCAAGGGCGTGAAGGAGCTGATGAAGCAG<br>TGGCAAGACCTGCAAGGCGAGATCGAAGCGCACACCGACGTGTACCACAA<br>CCTGGACGAGAACTCTCAGAAGATCCTGAGAAGCCTGGAGGGCAGCGACG<br>ACGCCGTGCTGTTACAGAGAAGGCTGGACAACATGAACTTCAAGTGGAGC<br>GAGCTGAGAAAGAAGAGCCTGAACATCAGAAGCCACCTGGAGGCTAGCAG<br>CGATCAGTGGAAGAGACTGCACCTGAGCCTGCAAGAGCTGCTGGTCTGGC<br>TTCAGTTGAAGGACGATGAGCTGAGCAGACAAGCCCCCATCGGCGGCGAC |

-continued

| SEQ ID NO | Description | SEQ |
|---|---|---|
| | | TTCCCCGCCGTGCAGAAGCAGAACGACGTGCATAGAGCCTTCAAGAGAGA |
| | | GCTGAAGACCAAGGAGCCCGTGATCATGAGCACCCTGGAAACGGTGAGAA |
| | | TCTTCCTGACCGAGCAGCCCCTGGAGGGCCTGGAGAAGCTGTACCAAGAG |
| | | CCTAGAGAGCTGCCCCCCGAGGAGAGAGCTCAGAACGTGACAAGACTGCT |
| | | GAGAAAGCAAGCCGAAGAGGTGAACACCGAGTGGGAGAAGCTGAACCTGC |
| | | ACAGCGCCGACTGGCAGAGAAAGATCGACGAAACCCTGGAGAGACTGAGA |
| | | GAATTGCAAGAGGCGACCGACGAGCTGGACCTGAAGCTGAGACAAGCCGA |
| | | GGTCATCAAGGGCAGCTGGCAGCCCGTGGGCGATCTATTAATTGACTCTC |
| | | TACAAGACCACCTGGAGAAAGTGAAGGCCCTGAGAGGCGAGATCGCCCCC |
| | | CTGAAGGAGAACGTGAGCCACGTGAATGATCTGGCACGTCAGCTGACCAC |
| | | CCTGGGCATACAACTGTCCCCCTATAACCTGAGCACACTGGAGGATTTGA |
| | | ATACTAGATGGAAGCTGCTGCAAGTGGCCGTGGAGGACAGAGTAAGACAA |
| | | TTACATGAGGCCCACAGAGACTTCGGCCCCGCTTCTCAGCACTTCCTGAG |
| | | CACAAGCGTGCAAGGCCCCTGGGAGAGAGCCATTTCCCCCAACAAGGTCC |
| | | CCTACTACATCAACCACGAGACACAGACCACCTGCTGGGACCACCCCAAG |
| | | ATGACCGAGCTGTATCAGAGCCTCGCCGATCTGAACAATGTGAGATTCAG |
| | | CGCCTACAGAACCGCCATGAAGCTGAGAAGACTGCAGAAGGCCCTGTGCC |
| | | TGGACTTATTAAGCCTGAGCGCCGCCTGCGACGCCCTGGATCAGCACAAC |
| | | CTGAAGCAAAACGACCAACCCATGGACATCCTGCAGATCATCAACTGCCT |
| | | CACCACCATATACGACAGACTGGAACAAGAGCACAACAACCTGGTGAACG |
| | | TGCCCCTGTGCGTGGACATGTGCCTGAACTGGCTGCTGAACGTGTACGAC |
| | | ACCGGCAGAACCGGCAGAATCAGAGTGCTGAGCTTCAAGACCGGCATCAT |
| | | CAGCCTGTGCAAGGCCCACCTGGAGGACAAATACAGATACCTTTTCAAAC |
| | | AAGTGGCTAGCAGCACCGGCTTCTGCGACCAAAGAAGACTGGGTCTGCTG |
| | | CTGCACGACAGCATTCAGATCCCTAGACAGCTGGGCGAGGTGGCTAGCTT |
| | | CGGCGGCAGCAACATCGAGCCTAGCGTGAGAAGCTGCTTTCAGTTCGCCA |
| | | ACAACAAGCCCGAGATAGAGGCAGCCCTCTTCTTAGACTGGATGAGACTG |
| | | GAGCCTCAGAGCATGGTATGGCTGCCGGTCCTGCACAGAGTGGCCGCCGC |
| | | CGAAACCGCCAAGCACCAAGCCAAGTGCAACATCTGCAAGGAGTGCCCCA |
| | | TCATCGGCTTCAGATACAGAAGCCTGAAGCACTTCAACTACGACATCTGT |
| | | CAGAGCTGCTTCTTCAGCGGCAGAGTGGCCAAGGGCCACAAGATGCACTA |
| | | CCCCATGGTGGAGTACTGCACCCCCACCACAAGCGGCGAGGACGTGAGAG |
| | | ACTTCGCCAAGGTGTTGAAGAATAAGTTTAGAACCAAGAGATACTTCGCC |
| | | AAGCACCCTAGAATGGGCTACCTGCCCGTGCAGACCGTGCTGGAGGGCGA |
| | | CAACATGGAAACCCCCGTGACCCTGATCAACTTCTGGCCCGTGGACAGCG |
| | | CCCCCGCTAGCAGCCCTCAGCTGAGCCACGACGACACCCACAGCAGAATC |
| | | GAGCACTACGCTAGCAGACTGGCCGAGATGGAGAACAGCAACGGCAGCTA |
| | | CCTGAACGACAGCATCAGCCCGAATGAGAGCATCGACGACGAGCACCTGC |
| | | TGATTCAGCACTACTGTCAGAGCCTGAACCAAGACAGCCCCCTGTCTCAG |
| | | CCTAGAAGCCCCGCTCAGATCCTGATCAGCCTGGAGAGCGAGGAGAGAGG |
| | | CGAGCTGGAGAGAATCCTAGCAGATCTGGAGGAAGAGAACAGAAACCTGC |
| | | AAGCCGAGTATGACCGACTGAAACAGCAACATGAGCACAAAGGCCTGAGC |
| | | CCACTGCCCTCCCCCCCCGAGATGATGCCCACAAGCCCTCAGAGCCCTAG |
| | | AGACGCCGAGCTGATCGCTGAAGCGAAGTTACTTAGACAACACAAGGGCA |
| | | GACTGGAGGCTAGAATGCAGATCCTGGAGGACCACAACAAGCAGCTGGAG |
| | | TCTCAGCTGCACAGACTGAGGCAGCTGCTGGAACAGCCCCAAGCCGAGGC |
| | | CAAAGTGAACGGCACCACCGTGAGCAGTCCTAGCACAAGCCTGCAGAGAA |
| | | GCGACAGCTCTCAGCCCATGCTGCTGAGAGTGGTGGGCTCTCAGACAAGC |
| | | GACAGCATGGGCGAGGAGGATCTGCTGAGTCCGCCCCAAGACACAAGCAC |
| | | CGGCCTGGAAGAGGTGATGGAGCAACTGAACAATAGCTTCCCTAGCAGCA |
| | | GAGGCAGAAACACCCCCGGCAAGCCCATGAGAGAGGACACCATGTGATGA |
| 3. | DMD-4 | ATGCTTTGGTGGGAAGAAGTCGAGGACTGCTACGAGCGCGAGGACGTGCA |
| | | GAAGAAAACCTTCACCAAATGGGTCAACGCCCAGTTCAGCAAGTTCGGCA |
| | | AGCAGCACATCGAGAACCTGTTCAGCGACCTGCAGGATGGCAGAAGGCTG |
| | | CTGGATCTGCTGGAAGGCCTGACAGGACAGAAGCTGCCCAAAGAGAAGGA |
| | | ACTTCAGCGACTTGAAGGAGAAAGTGAACGCCATCGAGAGAGAGAAGGCC |
| | | GAGAAGTTCAGAAAGTTGCAAGACGCCTCAAGAAGCGCCCAAGCCCTGGT |
| | | GGAGCAGATGGTTAACGAAGGCGTGAATGCCGACAGCATCAAGCAAGCTA |
| | | GCGAGCAGCTGAATAGCCGGTGGATTGAATTCTGTCAGCTGCTGAGCGAG |
| | | AGATTAAACTGGCTGGAGTATCAGAACAACATCATCGCCTTCTACAATCA |
| | | GCTGCAGCAACTAGAACAAATGACCACCACCGCCGAGAACTGGCTAAAGA |
| | | TTCAGCCCACCACCCCTAGCGAGCCCACCGCCATCAAATCTCAGCTGAAA |
| | | ATTTGCAAGGACGAAGTGAACAGACTGTCGGACCTGCAGCCTCAAATCGA |
| | | AAGACTGAAAATTCAGAGCATCGCACTTAAGGAGAAGGGCCAAGGACCCA |
| | | TGTTCCTGGACGCCGACTTCGTGGCCTTCACCAACCACTTCAAGCAAGTG |
| | | TTCAGCGACGTGCAAGCTAGAGAGAAGGAGCTGCAGACCATCTTCGACAC |
| | | CCTGCCCCCCATGAGATACCAAGAAACCATGAGCGCCATCAGAACCTGGG |
| | | TGCAGCAGAGCGAAACCAAGCTGAGCATCCCTCAGCTGAGCGTGACCGAC |
| | | TACGAGATCATGGAGCAAAGACTGGGAGAGCTGCAAGCCCTGCAGAGCAG |
| | | CCTGCAAGAGCAGCAGAGCGGCCTGTACTACCTGAGCACCACCGTGAAGG |
| | | AGATGTCGAAGAAAGCCCCGTCGGAGATCAGCAGAAAGTATCAGAGCGAG |
| | | TTCGAGGAGATCGAGGGCAGATGGAAGAAGCTGAGCAGCCAACTGGTGGA |
| | | ACACTGTCAGAAATTAGAAGAACAGATGAACAAGCTGAGAAAGATTCAGA |
| | | ACCACATTCAGACCCTGAAGAAGTGGATGGCCGAGGTGGACGTGTTCCTG |

-continued

| SEQ ID NO | Description | SEQ |
|---|---|---|
| | | AAAGAGGAGTGGCCCGCCCTGGGCGATTCCGAAATCTTAAAAAAGCAGCT |
| | | GAAGCAGTGCAGACTGCTGGTGTCAGATATCCAAACCATTCAACCAAGCC |
| | | TGAACAGCGTGAACGAAGGCGGGCAGAAGATCAAGAACGAGGCCGAGCCC |
| | | GAGTTCGCTAGCAGACTGGAAACCGAGCTGAAGGAGCTGAATACACAGTG |
| | | GGACCACATGTGTCAGCAAGTGTACGCTAGAAAGGAAGCGCTGAAGGGCG |
| | | GGCTGGAGAAGACCGTTAGCCTGCAAAAGGATCTGAGCGAGATGCACGAG |
| | | TGGATGACCCAAGCCGAGGAGGAGTACCTGGAGAGAGACTTCGAGTACAA |
| | | GACCCCCGACGAGCTGCAGAAGGCCGTCGAGGAAATGAAGAGAGCGAAGG |
| | | AGGAGGCTCAGCAGAAGGAAGCCAAGGTGAAGCTGCTGACTGAATCTGTC |
| | | AACAGTGTGATAGCTCAAGCACCCCCCGTTGCCCAAGAGGCACTAAAGAA |
| | | GGAGCTGGAAACTCTGACCACCAACTATCAGTGGCTGTGCACAAGACTGA |
| | | ACGGCAAGTGCAAGACCCTGGAGGAAGTGTGGGCCTGCTGGCACGAGCTG |
| | | CTGAGCTACCTGGAGAAGGCCAACAAGTGGCTGAACGAGGTGGAGTTCAA |
| | | GCTGAAGACCACCGAGAACATCCCCGGCGGCGCCGAGGAGATCAGCGAGG |
| | | TGCTGGACAGCCTGGAGAACCTGATGAGACACAGCGAGGACAACCCCAAT |
| | | CAGATCAGAATCCTGGCTCAGACCCTGACCGACGGCGGCGTGATGGACGA |
| | | GCTGATCAACGAGGAGCTGGAAACCTTTAACTCTAGATGGCGAGAACTGC |
| | | ACGAGGAGGCCGTGAGAAGACAGAAGCTGCTGGAGCAAAGCATTCAGAGC |
| | | GCCCAAGAAACCGAGAAGAGCCTGCACCTGATCCAAGAGAGCCTGACCTT |
| | | CATCGACAAGCAGCTGGCCGCCTACATCGCCGACAAGGTGGACGCCGCTC |
| | | AGATGCCACAAGAGGCTCAGAAGATTCAGTCCGATCTGACAAGCCACGAG |
| | | ATCAGCCTGGAGGAGATGAAAAAACACAACCAAGGCAAGGAGGCCGCTCA |
| | | GAGAGTGCTGTCTCAGATCGACGTGGCTCAGAAGAAGCTGCAAGACGTGA |
| | | GCATGAAGTTCAGACTGTTTCAGAAGCCCGCCAACTTCGAGCAGCGACTG |
| | | CAAGAGAGCAAGATGATCCTGGACGAGGTGAAGATGCACCTGCCCGCCCT |
| | | GGAAACCAAGAGCGTGGAGCAAGAGGTGGTGCAGTCTCAGTTGAACCACT |
| | | GCGTGAACCTGTACAAGAGCCTGTCGGAGGTCAAGAGTGAGGTCGAGATG |
| | | GTGATCAAAACTGGGAGACAGATCGTGCAAAAAAAGCAGACCGAGAACCC |
| | | CAAGGAGCTGGACGAGCGTGTTACCGCCCTGAAGCTGCACTACAACGAGC |
| | | TGGGCGCCAAGGTGACCGAGAGAAAGCAGCAGCTGGAGAAGTGCCTGAAG |
| | | CTGAGCAGAAAGATGAGAAAGGAGATGAACGTGCTGACCGAGTGGCTGGC |
| | | CGCCACCGACATGGAGCTGACCAAGAGAAGCGCCGTGGAGGGCATGCCTA |
| | | GCAACCTGGACAGCGAGGTGGCCTGGGGCAAGGCCACACAGAAGGAGATC |
| | | GAGAAGCAGAAGGTGCACCTGAAGAGCATCACCGAGGTGGGCGAGGCCCT |
| | | GAAGACCGTGCTGGGCAAGAAGGAAACCCTGGTGGAGGACAAGCTGAGCC |
| | | TGCTGAACTCGAACTGGATCGCCGTGACAAGCAGAGCCGAGGAGTGGCTG |
| | | AACCTGCTGTTAGAGTACCAAAAACACATGGAAACCTTCGATCAGAACGT |
| | | GGACCACATCACCAAGTGGATCATCCAAGCCGACACCCTGCTGGACGAAA |
| | | GCGAAAAGAAGAAGCCGCAACAAAAGGAGGATGTGCTGAAGAGACTGAAG |
| | | GCCGAACTGAACGATATCAGACCCAAGGTGGACAGCACACGGGACCAAGC |
| | | CGCCAACCTGATGGCCAACAGAGGCGACCACTGCAGAAAACTGGTGGAGC |
| | | CTCAGATCAGCGAGCTGAACCACAGATTCGCCGCCATCAGCCACAGAATC |
| | | AAAACCGGCAAAGCGAGCATCCCCTTGAAGGAACTGGAGCAATTTAACAG |
| | | CGACATCCAAAAATTGCTCGAACCACTGGAGGCCGAGATTCAGCAAGGCG |
| | | TGAACCTGAAGGAAGAGGACTTCAACAAGGACATGAACGAGGACAACGAG |
| | | GGCACCGTGAAAGAACTGCTGCAGAGAGGCGACAACCTGCAGCAGAGAAT |
| | | CACCGACGAGAGAAAGAGAGAGGAGATCAAGATCAAGCAGCAGCTGCTGC |
| | | AGACTAAGCACAACGCCCTGAAGGATCTGAGATCTCAGAGGAGAAAAAAG |
| | | GCTCTGGAAATTTCACATCAGTGGTATCAGTACAAGAGACAAGCAGACGA |
| | | CCTGCTGAAGTGCCTGGACGACATCGAGAAGAAGTTAGCTAGCCTGCCCG |
| | | AGCCTAGAGACGAGAGAAAGATCAAGGAGATCGACAGAGAGTTACAAAAG |
| | | AAGAAGGAGGAGCTGAATGCGGTAAGAAGACAAGCGGAAGGCCTGTCCGA |
| | | GGACGGCGCAGCCATGGCCGTGGAGCCCACACAGATTCAGCTCAGCAAGA |
| | | GATGGAGAGAGATCGAGAGCAAGTTCGCTCAGTTCAGAAGACTGAACTTC |
| | | GCTCAGATCCACACCGTGAGAGAGGAAACCATGATGGTGATGACCGAGGA |
| | | CATGCCCCTGGAGATCTCATACGTTCCTAGCACCTACCTGACCGAGATCA |
| | | CCCACGTGAGCCAAGCCCTGCTGGAGGTGGAGCAGCTGCTGAACGCCCCC |
| | | GACCTGTGCGCCAAGGACTTCGAGGACCTGTTCAAACAAGAGGAGAGCCT |
| | | GAAGAACATCAAGGACAGCCTGCAGCAAAGTAGCGGCAGAATCGACATCA |
| | | TCCACAGCAAGAAGACCGCCGCCCTGCAGAGCGCCACCCCCCGTGGAGAGA |
| | | GTGAAGCTTCAAGAGGCCCTTTCGCAGCTGGATTTTCAGTGGGAGAAGGT |
| | | GAACAAAATGTACAAGGACAGACAAGGCAGATTCGACAGAAGCGTGGAGA |
| | | AGTGGAGAAGATTCCACTACGACATCAAGATCTTCAATCAGTGGCTGACC |
| | | GAGGCAGAGCAGTTCCTGAGAAAGACACAGATCCCCGAGAACTGGGAGCA |
| | | CGCCAAGTACAAGTGGTACCTGAAGGAGCTGCAAGACGGCATCGGGCAGA |
| | | GACAGACCGTGGTGAGAACCCTGAACGCCACCGGCGAGGAGATCATCCAA |
| | | CAAAGCTCCAAAACCGACGCTAGCATCCTGCAAGAGAAACTGGGCAGCCT |
| | | GAACCTGAGATGGCAAGAGGTGTGCAAGCAGCTGAGCGACCGCAAAAAAC |
| | | GGTTAGAGGAGCAGAAGAACATCCTGAGCGAGTTTCAGCGGGACCTGAAC |
| | | GAGTTCGTGCTGTGGCTGGAGGAGGCCGATAACATCGCTAGCATCCCCCT |
| | | GGAGCCCGGCAAGGAGCAGCAGTTAAAAGAAAAACTTGAGCAAGTGAAGC |
| | | TGCTGGTGGAGCAGCACAAGAGTGCACGCCCTGAACAACGTGAACAAGGC |
| | | CCTGAGAGTGCTGCAGAACAACAACGTGGACCTGGTCAACATCGGCAGCA |
| | | CCGACATCGTGGACGGCAACCACAAACTGACCCTGGGCCTGATCTGGAAC |
| | | ATCATCCTGCACTGGCAAGTGAAGAACGTGATGAAGAACATCATGGCCGG |

-continued

| SEQ ID NO | Description | SEQ |
|---|---|---|
| | | CCTGCAGCAGACCAACAGCGAGAAGATTCTGCTGAGCTGGGTCCGACAGA<br>GCACCCCGGAATTACCCTCAAGTGAACGTGATCAACTTCACCACCTCTTGG<br>AGCGACGGACTGGCCCTGAATGCCCTGATCCACAGCCACAGACCTGACCT<br>GTTCGACTGGAACAGCGTCGTGTGTCAGCAGAGCGCCACACAGAGGCTGG<br>AACACGCCTTCAATATCGCCAGATACCAGCTGGGCATCGAGAAACTGCTG<br>GACCCCGAGGATGTGGACACCACCTATCCTGACAAGAAATCCATCCTCAT<br>GTACATCACCAGCCTGTTCCAGGTGCTGCCCCAGCAGGTTTCCATCGAGG<br>CCATTCAAGAGGTCGAGATGCTGCCCAGACCTCCTAAAGTGACCAAAGAG<br>GAACACTTCCAGCTGCACCACCAGATGCACTACTCTCAGCAGATCACCGT<br>GTCTCTGGCCCAGGGCTACGAGAGAACAAGCAGCCCCAAGCCTCGGTTCA<br>AGAGCTACGCCTATACACAGGCCGCCTACGTGACCACCAGCGATCCTACA<br>AGAAGCCCATTTCCTAGCCAGCATCTGGAAGCCCCTGAGGACAAGAGCTT<br>TGGCAGCAGCCTGATGGAAAGCGAAGTGAACCTGGACCGCTACCAGACAG<br>CCCTGGAAGAGGTTCTGAGCTGGCTGCTGTCTGCCGAGGATACACTGCAG<br>GCTCAGGGCGAGATCAGCAACGACGTGGAAGTGGTCAAGGACCAGTTTCA<br>CACCCACGAGGGCTACATGATGGACCTGACAGCCCACCAGGGCAGAGTGG<br>GCAATATTCTGCAGCTGGGCTCCAAGCTGATCGGCACAGGCAAGCTGAGC<br>GAGGACGAAGAGACAGAGGTGCAAGAGCAGATGAACCTGCTGAACAGCAG<br>ATGGGAGTGTCTGAGAGTGGCCAGCATGGAAAAGCAGAGCAACCTGCACC<br>GGGTGCTGATGGATCTCCAGAACCAGAAGCTGAAAGAGCTGAACGACTGG<br>CTGACCAAGACCGAGGAACGGACCCGGAAGATGGAAGAGGAACCTCTGGG<br>ACCCGACCTGGAAGATCTGAAAAGACAGGTGCAGCAGCATAAGGTGCTGC<br>AAGAGGACCTCGAACAAGAGCAAGTGCGCGTGAACAGCCTGACACACATG<br>GTGGTGGTCGTGGATGAGAGCAGCGGAGATCATGCCACAGCCGCTCTGGA<br>AGAACAGCTGAAGGTGCTGGGAGACAGATGGGCCAATATCTGCCGGTGGA<br>CCGAGGATAGATGGGTGCTGCTCCAGGACATCCTGCTGAAGTGGCAGCGG<br>CTGACAGAGGAACAGTGCCTGTTTAGCGCCTGGCTGTCCGAGAAAGAGGA<br>CGCCGTCAACAAGATCCACACCACCGGCTTCAAGGATCAGAATGAGATGC<br>TGAGCAGCCTGCAGAAACTGGCCGTGCTGAAGGCTGACCTGGAAAAGAAA<br>AAGCAGTCCATGGGCAAGCTGTACTCCCTGAAGCAGGACCTGCTGAGCAC<br>ACTGAAGAACAAGTCTGTGACCCAGAAAACCGAGGCCTGGCTGGACAACT<br>TCGCCCGGTGTTGGGATAACCTGGTGCAGAAGCTGGAAAAGTCCACCGCT<br>CAGATCTCTCAGGCCGTGACCACAACACAGCCTTCTCTGACCCAGACCAC<br>CGTGATGGAAACAGTGACCACAGTGACAACCCGCGAGCAGATCCTGGTCA<br>AGCACGCCCAAGAAGAACTGCCTCCTCCACCTCCTCAGAAGAAACGGCAG<br>ATCACAGTGGACAGCGAGATCCGGAAGAGACTGGACGTGGACATCACCGA<br>GCTGCACAGCTGGATCACCAGATCCGAAGCCGTGCTGCAGTCCCCTGAGT<br>TCGCCATCTTCAGAAAAGAGGGCAACTTCTCCGACCTGAAAGAGAAAGTC<br>AACGCCATCGAGAGAGAGAAGGCCGAGAAGTTCCGGAAGCTGCAGGACGC<br>CTCTAGATCTGCCCAGGCTCTGGTGGAACAGATGGTCAACGAAGGCGTGA<br>ACGCCGACAGCATCAAGCAGGCCTCAGAGCAGCTGAACTCCCGGTGGATC<br>GAGTTCTGTCAGCTCCTGAGCGAGAGACTGAACTGGCTGGAATACCAGAA<br>CAATATCATTGCCTTCTACAACCAGCTCCAGCAGCTCGAACAGATGACCA<br>CCACAGCCGAGAATTGGCTGAAGATCCAGCCTACCACACCTAGCGAGCCC<br>ACCGCCATTAAGAGCCAGCTGAAAATCTGCAAGGACGAAGTGAATCGGCT<br>GAGCGATCTGCAGCCCCAGATCGAAAGACTGAAAATCCAGTCTATCGCCC<br>TCAAAGAGAAAGGACAGGGCCCCATGTTCCTGGACGCCGATTTTGTGGCC<br>TTTACCAACCACTTCAAACAGGTGTTCTCCGACGTGCAGGCCCGGGAAAA<br>AGAGCTGCAGACCATCTTCGACACCCTGCCTCCAATGAGATACCAAGAGA<br>CAATGAGCGCCATCCGGACCTGGGTGCAGCAAAGCGAGACAAAGCTGAGC<br>ATCCCACAGCTGAGCGTGACCGACTACGAGATCATGGAACAGAGACTGGG<br>CGAACTGCAGGCCCTCCAGTCTAGCCTGCAAGAACAGCAGTCCGGCCTGT<br>ACTACCTGAGCACAACCGTGAAAGAGATGAGCAAGAAGGCCCCTAGCGAG<br>ATCTCCCGGAAGTACCAGAGCGAGTTCGAAGAGATCGAAGGCCGGTGGAA<br>GAAGCTGTCTAGCCAGCTGGTTGAGCACTGCCAGAAACTCGAAGAACAAA<br>TGAACAAGCTGCGCAAGATCCAGAATCACATCCAGACGCTGAAGAAATGG<br>ATGGCCGAGGTGGACGTGTTCCTGAAAGAAGAGTGGCCCGCTCTGGGCGA<br>CTCCGAGATTCTGAAGAAACAGCTCAAACAGTGCCGGCTGCTGGTGTCCG<br>ATATCCAGACAATCCAGCCAAGCCTGAACTCCGTGAATGAAGGCGGCCAG<br>AAGATCAAGAACGAGGCCGAGCCTGAGTTTGCCAGCAGACTGGAAACCGA<br>ACTGAAAGAACTCAACACCCAGTGGGACCACATGTGCCAGCAAGTGTACG<br>CCCGGAAAGAGGCCCTGAAAGGCGGACTCGAAAAGACTGTGTCTCTGCAG<br>AAAGACCTGTCTGAGATGCACGAGTGGATGACCCAGGCCGAAGAGGAATA<br>CCTGGAACGGGACTTCGAGTACAAGACCCCTGATGAGCTGCAAAAAGCCG<br>TCGAGGAAATGAAGCGGGCCAAAGAAGAGGCCCAGCAGAAAGAAGCCAAA<br>GTCAAGCTGCTGACCGAGTCCGTGAATAGCGTTATCGCTCAGGCCCCTCC<br>TGTGGCTCAAGAGGCTCTCAAGAAAGAACTGGAAACTCTGACCACCAACT<br>ACCAGTGGCTGTGCACCAGACTGAACGGCAAGTGCAAGACACTGGAAGAA<br>GTGTGGGCCTGCTGGCACGAACTGCTGTCCTATCTGGAAAAGGCCAACAA<br>GTGGCTGAACGAGGTGGAATTCAAGCTGAAAACCACCGAGAACATCCCTG<br>GCGGCGCTGAAGAGATTAGCGAGGTGCTGGACAGCCTGGAAAACCTGATG<br>AGACACAGCGAGGACAACCCCAATCAGATCAGAATCCTGGCTCAGACCCT<br>GACCGATGGCGGCGTGATGGACGAGCTGATCAACGAGGAACTCGAAACCT<br>TCAACAGCCGGTGGCGGGAACTGCACGAGGAAGCTGTTCGGAGGCAGAAG<br>TTGCTGGAACAGTCTATCCAGAGCGCACAAGAAACCGAGAAGTCCCTGCA |

-continued

| SEQ ID NO | Description | SEQ |
|---|---|---|
| | | CCTGATCCAAGAGAGCCTGACCTTCATCGACAAGCAGCTGGCCGCTTATA<br>TCGCCGACAAGGTGGACGCTGCTCAGATGCCCCAAGAGGCACAGAAGATT<br>CAGAGCGACCTGACCAGCCACGAGATTAGCCTGGAAGAAATGAAGAAGCA<br>CAACCAGGGCAAAGAGGCCGCTCAGAGAGTCCTGAGCCAGATCGATGTGG<br>CACAGAAAAAGCTCCAGGATGTGTCCATGAAGTTTCGGCTGTTTCAGAAG<br>CCCGCCAACTTCGAGCAGAGACTGCAAGAGTCCAAGATGATCCTGGACGA<br>AGTCAAAATGCATCTGCCCGCACTGGAAACAAAGTCCGTGGAACAAGAAG<br>TGGTGCAGTCCCAGCTGAACCACTGCGTGAACCTGTACAAGAGCCTGTCC<br>GAAGTGAAGTCTGAGGTGGAAATGGTCATCAAGACCGGCAGGCAGATCGT<br>CCAGAAGAAGCAGACCGAGAATCCCAAAGAACTCGACGAGAGAGTGACCG<br>CTCTGAAGCTGCACTACAATGAGCTGGGCGCCAAAGTGACCGAGCGGAAG<br>CAACAGCTTGAGAAGTGCCTGAAACTGTCTCGGAAGATGCGGAAAGAAAT<br>GAACGTGCTGACAGAGTGGCTGGCCGCCACCGATATGGAACTGACTAAGA<br>GAAGCGCCGTGGAAGGCATGCCCAGCAACCTGGATAGTGAAGTGGCCTGG<br>GGCAAAGCCACTCAGAAAGAGATTGAGAAGCAGAAGGTCCACCTGAAGTC<br>CATCACCGAAGTGGGCGAAGCCCTGAAAACCGTGCTGGGAAAGAAAGAGA<br>CACTGGTCGAGGACAAGCTGTCCCTGCTGAATTCCAACTGGATCGCCGTG<br>ACCTCCAGAGCTGAGGAATGGCTGAATCTGCTGCTTGAGTACCAGAAACA<br>CATGGAAACGTTCGACCAGAACGTCGACCACATCACAAAGTGGATCATCC<br>AGGCTGATACCCTGCTGGACGAGTCCGAGAAGAAGAAACCCCAACAAAAA<br>GAAGATGTGCTGAAGCGGCTGAAAGCCGAGCTGAATGACATCCGGCCTAA<br>GGTGGACAGCACCAGAGATCAGGCAGCCAACCTGATGGCCAACAGAGGCG<br>ACCACTGTCGGAAGCTCGTGGAACCTCAGATCAGCGAGCTTAACCACAGA<br>TTTGCCGCCATCAGCCACCGGATCAAGACAGGCAAGGCCAGCATTCCTCT<br>CAAAGAGCTTGAGCAGTTCAACAGCGACATCCAAAAGCTGCTCGAACCCC<br>TGGAAGCCGAGATCCAACAGGGCGTCAACCTCAAAGAAGAAGATTTCAAC<br>AAGGACATGAACGAGGACAATGAGGGCACCGTCAAAGAACTGCTGCAGCG<br>GGGCGATAATCTGCAGCAGCGGATTACCGATGAGCGCAAGCGGGAAGAGA<br>TCAAGATTAAGCAGCAGCTGCTGCAGACCAAGCACAACGCCCTGAAGGAC<br>CTGCGGAGCCAGAGAAGAAAGAAGGCCCTGGAAATCAGCCACCAGTGGTA<br>TCAGTACAAGCGGCAGGCCGACGACCTGCTGAAGTGCCTGGATGACATCG<br>AGAAGAAGCTGGCCTCTCTGCCCGAGCCTAGGGACGAGAGAAAGATCAAA<br>GAGATCGACCGCGAGCTGCAGAAAAAGAAAGAGGAACTGAACGCCGTCCG<br>CAGACAGGCCGAAGGACTTTCTGAAGATGGCGCCGCTATGGCCGTGGAAC<br>CCACACAGATTCAGCTGAGCAAGCGGTGGCGGGAAATCGAGAGCAAGTTC<br>GCCCAGTTCCGGCGGCTGAATTTCGCCCAGATCCACACCGTGCGGGAAGA<br>GACAATGATGGTCATGACAGAGGACATGCCCCTTGAGATCAGCTACGTGC<br>CCAGCACCTACCTGACCGAGATCACCCATGTGTCTCAGGCCCTGCTGGAA<br>GTGGAACAGCTGCTGAATGCCCCTGACCTGTGCGCCAAGGACTTCGAGGA<br>CCTGTTCAAGCAAGAGGAAAGCCTGAAGAACATCAAGGACAGCCTGCAGC<br>AGAGCAGCGGCCGGATCGATATCATCCACAGCAAGAAAACCGCCGCACTG<br>CAGAGCGCCACACCTGTGGAAAGAGTGAAGCTGCAAGAGGCCCTGAGCCA<br>GCTGGATTTCCAGTGGGAGAAAGTGAACAAGATGTACAAGGACCGGCAGG<br>GCAGATTCGACCGCAGCGTTGAAAAGTGGCGGCGGTTCCACTACGACATC<br>AAGATCTTCAACCAGTGGCTGACCGAGGCCGAGCAGTTCCTGAGAAAGAC<br>ACAGATCCCCGAGAACTGGGAGCACGCCAAGTACAAGTGGTATCTGAAAG<br>AGCTGCAGGACGGCATCGGCCAGAGACAGACAGTCGTGCGGACACTGAAT<br>GCCACCGGCGAGGAAATCATCCAGCAGTCCAGCAAGACCGACGCCAGCAT<br>CCTGCAAGAGAAGCTGGGCAGCCTGAACCTGCGGTGGCAAGAAGTGTGCA<br>AGCAGCTGAGCGACCGGAAGAAGCGGCTGGAAGAACAGAAGAATATCCTG<br>AGCGAGTTCCAGCGGGACCTGAACGAGTTCGTGCTGTGGCTCGAAGAGGC<br>CGACAATATCGCCAGCATTCCCCTGGAACCTGGCAAAGAGCAGCAGCTGA<br>AAGAAAAGCTGGAACAAGTGAAACTGCTGGTCGAGGAACTGCCCCTGAGA<br>CAGGGAATCCTGAAACAGCTGAACGAGACAGGCGGCCCTGTGCTGGTGTC<br>TGCCCCTATTTCTCCCGAGGAACAGGACAAGCTGGAAAACAAGCTGAAGC<br>AGACCAACCTGCAGTGGATCAAGGTGTCCAGAGCACTGCCTGAGAAGCAG<br>GGCGAGATCGAGGCCCAGATCAAGGACCTGGGACAGCTCGAAAAGAAGCT<br>TGAGGACCTCGAAGAACAGCTCAACCATCTGCTGCTTTGGCTGAGCCCCA<br>TCCGGAACCAGCTGGAAATCTACAACCAGCCTAATCAAGAGGGCCCCTTC<br>GACGTGAAAGAAACCGAGATTGCCGTGCAGGCCAAGCAGCCCGATGTGGA<br>AGAGATCCTGTCTAAGGGCCAGCACCTGTACAAAGAGAAGCCCGCCACAC<br>AGCCCGTGAAGCGGAAACTGGAAGATCTGAGCAGCGAGTGGAAGGCCGTG<br>AACCGGCTGCTGCAAGAACTGAGAGCCAAACAGCCTGATCTGGCCCCTGG<br>CCTGACAACAATTGGCGCCTCTCCTACACAGACCGTGACACTGGTCACAC<br>AGCCTGTGGTCACCAAAGAGACAGCCATCAGCAAACTGGAAATGCCCAGC<br>AGTCTGATGCTCGAAGTGCCCGCACTGGCCGACTTCAATAGAGCCTGGAC<br>CGAGCTGACCGACTGGCTCAGTCTGCTGGACCAAGTCATCAAGTCCCAGA<br>GAGTGATGGTCGGAGATCTTGAGGACATCAACGAGATGATCATTAAGCAG<br>AAAGCCACCATGCAGGACCTTGAGCAGAGAAGGCCCCAGCTTGAAGAACT<br>GATCACCGCCGCTCAGAACCTGAAAAACAAGACCAGCAATCAAGAAGCCC<br>GGACCATCATCACCGACCGGATCGAGAGAATCCAGAACCAGTGGGACGAA<br>GTGCAAGAGCATCTGCAGAACAGACGGCAGCAGCTCAATGAGATGCTGAA<br>GGACAGCACACAGTGGCTGGAAGCCAAAGAAGAAGCCGAGCAGGTTCTCG<br>GACAGGCCAGAGCTAAGCTGGAATCTTGGAAAGAGGGACCCTACACCGTC<br>GACGCCATCCAGAAGAAGATCACCGAGACAAAGCAGCTGGCCAAGGATCT |

-continued

| SEQ ID NO | Description | SEQ |
|---|---|---|
| | | GAGACAGTGGCAGACCAATGTGGACGTGGCCAACGACCTGGCTCTGAAGC<br>TGCTGAGAGACTACAGCGCCGACGACACCAGAAAGGTGCACATGATCACC<br>GAAAACATCAACGCCTCTTGGCGGAGCATCCACAAGCGGGTGTCAGAGAG<br>AGAAGCCGCTCTGGAAGAAACACATAGACTGCTCCAGCAGTTCCCACTCG<br>ACCTGGAAAAGTTCCTGGCCTGGCTGACAGAAGCCGAAACCACCGCTAAC<br>GTGCTCCAGGATGCCACCAGAAAAGAGCGGCTGTTGGAGGACAGCAAGGG<br>CGTCAAAGAACTCATGAAGCAGTGGCAGGATCTGCAAGGGGAGATTGAAG<br>CCCACACCGACGTGTACCACAACCTGGACGAGAACAGCCAGAAGATCCTG<br>CGGTCCCTGGAAGGCTCTGATGATGCTGTGCTGCTTCAGAGGCGGCTGGA<br>CAACATGAACTTCAAGTGGAGCGAGCTGCGGAAGAAGTCCCTGAACATCA<br>GAAGCCACCTGGAAGCCTCCAGCGACCAGTGGAAAAGACTGCACCTGTCT<br>CTCCAAGAGCTGCTCGTGTGGCTGCAGCTGAAGGATGACGAGCTGAGTAG<br>ACAGGCCCCTATCGGCGGAGATTTTCCCGCCGTGCAGAAACAGAACGACG<br>TGCACCGGGCCTTCAAGAGAGAGCTGAAAACAAAAGAACCCGTCATCATG<br>AGCACCCTGGAAACCGTGCGGATCTTTCTGACCGAGCAGCCTCTGGAAGG<br>ACTGGAAAAGCTGTACCAAGAGCCTAGAGAGCTGCCTCCTGAAGAAAGGG<br>CCCAGAACGTGACACGGCTGCTTAGAAAGCAGGCCGAGGAAGTGAACACC<br>GAATGGGAGAAGCTGAACCTCCACTCCGCCGACTGGCAGCGGAAGATCGA<br>TGAGACACTGGAACGGCTGCGGGAACTGCAAGAAGCCACAGACGAGCTGG<br>ACCTGAAACTGCGGCAGGCTGAAGTGATCAAAGGCTCCTGGCAGCCAGTG<br>GGCGATCTGCTGATCGATAGCCTGCAGGACCATCTGGAAAAAGTCAAGGC<br>CCTGCGGGGAGAGATCGCCCCTCTCAAAGAAAACGTGTCCCACGTGAACG<br>ATCTGGCCAGGCAGCTGACAACACTGGGCATCCAGCTGAGCCCTTACAAC<br>CTGTCTACCTTGGAGGACCTGAATACCCGGTGGAAGCTGCTCCAAGTGGC<br>CGTCGAGGATAGAGTGCGGCAGCTGCATGAGGCTCACAGAGATTTTGGAC<br>CCGCCAGCCAGCACTTCCTGAGCACATCTGTTCAAGGCCCCTGGGAGAGA<br>GCTATCAGCCCTAACAAGGTGCCCTACTACATCAACCACGAGACACAGAC<br>CACCTGTTGGGATCACCCCAAGATGACCGAACTGTATCAGTCCCTGGCCG<br>ACCTGAACAACGTGCGGTTTAGCGCCTACCGGACCGCCATGAAGCTGCGC<br>AGACTGCAGAAAGCTCTGTGCCTGGACCTGCTGTCTCTGAGCGCTGCTTG<br>TGATGCCCTGGACCAGCATAACCTCAAGCAGAACGACCAGCCTATGGACA<br>TCCTGCAGATCATCAACTGCCTGACCACCATCTACGACCGGCTCGAACAA<br>GAGCACAACAACCTGGTCAACGTGCCCCTGTGCGTGGACATGTGCCTGAA<br>TTGGCTGCTGAACGTGTACGACACCGGCAGAACCGGCAGGATCAGAGTGC<br>TGAGCTTCAAGACCGGCATCATCTCCCTGTGCAAGGCCCACCTTGAGGAT<br>AAGTACCGCTACCTGTTTAAGCAGGTCGCCAGCAGCACCGGCTTTTGCGA<br>CCAAAGAAGGCTGGGACTGCTGCTCCACGACAGCATTCAGATCCCTAGAC<br>AGCTGGGCGAAGTGGCCTCTTTCGGCGGCTCTAATATCGAGCCTAGCGTG<br>CGGAGCTGCTTCCAGTTCGCCAACAACAAGCCCGAGATTGAGGCCGCACT<br>GTTCCTGGACTGGATGAGACTGGAACCCCAGAGCATGGTCTGGCTGCCTG<br>TGCTGCATAGAGTGGCCGCAGCCGAAACAGCCAAGCACCAGGCCAAGTGC<br>AACATCTGCAAAGAGTGCCCCATCATCGGCTTCCGGTACAGATCCCTGAA<br>GCACTTCAACTACGATATCTGCCAGTCCTGCTTCTTCAGCGGCAGAGTGG<br>CCAAGGGCCACAAGATGCACTACCCCATGGTGGAATACTGCACCCCTACC<br>ACCTCTGGCGAGGACGTGCGGGATTTTGCCAAGGTGCTCAAGAACAAGTT<br>CCGGACCAAGCGCTACTTCGCTAAGCACCCCAGAATGGGCTACCTGCCAG<br>TGCAGACAGTGCTTGAGGGCGACAACATGGAAACCCCTGTGACTCTGATC<br>AACTTCTGGCCCGTGGATAGCGCCCCTGCTAGTTCTCCTCAGCTGTCTCA<br>CGACGATACCCACAGCAGAATCGAGCACTACGCCTCCAGACTGGCCGAGA<br>TGGAAAACAGCAACGGCAGCTACCTGAATGACAGCATCAGCCCCAACGAG<br>AGCATCGACGACGAACATCTGCTCATTCAGCACTACTGCCAGAGCCTGAA<br>TCAGGACAGCCCTCTGTCTCAGCCTAGAAGCCCTGCACAGATCCTGATCA<br>GCCTGGAAAGCGAGGAACGCGGCGAGCTGGAAAGAATCCTGGCAGACCTG<br>GAAGAGGAAAACCGGAACCTGCAGGCCGAATACGACAGACTCAAGCAGCA<br>GCACGAGCACAAGGGACTGTCTCCACTGCCTTCTCCACCTGAAATGATGC<br>CCACCTCTCCACAGAGCCCCAGAGATGCCGAGCTGATTGCCGAAGCCAAA<br>CTGCTGAGGCAGCACAAAGGCAGACTCGAAGCCAGAATGCAGATTCTCGA<br>AGATCACAACAAGCAGCTCGAATCCCAGCTGCACAGACTTAGGCAGCTGC<br>TGGAACAGCCTCAGGCAGAGGCCAAAGTGAATGGCACCACCGTGTCTAGC<br>CCTAGCACAAGCCTGCAGAGATCCGACAGCAGCCAGCCAATGCTTCTGAG<br>AGTCGTGGGCTCCCAGACCAGCGATTCTATGGGCGAAGAGGACCTGCTCA<br>GCCCTCCTCAGGATACAAGCACCGGCCTGGAAGAAGTGATGGAACAACTG<br>AACAACAGCTTCCCCAGCAGCAGAGGCAGAAACACCCCTGGCAAGCCCAT<br>GCGCGAGGACACCATGTGATAA |
| 4. | MHCK Promoter | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG |

-continued

| SEQ ID NO | Description | SEQ |
|---|---|---|
| | | CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>C |
| 5. | MHCK Promoter SF | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATC |
| 6. | MHCK7-hBGi-DMD-3-WPRE3-DTS | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>CATGCTGTGGTGGGAAGAGGTGGAGGACTGTTACGAGAGAGAGGACGTGC<br>AGAAGAAGACATTCACCAAGTGGGTGAACGCTCAGTTCAGCAAGTTCGGC<br>AAGCAGCACATCGAGAACCTGTTTAGCGATCTACAAGATGGCAGAAGACT<br>GCTGGACCTGCTGGAGGGCCTGACCGGGCAGAAGCTGCCCAAAGAAAAGG<br>GGTCTACAAGAGTGCACGCCCTGAACAACGTGAACAAGGCCCTGAGAGTG<br>CTGCAGAACAACAACGTGGACCTGGTGAACATCGGCAGCACCGACATCGT<br>GGACGGCAACCACAAGCTGACCCTGGGCCTGATCTGGAACATCATCCTGC<br>ACTGGCAAGTGAAGAACGTGATGAAGAACATCATGGCCGGCCTGCAGCAG<br>ACCAACAGCGAGAAGATCCTGCTGAGCTGGGTGAGACAGAGCACAAGAAA<br>CTACCCCCAAGTGAACGTGATCAACTTCACCACAAGCTGGAGCGACGGCC<br>TGGCCCTGAACGCCCTGATCCACAGCCACAGACCCGACCTGTTCGACTGG<br>AACAGCGTGGTGTGTCAGCAGAGCGCCACACAGAGACTGGAGCACGCCTT<br>CAACATCGCTAGATATCAGCTGGGCATCGAGAAGTTACTGGACCCCGAAG<br>ATGTGGACACCACCTACCCCGACAAGAAGAGCATCCTGATGTACATCACA<br>AGCCTGTTCCAAGTGCTGCCTCAGCAAGTGAGCATCGAGGCCATCCAAGA<br>AGTCGAGATGCTGCCTAGACCCCCCAAGGTGACCAAGGAGGAGCACTTTC<br>AGCTGCACCATCAGATGCACTACTCTCAGCAGATCACAGTCAGCTTGGCA<br>CAAGGCTACGAGAGAACAAGCAGCCCCAAGCCTAGATTCAAGAGCTACGC<br>CTACACCCAAGCCGCCTACGTGACCACAAGTGACCCCACAAGAAGCCCCT<br>TCCCTTCTCAGCACCTGGAGGCCCCCGAGGACAAGAGCTTCGGCAGCAGC<br>CTGATGGAGAGCGAGGTGAACCTGGACAGATATCAGACCGCGTTAGAAGA<br>AGTGTTGAGCTGGCTGCTGAGCGCCGAGGACACCCTGCAAGCCCAAGGCG |

-continued

| SEQ ID NO | Description | SEQ |
|---|---|---|
| | | AGATCAGCAACGATGTGGAGGTGGTGAAGGATCAGTTCCACACCCACGAG<br>GGCTACATGATGGACCTGACCGCCCACCAAGGCAGAGTGGGCAACATCCT<br>GCAGCTGGGCAGCAAGCTGATCGGCACCGGCAAGCTGAGCGAGGACGAGG<br>AAACCGAGGTTCAAGAGCAAATGAACCTGCTAAACAGCAGATGGGAGTGC<br>CTGAGAGTGGCTAGCATGGAAAAGCAGAGTAACCTGCACAGAGTGCTGAT<br>GGACCTGCAGAATCAGAAATTGAAAGAACTTAATGATTGGCTGACCAAGA<br>CCGAGGAGAGAACAAGAAAGATGGAGGAGGAGCCCCTGGGCCCCGACCTG<br>GAGGACCTGAAGAGACAAGTGCAGCAGCACAAGGTGCTGCAAGAGGACCT<br>GGAGCAAGAGCAAGTGAGAGTGAACTCTCTGACACACATGGTGGTGGTAG<br>TGGACGAGAGCAGCGGCGATCACGCTACCGCGGCGCTGGAAGAGCAGCTG<br>AAAGTGCTGGGCGACAGATGGGCCAACATCTGCAGATGGACCGAGGACAG<br>ATGGGTGCTGCTGCAAGACATCCTGCTGAAGTGGCAGAGACTGACCGAGG<br>AGCAGTGCCTGTTCAGCGCCTGGCTGAGCGAGAAGGAAGACGCTGTGAAC<br>AAGATCCACACCACCGGCTTCAAGGATCAGAACGAGATGCTGAGCTCCCT<br>CCAAAAGCTCGCAGTGCTGAAGGCCGACCTGGAAAAGAAAAAACAGTCGA<br>TGGGCAAGCTGTACAGCCTGAAGCAAGACCTGCTGAGCACCCTGAAGAAC<br>AAGAGCGTGACACAGAAGACCGAGGCCTGGCTGGACAACTTCGCTAGATG<br>CTGGGACAACCTGGTACAGAAGTTAGAGAAGTCTACCGCTCAGATCAGCC<br>AAGCCGTAACCACCACACAACCTAGCCTGACTCAGACCACCGTGATGGAA<br>ACCGTGACCACCGTGACAACCCGTGAGCAGATCCTGGTGAAGCACGCCCA<br>AGAGGAGCTGCCCCCCCCCCCCCTCAGAAGAAGAGACAGATCACCGTGG<br>ACTCAGAGATTCGCAAGAGACTGGACGTGGACATCACCGAGCTGCACAGC<br>TGGATCACAAGAAGCGAGGCCGTGCTGCAGAGCCCTGAGTTCGCGATCTT<br>TAGAAAGGAGGGCAACTTCAGCGACTTGAAGGAGAAAGTGAACGCCATCG<br>AGAGAGAGAAGGCCGAGAAGTTCAGAAAGTTGCAAGACGCCTCAAGAAGC<br>GCCCAAGCCCTGGTGGAGCAGATGGTTAACGAAGGCGTGAATGCCGACAG<br>CATCAAGCAAGCTAGCGAGCAGCTGAATAGCCGGTGGATTGAATTCTGTC<br>AGCTGCTGAGCGAGAGATTAAACTGGCTGGAGTATCAGAACAACATCATC<br>GCCTTCTACAATCAGCTGCAGCAACTAGAACAAATGACCACCACCGCCGA<br>GAACTGGCTAAAGATTCAGCCCACCACCCCTAGCGAGCCCACCGCCATCA<br>AATCTCAGCTGAAAATTTGCAAGGACGAAGTGAACAGACTGTCGGACCTG<br>CAGCCTCAAATCGAAAGACTGAAAATTCAGAGCATCGCACTTAAGGAGAA<br>GGGCCAAGGACCCATGTTCCTGGACGCCGACTTCGTGGCCTTCACCAACC<br>ACTTCAAGCAAGTGTTCAGCGACGTGCAAGCTAGAGAGAAGGAGCTGCAG<br>ACCATCTTCGACACCCTGCCCCCCATGAGATACCAAGAAACCATGAGCGC<br>CATCAGAACCTGGGTGCAGCAGAGCGAAACCAAGCTGAGCATCCCTCAGC<br>TGAGCGTGACCGACTACGAGATCATGGAGCAAAGACTGGGAGAGCTGCAA<br>GCCCTGCAGAGCAGCCTGCAAGAGCAGCAGAGCGGCCTGTACTACCTGAG<br>CACCACCGTGAAGGAGATGTCGAAGAAAGCCCCGTCGGAGATCAGCAGAA<br>AGTATCAGAGCGAGTTCGAGGAGATCGAGGGCAGATGGAAGAAGCTGAGC<br>AGCCAACTGGTGGAACACTGTCAGAAATTAGAAGAACAGATGAACAAGCT<br>GAGAAAGATTCAGAACCACATTCAGACCCTGAAGAAGTGGATGGCCGAGG<br>TGGACGTGTTCCTGAAAGAGGAGTGGCCCGCCCTGGGCGATTCCGAAATC<br>TTAAAAAAGCAGCTGAAGCAGTGCAGACTGCTGGTGTCAGATATCCAAAC<br>CATTCAACCAAGCCTGAACAGCGTGAACGAAGGCGGGCAGAAGATCAAGA<br>ACGAGGCCGAGCCCGAGTTCGCTAGCAGACTGGAAACCGAGCTGAAGGAG<br>CTGAATACACAGTGGGACCACATGTGTCAGCAAGTGTACGCTAGAAAGGA<br>AGCGCTGAAGGGCGGGCTGGAGAAGACCGTTAGCCTGCAAAAGGATCTGA<br>GCGAGATGCACGAGTGGATGACCCAAGCCGAGGAGGAGTACCTGGAGAGA<br>GACTTCGAGTACAAGACCCCCGACGAGCTGCAGAAGGCCGTCGAGGAAAT<br>GAAGAGAGCGAAGGAGGAGGCTCAGCAGAAGGAAGCCAAGGTGAAGCTGC<br>TGACTGAATCTGTCAACAGTGTGATAGCTCAAGCACCCCCCGTTGCCCAA<br>GAGGCACTAAAGAAGGAGCTGGAAACTCTGACCACCAACTATCAGTGGCT<br>GTGCACAAGACTGAACGGCAAGTGCAAGACCCTGGAGGAAGTGTGGGCCT<br>GCTGGCACGAGCTGCTGAGCTACCTGGAGAAGGCCAACAAGTGGCTGAAC<br>GAGGTGGAGTTCAAGCTGAAGACCACCGAGAACATCCCCGGCGGCGCCGA<br>GGAGATCAGCGAGGTGCTGGACAGCCTGGAGAACCTGATGAGACACAGCG<br>AGGACAACCCCAATCAGATCAGAATCCTGGCTCAGACCCTGACCGACGGC<br>GGCGTGATGGACGAGCTGATCAACGAGGAGCTGGAAACCTTTAACTCTAG<br>ATGGCGAGAACTGCACGAGGAGGCCGTGAGAAGACAGAAGCTGCTGGAGC<br>AAAGCATTCAGAGCGCCCAAGAAACCGAGAAGAGCCTGCACCTGATCCAA<br>GAGAGCCTGACCTTCATCGACAAGCAGCTGGCCGCCTACATCGCCGACAA<br>GGTGGACGCCGCTCAGATGCCACAAGAGGCTCAGAAGATTCAGTCCGATC<br>TGACAAGCCACGAGATCAGCCTGGAGGAGATGAAAAAACACAACCAAGGC<br>AAGGAGGCCGCTCAGAGAGTGCTGTCTCAGATCGACGTGGCTCAGAAGAA<br>GCTGCAAGACGTGAGCATGAAGTTCAGACTGTTTCAGAAGCCCGCCAACT<br>TCGAGCAGCGACTGCAAGAGAGCAAGATGATCCTGGACGAGGTGAAGATG<br>CACCTGCCCGCCCTGGAAACCAAGAGCGTGGAGCAAGAGGTGGTGCAGTC<br>TCAGTTGAACCACTGCGTGAACCTGTACAAGAGCCTGTCGGAGGTCAAGA<br>GTGAGGTCGAGATGGTGATCAAAACTGGGAGACAGATCGTGCAAAAAAAG<br>CAGACCGAGAACCCCAAGGAGCTGGACGAGCGTGTTACCGCCCTGAAGCT<br>GCACTACAACGAGCTGGGCGCCAAGGTGACCGAGAGAAAGCAGCAGCTGG<br>AGAAGTGCCTGAAGCTGAGCAGAAAGATGAGAAAGGAGATGAACGTGCTG<br>ACCGAGTGGCTGGCCGCCACCGACATGGAGCTGACCAAGAGAAGCGCCGT<br>GGAGGGCATGCCTAGCAACCTGGACAGCGAGGTGGCCTGGGGCAAGGCCA |

-continued

| SEQ ID NO | Description | SEQ |
|---|---|---|
| | | CACAGAAGGAGATCGAGAAGCAGAAGGTGCACCTGAAGAGCATCACCGAG<br>GTGGGCGAGGCCCTGAAGACCGTGCTGGGCAAGAAGGAAACCCTGGTGGA<br>GGACAAGCTGAGCCTGCTGAACTCGAACTGGATCGCCGTGACAAGCAGAG<br>CCGAGGAGTGGCTGAACCTGCTGTTAGAGTACCAAAAACACATGGAAACC<br>TTCGATCAGAACGTGGACCACATCACCAAGTGGATCATCCAAGCCGACAC<br>CCTGCTGGACGAAAGCGAAAAGAAGAAGCCGCAACAAAAGGAGGATGTGC<br>TGAAGAGACTGAAGGCCGAACTGAACGATATCAGACCCAAGGTGGACAGC<br>ACACGGGACCAAGCCGCCAACCTGATGGCCAACAGAGGCGACCACTGCAG<br>AAAACTGGTGGAGCCTCAGATCAGCGAGCTGAACCACAGATTCGCCGCCA<br>TCAGCCACAGAATCAAAACCGGCAAAGCGAGCATCCCCTTGAAGGAACTG<br>GAGCAATTTAACAGCGACATCCAAAAATTGCTCGAACCACTGGAGGCCGA<br>GATTCAGCAAGGCGTGAACCTGAAGGAAGAGGACTTCAACAAGGACATGA<br>ACGAGGACAACGAGGGCACCGTGAAAGAACTGCTGCAGAGAGGCGACAAC<br>CTGCAGCAGAGAATCACCGACGAGAGAAAGAGAGAGGAGATCAAGATCAA<br>GCAGCAGCTGCTGCAGACTAAGCACAACGCCCTGAAGGATCTGAGATCTC<br>AGAGGAGAAAAAAGGCTCTGGAAATTTCACATCAGTGGTATCAGTACAAG<br>AGACAAGCAGACGACCTGCTGAAGTGCCTGGACGACATCGAGAAGAAGTT<br>AGCTAGCCTGCCCGAGCCTAGAGACGAGAGAAAGATCAAGGAGATCGACA<br>GAGAGTTACAAAAGAAGAAGGAGGAGCTGAATGCGGTAAGAAGACAAGCG<br>GAAGGCCTGTCCGAGGACGGCGCAGCCATGGCCGTGGAGCCCACACAGAT<br>TCAGCTCAGCAAGAGATGGAGAGAGATCGAGAGCAAGTTCGCTCAGTTCA<br>GAAGACTGAACTTCGCTCAGATCCACACCGTGAGAGAGGAAACCATGATG<br>GTGATGACCGAGGACATGCCCCTGGAGATCTCATACGTTCCTAGCACCTA<br>CCTGACCGAGATCACCCACGTGAGCCAAGCCCTGCTGGAGGTGGAGCAGC<br>TGCTGAACGCCCCCGACCTGTGCGCCAAGGACTTCGAGGACCTGTTCAAA<br>CAAGAGGAGAGCCTGAAGAACATCAAGGACAGCCTGCAGCAAAGTAGCGG<br>CAGAATCGACATCATCCACAGCAAGAAGACCGCCGCCCTGCAGAGCGCCA<br>CCCCCGTGGAGAGAGTGAAGCTTCAAGAGGCCCTTTCGCAGCTGGATTTT<br>CAGTGGGAGAAGGTGAACAAAATGTACAAGGACAGACAAGGCAGATTCGA<br>CAGAAGCGTGGAGAAGTGGAGAAGATTCCACTACGACATCAAGATCTTCA<br>ATCAGTGGCTGACCGAGGCAGAGCAGTTCCTGAGAAAGACACAGATCCCC<br>GAGAACTGGGAGCACGCCAAGTACAAGTGGTACCTGAAGGAGCTGCAAGA<br>CGGCATCGGGCAGAGACAGACCGTGGTGAGAACCCTGAACGCCACCGGCG<br>AGGAGATCATCCAACAAAGCTCCAAAACCGACGCTAGCATCCTGCAAGAG<br>AAACTGGGCAGCCTGAACCTGAGATGGCAAGAGGTGTGCAAGCAGCTGAG<br>CGACCGCAAAAAACGGTTAGAGGAGCAGAAGAACATCCTGAGCGAGTTTC<br>AGCGGGACCTGAACGAGTTCGTGCTGTGGCTGGAGGAGGCCGATAACATC<br>GCTAGCATCCCCCTGGAGCCCGGCAAGGAGCAGCAGTTAAAAGAAAAACT<br>TGAGCAAGTGAAGCTGCTGGTGGAGGAGCTGCCCCTGAGACAAGGCATCC<br>TGAAGCAGCTGAACGAGACTGGCGGCCCCGTGCTGGTGAGCGCCCCCATC<br>AGCCCCGAGGAGCAAGACAAGCTGGAGAACAAGCTGAAGCAGACCAACCT<br>GCAGTGGATCAAGGTGAGCAGAGCCCTGCCCGAGAAGCAAGGCGAAATCG<br>AGGCCCAAATAAAGGACCTGGGGCAGCTGGAGAAGAAACTCGAAGACTTG<br>GAAGAACAACTCAACCACTTGCTGCTGTGGCTGAGCCCCATCAGAAATCA<br>GCTGGAGATCTACAATCAGCCCAACCAAGAGGGGCCATTCGACGTGAAGG<br>AAACCGAGATCGCCGTGCAAGCCAAGCAGCCCGATGTGGAGGAGATCCTG<br>AGCAAGGGGCAGCACCTGTACAAGGAGAAGCCCGCCACACAGCCCGTCAA<br>GCGTAAACTAGAGGATCTTTCCTCTGAGTGGAAGGCCGTGAACCGTCTGC<br>TACAAGAGCTGCGGGCTAAGCAACCCGACTTAGCGCCCGGCCTGACCACC<br>ATCGGTGCAAGCCCCACGCAGACCGTGACCCTGGTGACCCAACCCGTGGT<br>GACCAAGGAAACCGCCATCAGCAAGCTGGAGATGCCTAGCAGCCTGATGC<br>TGGAGGTGCCCGCCCTGGCCGACTTCAACAGAGCCTGGACCGAGCTGACC<br>GACTGGCTGAGCCTGCTGGACCAAGTGATCAAGTCTCAGAGAGTGATGGT<br>GGGCGATCTGGAGGACATCAATGAGATGATCATCAAGCAGAAGGCCACCA<br>TGCAAGACCTGGAGCAGAGAAGACCTCAGCTGGAGGAGCTGATCACCGCC<br>GCTCAGAACCTGAAAAACAAGACGAGCAACCAAGAGGCTAGAACCATCAT<br>CACCGACAGAATCGAGAGAATTCAGAATCAGTGGGACGAGGTGCAAGAGC<br>ACCTGCAGAACAGAAGACAGCAACTAAACGAAATGCTCAAGGACAGCACA<br>CAGTGGCTGGAGGCCAAGGAGGAGGCGGAGCAAGTGTTGGGCCAAGCTAG<br>AGCCAAGCTGGAGAGCTGGAAGGAGGGACCCTACACCGTGGACGCCATTC<br>AGAAGAAGATCACCGAAACCAAGCAGCTGGCCAAGGACCTGCGACAGTGG<br>CAGACCAACGTGGACGTGGCCAACGATCTTGCCCTGAAGCTGCTGCGCGA<br>CTATAGCGCCGACGACACAAGAAAGGTGCACATGATCACCGAGAACATCA<br>ACGCTAGCTGGCGTAGCATCCACAAGAGAGTGAGCGAGAGAGAGGCGGCT<br>TTGGAGGAAACCCATAGACTGCTGCAGCAGTTTCCCCTGGACCTGGAGAA<br>GTTCCTGGCCTGGCTGACCGAAGCCGAAACAACCGCCAACGTGCTGCAAG<br>ACGCCACAAGAAAGGAGAGACTGCTGGAGGACAGCAAGGGCGTGAAGGAG<br>CTGATGAAGCAGTGGCAAGACCTGCAAGGCGAGATCGAAGCGCACACCGA<br>CGTGTACCACAACCTGGACGAGAACTCTCAGAAGATCCTGAGAAGCCTGG<br>AGGGCAGCGACGACGCCGTGCTGTTACAGAGAAGGCTGGACAACATGAAC<br>TTCAAGTGGAGCGAGCTGAGAAAGAAGAGCCTGAACATCAGAAGCCACCT<br>GGAGGCTAGCAGCGATCAGTGGAAGAGACTGCACCTGAGCCTGCAAGAGC<br>TGCTGGTCTGGCTTCAGTTGAAGGACGATGAGCTGAGCAGACAAGCCCCC<br>ATCGGCGGCGACTTCCCCGCCGTGCAGAAGCAGAACGACGTGCATAGAGC<br>CTTCAAGAGAGAGCTGAAGACCAAGGAGCCCGTGATCATGAGCACCCTGG |

-continued

| SEQ ID NO | Description | SEQ |
|---|---|---|
| | | AAACGGTGAGAATCTTCCTGACCGAGCAGCCCCTGGAGGGCCTGGAGAAG<br>CTGTACCAAGAGCCTAGAGAGCTGCCCCCCGAGGAGAGAGCTCAGAACGT<br>GACAAGACTGCTGAGAAAGCAAGCCGAAGAGGTGAACACCGAGTGGGAGA<br>AGCTGAACCTGCACAGCGCCGACTGGCAGAGAAAGATCGACGAAACCCTG<br>GAGAGACTGAGAGAATTGCAAGAGGCGACCGACGAGCTGGACCTGAAGCT<br>GAGACAAGCCGAGGTCATCAAGGGCAGCTGGCAGCCCGTGGGCGATCTAT<br>TAATTGACTCTCTACAAGACCACCTGGAGAAAGTGAAGGCCCTGAGAGGC<br>GAGATCGCCCCCCTGAAGGAGAACGTGAGCCACGTGAATGATCTGGCACG<br>TCAGCTGACCACCCTGGGCATACAACTGTCCCCCTATAACCTGAGCACAC<br>TGGAGGATTTGAATACTAGATGGAAGCTGCTGCAAGTGGCCGTGGAGGAC<br>AGAGTAAGACAATTACATGAGGCCCACAGAGACTTCGGCCCCGCTTCTCA<br>GCACTTCCTGAGCACAAGCGTGCAAGGCCCCTGGGAGAGAGCCATTTCCC<br>CCAACAAGGTCCCCTACTACATCAACCACGAGACACAGACCACCTGCTGG<br>GACCACCCCAAGATGACCGAGCTGTATCAGAGCCTCGCCGATCTGAACAA<br>TGTGAGATTCAGCGCCTACAGAACCGCCATGAAGCTGAGAAGACTGCAGA<br>AGGCCCTGTGCCTGGACTTATTAAGCCTGAGCGCCGCCTGCGACGCCCTG<br>GATCAGCACAACCTGAAGCAAAACGACCAACCCATGGACATCCTGCAGAT<br>CATCAACTGCCTCACCACCATATACGACAGACTGGAACAAGAGCACAACA<br>ACCTGGTGAACGTGCCCCTGTGCGTGGACATGTGCCTGAACTGGCTGCTG<br>AACGTGTACGACACCGGCAGAACCGGCAGAATCAGAGTGCTGAGCTTCAA<br>GACCGGCATCATCAGCCTGTGCAAGGCCCACCTGGAGGACAAATACAGAT<br>ACCTTTTCAAACAAGTGGCTAGCAGCACCGGCTTCTGCGACCAAAGAAGA<br>CTGGGTCTGCTGCTGCACGACAGCATTCAGATCCCTAGACAGCTGGGCGA<br>GGTGGCTAGCTTCGGCGGCAGCAACATCGAGCCTAGCGTGAGAAGCTGCT<br>TTCAGTTCGCCAACAACAAGCCCGAGATAGAGGCAGCCCTCTTCTTAGAC<br>TGGATGAGACTGGAGCCTCAGAGCATGGTATGGCTGCCGGTCCTGCACAG<br>AGTGGCCGCCGCCGAAACCGCCAAGCACCAAGCCAAGTGCAACATCTGCA<br>AGGAGTGCCCCATCATCGGCTTCAGATACAGAAGCCTGAAGCACTTCAAC<br>TACGACATCTGTCAGAGCTGCTTCTTCAGCGGCAGAGTGGCCAAGGGCCA<br>CAAGATGCACTACCCCATGGTGGAGTACTGCACCCCCACCACAAGCGGCG<br>AGGACGTGAGAGACTTCGCCAAGGTGTTGAAGAATAAGTTTAGAACCAAG<br>AGATACTTCGCCAAGCACCCTAGAATGGGCTACCTGCCCGTGCAGACCGT<br>GCTGGAGGGCGACAACATGGAAACCCCCGTGACCCTGATCAACTTCTGGC<br>CCGTGGACAGCGCCCCCGCTAGCAGCCCTCAGCTGAGCCACGACGACACC<br>CACAGCAGAATCGAGCACTACGCTAGCAGACTGGCCGAGATGGAGAACAG<br>CAACGGCAGCTACCTGAACGACAGCATCAGCCCGAATGAGAGCATCGACG<br>ACGAGCACCTGCTGATTCAGCACTACTGTCAGAGCCTGAACCAAGACAGC<br>CCCCTGTCTCAGCCTAGAAGCCCCGCTCAGATCCTGATCAGCCTGGAGAG<br>CGAGGAGAGAGGCGAGCTGGAGAGAATCCTAGCAGATCTGGAGGAAGAGA<br>ACAGAAACCTGCAAGCCGAGTATGACCGACTGAAACAGCAACATGAGCAC<br>AAAGGCCTGAGCCCACTGCCCTCCCCCCCCGAGATGATGCCCACAAGCCC<br>TCAGAGCCCTAGAGACGCCGAGCTGATCGCTGAAGCGAAGTTACTTAGAC<br>AACACAAGGGCAGACTGGAGGCTAGAATGCAGATCCTGGAGGACCACAAC<br>AAGCAGCTGGAGTCTCAGCTGCACAGACTGAGGCAGCTGCTGGAACAGCC<br>CCAAGCCGAGGCCAAAGTGAACGGCACCACCGTGAGCAGTCCTAGCACAA<br>GCCTGCAGAGAAGCGACAGCTCTCAGCCCATGCTGCTGAGAGTGGTGGGC<br>TCTCAGACAAGCGACAGCATGGGCGAGGAGGATCTGCTGAGTCCGCCCCA<br>AGACACAAGCACCGGCCTGGAAGAGGTGATGGAGCAACTGAACAATAGCT<br>TCCCTAGCAGCAGAGGCAGAAACACCCCCGGCAAGCCCATGAGAGAGGAC<br>ACCATGTGATGACTCGAGAATCAACCTCTGGATTACAAAATTTGTGAAAG<br>ATTGACTGGTATTCTTAACTATGTTGCTCCTTTTACGCTATGTGGATACG<br>CTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTG<br>GCCCGTTGTCAGGCAACGTGGCGTGGTGTGCACTGTGTTTGCTGACGCAA<br>CCCCCACTGGTTGGGGCATTGCCACCACCTGTCAGCTCCTTTCCGGGACT<br>TTCGCTTTCCCCCTCCCTATTGCCACGGCGGAACTCATCGCCGCCTGCCT<br>TGCCCGCTGCTGGACAGGGGCTCGGCTGTTGGGCACTGACAATTCCGTGG<br>GGTGTGCCTTCTAGTTGCCAGCCATCTGTTGTTTGCCCCTCCCCCGTGCC<br>TTCCTTGACCCTGGAAGGTGCCACTCCCACTGTCCTTTCCTAATAAAATG<br>AGGAAATTGCATCGCATTGTCTGAGTAGGTGTCATTCTATTCTGGGGGGT<br>GGGGTGGGGCAGGACAGCAAGGGGGAGGATTGGGAAGACAATAGCAGGCA<br>TGCTGGGGATGCGGTGGGCTCTATGGAAGATGTCTACTGAGCTGTGCGA<br>TCCCTGCTGGGGACTTTCCGCTGGGGACTTTCCGCTGGGGACTTTCCGCC<br>TTCAGCTAAGGAAGCTACCAATATTTAGAGGTACATTTTGTTCTAGAACA<br>AAATGTACCGGTACATTTTGTTCTGGTACATTTTGTTCT |
| 7. | MHCK7-hBGi-DMD-4-WPRE3-DTS | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT |

-continued

| SEQ ID NO | Description | SEQ |
|---|---|---|
| | | GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>CATGCTTTGGTGGGAAGAAGTCGAGGACTGCTACGAGCGCGAGGACGTGC<br>AGAAGAAAACCTTCACCAAATGGGTCAACGCCCAGTTCAGCAAGTTCGGC<br>AAGCAGCACATCGAGAACCTGTTCAGCGACCTGCAGGATGGCAGAAGGCT<br>GCTGGATCTGCTGGAAGGCCTGACAGGACAGAAGCTGCCCAAAGAGAAGG<br>GCAGCACAAGAGTGCACGCCCTGAACAACGTGAACAAGGCCCTGAGAGTG<br>CTGCAGAACAACAACGTGGACCTGGTCAACATCGGCAGCACCGACATCGT<br>GGACGGCAACCACAAACTGACCCTGGGCCTGATCTGGAACATCATCCTGC<br>ACTGGCAAGTGAAGAACGTGATGAAGAACATCATGGCCGGCCTGCAGCAG<br>ACCAACAGCGAGAAGATTCTGCTGAGCTGGGTCCGACAGAGCACCCGGAA<br>TTACCCTCAAGTGAACGTGATCAACTTCACCACCTCTTGGAGCGACGGAC<br>TGGCCCTGAATGCCCTGATCCACAGCCACAGACCTGACCTGTTCGACTGG<br>AACAGCGTCGTGTGTCAGCAGAGCGCCACACAGAGGCTGGAACACGCCTT<br>CAATATCGCCAGATACCAGCTGGGCATCGAGAAACTGCTGGACCCCGAGG<br>ATGTGGACACCACCTATCCTGACAAGAAATCCATCCTCATGTACATCACC<br>AGCCTGTTCCAGGTGCTGCCCCAGCAGGTTTCCATCGAGGCCATTCAAGA<br>GGTCGAGATGCTGCCCAGACCTCCTAAAGTGACCAAAGAGGAACACTTCC<br>AGCTGCACCACCAGATGCACTACTCTCAGCAGATCACCGTGTCTCTGGCC<br>CAGGGCTACGAGAGAACAAGCAGCCCCAAGCCTCGGTTCAAGAGCTACGC<br>CTATACACAGGCCGCCTACGTGACCACCAGCGATCCTACAAGAAGCCCAT<br>TTCCTAGCCAGCATCTGGAAGCCCCTGAGGACAAGAGCTTTGGCAGCAGC<br>CTGATGGAAAGCGAAGTGAACCTGGACCGCTACCAGACAGCCCTGGAAGA<br>GGTTCTGAGCTGGCTGCTGTCTGCCGAGGATACACTGCAGGCTCAGGGCG<br>AGATCAGCAACGACGTGGAAGTGGTCAAGGACCAGTTTCACACCCACGAG<br>GGCTACATGATGGACCTGACAGCCCACCAGGGCAGAGTGGGCAATATTCT<br>GCAGCTGGGCTCCAAGCTGATCGGCACAGGCAAGCTGAGCGAGGACGAAG<br>AGACAGAGGTGCAAGAGCAGATGAACCTGCTGAACAGCAGATGGGAGTGT<br>CTGAGAGTGGCCAGCATGGAAAAGCAGAGCAACCTGCACCGGGTGCTGAT<br>GGATCTCCAGAACCAGAAGCTGAAAGAGCTGAACGACTGGCTGACCAAGA<br>CCGAGGAACGGACCCGGAAGATGGAAGAGGAACCTCTGGGACCCGACCTG<br>GAAGATCTGAAAAGACAGGTGCAGCAGCATAAGGTGCTGCAAGAGGACCT<br>CGAACAAGAGCAAGTGCGCGTGAACAGCCTGACACACATGGTGGTGGTCG<br>TGGATGAGAGCAGCGGAGATCATGCCACAGCCGCTCTGGAAGAACAGCTG<br>AAGGTGCTGGGAGACAGATGGGCCAATATCTGCCGGTGGACCGAGGATAG<br>ATGGGTGCTGCTCCAGGACATCCTGCTGAAGTGGCAGCGGCTGACAGAGG<br>AACAGTGCCTGTTTAGCGCCTGGCTGTCCGAGAAAGAGGACGCCGTCAAC<br>AAGATCCACACCACCGGCTTCAAGGATCAGAATGAGATGCTGAGCAGCCT<br>GCAGAAACTGGCCGTGCTGAAGGCTGACCTGGAAAAGAAAAAGCAGTCCA<br>TGGGCAAGCTGTACTCCCTGAAGCAGGACCTGCTGAGCACACTGAAGAAC<br>AAGTCTGTGACCCAGAAAACCGAGGCCTGGCTGGACAACTTCGCCCGGTG<br>TTGGGATAACCTGGTGCAGAAGCTGGAAAAGTCCACCGCTCAGATCTCTC<br>AGGCCGTGACCACAACACAGCCTTCTCTGACCCAGACCACCGTGATGGAA<br>ACAGTGACCACAGTGACAACCCGCGAGCAGATCCTGGTCAAGCACGCCCA<br>AGAAGAACTGCCTCCTCCACCTCCTCAGAAGAAACGGCAGATCACAGTGG<br>ACAGCGAGATCCGGAAGAGACTGGACGTGGACATCACCGAGCTGCACAGC<br>TGGATCACCAGATCCGAAGCCGTGCTGCAGTCCCCTGAGTTCGCCATCTT<br>CAGAAAAGAGGGCAACTTCTCCGACCTGAAAGAGAAAGTCAACGCCATCG<br>AGAGAGAGAAGGCCGAGAAGTTCCGGAAGCTGCAGGACGCCTCTAGATCT<br>GCCCAGGCTCTGGTGGAACAGATGGTCAACGAAGGCGTGAACGCCGACAG<br>CATCAAGCAGGCCTCAGAGCAGCTGAACTCCCGGTGGATCGAGTTCTGTC<br>AGCTCCTGAGCGAGAGACTGAACTGGCTGGAATACCAGAACAATATCATT<br>GCCTTCTACAACCAGCTCCAGCAGCTCGAACAGATGACCACCACAGCCGA<br>GAATTGGCTGAAGATCCAGCCTACCACACCTAGCGAGCCCACCGCCATTA<br>AGAGCCAGCTGAAAATCTGCAAGGACGAAGTGAATCGGCTGAGCGATCTG<br>CAGCCCCAGATCGAAAGACTGAAAATCCAGTCTATCGCCCTCAAAGAGAA<br>AGGACAGGGCCCCATGTTCCTGGACGCCGATTTTGTGGCCTTTACCAACC<br>ACTTCAAACAGGTGTTCTCCGACGTGCAGGCCCGGGAAAAAGAGCTGCAG<br>ACCATCTTCGACACCCTGCCTCCAATGAGATACCAAGAGACAATGAGCGC<br>CATCCGGACCTGGGTGCAGCAAAGCGAGACAAAGCTGAGCATCCCACAGC<br>TGAGCGTGACCGACTACGAGATCATGGAACAGAGACTGGGCGAACTGCAG<br>GCCCTCCAGTCTAGCCTGCAAGAACAGCAGTCCGGCCTGTACTACCTGAG<br>CACAACCGTGAAAGAGATGAGCAAGAAGGCCCCTAGCGAGATCTCCCGGA<br>AGTACCAGAGCGAGTTCGAAGAGATCGAAGGCCGGTGGAAGAAGCTGTCT<br>AGCCAGCTGGTTGAGCACTGCCAGAAACTCGAAGAACAAATGAACAAGCT |

-continued

| SEQ ID NO | Description | SEQ |
|---|---|---|
| | | GCGCAAGATCCAGAATCACATCCAGACGCTGAAGAAATGGATGGCCGAGG |
| | | TGGACGTGTTCCTGAAAGAAGAGTGGCCCGCTCTGGGCGACTCCGAGATT |
| | | CTGAAGAAACAGCTCAAACAGTGCCGGCTGCTGGTGTCCGATATCCAGAC |
| | | AATCCAGCCAAGCCTGAACTCCGTGAATGAAGGCGGCCAGAAGATCAAGA |
| | | ACGAGGCCGAGCCTGAGTTTGCCAGCAGACTGGAAACCGAACTGAAAGAA |
| | | CTCAACACCCAGTGGGACCACATGTGCCAGCAAGTGTACGCCCGGAAAGA |
| | | GGCCCTGAAAGGCGGACTCGAAAAGACTGTGTCTCTGCAGAAAGACCTGT |
| | | CTGAGATGCACGAGTGGATGACCCAGGCCGAAGAGGAATACCTGGAACGG |
| | | GACTTCGAGTACAAGACCCCTGATGAGCTGCAAAAAGCCGTCGAGGAAAT |
| | | GAAGCGGGCCAAAGAAGAGGCCCAGCAGAAAGAAGCCAAAGTCAAGCTGC |
| | | TGACCGAGTCCGTGAATAGCGTTATCGCTCAGGCCCCTCCTGTGGCTCAA |
| | | GAGGCTCTCAAGAAAGAACTGGAAACTCTGACCACCAACTACCAGTGGCT |
| | | GTGCACCAGACTGAACGGCAAGTGCAAGACACTGGAAGAAGTGTGGGCCT |
| | | GCTGGCACGAACTGCTGTCCTATCTGGAAAAGGCCAACAAGTGGCTGAAC |
| | | GAGGTGGAATTCAAGCTGAAAACCACCGAGAACATCCCTGGCGGCGCTGA |
| | | AGAGATTAGCGAGGTGCTGGACAGCCTGGAAAACCTGATGAGACACAGCG |
| | | AGGACAACCCCAATCAGATCAGAATCCTGGCTCAGACCCTGACCGATGGC |
| | | GGCGTGATGGACGAGCTGATCAACGAGGAACTCGAAACCTTCAACAGCCG |
| | | GTGGCGGGAACTGCACGAGGAAGCTGTTCGGAGGCAGAAGTTGCTGGAAC |
| | | AGTCTATCCAGAGCGCACAAGAAACCGAGAAGTCCCTGCACCTGATCCAA |
| | | GAGAGCCTGACCTTCATCGACAAGCAGCTGGCCGCTTATATCGCCGACAA |
| | | GGTGGACGCTGCTCAGATGCCCCAAGAGGCACAGAAGATTCAGAGCGACC |
| | | TGACCAGCCACGAGATTAGCCTGGAAGAAATGAAGAAGCACAACCAGGGC |
| | | AAAGAGGCCGCTCAGAGAGTCCTGAGCCAGATCGATGTGGCACAGAAAAA |
| | | GCTCCAGGATGTGTCCATGAAGTTTCGGCTGTTTCAGAAGCCCGCCAACT |
| | | TCGAGCAGAGACTGCAAGAGTCCAAGATGATCCTGGACGAAGTCAAAATG |
| | | CATCTGCCCGCACTGGAAACAAAGTCCGTGGAACAAGAAGTGGTGCAGTC |
| | | CCAGCTGAACCACTGCGTGAACCTGTACAAGAGCCTGTCCGAAGTGAAGT |
| | | CTGAGGTGGAAATGGTCATCAAGACCGGCAGGCAGATCGTCCAGAAGAAG |
| | | CAGACCGAGAATCCCAAAGAACTCGACGAGAGAGTGACCGCTCTGAAGCT |
| | | GCACTACAATGAGCTGGGCGCCAAAGTGACCGAGCGGAAGCAACAGCTTG |
| | | AGAAGTGCCTGAAACTGTCTCGGAAGATGCGGAAAGAAATGAACGTGCTG |
| | | ACAGAGTGGCTGGCCGCCACCGATATGGAACTGACTAAGAGAAGCGCCGT |
| | | GGAAGGCATGCCCAGCAACCTGGATAGTGAAGTGGCCTGGGGCAAAGCCA |
| | | CTCAGAAAGAGATTGAGAAGCAGAAGGTCCACCTGAAGTCCATCACCGAA |
| | | GTGGGCGAAGCCCTGAAAACCGTGCTGGGAAAGAAAGAGACACTGGTCGA |
| | | GGACAAGCTGTCCCTGCTGAATTCCAACTGGATCGCCGTGACCTCCAGAG |
| | | CTGAGGAATGGCTGAATCTGCTGCTTGAGTACCAGAAACACATGGAAACG |
| | | TTCGACCAGAACGTCGACCACATCACAAAGTGGATCATCCAGGCTGATAC |
| | | CCTGCTGGACGAGTCCGAGAAGAAGAAACCCCAACAAAAAGAAGATGTGC |
| | | TGAAGCGGCTGAAAGCCGAGCTGAATGACATCCGGCCTAAGGTGGACAGC |
| | | ACCAGAGATCAGGCAGCCAACCTGATGGCCAACAGAGGCGACCACTGTCG |
| | | GAAGCTCGTGGAACCTCAGATCAGCGAGCTTAACCACAGATTTGCCGCCA |
| | | TCAGCCACCGGATCAAGACAGGCAAGGCCAGCATTCCTCTCAAAGAGCTT |
| | | GAGCAGTTCAACAGCGACATCCAAAAGCTGCTCGAACCCCTGGAAGCCGA |
| | | GATCCAACAGGGCGTCAACCTCAAAGAAGAAGATTTCAACAAGGACATGA |
| | | ACGAGGACAATGAGGGCACCGTCAAAGAACTGCTGCAGCGGGGCGATAAT |
| | | CTGCAGCAGCGGATTACCGATGAGCGCAAGCGGGAAGAGATCAAGATTAA |
| | | GCAGCAGCTGCTGCAGACCAAGCACAACGCCCTGAAGGACCTGCGGAGCC |
| | | AGAGAAGAAAGAAGGCCCTGGAAATCAGCCACCAGTGGTATCAGTACAAG |
| | | CGGCAGGCCGACGACCTGCTGAAGTGCCTGGATGACATCGAGAAGAAGCT |
| | | GGCCTCTCTGCCCGAGCCTAGGGACGAGAGAAAGATCAAAGAGATCGACC |
| | | GCGAGCTGCAGAAAAAGAAAGAGGAACTGAACGCCGTCCGCAGACAGGCC |
| | | GAAGGACTTTCTGAAGATGGCGCCGCTATGGCCGTGGAACCCACACAGAT |
| | | TCAGCTGAGCAAGCGGTGGCGGGAAATCGAGAGCAAGTTCGCCCAGTTCC |
| | | GGCGGCTGAATTTCGCCCAGATCCACACCGTGCGGGAAGAGACAATGATG |
| | | GTCATGACAGAGGACATGCCCCTTGAGATCAGCTACGTGCCCAGCACCTA |
| | | CCTGACCGAGATCACCCATGTGTCTCAGGCCCTGCTGGAAGTGGAACAGC |
| | | TGCTGAATGCCCCTGACCTGTGCGCCAAGGACTTCGAGGACCTGTTCAAG |
| | | CAAGAGGAAAGCCTGAAGAACATCAAGGACAGCCTGCAGCAGAGCAGCGG |
| | | CCGGATCGATATCATCCACAGCAAGAAAACCGCCGCACTGCAGAGCGCCA |
| | | CACCTGTGGAAAGAGTGAAGCTGCAAGAGGCCCTGAGCCAGCTGGATTTC |
| | | CAGTGGGAGAAAGTGAACAAGATGTACAAGGACCGGCAGGGCAGATTCGA |
| | | CCGCAGCGTTGAAAAGTGGCGGCGGTTCCACTACGACATCAAGATCTTCA |
| | | ACCAGTGGCTGACCGAGGCCGAGCAGTTCCTGAGAAAGACACAGATCCCC |
| | | GAGAACTGGGAGCACGCCAAGTACAAGTGGTATCTGAAAGAGCTGCAGGA |
| | | CGGCATCGGCCAGAGACAGACAGTCGTGCGGACACTGAATGCCACCGGCG |
| | | AGGAAATCATCCAGCAGTCCAGCAAGACCGACGCCAGCATCCTGCAAGAG |
| | | AAGCTGGGCAGCCTGAACCTGCGGTGGCAAGAAGTGTGCAAGCAGCTGAG |
| | | CGACCGGAAGAAGCGGCTGGAAGAACAGAAGAATATCCTGAGCGAGTTCC |
| | | AGCGGGACCTGAACGAGTTCGTGCTGTGGCTCGAAGAGGCCGACAATATC |
| | | GCCAGCATTCCCCTGGAACCTGGCAAAGAGCAGCAGCTGAAAGAAAAGCT |
| | | GGAACAAGTGAAACTGCTGGTCGAGGAACTGCCCCTGAGACAGGGAATCC |
| | | TGAAACAGCTGAACGAGACAGGCGGCCCTGTGCTGGTGTCTGCCCCTATT |
| | | TCTCCCGAGGAACAGGACAAGCTGGAAAACAAGCTGAAGCAGACCAACCT |

-continued

| SEQ ID NO | Description | SEQ |
|---|---|---|
| | | GCAGTGGATCAAGGTGTCCAGAGCACTGCCTGAGAAGCAGGGCGAGATCG<br>AGGCCCAGATCAAGGACCTGGGACAGCTCGAAAAGAAGCTTGAGGACCTC<br>GAAGAACAGCTCAACCATCTGCTGCTTTGGCTGAGCCCCATCCGGAACCA<br>GCTGGAAATCTACAACCAGCCTAATCAAGAGGGCCCCTTCGACGTGAAAG<br>AAACCGAGATTGCCGTGCAGGCCAAGCAGCCCGATGTGGAAGAGATCCTG<br>TCTAAGGGCCAGCACCTGTACAAAGAGAAGCCCGCCACACAGCCCGTGAA<br>GCGGAAACTGGAAGATCTGAGCAGCGAGTGGAAGGCCGTGAACCGGCTGC<br>TGCAAGAACTGAGAGCCAAACAGCCTGATCTGGCCCCTGGCCTGACAACA<br>ATTGGCGCCTCTCCTACACAGACCGTGACACTGGTCACACAGCCTGTGGT<br>CACCAAAGAGACAGCCATCAGCAAACTGGAAATGCCCAGCAGTCTGATGC<br>TCGAAGTGCCCGCACTGGCCGACTTCAATAGAGCCTGGACCGAGCTGACC<br>GACTGGCTCAGTCTGCTGGACCAAGTCATCAAGTCCCAGAGAGTGATGGT<br>CGGAGATCTTGAGGACATCAACGAGATGATCATTAAGCAGAAAGCCACCA<br>TGCAGGACCTTGAGCAGAGAAGGCCCCAGCTTGAAGAACTGATCACCGCC<br>GCTCAGAACCTGAAAAACAAGACCAGCAATCAAGAAGCCCGGACCATCAT<br>CACCGACCGGATCGAGAGAATCCAGAACCAGTGGGACGAAGTGCAAGAGC<br>ATCTGCAGAACAGACGGCAGCAGCTCAATGAGATGCTGAAGGACAGCACA<br>CAGTGGCTGGAAGCCAAAGAAGAAGCCGAGCAGGTTCTCGGACAGGCCAG<br>AGCTAAGCTGGAATCTTGGAAAGAGGGACCCTACACCGTCGACGCCATCC<br>AGAAGAAGATCACCGAGACAAAGCAGCTGGCCAAGGATCTGAGACAGTGG<br>CAGACCAATGTGGACGTGGCCAACGACCTGGCTCTGAAGCTGCTGAGAGA<br>CTACAGCGCCGACGACACCAGAAAGGTGCACATGATCACCGAAAACATCA<br>ACGCCTCTTGGCGGAGCATCCACAAGCGGGTGTCAGAGAGAGAAGCCGCT<br>CTGGAAGAAACACATAGACTGCTCCAGCAGTTCCCACTCGACCTGGAAAA<br>GTTCCTGGCCTGGCTGACAGAAGCCGAAACCACCGCTAACGTGCTCCAGG<br>ATGCCACCAGAAAAGAGCGGCTGTTGGAGGACAGCAAGGGCGTCAAAGAA<br>CTCATGAAGCAGTGGCAGGATCTGCAAGGGGAGATTGAAGCCCACACCGA<br>CGTGTACCACAACCTGGACGAGAACAGCCAGAAGATCCTGCGGTCCCTGG<br>AAGGCTCTGATGATGCTGTGCTGCTTCAGAGGCGGCTGGACAACATGAAC<br>TTCAAGTGGAGCGAGCTGCGGAAGAAGTCCCTGAACATCAGAAGCCACCT<br>GGAAGCCTCCAGCGACCAGTGGAAAAGACTGCACCTGTCTCTCCAAGAGC<br>TGCTCGTGTGGCTGCAGCTGAAGGATGACGAGCTGAGTAGACAGGCCCCT<br>ATCGGCGGAGATTTTCCCGCCGTGCAGAAACAGAACGACGTGCACCGGGC<br>CTTCAAGAGAGAGCTGAAAACAAAAGAACCCGTCATCATGAGCACCCTGG<br>AAACCGTGCGGATCTTTCTGACCGAGCAGCCTCTGGAAGGACTGGAAAAG<br>CTGTACCAAGAGCCTAGAGAGCTGCCTCCTGAAGAAAGGGCCCAGAACGT<br>GACACGGCTGCTTAGAAAGCAGGCCGAGGAAGTGAACACCGAATGGGAGA<br>AGCTGAACCTCCACTCCGCCGACTGGCAGCGGAAGATCGATGAGACACTG<br>GAACGGCTGCGGGAACTGCAAGAAGCCACAGACGAGCTGGACCTGAAACT<br>GCGGCAGGCTGAAGTGATCAAAGGCTCCTGGCAGCCAGTGGGCGATCTGC<br>TGATCGATAGCCTGCAGGACCATCTGGAAAAAGTCAAGGCCCTGCGGGGA<br>GAGATCGCCCCTCTCAAAGAAAACGTGTCCCACGTGAACGATCTGGCCAG<br>GCAGCTGACAACACTGGGCATCCAGCTGAGCCCTTACAACCTGTCTACCT<br>TGGAGGACCTGAATACCCGGTGGAAGCTGCTCCAAGTGGCCGTCGAGGAT<br>AGAGTGCGGCAGCTGCATGAGGCTCACAGAGATTTTGGACCCGCCAGCCA<br>GCACTTCCTGAGCACATCTGTTCAAGGCCCCTGGGAGAGAGCTATCAGCC<br>CTAACAAGGTGCCCTACTACATCAACCACGAGACACAGACCACCTGTTGG<br>GATCACCCCAAGATGACCGAACTGTATCAGTCCCTGGCCGACCTGAACAA<br>CGTGCGGTTTAGCGCCTACCGGACCGCCATGAAGCTGCGCAGACTGCAGA<br>AAGCTCTGTGCCTGGACCTGCTGTCTCTGAGCGCTGCTTGTGATGCCCTG<br>GACCAGCATAACCTCAAGCAGAACGACCAGCCTATGGACATCCTGCAGAT<br>CATCAACTGCCTGACCACCATCTACGACCGGCTCGAACAAGAGCACAACA<br>ACCTGGTCAACGTGCCCCTGTGCGTGGACATGTGCCTGAATTGGCTGCTG<br>AACGTGTACGACACCGGCAGAACCGGCAGGATCAGAGTGCTGAGCTTCAA<br>GACCGGCATCATCTCCCTGTGCAAGGCCCACCTTGAGGATAAGTACCGCT<br>ACCTGTTTAAGCAGGTCGCCAGCAGCACCGGCTTTTGCGACCAAAGAAGG<br>CTGGGACTGCTGCTCCACGACAGCATTCAGATCCCTAGACAGCTGGGCGA<br>AGTGGCCTCTTTCGGCGGCTCTAATATCGAGCCTAGCGTGCGGAGCTGCT<br>TCCAGTTCGCCAACAACAAGCCCGAGATTGAGGCCGCACTGTTCCTGGAC<br>TGGATGAGACTGGAACCCCAGAGCATGGTCTGGCTGCCTGTGCTGCATAG<br>AGTGGCCGCAGCCGAAACAGCCAAGCACCAGGCCAAGTGCAACATCTGCA<br>AAGAGTGCCCCATCATCGGCTTCCGGTACAGATCCCTGAAGCACTTCAAC<br>TACGATATCTGCCAGTCCTGCTTCTTCAGCGGCAGAGTGGCCAAGGGCCA<br>CAAGATGCACTACCCCATGGTGGAATACTGCACCCCTACCACCTCTGGCG<br>AGGACGTGCGGGATTTTGCCAAGGTGCTCAAGAACAAGTTCCGGACCAAG<br>CGCTACTTCGCTAAGCACCCCAGAATGGGCTACCTGCCAGTGCAGACAGT<br>GCTTGAGGGCGACAACATGGAAACCCCTGTGACTCTGATCAACTTCTGGC<br>CCGTGGATAGCGCCCCTGCTAGTTCTCCTCAGCTGTCTCACGACGATACC<br>CACAGCAGAATCGAGCACTACGCCTCCAGACTGGCCGAGATGGAAAACAG<br>CAACGGCAGCTACCTGAATGACAGCATCAGCCCCAACGAGAGCATCGACG<br>ACGAACATCTGCTCATTCAGCACTACTGCCAGAGCCTGAATCAGGACAGC<br>CCTCTGTCTCAGCCTAGAAGCCCTGCACAGATCCTGATCAGCCTGGAAAG<br>CGAGGAACGCGGCGAGCTGGAAAGAATCCTGGCAGACCTGGAAGAGGAAA<br>ACCGGAACCTGCAGGCCGAATACGACAGACTCAAGCAGCAGCACGAGCAC<br>AAGGGACTGTCTCCACTGCCTTCTCCACCTGAAATGATGCCCACCTCTCC |

-continued

| SEQ ID NO | Description | SEQ |
|---|---|---|
| | | ACAGAGCCCCAGAGATGCCGAGCTGATTGCCGAAGCCAAACTGCTGAGGC<br>AGCACAAAGGCAGACTCGAAGCCAGAATGCAGATTCTCGAAGATCACAAC<br>AAGCAGCTCGAATCCCAGCTGCACAGACTTAGGCAGCTGCTGGAACAGCC<br>TCAGGCAGAGGCCAAAGTGAATGGCACCACCGTGTCTAGCCCTAGCACAA<br>GCCTGCAGAGATCCGACAGCAGCCAGCCAATGCTTCTGAGAGTCGTGGGC<br>TCCCAGACCAGCGATTCTATGGGCGAAGAGGACCTGCTCAGCCCTCCTCA<br>GGATACAAGCACCGGCCTGGAAGAAGTGATGGAACAACTGAACAACAGCT<br>TCCCCAGCAGCAGAGGCAGAAACACCCCTGGCAAGCCCATGCGCGAGGAC<br>ACCATGTGATAACTCGAGAATCAACCTCTGGATTACAAAATTTGTGAAAG<br>ATTGACTGGTATTCTTAACTATGTTGCTCCTTTTACGCTATGTGGATACG<br>CTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTG<br>GCCCGTTGTCAGGCAACGTGGCGTGGTGTGCACTGTGTTTGCTGACGCAA<br>CCCCCACTGGTTGGGGCATTGCCACCACCTGTCAGCTCCTTTCCGGGACT<br>TTCGCTTTCCCCCTCCCTATTGCCACGGCGGAACTCATCGCCGCCTGCCT<br>TGCCCGCTGCTGGACAGGGGCTCGGCTGTTGGGCACTGACAATTCCGTGG<br>GGTGTGCCTTCTAGTTGCCAGCCATCTGTTGTTTGCCCCTCCCCCGTGCC<br>TTCCTTGACCCTGGAAGGTGCCACTCCCACTGTCCTTTCCTAATAAAATG<br>AGGAAATTGCATCGCATTGTCTGAGTAGGTGTCATTCTATTCTGGGGGGT<br>GGGGTGGGGCAGGACAGCAAGGGGGAGGATTGGGAAGACAATAGCAGGCA<br>TGCTGGGGATGCGGTGGGCTCTATGGGAAGATGTCTACTGAGCTGTGCGA<br>TCCCTGCTGGGGACTTTCCGCTGGGGACTTTCCGCTGGGGACTTTCCGCC<br>TTCAGCTAAGGAAGCTACCAATATTTAGAGGTACATTTTGTTCTAGAACA<br>AAATGTACCGGTACATTTTGTTCTGGTACATTTTGTTCT |
| 8. | WPRE3 | AATCAACCTCTGGATTACAAAATTTGTGAAAGATTGACTGGTATTCTTAA<br>CTATGTTGCTCCTTTTACGCTATGTGGATACGCTGCTTTAATGCCTTTGT<br>ATCATGCTATTGCTTCCCGTATGGCTTTCATTTTCTCCTCCTTGTATAAA<br>TCCTGGTTGCTGTCTCTTTATGAGGAGTTGTGGCCCGTTGTCAGGCAACG<br>TGGCGTGGTGTGCACTGTGTTTGCTGACGCAACCCCCACTGGTTGGGGCA<br>TTGCCACCACCTGTCAGCTCCTTTCCGGGACTTTCGCTTTCCCCCTCCCT<br>ATTGCCACGGCGGAACTCATCGCCGCCTGCCTTGCCCGCTGCTGGACAGG<br>GGCTCGGCTGTTGGGCACTGACAATTCCGTGG |
| 9. | PolyA | TGTGCCTTCTAGTTGCCAGCCATCTGTTGTTTGCCCCTCCCCCGTGCCTT<br>CCTTGACCCTGGAAGGTGCCACTCCCACTGTCCTTTCCTAATAAAATGAG<br>GAAATTGCATCGCATTGTCTGAGTAGGTGTCATTCTATTCTGGGGGGTGG<br>GGTGGGGCAGGACAGCAAGGGGGAGGATTGGGAAGACAATAGCAGGCATG<br>CTGGGGATGCGGTGGGCTCTATGG |
| 10. | Post-Tx Reg. | AATCAACCTCTGGATTACAAAATTTGTGAAAGATTGACTGGTATTCTTAA<br>CTATGTTGCTCCTTTTACGCTATGTGGATACGCTGCTTTAATGCCTTTGT<br>ATCATGCTATTGCTTCCCGTATGGCTTTCATTTTCTCCTCCTTGTATAAA<br>TCCTGGTTGCTGTCTCTTTATGAGGAGTTGTGGCCCGTTGTCAGGCAACG<br>TGGCGTGGTGTGCACTGTGTTTGCTGACGCAACCCCCACTGGTTGGGGCA<br>TTGCCACCACCTGTCAGCTCCTTTCCGGGACTTTCGCTTTCCCCCTCCCT<br>ATTGCCACGGCGGAACTCATCGCCGCCTGCCTTGCCCGCTGCTGGACAGG<br>GGCTCGGCTGTTGGGCACTGACAATTCCGTGGGGTGTGCCTTCTAGTTGC<br>CAGCCATCTGTTGTTTGCCCCTCCCCCGTGCCTTCCTTGACCCTGGAAGG<br>TGCCACTCCCACTGTCCTTTCCTAATAAAATGAGGAAATTGCATCGCATT<br>GTCTGAGTAGGTGTCATTCTATTCTGGGGGGTGGGGTGGGGCAGGACAGC<br>AAGGGGGAGGATTGGGAAGACAATAGCAGGCATGCTGGGGATGCGGTGGG<br>CTCTATGG |
| 11. | DTS | GAGCTGTGCGATCCCTGCTGGGGACTTTCCGCTGGGGACTTTCCGCTGGG<br>GACTTTCCGCCTTCAGCTAAGGAAGCTACCAATATTTAGAGGTACATTTT<br>GTTCTAGAACAAAATGTACCGGTACATTTTGTTCTGGTACATTTTGTTCT |
| 12. | Post-Tx Reg. DTS | AATCAACCTCTGGATTACAAAATTTGTGAAAGATTGACTGGTATTCTTAA<br>CTATGTTGCTCCTTTTACGCTATGTGGATACGCTGCTTTAATGCCTTTGT<br>ATCATGCTATTGCTTCCCGTATGGCTTTCATTTTCTCCTCCTTGTATAAA<br>TCCTGGTTGCTGTCTCTTTATGAGGAGTTGTGGCCCGTTGTCAGGCAACG<br>TGGCGTGGTGTGCACTGTGTTTGCTGACGCAACCCCCACTGGTTGGGGCA<br>TTGCCACCACCTGTCAGCTCCTTTCCGGGACTTTCGCTTTCCCCCTCCCT<br>ATTGCCACGGCGGAACTCATCGCCGCCTGCCTTGCCCGCTGCTGGACAGG<br>GGCTCGGCTGTTGGGCACTGACAATTCCGTGGGGTGTGCCTTCTAGTTGC<br>CAGCCATCTGTTGTTTGCCCCTCCCCCGTGCCTTCCTTGACCCTGGAAGG<br>TGCCACTCCCACTGTCCTTTCCTAATAAAATGAGGAAATTGCATCGCATT<br>GTCTGAGTAGGTGTCATTCTATTCTGGGGGGTGGGGTGGGGCAGGACAGC<br>AAGGGGGAGGATTGGGAAGACAATAGCAGGCATGCTGGGGATGCGGTGGG<br>CTCTATGGGAAGATGTCTACTGAGCTGTGCGATCCCTGCTGGGGACTTTC<br>CGCTGGGGACTTTCCGCTGGGGACTTTCCGCCTTCAGCTAAGGAAGCTAC<br>CAATATTTAGAGGTACATTTTGTTCTAGAACAAAATGTACCGGTACATTT<br>TGTTCTGGTACATTTTGTTCT |

-continued

| SEQ ID NO | Description | SEQ |
|---|---|---|
| 13. | Dystrophin WT | MLWWEEVEDCYEREDVQKKTFTKWVNAQFSKFGKQHIENLFSDLQDGRRL<br>LDLLEGLTGQKLPKEKGSTRVHALNNVNKALRVLQNNNVDLVNIGSTDIV<br>DGNHKLTLGLIWNIILHWQVKNVMKNIMAGLQQTNSEKILLSWVRQSTRN<br>YPQVNVINFTTSWSDGLALNALIHSHRPDLFDWNSVVCQQSATQRLEHAF<br>NIARYQLGIEKLLDPEDVDTTYPDKKSILMYITSLFQVLPQQVSIEAIQE<br>VEMLPRPPKVTKEEHFQLHHQMHYSQQITVSLAQGYERTSSPKPRFKSYA<br>YTQAAYVTTSDPTRSPFPSQHLEAPEDKSFGSSLMESEVNLDRYQTALEE<br>VLSWLLSAEDTLQAQGEISNDVEVVKDQFHTHEGYMMDLTAHQGRVGNIL<br>QLGSKLIGTGKLSEDEETEVQEQMNLLNSRWECLRVASMEKQSNLHRVLM<br>DLQNQKLKELNDWLTKTEERTRKMEEEPLGPDLEDLKRQVQQHKVLQEDL<br>EQEQVRVNSLTHMVVVVDESSGDHATAALEEQLKVLGDRWANICRWTEDR<br>WVLLQDILLKWQRLTEEQCLFSAWLSEKEDAVNKIHTTGFKDQNEMLSSL<br>QKLAVLKADLEKKKQSMGKLYSLKQDLLSTLKNKSVTQKTEAWLDNFARC<br>WDNLVQKLEKSTAQISQAVTTTQPSLTQTTVMETVTTVTTREQILVKHAQ<br>EELPPPPPQKKRQITVDSEIRKRLDVDITELHSWITRSEAVLQSPEFAIF<br>RKEGNFSDLKEKVNAIEREKAEKFRKLQDASRSAQALVEQMVNEGVNADS<br>IKQASEQLNSRWIEFCQLLSERLNWLEYQNNIIAFYNQLQQLEQMTTTAE<br>NWLKIQPTTPSEPTAIKSQLKICKDEVNRLSDLQPQIERLKIQSIALKEK<br>GQGPMFLDADFVAFTNHFKQVFSDVQAREKELQTIFDTLPPMRYQETMSA<br>IRTWVQQSETKLSIPQLSVTDYEIMEQRLGELQALQSSLQEQQSGLYYLS<br>TTVKEMSKKAPSEISRKYQSEFEEIEGRWKKLSSQLVEHCQKLEEQMNKL<br>RKIQNHIQTLKKWMAEVDVFLKEEWPALGDSEILKKQLKQCRLLVSDIQT<br>IQPSLNSVNEGGQKIKNEAEPEFASRLETELKELNTQWDHMCQQVYARKE<br>ALKGGLEKTVSLQKDLSEMHEWMTQAEEEYLERDFEYKTPDELQKAVEEM<br>KRAKEEAQQKEAKVKLLTESVNSVIAQAPPVAQEALKKELETLTTNYQWL<br>CTRLNGKCKTLEEVWACWHELLSYLEKANKWLNEVEFKLKTTENIPGGAE<br>EISEVLDSLENLMRHSEDNPNQIRILAQTLTDGGVMDELINEELETFNSR<br>WRELHEEAVRRQKLLEQSIQSAQETEKSLHLIQESLTFIDKQLAAYIADK<br>VDAAQMPQEAQKIQSDLTSHEISLEEMKKHNQGKEAAQRVLSQIDVAQKK<br>LQDVSMKFRLFQKPANFEQRLQESKMILDEVKMHLPALETKSVEQEVVQS<br>QLNHCVNLYKSLSEVKSEVEMVIKTGRQIVQKKQTENPKELDERVTALKL<br>HYNELGAKVTERKQQLEKCLKLSRKMRKEMNVLTEWLAATDMELTKRSAV<br>EGMPSNLDSEVAWGKATQKEIEKQKVHLKSITEVGEALKTVLGKKETLVE<br>DKLSLLNSNWIAVTSRAEEWLNLLLEYQKHMETFDQNVDHITKWIIQADT<br>LLDESEKKKPQQKEDVLKRLKAELNDIRPKVDSTRDQAANLMANRGDHCR<br>KLVEPQISELNHRFAAISHRIKTGKASIPLKELEQFNSDIQKLLEPLEAE<br>IQQGVNLKEEDFNKDMNEDNEGTVKELLQRGDNLQQRITDERKREEIKIK<br>QQLLQTKHNALKDLRSQRRKKALEISHQWYQYKRQADDLLKCLDDIEKKL<br>ASLPEPRDERKIKEIDRELQKKKEELNAVRRQAEGLSEDGAAMAVEPTQI<br>QLSKRWREIESKFAQFRRLNFAQIHTVREETMMVMTEDMPLEISYVPSTY<br>LTEITHVSQALLEVEQLLNAPDLCAKDFEDLFKQEESLKNIKDSLQQSSG<br>RIDIIHSKKTAALQSATPVERVKLQEALSQLDFQWEKVNKMYKDRQGRFD<br>RSVEKWRRFHYDIKIFNQWLTEAEQFLRKTQIPENWEHAKYKWYLKELQD<br>GIGQRQTVVRTLNATGEEIIQQSSKTDASILQEKLGSLNLRWQEVCKQLS<br>DRKKRLEEQKNILSEFQRDLNEFVLWLEEADNIASIPLEPGKEQQLKEKL<br>EQVKLLVEELPLRQGILKQLNETGGPVLVSAPISPEEQDKLENKLKQTNL<br>QWIKVSRALPEKQGEIEAQIKDLGQLEKKLEDLEEQLNHLLLWLSPIRNQ<br>LEIYNQPNQEGPFDVKETEIAVQAKQPDVEEILSKGQHLYKEKPATQPVK<br>RKLEDLSSEWKAVNRLLQELRAKQPDLAPGLTTIGASPTQTVTLVTQPVV<br>TKETAISKLEMPSSLMLEVPALADFNRAWTELTDWLSLLDQVIKSQRVMV<br>GDLEDINEMIIKQKATMQDLEQRRPQLEELITAAQNLKNKTSNQEARTII<br>TDRIERIQNQWDEVQEHLQNRRQQLNEMLKDSTQWLEAKEEAEQVLGQAR<br>AKLESWKEGPYTVDAIQKKITETKQLAKDLRQWQTNVDVANDLALKLLRD<br>YSADDTRKVHMITENINASWRSIHKRVSEREAALEETHRLLQQFPLDLEK<br>FLAWLTEAETTANVLQDATRKERLLEDSKGVKELMKQWQDLQGEIEAHTD<br>VYHNLDENSQKILRSLEGSDDAVLLQRRLDNMNFKWSELRKKSLNIRSHL<br>EASSDQWKRLHLSLQELLVWLQLKDDELSRQAPIGGDFPAVQKQNDVHRA<br>FKRELKTKEPVIMSTLETVRIFLTEQPLEGLEKLYQEPRELPPEERAQNV<br>TRLLRKQAEEVNTEWEKLNLHSADWQRKIDETLERLRELQEATDELDLKL<br>RQAEVIKGSWQPVGDLLIDSLQDHLEKVKALRGEIAPLKENVSHVNDLAR<br>QLTTLGIQLSPYNLSTLEDLNTRWKLLQVAVEDRVRQLHEAHRDFGPASQ<br>HELSTSVQGPWERAISPNKVPYYINHETQTTCWDHPKMTELYQSLADLNN<br>VRFSAYRTAMKLRRLOKALCLDLLSLSAACDALDQHNLKQNDQPMDILQI<br>INCLTTIYDRLEQEHNNLVNVPLCVDMCLNWLLNVYDTGRTGRIRVLSFK<br>TGIISLCKAHLEDKYRYLFKQVASSTGFCDQRRLGLLLHDSIQIPRQLGE<br>VASFGGSNIEPSVRSCFQFANNKPEIEAALFLDWMRLEPQSMVWLPVLHR<br>VAAAETAKHQAKCNICKECPIIGFRYRSLKHFNYDICQSCFFSGRVAKGH<br>KMHYPMVEYCTPTTSGEDVRDFAKVLKNKFRTKRYFAKHPRMGYLPVQTV<br>LEGDNMETPVTLINFWPVDSAPASSPQLSHDDTHSRIEHYASRLAEMENS<br>NGSYLNDSISPNESIDDEHLLIQHYCQSLNQDSPLSQPRSPAQILISLES<br>EERGELERILADLEEENRNLQAEYDRLKQQHEHKGLSPLPSPPEMMPTSP<br>QSPRDAELIAEAKLLRQHKGRLEARMQILEDHNKQLESQLHRLRQLLEQP<br>QAEAKVNGTTVSSPSTSLQRSDSSQPMLLRVVGSQTSDSMGEEDLLSPPQ<br>DTSTGLEEVMEQLNNSFPSSRGRNTPGKPMREDTM** |

-continued

| SEQ ID NO | Description | SEQ |
|---|---|---|
| 14. | NP-CBA-hBGi-DMD-3-WPRE3-DTS | TCTGGATCCACTGCTTAAATACGGACGAGGACAGGGCCCTGTCTCCTCAG CTTCAGGCACCACCACTGACCTGGGACAGTGAATCGTAAGTACTAGCAGC TACAATCCAGCTACCATTCTGCTTTTATTTTATGGTTGGGATAAGGCTGG ATTATTCTGAGTCCAAGCTAGGCCCTTTTGCTAATCATGTTCATACCTCT TATCTTCCTCCCACAGCTCCTGGGCAACGTGCTGGTCTGTGTGCTGGCCC ATCACTTTGGCAAAGAATTGCGATCGCCACCATGCTGTGGTGGGAAGAGG TGGAGGACTGTTACGAGAGAGAGGACGTGCAGAAGAAGACATTCACCAAG TGGGTGAACGCTCAGTTCAGCAAGTTCGGCAAGCAGCACATCGAGAACCT GTTTAGCGATCTACAAGATGGCAGAAGACTGCTGGACCTGCTGGAGGGCC TGACCGGGCAGAAGCTGCCCAAAGAAAAGGGGTCTACAAGAGTGCACGCC CTGAACAACGTGAACAAGGCCCTGAGAGTGCTGCAGAACAACAACGTGGA CCTGGTGAACATCGGCAGCACCGACATCGTGGACGGCAACCCACAAGCTGA CCCTGGGCCTGATCTGGAACATCATCCTGCACTGGCAAGTGAAGAACGTG ATGAAGAACATCATGGCCGGCCTGCAGCAGACCAACAGCGAGAAGATCCT GCTGAGCTGGGTGAGACAGAGCACAAGAAACTACCCCCAAGTGAACGTGA TCAACTTCACCACAAGCTGGAGCGACGGCCTGGCCCTGAACGCCCTGATC CACAGCCACAGACCCGACCTGTTCGACTGGAACAGCGTGGTGTGTCAGCA GAGCGCCACACAGAGACTGGAGCACGCCTTCAACATCGCTAGATATCAGC TGGGCATCGAGAAGTTACTGGACCCCGAAGATGTGGACACCACCTACCCC GACAAGAAGAGCATCCTGATGTACATCACAAGCCTGTTCCAAGTGCTGCC TCAGCAAGTGAGCATCGAGGCCATCCAAGAAGTCGAGATGCTGCCTAGAC CCCCCAAGGTGACCAAGGAGGAGCACTTTCAGCTGCACCATCAGATGCAC TACTCTCAGCAGATCACAGTCAGCTTGGCACAAGGCTACGAGAGAACAAG CAGCCCCAAGCCTAGATTCAAGAGCTACGCCTACACCCAAGCCGCCTACG TGACCACAAGTGACCCCACAAGAAGCCCCTTCCCTTCTCAGCACCTGGAG GCCCCCGAGGACAAGAGCTTCGGCAGCAGCCTGATGGAGAGCGAGGTGAA CCTGGACAGATATCAGACCGCGTTAGAAGAAGTGTTGAGCTGGCTGCTGA GCGCCGAGGACACCCTGCAAGCCCAAGGCGAGATCAGCAACGATGTGGAG GTGGTGAAGGATCAGTTCCACACCCACGAGGGCTACATGATGGACCTGAC CGCCCACCAAGGCAGAGTGGGCAACATCCTGCAGCTGGGCAGCAAGCTGA TCGGCACCGGCAAGCTGAGCGAGGACGAGGAAACCGAGGTTCAAGAGCAA ATGAACCTGCTAAACAGCAGATGGGAGTGCCTGAGAGTGGCTAGCATGGA AAAGCAGAGTAACCTGCACAGAGTGCTGATGGACCTGCAGAATCAGAAAT TGAAAGAACTTAATGATTGGCTGACCAAGACCGAGGAGAGAACAAGAAAG ATGGAGGAGGAGCCCCTGGGCCCCGACCTGGAGGACCTGAAGAGACAAGT GCAGCAGCACAAGGTGCTGCAAGAGGACCTGGAGCAAGAGCAAGTGAGAG TGAACTCTCTGACACACATGGTGGTGGTAGTGGACGAGAGCAGCGGCGAT CACGCTACCGCGGCGCTGGAAGAGCAGCTGAAAGTGCTGGGCGACAGATG GGCCAACATCTGCAGATGGACCGAGGACAGATGGGTGCTGCTGCAAGACA TCCTGCTGAAGTGGCAGAGACTGACCGAGGAGCAGTGCCTGTTCAGCGCC TGGCTGAGCGAGAAGGAAGACGCTGTGAACAAGATCCACACCACCGGCTT CAAGGATCAGAACGAGATGCTGAGCTCCCTCCAAAAGCTCGCAGTGCTGA AGGCCGACCTGGAAAAGAAAAACAGTCGATGGGCAAGCTGTACAGCCTG AAGCAAGACCTGCTGAGCACCCTGAAGAACAAGAGCGTGACACAGAAGAC CGAGGCCTGGCTGGACAACTTCGCTAGATGCTGGGACAACCTGGTACAGA AGTTAGAGAAGTCTACCGCTCAGATCAGCCAAGCCGTAACCACCACACAA CCTAGCCTGACTCAGACCACCGTGATGGAAACCGTGACCACCGTGACAAC CCGTGAGCAGATCCTGGTGAAGCACGCCCAAGAGGAGCTGCCCCCCCCCC CCCCTCAGAAGAAGAGACAGATCACCGTGGACTCAGAGATTCGCAAGAGA CTGGACGTGGACATCACCGAGCTGCACAGCTGGATCACAAGAAGCGAGGC CGTGCTGCAGAGCCCTGAGTTCGCGATCTTTAGAAAGGAGGGCAACTTCA GCGACTTGAAGGAGAAAGTGAACGCCATCGAGAGAGAGAAGGCCGAGAAG TTCAGAAAGTTGCAAGACGCCTCAAGAAGCGCCCAAGCCCTGGTGGAGCA GATGGTTAACGAAGGCGTGAATGCCGACAGCATCAAGCAAGCTAGCGAGC AGCTGAATAGCCGGTGGATTGAATTCTGTCAGCTGCTGAGCGAGAGATTA AACTGGCTGGAGTATCAGAACAACATCATCGCCTTCTACAATCAGCTGCA GCAACTAGAACAAATGACCACCACCGCCGAGAACTGGCTAAAGATTCAGC CCACCACCCCTAGCGAGCCCACCGCCATCAAATCTCAGCTGAAAATTTGC AAGGACGAAGTGAACAGACTGTCGGACCTGCAGCCTCAAATCGAAAGACT GAAAATTCAGAGCATCGCACTTAAGGAGAAGGGCCAAGGACCCATGTTCC TGGACGCCGACTTCGTGGCCTTCACCAACCACTTCAAGCAAGTGTTCAGC GACGTGCAAGCTAGAGAGAAGGAGCTGCAGACCATCTTCGACACCCTGCC CCCCATGAGATACCAAGAAACCATGAGCGCCATCAGAACCTGGGTGCAGC AGAGCGAAACCAAGCTGAGCATCCCTCAGCTGAGCGTGACCGACTACGAG ATCATGGAGCAAAGACTGGGAGAGCTGCAAGCCCTGCAGAGCAGCCTGCA AGAGCAGCAGAGCGGCCTGTACTACCTGAGCACCACCGTGAAGGAGATGT CGAAGAAAGCCCCGTCGGAGATCAGCAGAAAGTATCAGAGCGAGTTCGAG GAGATCGAGGGCAGATGGAAGAAGCTGAGCAGCCAACTGGTGGAACACTG TCAGAAATTAGAAGAACAGATGAACAAGCTGAGAAAGATTCAGAACCACA TTCAGACCCTGAAGAAGTGGATGGCCGAGGTGGACGTGTTCCTGAAAGAG GAGTGGCCCGCCCTGGGCGATTCCGAAATCTTAAAAAAGCAGCTGAAGCA GTGCAGACTGCTGGTGTCAGATATCCAAACCATTCAACCAAGCCTGAACA GCGTGAACGAAGGCGGGCAGAAGATCAAGAACGAGGCCGAGCCCGAGTTC GCTAGCAGACTGGAAACCGAGCTGAAGGAGCTGAATACACAGTGGGACCA CATGTGTCAGCAAGTGTACGCTAGAAAGGAAGCGCTGAAGGGCGGGCTGG |

-continued

| SEQ ID NO | Description | SEQ |
|---|---|---|
| | | AGAAGACCGTTAGCCTGCAAAAGGATCTGAGCGAGATGCACGAGTGGATG |
| | | ACCCAAGCCGAGGAGGAGTACCTGGAGAGAGACTTCGAGTACAAGACCCC |
| | | CGACGAGCTGCAGAAGGCCGTCGAGGAAATGAAGAGAGCGAAGGAGGAGG |
| | | CTCAGCAGAAGGAAGCCAAGGTGAAGCTGCTGACTGAATCTGTCAACAGT |
| | | GTGATAGCTCAAGCACCCCCCGTTGCCCAAGAGGCACTAAAGAAGGAGCT |
| | | GGAAACTCTGACCACCAACTATCAGTGGCTGTGCACAAGACTGAACGGCA |
| | | AGTGCAAGACCCTGGAGGAAGTGTGGGCCTGCTGGCACGAGCTGCTGAGC |
| | | TACCTGGAGAAGGCCAACAAGTGGCTGAACGAGGTGGAGTTCAAGCTGAA |
| | | GACCACCGAGAACATCCCCGGCGGCGCCGAGGAGATCAGCGAGGTGCTGG |
| | | ACAGCCTGGAGAACCTGATGAGACACAGCGAGGACAACCCCAATCAGATC |
| | | AGAATCCTGGCTCAGACCCTGACCGACGGCGGCGTGATGGACGAGCTGAT |
| | | CAACGAGGAGCTGGAAACCTTTAACTCTAGATGGCGAGAACTGCACGAGG |
| | | AGGCCGTGAGAAGACAGAAGCTGCTGGAGCAAAGCATTCAGAGCGCCCAA |
| | | GAAACCGAGAAGAGCCTGCACCTGATCCAAGAGAGCCTGACCTTCATCGA |
| | | CAAGCAGCTGGCCGCCTACATCGCCGACAAGGTGGACGCCGCTCAGATGC |
| | | CACAAGAGGCTCAGAAGATTCAGTCCGATCTGACAAGCCACGAGATCAGC |
| | | CTGGAGGAGATGAAAAAACACAACCAAGGCAAGGAGGCCGCTCAGAGAGT |
| | | GCTGTCTCAGATCGACGTGGCTCAGAAGAAGCTGCAAGACGTGAGCATGA |
| | | AGTTCAGACTGTTTCAGAAGCCCGCCAACTTCGAGCAGCGACTGCAAGAG |
| | | AGCAAGATGATCCTGGACGAGGTGAAGATGCACCTGCCCGCCCTGGAAAC |
| | | CAAGAGCGTGGAGCAAGAGGTGGTGCAGTCTCAGTTGAACCACTGCGTGA |
| | | ACCTGTACAAGAGCCTGTCGGAGGTCAAGAGTGAGGTCGAGATGGTGATC |
| | | AAAACTGGGAGACAGATCGTGCAAAAAAAGCAGACCGAGAACCCCAAGGA |
| | | GCTGGACGAGCGTGTTACCGCCCTGAAGCTGCACTACAACGAGCTGGGCG |
| | | CCAAGGTGACCGAGAGAAAGCAGCAGCTGGAGAAGTGCCTGAAGCTGAGC |
| | | AGAAAGATGAGAAAGGAGATGAACGTGCTGACCGAGTGGCTGGCCGCCAC |
| | | CGACATGGAGCTGACCAAGAGAAGCGCCGTGGAGGGCATGCCTAGCAACC |
| | | TGGACAGCGAGGTGGCCTGGGGCAAGGCCACACAGAAGGAGATCGAGAAG |
| | | CAGAAGGTGCACCTGAAGAGCATCACCGAGGTGGGCGAGGCCCTGAAGAC |
| | | CGTGCTGGGCAAGAAGGAAACCCTGGTGGAGGACAAGCTGAGCCTGCTGA |
| | | ACTCGAACTGGATCGCCGTGACAAGCAGAGCCGAGGAGTGGCTGAACCTG |
| | | CTGTTAGAGTACCAAAAACACATGGAAACCTTCGATCAGAACGTGGACCA |
| | | CATCACCAAGTGGATCATCCAAGCCGACACCCTGCTGGACGAAAGCGAAA |
| | | AGAAGAAGCCGCAACAAAAGGAGGATGTGCTGAAGAGACTGAAGGCCGAA |
| | | CTGAACGATATCAGACCCAAGGTGGACAGCACACGGGACCAAGCCGCCAA |
| | | CCTGATGGCCAACAGAGGCGACCACTGCAGAAAACTGGTGGAGCCTCAGA |
| | | TCAGCGAGCTGAACCACAGATTCGCCGCCATCAGCCACAGAATCAAAACC |
| | | GGCAAAGCGAGCATCCCCTTGAAGGAACTGGAGCAATTTAACAGCGACAT |
| | | CCAAAAATTGCTCGAACCACTGGAGGCCGAGATTCAGCAAGGCGTGAACC |
| | | TGAAGGAAGAGGACTTCAACAAGGACATGAACGAGGACAACGAGGGCACC |
| | | GTGAAAGAACTGCTGCAGAGAGGCGACAACCTGCAGCAGAGAATCACCGA |
| | | CGAGAGAAAGAGAGAGGAGATCAAGATCAAGCAGCAGCTGCTGCAGACTA |
| | | AGCACAACGCCCTGAAGGATCTGAGATCTCAGAGGAGAAAAAAGGCTCTG |
| | | GAAATTTCACATCAGTGGTATCAGTACAAGAGACAAGCAGACGACCTGCT |
| | | GAAGTGCCTGGACGACATCGAGAAGAAGTTAGCTAGCCTGCCCGAGCCTA |
| | | GAGACGAGAGAAAGATCAAGGAGATCGACAGAGAGTTACAAAAGAAGAAG |
| | | GAGGAGCTGAATGCGGTAAGAAGACAAGCGGAAGGCCTGTCCGAGGACGG |
| | | CGCAGCCATGGCCGTGGAGCCCACACAGATTCAGCTCAGCAAGAGATGGA |
| | | GAGAGATCGAGAGCAAGTTCGCTCAGTTCAGAAGACTGAACTTCGCTCAG |
| | | ATCCACACCGTGAGAGAGGAAACCATGATGGTGATGACCGAGGACATGCC |
| | | CCTGGAGATCTCATACGTTCCTAGCACCTACCTGACCGAGATCACCCACG |
| | | TGAGCCAAGCCCTGCTGGAGGTGGAGCAGCTGCTGAACGCCCCCGACCTG |
| | | TGCGCCAAGGACTTCGAGGACCTGTTCAAACAAGAGGAGAGCCTGAAGAA |
| | | CATCAAGGACAGCCTGCAGCAAAGTAGCGGCAGAATCGACATCATCCACA |
| | | GCAAGAAGACCGCCGCCCTGCAGAGCGCCACCCCCGTGGAGAGAGTGAAG |
| | | CTTCAAGAGGCCCTTTCGCAGCTGGATTTTCAGTGGGAGAAGGTGAACAA |
| | | AATGTACAAGGACAGACAAGGCAGATTCGACAGAAGCGTGGAGAAGTGGA |
| | | GAAGATTCCACTACGACATCAAGATCTTCAATCAGTGGCTGACCGAGGCA |
| | | GAGCAGTTCCTGAGAAAGACACAGATCCCCGAGAACTGGGAGCACGCCAA |
| | | GTACAAGTGGTACCTGAAGGAGCTGCAAGACGGCATCGGGCAGAGACAGA |
| | | CCGTGGTGAGAACCCTGAACGCCACCGGCGAGGAGATCATCCAACAAAGC |
| | | TCCAAAACCGACGCTAGCATCCTGCAAGAGAAACTGGGCAGCCTGAACCT |
| | | GAGATGGCAAGAGGTGTGCAAGCAGCTGAGCGACCGCAAAAAACGGTTAG |
| | | AGGAGCAGAAGAACATCCTGAGCGAGTTTCAGCGGGACCTGAACGAGTTC |
| | | GTGCTGTGGCTGGAGGAGGCCGATAACATCGCTAGCATCCCCCTGGAGCC |
| | | CGGCAAGGAGCAGCAGTTAAAAGAAAAACTTGAGCAAGTGAAGCTGCTGG |
| | | TGGAGGAGCTGCCCCTGAGACAAGGCATCCTGAAGCAGCTGAACGAGACT |
| | | GGCGGCCCCGTGCTGGTGAGCGCCCCCATCAGCCCCGAGGAGCAAGACAA |
| | | GCTGGAGAACAAGCTGAAGCAGACCAACCTGCAGTGGATCAAGGTGAGCA |
| | | GAGCCCTGCCCGAGAAGCAAGGCGAAATCGAGGCCCAAATAAAGGACCTG |
| | | GGGCAGCTGGAGAAGAAACTCGAAGACTTGGAAGAACAACTCAACCACTT |
| | | GCTGCTGTGGCTGAGCCCCATCAGAAATCAGCTGGAGATCTACAATCAGC |
| | | CCAACCAAGAGGGGCCATTCGACGTGAAGGAAACCGAGATCGCCGTGCAA |
| | | GCCAAGCAGCCCGATGTGGAGGAGATCCTGAGCAAGGGGCAGCACCTGTA |
| | | CAAGGAGAAGCCCGCCACACAGCCCGTCAAGCGTAAACTAGAGGATCTTT |

-continued

| SEQ ID NO | Description | SEQ |
|---|---|---|
| | | CCTCTGAGTGGAAGGCCGTGAACCGTCTGCTACAAGAGCTGCGGGCTAAG |
| | | CAACCCGACTTAGCGCCCGGCCTGACCACCATCGGTGCAAGCCCCACGCA |
| | | GACCGTGACCCTGGTGACCCAACCCGTGGTGACCAAGGAAACCGCCATCA |
| | | GCAAGCTGGAGATGCCTAGCAGCCTGATGCTGGAGGTGCCCGCCCTGGCC |
| | | GACTTCAACAGAGCCTGGACCGAGCTGACCGACTGGCTGAGCCTGCTGGA |
| | | CCAAGTGATCAAGTCTCAGAGAGTGATGGTGGGCGATCTGGAGGACATCA |
| | | ATGAGATGATCATCAAGCAGAAGGCCACCATGCAAGACCTGGAGCAGAGA |
| | | AGACCTCAGCTGGAGGAGCTGATCACCGCCGCTCAGAACCTGAAAAACAA |
| | | GACGAGCAACCAAGAGGCTAGAACCATCATCACCGACAGAATCGAGAGAA |
| | | TTCAGAATCAGTGGGACGAGGTGCAAGAGCACCTGCAGAACAGAAGACAG |
| | | CAACTAAACGAAATGCTCAAGGACAGCACACAGTGGCTGGAGGCCAAGGA |
| | | GGAGGCGGAGCAAGTGTTGGGCCAAGCTAGAGCCAAGCTGGAGAGCTGGA |
| | | AGGAGGGACCCTACACCGTGGACGCCATTCAGAAGAAGATCACCGAAACC |
| | | AAGCAGCTGGCCAAGGACCTGCGACAGTGGCAGACCAACGTGGACGTGGC |
| | | CAACGATCTTGCCCTGAAGCTGCTGCGCGACTATAGCGCCGACGACACAA |
| | | GAAAGGTGCACATGATCACCGAGAACATCAACGCTAGCTGGCGTAGCATC |
| | | CACAAGAGAGTGAGCGAGAGAGAGGCGGCTTTGGAGGAAACCCATAGACT |
| | | GCTGCAGCAGTTTCCCCTGGACCTGGAGAAGTTCCTGGCCTGGCTGACCG |
| | | AAGCCGAAACAACCGCCAACGTGCTGCAAGACGCCACAAGAAAGGAGAGA |
| | | CTGCTGGAGGACAGCAAGGGCGTGAAGGAGCTGATGAAGCAGTGGCAAGA |
| | | CCTGCAAGGCGAGATCGAAGCGCACACCGACGTGTACCACAACCTGGACG |
| | | AGAACTCTCAGAAGATCCTGAGAAGCCTGGAGGGCAGCGACGACGCCGTG |
| | | CTGTTACAGAGAAGGCTGGACAACATGAACTTCAAGTGGAGCGAGCTGAG |
| | | AAAGAAGAGCCTGAACATCAGAAGCCACCTGGAGGCTAGCAGCGATCAGT |
| | | GGAAGAGACTGCACCTGAGCCTGCAAGAGCTGCTGGTCTGGCTTCAGTTG |
| | | AAGGACGATGAGCTGAGCAGACAAGCCCCCATCGGCGGCGACTTCCCCGC |
| | | CGTGCAGAAGCAGAACGACGTGCATAGAGCCTTCAAGAGAGAGCTGAAGA |
| | | CCAAGGAGCCCGTGATCATGAGCACCCTGGAAACGGTGAGAATCTTCCTG |
| | | ACCGAGCAGCCCCTGGAGGGCCTGGAGAAGCTGTACCAAGAGCCTAGAGA |
| | | GCTGCCCCCCGAGGAGAGAGCTCAGAACGTGACAAGACTGCTGAGAAAGC |
| | | AAGCCGAAGAGGTGAACACCGAGTGGGAGAAGCTGAACCTGCACAGCGCC |
| | | GACTGGCAGAGAAAGATCGACGAAACCCTGGAGAGACTGAGAGAATTGCA |
| | | AGAGGCGACCGACGAGCTGGACCTGAAGCTGAGACAAGCCGAGGTCATCA |
| | | AGGGCAGCTGGCAGCCCGTGGGCGATCTATTAATTGACTCTCTACAAGAC |
| | | CACCTGGAGAAAGTGAAGGCCCTGAGAGGCGAGATCGCCCCCCTGAAGGA |
| | | GAACGTGAGCCACGTGAATGATCTGGCACGTCAGCTGACCACCCTGGGCA |
| | | TACAACTGTCCCCCTATAACCTGAGCACACTGGAGGATTTGAATACTAGA |
| | | TGGAAGCTGCTGCAAGTGGCCGTGGAGGACAGAGTAAGACAATTACATGA |
| | | GGCCCACAGAGACTTCGGCCCCGCTTCTCAGCACTTCCTGAGCACAAGCG |
| | | TGCAAGGCCCCTGGGAGAGAGCCATTTCCCCCAACAAGGTCCCCTACTAC |
| | | ATCAACCACGAGACACAGACCACCTGCTGGGACCACCCCAAGATGACCGA |
| | | GCTGTATCAGAGCCTCGCCGATCTGAACAATGTGAGATTCAGCGCCTACA |
| | | GAACCGCCATGAAGCTGAGAAGACTGCAGAAGGCCCTGTGCCTGGACTTA |
| | | TTAAGCCTGAGCGCCGCCTGCGACGCCCTGGATCAGCACAACCTGAAGCA |
| | | AAACGACCAACCCATGGACATCCTGCAGATCATCAACTGCCTCACCACCA |
| | | TATACGACAGACTGGAACAAGAGCACAACAACCTGGTGAACGTGCCCCTG |
| | | TGCGTGGACATGTGCCTGAACTGGCTGCTGAACGTGTACGACACCGGCAG |
| | | AACCGGCAGAATCAGAGTGCTGAGCTTCAAGACCGGCATCATCAGCCTGT |
| | | GCAAGGCCCACCTGGAGGACAAATACAGATACCTTTTCAAACAAGTGGCT |
| | | AGCAGCACCGGCTTCTGCGACCAAAGAAGACTGGGTCTGCTGCTGCACGA |
| | | CAGCATTCAGATCCCTAGACAGCTGGGCGAGGTGGCTAGCTTCGGCGGCA |
| | | GCAACATCGAGCCTAGCGTGAGAAGCTGCTTTCAGTTCGCCAACAACAAG |
| | | CCCGAGATAGAGGCAGCCCTCTTCTTAGACTGGATGAGACTGGAGCCTCA |
| | | GAGCATGGTATGGCTGCCGGTCCTGCACAGAGTGGCCGCCGCCGAAACCG |
| | | CCAAGCACCAAGCCAAGTGCAACATCTGCAAGGAGTGCCCCATCATCGGC |
| | | TTCAGATACAGAAGCCTGAAGCACTTCAACTACGACATCTGTCAGAGCTG |
| | | CTTCTTCAGCGGCAGAGTGGCCAAGGGCCACAAGATGCACTACCCCATGG |
| | | TGGAGTACTGCACCCCCACCACAAGCGGCGAGGACGTGAGAGACTTCGCC |
| | | AAGGTGTTGAAGAATAAGTTTAGAACCAAGAGATACTTCGCCAAGCACCC |
| | | TAGAATGGGCTACCTGCCCGTGCAGACCGTGCTGGAGGGCGACAACATGG |
| | | AAACCCCCGTGACCCTGATCAACTTCTGGCCCGTGGACAGCGCCCCCGCT |
| | | AGCAGCCCTCAGCTGAGCCACGACGACACCCACAGCAGAATCGAGCACTA |
| | | CGCTAGCAGACTGGCCGAGATGGAGAACAGCAACGGCAGCTACCTGAACG |
| | | ACAGCATCAGCCCGAATGAGAGCATCGACGACGAGCACCTGCTGATTCAG |
| | | CACTACTGTCAGAGCCTGAACCAAGACAGCCCCCTGTCTCAGCCTAGAAG |
| | | CCCCGCTCAGATCCTGATCAGCCTGGAGAGCGAGGAGAGAGGCGAGCTGG |
| | | AGAGAATCCTAGCAGATCTGGAGGAAGAGAACAGAAACCTGCAAGCCGAG |
| | | TATGACCGACTGAAACAGCAACATGAGCACAAAGGCCTGAGCCCACTGCC |
| | | CTCCCCCCCCGAGATGATGCCCACAAGCCCTCAGAGCCCTAGAGACGCCG |
| | | AGCTGATCGCTGAAGCGAAGTTACTTAGACAACACAAGGGCAGACTGGAG |
| | | GCTAGAATGCAGATCCTGGAGGACCACAACAAGCAGCTGGAGTCTCAGCT |
| | | GCACAGACTGAGGCAGCTGCTGGAACAGCCCCAAGCCGAGGCCAAAGTGA |
| | | ACGGCACCACCGTGAGCAGTCCTAGCACAAGCCTGCAGAGAAGCGACAGC |
| | | TCTCAGCCCATGCTGCTGAGAGTGGTGGGCTCTCAGACAAGCGACAGCAT |
| | | GGGCGAGGAGGATCTGCTGAGTCCGCCCCAAGACACAAGCACCGGCCTGG |

-continued

| SEQ ID NO | Description | SEQ |
|---|---|---|
| | | AAGAGGTGATGGAGCAACTGAACAATAGCTTCCCTAGCAGCAGAGGCAGA<br>AACACCCCCGGCAAGCCCATGAGAGAGGACACCATGTGATGACTCGAGAA<br>TCAACCTCTGGATTACAAAATTTGTGAAAGATTGACTGGTATTCTTAACT<br>ATGTTGCTCCTTTTACGCTATGTGGATACGCTGCTTTAATGCCTTTGTAT<br>CATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTG<br>GCGTGGTGTGCACTGTGTTTGCTGACGCAACCCCCACTGGTTGGGGCATT<br>GCCACCACCTGTCAGCTCCTTTCCGGGACTTTCGCTTTCCCCCTCCCTAT<br>TGCCACGGCGGAACTCATCGCCGCCTGCCTTGCCCGCTGCTGGACAGGGG<br>CTCGGCTGTTGGGCACTGACAATTCCGTGGGGTGTGCCTTCTAGTTGCCA<br>GCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAA<br>GGGGGAGGATTGGGAAGACAATAGCAGGCATGCTGGGGATGCGGTGGGCT<br>CTATGGGAAGATGTCTACTGAGCTGTGCGATCCCTGCTGGGGACTTTCCG<br>CTGGGGACTTTCCGCTGGGGACTTTCCGCCTTCAGCTAAGGAAGCTACCA<br>ATATTTAGAGGTACATTTTGTTCTAGAACAAAATGTACCGGTACATTTTG<br>TTCTGGTACATTTTGTTCTATTAAGGACAACGTAAGTATAGCGCATAGAC<br>ACGTGGCGCCATCGGATCCCGGGCCCGTGGCTTGTTGTCCACAACCATTA<br>AACCTTAAAAGCTTTAAAAGCCTTATATATTCTTTTTTTTCTTATAAAAC<br>TTAAAACCTTAGAGGCTATTTAAGTTGCTGATTTATATTAATTTTATTGT<br>TCAAACATGAGAGCTTAGTACGTGAAACATGAGAGCTTAGTACATTAGCC<br>ATGAGAGCTTAGTACATTAGCCATGAGGGTTTAGTTCATTAAACATGAGA<br>GCTTAGTACATTAAACATGAGAGCTTAGTACATTAAACATGAGAGCTTAG<br>TACATACTATCAACAGGTTGAACTGCTGATCTGTACAGTAGAATTGGTAA<br>AGAGAGTTGTGTAAAATATTGAGTTCGCACATCTTGTTGTCTGATTATTG<br>ATTTTTGGCGAAACCATTTGATCATATGACAAGATGTGTATCTACCTTAA<br>CTTAATGATTTTGATAAAAATCATTATGCGGCCGCCGTTACATAACTTAC<br>GGTAAATGGCCCGCCTGGCTGACCGCCCAACGACCCCCGCCCATTGACGT<br>CAATAATGACGTATGTTCCCATAGTAACGCCAATAGGGACTTTCCATTGA<br>CGTCAATGGGTGGAGTATTTACGGTAAACTGCCCACTTGGCAGTACATCA<br>AGTGTATCATATGCCAAGTACGCCCCCTATTGACGTCAATGACGGTAAAT<br>GGCCCGCCTGGCATTATGCCCAGTACATGACCTTATGGGACTTTCCTACT<br>TGGCAGTACATCTACGTATTAGTCATCGCTATTACCATGGTCGAGGTGAG<br>CCCCACGTTCTGCTTCACTCTCCCCATCTCCCCCCCCTCCCCACCCCCAA<br>TTTTGTATTTATTTATTTTTTAATTATTTTGTGCAGCGATGGGGGCGGGG<br>GGGGGGGGGGCGCGCGCCAGGCGGGGCGGGGCGGGGCGAGGGGGGGGCGG<br>GGCGAGGCGGAGAGGTGCGGCGGCAGCCAATCAGAGCGGCGCGCTCCGAA<br>AGTTTCCTTTTATGGCGAGGCGGCGGCGGCGGCGGCCCTATAAAAAGCGA<br>AGCGCGCGGCGGGCGGGAGTC |
| 15. | NP-CBA-<br>hBGi-DMD-<br>4-WPRE3- DTS | TCTGGATCCACTGCTTAAATACGGACGAGGACAGGGCCCTGTCTCCTCAG<br>CTTCAGGCACCACCACTGACCTGGGACAGTGAATCGTAAGTACTAGCAGC<br>TACAATCCAGCTACCATTCTGCTTTTATTTTATGGTTGGGATAAGGCTGG<br>ATTATTCTGAGTCCAAGCTAGGCCCTTTTGCTAATCATGTTCATACCTCT<br>TATCTTCCTCCCACAGCTCCTGGGCAACGTGCTGGTCTGTGTGCTGGCCC<br>ATCACTTTGGCAAAGAATTGCGATCGCCACCATGCTTTGGTGGGAAGAAG<br>TCGAGGACTGCTACGAGCGCGAGGACGTGCAGAAGAAAACCTTCACCAAA<br>TGGGTCAACGCCCAGTTCAGCAAGTTCGGCAAGCAGCACATCGAGAACCT<br>GTTCAGCGACCTGCAGGATGGCAGAAGGCTGCTGGATCTGCTGGAAGGCC<br>TGACAGGACAGAAGCTGCCCAAAGAGAAGGGCAGCACAAGAGTGCACGCC<br>CTGAACAACGTGAACAAGGCCCTGAGAGTGCTGCAGAACAACAACGTGGA<br>CCTGGTCAACATCGGCAGCACCGACATCGTGGACGGCAACCACAAACTGA<br>CCCTGGGCCTGATCTGGAACATCATCCTGCACTGGCAAGTGAAGAACGTG<br>ATGAAGAACATCATGGCCGGCCTGCAGCAGACCAACAGCGAGAAGATTCT<br>GCTGAGCTGGGTCCGACAGAGCACCCGGAATTACCCTCAAGTGAACGTGA<br>TCAACTTCACCACCTCTTGGAGCGACGGACTGGCCCTGAATGCCCTGATC<br>CACAGCCACAGACCTGACCTGTTCGACTGGAACAGCGTCGTGTGTCAGCA<br>GAGCGCCACACAGAGGCTGGAACACGCCTTCAATATCGCCAGATACCAGC<br>TGGGCATCGAGAAACTGCTGGACCCCGAGGATGTGGACACCACCTATCCT<br>GACAAGAAATCCATCCTCATGTACATCACCAGCCTGTTCCAGGTGCTGCC<br>CCAGCAGGTTTCCATCGAGGCCATTCAAGAGGTCGAGATGCTGCCCAGAC<br>CTCCTAAAGTGACCAAAGAGGAACACTTCCAGCTGCACCACCAGATGCAC<br>TACTCTCAGCAGATCACCGTGTCTCTGGCCCAGGGCTACGAGAGAACAAG<br>CAGCCCCAAGCCTCGGTTCAAGAGCTACGCCTATACACAGGCCGCCTACG<br>TGACCACCAGCGATCCTACAAGAAGCCCATTTCCTAGCCAGCATCTGGAA<br>GCCCCTGAGGACAAGAGCTTTGGCAGCAGCCTGATGGAAAGCGAAGTGAA<br>CCTGGACCGCTACCAGACAGCCCTGGAAGAGGTTCTGAGCTGGCTGCTGT<br>CTGCCGAGGATACACTGCAGGCTCAGGGCGAGATCAGCAACGACGTGGAA<br>GTGGTCAAGGACCAGTTTCACACCCACGAGGGCTACATGATGGACCTGAC<br>AGCCCACCAGGGCAGAGTGGGCAATATTCTGCAGCTGGGCTCCAAGCTGA<br>TCGGCACAGGCAAGCTGAGCGAGGACGAAGAGACAGAGGTGCAAGAGCAG<br>ATGAACCTGCTGAACAGCAGATGGGAGTGTCTGAGAGTGGCCAGCATGGA<br>AAAGCAGAGCAACCTGCACCGGGTGCTGATGGATCTCCAGAACCAGAAGC<br>TGAAAGAGCTGAACGACTGGCTGACCAAGACCGAGGAACGGACCCGGAAG |

-continued

| SEQ ID NO | Description | SEQ |
|---|---|---|
| | | ATGGAAGAGGAACCTCTGGGACCCGACCTGGAAGATCTGAAAAGACAGGT<br>GCAGCAGCATAAGGTGCTGCAAGAGGACCTCGAACAAGAGCAAGTGCGCG<br>TGAACAGCCTGACACACATGGTGGTCGTGGATGAGAGCAGCGGAGAT<br>CATGCCACAGCCGCTCTGGAAGAACAGCTGAAGGTGCTGGGAGACAGATG<br>GGCCAATATCTGCCGGTGGACCGAGGATAGATGGGTGCTGCTCCAGGACA<br>TCCTGCTGAAGTGGCAGCGGCTGACAGAGGAACAGTGCCTGTTTAGCGCC<br>TGGCTGTCCGAGAAAGAGGACGCCGTCAACAAGATCCACACCACCGGCTT<br>CAAGGATCAGAATGAGATGCTGAGCAGCCTGCAGAAACTGGCCGTGCTGA<br>AGGCTGACCTGGAAAAGAAAAAGCAGTCCATGGGCAAGCTGTACTCCCTG<br>AAGCAGGACCTGCTGAGCACACTGAAGAACAAGTCTGTGACCCAGAAAAC<br>CGAGGCCTGGCTGGACAACTTCGCCCGGTGTTGGGATAACCTGGTGCAGA<br>AGCTGGAAAAGTCCACCGCTCAGATCTCTCAGGCCGTGACCACAACACAG<br>CCTTCTCTGACCCAGACCACCGTGATGGAAACAGTGACCACAGTGACAAC<br>CCGCGAGCAGATCCTGGTCAAGCACGCCCAAGAAGAACTGCCTCCTCCAC<br>CTCCTCAGAAGAAACGGCAGATCACAGTGGACAGCGAGATCCGGAAGAGA<br>CTGGACGTGGACATCACCGAGCTGCACAGCTGGATCACCAGATCCGAAGC<br>CGTGCTGCAGTCCCCTGAGTTCGCCATCTTCAGAAAAGAGGGCAACTTCT<br>CCGACCTGAAAGAGAAAGTCAACGCCATCGAGAGAGAGAAGGCCGAGAAG<br>TTCCGGAAGCTGCAGGACGCCTCTAGATCTGCCCAGGCTCTGGTGGAACA<br>GATGGTCAACGAAGGCGTGAACGCCGACAGCATCAAGCAGGCCTCAGAGC<br>AGCTGAACTCCCGGTGGATCGAGTTCTGTCAGCTCCTGAGCGAGAGACTG<br>AACTGGCTGGAATACCAGAACAATATCATTGCCTTCTACAACCAGCTCCA<br>GCAGCTCGAACAGATGACCACCACAGCCGAGAATTGGCTGAAGATCCAGC<br>CTACCACACCTAGCGAGCCCACCGCCATTAAGAGCCAGCTGAAAATCTGC<br>AAGGACGAAGTGAATCGGCTGAGCGATCTGCAGCCCCAGATCGAAAGACT<br>GAAAATCCAGTCTATCGCCCTCAAAGAGAAAGGACAGGGCCCCATGTTCC<br>TGGACGCCGATTTTGTGGCCTTTACCAACCACTTCAAACAGGTGTTCTCC<br>GACGTGCAGGCCCGGGAAAAAGAGCTGCAGACCATCTTCGACACCCTGCC<br>TCCAATGAGATACCAAGAGACAATGAGCGCCATCCGGACCTGGGTGCAGC<br>AAAGCGAGACAAAGCTGAGCATCCCACAGCTGAGCGTGACCGACTACGAG<br>ATCATGGAACAGAGACTGGGCGAACTGCAGGCCCTCCAGTCTAGCCTGCA<br>AGAACAGCAGTCCGGCCTGTACTACCTGAGCACAACCGTGAAAGAGATGA<br>GCAAGAAGGCCCCTAGCGAGATCTCCCGGAAGTACCAGAGCGAGTTCGAA<br>GAGATCGAAGGCCGGTGGAAGAAGCTGTCTAGCCAGCTGGTTGAGCACTG<br>CCAGAAACTCGAAGAACAAATGAACAAGCTGCGCAAGATCCAGAATCACA<br>TCCAGACGCTGAAGAAATGGATGGCCGAGGTGGACGTGTTCCTGAAAGAA<br>GAGTGGCCCGCTCTGGGCGACTCCGAGATTCTGAAGAAACAGCTCAAACA<br>GTGCCGGCTGCTGGTGTCCGATATCCAGACAATCCAGCCAAGCCTGAACT<br>CCGTGAATGAAGGCGGCCAGAAGATCAAGAACGAGGCCGAGCCTGAGTTT<br>GCCAGCAGACTGGAAACCGAACTGAAAGAACTCAACACCCAGTGGGACCA<br>CATGTGCCAGCAAGTGTACGCCCGGAAAGAGGCCCTGAAAGGCGGACTCG<br>AAAAGACTGTGTCTCTGCAGAAAGACCTGTCTGAGATGCACGAGTGGATG<br>ACCCAGGCCGAAGAGGAATACCTGGAACGGGACTTCGAGTACAAGACCCC<br>TGATGAGCTGCAAAAAGCCGTCGAGGAAATGAAGCGGGCCAAAGAAGAGG<br>CCCAGCAGAAAGAAGCCAAAGTCAAGCTGCTGACCGAGTCCGTGAATAGC<br>GTTATCGCTCAGGCCCCTCCTGTGGCTCAAGAGGCTCTCAAGAAAGAACT<br>GGAAACTCTGACCACCAACTACCAGTGGCTGTGCACCAGACTGAACGGCA<br>AGTGCAAGACACTGGAAGAAGTGTGGGCCTGCTGGCACGAACTGCTGTCC<br>TATCTGGAAAAGGCCAACAAGTGGCTGAACGAGGTGGAATTCAAGCTGAA<br>AACCACCGAGAACATCCCTGGCGGCGCTGAAGAGATTAGCGAGGTGCTGG<br>ACAGCCTGGAAAACCTGATGAGACACAGCGAGGACAACCCCAATCAGATC<br>AGAATCCTGGCTCAGACCCTGACCGATGGCGGCGTGATGGACGAGCTGAT<br>CAACGAGGAACTCGAAACCTTCAACAGCCGGTGGCGGGAACTGCACGAGG<br>AAGCTGTTCGGAGGCAGAAGTTGCTGGAACAGTCTATCCAGAGCGCACAA<br>GAAACCGAGAAGTCCCTGCACCTGATCCAAGAGAGCCTGACCTTCATCGA<br>CAAGCAGCTGGCCGCTTATATCGCCGACAAGGTGGACGCTGCTCAGATGC<br>CCCAAGAGGCACAGAAGATTCAGAGCGACCTGACCAGCCACGAGATTAGC<br>CTGGAAGAAATGAAGAAGCACAACCAGGGCAAAGAGGCCGCTCAGAGAGT<br>CCTGAGCCAGATCGATGTGGCACAGAAAAAGCTCCAGGATGTGTCCATGA<br>AGTTTCGGCTGTTTCAGAAGCCCGCCAACTTCGAGCAGAGACTGCAAGAG<br>TCCAAGATGATCCTGGACGAAGTCAAAATGCATCTGCCCGCACTGGAAAC<br>AAAGTCCGTGGAACAAGAAGTGGTGCAGTCCCAGCTGAACCACTGCGTGA<br>ACCTGTACAAGAGCCTGTCCGAAGTGAAGTCTGAGGTGGAAATGGTCATC<br>AAGACCGGCAGGCAGATCGTCCAGAAGAAGCAGACCGAGAATCCCAAAGA<br>ACTCGACGAGAGAGTGACCGCTCTGAAGCTGCACTACAATGAGCTGGGCG<br>CCAAAGTGACCGAGCGGAAGCAACAGCTTGAGAAGTGCCTGAAACTGTCT<br>CGGAAGATGCGGAAAGAAATGAACGTGCTGACAGAGTGGCTGGCCGCCAC<br>CGATATGGAACTGACTAAGAGAAGCGCCGTGGAAGGCATGCCCAGCAACC<br>TGGATAGTGAAGTGGCCTGGGGCAAAGCCACTCAGAAAGAGATTGAGAAG<br>CAGAAGGTCCACCTGAAGTCCATCACCGAAGTGGGCGAAGCCCTGAAAAC<br>CGTGCTGGGAAAGAAAGAGACACTGGTCGAGGACAAGCTGTCCCTGCTGA<br>ATTCCAACTGGATCGCCGTGACCTCCAGAGCTGAGGAATGGCTGAATCTG<br>CTGCTTGAGTACCAGAAACACATGGAAACGTTCGACCAGAACGTCGACCA<br>CATCACAAAGTGGATCATCCAGGCTGATACCCTGCTGGACGAGTCCGAGA<br>AGAAGAAACCCCAACAAAAAGAAGATGTGCTGAAGCGGCTGAAAGCCGAG |

-continued

| SEQ ID NO | Description | SEQ |
|---|---|---|
| | | CTGAATGACATCCGGCCTAAGGTGGACAGCACCAGAGATCAGGCAGCCAA<br>CCTGATGGCCAACAGAGGCGACCACTGTCGGAAGCTCGTGGAACCTCAGA<br>TCAGCGAGCTTAACCACAGATTTGCCGCCATCAGCCACCGGATCAAGACA<br>GGCAAGGCCAGCATTCCTCTCAAAGAGCTTGAGCAGTTCAACAGCGACAT<br>CCAAAAGCTGCTCGAACCCCTGGAAGCCGAGATCCAACAGGGCGTCAACC<br>TCAAAGAAGAAGATTTCAACAAGGACATGAACGAGGACAATGAGGGCACC<br>GTCAAAGAACTGCTGCAGCGGGGCGATAATCTGCAGCAGCGGATTACCGA<br>TGAGCGCAAGCGGGAAGAGATCAAGATTAAGCAGCAGCTGCTGCAGACCA<br>AGCACAACGCCCTGAAGGACCTGCGGAGCCAGAGAAGAAAGAAGGCCCTG<br>GAAATCAGCCACCAGTGGTATCAGTACAAGCGGCAGGCCGACGACCTGCT<br>GAAGTGCCTGGATGACATCGAGAAGAAGCTGGCCTCTCTGCCCGAGCCTA<br>GGGACGAGAGAAAGATCAAAGAGATCGACCGCGAGCTGCAGAAAAAGAAA<br>GAGGAACTGAACGCCGTCCGCAGACAGGCCGAAGGACTTTCTGAAGATGG<br>CGCCGCTATGGCCGTGGAACCCACACAGATTCAGCTGAGCAAGCGGTGGC<br>GGGAAATCGAGAGCAAGTTCGCCCAGTTCCGGCGGCTGAATTTCGCCCAG<br>ATCCACACCGTGCGGGAAGAGACAATGATGGTCATGACAGAGGACATGCC<br>CCTTGAGATCAGCTACGTGCCCAGCACCTACCTGACCGAGATCACCCATG<br>TGTCTCAGGCCCTGCTGGAAGTGGAACAGCTGCTGAATGCCCCTGACCTG<br>TGCGCCAAGGACTTCGAGGACCTGTTCAAGCAAGAGGAAAGCCTGAAGAA<br>CATCAAGGACAGCCTGCAGCAGAGCAGCGGCCGGATCGATATCATCCACA<br>GCAAGAAAACCGCCGCACTGCAGAGCGCCACACCTGTGGAAAGAGTGAAG<br>CTGCAAGAGGCCCTGAGCCAGCTGGATTTCCAGTGGGAGAAAGTGAACAA<br>GATGTACAAGGACCGGCAGGGCAGATTCGACCGCAGCGTTGAAAAGTGGC<br>GGCGGTTCCACTACGACATCAAGATCTTCAACCAGTGGCTGACCGAGGCC<br>GAGCAGTTCCTGAGAAAGACACAGATCCCCGAGAACTGGGAGCACGCCAA<br>GTACAAGTGGTATCTGAAAGAGCTGCAGGACGGCATCGGCCAGAGACAGA<br>CAGTCGTGCGGACACTGAATGCCACCGGCGAGGAAATCATCCAGCAGTCC<br>AGCAAGACCGACGCCAGCATCCTGCAAGAGAAGCTGGGCAGCCTGAACCT<br>GCGGTGGCAAGAAGTGTGCAAGCAGCTGAGCGACCGGAAGAAGCGGCTGG<br>AAGAACAGAAGAATATCCTGAGCGAGTTCCAGCGGGACCTGAACGAGTTC<br>GTGCTGTGGCTCGAAGAGGCCGACAATATCGCCAGCATTCCCCTGGAACC<br>TGGCAAAGAGCAGCAGCTGAAAGAAAAGCTGGAACAAGTGAAACTGCTGG<br>TCGAGGAACTGCCCCTGAGACAGGGAATCCTGAAACAGCTGAACGAGACA<br>GGCGGCCCTGTGCTGGTGTCTGCCCCTATTTCTCCCGAGGAACAGGACAA<br>GCTGGAAAACAAGCTGAAGCAGACCAACCTGCAGTGGATCAAGGTGTCCA<br>GAGCACTGCCTGAGAAGCAGGGCGAGATCGAGGCCCAGATCAAGGACCTG<br>GGACAGCTCGAAAAGAAGCTTGAGGACCTCGAAGAACAGCTCAACCATCT<br>GCTGCTTTGGCTGAGCCCCATCCGGAACCAGCTGGAAATCTACAACCAGC<br>CTAATCAAGAGGGCCCCTTCGACGTGAAAGAAACCGAGATTGCCGTGCAG<br>GCCAAGCAGCCCGATGTGGAAGAGATCCTGTCTAAGGGCCAGCACCTGTA<br>CAAAGAGAAGCCCGCCACACAGCCCGTGAAGCGGAAACTGGAAGATCTGA<br>GCAGCGAGTGGAAGGCCGTGAACCGGCTGCTGCAAGAACTGAGAGCCAAA<br>CAGCCTGATCTGGCCCCTGGCCTGACAACAATTGGCGCCTCTCCTACACA<br>GACCGTGACACTGGTCACACAGCCTGTGGTCACCAAAGAGACAGCCATCA<br>GCAAACTGGAAATGCCCAGCAGTCTGATGCTCGAAGTGCCCGCACTGGCC<br>GACTTCAATAGAGCCTGGACCGAGCTGACCGACTGGCTCAGTCTGCTGGA<br>CCAAGTCATCAAGTCCCAGAGAGTGATGGTCGGAGATCTTGAGGACATCA<br>ACGAGATGATCATTAAGCAGAAAGCCACCATGCAGGACCTTGAGCAGAGA<br>AGGCCCCAGCTTGAAGAACTGATCACCGCCGCTCAGAACCTGAAAAACAA<br>GACCAGCAATCAAGAAGCCCGGACCATCATCACCGACCGGATCGAGAGAA<br>TCCAGAACCAGTGGGACGAAGTGCAAGAGCATCTGCAGAACAGACGGCAG<br>CAGCTCAATGAGATGCTGAAGGACAGCACACAGTGGCTGGAAGCCAAAGA<br>AGAAGCCGAGCAGGTTCTCGGACAGGCCAGAGCTAAGCTGGAATCTTGGA<br>AAGAGGGACCCTACACCGTCGACGCCATCCAGAAGAAGATCACCGAGACA<br>AAGCAGCTGGCCAAGGATCTGAGACAGTGGCAGACCAATGTGGACGTGGC<br>CAACGACCTGGCTCTGAAGCTGCTGAGAGACTACAGCGCCGACGACACCA<br>GAAAGGTGCACATGATCACCGAAAACATCAACGCCTCTTGGCGGAGCATC<br>CACAAGCGGGTGTCAGAGAGAGAAGCCGCTCTGGAAGAAACACATAGACT<br>GCTCCAGCAGTTCCCACTCGACCTGGAAAAGTTCCTGGCCTGGCTGACAG<br>AAGCCGAAACCACCGCTAACGTGCTCCAGGATGCCACCAGAAAAGAGCGG<br>CTGTTGGAGGACAGCAAGGGCGTCAAAGAACTCATGAAGCAGTGGCAGGA<br>TCTGCAAGGGGAGATTGAAGCCCACACCGACGTGTACCACAACCTGGACG<br>AGAACAGCCAGAAGATCCTGCGGTCCCTGGAAGGCTCTGATGATGCTGTG<br>CTGCTTCAGAGGCGGCTGGACAACATGAACTTCAAGTGGAGCGAGCTGCG<br>GAAGAAGTCCCTGAACATCAGAAGCCACCTGGAAGCCTCCAGCGACCAGT<br>GGAAAAGACTGCACCTGTCTCTCCAAGAGCTGCTCGTGTGGCTGCAGCTG<br>AAGGATGACGAGCTGAGTAGACAGGCCCCTATCGGCGGAGATTTTCCCGC<br>CGTGCAGAAACAGAACGACGTGCACCGGGCCTTCAAGAGAGAGCTGAAAA<br>CAAAAGAACCCGTCATCATGAGCACCCTGGAAACCGTGCGGATCTTTCTG<br>ACCGAGCAGCCTCTGGAAGGACTGGAAAAGCTGTACCAAGAGCCTAGAGA<br>GCTGCCTCCTGAAGAAAGGGCCCAGAACGTGACACGGCTGCTTAGAAAGC<br>AGGCCGAGGAAGTGAACACCGAATGGGAGAAGCTGAACCTCCACTCCGCC<br>GACTGGCAGCGGAAGATCGATGAGACACTGGAACGGCTGCGGGAACTGCA<br>AGAAGCCACAGACGAGCTGGACCTGAAACTGCGGCAGGCTGAAGTGATCA<br>AAGGCTCCTGGCAGCCAGTGGGCGATCTGCTGATCGATAGCCTGCAGGAC |

-continued

| SEQ ID NO | Description | SEQ |
|---|---|---|
| | | CATCTGGAAAAAGTCAAGGCCCTGCGGGGAGAGATCGCCCCTCTCAAAGA |
| | | AAACGTGTCCCACGTGAACGATCTGGCCAGGCAGCTGACAACACTGGGCA |
| | | TCCAGCTGAGCCCTTACAACCTGTCTACCTTGGAGGACCTGAATACCCGG |
| | | TGGAAGCTGCTCCAAGTGGCCGTCGAGGATAGAGTGCGGCAGCTGCATGA |
| | | GGCTCACAGAGATTTTGGACCCGCCAGCCAGCACTTCCTGAGCACATCTG |
| | | TTCAAGGCCCCTGGGAGAGAGCTATCAGCCCTAACAAGGTGCCCTACTAC |
| | | ATCAACCACGAGACACAGACCACCTGTTGGGATCACCCCAAGATGACCGA |
| | | ACTGTATCAGTCCCTGGCCGACCTGAACAACGTGCGGTTTAGCGCCTACC |
| | | GGACCGCCATGAAGCTGCGCAGACTGCAGAAAGCTCTGTGCCTGGACCTG |
| | | CTGTCTCTGAGCGCTGCTTGTGATGCCCTGGACCAGCATAACCTCAAGCA |
| | | GAACGACCAGCCTATGGACATCCTGCAGATCATCAACTGCCTGACCACCA |
| | | TCTACGACCGGCTCGAACAAGAGCACAACAACCTGGTCAACGTGCCCCTG |
| | | TGCGTGGACATGTGCCTGAATTGGCTGCTGAACGTGTACGACACCGGCAG |
| | | AACCGGCAGGATCAGAGTGCTGAGCTTCAAGACCGGCATCATCTCCCTGT |
| | | GCAAGGCCCACCTTGAGGATAAGTACCGCTACCTGTTTAAGCAGGTCGCC |
| | | AGCAGCACCGGCTTTTGCGACCAAAGAAGGCTGGGACTGCTGCTCCACGA |
| | | CAGCATTCAGATCCCTAGACAGCTGGGCGAAGTGGCCTCTTTCGGCGGCT |
| | | CTAATATCGAGCCTAGCGTGCGGAGCTGCTTCCAGTTCGCCAACAACAAG |
| | | CCCGAGATTGAGGCCGCACTGTTCCTGGACTGGATGAGACTGGAACCCCA |
| | | GAGCATGGTCTGGCTGCCTGTGCTGCATAGAGTGGCCGCAGCCGAAACAG |
| | | CCAAGCACCAGGCCAAGTGCAACATCTGCAAAGAGTGCCCCATCATCGGC |
| | | TTCCGGTACAGATCCCTGAAGCACTTCAACTACGATATCTGCCAGTCCTG |
| | | CTTCTTCAGCGGCAGAGTGGCCAAGGGCCACAAGATGCACTACCCCATGG |
| | | TGGAATACTGCACCCCTACCACCTCTGGCGAGGACGTGCGGGATTTTGCC |
| | | AAGGTGCTCAAGAACAAGTTCCGGACCAAGCGCTACTTCGCTAAGCACCC |
| | | CAGAATGGGCTACCTGCCAGTGCAGACAGTGCTTGAGGGCGACAACATGG |
| | | AAACCCCTGTGACTCTGATCAACTTCTGGCCCGTGGATAGCGCCCCTGCT |
| | | AGTTCTCCTCAGCTGTCTCACGACGATACCCACAGCAGAATCGAGCACTA |
| | | CGCCTCCAGACTGGCCGAGATGGAAAACAGCAACGGCAGCTACCTGAATG |
| | | ACAGCATCAGCCCCAACGAGAGCATCGACGACGAACATCTGCTCATTCAG |
| | | CACTACTGCCAGAGCCTGAATCAGGACAGCCCTCTGTCTCAGCCTAGAAG |
| | | CCCTGCACAGATCCTGATCAGCCTGGAAAGCGAGGAACGCGGCGAGCTGG |
| | | AAAGAATCCTGGCAGACCTGGAAGAGGAAAACCGGAACCTGCAGGCCGAA |
| | | TACGACAGACTCAAGCAGCAGCACGAGCACAAGGGACTGTCTCCACTGCC |
| | | TTCTCCACCTGAAATGATGCCCACCTCTCCACAGAGCCCCAGAGATGCCG |
| | | AGCTGATTGCCGAAGCCAAACTGCTGAGGCAGCACAAAGGCAGACTCGAA |
| | | GCCAGAATGCAGATTCTCGAAGATCACAACAAGCAGCTCGAATCCCAGCT |
| | | GCACAGACTTAGGCAGCTGCTGGAACAGCCTCAGGCAGAGGCCAAAGTGA |
| | | ATGGCACCACCGTGTCTAGCCCTAGCACAAGCCTGCAGAGATCCGACAGC |
| | | AGCCAGCCAATGCTTCTGAGAGTCGTGGGCTCCCAGACCAGCGATTCTAT |
| | | GGGCGAAGAGGACCTGCTCAGCCCTCCTCAGGATACAAGCACCGGCCTGG |
| | | AAGAAGTGATGGAACAACTGAACAACAGCTTCCCCAGCAGCAGAGGCAGA |
| | | AACACCCCTGGCAAGCCCATGCGCGAGGACACCATGTGATAACTCGAGAA |
| | | TCAACCTCTGGATTACAAAATTTGTGAAAGATTGACTGGTATTCTTAACT |
| | | ATGTTGCTCCTTTTACGCTATGTGGATACGCTGCTTTAATGCCTTTGTAT |
| | | CATGCTATTGCTTCCCGTATGGCTTTCATTTTCTCCTCCTTGTATAAATC |
| | | CTGGTTGCTGTCTCTTTATGAGGAGTTGTGGCCCGTTGTCAGGCAACGTG |
| | | GCGTGGTGTGCACTGTGTTTGCTGACGCAACCCCCACTGGTTGGGGCATT |
| | | GCCACCACCTGTCAGCTCCTTTCCGGGACTTTCGCTTTCCCCCTCCCTAT |
| | | TGCCACGGCGGAACTCATCGCCGCCTGCCTTGCCCGCTGCTGGACAGGGG |
| | | CTCGGCTGTTGGGCACTGACAATTCCGTGGGGTGTGCCTTCTAGTTGCCA |
| | | GCCATCTGTTGTTTGCCCCTCCCCCGTGCCTTCCTTGACCCTGGAAGGTG |
| | | CCACTCCCACTGTCCTTTCCTAATAAAATGAGGAAATTGCATCGCATTGT |
| | | CTGAGTAGGTGTCATTCTATTCTGGGGGGTGGGGTGGGGCAGGACAGCAA |
| | | GGGGGAGGATTGGGAAGACAATAGCAGGCATGCTGGGGATGCGGTGGGCT |
| | | CTATGGGAAGATGTCTACTGAGCTGTGCGATCCCTGCTGGGGACTTTCCG |
| | | CTGGGGACTTTCCGCTGGGGACTTTCCGCCTTCAGCTAAGGAAGCTACCA |
| | | ATATTTAGAGGTACATTTTGTTCTAGAACAAAATGTACCGGTACATTTTG |
| | | TTCTGGTACATTTTGTTCTATTAAGGACAACGTAAGTATAGCGCATAGAC |
| | | ACCTAGCTGGCTTGTTGTCCACAACCATTAAACCTTAAAAGCTTTAAAAG |
| | | CCTTATATATTCTTTTTTTTCTTATAAAACTTAAAACCTTAGAGGCTATT |
| | | TAAGTTGCTGATTTATATTAATTTTATTGTTCAAACATGAGAGCTTAGTA |
| | | CGTGAAACATGAGAGCTTAGTACATTAGCCATGAGAGCTTAGTACATTAG |
| | | CCATGAGGGTTTAGTTCATTAAACATGAGAGCTTAGTACATTAAACATGA |
| | | GAGCTTAGTACATTAAACATGAGAGCTTAGTACATACTATCAACAGGTTG |
| | | AACTGCTGATCTGTACAGTAGAATTGGTAAAGAGAGTTGTGTAAAATATT |
| | | GAGTTCGCACATCTTGTTGTCTGATTATTGATTTTTGGCGAAACCATTTG |
| | | ATCATATGACAAGATGTGTATCTACCTTAACTTAATGATTTTGATAAAAA |
| | | TCATTACGAATGCATGCGGCCGCCGTTACATAACTTACGGTAAATGGCCC |
| | | GCCTGGCTGACCGCCCAACGACCCCCGCCCATTGACGTCAATAATGACGT |
| | | ATGTTCCCATAGTAACGCCAATAGGGACTTTCCATTGACGTCAATGGGTG |
| | | GAGTATTTACGGTAAACTGCCCACTTGGCAGTACATCAAGTGTATCATAT |
| | | GCCAAGTACGCCCCCTATTGACGTCAATGACGGTAAATGGCCCGCCTGGC |
| | | ATTATGCCCAGTACATGACCTTATGGGACTTTCCTACTTGGCAGTACATC |
| | | TACGTATTAGTCATCGCTATTACCATGGTCGAGGTGAGCCCCACGTTCTG |

-continued

| SEQ ID NO | Description | SEQ |
|---|---|---|
| | | CTTCACTCTCCCCATCTCCCCCCCCTCCCCACCCCCAATTTTGTATTTAT<br>TTATTTTTTAATTATTTTGTGCAGCGATGGGGGCGGGGGGGGGGGGGGCG<br>CGCGCCAGGCGGGGCGGGGCGGGGCGAGGGGCGGGGCGGGGCGAGGCGGA<br>GAGGTGCGGCGGCAGCCAATCAGAGCGGCGCGCTCCGAAAGTTTCCTTTT<br>ATGGCGAGGCGGCGGCGGCGGCGGCCCTATAAAAAGCGAAGCGCGCGGCG<br>GGCGGGAGTC |
| 16. | NP- MHCK7-<br>hBGi-DMD-<br>3-WPRE3- DTS | TCTGGATCCACTGCTTAAATACGGACGAGGACAGGGCCCTGTCTCCTCAG<br>CTTCAGGCACCACCACTGACCTGGGACAGTGAATCGTAAGTACTAGCAGC<br>TACAATCCAGCTACCATTCTGCTTTTATTTTATGGTTGGGATAAGGCTGG<br>ATTATTCTGAGTCCAAGCTAGGCCCTTTTGCTAATCATGTTCATACCTCT<br>TATCTTCCTCCCACAGCTCCTGGGCAACGTGCTGGTCTGTGTGCTGGCCC<br>ATCACTTTGGCAAAGAATTGCGATCGCCACCATGCTGTGGTGGGAAGAGG<br>TGGAGGACTGTTACGAGAGAGAGGACGTGCAGAAGAAGACATTCACCAAG<br>TGGGTGAACGCTCAGTTCAGCAAGTTCGGCAAGCAGCACATCGAGAACCT<br>GTTTAGCGATCTACAAGATGGCAGAAGACTGCTGGACCTGCTGGAGGGCC<br>TGACCGGGCAGAAGCTGCCCAAAGAAAAGGGGTCTACAAGAGTGCACGCC<br>CTGAACAACGTGAACAAGGCCCTGAGAGTGCTGCAGAACAACAACGTGGA<br>CCTGGTGAACATCGGCAGCACCGACATCGTGGACGGCAACCACAAGCTGA<br>CCCTGGGCCTGATCTGGAACATCATCCTGCACTGGCAAGTGAAGAACGTG<br>ATGAAGAACATCATGGCCGGCCTGCAGCAGACCAACAGCGAGAAGATCCT<br>GCTGAGCTGGGTGAGACAGAGCACAAGAAACTACCCCCAAGTGAACGTGA<br>TCAACTTCACCACAAGCTGGAGCGACGGCCTGGCCCTGAACGCCCTGATC<br>CACAGCCACAGACCCGACCTGTTCGACTGGAACAGCGTGGTGTGTCAGCA<br>GAGCGCCACACAGAGACTGGAGCACGCCTTCAACATCGCTAGATATCAGC<br>TGGGCATCGAGAAGTTACTGGACCCCGAAGATGTGGACACCACCTACCCC<br>GACAAGAAGAGCATCCTGATGTACATCACAAGCCTGTTCCAAGTGCTGCC<br>TCAGCAAGTGAGCATCGAGGCCATCCAAGAAGTCGAGATGCTGCCTAGAC<br>CCCCCAAGGTGACCAAGGAGGAGCACTTTCAGCTGCACCATCAGATGCAC<br>TACTCTCAGCAGATCACAGTCAGCTTGGCACAAGGCTACGAGAGAACAAG<br>CAGCCCCAAGCCTAGATTCAAGAGCTACGCCTACACCCAAGCCGCCTACG<br>TGACCACAAGTGACCCCACAAGAAGCCCCTTCCCTTCTCAGCACCTGGAG<br>GCCCCCGAGGACAAGAGCTTCGGCAGCAGCCTGATGGAGAGCGAGGTGAA<br>CCTGGACAGATATCAGACCGCGTTAGAAGAAGTGTTGAGCTGGCTGCTGA<br>GCGCCGAGGACACCCTGCAAGCCCAAGGCGAGATCAGCAACGATGTGGAG<br>GTGGTGAAGGATCAGTTCCACACCCACGAGGGCTACATGATGGACCTGAC<br>CGCCCACCAAGGCAGAGTGGGCAACATCCTGCAGCTGGGCAGCAAGCTGA<br>TCGGCACCGGCAAGCTGAGCGAGGACGAGGAAACCGAGGTTCAAGAGCAA<br>ATGAACCTGCTAAACAGCAGATGGGAGTGCCTGAGAGTGGCTAGCATGGA<br>AAAGCAGAGTAACCTGCACAGAGTGCTGATGGACCTGCAGAATCAGAAAT<br>TGAAAGAACTTAATGATTGGCTGACCAAGACCGAGGAGAGAACAAGAAAG<br>ATGGAGGAGGAGCCCCTGGGCCCCGACCTGGAGGACCTGAAGAGACAAGT<br>GCAGCAGCACAAGGTGCTGCAAGAGGACCTGGAGCAAGAGCAAGTGAGAG<br>TGAACTCTCTGACACACATGGTGGTGGTAGTGGACGAGAGCAGCGGCGAT<br>CACGCTACCGCGGCGCTGGAAGAGCAGCTGAAAGTGCTGGGCGACAGATG<br>GGCCAACATCTGCAGATGGACCGAGGACAGATGGGTGCTGCTGCAAGACA<br>TCCTGCTGAAGTGGCAGAGACTGACCGAGGAGCAGTGCCTGTTCAGCGCC<br>TGGCTGAGCGAGAAGGAAGACGCTGTGAACAAGATCCACACCACCGGCTT<br>CAAGGATCAGAACGAGATGCTGAGCTCCCTCCAAAAGCTCGCAGTGCTGA<br>AGGCCGACCTGGAAAAGAAAAAACAGTCGATGGGCAAGCTGTACAGCCTG<br>AAGCAAGACCTGCTGAGCACCCTGAAGAACAAGAGCGTGACACAGAAGAC<br>CGAGGCCTGGCTGGACAACTTCGCTAGATGCTGGGACAACCTGGTACAGA<br>AGTTAGAGAAGTCTACCGCTCAGATCAGCCAAGCCGTAACCACCACACAA<br>CCTAGCCTGACTCAGACCACCGTGATGGAAACCGTGACCACCGTGACAAC<br>CCGTGAGCAGATCCTGGTGAAGCACGCCCAAGAGGAGCTGCCCCCCCCCC<br>CCCCTCAGAAGAAGAGACAGATCACCGTGGACTCAGAGATTCGCAAGAGA<br>CTGGACGTGGACATCACCGAGCTGCACAGCTGGATCACAAGAAGCGAGGC<br>CGTGCTGCAGAGCCCTGAGTTCGCGATCTTTAGAAAGGAGGGCAACTTCA<br>GCGACTTGAAGGAGAAAGTGAACGCCATCGAGAGAGAGAAGGCCGAGAAG<br>TTCAGAAAGTTGCAAGACGCCTCAAGAAGCGCCCAAGCCCTGGTGGAGCA<br>GATGGTTAACGAAGGCGTGAATGCCGACAGCATCAAGCAAGCTAGCGAGC<br>AGCTGAATAGCCGGTGGATTGAATTCTGTCAGCTGCTGAGCGAGAGATTA<br>AACTGGCTGGAGTATCAGAACAACATCATCGCCTTCTACAATCAGCTGCA<br>GCAACTAGAACAAATGACCACCACCGCCGAGAACTGGCTAAAGATTCAGC<br>CCACCACCCCTAGCGAGCCCACCGCCATCAAATCTCAGCTGAAAATTTGC<br>AAGGACGAAGTGAACAGACTGTCGGACCTGCAGCCTCAAATCGAAAGACT<br>GAAAATTCAGAGCATCGCACTTAAGGAGAAGGGCCAAGGACCCATGTTCC<br>TGGACGCCGACTTCGTGGCCTTCACCAACCACTTCAAGCAAGTGTTCAGC<br>GACGTGCAAGCTAGAGAGAAGGAGCTGCAGACCATCTTCGACACCCTGCC<br>CCCCATGAGATACCAAGAAACCATGAGCGCCATCAGAACCTGGGTGCAGC<br>AGAGCGAAACCAAGCTGAGCATCCCTCAGCTGAGCGTGACCGACTACGAG<br>ATCATGGAGCAAAGACTGGGAGAGCTGCAAGCCCTGCAGAGCAGCCTGCA<br>AGAGCAGCAGAGCGGCCTGTACTACCTGAGCACCACCGTGAAGGAGATGT<br>CGAAGAAAGCCCCGTCGGAGATCAGCAGAAAGTATCAGAGCGAGTTCGAG<br>GAGATCGAGGGCAGATGGAAGAAGCTGAGCAGCCAACTGGTGGAACACTG |

-continued

| SEQ ID NO | Description | SEQ |
|---|---|---|
| | | TCAGAAATTAGAAGAACAGATGAACAAGCTGAGAAAGATTCAGAACCACA<br>TTCAGACCCTGAAGAAGTGGATGGCCGAGGTGGACGTGTTCCTGAAAGAG<br>GAGTGGCCCGCCCTGGGCGATTCCGAAATCTTAAAAAGCAGCTGAAGCA<br>GTGCAGACTGCTGGTGTCAGATATCCAAACCATTCAACCAAGCCTGAACA<br>GCGTGAACGAAGGCGGGCAGAAGATCAAGAACGAGGCCGAGCCCGAGTTC<br>GCTAGCAGACTGGAAACCGAGCTGAAGGAGCTGAATACACAGTGGGACCA<br>CATGTGTCAGCAAGTGTACGCTAGAAAGGAAGCGCTGAAGGGCGGGCTGG<br>AGAAGACCGTTAGCCTGCAAAAGGATCTGAGCGAGATGCACGAGTGGATG<br>ACCCAAGCCGAGGAGGAGTACCTGGAGAGAGACTTCGAGTACAAGACCCC<br>CGACGAGCTGCAGAAGGCCGTCGAGGAAATGAAGAGAGCGAAGGAGGAGG<br>CTCAGCAGAAGGAAGCCAAGGTGAAGCTGCTGACTGAATCTGTCAACAGT<br>GTGATAGCTCAAGCACCCCCCGTTGCCCAAGAGGCACTAAAGAAGGAGCT<br>GGAAACTCTGACCACCAACTATCAGTGGCTGTGCACAAGACTGAACGGCA<br>AGTGCAAGACCCTGGAGGAAGTGTGGGCCTGCTGGCACGAGCTGCTGAGC<br>TACCTGGAGAAGGCCAACAAGTGGCTGAACGAGGTGGAGTTCAAGCTGAA<br>GACCACCGAGAACATCCCCGGCGGCGCCGAGGAGATCAGCGAGGTGCTGG<br>ACAGCCTGGAGAACCTGATGAGACACAGCGAGGACAACCCCAATCAGATC<br>AGAATCCTGGCTCAGACCCTGACCGACGGCGGCGTGATGGACGAGCTGAT<br>CAACGAGGAGCTGGAAACCTTTAACTCTAGATGGCGAGAACTGCACGAGG<br>AGGCCGTGAGAAGACAGAAGCTGCTGGAGCAAAGCATTCAGAGCGCCCAA<br>GAAACCGAGAAGAGCCTGCACCTGATCCAAGAGAGCCTGACCTTCATCGA<br>CAAGCAGCTGGCCGCCTACATCGCCGACAAGGTGGACGCCGCTCAGATGC<br>CACAAGAGGCTCAGAAGATTCAGTCCGATCTGACAAGCCACGAGATCAGC<br>CTGGAGGAGATGAAAAAACACAACCAAGGCAAGGAGGCCGCTCAGAGAGT<br>GCTGTCTCAGATCGACGTGGCTCAGAAGAAGCTGCAAGACGTGAGCATGA<br>AGTTCAGACTGTTTCAGAAGCCCGCCAACTTCGAGCAGCGACTGCAAGAG<br>AGCAAGATGATCCTGGACGAGGTGAAGATGCACCTGCCCGCCCTGGAAAC<br>CAAGAGCGTGGAGCAAGAGGTGGTGCAGTCTCAGTTGAACCACTGCGTGA<br>ACCTGTACAAGAGCCTGTCGGAGGTCAAGAGTGAGGTCGAGATGGTGATC<br>AAAACTGGGAGACAGATCGTGCAAAAAAAGCAGACCGAGAACCCCAAGGA<br>GCTGGACGAGCGTGTTACCGCCCTGAAGCTGCACTACAACGAGCTGGGCG<br>CCAAGGTGACCGAGAGAAAGCAGCAGCTGGAGAAGTGCCTGAAGCTGAGC<br>AGAAAGATGAGAAAGGAGATGAACGTGCTGACCGAGTGGCTGGCCGCCAC<br>CGACATGGAGCTGACCAAGAGAAGCGCCGTGGAGGGCATGCCTAGCAACC<br>TGGACAGCGAGGTGGCCTGGGGCAAGGCCACACAGAAGGAGATCGAGAAG<br>CAGAAGGTGCACCTGAAGAGCATCACCGAGGTGGGCGAGGCCCTGAAGAC<br>CGTGCTGGGCAAGAAGGAAACCCTGGTGGAGGACAAGCTGAGCCTGCTGA<br>ACTCGAACTGGATCGCCGTGACAAGCAGAGCCGAGGAGTGGCTGAACCTG<br>CTGTTAGAGTACCAAAAACACATGGAAACCTTCGATCAGAACGTGGACCA<br>CATCACCAAGTGGATCATCCAAGCCGACACCCTGCTGGACGAAAGCGAAA<br>AGAAGAAGCCGCAACAAAAGGAGGATGTGCTGAAGAGACTGAAGGCCGAA<br>CTGAACGATATCAGACCCAAGGTGGACAGCACACGGGACCAAGCCGCCAA<br>CCTGATGGCCAACAGAGGCGACCACTGCAGAAAACTGGTGGAGCCTCAGA<br>TCAGCGAGCTGAACCACAGATTCGCCGCCATCAGCCACAGAATCAAAACC<br>GGCAAAGCGAGCATCCCCTTGAAGGAACTGGAGCAATTTAACAGCGACAT<br>CCAAAAATTGCTCGAACCACTGGAGGCCGAGATTCAGCAAGGCGTGAACC<br>TGAAGGAAGAGGACTTCAACAAGGACATGAACGAGGACAACGAGGGCACC<br>GTGAAAGAACTGCTGCAGAGAGGCGACAACCTGCAGCAGAGAATCACCGA<br>CGAGAGAAAGAGAGAGGAGATCAAGATCAAGCAGCAGCTGCTGCAGACTA<br>AGCACAACGCCCTGAAGGATCTGAGATCTCAGAGGAGAAAAAAGGCTCTG<br>GAAATTTCACATCAGTGGTATCAGTACAAGAGACAAGCAGACGACCTGCT<br>GAAGTGCCTGGACGACATCGAGAAGAAGTTAGCTAGCCTGCCCGAGCCTA<br>GAGACGAGAGAAAGATCAAGGAGATCGACAGAGAGTTACAAAAGAAGAAG<br>GAGGAGCTGAATGCGGTAAGAAGACAAGCGGAAGGCCTGTCCGAGGACGG<br>CGCAGCCATGGCCGTGGAGCCCACACAGATTCAGCTCAGCAAGAGATGGA<br>GAGAGATCGAGAGCAAGTTCGCTCAGTTCAGAAGACTGAACTTCGCTCAG<br>ATCCACACCGTGAGAGAGGAAACCATGATGGTGATGACCGAGGACATGCC<br>CCTGGAGATCTCATACGTTCCTAGCACCTACCTGACCGAGATCACCCACG<br>TGAGCCAAGCCCTGCTGGAGGTGGAGCAGCTGCTGAACGCCCCCGACCTG<br>TGCGCCAAGGACTTCGAGGACCTGTTCAAACAAGAGGAGAGCCTGAAGAA<br>CATCAAGGACAGCCTGCAGCAAAGTAGCGGCAGAATCGACATCATCCACA<br>GCAAGAAGACCGCCGCCCTGCAGAGCGCCACCCCCGTGGAGAGAGTGAAG<br>CTTCAAGAGGCCCTTTCGCAGCTGGATTTTCAGTGGGAGAAGGTGAACAA<br>AATGTACAAGGACAGACAAGGCAGATTCGACAGAAGCGTGGAGAAGTGGA<br>GAAGATTCCACTACGACATCAAGATCTTCAATCAGTGGCTGACCGAGGCA<br>GAGCAGTTCCTGAGAAAGACACAGATCCCCGAGAACTGGGAGCACGCCAA<br>GTACAAGTGGTACCTGAAGGAGCTGCAAGACGGCATCGGGCAGAGACAGA<br>CCGTGGTGAGAACCCTGAACGCCACCGGCGAGGAGATCATCCAACAAAGC<br>TCCAAAACCGACGCTAGCATCCTGCAAGAGAAACTGGGCAGCCTGAACCT<br>GAGATGGCAAGAGGTGTGCAAGCAGCTGAGCGACCGCAAAAAACGGTTAG<br>AGGAGCAGAAGAACATCCTGAGCGAGTTTCAGCGGGACCTGAACGAGTTC<br>GTGCTGTGGCTGGAGGAGGCCGATAACATCGCTAGCATCCCCCTGGAGCC<br>CGGCAAGGAGCAGCAGTTAAAAGAAAAACTTGAGCAAGTGAAGCTGCTGG<br>TGGAGGAGCTGCCCCTGAGACAAGGCATCCTGAAGCAGCTGAACGAGACT<br>GGCGGCCCCGTGCTGGTGAGCGCCCCCATCAGCCCCGAGGAGCAAGACAA |

-continued

| SEQ ID NO | Description | SEQ |
|---|---|---|
| | | GCTGGAGAACAAGCTGAAGCAGACCAACCTGCAGTGGATCAAGGTGAGCA<br>GAGCCCTGCCCGAGAAGCAAGGCGAAATCGAGGCCCAAATAAAGGACCTG<br>GGGCAGCTGGAGAAGAAACTCGAAGACTTGGAAGAACAACTCAACCACTT<br>GCTGCTGTGGCTGAGCCCCATCAGAAATCAGCTGGAGATCTACAATCAGC<br>CCAACCAAGAGGGGCCATTCGACGTGAAGGAAACCGAGATCGCCGTGCAA<br>GCCAAGCAGCCCGATGTGGAGGAGATCCTGAGCAAGGGGCAGCACCTGTA<br>CAAGGAGAAGCCCGCCACACAGCCCGTCAAGCGTAAACTAGAGGATCTTT<br>CCTCTGAGTGGAAGGCCGTGAACCGTCTGCTACAAGAGCTGCGGGCTAAG<br>CAACCCGACTTAGCGCCCGGCCTGACCACCATCGGTGCAAGCCCCACGCA<br>GACCGTGACCCTGGTGACCCAACCCGTGGTGACCAAGGAAACCGCCATCA<br>GCAAGCTGGAGATGCCTAGCAGCCTGATGCTGGAGGTGCCCGCCCTGGCC<br>GACTTCAACAGAGCCTGGACCGAGCTGACCGACTGGCTGAGCCTGCTGGA<br>CCAAGTGATCAAGTCTCAGAGAGTGATGGTGGGCGATCTGGAGGACATCA<br>ATGAGATGATCATCAAGCAGAAGGCCACCATGCAAGACCTGGAGCAGAGA<br>AGACCTCAGCTGGAGGAGCTGATCACCGCCGCTCAGAACCTGAAAAACAA<br>GACGAGCAACCAAGAGGCTAGAACCATCATCACCGACAGAATCGAGAGAA<br>TTCAGAATCAGTGGGACGAGGTGCAAGAGCACCTGCAGAACAGAAGACAG<br>CAACTAAACGAAATGCTCAAGGACAGCACACAGTGGCTGGAGGCCAAGGA<br>GGAGGCGGAGCAAGTGTTGGGCCAAGCTAGAGCCAAGCTGGAGAGCTGGA<br>AGGAGGGACCCTACACCGTGGACGCCATTCAGAAGAAGATCACCGAAACC<br>AAGCAGCTGGCCAAGGACCTGCGACAGTGGCAGACCAACGTGGACGTGGC<br>CAACGATCTTGCCCTGAAGCTGCTGCGCGACTATAGCGCCGACGACACAA<br>GAAAGGTGCACATGATCACCGAGAACATCAACGCTAGCTGGCGTAGCATC<br>CACAAGAGAGTGAGCGAGAGAGAGGCGGCTTTGGAGGAAACCCATAGACT<br>GCTGCAGCAGTTTCCCCTGGACCTGGAGAAGTTCCTGGCCTGGCTGACCG<br>AAGCCGAAACAACCGCCAACGTGCTGCAAGACGCCACAAGAAAGGAGAGA<br>CTGCTGGAGGACAGCAAGGGCGTGAAGGAGCTGATGAAGCAGTGGCAAGA<br>CCTGCAAGGCGAGATCGAAGCGCACACCGACGTGTACCACAACCTGGACG<br>AGAACTCTCAGAAGATCCTGAGAAGCCTGGAGGGCAGCGACGACGCCGTG<br>CTGTTACAGAGAAGGCTGGACAACATGAACTTCAAGTGGAGCGAGCTGAG<br>AAAGAAGAGCCTGAACATCAGAAGCCACCTGGAGGCTAGCAGCGATCAGT<br>GGAAGAGACTGCACCTGAGCCTGCAAGAGCTGCTGGTCTGGCTTCAGTTG<br>AAGGACGATGAGCTGAGCAGACAAGCCCCCATCGGCGGCGACTTCCCCGC<br>CGTGCAGAAGCAGAACGACGTGCATAGAGCCTTCAAGAGAGAGCTGAAGA<br>CCAAGGAGCCCGTGATCATGAGCACCCTGGAAACGGTGAGAATCTTCCTG<br>ACCGAGCAGCCCCTGGAGGGCCTGGAGAAGCTGTACCAAGAGCCTAGAGA<br>GCTGCCCCCCGAGGAGAGAGCTCAGAACGTGACAAGACTGCTGAGAAAGC<br>AAGCCGAAGAGGTGAACACCGAGTGGGAGAAGCTGAACCTGCACAGCGCC<br>GACTGGCAGAGAAAGATCGACGAAACCCTGGAGAGACTGAGAGAATTGCA<br>AGAGGCGACCGACGAGCTGGACCTGAAGCTGAGACAAGCCGAGGTCATCA<br>AGGGCAGCTGGCAGCCCGTGGGCGATCTATTAATTGACTCTCTACAAGAC<br>CACCTGGAGAAAGTGAAGGCCCTGAGAGGCGAGATCGCCCCCCTGAAGGA<br>GAACGTGAGCCACGTGAATGATCTGGCACGTCAGCTGACCACCCTGGGCA<br>TACAACTGTCCCCCTATAACCTGAGCACACTGGAGGATTTGAATACTAGA<br>TGGAAGCTGCTGCAAGTGGCCGTGGAGGACAGAGTAAGACAATTACATGA<br>GGCCCACAGAGACTTCGGCCCCGCTTCTCAGCACTTCCTGAGCACAAGCG<br>TGCAAGGCCCCTGGGAGAGAGCCATTTCCCCCAACAAGGTCCCCTACTAC<br>ATCAACCACGAGACACAGACCACCTGCTGGGACCACCCCAAGATGACCGA<br>GCTGTATCAGAGCCTCGCCGATCTGAACAATGTGAGATTCAGCGCCTACA<br>GAACCGCCATGAAGCTGAGAAGACTGCAGAAGGCCCTGTGCCTGGACTTA<br>TTAAGCCTGAGCGCCGCCTGCGACGCCCTGGATCAGCACAACCTGAAGCA<br>AAACGACCAACCCATGGACATCCTGCAGATCATCAACTGCCTCACCACCA<br>TATACGACAGACTGGAACAAGAGCACAACAACCTGGTGAACGTGCCCCTG<br>TGCGTGGACATGTGCCTGAACTGGCTGCTGAACGTGTACGACACCGGCAG<br>AACCGGCAGAATCAGAGTGCTGAGCTTCAAGACCGGCATCATCAGCCTGT<br>GCAAGGCCCACCTGGAGGACAAATACAGATACCTTTTCAAACAAGTGGCT<br>AGCAGCACCGGCTTCTGCGACCAAAGAAGACTGGGTCTGCTGCTGCACGA<br>CAGCATTCAGATCCCTAGACAGCTGGGCGAGGTGGCTAGCTTCGGCGGCA<br>GCAACATCGAGCCTAGCGTGAGAAGCTGCTTTCAGTTCGCCAACAACAAG<br>CCCGAGATAGAGGCAGCCCTCTTCTTAGACTGGATGAGACTGGAGCCTCA<br>GAGCATGGTATGGCTGCCGGTCCTGCACAGAGTGGCCGCCGCCGAAACCG<br>CCAAGCACCAAGCCAAGTGCAACATCTGCAAGGAGTGCCCCATCATCGGC<br>TTCAGATACAGAAGCCTGAAGCACTTCAACTACGACATCTGTCAGAGCTG<br>CTTCTTCAGCGGCAGAGTGGCCAAGGGCCACAAGATGCACTACCCCATGG<br>TGGAGTACTGCACCCCCACCACAAGCGGCGAGGACGTGAGAGACTTCGCC<br>AAGGTGTTGAAGAATAAGTTTAGAACCAAGAGATACTTCGCCAAGCACCC<br>TAGAATGGGCTACCTGCCCGTGCAGACCGTGCTGGAGGGCGACAACATGG<br>AAACCCCCGTGACCCTGATCAACTTCTGGCCCGTGGACAGCGCCCCCGCT<br>AGCAGCCCTCAGCTGAGCCACGACGACACCCACAGCAGAATCGAGCACTA<br>CGCTAGCAGACTGGCCGAGATGGAGAACAGCAACGGCAGCTACCTGAACG<br>ACAGCATCAGCCCGAATGAGAGCATCGACGACGAGCACCTGCTGATTCAG<br>CACTACTGTCAGAGCCTGAACCAAGACAGCCCCCTGTCTCAGCCTAGAAG<br>CCCCGCTCAGATCCTGATCAGCCTGGAGAGCGAGGAGAGAGGCGAGCTGG<br>AGAGAATCCTAGCAGATCTGGAGGAAGAGAACAGAAACCTGCAAGCCGAG<br>TATGACCGACTGAAACAGCAACATGAGCACAAAGGCCTGAGCCCACTGCC |

-continued

| SEQ ID NO | Description | SEQ |
|---|---|---|
| | | CTCCCCCCCCGAGATGATGCCCACAAGCCCTCAGAGCCCTAGAGACGCCG<br>AGCTGATCGCTGAAGCGAAGTTACTTAGACAACACAAGGGCAGACTGGAG<br>GCTAGAATGCAGATCCTGGAGGACCACAACAAGCAGCTGGAGTCTCAGCT<br>GCACAGACTGAGGCAGCTGCTGGAACAGCCCCAAGCCGAGGCCAAAGTGA<br>ACGGCACCACCGTGAGCAGTCCTAGCACAAGCCTGCAGAGAAGCGACAGC<br>TCTCAGCCCATGCTGCTGAGAGTGGTGGGCTCTCAGACAAGCGACAGCAT<br>GGGCGAGGAGGATCTGCTGAGTCCGCCCCAAGACACAAGCACCGGCCTGG<br>AAGAGGTGATGGAGCAACTGAACAATAGCTTCCCTAGCAGCAGAGGCAGA<br>AACACCCCCGGCAAGCCCATGAGAGAGGACACCATGTGATGACTCGAGAA<br>TCAACCTCTGGATTACAAAATTTGTGAAAGATTGACTGGTATTCTTAACT<br>ATGTTGCTCCTTTTACGCTATGTGGATACGCTGCTTTAATGCCTTTGTAT<br>CATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTG<br>GCGTGGTGTGCACTGTGTTTGCTGACGCAACCCCCACTGGTTGGGGCATT<br>GCCACCACCTGTCAGCTCCTTTCCGGGACTTTCGCTTTCCCCCTCCCTAT<br>TGCCACGGCGGAACTCATCGCCGCCTGCCTTGCCCGCTGCTGGACAGGGG<br>CTCGGCTGTTGGGCACTGACAATTCCGTGGGGTGTGCCTTCTAGTTGCCA<br>GCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAA<br>GGGGGAGGATTGGGAAGACAATAGCAGGCATGCTGGGGATGCGGTGGGCT<br>CTATGGGAAGATGTCTACTGAGCTGTGCGATCCCTGCTGGGGACTTTCCG<br>CTGGGGACTTTCCGCTGGGGACTTTCCGCCTTCAGCTAAGGAAGCTACCA<br>ATATTTAGAGGTACATTTTGTTCTAGAACAAAATGTACCGGTACATTTTG<br>TTCTGGTACATTTTGTTCTATTAAGGACAACGTAAGTATAGCGCATAGAC<br>ACGTGGCGCCATCGGATCCCGGGCCCGTGGCTTGTTGTCCACAACCATTA<br>AACCTTAAAAGCTTTAAAAGCCTTATATATTCTTTTTTTTCTTATAAAAC<br>TTAAAACCTTAGAGGCTATTTAAGTTGCTGATTTATATTAATTTTATTGT<br>TCAAACATGAGAGCTTAGTACGTGAAACATGAGAGCTTAGTACATTAGCC<br>ATGAGAGCTTAGTACATTAGCCATGAGGGTTTAGTTCATTAAACATGAGA<br>GCTTAGTACATTAAACATGAGAGCTTAGTACATTAAACATGAGAGCTTAG<br>TACATACTATCAACAGGTTGAACTGCTGATCTGTACAGTAGAATTGGTAA<br>AGAGAGTTGTGTAAAATATTGAGTTCGCACATCTTGTTGTCTGATTATTG<br>ATTTTTGGCGAAACCATTTGATCATATGACAAGATGTGTATCTACCTTAA<br>CTTAATGATTTTGATAAAAATCATTATCTAGAAGCTGCATGTCTAAGCTA<br>GACCCTTCAGATTAAAAATAACTGAGGTAAGGGCCTGGGTAGGGGAGGTG<br>GTGTGAGACGCTCCTGTCTCTCCTCTATCTGCCCATCGGCCCTTTGGGGA<br>GGAGGAATGTGCCCAAGGACTAAAAAAAGGCCATGGAGCCAGAGGGGCGA<br>GGGCAACAGACCTTTCATGGGCAAACCTTGGGGCCCTGCTGTCTAGCATG<br>CCCCACTACGGGTCTAGGCTGCCCATGTAAGGAGGCAAGGCCTGGGGACA<br>CCCGAGATGCCTGGTTATAATTAACCCAGACATGTGGCTGCCCCCCCCCC<br>CCCAACACCTGCTGCCTCTAAAAATAACCCTGTCCCTGGTGGATCCCCTG<br>CATGCGAAGATCTTCGAACAAGGCTGTGGGGGACTGAGGGCAGGCTGTAA<br>CAGGCTTGGGGGCCAGGGCTTATACGTGCCTGGGACTCCCAAAGTATTAC<br>TGTTCCATGTTCCCGGCGAAGGGCCAGCTGTCCCCCGCCAGCTAGACTCA<br>GCACTTAGTTTAGGAACCAGTGAGCAAGTCAGCCCTTGGGGCAGCCCATA<br>CAAGGCCATGGGGCTGGGCAAGCTGCACGCCTGGGTCCGGGGTGGGCACG<br>GTGCCCGGGCAACGAGCTGAAAGCTCATCTGCTCTCAGGGGCCCCTCCCT<br>GGGGACAGCCCCTCCTGGCTAGTCACACCCTGTAGGCTCCTCTATATAAC<br>CCAGGGGCACAGGGGCTGCCCTCATTCTACCACCACCTCCACAGCAC |
| 17. | NP-MHCK7-hBGi-DMD-4-WPRE3-DTS | TCTGGATCCACTGCTTAAATACGGACGAGGACAGGGCCCTGTCTCCTCAG<br>CTTCAGGCACCACCACTGACCTGGGACAGTGAATCGTAAGTACTAGCAGC<br>TACAATCCAGCTACCATTCTGCTTTTATTTTATGGTTGGGATAAGGCTGG<br>ATTATTCTGAGTCCAAGCTAGGCCCTTTTGCTAATCATGTTCATACCTCT<br>TATCTTCCTCCCACAGCTCCTGGGCAACGTGCTGGTCTGTGTGCTGGCCC<br>ATCACTTTGGCAAAGAATTGCGATCTTCACCAAATGGTCAACGCCCAGT<br>TCAGCAAGTTCGGCAAGCAGCACATCGAGAACCTGTTCAGCGGCCACCAT<br>GCTTTGGTGGGAAGAAGTCGAGGACTGCTACGAGCGCGAGGACGTGCAGA<br>AGAAAACCACCTGCAGGATGGCAGAAGGCTGCTGGATCTGCTGGAAGGCC<br>TGACAGGACAGAAGCTGCCCAAAGAGAAGGGCAGCACAAGAGTGCACGCC<br>CTGAACAACGTGAACAAGGCCCTGAGAGTGCTGCAGAACAACAACGTGGA<br>CCTGGTCAACATCGGCAGCACCGACATCGTGGACGGCAACCACAAACTGA<br>CCCTGGGCCTGATCTGGAACATCATCCTGCACTGGCAAGTGAAGAACGTG<br>ATGAAGAACATCATGGCCGGCCTGCAGCAGACCAACAGCGAGAAGATTCT<br>GCTGAGCTGGGTCCGACAGAGCACCCGGAATTACCCTCAAGTGAACGTGA<br>TCAACTTCACCACCTCTTGGAGCGACGGACTGGCCCTGAATGCCCTGATC<br>CACAGCCACAGACCTGACCTGTTCGACTGGAACAGCGTCGTGTGTCAGCA<br>GAGCGCCACACAGAGGCTGGAACACGCCTTCAATATCGCCAGATACCAGC<br>TGGGCATCGAGAAACTGCTGGACCCCGAGGATGTGGACACCACCTATCCT<br>GACAAGAAATCCATCCTCATGTACATCACCAGCCTGTTCCAGGTGCTGCC<br>CCAGCAGGTTTCCATCGAGGCCATTCAAGAGGTCGAGATGCTGCCCAGAC<br>CTCCTAAAGTGACCAAAGAGGAACACTTCCAGCTGCACCACCAGATGCAC<br>TACTCTCAGCAGATCACCGTGTCTCTGGCCCAGGGCTACGAGAGAACAAG<br>CAGCCCCAAGCCTCGGTTCAAGAGCTACGCCTATACACAGGCCGCCTACG |

-continued

| SEQ ID NO | Description | SEQ |
|---|---|---|
| | | TGACCACCAGCGATCCTACAAGAAGCCCATTTCCTAGCCAGCATCTGGAA GCCCCTGAGGACAAGAGCTTTGGCAGCAGCCTGATGGAAAGCGAAGTGAA CCTGGACCGCTACCAGACAGCCCTGGAAGAGGTTCTGAGCTGGCTGCTGT CTGCCGAGGATACACTGCAGGCTCAGGGCGAGATCAGCAACGACGTGGAA GTGGTCAAGGACCAGTTTCACACCCACGAGGGCTACATGATGGACCTGAC AGCCCACCAGGGCAGAGTGGGCAATATTCTGCAGCTGGGCTCCAAGCTGA TCGGCACAGGCAAGCTGAGCGAGGACGAAGAGACAGAGGTGCAAGAGCAG ATGAACCTGCTGAACAGCAGATGGGAGTGTCTGAGAGTGGCCAGCATGGA AAAGCAGAGCAACCTGCACCGGGTGCTGATGGATCTCCAGAACCAGAAGC TGAAAGAGCTGAACGACTGGCTGACCAAGACCGAGGAACGGACCCGGAAG ATGGAAGAGGAACCTCTGGGACCCGACCTGGAAGATCTGAAAAGACAGGT GCAGCAGCATAAGGTGCTGCAAGAGGACCTCGAACAAGAGCAAGTGCGCG TGAACAGCCTGACACACATGGTGGTGGTCGTGGATGAGAGCAGCGGAGAT CATGCCACAGCCGCTCTGGAAGAACAGCTGAAGGTGCTGGGAGACAGATG GGCCAATATCTGCCGGTGGACCGAGGATAGATGGGTGCTGCTCCAGGACA TCCTGCTGAAGTGGCAGCGGCTGACAGAGGAACAGTGCCTGTTTAGCGCC TGGCTGTCCGAGAAAGAGGACGCCGTCAACAAGATCCACACCACCGGCTT CAAGGATCAGAATGAGATGCTGAGCAGCCTGCAGAAACTGGCCGTGCTGA AGGCTGACCTGGAAAAGAAAAAGCAGTCCATGGGCAAGCTGTACTCCCTG AAGCAGGACCTGCTGAGCACACTGAAGAACAAGTCTGTGACCCAGAAAAC CGAGGCCTGGCTGGACAACTTCGCCCGGTGTTGGGATAACCTGGTGCAGA AGCTGGAAAAGTCCACCGCTCAGATCTCTCAGGCCGTGACCACAACACAG CCTTCTCTGACCCAGACCACCGTGATGGAAACAGTGACCACAGTGACAAC CCGCGAGCAGATCCTGGTCAAGCACGCCCAAGAAGAACTGCCTCCTCCAC CTCCTCAGAAGAAACGGCAGATCACAGTGGACAGCGAGATCCGGAAGAGA CTGGACGTGGACATCACCGAGCTGCACAGCTGGATCACCAGATCCGAAGC CGTGCTGCAGTCCCCTGAGTTCGCCATCTTCAGAAAAGAGGGCAACTTCT CCGACCTGAAAGAGAAAGTCAACGCCATCGAGAGAGAGAAGGCCGAGAAG TTCCGGAAGCTGCAGGACGCCTCTAGATCTGCCCAGGCTCTGGTGGAACA GATGGTCAACGAAGGCGTGAACGCCGACAGCATCAAGCAGGCCTCAGAGC AGCTGAACTCCCGGTGGATCGAGTTCTGTCAGCTCCTGAGCGAGAGACTG AACTGGCTGGAATACCAGAACAATATCATTGCCTTCTACAACCAGCTCCA GCAGCTCGAACAGATGACCACCACAGCCGAGAATTGGCTGAAGATCCAGC CTACCACACCTAGCGAGCCCACCGCCATTAAGAGCCAGCTGAAAATCTGC AAGGACGAAGTGAATCGGCTGAGCGATCTGCAGCCCCAGATCGAAAGACT GAAAATCCAGTCTATCGCCCTCAAAGAGAAAGGACAGGGCCCCATGTTCC TGGACGCCGATTTTGTGGCCTTTACCAACCACTTCAAACAGGTGTTCTCC GACGTGCAGGCCCGGGAAAAAGAGCTGCAGACCATCTTCGACACCCTGCC TCCAATGAGATACCAAGAGACAATGAGCGCCATCCGGACCTGGGTGCAGC AAAGCGAGACAAAGCTGAGCATCCCACAGCTGAGCGTGACCGACTACGAG ATCATGGAACAGAGACTGGGCGAACTGCAGGCCCTCCAGTCTAGCCTGCA AGAACAGCAGTCCGGCCTGTACTACCTGAGCACAACCGTGAAAGAGATGA GCAAGAAGGCCCCTAGCGAGATCTCCCGGAAGTACCAGAGCGAGTTCGAA GAGATCGAAGGCCGGTGGAAGAAGCTGTCTAGCCAGCTGGTTGAGCACTG CCAGAAACTCGAAGAACAAATGAACAAGCTGCGCAAGATCCAGAATCACA TCCAGACGCTGAAGAAATGGATGGCCGAGGTGGACGTGTTCCTGAAAGAA GAGTGGCCCGCTCTGGGCGACTCCGAGATTCTGAAGAAACAGCTCAAACA GTGCCGGCTGCTGGTGTCCGATATCCAGACAATCCAGCCAAGCCTGAACT CCGTGAATGAAGGCGGCCAGAAGATCAAGAACGAGGCCGAGCCTGAGTTT GCCAGCAGACTGGAAACCGAACTGAAAGAACTCAACACCCAGTGGGACCA CATGTGCCAGCAAGTGTACGCCCGGAAAGAGGCCCTGAAAGGCGGACTCG AAAAGACTGTGTCTCTGCAGAAAGACCTGTCTGAGATGCACGAGTGGATG ACCCAGGCCGAAGAGGAATACCTGGAACGGGACTTCGAGTACAAGACCCC TGATGAGCTGCAAAAAGCCGTCGAGGAAATGAAGCGGGCCAAAGAAGAGG CCCAGCAGAAAGAAGCCAAAGTCAAGCTGCTGACCGAGTCCGTGAATAGC GTTATCGCTCAGGCCCCTCCTGTGGCTCAAGAGGCTCTCAAGAAAGAACT GGAAACTCTGACCACCAACTACCAGTGGCTGTGCACCAGACTGAACGGCA AGTGCAAGACACTGGAAGAAGTGTGGGCCTGCTGGCACGAACTGCTGTCC TATCTGGAAAAGGCCAACAAGTGGCTGAACGAGGTGGAATTCAAGCTGAA AACCACCGAGAACATCCCTGGCGGCGCTGAAGAGATTAGCGAGGTGCTGG ACAGCCTGGAAAACCTGATGAGACACAGCGAGGACAACCCCAATCAGATC AGAATCCTGGCTCAGACCCTGACCGATGGCGGCGTGATGGACGAGCTGAT CAACGAGGAACTCGAAACCTTCAACAGCCGGTGGCGGGAACTGCACGAGG AAGCTGTTCGGAGGCAGAAGTTGCTGGAACAGTCTATCCAGAGCGCACAA GAAACCGAGAAGTCCCTGCACCTGATCCAAGAGAGCCTGACCTTCATCGA CAAGCAGCTGGCCGCTTATATCGCCGACAAGGTGGACGCTGCTCAGATGC CCCAAGAGGCACAGAAGATTCAGAGCGACCTGACCAGCCACGAGATTAGC CTGGAAGAAATGAAGAAGCACAACCAGGGCAAAGAGGCCGCTCAGAGAGT CCTGAGCCAGATCGATGTGGCACAGAAAAAGCTCCAGGATGTGTCCATGA AGTTTCGGCTGTTTCAGAAGCCCGCCAACTTCGAGCAGAGACTGCAAGAG TCCAAGATGATCCTGGACGAAGTCAAAATGCATCTGCCCGCACTGGAAAC AAAGTCCGTGGAACAAGAAGTGGTGCAGTCCCAGCTGAACCACTGCGTGA ACCTGTACAAGAGCCTGTCCGAAGTGAAGTCTGAGGTGGAAATGGTCATC AAGACCGGCAGGCAGATCGTCCAGAAGAAGCAGACCGAGAATCCCAAAGA ACTCGACGAGAGAGTGACCGCTCTGAAGCTGCACTACAATGAGCTGGGCG |

-continued

| SEQ ID NO | Description | SEQ |
|---|---|---|
| | | CCAAAGTGACCGAGCGGAAGCAACAGCTTGAGAAGTGCCTGAAACTGTCT |
| | | CGGAAGATGCGGAAAGAAATGAACGTGCTGACAGAGTGGCTGGCCGCCAC |
| | | CGATATGGAACTGACTAAGAGAAGCGCCGTGGAAGGCATGCCCAGCAACC |
| | | TGGATAGTGAAGTGGCCTGGGGCAAAGCCACTCAGAAAGAGATTGAGAAG |
| | | CAGAAGGTCCACCTGAAGTCCATCACCGAAGTGGGCGAAGCCCTGAAAAC |
| | | CGTGCTGGGAAAGAAAGAGACACTGGTCGAGGACAAGCTGTCCCTGCTGA |
| | | ATTCCAACTGGATCGCCGTGACCTCCAGAGCTGAGGAATGGCTGAATCTG |
| | | CTGCTTGAGTACCAGAAACACATGGAAACGTTCGACCAGAACGTCGACCA |
| | | CATCACAAAGTGGATCATCCAGGCTGATACCCTGCTGGACGAGTCCGAGA |
| | | AGAAGAAACCCCAACAAAAAGAAGATGTGCTGAAGCGGCTGAAAGCCGAG |
| | | CTGAATGACATCCGGCCTAAGGTGGACAGCACCAGAGATCAGGCAGCCAA |
| | | CCTGATGGCCAACAGAGGCGACCACTGTCGGAAGCTCGTGGAACCTCAGA |
| | | TCAGCGAGCTTAACCACAGATTTGCCGCCATCAGCCACCGGATCAAGACA |
| | | GGCAAGGCCAGCATTCCTCTCAAAGAGCTTGAGCAGTTCAACAGCGACAT |
| | | CCAAAAGCTGCTCGAACCCCTGGAAGCCGAGATCCAACAGGGCGTCAACC |
| | | TCAAAGAAGAAGATTTCAACAAGGACATGAACGAGGACAATGAGGGCACC |
| | | GTCAAAGAACTGCTGCAGCGGGGCGATAATCTGCAGCAGCGGATTACCGA |
| | | TGAGCGCAAGCGGGAAGAGATCAAGATTAAGCAGCAGCTGCTGCAGACCA |
| | | AGCACAACGCCCTGAAGGACCTGCGGAGCCAGAGAAGAAAGAAGGCCCTG |
| | | GAAATCAGCCACCAGTGGTATCAGTACAAGCGGCAGGCCGACGACCTGCT |
| | | GAAGTGCCTGGATGACATCGAGAAGAAGCTGGCCTCTCTGCCCGAGCCTA |
| | | GGGACGAGAGAAAGATCAAAGAGATCGACCGCGAGCTGCAGAAAAAGAAA |
| | | GAGGAACTGAACGCCGTCCGCAGACAGGCCGAAGGACTTTCTGAAGATGG |
| | | CGCCGCTATGGCCGTGGAACCCACACAGATTCAGCTGAGCAAGCGGTGGC |
| | | GGGAAATCGAGAGCAAGTTCGCCCAGTTCCGGCGGCTGAATTTCGCCCAG |
| | | ATCCACACCGTGCGGGAAGAGACAATGATGGTCATGACAGAGGACATGCC |
| | | CCTTGAGATCAGCTACGTGCCCAGCACCTACCTGACCGAGATCACCCATG |
| | | TGTCTCAGGCCCTGCTGGAAGTGGAACAGCTGCTGAATGCCCCTGACCTG |
| | | TGCGCCAAGGACTTCGAGGACCTGTTCAAGCAAGAGGAAAGCCTGAAGAA |
| | | CATCAAGGACAGCCTGCAGCAGAGCAGCGGCCGGATCGATATCATCCACA |
| | | GCAAGAAAACCGCCGCACTGCAGAGCGCCACACCTGTGGAAAGAGTGAAG |
| | | CTGCAAGAGGCCCTGAGCCAGCTGGATTTCCAGTGGGAGAAAGTGAACAA |
| | | GATGTACAAGGACCGGCAGGGCAGATTCGACCGCAGCGTTGAAAAGTGGC |
| | | GGCGGTTCCACTACGACATCAAGATCTTCAACCAGTGGCTGACCGAGGCC |
| | | GAGCAGTTCCTGAGAAAGACACAGATCCCCGAGAACTGGGAGCACGCCAA |
| | | GTACAAGTGGTATCTGAAAGAGCTGCAGGACGGCATCGGCCAGAGACAGA |
| | | CAGTCGTGCGGACACTGAATGCCACCGGCGAGGAAATCATCCAGCAGTCC |
| | | AGCAAGACCGACGCCAGCATCCTGCAAGAGAAGCTGGGCAGCCTGAACCT |
| | | GCGGTGGCAAGAAGTGTGCAAGCAGCTGAGCGACCGGAAGAAGCGGCTGG |
| | | AAGAACAGAAGAATATCCTGAGCGAGTTCCAGCGGGACCTGAACGAGTTC |
| | | GTGCTGTGGCTCGAAGAGGCCGACAATATCGCCAGCATTCCCCTGGAACC |
| | | TGGCAAAGAGCAGCAGCTGAAAGAAAAGCTGGAACAAGTGAAACTGCTGG |
| | | TCGAGGAACTGCCCCTGAGACAGGGAATCCTGAAACAGCTGAACGAGACA |
| | | GGCGGCCCTGTGCTGGTGTCTGCCCCTATTTCTCCCGAGGAACAGGACAA |
| | | GCTGGAAAACAAGCTGAAGCAGACCAACCTGCAGTGGATCAAGGTGTCCA |
| | | GAGCACTGCCTGAGAAGCAGGGCGAGATCGAGGCCCAGATCAAGGACCTG |
| | | GGACAGCTCGAAAAGAAGCTTGAGGACCTCGAAGAACAGCTCAACCATCT |
| | | GCTGCTTTGGCTGAGCCCCATCCGGAACCAGCTGGAAATCTACAACCAGC |
| | | CTAATCAAGAGGGCCCCTTCGACGTGAAAGAAACCGAGATTGCCGTGCAG |
| | | GCCAAGCAGCCCGATGTGGAAGAGATCCTGTCTAAGGGCCAGCACCTGTA |
| | | CAAAGAGAAGCCCGCCACACAGCCCGTGAAGCGGAAACTGGAAGATCTGA |
| | | GCAGCGAGTGGAAGGCCGTGAACCGGCTGCTGCAAGAACTGAGAGCCAAA |
| | | CAGCCTGATCTGGCCCCTGGCCTGACAACAATTGGCGCCTCTCCTACACA |
| | | GACCGTGACACTGGTCACACAGCCTGTGGTCACCAAAGAGACAGCCATCA |
| | | GCAAACTGGAAATGCCCAGCAGTCTGATGCTCGAAGTGCCCGCACTGGCC |
| | | GACTTCAATAGAGCCTGGACCGAGCTGACCGACTGGCTCAGTCTGCTGGA |
| | | CCAAGTCATCAAGTCCCAGAGAGTGATGGTCGGAGATCTTGAGGACATCA |
| | | ACGAGATGATCATTAAGCAGAAAGCCACCATGCAGGACCTTGAGCAGAGA |
| | | AGGCCCCAGCTTGAAGAACTGATCACCGCCGCTCAGAACCTGAAAAACAA |
| | | GACCAGCAATCAAGAAGCCCGGACCATCATCACCGACCGGATCGAGAGAA |
| | | TCCAGAACCAGTGGGACGAAGTGCAAGAGCATCTGCAGAACAGACGGCAG |
| | | CAGCTCAATGAGATGCTGAAGGACAGCACACAGTGGCTGGAAGCCAAAGA |
| | | AGAAGCCGAGCAGGTTCTCGGACAGGCCAGAGCTAAGCTGGAATCTTGGA |
| | | AAGAGGGACCCTACACCGTCGACGCCATCCAGAAGAAGATCACCGAGACA |
| | | AAGCAGCTGGCCAAGGATCTGAGACAGTGGCAGACCAATGTGGACGTGGC |
| | | CAACGACCTGGCTCTGAAGCTGCTGAGAGACTACAGCGCCGACGACACCA |
| | | GAAAGGTGCACATGATCACCGAAAACATCAACGCCTCTTGGCGGAGCATC |
| | | CACAAGCGGGTGTCAGAGAGAGAAGCCGCTCTGGAAGAAACACATAGACT |
| | | GCTCCAGCAGTTCCCACTCGACCTGGAAAAGTTCCTGGCCTGGCTGACAG |
| | | AAGCCGAAACCACCGCTAACGTGCTCCAGGATGCCACCAGAAAAGAGCGG |
| | | CTGTTGGAGGACAGCAAGGGCGTCAAAGAACTCATGAAGCAGTGGCAGGA |
| | | TCTGCAAGGGGAGATTGAAGCCCACACCGACGTGTACCACAACCTGGACG |
| | | AGAACAGCCAGAAGATCCTGCGGTCCCTGGAAGGCTCTGATGATGCTGTG |
| | | CTGCTTCAGAGGCGGCTGGACAACATGAACTTCAAGTGGAGCGAGCTGCG |
| | | GAAGAAGTCCCTGAACATCAGAAGCCACCTGGAAGCCTCCAGCGACCAGT |

-continued

| SEQ ID NO | Description | SEQ |
|---|---|---|
| | | GGAAAAGACTGCACCTGTCTCTCCAAGAGCTGCTCGTGTGGCTGCAGCTG<br>AAGGATGACGAGCTGAGTAGACAGGCCCCTATCGGCGGAGATTTTCCCGC<br>CGTGCAGAAACAGAACGACGTGCACCGGGCCTTCAAGAGAGAGCTGAAAA<br>CAAAAGAACCCGTCATCATGAGCACCCTGGAAACCGTGCGGATCTTTCTG<br>ACCGAGCAGCCTCTGGAAGGACTGGAAAAGCTGTACCAAGAGCCTAGAGA<br>GCTGCCTCCTGAAGAAAGGGCCCAGAACGTGACACGGCTGCTTAGAAAGC<br>AGGCCGAGGAAGTGAACACCGAATGGGAGAAGCTGAACCTCCACTCCGCC<br>GACTGGCAGCGGAAGATCGATGAGACACTGGAACGGCTGCGGGAACTGCA<br>AGAAGCCACAGACGAGCTGGACCTGAAACTGCGGCAGGCTGAAGTGATCA<br>AAGGCTCCTGGCAGCCAGTGGGCGATCTGCTGATCGATAGCCTGCAGGAC<br>CATCTGGAAAAAGTCAAGGCCCTGCGGGGAGAGATCGCCCCTCTCAAAGA<br>AAACGTGTCCCACGTGAACGATCTGGCCAGGCAGCTGACAACACTGGGCA<br>TCCAGCTGAGCCCTTACAACCTGTCTACCTTGGAGGACCTGAATACCCGG<br>TGGAAGCTGCTCCAAGTGGCCGTCGAGGATAGAGTGCGGCAGCTGCATGA<br>GGCTCACAGAGATTTTGGACCCGCCAGCCAGCACTTCCTGAGCACATCTG<br>TTCAAGGCCCCTGGGAGAGAGCTATCAGCCCTAACAAGGTGCCCTACTAC<br>ATCAACCACGAGACACAGACCACCTGTTGGGATCACCCCAAGATGACCGA<br>ACTGTATCAGTCCCTGGCCGACCTGAACAACGTGCGGTTTAGCGCCTACC<br>GGACCGCCATGAAGCTGCGCAGACTGCAGAAAGCTCTGTGCCTGGACCTG<br>CTGTCTCTGAGCGCTGCTTGTGATGCCCTGGACCAGCATAACCTCAAGCA<br>GAACGACCAGCCTATGGACATCCTGCAGATCATCAACTGCCTGACCACCA<br>TCTACGACCGGCTCGAACAAGAGCACAACAACCTGGTCAACGTGCCCCTG<br>TGCGTGGACATGTGCCTGAATTGGCTGCTGAACGTGTACGACACCGGCAG<br>AACCGGCAGGATCAGAGTGCTGAGCTTCAAGACCGGCATCATCTCCCTGT<br>GCAAGGCCCACCTTGAGGATAAGTACCGCTACCTGTTTAAGCAGGTCGCC<br>AGCAGCACCGGCTTTTGCGACCAAAGAAGGCTGGGACTGCTGCTCCACGA<br>CAGCATTCAGATCCCTAGACAGCTGGGCGAAGTGGCCTCTTTCGGCGGCT<br>CTAATATCGAGCCTAGCGTGCGGAGCTGCTTCCAGTTCGCCAACAACAAG<br>CCCGAGATTGAGGCCGCACTGTTCCTGGACTGGATGAGACTGGAACCCCA<br>GAGCATGGTCTGGCTGCCTGTGCTGCATAGAGTGGCCGCAGCCGAAACAG<br>CCAAGCACCAGGCCAAGTGCAACATCTGCAAAGAGTGCCCCATCATCGGC<br>TTCCGGTACAGATCCCTGAAGCACTTCAACTACGATATCTGCCAGTCCTG<br>CTTCTTCAGCGGCAGAGTGGCCAAGGGCCACAAGATGCACTACCCCATGG<br>TGGAATACTGCACCCCTACCACCTCTGGCGAGGACGTGCGGGATTTTGCC<br>AAGGTGCTCAAGAACAAGTTCCGGACCAAGCGCTACTTCGCTAAGCACCC<br>CAGAATGGGCTACCTGCCAGTGCAGACAGTGCTTGAGGGCGACAACATGG<br>AAACCCCTGTGACTCTGATCAACTTCTGGCCCGTGGATAGCGCCCCTGCT<br>AGTTCTCCTCAGCTGTCTCACGACGATACCCACAGCAGAATCGAGCACTA<br>CGCCTCCAGACTGGCCGAGATGGAAAACAGCAACGGCAGCTACCTGAATG<br>ACAGCATCAGCCCCAACGAGAGCATCGACGACGAACATCTGCTCATTCAG<br>CACTACTGCCAGAGCCTGAATCAGGACAGCCCTCTGTCTCAGCCTAGAAG<br>CCCTGCACAGATCCTGATCAGCCTGGAAAGCGAGGAACGCGGCGAGCTGG<br>AAAGAATCCTGGCAGACCTGGAAGAGGAAAACCGGAACCTGCAGGCCGAA<br>TACGACAGACTCAAGCAGCAGCACGAGCACAAGGGACTGTCTCCACTGCC<br>TTCTCCACCTGAAATGATGCCCACCTCTCCACAGAGCCCCAGAGATGCCG<br>AGCTGATTGCCGAAGCCAAACTGCTGAGGCAGCACAAAGGCAGACTCGAA<br>GCCAGAATGCAGATTCTCGAAGATCACAACAAGCAGCTCGAATCCCAGCT<br>GCACAGACTTAGGCAGCTGCTGGAACAGCCTCAGGCAGAGGCCAAAGTGA<br>ATGGCACCACCGTGTCTAGCCCTAGCACAAGCCTGCAGAGATCCGACAGC<br>AGCCAGCCAATGCTTCTGAGAGTCGTGGGCTCCCAGACCAGCGATTCTAT<br>GGGCGAAGAGGACCTGCTCAGCCCTCCTCAGGATACAAGCACCGGCCTGG<br>AAGAAGTGATGGAACAACTGAACAACAGCTTCCCCAGCAGCAGAGGCAGA<br>AACACCCCTGGCAAGCCCATGCGCGAGGACACCATGTGATAACTCGAGAA<br>TCAACCTCTGGATTACAAAATTTGTGAAAGATTGACTGGTATTCTTAACT<br>ATGTTGCTCCTTTTACGCTATGTGGATACGCTGCTTTAATGCCTTTGTAT<br>CATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTG<br>GCGTGGTGTGCACTGTGTTTGCTGACGCAACCCCCACTGGTTGGGGCATT<br>GCCACCACCTGTCAGCTCCTTTCCGGGACTTTCGCTTTCCCCCTCCCTAT<br>TGCCACGGCGGAACTCATCGCCGCCTGCCTTGCCCGCTGCTGGACAGGGG<br>CTCGGCTGTTGGGCACTGACAATTCCGTGGGGTGTGCCTTCTAGTTGCCA<br>GCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAA<br>GGGGGAGGATTGGGAAGACAATAGCAGGCATGCTGGGGATGCGGTGGGCT<br>CTATGGGAAGATGTCTACTGAGCTGTGCGATCCCTGCTGGGGACTTTCCG<br>CTGGGGACTTTCCGCTGGGGACTTTCCGCCTTCAGCTAAGGAAGCTACCA<br>ATATTTAGAGGTACATTTTGTTCTAGAACAAAATGTACCGGTACATTTTG<br>TTCTGGTACATTTTGTTCTATTAAGGACAACGTAAGTATAGCGCATAGAC<br>ACCTAGCTGGCTTGTTGTCCACAACCATTAAACCTTAAAAGCTTTAAAAG<br>CCTTATATATTCTTTTTTTTCTTATAAAACTTAAAACCTTAGAGGCTATT<br>TAAGTTGCTGATTTATATTAATTTTATTGTTCAAACATGAGAGCTTAGTA<br>CGTGAAACATGAGAGCTTAGTACATTAGCCATGAGAGCTTAGTACATTAG<br>CCATGAGGGTTTAGTTCATTAAACATGAGAGCTTAGTACATTAAACATGA<br>GAGCTTAGTACATTAAACATGAGAGCTTAGTACATACTATCAACAGGTTG |

-continued

| SEQ ID NO | Description | SEQ |
|---|---|---|
| | | AACTGCTGATCTGTACAGTAGAATTGGTAAAGAGAGTTGTGTAAAATATT<br>GAGTTCGCACATCTTGTTGTCTGATTATTGATTTTTGGCGAAACCATTTG<br>ATCATATGACAAGATGTGTATCTACCTTAACTTAATGATTTTGATAAAAA<br>TCATTACGAATGCATCTAGAAGCTGCATGTCTAAGCTAGACCCTTCAGAT<br>TAAAAATAACTGAGGTAAGGGCCTGGGTAGGGGAGGTGGTGTGAGACGCT<br>CCTGTCTCTCCTCTATCTGCCCATCGGCCCTTTGGGGAGGAGGAATGTGC<br>CCAAGGACTAAAAAAAGGCCATGGAGCCAGAGGGGCGAGGGCAACAGACC<br>TTTCATGGGCAAACCTTGGGGCCCTGCTGTCTAGCATGCCCCACTACGGG<br>TCTAGGCTGCCCATGTAAGGAGGCAAGGCCTGGGGACACCCGAGATGCCT<br>GGTTATAATTAACCCAGACATGTGGCTGCCCCCCCCCCCCCAACACCTGC<br>TGCCTCTAAAAATAACCCTGTCCCTGGTGGATCCCCTGCATGCGAAGATC<br>TTCGAACAAGGCTGTGGGGGACTGAGGGCAGGCTGTAACAGGCTTGGGGG<br>CCAGGGCTTATACGTGCCTGGGACTCCCAAAGTATTACTGTTCCATGTTC<br>CCGGCGAAGGGCCAGCTGTCCCCCGCCAGCTAGACTCAGCACTTAGTTTA<br>GGAACCAGTGAGCAAGTCAGCCCTTGGGGCAGCCCATACAAGGCCATGGG<br>GCTGGGCAAGCTGCACGCCTGGGTCCGGGGTGGGCACGGTGCCCGGGCAA<br>CGAGCTGAAAGCTCATCTGCTCTCAGGGGCCCCTCCCTGGGGACAGCCCC<br>TCCTGGCTAGTCACACCCTGTAGGCTCCTCTATATAACCCAGGGGCACAG<br>GGGCTGCCCTCATTCTACCACCACCTCCACAGCAC |
| 18. | CBA | CGTTACATAACTTACGGTAAATGGCCCGCCTGGCTGACCGCCCAACGACC<br>CCCGCCCATTGACGTCAATAATGACGTATGTTCCCATAGTAACGCCAATA<br>GGGACTTTCCATTGACGTCAATGGGTGGAGTATTTACGGTAAACTGCCCA<br>CTTGGCAGTACATCAAGTGTATCATATGCCAAGTACGCCCCCTATTGACG<br>TCAATGACGGTAAATGGCCCGCCTGGCATTATGCCCAGTACATGACCTTA<br>TGGGACTTTCCTACTTGGCAGTACATCTACGTATTAGTCATCGCTATTAC<br>CATGGTCGAGGTGAGCCCCACGTTCTGCTTCACTCTCCCCATCTCCCCCC<br>CCTCCCCACCCCCAATTTTGTATTTATTTATTTTTTAATTATTTTGTGCA<br>GCGATGGGGGCGGGGGGGGGGGGGGGGCGCGCCAGGCGGGGCGGGGCGGG<br>GCGAGGGGCGGGGCGGGGCGAGGCGGAGAGGTGCGGCGGCAGCCAATCAGA<br>GCGGCGCGCTCCGAAAGTTTCCTTTTATGGCGAGGCGGCGGCGGCGGCGG<br>CCCTATAAAAAGCGAAGCGCGCGGCGGGCGGGAGTCTCTGGATCCACTGC<br>TTAAATACGGACGAGGACAGGGCCCTGTCTCCTCAGCTTCAGGCACCACC<br>ACTGACCTGGGACAGTGAATCGTAAGTACTAGCAGCTACAATCCAGCTAC<br>CATTCTGCTTTTATTTTATGGTTGGGATAAGGCTGGATTATTCTGAGTCC<br>AAGCTAGGCCCTTTTGCTAATCATGTTCATACCTCTTATCTTCCTCCCAC<br>AGCTCCTGGGCAACGTGCTGGTCTGTGTGCTGGCCCATCACTTTGGCAAA<br>GAATTGCGATCGCCACC |
| 19. | DMD-1 | ATGCTGTGGTGGGAAGAGGTGGAGGATTGCTACGAGCGGGAGGATGTGCA<br>GAAAAAGACTTTCACCAAGTGGGTAAATGCTCAGTTCTCTAAGTTCGGGA<br>AGCAACACATCGAGAACTTGTTTTCCGACCTCCAGGATGGCAGGCGCCTG<br>CTTGACTTGCTGGAGGGTCTGACTGGTCAGAAGCTCCCTAAGGAGAAGGG<br>CAGCACCAGAGTTCACGCTCTGAATAACGTTAACAAAGCCCTGAGGGTCC<br>TCCAGAATAACAATGTAGACCTGGTGAACATCGGTTCTACCGACATCGTG<br>GACGGGAATCATAAACTGACCTTGGGGCTCATCTGGAACATTATCTTGCA<br>CTGGCAGGTGAAGAACGTCATGAAGAATATCATGGCCGGGCTGCAACAGA<br>CCAACTCCGAAAAGATTTTGCTCAGCTGGGTGCGCCAGTCCACCCGCAAT<br>TATCCACAAGTCAACGTTATCAATTTCACCACTAGTTGGAGTGATGGCCT<br>CGCCCTGAACGCCTTGATCCACAGTCACCGCCCCGACCTGTTTGACTGGA<br>ACTCTGTGGTTTGCCAACAGAGCGCTACCCAGCGTCTCGAACATGCTTTC<br>AATATCGCTAGATACCAGCTCGGTATCGAGAAGCTGTTGGATCCTGAGGA<br>CGTAGACACGACCTACCCCGATAAAAAGAGCATCCTGATGTATATCACTT<br>CTCTGTTTCAGGTGCTTCCTCAACAGGTGTCCATTGAAGCCATCCAAGAG<br>GTCGAAATGCTGCCCAGGCCCCCTAAGGTGACAAAAGAAGAGCATTTCCA<br>GCTGCATCACCAGATGCATTACAGTCAACAGATTACCGTCAGCTTGGCTC<br>AGGGATATGAGCGCACGTCCTCTCCTAAGCCCAGATTTAAGTCCTACGCA<br>TATACCCAGGCTGCCTACGTGACCACTTCCGACCCAACTAGGAGCCCCTT<br>TCCCTCCCAACACCTGGAGGCCCCTGAGGACAAAAGCTTCGGATCTAGTC<br>TGATGGAGTCCGAGGTGAATCTGGATCGGTACCAAACTGCTCTGGAGGAA<br>GTGCTGTCCTGGCTTCTGTCCGCTGAAGACACCCTGCAGGCGCAAGGTGA<br>GATTTCTAACGACGTCGAGGTCGTGAAGGATCAGTTCCACACTCATGAGG<br>GCTACATGATGGACTTGACAGCTCACCAGGGAAGAGTTGGTAACATCCTG<br>CAGCTTGGCTCCAAGTTGATTGGCACGGGAAAGCTTAGCGAGGACGAGGA<br>AACCGAGGTACAGGAGCAGATGAACTTGCTGAATTCCCGCTGGGAGTGCC<br>TGAGAGTTGCGTCCATGGAAAAGCAGTCAAACCTTCACAGAGTGCTGATG<br>GACCTTCAGAACCAGAAGCTGAAGGAGCTGAACGATTGGCTGACAAAGAC<br>CGAGGAACGCACAAGAAAAATGGAAGAGGAACCTCTGGGACCTGATCTGG<br>AGGATCTGAAGCGCCAGGTCCAACAGCATAAGGTGCTGCAGGAGGATTTG<br>GAGCAGGAGCAGGTGCGGGTCAACAGCCTGACACATATGGTGGTTGTGGT<br>CGATGAGTCCTCTGGCGATCATGCTACCGCAGCGCTGGAAGAGCAGCTGA<br>AGGTGCTGGGGGATCGCTGGGCCAACATTTGCAGATGGACAGAAGACCGG<br>TGGGTCCTGCTTCAAGATATCCTGCTCAAGTGGCAGCGCCTGACTGAAGA<br>GCAGTGCCTGTTCTCAGCTTGGTTGAGCGAAAAAGAGGACGCAGTTAACA<br>AGATCCATACCACAGGCTTCAAGGATCAGAATGAGATGCTGAGCTCACTG |

-continued

| SEQ ID NO | Description | SEQ |
|---|---|---|
| | | CAGAAGCTGGCTGTGCTGAAGGCCGACTTGGAGAAGAAAAAGCAGTCCAT<br>GGGCAAACTGTATAGCCTGAAGCAGGACCTGCTCAGCACCCTGAAGAACA<br>AAAGCGTTACGCAGAAAACTGAGGCCTGGTTGGACAACTTTGCTCGCTGC<br>TGGGATAACCTTGTGCAGAAGCTGGAAAAGTCAACCGCACAGATCTCCCA<br>GGCTGTGACCACTACGCAGCCTAGCTTGACCCAGACAACCGTTATGGAAA<br>CCGTGACAACCGTGACAACGAGAGAGCAAATCCTGGTTAAGCATGCCCAG<br>GAGGAACTGCCGCCACCCCCGCCTCAGAAGAAACGGCAGATTACGGTGGA<br>CAGCGAGATCCGCAAGAGGCTGGACGTCGACATCACTGAGCTCCACTCAT<br>GGATCACGCGGAGTGAGGCCGTGCTGCAGTCTCCCGAGTTCGCTATTTTC<br>CGCAAGGAGGGAAACTTCTCTGACTTGAAAGAGAAGGTGAATGCCATCGA<br>GCGTGAAAAGGCAGAAAAGTTCAGAAAGCTGCAGGACGCCTCTCGCTCTG<br>CGCAGGCCCTGGTGGAGCAGATGGTCAACGAGGGTGTTAACGCTGACAGC<br>ATCAAACAGGCAAGCGAACAGCTGAACTCCAGATGGATCGAATTTTGCCA<br>ACTGCTCTCCGAACGCCTCAACTGGTTGGAGTACCAGAACAATATTATCG<br>CTTTTTACAACCAGCTGCAGCAACTGGAGCAGATGACAACTACCGCCGAA<br>AACTGGCTGAAAATTCAGCCAACCACACCGTCCGAGCCAACTGCGATCAA<br>GTCTCAGCTGAAGATCTGCAAGGACGAAGTGAACCGTCTTAGCGACTTGC<br>AACCCCAGATTGAACGGCTCAAGATTCAGTCTATTGCTCTGAAGGAGAAG<br>GGTCAGGGTCCGATGTTCCTGGATGCAGATTTTGTCGCATTTACCAATCA<br>CTTCAAACAGGTGTTTAGTGACGTCCAGGCGCGCGAGAAAGAGCTGCAGA<br>CTATTTTTGACACCCTGCCTCCCATGAGGTACCAGGAGACAATGAGTGCC<br>ATTCGCACCTGGGTGCAACAGTCCGAGACGAAATTGTCAATCCCACAGCT<br>GTCCGTGACAGACTACGAGATTATGGAGCAACGGTTGGGGGAGCTGCAGG<br>CTCTTCAGAGTTCCCTGCAGGAGCAACAGAGCGGACTGTACTATCTTTCC<br>ACTACCGTGAAGGAAATGAGTAAGAAAGCCCCTTCCGAGATCAGCCGCAA<br>ATACCAGTCTGAATTCGAAGAGATCGAGGGACGCTGGAAAAAGCTGTCAA<br>GCCAGCTGGTCGAGCACTGTCAGAAGCTGGAAGAGCAGATGAACAAGCTG<br>CGTAAAATCCAGAACCATATTCAGACCCTCAAGAAATGGATGGCAGAAGT<br>TGACGTGTTTCTGAAGGAAGAGTGGCCTGCCCTCGGCGATAGCGAAATCC<br>TTAAGAAACAACTCAAGCAGTGCCGCCTCCTGGTGTCCGATATTCAGACA<br>ATCCAGCCTTCCCTGAACAGCGTTAATGAGGGCGGACAGAAAATTAAAAA<br>CGAGGCCGAACCCGAGTTCGCTTCTCGCCTGGAGACTGAACTGAAGGAGC<br>TGAATACCCAGTGGGACCATATGTGTCAACAGGTCTACGCACGCAAAGAG<br>GCACTGAAGGGCGGTCTGGAGAAGACTGTCTCACTCCAGAAGGACCTGAG<br>CGAGATGCACGAGTGGATGACCCAGGCCGAAGAGGAATACCTGGAGCGTG<br>ATTTTGAGTATAAGACCCCAGACGAACTCCAGAAAGCCGTTGAAGAGATG<br>AAGAGGGCTAAGGAGGAAGCCCAACAGAAGGAGGCGAAAGTGAAGCTCCT<br>GACAGAGTCCGTGAACTCCGTCATCGCTCAAGCTCCTCCCGTGGCTCAGG<br>AGGCCCTCAAGAAAGAGCTGGAAACTCTGACCACAAATTACCAGTGGTTG<br>TGTACCCGCTTGAACGGTAAGTGCAAGACCCTGGAAGAGGTGTGGGCCTG<br>CTGGCACGAGCTCCTGTCCTATCTTGAGAAGGCGAACAAATGGCTGAACG<br>AAGTGGAATTCAAGTTGAAAACAACTGAGAACATTCCGGGAGGCGCTGAG<br>GAAATCTCTGAGGTGCTGGACTCTCTGGAAAATCTGATGCGTCATTCTGA<br>AGACAATCCTAACCAGATCAGGATTCTGGCACAGACCCTCACTGACGGAG<br>GCGTTATGGACGAACTTATCAACGAGGAACTGGAGACATTCAATTCCCGT<br>TGGCGTGAGCTGCACGAAGAGGCCGTGCGCCGTCAGAAGTTGCTGGAACA<br>GTCTATCCAGTCCGCCCAGGAGACAGAGAAATCTCTCCACCTGATCCAGG<br>AGAGTCTGACGTTTATCGATAAGCAGCTGGCTGCCTACATCGCCGACAAG<br>GTGGACGCTGCCCAGATGCCCCAAGAGGCTCAGAAGATCCAGTCCGACCT<br>GACGTCTCATGAAATCAGCCTGGAAGAGATGAAAAAGCACAACCAGGGCA<br>AAGAGGCTGCCCAGCGCGTCCTCTCCCAGATTGACGTGGCTCAGAAAAAG<br>TTGCAGGACGTGAGCATGAAGTTTAGGCTGTTCCAGAAACCCGCCAACTT<br>CGAACAGAGACTGCAGGAGTCTAAGATGATCCTGGATGAGGTCAAGATGC<br>ACCTCCCTGCTCTGGAAACAAAATCTGTGGAGCAGGAGGTCGTGCAGTCA<br>CAACTGAACCATTGTGTGAACCTCTACAAGTCTCTCAGCGAGGTGAAGTC<br>CGAGGTCGAGATGGTGATCAAGACCGGACGCCAGATTGTGCAGAAAAAGC<br>AGACAGAGAACCCCAAAGGAGCTGGACGAACGGGTGACCGCCCTGAAGCTC<br>CACTACAACGAGTTGGGTGCCAAAGTCACTGAAAGAAAGCAACAGCTGGA<br>GAAGTGTCTGAAGCTGAGCCGCAAGATGCGCAAAGAAATGAACGTCTTGA<br>CCGAGTGGTTGGCGGCCACCGACATGGAGCTGACCAAGAGATCCGCTGTG<br>GAGGGCATGCCCTCCAACCTTGACTCAGAGGTGGCCTGGGGCAAGGCCAC<br>ACAGAAGGAGATCGAAAAACAGAAGGTGCATCTTAAATCAATCACTGAGG<br>TGGGCGAAGCTCTGAAGACAGTGCTGGGCAAGAAAGAGACACTTGTAGAG<br>GACAAGCTCTCCCTTCTGAATAGCAATTGGATCGCCGTAACTAGTCGCGC<br>GGAGGAATGGCTGAACCTCCTGTTGGAATACCAGAAACACATGGAAACCT<br>TCGATCAGAACGTGGACCATATTACCAAGTGGATTATCCAGGCTGACACT<br>CTCCTGGACGAGTCTGAGAAAAAGAAACCCCAGCAAAAGGAAGATGTGCT<br>GAAGCGCCTGAAGGCGGAATTGAACGACATCCGCCCGAAGGTTGATTCCA<br>CCCGCGACCAAGCGGCCAACCTTATGGCTAACCGCGGGGACCATTGCAGA<br>AAACTGGTGGAACCGCAGATCTCTGAGCTGAACCACAGATTCGCCGCGAT<br>TTCTCACAGAATTAAGACTGGCAAGGCCTCCATCCCTCTGAAAGAGCTGG<br>AGCAGTTCAACTCTGATATTCAGAAGCTTCTGGAGCCCCTGGAGGCAGAA<br>ATCCAACAGGGCGTCAACCTGAAAGAGGAAGACTTTAATAAGGACATGAA<br>TGAGGATAACGAAGGTACCGTCAAGGAGCTCCTGCAGAGGGGCGACAATC<br>TGCAGCAAAGAATCACTGACGAACGTAAGCGCGAAGAGATTAAGATCAAG |

-continued

| SEQ ID NO | Description | SEQ |
|---|---|---|
| | | CAACAGCTGTTGCAGACTAAGCACAACGCCCTGAAGGATCTGAGGTCCCA |
| | | GCGCAGGAAAAAGGCCCTGGAGATTTCCCACCAGTGGTACCAGTACAAGC |
| | | GCCAGGCCGATGACCTTCTGAAGTGCCTCGACGATATCGAGAAAAAGCTG |
| | | GCCTCACTGCCCGAGCCCCGCGACGAGCGCAAGATCAAGGAGATTGACCG |
| | | TGAGCTCCAGAAGAAAAAGGAGGAACTGAACGCGGTGCGCAGACAGGCCG |
| | | AGGGCCTCTCCGAGGACGGCGCTGCGATGGCTGTTGAGCCCACTCAGATC |
| | | CAACTGAGCAAGCGGTGGAGAGAGATCGAGTCTAAGTTCGCGCAATTTAG |
| | | GCGCCTCAACTTCGCCCAGATTCACACGGTCCGTGAGGAAACGATGATGG |
| | | TGATGACAGAGGATATGCCACTGGAAATCAGCTACGTGCCCAGTACATAT |
| | | CTCACCGAAATCACCCATGTGTCCCAGGCTCTCCTGGAGGTGGAACAGTT |
| | | GCTCAACGCTCCCGACTTGTGCGCTAAGGACTTCGAGGACCTGTTCAAGC |
| | | AGGAAGAGAGCCTGAAAAACATTAAGGACTCCCTGCAACAGTCAAGCGGC |
| | | CGCATCGATATCATTCATTCTAAGAAAACCGCTGCCCTGCAGTCTGCAAC |
| | | CCCCGTAGAGCGCGTCAAACTGCAGGAAGCTCTCAGCCAACTGGATTTCC |
| | | AGTGGGAGAAGGTGAACAAGATGTATAAGGATCGTCAGGGCCGGTTCGAC |
| | | CGCTCTGTGGAGAAGTGGCGCCGTTTCCACTACGATATCAAGATTTTCAA |
| | | TCAATGGTTGACCGAGGCAGAGCAGTTCCTCAGAAAGACACAGATCCCTG |
| | | AAAATTGGGAGCATGCCAAGTACAAGTGGTATCTGAAGGAGCTGCAGGAC |
| | | GGGATCGGACAACGTCAGACCGTGGTCCGCACCCTGAACGCAACCGGCGA |
| | | GGAAATTATCCAACAGTCTAGCAAGACAGATGCTAGCATCCTCCAGGAGA |
| | | AGCTCGGAAGCCTCAACCTTCGCTGGCAGGAGGTGTGCAAGCAGCTGTCA |
| | | GACAGGAAGAAACGCCTGGAGGAACAGAAGAACATCCTTTCAGAGTTCCA |
| | | GAGAGATCTGAACGAATTCGTGCTTTGGCTTGAAGAGGCCGATAACATCG |
| | | CAAGCATCCCACTGGAGCCTGGTAAGGAACAGCAATTGAAGGAGAAGCTG |
| | | GAGCAGGTAAAGCTGCTCGTGGAAGAGCTGCCTCTGAGGCAGGGAATTCT |
| | | CAAGCAGCTCAACGAGACTGGGGGCCCGGTTTTGGTGAGCGCCCCAATTA |
| | | GCCCAGAAGAGCAGGACAAGTTGGAGAACAAGCTGAAGCAGACCAACCTG |
| | | CAGTGGATCAAGGTGTCCCGCGCACTGCCCGAAAAGCAGGGAGAGATTGA |
| | | GGCCCAGATCAAGGATCTGGGACAGCTGGAGAAAAAGCTGGAAGACCTGG |
| | | AGGAACAGCTGAACCATTTGCTCCTGTGGTTGTCCCCCATCAGAAATCAG |
| | | CTGGAAATCTACAACCAACCGAACCAGGAAGGTCCGTTTGATGTTAAGGA |
| | | AACCGAGATCGCTGTGCAGGCGAAGCAGCCTGACGTAGAAGAGATCCTGT |
| | | CAAAGGGACAGCACCTCTACAAGGAGAAGCCCGCCACCCAGCCAGTCAAG |
| | | CGGAAGCTCGAAGACCTGTCCAGCGAGTGGAAAGCCGTCAACCGCCTCCT |
| | | GCAAGAGCTGCGTGCCAAGCAACCGGACCTGGCGCCAGGTCTGACTACCA |
| | | TTGGCGCAAGTCCTACCCAGACTGTCACCCTGGTGACCCAACCCGTTGTG |
| | | ACAAAGGAAACCGCCATCAGCAAGCTGGAGATGCCTAGCTCTTTGATGCT |
| | | GGAGGTTCCCGCCCTCGCCGACTTCAACCGTGCTTGGACAGAACTGACCG |
| | | ACTGGCTGTCCCTCCTGGACCAAGTGATCAAGAGCCAGCGCGTGATGGTG |
| | | GGTGATCTTGAGGATATTAACGAAATGATTATCAAGCAGAAGGCCACCAT |
| | | GCAGGACTTGGAGCAGAGGCGCCCCCAGTTGGAGGAACTGATCACCGCCG |
| | | CGCAGAATCTGAAAAACAAAACTTCCAATCAGGAAGCGAGAACCATCATT |
| | | ACAGACAGAATTGAGAGAATTCAAAACCAGTGGGACGAAGTGCAAGAACA |
| | | CCTCCAGAACCGGCGTCAACAGCTGAACGAGATGCTGAAGGATTCCACTC |
| | | AATGGCTGGAAGCTAAGGAAGAGGCCGAGCAGGTCCTTGGACAGGCACGC |
| | | GCTAAGCTGGAGTCCTGGAAAGAAGGCCCCTATACAGTGGACGCAATTCA |
| | | AAAGAAAATCACCGAGACGAAGCAACTGGCCAAGGACCTGAGACAGTGGC |
| | | AAACCAACGTTGATGTGGCTAATGACCTGGCCTTGAAGCTCCTGCGTGAC |
| | | TACTCCGCGGATGACACTAGAAAGGTGCACATGATCACCGAGAATATCAA |
| | | CGCTAGCTGGCGCTCCATCCATAAGCGTGTGAGTGAGCGCGAAGCCGCTC |
| | | TGGAGGAAACCCATCGCCTGCTTCAACAGTTTCCTTTGGACCTGGAAAAG |
| | | TTCCTGGCCTGGCTCACAGAAGCCGAGACAACCGCCAACGTGCTGCAGGA |
| | | CGCCACCCGTAAGGAGCGCTTGCTGGAGGATAGTAAGGGGGTGAAGGAGT |
| | | TGATGAAGCAGTGGCAAGATCTGCAGGGGGAAATCGAGGCACATACCGAC |
| | | GTCTATCATAACCTGGATGAGAATTCCCAGAAAATCCTGCGCAGCTTGGA |
| | | GGGCAGTGATGACGCGGTGCTTCTGCAACGGCGCTTGGACAACATGAACT |
| | | TCAAGTGGTCCGAGTTGCGTAAAAAGAGTCTGAACATTCGCTCCCACCTG |
| | | GAGGCTTCTAGTGACCAGTGGAAGCGCCTGCACCTGAGCCTGCAAGAACT |
| | | GCTCGTGTGGCTGCAACTGAAGGATGACGAGTTGAGTCGTCAGGCCCCTA |
| | | TCGGAGGTGACTTTCCGGCTGTCCAGAAACAGAACGACGTGCATAGGGCA |
| | | TTTAAGCGCGAGTTGAAGACAAAGGAGCCAGTCATTATGTCCACGCTGGA |
| | | AACCGTGCGCATTTTCCTGACTGAGCAGCCTCTGGAGGGGCTGGAGAAGC |
| | | TGTACCAGGAGCCTCGCGAGTTGCCCCCTGAAGAGCGTGCCCAGAATGTG |
| | | ACCCGCCTGTTGCGTAAGCAGGCCGAGGAAGTGAACACCGAGTGGGAGAA |
| | | GCTGAACCTGCATTCCGCGGATTGGCAGAGGAAGATTGACGAGACGCTGG |
| | | AGAGGCTCCGTGAGTTGCAGGAGGCAACCGACGAACTGGACCTCAAGCTG |
| | | CGTCAAGCAGAGGTGATCAAGGGGAGTTGGCAGCCGGTCGGCGATTTGCT |
| | | GATCGACTCCCTGCAGGATCACCTGGAAAAGGTTAAAGCTTTGCGCGGGG |
| | | AAATTGCCCCGCTGAAGGAGAACGTGAGCCACGTTAACGATCTGGCCAGA |
| | | CAGCTGACCACTCTGGGTATCCAGCTGAGCCCGTACAATCTGAGCACCCT |
| | | CGAAGACTTGAATACGAGATGGAAACTCCTGCAGGTGGCAGTGGAGGACA |
| | | GGGTGCGCCAATTGCACGAGGCCCACCGGGACTTTGGACCGGCCAGCCAG |
| | | CATTTCCTCAGTACCTCTGTTCAGGGCCCGTGGGAGCGGGCCATCTCCCC |
| | | CAACAAGGTCCCCTATTACATCAACCATGAAACCCAGACTACCTGTTGGG |
| | | ACCACCCTAAAATGACTGAGTTGTATCAATCTCTGGCCGACTTGAATAAC |

-continued

| SEQ ID NO | Description | SEQ |
|---|---|---|
| | | GTGCGCTTCTCAGCCTACAGGACTGCAATGAAACTCAGACGCCTCCAAAA GGCCCTTTGTCTGGACTTGCTGTCCCTTAGCGCTGCCTGTGATGCTCTGG ATCAGCACAATTTGAAACAAAACGACCAGCCGATGGACATCCTCCAGATT ATCAACTGCCTGACTACCATCTACGACAGACTGGAACAGGAGCATAATAA CCTGGTGAACGTCCCCCTGTGCGTGGACATGTGCCTGAACTGGCTGCTCA ATGTGTATGACACGGGTAGAACAGGACGGATCAGGGTCCTGTCCTTTAAG ACCGGTATCATTTCTCTGTGTAAGGCACATCTGGAGGACAAGTACCGCTA CCTGTTTAAGCAGGTCGCCAGCTCCACTGGCTTCTGCGATCAAAGGCGGC TGGGTCTGCTCCTGCACGACTCCATTCAGATCCCGAGACAGTTGGGTGAA GTGGCGTCCTTCGGCGGTTCTAATATCGAGCCTAGCGTCCGCAGCTGTTT CCAATTCGCCAATAACAAGCCGGAGATCGAAGCGGCCCTTTTCCTGGACT GGATGCGTCTGGAACCTCAGAGCATGGTTTGGCTTCCGGTGCTTCATCGC GTGGCCGCTGCCGAAACCGCTAAACATCAGGCCAAATGTAACATCTGTAA GGAATGCCCGATTATCGGTTTCCGGTACCGTAGCCTCAAGCATTTCAACT ATGATATTTGTCAATCTTGCTTCTTTAGCGGACGGGTGGCCAAAGGCCAC AAAATGCACTACCCGATGGTCGAGTATTGCACTCCTACAACCTCCGGCGA GGACGTGCGCGATTTTGCCAAAGTGCTGAAAAACAAGTTTAGAACCAAGC GTTACTTTGCCAAGCATCCACGTATGGGCTACCTGCCTGTCCAGACCGTT CTGGAAGGTGATAACATGGAGACACCCGTGACTTTGATTAACTTTTGGCC AGTAGACTCTGCTCCGGCAAGCTCCCCTCAGCTCTCCCACGATGACACTC ACAGCCGTATCGAGCACTACGCCTCTCGCCTGGCTGAGATGGAGAACTCT AACGGTTCATACCTGAATGACAGTATCTCCCCAAACGAGAGTATCGATGA CGAACATCTGCTCATTCAGCATTACTGTCAATCCTTGAATCAGGACAGCC CCCTGTCCCAGCCACGGTCCCCGGCCCAGATCCTGATTTCACTGGAGTCC GAAGAGAGAGGGGAACTGGAAAGGATCCTCGCTGACCTGGAAGAGGAAAA CCGGAACCTGCAGGCTGAATACGACCGCTTGAAGCAGCAACACGAGCACA AGGGCTTGAGCCCGTTGCCAAGCCCTCCGGAGATGATGCCAACTAGCCCT CAGAGCCCACGGGATGCCGAGCTCATCGCTGAAGCTAAGTTGCTGAGACA GCACAAGGGACGTCTGGAGGCCCGCATGCAGATCCTGGAGGATCATAATA AACAGTTGGAGAGCCAACTGCATAGGCTGCGCCAGCTCCTGGAGCAGCCA CAGGCCGAGGCTAAGGTCAACGGAACTACCGTTTCCAGCCCGTCCACATC TCTGCAGCGCTCAGATAGTTCCCAGCCTATGTTGCTGAGAGTGGTTGGAT CTCAGACCTCCGACTCAATGGGCGAAGAGGACTTGCTGTCTCCCCCACAG GACACTAGCACAGGACTCGAAGAGGTGATGGAACAGCTCAATAACTCTTT TCCTTCTAGTCGGGGTCGCAATACCCCTGGAAAGCCCATGCGCGAAGACA CCATGTAATAG |
| 20. | DMD-5 | ATGCTGTGGTGGGAGGAAGTTGAAGATTGTTATGAGAGAGAAGATGTCCA GAAAAAGACCTTTACCAAATGGGTGAACGCACAGTTCTCCAAATTTGGGA AACAGCATATAGAAAATTTGTTCAGCGATCTTCAGGATGGGCGCAGGTTG CTTGACCTTCTGGAAGGACTGACCGGGCAGAAGCTGCCCAAAGAGAAAGG GTCTACCAGAGTTCACGCTCTGAACAACGTGAATAAGGCACTGCGAGTCC TGCAAAATAACAACGTCGACCTGGTGAACATAGGCAGCACTGATATTGTT GATGGGAACCATAAACTCACACTGGGTCTGATTTGGAATATTATACTGCA CTGGCAGGTCAAAAATGTTATGAAAAATATTATGGCCGGGCTTCAACAGA CCAATTCCGAGAAGATCCTGCTGTCTTGGGTTAGGCAGTCCACGAGGAAC TACCCTCAAGTGAACGTTATTAACTTCACAACATCATGGAGTGATGGACT TGCCCTGAACGCCTTGATCCACTCCCATAGGCCAGACCTGTTCGATTGGA ATAGCGTAGTCTGTCAGCAGAGTGCTACACAACGCCTGGAACACGCCTTT AACATAGCCAGGTATCAGCTTGGAATTGAGAAACTCCTCGACCCTGAAGA CGTAGACACCACTTACCCCGACAAAAAATCCATTCTTATGTACATAACTT CCTTGTTTCAGGTTCTCCCCCAGCAGGTGTCCATCGAGGCTATACAGGAG GTCGAAATGCTCCCCAGACCCCCTAAGGTCACGAAGGAAGAGCACTTCCA ACTGCACCATCAGATGCACTACAGTCAACAGATCACTGTGAGTCTCGCAC AGGGGTACGAAAGGACCAGCTCCCCTAAACCCCGCTTCAAGTCCTACGCC TATACTCAGGCAGCTTACGTAACCACAAGTGACCCCACGCGGTCACCCTT CCCAAGCCAGCACCTGGAGGCTCCCGAGGACAAAAGCTTTGGATCATCCC TGATGGAATCTGAAGTCAATCTCGATAGGTACCAAACCGCTCTGGAGGAG GTCCTCAGTTGGCTCCTTTCAGCTGAAGATACTCTGCAGGCACAGGGTGA GATCAGCAATGACGTGGAGGTAGTGAAAGATCAGTTTCACACTCACGAGG GCTATATGATGGACCTGACAGCCCATCAAGGTCGCGTTGGCAATATCCTG CAGTTGGGGTCCAAACTGATTGGTACCGGTAAGTTGTCCGAGGACGAAGA GACAGAAGTGCAGGAGCAGATGAACCTGCTTAATTCTAGATGGGAATGCC TCCGCGTGGCCTCTATGGAGAAGCAGTCCAATCTCCATCGGGTTCTCATG GACTTGCAGAATCAGAAGCTGAAGGAACTCAACGACTGGTTGACCAAGAC TGAGGAGCGCACCAGAAAGATGGAGGAGGAGCCACTCGGTCCTGATCTTG AAGATCTGAAACGACAAGTTCAGCAGCACAAGGTCCTGCAGGAGGATCTC GAACAGGAGCAGGTCCGGGTGAACAGCCTGACCCATATGGTTGTCGTTGT CGACGAGTCAAGTGGGGACCATGCTACGGCTGCGCTTGAGGAACAGCTGA AGGTCTTGGGCGATAGATGGGCGAATATCTGCCGCTGGACTGAAGATAGA TGGGTGCTGCTGCAGGATATTCTTTTGAAGTGGCAGCGGTTGACCGAAGA ACAATGCTTGTTTAGCGCCTGGCTGAGTGAGAAAGAGGATGCGGTGAATA AGATACACACTACTGGCTTCAAAGACCAGAATGAAATGCTTAGCAGCCTG CAGAAACTTGCGGTTCTTAAGGCCGACTTGGAAAAGAAAAAGCAGTCAAT GGGTAAGCTGTACTCACTCAAGCAGGACCTGCTGTCAACTTTGAAGAACA |

-continued

| SEQ ID NO | Description | SEQ |
|---|---|---|
| | | AGAGCGTCACGCAAAAGACTGAGGCCTGGCTCGACAATTTTGCTAGGTGC<br>TGGGATAACCTGGTGCAGAAGTTGGAAAAGTCCACTGCTCAGATCTCTCA<br>AGCCGTGACTACTACCCAGCCCAGCCTGACACAGACTACCGTCATGGAAA<br>CCGTTACCACTGTGACGACTAGGGAGCAGATACTCGTTAAGCACGCTCAA<br>GAGGAATTGCCGCCACCTCCTCCCCAAAAGAAACGCCAGATTACCGTCGA<br>CTCTGAAATACGCAAGAGACTGGATGTGGACATCACGGAACTGCACTCTT<br>GGATTACCAGAAGCGAGGCAGTCCTCCAGAGCCCCGAGTTTGCGATCTTC<br>AGGAAGGAAGGCAACTTTTCAGATCTGAAGGAAAAGGTGAACGCCATCGA<br>GCGCGAGAAAGCCGAGAAGTTCCGCAAACTGCAGGATGCGAGCCGGTCTG<br>CTCAGGCCTTGGTGGAGCAAATGGTGAATGAAGGCGTAAATGCGGACAGC<br>ATCAAGCAGGCCTCCGAGCAGCTCAATTCAAGATGGATCGAGTTCTGTCA<br>GCTGCTCAGCGAGCGATTGAACTGGCTGGAGTATCAAAATAACATAATCG<br>CGTTTTACAACCAGCTGCAACAGCTGGAACAGATGACGACTACTGCAGAG<br>AACTGGCTTAAAATCCAGCCTACAACTCCTTCTGAACCCACAGCAATCAA<br>AAGCCAGCTCAAGATCTGCAAGGACGAAGTCAACCGCCTCTCCGATTTGC<br>AGCCTCAGATAGAACGACTCAAGATCCAAAGTATCGCACTCAAAGAAAAG<br>GGGCAAGGCCCTATGTTTCTCGATGCTGATTTTGTGGCTTTCACCAACCA<br>TTTTAAGCAAGTGTTTTCAGATGTGCAAGCCCGGGAAAAGGAACTGCAAA<br>CCATTTTTGATACCCTGCCTCCAATGCGGTACCAGGAGACTATGTCTGCA<br>ATTCGCACCTGGGTGCAACAAAGCGAGACGAAACTTTCTATTCCACAACT<br>GTCCGTGACAGACTACGAAATTATGGAACAGCGACTGGGAGAACTCCAAG<br>CCCTTCAGTCCAGCCTTCAGGAGCAGCAGTCAGGATTGTACTATCTGTCA<br>ACCACCGTGAAGGAAATGTCAAAAAAGGCTCCCTCCGAAATATCTCGCAA<br>GTATCAGTCTGAGTTTGAAGAGATTGAAGGGAGATGGAAGAAACTGTCCT<br>CACAGCTGGTTGAGCACTGTCAGAAGTTGGAAGAGCAGATGAACAAGTTG<br>CGCAAGATTCAAAATCACATACAGACACTCAAAAAGTGGATGGCGGAGGT<br>TGACGTCTTCCTTAAAGAGGAGTGGCCAGCCCTGGGCGACTCAGAGATCC<br>TGAAAAAGCAACTGAAACAGTGCCGACTGCTGGTGTCCGACATCCAGACA<br>ATACAGCCAAGTTTGAATAGCGTGAATGAGGGTGGACAAAAAATCAAAAA<br>CGAGGCTGAGCCCGAGTTCGCCTCCAGATTGGAAACCGAGCTGAAGGAAC<br>TTAATACACAGTGGGATCATATGTGTCAGCAGGTTTATGCCCGGAAGGAA<br>GCACTGAAAGGGGGGCTGGAGAAAACCGTGAGCCTTCAGAAGGACCTTAG<br>CGAGATGCACGAGTGGATGACCCAGGCGGAGGAAGAGTATCTCGAACGGG<br>ATTTTGAGTATAAGACACCAGATGAACTTCAGAAGGCAGTCGAAGAGATG<br>AAACGGGCAAAGGAAGAGGCTCAGCAGAAGGAAGCAAAGGTTAAACTTCT<br>GACAGAATCCGTTAACAGCGTTATAGCCCAAGCTCCCCCCGTTGCCCAGG<br>AAGCTCTTAAAAAGGAACTGGAAACACTGACAACAAACTACCAGTGGCTG<br>TGCACCCGCTTGAACGGCAAATGCAAAACCCTGGAAGAGGTCTGGGCTTG<br>TTGGCATGAACTCCTGTCATACCTGGAAAAAGCTAATAAGTGGCTGAATG<br>AGGTGGAGTTTAAATTGAAAACGACCGAAAACATCCCTGGCGGTGCAGAG<br>GAGATATCTGAGGTGCTCGATAGCCTGGAGAATCTTATGAGGCATAGCGA<br>GGATAACCCCAACCAGATTAGGATACTGGCCCAAACTCTGACCGACGGCG<br>GAGTGATGGACGAGCTGATAAACGAGGAACTGGAAACCTTTAATTCACGC<br>TGGCGAGAACTTCACGAGGAGGCAGTCAGGCGCCAGAAACTGCTGGAGCA<br>GTCCATCCAGAGTGCCCAGGAGACTGAGAAGTCACTTCATCTGATCCAGG<br>AGAGTTTGACGTTTATCGACAAGCAGCTTGCCGCCTACATTGCAGACAAG<br>GTCGATGCTGCTCAGATGCCGCAAGAGGCTCAGAAAATCCAGAGCGACCT<br>GACAAGCCACGAGATTAGCCTGGAGGAAATGAAAAAGCACAACCAGGGTA<br>AAGAGGCCGCCCAGCGGGTTCTGAGCCAGATCGATGTCGCACAGAAGAAA<br>CTCCAAGATGTAAGCATGAAGTTCCGACTGTTTCAGAAACCAGCGAACTT<br>TGAGCAGCGACTGCAGGAGTCTAAAATGATCCTCGATGAGGTGAAAATGC<br>ATCTGCCAGCCCTGGAAACTAAGAGCGTGGAGCAGGAGGTGGTTCAGAGT<br>CAGCTGAACCACTGCGTAAACCTCTATAAAAGTCTTAGTGAAGTGAAGAG<br>CGAGGTGGAGATGGTGATTAAGACTGGTAGACAGATTGTACAGAAAAAGC<br>AGACGGAGAACCCCAAAGAGTTGGATGAACGGGTGACAGCCCTTAAGCTC<br>CACTATAACGAGCTGGGAGCCAAAGTGACTGAGAGAAAGCAGCAACTTGA<br>AAAATGTCTGAAGCTGAGCAGAAAGATGCGGAAGGAAATGAATGTGCTGA<br>CAGAGTGGCTGGCTGCGACCGACATGGAACTTACAAAGAGGAGCGCCGTG<br>GAAGGCATGCCTTCCAATCTGGATAGTGAGGTCGCTTGGGGCAAAGCTAC<br>ACAGAAGGAAATTGAGAAGCAAAAAGTGCATCTTAAGAGCATTACTGAAG<br>TTGGCGAGGCTTTGAAAACCGTCCTCGGCAAGAAAGAGACTCTGGTAGAA<br>GATAAACTCTCACTGCTGAACTCAAACTGGATCGCAGTCACTAGTCGGGC<br>CGAAGAGTGGCTGAATTTGCTGTTGGAGTACCAAAAGCATATGGAGACTT<br>TCGATCAGAATGTCGACCACATTACGAAGTGGATAATCCAGGCGGACACA<br>CTGTTGGATGAGTCCGAGAAAAAGAAACCTCAGCAGAAGGAAGACGTGCT<br>CAAACGACTCAAAGCCGAACTGAACGACATCAGGCCCAAAGTTGATTCCA<br>CCCGGGATCAAGCGGCCAATCTCATGGCCAACCGGGGGGATCACTGCAGA<br>AAGTTGGTAGAACCTCAGATAAGCGAACTTAATCATAGATTTGCCGCCAT<br>ATCACATAGGATTAAGACCGGTAAGGCTTCAATCCCCCTGAAGGAACTCG<br>AACAGTTTAATAGTGACATCCAGAAGCTCCTGGAGCCTCTCGAAGCCGAG<br>ATTCAACAGGGTGTAAACCTTAAGGAAGAGGATTTTAATAAGGATATGAA<br>TGAGGACAATGAAGGCACGGTCAAAGAGCTCCTCCAGAGGGGAGACAATT<br>TGCAGCAGCGGATCACCGATGAACGCAAACGCGAAGAGATCAAAATTAAG<br>CAGCAGCTCCTCCAAACAAAGCACAATGCCCTTAAAGACCTCAGAAGCCA<br>GCGGCGGAAAAAGGCTCTGGAAATCAGCCATCAATGGTATCAGTACAAGC |

-continued

| SEQ ID NO | Description | SEQ |
|---|---|---|
| | | GGCAAGCGGACGATCTCCTGAAATGTCTGGATGATATCGAGAAAAAACTG<br>GCCAGTCTGCCAGAGCCCAGAGATGAGCGCAAAATCAAGGAAATCGACAG<br>GGAGCTTCAGAAGAAAAAAGAGGAGCTGAACGCCGTCCGAAGGCAGGCCG<br>AAGGGCTGTCAGAAGATGGGGCCGCCATGGCAGTGGAACCTACCCAGATT<br>CAACTGTCCAAGCGCTGGAGAGAGATTGAAAGTAAGTTCGCACAATTCCG<br>GAGGCTTAATTTTGCTCAGATTCACACAGTTAGGGAGGAAACCATGATGG<br>TGATGACCGAAGACATGCCACTCGAAATCAGCTACGTCCCTAGCACATAT<br>CTCACGGAGATTACCCACGTGTCCCAGGCACTGCTGGAAGTCGAGCAATT<br>GTTGAACGCCCCTGATCTCTGCGCCAAGGATTTCGAAGACTTGTTCAAGC<br>AAGAGGAAAGCCTCAAGAACATCAAAGACAGTCTTCAGCAGTCCTCAGGC<br>AGAATTGATATTATCCACTCCAAGAAAACAGCCGCTCTCCAGAGCGCTAC<br>CCCTGTCGAACGAGTGAAACTGCAAGAGGCCTTGTCTCAGTTGGACTTCC<br>AGTGGGAGAAAGTCAACAAGATGTACAAGGACAGGCAGGGTCGGTTCGAC<br>CGGAGCGTCGAAAAATGGCGGAGATTCCATTATGACATCAAGATATTCAA<br>TCAGTGGCTTACAGAGGCGGAGCAATTTTTGAGAAAGACGCAGATTCCCG<br>AAAACTGGGAGCATGCCAAGTACAAGTGGTACCTCAAAGAGCTCCAGGAT<br>GGAATCGGCCAGAGACAGACCGTAGTTAGAACACTGAACGCAACTGGAGA<br>AGAGATTATCCAGCAGTCCTCCAAAACTGACGCCTCTATCCTCCAGGAGA<br>AGCTTGGCAGCCTTAACCTGCGGTGGCAGGAGGTGTGTAAACAACTGTCA<br>GATAGGAAAAAAAGACTTGAGGAACAGAAGAACATTCTGAGCGAGTTCCA<br>ACGAGATCTCAACGAGTTCGTACTGTGGCTGGAGGAGGCCGACAACATCG<br>CTTCAATCCCCCTGGAACCCGGCAAGGAACAGCAGCTTAAGGAAAAATTG<br>GAACAGGTAAAACTGTTGGTAGAGGAGCTCCCATTGCGGCAGGGCATTCT<br>CAAGCAGCTGAATGAAACTGGAGGTCCCGTTCTGGTCAGTGCGCCCATAA<br>GCCCGGAAGAGCAGGACAAGTTGGAAAACAAGCTGAAGCAAACAAATCTG<br>CAGTGGATCAAAGTGAGCCGGGCTCTTCCAGAAAAGCAAGGCGAGATTGA<br>AGCCCAGATTAAGGATCTTGGCCAGCTTGAGAAAAAGCTGGAGGATCTGG<br>AAGAGCAGCTGAACCATTTGCTTCTGTGGCTGAGTCCCATTAGAAACCAG<br>CTGGAAATCTACAACCAGCCAAACCAAGAGGGCCCTTTCGACGTCAAGGA<br>AACTGAGATAGCAGTCCAGGCAAAACAGCCCGATGTCGAAGAAATCTTGT<br>CTAAGGGGCAGCACCTCTACAAAGAGAAACCTGCCACCCAGCCCGTGAAG<br>AGAAAACTGGAAGACCTCTCTTCAGAGTGGAAGGCTGTAAACAGGTTGCT<br>CCAGGAGCTGAGAGCTAAGCAACCTGACCTCGCACCCGGCCTGACTACTA<br>TTGGCGCCAGCCCGACCCAAACCGTCACACTGGTGACCCAGCCTGTAGTC<br>ACAAAAGAAACCGCCATCTCCAAACTGGAGATGCCTTCAAGCCTGATGCT<br>GGAGGTGCCTGCTCTGGCCGATTTCAACAGAGCCTGGACAGAGCTGACAG<br>ACTGGCTGTCTCTGCTCGACCAAGTGATAAAGTCACAGCGCGTCATGGTG<br>GGTGACCTGGAGGACATCAATGAGATGATCATAAAGCAAAAGGCTACCAT<br>GCAGGACTTGGAGCAGCGCAGGCCGCAGTTGGAAGAACTGATTACAGCAG<br>CCCAGAACCTCAAGAACAAGACTTCAAATCAGGAGGCAAGGACCATCATA<br>ACAGATAGAATCGAGAGGATTCAGAACCAATGGGATGAGGTGCAGGAGCA<br>CCTGCAGAACAGAAGGCAGCAGCTGAACGAAATGCTGAAAGACTCCACAC<br>AGTGGCTGGAGGCCAAAGAGGAGGCAGAACAGGTGCTGGGCCAGGCTAGG<br>GCCAAGCTGGAAAGTTGGAAGGAAGGGCCCTACACCGTGGACGCCATACA<br>GAAGAAAATAACGGAGACAAAACAGCTGGCCAAAGACCTCCGCCAATGGC<br>AGACCAACGTAGACGTCGCCAATGACCTGGCACTCAAGTTGTTGAGAGAT<br>TATTCCGCAGATGACACCCGAAAAGTACACATGATCACTGAGAATATCAA<br>CGCCAGTTGGCGGAGCATTCACAAACGGGTGAGCGAGAGAGAAGCCGCCC<br>TTGAGGAGACGCATCGCCTTTTGCAGCAATTTCCGCTTGACCTGGAAAAG<br>TTTCTGGCTTGGTTGACAGAGGCCGAGACAACTGCTAACGTGCTGCAAGA<br>TGCCACCCGCAAAGAGCGGCTTCTTGAGGACTCTAAAGGGGTGAAAGAAT<br>TGATGAAGCAGTGGCAGGACCTCCAGGGCGAAATCGAGGCCCATACTGAT<br>GTCTACCACAACCTGGATGAAAATAGTCAGAAAATCCTGAGATCCCTGGA<br>AGGGAGTGATGATGCGGTGCTGCTGCAGCGCCGACTCGATAACATGAACT<br>TTAAGTGGTCTGAACTCCGGAAAAAAAGCCTGAACATTCGGAGCCATCTG<br>GAGGCTTCTTCTGATCAGTGGAAGAGACTTCATCTGTCCTTGCAGGAGCT<br>TCTGGTGTGGCTGCAGCTGAAAGACGACGAGCTGTCAAGGCAGGCACCAA<br>TAGGGGGCGACTTCCCCGCTGTTCAGAAACAAAATGATGTGCACAGGGCA<br>TTCAAGCGGGAACTGAAGACGAAAGAACCAGTGATTATGAGOACTCTGGA<br>GACGGTACGCATCTTTCTGACCGAGCAGCCACTTGAAGGCCTCGAAAAGT<br>TGTACCAGGAGCCACGGGAATTGCCTCCCGAAGAACGGGCTCAGAATGTT<br>ACCCGACTGCTTCGCAAGCAGGCTGAGGAAGTGAACACTGAGTGGGAAAA<br>ACTGAATCTGCACAGTGCCGATTGGCAGCGCAAAATTGACGAGACATTGG<br>AGCGCTTGCGGGAGCTGCAGGAAGCCACAGATGAACTTGATCTGAAACTC<br>AGACAGGCCGAGGTCATAAAGGGTTCTTGGCAACCCGTAGGCGACCTTTT<br>GATTGACTCACTGCAGGATCATCTGGAGAAAGTAAAGGCGCTGCGGGGGG<br>AAATTGCTCCGCTGAAGGAAAACGTGAGCCATGTGAATGATCTGGCTCGG<br>CAATTGACTACCCTGGGTATCCAGCTGTCCCCCTACAATCTGAGCACTCT<br>CGAAGACCTCAACACAAGATGGAAACTGCTGCAGGTCGCCGTGGAGGACA<br>GGGTGAGGCAGCTGCATGAGGCACACAGGGACTTCGGTCCGGCAAGCCAA<br>CACTTCCTGTCTACTTCTGTTCAAGGGCCTTGGGAACGCGCTATTTCCCC<br>AAACAAAGTGCCGTACTATATTAACCATGAAACTCAGACAACCTGCTGGG<br>ATCATCCTAAAATGACTGAGCTGTACCAGAGCCTCGCCGATCTGAATAAC<br>GTGAGGTTTAGCGCATACAGAACCGCAATGAAGCTCAGGAGACTGCAGAA<br>GGCACTTTGCCTGGACCTCCTGAGCCTCTCCGCTGCCTGCGATGCCCTCG |

| SEQ ID NO | Description | SEQ |
|---|---|---|
| | | ACCAGCACAACCTGAAGCAGAATGATCAGCCTATGGACATCCTGCAAATC ATAAATTGTCTGACGACAATCTACGACCGGCTCGAACAGGAGCACAATAA TCTCGTGAACGTTCCACTTTGTGTGGATATGTGTCTCAACTGGCTGTTGA ACGTCTATGACACCGGGAGAACTGGAAGGATCCGCGTTCTGTCCTTTAAG ACTGGAATCATCAGCTTGTGTAAGGCGCACCTTGAGGACAAATATCGATA CCTGTTTAAGCAGGTTGCAAGCTCCACTGGATTCTGCGACCAGAGGCGCC TCGGGCTGCTGCTTCATGATAGTATCCAAATCCCACGCCAACTCGGAGAG GTGGCAAGCTTCGGCGGGAGCAATATTGAGCCAAGCGTCAGATCTTGTTT CCAGTTTGCCAACAATAAGCCTGAGATCGAAGCCGCACTGTTTTTGGATT GGATGCGGTTGGAGCCCCAGAGTATGGTGTGGTTGCCCGTGCTGCATAGG GTCGCTGCCGCTGAAACCGCCAAACACCAGGCCAAGTGCAATATTTGCAA GGAATGTCCCATCATCGGGTTTAGATACCGGAGCCTGAAGCACTTCAATT ATGATATCTGCCAGTCTTGTTTTTTTTCCGGCCGAGTTGCTAAGGGACAC AAGATGCATTACCCAATGGTGGAATATTGTACGCCAACCACCAGCGGCGA AGATGTCAGAGATTTTGCAAAAGTACTCAAGAACAAGTTCCGCACCAAGC GATATTTCGCGAAGCACCCCCGGATGGGCTACCTCCCAGTGCAGACGGTT CTGGAAGGCGATAACATGGAAACTCCAGTCACCCTGATCAATTTCTGGCC TGTGGACTCTGCGCCTGCCTCTTCACCTCAGCTCTCCCACGATGACACCC ATTCCAGAATCGAGCACTACGCGTCTCGACTGGCGGAGATGGAGAACAGC AATGGTTCTTACCTCAATGACAGCATTAGCCCCAACGAAAGCATCGATGA CGAGCACCTCTTGATTCAACACTACTGCCAGTCCCTGAATCAGGACAGTC CTCTGTCCCAACCCAGGAGCCCAGCCCAGATACTGATCTCTCTCGAATCA GAAGAAAGAGGGGAGTTGGAGCGAATTTTGGCCGACCTGGAGGAGGAGAA TAGAAATCTTCAGGCCGAGTACGATAGACTGAAGCAGCAGCACGAGCACA AGGGCCTTTCTCCACTGCCCTCTCCACCGGAAATGATGCCAACCTCCCCT CAAAGTCCCAGGGACGCTGAGCTCATTGCCGAGGCAAAGCTGTTGCGCCA GCACAAAGGACGCCTGGAGGCGAGAATGCAGATCCTGGAAGACCATAACA AGCAGCTTGAGTCTCAGCTGCACCGACTTAGACAGCTGTTGGAGCAGCCA CAAGCGGAAGCAAAGGTCAATGGAACTACCGTGAGTTCCCCCAGTACAAG TCTGCAGCGCTCTGACTCAAGCCAGCCAATGCTGCTCCGGGTAGTCGGTT CTCAGACTAGTGATTCAATGGGGGAGGAGGATCTTCTTTCCCCACCCCAA GACACCTCAACAGGGCTTGAGGAAGTGATGGAGCAGCTGAACAACTCCTT CCCCTCTTCACGGGGGAGAAATACTCCTGGGAAGCCTATGAGAGAGGATA CCATGTAATGA |
| 21. | DTS CBA-hBGi-DMD-1-WPRE3- | CGTTACATAACTTACGGTAAATGGCCCGCCTGGCTGACCGCCCAACGACC CCCGCCCATTGACGTCAATAATGACGTATGTTCCCATAGTAACGCCAATA GGGACTTTCCATTGACGTCAATGGGTGGAGTATTTACGGTAAACTGCCCA CTTGGCAGTACATCAAGTGTATCATATGCCAAGTACGCCCCCTATTGACG TCAATGACGGTAAATGGCCCGCCTGGCATTATGCCCAGTACATGACCTTA TGGGACTTTCCTACTTGGCAGTACATCTACGTATTAGTCATCGCTATTAC CATGGTCGAGGTGAGCCCCACGTTCTGCTTCACTCTCCCCATCTCCCCCC CCTCCCCACCCCCAATTTTGTATTTATTTATTTTTTAATTATTTTGTGCA GCGATGGGGGCGGGGGGGGGGGGGGGGCGCGCCAGGCGGGGCGGGGCGGG GCGAGGGGCGGGGCGGGGCGAGGCGGAGAGGTGCGGCGGCAGCCAATCAGA GCGGCGCGCTCCGAAAGTTTCCTTTTATGGCGAGGCGGCGGCGGCGGCGG CCCTATAAAAAGCGAAGCGCGCGGCGGGCGGGAGTCTCTGGATCCACTGC TTAAATACGGACGAGGACAGGGCCCTGTCTCCTCAGCTTCAGGCACCACC ACTGACCTGGGACAGTGAATCGTAAGTACTAGCAGCTACAATCCAGCTAC CATTCTGCTTTTATTTTATGGTTGGGATAAGGCTGGATTATTCTGAGTCC AAGCTAGGCCCTTTTGCTAATCATGTTCATACCTCTTATCTTCCTCCCAC AGCTCCTGGGCAACGTGCTGGTCTGTGTGCTGGCCCATCACTTTGGCAAA GAATTGCGATCGCCACCATGCTGTGGTGGGAAGAGGTGGAGGATTGCTAC GAGCGGGAGGATGTGCAGAAAAAGACTTTCACCAAGTGGGTAAATGCTCA GTTCTCTAAGTTCGGGAAGCAACACATCGAGAACTTGTTTTCCGACCTCC AGGATGGCAGGCGCCTGCTTGACTTGCTGGAGGGTCTGACTGGTCAGAAG CTCCCTAAGGAGAAGGGCAGCACCAGAGTTCACGCTCTGAATAACGTTAA CAAAGCCCTGAGGGTCCTCCAGAATAACAATGTAGACCTGGTGAACATCG GTTCTACCGACATCGTGGACGGGAATCATAAACTGACCTTGGGGCTCATC TGGAACATTATCTTGCACTGGCAGGTGAAGAACGTCATGAAGAATATCAT GGCCGGGCTGCAACAGACCAACTCCGAAAAGATTTTGCTCAGCTGGGTGC GCCAGTCCACCCGCAATTATCCACAAGTCAACGTTATCAATTTCACCACT AGTTGGAGTGATGGCCTCGCCCTGAACGCCTTGATCCACAGTCACCGCCC CGACCTGTTTGACTGGAACTCTGTGGTTTGCCAACAGAGCGCTACCCAGC GTCTCGAACATGCTTTCAATATCGCTAGATACCAGCTCGGTATCGAGAAG CTGTTGGATCCTGAGGACGTAGACACGACCTACCCCGATAAAAAGAGCAT CCTGATGTATATCACTTCTCTGTTTCAGGTGCTTCCTCAACAGGTGTCCA TTGAAGCCATCCAAGAGGTCGAAATGCTGCCCAGGCCCCCTAAGGTGACA AAAGAAGAGCATTTCCAGCTGCATCACCAGATGCATTACAGTCAACAGAT TACCGTCAGCTTGGCTCAGGGATATGAGCGCACGTCCTCTCCTAAGCCCA GATTTAAGTCCTACGCATATACCCAGGCTGCCTACGTGACCACTTCCGAC CCAACTAGGAGCCCCTTTCCCTCCCAACACCTGGAGGCCCCTGAGGACAA AAGCTTCGGATCTAGTCTGATGGAGTCCGAGGTGAATCTGGATCGGTACC AAACTGCTCTGGAGGAAGTGCTGTCCTGGCTTCTGTCCGCTGAAGACACC CTGCAGGCGCAAGGTGAGATTTCTAACGACGTCGAGGTCGTGAAGGATCA |

-continued

| SEQ ID NO | Description | SEQ |
|---|---|---|
| | | GTTCCACACTCATGAGGGCTACATGATGGACTTGACAGCTCACCAGGGAA<br>GAGTTGGTAACATCCTGCAGCTTGGCTCCAAGTTGATTGGCACGGGAAAG<br>CTTAGCGAGGACGAGGAAACCGAGGTACAGGAGCAGATGAACTTGCTGAA<br>TTCCCGCTGGGAGTGCCTGAGAGTTGCGTCCATGGAAAAGCAGTCAAACC<br>TTCACAGAGTGCTGATGGACCTTCAGAACCAGAAGCTGAAGGAGCTGAAC<br>GATTGGCTGACAAAGACCGAGGAACGCACAAGAAAAATGGAAGAGGAACC<br>TCTGGGACCTGATCTGGAGGATCTGAAGCGCCAGGTCCAACAGCATAAGG<br>TGCTGCAGGAGGATTTGGAGCAGGAGCAGGTGCGGGTCAACAGCCTGACA<br>CATATGGTGGTTGTGGTCGATGAGTCCTCTGGCGATCATGCTACCGCAGC<br>GCTGGAAGAGCAGCTGAAGGTGCTGGGGGATCGCTGGGCCAACATTTGCA<br>GATGGACAGAAGACCGGTGGGTCCTGCTTCAAGATATCCTGCTCAAGTGG<br>CAGCGCCTGACTGAAGAGCAGTGCCTGTTCTCAGCTTGGTTGAGCGAAAA<br>AGAGGACGCAGTTAACAAGATCCATACCACAGGCTTCAAGGATCAGAATG<br>AGATGCTGAGCTCACTGCAGAAGCTGGCTGTGCTGAAGGCCGACTTGGAG<br>AAGAAAAAGCAGTCCATGGGCAAACTGTATAGCCTGAAGCAGGACCTGCT<br>CAGCACCCTGAAGAACAAAAGCGTTACGCAGAAAACTGAGGCCTGGTTGG<br>ACAACTTTGCTCGCTGCTGGGATAACCTTGTGCAGAAGCTGGAAAAGTCA<br>ACCGCACAGATCTCCCAGGCTGTGACCACTACGCAGCCTAGCTTGACCCA<br>GACAACCGTTATGGAAACCGTGACAACCGTGACAACGAGAGAGCAAATCC<br>TGGTTAAGCATGCCCAGGAGGAACTGCCGCCACCCCCGCCTCAGAAGAAA<br>CGGCAGATTACGGTGGACAGCGAGATCCGCAAGAGGCTGGACGTCGACAT<br>CACTGAGCTCCACTCATGGATCACGCGGAGTGAGGCCGTGCTGCAGTCTC<br>CCGAGTTCGCTATTTTCCGCAAGGAGGGAAACTTCTCTGACTTGAAAGAG<br>AAGGTGAATGCCATCGAGCGTGAAAAGGCAGAAAAGTTCAGAAAGCTGCA<br>GGACGCCTCTCGCTCTGCGCAGGCCCTGGTGGAGCAGATGGTCAACGAGG<br>GTGTTAACGCTGACAGCATCAAACAGGCAAGCGAACAGCTGAACTCCAGA<br>TGGATCGAATTTTGCCAACTGCTCTCCGAACGCCTCAACTGGTTGGAGTA<br>CCAGAACAATATTATCGCTTTTTACAACCAGCTGCAGCAACTGGAGCAGA<br>TGACAACTACCGCCGAAAACTGGCTGAAAATTCAGCCAACCACACCGTCC<br>GAGCCAACTGCGATCAAGTCTCAGCTGAAGATCTGCAAGGACGAAGTGAA<br>CCGTCTTAGCGACTTGCAACCCCAGATTGAACGGCTCAAGATTCAGTCTA<br>TTGCTCTGAAGGAGAAGGGTCAGGGTCCGATGTTCCTGGATGCAGATTTT<br>GTCGCATTTACCAATCACTTCAAACAGGTGTTTAGTGACGTCCAGGCGCG<br>CGAGAAAGAGCTGCAGACTATTTTTGACACCCTGCCTCCCATGAGGTACC<br>AGGAGACAATGAGTGCCATTCGCACCTGGGTGCAACAGTCCGAGACGAAA<br>TTGTCAATCCCACAGCTGTCCGTGACAGACTACGAGATTATGGAGCAACG<br>GTTGGGGGAGCTGCAGGCTCTTCAGAGTTCCCTGCAGGAGCAACAGAGCG<br>GACTGTACTATCTTTCCACTACCGTGAAGGAAATGAGTAAGAAAGCCCCT<br>TCCGAGATCAGCCGCAAATACCAGTCTGAATTCGAAGAGATCGAGGGACG<br>CTGGAAAAAGCTGTCAAGCCAGCTGGTCGAGCACTGTCAGAAGCTGGAAG<br>AGCAGATGAACAAGCTGCGTAAAATCCAGAACCATATTCAGACCCTCAAG<br>AAATGGATGGCAGAAGTTGACGTGTTTCTGAAGGAAGAGTGGCCTGCCCT<br>CGGCGATAGCGAAATCCTTAAGAAACAACTCAAGCAGTGCCGCCTCCTGG<br>TGTCCGATATTCAGACAATCCAGCCTTCCCTGAACAGCGTTAATGAGGGC<br>GGACAGAAAATTAAAAACGAGGCCGAACCCGAGTTCGCTTCTCGCCTGGA<br>GACTGAACTGAAGGAGCTGAATACCCAGTGGGACCATATGTGTCAACAGG<br>TCTACGCACGCAAAGAGGCACTGAAGGGCGGTCTGGAGAAGACTGTCTCA<br>CTCCAGAAGGACCTGAGCGAGATGCACGAGTGGATGACCCAGGCCGAAGA<br>GGAATACCTGGAGCGTGATTTTGAGTATAAGACCCCAGACGAACTCCAGA<br>AAGCCGTTGAAGAGATGAAGAGGGCTAAGGAGGAAGCCCAACAGAAGGAG<br>GCGAAAGTGAAGCTCCTGACAGAGTCCGTGAACTCCGTCATCGCTCAAGC<br>TCCTCCCGTGGCTCAGGAGGCCCTCAAGAAAGAGCTGGAAACTCTGACCA<br>CAAATTACCAGTGGTTGTGTACCCGCTTGAACGGTAAGTGCAAGACCCTG<br>GAAGAGGTGTGGGCCTGCTGGCACGAGCTCCTGTCCTATCTTGAGAAGGC<br>GAACAAATGGCTGAACGAAGTGGAATTCAAGTTGAAAACAACTGAGAACA<br>TTCCGGGAGGCGCTGAGGAAATCTCTGAGGTGCTGGACTCTCTGGAAAAT<br>CTGATGCGTCATTCTGAAGACAATCCTAACCAGATCAGGATTCTGGCACA<br>GACCCTCACTGACGGAGGCGTTATGGACGAACTTATCAACGAGGAACTGG<br>AGACATTCAATTCCCGTTGGCGTGAGCTGCACGAAGAGGCCGTGCGCCGT<br>CAGAAGTTGCTGGAACAGTCTATCCAGTCCGCCCAGGAGACAGAGAAATC<br>TCTCCACCTGATCCAGGAGAGTCTGACGTTTATCGATAAGCAGCTGGCTG<br>CCTACATCGCCGACAAGGTGGACGCTGCCCAGATGCCCCAAGAGGCTCAG<br>AAGATCCAGTCCGACCTGACGTCTCATGAAATCAGCCTGGAAGAGATGAA<br>AAAGCACAACCAGGGCAAAGAGGCTGCCCAGCGCGTCCTCTCCCAGATTG<br>ACGTGGCTCAGAAAAAGTTGCAGGACGTGAGCATGAAGTTTAGGCTGTTC<br>CAGAAACCCGCCAACTTCGAACAGAGACTGCAGGAGTCTAAGATGATCCT<br>GGATGAGGTCAAGATGCACCTCCCTGCTCTGGAAACAAAATCTGTGGAGC<br>AGGAGGTCGTGCAGTCACAACTGAACCATTGTGTGAACCTCTACAAGTCT<br>CTCAGCGAGGTGAAGTCCGAGGTCGAGATGGTGATCAAGACCGGACGCCA<br>GATTGTGCAGAAAAAGCAGACAGAGAACCCCAAAGGAGCTGGACGAACGGG<br>TGACCGCCCTGAAGCTCCACTACAACGAGTTGGGTGCCAAAGTCACTGAA<br>AGAAAGCAACAGCTGGAGAAGTGTCTGAAGCTGAGCCGCAAGATGCGCAA<br>AGAAATGAACGTCTTGACCGAGTGGTTGGCGGCCACCGACATGGAGCTGA<br>CCAAGAGATCCGCTGTGGAGGGCATGCCCTCCAACCTTGACTCAGAGGTG<br>GCCTGGGGCAAGGCCACACAGAAGGAGATCGAAAAACAGAAGGTGCATCT |

-continued

| SEQ ID NO | Description | SEQ |
|---|---|---|
| | | TAAATCAATCACTGAGGTGGGCGAAGCTCTGAAGACAGTGCTGGGCAAGA<br>AAGAGACACTTGTAGAGGACAAGCTCTCCCTTCTGAATAGCAATTGGATC<br>GCCGTAACTAGTCGCGCGGAGGAATGGCTGAACCTCCTGTTGGAATACCA<br>GAAACACATGGAAACCTTCGATCAGAACGTGGACCATATTACCAAGTGGA<br>TTATCCAGGCTGACACTCTCCTGGACGAGTCTGAGAAAAAGAAACCCCAG<br>CAAAAGGAAGATGTGCTGAAGCGCCTGAAGGCGGAATTGAACGACATCCG<br>CCCGAAGGTTGATTCCACCCGCGACCAAGCGGCCAACCTTATGGCTAACC<br>GCGGGGACCATTGCAGAAAACTGGTGGAACCGCAGATCTCTGAGCTGAAC<br>CACAGATTCGCCGCGATTTCTCACAGAATTAAGACTGGCAAGGCCTCCAT<br>CCCTCTGAAAGAGCTGGAGCAGTTCAACTCTGATATTCAGAAGCTTCTGG<br>AGCCCCTGGAGGCAGAAATCCAACAGGGCGTCAACCTGAAAGAGGAAGAC<br>TTTAATAAGGACATGAATGAGGATAACGAAGGTACCGTCAAGGAGCTCCT<br>GCAGAGGGGCGACAATCTGCAGCAAAGAATCACTGACGAACGTAAGCGCG<br>AAGAGATTAAGATCAAGCAACAGCTGTTGCAGACTAAGCACAACGCCCTG<br>AAGGATCTGAGGTCCCAGCGCAGGAAAAAGGCCCTGGAGATTTCCCACCA<br>GTGGTACCAGTACAAGCGCCAGGCCGATGACCTTCTGAAGTGCCTCGACG<br>ATATCGAGAAAAAGCTGGCCTCACTGCCCGAGCCCCGCGACGAGCGCAAG<br>ATCAAGGAGATTGACCGTGAGCTCCAGAAGAAAAAGGAGGAACTGAACGC<br>GGTGCGCAGACAGGCCGAGGGCCTCTCCGAGGACGGCGCTGCGATGGCTG<br>TTGAGCCCACTCAGATCCAACTGAGCAAGCGGTGGAGAGAGATCGAGTCT<br>AAGTTCGCGCAATTTAGGCGCCTCAACTTCGCCCAGATTCACACGGTCCG<br>TGAGGAAACGATGATGGTGATGACAGAGGATATGCCACTGGAAATCAGCT<br>ACGTGCCCAGTACATATCTCACCGAAATCACCCATGTGTCCCAGGCTCTC<br>CTGGAGGTGGAACAGTTGCTCAACGCTCCCGACTTGTGCGCTAAGGACTT<br>CGAGGACCTGTTCAAGCAGGAAGAGAGCCTGAAAAACATTAAGGACTCCC<br>TGCAACAGTCAAGCGGCCGCATCGATATCATTCATTCTAAGAAAACCGCT<br>GCCCTGCAGTCTGCAACCCCCGTAGAGCGCGTCAAACTGCAGGAAGCTCT<br>CAGCCAACTGGATTTCCAGTGGGAGAAGGTGAACAAGATGTATAAGGATC<br>GTCAGGGCCGGTTCGACCGCTCTGTGGAGAAGTGGCGCCGTTTCCACTAC<br>GATATCAAGATTTTCAATCAATGGTTGACCGAGGCAGAGCAGTTCCTCAG<br>AAAGACACAGATCCCTGAAAATTGGGAGCATGCCAAGTACAAGTGGTATC<br>TGAAGGAGCTGCAGGACGGGATCGGACAACGTCAGACCGTGGTCCGCACC<br>CTGAACGCAACCGGCGAGGAAATTATCCAACAGTCTAGCAAGACAGATGC<br>TAGCATCCTCCAGGAGAAGCTCGGAAGCCTCAACCTTCGCTGGCAGGAGG<br>TGTGCAAGCAGCTGTCAGACAGGAAGAAACGCCTGGAGGAACAGAAGAAC<br>ATCCTTTCAGAGTTCCAGAGAGATCTGAACGAATTCGTGCTTTGGCTTGA<br>AGAGGCCGATAACATCGCAAGCATCCCACTGGAGCCTGGTAAGGAACAGC<br>AATTGAAGGAGAAGCTGGAGCAGGTAAAGCTGCTCGTGGAAGAGCTGCCT<br>CTGAGGCAGGGAATTCTCAAGCAGCTCAACGAGACTGGGGGCCCGGTTTT<br>GGTGAGCGCCCCAATTAGCCCAGAAGAGCAGGACAAGTTGGAGAACAAGC<br>TGAAGCAGACCAACCTGCAGTGGATCAAGGTGTCCCGCGCACTGCCCGAA<br>AAGCAGGGAGAGATTGAGGCCCAGATCAAGGATCTGGGACAGCTGGAGAA<br>AAAGCTGGAAGACCTGGAGGAACAGCTGAACCATTTGCTCCTGTGGTTGT<br>CCCCCATCAGAAATCAGCTGGAAATCTACAACCAACCGAACCAGGAAGGT<br>CCGTTTGATGTTAAGGAAACCGAGATCGCTGTGCAGGCGAAGCAGCCTGA<br>CGTAGAAGAGATCCTGTCAAAGGGACAGCACCTCTACAAGGAGAAGCCCG<br>CCACCCAGCCAGTCAAGCGGAAGCTCGAAGACCTGTCCAGCGAGTGGAAA<br>GCCGTCAACCGCCTCCTGCAAGAGCTGCGTGCCAAGCAACCGGACCTGGC<br>GCCAGGTCTGACTACCATTGGCGCAAGTCCTACCCAGACTGTCACCCTGG<br>TGACCCAACCCGTTGTGACAAAGGAAACCGCCATCAGCAAGCTGGAGATG<br>CCTAGCTCTTTGATGCTGGAGGTTCCCGCCCTCGCCGACTTCAACCGTGC<br>TTGGACAGAACTGACCGACTGGCTGTCCCTCCTGGACCAAGTGATCAAGA<br>GCCAGCGCGTGATGGTGGGTGATCTTGAGGATATTAACGAAATGATTATC<br>AAGCAGAAGGCCACCATGCAGGACTTGGAGCAGAGGCGCCCCCAGTTGGA<br>GGAACTGATCACCGCCGCGCAGAATCTGAAAAACAAAACTTCCAATCAGG<br>AAGCGAGAACCATCATTACAGACAGAATTGAGAGAATTCAAAACCAGTGG<br>GACGAAGTGCAAGAACACCTCCAGAACCGGCGTCAACAGCTGAACGAGAT<br>GCTGAAGGATTCCACTCAATGGCTGGAAGCTAAGGAAGAGGCCGAGCAGG<br>TCCTTGGACAGGCACGCGCTAAGCTGGAGTCCTGGAAAGAAGGCCCCTAT<br>ACAGTGGACGCAATTCAAAAGAAAATCACCGAGACGAAGCAACTGGCCAA<br>GGACCTGAGACAGTGGCAAACCAACGTTGATGTGGCTAATGACCTGGCCT<br>TGAAGCTCCTGCGTGACTACTCCGCGGATGACACTAGAAAGGTGCACATG<br>ATCACCGAGAATATCAACGCTAGCTGGCGCTCCATCCATAAGCGTGTGAG<br>TGAGCGCGAAGCCGCTCTGGAGGAAACCCATCGCCTGCTTCAACAGTTTC<br>CTTTGGACCTGGAAAAGTTCCTGGCCTGGCTCACAGAAGCCGAGACAACC<br>GCCAACGTGCTGCAGGACGCCACCCGTAAGGAGCGCTTGCTGGAGGATAG<br>TAAGGGGGTGAAGGAGTTGATGAAGCAGTGGCAAGATCTGCAGGGGGAAA<br>TCGAGGCACATACCGACGTCTATCATAACCTGGATGAGAATTCCCAGAAA<br>ATCCTGCGCAGCTTGGAGGGCAGTGATGACGCGGTGCTTCTGCAACGGCG<br>CTTGGACAACATGAACTTCAAGTGGTCCGAGTTGCGTAAAAAGAGTCTGA<br>ACATTCGCTCCCACCTGGAGGCTTCTAGTGACCAGTGGAAGCGCCTGCAC<br>CTGAGCCTGCAAGAACTGCTCGTGTGGCTGCAACTGAAGGATGACGAGTT<br>GAGTCGTCAGGCCCCTATCGGAGGTGACTTTCCGGCTGTCCAGAAACAGA<br>ACGACGTGCATAGGGCATTTAAGCGCGAGTTGAAGACAAAGGAGCCAGTC<br>ATTATGTCCACGCTGGAAACCGTGCGCATTTTCCTGACTGAGCAGCCTCT |

-continued

| SEQ ID NO | Description | SEQ |
|---|---|---|
| | | GGAGGGGCTGGAGAAGCTGTACCAGGAGCCTCGCGAGTTGCCCCCTGAAG AGCGTGCCCAGAATGTGACCCGCCTGTTGCGTAAGCAGGCCGAGGAAGTG AACACCGAGTGGGAGAAGCTGAACCTGCATTCCGCGGATTGGCAGAGGAA GATTGACGAGACGCTGGAGAGGCTCCGTGAGTTGCAGGAGGCAACCGACG AACTGGACCTCAAGCTGCGTCAAGCAGAGGTGATCAAGGGGAGTTGGCAG CCGGTCGGCGATTTGCTGATCGACTCCCTGCAGGATCACCTGGAAAAGGT TAAAGCTTTGCGCGGGGAAATTGCCCCGCTGAAGGAGAACGTGAGCCACG TTAACGATCTGGCCAGACAGCTGACCACTCTGGGTATCCAGCTGAGCCCG TACAATCTGAGCACCCTCGAAGACTTGAATACGAGATGGAAACTCCTGCA GGTGGCAGTGGAGGACAGGGTGCGCCAATTGCACGAGGCCCACCGGGACT TTGGACCGGCCAGCCAGCATTTCCTCAGTACCTCTGTTCAGGGCCCGTGG GAGCGGGCCATCTCCCCCAACAAGGTCCCCTATTACATCAACCATGAAAC CCAGACTACCTGTTGGGACCACCCTAAAATGACTGAGTTGTATCAATCTC TGGCCGACTTGAATAACGTGCGCTTCTCAGCCTACAGGACTGCAATGAAA CTCAGACGCCTCCAAAAGGCCCTTTGTCTGGACTTGCTGTCCCTTAGCGC TGCCTGTGATGCTCTGGATCAGCACAATTTGAAACAAAACGACCAGCCGA TGGACATCCTCCAGATTATCAACTGCCTGACTACCATCTACGACAGACTG GAACAGGAGCATAATAACCTGGTGAACGTCCCCCTGTGCGTGGACATGTG CCTGAACTGGCTGCTCAATGTGTATGACACGGGTAGAACAGGACGGATCA GGGTCCTGTCCTTTAAGACCGGTATCATTTCTCTGTGTAAGGCACATCTG GAGGACAAGTACCGCTACCTGTTTAAGCAGGTCGCCAGCTCCACTGGCTT CTGCGATCAAAGGCGGCTGGGTCTGCTCCTGCACGACTCCATTCAGATCC CGAGACAGTTGGGTGAAGTGGCGTCCTTCGGCGGTTCTAATATCGAGCCT AGCGTCCGCAGCTGTTTCCAATTCGCCAATAACAAGCCGGAGATCGAAGC GGCCCTTTTCCTGGACTGGATGCGTCTGGAACCTCAGAGCATGGTTTGGC TTCCGGTGCTTCATCGCGTGGCCGCTGCCGAAACCGCTAAACATCAGGCC AAATGTAACATCTGTAAGGAATGCCCGATTATCGGTTTCCGGTACCGTAG CCTCAAGCATTTCAACTATGATATTTGTCAATCTTGCTTCTTTAGCGGAC GGGTGGCCAAAGGCCACAAAATGCACTACCCGATGGTCGAGTATTGCACT CCTACAACCTCCGGCGAGGACGTGCGCGATTTTGCCAAAGTGCTGAAAAA CAAGTTTAGAACCAAGCGTTACTTTGCCAAGCATCCACGTATGGGCTACC TGCCTGTCCAGACCGTTCTGGAAGGTGATAACATGGAGACACCCGTGACT TTGATTAACTTTTGGCCAGTAGACTCTGCTCCGGCAAGCTCCCCTCAGCT CTCCCACGATGACACTCACAGCCGTATCGAGCACTACGCCTCTCGCCTGG CTGAGATGGAGAACTCTAACGGTTCATACCTGAATGACAGTATCTCCCCA AACGAGAGTATCGATGACGAACATCTGCTCATTCAGCATTACTGTCAATC CTTGAATCAGGACAGCCCCCTGTCCCAGCCACGGTCCCCGGCCCAGATCC TGATTTCACTGGAGTCCGAAGAGAGAGGGGAACTGGAAAGGATCCTCGCT GACCTGGAAGAGGAAAACCGGAACCTGCAGGCTGAATACGACCGCTTGAA GCAGCAACACGAGCACAAGGGCTTGAGCCCGTTGCCAAGCCCTCCGGAGA TGATGCCAACTAGCCCTCAGAGCCCACGGGATGCCGAGCTCATCGCTGAA GCTAAGTTGCTGAGACAGCACAAGGGACGTCTGGAGGCCCGCATGCAGAT CCTGGAGGATCATAATAAACAGTTGGAGAGCCAACTGCATAGGCTGCGCC AGCTCCTGGAGCAGCCACAGGCCGAGGCTAAGGTCAACGGAACTACCGTT TCCAGCCCGTCCACATCTCTGCAGCGCTCAGATAGTTCCCAGCCTATGTT GCTGAGAGTGGTTGGATCTCAGACCTCCGACTCAATGGGCGAAGAGGACT TGCTGTCTCCCCCACAGGACACTAGCACAGGACTCGAAGAGGTGATGGAA CAGCTCAATAACTCTTTTCCTTCTAGTCGGGGTCGCAATACCCCTGGAAA GCCCATGCGCGAAGACACCATGTAATAGCTCGAGAATCAACCTCTGGATT ACAAAATTTGTGAAAGATTGACTGGTATTCTTAACTATGTTGCTCCTTTT ACGCTATGTGGATACGCTGCTTTAATGCCTTTGTATCATGCTATTGCTTC CCGTATGGCTTTCATTTTCTCCTCCTTGTATAAATCCTGGTTGCTGTCTC TTTATGAGGAGTTGTGGCCCGTTGTCAGGCAACGTGGCGTGGTGTGCACT GTGTTTGCTGACGCAACCCCCACTGGTTGGGGCATTGCCACCACCTGTCA GCTCCTTTCCGGGACTTTCGCTTTCCCCCTCCCTATTGCCACGGCGGAAC TCATCGCCGCCTGCCTTGCCCGCTGCTGGACAGGGGCTCGGCTGTTGGGC ACTGACAATTCCGTGGGGTGTGCCTTCTAGTTGCCAGCCATCTGTTGTTT GCCCCTCCCCCGTGCCTTCCTTGACCCTGGAAGGTGCCACTCCCACTGTC CTTTCCTAATAAAATGAGGAAATTGCATCGCATTGTCTGAGTAGGTGTCA TTCTATTCTGGGGGGTGGGGTGGGGCAGGACAGCAAGGGGGAGGATTGGG AAGACAATAGCAGGCATGCTGGGGATGCGGTGGGCTCTATGGGAAGATGT CTACTGAGCTGTGCGATCCCTGCTGGGGACTTTCCGCTGGGGACTTTCCG CTGGGGACTTTCCGCCTTCAGCTAAGGAAGCTACCAATATTTAGAGGTAC ATTTTGTTCTAGAACAAAATGTACCGGTACATTTTGTTCTGGTACATTTT GTTCT |
| 22. | CBA-hBGi-DMD-3-WPRE3-DTS | CGTTACATAACTTACGGTAAATGGCCCGCCTGGCTGACCGCCCAACGACC CCCGCCCATTGACGTCAATAATGACGTATGTTCCCATAGTAACGCCAATA GGGACTTTCCATTGACGTCAATGGGTGGAGTATTTACGGTAAACTGCCCA CTTGGCAGTACATCAAGTGTATCATATGCCAAGTACGCCCCCTATTGACG TCAATGACGGTAAATGGCCCGCCTGGCATTATGCCCAGTACATGACCTTA TGGGACTTTCCTACTTGGCAGTACATCTACGTATTAGTCATCGCTATTAC CATGGTCGAGGTGAGCCCCACGTTCTGCTTCACTCTCCCCATCTCCCCCC CCTCCCCACCCCCAATTTTGTATTTATTTATTTTTTAATTATTTTGTGCA GCGATGGGGGCGGGGGGGGGGGGGGGGCGCGCCAGGCGGGGCGGGGCGGGG |

-continued

| SEQ ID NO | Description | SEQ |
|---|---|---|
| | | CGAGGGGCGGGGCGGGGCGAGGCGGAGAGGTGCGGCGGCAGCCAATCAGA<br>GCGGCGCGCTCCGAAAGTTTCCTTTTATGGCGAGGCGGCGGCGGCGGCGG<br>CCCTATAAAAAGCGAAGCGCGCGGCGGGCGGGAGTCTCTGGATCCACTGC<br>TTAAATACGGACGAGGACAGGGCCCTGTCTCCTCAGCTTCAGGCACCACC<br>ACTGACCTGGGACAGTGAATCGTAAGTACTAGCAGCTACAATCCAGCTAC<br>CATTCTGCTTTTATTTTATGGTTGGGATAAGGCTGGATTATTCTGAGTCC<br>AAGCTAGGCCCTTTTGCTAATCATGTTCATACCTCTTATCTTCCTCCCAC<br>AGCTCCTGGGCAACGTGCTGGTCTGTGTGCTGGCCCATCACTTTGGCAAA<br>GAATTGCGATCGCCACCATGCTGTGGTGGGAAGAGGTGGAGGACTGTTAC<br>GAGAGAGAGGACGTGCAGAAGAAGACATTCACCAAGTGGGTGAACGCTCA<br>GTTCAGCAAGTTCGGCAAGCAGCACATCGAGAACCTGTTTAGCGATCTAC<br>AAGATGGCAGAAGACTGCTGGACCTGCTGGAGGGCCTGACCGGGCAGAAG<br>CTGCCCAAAGAAAAGGGGTCTACAAGAGTGCACGCCCTGAACAACGTGAA<br>CAAGGCCCTGAGAGTGCTGCAGAACAACAACGTGGACCTGGTGAACATCG<br>GCAGCACCGACATCGTGGACGGCAACCACAAGCTGACCCTGGGCCTGATC<br>TGGAACATCATCCTGCACTGGCAAGTGAAGAACGTGATGAAGAACATCAT<br>GGCCGGCCTGCAGCAGACCAACAGCGAGAAGATCCTGCTGAGCTGGGTGA<br>GACAGAGCACAAGAAACTACCCCCAAGTGAACGTGATCAACTTCACCACA<br>AGCTGGAGCGACGGCCTGGCCCTGAACGCCCTGATCCACAGCCACAGACC<br>CGACCTGTTCGACTGGAACAGCGTGGTGTGTCAGCAGAGCGCCACACAGA<br>GACTGGAGCACGCCTTCAACATCGCTAGATATCAGCTGGGCATCGAGAAG<br>TTACTGGACCCCGAAGATGTGGACACCACCTACCCCGACAAGAAGAGCAT<br>CCTGATGTACATCACAAGCCTGTTCCAAGTGCTGCCTCAGCAAGTGAGCA<br>TCGAGGCCATCCAAGAAGTCGAGATGCTGCCTAGACCCCCCAAGGTGACC<br>AAGGAGGAGCACTTTCAGCTGCACCATCAGATGCACTACTCTCAGCAGAT<br>CACAGTCAGCTTGGCACAAGGCTACGAGAGAACAAGCAGCCCCAAGCCTA<br>GATTCAAGAGCTACGCCTACACCCAAGCCGCCTACGTGACCACAAGTGAC<br>CCCACAAGAAGCCCCTTCCCTTCTCAGCACCTGGAGGCCCCCGAGGACAA<br>GAGCTTCGGCAGCAGCCTGATGGAGAGCGAGGTGAACCTGGACAGATATC<br>AGACCGCGTTAGAAGAAGTGTTGAGCTGGCTGCTGAGCGCCGAGGACACC<br>CTGCAAGCCCAAGGCGAGATCAGCAACGATGTGGAGGTGGTGAAGGATCA<br>GTTCCACACCCACGAGGGCTACATGATGGACCTGACCGCCCACCAAGGCA<br>GAGTGGGCAACATCCTGCAGCTGGGCAGCAAGCTGATCGGCACCGGCAAG<br>CTGAGCGAGGACGAGGAAACCGAGGTTCAAGAGCAAATGAACCTGCTAAA<br>CAGCAGATGGGAGTGCCTGAGAGTGGCTAGCATGGAAAAGCAGAGTAACC<br>TGCACAGAGTGCTGATGGACCTGCAGAATCAGAAATTGAAAGAACTTAAT<br>GATTGGCTGACCAAGACCGAGGAGAGAACAAGAAAGATGGAGGAGGAGCC<br>CCTGGGCCCCGACCTGGAGGACCTGAAGAGACAAGTGCAGCAGCACAAGG<br>TGCTGCAAGAGGACCTGGAGCAAGAGCAAGTGAGAGTGAACTCTCTGACA<br>CACATGGTGGTGGTAGTGGACGAGAGCAGCGGCGATCACGCTACCGCGGC<br>GCTGGAAGAGCAGCTGAAAGTGCTGGGCGACAGATGGGCCAACATCTGCA<br>GATGGACCGAGGACAGATGGGTGCTGCTGCAAGACATCCTGCTGAAGTGG<br>CAGAGACTGACCGAGGAGCAGTGCCTGTTCAGCGCCTGGCTGAGCGAGAA<br>GGAAGACGCTGTGAACAAGATCCACACCACCGGCTTCAAGGATCAGAACG<br>AGATGCTGAGCTCCCTCCAAAAGCTCGCAGTGCTGAAGGCCGACCTGGAA<br>AAGAAAAAACAGTCGATGGGCAAGCTGTACAGCCTGAAGCAAGACCTGCT<br>GAGCACCCTGAAGAACAAGAGCGTGACACAGAAGACCGAGGCCTGGCTGG<br>ACAACTTCGCTAGATGCTGGGACAACCTGGTACAGAAGTTAGAGAAGTCT<br>ACCGCTCAGATCAGCCAAGCCGTAACCACCACACAACCTAGCCTGACTCA<br>GACCACCGTGATGGAAACCGTGACCACCGTGACAACCCGTGAGCAGATCC<br>TGGTGAAGCACGCCCAAGAGGAGCTGCCCCCCCCCCCCCCTCAGAAGAAG<br>AGACAGATCACCGTGGACTCAGAGATTCGCAAGAGACTGGACGTGGACAT<br>CACCGAGCTGCACAGCTGGATCACAAGAAGCGAGGCCGTGCTGCAGAGCC<br>CTGAGTTCGCGATCTTTAGAAAGGAGGGCAACTTCAGCGACTTGAAGGAG<br>AAAGTGAACGCCATCGAGAGAGAGAAGGCCGAGAAGTTCAGAAAGTTGCA<br>AGACGCCTCAAGAAGCGCCCAAGCCCTGGTGGAGCAGATGGTTAACGAAG<br>GCGTGAATGCCGACAGCATCAAGCAAGCTAGCGAGCAGCTGAATAGCCGG<br>TGGATTGAATTCTGTCAGCTGCTGAGCGAGAGATTAAACTGGCTGGAGTA<br>TCAGAACAACATCATCGCCTTCTACAATCAGCTGCAGCAACTAGAACAAA<br>TGACCACCACCGCCGAGAACTGGCTAAAGATTCAGCCCACCACCCCTAGC<br>GAGCCCACCGCCATCAAATCTCAGCTGAAAATTTGCAAGGACGAAGTGAA<br>CAGACTGTCGGACCTGCAGCCTCAAATCGAAAGACTGAAAATTCAGAGCA<br>TCGCACTTAAGGAGAAGGGCCAAGGACCCATGTTCCTGGACGCCGACTTC<br>GTGGCCTTCACCAACCACTTCAAGCAAGTGTTCAGCGACGTGCAAGCTAG<br>AGAGAAGGAGCTGCAGACCATCTTCGACACCCTGCCCCCCATGAGATACC<br>AAGAAACCATGAGCGCCATCAGAACCTGGGTGCAGCAGAGCGAAACCAAG<br>CTGAGCATCCCTCAGCTGAGCGTGACCGACTACGAGATCATGGAGCAAAG<br>ACTGGGAGAGCTGCAAGCCCTGCAGAGCAGCCTGCAAGAGCAGCAGAGCG<br>GCCTGTACTACCTGAGCACCACCGTGAAGGAGATGTCGAAGAAAGCCCCG<br>TCGGAGATCAGCAGAAAGTATCAGAGCGAGTTCGAGGAGATCGAGGGCAG<br>ATGGAAGAAGCTGAGCAGCCAACTGGTGGAACACTGTCAGAAATTAGAAG<br>AACAGATGAACAAGCTGAGAAAGATTCAGAACCACATTCAGACCCTGAAG<br>AAGTGGATGGCCGAGGTGGACGTGTTCCTGAAAGAGGAGTGGCCCGCCCT<br>GGGCGATTCCGAAATCTTAAAAAAGCAGCTGAAGCAGTGCAGACTGCTGG<br>TGTCAGATATCCAAACCATTCAACCAAGCCTGAACAGCGTGAACGAAGGG |

-continued

| SEQ ID NO | Description | SEQ |
|---|---|---|
| | | GGCAGAAGATCAAGAACGAGGCCGAGCCCGAGTTCGCTAGCAGACTGGAA ACCGAGCTGAAGGAGCTGAATACACAGTGGGACCACATGTGTCAGCAAGT GTACGCTAGAAAGGAAGCGCTGAAGGGCGGGCTGGAGAAGACCGTTAGCC TGCAAAAGGATCTGAGCGAGATGCACGAGTGGATGACCCAAGCCGAGGAG GAGTACCTGGAGAGAGACTTCGAGTACAAGACCCCCGACGAGCTGCAGAA GGCCGTCGAGGAAATGAAGAGAGCGAAGGAGGAGGCTCAGCAGAAGGAAG CCAAGGTGAAGCTGCTGACTGAATCTGTCAACAGTGTGATAGCTCAAGCA CCCCCCGTTGCCCAAGAGGCACTAAAGAAGGAGCTGGAAACTCTGACCAC CAACTATCAGTGGCTGTGCACAAGACTGAACGGCAAGTGCAAGACCCTGG AGGAAGTGTGGGCCTGCTGGCACGAGCTGCTGAGCTACCTGGAGAAGGCC AACAAGTGGCTGAACGAGGTGGAGTTCAAGCTGAAGACCACCGAGAACAT CCCCGGCGGCGCCGAGGAGATCAGCGAGGTGCTGGACAGCCTGGAGAACC TGATGAGACACAGCGAGGACAACCCCAATCAGATCAGAATCCTGGCTCAG ACCCTGACCGACGGCGGCGTGATGGACGAGCTGATCAACGAGGAGCTGGA AACCTTTAACTCTAGATGGCGAGAACTGCACGAGGAGGCCGTGAGAAGAC AGAAGCTGCTGGAGCAAAGCATTCAGAGCGCCCAAGAAACCGAGAAGAGC CTGCACCTGATCCAAGAGAGCCTGACCTTCATCGACAAGCAGCTGGCCGC CTACATCGCCGACAAGGTGGACGCCGCTCAGATGCCACAAGAGGCTCAGA AGATTCAGTCCGATCTGACAAGCCACGAGATCAGCCTGGAGGAGATGAAA AAACACAACCAAGGCAAGGAGGCCGCTCAGAGAGTGCTGTCTCAGATCGA CGTGGCTCAGAAGAAGCTGCAAGACGTGAGCATGAAGTTCAGACTGTTTC AGAAGCCCGCCAACTTCGAGCAGCGACTGCAAGAGAGCAAGATGATCCTG GACGAGGTGAAGATGCACCTGCCCGCCCTGGAAACCAAGAGCGTGGAGCA AGAGGTGGTGCAGTCTCAGTTGAACCACTGCGTGAACCTGTACAAGAGCC TGTCGGAGGTCAAGAGTGAGGTCGAGATGGTGATCAAAACTGGGAGACAG ATCGTGCAAAAAAAGCAGACCGAGAACCCCAAGGAGCTGGACGAGCGTGT TACCGCCCTGAAGCTGCACTACAACGAGCTGGGCGCCAAGGTGACCGAGA GAAAGCAGCAGCTGGAGAAGTGCCTGAAGCTGAGCAGAAAGATGAGAAAG GAGATGAACGTGCTGACCGAGTGGCTGGCCGCCACCGACATGGAGCTGAC CAAGAGAAGCGCCGTGGAGGGCATGCCTAGCAACCTGGACAGCGAGGTGG CCTGGGGCAAGGCCACACAGAAGGAGATCGAGAAGCAGAAGGTGCACCTG AAGAGCATCACCGAGGTGGGCGAGGCCCTGAAGACCGTGCTGGGCAAGAA GGAAACCCTGGTGGAGGACAAGCTGAGCCTGCTGAACTCGAACTGGATCG CCGTGACAAGCAGAGCCGAGGAGTGGCTGAACCTGCTGTTAGAGTACCAA AAACACATGGAAACCTTCGATCAGAACGTGGACCACATCACCAAGTGGAT CATCCAAGCCGACACCCTGCTGGACGAAAGCGAAAAGAAGAAGCCGCAAC AAAAGGAGGATGTGCTGAAGAGACTGAAGGCCGAACTGAACGATATCAGA CCCAAGGTGGACAGCACACGGGACCAAGCCGCCAACCTGATGGCCAACAG AGGCGACCACTGCAGAAAACTGGTGGAGCCTCAGATCAGCGAGCTGAACC ACAGATTCGCCGCCATCAGCCACAGAATCAAAACCGGCAAAGCGAGCATC CCCTTGAAGGAACTGGAGCAATTTAACAGCGACATCCAAAAATTGCTCGA ACCACTGGAGGCCGAGATTCAGCAAGGCGTGAACCTGAAGGAAGAGGACT TCAACAAGGACATGAACGAGGACAACGAGGGCACCGTGAAAGAACTGCTG CAGAGAGGCGACAACCTGCAGCAGAGAATCACCGACGAGAGAAAGAGAGA GGAGATCAAGATCAAGCAGCAGCTGCTGCAGACTAAGCACAACGCCCTGA AGGATCTGAGATCTCAGAGGAGAAAAAAGGCTCTGGAAATTTCACATCAG TGGTATCAGTACAAGAGACAAGCAGACGACCTGCTGAAGTGCCTGGACGA CATCGAGAAGAAGTTAGCTAGCCTGCCCGAGCCTAGAGACGAGAGAAAGA TCAAGGAGATCGACAGAGAGTTACAAAAGAAGAAGGAGGAGCTGAATGCG GTAAGAAGACAAGCGGAAGGCCTGTCCGAGGACGGCGCAGCCATGGCCGT GGAGCCCACACAGATTCAGCTCAGCAAGAGATGGAGAGAGATCGAGAGCA AGTTCGCTCAGTTCAGAAGACTGAACTTCGCTCAGATCCACACCGTGAGA GAGGAAACCATGATGGTGATGACCGAGGACATGCCCCTGGAGATCTCATA CGTTCCTAGCACCTACCTGACCGAGATCACCCACGTGAGCCAAGCCCTGC TGGAGGTGGAGCAGCTGCTGAACGCCCCCGACCTGTGCGCCAAGGACTTC GAGGACCTGTTCAAACAAGAGGAGAGCCTGAAGAACATCAAGGACAGCCT GCAGCAAAGTAGCGGCAGAATCGACATCATCCACAGCAAGAAGACCGCCG CCCTGCAGAGCGCCACCCCCGTGGAGAGAGTGAAGCTTCAAGAGGCCCTT TCGCAGCTGGATTTTCAGTGGGAGAAGGTGAACAAAATGTACAAGGACAG ACAAGGCAGATTCGACAGAAGCGTGGAGAAGTGGAGAAGATTCCACTACG ACATCAAGATCTTCAATCAGTGGCTGACCGAGGCAGAGCAGTTCCTGAGA AAGACACAGATCCCCGAGAACTGGGAGCACGCCAAGTACAAGTGGTACCT GAAGGAGCTGCAAGACGGCATCGGGCAGAGACAGACCGTGGTGAGAACCC TGAACGCCACCGGCGAGGAGATCATCCAACAAAGCTCCAAAACCGACGCT AGCATCCTGCAAGAGAAACTGGGCAGCCTGAACCTGAGATGGCAAGAGGT GTGCAAGCAGCTGAGCGACCGCAAAAAACGGTTAGAGGAGCAGAAGAACA TCCTGAGCGAGTTTCAGCGGGACCTGAACGAGTTCGTGCTGTGGCTGGAG GAGGCCGATAACATCGCTAGCATCCCCCTGGAGCCCGGCAAGGAGCAGCA GTTAAAAGAAAAACTTGAGCAAGTGAAGCTGCTGGTGGAGGAGCTGCCCC TGAGACAAGGCATCCTGAAGCAGCTGAACGAGACTGGCGGCCCCGTGCTG GTGAGCGCCCCCATCAGCCCCGAGGAGCAAGACAAGCTGGAGAACAAGCT GAAGCAGACCAACCTGCAGTGGATCAAGGTGAGCAGAGCCCTGCCCGAGA AGCAAGGCGAAATCGAGGCCCAAATAAAGGACCTGGGGCAGCTGGAGAAG AAACTCGAAGACTTGGAAGAACAACTCAACCACTTGCTGCTGTGGCTGAG CCCCATCAGAAATCAGCTGGAGATCTACAATCAGCCCAACCAAGAGGGGC |

-continued

| SEQ ID NO | Description | SEQ |
|---|---|---|
| | | CATTCGACGTGAAGGAAACCGAGATCGCCGTGCAAGCCAAGCAGCCCGAT<br>GTGGAGGAGATCCTGAGCAAGGGGCAGCACCTGTACAAGGAGAAGCCCGC<br>CACACAGCCCGTCAAGCGTAAACTAGAGGATCTTTCCTCTGAGTGGAAGG<br>CCGTGAACCGTCTGCTACAAGAGCTGCGGGCTAAGCAACCCGACTTAGCG<br>CCCGGCCTGACCACCATCGGTGCAAGCCCCACGCAGACCGTGACCCTGGT<br>GACCCAACCCGTGGTGACCAAGGAAACCGCCATCAGCAAGCTGGAGATGC<br>CTAGCAGCCTGATGCTGGAGGTGCCCGCCCTGGCCGACTTCAACAGAGCC<br>TGGACCGAGCTGACCGACTGGCTGAGCCTGCTGGACCAAGTGATCAAGTC<br>TCAGAGAGTGATGGTGGGCGATCTGGAGGACATCAATGAGATGATCATCA<br>AGCAGAAGGCCACCATGCAAGACCTGGAGCAGAGAAGACCTCAGCTGGAG<br>GAGCTGATCACCGCCGCTCAGAACCTGAAAAACAAGACGAGCAACCAAGA<br>GGCTAGAACCATCATCACCGACAGAATCGAGAGAATTCAGAATCAGTGGG<br>ACGAGGTGCAAGAGCACCTGCAGAACAGAAGACAGCAACTAAACGAAATG<br>CTCAAGGACAGCACACAGTGGCTGGAGGCCAAGGAGGAGGCGGAGCAAGT<br>GTTGGGCCAAGCTAGAGCCAAGCTGGAGAGCTGGAAGGAGGGACCCTACA<br>CCGTGGACGCCATTCAGAAGAAGATCACCGAAACCAAGCAGCTGGCCAAG<br>GACCTGCGACAGTGGCAGACCAACGTGGACGTGGCCAACGATCTTGCCCT<br>GAAGCTGCTGCGCGACTATAGCGCCGACGACACAAGAAAGGTGCACATGA<br>TCACCGAGAACATCAACGCTAGCTGGCGTAGCATCCACAAGAGAGTGAGC<br>GAGAGAGAGGCGGCTTTGGAGGAAACCCATAGACTGCTGCAGCAGTTTCC<br>CCTGGACCTGGAGAAGTTCCTGGCCTGGCTGACCGAAGCCGAAACAACCG<br>CCAACGTGCTGCAAGACGCCACAAGAAAGGAGAGACTGCTGGAGGACAGC<br>AAGGGCGTGAAGGAGCTGATGAAGCAGTGGCAAGACCTGCAAGGCGAGAT<br>CGAAGCGCACACCGACGTGTACCACAACCTGGACGAGAACTCTCAGAAGA<br>TCCTGAGAAGCCTGGAGGGCAGCGACGACGCCGTGCTGTTACAGAGAAGG<br>CTGGACAACATGAACTTCAAGTGGAGCGAGCTGAGAAAGAAGAGCCTGAA<br>CATCAGAAGCCACCTGGAGGCTAGCAGCGATCAGTGGAAGAGACTGCACC<br>TGAGCCTGCAAGAGCTGCTGGTCTGGCTTCAGTTGAAGGACGATGAGCTG<br>AGCAGACAAGCCCCCATCGGCGGCGACTTCCCCGCCGTGCAGAAGCAGAA<br>CGACGTGCATAGAGCCTTCAAGAGAGAGCTGAAGACCAAGGAGCCCGTGA<br>TCATGAGCACCCTGGAAACGGTGAGAATCTTCCTGACCGAGCAGCCCCTG<br>GAGGGCCTGGAGAAGCTGTACCAAGAGCCTAGAGAGCTGCCCCCCGAGGA<br>GAGAGCTCAGAACGTGACAAGACTGCTGAGAAAGCAAGCCGAAGAGGTGA<br>ACACCGAGTGGGAGAAGCTGAACCTGCACAGCGCCGACTGGCAGAGAAAG<br>ATCGACGAAACCCTGGAGAGACTGAGAGAATTGCAAGAGGCGACCGACGA<br>GCTGGACCTGAAGCTGAGACAAGCCGAGGTCATCAAGGGCAGCTGGCAGC<br>CCGTGGGCGATCTATTAATTGACTCTCTACAAGACCACCTGGAGAAAGTG<br>AAGGCCCTGAGAGGCGAGATCGCCCCCCTGAAGGAGAACGTGAGCCACGT<br>GAATGATCTGGCACGTCAGCTGACCACCCTGGGCATACAACTGTCCCCCT<br>ATAACCTGAGCACACTGGAGGATTTGAATACTAGATGGAAGCTGCTGCAA<br>GTGGCCGTGGAGGACAGAGTAAGACAATTACATGAGGCCCACAGAGACTT<br>CGGCCCCGCTTCTCAGCACTTCCTGAGCACAAGCGTGCAAGGCCCCTGGG<br>AGAGAGCCATTTCCCCCAACAAGGTCCCCTACTACATCAACCACGAGACA<br>CAGACCACCTGCTGGGACCACCCCAAGATGACCGAGCTGTATCAGAGCCT<br>CGCCGATCTGAACAATGTGAGATTCAGCGCCTACAGAACCGCCATGAAGC<br>TGAGAAGACTGCAGAAGGCCCTGTGCCTGGACTTATTAAGCCTGAGCGCC<br>GCCTGCGACGCCCTGGATCAGCACAACCTGAAGCAAAACGACCAACCCAT<br>GGACATCCTGCAGATCATCAACTGCCTCACCACCATATACGACAGACTGG<br>AACAAGAGCACAACAACCTGGTGAACGTGCCCCTGTGCGTGGACATGTGC<br>CTGAACTGGCTGCTGAACGTGTACGACACCGGCAGAACCGGCAGAATCAG<br>AGTGCTGAGCTTCAAGACCGGCATCATCAGCCTGTGCAAGGCCCACCTGG<br>AGGACAAATACAGATACCTTTTCAAACAAGTGGCTAGCAGCACCGGCTTC<br>TGCGACCAAAGAAGACTGGGTCTGCTGCTGCACGACAGCATTCAGATCCC<br>TAGACAGCTGGGCGAGGTGGCTAGCTTCGGCGGCAGCAACATCGAGCCTA<br>GCGTGAGAAGCTGCTTTCAGTTCGCCAACAACAAGCCCGAGATAGAGGCA<br>GCCCTCTTCTTAGACTGGATGAGACTGGAGCCTCAGAGCATGGTATGGCT<br>GCCGGTCCTGCACAGAGTGGCCGCCGCCGAAACCGCCAAGCACCAAGCCA<br>AGTGCAACATCTGCAAGGAGTGCCCCATCATCGGCTTCAGATACAGAAGC<br>CTGAAGCACTTCAACTACGACATCTGTCAGAGCTGCTTCTTCAGCGGCAG<br>AGTGGCCAAGGGCCACAAGATGCACTACCCCATGGTGGAGTACTGCACCC<br>CCACCACAAGCGGCGAGGACGTGAGAGACTTCGCCAAGGTGTTGAAGAAT<br>AAGTTTAGAACCAAGAGATACTTCGCCAAGCACCCTAGAATGGGCTACCT<br>GCCCGTGCAGACCGTGCTGGAGGGCGACAACATGGAAACCCCCGTGACCC<br>TGATCAACTTCTGGCCCGTGGACAGCGCCCCCGCTAGCAGCCCTCAGCTG<br>AGCCACGACGACACCCACAGCAGAATCGAGCACTACGCTAGCAGACTGGC<br>CGAGATGGAGAACAGCAACGGCAGCTACCTGAACGACAGCATCAGCCCGA<br>ATGAGAGCATCGACGACGAGCACCTGCTGATTCAGCACTACTGTCAGAGC<br>CTGAACCAAGACAGCCCCCTGTCTCAGCCTAGAAGCCCCGCTCAGATCCT<br>GATCAGCCTGGAGAGCGAGGAGAGAGGCGAGCTGGAGAGAATCCTAGCAG<br>ATCTGGAGGAAGAGAACAGAAACCTGCAAGCCGAGTATGACCGACTGAAA<br>CAGCAACATGAGCACAAAGGCCTGAGCCCACTGCCCTCCCCCCCCGAGAT<br>GATGCCCACAAGCCCTCAGAGCCCTAGAGACGCCGAGCTGATCGCTGAAG<br>CGAAGTTACTTAGACAACACAAGGGCAGACTGGAGGCTAGAATGCAGATC<br>CTGGAGGACCACAACAAGCAGCTGGAGTCTCAGCTGCACAGACTGAGGCA<br>GCTGCTGGAACAGCCCCAAGCCGAGGCCAAAGTGAACGGCACCACCGTGA |

| SEQ ID NO | Description | SEQ |
|---|---|---|
| | | GCAGTCCTAGCACAAGCCTGCAGAGAAGCGACAGCTCTCAGCCCATGCTG<br>CTGAGAGTGGTGGGCTCTCAGACAAGCGACAGCATGGGCGAGGAGGATCT<br>GCTGAGTCCGCCCCAAGACACAAGCACCGGCCTGGAAGAGGTGATGGAGC<br>AACTGAACAATAGCTTCCCTAGCAGCAGAGGCAGAAACACCCCCGGCAAG<br>CCCATGAGAGAGGACACCATGTGATGACTCGAGAATCAACCTCTGGATTA<br>CAAAATTTGTGAAAGATTGACTGGTATTCTTAACTATGTTGCTCCTTTTA<br>CGCTATGTGGATACGCTGCTTTAATGCCTTTGTATCATGCTATTGCTTCC<br>CGTATGGCTTTCATTTTCTCCTCCTTGTATAAATCCTGGTTGCTGTCTCT<br>TTATGAGGAGTTGTGGCCCGTTGTCAGGCAACGTGGCGTGGTGTGCACTG<br>TGTTTGCTGACGCAACCCCCACTGGTTGGGGCATTGCCACCACCTGTCAG<br>CTCCTTTCCGGGACTTTCGCTTTCCCCCTCCCTATTGCCACGGCGGAACT<br>CATCGCCGCCTGCCTTGCCCGCTGCTGGACAGGGGCTCGGCTGTTGGGCA<br>CTGACAATTCCGTGGGGTGTGCCTTCTAGTTGCCAGCCATCTGTTGTTTG<br>CCCCTCCCCCGTGCCTTCCTTGACCCTGGAAGGTGCCACTCCCACTGTCC<br>TTTCCTAATAAAATGAGGAAATTGCATCGCATTGTCTGAGTAGGTGTCAT<br>TCTATTCTGGGGGGTGGGGTGGGGCAGGACAGCAAGGGGGAGGATTGGGA<br>AGACAATAGCAGGCATGCTGGGGATGCGGTGGGCTCTATGGGAAGATGTC<br>TACTGAGCTGTGCGATCCCTGCTGGGGACTTTCCGCTGGGGACTTTCCGC<br>TGGGGACTTTCCGCCTTCAGCTAAGGAAGCTACCAATATTTAGAGGTACA<br>TTTTGTTCTAGAACAAAATGTACCGGTACATTTTGTTCTGGTACATTTTG<br>TTCT |
| 23. | CBA-hBGi-<br>DMD-4-<br>WPRE3-<br>DTS | CGTTACATAACTTACGGTAAATGGCCCGCCTGGCTGACCGCCCAACGACC<br>CCCGCCCATTGACGTCAATAATGACGTATGTTCCCATAGTAACGCCAATA<br>GGGACTTTCCATTGACGTCAATGGGTGGAGTATTTACGGTAAACTGCCCA<br>CTTGGCAGTACATCAAGTGTATCATATGCCAAGTACGCCCCCTATTGACG<br>TCAATGACGGTAAATGGCCCGCCTGGCATTATGCCCAGTACATGACCTTA<br>TGGGACTTTCCTACTTGGCAGTACATCTACGTATTAGTCATCGCTATTAC<br>CATGGTCGAGGTGAGCCCCACGTTCTGCTTCACTCTCCCCATCTCCCCCC<br>CCTCCCCACCCCCAATTTTGTATTTATTTATTTTTTAATTATTTTGTGCA<br>GCGATGGGGGCGGGGGGGGGGGGGGGGCGCGCCAGGCGGGGCGGGGCGGG<br>GCGAGGGGGGGGCGGGGCGAGGCGGAGAGGTGCGGCGGCAGCCAATCAGA<br>GCGGCGCGCTCCGAAAGTTTCCTTTTATGGCGAGGCGGCGGCGGCGGCGG<br>CCCTATAAAAAGCGAAGCGCGCGGCGGGCGGGAGTCTCTGGATCCACTGC<br>TTAAATACGGACGAGGACAGGGCCCTGTCTCCTCAGCTTCAGGCACCACC<br>ACTGACCTGGGACAGTGAATCGTAAGTACTAGCAGCTACAATCCAGCTAC<br>CATTCTGCTTTTATTTTATGGTTGGGATAAGGCTGGATTATTCTGAGTCC<br>AAGCTAGGCCCTTTTGCTAATCATGTTCATACCTCTTATCTTCCTCCCAC<br>AGCTCCTGGGCAACGTGCTGGTCTGTGTGCTGGCCCATCACTTTGGCAAA<br>GAATTGCGATCGCCACCATGCTTTGGTGGGAAGAAGTCGAGGACTGCTAC<br>GAGCGCGAGGACGTGCAGAAGAAAACCTTCACCAAATGGGTCAACGCCCA<br>GTTCAGCAAGTTCGGCAAGCAGCACATCGAGAACCTGTTCAGCGACCTGC<br>AGGATGGCAGAAGGCTGCTGGATCTGCTGGAAGGCCTGACAGGACAGAAG<br>CTGCCCAAAGAGAAGGGCAGCACAAGAGTGCACGCCCTGAACAACGTGAA<br>CAAGGCCCTGAGAGTGCTGCAGAACAACAACGTGGACCTGGTCAACATCG<br>GCAGCACCGACATCGTGGACGGCAACCACAAACTGACCCTGGGCCTGATC<br>TGGAACATCATCCTGCACTGGCAAGTGAAGAACGTGATGAAGAACATCAT<br>GGCCGGCCTGCAGCAGACCAACAGCGAGAAGATTCTGCTGAGCTGGGTCC<br>GACAGAGCACCCGGAATTACCCTCAAGTGAACGTGATCAACTTCACCACC<br>TCTTGGAGCGACGGACTGGCCCTGAATGCCCTGATCCACAGCCACAGACC<br>TGACCTGTTCGACTGGAACAGCGTCGTGTGTCAGCAGAGCGCCACACAGA<br>GGCTGGAACACGCCTTCAATATCGCCAGATACCAGCTGGGCATCGAGAAA<br>CTGCTGGACCCCGAGGATGTGGACACCACCTATCCTGACAAGAAATCCAT<br>CCTCATGTACATCACCAGCCTGTTCCAGGTGCTGCCCCAGCAGGTTTCCA<br>TCGAGGCCATTCAAGAGGTCGAGATGCTGCCCAGACCTCCTAAAGTGACC<br>AAAGAGGAACACTTCCAGCTGCACCACCAGATGCACTACTCTCAGCAGAT<br>CACCGTGTCTCTGGCCCAGGGCTACGAGAGAACAAGCAGCCCCAAGCCTC<br>GGTTCAAGAGCTACGCCTATACACAGGCCGCCTACGTGACCACCAGCGAT<br>CCTACAAGAAGCCCATTTCCTAGCCAGCATCTGGAAGCCCCTGAGGACAA<br>GAGCTTTGGCAGCAGCCTGATGGAAAGCGAAGTGAACCTGGACCGCTACC<br>AGACAGCCCTGGAAGAGGTTCTGAGCTGGCTGCTGTCTGCCGAGGATACA<br>CTGCAGGCTCAGGGCGAGATCAGCAACGACGTGGAAGTGGTCAAGGACCA<br>GTTTCACACCCACGAGGGCTACATGATGGACCTGACAGCCCACCAGGGCA<br>GAGTGGGCAATATTCTGCAGCTGGGCTCCAAGCTGATCGGCACAGGCAAG<br>CTGAGCGAGGACGAAGAGACAGAGGTGCAAGAGCAGATGAACCTGCTGAA<br>CAGCAGATGGGAGTGTCTGAGAGTGGCCAGCATGGAAAAGCAGAGCAACC<br>TGCACCGGGTGCTGATGGATCTCCAGAACCAGAAGCTGAAAGAGCTGAAC<br>GACTGGCTGACCAAGACCGAGGAACGGACCCGGAAGATGGAAGAGGAACC<br>TCTGGGACCCGACCTGGAAGATCTGAAAAGACAGGTGCAGCAGCATAAGG<br>TGCTGCAAGAGGACCTCGAACAAGAGCAAGTGCGCGTGAACAGCCTGACA<br>CACATGGTGGTGGTCGTGGATGAGAGCAGCGGAGATCATGCCACAGCCGC<br>TCTGGAAGAACAGCTGAAGGTGCTGGGAGACAGATGGGCCAATATCTGCC<br>GGTGGACCGAGGATAGATGGGTGCTGCTCCAGGACATCCTGCTGAAGTGG<br>CAGCGGCTGACAGAGGAACAGTGCCTGTTTAGCGCCTGGCTGTCCGAGAA<br>AGAGGACGCCGTCAACAAGATCCACACCACCGGCTTCAAGGATCAGAATG |

-continued

| SEQ ID NO | Description | SEQ |
|---|---|---|
| | | AGATGCTGAGCAGCCTGCAGAAACTGGCCGTGCTGAAGGCTGACCTGGAA<br>AAGAAAAAGCAGTCCATGGGCAAGCTGTACTCCCTGAAGCAGGACCTGCT<br>GAGCACACTGAAGAACAAGTCTGTGACCCAGAAAACCGAGGCCTGGCTGG<br>ACAACTTCGCCCGGTGTTGGGATAACCTGGTGCAGAAGCTGGAAAAGTCC<br>ACCGCTCAGATCTCTCAGGCCGTGACCACAACACAGCCTTCTCTGACCCA<br>GACCACCGTGATGGAAACAGTGACCACAGTGACAACCCGCGAGCAGATCC<br>TGGTCAAGCACGCCCAAGAAGAACTGCCTCCTCCACCTCCTCAGAAGAAA<br>CGGCAGATCACAGTGGACAGCGAGATCCGGAAGAGACTGGACGTGGACAT<br>CACCGAGCTGCACAGCTGGATCACCAGATCCGAAGCCGTGCTGCAGTCCC<br>CTGAGTTCGCCATCTTCAGAAAAGAGGGCAACTTCTCCGACCTGAAAGAG<br>AAAGTCAACGCCATCGAGAGAGAGAAGGCCGAGAAGTTCCGGAAGCTGCA<br>GGACGCCTCTAGATCTGCCCAGGCTCTGGTGGAACAGATGGTCAACGAAG<br>GCGTGAACGCCGACAGCATCAAGCAGGCCTCAGAGCAGCTGAACTCCCGG<br>TGGATCGAGTTCTGTCAGCTCCTGAGCGAGAGACTGAACTGGCTGGAATA<br>CCAGAACAATATCATTGCCTTCTACAACCAGCTCCAGCAGCTCGAACAGA<br>TGACCACCACAGCCGAGAATTGGCTGAAGATCCAGCCTACCACACCTAGC<br>GAGCCCACCGCCATTAAGAGCCAGCTGAAAATCTGCAAGGACGAAGTGAA<br>TCGGCTGAGCGATCTGCAGCCCCAGATCGAAAGACTGAAAATCCAGTCTA<br>TCGCCCTCAAAGAGAAAGGACAGGGCCCCATGTTCCTGGACGCCGATTTT<br>GTGGCCTTTACCAACCACTTCAAACAGGTGTTCTCCGACGTGCAGGCCCG<br>GGAAAAAGAGCTGCAGACCATCTTCGACACCCTGCCTCCAATGAGATACC<br>AAGAGACAATGAGCGCCATCCGGACCTGGGTGCAGCAAAGCGAGACAAAG<br>CTGAGCATCCCACAGCTGAGCGTGACCGACTACGAGATCATGGAACAGAG<br>ACTGGGCGAACTGCAGGCCCTCCAGTCTAGCCTGCAAGAACAGCAGTCCG<br>GCCTGTACTACCTGAGCACAACCGTGAAAGAGATGAGCAAGAAGGCCCCT<br>AGCGAGATCTCCCGGAAGTACCAGAGCGAGTTCGAAGAGATCGAAGGCCG<br>GTGGAAGAAGCTGTCTAGCCAGCTGGTTGAGCACTGCCAGAAACTCGAAG<br>AACAAATGAACAAGCTGCGCAAGATCCAGAATCACATCCAGACGCTGAAG<br>AAATGGATGGCCGAGGTGGACGTGTTCCTGAAAGAAGAGTGGCCCGCTCT<br>GGGCGACTCCGAGATTCTGAAGAAACAGCTCAAACAGTGCCGGCTGCTGG<br>TGTCCGATATCCAGACAATCCAGCCAAGCCTGAACTCCGTGAATGAAGGC<br>GGCCAGAAGATCAAGAACGAGGCCGAGCCTGAGTTTGCCAGCAGACTGGA<br>AACCGAACTGAAAGAACTCAACACCCAGTGGGACCACATGTGCCAGCAAG<br>TGTACGCCCGGAAAGAGGCCCTGAAAGGCGGACTCGAAAAGACTGTGTCT<br>CTGCAGAAAGACCTGTCTGAGATGCACGAGTGGATGACCCAGGCCGAAGA<br>GGAATACCTGGAACGGGACTTCGAGTACAAGACCCCTGATGAGCTGCAAA<br>AAGCCGTCGAGGAAATGAAGCGGGCCAAAGAAGAGGCCCAGCAGAAAGAA<br>GCCAAAGTCAAGCTGCTGACCGAGTCCGTGAATAGCGTTATCGCTCAGGC<br>CCCTCCTGTGGCTCAAGAGGCTCTCAAGAAAGAACTGGAAACTCTGACCA<br>CCAACTACCAGTGGCTGTGCACCAGACTGAACGGCAAGTGCAAGACACTG<br>GAAGAAGTGTGGGCCTGCTGGCACGAACTGCTGTCCTATCTGGAAAAGGC<br>CAACAAGTGGCTGAACGAGGTGGAATTCAAGCTGAAAACCACCGAGAACA<br>TCCCTGGCGGCGCTGAAGAGATTAGCGAGGTGCTGGACAGCCTGGAAAAC<br>CTGATGAGACACAGCGAGGACAACCCCAATCAGATCAGAATCCTGGCTCA<br>GACCCTGACCGATGGCGGCGTGATGGACGAGCTGATCAACGAGGAACTCG<br>AAACCTTCAACAGCCGGTGGCGGGAACTGCACGAGGAAGCTGTTCGGAGG<br>CAGAAGTTGCTGGAACAGTCTATCCAGAGCGCACAAGAAACCGAGAAGTC<br>CCTGCACCTGATCCAAGAGAGCCTGACCTTCATCGACAAGCAGCTGGCCG<br>CTTATATCGCCGACAAGGTGGACGCTGCTCAGATGCCCCAAGAGGCACAG<br>AAGATTCAGAGCGACCTGACCAGCCACGAGATTAGCCTGGAAGAAATGAA<br>GAAGCACAACCAGGGCAAAGAGGCCGCTCAGAGAGTCCTGAGCCAGATCG<br>ATGTGGCACAGAAAAAGCTCCAGGATGTGTCCATGAAGTTTCGGCTGTTT<br>CAGAAGCCCGCCAACTTCGAGCAGAGACTGCAAGAGTCCAAGATGATCCT<br>GGACGAAGTCAAAATGCATCTGCCCGCACTGGAAACAAAGTCCGTGGAAC<br>AAGAAGTGGTGCAGTCCCAGCTGAACCACTGCGTGAACCTGTACAAGAGC<br>CTGTCCGAAGTGAAGTCTGAGGTGGAAATGGTCATCAAGACCGGCAGGCA<br>GATCGTCCAGAAGAAGCAGACCGAGAATCCCAAAGAACTCGACGAGAGAG<br>TGACCGCTCTGAAGCTGCACTACAATGAGCTGGGCGCCAAAGTGACCGAG<br>CGGAAGCAACAGCTTGAGAAGTGCCTGAAACTGTCTCGGAAGATGCGGAA<br>AGAAATGAACGTGCTGACAGAGTGGCTGGCCGCCACCGATATGGAACTGA<br>CTAAGAGAAGCGCCGTGGAAGGCATGCCCAGCAACCTGGATAGTGAAGTG<br>GCCTGGGGCAAAGCCACTCAGAAAGAGATTGAGAAGCAGAAGGTCCACCT<br>GAAGTCCATCACCGAAGTGGGCGAAGCCCTGAAAACCGTGCTGGGAAAGA<br>AAGAGACACTGGTCGAGGACAAGCTGTCCCTGCTGAATTCCAACTGGATC<br>GCCGTGACCTCCAGAGCTGAGGAATGGCTGAATCTGCTGCTTGAGTACCA<br>GAAACACATGGAAACGTTCGACCAGAACGTCGACCACATCACAAAGTGGA<br>TCATCCAGGCTGATACCCTGCTGGACGAGTCCGAGAAGAAGAAACCCCAA<br>CAAAAAGAAGATGTGCTGAAGCGGCTGAAAGCCGAGCTGAATGACATCCG<br>GCCTAAGGTGGACAGCACCAGAGATCAGGCAGCCAACCTGATGGCCAACA<br>GAGGCGACCACTGTCGGAAGCTCGTGGAACCTCAGATCAGCGAGCTTAAC<br>CACAGATTTGCCGCCATCAGCCACCGGATCAAGACAGGCAAGGCCAGCAT<br>TCCTCTCAAAGAGCTTGAGCAGTTCAACAGCGACATCCAAAAGCTGCTCG<br>AACCCCTGGAAGCCGAGATCCAACAGGGCGTCAACCTCAAAGAAGAAGAT<br>TTCAACAAGGACATGAACGAGGACAATGAGGGCACCGTCAAAGAACTGCT<br>GCAGCGGGGCGATAATCTGCAGCAGCGGATTACCGATGAGCGCAAGCGGG |

| SEQ ID NO | Description | SEQ |
|---|---|---|
| | | AAGAGATCAAGATTAAGCAGCAGCTGCTGCAGACCAAGCACAACGCCCTG<br>AAGGACCTGCGGAGCCAGAGAAGAAAGAAGGCCCTGGAAATCAGCCACCA<br>GTGGTATCAGTACAAGCGGCAGGCCGACGACCTGCTGAAGTGCCTGGATG<br>ACATCGAGAAGAAGCTGGCCTCTCTGCCCGAGCCTAGGGACGAGAGAAAG<br>ATCAAAGAGATCGACCGCGAGCTGCAGAAAAAGAAAGAGGAACTGAACGC<br>CGTCCGCAGACAGGCCGAAGGACTTTCTGAAGATGGCGCCGCTATGGCCG<br>TGGAACCCACACAGATTCAGCTGAGCAAGCGGTGGCGGGAAATCGAGAGC<br>AAGTTCGCCCAGTTCCGGCGGCTGAATTTCGCCCAGATCCACACCGTGCG<br>GGAAGAGACAATGATGGTCATGACAGAGGACATGCCCCTTGAGATCAGCT<br>ACGTGCCCAGCACCTACCTGACCGAGATCACCCATGTGTCTCAGGCCCTG<br>CTGGAAGTGGAACAGCTGCTGAATGCCCCTGACCTGTGCGCCAAGGACTT<br>CGAGGACCTGTTCAAGCAAGAGGAAAGCCTGAAGAACATCAAGGACAGCC<br>TGCAGCAGAGCAGCGGCCGGATCGATATCATCCACAGCAAGAAAACCGCC<br>GCACTGCAGAGCGCCACACCTGTGGAAAGAGTGAAGCTGCAAGAGGCCCT<br>GAGCCAGCTGGATTTCCAGTGGGAGAAAGTGAACAAGATGTACAAGGACC<br>GGCAGGGCAGATTCGACCGCAGCGTTGAAAAGTGGCGGCGGTTCCACTAC<br>GACATCAAGATCTTCAACCAGTGGCTGACCGAGGCCGAGCAGTTCCTGAG<br>AAAGACACAGATCCCCGAGAACTGGGAGCACGCCAAGTACAAGTGGTATC<br>TGAAAGAGCTGCAGGACGGCATCGGCCAGAGACAGACAGTCGTGCGGACA<br>CTGAATGCCACCGGCGAGGAAATCATCCAGCAGTCCAGCAAGACCGACGC<br>CAGCATCCTGCAAGAGAAGCTGGGCAGCCTGAACCTGCGGTGGCAAGAAG<br>TGTGCAAGCAGCTGAGCGACCGGAAGAAGCGGCTGGAAGAACAGAAGAAT<br>ATCCTGAGCGAGTTCCAGCGGGACCTGAACGAGTTCGTGCTGTGGCTCGA<br>AGAGGCCGACAATATCGCCAGCATTCCCCTGGAACCTGGCAAAGAGCAGC<br>AGCTGAAAGAAAAGCTGGAACAAGTGAAACTGCTGGTCGAGGAACTGCCC<br>CTGAGACAGGGAATCCTGAAACAGCTGAACGAGACAGGCGGCCCTGTGCT<br>GGTGTCTGCCCCTATTTCTCCCGAGGAACAGGACAAGCTGGAAAACAAGC<br>TGAAGCAGACCAACCTGCAGTGGATCAAGGTGTCCAGAGCACTGCCTGAG<br>AAGCAGGGCGAGATCGAGGCCCAGATCAAGGACCTGGGACAGCTCGAAAA<br>GAAGCTTGAGGACCTCGAAGAACAGCTCAACCATCTGCTGCTTTGGCTGA<br>GCCCCATCCGGAACCAGCTGGAAATCTACAACCAGCCTAATCAAGAGGGC<br>CCCTTCGACGTGAAAGAAACCGAGATTGCCGTGCAGGCCAAGCAGCCCGA<br>TGTGGAAGAGATCCTGTCTAAGGGCCAGCACCTGTACAAAGAGAAGCCCG<br>CCACACAGCCCGTGAAGCGGAAACTGGAAGATCTGAGCAGCGAGTGGAAG<br>GCCGTGAACCGGCTGCTGCAAGAACTGAGAGCCAAACAGCCTGATCTGGC<br>CCCTGGCCTGACAACAATTGGCGCCTCTCCTACACAGACCGTGACACTGG<br>TCACACAGCCTGTGGTCACCAAAGAGACAGCCATCAGCAAACTGGAAATG<br>CCCAGCAGTCTGATGCTCGAAGTGCCCGCACTGGCCGACTTCAATAGAGC<br>CTGGACCGAGCTGACCGACTGGCTCAGTCTGCTGGACCAAGTCATCAAGT<br>CCCAGAGAGTGATGGTCGGAGATCTTGAGGACATCAACGAGATGATCATT<br>AAGCAGAAAGCCACCATGCAGGACCTTGAGCAGAGAAGGCCCCAGCTTGA<br>AGAACTGATCACCGCCGCTCAGAACCTGAAAAACAAGACCAGCAATCAAG<br>AAGCCCGGACCATCATCACCGACCGGATCGAGAGAATCCAGAACCAGTGG<br>GACGAAGTGCAAGAGCATCTGCAGAACAGACGGCAGCAGCTCAATGAGAT<br>GCTGAAGGACAGCACACAGTGGCTGGAAGCCAAAGAAGAAGCCGAGCAGG<br>TTCTCGGACAGGCCAGAGCTAAGCTGGAATCTTGGAAAGAGGGACCCTAC<br>ACCGTCGACGCCATCCAGAAGAAGATCACCGAGACAAAGCAGCTGGCCAA<br>GGATCTGAGACAGTGGCAGACCAATGTGGACGTGGCCAACGACCTGGCTC<br>TGAAGCTGCTGAGAGACTACAGCGCCGACGACACCAGAAAGGTGCACATG<br>ATCACCGAAAACATCAACGCCTCTTGGCGGAGCATCCACAAGCGGGTGTC<br>AGAGAGAGAAGCCGCTCTGGAAGAAACACATAGACTGCTCCAGCAGTTCC<br>CACTCGACCTGGAAAAGTTCCTGGCCTGGCTGACAGAAGCCGAAACCACC<br>GCTAACGTGCTCCAGGATGCCACCAGAAAAGAGCGGCTGTTGGAGGACAG<br>CAAGGGCGTCAAAGAACTCATGAAGCAGTGGCAGGATCTGCAAGGGGAGA<br>TTGAAGCCCACACCGACGTGTACCACAACCTGGACGAGAACAGCCAGAAG<br>ATCCTGCGGTCCCTGGAAGGCTCTGATGATGCTGTGCTGCTTCAGAGGCG<br>GCTGGACAACATGAACTTCAAGTGGAGCGAGCTGCGGAAGAAGTCCCTGA<br>ACATCAGAAGCCACCTGGAAGCCTCCAGCGACCAGTGGAAAAGACTGCAC<br>CTGTCTCTCCAAGAGCTGCTCGTGTGGCTGCAGCTGAAGGATGACGAGCT<br>GAGTAGACAGGCCCCTATCGGCGGAGATTTTCCCGCCGTGCAGAAACAGA<br>ACGACGTGCACCGGGCCTTCAAGAGAGAGCTGAAAAAAAAGAACCCGTCA<br>TCATGAGCACCCTGGAAACCGTGCGGATCTTTCTGACCGAGCAGCCTCTG<br>GAAGGACTGGAAAAGCTGTACCAAGAGCCTAGAGAGCTGCCTCCTGAAGA<br>AAGGGCCCAGAACGTGACACGGCTGCTTAGAAAGCAGGCCGAGGAAGTGA<br>ACACCGAATGGGAGAAGCTGAACCTCCACTCCGCCGACTGGCAGCGGAAG<br>ATCGATGAGACACTGGAACGGCTGCGGGAACTGCAAGAAGCCACAGACGA<br>GCTGGACCTGAAACTGCGGCAGGCTGAAGTGATCAAAGGCTCCTGGCAGC<br>CAGTGGGCGATCTGCTGATCGATAGCCTGCAGGACCATCTGGAAAAAGTC<br>AAGGCCCTGCGGGGAGAGATCGCCCCTCTCAAAGAAAACGTGTCCCACGT<br>GAACGATCTGGCCAGGCAGCTGACAACACTGGGCATCCAGCTGAGCCCTT<br>ACAACCTGTCTACCTTGGAGGACCTGAATACCCGGTGGAAGCTGCTCCAA<br>GTGGCCGTCGAGGATAGAGTGCGGCAGCTGCATGAGGCTCACAGAGATTT<br>TGGACCCGCCAGCCAGCACTTCCTGAGCACATCTGTTCAAGGCCCCTGGG<br>AGAGAGCTATCAGCCCTAACAAGGTGCCCTACTACATCAACCACGAGACA<br>CAGACCACCTGTTGGGATCACCCCAAGATGACCGAACTGTATCAGTCCCT |

-continued

| SEQ ID NO | Description | SEQ |
|---|---|---|
| | | GGCCGACCTGAACAACGTGCGGTTTAGCGCCTACCGGACCGCCATGAAGC TGCGCAGACTGCAGAAAGCTCTGTGCCTGGACCTGCTGTCTCTGAGCGCT GCTTGTGATGCCCTGGACCAGCATAACCTCAAGCAGAACGACCAGCCTAT GGACATCCTGCAGATCATCAACTGCCTGACCACCATCTACGACCGGCTCG AACAAGAGCACAACAACCTGGTCAACGTGCCCCTGTGCGTGGACATGTGC CTGAATTGGCTGCTGAACGTGTACGACACCGGCAGAACCGGCAGGATCAG AGTGCTGAGCTTCAAGACCGGCATCATCTCCCTGTGCAAGGCCCACCTTG AGGATAAGTACCGCTACCTGTTTAAGCAGGTCGCCAGCAGCACCGGCTTT TGCGACCAAAGAAGGCTGGGACTGCTGCTCCACGACAGCATTCAGATCCC TAGACAGCTGGGCGAAGTGGCCTCTTTCGGCGGCTCTAATATCGAGCCTA GCGTGCGGAGCTGCTTCCAGTTCGCCAACAACAAGCCCGAGATTGAGGCC GCACTGTTCCTGGACTGGATGAGACTGGAACCCCAGAGCATGGTCTGGCT GCCTGTGCTGCATAGAGTGGCCGCAGCCGAAACAGCCAAGCACCAGGCCA AGTGCAACATCTGCAAAGAGTGCCCCATCATCGGCTTCCGGTACAGATCC CTGAAGCACTTCAACTACGATATCTGCCAGTCCTGCTTCTTCAGCGGCAG AGTGGCCAAGGGCCACAAGATGCACTACCCCATGGTGGAATACTGCACCC CTACCACCTCTGGCGAGGACGTGCGGGATTTTGCCAAGGTGCTCAAGAAC AAGTTCCGGACCAAGCGCTACTTCGCTAAGCACCCCAGAATGGGCTACCT GCCAGTGCAGACAGTGCTTGAGGGCGACAACATGGAAACCCCTGTGACTC TGATCAACTTCTGGCCCGTGGATAGCGCCCCTGCTAGTTCTCCTCAGCTG TCTCACGACGATACCCACAGCAGAATCGAGCACTACGCCTCCAGACTGGC CGAGATGGAAAACAGCAACGGCAGCTACCTGAATGACAGCATCAGCCCCA ACGAGAGCATCGACGACGAACATCTGCTCATTCAGCACTACTGCCAGAGC CTGAATCAGGACAGCCCTCTGTCTCAGCCTAGAAGCCCTGCACAGATCCT GATCAGCCTGGAAAGCGAGGAACGCGGCGAGCTGGAAAGAATCCTGGCAG ACCTGGAAGAGGAAAACCGGAACCTGCAGGCCGAATACGACAGACTCAAG CAGCAGCACGAGCACAAGGGACTGTCTCCACTGCCTTCTCCACCTGAAAT GATGCCCACCTCTCCACAGAGCCCCAGAGATGCCGAGCTGATTGCCGAAG CCAAACTGCTGAGGCAGCACAAAGGCAGACTCGAAGCCAGAATGCAGATT CTCGAAGATCACAACAAGCAGCTCGAATCCCAGCTGCACAGACTTAGGCA GCTGCTGGAACAGCCTCAGGCAGAGGCCAAAGTGAATGGCACCACCGTGT CTAGCCCTAGCACAAGCCTGCAGAGATCCGACAGCAGCCAGCCAATGCTT CTGAGAGTCGTGGGCTCCCAGACCAGCGATTCTATGGGCGAAGAGGACCT GCTCAGCCCTCCTCAGGATACAAGCACCGGCCTGGAAGAAGTGATGGAAC AACTGAACAACAGCTTCCCCAGCAGCAGAGGCAGAAACACCCCTGGCAAG CCCATGCGCGAGGACACCATGTGATAACTCGAGAATCAACCTCTGGATTA CAAAATTTGTGAAAGATTGACTGGTATTCTTAACTATGTTGCTCCTTTTA CGCTATGTGGATACGCTGCTTTAATGCCTTTGTATCATGCTATTGCTTCC CGTATGGCTTTCATTTTCTCCTCCTTGTATAAATCCTGGTTGCTGTCTCT TTATGAGGAGTTGTGGCCCGTTGTCAGGCAACGTGGCGTGGTGTGCACTG TGTTTGCTGACGCAACCCCCACTGGTTGGGGCATTGCCACCACCTGTCAG CTCCTTTCCGGGACTTTCGCTTTCCCCCTCCCTATTGCCACGGCGGAACT CATCGCCGCCTGCCTTGCCCGCTGCTGGACAGGGGCTCGGCTGTTGGGCA CTGACAATTCCGTGGGGTGTGCCTTCTAGTTGCCAGCCATCTGTTGTTTG CCCCTCCCCCGTGCCTTCCTTGACCCTGGAAGGTGCCACTCCCACTGTCC TTTCCTAATAAAATGAGGAAATTGCATCGCATTGTCTGAGTAGGTGTCAT TCTATTCTGGGGGGTGGGGTGGGGCAGGACAGCAAGGGGGAGGATTGGGA AGACAATAGCAGGCATGCTGGGGATGCGGTGGGCTCTATGGGAAGATGTC TACTGAGCTGTGCGATCCCTGCTGGGGACTTTCCGCTGGGGACTTTCCGC TGGGGACTTTCCGCCTTCAGCTAAGGAAGCTACCAATATTTAGAGGTACA TTTTGTTCTAGAACAAAATGTACCGGTACATTTTGTTCTGGTACATTTTG TTCT |
| 24. | CBA-hBGi-DMD-5-WPRE3-DTS | CGTTACATAACTTACGGTAAATGGCCCGCCTGGCTGACCGCCCAACGACC CCCGCCCATTGACGTCAATAATGACGTATGTTCCCATAGTAACGCCAATA GGGACTTTCCATTGACGTCAATGGGTGGAGTATTTACGGTAAACTGCCCA CTTGGCAGTACATCAAGTGTATCATATGCCAAGTACGCCCCCTATTGACG TCAATGACGGTAAATGGCCCGCCTGGCATTATGCCCAGTACATGACCTTA TGGGACTTTCCTACTTGGCAGTACATCTACGTATTAGTCATCGCTATTAC CATGGTCGAGGTGAGCCCCACGTTCTGCTTCACTCTCCCCATCTCCCCCC CCTCCCCACCCCCAATTTTGTATTTATTTATTTTTTAATTATTTTGTGCA GCGATGGGGGCGGGGGGGGGGGGGGGGCGCGCCAGGCGGGGCGGGGCGGG GCGAGGGGCGGGGCGGGGCGAGGCGGAGAGGTGCGGCGGCAGCCAATCAG AGCGGCGCGCTCCGAAAGTTTCCTTTTATGGCGAGGCGGCGGCGGCGGCG GCCCTATAAAAAGCGAAGCGCGCGGCGGGGGAGTCTCTGGATCCACTGC TTAAATACGGACGAGGACAGGGCCCTGTCTCCTCAGCTTCAGGCACCACC ACTGACCTGGGACAGTGAATCGTAAGTACTAGCAGCTACAATCCAGCTAC CATTCTGCTTTTATTTTATGGTTGGGATAAGGCTGGATTATTCTGAGTCC AAGCTAGGCCCTTTTGCTAATCATGTTCATACCTCTTATCTTCCTCCCAC AGCTCCTGGGCAACGTGCTGGTCTGTGTGCTGGCCCATCACTTTGGCAAA GAATTGCGATCGCCACCATGCTGTGGTGGGAGGAAGTTGAAGATTGTTAT GAGAGAGAAGATGTCCAGAAAAAGACCTTTACCAAATGGGTGAACGCACA GTTCTCCAAATTTGGGAAACAGCATATAGAAAATTTGTTCAGCGATCTTC AGGATGGGCGCAGGTTGCTTGACCTTCTGGAAGGACTGACCGGGCAGAAG CTGCCCAAAGAGAAAGGGTCTACCAGAGTTCACGCTCTGAACAACGTGAA |

-continued

| SEQ ID NO | Description | SEQ |
|---|---|---|
| | | TAAGGCACTGCGAGTCCTGCAAAATAACAACGTCGACCTGGTGAACATAG |
| | | GCAGCACTGATATTGTTGATGGGAACCATAAACTCACACTGGGTCTGATT |
| | | TGGAATATTATACTGCACTGGCAGGTCAAAAATGTTATGAAAAATATTAT |
| | | GGCCGGGCTTCAACAGACCAATTCCGAGAAGATCCTGCTGTCTTGGGTTA |
| | | GGCAGTCCACGAGGAACTACCCTCAAGTGAACGTTATTAACTTCACAACA |
| | | TCATGGAGTGATGGACTTGCCCTGAACGCCTTGATCCACTCCCATAGGCC |
| | | AGACCTGTTCGATTGGAATAGCGTAGTCTGTCAGCAGAGTGCTACACAAC |
| | | GCCTGGAACACGCCTTTAACATAGCCAGGTATCAGCTTGGAATTGAGAAA |
| | | CTCCTCGACCCTGAAGACGTAGACACCACTTACCCCGACAAAAAATCCAT |
| | | TCTTATGTACATAACTTCCTTGTTTCAGGTTCTCCCCCAGCAGGTGTCCA |
| | | TCGAGGCTATACAGGAGGTCGAAATGCTCCCCAGACCCCCTAAGGTCACG |
| | | AAGGAAGAGCACTTCCAACTGCACCATCAGATGCACTACAGTCAACAGAT |
| | | CACTGTGAGTCTCGCACAGGGGTACGAAAGGACCAGCTCCCCTAAACCCC |
| | | GCTTCAAGTCCTACGCCTATACTCAGGCAGCTTACGTAACCACAAGTGAC |
| | | CCCACGCGGTCACCCTTCCCAAGCCAGCACCTGGAGGCTCCCGAGGACAA |
| | | AAGCTTTGGATCATCCCTGATGGAATCTGAAGTCAATCTCGATAGGTACC |
| | | AAACCGCTCTGGAGGAGGTCCTCAGTTGGCTCCTTTCAGCTGAAGATACT |
| | | CTGCAGGCACAGGGTGAGATOAGCAATGACGTGGAGGTAGTGAAAGATCA |
| | | GTTTCACACTCACGAGGGCTATATGATGGACCTGACAGCCCATCAAGGTC |
| | | GCGTTGGCAATATCCTGCAGTTGGGGTCCAAACTGATTGGTACCGGTAAG |
| | | TTGTCCGAGGACGAAGAGACAGAAGTGCAGGAGCAGATGAACCTGCTTAA |
| | | TTCTAGATGGGAATGCCTCCGCGTGGCCTCTATGGAGAAGCAGTCCAATC |
| | | TCCATCGGGTTCTCATGGACTTGCAGAATCAGAAGCTGAAGGAACTCAAC |
| | | GACTGGTTGACCAAGACTGAGGAGCGCACCAGAAAGATGGAGGAGGAGCC |
| | | ACTCGGTCCTGATCTTGAAGATCTGAAACGACAAGTTCAGCAGCACAAGG |
| | | TCCTGCAGGAGGATCTCGAACAGGAGCAGGTCCGGGTGAACAGCCTGACC |
| | | CATATGGTTGTCGTTGTCGACGAGTCAAGTGGGGACCATGCTACGGCTGC |
| | | GCTTGAGGAACAGCTGAAGGTCTTGGGCGATAGATGGGCGAATATCTGCC |
| | | GCTGGACTGAAGATAGATGGGTGCTGCTGCAGGATATTCTTTTGAAGTGG |
| | | CAGCGGTTGACCGAAGAACAATGCTTGTTTAGCGCCTGGCTGAGTGAGAA |
| | | AGAGGATGCGGTGAATAAGATACACACTACTGGCTTCAAAGACCAGAATG |
| | | AAATGCTTAGCAGCCTGCAGAAACTTGCGGTTCTTAAGGCCGACTTGGAA |
| | | AAGAAAAAGCAGTCAATGGGTAAGCTGTACTCACTCAAGCAGGACCTGCT |
| | | GTCAACTTTGAAGAACAAGAGCGTCACGCAAAAGACTGAGGCCTGGCTCG |
| | | ACAATTTTGCTAGGTGCTGGGATAACCTGGTGCAGAAGTTGGAAAAGTCC |
| | | ACTGCTCAGATCTCTCAAGCCGTGACTACTACCCAGCCCAGCCTGACACA |
| | | GACTACCGTCATGGAAACCGTTACCACTGTGACGACTAGGGAGCAGATAC |
| | | TCGTTAAGCACGCTCAAGAGGAATTGCCGCCACCTCCTCCCCAAAAGAAA |
| | | CGCCAGATTACCGTCGACTCTGAAATACGCAAGAGACTGGATGTGGACAT |
| | | CACGGAACTGCACTCTTGGATTACCAGAAGCGAGGCAGTCCTCCAGAGCC |
| | | CCGAGTTTGCGATCTTCAGGAAGGAAGGCAACTTTTCAGATCTGAAGGAA |
| | | AAGGTGAACGCCATCGAGCGCGAGAAAGCCGAGAAGTTCCGCAAACTGCA |
| | | GGATGCGAGCCGGTCTGCTCAGGCCTTGGTGGAGCAAATGGTGAATGAAG |
| | | GCGTAAATGCGGACAGCATCAAGCAGGCCTCCGAGCAGCTCAATTCAAGA |
| | | TGGATCGAGTTCTGTCAGCTGCTCAGCGAGCGATTGAACTGGCTGGAGTA |
| | | TCAAAATAACATAATCGCGTTTTACAACCAGCTGCAACAGCTGGAACAGA |
| | | TGACGACTACTGCAGAGAACTGGCTTAAAATCCAGCCTACAACTCCTTCT |
| | | GAACCCACAGCAATCAAAAGCCAGCTCAAGATCTGCAAGGACGAAGTCAA |
| | | CCGCCTCTCCGATTTGCAGCCTCAGATAGAACGACTCAAGATCCAAAGTA |
| | | TCGCACTCAAAGAAAAGGGGCAAGGCCCTATGTTTCTCGATGCTGATTTT |
| | | GTGGCTTTCACCAACCATTTTAAGCAAGTGTTTTCAGATGTGCAAGCCCG |
| | | GGAAAAGGAACTGCAAACCATTTTTGATACCCTGCCTCCAATGCGGTACC |
| | | AGGAGACTATGTCTGCAATTCGCACCTGGGTGCAACAAAGCGAGACGAAA |
| | | CTTTCTATTCCACAACTGTCCGTGACAGACTACGAAATTATGGAACAGCG |
| | | ACTGGGAGAACTCCAAGCCCTTCAGTCCAGCCTTCAGGAGCAGCAGTCAG |
| | | GATTGTACTATCTGTCAACCACCGTGAAGGAAATGTCAAAAAAGGCTCCC |
| | | TCCGAAATATCTCGCAAGTATCAGTCTGAGTTTGAAGAGATTGAAGGGAG |
| | | ATGGAAGAAACTGTCCTCACAGCTGGTTGAGCACTGTCAGAAGTTGGAAG |
| | | AGCAGATGAACAAGTTGCGCAAGATTCAAAATCACATACAGACACTCAAA |
| | | AAGTGGATGGCGGAGGTTGACGTCTTCCTTAAAGAGGAGTGGCCAGCCCT |
| | | GGGCGACTCAGAGATCCTGAAAAAGCAACTGAAACAGTGCCGACTGCTGG |
| | | TGTCCGACATCCAGACAATACAGCCAAGTTTGAATAGCGTGAATGAGGGT |
| | | GGACAAAAAATCAAAAACGAGGCTGAGCCCGAGTTCGCCTCCAGATTGGA |
| | | AACCGAGCTGAAGGAACTTAATACACAGTGGGATCATATGTGTCAGCAGG |
| | | TTTATGCCCGGAAGGAAGCACTGAAAGGGGGGCTGGAGAAAACCGTGAGC |
| | | CTTCAGAAGGACCTTAGCGAGATGCACGAGTGGATGACCCAGGCGGAGGA |
| | | AGAGTATCTCGAACGGGATTTTGAGTATAAGACACCAGATGAACTTCAGA |
| | | AGGCAGTCGAAGAGATGAAACGGGCAAAGGAAGAGGCTCAGCAGAAGGAA |
| | | GCAAAGGTTAAACTTCTGACAGAATCCGTTAACAGCGTTATAGCCCAAGC |
| | | TCCCCCCGTTGCCCAGGAAGCTCTTAAAAAGGAACTGGAAACACTGACAA |
| | | CAAACTACCAGTGGCTGTGCACCCGCTTGAACGGCAAATGCAAAACCCTG |
| | | GAAGAGGTCTGGGCTTGTTGGCATGAACTCCTGTCATACCTGGAAAAAGC |
| | | TAATAAGTGGCTGAATGAGGTGGAGTTTAAATTGAAAACGACCGAAAACA |
| | | TCCCTGGCGGTGCAGAGGAGATATCTGAGGTGCTCGATAGCCTGGAGAAT |
| | | CTTATGAGGCATAGCGAGGATAACCCCAACCAGATTAGGATACTGGCCCA |

-continued

| SEQ ID NO | Description | SEQ |
|---|---|---|
| | | AACTCTGACCGACGGCGGAGTGATGGACGAGCTGATAAACGAGGAACTGG AAACCTTTAATTCACGCTGGCGAGAACTTCACGAGGAGGCAGTCAGGCGC CAGAAACTGCTGGAGCAGTCCATCCAGAGTGCCCAGGAGACTGAGAAGTC ACTTCATCTGATCCAGGAGAGTTTGACGTTTATCGACAAGCAGCTTGCCG CCTACATTGCAGACAAGGTCGATGCTGCTCAGATGCCGCAAGAGGCTCAG AAAATCCAGAGCGACCTGACAAGCCACGAGATTAGCCTGGAGGAAATGAA AAAGCACAACCAGGGTAAAGAGGCCGCCCAGCGGGTTCTGAGCCAGATCG ATGTCGCACAGAAGAAACTCCAAGATGTAAGCATGAAGTTCCGACTGTTT CAGAAACCAGCGAACTTTGAGCAGCGACTGCAGGAGTCTAAAATGATCCT CGATGAGGTGAAAATGCATCTGCCAGCCCTGGAAACTAAGAGCGTGGAGC AGGAGGTGGTTCAGAGTCAGCTGAACCACTGCGTAAACCTCTATAAAAGT CTTAGTGAAGTGAAGAGCGAGGTGGAGATGGTGATTAAGACTGGTAGACA GATTGTACAGAAAAAGCAGACGGAGAACCCCAAAGAGTTGGATGAACGGG TGACAGCCCTTAAGCTCCACTATAACGAGCTGGGAGCCAAAGTGACTGAG AGAAAGCAGCAACTTGAAAAATGTCTGAAGCTGAGCAGAAAGATGCGGAA GGAAATGAATGTGCTGACAGAGTGGCTGGCTGCGACCGACATGGAACTTA CAAAGAGGAGCGCCGTGGAAGGCATGCCTTCCAATCTGGATAGTGAGGTC GCTTGGGGCAAAGCTACACAGAAGGAAATTGAGAAGCAAAAAGTGCATCT TAAGAGCATTACTGAAGTTGGCGAGGCTTTGAAAACCGTCCTCGGCAAGA AAGAGACTCTGGTAGAAGATAAACTCTCACTGCTGAACTCAAACTGGATC GCAGTCACTAGTCGGGCCGAAGAGTGGCTGAATTTGCTGTTGGAGTACCA AAAGCATATGGAGACTTTCGATCAGAATGTCGACCACATTACGAAGTGGA TAATCCAGGCGGACACACTGTTGGATGAGTCCGAGAAAAAGAAACCTCAG CAGAAGGAAGACGTGCTCAAACGACTCAAAGCCGAACTGAACGACATCAG GCCCAAAGTTGATTCCACCCGGGATCAAGCGGCCAATCTCATGGCCAACC GGGGGGATCACTGCAGAAAGTTGGTAGAACCTCAGATAAGCGAACTTAAT CATAGATTTGCCGCCATATCACATAGGATTAAGACCGGTAAGGCTTCAAT CCCCCTGAAGGAACTCGAACAGTTTAATAGTGACATCCAGAAGCTCCTGG AGCCTCTCGAAGCCGAGATTCAACAGGGTGTAAACCTTAAGGAAGAGGAT TTTAATAAGGATATGAATGAGGACAATGAAGGCACGGTCAAAGAGCTCCT CCAGAGGGGAGACAATTTGCAGCAGCGGATCACCGATGAACGCAAACGCG AAGAGATCAAAATTAAGCAGCAGCTCCTCCAAACAAAGCACAATGCCCTT AAAGACCTCAGAAGCCAGCGGCGGAAAAAGGCTCTGGAAATCAGCCATCA ATGGTATCAGTACAAGCGGCAAGCGGACGATCTCCTGAAATGTCTGGATG ATATCGAGAAAAAACTGGCCAGTCTGCCAGAGCCCAGAGATGAGCGCAAA ATCAAGGAAATCGACAGGGAGCTTCAGAAGAAAAAAGAGGAGCTGAACGC CGTCCGAAGGCAGGCCGAAGGGCTGTCAGAAGATGGGGCCGCCATGGCAG TGGAACCTACCCAGATTCAACTGTCCAAGCGCTGGAGAGAGATTGAAAGT AAGTTCGCACAATTCCGGAGGCTTAATTTTGCTCAGATTCACACAGTTAG GGAGGAAACCATGATGGTGATGACCGAAGACATGCCACTCGAAATCAGCT ACGTCCCTAGCACATATCTCACGGAGATTACCCACGTGTCCCAGGCACTG CTGGAAGTCGAGCAATTGTTGAACGCCCCTGATCTCTGCGCCAAGGATTT CGAAGACTTGTTCAAGCAAGAGGAAAGCCTCAAGAACATCAAAGACAGTC TTCAGCAGTCCTCAGGCAGAATTGATATTATCCACTCCAAGAAAACAGCC GCTCTCCAGAGCGCTACCCCTGTCGAACGAGTGAAACTGCAAGAGGCCTT GTCTCAGTTGGACTTCCAGTGGGAGAAAGTCAACAAGATGTACAAGGACA GGCAGGGTCGGTTCGACCGGAGCGTCGAAAAATGGCGGAGATTCCATTAT GACATCAAGATATTCAATCAGTGGCTTACAGAGGCGGAGCAATTTTTGAG AAAGACGCAGATTCCCGAAAACTGGGAGCATGCCAAGTACAAGTGGTACC TCAAAGAGCTCCAGGATGGAATCGGCCAGAGACAGACCGTAGTTAGAACA CTGAACGCAACTGGAGAAGAGATTATCCAGCAGTCCTCCAAAACTGACGC CTCTATCCTCCAGGAGAAGCTTGGCAGCCTTAACCTGCGGTGGCAGGAGG TGTGTAAACAACTGTCAGATAGGAAAAAAAGACTTGAGGAACAGAAGAAC ATTCTGAGCGAGTTCCAACGAGATCTCAACGAGTTCGTACTGTGGCTGGA GGAGGCCGACAACATCGCTTCAATCCCCCTGGAACCCGGCAAGGAACAGC AGCTTAAGGAAAAATTGGAACAGGTAAAACTGTTGGTAGAGGAGCTCCCA TTGCGGCAGGGCATTCTCAAGCAGCTGAATGAAACTGGAGGTCCCGTTCT GGTCAGTGCGCCCATAAGCCCGGAAGAGCAGGACAAGTTGGAAAACAAGC TGAAGCAAACAAATCTGCAGTGGATCAAAGTGAGCCGGGCTCTTCCAGAA AAGCAAGGCGAGATTGAAGCCCAGATTAAGGATCTTGGCCAGCTTGAGAA AAAGCTGGAGGATCTGGAAGAGCAGCTGAACCATTTGCTTCTGTGGCTGA GTCCCATTAGAAACCAGCTGGAAATCTACAACCAGCCAAACCAAGAGGGC CCTTTCGACGTCAAGGAAACTGAGATAGCAGTCCAGGCAAAACAGCCCGA TGTCGAAGAAATCTTGTCTAAGGGGCAGCACCTCTACAAAGAGAAACCTG CCACCCAGCCCGTGAAGAGAAAACTGGAAGACCTCTCTTCAGAGTGGAAG GCTGTAAACAGGTTGCTCCAGGAGCTGAGAGCTAAGCAACCTGACCTCGC ACCCGGCCTGACTACTATTGGCGCCAGCCCGACCCAAACCGTCACACTGG TGACCCAGCCTGTAGTCACAAAAGAAACCGCCATCTCCAAACTGGAGATG CCTTCAAGCCTGATGCTGGAGGTGCCTGCTCTGGCCGATTTCAACAGAGC CTGGACAGAGCTGACAGACTGGCTGTCTCTGCTCGACCAAGTGATAAAGT CACAGCGCGTCATGGTGGGTGACCTGGAGGACATCAATGAGATGATCATA AAGCAAAAGGCTACCATGCAGGACTTGGAGCAGCGCAGGCCGCAGTTGGA AGAACTGATTACAGCAGCCCAGAACCTCAAGAACAAGACTTCAAATCAGG AGGCAAGGACCATCATAACAGATAGAATCGAGAGGATTCAGAACCAATGG GATGAGGTGCAGGAGCACCTGCAGAACAGAAGGCAGCAGCTGAACGAAAT |

-continued

| SEQ ID NO | Description | SEQ |
|---|---|---|
| | | GCTGAAAGACTCCACACAGTGGCTGGAGGCCAAAGAGGAGGCAGAACAGG<br>TGCTGGGCCAGGCTAGGGCCAAGCTGGAAAGTTGGAAGGAAGGGCCCTAC<br>ACCGTGGACGCCATACAGAAGAAAATAACGGAGACAAAACAGCTGGCCAA<br>AGACCTCCGCCAATGGCAGACCAACGTAGACGTCGCCAATGACCTGGCAC<br>TCAAGTTGTTGAGAGATTATTCCGCAGATGACACCCGAAAAGTACACATG<br>ATCACTGAGAATATCAACGCCAGTTGGCGGAGCATTCACAAACGGGTGAG<br>CGAGAGAGAAGCCGCCCTTGAGGAGACGCATCGCCTTTTGCAGCAATTTC<br>CGCTTGACCTGGAAAAGTTTCTGGCTTGGTTGACAGAGGCCGAGACAACT<br>GCTAACGTGCTGCAAGATGCCACCCGCAAAGAGCGGCTTCTTGAGGACTC<br>TAAAGGGGTGAAAGAATTGATGAAGCAGTGGCAGGACCTCCAGGGCGAAA<br>TCGAGGCCCATACTGATGTCTACCACAACCTGGATGAAAATAGTCAGAAA<br>ATCCTGAGATCCCTGGAAGGGAGTGATGATGCGGTGCTGCTGCAGCGCCG<br>ACTCGATAACATGAACTTTAAGTGGTCTGAACTCCGGAAAAAAAGCCTGA<br>ACATTCGGAGCCATCTGGAGGCTTCTTCTGATCAGTGGAAGAGACTTCAT<br>CTGTCCTTGCAGGAGCTTCTGGTGTGGCTGCAGCTGAAAGACGACGAGCT<br>GTCAAGGCAGGCACCAATAGGGGGCGACTTCCCCGCTGTTCAGAAACAAA<br>ATGATGTGCACAGGGCATTCAAGCGGGAACTGAAGACGAAAGAACCAGTG<br>ATTATGAGCACTCTGGAGACGGTACGCATCTTTCTGACCGAGCAGCCACT<br>TGAAGGCCTCGAAAAGTTGTACCAGGAGCCACGGGAATTGCCTCCCGAAG<br>AACGGGCTCAGAATGTTACCCGACTGCTTCGCAAGCAGGCTGAGGAAGTG<br>AACACTGAGTGGGAAAAACTGAATCTGCACAGTGCCGATTGGCAGCGCAA<br>AATTGACGAGACATTGGAGCGCTTGCGGGAGCTGCAGGAAGCCACAGATG<br>AACTTGATCTGAAACTCAGACAGGCCGAGGTCATAAAGGGTTCTTGGCAA<br>CCCGTAGGCGACCTTTTGATTGACTCACTGCAGGATCATCTGGAGAAAGT<br>AAAGGCGCTGCGGGGGGAAATTGCTCCGCTGAAGGAAAACGTGAGCCATG<br>TGAATGATCTGGCTCGGCAATTGACTACCCTGGGTATCCAGCTGTCCCCC<br>TACAATCTGAGCACTCTCGAAGACCTCAACACAAGATGGAAACTGCTGCA<br>GGTCGCCGTGGAGGACAGGGTGAGGCAGCTGCATGAGGCACACAGGGACT<br>TCGGTCCGGCAAGCCAACACTTCCTGTCTACTTCTGTTCAAGGGCCTTGG<br>GAACGCGCTATTTCCCCAAACAAAGTGCCGTACTATATTAACCATGAAAC<br>TCAGACAACCTGCTGGGATCATCCTAAAATGACTGAGCTGTACCAGAGCC<br>TCGCCGATCTGAATAACGTGAGGTTTAGCGCATACAGAACCGCAATGAAG<br>CTCAGGAGACTGCAGAAGGCACTTTGCCTGGACCTCCTGAGCCTCTCCGC<br>TGCCTGCGATGCCCTCGACCAGCACAACCTGAAGCAGAATGATCAGCCTA<br>TGGACATCCTGCAAATCATAAATTGTCTGACGACAATCTACGACCGGCTC<br>GAACAGGAGCACAATAATCTCGTGAACGTTCCACTTTGTGTGGATATGTG<br>TCTCAACTGGCTGTTGAACGTCTATGACACCGGGAGAACTGGAAGGATCC<br>GCGTTCTGTCCTTTAAGACTGGAATCATCAGCTTGTGTAAGGCGCACCTT<br>GAGGACAAATATCGATACCTGTTTAAGCAGGTTGCAAGCTCCACTGGATT<br>CTGCGACCAGAGGCGCCTCGGGCTGCTGCTTCATGATAGTATCCAAATCC<br>CACGCCAACTCGGAGAGGTGGCAAGCTTCGGCGGGAGCAATATTGAGCCA<br>AGCGTCAGATCTTGTTTCCAGTTTGCCAACAATAAGCCTGAGATCGAAGC<br>CGCACTGTTTTTGGATTGGATGCGGTTGGAGCCCCAGAGTATGGTGTGGT<br>TGCCCGTGCTGCATAGGGTCGCTGCCGCTGAAACCGCCAAACACCAGGCC<br>AAGTGCAATATTTGCAAGGAATGTCCCATCATCGGGTTTAGATACCGGAG<br>CCTGAAGCACTTCAATTATGATATCTGCCAGTCTTGTTTTTTTTCCGGCC<br>GAGTTGCTAAGGGACACAAGATGCATTACCCAATGGTGGAATATTGTACG<br>CCAACCACCAGCGGCGAAGATGTCAGAGATTTTGCAAAAGTACTCAAGAA<br>CAAGTTCCGCACCAAGCGATATTTCGCGAAGCACCCCCGGATGGGCTACC<br>TCCCAGTGCAGACGGTTCTGGAAGGCGATAACATGGAAACTCCAGTCACC<br>CTGATCAATTTCTGGCCTGTGGACTCTGCGCCTGCCTCTTCACCTCAGCT<br>CTCCCACGATGACACCCATTCCAGAATCGAGCACTACGCGTCTCGACTGG<br>CGGAGATGGAGAACAGCAATGGTTCTTACCTCAATGACAGCATTAGCCCC<br>AACGAAAGCATCGATGACGAGCACCTCTTGATTCAACACTACTGCCAGTC<br>CCTGAATCAGGACAGTCCTCTGTCCCAACCCAGGAGCCCAGCCCAGATAC<br>TGATCTCTCTCGAATCAGAAGAAAGAGGGGAGTTGGAGCGAATTTTGGCC<br>GACCTGGAGGAGGAGAATAGAAATCTTCAGGCCGAGTACGATAGACTGAA<br>GCAGCAGCACGAGCACAAGGGCCTTTCTCCACTGCCCTCTCCACCGGAAA<br>TGATGCCAACCTCCCCTCAAAGTCCCAGGGACGCTGAGCTCATTGCCGAG<br>GCAAAGCTGTTGCGCCAGCACAAAGGACGCCTGGAGGCGAGAATGCAGAT<br>CCTGGAAGACCATAACAAGCAGCTTGAGTCTCAGCTGCACCGACTTAGAC<br>AGCTGTTGGAGCAGCCACAAGCGGAAGCAAAGGTCAATGGAACTACCGTG<br>AGTTCCCCCAGTACAAGTCTGCAGCGCTCTGACTCAAGCCAGCCAATGCT<br>GCTCCGGGTAGTCGGTTCTCAGACTAGTGATTCAATGGGGGAGGAGGATC<br>TTCTTTCCCCACCCCAAGACACCTCAACAGGGCTTGAGGAAGTGATGGAG<br>CAGCTGAACAACTCCTTCCCCTCTTCACGGGGGAGAAATACTCCTGGGAA<br>GCCTATGAGAGAGGATACCATGTAATGACTCGAGAATCAACCTCTGGATT<br>ACAAAATTTGTGAAAGATTGACTGGTATTCTTAACTATGTTGCTCCTTTT<br>ACGCTATGTGGATACGCTGCTTTAATGCCTTTGTATCATGCTATTGCTTC<br>CCGTATGGCTTTCATTTTCTCCTCCTTGTATAAATCCTGGTTGCTGTCTC<br>TTTATGAGGAGTTGTGGCCCGTTGTCAGGCAACGTGGCGTGGTGTGCACT<br>GTGTTTGCTGACGCAACCCCCACTGGTTGGGGCATTGCCACCACCTGTCA<br>GCTCCTTTCCGGGACTTTCGCTTTCCCCCTCCCTATTGCCACGGCGGAAC<br>TCATCGCCGCCTGCCTTGCCCGCTGCTGGACAGGGGCTCGGCTGTTGGGC<br>ACTGACAATTCCGTGGGGTGTGCCTTCTAGTTGCCAGCCATCTGTTGTTT |

-continued

| SEQ ID NO | Description | SEQ |
|---|---|---|
| | | GCCCCTCCCCCGTGCCTTCCTTGACCCTGGAAGGTGCCACTCCCACTGTC |
| | | CTTTCCTAATAAAATGAGGAAATTGCATCGCATTGTCTGAGTAGGTGTCA |
| | | TTCTATTCTGGGGGGTGGGGTGGGGCAGGACAGCAAGGGGGAGGATTGGG |
| | | AAGACAATAGCAGGCATGCTGGGGATGCGGTGGGCTCTATGGGAAGATGT |
| | | CTACTGAGCTGTGCGATCCCTGCTGGGGACTTTCCGCTGGGGACTTTCCG |
| | | CTGGGGACTTTCCGCCTTCAGCTAAGGAAGCTACCAATATTTAGAGGTAC |
| | | ATTTTGTTCTAGAACAAAATGTACCGGTACATTTTGTTCTGGTACATTTT |
| | | GTTCT |
| 25. | MHCK7-hBGi- | CTAGAAGCTGCATGTCTAAGCTAGACCCTTCAGATTAAAAATAACTGAGG |
| | DMD- | TAAGGGCCTGGGTAGGGGAGGTGGTGTGAGACGCTCCTGTCTCTCCTCTA |
| | 1-WPRE3- | TCTGCCCATCGGCCCTTTGGGGAGGAGGAATGTGCCCAAGGACTAAAAAA |
| | DTS | AGGCCATGGAGCCAGAGGGGCGAGGGCAACAGACCTTTCATGGGCAAACC |
| | | TTGGGGCCCTGCTGTCTAGCATGCCCCACTACGGGTCTAGGCTGCCCATG |
| | | TAAGGAGGCAAGGCCTGGGGACACCCGAGATGCCTGGTTATAATTAACCC |
| | | AGACATGTGGCTGCCCCCCCCCCCCCAACACCTGCTGCCTCTAAAAATAA |
| | | CCCTGTCCCTGGTGGATCCCCTGCATGCGAAGATCTTCGAACAAGGCTGT |
| | | GGGGGACTGAGGGCAGGCTGTAACAGGCTTGGGGGCCAGGGCTTATACGT |
| | | GCCTGGGACTCCCAAAGTATTACTGTTCCATGTTCCCGGCGAAGGGCCAG |
| | | CTGTCCCCCGCCAGCTAGACTCAGCACTTAGTTTAGGAACCAGTGAGCAA |
| | | GTCAGCCCTTGGGGCAGCCCATACAAGGCCATGGGGCTGGGCAAGCTGCA |
| | | CGCCTGGGTCCGGGGTGGGCACGGTGCCCGGGCAACGAGCTGAAAGCTCA |
| | | TCTGCTCTCAGGGGCCCCTCCCTGGGGACAGCCCCTCCTGGCTAGTCACA |
| | | CCCTGTAGGCTCCTCTATATAACCCAGGGGCACAGGGGCTGCCCTCATTC |
| | | TACCACCACCTCCACAGCACTCTGGATCCACTGCTTAAATACGGACGAGG |
| | | ACAGGGCCCTGTCTCCTCAGCTTCAGGCACCACCACTGACCTGGGACAGT |
| | | GAATCGTAAGTACTAGCAGCTACAATCCAGCTACCATTCTGCTTTTATTT |
| | | TATGGTTGGGATAAGGCTGGATTATTCTGAGTCCAAGCTAGGCCCTTTTG |
| | | CTAATCATGTTCATACCTCTTATCTTCCTCCCACAGCTCCTGGGCAACGT |
| | | GCTGGTCTGTGTGCTGGCCCATCACTTTGGCAAAGAATTGCGATCGCCAC |
| | | CATGCTGTGGTGGGAAGAGGTGGAGGATTGCTACGAGCGGGAGGATGTGC |
| | | AGAAAAAGACTTTCACCAAGTGGGTAAATGCTCAGTTCTCTAAGTTCGGG |
| | | AAGCAACACATCGAGAACTTGTTTTCCGACCTCCAGGATGGCAGGCGCCT |
| | | GCTTGACTTGCTGGAGGGTCTGACTGGTCAGAAGCTCCCTAAGGAGAAGG |
| | | GCAGCACCAGAGTTCACGCTCTGAATAACGTTAACAAAGCCCTGAGGGTC |
| | | CTCCAGAATAACAATGTAGACCTGGTGAACATCGGTTCTACCGACATCGT |
| | | GGACGGGAATCATAAACTGACCTTGGGGCTCATCTGGAACATTATCTTGC |
| | | ACTGGCAGGTGAAGAACGTCATGAAGAATATCATGGCCGGGCTGCAACAG |
| | | ACCAACTCCGAAAAGATTTTGCTCAGCTGGGTGCGCCAGTCCACCCGCAA |
| | | TTATCCACAAGTCAACGTTATCAATTTCACCACTAGTTGGAGTGATGGCC |
| | | TCGCCCTGAACGCCTTGATCCACAGTCACCGCCCCGACCTGTTTGACTGG |
| | | AACTCTGTGGTTTGCCAACAGAGCGCTACCCAGCGTCTCGAACATGCTTT |
| | | CAATATCGCTAGATACCAGCTCGGTATCGAGAAGCTGTTGGATCCTGAGG |
| | | ACGTAGACACGACCTACCCCGATAAAAAGAGCATCCTGATGTATATCACT |
| | | TCTCTGTTTCAGGTGCTTCCTCAACAGGTGTCCATTGAAGCCATCCAAGA |
| | | GGTCGAAATGCTGCCCAGGCCCCCTAAGGTGACAAAAGAAGAGCATTTCC |
| | | AGCTGCATCACCAGATGCATTACAGTCAACAGATTACCGTCAGCTTGGCT |
| | | CAGGGATATGAGCGCACGTCCTCTCCTAAGCCCAGATTTAAGTCCTACGC |
| | | ATATACCCAGGCTGCCTACGTGACCACTTCCGACCCAACTAGGAGCCCCT |
| | | TTCCCTCCCAACACCTGGAGGCCCCTGAGGACAAAAGCTTCGGATCTAGT |
| | | CTGATGGAGTCCGAGGTGAATCTGGATCGGTACCAAACTGCTCTGGAGGA |
| | | AGTGCTGTCCTGGCTTCTGTCCGCTGAAGACACCCTGCAGGCGCAAGGTG |
| | | AGATTTCTAACGACGTCGAGGTCGTGAAGGATCAGTTCCACACTCATGAG |
| | | GGCTACATGATGGACTTGACAGCTCACCAGGGAAGAGTTGGTAACATCCT |
| | | GCAGCTTGGCTCCAAGTTGATTGGCACGGGAAAGCTTAGCGAGGACGAGG |
| | | AAACCGAGGTACAGGAGCAGATGAACTTGCTGAATTCCCGCTGGGAGTGC |
| | | CTGAGAGTTGCGTCCATGGAAAAGCAGTCAAACCTTCACAGAGTGCTGAT |
| | | GGACCTTCAGAACCAGAAGCTGAAGGAGCTGAACGATTGGCTGACAAAGA |
| | | CCGAGGAACGCACAAGAAAAATGGAAGAGGAACCTCTGGGACCTGATCTG |
| | | GAGGATCTGAAGCGCCAGGTCCAACAGCATAAGGTGCTGCAGGAGGATTT |
| | | GGAGCAGGAGCAGGTGCGGGTCAACAGCCTGACACATATGGTGGTTGTGG |
| | | TCGATGAGTCCTCTGGCGATCATGCTACCGCAGCGCTGGAAGAGCAGCTG |
| | | AAGGTGCTGGGGGATCGCTGGGCCAACATTTGCAGATGGACAGAAGACCG |
| | | GTGGGTCCTGCTTCAAGATATCCTGCTCAAGTGGCAGCGCCTGACTGAAG |
| | | AGCAGTGCCTGTTCTCAGCTTGGTTGAGCGAAAAAGAGGACGCAGTTAAC |
| | | AAGATCCATACCACAGGCTTCAAGGATCAGAATGAGATGCTGAGCTCACT |
| | | GCAGAAGCTGGCTGTGCTGAAGGCCGACTTGGAGAAGAAAAAGCAGTCCA |
| | | TGGGCAAACTGTATAGCCTGAAGCAGGACCTGCTCAGCACCCTGAAGAAC |
| | | AAAAGCGTTACGCAGAAAACTGAGGCCTGGTTGGACAACTTTGCTCGCTG |
| | | CTGGGATAACCTTGTGCAGAAGCTGGAAAAGTCAACCGCACAGATCTCCC |
| | | AGGCTGTGACCACTACGCAGCCTAGCTTGACCCAGACAACCGTTATGGAA |
| | | ACCGTGACAACCGTGACAACGAGAGAGCAAATCCTGGTTAAGCATGCCCA |
| | | GGAGGAACTGCCGCCACCCCCGCCTCAGAAGAAACGGCAGATTACGGTGG |
| | | ACAGCGAGATCCGCAAGAGGCTGGACGTCGACATCACTGAGCTCCACTCA |
| | | TGGATCACGCGGAGTGAGGCCGTGCTGCAGTCTCCCGAGTTCGCTATTTT |

| SEQ ID NO | Description | SEQ |
|---|---|---|
| | | CCGCAAGGAGGGAAACTTCTCTGACTTGAAAGAGAAGGTGAATGCCATCG<br>AGCGTGAAAAGGCAGAAAAGTTCAGAAAGCTGCAGGACGCCTCTCGCTCT<br>GCGCAGGCCCTGGTGGAGCAGATGGTCAACGAGGGTGTTAACGCTGACAG<br>CATCAAACAGGCAAGCGAACAGCTGAACTCCAGATGGATCGAATTTTGCC<br>AACTGCTCTCCGAACGCCTCAACTGGTTGGAGTACCAGAACAATATTATC<br>GCTTTTTACAACCAGCTGCAGCAACTGGAGCAGATGACAACTACCGCCGA<br>AAACTGGCTGAAAATTCAGCCAACCACACCGTCCGAGCCAACTGCGATCA<br>AGTCTCAGCTGAAGATCTGCAAGGACGAAGTGAACCGTCTTAGCGACTTG<br>CAACCCCAGATTGAACGGCTCAAGATTCAGTCTATTGCTCTGAAGGAGAA<br>GGGTCAGGGTCCGATGTTCCTGGATGCAGATTTTGTCGCATTTACCAATC<br>ACTTCAAACAGGTGTTTAGTGACGTCCAGGCGCGCGAGAAAGAGCTGCAG<br>ACTATTTTTGACACCCTGCCTCCCATGAGGTACCAGGAGACAATGAGTGC<br>CATTCGCACCTGGGTGCAACAGTCCGAGACGAAATTGTCAATCCCACAGC<br>TGTCCGTGACAGACTACGAGATTATGGAGCAACGGTTGGGGGAGCTGCAG<br>GCTCTTCAGAGTTCCCTGCAGGAGCAACAGAGCGGACTGTACTATCTTTC<br>CACTACCGTGAAGGAAATGAGTAAGAAAGCCCCTTCCGAGATCAGCCGCA<br>AATACCAGTCTGAATTCGAAGAGATCGAGGGACGCTGGAAAAAGCTGTCA<br>AGCCAGCTGGTCGAGCACTGTCAGAAGCTGGAAGAGCAGATGAACAAGCT<br>GCGTAAAATCCAGAACCATATTCAGACCCTCAAGAAATGGATGGCAGAAG<br>TTGACGTGTTTCTGAAGGAAGAGTGGCCTGCCCTCGGCGATAGCGAAATC<br>CTTAAGAAACAACTCAAGCAGTGCCGCCTCCTGGTGTCCGATATTCAGAC<br>AATCCAGCCTTCCCTGAACAGCGTTAATGAGGGCGGACAGAAAATTAAAA<br>ACGAGGCCGAACCCGAGTTCGCTTCTCGCCTGGAGACTGAACTGAAGGAG<br>CTGAATACCCAGTGGGACCATATGTGTCAACAGGTCTACGCACGCAAAGA<br>GGCACTGAAGGGCGGTCTGGAGAAGACTGTCTCACTCCAGAAGGACCTGA<br>GCGAGATGCACGAGTGGATGACCCAGGCCGAAGAGGAATACCTGGAGCGT<br>GATTTTGAGTATAAGACCCCAGACGAACTCCAGAAAGCCGTTGAAGAGAT<br>GAAGAGGGCTAAGGAGGAAGCCCAACAGAAGGAGGCGAAAGTGAAGCTCC<br>TGACAGAGTCCGTGAACTCCGTCATCGCTCAAGCTCCTCCCGTGGCTCAG<br>GAGGCCCTCAAGAAAGAGCTGGAAACTCTGACCACAAATTACCAGTGGTT<br>GTGTACCCGCTTGAACGGTAAGTGCAAGACCCTGGAAGAGGTGTGGGCCT<br>GCTGGCACGAGCTCCTGTCCTATCTTGAGAAGGCGAACAAATGGCTGAAC<br>GAAGTGGAATTCAAGTTGAAAACAACTGAGAACATTCCGGGAGGCGCTGA<br>GGAAATCTCTGAGGTGCTGGACTCTCTGGAAAATCTGATGCGTCATTCTG<br>AAGACAATCCTAACCAGATCAGGATTCTGGCACAGACCCTCACTGACGGA<br>GGCGTTATGGACGAACTTATCAACGAGGAACTGGAGACATTCAATTCCCG<br>TTGGCGTGAGCTGCACGAAGAGGCCGTGCGCCGTCAGAAGTTGCTGGAAC<br>AGTCTATCCAGTCCGCCCAGGAGACAGAGAAATCTCTCCACCTGATCCAG<br>GAGAGTCTGACGTTTATCGATAAGCAGCTGGCTGCCTACATCGCCGACAA<br>GGTGGACGCTGCCCAGATGCCCCAAGAGGCTCAGAAGATCCAGTCCGACC<br>TGACGTCTCATGAAATCAGCCTGGAAGAGATGAAAAAGCACAACCAGGGC<br>AAAGAGGCTGCCCAGCGCGTCCTCTCCCAGATTGACGTGGCTCAGAAAAA<br>GTTGCAGGACGTGAGCATGAAGTTTAGGCTGTTCCAGAAACCCGCCAACT<br>TCGAACAGAGACTGCAGGAGTCTAAGATGATCCTGGATGAGGTCAAGATG<br>CACCTCCCTGCTCTGGAAACAAAATCTGTGGAGCAGGAGGTCGTGCAGTC<br>ACAACTGAACCATTGTGTGAACCTCTACAAGTCTCTCAGCGAGGTGAAGT<br>CCGAGGTCGAGATGGTGATCAAGACCGGACGCCAGATTGTGCAGAAAAAG<br>CAGACAGAGAACCCAAAGGAGCTGGACGAACGGGTGACCGCCCTGAAGCT<br>CCACTACAACGAGTTGGGTGCCAAAGTCACTGAAAGAAAGCAACAGCTGG<br>AGAAGTGTCTGAAGCTGAGCCGCAAGATGCGCAAAGAAATGAACGTCTTG<br>ACCGAGTGGTTGGCGGCCACCGACATGGAGCTGACCAAGAGATCCGCTGT<br>GGAGGGCATGCCCTCCAACCTTGACTCAGAGGTGGCCTGGGGCAAGGCCA<br>CACAGAAGGAGATCGAAAAACAGAAGGTGCATCTTAAATCAATCACTGAG<br>GTGGGCGAAGCTCTGAAGACAGTGCTGGGCAAGAAAGAGACACTTGTAGA<br>GGACAAGCTCTCCCTTCTGAATAGCAATTGGATCGCCGTAACTAGTCGCG<br>CGGAGGAATGGCTGAACCTCCTGTTGGAATACCAGAAACACATGGAAACC<br>TTCGATCAGAACGTGGACCATATTACCAAGTGGATTATCCAGGCTGACAC<br>TCTCCTGGACGAGTCTGAGAAAAAGAAACCCCAGCAAAAGGAAGATGTGC<br>TGAAGCGCCTGAAGGCGGAATTGAACGACATCCGCCCGAAGGTTGATTCC<br>ACCCGCGACCAAGCGGCCAACCTTATGGCTAACCGCGGGGACCATTGCAG<br>AAAACTGGTGGAACCGCAGATCTCTGAGCTGAACCACAGATTCGCCGCGA<br>TTTCTCACAGAATTAAGACTGGCAAGGCCTCCATCCCTCTGAAAGAGCTG<br>GAGCAGTTCAACTCTGATATTCAGAAGCTTCTGGAGCCCCTGGAGGCAGA<br>AATCCAACAGGGCGTCAACCTGAAAGAGGAAGACTTTAATAAGGACATGA<br>ATGAGGATAACGAAGGTACCGTCAAGGAGCTCCTGCAGAGGGGCGACAAT<br>CTGCAGCAAAGAATCACTGACGAACGTAAGCGCGAAGAGATTAAGATCAA<br>GCAACAGCTGTTGCAGACTAAGCACAACGCCCTGAAGGATCTGAGGTCCC<br>AGCGCAGGAAAAAGGCCCTGGAGATTTCCCACCAGTGGTACCAGTACAAG<br>CGCCAGGCCGATGACCTTCTGAAGTGCCTCGACGATATCGAGAAAAAGCT<br>GGCCTCACTGCCCGAGCCCCGCGACGAGCGCAAGATCAAGGAGATTGACC<br>GTGAGCTCCAGAAGAAAAAGGAGGAACTGAACGCGGTGCGCAGACAGGCC<br>GAGGGCCTCTCCGAGGACGGCGCTGCGATGGCTGTTGAGCCCACTCAGAT<br>CCAACTGAGCAAGCGGTGGAGAGAGATCGAGTCTAAGTTCGCGCAATTTA<br>GGCGCCTCAACTTCGCCCAGATTCACACGGTCCGTGAGGAAACGATGATG<br>GTGATGACAGAGGATATGCCACTGGAAATCAGCTACGTGCCCAGTACATA |

-continued

| SEQ ID NO | Description | SEQ |
|---|---|---|
| | | TCTCACCGAAATCACCCATGTGTCCCAGGCTCTCCTGGAGGTGGAACAGT<br>TGCTCAACGCTCCCGACTTGTGCGCTAAGGACTTCGAGGACCTGTTCAAG<br>CAGGAAGAGAGCCTGAAAAACATTAAGGACTCCCTGCAACAGTCAAGCGG<br>CCGCATCGATATCATTCATTCTAAGAAAACCGCTGCCCTGCAGTCTGCAA<br>CCCCCGTAGAGCGCGTCAAACTGCAGGAAGCTCTCAGCCAACTGGATTTC<br>CAGTGGGAGAAGGTGAACAAGATGTATAAGGATCGTCAGGGCCGGTTCGA<br>CCGCTCTGTGGAGAAGTGGCGCCGTTTCCACTACGATATCAAGATTTTCA<br>ATCAATGGTTGACCGAGGCAGAGCAGTTCCTCAGAAAGACACAGATCCCT<br>GAAAATTGGGAGCATGCCAAGTACAAGTGGTATCTGAAGGAGCTGCAGGA<br>CGGGATCGGACAACGTCAGACCGTGGTCCGCACCCTGAACGCAACCGGCG<br>AGGAAATTATCCAACAGTCTAGCAAGACAGATGCTAGCATCCTCCAGGAG<br>AAGCTCGGAAGCCTCAACCTTCGCTGGCAGGAGGTGTGCAAGCAGCTGTC<br>AGACAGGAAGAAACGCCTGGAGGAACAGAAGAACATCCTTTCAGAGTTCC<br>AGAGAGATCTGAACGAATTCGTGCTTTGGCTTGAAGAGGCCGATAACATC<br>GCAAGCATCCCACTGGAGCCTGGTAAGGAACAGCAATTGAAGGAGAAGCT<br>GGAGCAGGTAAAGCTGCTCGTGGAAGAGCTGCCTCTGAGGCAGGGAATTC<br>TCAAGCAGCTCAACGAGACTGGGGGCCCGGTTTTGGTGAGCGCCCCAATT<br>AGCCCAGAAGAGCAGGACAAGTTGGAGAACAAGCTGAAGCAGACCAACCT<br>GCAGTGGATCAAGGTGTCCCGCGCACTGCCCGAAAAGCAGGGAGAGATTG<br>AGGCCCAGATCAAGGATCTGGGACAGCTGGAGAAAAAGCTGGAAGACCTG<br>GAGGAACAGCTGAACCATTTGCTCCTGTGGTTGTCCCCCATCAGAAATCA<br>GCTGGAAATCTACAACCAACCGAACCAGGAAGGTCCGTTTGATGTTAAGG<br>AAACCGAGATCGCTGTGCAGGCGAAGCAGCCTGACGTAGAAGAGATCCTG<br>TCAAAGGGACAGCACCTCTACAAGGAGAAGCCCGCCACCCAGCCAGTCAA<br>GCGGAAGCTCGAAGACCTGTCCAGCGAGTGGAAAGCCGTCAACCGCCTCC<br>TGCAAGAGCTGCGTGCCAAGCAACCGGACCTGGCGCCAGGTCTGACTACC<br>ATTGGCGCAAGTCCTACCCAGACTGTCACCCTGGTGACCCAACCCGTTGT<br>GACAAAGGAAACCGCCATCAGCAAGCTGGAGATGCCTAGCTCTTTGATGC<br>TGGAGGTTCCCGCCCTCGCCGACTTCAACCGTGCTTGGACAGAACTGACC<br>GACTGGCTGTCCCTCCTGGACCAAGTGATCAAGAGCCAGCGCGTGATGGT<br>GGGTGATCTTGAGGATATTAACGAAATGATTATCAAGCAGAAGGCCACCA<br>TGCAGGACTTGGAGCAGAGGCGCCCCCAGTTGGAGGAACTGATCACCGCC<br>GCGCAGAATCTGAAAAACAAAACTTCCAATCAGGAAGCGAGAACCATCAT<br>TACAGACAGAATTGAGAGAATTCAAAACCAGTGGGACGAAGTGCAAGAAC<br>ACCTCCAGAACCGGCGTCAACAGCTGAACGAGATGCTGAAGGATTCCACT<br>CAATGGCTGGAAGCTAAGGAAGAGGCCGAGCAGGTCCTTGGACAGGCACG<br>CGCTAAGCTGGAGTCCTGGAAAGAAGGCCCCTATACAGTGGACGCAATTC<br>AAAAGAAAATCACCGAGACGAAGCAACTGGCCAAGGACCTGAGACAGTGG<br>CAAACCAACGTTGATGTGGCTAATGACCTGGCCTTGAAGCTCCTGCGTGA<br>CTACTCCGCGGATGACACTAGAAAGGTGCACATGATCACCGAGAATATCA<br>ACGCTAGCTGGCGCTCCATCCATAAGCGTGTGAGTGAGCGCGAAGCCGCT<br>CTGGAGGAAACCCATCGCCTGCTTCAACAGTTTCCTTTGGACCTGGAAAA<br>GTTCCTGGCCTGGCTCACAGAAGCCGAGACAACCGCCAACGTGCTGCAGG<br>ACGCCACCCGTAAGGAGCGCTTGCTGGAGGATAGTAAGGGGGTGAAGGAG<br>TTGATGAAGCAGTGGCAAGATCTGCAGGGGGAAATCGAGGCACATACCGA<br>CGTCTATCATAACCTGGATGAGAATTCCCAGAAAATCCTGCGCAGCTTGG<br>AGGGCAGTGATGACGCGGTGCTTCTGCAACGGCGCTTGGACAACATGAAC<br>TTCAAGTGGTCCGAGTTGCGTAAAAAGAGTCTGAACATTCGCTCCCACCT<br>GGAGGCTTCTAGTGACCAGTGGAAGCGCCTGCACCTGAGCCTGCAAGAAC<br>TGCTCGTGTGGCTGCAACTGAAGGATGACGAGTTGAGTCGTCAGGCCCCT<br>ATCGGAGGTGACTTTCCGGCTGTCCAGAAACAGAACGACGTGCATAGGGC<br>ATTTAAGCGCGAGTTGAAGACAAAGGAGCCAGTCATTATGTCCACGCTGG<br>AAACCGTGCGCATTTTCCTGACTGAGCAGCCTCTGGAGGGGCTGGAGAAG<br>CTGTACCAGGAGCCTCGCGAGTTGCCCCCTGAAGAGCGTGCCCAGAATGT<br>GACCCGCCTGTTGCGTAAGCAGGCCGAGGAAGTGAACACCGAGTGGGAGA<br>AGCTGAACCTGCATTCCGCGGATTGGCAGAGGAAGATTGACGAGACGCTG<br>GAGAGGCTCCGTGAGTTGCAGGAGGCAACCGACGAACTGGACCTCAAGCT<br>GCGTCAAGCAGAGGTGATCAAGGGGAGTTGGCAGCCGGTCGGCGATTTGC<br>TGATCGACTCCCTGCAGGATCACCTGGAAAAGGTTAAAGCTTTGCGCGGG<br>GAAATTGCCCCGCTGAAGGAGAACGTGAGCCACGTTAACGATCTGGCCAG<br>ACAGCTGACCACTCTGGGTATCCAGCTGAGCCCGTACAATCTGAGCACCC<br>TCGAAGACTTGAATACGAGATGGAAACTCCTGCAGGTGGCAGTGGAGGAC<br>AGGGTGCGCCAATTGCACGAGGCCCACCGGGACTTTGGACCGGCCAGCCA<br>GCATTTCCTCAGTACCTCTGTTCAGGGCCCGTGGGAGCGGGCCATCTCCC<br>CCAACAAGGTCCCCTATTACATCAACCATGAAACCCAGACTACCTGTTGG<br>GACCACCCTAAAATGACTGAGTTGTATCAATCTCTGGCCGACTTGAATAA<br>CGTGCGCTTCTCAGCCTACAGGACTGCAATGAAACTCAGACGCCTCCAAA<br>AGGCCCTTTGTCTGGACTTGCTGTCCCTTAGCGCTGCCTGTGATGCTCTG<br>GATCAGCACAATTTGAAACAAAACGACCAGCCGATGGACATCCTCCAGAT<br>TATCAACTGCCTGACTACCATCTACGACAGACTGGAACAGGAGCATAATA<br>ACCTGGTGAACGTCCCCCTGTGCGTGGACATGTGCCTGAACTGGCTGCTC<br>AATGTGTATGACACGGGTAGAACAGGACGGATCAGGGTCCTGTCCTTTAA<br>GACCGGTATCATTTCTCTGTGTAAGGCACATCTGGAGGACAAGTACCGCT<br>ACCTGTTTAAGCAGGTCGCCAGCTCCACTGGCTTCTGCGATCAAAGGCGG<br>CTGGGTCTGCTCCTGCACGACTCCATTCAGATCCCGAGACAGTTGGGTGA |

-continued

| SEQ ID NO | Description | SEQ |
|---|---|---|
| | | AGTGGCGTCCTTCGGCGGTTCTAATATCGAGCCTAGCGTCCGCAGCTGTT<br>TCCAATTCGCCAATAACAAGCCGGAGATCGAAGCGGCCCTTTTCCTGGAC<br>TGGATGCGTCTGGAACCTCAGAGCATGGTTTGGCTTCCGGTGCTTCATCG<br>CGTGGCCGCTGCCGAAACCGCTAAACATCAGGCCAAATGTAACATCTGTA<br>AGGAATGCCCGATTATCGGTTTCCGGTACCGTAGCCTCAAGCATTTCAAC<br>TATGATATTTGTCAATCTTGCTTCTTTAGCGGACGGGTGGCCAAAGGCCA<br>CAAAATGCACTACCCGATGGTCGAGTATTGCACTCCTACAACCTCCGGCG<br>AGGACGTGCGCGATTTTGCCAAAGTGCTGAAAAACAAGTTTAGAACCAAG<br>CGTTACTTTGCCAAGCATCCACGTATGGGCTACCTGCCTGTCCAGACCGT<br>TCTGGAAGGTGATAACATGGAGACACCCGTGACTTTGATTAACTTTTGGC<br>CAGTAGACTCTGCTCCGGCAAGCTCCCCTCAGCTCTCCCACGATGACACT<br>CACAGCCGTATCGAGCACTACGCCTCTCGCCTGGCTGAGATGGAGAACTC<br>TAACGGTTCATACCTGAATGACAGTATCTCCCCAAACGAGAGTATCGATG<br>ACGAACATCTGCTCATTCAGCATTACTGTCAATCCTTGAATCAGGACAGC<br>CCCCTGTCCCAGCCACGGTCCCCGGCCCAGATCCTGATTTCACTGGAGTC<br>CGAAGAGAGAGGGGAACTGGAAAGGATCCTCGCTGACCTGGAAGAGGAAA<br>ACCGGAACCTGCAGGCTGAATACGACCGCTTGAAGCAGCAACACGAGCAC<br>AAGGGCTTGAGCCCGTTGCCAAGCCCTCCGGAGATGATGCCAACTAGCCC<br>TCAGAGCCCACGGGATGCCGAGCTCATCGCTGAAGCTAAGTTGCTGAGAC<br>AGCACAAGGGACGTCTGGAGGCCCGCATGCAGATCCTGGAGGATCATAAT<br>AAACAGTTGGAGAGCCAACTGCATAGGCTGCGCCAGCTCCTGGAGCAGCC<br>ACAGGCCGAGGCTAAGGTCAACGGAACTACCGTTTCCAGCCCGTCCACAT<br>CTCTGCAGCGCTCAGATAGTTCCCAGCCTATGTTGCTGAGAGTGGTTGGA<br>TCTCAGACCTCCGACTCAATGGGCGAAGAGGACTTGCTGTCTCCCCCACA<br>GGACACTAGCACAGGACTCGAAGAGGTGATGGAACAGCTCAATAACTCTT<br>TTCCTTCTAGTCGGGGTCGCAATACCCCTGGAAAGCCCATGCGCGAAGAC<br>ACCATGTAATAGCTCGAGAATCAACCTCTGGATTACAAAATTTGTGAAAG<br>ATTGACTGGTATTCTTAACTATGTTGCTCCTTTTACGCTATGTGGATACG<br>CTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTG<br>GCCCGTTGTCAGGCAACGTGGCGTGGTGTGCACTGTGTTTGCTGACGCAA<br>CCCCCACTGGTTGGGGCATTGCCACCACCTGTCAGCTCCTTTCCGGGACT<br>TTCGCTTTCCCCCTCCCTATTGCCACGGCGGAACTCATCGCCGCCTGCCT<br>TGCCCGCTGCTGGACAGGGGCTCGGCTGTTGGGCACTGACAATTCCGTGG<br>GGTGTGCCTTCTAGTTGCCAGCCATCTGTTGTTTGCCCCTCCCCCGTGCC<br>TTCCTTGACCCTGGAAGGTGCCACTCCCACTGTCCTTTCCTAATAAAATG<br>AGGAAATTGCATCGCATTGTCTGAGTAGGTGTCATTCTATTCTGGGGGGT<br>GGGGTGGGGCAGGACAGCAAGGGGGAGGATTGGGAAGACAATAGCAGGCA<br>TGCTGGGGATGCGGTGGGCTCTATGGGAAGATGTCTACTGAGCTGTGCGA<br>TCCCTGCTGGGGACTTTCCGCTGGGGACTTTCCGCTGGGGACTTTCCGCC<br>TTCAGCTAAGGAAGCTACCAATATTTAGAGGTACATTTTGTTCTAGAACA<br>AAATGTACCGGTACATTTTGTTCTGGTACATTTTGTTCT |
| 26. | MHCK7-hBGi-DMD-3-WPRE3-DTS | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>CATGCTGTGGTGGGAAGAGGTGGAGGACTGTTACGAGAGAGAGGACGTGC<br>AGAAGAAGACATTCACCAAGTGGGTGAACGCTCAGTTCAGCAAGTTCGGC<br>AAGCAGCACATCGAGAACCTGTTTAGCGATCTACAAGATGGCAGAAGACT<br>GCTGGACCTGCTGGAGGGCCTGACCGGGCAGAAGCTGCCCAAAGAAAAGG<br>GGTCTACAAGAGTGCACGCCCTGAACAACGTGAACAAGGCCCTGAGAGTG<br>CTGCAGAACAACAACGTGGACCTGGTGAACATCGGCAGCACCGACATCGT<br>GGACGGCAACCACAAGCTGACCCTGGGCCTGATCTGGAACATCATCCTGC<br>ACTGGCAAGTGAAGAACGTGATGAAGAACATCATGGCCGGCCTGCAGCAG<br>ACCAACAGCGAGAAGATCCTGCTGAGCTGGGTGAGACAGAGCACAAGAAA<br>CTACCCCCAAGTGAACGTGATCAACTTCACCACAAGCTGGAGCGACGGCC<br>TGGCCCTGAACGCCCTGATCCACAGCCACAGACCCGACCTGTTCGACTGG |

-continued

| SEQ ID NO | Description | SEQ |
|---|---|---|
| | | AACAGCGTGGTGTGTCAGCAGAGCGCCACACAGAGACTGGAGCACGCCTT<br>CAACATCGCTAGATATCAGCTGGGCATCGAGAAGTTACTGGACCCCGAAG<br>ATGTGGACACCACCTACCCCGACAAGAAGAGCATCCTGATGTACATCACA<br>AGCCTGTTCCAAGTGCTGCCTCAGCAAGTGAGCATCGAGGCCATCCAAGA<br>AGTCGAGATGCTGCCTAGACCCCCCAAGGTGACCAAGGAGGAGCACTTTC<br>AGCTGCACCATCAGATGCACTACTCTCAGCAGATCACAGTCAGCTTGGCA<br>CAAGGCTACGAGAGAACAAGCAGCCCCAAGCCTAGATTCAAGAGCTACGC<br>CTACACCCAAGCCGCCTACGTGACCACAAGTGACCCCACAAGAAGCCCCT<br>TCCCTTCTCAGCACCTGGAGGCCCCCGAGGACAAGAGCTTCGGCAGCAGC<br>CTGATGGAGAGCGAGGTGAACCTGGACAGATATCAGACCGCGTTAGAAGA<br>AGTGTTGAGCTGGCTGCTGAGCGCCGAGGACACCCTGCAAGCCCAAGGCG<br>AGATCAGCAACGATGTGGAGGTGGTGAAGGATCAGTTCCACACCCACGAG<br>GGCTACATGATGGACCTGACCGCCCACCAAGGCAGAGTGGGCAACATCCT<br>GCAGCTGGGCAGCAAGCTGATCGGCACCGGCAAGCTGAGCGAGGACGAGG<br>AAACCGAGGTTCAAGAGCAAATGAACCTGCTAAACAGCAGATGGGAGTGC<br>CTGAGAGTGGCTAGCATGGAAAAGCAGAGTAACCTGCACAGAGTGCTGAT<br>GGACCTGCAGAATCAGAAATTGAAAGAACTTAATGATTGGCTGACCAAGA<br>CCGAGGAGAGAACAAGAAAGATGGAGGAGGAGCCCCTGGGCCCCGACCTG<br>GAGGACCTGAAGAGACAAGTGCAGCAGCACAAGGTGCTGCAAGAGGACCT<br>GGAGCAAGAGCAAGTGAGAGTGAACTCTCTGACACACATGGTGGTGGTAG<br>TGGACGAGAGCAGCGGCGATCACGCTACCGCGGCGCTGGAAGAGCAGCTG<br>AAAGTGCTGGGCGACAGATGGGCCAACATCTGCAGATGGACCGAGGACAG<br>ATGGGTGCTGCTGCAAGACATCCTGCTGAAGTGGCAGAGACTGACCGAGG<br>AGCAGTGCCTGTTCAGCGCCTGGCTGAGCGAGAAGGAAGACGCTGTGAAC<br>AAGATCCACACCACCGGCTTCAAGGATCAGAACGAGATGCTGAGCTCCCT<br>CCAAAAGCTCGCAGTGCTGAAGGCCGACCTGGAAAAGAAAAAACAGTCGA<br>TGGGCAAGCTGTACAGCCTGAAGCAAGACCTGCTGAGCACCCTGAAGAAC<br>AAGAGCGTGACACAGAAGACCGAGGCCTGGCTGGACAACTTCGCTAGATG<br>CTGGGACAACCTGGTACAGAAGTTAGAGAAGTCTACCGCTCAGATCAGCC<br>AAGCCGTAACCACCACACAACCTAGCCTGACTCAGACCACCGTGATGGAA<br>ACCGTGACCACCGTGACAACCCGTGAGCAGATCCTGGTGAAGCACGCCCA<br>AGAGGAGCTGCCCCCCCCCCCCCCTCAGAAGAAGAGACAGATCACCGTGG<br>ACTCAGAGATTCGCAAGAGACTGGACGTGGACATCACCGAGCTGCACAGC<br>TGGATCACAAGAAGCGAGGCCGTGCTGCAGAGCCCTGAGTTCGCGATCTT<br>TAGAAAGGAGGGCAACTTCAGCGACTTGAAGGAGAAAGTGAACGCCATCG<br>AGAGAGAGAAGGCCGAGAAGTTCAGAAAGTTGCAAGACGCCTCAAGAAGC<br>GCCCAAGCCCTGGTGGAGCAGATGGTTAACGAAGGCGTGAATGCCGACAG<br>CATCAAGCAAGCTAGCGAGCAGCTGAATAGCCGGTGGATTGAATTCTGTC<br>AGCTGCTGAGCGAGAGATTAAACTGGCTGGAGTATCAGAACAACATCATC<br>GCCTTCTACAATCAGCTGCAGCAACTAGAACAAATGACCACCACCGCCGA<br>GAACTGGCTAAAGATTCAGCCCACCACCCCTAGCGAGCCCACCGCCATCA<br>AATCTCAGCTGAAAATTTGCAAGGACGAAGTGAACAGACTGTCGGACCTG<br>CAGCCTCAAATCGAAAGACTGAAAATTCAGAGCATCGCACTTAAGGAGAA<br>GGGCCAAGGACCCATGTTCCTGGACGCCGACTTCGTGGCCTTCACCAACC<br>ACTTCAAGCAAGTGTTCAGCGACGTGCAAGCTAGAGAGAAGGAGCTGCAG<br>ACCATCTTCGACACCCTGCCCCCCATGAGATACCAAGAAACCATGAGCGC<br>CATCAGAACCTGGGTGCAGCAGAGCGAAACCAAGCTGAGCATCCCTCAGC<br>TGAGCGTGACCGACTACGAGATCATGGAGCAAAGACTGGGAGAGCTGCAA<br>GCCCTGCAGAGCAGCCTGCAAGAGCAGCAGAGCGGCCTGTACTACCTGAG<br>CACCACCGTGAAGGAGATGTCGAAGAAAGCCCCGTCGGAGATCAGCAGAA<br>AGTATCAGAGCGAGTTCGAGGAGATCGAGGGCAGATGGAAGAAGCTGAGC<br>AGCCAACTGGTGGAACACTGTCAGAAATTAGAAGAACAGATGAACAAGCT<br>GAGAAAGATTCAGAACCACATTCAGACCCTGAAGAAGTGGATGGCCGAGG<br>TGGACGTGTTCCTGAAAGAGGAGTGGCCCGCCCTGGGCGATTCCGAAATC<br>TTAAAAAAGCAGCTGAAGCAGTGCAGACTGCTGGTGTCAGATATCCAAAC<br>CATTCAACCAAGCCTGAACAGCGTGAACGAAGGCGGGCAGAAGATCAAGA<br>ACGAGGCCGAGCCCGAGTTCGCTAGCAGACTGGAAACCGAGCTGAAGGAG<br>CTGAATACACAGTGGGACCACATGTGTCAGCAAGTGTACGCTAGAAAGGA<br>AGCGCTGAAGGGCGGGCTGGAGAAGACCGTTAGCCTGCAAAAGGATCTGA<br>GCGAGATGCACGAGTGGATGACCCAAGCCGAGGAGGAGTACCTGGAGAGA<br>GACTTCGAGTACAAGACCCCCGACGAGCTGCAGAAGGCCGTCGAGGAAAT<br>GAAGAGAGCGAAGGAGGAGGCTCAGCAGAAGGAAGCCAAGGTGAAGCTGC<br>TGACTGAATCTGTCAACAGTGTGATAGCTCAAGCACCCCCCGTTGCCCAA<br>GAGGCACTAAAGAAGGAGCTGGAAACTCTGACCACCAACTATCAGTGGCT<br>GTGCACAAGACTGAACGGCAAGTGCAAGACCCTGGAGGAAGTGTGGGCCT<br>GCTGGCACGAGCTGCTGAGCTACCTGGAGAAGGCCAACAAGTGGCTGAAC<br>GAGGTGGAGTTCAAGCTGAAGACCACCGAGAACATCCCCGGCGGCGCCGA<br>GGAGATCAGCGAGGTGCTGGACAGCCTGGAGAACCTGATGAGACACAGCG<br>AGGACAACCCCAATCAGATCAGAATCCTGGCTCAGACCCTGACCGACGGC<br>GGCGTGATGGACGAGCTGATCAACGAGGAGCTGGAAACCTTTAACTCTAG<br>ATGGCGAGAACTGCACGAGGAGGCCGTGAGAAGACAGAAGCTGCTGGAGC<br>AAAGCATTCAGAGCGCCCAAGAAACCGAGAAGAGCCTGCACCTGATCCAA<br>GAGAGCCTGACCTTCATCGACAAGCAGCTGGCCGCCTACATCGCCGACAA<br>GGTGGACGCCGCTCAGATGCCACAAGAGGCTCAGAAGATTCAGTCCGATC<br>TGACAAGCCACGAGATCAGCCTGGAGGAGATGAAAAAACACAACCAAGGC |

-continued

| SEQ ID NO | Description | SEQ |
|---|---|---|
| | | AAGGAGGCCGCTCAGAGAGTGCTGTCTCAGATCGACGTGGCTCAGAAGAA |
| | | GCTGCAAGACGTGAGCATGAAGTTCAGACTGTTTCAGAAGCCCGCCAACT |
| | | TCGAGCAGCGACTGCAAGAGAGCAAGATGATCCTGGACGAGGTGAAGATG |
| | | CACCTGCCCGCCCTGGAAACCAAGAGCGTGGAGCAAGAGGTGGTGCAGTC |
| | | TCAGTTGAACCACTGCGTGAACCTGTACAAGAGCCTGTCGGAGGTCAAGA |
| | | GTGAGGTCGAGATGGTGATCAAAACTGGGAGACAGATCGTGCAAAAAAAG |
| | | CAGACCGAGAACCCCAAGGAGCTGGACGAGCGTGTTACCGCCCTGAAGCT |
| | | GCACTACAACGAGCTGGGCGCCAAGGTGACCGAGAGAAAGCAGCAGCTGG |
| | | AGAAGTGCCTGAAGCTGAGCAGAAAGATGAGAAAGGAGATGAACGTGCTG |
| | | ACCGAGTGGCTGGCCGCCACCGACATGGAGCTGACCAAGAGAAGCGCCGT |
| | | GGAGGGCATGCCTAGCAACCTGGACAGCGAGGTGGCCTGGGGCAAGGCCA |
| | | CACAGAAGGAGATCGAGAAGCAGAAGGTGCACCTGAAGAGCATCACCGAG |
| | | GTGGGCGAGGCCCTGAAGACCGTGCTGGGCAAGAAGGAAACCCTGGTGGA |
| | | GGACAAGCTGAGCCTGCTGAACTCGAACTGGATCGCCGTGACAAGCAGAG |
| | | CCGAGGAGTGGCTGAACCTGCTGTTAGAGTACCAAAAACACATGGAAACC |
| | | TTCGATCAGAACGTGGACCACATCACCAAGTGGATCATCCAAGCCGACAC |
| | | CCTGCTGGACGAAAGCGAAAAGAAGAAGCCGCAACAAAAGGAGGATGTGC |
| | | TGAAGAGACTGAAGGCCGAACTGAACGATATCAGACCCAAGGTGGACAGC |
| | | ACACGGGACCAAGCCGCCAACCTGATGGCCAACAGAGGCGACCACTGCAG |
| | | AAAACTGGTGGAGCCTCAGATCAGCGAGCTGAACCACAGATTCGCCGCCA |
| | | TCAGCCACAGAATCAAAACCGGCAAAGCGAGCATCCCCTTGAAGGAACTG |
| | | GAGCAATTTAACAGCGACATCCAAAAATTGCTCGAACCACTGGAGGCCGA |
| | | GATTCAGCAAGGCGTGAACCTGAAGGAAGAGGACTTCAACAAGGACATGA |
| | | ACGAGGACAACGAGGGCACCGTGAAAGAACTGCTGCAGAGAGGCGACAAC |
| | | CTGCAGCAGAGAATCACCGACGAGAGAAAGAGAGAGGAGATCAAGATCAA |
| | | GCAGCAGCTGCTGCAGACTAAGCACAACGCCCTGAAGGATCTGAGATCTC |
| | | AGAGGAGAAAAAAGGCTCTGGAAATTTCACATCAGTGGTATCAGTACAAG |
| | | AGACAAGCAGACGACCTGCTGAAGTGCCTGGACGACATCGAGAAGAAGTT |
| | | AGCTAGCCTGCCCGAGCCTAGAGACGAGAGAAAGATCAAGGAGATCGACA |
| | | GAGAGTTACAAAAGAAGAAGGAGGAGCTGAATGCGGTAAGAAGACAAGCG |
| | | GAAGGCCTGTCCGAGGACGGCGCAGCCATGGCCGTGGAGCCCACACAGAT |
| | | TCAGCTCAGCAAGAGATGGAGAGAGATCGAGAGCAAGTTCGCTCAGTTCA |
| | | GAAGACTGAACTTCGCTCAGATCCACACCGTGAGAGAGGAAACCATGATG |
| | | GTGATGACCGAGGACATGCCCCTGGAGATCTCATACGTTCCTAGCACCTA |
| | | CCTGACCGAGATCACCCACGTGAGCCAAGCCCTGCTGGAGGTGGAGCAGC |
| | | TGCTGAACGCCCCCGACCTGTGCGCCAAGGACTTCGAGGACCTGTTCAAA |
| | | CAAGAGGAGAGCCTGAAGAACATCAAGGACAGCCTGCAGCAAAGTAGCGG |
| | | CAGAATCGACATCATCCACAGCAAGAAGACCGCCGCCCTGCAGAGCGCCA |
| | | CCCCCGTGGAGAGAGTGAAGCTTCAAGAGGCCCTTTCGCAGCTGGATTTT |
| | | CAGTGGGAGAAGGTGAACAAAATGTACAAGGACAGACAAGGCAGATTCGA |
| | | CAGAAGCGTGGAGAAGTGGAGAAGATTCCACTACGACATCAAGATCTTCA |
| | | ATCAGTGGCTGACCGAGGCAGAGCAGTTCCTGAGAAAGACACAGATCCCC |
| | | GAGAACTGGGAGCACGCCAAGTACAAGTGGTACCTGAAGGAGCTGCAAGA |
| | | CGGCATCGGGCAGAGACAGACCGTGGTGAGAACCCTGAACGCCACCGGCG |
| | | AGGAGATCATCCAACAAAGCTCCAAAACCGACGCTAGCATCCTGCAAGAG |
| | | AAACTGGGCAGCCTGAACCTGAGATGGCAAGAGGTGTGCAAGCAGCTGAG |
| | | CGACCGCAAAAAACGGTTAGAGGAGCAGAAGAACATCCTGAGCGAGTTTC |
| | | AGCGGGACCTGAACGAGTTCGTGCTGTGGCTGGAGGAGGCCGATAACATC |
| | | GCTAGCATCCCCCTGGAGCCCGGCAAGGAGCAGCAGTTAAAAGAAAAACT |
| | | TGAGCAAGTGAAGCTGCTGGTGGAGGAGCTGCCCCTGAGACAAGGCATCC |
| | | TGAAGCAGCTGAACGAGACTGGCGGCCCCGTGCTGGTGAGCGCCCCCATC |
| | | AGCCCCGAGGAGCAAGACAAGCTGGAGAACAAGCTGAAGCAGACCAACCT |
| | | GCAGTGGATCAAGGTGAGCAGAGCCCTGCCCGAGAAGCAAGGCGAAATCG |
| | | AGGCCCAAATAAAGGACCTGGGGCAGCTGGAGAAGAAACTCGAAGACTTG |
| | | GAAGAACAACTCAACCACTTGCTGCTGTGGCTGAGCCCCATCAGAAATCA |
| | | GCTGGAGATCTACAATCAGCCCAACCAAGAGGGGCCATTCGACGTGAAGG |
| | | AAACCGAGATCGCCGTGCAAGCCAAGCAGCCCGATGTGGAGGAGATCCTG |
| | | AGCAAGGGGCAGCACCTGTACAAGGAGAAGCCCGCCACACAGCCCGTCAA |
| | | GCGTAAACTAGAGGATCTTTCCTCTGAGTGGAAGGCCGTGAACCGTCTGC |
| | | TACAAGAGCTGCGGGCTAAGCAACCCGACTTAGCGCCCGGCCTGACCACC |
| | | ATCGGTGCAAGCCCCACGCAGACCGTGACCCTGGTGACCCAACCCGTGGT |
| | | GACCAAGGAAACCGCCATCAGCAAGCTGGAGATGCCTAGCAGCCTGATGC |
| | | TGGAGGTGCCCGCCCTGGCCGACTTCAACAGAGCCTGGACCGAGCTGACC |
| | | GACTGGCTGAGCCTGCTGGACCAAGTGATCAAGTCTCAGAGAGTGATGGT |
| | | GGGCGATCTGGAGGACATCAATGAGATGATCATCAAGCAGAAGGCCACCA |
| | | TGCAAGACCTGGAGCAGAGAAGACCTCAGCTGGAGGAGCTGATCACCGCC |
| | | GCTCAGAACCTGAAAAACAAGACGAGCAACCAAGAGGCTAGAACCATCAT |
| | | CACCGACAGAATCGAGAGAATTCAGAATCAGTGGGACGAGGTGCAAGAGC |
| | | ACCTGCAGAACAGAAGACAGCAACTAAACGAAATGCTCAAGGACAGCACA |
| | | CAGTGGCTGGAGGCCAAGGAGGAGGCGGAGCAAGTGTTGGGCCAAGCTAG |
| | | AGCCAAGCTGGAGAGCTGGAAGGAGGGACCCTACACCGTGGACGCCATTC |
| | | AGAAGAAGATCACCGAAACCAAGCAGCTGGCCAAGGACCTGCGACAGTGG |
| | | CAGACCAACGTGGACGTGGCCAACGATCTTGCCCTGAAGCTGCTGCGCGA |
| | | CTATAGCGCCGACGACACAAGAAAGGTGCACATGATCACCGAGAACATCA |
| | | ACGCTAGCTGGCGTAGCATCCACAAGAGAGTGAGCGAGAGAGAGGCGGCT |

-continued

| SEQ ID NO | Description | SEQ |
|---|---|---|
| | | TTGGAGGAAACCCATAGACTGCTGCAGCAGTTTCCCCTGGACCTGGAGAA<br>GTTCCTGGCCTGGCTGACCGAAGCCGAAACAACCGCCAACGTGCTGCAAG<br>ACGCCACAAGAAAGGAGAGACTGCTGGAGGACAGCAAGGGCGTGAAGGAG<br>CTGATGAAGCAGTGGCAAGACCTGCAAGGCGAGATCGAAGCGCACACCGA<br>CGTGTACCACAACCTGGACGAGAACTCTCAGAAGATCCTGAGAAGCCTGG<br>AGGGCAGCGACGACGCCGTGCTGTTACAGAGAAGGCTGGACAACATGAAC<br>TTCAAGTGGAGCGAGCTGAGAAAGAAGAGCCTGAACATCAGAAGCCACCT<br>GGAGGCTAGCAGCGATCAGTGGAAGAGACTGCACCTGAGCCTGCAAGAGC<br>TGCTGGTCTGGCTTCAGTTGAAGGACGATGAGCTGAGCAGACAAGCCCCC<br>ATCGGCGGCGACTTCCCCGCCGTGCAGAAGCAGAACGACGTGCATAGAGC<br>CTTCAAGAGAGAGCTGAAGACCAAGGAGCCCGTGATCATGAGCACCCTGG<br>AAACGGTGAGAATCTTCCTGACCGAGCAGCCCCTGGAGGGCCTGGAGAAG<br>CTGTACCAAGAGCCTAGAGAGCTGCCCCCCGAGGAGAGAGCTCAGAACGT<br>GACAAGACTGCTGAGAAAGCAAGCCGAAGAGGTGAACACCGAGTGGGAGA<br>AGCTGAACCTGCACAGCGCCGACTGGCAGAGAAAGATCGACGAAACCCTG<br>GAGAGACTGAGAGAATTGCAAGAGGCGACCGACGAGCTGGACCTGAAGCT<br>GAGACAAGCCGAGGTCATCAAGGGCAGCTGGCAGCCCGTGGGCGATCTAT<br>TAATTGACTCTCTACAAGACCACCTGGAGAAAGTGAAGGCCCTGAGAGGC<br>GAGATCGCCCCCCTGAAGGAGAACGTGAGCCACGTGAATGATCTGGCACG<br>TCAGCTGACCACCCTGGGCATACAACTGTCCCCCTATAACCTGAGCACAC<br>TGGAGGATTTGAATACTAGATGGAAGCTGCTGCAAGTGGCCGTGGAGGAC<br>AGAGTAAGACAATTACATGAGGCCCACAGAGACTTCGGCCCCGCTTCTCA<br>GCACTTCCTGAGCACAAGCGTGCAAGGCCCCTGGGAGAGAGCCATTTCCC<br>CCAACAAGGTCCCCTACTACATCAACCACGAGACACAGACCACCTGCTGG<br>GACCACCCCAAGATGACCGAGCTGTATCAGAGCCTCGCCGATCTGAACAA<br>TGTGAGATTCAGCGCCTACAGAACCGCCATGAAGCTGAGAAGACTGCAGA<br>AGGCCCTGTGCCTGGACTTATTAAGCCTGAGCGCCGCCTGCGACGCCCTG<br>GATCAGCACAACCTGAAGCAAAACGACCAACCCATGGACATCCTGCAGAT<br>CATCAACTGCCTCACCACCATATACGACAGACTGGAACAAGAGCACAACA<br>ACCTGGTGAACGTGCCCCTGTGCGTGGACATGTGCCTGAACTGGCTGCTG<br>AACGTGTACGACACCGGCAGAACCGGCAGAATCAGAGTGCTGAGCTTCAA<br>GACCGGCATCATCAGCCTGTGCAAGGCCCACCTGGAGGACAAATACAGAT<br>ACCTTTTCAAACAAGTGGCTAGCAGCACCGGCTTCTGCGACCAAAGAAGA<br>CTGGGTCTGCTGCTGCACGACAGCATTCAGATCCCTAGACAGCTGGGCGA<br>GGTGGCTAGCTTCGGCGGCAGCAACATCGAGCCTAGCGTGAGAAGCTGCT<br>TTCAGTTCGCCAACAACAAGCCCGAGATAGAGGCAGCCCTCTTCTTAGAC<br>TGGATGAGACTGGAGCCTCAGAGCATGGTATGGCTGCCGGTCCTGCACAG<br>AGTGGCCGCCGCCGAAACCGCCAAGCACCAAGCCAAGTGCAACATCTGCA<br>AGGAGTGCCCCATCATCGGCTTCAGATACAGAAGCCTGAAGCACTTCAAC<br>TACGACATCTGTCAGAGCTGCTTCTTCAGCGGCAGAGTGGCCAAGGGCCA<br>CAAGATGCACTACCCCATGGTGGAGTACTGCACCCCCACCACAAGCGGCG<br>AGGACGTGAGAGACTTCGCCAAGGTGTTGAAGAATAAGTTTAGAACCAAG<br>AGATACTTCGCCAAGCACCCTAGAATGGGCTACCTGCCCGTGCAGACCGT<br>GCTGGAGGGCGACAACATGGAAACCCCCGTGACCCTGATCAACTTCTGGC<br>CCGTGGACAGCGCCCCCGCTAGCAGCCCTCAGCTGAGCCACGACGACACC<br>CACAGCAGAATCGAGCACTACGCTAGCAGACTGGCCGAGATGGAGAACAG<br>CAACGGCAGCTACCTGAACGACAGCATCAGCCCGAATGAGAGCATCGACG<br>ACGAGCACCTGCTGATTCAGCACTACTGTCAGAGCCTGAACCAAGACAGC<br>CCCCTGTCTCAGCCTAGAAGCCCCGCTCAGATCCTGATCAGCCTGGAGAG<br>CGAGGAGAGAGGCGAGCTGGAGAGAATCCTAGCAGATCTGGAGGAAGAGA<br>ACAGAAACCTGCAAGCCGAGTATGACCGACTGAAACAGCAACATGAGCAC<br>AAAGGCCTGAGCCCACTGCCCTCCCCCCCCGAGATGATGCCCACAAGCCC<br>TCAGAGCCCTAGAGACGCCGAGCTGATCGCTGAAGCGAAGTTACTTAGAC<br>AACACAAGGGCAGACTGGAGGCTAGAATGCAGATCCTGGAGGACCACAAC<br>AAGCAGCTGGAGTCTCAGCTGCACAGACTGAGGCAGCTGCTGGAACAGCC<br>CCAAGCCGAGGCCAAAGTGAACGGCACCACCGTGAGCAGTCCTAGCACAA<br>GCCTGCAGAGAAGCGACAGCTCTCAGCCCATGCTGCTGAGAGTGGTGGGC<br>TCTCAGACAAGCGACAGCATGGGCGAGGAGGATCTGCTGAGTCCGCCCCA<br>AGACACAAGCACCGGCCTGGAAGAGGTGATGGAGCAACTGAACAATAGCT<br>TCCCTAGCAGCAGAGGCAGAAACACCCCCGGCAAGCCCATGAGAGAGGAC<br>ACCATGTGATGACTCGAGAATCAACCTCTGGATTACAAAATTTGTGAAAG<br>ATTGACTGGTATTCTTAACTATGTTGCTCCTTTTACGCTATGTGGATACG<br>CTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTG<br>GCCCGTTGTCAGGCAACGTGGCGTGGTGTGCACTGTGTTTGCTGACGCAA<br>CCCCCACTGGTTGGGGCATTGCCACCACCTGTCAGCTCCTTTCCGGGACT<br>TTCGCTTTCCCCCTCCCTATTGCCACGGCGGAACTCATCGCCGCCTGCCT<br>TGCCCGCTGCTGGACAGGGGCTCGGCTGTTGGGCACTGACAATTCCGTGG<br>GGTGTGCCTTCTAGTTGCCAGCCATCTGTTGTTTGCCCCTCCCCCGTGCC<br>TTCCTTGACCCTGGAAGGTGCCACTCCCACTGTCCTTTCCTAATAAAATG<br>AGGAAATTGCATCGCATTGTCTGAGTAGGTGTCATTCTATTCTGGGGGGT<br>GGGGTGGGGCAGGACAGCAAGGGGGAGGATTGGGAAGACAATAGCAGGCA<br>TGCTGGGGATGCGGTGGGCTCTATGGGAAGATGTCTACTGAGCTGTGCGA |

-continued

| SEQ ID NO | Description | SEQ |
|---|---|---|
| | | TCCCTGCTGGGGACTTTCCGCTGGGGACTTTCCGCTGGGGACTTTCCGCC TTCAGCTAAGGAAGCTACCAATATTTAGAGGTACATTTTGTTCTAGAACA AAATGTACCGGTACATTTTGTTCTGGTACATTTTGTTCT |
| 27. | MHCK7-hBGi-DMD-4-WPRE3-DTS | CTAGAAGCTGCATGTCTAAGCTAGACCCTTCAGATTAAAAATAACTGAGG TAAGGGCCTGGGTAGGGGAGGTGGTGTGAGACGCTCCTGTCTCTCCTCTA TCTGCCCATCGGCCCTTTGGGGAGGAGGAATGTGCCCAAGGACTAAAAAA AGGCCATGGAGCCAGAGGGGCGAGGGCAACAGACCTTTCATGGGCAAACC TTGGGGCCCTGCTGTCTAGCATGCCCCACTACGGGTCTAGGCTGCCCATG TAAGGAGGCAAGGCCTGGGGACACCCGAGATGCCTGGTTATAATTAACCC AGACATGTGGCTGCCCCCCCCCCCCCAACACCTGCTGCCTCTAAAAATAA CCCTGTCCCTGGTGGATCCCCTGCATGCGAAGATCTTCGAACAAGGCTGT GGGGGACTGAGGGCAGGCTGTAACAGGCTTGGGGGCCAGGGCTTATACGT GCCTGGGACTCCCAAAGTATTACTGTTCCATGTTCCCGGCGAAGGGCCAG CTGTCCCCCGCCAGCTAGACTCAGCACTTAGTTTAGGAACCAGTGAGCAA GTCAGCCCTTGGGGCAGCCCATACAAGGCCATGGGGCTGGGCAAGCTGCA CGCCTGGGTCCGGGGTGGGCACGGTGCCCGGGCAACGAGCTGAAAGCTCA TCTGCTCTCAGGGGCCCCTCCCTGGGGACAGCCCCTCCTGGCTAGTCACA CCCTGTAGGCTCCTCTATATAACCCAGGGGCACAGGGGCTGCCCTCATTC TACCACCACCTCCACAGCACTCTGGATCCACTGCTTAAATACGGACGAGG ACAGGGCCCTGTCTCCTCAGCTTCAGGCACCACCACTGACCTGGGACAGT GAATCGTAAGTACTAGCAGCTACAATCCAGCTACCATTCTGCTTTTATTT TATGGTTGGGATAAGGCTGGATTATTCTGAGTCCAAGCTAGGCCCTTTTG CTAATCATGTTCATACCTCTTATCTTCCTCCCACAGCTCCTGGGCAACGT GCTGGTCTGTGTGCTGGCCCATCACTTTGGCAAAGAATTGCGATCGCCAC CATGCTTTGGTGGGAAGAAGTCGAGGACTGCTACGAGCGCGAGGACGTGC AGAAGAAAACCTTCACCAAATGGGTCAACGCCCAGTTCAGCAAGTTCGGC AAGCAGCACATCGAGAACCTGTTCAGCGACCTGCAGGATGGCAGAAGGCT GCTGGATCTGCTGGAAGGCCTGACAGGACAGAAGCTGCCCAAAGAGAAGG GCAGCACAAGAGTGCACGCCCTGAACAACGTGAACAAGGCCCTGAGAGTG CTGCAGAACAACAACGTGGACCTGGTCAACATCGGCAGCACCGACATCGT GGACGGCAACCACAAACTGACCCTGGGCCTGATCTGGAACATCATCCTGC ACTGGCAAGTGAAGAACGTGATGAAGAACATCATGGCCGGCCTGCAGCAG ACCAACAGCGAGAAGATTCTGCTGAGCTGGGTCCGACAGAGCACCCGGAA TTACCCTCAAGTGAACGTGATCAACTTCACCACCTCTTGGAGCGACGGAC TGGCCCTGAATGCCCTGATCCACAGCCACAGACCTGACCTGTTCGACTGG AACAGCGTCGTGTGTCAGCAGAGCGCCACACAGAGGCTGGAACACGCCTT CAATATCGCCAGATACCAGCTGGGCATCGAGAAACTGCTGGACCCCGAGG ATGTGGACACCACCTATCCTGACAAGAAATCCATCCTCATGTACATCACC AGCCTGTTCCAGGTGCTGCCCCAGCAGGTTTCCATCGAGGCCATTCAAGA GGTCGAGATGCTGCCCAGACCTCCTAAAGTGACCAAAGAGGAACACTTCC AGCTGCACCACCAGATGCACTACTCTCAGCAGATCACCGTGTCTCTGGCC CAGGGCTACGAGAGAACAAGCAGCCCCAAGCCTCGGTTCAAGAGCTACGC CTATACACAGGCCGCCTACGTGACCACCAGCGATCCTACAAGAAGCCCAT TTCCTAGCCAGCATCTGGAAGCCCCTGAGGACAAGAGCTTTGGCAGCAGC CTGATGGAAAGCGAAGTGAACCTGGACCGCTACCAGACAGCCCTGGAAGA GGTTCTGAGCTGGCTGCTGTCTGCCGAGGATACACTGCAGGCTCAGGGCG AGATCAGCAACGACGTGGAAGTGGTCAAGGACCAGTTTCACACCCACGAG GGCTACATGATGGACCTGACAGCCCACCAGGGCAGAGTGGGCAATATTCT GCAGCTGGGCTCCAAGCTGATCGGCACAGGCAAGCTGAGCGAGGACGAAG AGACAGAGGTGCAAGAGCAGATGAACCTGCTGAACAGCAGATGGGAGTGT CTGAGAGTGGCCAGCATGGAAAAGCAGAGCAACCTGCACCGGGTGCTGAT GGATCTCCAGAACCAGAAGCTGAAAGAGCTGAACGACTGGCTGACCAAGA CCGAGGAACGGACCCGGAAGATGGAAGAGGAACCTCTGGGACCCGACCTG GAAGATCTGAAAAGACAGGTGCAGCAGCATAAGGTGCTGCAAGAGGACCT CGAACAAGAGCAAGTGCGCGTGAACAGCCTGACACACATGGTGGTGGTCG TGGATGAGAGCAGCGGAGATCATGCCACAGCCGCTCTGGAAGAACAGCTG AAGGTGCTGGGAGACAGATGGGCCAATATCTGCCGGTGGACCGAGGATAG ATGGGTGCTGCTCCAGGACATCCTGCTGAAGTGGCAGCGGCTGACAGAGG AACAGTGCCTGTTTAGCGCCTGGCTGTCCGAGAAAGAGGACGCCGTCAAC AAGATCCACACCACCGGCTTCAAGGATCAGAATGAGATGCTGAGCAGCCT GCAGAAACTGGCCGTGCTGAAGGCTGACCTGGAAAAGAAAAAGCAGTCCA TGGGCAAGCTGTACTCCCTGAAGCAGGACCTGCTGAGCACACTGAAGAAC AAGTCTGTGACCCAGAAAACCGAGGCCTGGCTGGACAACTTCGCCCGGTG TTGGGATAACCTGGTGCAGAAGCTGGAAAAGTCCACCGCTCAGATCTCTC AGGCCGTGACCACAACACAGCCTTCTCTGACCCAGACCACCGTGATGGAA ACAGTGACCACAGTGACAACCCGCGAGCAGATCCTGGTCAAGCACGCCCA AGAAGAACTGCCTCCTCCACCTCCTCAGAAGAAACGGCAGATCACAGTGG ACAGCGAGATCCGGAAGAGACTGGACGTGGACATCACCGAGCTGCACAGC TGGATCACCAGATCCGAAGCCGTGCTGCAGTCCCCTGAGTTCGCCATCTT CAGAAAAGAGGGCAACTTCTCCGACCTGAAAGAGAAAGTCAACGCCATCG AGAGAGAGAAGGCCGAGAAGTTCCGGAAGCTGCAGGACGCCTCTAGATCT GCCCAGGCTCTGGTGGAACAGATGGTCAACGAAGGCGTGAACGCCGACAG CATCAAGCAGGCCTCAGAGCAGCTGAACTCCCGGTGGATCGAGTTCTGTC AGCTCCTGAGCGAGAGACTGAACTGGCTGGAATACCAGAACAATATCATT |

-continued

| SEQ ID NO | Description | SEQ |
|---|---|---|
| | | GCCTTCTACAACCAGCTCCAGCAGCTCGAACAGATGACCACCACAGCCGA<br>GAATTGGCTGAAGATCCAGCCTACCACACCTAGCGAGCCCACCGCCATTA<br>AGAGCCAGCTGAAAATCTGCAAGGACGAAGTGAATCGGCTGAGCGATCTG<br>CAGCCCCAGATCGAAAGACTGAAAATCCAGTCTATCGCCCTCAAAGAGAA<br>AGGACAGGGCCCCATGTTCCTGGACGCCGATTTTGTGGCCTTTACCAACC<br>ACTTCAAACAGGTGTTCTCCGACGTGCAGGCCCGGGAAAAAGAGCTGCAG<br>ACCATCTTCGACACCCTGCCTCCAATGAGATACCAAGAGACAATGAGCGC<br>CATCCGGACCTGGGTGCAGCAAAGCGAGACAAAGCTGAGCATCCCACAGC<br>TGAGCGTGACCGACTACGAGATCATGGAACAGAGACTGGGCGAACTGCAG<br>GCCCTCCAGTCTAGCCTGCAAGAACAGCAGTCCGGCCTGTACTACCTGAG<br>CACAACCGTGAAAGAGATGAGCAAGAAGGCCCCTAGCGAGATCTCCCGGA<br>AGTACCAGAGCGAGTTCGAAGAGATCGAAGGCCGGTGGAAGAAGCTGTCT<br>AGCCAGCTGGTTGAGCACTGCCAGAAACTCGAAGAACAAATGAACAAGCT<br>GCGCAAGATCCAGAATCACATCCAGACGCTGAAGAAATGGATGGCCGAGG<br>TGGACGTGTTCCTGAAAGAAGAGTGGCCCGCTCTGGGCGACTCCGAGATT<br>CTGAAGAAACAGCTCAAACAGTGCCGGCTGCTGGTGTCCGATATCCAGAC<br>AATCCAGCCAAGCCTGAACTCCGTGAATGAAGGCGGCCAGAAGATCAAGA<br>ACGAGGCCGAGCCTGAGTTTGCCAGCAGACTGGAAACCGAACTGAAAGAA<br>CTCAACACCCAGTGGGACCACATGTGCCAGCAAGTGTACGCCCGGAAAGA<br>GGCCCTGAAAGGCGGACTCGAAAAGACTGTGTCTCTGCAGAAAGACCTGT<br>CTGAGATGCACGAGTGGATGACCCAGGCCGAAGAGGAATACCTGGAACGG<br>GACTTCGAGTACAAGACCCCTGATGAGCTGCAAAAAGCCGTCGAGGAAAT<br>GAAGCGGGCCAAAGAAGAGGCCCAGCAGAAAGAAGCCAAAGTCAAGCTGC<br>TGACCGAGTCCGTGAATAGCGTTATCGCTCAGGCCCCTCCTGTGGCTCAA<br>GAGGCTCTCAAGAAAGAACTGGAAACTCTGACCACCAACTACCAGTGGCT<br>GTGCACCAGACTGAACGGCAAGTGCAAGACACTGGAAGAAGTGTGGGCCT<br>GCTGGCACGAACTGCTGTCCTATCTGGAAAAGGCCAACAAGTGGCTGAAC<br>GAGGTGGAATTCAAGCTGAAAACCACCGAGAACATCCCTGGCGGCGCTGA<br>AGAGATTAGCGAGGTGCTGGACAGCCTGGAAAACCTGATGAGACACAGCG<br>AGGACAACCCCAATCAGATCAGAATCCTGGCTCAGACCCTGACCGATGGC<br>GGCGTGATGGACGAGCTGATCAACGAGGAACTCGAAACCTTCAACAGCCG<br>GTGGCGGGAACTGCACGAGGAAGCTGTTCGGAGGCAGAAGTTGCTGGAAC<br>AGTCTATCCAGAGCGCACAAGAAACCGAGAAGTCCCTGCACCTGATCCAA<br>GAGAGCCTGACCTTCATCGACAAGCAGCTGGCCGCTTATATCGCCGACAA<br>GGTGGACGCTGCTCAGATGCCCCAAGAGGCACAGAAGATTCAGAGCGACC<br>TGACCAGCCACGAGATTAGCCTGGAAGAAATGAAGAAGCACAACCAGGGC<br>AAAGAGGCCGCTCAGAGAGTCCTGAGCCAGATCGATGTGGCACAGAAAAA<br>GCTCCAGGATGTGTCCATGAAGTTTCGGCTGTTTCAGAAGCCCGCCAACT<br>TCGAGCAGAGACTGCAAGAGTCCAAGATGATCCTGGACGAAGTCAAAATG<br>CATCTGCCCGCACTGGAAACAAAGTCCGTGGAACAAGAAGTGGTGCAGTC<br>CCAGCTGAACCACTGCGTGAACCTGTACAAGAGCCTGTCCGAAGTGAAGT<br>CTGAGGTGGAAATGGTCATCAAGACCGGCAGGCAGATCGTCCAGAAGAAG<br>CAGACCGAGAATCCCAAAGAACTCGACGAGAGAGTGACCGCTCTGAAGCT<br>GCACTACAATGAGCTGGGCGCCAAAGTGACCGAGCGGAAGCAACAGCTTG<br>AGAAGTGCCTGAAACTGTCTCGGAAGATGCGGAAAGAAATGAACGTGCTG<br>ACAGAGTGGCTGGCCGCCACCGATATGGAACTGACTAAGAGAAGCGCCGT<br>GGAAGGCATGCCCAGCAACCTGGATAGTGAAGTGGCCTGGGGCAAAGCCA<br>CTCAGAAAGAGATTGAGAAGCAGAAGGTCCACCTGAAGTCCATCACCGAA<br>GTGGGCGAAGCCCTGAAAACCGTGCTGGGAAAGAAAGAGACACTGGTCGA<br>GGACAAGCTGTCCCTGCTGAATTCCAACTGGATCGCCGTGACCTCCAGAG<br>CTGAGGAATGGCTGAATCTGCTGCTTGAGTACCAGAAACACATGGAAACG<br>TTCGACCAGAACGTCGACCACATCACAAAGTGGATCATCCAGGCTGATAC<br>CCTGCTGGACGAGTCCGAGAAGAAGAAACCCCAACAAAAAGAAGATGTGC<br>TGAAGCGGCTGAAAGCCGAGCTGAATGACATCCGGCCTAAGGTGGACAGC<br>ACCAGAGATCAGGCAGCCAACCTGATGGCCAACAGAGGCGACCACTGTCG<br>GAAGCTCGTGGAACCTCAGATCAGCGAGCTTAACCACAGATTTGCCGCCA<br>TCAGCCACCGGATCAAGACAGGCAAGGCCAGCATTCCTCTCAAAGAGCTT<br>GAGCAGTTCAACAGCGACATCCAAAAGCTGCTCGAACCCCTGGAAGCCGA<br>GATCCAACAGGGCGTCAACCTCAAAGAAGAAGATTTCAACAAGGACATGA<br>ACGAGGACAATGAGGGCACCGTCAAAGAACTGCTGCAGCGGGGCGATAAT<br>CTGCAGCAGCGGATTACCGATGAGCGCAAGCGGGAAGAGATCAAGATTAA<br>GCAGCAGCTGCTGCAGACCAAGCACAACGCCCTGAAGGACCTGCGGAGCC<br>AGAGAAGAAAGAAGGCCCTGGAAATCAGCCACCAGTGGTATCAGTACAAG<br>CGGCAGGCCGACGACCTGCTGAAGTGCCTGGATGACATCGAGAAGAAGCT<br>GGCCTCTCTGCCCGAGCCTAGGGACGAGAGAAAGATCAAAGAGATCGACC<br>GCGAGCTGCAGAAAAAGAAAGAGGAACTGAACGCCGTCCGCAGACAGGCC<br>GAAGGACTTTCTGAAGATGGCGCCGCTATGGCCGTGGAACCCACACAGAT<br>TCAGCTGAGCAAGCGGTGGCGGGAAATCGAGAGCAAGTTCGCCCAGTTCC<br>GGCGGCTGAATTTCGCCCAGATCCACACCGTGCGGGAAGAGACAATGATG<br>GTCATGACAGAGGACATGCCCCTTGAGATCAGCTACGTGCCCAGCACCTA<br>CCTGACCGAGATCACCCATGTGTCTCAGGCCCTGCTGGAAGTGGAACAGC<br>TGCTGAATGCCCCTGACCTGTGCGCCAAGGACTTCGAGGACCTGTTCAAG<br>CAAGAGGAAAGCCTGAAGAACATCAAGGACAGCCTGCAGCAGAGCAGCGG<br>CCGGATCGATATCATCCACAGCAAGAAAACCGCCGCACTGCAGAGCGCCA<br>CACCTGTGGAAAGAGTGAAGCTGCAAGAGGCCCTGAGCCAGCTGGATTTC |

-continued

| SEQ ID NO | Description | SEQ |
|---|---|---|
| | | CAGTGGGAGAAAGTGAACAAGATGTACAAGGACCGGCAGGGCAGATTCGA |
| | | CCGCAGCGTTGAAAAGTGGCGGCGGTTCCACTACGACATCAAGATCTTCA |
| | | ACCAGTGGCTGACCGAGGCCGAGCAGTTCCTGAGAAAGACACAGATCCCC |
| | | GAGAACTGGGAGCACGCCAAGTACAAGTGGTATCTGAAAGAGCTGCAGGA |
| | | CGGCATCGGCCAGAGACAGACAGTCGTGCGGACACTGAATGCCACCGGCG |
| | | AGGAAATCATCCAGCAGTCCAGCAAGACCGACGCCAGCATCCTGCAAGAG |
| | | AAGCTGGGCAGCCTGAACCTGCGGTGGCAAGAAGTGTGCAAGCAGCTGAG |
| | | CGACCGGAAGAAGCGGCTGGAAGAACAGAAGAATATCCTGAGCGAGTTCC |
| | | AGCGGGACCTGAACGAGTTCGTGCTGTGGCTCGAAGAGGCCGACAATATC |
| | | GCCAGCATTCCCCTGGAACCTGGCAAAGAGCAGCAGCTGAAAGAAAAGCT |
| | | GGAACAAGTGAAACTGCTGGTCGAGGAACTGCCCCTGAGACAGGGAATCC |
| | | TGAAACAGCTGAACGAGACAGGCGGCCCTGTGCTGGTGTCTGCCCCTATT |
| | | TCTCCCGAGGAACAGGACAAGCTGGAAAACAAGCTGAAGCAGACCAACCT |
| | | GCAGTGGATCAAGGTGTCCAGAGCACTGCCTGAGAAGCAGGGCGAGATCG |
| | | AGGCCCAGATCAAGGACCTGGGACAGCTCGAAAAGAAGCTTGAGGACCTC |
| | | GAAGAACAGCTCAACCATCTGCTGCTTTGGCTGAGCCCCATCCGGAACCA |
| | | GCTGGAAATCTACAACCAGCCTAATCAAGAGGGCCCCTTCGACGTGAAAG |
| | | AAACCGAGATTGCCGTGCAGGCCAAGCAGCCCGATGTGGAAGAGATCCTG |
| | | TCTAAGGGCCAGCACCTGTACAAAGAGAAGCCCGCCACACAGCCCGTGAA |
| | | GCGGAAACTGGAAGATCTGAGCAGCGAGTGGAAGGCCGTGAACCGGCTGC |
| | | TGCAAGAACTGAGAGCCAAACAGCCTGATCTGGCCCCTGGCCTGACAACA |
| | | ATTGGCGCCTCTCCTACACAGACCGTGACACTGGTCACACAGCCTGTGGT |
| | | CACCAAAGAGACAGCCATCAGCAAACTGGAAATGCCCAGCAGTCTGATGC |
| | | TCGAAGTGCCCGCACTGGCCGACTTCAATAGAGCCTGGACCGAGCTGACC |
| | | GACTGGCTCAGTCTGCTGGACCAAGTCATCAAGTCCCAGAGAGTGATGGT |
| | | CGGAGATCTTGAGGACATCAACGAGATGATCATTAAGCAGAAAGCCACCA |
| | | TGCAGGACCTTGAGCAGAGAAGGCCCCAGCTTGAAGAACTGATCACCGCC |
| | | GCTCAGAACCTGAAAAACAAGACCAGCAATCAAGAAGCCCGGACCATCAT |
| | | CACCGACCGGATCGAGAGAATCCAGAACCAGTGGGACGAAGTGCAAGAGC |
| | | ATCTGCAGAACAGACGGCAGCAGCTCAATGAGATGCTGAAGGACAGCACA |
| | | CAGTGGCTGGAAGCCAAAGAAGAAGCCGAGCAGGTTCTCGGACAGGCCAG |
| | | AGCTAAGCTGGAATCTTGGAAAGAGGGACCCTACACCGTCGACGCCATCC |
| | | AGAAGAAGATCACCGAGACAAAGCAGCTGGCCAAGGATCTGAGACAGTGG |
| | | CAGACCAATGTGGACGTGGCCAACGACCTGGCTCTGAAGCTGCTGAGAGA |
| | | CTACAGCGCCGACGACACCAGAAAGGTGCACATGATCACCGAAAACATCA |
| | | ACGCCTCTTGGCGGAGCATCCACAAGCGGGTGTCAGAGAGAGAAGCCGCT |
| | | CTGGAAGAAACACATAGACTGCTCCAGCAGTTCCCACTCGACCTGGAAAA |
| | | GTTCCTGGCCTGGCTGACAGAAGCCGAAACCACCGCTAACGTGCTCCAGG |
| | | ATGCCACCAGAAAAGAGCGGCTGTTGGAGGACAGCAAGGGCGTCAAAGAA |
| | | CTCATGAAGCAGTGGCAGGATCTGCAAGGGGAGATTGAAGCCCACACCGA |
| | | CGTGTACCACAACCTGGACGAGAACAGCCAGAAGATCCTGCGGTCCCTGG |
| | | AAGGCTCTGATGATGCTGTGCTGCTTCAGAGGCGGCTGGACAACATGAAC |
| | | TTCAAGTGGAGCGAGCTGCGGAAGAAGTCCCTGAACATCAGAAGCCACCT |
| | | GGAAGCCTCCAGCGACCAGTGGAAAAGACTGCACCTGTCTCTCCAAGAGC |
| | | TGCTCGTGTGGCTGCAGCTGAAGGATGACGAGCTGAGTAGACAGGCCCCT |
| | | ATCGGCGGAGATTTTCCCGCCGTGCAGAAACAGAACGACGTGCACCGGGC |
| | | CTTCAAGAGAGAGCTGAAAACAAAAGAACCCGTCATCATGAGCACCCTGG |
| | | AAACCGTGCGGATCTTTCTGACCGAGCAGCCTCTGGAAGGACTGGAAAAG |
| | | CTGTACCAAGAGCCTAGAGAGCTGCCTCCTGAAGAAAGGGCCCAGAACGT |
| | | GACACGGCTGCTTAGAAAGCAGGCCGAGGAAGTGAACACCGAATGGGAGA |
| | | AGCTGAACCTCCACTCCGCCGACTGGCAGCGGAAGATCGATGAGACACTG |
| | | GAACGGCTGCGGGAACTGCAAGAAGCCACAGACGAGCTGGACCTGAAACT |
| | | GCGGCAGGCTGAAGTGATCAAAGGCTCCTGGCAGCCAGTGGGCGATCTGC |
| | | TGATCGATAGCCTGCAGGACCATCTGGAAAAAGTCAAGGCCCTGCGGGGA |
| | | GAGATCGCCCCTCTCAAAGAAAACGTGTCCCACGTGAACGATCTGGCCAG |
| | | GCAGCTGACAACACTGGGCATCCAGCTGAGCCCTTACAACCTGTCTACCT |
| | | TGGAGGACCTGAATACCCGGTGGAAGCTGCTCCAAGTGGCCGTCGAGGAT |
| | | AGAGTGCGGCAGCTGCATGAGGCTCACAGAGATTTTGGACCCGCCAGCCA |
| | | GCACTTCCTGAGCACATCTGTTCAAGGCCCCTGGGAGAGAGCTATCAGCC |
| | | CTAACAAGGTGCCCTACTACATCAACCACGAGACACAGACCACCTGTTGG |
| | | GATCACCCCAAGATGACCGAACTGTATCAGTCCCTGGCCGACCTGAACAA |
| | | CGTGCGGTTTAGCGCCTACCGGACCGCCATGAAGCTGCGCAGACTGCAGA |
| | | AAGCTCTGTGCCTGGACCTGCTGTCTCTGAGCGCTGCTTGTGATGCCCTG |
| | | GACCAGCATAACCTCAAGCAGAACGACCAGCCTATGGACATCCTGCAGAT |
| | | CATCAACTGCCTGACCACCATCTACGACCGGCTCGAACAAGAGCACAACA |
| | | ACCTGGTCAACGTGCCCCTGTGCGTGGACATGTGCCTGAATTGGCTGCTG |
| | | AACGTGTACGACACCGGCAGAACCGGCAGGATCAGAGTGCTGAGCTTCAA |
| | | GACCGGCATCATCTCCCTGTGCAAGGCCCACCTTGAGGATAAGTACCGCT |
| | | ACCTGTTTAAGCAGGTCGCCAGCAGCACCGGCTTTTGCGACCAAAGAAGG |
| | | CTGGGACTGCTGCTCCACGACAGCATTCAGATCCCTAGACAGCTGGGCGA |
| | | AGTGGCCTCTTTCGGCGGCTCTAATATCGAGCCTAGCGTGCGGAGCTGCT |
| | | TCCAGTTCGCCAACAACAAGCCCGAGATTGAGGCCGCACTGTTCCTGGAC |
| | | TGGATGAGACTGGAACCCCAGAGCATGGTCTGGCTGCCTGTGCTGCATAG |
| | | AGTGGCCGCAGCCGAAACAGCCAAGCACCAGGCCAAGTGCAACATCTGCA |
| | | AAGAGTGCCCCATCATCGGCTTCCGGTACAGATCCCTGAAGCACTTCAAC |

-continued

| SEQ ID NO | Description | SEQ |
|---|---|---|
| | | TACGATATCTGCCAGTCCTGCTTCTTCAGCGGCAGAGTGGCCAAGGGCCA CAAGATGCACTACCCCATGGTGGAATACTGCACCCCTACCACCTCTGGCG AGGACGTGCGGGATTTTGCCAAGGTGCTCAAGAACAAGTTCCGGACCAAG CGCTACTTCGCTAAGCACCCCAGAATGGGCTACCTGCCAGTGCAGACAGT GCTTGAGGGCGACAACATGGAAACCCCTGTGACTCTGATCAACTTCTGGC CCGTGGATAGCGCCCCTGCTAGTTCTCCTCAGCTGTCTCACGACGATACC CACAGCAGAATCGAGCACTACGCCTCCAGACTGGCCGAGATGGAAAACAG CAACGGCAGCTACCTGAATGACAGCATCAGCCCCAACGAGAGCATCGACG ACGAACATCTGCTCATTCAGCACTACTGCCAGAGCCTGAATCAGGACAGC CCTCTGTCTCAGCCTAGAAGCCCTGCACAGATCCTGATCAGCCTGGAAAG CGAGGAACGCGGCGAGCTGGAAAGAATCCTGGCAGACCTGGAAGAGGAAA ACCGGAACCTGCAGGCCGAATACGACAGACTCAAGCAGCAGCACGAGCAC AAGGGACTGTCTCCACTGCCTTCTCCACCTGAAATGATGCCCACCTCTCC ACAGAGCCCCAGAGATGCCGAGCTGATTGCCGAAGCCAAACTGCTGAGGC AGCACAAAGGCAGACTCGAAGCCAGAATGCAGATTCTCGAAGATCACAAC AAGCAGCTCGAATCCCAGCTGCACAGACTTAGGCAGCTGCTGGAACAGCC TCAGGCAGAGGCCAAAGTGAATGGCACCACCGTGTCTAGCCCTAGCACAA GCCTGCAGAGATCCGACAGCAGCCAGCCAATGCTTCTGAGAGTCGTGGGC TCCCAGACCAGCGATTCTATGGGCGAAGAGGACCTGCTCAGCCCTCCTCA GGATACAAGCACCGGCCTGGAAGAAGTGATGGAACAACTGAACAACAGCT TCCCCAGCAGCAGAGGCAGAAACACCCCTGGCAAGCCCATGCGCGAGGAC ACCATGTGATAACTCGAGAATCAACCTCTGGATTACAAAATTTGTGAAAG ATTGACTGGTATTCTTAACTATGTTGCTCCTTTTACGCTATGTGGATACG CTGCTTTAATGCCTTTGTATCATGCTATTGCTTCCCGTATGGCTTTCATT TTCTCCTCCTTGTATAAATCCTGGTTGCTGTCTCTTTATGAGGAGTTGTG GCCCGTTGTCAGGCAACGTGGCGTGGTGTGCACTGTGTTTGCTGACGCAA CCCCCACTGGTTGGGGCATTGCCACCACCTGTCAGCTCCTTTCCGGGACT TTCGCTTTCCCCCTCCCTATTGCCACGGCGGAACTCATCGCCGCCTGCCT TGCCCGCTGCTGGACAGGGGCTCGGCTGTTGGGCACTGACAATTCCGTGG GGTGTGCCTTCTAGTTGCCAGCCATCTGTTGTTTGCCCCTCCCCCGTGCC TTCCTTGACCCTGGAAGGTGCCACTCCCACTGTCCTTTCCTAATAAAATG AGGAAATTGCATCGCATTGTCTGAGTAGGTGTCATTCTATTCTGGGGGGT GGGGTGGGGCAGGACAGCAAGGGGGAGGATTGGGAAGACAATAGCAGGCA TGCTGGGGATGCGGTGGGCTCTATGGGAAGATGTCTACTGAGCTGTGCGA TCCCTGCTGGGGACTTTCCGCTGGGGACTTTCCGCTGGGGACTTTCCGCC TTCAGCTAAGGAAGCTACCAATATTTAGAGGTACATTTTGTTCTAGAACA AAATGTACCGGTACATTTTGTTCTGGTACATTTTGTTCT |
| 28. | MHCK7-hBGi-DMD-5-WPRE3-DTS | CTAGAAGCTGCATGTCTAAGCTAGACCCTTCAGATTAAAAATAACTGAGG TAAGGGCCTGGGTAGGGGAGGTGGTGTGAGACGCTCCTGTCTCTCCTCTA TCTGCCCATCGGCCCTTTGGGGAGGAGGAATGTGCCCAAGGACTAAAAAA AGGCCATGGAGCCAGAGGGGCGAGGGCAACAGACCTTTCATGGGCAAACC TTGGGGCCCTGCTGTCTAGCATGCCCCACTACGGGTCTAGGCTGCCCATG TAAGGAGGCAAGGCCTGGGGACACCCGAGATGCCTGGTTATAATTAACCC AGACATGTGGCTGCCCCCCCCCCCCCAACACCTGCTGCCTCTAAAAATAA CCCTGTCCCTGGTGGATCCCCTGCATGCGAAGATCTTCGAACAAGGCTGT GGGGGACTGAGGGCAGGCTGTAACAGGCTTGGGGGCCAGGGCTTATACGT GCCTGGGACTCCCAAAGTATTACTGTTCCATGTTCCCGGCGAAGGGCCAG CTGTCCCCCGCCAGCTAGACTCAGCACTTAGTTTAGGAACCAGTGAGCAA GTCAGCCCTTGGGGCAGCCCATACAAGGCCATGGGGCTGGGCAAGCTGCA CGCCTGGGTCCGGGGTGGGCACGGTGCCCGGGCAACGAGCTGAAAGCTCA TCTGCTCTCAGGGGCCCCTCCCTGGGGACAGCCCCTCCTGGCTAGTCACA CCCTGTAGGCTCCTCTATATAACCCAGGGGCACAGGGGCTGCCCTCATTC TACCACCACCTCCACAGCACTCTGGATCCACTGCTTAAATACGGACGAGG ACAGGGCCCTGTCTCCTCAGCTTCAGGCACCACCACTGACCTGGGACAGT GAATCGTAAGTACTAGCAGCTACAATCCAGCTACCATTCTGCTTTTATTT TATGGTTGGGATAAGGCTGGATTATTCTGAGTCCAAGCTAGGCCCTTTTG CTAATCATGTTCATACCTCTTATCTTCCTCCCACAGCTCCTGGGCAACGT GCTGGTCTGTGTGCTGGCCCATCACTTTGGCAAAGAATTGCGATCGCCAC CATGCTGTGGTGGGAGGAAGTTGAAGATTGTTATGAGAGAGAAGATGTCC AGAAAAAGACCTTTACCAAATGGGTGAACGCACAGTTCTCCAAATTTGGG AAACAGCATATAGAAAATTTGTTCAGCGATCTTCAGGATGGGCGCAGGTT GCTTGACCTTCTGGAAGGACTGACCGGGCAGAAGCTGCCCAAAGAGAAAG GGTCTACCAGAGTTCACGCTCTGAACAACGTGAATAAGGCACTGCGAGTC CTGCAAAATAACAACGTCGACCTGGTGAACATAGGCAGCACTGATATTGT TGATGGGAACCATAAACTCACACTGGGTCTGATTTGGAATATTATACTGC ACTGGCAGGTCAAAAATGTTATGAAAAATATTATGGCCGGGCTTCAACAG ACCAATTCCGAGAAGATCCTGCTGTCTTGGGTTAGGCAGTCCACGAGGAA CTACCCTCAAGTGAACGTTATTAACTTCACAACATCATGGAGTGATGGAC TTGCCCTGAACGCCTTGATCCACTCCCATAGGCCAGACCTGTTCGATTGG AATAGCGTAGTCTGTCAGCAGAGTGCTACACAACGCCTGGAACACGCCTT TAACATAGCCAGGTATCAGCTTGGAATTGAGAAACTCCTCGACCCTGAAG ACGTAGACACCACTTACCCCGACAAAAAATCCATTCTTATGTACATAACT TCCTTGTTTCAGGTTCTCCCCCAGCAGGTGTCCATCGAGGCTATACAGGA GGTCGAAATGCTCCCCAGACCCCCTAAGGTCACGAAGGAAGAGCACTTCC |

-continued

| SEQ ID NO | Description | SEQ |
|---|---|---|
| | | AACTGCACCATCAGATGCACTACAGTCAACAGATCACTGTGAGTCTCGCA<br>CAGGGGTACGAAAGGACCAGCTCCCCTAAACCCCGCTTCAAGTCCTACGC<br>CTATACTCAGGCAGCTTACGTAACCACAAGTGACCCCACGCGGTCACCCT<br>TCCCAAGCCAGCACCTGGAGGCTCCCGAGGACAAAAGCTTTGGATCATCC<br>CTGATGGAATCTGAAGTCAATCTCGATAGGTACCAAACCGCTCTGGAGGA<br>GGTCCTCAGTTGGCTCCTTTCAGCTGAAGATACTCTGCAGGCACAGGGTG<br>AGATCAGCAATGACGTGGAGGTAGTGAAAGATCAGTTTCACACTCACGAG<br>GGCTATATGATGGACCTGACAGCCCATCAAGGTCGCGTTGGCAATATCCT<br>GCAGTTGGGGTCCAAACTGATTGGTACCGGTAAGTTGTCCGAGGACGAAG<br>AGACAGAAGTGCAGGAGCAGATGAACCTGCTTAATTCTAGATGGGAATGC<br>CTCCGCGTGGCCTCTATGGAGAAGCAGTCCAATCTCCATCGGGTTCTCAT<br>GGACTTGCAGAATCAGAAGCTGAAGGAACTCAACGACTGGTTGACCAAGA<br>CTGAGGAGCGCACCAGAAAGATGGAGGAGGAGCCACTCGGTCCTGATCTT<br>GAAGATCTGAAACGACAAGTTCAGCAGCACAAGGTCCTGCAGGAGGATCT<br>CGAACAGGAGCAGGTCCGGGTGAACAGCCTGACCCATATGGTTGTCGTTG<br>TCGACGAGTCAAGTGGGGACCATGCTACGGCTGCGCTTGAGGAACAGCTG<br>AAGGTCTTGGGCGATAGATGGGCGAATATCTGCCGCTGGACTGAAGATAG<br>ATGGGTGCTGCTGCAGGATATTCTTTTGAAGTGGCAGCGGTTGACCGAAG<br>AACAATGCTTGTTTAGCGCCTGGCTGAGTGAGAAAGAGGATGCGGTGAAT<br>AAGATACACACTACTGGCTTCAAAGACCAGAATGAAATGCTTAGCAGCCT<br>GCAGAAACTTGCGGTTCTTAAGGCCGACTTGGAAAAGAAAAAGCAGTCAA<br>TGGGTAAGCTGTACTCACTCAAGCAGGACCTGCTGTCAACTTTGAAGAAC<br>AAGAGCGTCACGCAAAAGACTGAGGCCTGGCTCGACAATTTTGCTAGGTG<br>CTGGGATAACCTGGTGCAGAAGTTGGAAAAGTCCACTGCTCAGATCTCTC<br>AAGCCGTGACTACTACCCAGCCCAGCCTGACACAGACTACCGTCATGGAA<br>ACCGTTACCACTGTGACGACTAGGGAGCAGATACTCGTTAAGCACGCTCA<br>AGAGGAATTGCCGCCACCTCCTCCCCAAAAGAAACGCCAGATTACCGTCG<br>ACTCTGAAATACGCAAGAGACTGGATGTGGACATCACGGAACTGCACTCT<br>TGGATTACCAGAAGCGAGGCAGTCCTCCAGAGCCCCGAGTTTGCGATCTT<br>CAGGAAGGAAGGCAACTTTTCAGATCTGAAGGAAAAGGTGAACGCCATCG<br>AGCGCGAGAAAGCCGAGAAGTTCCGCAAACTGCAGGATGCGAGCCGGTCT<br>GCTCAGGCCTTGGTGGAGCAAATGGTGAATGAAGGCGTAAATGCGGACAG<br>CATCAAGCAGGCCTCCGAGCAGCTCAATTCAAGATGGATCGAGTTCTGTC<br>AGCTGCTCAGCGAGCGATTGAACTGGCTGGAGTATCAAAATAACATAATC<br>GCGTTTTACAACCAGCTGCAACAGCTGGAACAGATGACGACTACTGCAGA<br>GAACTGGCTTAAAATCCAGCCTACAACTCCTTCTGAACCCACAGCAATCA<br>AAAGCCAGCTCAAGATCTGCAAGGACGAAGTCAACCGCCTCTCCGATTTG<br>CAGCCTCAGATAGAACGACTCAAGATCCAAAGTATCGCACTCAAAGAAAA<br>GGGGCAAGGCCCTATGTTTCTCGATGCTGATTTTGTGGCTTTCACCAACC<br>ATTTTAAGCAAGTGTTTTCAGATGTGCAAGCCCGGGAAAAGGAACTGCAA<br>ACCATTTTTGATACCCTGCCTCCAATGCGGTACCAGGAGACTATGTCTGC<br>AATTCGCACCTGGGTGCAACAAAGCGAGACGAAACTTTCTATTCCACAAC<br>TGTCCGTGACAGACTACGAAATTATGGAACAGCGACTGGGAGAACTCCAA<br>GCCCTTCAGTCCAGCCTTCAGGAGCAGCAGTCAGGATTGTACTATCTGTC<br>AACCACCGTGAAGGAAATGTCAAAAAAGGCTCCCTCCGAAATATCTCGCA<br>AGTATCAGTCTGAGTTTGAAGAGATTGAAGGGAGATGGAAGAAACTGTCC<br>TCACAGCTGGTTGAGCACTGTCAGAAGTTGGAAGAGCAGATGAACAAGTT<br>GCGCAAGATTCAAAATCACATACAGACACTCAAAAAGTGGATGGCGGAGG<br>TTGACGTCTTCCTTAAAGAGGAGTGGCCAGCCCTGGGCGACTCAGAGATC<br>CTGAAAAAGCAACTGAAACAGTGCCGACTGCTGGTGTCCGACATCCAGAC<br>AATACAGCCAAGTTTGAATAGCGTGAATGAGGGTGGACAAAAAATCAAAA<br>ACGAGGCTGAGCCCGAGTTCGCCTCCAGATTGGAAACCGAGCTGAAGGAA<br>CTTAATACACAGTGGGATCATATGTGTCAGCAGGTTTATGCCCGGAAGGA<br>AGCACTGAAAGGGGGGCTGGAGAAAACCGTGAGCCTTCAGAAGGACCTTA<br>GCGAGATGCACGAGTGGATGACCCAGGCGGAGGAAGAGTATCTCGAACGG<br>GATTTTGAGTATAAGACACCAGATGAACTTCAGAAGGCAGTCGAAGAGAT<br>GAAACGGGCAAAGGAAGAGGCTCAGCAGAAGGAAGCAAAGGTTAAACTTC<br>TGACAGAATCCGTTAACAGCGTTATAGCCCAAGCTCCCCCCGTTGCCCAG<br>GAAGCTCTTAAAAAGGAACTGGAAACACTGACAACAAACTACCAGTGGCT<br>GTGCACCCGCTTGAACGGCAAATGCAAAACCCTGGAAGAGGTCTGGGCTT<br>GTTGGCATGAACTCCTGTCATACCTGGAAAAAGCTAATAAGTGGCTGAAT<br>GAGGTGGAGTTTAAATTGAAAACGACCGAAAACATCCCTGGCGGTGCAGA<br>GGAGATATCTGAGGTGCTCGATAGCCTGGAGAATCTTATGAGGCATAGCG<br>AGGATAACCCCAACCAGATTAGGATACTGGCCCAAACTCTGACCGACGGC<br>GGAGTGATGGACGAGCTGATAAACGAGGAACTGGAAACCTTTAATTCACG<br>CTGGCGAGAACTTCACGAGGAGGCAGTCAGGCGCCAGAAACTGCTGGAGC<br>AGTCCATCCAGAGTGCCCAGGAGACTGAGAAGTCACTTCATCTGATCCAG<br>GAGAGTTTGACGTTTATCGACAAGCAGCTTGCCGCCTACATTGCAGACAA<br>GGTCGATGCTGCTCAGATGCCGCAAGAGGCTCAGAAAATCCAGAGCGACC<br>TGACAAGCCACGAGATTAGCCTGGAGGAAATGAAAAAGCACAACCAGGGT<br>AAAGAGGCCGCCCAGCGGGTTCTGAGCCAGATCGATGTCGCACAGAAGAA<br>ACTCCAAGATGTAAGCATGAAGTTCCGACTGTTTCAGAAACCAGCGAACT<br>TTGAGCAGCGACTGCAGGAGTCTAAAATGATCCTCGATGAGGTGAAAATG<br>CATCTGCCAGCCCTGGAAACTAAGAGCGTGGAGCAGGAGGTGGTTCAGAG<br>TCAGCTGAACCACTGCGTAAACCTCTATAAAAGTCTTAGTGAAGTGAAGA |

-continued

| SEQ ID NO | Description | SEQ |
|---|---|---|
| | | GCGAGGTGGAGATGGTGATTAAGACTGGTAGACAGATTGTACAGAAAAAG<br>CAGACGGAGAACCCCAAAGAGTTGGATGAACGGGTGACAGCCCTTAAGCT<br>CCACTATAACGAGCTGGGAGCCAAAGTGACTGAGAGAAAGCAGCAACTTG<br>AAAAATGTCTGAAGCTGAGCAGAAAGATGCGGAAGGAAATGAATGTGCTG<br>ACAGAGTGGCTGGCTGCGACCGACATGGAACTTACAAAGAGGAGCGCCGT<br>GGAAGGCATGCCTTCCAATCTGGATAGTGAGGTCGCTTGGGGCAAAGCTA<br>CACAGAAGGAAATTGAGAAGCAAAAAGTGCATCTTAAGAGCATTACTGAA<br>GTTGGCGAGGCTTTGAAAACCGTCCTCGGCAAGAAAGAGACTCTGGTAGA<br>AGATAAACTCTCACTGCTGAACTCAAACTGGATCGCAGTCACTAGTCGGG<br>CCGAAGAGTGGCTGAATTTGCTGTTGGAGTACCAAAAGCATATGGAGACT<br>TTCGATCAGAATGTCGACCACATTACGAAGTGGATAATCCAGGCGGACAC<br>ACTGTTGGATGAGTCCGAGAAAAAGAAACCTCAGCAGAAGGAAGACGTGC<br>TCAAACGACTCAAAGCCGAACTGAACGACATCAGGCCCAAAGTTGATTCC<br>ACCCGGGATCAAGCGGCCAATCTCATGGCCAACCGGGGGGATCACTGCAG<br>AAAGTTGGTAGAACCTCAGATAAGCGAACTTAATCATAGATTTGCCGCCA<br>TATCACATAGGATTAAGACCGGTAAGGCTTCAATCCCCCTGAAGGAACTC<br>GAACAGTTTAATAGTGACATCCAGAAGCTCCTGGAGCCTCTCGAAGCCGA<br>GATTCAACAGGGTGTAAACCTTAAGGAAGAGGATTTTAATAAGGATATGA<br>ATGAGGACAATGAAGGCACGGTCAAAGAGCTCCTCCAGAGGGGAGACAAT<br>TTGCAGCAGCGGATCACCGATGAACGCAAACGCGAAGAGATCAAAATTAA<br>GCAGCAGCTCCTCCAAACAAAGCACAATGCCCTTAAAGACCTCAGAAGCC<br>AGCGGCGGAAAAAGGCTCTGGAAATCAGCCATCAATGGTATCAGTACAAG<br>CGGCAAGCGGACGATCTCCTGAAATGTCTGGATGATATCGAGAAAAAACT<br>GGCCAGTCTGCCAGAGCCCAGAGATGAGCGCAAAATCAAGGAAATCGACA<br>GGGAGCTTCAGAAGAAAAAAGAGGAGCTGAACGCCGTCCGAAGGCAGGCC<br>GAAGGGCTGTCAGAAGATGGGGCCGCCATGGCAGTGGAACCTACCCAGAT<br>TCAACTGTCCAAGCGCTGGAGAGAGATTGAAAGTAAGTTCGCACAATTCC<br>GGAGGCTTAATTTTGCTCAGATTCACACAGTTAGGGAGGAAACCATGATG<br>GTGATGACCGAAGACATGCCACTCGAAATCAGCTACGTCCCTAGCACATA<br>TCTCACGGAGATTACCCACGTGTCCCAGGCACTGCTGGAAGTCGAGCAAT<br>TGTTGAACGCCCCTGATCTCTGCGCCAAGGATTTCGAAGACTTGTTCAAG<br>CAAGAGGAAAGCCTCAAGAACATCAAAGACAGTCTTCAGCAGTCCTCAGG<br>CAGAATTGATATTATCCACTCCAAGAAAACAGCCGCTCTCCAGAGCGCTA<br>CCCCTGTCGAACGAGTGAAACTGCAAGAGGCCTTGTCTCAGTTGGACTTC<br>CAGTGGGAGAAAGTCAACAAGATGTACAAGGACAGGCAGGGTCGGTTCGA<br>CCGGAGCGTCGAAAAATGGCGGAGATTCCATTATGACATCAAGATATTCA<br>ATCAGTGGCTTACAGAGGCGGAGCAATTTTTGAGAAAGACGCAGATTCCC<br>GAAAACTGGGAGCATGCCAAGTACAAGTGGTACCTCAAAGAGCTCCAGGA<br>TGGAATCGGCCAGAGACAGACCGTAGTTAGAACACTGAACGCAACTGGAG<br>AAGAGATTATCCAGCAGTCCTCCAAAACTGACGCCTCTATCCTCCAGGAG<br>AAGCTTGGCAGCCTTAACCTGCGGTGGCAGGAGGTGTGTAAACAACTGTC<br>AGATAGGAAAAAAAGACTTGAGGAACAGAAGAACATTCTGAGCGAGTTCC<br>AACGAGATCTCAACGAGTTCGTACTGTGGCTGGAGGAGGCCGACAACATC<br>GCTTCAATCCCCCTGGAACCCGGCAAGGAACAGCAGCTTAAGGAAAAATT<br>GGAACAGGTAAAACTGTTGGTAGAGGAGCTCCCATTGCGGCAGGGCATTC<br>TCAAGCAGCTGAATGAAACTGGAGGTCCCGTTCTGGTCAGTGCGCCCATA<br>AGCCCGGAAGAGCAGGACAAGTTGGAAAACAAGCTGAAGCAAACAAATCT<br>GCAGTGGATCAAAGTGAGCCGGGCTCTTCCAGAAAAGCAAGGCGAGATTG<br>AAGCCCAGATTAAGGATCTTGGCCAGCTTGAGAAAAAGCTGGAGGATCTG<br>GAAGAGCAGCTGAACCATTTGCTTCTGTGGCTGAGTCCCATTAGAAACCA<br>GCTGGAAATCTACAACCAGCCAAACCAAGAGGGCCCCTTTCGACGTCAAGG<br>AAACTGAGATAGCAGTCCAGGCAAAACAGCCCGATGTCGAAGAAATCTTG<br>TCTAAGGGGCAGCACCTCTACAAAGAGAAACCTGCCACCCAGCCCGTGAA<br>GAGAAAACTGGAAGACCTCTCTTCAGAGTGGAAGGCTGTAAACAGGTTGC<br>TCCAGGAGCTGAGAGCTAAGCAACCTGACCTCGCACCCGGCCTGACTACT<br>ATTGGCGCCAGCCCGACCCAAACCGTCACACTGGTGACCCAGCCTGTAGT<br>CACAAAAGAAACCGCCATCTCCAAACTGGAGATGCCTTCAAGCCTGATGC<br>TGGAGGTGCCTGCTCTGGCCGATTTCAACAGAGCCTGGACAGAGCTGACA<br>GACTGGCTGTCTCTGCTCGACCAAGTGATAAAGTCACAGCGCGTCATGGT<br>GGGTGACCTGGAGGACATCAATGAGATGATCATAAAGCAAAAGGCTACCA<br>TGCAGGACTTGGAGCAGCGCAGGCCGCAGTTGGAAGAACTGATTACAGCA<br>GCCCAGAACCTCAAGAACAAGACTTCAAATCAGGAGGCAAGGACCATCAT<br>AACAGATAGAATCGAGAGGATTCAGAACCAATGGGATGAGGTGCAGGAGC<br>ACCTGCAGAACAGAAGGCAGCAGCTGAACGAAATGCTGAAAGACTCCACA<br>CAGTGGCTGGAGGCCAAAGAGGAGGCAGAACAGGTGCTGGGCCAGGCTAG<br>GGCCAAGCTGGAAAGTTGGAAGGAAGGGCCCTACACCGTGGACGCCATAC<br>AGAAGAAAATAACGGAGACAAAACAGCTGGCCAAAGACCTCCGCCAATGG<br>CAGACCAACGTAGACGTCGCCAATGACCTGGCACTCAAGTTGTTGAGAGA<br>TTATTCCGCAGATGACACCCGAAAAGTACACATGATCACTGAGAATATCA<br>ACGCCAGTTGGCGGAGCATTCACAAACGGGTGAGCGAGAGAGAAGCCGCC<br>CTTGAGGAGACGCATCGCCTTTTGCAGCAATTTCCGCTTGACCTGGAAAA<br>GTTTCTGGCTTGGTTGACAGAGGCCGAGACAACTGCTAACGTGCTGCAAG<br>ATGCCACCCGCAAAGAGCGGCTTCTTGAGGACTCTAAAGGGGTGAAAGAA<br>TTGATGAAGCAGTGGCAGGACCTCCAGGGCGAAATCGAGGCCCATACTGA<br>TGTCTACCACAACCTGGATGAAAATAGTCAGAAAATCCTGAGATCCCTGG |

-continued

| SEQ ID NO | Description | SEQ |
|---|---|---|
| | | AAGGGAGTGATGATGCGGTGCTGCTGCAGCGCCGACTCGATAACATGAAC TTTAAGTGGTCTGAACTCCGGAAAAAAAGCCTGAACATTCGGAGCCATCT GGAGGCTTCTTCTGATCAGTGGAAGAGACTTCATCTGTCCTTGCAGGAGC TTCTGGTGTGGCTGCAGCTGAAAGACGACGAGCTGTCAAGGCAGGCACCA ATAGGGGGCGACTTCCCCGCTGTTCAGAAACAAAATGATGTGCACAGGGC ATTCAAGCGGGAACTGAAGACGAAAGAACCAGTGATTATGAGCACTCTGG AGACGGTACGCATCTTTCTGACCGAGCAGCCACTTGAAGGCCTCGAAAAG TTGTACCAGGAGCCACGGGAATTGCCTCCCGAAGAACGGGCTCAGAATGT TACCCGACTGCTTCGCAAGCAGGCTGAGGAAGTGAACACTGAGTGGGAAA AACTGAATCTGCACAGTGCCGATTGGCAGCGCAAAATTGACGAGACATTG GAGCGCTTGCGGGAGCTGCAGGAAGCCACAGATGAACTTGATCTGAAACT CAGACAGGCCGAGGTCATAAAGGGTTCTTGGCAACCCGTAGGCGACCTTT TGATTGACTCACTGCAGGATCATCTGGAGAAAGTAAAGGCGCTGCGGGGG GAAATTGCTCCGCTGAAGGAAAACGTGAGCCATGTGAATGATCTGGCTCG GCAATTGACTACCCTGGGTATCCAGCTGTCCCCCTACAATCTGAGCACTC TCGAAGACCTCAACACAAGATGGAAACTGCTGCAGGTCGCCGTGGAGGAC AGGGTGAGGCAGCTGCATGAGGCACACAGGGACTTCGGTCCGGCAAGCCA ACACTTCCTGTCTACTTCTGTTCAAGGGCCTTGGGAACGCGCTATTTCCC CAAACAAAGTGCCGTACTATATTAACCATGAAACTCAGACAACCTGCTGG GATCATCCTAAAATGACTGAGCTGTACCAGAGCCTCGCCGATCTGAATAA CGTGAGGTTTAGCGCATACAGAACCGCAATGAAGCTCAGGAGACTGCAGA AGGCACTTTGCCTGGACCTCCTGAGCCTCTCCGCTGCCTGCGATGCCCTC GACCAGCACAACCTGAAGCAGAATGATCAGCCTATGGACATCCTGCAAAT CATAAATTGTCTGACGACAATCTACGACCGGCTCGAACAGGAGCACAATA ATCTCGTGAACGTTCCACTTTGTGTGGATATGTGTCTCAACTGGCTGTTG AACGTCTATGACACCGGGAGAACTGGAAGGATCCGCGTTCTGTCCTTTAA GACTGGAATCATCAGCTTGTGTAAGGCGCACCTTGAGGACAAATATCGAT ACCTGTTTAAGCAGGTTGCAAGCTCCACTGGATTCTGCGACCAGAGGCGC CTCGGGCTGCTGCTTCATGATAGTATCCAAATCCCACGCCAACTCGGAGA GGTGGCAAGCTTCGGCGGGAGCAATATTGAGCCAAGCGTCAGATCTTGTT TCCAGTTTGCCAACAATAAGCCTGAGATCGAAGCCGCACTGTTTTTGGAT TGGATGCGGTTGGAGCCCCAGAGTATGGTGTGGTTGCCCGTGCTGCATAG GGTCGCTGCCGCTGAAACCGCCAAACACCAGGCCAAGTGCAATATTTGCA AGGAATGTCCCATCATCGGGTTTAGATACCGGAGCCTGAAGCACTTCAAT TATGATATCTGCCAGTCTTGTTTTTTTTCCGGCCGAGTTGCTAAGGGACA CAAGATGCATTACCCAATGGTGGAATATTGTACGCCAACCACCAGCGGCG AAGATGTCAGAGATTTTGCAAAAGTACTCAAGAACAAGTTCCGCACCAAG CGATATTTCGCGAAGCACCCCCGGATGGGCTACCTCCCAGTGCAGACGGT TCTGGAAGGCGATAACATGGAAACTCCAGTCACCCTGATCAATTTCTGGC CTGTGGACTCTGCGCCTGCCTCTTCACCTCAGCTCTCCCACGATGACACC CATTCCAGAATCGAGCACTACGCGTCTCGACTGGCGGAGATGGAGAACAG CAATGGTTCTTACCTCAATGACAGCATTAGCCCCAACGAAAGCATCGATG ACGAGCACCTCTTGATTCAACACTACTGCCAGTCCCTGAATCAGGACAGT CCTCTGTCCCAACCCAGGAGCCCAGCCCAGATACTGATCTCTCTCGAATC AGAAGAAAGAGGGGAGTTGGAGCGAATTTTGGCCGACCTGGAGGAGGAGA ATAGAAATCTTCAGGCCGAGTACGATAGACTGAAGCAGCAGCACGAGCAC AAGGGCCTTTCTCCACTGCCCTCTCCACCGGAAATGATGCCAACCTCCCC TCAAAGTCCCAGGGACGCTGAGCTCATTGCCGAGGCAAAGCTGTTGCGCC AGCACAAAGGACGCCTGGAGGCGAGAATGCAGATCCTGGAAGACCATAAC AAGCAGCTTGAGTCTCAGCTGCACCGACTTAGACAGCTGTTGGAGCAGCC ACAAGCGGAAGCAAAGGTCAATGGAACTACCGTGAGTTCCCCCAGTACAA GTCTGCAGCGCTCTGACTCAAGCCAGCCAATGCTGCTCCGGGTAGTCGGT TCTCAGACTAGTGATTCAATGGGGGAGGAGGATCTTCTTTCCCCACCCCA AGACACCTCAACAGGGCTTGAGGAAGTGATGGAGCAGCTGAACAACTCCT TCCCCTCTTCACGGGGGAGAAATACTCCTGGGAAGCCTATGAGAGAGGAT ACCATGTAATGACTCGAGAATCAACCTCTGGATTACAAAATTTGTGAAAG ATTGACTGGTATTCTTAACTATGTTGCTCCTTTTACGCTATGTGGATACG CTGCTTTAATGCCTTTGTATCATGCTATTGCTTCCCGTATGGCTTTCATT TTCTCCTCCTTGTATAAATCCTGGTTGCTGTCTCTTTATGAGGAGTTGTG GCCCGTTGTCAGGCAACGTGGCGTGGTGTGCACTGTGTTTGCTGACGCAA CCCCCACTGGTTGGGGCATTGCCACCACCTGTCAGCTCCTTTCCGGGACT TTCGCTTTCCCCCTCCCTATTGCCACGGCGGAACTCATCGCCGCCTGCCT TGCCCGCTGCTGGACAGGGGCTCGGCTGTTGGGCACTGACAATTCCGTGG GGTGTGCCTTCTAGTTGCCAGCCATCTGTTGTTTGCCCCTCCCCCGTGCC TTCCTTGACCCTGGAAGGTGCCACTCCCACTGTCCTTTCCTAATAAAATG AGGAAATTGCATCGCATTGTCTGAGTAGGTGTCATTCTATTCTGGGGGGT GGGGTGGGGCAGGACAGCAAGGGGGAGGATTGGGAAGACAATAGCAGGCA TGCTGGGGATGCGGTGGGCTCTATGGGAAGATGTCTACTGAGCTGTGCGA TCCCTGCTGGGGACTTTCCGCTGGGGACTTTCCGCTGGGGACTTTCCGCC TTCAGCTAAGGAAGCTACCAATATTTAGAGGTACATTTTGTTCTAGAACA AAATGTACCGGTACATTTTGTTCTGGTACATTTTGTTCT |
| 29. | Fluc-DTS NP-CBA- | TGCATGCGGCCGCCGTTACATAACTTACGGTAAATGGCCCGCCTGGCTGA CCGCCCAACGACCCCCGCCCATTGACGTCAATAATGACGTATGTTCCCAT AGTAACGCCAATAGGGACTTTCCATTGACGTCAATGGGTGGAGTATTTAC |

-continued

| SEQ ID NO | Description | SEQ |
|---|---|---|
| | hBGi-<br>EGFP-P2A-<br>WPRE3- | GGTAAACTGCCCACTTGGCAGTACATCAAGTGTATCATATGCCAAGTACG<br>CCCCCTATTGACGTCAATGACGGTAAATGGCCCGCCTGGCATTATGCCCA<br>GTACATGACCTTATGGGACTTTCCTACTTGGCAGTACATCTACGTATTAG<br>TCATCGCTATTACCATGGTCGAGGTGAGCCCCACGTTCTGCTTCACTCTC<br>CCCATCTCCCCCCCCTCCCCACCCCCAATTTTGTATTTATTTATTTTTTA<br>ATTATTTTGTGCAGCGATGGGGGCGGGGGGGGGGGGGGCGCGCGCCAGGC<br>GGGGCGGGGCGGGGCGAGGGGCGGGGCGGGGCGAGGCGGAGAGGTGCGGC<br>GGCAGCCAATCAGAGCGGCGCGCTCCGAAAGTTTCCTTTTATGGCGAGGC<br>GGCGGCGGCGGCGGCCCTATAAAAAGCGAAGCGCGCGGCGGGCGGGAGTC<br>TCTGGATCCACTGCTTAAATACGGACGAGGACAGGGCCCTGTCTCCTCAG<br>CTTCAGGCACCACCACTGACCTGGGACAGTGAATCGTAAGTACTAGCAGC<br>TACAATCCAGCTACCATTCTGCTTTTATTTTATGGTTGGGATAAGGCTGG<br>ATTATTCTGAGTCCAAGCTAGGCCCTTTTGCTAATCATGTTCATACCTCT<br>TATCTTCCTCCCACAGCTCCTGGGCAACGTGCTGGTCTGTGTGCTGGCCC<br>ATCACTTTGGCAAAGAATTGCGATCGCCACCATGGTGAGCAAGGGCGAGG<br>AGCTGTTCACCGGGGTGGTGCCCATCCTGGTCGAGCTGGACGGCGACGTA<br>AACGGCCACAAGTTCAGCGTGTCCGGCGAGGGCGAGGGCGATGCCACCTA<br>CGGCAAGCTGACCCTGAAGTTCATCTGCACCACCGGCAAGCTGCCCGTGC<br>CCTGGCCCACCCTCGTGACCACCCTGACCTACGGCGTGCAGTGCTTCAGC<br>CGCTACCCCGACCACATGAAGCAGCACGACTTCTTCAAGTCCGCCATGCC<br>CGAAGGCTACGTCCAGGAGCGCACCATCTTCTTCAAGGACGACGGCAACT<br>ACAAGACCCGCGCCGAGGTGAAGTTCGAGGGCGACACCCTGGTGAACCGC<br>ATCGAGCTGAAGGGCATCGACTTCAAGGAGGACGGCAACATCCTGGGGCA<br>CAAGCTGGAGTACAACTACAACAGCCACAACGTCTATATCATGGCCGACA<br>AGCAGAAGAACGGCATCAAGGTGAACTTCAAGATCCGCCACAACATCGAG<br>GACGGCAGCGTGCAGCTCGCCGACCACTACCAGCAGAACACCCCCATCGG<br>CGACGGCCCCGTGCTGCTGCCCGACAACCACTACCTGAGCACCCAGTCCG<br>CCCTGAGCAAAGACCCCAACGAGAAGCGCGATCACATGGTCCTGCTGGAG<br>TTCGTGACCGCCGCCGGGATCACTCTCGGCATGGACGAGCTGTACAAGAA<br>TCGCGCTACTAACTTCAGCCTGCTGAAGCAGGCTGGAGACGTGGAGGAGA<br>ACCCTGGACCTATGGAAGACGCCAAAAACATAAAGAAAGGCCCGGCGCCA<br>TTCTATCCGCTGGAAGATGGAACCGCTGGAGAGCAACTGCATAAGGCTAT<br>GAAGAGATACGCCCTGGTTCCTGGAACAATTGCTTTTACAGATGCACATA<br>TCGAGGTGGACATCACTTACGCTGAGTACTTCGAAATGTCCGTTCGGTTG<br>GCAGAAGCTATGAAACGATATGGGCTGAATACAAATCACAGAATCGTCGT<br>ATGCAGTGAAAACTCTCTTCAATTCTTTATGCCGGTGTTGGGCGCGTTAT<br>TTATCGGAGTTGCAGTTGCGCCCGCGAACGACATTTATAATGAACGTGAA<br>TTGCTCAACAGTATGGGCATTTCGCAGCCTACCGTGGTGTTCGTTTCCAA<br>AAAGGGGTTGCAAAAAATTTTGAACGTGCAAAAAAAGCTCCCAATCATCC<br>AAAAAATTATTATCATGGATTCTAAAACGGATTACCAGGGATTTCAGTCG<br>ATGTACACGTTCGTCACATCTCATCTACCTCCCGGTTTTAATGAATACGA<br>TTTTGTGCCAGAGTCCTTCGATAGGGACAAGACAATTGCACTGATCATGA<br>ACTCCTCTGGATCTACTGGTCTGCCTAAAGGTGTCGCTCTGCCTCATAGA<br>ACTGCCTGCGTGAGATTCTCGCATGCCAGAGATCCTATTTTTGGCAATCA<br>AATCATTCCGGATACTGCGATTTTAAGTGTTGTTCCATTCCATCACGGTT<br>TTGGAATGTTTACTACACTCGGATATTTGATATGTGGATTTCGAGTCGTC<br>TTAATGTATAGATTTGAAGAAGAGCTGTTTCTGAGGAGCCTTCAGGATTA<br>CAAGATTCAAAGTGCGCTGCTGGTGCCAACCCTATTCTCCTTCTTCGCCA<br>AAAGCACTCTGATTGACAAATACGATTTATCTAATTTACACGAAATTGCT<br>TCTGGTGGCGCTCCCCTCTCTAAGGAAGTCGGGGAAGCGGTTGCCAAGAG<br>GTTCCATCTGCCAGGTATCAGGCAAGGATATGGGCTCACTGAGACTACAT<br>CAGCTATTCTGATTACACCCGAGGGGGATGATAAACCGGGCGCGGTCGGT<br>AAAGTTGTTCCATTTTTTGAAGCGAAGGTTGTGGATCTGGATACCGGGAA<br>AACGCTGGGCGTTAATCAAAGAGGCGAACTGTGTGTGAGAGGTCCTATGA<br>TTATGTCCGGTTATGTAAACAATCCGGAAGCGACCAACGCCTTGATTGAC<br>AAGGATGGATGGCTACATTCTGGAGACATAGCTTACTGGGACGAAGACGA<br>ACACTTCTTCATCGTTGACCGCCTGAAGTCTCTGATTAAGTACAAAGGCT<br>ATCAGGTGGCTCCCGCTGAATTGGAATCCATCTTGCTCCAACACCCCAAC<br>ATCTTCGACGCAGGTGTCGCAGGTCTTCCCGACGATGACGCCGGTGAACT<br>TCCCGCCGCCGTTGTTGTTTTGGAGCACGGAAAGACGATGACGGAAAAAG<br>AGATCGTGGATTACGTCGCCAGTCAAGTAACAACCGCGAAAAAGTTGCGC<br>GGAGGAGTTGTGTTTGTGGACGAAGTACCGAAAGGTCTTACCGGAAAACT<br>CGACGCAAGAAAAATCAGAGAGATCCTCATAAAGGCCAAGAAGGGCGGAA<br>AGATCGCCGTGTAACTCGAGAATCAACCTCTGGATTACAAAATTTGTGAA<br>AGATTGACTGGTATTCTTAACTATGTTGCTCCTTTTACGCTATGTGGATA<br>CGCTGCTTTAATGCCTTTGTATCATGCTATTGCTTCCCGTATGGCTTTCA<br>TTTTCTCCTCCTTGTATAAATCCTGGTTGCTGTCTCTTTATGAGGAGTTG<br>TGGCCCGTTGTCAGGCAACGTGGCGTGGTGTGCACTGTGTTTGCTGACGC<br>AACCCCCACTGGTTGGGGCATTGCCACCACCTGTCAGCTCCTTTCCGGGA<br>CTTTCGCTTTCCCCCTCCCTATTGCCACGGCGGAACTCATCGCCGCCTGC<br>CTTGCCCGCTGCTGGACAGGGGCTCGGCTGTTGGGCACTGACAATTCCGT<br>GGGGTGTGCCTTCTAGTTGCCAGCCATCTGTTGTTTGCCCCTCCCCCGTG<br>CCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGG<br>GTGGGGTGGGGCAGGACAGCAAGGGGGAGGATTGGGAAGACAATAGCAGG |

-continued

| SEQ ID NO | Description | SEQ |
|---|---|---|
| | | CATGCTGGGGATGCGGTGGGCTCTATGGGAAGATGTCTACTGAGCTGTGC<br>GATCCCTGCTGGGGACTTTCCGCTGGGGACTTTCCGCTGGGGACTTTCCG<br>CCTTCAGCTAAGGAAGCTACCAATATTTAGAGGTACATTTTGTTCTAGAA<br>CAAAATGTACCGGTACATTTTGTTCTGGTACATTTTGTTCTATTAAGGAC<br>AACGTAAGTATAGCGCATAGACACGTGGCGCCATCGGATCCCGGGTGGCT<br>TGTTGTCCACAACCATTAAACCTTAAAAGCTTTAAAAGCCTTATATATTC<br>TTTTTTTTCTTATAAAACTTAAAACCTTAGAGGCTATTTAAGTTGCTGAT<br>TTATATTAATTTTATTGTTCAAACATGAGAGCTTAGTACGTGAAACATGA<br>GAGCTTAGTACATTAGCCATGAGAGCTTAGTACATTAGCCATGAGGGTTT<br>AGTTCATTAAACATGAGAGCTTAGTACATTAAACATGAGAGCTTAGTACA<br>TTAAACATGAGAGCTTAGTACATACTATCAACAGGTTGAACTGCTGATCT<br>GTACAGTAGAATTGGTAAAGAGAGTTGTGTAAAATATTGAGTTCGCACAT<br>CTTGTTGTCTGATTATTGATTTTTGGCGAAACCATTTGATCATATGACAA<br>GATGTGTATCTACCTTAACTTAATGATTTTGATAAAAATCATTA |
| 30. | NP-<br>DTS<br>MHCK7-<br>hBGi-<br>JEGFP-P2A-<br>Fluc-<br>WPRE3- | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>CATGGTGAGCAAGGGCGAGGAGCTGTTCACCGGGGTGGTGCCCATCCTGG<br>TCGAGCTGGACGGCGACGTAAACGGCCACAAGTTCAGCGTGTCCGGCGAG<br>GGCGAGGGCGATGCCACCTACGGCAAGCTGACCCTGAAGTTCATCTGCAC<br>CACCGGCAAGCTGCCCGTGCCCTGGCCCACCCTCGTGACCACCCTGACCT<br>ACGGCGTGCAGTGCTTCAGCCGCTACCCCGACCACATGAAGCAGCACGAC<br>TTCTTCAAGTCCGCCATGCCCGAAGGCTACGTCCAGGAGCGCACCATCTT<br>CTTCAAGGACGACGGCAACTACAAGACCCGCGCCGAGGTGAAGTTCGAGG<br>GCGACACCCTGGTGAACCGCATCGAGCTGAAGGGCATCGACTTCAAGGAG<br>GACGGCAACATCCTGGGGCACAAGCTGGAGTACAACTACAACAGCCACAA<br>CGTCTATATCATGGCCGACAAGCAGAAGAACGGCATCAAGGTGAACTTCA<br>AGATCCGCCACAACATCGAGGACGGCAGCGTGCAGCTCGCCGACCACTAC<br>CAGCAGAACACCCCCATCGGCGACGGCCCCGTGCTGCTGCCCGACAACCA<br>CTACCTGAGCACCCAGTCCGCCCTGAGCAAAGACCCCAACGAGAAGCGCG<br>ATCACATGGTCCTGCTGGAGTTCGTGACCGCCGCCGGGATCACTCTCGGC<br>ATGGACGAGCTGTACAAGAATCGCGCTACTAACTTCAGCCTGCTGAAGCA<br>GGCTGGAGACGTGGAGGAGAACCCTGGACCTATGGAAGACGCCAAAAACA<br>TAAAGAAAGGCCCGGCGCCATTCTATCCGCTGGAAGATGGAACCGCTGGA<br>GAGCAACTGCATAAGGCTATGAAGAGATACGCCCTGGTTCCTGGAACAAT<br>TGCTTTTACAGATGCACATATCGAGGTGGACATCACTTACGCTGAGTACT<br>TCGAAATGTCCGTTCGGTTGGCAGAAGCTATGAAACGATATGGGCTGAAT<br>ACAAATCACAGAATCGTCGTATGCAGTGAAAACTCTCTTCAATTCTTTAT<br>GCCGGTGTTGGGCGCGTTATTTATCGGAGTTGCAGTTGCGCCCGCGAACG<br>ACATTTATAATGAACGTGAATTGCTCAACAGTATGGGCATTTCGCAGCCT<br>ACCGTGGTGTTCGTTTCCAAAAAGGGGTTGCAAAAAATTTTGAACGTGCA<br>AAAAAAGCTCCCAATCATCCAAAAAATTATTATCATGGATTCTAAAACGG<br>ATTACCAGGGATTTCAGTCGATGTACACGTTCGTCACATCTCATCTACCT<br>CCCGGTTTTAATGAATACGATTTTGTGCCAGAGTCCTTCGATAGGGACAA<br>GACAATTGCACTGATCATGAACTCCTCTGGATCTACTGGTCTGCCTAAAG<br>GTGTCGCTCTGCCTCATAGAACTGCCTGCGTGAGATTCTCGCATGCCAGA<br>GATCCTATTTTTGGCAATCAAATCATTCCGGATACTGCGATTTTAAGTGT<br>TGTTCCATTCCATCACGGTTTTGGAATGTTTACTACACTCGGATATTTGA<br>TATGTGGATTTCGAGTCGTCTTAATGTATAGATTTGAAGAAGAGCTGTTT<br>CTGAGGAGCCTTCAGGATTACAAGATTCAAAGTGCGCTGCTGGTGCCAAC<br>CCTATTCTCCTTCTTCGCCAAAAGCACTCTGATTGACAAATACGATTTAT<br>CTAATTTACACGAAATTGCTTCTGGTGGCGCTCCCCTCTCTAAGGAAGTC<br>GGGGAAGCGGTTGCCAAGAGGTTCCATCTGCCAGGTATCAGGCAAGGATA<br>TGGGCTCACTGAGACTACATCAGCTATTCTGATTACACCCGAGGGGGATG<br>ATAAACCGGGCGCGGTCGGTAAAGTTGTTCCATTTTTTGAAGCGAAGGTT<br>GTGGATCTGGATACCGGGAAAACGCTGGGCGTTAATCAAAGAGGCGAACT |

-continued

| SEQ ID NO | Description | SEQ |
|---|---|---|
| | | GTGTGTGAGAGGTCCTATGATTATGTCCGGTTATGTAAACAATCCGGAAG CGACCAACGCCTTGATTGACAAGGATGGATGGCTACATTCTGGAGACATA GCTTACTGGGACGAAGACGAACACTTCTTCATCGTTGACCGCCTGAAGTC TCTGATTAAGTACAAAGGCTATCAGGTGGCTCCCGCTGAATTGGAATCCA TCTTGCTCCAACACCCCAACATCTTCGACGCAGGTGTCGCAGGTCTTCCC GACGATGACGCCGGTGAACTTCCCGCCGCCGTTGTTGTTTTGGAGCACGG AAAGACGATGACGGAAAAAGAGATCGTGGATTACGTCGCCAGTCAAGTAA CAACCGCGAAAAAGTTGCGCGGAGGAGTTGTGTTTGTGGACGAAGTACCG AAAGGTCTTACCGGAAAACTCGACGCAAGAAAAATCAGAGAGATCCTCAT AAAGGCCAAGAAGGGCGGAAAGATCGCCGTGTAACTCGAGAATCAACCTC TGGATTACAAAATTTGTGAAAGATTGACTGGTATTCTTAACTATGTTGCT CCTTTTACGCTATGTGGATACGCTGCTTTAATGCCTTTGTATCATGCTAT TGCTTCCCGTATGGCTTTCATTTTCTCCTCCTTGTATAAATCCTGGTTGC TGTCTCTTTATGAGGAGTTGTGGCCCGTTGTCAGGCAACGTGGCGTGGTG TGCACTGTGTTTGCTGACGCAACCCCCACTGGTTGGGGCATTGCCACCAC CTGTCAGCTCCTTTCCGGGACTTTCGCTTTCCCCCTCCCTATTGCCACGG CGGAACTCATCGCCGCCTGCCTTGCCCGCTGCTGGACAGGGGCTCGGCTG TTGGGCACTGACAATTCCGTGGGGTGTGCCTTCTAGTTGCCAGCCATCTG TTGTTTGCCCCTCCCCCGTGCCTTCCTTGACCCTGGAAGGTGCCACTCCC ACTGTCCTTTCCTAATAAAATGAGGAAATTGCATCGCATTGTCTGAGTAG GTGTCATTCTATTCTGGGGGGTGGGGTGGGGCAGGACAGCAAGGGGGAGG ATTGGGAAGACAATAGCAGGCATGCTGGGGATGCGGTGGGCTCTATGGGA AGATGTCTACTGAGCTGTGCGATCCCTGCTGGGGACTTTCCGCTGGGGAC TTTCCGCTGGGGACTTTCCGCCTTCAGCTAAGGAAGCTACCAATATTTAG AGGTACATTTTGTTCTAGAACAAAATGTACCGGTACATTTTGTTCTGGTA CATTTTGTTCTATTAAGGACAACGTAAGTATAGCGCATAGACACGTGGCG CCATCGGATCCCGGGCCCGTCGACTTAAGTGGCTTGTTGTCCACAACCAT TAAACCTTAAAAGCTTTAAAAGCCTTATATATTCTTTTTTTTCTTATAAA ACTTAAAACCTTAGAGGCTATTTAAGTTGCTGATTTATATTAATTTTATT GTTCAAACATGAGAGCTTAGTACGTGAAACATGAGAGCTTAGTACATTAG CCATGAGAGCTTAGTACATTAGCCATGAGGGTTTAGTTCATTAAACATGA GAGCTTAGTACATTAAACATGAGAGCTTAGTACATTAAACATGAGAGCTT AGTACATACTATCAACAGGTTGAACTGCTGATCTGTACAGTAGAATTGGT AAAGAGAGTTGTGTAAAATATTGAGTTCGCACATCTTGTTGTCTGATTAT TGATTTTTGGCGAAACCATTTGATCATATGACAAGATGTGTATCTACCTT AACTTAATGATTTTGATAAAAATCATTAGCGGCCGC |
| 31. | pUC57-CBA-hBGi-DMD-4-WPRE3-DTS | TCTGGATCCACTGCTTAAATACGGACGAGGACAGGGCCCTGTCTCCTCAG CTTCAGGCACCACCACTGACCTGGGACAGTGAATCGTAAGTACTAGCAGC TACAATCCAGCTACCATTCTGCTTTTATTTTATGGTTGGGATAAGGCTGG ATTATTCTGAGTCCAAGCTAGGCCCTTTTGCTAATCATGTTCATACCTCT TATCTTCCTCCCACAGCTCCTGGGCAACGTGCTGGTCTGTGTGCTGGCCC ATCACTTTGGCAAAGAATTGCGATCGCCACCATGCTTTGGTGGGAAGAAG TCGAGGACTGCTACGAGCGCGAGGACGTGCAGAAGAAAACCTTCACCAAA TGGGTCAACGCCCAGTTCAGCAAGTTCGGCAAGCAGCACATCGAGAACCT GTTCAGCGACCTGCAGGATGGCAGAAGGCTGCTGGATCTGCTGGAAGGCC TGACAGGACAGAAGCTGCCCAAAGAGAAGGGCAGCACAAGAGTGCACGCC CTGAACAACGTGAACAAGGCCCTGAGAGTGCTGCAGAACAACAACGTGGA CCTGGTCAACATCGGCAGCACCGACATCGTGGACGGCAACCACAAACTGA CCCTGGGCCTGATCTGGAACATCATCCTGCACTGGCAAGTGAAGAACGTG ATGAAGAACATCATGGCCGGCCTGCAGCAGACCAACAGCGAGAAGATTCT GCTGAGCTGGGTCCGACAGAGCACCCGGAATTACCCTCAAGTGAACGTGA TCAACTTCACCACCTCTTGGAGCGACGGACTGGCCCTGAATGCCCTGATC CACAGCCACAGACCTGACCTGTTCGACTGGAACAGCGTCGTGTGTCAGCA GAGCGCCACACAGAGGCTGGAACACGCCTTCAATATCGCCAGATACCAGC TGGGCATCGAGAAACTGCTGGACCCCGAGGATGTGGACACCACCTATCCT GACAAGAAATCCATCCTCATGTACATCACCAGCCTGTTCCAGGTGCTGCC CCAGCAGGTTTCCATCGAGGCCATTCAAGAGGTCGAGATGCTGCCCAGAC CTCCTAAAGTGACCAAAGAGGAACACTTCCAGCTGCACCACCAGATGCAC TACTCTCAGCAGATCACCGTGTCTCTGGCCCAGGGCTACGAGAGAACAAG CAGCCCCAAGCCTCGGTTCAAGAGCTACGCCTATACACAGGCCGCCTACG TGACCACCAGCGATCCTACAAGAAGCCCATTTCCTAGCCAGCATCTGGAA GCCCCTGAGGACAAGAGCTTTGGCAGCAGCCTGATGGAAAGCGAAGTGAA CCTGGACCGCTACCAGACAGCCCTGGAAGAGGTTCTGAGCTGGCTGCTGT CTGCCGAGGATACACTGCAGGCTCAGGGCGAGATCAGCAACGACGTGGAA GTGGTCAAGGACCAGTTTCACACCCACGAGGGCTACATGATGGACCTGAC AGCCCACCAGGGCAGAGTGGGCAATATTCTGCAGCTGGGCTCCAAGCTGA TCGGCACAGGCAAGCTGAGCGAGGACGAAGAGACAGAGGTGCAAGAGCAG ATGAACCTGCTGAACAGCAGATGGGAGTGTCTGAGAGTGGCCAGCATGGA AAAGCAGAGCAACCTGCACCGGGTGCTGATGGATCTCCAGAACCAGAAGC TGAAAGAGCTGAACGACTGGCTGACCAAGACCGAGGAACGGACCCGGAAG ATGGAAGAGGAACCTCTGGGACCCGACCTGGAAGATCTGAAAAGACAGGT GCAGCAGCATAAGGTGCTGCAAGAGGACCTCGAACAAGAGCAAGTGCGCG TGAACAGCCTGACACACATGGTGGTGGTCGTGGATGAGAGCAGCGGAGAT CATGCCACAGCCGCTCTGGAAGAACAGCTGAAGGTGCTGGGAGACAGATG |

-continued

| SEQ ID NO | Description | SEQ |
|---|---|---|
| | | GGCCAATATCTGCCGGTGGACCGAGGATAGATGGGTGCTGCTCCAGGACA<br>TCCTGCTGAAGTGGCAGCGGCTGACAGAGGAACAGTGCCTGTTTAGCGCC<br>TGGCTGTCCGAGAAAGAGGACGCCGTCAACAAGATCCACACCACCGGCTT<br>CAAGGATCAGAATGAGATGCTGAGCAGCCTGCAGAAACTGGCCGTGCTGA<br>AGGCTGACCTGGAAAAGAAAAAGCAGTCCATGGGCAAGCTGTACTCCCTG<br>AAGCAGGACCTGCTGAGCACACTGAAGAACAAGTCTGTGACCCAGAAAAC<br>CGAGGCCTGGCTGGACAACTTCGCCCGGTGTTGGGATAACCTGGTGCAGA<br>AGCTGGAAAAGTCCACCGCTCAGATCTCTCAGGCCGTGACCACAACACAG<br>CCTTCTCTGACCCAGACCACCGTGATGGAAACAGTGACCACAGTGACAAC<br>CCGCGAGCAGATCCTGGTCAAGCACGCCCAAGAAGAACTGCCTCCTCCAC<br>CTCCTCAGAAGAAACGGCAGATCACAGTGGACAGCGAGATCCGGAAGAGA<br>CTGGACGTGGACATCACCGAGCTGCACAGCTGGATCACCAGATCCGAAGC<br>CGTGCTGCAGTCCCCTGAGTTCGCCATCTTCAGAAAAGAGGGCAACTTCT<br>CCGACCTGAAAGAGAAAGTCAACGCCATCGAGAGAGAGAAGGCCGAGAAG<br>TTCCGGAAGCTGCAGGACGCCTCTAGATCTGCCCAGGCTCTGGTGGAACA<br>GATGGTCAACGAAGGCGTGAACGCCGACAGCATCAAGCAGGCCTCAGAGC<br>AGCTGAACTCCCGGTGGATCGAGTTCTGTCAGCTCCTGAGCGAGAGACTG<br>AACTGGCTGGAATACCAGAACAATATCATTGCCTTCTACAACCAGCTCCA<br>GCAGCTCGAACAGATGACCACCACAGCCGAGAATTGGCTGAAGATCCAGC<br>CTACCACACCTAGCGAGCCCACCGCCATTAAGAGCCAGCTGAAAATCTGC<br>AAGGACGAAGTGAATCGGCTGAGCGATCTGCAGCCCCAGATCGAAAGACT<br>GAAAATCCAGTCTATCGCCCTCAAAGAGAAAGGACAGGGCCCCATGTTCC<br>TGGACGCCGATTTTGTGGCCTTTACCAACCACTTCAAACAGGTGTTCTCC<br>GACGTGCAGGCCCGGGAAAAAGAGCTGCAGACCATCTTCGACACCCTGCC<br>TCCAATGAGATACCAAGAGACAATGAGCGCCATCCGGACCTGGGTGCAGC<br>AAAGCGAGACAAAGCTGAGCATCCCACAGCTGAGCGTGACCGACTACGAG<br>ATCATGGAACAGAGACTGGGCGAACTGCAGGCCCTCCAGTCTAGCCTGCA<br>AGAACAGCAGTCCGGCCTGTACTACCTGAGCACAACCGTGAAAGAGATGA<br>GCAAGAAGGCCCCTAGCGAGATCTCCCGGAAGTACCAGAGCGAGTTCGAA<br>GAGATCGAAGGCCGGTGGAAGAAGCTGTCTAGCCAGCTGGTTGAGCACTG<br>CCAGAAACTCGAAGAACAAATGAACAAGCTGCGCAAGATCCAGAATCACA<br>TCCAGACGCTGAAGAAATGGATGGCCGAGGTGGACGTGTTCCTGAAAGAA<br>GAGTGGCCCGCTCTGGGCGACTCCGAGATTCTGAAGAAACAGCTCAAACA<br>GTGCCGGCTGCTGGTGTCCGATATCCAGACAATCCAGCCAAGCCTGAACT<br>CCGTGAATGAAGGCGGCCAGAAGATCAAGAACGAGGCCGAGCCTGAGTTT<br>GCCAGCAGACTGGAAACCGAACTGAAAGAACTCAACACCCAGTGGGACCA<br>CATGTGCCAGCAAGTGTACGCCCGGAAAGAGGCCCTGAAAGGCGGACTCG<br>AAAAGACTGTGTCTCTGCAGAAAGACCTGTCTGAGATGCACGAGTGGATG<br>ACCCAGGCCGAAGAGGAATACCTGGAACGGGACTTCGAGTACAAGACCCC<br>TGATGAGCTGCAAAAAGCCGTCGAGGAAATGAAGCGGGCCAAAGAAGAGG<br>CCCAGCAGAAAGAAGCCAAAGTCAAGCTGCTGACCGAGTCCGTGAATAGC<br>GTTATCGCTCAGGCCCCTCCTGTGGCTCAAGAGGCTCTCAAGAAAGAACT<br>GGAAACTCTGACCACCAACTACCAGTGGCTGTGCACCAGACTGAACGGCA<br>AGTGCAAGACACTGGAAGAAGTGTGGGCCTGCTGGCACGAACTGCTGTCC<br>TATCTGGAAAAGGCCAACAAGTGGCTGAACGAGGTGGAATTCAAGCTGAA<br>AACCACCGAGAACATCCCTGGCGGCGCTGAAGAGATTAGCGAGGTGCTGG<br>ACAGCCTGGAAAACCTGATGAGACACAGCGAGGACAACCCCAATCAGATC<br>AGAATCCTGGCTCAGACCCTGACCGATGGCGGCGTGATGGACGAGCTGAT<br>CAACGAGGAACTCGAAACCTTCAACAGCCGGTGGCGGGAACTGCACGAGG<br>AAGCTGTTCGGAGGCAGAAGTTGCTGGAACAGTCTATCCAGAGCGCACAA<br>GAAACCGAGAAGTCCCTGCACCTGATCCAAGAGAGCCTGACCTTCATCGA<br>CAAGCAGCTGGCCGCTTATATCGCCGACAAGGTGGACGCTGCTCAGATGC<br>CCCAAGAGGCACAGAAGATTCAGAGCGACCTGACCAGCCACGAGATTAGC<br>CTGGAAGAAATGAAGAAGCACAACCAGGGCAAAGAGGCCGCTCAGAGAGT<br>CCTGAGCCAGATCGATGTGGCACAGAAAAAGCTCCAGGATGTGTCCATGA<br>AGTTTCGGCTGTTTCAGAAGCCCGCCAACTTCGAGCAGAGACTGCAAGAG<br>TCCAAGATGATCCTGGACGAAGTCAAAATGCATCTGCCCGCACTGGAAAC<br>AAAGTCCGTGGAACAAGAAGTGGTGCAGTCCCAGCTGAACCACTGCGTGA<br>ACCTGTACAAGAGCCTGTCCGAAGTGAAGTCTGAGGTGGAAATGGTCATC<br>AAGACCGGCAGGCAGATCGTCCAGAAGAAGCAGACCGAGAATCCCAAAGA<br>ACTCGACGAGAGAGTGACCGCTCTGAAGCTGCACTACAATGAGCTGGGCG<br>CCAAAGTGACCGAGCGGAAGCAACAGCTTGAGAAGTGCCTGAAACTGTCT<br>CGGAAGATGCGGAAAGAAATGAACGTGCTGACAGAGTGGCTGGCCGCCAC<br>CGATATGGAACTGACTAAGAGAAGCGCCGTGGAAGGCATGCCCAGCAACC<br>TGGATAGTGAAGTGGCCTGGGGCAAAGCCACTCAGAAAGAGATTGAGAAG<br>CAGAAGGTCCACCTGAAGTCCATCACCGAAGTGGGCGAAGCCCTGAAAAC<br>CGTGCTGGGAAAGAAAGAGACACTGGTCGAGGACAAGCTGTCCCTGCTGA<br>ATTCCAACTGGATCGCCGTGACCTCCAGAGCTGAGGAATGGCTGAATCTG<br>CTGCTTGAGTACCAGAAACACATGGAAACGTTCGACCAGAACGTCGACCA<br>CATCACAAAGTGGATCATCCAGGCTGATACCCTGCTGGACGAGTCCGAGA<br>AGAAGAAACCCCAACAAAAAGAAGATGTGCTGAAGCGGCTGAAAGCCGAG<br>CTGAATGACATCCGGCCTAAGGTGGACAGCACCAGAGATCAGGCAGCCAA<br>CCTGATGGCCAACAGAGGCGACCACTGTCGGAAGCTCGTGGAACCTCAGA<br>TCAGCGAGCTTAACCACAGATTTGCCGCCATCAGCCACCGGATCAAGACA<br>GGCAAGGCCAGCATTCCTCTCAAAGAGCTTGAGCAGTTCAACAGCGACAT |

-continued

| SEQ ID NO | Description | SEQ |
|---|---|---|
| | | CCAAAAGCTGCTCGAACCCCTGGAAGCCGAGATCCAACAGGGCGTCAACC<br>TCAAAGAAGAAGATTTCAACAAGGACATGAACGAGGACAATGAGGGCACC<br>GTCAAAGAACTGCTGCAGCGGGGCGATAATCTGCAGCAGCGGATTACCGA<br>TGAGCGCAAGCGGGAAGAGATCAAGATTAAGCAGCAGCTGCTGCAGACCA<br>AGCACAACGCCCTGAAGGACCTGCGGAGCCAGAGAAGAAAGAAGGCCCTG<br>GAAATCAGCCACCAGTGGTATCAGTACAAGCGGCAGGCCGACGACCTGCT<br>GAAGTGCCTGGATGACATCGAGAAGAAGCTGGCCTCTCTGCCCGAGCCTA<br>GGGACGAGAGAAAGATCAAAGAGATCGACCGCGAGCTGCAGAAAAAGAAA<br>GAGGAACTGAACGCCGTCCGCAGACAGGCCGAAGGACTTTCTGAAGATGG<br>CGCCGCTATGGCCGTGGAACCCACACAGATTCAGCTGAGCAAGCGGTGGC<br>GGGAAATCGAGAGCAAGTTCGCCCAGTTCCGGCGGCTGAATTTCGCCCAG<br>ATCCACACCGTGCGGGAAGAGACAATGATGGTCATGACAGAGGACATGCC<br>CCTTGAGATCAGCTACGTGCCCAGCACCTACCTGACCGAGATCACCCATG<br>TGTCTCAGGCCCTGCTGGAAGTGGAACAGCTGCTGAATGCCCCTGACCTG<br>TGCGCCAAGGACTTCGAGGACCTGTTCAAGCAAGAGGAAAGCCTGAAGAA<br>CATCAAGGACAGCCTGCAGCAGAGCAGCGGCCGGATCGATATCATCCACA<br>GCAAGAAAACCGCCGCACTGCAGAGCGCCACACCTGTGGAAAGAGTGAAG<br>CTGCAAGAGGCCCTGAGCCAGCTGGATTTCCAGTGGGAGAAAGTGAACAA<br>GATGTACAAGGACCGGCAGGGCAGATTCGACCGCAGCGTTGAAAAGTGGC<br>GGCGGTTCCACTACGACATCAAGATCTTCAACCAGTGGCTGACCGAGGCC<br>GAGCAGTTCCTGAGAAAGACACAGATCCCCGAGAACTGGGAGCACGCCAA<br>GTACAAGTGGTATCTGAAAGAGCTGCAGGACGGCATCGGCCAGAGACAGA<br>CAGTCGTGCGGACACTGAATGCCACCGGCGAGGAAATCATCCAGCAGTCC<br>AGCAAGACCGACGCCAGCATCCTGCAAGAGAAGCTGGGCAGCCTGAACCT<br>GCGGTGGCAAGAAGTGTGCAAGCAGCTGAGCGACCGGAAGAAGCGGCTGG<br>AAGAACAGAAGAATATCCTGAGCGAGTTCCAGCGGGACCTGAACGAGTTC<br>GTGCTGTGGCTCGAAGAGGCCGACAATATCGCCAGCATTCCCCTGGAACC<br>TGGCAAAGAGCAGCAGCTGAAAGAAAAGCTGGAACAAGTGAAACTGCTGG<br>TCGAGGAACTGCCCCTGAGACAGGGAATCCTGAAACAGCTGAACGAGACA<br>GGCGGCCCTGTGCTGGTGTCTGCCCCTATTTCTCCCGAGGAACAGGACAA<br>GCTGGAAAACAAGCTGAAGCAGACCAACCTGCAGTGGATCAAGGTGTCCA<br>GAGCACTGCCTGAGAAGCAGGGCGAGATCGAGGCCCAGATCAAGGACCTG<br>GGACAGCTCGAAAAGAAGCTTGAGGACCTCGAAGAACAGCTCAACCATCT<br>GCTGCTTTGGCTGAGCCCCATCCGGAACCAGCTGGAAATCTACAACCAGC<br>CTAATCAAGAGGGCCCCTTCGACGTGAAAGAAACCGAGATTGCCGTGCAG<br>GCCAAGCAGCCCGATGTGGAAGAGATCCTGTCTAAGGGCCAGCACCTGTA<br>CAAAGAGAAGCCCGCCACACAGCCCGTGAAGCGGAAACTGGAAGATCTGA<br>GCAGCGAGTGGAAGGCCGTGAACCGGCTGCTGCAAGAACTGAGAGCCAAA<br>CAGCCTGATCTGGCCCCTGGCCTGACAACAATTGGCGCCTCTCCTACACA<br>GACCGTGACACTGGTCACACAGCCTGTGGTCACCAAAGAGACAGCCATCA<br>GCAAACTGGAAATGCCCAGCAGTCTGATGCTCGAAGTGCCCGCACTGGCC<br>GACTTCAATAGAGCCTGGACCGAGCTGACCGACTGGCTCAGTCTGCTGGA<br>CCAAGTCATCAAGTCCCAGAGAGTGATGGTCGGAGATCTTGAGGACATCA<br>ACGAGATGATCATTAAGCAGAAAGCCACCATGCAGGACCTTGAGCAGAGA<br>AGGCCCCAGCTTGAAGAACTGATCACCGCCGCTCAGAACCTGAAAAACAA<br>GACCAGCAATCAAGAAGCCCGGACCATCATCACCGACCGGATCGAGAGAA<br>TCCAGAACCAGTGGGACGAAGTGCAAGAGCATCTGCAGAACAGACGGCAG<br>CAGCTCAATGAGATGCTGAAGGACAGCACACAGTGGCTGGAAGCCAAAGA<br>AGAAGCCGAGCAGGTTCTCGGACAGGCCAGAGCTAAGCTGGAATCTTGGA<br>AAGAGGGACCCTACACCGTCGACGCCATCCAGAAGAAGATCACCGAGACA<br>AAGCAGCTGGCCAAGGATCTGAGACAGTGGCAGACCAATGTGGACGTGGC<br>CAACGACCTGGCTCTGAAGCTGCTGAGAGACTACAGCGCCGACGACACCA<br>GAAAGGTGCACATGATCACCGAAAACATCAACGCCTCTTGGCGGAGCATC<br>CACAAGCGGGTGTCAGAGAGAGAAGCCGCTCTGGAAGAAACACATAGACT<br>GCTCCAGCAGTTCCCACTCGACCTGGAAAAGTTCCTGGCCTGGCTGACAG<br>AAGCCGAAACCACCGCTAACGTGCTCCAGGATGCCACCAGAAAAGAGCGG<br>CTGTTGGAGGACAGCAAGGGCGTCAAAGAACTCATGAAGCAGTGGCAGGA<br>TCTGCAAGGGGAGATTGAAGCCCACACCGACGTGTACCACAACCTGGACG<br>AGAACAGCCAGAAGATCCTGCGGTCCCTGGAAGGCTCTGATGATGCTGTG<br>CTGCTTCAGAGGCGGCTGGACAACATGAACTTCAAGTGGAGCGAGCTGCG<br>GAAGAAGTCCCTGAACATCAGAAGCCACCTGGAAGCCTCCAGCGACCAGT<br>GGAAAAGACTGCACCTGTCTCTCCAAGAGCTGCTCGTGTGGCTGCAGCTG<br>AAGGATGACGAGCTGAGTAGACAGGCCCCTATCGGCGGAGATTTTCCCGC<br>CGTGCAGAAACAGAACGACGTGCACCGGGCCTTCAAGAGAGAGCTGAAAA<br>CAAAAGAACCCGTCATCATGAGCACCCTGGAAACCGTGCGGATCTTTCTG<br>ACCGAGCAGCCTCTGGAAGGACTGGAAAAGCTGTACCAAGAGCCTAGAGA<br>GCTGCCTCCTGAAGAAAGGGCCCAGAACGTGACACGGCTGCTTAGAAAGC<br>AGGCCGAGGAAGTGAACACCGAATGGGAGAAGCTGAACCTCCACTCCGCC<br>GACTGGCAGCGGAAGATCGATGAGACACTGGAACGGCTGCGGGAACTGCA<br>AGAAGCCACAGACGAGCTGGACCTGAAACTGCGGCAGGCTGAAGTGATCA<br>AAGGCTCCTGGCAGCCAGTGGGCGATCTGCTGATCGATAGCCTGCAGGAC<br>CATCTGGAAAAAGTCAAGGCCCTGCGGGGAGAGATCGCCCCTCTCAAAGA<br>AAACGTGTCCCACGTGAACGATCTGGCCAGGCAGCTGACAACACTGGGCA<br>TCCAGCTGAGCCCTTACAACCTGTCTACCTTGGAGGACCTGAATACCCGG<br>TGGAAGCTGCTCCAAGTGGCCGTCGAGGATAGAGTGCGGCAGCTGCATGA |

-continued

| SEQ ID NO | Description | SEQ |
|---|---|---|
| | | GGCTCACAGAGATTTTGGACCCGCCAGCCAGCACTTCCTGAGCACATCTG<br>TTCAAGGCCCCTGGGAGAGAGCTATCAGCCCTAACAAGGTGCCCTACTAC<br>ATCAACCACGAGACACAGACCACCTGTTGGGATCACCCCAAGATGACCGA<br>ACTGTATCAGTCCCTGGCCGACCTGAACAACGTGCGGTTTAGCGCCTACC<br>GGACCGCCATGAAGCTGCGCAGACTGCAGAAAGCTCTGTGCCTGGACCTG<br>CTGTCTCTGAGCGCTGCTTGTGATGCCCTGGACCAGCATAACCTCAAGCA<br>GAACGACCAGCCTATGGACATCCTGCAGATCATCAACTGCCTGACCACCA<br>TCTACGACCGGCTCGAACAAGAGCACAACAACCTGGTCAACGTGCCCCTG<br>TGCGTGGACATGTGCCTGAATTGGCTGCTGAACGTGTACGACACCGGCAG<br>AACCGGCAGGATCAGAGTGCTGAGCTTCAAGACCGGCATCATCTCCCTGT<br>GCAAGGCCCACCTTGAGGATAAGTACCGCTACCTGTTTAAGCAGGTCGCC<br>AGCAGCACCGGCTTTTGCGACCAAAGAAGGCTGGGACTGCTGCTCCACGA<br>CAGCATTCAGATCCCTAGACAGCTGGGCGAAGTGGCCTCTTTCGGCGGCT<br>CTAATATCGAGCCTAGCGTGCGGAGCTGCTTCCAGTTCGCCAACAACAAG<br>CCCGAGATTGAGGCCGCACTGTTCCTGGACTGGATGAGACTGGAACCCCA<br>GAGCATGGTCTGGCTGCCTGTGCTGCATAGAGTGGCCGCAGCCGAAACAG<br>CCAAGCACCAGGCCAAGTGCAACATCTGCAAAGAGTGCCCCATCATCGGC<br>TTCCGGTACAGATCCCTGAAGCACTTCAACTACGATATCTGCCAGTCCTG<br>CTTCTTCAGCGGCAGAGTGGCCAAGGGCCACAAGATGCACTACCCCATGG<br>TGGAATACTGCACCCCTACCACCTCTGGCGAGGACGTGCGGGATTTTGCC<br>AAGGTGCTCAAGAACAAGTTCCGGACCAAGCGCTACTTCGCTAAGCACCC<br>CAGAATGGGCTACCTGCCAGTGCAGACAGTGCTTGAGGGCGACAACATGG<br>AAACCCCTGTGACTCTGATCAACTTCTGGCCCGTGGATAGCGCCCCTGCT<br>AGTTCTCCTCAGCTGTCTCACGACGATACCCACAGCAGAATCGAGCACTA<br>CGCCTCCAGACTGGCCGAGATGGAAAACAGCAACGGCAGCTACCTGAATG<br>ACAGCATCAGCCCCAACGAGAGCATCGACGACGAACATCTGCTCATTCAG<br>CACTACTGCCAGAGCCTGAATCAGGACAGCCCTCTGTCTCAGCCTAGAAG<br>CCCTGCACAGATCCTGATCAGCCTGGAAAGCGAGGAACGCGGCGAGCTGG<br>AAAGAATCCTGGCAGACCTGGAAGAGGAAAACCGGAACCTGCAGGCCGAA<br>TACGACAGACTCAAGCAGCAGCACGAGCACAAGGGACTGTCTCCACTGCC<br>TTCTCCACCTGAAATGATGCCCACCTCTCCACAGAGCCCCAGAGATGCCG<br>AGCTGATTGCCGAAGCCAAACTGCTGAGGCAGCACAAAGGCAGACTCGAA<br>GCCAGAATGCAGATTCTCGAAGATCACAACAAGCAGCTCGAATCCCAGCT<br>GCACAGACTTAGGCAGCTGCTGGAACAGCCTCAGGCAGAGGCCAAAGTGA<br>ATGGCACCACCGTGTCTAGCCCTAGCACAAGCCTGCAGAGATCCGACAGC<br>AGCCAGCCAATGCTTCTGAGAGTCGTGGGCTCCCAGACCAGCGATTCTAT<br>GGGCGAAGAGGACCTGCTCAGCCCTCCTCAGGATACAAGCACCGGCCTGG<br>AAGAAGTGATGGAACAACTGAACAACAGCTTCCCCAGCAGCAGAGGCAGA<br>AACACCCCTGGCAAGCCCATGCGCGAGGACACCATGTGATAACTCGAGAA<br>TCAACCTCTGGATTACAAAATTTGTGAAAGATTGACTGGTATTCTTAACT<br>ATGTTGCTCCTTTTACGCTATGTGGATACGCTGCTTTAATGCCTTTGTAT<br>CATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTG<br>GCGTGGTGTGCACTGTGTTTGCTGACGCAACCCCCACTGGTTGGGGCATT<br>GCCACCACCTGTCAGCTCCTTTCCGGGACTTTCGCTTTCCCCCTCCCTAT<br>TGCCACGGCGGAACTCATCGCCGCCTGCCTTGCCCGCTGCTGGACAGGGG<br>CTCGGCTGTTGGGCACTGACAATTCCGTGGGGTGTGCCTTCTAGTTGCCA<br>GCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAA<br>GGGGGAGGATTGGGAAGACAATAGCAGGCATGCTGGGGATGCGGTGGGCT<br>CTATGGGAAGATGTCTACTGAGCTGTGCGATCCCTGCTGGGGACTTTCCG<br>CTGGGGACTTTCCGCTGGGGACTTTCCGCCTTCAGCTAAGGAAGCTACCA<br>ATATTTAGAGGTACATTTTGTTCTAGAACAAAATGTACCGGTACATTTTG<br>TTCTGGTACATTTTGTTCTATTAAGGACAACGTAAGTATAGCGCATAGAC<br>ACGTGGCGCCATCGGATCCCGGGCCCGTCGACTGCAGAGGCCTGCATGCA<br>AGCTTGGCGTAATCATGGTCATAGCTGTTTCCTGTGTGAAATTGTTATCC<br>GCTCACAATTCCACACAACATACGAGCCGGAAGCATAAAGTGTAAAGCCT<br>GGGGTGCCTAATGAGTGAGCTAACTCACATTAATTGCGTTGCGCTCACTG<br>CCCGCTTTCCAGTCGGGAAACCTGTCGTGCCAGCTGCATTAATGAATCGG<br>CCAACGCGCGGGGAGAGGCGGTTTGCGTATTGGGCGCTCTTCCGCTTCCT<br>CGCTCACTGACTCGCTGCGCTCGGTCGTTCGGCTGCGGCGAGCGGTATCA<br>GCTCACTCAAAGGCGGTAATACGGTTATCCACAGAATCAGGGGATAACGC<br>AGGAAAGAACATGTGAGCAAAAGGCCAGCAAAAGGCCAGGAACCGTAAAA<br>AGGCCGCGTTGCTGGCGTTTTTCCATAGGCTCCGCCCCCCTGACGAGCAT<br>CACAAAAATCGACGCTCAAGTCAGAGGTGGCGAAACCCGACAGGACTATA<br>AAGATACCAGGCGTTTCCCCCTGGAAGCTCCCTCGTGCGCTCTCCTGTTC<br>CGACCCTGCCGCTTACCGGATACCTGTCCGCCTTTCTCCCTTCGGGAAGC<br>GTGGCGCTTTCTCATAGCTCACGCTGTAGGTATCTCAGTTCGGTGTAGGT<br>CGTTCGCTCCAAGCTGGGCTGTGTGCACGAACCCCCCGTTCAGCCCGACC<br>GCTGCGCCTTATCCGGTAACTATCGTCTTGAGTCCAACCCGGTAAGACAC<br>GACTTATCGCCACTGGCAGCAGCCACTGGTAACAGGATTAGCAGAGCGAG<br>GTATGTAGGCGGTGCTACAGAGTTCTTGAAGTGGTGGCCTAACTACGGCT<br>ACACTAGAAGAACAGTATTTGGTATCTGCGCTCTGCTGAAGCCAGTTACC<br>TTCGGAAAAAGAGTTGGTAGCTCTTGATCCGGCAAACAAACCACCGCTGG |

| SEQ ID NO | Description | SEQ |
|---|---|---|
| | | TAGCGGTGGTTTTTTTGTTTGCAAGCAGCAGATTACGCGCAGAAAAAAAG GATCTCAAGAAGATCCTTTGATCTTTTCTACGGGGTCTGACGCTCAGTGG AACGAAAACTCACGTTAAGGGATTTTGGTCATGAGATTATCAAAAAGGAT CTTCACCTAGATCCTTTTAAATTAAAAATGAAGTTTTAAATCAATCTAAA GTATATATGAGTAAACTTGGTCTGACAGTTACCAATGCTTAATCAGTGAG GCACCTATCTCAGCGATCTGTCTATTTCGTTCATCCATAGTTGCCTGACT CCCCGTCGTGTAGATAACTACGATACGGGAGGGCTTACCATCTGGCCCCA GTGCTGCAATGATACCGCGAGACCCACGCTCACCGGCTCCAGATTTATCA GCAATAAACCAGCCAGCCGGAAGGGCCGAGCGCAGAAGTGGTCCTGCAAC TTTATCCGCCTCCATCCAGTCTATTAATTGTTGCCGGGAAGCTAGAGTAA GTAGTTCGCCAGTTAATAGTTTGCGCAACGTTGTTGCCATTGCTACAGGC ATCGTGGTGTCACGCTCGTCGTTTGGTATGGCTTCATTCAGCTCCGGTTC CCAACGATCAAGGCGAGTTACATGATCCCCCATGTTGTGCAAAAAAGCGG TTAGCTCCTTCGGTCCTCCGATCGTTGTCAGAAGTAAGTTGGCCGCAGTG TTATCACTCATGGTTATGGCAGCACTGCATAATTCTCTTACTGTCATGCC ATCCGTAAGATGCTTTTCTGTGACTGGTGAGTACTCAACCAAGTCATTCT GAGAATAGTGTATGCGGCGACCGAGTTGCTCTTGCCCGGCGTCAATACGG GATAATACCGCGCCACATAGCAGAACTTTAAAAGTGCTCATCATTGGAAA ACGTTCTTCGGGGCGAAAACTCTCAAGGATCTTACCGCTGTTGAGATCCA GTTCGATGTAACCCACTCGTGCACCCAACTGATCTTCAGCATCTTTTACT TTCACCAGCGTTTCTGGGTGAGCAAAAACAGGAAGGCAAAATGCCGCAAA AAAGGGAATAAGGGCGACACGGAAATGTTGAATACTCATACTCTTCCTTT TTCAATATTATTGAAGCATTTATCAGGGTTATTGTCTCATGAGCGGATAC ATATTTGAATGTATTTAGAAAAATAAACAAATAGGGGTTCCGCGCACATT TCCCCGAAAAGTGCCACCTGACGTCTAAGAAACCATTATTATCATGACAT TAACCTATAAAAATAGGCGTATCACGAGGCCCTTTCGTCTCGCGCGTTTC GGTGATGACGGTGAAAACCTCTGACACATGCAGCTCCCGGAGACGGTCAC AGCTTGTCTGTAAGCGGATGCCGGGAGCAGACAAGCCCGTCAGGGCGCGT CAGCGGGTGTTGGCGGGTGTCGGGGCTGGCTTAACTATGCGGCATCAGAG CAGATTGTACTGAGAGTGCACCATATGCGGTGTGAAATACCGCACAGATG CGTAAGGAGAAAATACCGCATCAGGCGCCATTCGCCATTCAGGCTGCGCA ACTGTTGGGAAGGGCGATCGGTGCGGGCCTCTTCGCTATTACGCCAGCTG GCGAAAGGGGGATGTGCTGCAAGGCGATTAAGTTGGGTAACGCCAGGGTT TTCCCAGTCACGACGTTGTAAAACGACGGCCAGTGAATTCGAGCTCGGTA CCTCGCGAATGCATGCGGCCGCCGTTACATAACTTACGGTAAATGGCCCG CCTGGCTGACCGCCCAACGACCCCCGCCCATTGACGTCAATAATGACGTA TGTTCCCATAGTAACGCCAATAGGGACTTTCCATTGACGTCAATGGGTGG AGTATTTACGGTAAACTGCCCACTTGGCAGTACATCAAGTGTATCATATG CCAAGTACGCCCCCTATTGACGTCAATGACGGTAAATGGCCCGCCTGGCA TTATGCCCAGTACATGACCTTATGGGACTTTCCTACTTGGCAGTACATCT ACGTATTAGTCATCGCTATTACCATGGTCGAGGTGAGCCCCACGTTCTGC TTCACTCTCCCCATCTCCCCCCCCTCCCCACCCCCAATTTTGTATTTATT TATTTTTTAATTATTTTGTGCAGCGATGGGGGCGGGGGGGGGGGGGGCGC GCGCCAGGCGGGGCGGGGCGGGGCGAGGGGCGGGGCGGGGCGAGGCGGAG AGGTGCGGCGGCAGCCAATCAGAGCGGCGCGCTCCGAAAGTTTCCTTTTA TGGCGAGGCGGCGGCGGCGGCGGCCCTATAAAAAGCGAAGCGCGCGGCGG GCGGGAGTC |
| 32. | pUC57-MHCK7-hBGi-DMD4-WPRE3-DTS | TCTGGATCCACTGCTTAAATACGGACGAGGACAGGGCCCTGTCTCCTCAG CTTCAGGCACCACCACTGACCTGGGACAGTGAATCGTAAGTACTAGCAGC TACAATCCAGCTACCATTCTGCTTTTATTTTATGGTTGGGATAAGGCTGG ATTATTCTGAGTCCAAGCTAGGCCCTTTTGCTAATCATGTTCATACCTCT TATCTTCCTCCCACAGCTCCTGGGCAACGTGCTGGTCTGTGTGCTGGCCC ATCACTTTGGCAAAGAATTGCGATCGCCACCATGCTTTGGTGGGAAGAAG TCGAGGACTGCTACGAGCGCGAGGACGTGCAGAAGAAAACCTTCACCAAA TGGGTCAACGCCCAGTTCAGCAAGTTCGGCAAGCAGCACATCGAGAACCT GTTCAGCGACCTGCAGGATGGCAGAAGGCTGCTGGATCTGCTGGAAGGCC TGACAGGACAGAAGCTGCCCAAAGAGAAGGGCAGCACAAGAGTGCACGCC CTGAACAACGTGAACAAGGCCCTGAGAGTGCTGCAGAACAACAACGTGGA CCTGGTCAACATCGGCAGCACCGACATCGTGGACGGCAACCACAAACTGA CCCTGGGCCTGATCTGGAACATCATCCTGCACTGGCAAGTGAAGAACGTG ATGAAGAACATCATGGCCGGCCTGCAGCAGACCAACAGCGAGAAGATTCT GCTGAGCTGGGTCCGACAGAGCACCCGGAATTACCCTCAAGTGAACGTGA TCAACTTCACCACCTCTTGGAGCGACGGACTGGCCCTGAATGCCCTGATC CACAGCCACAGACCTGACCTGTTCGACTGGAACAGCGTCGTGTGTCAGCA GAGCGCCACACAGAGGCTGGAACACGCCTTCAATATCGCCAGATACCAGC TGGGCATCGAGAAACTGCTGGACCCCGAGGATGTGGACACCACCTATCCT GACAAGAAATCCATCCTCATGTACATCACCAGCCTGTTCCAGGTGCTGCC CCAGCAGGTTTCCATCGAGGCCATTCAAGAGGTCGAGATGCTGCCCAGAC CTCCTAAAGTGACCAAAGAGGAACACTTCCAGCTGCACCACCAGATGCAC TACTCTCAGCAGATCACCGTGTCTCTGGCCCAGGGCTACGAGAGAACAAG CAGCCCCAAGCCTCGGTTCAAGAGCTACGCCTATACACAGGCCGCCTACG TGACCACCAGCGATCCTACAAGAAGCCCATTTCCTAGCCAGCATCTGGAA GCCCCTGAGGACAAGAGCTTTGGCAGCAGCCTGATGGAAAGCGAAGTGAA CCTGGACCGCTACCAGACAGCCCTGGAAGAGGTTCTGAGCTGGCTGCTGT |

-continued

| SEQ ID NO | Description | SEQ |
|---|---|---|
| | | CTGCCGAGGATACACTGCAGGCTCAGGGCGAGATCAGCAACGACGTGGAA |
| | | GTGGTCAAGGACCAGTTTCACACCCACGAGGGCTACATGATGGACCTGAC |
| | | AGCCCACCAGGGCAGAGTGGGCAATATTCTGCAGCTGGGCTCCAAGCTGA |
| | | TCGGCACAGGCAAGCTGAGCGAGGACGAAGAGACAGAGGTGCAAGAGCAG |
| | | ATGAACCTGCTGAACAGCAGATGGGAGTGTCTGAGAGTGGCCAGCATGGA |
| | | AAAGCAGAGCAACCTGCACCGGGTGCTGATGGATCTCCAGAACCAGAAGC |
| | | TGAAAGAGCTGAACGACTGGCTGACCAAGACCGAGGAACGGACCCGGAAG |
| | | ATGGAAGAGGAACCTCTGGGACCCGACCTGGAAGATCTGAAAAGACAGGT |
| | | GCAGCAGCATAAGGTGCTGCAAGAGGACCTCGAACAAGAGCAAGTGCGCG |
| | | TGAACAGCCTGACACACATGGTGGTGGTCGTGGATGAGAGCAGCGGAGAT |
| | | CATGCCACAGCCGCTCTGGAAGAACAGCTGAAGGTGCTGGGAGACAGATG |
| | | GGCCAATATCTGCCGGTGGACCGAGGATAGATGGGTGCTGCTCCAGGACA |
| | | TCCTGCTGAAGTGGCAGCGGCTGACAGAGGAACAGTGCCTGTTTAGCGCC |
| | | TGGCTGTCCGAGAAAGAGGACGCCGTCAACAAGATCCACACCACCGGCTT |
| | | CAAGGATCAGAATGAGATGCTGAGCAGCCTGCAGAAACTGGCCGTGCTGA |
| | | AGGCTGACCTGGAAAAGAAAAAGCAGTCCATGGGCAAGCTGTACTCCCTG |
| | | AAGCAGGACCTGCTGAGCACACTGAAGAACAAGTCTGTGACCCAGAAAAC |
| | | CGAGGCCTGGCTGGACAACTTCGCCCGGTGTTGGGATAACCTGGTGCAGA |
| | | AGCTGGAAAAGTCCACCGCTCAGATCTCTCAGGCCGTGACCACAACACAG |
| | | CCTTCTCTGACCCAGACCACCGTGATGGAAACAGTGACCACAGTGACAAC |
| | | CCGCGAGCAGATCCTGGTCAAGCACGCCCAAGAAGAACTGCCTCCTCCAC |
| | | CTCCTCAGAAGAAACGGCAGATCACAGTGGACAGCGAGATCCGGAAGAGA |
| | | CTGGACGTGGACATCACCGAGCTGCACAGCTGGATCACCAGATCCGAAGC |
| | | CGTGCTGCAGTCCCCTGAGTTCGCCATCTTCAGAAAAGAGGGCAACTTCT |
| | | CCGACCTGAAAGAGAAAGTCAACGCCATCGAGAGAGAGAAGGCCGAGAAG |
| | | TTCCGGAAGCTGCAGGACGCCTCTAGATCTGCCCAGGCTCTGGTGGAACA |
| | | GATGGTCAACGAAGGCGTGAACGCCGACAGCATCAAGCAGGCCTCAGAGC |
| | | AGCTGAACTCCCGGTGGATCGAGTTCTGTCAGCTCCTGAGCGAGAGACTG |
| | | AACTGGCTGGAATACCAGAACAATATCATTGCCTTCTACAACCAGCTCCA |
| | | GCAGCTCGAACAGATGACCACCACAGCCGAGAATTGGCTGAAGATCCAGC |
| | | CTACCACACCTAGCGAGCCCACCGCCATTAAGAGCCAGCTGAAAATCTGC |
| | | AAGGACGAAGTGAATCGGCTGAGCGATCTGCAGCCCCAGATCGAAAGACT |
| | | GAAAATCCAGTCTATCGCCCTCAAAGAGAAAGGACAGGGCCCCATGTTCC |
| | | TGGACGCCGATTTTGTGGCCTTTACCAACCACTTCAAACAGGTGTTCTCC |
| | | GACGTGCAGGCCCGGGAAAAAGAGCTGCAGACCATCTTCGACACCCTGCC |
| | | TCCAATGAGATACCAAGAGACAATGAGCGCCATCCGGACCTGGGTGCAGC |
| | | AAAGCGAGACAAAGCTGAGCATCCCACAGCTGAGCGTGACCGACTACGAG |
| | | ATCATGGAACAGAGACTGGGCGAACTGCAGGCCCTCCAGTCTAGCCTGCA |
| | | AGAACAGCAGTCCGGCCTGTACTACCTGAGCACAACCGTGAAAGAGATGA |
| | | GCAAGAAGGCCCCTAGCGAGATCTCCCGGAAGTACCAGAGCGAGTTCGAA |
| | | GAGATCGAAGGCCGGTGGAAGAAGCTGTCTAGCCAGCTGGTTGAGCACTG |
| | | CCAGAAACTCGAAGAACAAATGAACAAGCTGCGCAAGATCCAGAATCACA |
| | | TCCAGACGCTGAAGAAATGGATGGCCGAGGTGGACGTGTTCCTGAAAGAA |
| | | GAGTGGCCCGCTCTGGGCGACTCCGAGATTCTGAAGAAACAGCTCAAACA |
| | | GTGCCGGCTGCTGGTGTCCGATATCCAGACAATCCAGCCAAGCCTGAACT |
| | | CCGTGAATGAAGGCGGCCAGAAGATCAAGAACGAGGCCGAGCCTGAGTTT |
| | | GCCAGCAGACTGGAAACCGAACTGAAAGAACTCAACACCCAGTGGGACCA |
| | | CATGTGCCAGCAAGTGTACGCCCGGAAAGAGGCCCTGAAAGGCGGACTCG |
| | | AAAAGACTGTGTCTCTGCAGAAAGACCTGTCTGAGATGCACGAGTGGATG |
| | | ACCCAGGCCGAAGAGGAATACCTGGAACGGGACTTCGAGTACAAGACCCC |
| | | TGATGAGCTGCAAAAAGCCGTCGAGGAAATGAAGCGGGCCAAAGAAGAGG |
| | | CCCAGCAGAAAGAAGCCAAAGTCAAGCTGCTGACCGAGTCCGTGAATAGC |
| | | GTTATCGCTCAGGCCCCTCCTGTGGCTCAAGAGGCTCTCAAGAAAGAACT |
| | | GGAAACTCTGACCACCAACTACCAGTGGCTGTGCACCAGACTGAACGGCA |
| | | AGTGCAAGACACTGGAAGAAGTGTGGGCCTGCTGGCACGAACTGCTGTCC |
| | | TATCTGGAAAAGGCCAACAAGTGGCTGAACGAGGTGGAATTCAAGCTGAA |
| | | AACCACCGAGAACATCCCTGGCGGCGCTGAAGAGATTAGCGAGGTGCTGG |
| | | ACAGCCTGGAAAACCTGATGAGACACAGCGAGGACAACCCCAATCAGATC |
| | | AGAATCCTGGCTCAGACCCTGACCGATGGCGGCGTGATGGACGAGCTGAT |
| | | CAACGAGGAACTCGAAACCTTCAACAGCCGGTGGCGGGAACTGCACGAGG |
| | | AAGCTGTTCGGAGGCAGAAGTTGCTGGAACAGTCTATCCAGAGCGCACAA |
| | | GAAACCGAGAAGTCCCTGCACCTGATCCAAGAGAGCCTGACCTTCATCGA |
| | | CAAGCAGCTGGCCGCTTATATCGCCGACAAGGTGGACGCTGCTCAGATGC |
| | | CCCAAGAGGCACAGAAGATTCAGAGCGACCTGACCAGCCACGAGATTAGC |
| | | CTGGAAGAAATGAAGAAGCACAACCAGGGCAAAGAGGCCGCTCAGAGAGT |
| | | CCTGAGCCAGATCGATGTGGCACAGAAAAAGCTCCAGGATGTGTCCATGA |
| | | AGTTTCGGCTGTTTCAGAAGCCCGCCAACTTCGAGCAGAGACTGCAAGAG |
| | | TCCAAGATGATCCTGGACGAAGTCAAAATGCATCTGCCCGCACTGGAAAC |
| | | AAAGTCCGTGGAACAAGAAGTGGTGCAGTCCCAGCTGAACCACTGCGTGA |
| | | ACCTGTACAAGAGCCTGTCCGAAGTGAAGTCTGAGGTGGAAATGGTCATC |
| | | AAGACCGGCAGGCAGATCGTCCAGAAGAAGCAGACCGAGAATCCCAAAGA |
| | | ACTCGACGAGAGAGTGACCGCTCTGAAGCTGCACTACAATGAGCTGGGCG |
| | | CCAAAGTGACCGAGCGGAAGCAACAGCTTGAGAAGTGCCTGAAACTGTCT |
| | | CGGAAGATGCGGAAAGAAATGAACGTGCTGACAGAGTGGCTGGCCGCCAC |
| | | CGATATGGAACTGACTAAGAGAAGCGCCGTGGAAGGCATGCCCAGCAACC |

-continued

| SEQ ID NO | Description | SEQ |
|---|---|---|
| | | TGGATAGTGAAGTGGCCTGGGGCAAAGCCACTCAGAAAGAGATTGAGAAG |
| | | CAGAAGGTCCACCTGAAGTCCATCACCGAAGTGGGCGAAGCCCTGAAAAC |
| | | CGTGCTGGGAAAGAAAGAGACACTGGTCGAGGACAAGCTGTCCCTGCTGA |
| | | ATTCCAACTGGATCGCCGTGACCTCCAGAGCTGAGGAATGGCTGAATCTG |
| | | CTGCTTGAGTACCAGAAACACATGGAAACGTTCGACCAGAACGTCGACCA |
| | | CATCACAAAGTGGATCATCCAGGCTGATACCCTGCTGGACGAGTCCGAGA |
| | | AGAAGAAACCCCAACAAAAAGAAGATGTGCTGAAGCGGCTGAAAGCCGAG |
| | | CTGAATGACATCCGGCCTAAGGTGGACAGCACCAGAGATCAGGCAGCCAA |
| | | CCTGATGGCCAACAGAGGCGACCACTGTCGGAAGCTCGTGGAACCTCAGA |
| | | TCAGCGAGCTTAACCACAGATTTGCCGCCATCAGCCACCGGATCAAGACA |
| | | GGCAAGGCCAGCATTCCTCTCAAAGAGCTTGAGCAGTTCAACAGCGACAT |
| | | CCAAAAGCTGCTCGAACCCCTGGAAGCCGAGATCCAACAGGGCGTCAACC |
| | | TCAAAGAAGAAGATTTCAACAAGGACATGAACGAGGACAATGAGGGCACC |
| | | GTCAAAGAACTGCTGCAGCGGGGCGATAATCTGCAGCAGCGGATTACCGA |
| | | TGAGCGCAAGCGGGAAGAGATCAAGATTAAGCAGCAGCTGCTGCAGACCA |
| | | AGCACAACGCCCTGAAGGACCTGCGGAGCCAGAGAAGAAAGAAGGCCCTG |
| | | GAAATCAGCCACCAGTGGTATCAGTACAAGCGGCAGGCCGACGACCTGCT |
| | | GAAGTGCCTGGATGACATCGAGAAGAAGCTGGCCTCTCTGCCCGAGCCTA |
| | | GGGACGAGAGAAAGATCAAAGAGATCGACCGCGAGCTGCAGAAAAAGAAA |
| | | GAGGAACTGAACGCCGTCCGCAGACAGGCCGAAGGACTTTCTGAAGATGG |
| | | CGCCGCTATGGCCGTGGAACCCACACAGATTCAGCTGAGCAAGCGGTGGC |
| | | GGGAAATCGAGAGCAAGTTCGCCCAGTTCCGGCGGCTGAATTTCGCCCAG |
| | | ATCCACACCGTGCGGGAAGAGACAATGATGGTCATGACAGAGGACATGCC |
| | | CCTTGAGATCAGCTACGTGCCCAGCACCTACCTGACCGAGATCACCCATG |
| | | TGTCTCAGGCCCTGCTGGAAGTGGAACAGCTGCTGAATGCCCCTGACCTG |
| | | TGCGCCAAGGACTTCGAGGACCTGTTCAAGCAAGAGGAAAGCCTGAAGAA |
| | | CATCAAGGACAGCCTGCAGCAGAGCAGCGGCCGGATCGATATCATCCACA |
| | | GCAAGAAAACCGCCGCACTGCAGAGCGCCACACCTGTGGAAAGAGTGAAG |
| | | CTGCAAGAGGCCCTGAGCCAGCTGGATTTCCAGTGGGAGAAAGTGAACAA |
| | | GATGTACAAGGACCGGCAGGGCAGATTCGACCGCAGCGTTGAAAAGTGGC |
| | | GGCGGTTCCACTACGACATCAAGATCTTCAACCAGTGGCTGACCGAGGCC |
| | | GAGCAGTTCCTGAGAAAGACACAGATCCCCGAGAACTGGGAGCACGCCAA |
| | | GTACAAGTGGTATCTGAAAGAGCTGCAGGACGGCATCGGCCAGAGACAGA |
| | | CAGTCGTGCGGACACTGAATGCCACCGGCGAGGAAATCATCCAGCAGTCC |
| | | AGCAAGACCGACGCCAGCATCCTGCAAGAGAAGCTGGGCAGCCTGAACCT |
| | | GCGGTGGCAAGAAGTGTGCAAGCAGCTGAGCGACCGGAAGAAGCGGCTGG |
| | | AAGAACAGAAGAATATCCTGAGCGAGTTCCAGCGGGACCTGAACGAGTTC |
| | | GTGCTGTGGCTCGAAGAGGCCGACAATATCGCCAGCATTCCCCTGGAACC |
| | | TGGCAAAGAGCAGCAGCTGAAAGAAAAGCTGGAACAAGTGAAACTGCTGG |
| | | TCGAGGAACTGCCCCTGAGACAGGGAATCCTGAAACAGCTGAACGAGACA |
| | | GGCGGCCCTGTGCTGGTGTCTGCCCCTATTTCTCCCGAGGAACAGGACAA |
| | | GCTGGAAAACAAGCTGAAGCAGACCAACCTGCAGTGGATCAAGGTGTCCA |
| | | GAGCACTGCCTGAGAAGCAGGGCGAGATCGAGGCCCAGATCAAGGACCTG |
| | | GGACAGCTCGAAAAGAAGCTTGAGGACCTCGAAGAACAGCTCAACCATCT |
| | | GCTGCTTTGGCTGAGCCCCATCCGGAACCAGCTGGAAATCTACAACCAGC |
| | | CTAATCAAGAGGGCCCCTTCGACGTGAAAGAAACCGAGATTGCCGTGCAG |
| | | GCCAAGCAGCCCGATGTGGAAGAGATCCTGTCTAAGGGCCAGCACCTGTA |
| | | CAAAGAGAAGCCCGCCACACAGCCCGTGAAGCGGAAACTGGAAGATCTGA |
| | | GCAGCGAGTGGAAGGCCGTGAACCGGCTGCTGCAAGAACTGAGAGCCAAA |
| | | CAGCCTGATCTGGCCCCTGGCCTGACAACAATTGGCGCCTCTCCTACACA |
| | | GACCGTGACACTGGTCACACAGCCTGTGGTCACCAAAGAGACAGCCATCA |
| | | GCAAACTGGAAATGCCCAGCAGTCTGATGCTCGAAGTGCCCGCACTGGCC |
| | | GACTTCAATAGAGCCTGGACCGAGCTGACCGACTGGCTCAGTCTGCTGGA |
| | | CCAAGTCATCAAGTCCCAGAGAGTGATGGTCGGAGATCTTGAGGACATCA |
| | | ACGAGATGATCATTAAGCAGAAAGCCACCATGCAGGACCTTGAGCAGAGA |
| | | AGGCCCCAGCTTGAAGAACTGATCACCGCCGCTCAGAACCTGAAAAACAA |
| | | GACCAGCAATCAAGAAGCCCGGACCATCATCACCGACCGGATCGAGAGAA |
| | | TCCAGAACCAGTGGGACGAAGTGCAAGAGCATCTGCAGAACAGACGGCAG |
| | | CAGCTCAATGAGATGCTGAAGGACAGCACACAGTGGCTGGAAGCCAAAGA |
| | | AGAAGCCGAGCAGGTTCTCGGACAGGCCAGAGCTAAGCTGGAATCTTGGA |
| | | AAGAGGGACCCTACACCGTCGACGCCATCCAGAAGAAGATCACCGAGACA |
| | | AAGCAGCTGGCCAAGGATCTGAGACAGTGGCAGACCAATGTGGACGTGGC |
| | | CAACGACCTGGCTCTGAAGCTGCTGAGAGACTACAGCGCCGACGACACCA |
| | | GAAAGGTGCACATGATCACCGAAAACATCAACGCCTCTTGGCGGAGCATC |
| | | CACAAGCGGGTGTCAGAGAGAGAAGCCGCTCTGGAAGAAACACATAGACT |
| | | GCTCCAGCAGTTCCCACTCGACCTGGAAAAGTTCCTGGCCTGGCTGACAG |
| | | AAGCCGAAACCACCGCTAACGTGCTCCAGGATGCCACCAGAAAAGAGCGG |
| | | CTGTTGGAGGACAGCAAGGGCGTCAAAGAACTCATGAAGCAGTGGCAGGA |
| | | TCTGCAAGGGGAGATTGAAGCCCACACCGACGTGTACCACAACCTGGACG |
| | | AGAACAGCCAGAAGATCCTGCGGTCCCTGGAAGGCTCTGATGATGCTGTG |
| | | CTGCTTCAGAGGCGGCTGGACAACATGAACTTCAAGTGGAGCGAGCTGCG |
| | | GAAGAAGTCCCTGAACATCAGAAGCCACCTGGAAGCCTCCAGCGACCAGT |
| | | GGAAAAGACTGCACCTGTCTCTCCAAGAGCTGCTCGTGTGGCTGCAGCTG |
| | | AAGGATGACGAGCTGAGTAGACAGGCCCCTATCGGCGGAGATTTTCCCGC |
| | | CGTGCAGAAACAGAACGACGTGCACCGGGCCTTCAAGAGAGAGCTGAAAA |

-continued

| SEQ ID NO | Description | SEQ |
|---|---|---|
| | | CAAAAGAACCCGTCATCATGAGCACCCTGGAAACCGTGCGGATCTTTCTG<br>ACCGAGCAGCCTCTGGAAGGACTGGAAAAGCTGTACCAAGAGCCTAGAGA<br>GCTGCCTCCTGAAGAAAGGGCCCAGAACGTGACACGGCTGCTTAGAAAGC<br>AGGCCGAGGAAGTGAACACCGAATGGGAGAAGCTGAACCTCCACTCCGCC<br>GACTGGCAGCGGAAGATCGATGAGACACTGGAACGGCTGCGGGAACTGCA<br>AGAAGCCACAGACGAGCTGGACCTGAAACTGCGGCAGGCTGAAGTGATCA<br>AAGGCTCCTGGCAGCCAGTGGGCGATCTGCTGATCGATAGCCTGCAGGAC<br>CATCTGGAAAAAGTCAAGGCCCTGCGGGGAGAGATCGCCCCTCTCAAAGA<br>AAACGTGTCCCACGTGAACGATCTGGCCAGGCAGCTGACAACACTGGGCA<br>TCCAGCTGAGCCCTTACAACCTGTCTACCTTGGAGGACCTGAATACCCGG<br>TGGAAGCTGCTCCAAGTGGCCGTCGAGGATAGAGTGCGGCAGCTGCATGA<br>GGCTCACAGAGATTTTGGACCCGCCAGCCAGCACTTCCTGAGCACATCTG<br>TTCAAGGCCCCTGGGAGAGAGCTATCAGCCCTAACAAGGTGCCCTACTAC<br>ATCAACCACGAGACACAGACCACCTGTTGGGATCACCCCAAGATGACCGA<br>ACTGTATCAGTCCCTGGCCGACCTGAACAACGTGCGGTTTAGCGCCTACC<br>GGACCGCCATGAAGCTGCGCAGACTGCAGAAAGCTCTGTGCCTGGACCTG<br>CTGTCTCTGAGCGCTGCTTGTGATGCCCTGGACCAGCATAACCTCAAGCA<br>GAACGACCAGCCTATGGACATCCTGCAGATCATCAACTGCCTGACCACCA<br>TCTACGACCGGCTCGAACAAGAGCACAACAACCTGGTCAACGTGCCCCTG<br>TGCGTGGACATGTGCCTGAATTGGCTGCTGAACGTGTACGACACCGGCAG<br>AACCGGCAGGATCAGAGTGCTGAGCTTCAAGACCGGCATCATCTCCCTGT<br>GCAAGGCCCACCTTGAGGATAAGTACCGCTACCTGTTTAAGCAGGTCGCC<br>AGCAGCACCGGCTTTTGCGACCAAAGAAGGCTGGGACTGCTGCTCCACGA<br>CAGCATTCAGATCCCTAGACAGCTGGGCGAAGTGGCCTCTTTCGGCGGCT<br>CTAATATCGAGCCTAGCGTGCGGAGCTGCTTCCAGTTCGCCAACAACAAG<br>CCCGAGATTGAGGCCGCACTGTTCCTGGACTGGATGAGACTGGAACCCCA<br>GAGCATGGTCTGGCTGCCTGTGCTGCATAGAGTGGCCGCAGCCGAAACAG<br>CCAAGCACCAGGCCAAGTGCAACATCTGCAAAGAGTGCCCCATCATCGGC<br>TTCCGGTACAGATCCCTGAAGCACTTCAACTACGATATCTGCCAGTCCTG<br>CTTCTTCAGCGGCAGAGTGGCCAAGGGCCACAAGATGCACTACCCCATGG<br>TGGAATACTGCACCCCTACCACCTCTGGCGAGGACGTGCGGGATTTTGCC<br>AAGGTGCTCAAGAACAAGTTCCGGACCAAGCGCTACTTCGCTAAGCACCC<br>CAGAATGGGCTACCTGCCAGTGCAGACAGTGCTTGAGGGCGACAACATGG<br>AAACCCCTGTGACTCTGATCAACTTCTGGCCCGTGGATAGCGCCCCTGCT<br>AGTTCTCCTCAGCTGTCTCACGACGATACCCACAGCAGAATCGAGCACTA<br>CGCCTCCAGACTGGCCGAGATGGAAAACAGCAACGGCAGCTACCTGAATG<br>ACAGCATCAGCCCCAACGAGAGCATCGACGACGAACATCTGCTCATTCAG<br>CACTACTGCCAGAGCCTGAATCAGGACAGCCCTCTGTCTCAGCCTAGAAG<br>CCCTGCACAGATCCTGATCAGCCTGGAAAGCGAGGAACGCGGCGAGCTGG<br>AAAGAATCCTGGCAGACCTGGAAGAGGAAAACCGGAACCTGCAGGCCGAA<br>TACGACAGACTCAAGCAGCAGCACGAGCACAAGGGACTGTCTCCACTGCC<br>TTCTCCACCTGAAATGATGCCCACCTCTCCACAGAGCCCCAGAGATGCCG<br>AGCTGATTGCCGAAGCCAAACTGCTGAGGCAGCACAAAGGCAGACTCGAA<br>GCCAGAATGCAGATTCTCGAAGATCACAACAAGCAGCTCGAATCCCAGCT<br>GCACAGACTTAGGCAGCTGCTGGAACAGCCTCAGGCAGAGGCCAAAGTGA<br>ATGGCACCACCGTGTCTAGCCCTAGCACAAGCCTGCAGAGATCCGACAGC<br>AGCCAGCCAATGCTTCTGAGAGTCGTGGGCTCCCAGACCAGCGATTCTAT<br>GGGCGAAGAGGACCTGCTCAGCCCTCCTCAGGATACAAGCACCGGCCTGG<br>AAGAAGTGATGGAACAACTGAACAACAGCTTCCCCAGCAGCAGAGGCAGA<br>AACACCCCTGGCAAGCCCATGCGCGAGGACACCATGTGATAACTCGAGAA<br>TCAACCTCTGGATTACAAAATTTGTGAAAGATTGACTGGTATTCTTAACT<br>ATGTTGCTCCTTTTACGCTATGTGGATACGCTGCTTTAATGCCTTTGTAT<br>CATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTG<br>GCGTGGTGTGCACTGTGTTTGCTGACGCAACCCCCACTGGTTGGGGCATT<br>GCCACCACCTGTCAGCTCCTTTCCGGGACTTTCGCTTTCCCCCTCCCTAT<br>TGCCACGGCGGAACTCATCGCCGCCTGCCTTGCCCGCTGCTGGACAGGGG<br>CTCGGCTGTTGGGCACTGACAATTCCGTGGGGTGTGCCTTCTAGTTGCCA<br>GCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAA<br>GGGGGAGGATTGGGAAGACAATAGCAGGCATGCTGGGGATGCGGTGGGCT<br>CTATGGGAAGATGTCTACTGAGCTGTGCGATCCCTGCTGGGGACTTTCCG<br>CTGGGGACTTTCCGCTGGGGACTTTCCGCCTTCAGCTAAGGAAGCTACCA<br>ATATTTAGAGGTACATTTTGTTCTAGAACAAAATGTACCGGTACATTTTG<br>TTCTGGTACATTTTGTTCTATTAAGGACAACGTAAGTATAGCGCATAGAC<br>ACGTGGCGCCATCGGATCCCGGGCCCGTCGACTGCAGAGGCCTGCATGCA<br>AGCTTGGCGTAATCATGGTCATAGCTGTTTCCTGTGTGAAATTGTTATCC<br>GCTCACAATTCCACACAACATACGAGCCGGAAGCATAAAGTGTAAAGCCT<br>GGGGTGCCTAATGAGTGAGCTAACTCACATTAATTGCGTTGCGCTCACTG<br>CCCGCTTTCCAGTCGGGAAACCTGTCGTGCCAGCTGCATTAATGAATCGG<br>CCAACGCGCGGGGAGAGGCGGTTTGCGTATTGGGCGCTCTTCCGCTTCCT<br>CGCTCACTGACTCGCTGCGCTCGGTCGTTCGGCTGCGGCGAGCGGTATCA<br>GCTCACTCAAAGGCGGTAATACGGTTATCCACAGAATCAGGGGATAACGC<br>AGGAAAGAACATGTGAGCAAAAGGCCAGCAAAAGGCCAGGAACCGTAAAA |

-continued

| SEQ ID NO | Description | SEQ |
|---|---|---|
| | | AGGCCGCGTTGCTGGCGTTTTTCCATAGGCTCCGCCCCCCTGACGAGCAT CACAAAAATCGACGCTCAAGTCAGAGGTGGCGAAACCCGACAGGACTATA AAGATACCAGGCGTTTCCCCCTGGAAGCTCCCTCGTGCGCTCTCCTGTTC CGACCCTGCCGCTTACCGGATACCTGTCCGCCTTTCTCCCTTCGGGAAGC GTGGCGCTTTCTCATAGCTCACGCTGTAGGTATCTCAGTTCGGTGTAGGT CGTTCGCTCCAAGCTGGGCTGTGTGCACGAACCCCCCGTTCAGCCCGACC GCTGCGCCTTATCCGGTAACTATCGTCTTGAGTCCAACCCGGTAAGACAC GACTTATCGCCACTGGCAGCAGCCACTGGTAACAGGATTAGCAGAGCGAG GTATGTAGGCGGTGCTACAGAGTTCTTGAAGTGGTGGCCTAACTACGGCT ACACTAGAAGAACAGTATTTGGTATCTGCGCTCTGCTGAAGCCAGTTACC TTCGGAAAAAGAGTTGGTAGCTCTTGATCCGGCAAACAAACCACCGCTGG TAGCGGTGGTTTTTTTGTTTGCAAGCAGCAGATTACGCGCAGAAAAAAAG GATCTCAAGAAGATCCTTTGATCTTTTCTACGGGGTCTGACGCTCAGTGG AACGAAAACTCACGTTAAGGGATTTTGGTCATGAGATTATCAAAAAGGAT CTTCACCTAGATCCTTTTAAATTAAAAATGAAGTTTTAAATCAATCTAAA GTATATATGAGTAAACTTGGTCTGACAGTTACCAATGCTTAATCAGTGAG GCACCTATCTCAGCGATCTGTCTATTTCGTTCATCCATAGTTGCCTGACT CCCCGTCGTGTAGATAACTACGATACGGGAGGGCTTACCATCTGGCCCCA GTGCTGCAATGATACCGCGAGACCCACGCTCACCGGCTCCAGATTTATCA GCAATAAACCAGCCAGCCGGAAGGGCCGAGCGCAGAAGTGGTCCTGCAAC TTTATCCGCCTCCATCCAGTCTATTAATTGTTGCCGGGAAGCTAGAGTAA GTAGTTCGCCAGTTAATAGTTTGCGCAACGTTGTTGCCATTGCTACAGGC ATCGTGGTGTCACGCTCGTCGTTTGGTATGGCTTCATTCAGCTCCGGTTC CCAACGATCAAGGCGAGTTACATGATCCCCCATGTTGTGCAAAAAAGCGG TTAGCTCCTTCGGTCCTCCGATCGTTGTCAGAAGTAAGTTGGCCGCAGTG TTATCACTCATGGTTATGGCAGCACTGCATAATTCTCTTACTGTCATGCC ATCCGTAAGATGCTTTTCTGTGACTGGTGAGTACTCAACCAAGTCATTCT GAGAATAGTGTATGCGGCGACCGAGTTGCTCTTGCCCGGCGTCAATACGG GATAATACCGCGCCACATAGCAGAACTTTAAAAGTGCTCATCATTGGAAA ACGTTCTTCGGGGCGAAAACTCTCAAGGATCTTACCGCTGTTGAGATCCA GTTCGATGTAACCCACTCGTGCACCCAACTGATCTTCAGCATCTTTTACT TTCACCAGCGTTTCTGGGTGAGCAAAAACAGGAAGGCAAAATGCCGCAAA AAAGGGAATAAGGGCGACACGGAAATGTTGAATACTCATACTCTTCCTTT TTCAATATTATTGAAGCATTTATCAGGGTTATTGTCTCATGAGCGGATAC ATATTTGAATGTATTTAGAAAAATAAACAAATAGGGGTTCCGCGCACATT TCCCCGAAAAGTGCCACCTGACGTCTAAGAAACCATTATTATCATGACAT TAACCTATAAAAATAGGCGTATCACGAGGCCCTTTCGTCTCGCGCGTTTC GGTGATGACGGTGAAAACCTCTGACACATGCAGCTCCCGGAGACGGTCAC AGCTTGTCTGTAAGCGGATGCCGGGAGCAGACAAGCCCGTCAGGGCGCGT CAGCGGGTGTTGGCGGGTGTCGGGGCTGGCTTAACTATGCGGCATCAGAG CAGATTGTACTGAGAGTGCACCATATGCGGTGTGAAATACCGCACAGATG CGTAAGGAGAAAATACCGCATCAGGCGCCATTCGCCATTCAGGCTGCGCA ACTGTTGGGAAGGGCGATCGGTGCGGGCCTCTTCGCTATTACGCCAGCTG GCGAAAGGGGGATGTGCTGCAAGGCGATTAAGTTGGGTAACGCCAGGGTT TTCCCAGTCACGACGTTGTAAAACGACGGCCAGTGAATTCGAGCTCGGTA CCTCGCGAATGCATCTAGAAGCTGCATGTCTAAGCTAGACCCTTCAGATT AAAAATAACTGAGGTAAGGGCCTGGGTAGGGGAGGTGGTGTGAGACGCTC CTGTCTCTCCTCTATCTGCCCATCGGCCCTTTGGGGAGGAGGAATGTGCC CAAGGACTAAAAAAAGGCCATGGAGCCAGAGGGGCGAGGGCAACAGACCT TTCATGGGCAAACCTTGGGGCCCTGCTGTCTAGCATGCCCCACTACGGGT CTAGGCTGCCCATGTAAGGAGGCAAGGCCTGGGGACACCCGAGATGCCTG GTTATAATTAACCCAGACATGTGGCTGCCCCCCCCCCCCCAACACCTGCT GCCTCTAAAAATAACCCTGTCCCTGGTGGATCCCCTGCATGCGAAGATCT TCGAACAAGGCTGTGGGGGACTGAGGGCAGGCTGTAACAGGCTTGGGGGC CAGGGCTTATACGTGCCTGGGACTCCCAAAGTATTACTGTTCCATGTTCC CGGCGAAGGGCCAGCTGTCCCCCGCCAGCTAGACTCAGCACTTAGTTTAG GAACCAGTGAGCAAGTCAGCCCTTGGGGCAGCCCATACAAGGCCATGGGG CTGGGCAAGCTGCACGCCTGGGTCCGGGGTGGGCACGGTGCCCGGGCAAC GAGCTGAAAGCTCATCTGCTCTCAGGGGCCCCTCCCTGGGGACAGCCCCT CCTGGCTAGTCACACCCTGTAGGCTCCTCTATATAACCCAGGGGCACAGG GGCTGCCCTCATTCTACCACCACCTCCACAGCAC |
| 33. | NP-MHCK7-hBGi-mafaDMD | AGCTCGGTACCTCGCGAATGCATCTAGAAGCTGCATGTCTAAGCTAGACC CTTCAGATTAAAAATAACTGAGGTAAGGGCCTGGGTAGGGGAGGTGGTGT GAGACGCTCCTGTCTCTCCTCTATCTGCCCATCGGCCCTTTGGGGAGGAG GAATGTGCCCAAGGACTAAAAAAAGGCCATGGAGCCAGAGGGGCGAGGGC AACAGACCTTTCATGGGCAAACCTTGGGGCCCTGCTGTCTAGCATGCCCC ACTACGGGTCTAGGCTGCCCATGTAAGGAGGCAAGGCCTGGGGACACCCG AGATGCCTGGTTATAATTAACCCAGACATGTGGCTGCCCCCCCCCCCCCA ACACCTGCTGCCTCTAAAAATAACCCTGTCCCTGGTGGATCCCCTGCATG CGAAGATCTTCGAACAAGGCTGTGGGGGACTGAGGGCAGGCTGTAACAGG CTTGGGGGCCAGGGCTTATACGTGCCTGGGACTCCCAAAGTATTACTGTT CCATGTTCCCGGCGAAGGGCCAGCTGTCCCCCGCCAGCTAGACTCAGCAC TTAGTTTAGGAACCAGTGAGCAAGTCAGCCCTTGGGGCAGCCCATACAAG GCCATGGGGCTGGGCAAGCTGCACGCCTGGGTCCGGGGTGGGCACGGTGC |

-continued

| SEQ ID NO | Description | SEQ |
|---|---|---|
| | | CCGGGCAACGAGCTGAAAGCTCATCTGCTCTCAGGGGCCCCTCCCTGGGG<br>ACAGCCCCTCCTGGCTAGTCACACCCTGTAGGCTCCTCTATATAACCCAG<br>GGGCACAGGGGCTGCCCTCATTCTACCACCACCTCCACAGCACTCTGGAT<br>CCACTGCTTAAATACGGACGAGGACAGGGCCCTGTCTCCTCAGCTTCAGG<br>CACCACCACTGACCTGGGACAGTGAATCGTAAGTACTAGCAGCTACAATC<br>CAGCTACCATTCTGCTTTTATTTTATGGTTGGGATAAGGCTGGATTATTC<br>TGAGTCCAAGCTAGGCCCTTTTGCTAATCATGTTCATACCTCTTATCTTC<br>CTCCCACAGCTCCTGGGCAACGTGCTGGTCTGTGTGCTGGCCCATCACTT<br>TGGCAAAGAATTGCGATCGCCACCATGCTGTGGTGGGAGGAGGTGGAGGA<br>TTGCTACGAGAGGGAAGATGTCCAGAAGAAAACCTTCACCAAGTGGGTGA<br>ACGCCCAGTTTAGCAAGTTCGGCAAGCAGCACATCGAGAACCTGTTTAGC<br>GACCTGCAGGACGGCAGAAGGCTGCTGGACCTCCTGGAGGGGCTGACCGG<br>CCAGAAGCTGCCCAAGGAAAAGGGCAGCACCAGGGTGCACGCCCTGAATA<br>ACGTGAACAAGGCCCTGAGAGTGCTGCAGAACAACAACGTGGACCTGGTG<br>AACATCGGCAGCACCGACATCGTGGACGGCAACCACAAGCTGACCCTGGG<br>CCTGATCTGGAATATCATCCTGCACTGGCAGGTGAAGAACGTGATGAAGA<br>ACATCATGGCCGGCCTGCAGCAGACCAACAGCGAGAAGATCCTGCTGAGC<br>TGGGTGAGACAGAGCACCAGGAACTACCCCCAGGTGAACGTGATCAACTT<br>CACCACCAGCTGGAGCGACGGGCTGGCCCTGAACGCCCTGATCCACAGCC<br>ACAGGCCCGACCTGTTCGACTGGAACAGCGTGGTGTGCCAACAGAGCGCC<br>ACGCAGAGGCTGGAGCACGCCTTCAACATCGCCAGATACCAGCTGGGCAT<br>CGAGAAGCTGTTGGACCCCGAGGACGTGGCCACCACCTACCCCGACAAGA<br>AGAGCATCCTGATGTACATCACCAGCCTGTTCCAGGTGCTGCCCCAGCAG<br>GTGAGCATCGAGGCCATCCAGGAGGTGGAGATGCTGCCCAGGCCCCCCAA<br>GGTGACAAAGGAGGAGCACTTCCAGCTGCACCACCAGATGCACTACAGCC<br>AGCAGATCACGGTGTCACTGGCCCAGGGCTACGAGAGGACCAGCAGCCCC<br>AAGCCCAGATTCAAGAGCTACGCCTACACCCAGGCCGCCTACGTGACCAC<br>CAGCGACCCCACCAGGTCCCCCTTCCCCAGCCAGCACCTGGAGGCCCCCG<br>AGGATAAGAGTTTCGGCAGCAGCCTCATGGAGAGCGAAGTGAACCTGGAC<br>AGATACCAGACCGCCCTCGAAGAGGTGCTGAGCTGGCTGCTGAGCGCCGA<br>GGATACCCTGCAGGCCCAGGGCGAGATCAGCAACGACGTGGAGGTGGTGA<br>AGGAGCAGTTCCACGCCCACGAGGGCTACATGATGGACCTGACCGCCCAC<br>CAGGGCAGGGTGGGCAACATCCTCCAACTGGGCAGCCAGCTGATCGGCAC<br>CGGCAAGCTGAGCGAGGACGAGGAGACTGAGGTGCAGGAGCAGATGAACC<br>TGCTGAACAGCAGGTGGGAGTGCCTGAGGGTGGCCAGCATGGAGAAACAG<br>TCCAACCTGCACAGGGTCCTGATGGACCTGCAGAACCAGAAGCTCAAGGA<br>ACTCAACGACTGGCTGACCAAGACCGAGGAGAGAACCAGGAAGATGGAGG<br>AGGAGCCCCTGGGCCCCGACCTGGAGGACCTGAAGAGGCAGGTGCAGCAG<br>CACAAGGTGCTGCAGGAGGATCTGGAGCAGGAACAGGTGAGGGTGAACAG<br>CCTGACCCACATGGTGGTGGTCGTGGACGAGAGCAGCGGCGACCATGCCA<br>CCGCCGCTCTGGAGGAGCAACTGAAGGTGCTGGGCGACAGATGGGCCAAC<br>ATCTGCAGATGGACCGAGGACAGGTGGGTGCTGCTCCAGGACATCCTCCT<br>GAAGTGGCAGAGGCTGACAGAGGAGCAGTGCCTGTTCAGCGCCTGGCTGA<br>GCGAGAAGGAGGACGTGGTGAACAGGATCCACACCACCGGCTTCAAGGAC<br>CAGAACGAGATGCTCAGCAGCCTGCAAAAGCTGGCCGTCCTGAAGGCCGA<br>CTTGGAGAAAAAGAAGCAGAGCATGGACAAGCTGTACAGCCTGAAGCAGG<br>ACCTCCTGAGCACCCTGAAGAACAAGAGTGTGACCCAGAAGATGGAGGCG<br>TGGCTGGAGAACTTCGCCAGGTGCTGGGACAACCTGGTGCAGAAGCTGGA<br>GAAGAGCACCGCCCAGATTAGCCAGGCCGTGACCACCACCCAGCCTAGCC<br>TGACCCAGACCACGGTGATGGAGACTGTGACCATGGTGACCACCAGGGAG<br>CAGATCCTGGTGAAGCACGCCCAGGAGGAACTCCCCCCCCCCCCGCCCCA<br>GAAGAAGAGACAGATCACCGTGGACTCCGAGATCAGGAAGAGGCTCGACG<br>TGGACATCACCGAACTGCATAGCTGGATCACCAGAAGCGAGGCCGTGCTG<br>CAGAGCCCCGAGTTCGCGATCTACAGGAAGGAGGGCAACTTCAGCGACCT<br>GAAGGAAAAGGTGAACGCCATCGAGAGGGAGAAGGCCGAGAAGTTCAGGA<br>AGCTCCAGGACGCCAGCAGGAGCGCCCAGGTGCTGGTGGAGCAGATGGTG<br>AACGAGGGGGTGAACGCCGACAGCATTAGGCAGGCCAGTGAGCAGCTGAA<br>TAGCAGGTGGATCGAGTTCTGCCAGCTGCTCAGCGAGAGGCTCAACTGGC<br>TGGAGTACCAGAACAACATTATCACCTTCTACAACCAGCTGCAGCAGCTG<br>GAGCAGATGACCACCACCGCCGAGAACTGGCTGAAGATCCAGCCCACCAC<br>CCCCAGCGAGCCCACCGCCATCAAGAGTCAGCTGAAGATCTGCAAGGACG<br>AGGTGAACAGACTGAGCGCCCTGCAGCCCCAGATCGAGAGACTCAAGATC<br>CAGTCCATCACCCTGAAGGAGAAGGGCCAGGGCCCCATGTTCCTGGACGC<br>CGACTTCGTGGCCTTCACCAACCACTTCAGCCAGGTGTTCAGCGACATGC<br>AGGCCAGGGAGAAGGAGCTGCAGACCATCTTCGACACCCTGCCCCCCATG<br>AGGTACCAAGAAACCATGAGCGCCATCAGGACCTGGGTGCAGCAGAGCGA<br>GACTAAGCTGAGCATCCCCCAGCTGAGCGTGACCGACTACGAGATCATGG<br>AGCAGAGACTGGGCGAGCTGCAGGTGCTGCAAAGCAGCCTGCAGGAGCAA<br>CAGAGCGGCCTGAACTACCTGAGCACCACCGTTAAGGAGATGAGCAAGAA<br>GGCCCCCAGCGAAATCAGCAGGAAGTACCAGCTGGAGTTCGAGGAAATCG<br>AGACAAGGTGGAAGAAGCTCTCCAGCCAGCTGGCCGAGCACTGCCAGAAG<br>TTGGAGGAGCAAATGAACAAGCTGAGAAAAATCCAGAACCACATCCAGAC<br>CCTGAAGAAGTGGATGGCCGAGGTGGACGTGTTCCTCAAGGAGGAGTGGC<br>CCGCCCTGGGCGACTCCGAGATTCTCAAAAAGCAGCTGAAGCAGTGTAGG<br>CTGCTGGTGAACGACATCCAGACCATCCAGCCCAGCCTGAACAGCGTGAA |

-continued

| SEQ ID NO | Description | SEQ |
|---|---|---|
| | | CGAGGGCGGCCAGAAGATCAAGAACGAGGCCGAGCCCGAGTTCGCCCTGA<br>GGCTGGAGATCGAGCTGAAGGAGCTGAACACCCAGTGGGACCACATGTGC<br>CAGCAGGTGTACGCCAGGAAGGAGGCCCTGAAGGGCGGCCTGGAAAAGAC<br>CGTGAGCCTGCAGAAGGACCTCAGCGAGATGCACGAGTGGATGACCCAGG<br>CCGAGGAGGAGTACCTGGAGAGGGACTTCGAGTACAAGACCCCCGACGAA<br>CTGCAGAAGGCCGTGGAAGAGATGAAGAGGGCCAAGGAGGAGGCCCAACA<br>AAAGGAGGCCAAGGTGAAGCTGCTGACAGAGAGCGTGAATAGCGTGATCG<br>CCCAGGCCCCTCCCGTGGCCCAGGAGGCGCTGAAGAAGGAACTGGAAACC<br>CTGACCACCAACTACCAGTGGCTGTGCACCAGGCTGAACGGCAAGTGCAA<br>GACCCTGGAGGAGGTGTGGGCCTGCTGGCACGAGCTGCTGAGCTACCTGG<br>AAAAGGCCAACAAGTGGCTGAACGAGGTGGAGTTCAAGCTGAAAACGACC<br>GAGAACATCCCCGGCGGCGCCGAGGAGATCAGCGAGGTGCTGCACAGCCT<br>GGAGAACCTGATGCAGCACAGCGAGGATAACCCCAACCAGATCAGGATCC<br>TGGCCCAGACCCTGACCGACGGCGGCGTGATGGACGAACTCATCAACGAG<br>GAGCTGGAAACCTTCAACTCCAGATGGAGGGAGCTGCACGAGGAGGCCGT<br>GAGGAGACAGAAGCTGCTCGAACAGAGCATCCAGAGCGCCCAGGAGATCG<br>AAAAGAGCCTGCACCTGATCCAGGAGAGCCTGACCTTCATCGACAAGCAG<br>CTGACCGCCTACATCGCCGACAAGGTGGACGCCGCCCAGATGCCCCAGGA<br>GGCCCAGAAGATCCAGAGCGACCTGACCAGCCACGAGATCAGCCTGGAGG<br>AGATGAAGAAGCACAACCAGGGCAAGGAGGCCGCCCAGAGGGTGCTGTCC<br>CAGATCGACGTGGCCCAGAAGAAGCTGCAGGACGTGAGCATGAAGTTCCG<br>GCTGTTCCAAAAGCCCGCGAACTTCGAACAGAGGCTGCAGGAGAGCAAGA<br>TGATCCTGGACGAGGTCAAGATGCACCTGCCCGCCCTGGAAACCAAGAGT<br>GTGGAGCAGGAGGTGGTGCAGAGCCAGCTCAACCACTGCGTGAACCTGTA<br>CAAGAGCCTGAGCGAGGTGAAGAGTGAGGTCGAGATGGTGATTAAGACCG<br>GGAGGCAGATCGTGCAGAAAAAGCAGACCGAGAACCCCAAAGAGCTGGAC<br>GAGAGGGTGACCGCCCTGAAACTGCACTACAACGAGCTGGGCGCCAAGGT<br>GACCGAGAGGAAGCAGCAGCTTGAGAAGTGCCTGAAGCTGTCCAGGAAGA<br>TGAGGAAGGAGATGAACGTGCTGACCGAGTGGCTGGCCGCCACCGACATG<br>GAGCTGACCAAGAGGAGCGCCGTGGAGGGGATGCCCAGCAACCTGGACAG<br>CGAGGTGGCCTGGGGCAAGGCCACCCAGAAGGAGATCGAGAAGCAGAAGG<br>TGCACCTGAAGAGTATCACCGAGGTGGGGGAGGCCCTCAAGACCGTGCTG<br>GGCAAGAAGGAGACACTGGTGGAGGATAAGCTGAGCCTCCTGAACAGCAA<br>CTGGATCGCCGTGACCAGCAGGGCCGAGGAGTGGCTGAACCTGCTGCTGG<br>AGTATCAAAAGCACATGGAGACATTCGACCAGAACGTGGACCACATCACC<br>AAGTGGATCATCCAGGCCGACACCCTGCTCGACGAGAGCGAAAAGAAGAA<br>GAGCCAGCAGAAGGAGGATGTGTTGAAGAGGCTGAAGGCCGAGCTGAACG<br>ACATCAGGCCCAAGGTGGACAGCACCAGGGACCAGGCCGCCAACCTGATG<br>GCCAACAGGGGCGACCACTGCAGGAAGCTGGTGGAGCCCCAGATCAGCGA<br>GCTGAACCACAGGTTCGCCGCCATCAGCCACAGGATCAAGACCGGCAAGG<br>CCAGTATCCCCCTCAAGGAGCTGGAGCAGTTCAACAGCGACATCCAGAAG<br>CTGCTGGAGCCTCTGGAGGCCGAGATCCAGCAGGGCGTGAACCTGAAGGA<br>GGAGGATTTCAACAAGGACATGAACGAGGATAACGAGGGCACCGTGAAGG<br>AGTTGCTCCAGAGGGGCGACAACCTGCAGCAGAGGATCACCGATGAGAGA<br>AAGAGGGAGGAGATCAAGATCAAGCAGCAACTGCTCCAGACCAAGCACAA<br>CGCCCTGAAGGACCTGAGATCCCAGAGGAGGAAGAAGGCCCTGGAGATCA<br>GCCACCAGTGGTACCAGTACAAGCGGCAGGCCGACGACCTGCTGAAGTGC<br>CTGGACGACATCGAGAAGAAGCTGGCCAGCCTGCCCGAGCCCAGGGACGA<br>GAGAAAGATTAAGGAGATCGACAGGGAGCTGCAGAAGAAGAAGGAGGAGC<br>TGAACGCCGTGAGGAGGCAGGCCGAGGGCCTGAGCGAAGATGGCGCCGCC<br>ATGGCCGTGGAGCCCACCCAGATCCAGCTGTCCAAGAGGTGGAGGGAGAT<br>CGAGAGCAAGTTCGCCCAATTCAGGAGGCTGAACTTCGCCCAGATCCACA<br>CCGTGAGGGAGGAAACCATGATGGTGATGACCGAGGATATGCCCCTGGAA<br>ATCAGCTACGTGCCCAGCACCTACCTGACCGAGATCACCCACGTGAGCCA<br>GGCCCTGAGCGAAGTGGAGCAGCTGCTGAACGCCCCCGACCTGTGCGCCA<br>AGGACTTCGAGGATCTGTTTAAGCAGGAGGAGAGCCTCAAGAACATCAAG<br>GACATCCTGCAGCAAAGCTCCGGCAGGATCGACATCATCCACAGCAAGAA<br>AACCGCCGCCCTGCAGAGCGCCACCCCCGTGGAGAGAGTCAAGCTGCAGG<br>AAGCCCTGAGCCAGATCGACTTCCAGTGGGAGAAGGTCAACAAGATGTAC<br>AAGGACAGACAGGGCAGGTTCGACAGAAGCGTGGAGAAGTGGAGGAGGTT<br>CCACTACGACATCAAGATCTTCAACCAGTGGCTGACCGAAGCCGAGCAGT<br>TCCTGAGGAAAACCCAGATCCCCGAGAACTGGGAGCACGCCAAGTACAAG<br>TGGTACCTGAAGGAACTCCAGGATGGCATCGGCCAGAGGCAGACCGTGGT<br>GAGGACCCTGAATGCCACCGGCGAGGAGATCATCCAGCAAAGCAGCAAGA<br>CCGACGCCAGCATCCTGCAGGAGAAACTCGGCAGCCTGAACCTGAGGTGG<br>CAGGAGGTGTGCAAGCAGCTGAGCGAGAGGAAGAAGAGGCTGGAGGAGCA<br>GAAGAACATCCTGAGCGAGTTCCAGAGGGACCTGAACGAGTTCGTGCTGT<br>GGCTGGAGGAGGCCGACAACATCGCCTCCATCCCCCTGGAGCCCGGCAAC<br>GAGCAACAGCTGAAAGAGAAGCTGGAGCAGGTCAAGCTGCTGGTGGAGGA<br>GCTGCCCCTGAGGCAGGGCATCCTGAAGCAGCTGAACGAAACCGGCGGCC<br>CCGTGCTGGTGAGCGCCCCCATCAGCCCCGAGGAGCAGGACAAGCTGGAG<br>AACAAGCTGAAGAGAACCAACCTGCAGTGGATCAAGGTGAGCAGGGCCCT<br>GCCCGAGAAGCAAGGCGAGATAGAGGCCCAGATCAAGGACCTGGGCCAAC<br>TGGAAAAGAAGCTGGAGGATCTCGAAGAACAGCTGAACCACCTGCTGCTG<br>TGGCTGAGCCCCATCAGGAACCAGCTGGAGATCTATAACCAGCCCAACCA |

-continued

| SEQ ID NO | Description | SEQ |
| --- | --- | --- |
| | | GGAGGGCCCCTTCGACATCAAGGAGACAGAGATCGCCGTGCAGGCCAAGC |
| | | AGCCCGACGTGGAGGGCATCCTGTCCAAGGGCCAGAGGCTGTACAAGGAG |
| | | AAGCCCGCCACACAGCCCGTGAAGAGAAAGCTGGAAGATCTCAGCAGCGA |
| | | GTGGAAAACCGTGAACCATCTGCTGCAGGAGCTGAGGGCCAAGCAACCCG |
| | | ACCTGGCCCCCGGCCTGACCACCGTGGGCGCTAGCCCCAGCCAGACCGTG |
| | | ACCCTGGTGACCCAGCCCGTGGTGACCAAGGAAACCGCCATCAGCAAGCT |
| | | GGAGATGCCCAGCAGCCTGATGCTGGAGGTGCCTGCCCTGGCCGACTTCA |
| | | ACAGGGCCTGGACCGAGCTGACAGAGTGGCTGAGCCTGCTGGGCAGGGTG |
| | | ATCAAGAGCCAGAGGGTGATGGTGGGCGACCTGGAAGATATCAACGAGAT |
| | | GATCATCAAGCAGAAGGCCACCGTGCAGGACCTGGAGCAGAGAAGGCCCC |
| | | AGCTGGAGGAGCTGATCACCGCCGCCCAGAACCTGAAGAATAAGACCAGC |
| | | AACCAGGAGGCCAGGACAATCATCACCGACAGAATCGAGAGGATCCAGAA |
| | | CCAGTGGGACGAAGTGCAGGAGCACCTGCAGAACAGGAGGCAGCAGCTCA |
| | | ACGAGATGCTGAAGGACAGCACCCAGTGGCTGGAAGCCAAGGAGGAAGCT |
| | | GAGCAGGTGCTGGGCCAGGCCAGGGCCAAGCTGGAGAGCTGGAAGGAAGG |
| | | CCCCTACACCATCGACGCCATCCAGAAGAAGATCACCGAAACCAAGCAGC |
| | | TGGCCAAGGACCTGAGGCAGTGGCAGATCAACGTGGACGTGGCCAACGAC |
| | | CTGGCCCTGAAGCTGCTGCGGGACTACAGCGCCGACGACACCAGGAAGGT |
| | | GCACATGATCACCGAAAACATCAACGCCAGCTGGGGGAGCATCCACAAGA |
| | | GGGTGAGCGAGCAGGAGGCCGCGCTGGAGGAAACCCACAGGCTGCTGCAG |
| | | CAGTTCCCCCTGGACCTCGAAAAGTTCCTGGCCTGGCTGACCGAGGCCGA |
| | | GACAACCGCCAACGTGCTGCAGGACGCTACCAGGAAGGAGAGGCTGCTGG |
| | | AGGATAGCAAGGGCGTGAAGGAACTCATGAAGCAGTGGCAGGACCTGCAG |
| | | GGCGAGATTGAGGCCCACACCGACGTGTACCACAACCTGGACGAGAACAG |
| | | CCAGAAGGTCCTGAGGAGCTTGGAGGGCAGCGACGACGCCGTGCTGCTGC |
| | | AGAGAAGGCTGGACAACATGAACTTCAAGTGGAGCGAGCTGAGGAAGAAG |
| | | TCCCTGAACATTAGAAGCCACCTGGAGGCTAGTAGCGACCAGTGGAAAAG |
| | | GCTGCACCTGAGCCTCCAGGAGCTGCTCGTGTGGCTGCAGCTGAAGGACG |
| | | ACGAGCTGAGCAGACAGACCCCCATCGGCGGCGACTTCCCCGCCGTGCAG |
| | | AAGCAGAACGACGTGCACAGGGCTTTCAAGAGGGAGCTGAAAACCAAGGA |
| | | GCCCGTGATCATGAGCACCCTGGAGACAGTGAGGATCTTCCTCACCGAGC |
| | | AGCCCCTGGAGGGCCTGGAGAAGCTGTACCAGGAGCCCAGGGAGCTGCCC |
| | | CCCGAGGAGAGAGCGCAGAACGTGACCAGACTGCTGAGGAAGCAGGCCGA |
| | | GGAAGTGAACACCGAGTGGGAGAAGCTGAACCTGCACAGCACCGACTGGC |
| | | AGAGGAAGATCGACGAAACCCTGGAGAGGCTGCAAGAGCTGCAGGAGGCC |
| | | ATGGACGAGCTGGACCTGAAACTGAGACAGGCCGAGGTGATCAAGGGCAG |
| | | CTGGCAGCCCGTCGGCGACCTGCTGATCGACAGCCTCCAGGACCACCTGG |
| | | AAAAAGTGAAGGCCCTGAGGGGCGAGATCGCCCCTCTGAAGGAGAACGTG |
| | | AGCCACGTGAACGACCTCGCCAGACAGCTGACCACCCTGGGCATCCAGCT |
| | | GAGCCCCTACAACCTCAGCACCCTGGAAGATCTGAACACCAGGTGGAAGC |
| | | TGCTGCAGGTGGCCGTCGAGGACAGGGTGAGGCAGCTCCACGAGGCCCAC |
| | | AGGGACTTCGGCCCCGCCAGCCAGCACTTCCTGAGCACCAGCGTGCAGGG |
| | | CCCCTGGGAGAGAGCCATCAGCCCGAACAAGGTGCCCTACTACATCAACC |
| | | ACGAAACCCAGACCACCTGCTGGGACCACCCCAAGATGACCGAGCTGTAC |
| | | CAGAGCCTGGCCGACCTGAACAATGTGAGATTCTCCGCCTACAGAACCGC |
| | | CATGAAGCTGAGGAGGCTCCAGAAGGCCCTGTGCCTGGACCTGCTGAGCC |
| | | TGAGCGCCGCCTGCGACGCCCTGGACCAGCACAACCTGAAGCAAAACGAC |
| | | CAGCCCATGGACATCCTCCAGATCATCAACTGCCTGACCACCATCTACGA |
| | | CAGACTGGAGCAGGAGCACAACAACCTGGTGAACGTGCCCCTGTGCGTGG |
| | | ACATGTGCCTGAACTGGCTGCTGAACGTGTACGACACCGGCAGGACCGGC |
| | | AGAATCAGAGTGCTGAGCTTCAAGACCGGGATCATCAGCCTGTGCAAGGC |
| | | CCACCTGGAGGACAAGTACAGGTACCTGTTCAAGCAGGTCAGCAGCAGCA |
| | | CCGGCTTCTGCGACCAGAGACGGCTGGGCCTGCTGCTGCACGACAGCATC |
| | | CAGATCCCCAGACAGCTGGGCGAGGTGGCCAGCTTCGGCGGCAGCAACAT |
| | | CGAGCCCAGCGTGAGAAGCTGCTTCCAGTTCGCCAACAACAAGCCCGAGA |
| | | TCGAGGCCGCCCTGTTCCTGGACTGGATGAGGCTGGAGCCCCAAAGCATG |
| | | GTGTGGCTGCCCGTGCTGCACAGGGTGGCCGCCGCCGAGACAGCCAAGCA |
| | | CCAGGCCAAGTGCAACATCTGCAAGGAGTGCCCCATCATCGGCTTCAGGT |
| | | ACAGGAGCCTGAAGCACTTCAACTACGACATCTGCCAGAGCTGCTTCTTC |
| | | AGCGGCAGGGTGGCCAAGGGCCACAAGATGCACTACCCCATGGTGGAGTA |
| | | CTGCACCCCCACCACCAGCGGCGAGGATGTGAGAGACTTCGCCAAGGTGC |
| | | TGAAAAACAAGTTCAGGACCAAGAGGTACTTCGCCAAGCACCCCAGAATG |
| | | GGCTACCTGCCCGTGCAGACCGTCCTGGAGGGCGACAACATGGAGACACC |
| | | CGTGACCCTGATCAACTTCTGGCCCGTGGACAGCGCCCCCGCCAGCAGCC |
| | | CTCAGCTGAGCCACGACGACACCCACAGCAGGATCGAGCACTACGCCAGC |
| | | AGGCTGGCCGAGATGGAGAACAGCAACGGCAGCTACCTGAACGACAGCAT |
| | | CAGCCCCAACGAGAGCATCGACGACGAGCACCTGCTGATCCAGCACTACT |
| | | GCCAGAGCCTGAACCAGGACAGCCCCCTGAGCCAGCCCAGGTCCCCCGCC |
| | | CAGATCCTGATCAGCCTCGAAAGCGAGGAGAGGGGCGAGCTGGAGAGAAT |
| | | CCTGGCCGATCTGGAGGAGGAGAACAGGAACCTGCAGGCCGAGTACGACA |
| | | GGCTGAAGCAGCAGCACGAGCACAAGGGCCTGAGCCCCCTGCCCAGCCCC |
| | | CCCGAGATGATGCCCACCAGCCCCCAGAGCCCCAGGGACGCCGAGCTGAT |
| | | CGCCGAGGCGAAGCTGCTGAGGCAGCACAAGGGCAGGCTGGAGGCCAGGA |
| | | TGCAGATCCTGGAGGACCACAACAAGCAGCTGGAGAGCCAGCTGCACAGA |
| | | CTGAGGCAGCTGCTTGAGCAGCCCCAGGCCGAAGCCAAGGTGAACGGCAC |

| SEQ ID NO | Description | SEQ |
|---|---|---|
| | | CACCGTCAGCAGCCCCAGCACCAGCCTGCAGAGGAGCGACAGCAGCCAGC |
| | | CCATGCTGCTGAGGGTGGTGGGCAGCCAGACCAGCGACAGCATGGGCGAG |
| | | GAGGATGTGCTGAGCCCCCCCCAGGACACCAGCACCGGCCTGGAGGAAGT |
| | | GATGGAGCAGCTGAACAACAGCTTCCCCAGCAGCAGGGGCAGGAACACCC |
| | | CCGGCAAGCCCATGAGGGAGGACACCATGGATTACAAGGATGACGATGAC |
| | | AAGTGATAACTCGAGAATCAACCTCTGGATTACAAAATTTGTGAAAGATT |
| | | GACTGGTATTCTTAACTATGTTGCTCCTTTTACGCTATGTGGATACGCTG |
| | | CTTTAATGCCTTTGTATCATGCTATTGCTTCCCGTATGGCTTTCATTTTC |
| | | TCCTCCTTGTATAAATCCTGGTTGCTGTCTCTTTATGAGGAGTTGTGGCC |
| | | CGTTGTCAGGCAACGTGGCGTGGTGTGCACTGTGTTTGCTGACGCAACCC |
| | | CCACTGGTTGGGGCATTGCCACCACCTGTCAGCTCCTTTCCGGGACTTTC |
| | | GCTTTCCCCCTCCCTATTGCCACGGCGGAACTCATCGCCGCCTGCCTTGC |
| | | CCGCTGCTGGACAGGGGCTCGGCTGTTGGGCACTGACAATTCCGTGGGGT |
| | | GTGCCTTCTAGTTGCCAGCCATCTGTTGTTTGCCCCTCCCCCGTGCCTTC |
| | | CTTGACCCTGGAAGGTGCCACTCCCACTGTCCTTTCCTAATAAAATGAGG |
| | | AAATTGCATCGCATTGTCTGAGTAGGTGTCATTCTATTCTGGGGGGTGGG |
| | | GTGGGGCAGGACAGCAAGGGGGAGGATTGGGAAGACAATAGCAGGCATGC |
| | | TGGGGATGCGGTGGGCTCTATGGGAAGATGTCTACTGAGCTGTGCGATCC |
| | | CTGCTGGGGACTTTCCGCTGGGGACTTTCCGCTGGGGACTTTCCGCCTTC |
| | | AGCTAAGGAAGCTACCAATATTTAGAGGTACATTTTGTTCTAGAACAAAA |
| | | TGTACCGGTACATTTTGTTCTGGTACATTTTGTTCTATTAAGGACCGGGC |
| | | GCGCCGTTTAAACTGGCTTGTTGTCCACAACCATTAAACCTTAAAAGCTT |
| | | TAAAAGCCTTATATATTCTTTTTTTTCTTATAAAACTTAAAACCTTAGAG |
| | | GCTATTTAAGTTGCTGATTTATATTAATTTTATTGTTCAAACATGAGAGC |
| | | TTAGTACGTGAAACATGAGAGCTTAGTACATTAGCCATGAGAGCTTAGTA |
| | | CATTAGCCATGAGGGTTTAGTTCATTAAACATGAGAGCTTAGTACATTAA |
| | | ACATGAGAGCTTAGTACATTAAACATGAGAGCTTAGTACATACTATCAAC |
| | | AGGTTGAACTGCTGATCTGTACAGTAGAATTGGTAAAGAGAGTTGTGTAA |
| | | AATATTGAGTTCGCACATCTTGTTGTCTGATTATTGATTTTTGGCGAAAC |
| | | CATTTGATCATATGACAAGATGTGTATCTACCTTAACTTAATGATTTTGA |
| | | TAAAAATCATTAGGCGCGCCGAAGAGCG |
| 34. | MHCK7-hBGi-DMD-4 -- | CTAGAAGCTGCATGTCTAAGCTAGACCCTTCAGATTAAAAATAACTGAGG |
| | | TAAGGGCCTGGGTAGGGGAGGTGGTGTGAGACGCTCCTGTCTCTCCTCTA |
| | | TCTGCCCATCGGCCCTTTGGGGAGGAGGAATGTGCCCAAGGACTAAAAAA |
| | | AGGCCATGGAGCCAGAGGGGCGAGGGCAACAGACCTTTCATGGGCAAACC |
| | | TTGGGGCCCTGCTGTCTAGCATGCCCCACTACGGGTCTAGGCTGCCCATG |
| | | TAAGGAGGCAAGGCCTGGGGACACCCGAGATGCCTGGTTATAATTAACCC |
| | | AGACATGTGGCTGCCCCCCCCCCCCCAACACCTGCTGCCTCTAAAAATAA |
| | | CCCTGTCCCTGGTGGATCCCCTGCATGCGAAGATCTTCGAACAAGGCTGT |
| | | GGGGGACTGAGGGCAGGCTGTAACAGGCTTGGGGGCCAGGGCTTATACGT |
| | | GCCTGGGACTCCCAAAGTATTACTGTTCCATGTTCCCGGCGAAGGGCCAG |
| | | CTGTCCCCCGCCAGCTAGACTCAGCACTTAGTTTAGGAACCAGTGAGCAA |
| | | GTCAGCCCTTGGGGCAGCCCATACAAGGCCATGGGGCTGGGCAAGCTGCA |
| | | CGCCTGGGTCCGGGGTGGGCACGGTGCCCGGGCAACGAGCTGAAAGCTCA |
| | | TCTGCTCTCAGGGGCCCCTCCCTGGGGACAGCCCCTCCTGGCTAGTCACA |
| | | CCCTGTAGGCTCCTCTATATAACCCAGGGGCACAGGGGCTGCCCTCATTC |
| | | TACCACCACCTCCACAGCACTCTGGATCCACTGCTTAAATACGGACGAGG |
| | | ACAGGGCCCTGTCTCCTCAGCTTCAGGCACCACCACTGACCTGGGACAGT |
| | | GAATCGTAAGTACTAGCAGCTACAATCCAGCTACCATTCTGCTTTTATTT |
| | | TATGGTTGGGATAAGGCTGGATTATTCTGAGTCCAAGCTAGGCCCTTTTG |
| | | CTAATCATGTTCATACCTCTTATCTTCCTCCCACAGCTCCTGGGCAACGT |
| | | GCTGGTCTGTGTGCTGGCCCATCACTTTGGCAAAGAATTGCGATCGCCAC |
| | | CATGCTTTGGTGGGAAGAAGTCGAGGACTGCTACGAGCGCGAGGACGTGC |
| | | AGAAGAAAACCTTCACCAAATGGGTCAACGCCCAGTTCAGCAAGTTCGGC |
| | | AAGCAGCACATCGAGAACCTGTTCAGCGACCTGCAGGATGGCAGAAGGCT |
| | | GCTGGATCTGCTGGAAGGCCTGACAGGACAGAAGCTGCCCAAAGAGAAGG |
| | | GCAGCACAAGAGTGCACGCCCTGAACAACGTGAACAAGGCCCTGAGAGTG |
| | | CTGCAGAACAACAACGTGGACCTGGTCAACATCGGCAGCACCGACATCGT |
| | | GGACGGCAACCACAAACTGACCCTGGGCCTGATCTGGAACATCATCCTGC |
| | | ACTGGCAAGTGAAGAACGTGATGAAGAACATCATGGCCGGCCTGCAGCAG |
| | | ACCAACAGCGAGAAGATTCTGCTGAGCTGGGTCCGACAGAGCACCCGGAA |
| | | TTACCCTCAAGTGAACGTGATCAACTTCACCACCTCTTGGAGCGACGGAC |
| | | TGGCCCTGAATGCCCTGATCCACAGCCACAGACCTGACCTGTTCGACTGG |
| | | AACAGCGTCGTGTGTCAGCAGAGCGCCACACAGAGGCTGGAACACGCCTT |
| | | CAATATCGCCAGATACCAGCTGGGCATCGAGAAACTGCTGGACCCCGAGG |
| | | ATGTGGACACCACCTATCCTGACAAGAAATCCATCCTCATGTACATCACC |
| | | AGCCTGTTCCAGGTGCTGCCCCAGCAGGTTTCCATCGAGGCCATTCAAGA |
| | | GGTCGAGATGCTGCCCAGACCTCCTAAAGTGACCAAAGAGGAACACTTCC |
| | | AGCTGCACCACCAGATGCACTACTCTCAGCAGATCACCGTGTCTCTGGCC |
| | | CAGGGCTACGAGAGAACAAGCAGCCCCAAGCCTCGGTTCAAGAGCTACGC |
| | | CTATACACAGGCCGCCTACGTGACCACCAGCGATCCTACAAGAAGCCCAT |
| | | TTCCTAGCCAGCATCTGGAAGCCCCTGAGGACAAGAGCTTTGGCAGCAGC |
| | | CTGATGGAAAGCGAAGTGAACCTGGACCGCTACCAGACAGCCCTGGAAGA |
| | | GGTTCTGAGCTGGCTGCTGTCTGCCGAGGATACACTGCAGGCTCAGGGCG |

-continued

| SEQ ID NO | Description | SEQ |
|---|---|---|
| | | AGATCAGCAACGACGTGGAAGTGGTCAAGGACCAGTTTCACACCCACGAG<br>GGCTACATGATGGACCTGACAGCCCACCAGGGCAGAGTGGGCAATATTCT<br>GCAGCTGGGCTCCAAGCTGATCGGCACAGGCAAGCTGAGCGAGGACGAAG<br>AGACAGAGGTGCAAGAGCAGATGAACCTGCTGAACAGCAGATGGGAGTGT<br>CTGAGAGTGGCCAGCATGGAAAAGCAGAGCAACCTGCACCGGGTGCTGAT<br>GGATCTCCAGAACCAGAAGCTGAAAGAGCTGAACGACTGGCTGACCAAGA<br>CCGAGGAACGGACCCGGAAGATGGAAGAGGAACCTCTGGGACCCGACCTG<br>GAAGATCTGAAAAGACAGGTGCAGCAGCATAAGGTGCTGCAAGAGGACCT<br>CGAACAAGAGCAAGTGCGCGTGAACAGCCTGACACACATGGTGGTGGTCG<br>TGGATGAGAGCAGCGGAGATCATGCCACAGCCGCTCTGGAAGAACAGCTG<br>AAGGTGCTGGGAGACAGATGGGCCAATATCTGCCGGTGGACCGAGGATAG<br>ATGGGTGCTGCTCCAGGACATCCTGCTGAAGTGGCAGCGGCTGACAGAGG<br>AACAGTGCCTGTTTAGCGCCTGGCTGTCCGAGAAAGAGGACGCCGTCAAC<br>AAGATCCACACCACCGGCTTCAAGGATCAGAATGAGATGCTGAGCAGCCT<br>GCAGAAACTGGCCGTGCTGAAGGCTGACCTGGAAAAGAAAAAGCAGTCCA<br>TGGGCAAGCTGTACTCCCTGAAGCAGGACCTGCTGAGCACACTGAAGAAC<br>AAGTCTGTGACCCAGAAAACCGAGGCCTGGCTGGACAACTTCGCCCGGTG<br>TTGGGATAACCTGGTGCAGAAGCTGGAAAAGTCCACCGCTCAGATCTCTC<br>AGGCCGTGACCACAACACAGCCTTCTCTGACCCAGACCACCGTGATGGAA<br>ACAGTGACCACAGTGACAACCCGCGAGCAGATCCTGGTCAAGCACGCCCA<br>AGAAGAACTGCCTCCTCCACCTCCTCAGAAGAAACGGCAGATCACAGTGG<br>ACAGCGAGATCCGGAAGAGACTGGACGTGGACATCACCGAGCTGCACAGC<br>TGGATCACCAGATCCGAAGCCGTGCTGCAGTCCCCTGAGTTCGCCATCTT<br>CAGAAAAGAGGGCAACTTCTCCGACCTGAAAGAGAAAGTCAACGCCATCG<br>AGAGAGAGAAGGCCGAGAAGTTCCGGAAGCTGCAGGACGCCTCTAGATCT<br>GCCCAGGCTCTGGTGGAACAGATGGTCAACGAAGGCGTGAACGCCGACAG<br>CATCAAGCAGGCCTCAGAGCAGCTGAACTCCCGGTGGATCGAGTTCTGTC<br>AGCTCCTGAGCGAGAGACTGAACTGGCTGGAATACCAGAACAATATCATT<br>GCCTTCTACAACCAGCTCCAGCAGCTCGAACAGATGACCACCACAGCCGA<br>GAATTGGCTGAAGATCCAGCCTACCACACCTAGCGAGCCCACCGCCATTA<br>AGAGCCAGCTGAAAATCTGCAAGGACGAAGTGAATCGGCTGAGCGATCTG<br>CAGCCCCAGATCGAAAGACTGAAAATCCAGTCTATCGCCCTCAAAGAGAA<br>AGGACAGGGCCCCATGTTCCTGGACGCCGATTTTGTGGCCTTTACCAACC<br>ACTTCAAACAGGTGTTCTCCGACGTGCAGGCCCGGGAAAAAGAGCTGCAG<br>ACCATCTTCGACACCCTGCCTCCAATGAGATACCAAGAGACAATGAGCGC<br>CATCCGGACCTGGGTGCAGCAAAGCGAGACAAAGCTGAGCATCCCACAGC<br>TGAGCGTGACCGACTACGAGATCATGGAACAGAGACTGGGCGAACTGCAG<br>GCCCTCCAGTCTAGCCTGCAAGAACAGCAGTCCGGCCTGTACTACCTGAG<br>CACAACCGTGAAAGAGATGAGCAAGAAGGCCCCTAGCGAGATCTCCCGGA<br>AGTACCAGAGCGAGTTCGAAGAGATCGAAGGCCGGTGGAAGAAGCTGTCT<br>AGCCAGCTGGTTGAGCACTGCCAGAAACTCGAAGAACAAATGAACAAGCT<br>GCGCAAGATCCAGAATCACATCCAGACGCTGAAGAAATGGATGGCCGAGG<br>TGGACGTGTTCCTGAAAGAAGAGTGGCCCGCTCTGGGCGACTCCGAGATT<br>CTGAAGAAACAGCTCAAACAGTGCCGGCTGCTGGTGTCCGATATCCAGAC<br>AATCCAGCCAAGCCTGAACTCCGTGAATGAAGGCGGCCAGAAGATCAAGA<br>ACGAGGCCGAGCCTGAGTTTGCCAGCAGACTGGAAACCGAACTGAAAGAA<br>CTCAACACCCAGTGGGACCACATGTGCCAGCAAGTGTACGCCCGGAAAGA<br>GGCCCTGAAAGGCGGACTCGAAAAGACTGTGTCTCTGCAGAAAGACCTGT<br>CTGAGATGCACGAGTGGATGACCCAGGCCGAAGAGGAATACCTGGAACGG<br>GACTTCGAGTACAAGACCCCTGATGAGCTGCAAAAAGCCGTCGAGGAAAT<br>GAAGCGGGCCAAAGAAGAGGCCCAGCAGAAAGAAGCCAAAGTCAAGCTGC<br>TGACCGAGTCCGTGAATAGCGTTATCGCTCAGGCCCCTCCTGTGGCTCAA<br>GAGGCTCTCAAGAAAGAACTGGAAACTCTGACCACCAACTACCAGTGGCT<br>GTGCACCAGACTGAACGGCAAGTGCAAGACACTGGAAGAAGTGTGGGCCT<br>GCTGGCACGAACTGCTGTCCTATCTGGAAAAGGCCAACAAGTGGCTGAAC<br>GAGGTGGAATTCAAGCTGAAAACCACCGAGAACATCCCTGGCGGCGCTGA<br>AGAGATTAGCGAGGTGCTGGACAGCCTGGAAAACCTGATGAGACACAGCG<br>AGGACAACCCCAATCAGATCAGAATCCTGGCTCAGACCCTGACCGATGGC<br>GGCGTGATGGACGAGCTGATCAACGAGGAACTCGAAACCTTCAACAGCCG<br>GTGGCGGGAACTGCACGAGGAAGCTGTTCGGAGGCAGAAGTTGCTGGAAC<br>AGTCTATCCAGAGCGCACAAGAAACCGAGAAGTCCCTGCACCTGATCCAA<br>GAGAGCCTGACCTTCATCGACAAGCAGCTGGCCGCTTATATCGCCGACAA<br>GGTGGACGCTGCTCAGATGCCCCAAGAGGCACAGAAGATTCAGAGCGACC<br>TGACCAGCCACGAGATTAGCCTGGAAGAAATGAAGAAGCACAACCAGGGC<br>AAAGAGGCCGCTCAGAGAGTCCTGAGCCAGATCGATGTGGCACAGAAAAA<br>GCTCCAGGATGTGTCCATGAAGTTTCGGCTGTTTCAGAAGCCCGCCAACT<br>TCGAGCAGAGACTGCAAGAGTCCAAGATGATCCTGGACGAAGTCAAAATG<br>CATCTGCCCGCACTGGAAACAAAGTCCGTGGAACAAGAAGTGGTGCAGTC<br>CCAGCTGAACCACTGCGTGAACCTGTACAAGAGCCTGTCCGAAGTGAAGT<br>CTGAGGTGGAAATGGTCATCAAGACCGGCAGGCAGATCGTCCAGAAGAAG<br>CAGACCGAGAATCCCAAAGAACTCGACGAGAGAGTGACCGCTCTGAAGCT<br>GCACTACAATGAGCTGGGCGCCAAAGTGACCGAGCGGAAGCAACAGCTTG<br>AGAAGTGCCTGAAACTGTCTCGGAAGATGCGGAAAGAAATGAACGTGCTG<br>ACAGAGTGGCTGGCCGCCACCGATATGGAACTGACTAAGAGAAGCGCCGT<br>GGAAGGCATGCCCAGCAACCTGGATAGTGAAGTGGCCTGGGGCAAAGCCA |

-continued

| SEQ ID NO | Description | SEQ |
|---|---|---|
| | | CTCAGAAAGAGATTGAGAAGCAGAAGGTCCACCTGAAGTCCATCACCGAA<br>GTGGGCGAAGCCCTGAAAACCGTGCTGGGAAAGAAAGAGACACTGGTCGA<br>GGACAAGCTGTCCCTGCTGAATTCCAACTGGATCGCCGTGACCTCCAGAG<br>CTGAGGAATGGCTGAATCTGCTGCTTGAGTACCAGAAACACATGGAAACG<br>TTCGACCAGAACGTCGACCACATCACAAAGTGGATCATCCAGGCTGATAC<br>CCTGCTGGACGAGTCCGAGAAGAAGAAACCCCAACAAAAAGAAGATGTGC<br>TGAAGCGGCTGAAAGCCGAGCTGAATGACATCCGGCCTAAGGTGGACAGC<br>ACCAGAGATCAGGCAGCCAACCTGATGGCCAACAGAGGCGACCACTGTCG<br>GAAGCTCGTGGAACCTCAGATCAGCGAGCTTAACCACAGATTTGCCGCCA<br>TCAGCCACCGGATCAAGACAGGCAAGGCCAGCATTCCTCTCAAAGAGCTT<br>GAGCAGTTCAACAGCGACATCCAAAAGCTGCTCGAACCCCTGGAAGCCGA<br>GATCCAACAGGGCGTCAACCTCAAAGAAGAAGATTTCAACAAGGACATGA<br>ACGAGGACAATGAGGGCACCGTCAAAGAACTGCTGCAGCGGGGCGATAAT<br>CTGCAGCAGCGGATTACCGATGAGCGCAAGCGGGAAGAGATCAAGATTAA<br>GCAGCAGCTGCTGCAGACCAAGCACAACGCCCTGAAGGACCTGCGGAGCC<br>AGAGAAGAAAGAAGGCCCTGGAAATCAGCCACCAGTGGTATCAGTACAAG<br>CGGCAGGCCGACGACCTGCTGAAGTGCCTGGATGACATCGAGAAGAAGCT<br>GGCCTCTCTGCCCGAGCCTAGGGACGAGAGAAAGATCAAAGAGATCGACC<br>GCGAGCTGCAGAAAAAGAAAGAGGAACTGAACGCCGTCCGCAGACAGGCC<br>GAAGGACTTTCTGAAGATGGCGCCGCTATGGCCGTGGAACCCACACAGAT<br>TCAGCTGAGCAAGCGGTGGCGGGAAATCGAGAGCAAGTTCGCCCAGTTCC<br>GGCGGCTGAATTTCGCCCAGATCCACACCGTGCGGGAAGAGACAATGATG<br>GTCATGACAGAGGACATGCCCCTTGAGATCAGCTACGTGCCCAGCACCTA<br>CCTGACCGAGATCACCCATGTGTCTCAGGCCCTGCTGGAAGTGGAACAGC<br>TGCTGAATGCCCCTGACCTGTGCGCCAAGGACTTCGAGGACCTGTTCAAG<br>CAAGAGGAAAGCCTGAAGAACATCAAGGACAGCCTGCAGCAGAGCAGCGG<br>CCGGATCGATATCATCCACAGCAAGAAAACCGCCGCACTGCAGAGCGCCA<br>CACCTGTGGAAAGAGTGAAGCTGCAAGAGGCCCTGAGCCAGCTGGATTTC<br>CAGTGGGAGAAAGTGAACAAGATGTACAAGGACCGGCAGGGCAGATTCGA<br>CCGCAGCGTTGAAAAGTGGCGGCGGTTCCACTACGACATCAAGATCTTCA<br>ACCAGTGGCTGACCGAGGCCGAGCAGTTCCTGAGAAAGACACAGATCCCC<br>GAGAACTGGGAGCACGCCAAGTACAAGTGGTATCTGAAAGAGCTGCAGGA<br>CGGCATCGGCCAGAGACAGACAGTCGTGCGGACACTGAATGCCACCGGCG<br>AGGAAATCATCCAGCAGTCCAGCAAGACCGACGCCAGCATCCTGCAAGAG<br>AAGCTGGGCAGCCTGAACCTGCGGTGGCAAGAAGTGTGCAAGCAGCTGAG<br>CGACCGGAAGAAGCGGCTGGAAGAACAGAAGAATATCCTGAGCGAGTTCC<br>AGCGGGACCTGAACGAGTTCGTGCTGTGGCTCGAAGAGGCCGACAATATC<br>GCCAGCATTCCCCTGGAACCTGGCAAAGAGCAGCAGCTGAAAGAAAAGCT<br>GGAACAAGTGAAACTGCTGGTCGAGGAACTGCCCCTGAGACAGGGAATCC<br>TGAAACAGCTGAACGAGACAGGCGGCCCTGTGCTGGTGTCTGCCCCTATT<br>TCTCCCGAGGAACAGGACAAGCTGGAAAACAAGCTGAAGCAGACCAACCT<br>GCAGTGGATCAAGGTGTCCAGAGCACTGCCTGAGAAGCAGGGCGAGATCG<br>AGGCCCAGATCAAGGACCTGGGACAGCTCGAAAAGAAGCTTGAGGACCTC<br>GAAGAACAGCTCAACCATCTGCTGCTTTGGCTGAGCCCCATCCGGAACCA<br>GCTGGAAATCTACAACCAGCCTAATCAAGAGGGCCCCTTCGACGTGAAAG<br>AAACCGAGATTGCCGTGCAGGCCAAGCAGCCCGATGTGGAAGAGATCCTG<br>TCTAAGGGCCAGCACCTGTACAAAGAGAAGCCCGCCACACAGCCCGTGAA<br>GCGGAAACTGGAAGATCTGAGCAGCGAGTGGAAGGCCGTGAACCGGCTGC<br>TGCAAGAACTGAGAGCCAAACAGCCTGATCTGGCCCCTGGCCTGACAACA<br>ATTGGCGCCTCTCCTACACAGACCGTGACACTGGTCACACAGCCTGTGGT<br>CACCAAAGAGACAGCCATCAGCAAACTGGAAATGCCCAGCAGTCTGATGC<br>TCGAAGTGCCCGCACTGGCCGACTTCAATAGAGCCTGGACCGAGCTGACC<br>GACTGGCTCAGTCTGCTGGACCAAGTCATCAAGTCCCAGAGAGTGATGGT<br>CGGAGATCTTGAGGACATCAACGAGATGATCATTAAGCAGAAAGCCACCA<br>TGCAGGACCTTGAGCAGAGAAGGCCCCAGCTTGAAGAACTGATCACCGCC<br>GCTCAGAACCTGAAAAACAAGACCAGCAATCAAGAAGCCCGGACCATCAT<br>CACCGACCGGATCGAGAGAATCCAGAACCAGTGGGACGAAGTGCAAGAGC<br>ATCTGCAGAACAGACGGCAGCAGCTCAATGAGATGCTGAAGGACAGCACA<br>CAGTGGCTGGAAGCCAAAGAAGAAGCCGAGCAGGTTCTCGGACAGGCCAG<br>AGCTAAGCTGGAATCTTGGAAAGAGGGACCCTACACCGTCGACGCCATCC<br>AGAAGAAGATCACCGAGACAAAGCAGCTGGCCAAGGATCTGAGACAGTGG<br>CAGACCAATGTGGACGTGGCCAACGACCTGGCTCTGAAGCTGCTGAGAGA<br>CTACAGCGCCGACGACACCAGAAAGGTGCACATGATCACCGAAAACATCA<br>ACGCCTCTTGGCGGAGCATCCACAAGCGGGTGTCAGAGAGAGAAGCCGCT<br>CTGGAAGAAACACATAGACTGCTCCAGCAGTTCCCACTCGACCTGGAAAA<br>GTTCCTGGCCTGGCTGACAGAAGCCGAAACCACCGCTAACGTGCTCCAGG<br>ATGCCACCAGAAAAGAGCGGCTGTTGGAGGACAGCAAGGGCGTCAAAGAA<br>CTCATGAAGCAGTGGCAGGATCTGCAAGGGGAGATTGAAGCCCACACCGA<br>CGTGTACCACAACCTGGACGAGAACAGCCAGAAGATCCTGCGGTCCCTGG<br>AAGGCTCTGATGATGCTGTGCTGCTTCAGAGGCGGCTGGACAACATGAAC<br>TTCAAGTGGAGCGAGCTGCGGAAGAAGTCCCTGAACATCAGAAGCCACCT<br>GGAAGCCTCCAGCGACCAGTGGAAAAGACTGCACCTGTCTCTCCAAGAGC<br>TGCTCGTGTGGCTGCAGCTGAAGGATGACGAGCTGAGTAGACAGGCCCCT<br>ATCGGCGGAGATTTTCCCGCCGTGCAGAAACAGAACGACGTGCACCGGGC<br>CTTCAAGAGAGAGCTGAAAACAAAAGAACCCGTCATCATGAGCACCCTGG |

-continued

| SEQ ID NO | Description | SEQ |
|---|---|---|
| | | AAACCGTGCGGATCTTTCTGACCGAGCAGCCTCTGGAAGGACTGGAAAAG<br>CTGTACCAAGAGCCTAGAGAGCTGCCTCCTGAAGAAAGGGCCCAGAACGT<br>GACACGGCTGCTTAGAAAGCAGGCCGAGGAAGTGAACACCGAATGGGAGA<br>AGCTGAACCTCCACTCCGCCGACTGGCAGCGGAAGATCGATGAGACACTG<br>GAACGGCTGCGGGAACTGCAAGAAGCCACAGACGAGCTGGACCTGAAACT<br>GCGGCAGGCTGAAGTGATCAAAGGCTCCTGGCAGCCAGTGGGCGATCTGC<br>TGATCGATAGCCTGCAGGACCATCTGGAAAAAGTCAAGGCCCTGCGGGGA<br>GAGATCGCCCCTCTCAAAGAAAACGTGTCCCACGTGAACGATCTGGCCAG<br>GCAGCTGACAACACTGGGCATCCAGCTGAGCCCTTACAACCTGTCTACCT<br>TGGAGGACCTGAATACCCGGTGGAAGCTGCTCCAAGTGGCCGTCGAGGAT<br>AGAGTGCGGCAGCTGCATGAGGCTCACAGAGATTTTGGACCCGCCAGCCA<br>GCACTTCCTGAGCACATCTGTTCAAGGCCCCTGGGAGAGAGCTATCAGCC<br>CTAACAAGGTGCCCTACTACATCAACCACGAGACACAGACCACCTGTTGG<br>GATCACCCCAAGATGACCGAACTGTATCAGTCCCTGGCCGACCTGAACAA<br>CGTGCGGTTTAGCGCCTACCGGACCGCCATGAAGCTGCGCAGACTGCAGA<br>AAGCTCTGTGCCTGGACCTGCTGTCTCTGAGCGCTGCTTGTGATGCCCTG<br>GACCAGCATAACCTCAAGCAGAACGACCAGCCTATGGACATCCTGCAGAT<br>CATCAACTGCCTGACCACCATCTACGACCGGCTCGAACAAGAGCACAACA<br>ACCTGGTCAACGTGCCCCTGTGCGTGGACATGTGCCTGAATTGGCTGCTG<br>AACGTGTACGACACCGGCAGAACCGGCAGGATCAGAGTGCTGAGCTTCAA<br>GACCGGCATCATCTCCCTGTGCAAGGCCCACCTTGAGGATAAGTACCGCT<br>ACCTGTTTAAGCAGGTCGCCAGCAGCACCGGCTTTTGCGACCAAAGAAGG<br>CTGGGACTGCTGCTCCACGACAGCATTCAGATCCCTAGACAGCTGGGCGA<br>AGTGGCCTCTTTCGGCGGCTCTAATATCGAGCCTAGCGTGCGGAGCTGCT<br>TCCAGTTCGCCAACAACAAGCCCGAGATTGAGGCCGCACTGTTCCTGGAC<br>TGGATGAGACTGGAACCCCAGAGCATGGTCTGGCTGCCTGTGCTGCATAG<br>AGTGGCCGCAGCCGAAACAGCCAAGCACCAGGCCAAGTGCAACATCTGCA<br>AAGAGTGCCCCATCATCGGCTTCCGGTACAGATCCCTGAAGCACTTCAAC<br>TACGATATCTGCCAGTCCTGCTTCTTCAGCGGCAGAGTGGCCAAGGGCCA<br>CAAGATGCACTACCCCATGGTGGAATACTGCACCCCTACCACCTCTGGCG<br>AGGACGTGCGGGATTTTGCCAAGGTGCTCAAGAACAAGTTCCGGACCAAG<br>CGCTACTTCGCTAAGCACCCCAGAATGGGCTACCTGCCAGTGCAGACAGT<br>GCTTGAGGGCGACAACATGGAAACCCCTGTGACTCTGATCAACTTCTGGC<br>CCGTGGATAGCGCCCCTGCTAGTTCTCCTCAGCTGTCTCACGACGATACC<br>CACAGCAGAATCGAGCACTACGCCTCCAGACTGGCCGAGATGGAAAACAG<br>CAACGGCAGCTACCTGAATGACAGCATCAGCCCCAACGAGAGCATCGACG<br>ACGAACATCTGCTCATTCAGCACTACTGCCAGAGCCTGAATCAGGACAGC<br>CCTCTGTCTCAGCCTAGAAGCCCTGCACAGATCCTGATCAGCCTGGAAAG<br>CGAGGAACGCGGCGAGCTGGAAAGAATCCTGGCAGACCTGGAAGAGGAAA<br>ACCGGAACCTGCAGGCCGAATACGACAGACTCAAGCAGCAGCACGAGCAC<br>AAGGGACTGTCTCCACTGCCTTCTCCACCTGAAATGATGCCCACCTCTCC<br>ACAGAGCCCCAGAGATGCCGAGCTGATTGCCGAAGCCAAACTGCTGAGGC<br>AGCACAAAGGCAGACTCGAAGCCAGAATGCAGATTCTCGAAGATCACAAC<br>AAGCAGCTCGAATCCCAGCTGCACAGACTTAGGCAGCTGCTGGAACAGCC<br>TCAGGCAGAGGCCAAAGTGAATGGCACCACCGTGTCTAGCCCTAGCACAA<br>GCCTGCAGAGATCCGACAGCAGCCAGCCAATGCTTCTGAGAGTCGTGGGC<br>TCCCAGACCAGCGATTCTATGGGCGAAGAGGACCTGCTCAGCCCTCCTCA<br>GGATACAAGCACCGGCCTGGAAGAAGTGATGGAACAACTGAACAACAGCT<br>TCCCCAGCAGCAGAGGCAGAAACACCCCTGGCAAGCCCATGCGCGAGGAC<br>ACCATGTGATAA |
| 35. | MHCK7-<br>hBGi-DMD-<br>4-WPRE3- | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>CATGCTTTGGTGGGAAGAAGTCGAGGACTGCTACGAGCGCGAGGACGTGC<br>AGAAGAAAACCTTCACCAAATGGGTCAACGCCCAGTTCAGCAAGTTCGGC<br>AAGCAGCACATCGAGAACCTGTTCAGCGACCTGCAGGATGGCAGAAGGCT |

-continued

| SEQ ID NO | Description | SEQ |
|---|---|---|
| | | GCTGGATCTGCTGGAAGGCCTGACAGGACAGAAGCTGCCCAAAGAGAAGG |
| | | GCAGCACAAGAGTGCACGCCCTGAACAACGTGAACAAGGCCCTGAGAGTG |
| | | CTGCAGAACAACAACGTGGACCTGGTCAACATCGGCAGCACCGACATCGT |
| | | GGACGGCAACCACAAACTGACCCTGGGCCTGATCTGGAACATCATCCTGC |
| | | ACTGGCAAGTGAAGAACGTGATGAAGAACATCATGGCCGGCCTGCAGCAG |
| | | ACCAACAGCGAGAAGATTCTGCTGAGCTGGGTCCGACAGAGCACCCGGAA |
| | | TTACCCTCAAGTGAACGTGATCAACTTCACCACCTCTTGGAGCGACGGAC |
| | | TGGCCCTGAATGCCCTGATCCACAGCCACAGACCTGACCTGTTCGACTGG |
| | | AACAGCGTCGTGTGTCAGCAGAGCGCCACACAGAGGCTGGAACACGCCTT |
| | | CAATATCGCCAGATACCAGCTGGGCATCGAGAAACTGCTGGACCCCGAGG |
| | | ATGTGGACACCACCTATCCTGACAAGAAATCCATCCTCATGTACATCACC |
| | | AGCCTGTTCCAGGTGCTGCCCCAGCAGGTTTCCATCGAGGCCATTCAAGA |
| | | GGTCGAGATGCTGCCCAGACCTCCTAAAGTGACCAAAGAGGAACACTTCC |
| | | AGCTGCACCACCAGATGCACTACTCTCAGCAGATCACCGTGTCTCTGGCC |
| | | CAGGGCTACGAGAGAACAAGCAGCCCCAAGCCTCGGTTCAAGAGCTACGC |
| | | CTATACACAGGCCGCCTACGTGACCACCAGCGATCCTACAAGAAGCCCAT |
| | | TTCCTAGCCAGCATCTGGAAGCCCCTGAGGACAAGAGCTTTGGCAGCAGC |
| | | CTGATGGAAAGCGAAGTGAACCTGGACCGCTACCAGACAGCCCTGGAAGA |
| | | GGTTCTGAGCTGGCTGCTGTCTGCCGAGGATACACTGCAGGCTCAGGGCG |
| | | AGATCAGCAACGACGTGGAAGTGGTCAAGGACCAGTTTCACACCCACGAG |
| | | GGCTACATGATGGACCTGACAGCCCACCAGGGCAGAGTGGGCAATATTCT |
| | | GCAGCTGGGCTCCAAGCTGATCGGCACAGGCAAGCTGAGCGAGGACGAAG |
| | | AGACAGAGGTGCAAGAGCAGATGAACCTGCTGAACAGCAGATGGGAGTGT |
| | | CTGAGAGTGGCCAGCATGGAAAAGCAGAGCAACCTGCACCGGGTGCTGAT |
| | | GGATCTCCAGAACCAGAAGCTGAAAGAGCTGAACGACTGGCTGACCAAGA |
| | | CCGAGGAACGGACCCGGAAGATGGAAGAGGAACCTCTGGGACCCGACCTG |
| | | GAAGATCTGAAAAGACAGGTGCAGCAGCATAAGGTGCTGCAAGAGGACCT |
| | | CGAACAAGAGCAAGTGCGCGTGAACAGCCTGACACACATGGTGGTGGTCG |
| | | TGGATGAGAGCAGCGGAGATCATGCCACAGCCGCTCTGGAAGAACAGCTG |
| | | AAGGTGCTGGGAGACAGATGGGCCAATATCTGCCGGTGGACCGAGGATAG |
| | | ATGGGTGCTGCTCCAGGACATCCTGCTGAAGTGGCAGCGGCTGACAGAGG |
| | | AACAGTGCCTGTTTAGCGCCTGGCTGTCCGAGAAAGAGGACGCCGTCAAC |
| | | AAGATCCACACCACCGGCTTCAAGGATCAGAATGAGATGCTGAGCAGCCT |
| | | GCAGAAACTGGCCGTGCTGAAGGCTGACCTGGAAAAGAAAAAGCAGTCCA |
| | | TGGGCAAGCTGTACTCCCTGAAGCAGGACCTGCTGAGCACACTGAAGAAC |
| | | AAGTCTGTGACCCAGAAAACCGAGGCCTGGCTGGACAACTTCGCCCGGTG |
| | | TTGGGATAACCTGGTGCAGAAGCTGGAAAAGTCCACCGCTCAGATCTCTC |
| | | AGGCCGTGACCACAACACAGCCTTCTCTGACCCAGACCACCGTGATGGAA |
| | | ACAGTGACCACAGTGACAACCCGCGAGCAGATCCTGGTCAAGCACGCCCA |
| | | AGAAGAACTGCCTCCTCCACCTCCTCAGAAGAAACGGCAGATCACAGTGG |
| | | ACAGCGAGATCCGGAAGAGACTGGACGTGGACATCACCGAGCTGCACAGC |
| | | TGGATCACCAGATCCGAAGCCGTGCTGCAGTCCCCTGAGTTCGCCATCTT |
| | | CAGAAAAGAGGGCAACTTCTCCGACCTGAAAGAGAAAGTCAACGCCATCG |
| | | AGAGAGAGAAGGCCGAGAAGTTCCGGAAGCTGCAGGACGCCTCTAGATCT |
| | | GCCCAGGCTCTGGTGGAACAGATGGTCAACGAAGGCGTGAACGCCGACAG |
| | | CATCAAGCAGGCCTCAGAGCAGCTGAACTCCCGGTGGATCGAGTTCTGTC |
| | | AGCTCCTGAGCGAGAGACTGAACTGGCTGGAATACCAGAACAATATCATT |
| | | GCCTTCTACAACCAGCTCCAGCAGCTCGAACAGATGACCACCACAGCCGA |
| | | GAATTGGCTGAAGATCCAGCCTACCACACCTAGCGAGCCCACCGCCATTA |
| | | AGAGCCAGCTGAAAATCTGCAAGGACGAAGTGAATCGGCTGAGCGATCTG |
| | | CAGCCCCAGATCGAAAGACTGAAAATCCAGTCTATCGCCCTCAAAGAGAA |
| | | AGGACAGGGCCCCATGTTCCTGGACGCCGATTTTGTGGCCTTTACCAACC |
| | | ACTTCAAACAGGTGTTCTCCGACGTGCAGGCCCGGGAAAAAGAGCTGCAG |
| | | ACCATCTTCGACACCCTGCCTCCAATGAGATACCAAGAGACAATGAGCGC |
| | | CATCCGGACCTGGGTGCAGCAAAGCGAGACAAAGCTGAGCATCCCACAGC |
| | | TGAGCGTGACCGACTACGAGATCATGGAACAGAGACTGGGCGAACTGCAG |
| | | GCCCTCCAGTCTAGCCTGCAAGAACAGCAGTCCGGCCTGTACTACCTGAG |
| | | CACAACCGTGAAAGAGATGAGCAAGAAGGCCCCTAGCGAGATCTCCCGGA |
| | | AGTACCAGAGCGAGTTCGAAGAGATCGAAGGCCGGTGGAAGAAGCTGTCT |
| | | AGCCAGCTGGTTGAGCACTGCCAGAAACTCGAAGAACAAATGAACAAGCT |
| | | GCGCAAGATCCAGAATCACATCCAGACGCTGAAGAAATGGATGGCCGAGG |
| | | TGGACGTGTTCCTGAAAGAAGAGTGGCCCGCTCTGGGCGACTCCGAGATT |
| | | CTGAAGAAACAGCTCAAACAGTGCCGGCTGCTGGTGTCCGATATCCAGAC |
| | | AATCCAGCCAAGCCTGAACTCCGTGAATGAAGGCGGCCAGAAGATCAAGA |
| | | ACGAGGCCGAGCCTGAGTTTGCCAGCAGACTGGAAACCGAACTGAAAGAA |
| | | CTCAACACCCAGTGGGACCACATGTGCCAGCAAGTGTACGCCCGGAAAGA |
| | | GGCCCTGAAAGGCGGACTCGAAAAGACTGTGTCTCTGCAGAAAGACCTGT |
| | | CTGAGATGCACGAGTGGATGACCCAGGCCGAAGAGGAATACCTGGAACGG |
| | | GACTTCGAGTACAAGACCCCTGATGAGCTGCAAAAAGCCGTCGAGGAAAT |
| | | GAAGCGGGCCAAAGAAGAGGCCCAGCAGAAAGAAGCCAAAGTCAAGCTGC |
| | | TGACCGAGTCCGTGAATAGCGTTATCGCTCAGGCCCCTCCTGTGGCTCAA |
| | | GAGGCTCTCAAGAAAGAACTGGAAACTCTGACCACCAACTACCAGTGGCT |
| | | GTGCACCAGACTGAACGGCAAGTGCAAGACACTGGAAGAAGTGTGGGCCT |
| | | GCTGGCACGAACTGCTGTCCTATCTGGAAAAGGCCAACAAGTGGCTGAAC |
| | | GAGGTGGAATTCAAGCTGAAAACCACCGAGAACATCCCTGGCGGCGCTGA |

-continued

| SEQ ID NO | Description | SEQ |
|---|---|---|
| | | AGAGATTAGCGAGGTGCTGGACAGCCTGGAAAACCTGATGAGACACAGCG<br>AGGACAACCCCAATCAGATCAGAATCCTGGCTCAGACCCTGACCGATGGC<br>GGCGTGATGGACGAGCTGATCAACGAGGAACTCGAAACCTTCAACAGCCG<br>GTGGCGGGAACTGCACGAGGAAGCTGTTCGGAGGCAGAAGTTGCTGGAAC<br>AGTCTATCCAGAGCGCACAAGAAACCGAGAAGTCCCTGCACCTGATCCAA<br>GAGAGCCTGACCTTCATCGACAAGCAGCTGGCCGCTTATATCGCCGACAA<br>GGTGGACGCTGCTCAGATGCCCCAAGAGGCACAGAAGATTCAGAGCGACC<br>TGACCAGCCACGAGATTAGCCTGGAAGAAATGAAGAAGCACAACCAGGGC<br>AAAGAGGCCGCTCAGAGAGTCCTGAGCCAGATCGATGTGGCACAGAAAAA<br>GCTCCAGGATGTGTCCATGAAGTTTCGGCTGTTTCAGAAGCCCGCCAACT<br>TCGAGCAGAGACTGCAAGAGTCCAAGATGATCCTGGACGAAGTCAAAATG<br>CATCTGCCCGCACTGGAAACAAAGTCCGTGGAACAAGAAGTGGTGCAGTC<br>CCAGCTGAACCACTGCGTGAACCTGTACAAGAGCCTGTCCGAAGTGAAGT<br>CTGAGGTGGAAATGGTCATCAAGACCGGCAGGCAGATCGTCCAGAAGAAG<br>CAGACCGAGAATCCCAAAGAACTCGACGAGAGAGTGACCGCTCTGAAGCT<br>GCACTACAATGAGCTGGGCGCCAAAGTGACCGAGCGGAAGCAACAGCTTG<br>AGAAGTGCCTGAAACTGTCTCGGAAGATGCGGAAAGAAATGAACGTGCTG<br>ACAGAGTGGCTGGCCGCCACCGATATGGAACTGACTAAGAGAAGCGCCGT<br>GGAAGGCATGCCCAGCAACCTGGATAGTGAAGTGGCCTGGGGCAAAGCCA<br>CTCAGAAAGAGATTGAGAAGCAGAAGGTCCACCTGAAGTCCATCACCGAA<br>GTGGGCGAAGCCCTGAAAACCGTGCTGGGAAAGAAAGAGACACTGGTCGA<br>GGACAAGCTGTCCCTGCTGAATTCCAACTGGATCGCCGTGACCTCCAGAG<br>CTGAGGAATGGCTGAATCTGCTGCTTGAGTACCAGAAACACATGGAAACG<br>TTCGACCAGAACGTCGACCACATCACAAAGTGGATCATCCAGGCTGATAC<br>CCTGCTGGACGAGTCCGAGAAGAAGAAACCCCAACAAAAAGAAGATGTGC<br>TGAAGCGGCTGAAAGCCGAGCTGAATGACATCCGGCCTAAGGTGGACAGC<br>ACCAGAGATCAGGCAGCCAACCTGATGGCCAACAGAGGCGACCACTGTCG<br>GAAGCTCGTGGAACCTCAGATCAGCGAGCTTAACCACAGATTTGCCGCCA<br>TCAGCCACCGGATCAAGACAGGCAAGGCCAGCATTCCTCTCAAAGAGCTT<br>GAGCAGTTCAACAGCGACATCCAAAAGCTGCTCGAACCCCTGGAAGCCGA<br>GATCCAACAGGGCGTCAACCTCAAAGAAGAAGATTTCAACAAGGACATGA<br>ACGAGGACAATGAGGGCACCGTCAAAGAACTGCTGCAGCGGGGCGATAAT<br>CTGCAGCAGCGGATTACCGATGAGCGCAAGCGGGAAGAGATCAAGATTAA<br>GCAGCAGCTGCTGCAGACCAAGCACAACGCCCTGAAGGACCTGCGGAGCC<br>AGAGAAGAAAGAAGGCCCTGGAAATCAGCCACCAGTGGTATCAGTACAAG<br>CGGCAGGCCGACGACCTGCTGAAGTGCCTGGATGACATCGAGAAGAAGCT<br>GGCCTCTCTGCCCGAGCCTAGGGACGAGAGAAAGATCAAAGAGATCGACC<br>GCGAGCTGCAGAAAAAGAAAGAGGAACTGAACGCCGTCCGCAGACAGGCC<br>GAAGGACTTTCTGAAGATGGCGCCGCTATGGCCGTGGAACCCACACAGAT<br>TCAGCTGAGCAAGCGGTGGCGGGAAATCGAGAGCAAGTTCGCCCAGTTCC<br>GGCGGCTGAATTTCGCCCAGATCCACACCGTGCGGGAAGAGACAATGATG<br>GTCATGACAGAGGACATGCCCCTTGAGATCAGCTACGTGCCCAGCACCTA<br>CCTGACCGAGATCACCCATGTGTCTCAGGCCCTGCTGGAAGTGGAACAGC<br>TGCTGAATGCCCCTGACCTGTGCGCCAAGGACTTCGAGGACCTGTTCAAG<br>CAAGAGGAAAGCCTGAAGAACATCAAGGACAGCCTGCAGCAGAGCAGCGG<br>CCGGATCGATATCATCCACAGCAAGAAAACCGCCGCACTGCAGAGCGCCA<br>CACCTGTGGAAAGAGTGAAGCTGCAAGAGGCCCTGAGCCAGCTGGATTTC<br>CAGTGGGAGAAAGTGAACAAGATGTACAAGGACCGGCAGGGCAGATTCGA<br>CCGCAGCGTTGAAAAGTGGCGGCGGTTCCACTACGACATCAAGATCTTCA<br>ACCAGTGGCTGACCGAGGCCGAGCAGTTCCTGAGAAAGACACAGATCCCC<br>GAGAACTGGGAGCACGCCAAGTACAAGTGGTATCTGAAAGAGCTGCAGGA<br>CGGCATCGGCCAGAGACAGACAGTCGTGCGGACACTGAATGCCACCGGCG<br>AGGAAATCATCCAGCAGTCCAGCAAGACCGACGCCAGCATCCTGCAAGAG<br>AAGCTGGGCAGCCTGAACCTGCGGTGGCAAGAAGTGTGCAAGCAGCTGAG<br>CGACCGGAAGAAGCGGCTGGAAGAACAGAAGAATATCCTGAGCGAGTTCC<br>AGCGGGACCTGAACGAGTTCGTGCTGTGGCTCGAAGAGGCCGACAATATC<br>GCCAGCATTCCCCTGGAACCTGGCAAAGAGCAGCAGCTGAAAGAAAAGCT<br>GGAACAAGTGAAACTGCTGGTCGAGGAACTGCCCCTGAGACAGGGAATCC<br>TGAAACAGCTGAACGAGACAGGCGGCCCTGTGCTGGTGTCTGCCCCTATT<br>TCTCCCGAGGAACAGGACAAGCTGGAAAACAAGCTGAAGCAGACCAACCT<br>GCAGTGGATCAAGGTGTCCAGAGCACTGCCTGAGAAGCAGGGCGAGATCG<br>AGGCCCAGATCAAGGACCTGGGACAGCTCGAAAAGAAGCTTGAGGACCTC<br>GAAGAACAGCTCAACCATCTGCTGCTTTGGCTGAGCCCCATCCGGAACCA<br>GCTGGAAATCTACAACCAGCCTAATCAAGAGGGCCCCTTCGACGTGAAAG<br>AAACCGAGATTGCCGTGCAGGCCAAGCAGCCCGATGTGGAAGAGATCCTG<br>TCTAAGGGCCAGCACCTGTACAAAGAGAAGCCCGCCACACAGCCCGTGAA<br>GCGGAAACTGGAAGATCTGAGCAGCGAGTGGAAGGCCGTGAACCGGCTGC<br>TGCAAGAACTGAGAGCCAAACAGCCTGATCTGGCCCCTGGCCTGACAACA<br>ATTGGCGCCTCTCCTACACAGACCGTGACACTGGTCACACAGCCTGTGGT<br>CACCAAAGAGACAGCCATCAGCAAACTGGAAATGCCCAGCAGTCTGATGC<br>TCGAAGTGCCCGCACTGGCCGACTTCAATAGAGCCTGGACCGAGCTGACC<br>GACTGGCTCAGTCTGCTGGACCAAGTCATCAAGTCCCAGAGAGTGATGGT<br>CGGAGATCTTGAGGACATCAACGAGATGATCATTAAGCAGAAAGCCACCA<br>TGCAGGACCTTGAGCAGAGAAGGCCCCAGCTTGAAGAACTGATCACCGCC<br>GCTCAGAACCTGAAAAACAAGACCAGCAATCAAGAAGCCCGGACCATCAT |

-continued

| SEQ ID NO | Description | SEQ |
|---|---|---|
| | | CACCGACCGGATCGAGAGAATCCAGAACCAGTGGGACGAAGTGCAAGAGC ATCTGCAGAACAGACGGCAGCAGCTCAATGAGATGCTGAAGGACAGCACA CAGTGGCTGGAAGCCAAAGAAGAAGCCGAGCAGGTTCTCGGACAGGCCAG AGCTAAGCTGGAATCTTGGAAAGAGGGACCCTACACCGTCGACGCCATCC AGAAGAAGATCACCGAGACAAAGCAGCTGGCCAAGGATCTGAGACAGTGG CAGACCAATGTGGACGTGGCCAACGACCTGGCTCTGAAGCTGCTGAGAGA CTACAGCGCCGACGACACCAGAAAGGTGCACATGATCACCGAAAACATCA ACGCCTCTTGGCGGAGCATCCACAAGCGGGTGTCAGAGAGAGAAGCCGCT CTGGAAGAAACACATAGACTGCTCCAGCAGTTCCCACTCGACCTGGAAAA GTTCCTGGCCTGGCTGACAGAAGCCGAAACCACCGCTAACGTGCTCCAGG ATGCCACCAGAAAAGAGCGGCTGTTGGAGGACAGCAAGGGCGTCAAAGAA CTCATGAAGCAGTGGCAGGATCTGCAAGGGGAGATTGAAGCCCACACCGA CGTGTACCACAACCTGGACGAGAACAGCCAGAAGATCCTGCGGTCCCTGG AAGGCTCTGATGATGCTGTGCTGCTTCAGAGGCGGCTGGACAACATGAAC TTCAAGTGGAGCGAGCTGCGGAAGAAGTCCCTGAACATCAGAAGCCACCT GGAAGCCTCCAGCGACCAGTGGAAAAGACTGCACCTGTCTCTCCAAGAGC TGCTCGTGTGGCTGCAGCTGAAGGATGACGAGCTGAGTAGACAGGCCCCT ATCGGCGGAGATTTTCCCGCCGTGCAGAAACAGAACGACGTGCACCGGGC CTTCAAGAGAGAGCTGAAAACAAAAGAACCCGTCATCATGAGCACCCTGG AAACCGTGCGGATCTTTCTGACCGAGCAGCCTCTGGAAGGACTGGAAAAG CTGTACCAAGAGCCTAGAGAGCTGCCTCCTGAAGAAAGGGCCCAGAACGT GACACGGCTGCTTAGAAAGCAGGCCGAGGAAGTGAACACCGAATGGGAGA AGCTGAACCTCCACTCCGCCGACTGGCAGCGGAAGATCGATGAGACACTG GAACGGCTGCGGGAACTGCAAGAAGCCACAGACGAGCTGGACCTGAAACT GCGGCAGGCTGAAGTGATCAAAGGCTCCTGGCAGCCAGTGGGCGATCTGC TGATCGATAGCCTGCAGGACCATCTGGAAAAAGTCAAGGCCCTGCGGGGA GAGATCGCCCCTCTCAAAGAAAACGTGTCCCACGTGAACGATCTGGCCAG GCAGCTGACAACACTGGGCATCCAGCTGAGCCCTTACAACCTGTCTACCT TGGAGGACCTGAATACCCGGTGGAAGCTGCTCCAAGTGGCCGTCGAGGAT AGAGTGCGGCAGCTGCATGAGGCTCACAGAGATTTTGGACCCGCCAGCCA GCACTTCCTGAGCACATCTGTTCAAGGCCCCTGGGAGAGAGCTATCAGCC CTAACAAGGTGCCCTACTACATCAACCACGAGACACAGACCACCTGTTGG GATCACCCCAAGATGACCGAACTGTATCAGTCCCTGGCCGACCTGAACAA CGTGCGGTTTAGCGCCTACCGGACCGCCATGAAGCTGCGCAGACTGCAGA AAGCTCTGTGCCTGGACCTGCTGTCTCTGAGCGCTGCTTGTGATGCCCTG GACCAGCATAACCTCAAGCAGAACGACCAGCCTATGGACATCCTGCAGAT CATCAACTGCCTGACCACCATCTACGACCGGCTCGAACAAGAGCACAACA ACCTGGTCAACGTGCCCCTGTGCGTGGACATGTGCCTGAATTGGCTGCTG AACGTGTACGACACCGGCAGAACCGGCAGGATCAGAGTGCTGAGCTTCAA GACCGGCATCATCTCCCTGTGCAAGGCCCACCTTGAGGATAAGTACCGCT ACCTGTTTAAGCAGGTCGCCAGCAGCACCGGCTTTTGCGACCAAAGAAGG CTGGGACTGCTGCTCCACGACAGCATTCAGATCCCTAGACAGCTGGGCGA AGTGGCCTCTTTCGGCGGCTCTAATATCGAGCCTAGCGTGCGGAGCTGCT TCCAGTTCGCCAACAACAAGCCCGAGATTGAGGCCGCACTGTTCCTGGAC TGGATGAGACTGGAACCCCAGAGCATGGTCTGGCTGCCTGTGCTGCATAG AGTGGCCGCAGCCGAAACAGCCAAGCACCAGGCCAAGTGCAACATCTGCA AAGAGTGCCCCATCATCGGCTTCCGGTACAGATCCCTGAAGCACTTCAAC TACGATATCTGCCAGTCCTGCTTCTTCAGCGGCAGAGTGGCCAAGGGCCA CAAGATGCACTACCCCATGGTGGAATACTGCACCCCTACCACCTCTGGCG AGGACGTGCGGGATTTTGCCAAGGTGCTCAAGAACAAGTTCCGGACCAAG CGCTACTTCGCTAAGCACCCCAGAATGGGCTACCTGCCAGTGCAGACAGT GCTTGAGGGCGACAACATGGAAACCCCTGTGACTCTGATCAACTTCTGGC CCGTGGATAGCGCCCCTGCTAGTTCTCCTCAGCTGTCTCACGACGATACC CACAGCAGAATCGAGCACTACGCCTCCAGACTGGCCGAGATGGAAAACAG CAACGGCAGCTACCTGAATGACAGCATCAGCCCCAACGAGAGCATCGACG ACGAACATCTGCTCATTCAGCACTACTGCCAGAGCCTGAATCAGGACAGC CCTCTGTCTCAGCCTAGAAGCCCTGCACAGATCCTGATCAGCCTGGAAAG CGAGGAACGCGGCGAGCTGGAAAGAATCCTGGCAGACCTGGAAGAGGAAA ACCGGAACCTGCAGGCCGAATACGACAGACTCAAGCAGCAGCACGAGCAC AAGGGACTGTCTCCACTGCCTTCTCCACCTGAAATGATGCCCACCTCTCC ACAGAGCCCCAGAGATGCCGAGCTGATTGCCGAAGCCAAACTGCTGAGGC AGCACAAAGGCAGACTCGAAGCCAGAATGCAGATTCTCGAAGATCACAAC AAGCAGCTCGAATCCCAGCTGCACAGACTTAGGCAGCTGCTGGAACAGCC TCAGGCAGAGGCCAAAGTGAATGGCACCACCGTGTCTAGCCCTAGCACAA GCCTGCAGAGATCCGACAGCAGCCAGCCAATGCTTCTGAGAGTCGTGGGC TCCCAGACCAGCGATTCTATGGGCGAAGAGGACCTGCTCAGCCCTCCTCA GGATACAAGCACCGGCCTGGAAGAAGTGATGGAACAACTGAACAACAGCT TCCCCAGCAGCAGAGGCAGAAACACCCCTGGCAAGCCCATGCGCGAGGAC ACCATGTGATAACTCGAGAATCAACCTCTGGATTACAAAATTTGTGAAAG ATTGACTGGTATTCTTAACTATGTTGCTCCTTTTACGCTATGTGGATACG CTGCTTTAATGCCTTTGTATCATGCTATTGCTTCCCGTATGGCTTTCATT TTCTCCTCCTTGTATAAATCCTGGTTGCTGTCTCTTTATGAGGAGTTGTG GCCCGTTGTCAGGCAACGTGGCGTGGTGTGCACTGTGTTTGCTGACGCAA |

| SEQ ID NO | Description | SEQ |
|---|---|---|
| | | CCCCCACTGGTTGGGGCATTGCCACCACCTGTCAGCTCCTTTCCGGGACT<br>TTCGCTTTCCCCCTCCCTATTGCCACGGCGGAACTCATCGCCGCCTGCCT<br>TGCCCGCTGCTGGACAGGGGCTCGGCTGTTGGGCACTGACAATTCCGTGG |
| 36. | MHCK7-hBGi-DMD-4-WPRE3-Poly A | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT<br>GCTGGTCTGTGTGCTGGCCCATCACTTTGGCAAAGAATTGCGATCGCCAC<br>CATGCTTTGGTGGGAAGAAGTCGAGGACTGCTACGAGCGCGAGGACGTGC<br>AGAAGAAAACCTTCACCAAATGGGTCAACGCCCAGTTCAGCAAGTTCGGC<br>AAGCAGCACATCGAGAACCTGTTCAGCGACCTGCAGGATGGCAGAAGGCT<br>GCTGGATCTGCTGGAAGGCCTGACAGGACAGAAGCTGCCCAAAGAGAAGG<br>GCAGCACAAGAGTGCACGCCCTGAACAACGTGAACAAGGCCCTGAGAGTG<br>CTGCAGAACAACAACGTGGACCTGGTCAACATCGGCAGCACCGACATCGT<br>GGACGGCAACCACAAACTGACCCTGGGCCTGATCTGGAACATCATCCTGC<br>ACTGGCAAGTGAAGAACGTGATGAAGAACATCATGGCCGGCCTGCAGCAG<br>ACCAACAGCGAGAAGATTCTGCTGAGCTGGGTCCGACAGAGCACCCGGAA<br>TTACCCTCAAGTGAACGTGATCAACTTCACCACCTCTTGGAGCGACGGAC<br>TGGCCCTGAATGCCCTGATCCACAGCCACAGACCTGACCTGTTCGACTGG<br>AACAGCGTCGTGTGTCAGCAGAGCGCCACACAGAGGCTGGAACACGCCTT<br>CAATATCGCCAGATACCAGCTGGGCATCGAGAAACTGCTGGACCCCGAGG<br>ATGTGGACACCACCTATCCTGACAAGAAATCCATCCTCATGTACATCACC<br>AGCCTGTTCCAGGTGCTGCCCCAGCAGGTTTCCATCGAGGCCATTCAAGA<br>GGTCGAGATGCTGCCCAGACCTCCTAAAGTGACCAAAGAGGAACACTTCC<br>AGCTGCACCACCAGATGCACTACTCTCAGCAGATCACCGTGTCTCTGGCC<br>CAGGGCTACGAGAGAACAAGCAGCCCCAAGCCTCGGTTCAAGAGCTACGC<br>CTATACACAGGCCGCCTACGTGACCACCAGCGATCCTACAAGAAGCCCAT<br>TTCCTAGCCAGCATCTGGAAGCCCCTGAGGACAAGAGCTTTGGCAGCAGC<br>CTGATGGAAAGCGAAGTGAACCTGGACCGCTACCAGACAGCCCTGGAAGA<br>GGTTCTGAGCTGGCTGCTGTCTGCCGAGGATACACTGCAGGCTCAGGGCG<br>AGATCAGCAACGACGTGGAAGTGGTCAAGGACCAGTTTCACACCCACGAG<br>GGCTACATGATGGACCTGACAGCCCACCAGGGCAGAGTGGGCAATATTCT<br>GCAGCTGGGCTCCAAGCTGATCGGCACAGGCAAGCTGAGCGAGGACGAAG<br>AGACAGAGGTGCAAGAGCAGATGAACCTGCTGAACAGCAGATGGGAGTGT<br>CTGAGAGTGGCCAGCATGGAAAAGCAGAGCAACCTGCACCGGGTGCTGAT<br>GGATCTCCAGAACCAGAAGCTGAAAGAGCTGAACGACTGGCTGACCAAGA<br>CCGAGGAACGGACCCGGAAGATGGAAGAGGAACCTCTGGGACCCGACCTG<br>GAAGATCTGAAAAGACAGGTGCAGCAGCATAAGGTGCTGCAAGAGGACCT<br>CGAACAAGAGCAAGTGCGCGTGAACAGCCTGACACACATGGTGGTGGTCG<br>TGGATGAGAGCAGCGGAGATCATGCCACAGCCGCTCTGGAAGAACAGCTG<br>AAGGTGCTGGGAGACAGATGGGCCAATATCTGCCGGTGGACCGAGGATAG<br>ATGGGTGCTGCTCCAGGACATCCTGCTGAAGTGGCAGCGGCTGACAGAGG<br>AACAGTGCCTGTTTAGCGCCTGGCTGTCCGAGAAAGAGGACGCCGTCAAC<br>AAGATCCACACCACCGGCTTCAAGGATCAGAATGAGATGCTGAGCAGCCT<br>GCAGAAACTGGCCGTGCTGAAGGCTGACCTGGAAAAGAAAAAGCAGTCCA<br>TGGGCAAGCTGTACTCCCTGAAGCAGGACCTGCTGAGCACACTGAAGAAC<br>AAGTCTGTGACCCAGAAAACCGAGGCCTGGCTGGACAACTTCGCCCGGTG<br>TTGGGATAACCTGGTGCAGAAGCTGGAAAAGTCCACCGCTCAGATCTCTC<br>AGGCCGTGACCACAACACAGCCTTCTCTGACCCAGACCACCGTGATGGAA<br>ACAGTGACCACAGTGACAACCCGCGAGCAGATCCTGGTCAAGCACGCCCA<br>AGAAGAACTGCCTCCTCCACCTCCTCAGAAGAAACGGCAGATCACAGTGG<br>ACAGCGAGATCCGGAAGAGACTGGACGTGGACATCACCGAGCTGCACAGC<br>TGGATCACCAGATCCGAAGCCGTGCTGCAGTCCCCTGAGTTCGCCATCTT<br>CAGAAAAGAGGGCAACTTCTCCGACCTGAAAGAGAAAGTCAACGCCATCG<br>AGAGAGAGAAGGCCGAGAAGTTCCGGAAGCTGCAGGACGCCTCTAGATCT<br>GCCCAGGCTCTGGTGGAACAGATGGTCAACGAAGGCGTGAACGCCGACAG<br>CATCAAGCAGGCCTCAGAGCAGCTGAACTCCCGGTGGATCGAGTTCTGTC<br>AGCTCCTGAGCGAGAGACTGAACTGGCTGGAATACCAGAACAATATCATT |

-continued

| SEQ ID NO | Description | SEQ |
|---|---|---|
| | | GCCTTCTACAACCAGCTCCAGCAGCTCGAACAGATGACCACCACAGCCGA<br>GAATTGGCTGAAGATCCAGCCTACCACACCTAGCGAGCCCACCGCCATTA<br>AGAGCCAGCTGAAAATCTGCAAGGACGAAGTGAATCGGCTGAGCGATCTG<br>CAGCCCCAGATCGAAAGACTGAAAATCCAGTCTATCGCCCTCAAAGAGAA<br>AGGACAGGGCCCCATGTTCCTGGACGCCGATTTTGTGGCCTTTACCAACC<br>ACTTCAAACAGGTGTTCTCCGACGTGCAGGCCCGGGAAAAAGAGCTGCAG<br>ACCATCTTCGACACCCTGCCTCCAATGAGATACCAAGAGACAATGAGCGC<br>CATCCGGACCTGGGTGCAGCAAAGCGAGACAAAGCTGAGCATCCCACAGC<br>TGAGCGTGACCGACTACGAGATCATGGAACAGAGACTGGGCGAACTGCAG<br>GCCCTCCAGTCTAGCCTGCAAGAACAGCAGTCCGGCCTGTACTACCTGAG<br>CACAACCGTGAAAGAGATGAGCAAGAAGGCCCCTAGCGAGATCTCCCGGA<br>AGTACCAGAGCGAGTTCGAAGAGATCGAAGGCCGGTGGAAGAAGCTGTCT<br>AGCCAGCTGGTTGAGCACTGCCAGAAACTCGAAGAACAAATGAACAAGCT<br>GCGCAAGATCCAGAATCACATCCAGACGCTGAAGAAATGGATGGCCGAGG<br>TGGACGTGTTCCTGAAAGAAGAGTGGCCCGCTCTGGGCGACTCCGAGATT<br>CTGAAGAAACAGCTCAAACAGTGCCGGCTGCTGGTGTCCGATATCCAGAC<br>AATCCAGCCAAGCCTGAACTCCGTGAATGAAGGCGGCCAGAAGATCAAGA<br>ACGAGGCCGAGCCTGAGTTTGCCAGCAGACTGGAAACCGAACTGAAAGAA<br>CTCAACACCCAGTGGGACCACATGTGCCAGCAAGTGTACGCCCGGAAAGA<br>GGCCCTGAAAGGCGGACTCGAAAAGACTGTGTCTCTGCAGAAAGACCTGT<br>CTGAGATGCACGAGTGGATGACCCAGGCCGAAGAGGAATACCTGGAACGG<br>GACTTCGAGTACAAGACCCCTGATGAGCTGCAAAAAGCCGTCGAGGAAAT<br>GAAGCGGGCCAAAGAAGAGGCCCAGCAGAAAGAAGCCAAAGTCAAGCTGC<br>TGACCGAGTCCGTGAATAGCGTTATCGCTCAGGCCCCTCCTGTGGCTCAA<br>GAGGCTCTCAAGAAAGAACTGGAAACTCTGACCACCAACTACCAGTGGCT<br>GTGCACCAGACTGAACGGCAAGTGCAAGACACTGGAAGAAGTGTGGGCCT<br>GCTGGCACGAACTGCTGTCCTATCTGGAAAAGGCCAACAAGTGGCTGAAC<br>GAGGTGGAATTCAAGCTGAAAACCACCGAGAACATCCCTGGCGGCGCTGA<br>AGAGATTAGCGAGGTGCTGGACAGCCTGGAAAACCTGATGAGACACAGCG<br>AGGACAACCCCAATCAGATCAGAATCCTGGCTCAGACCCTGACCGATGGC<br>GGCGTGATGGACGAGCTGATCAACGAGGAACTCGAAACCTTCAACAGCCG<br>GTGGCGGGAACTGCACGAGGAAGCTGTTCGGAGGCAGAAGTTGCTGGAAC<br>AGTCTATCCAGAGCGCACAAGAAACCGAGAAGTCCCTGCACCTGATCCAA<br>GAGAGCCTGACCTTCATCGACAAGCAGCTGGCCGCTTATATCGCCGACAA<br>GGTGGACGCTGCTCAGATGCCCCAAGAGGCACAGAAGATTCAGAGCGACC<br>TGACCAGCCACGAGATTAGCCTGGAAGAAATGAAGAAGCACAACCAGGGC<br>AAAGAGGCCGCTCAGAGAGTCCTGAGCCAGATCGATGTGGCACAGAAAAA<br>GCTCCAGGATGTGTCCATGAAGTTTCGGCTGTTTCAGAAGCCCGCCAACT<br>TCGAGCAGAGACTGCAAGAGTCCAAGATGATCCTGGACGAAGTCAAAATG<br>CATCTGCCCGCACTGGAAACAAAGTCCGTGGAACAAGAAGTGGTGCAGTC<br>CCAGCTGAACCACTGCGTGAACCTGTACAAGAGCCTGTCCGAAGTGAAGT<br>CTGAGGTGGAAATGGTCATCAAGACCGGCAGGCAGATCGTCCAGAAGAAG<br>CAGACCGAGAATCCCAAAGAACTCGACGAGAGAGTGACCGCTCTGAAGCT<br>GCACTACAATGAGCTGGGCGCCAAAGTGACCGAGCGGAAGCAACAGCTTG<br>AGAAGTGCCTGAAACTGTCTCGGAAGATGCGGAAAGAAATGAACGTGCTG<br>ACAGAGTGGCTGGCCGCCACCGATATGGAACTGACTAAGAGAAGCGCCGT<br>GGAAGGCATGCCCAGCAACCTGGATAGTGAAGTGGCCTGGGGCAAAGCCA<br>CTCAGAAAGAGATTGAGAAGCAGAAGGTCCACCTGAAGTCCATCACCGAA<br>GTGGGCGAAGCCCTGAAAACCGTGCTGGGAAAGAAAGAGACACTGGTCGA<br>GGACAAGCTGTCCCTGCTGAATTCCAACTGGATCGCCGTGACCTCCAGAG<br>CTGAGGAATGGCTGAATCTGCTGCTTGAGTACCAGAAACACATGGAAACG<br>TTCGACCAGAACGTCGACCACATCACAAAGTGGATCATCCAGGCTGATAC<br>CCTGCTGGACGAGTCCGAGAAGAAGAAACCCCAACAAAAAGAAGATGTGC<br>TGAAGCGGCTGAAAGCCGAGCTGAATGACATCCGGCCTAAGGTGGACAGC<br>ACCAGAGATCAGGCAGCCAACCTGATGGCCAACAGAGGCGACCACTGTCG<br>GAAGCTCGTGGAACCTCAGATCAGCGAGCTTAACCACAGATTTGCCGCCA<br>TCAGCCACCGGATCAAGACAGGCAAGGCCAGCATTCCTCTCAAAGAGCTT<br>GAGCAGTTCAACAGCGACATCCAAAAGCTGCTCGAACCCCTGGAAGCCGA<br>GATCCAACAGGGCGTCAACCTCAAAGAAGAAGATTTCAACAAGGACATGA<br>ACGAGGACAATGAGGGCACCGTCAAAGAACTGCTGCAGCGGGGCGATAAT<br>CTGCAGCAGCGGATTACCGATGAGCGCAAGCGGGAAGAGATCAAGATTAA<br>GCAGCAGCTGCTGCAGACCAAGCACAACGCCCTGAAGGACCTGCGGAGCC<br>AGAGAAGAAAGAAGGCCCTGGAAATCAGCCACCAGTGGTATCAGTACAAG<br>CGGCAGGCCGACGACCTGCTGAAGTGCCTGGATGACATCGAGAAGAAGCT<br>GGCCTCTCTGCCCGAGCCTAGGGACGAGAGAAAGATCAAAGAGATCGACC<br>GCGAGCTGCAGAAAAAGAAAGAGGAACTGAACGCCGTCCGCAGACAGGCC<br>GAAGGACTTTCTGAAGATGGCGCCGCTATGGCCGTGGAACCCACACAGAT<br>TCAGCTGAGCAAGCGGTGGCGGGAAATCGAGAGCAAGTTCGCCCAGTTCC<br>GGCGGCTGAATTTCGCCCAGATCCACACCGTGCGGGAAGAGACAATGATG<br>GTCATGACAGAGGACATGCCCCTTGAGATCAGCTACGTGCCCAGCACCTA<br>CCTGACCGAGATCACCCATGTGTCTCAGGCCCTGCTGGAAGTGGAACAGC<br>TGCTGAATGCCCCTGACCTGTGCGCCAAGGACTTCGAGGACCTGTTCAAG<br>CAAGAGGAAAGCCTGAAGAACATCAAGGACAGCCTGCAGCAGAGCAGCGG<br>CCGGATCGATATCATCCACAGCAAGAAAACCGCCGCACTGCAGAGCGCCA<br>CACCTGTGGAAAGAGTGAAGCTGCAAGAGGCCCTGAGCCAGCTGGATTTC |

-continued

| SEQ ID NO | Description | SEQ |
|---|---|---|
| | | CAGTGGGAGAAAGTGAACAAGATGTACAAGGACCGGCAGGGCAGATTCGA<br>CCGCAGCGTTGAAAAGTGGCGGCGGTTCCACTACGACATCAAGATCTTCA<br>ACCAGTGGCTGACCGAGGCCGAGCAGTTCCTGAGAAAGACACAGATCCCC<br>GAGAACTGGGAGCACGCCAAGTACAAGTGGTATCTGAAAGAGCTGCAGGA<br>CGGCATCGGCCAGAGACAGACAGTCGTGCGGACACTGAATGCCACCGGCG<br>AGGAAATCATCCAGCAGTCCAGCAAGACCGACGCCAGCATCCTGCAAGAG<br>AAGCTGGGCAGCCTGAACCTGCGGTGGCAAGAAGTGTGCAAGCAGCTGAG<br>CGACCGGAAGAAGCGGCTGGAAGAACAGAAGAATATCCTGAGCGAGTTCC<br>AGCGGGACCTGAACGAGTTCGTGCTGTGGCTCGAAGAGGCCGACAATATC<br>GCCAGCATTCCCCTGGAACCTGGCAAAGAGCAGCAGCTGAAAGAAAAGCT<br>GGAACAAGTGAAACTGCTGGTCGAGGAACTGCCCCTGAGACAGGGAATCC<br>TGAAACAGCTGAACGAGACAGGCGGCCCTGTGCTGGTGTCTGCCCCTATT<br>TCTCCCGAGGAACAGGACAAGCTGGAAAACAAGCTGAAGCAGACCAACCT<br>GCAGTGGATCAAGGTGTCCAGAGCACTGCCTGAGAAGCAGGGCGAGATCG<br>AGGCCCAGATCAAGGACCTGGGACAGCTCGAAAAGAAGCTTGAGGACCTC<br>GAAGAACAGCTCAACCATCTGCTGCTTTGGCTGAGCCCCATCCGGAACCA<br>GCTGGAAATCTACAACCAGCCTAATCAAGAGGGCCCCTTCGACGTGAAAG<br>AAACCGAGATTGCCGTGCAGGCCAAGCAGCCCGATGTGGAAGAGATCCTG<br>TCTAAGGGCCAGCACCTGTACAAAGAGAAGCCCGCCACACAGCCCGTGAA<br>GCGGAAACTGGAAGATCTGAGCAGCGAGTGGAAGGCCGTGAACCGGCTGC<br>TGCAAGAACTGAGAGCCAAACAGCCTGATCTGGCCCCTGGCCTGACAACA<br>ATTGGCGCCTCTCCTACACAGACCGTGACACTGGTCACACAGCCTGTGGT<br>CACCAAAGAGACAGCCATCAGCAAACTGGAAATGCCCAGCAGTCTGATGC<br>TCGAAGTGCCCGCACTGGCCGACTTCAATAGAGCCTGGACCGAGCTGACC<br>GACTGGCTCAGTCTGCTGGACCAAGTCATCAAGTCCCAGAGAGTGATGGT<br>CGGAGATCTTGAGGACATCAACGAGATGATCATTAAGCAGAAAGCCACCA<br>TGCAGGACCTTGAGCAGAGAAGGCCCCAGCTTGAAGAACTGATCACCGCC<br>GCTCAGAACCTGAAAAACAAGACCAGCAATCAAGAAGCCCGGACCATCAT<br>CACCGACCGGATCGAGAGAATCCAGAACCAGTGGGACGAAGTGCAAGAGC<br>ATCTGCAGAACAGACGGCAGCAGCTCAATGAGATGCTGAAGGACAGCACA<br>CAGTGGCTGGAAGCCAAAGAAGAAGCCGAGCAGGTTCTCGGACAGGCCAG<br>AGCTAAGCTGGAATCTTGGAAAGAGGGACCCTACACCGTCGACGCCATCC<br>AGAAGAAGATCACCGAGACAAAGCAGCTGGCCAAGGATCTGAGACAGTGG<br>CAGACCAATGTGGACGTGGCCAACGACCTGGCTCTGAAGCTGCTGAGAGA<br>CTACAGCGCCGACGACACCAGAAAGGTGCACATGATCACCGAAAACATCA<br>ACGCCTCTTGGCGGAGCATCCACAAGCGGGTGTCAGAGAGAGAAGCCGCT<br>CTGGAAGAAACACATAGACTGCTCCAGCAGTTCCCACTCGACCTGGAAAA<br>GTTCCTGGCCTGGCTGACAGAAGCCGAAACCACCGCTAACGTGCTCCAGG<br>ATGCCACCAGAAAAGAGCGGCTGTTGGAGGACAGCAAGGGCGTCAAAGAA<br>CTCATGAAGCAGTGGCAGGATCTGCAAGGGGAGATTGAAGCCCACACCGA<br>CGTGTACCACAACCTGGACGAGAACAGCCAGAAGATCCTGCGGTCCCTGG<br>AAGGCTCTGATGATGCTGTGCTGCTTCAGAGGCGGCTGGACAACATGAAC<br>TTCAAGTGGAGCGAGCTGCGGAAGAAGTCCCTGAACATCAGAAGCCACCT<br>GGAAGCCTCCAGCGACCAGTGGAAAAGACTGCACCTGTCTCTCCAAGAGC<br>TGCTCGTGTGGCTGCAGCTGAAGGATGACGAGCTGAGTAGACAGGCCCCT<br>ATCGGCGGAGATTTTCCCGCCGTGCAGAAACAGAACGACGTGCACCGGGC<br>CTTCAAGAGAGAGCTGAAAACAAAAGAACCCGTCATCATGAGCACCCTGG<br>AAACCGTGCGGATCTTTCTGACCGAGCAGCCTCTGGAAGGACTGGAAAAG<br>CTGTACCAAGAGCCTAGAGAGCTGCCTCCTGAAGAAAGGGCCCAGAACGT<br>GACACGGCTGCTTAGAAAGCAGGCCGAGGAAGTGAACACCGAATGGGAGA<br>AGCTGAACCTCCACTCCGCCGACTGGCAGCGGAAGATCGATGAGACACTG<br>GAACGGCTGCGGGAACTGCAAGAAGCCACAGACGAGCTGGACCTGAAACT<br>GCGGCAGGCTGAAGTGATCAAAGGCTCCTGGCAGCCAGTGGGCGATCTGC<br>TGATCGATAGCCTGCAGGACCATCTGGAAAAAGTCAAGGCCCTGCGGGGA<br>GAGATCGCCCCTCTCAAAGAAAACGTGTCCCACGTGAACGATCTGGCCAG<br>GCAGCTGACAACACTGGGCATCCAGCTGAGCCCTTACAACCTGTCTACCT<br>TGGAGGACCTGAATACCCGGTGGAAGCTGCTCCAAGTGGCCGTCGAGGAT<br>AGAGTGCGGCAGCTGCATGAGGCTCACAGAGATTTTGGACCCGCCAGCCA<br>GCACTTCCTGAGCACATCTGTTCAAGGCCCCTGGGAGAGAGCTATCAGCC<br>CTAACAAGGTGCCCTACTACATCAACCACGAGACACAGACCACCTGTTGG<br>GATCACCCCAAGATGACCGAACTGTATCAGTCCCTGGCCGACCTGAACAA<br>CGTGCGGTTTAGCGCCTACCGGACCGCCATGAAGCTGCGCAGACTGCAGA<br>AAGCTCTGTGCCTGGACCTGCTGTCTCTGAGCGCTGCTTGTGATGCCCTG<br>GACCAGCATAACCTCAAGCAGAACGACCAGCCTATGGACATCCTGCAGAT<br>CATCAACTGCCTGACCACCATCTACGACCGGCTCGAACAAGAGCACAACA<br>ACCTGGTCAACGTGCCCCTGTGCGTGGACATGTGCCTGAATTGGCTGCTG<br>AACGTGTACGACACCGGCAGAACCGGCAGGATCAGAGTGCTGAGCTTCAA<br>GACCGGCATCATCTCCCTGTGCAAGGCCCACCTTGAGGATAAGTACCGCT<br>ACCTGTTTAAGCAGGTCGCCAGCAGCACCGGCTTTTGCGACCAAAGAAGG<br>CTGGGACTGCTGCTCCACGACAGCATTCAGATCCCTAGACAGCTGGGCGA<br>AGTGGCCTCTTTCGGCGGCTCTAATATCGAGCCTAGCGTGCGGAGCTGCT<br>TCCAGTTCGCCAACAACAAGCCCGAGATTGAGGCCGCACTGTTCCTGGAC<br>TGGATGAGACTGGAACCCCAGAGCATGGTCTGGCTGCCTGTGCTGCATAG<br>AGTGGCCGCAGCCGAAACAGCCAAGCACCAGGCCAAGTGCAACATCTGCA<br>AAGAGTGCCCCATCATCGGCTTCCGGTACAGATCCCTGAAGCACTTCAAC |

-continued

| SEQ ID NO | Description | SEQ |
|---|---|---|
| | | TACGATATCTGCCAGTCCTGCTTCTTCAGCGGCAGAGTGGCCAAGGGCCA CAAGATGCACTACCCCATGGTGGAATACTGCACCCCTACCACCTCTGGCG AGGACGTGCGGGATTTTGCCAAGGTGCTCAAGAACAAGTTCCGGACCAAG CGCTACTTCGCTAAGCACCCCAGAATGGGCTACCTGCCAGTGCAGACAGT GCTTGAGGGCGACAACATGGAAACCCCTGTGACTCTGATCAACTTCTGGC CCGTGGATAGCGCCCCTGCTAGTTCTCCTCAGCTGTCTCACGACGATACC CACAGCAGAATCGAGCACTACGCCTCCAGACTGGCCGAGATGGAAAACAG CAACGGCAGCTACCTGAATGACAGCATCAGCCCCAACGAGAGCATCGACG ACGAACATCTGCTCATTCAGCACTACTGCCAGAGCCTGAATCAGGACAGC CCTCTGTCTCAGCCTAGAAGCCCTGCACAGATCCTGATCAGCCTGGAAAG CGAGGAACGCGGCGAGCTGGAAAGAATCCTGGCAGACCTGGAAGAGGAAA ACCGGAACCTGCAGGCCGAATACGACAGACTCAAGCAGCAGCACGAGCAC AAGGGACTGTCTCCACTGCCTTCTCCACCTGAAATGATGCCCACCTCTCC ACAGAGCCCCAGAGATGCCGAGCTGATTGCCGAAGCCAAACTGCTGAGGC AGCACAAAGGCAGACTCGAAGCCAGAATGCAGATTCTCGAAGATCACAAC AAGCAGCTCGAATCCCAGCTGCACAGACTTAGGCAGCTGCTGGAACAGCC TCAGGCAGAGGCCAAAGTGAATGGCACCACCGTGTCTAGCCCTAGCACAA GCCTGCAGAGATCCGACAGCAGCCAGCCAATGCTTCTGAGAGTCGTGGGC TCCCAGACCAGCGATTCTATGGGCGAAGAGGACCTGCTCAGCCCTCCTCA GGATACAAGCACCGGCCTGGAAGAAGTGATGGAACAACTGAACAACAGCT TCCCCAGCAGCAGAGGCAGAAACACCCCTGGCAAGCCCATGCGCGAGGAC ACCATGTGATAACTCGAGAATCAACCTCTGGATTACAAAATTTGTGAAAG ATTGACTGGTATTCTTAACTATGTTGCTCCTTTTACGCTATGTGGATACG CTGCTTTAATGCCTTTGTATCATGCTATTGCTTCCCGTATGGCTTTCATT TTCTCCTCCTTGTATAAATCCTGGTTGCTGTCTCTTTATGAGGAGTTGTG GCCCGTTGTCAGGCAACGTGGCGTGGTGTGCACTGTGTTTGCTGACGCAA CCCCCACTGGTTGGGGCATTGCCACCACCTGTCAGCTCCTTTCCGGGACT TTCGCTTTCCCCCTCCCTATTGCCACGGCGGAACTCATCGCCGCCTGCCT TGCCCGCTGCTGGACAGGGGCTCGGCTGTTGGGCACTGACAATTCCGTGG GGTGTGCCTTCTAGTTGCCAGCCATCTGTTGTTTGCCCCTCCCCCGTGCC TTCCTTGACCCTGGAAGGTGCCACTCCCACTGTCCTTTCCTAATAAAATG AGGAAATTGCATCGCATTGTCTGAGTAGGTGTCATTCTATTCTGGGGGGT GGGGTGGGGCAGGACAGCAAGGGGGAGGATTGGGAAGACAATAGCAGGCA TGCTGGGGATGCGGTGGGCTCTATGG |
| 37. | CMV enhancer-CBA Promoter-AAT Exon-hBGI-hBG Exon | CGTTACATAACTTACGGTAAATGGCCCGCCTGGCTGACCGCCCAACGACC CCCGCCCATTGACGTCAATAATGACGTATGTTCCCATAGTAACGCCAATA GGGACTTTCCATTGACGTCAATGGGTGGAGTATTTACGGTAAACTGCCCA CTTGGCAGTACATCAAGTGTATCATATGCCAAGTACGCCCCCTATTGACG TCAATGACGGTAAATGGCCCGCCTGGCATTATGCCCAGTACATGACCTTA TGGGACTTTCCTACTTGGCAGTACATCTACGTATTAGTCATCGCTATTAC CATGGTCGAGGTGAGCCCCACGTTCTGCTTCACTCTCCCCATCTCCCCCC CCTCCCCACCCCCAATTTTGTATTTATTTATTTTTTAATTATTTTGTGCA GCGATGGGGGCGGGGGGGGGGGGGGGGCGCGCCAGGCGGGGCGGGGCGGG GCGAGGGGCGGGGCGGGGCGAGGCGGAGAGGTGCGGCGGCAGCCAATCAG AGCGGCGCGCTCCGAAAGTTTCCTTTTATGGCGAGGCGGCGGCGGCGGCG GCCCTATAAAAAGCGAAGCGCGCGGCGGGCGGGAGTCTCTGGATCCACTG CTTAAATACGGACGAGGACAGGGCCCTGTCTCCTCAGCTTCAGGCACCAC CACTGACCTGGGACAGTGAATCGTAAGTACTAGCAGCTACAATCCAGCTA CCATTCTGCTTTTATTTTATGGTTGGGATAAGGCTGGATTATTCTGAGTC CAAGCTAGGCCCTTTTGCTAATCATGTTCATACCTCTTATCTTCCTCCCA CAGCTCCTGGGCAACGTGCTGGTCTGTGTGCTGGCCCATCACTTTGGCAA AGAATTGCGATCGCCACC |
| 38. | CMV enhancer-CBA Promoter-AAT Exon | CGTTACATAACTTACGGTAAATGGCCCGCCTGGCTGACCGCCCAACGACC CCCGCCCATTGACGTCAATAATGACGTATGTTCCCATAGTAACGCCAATA GGGACTTTCCATTGACGTCAATGGGTGGAGTATTTACGGTAAACTGCCCA CTTGGCAGTACATCAAGTGTATCATATGCCAAGTACGCCCCCTATTGACG TCAATGACGGTAAATGGCCCGCCTGGCATTATGCCCAGTACATGACCTTA TGGGACTTTCCTACTTGGCAGTACATCTACGTATTAGTCATCGCTATTAC CATGGTCGAGGTGAGCCCCACGTTCTGCTTCACTCTCCCCATCTCCCCCC CCTCCCCACCCCCAATTTTGTATTTATTTATTTTTTAATTATTTTGTGCA GCGATGGGGGCGGGGGGGGGGGGGGGGCGCGCCAGGCGGGGGGGGGCGGG GCGAGGGGCGGGGCGGGGCGAGGCGGAGAGGTGCGGCGGCAGCCAATCAG AGCGGCGCGCTCCGAAAGTTTCCTTTTATGGCGAGGCGGCGGCGGCGGCG GCCCTATAAAAAGCGAAGCGCGCGGCGGGCGGGAGTCTCTGGATCCACTG CTTAAATACGGACGAGGACAGGGCCCTGTCTCCTCAGCTTCAGGCACCAC CACTGACCTGGGACAGTGAATC |
| 39. | CBA Promoter-AAT Exon | TGGTCGAGGTGAGCCCCACGTTCTGCTTCACTCTCCCCATCTCCCCCCCC TCCCCACCCCCAATTTTGTATTTATTTATTTTTTAATTATTTTGTGCAGC GATGGGGGCGGGGGGGGGGGGGGGGCGCGCCAGGCGGGGCGGGGCGGGGC GAGGGGCGGGGCGGGGCGAGGCGGAGAGGTGCGGCGGCAGCCAATCAGAG CGGCGCGCTCCGAAAGTTTCCTTTTATGGCGAGGCGGCGGCGGCGGCGGC CCTATAAAAAGCGAAGCGCGCGGCGGGCGGGAGTCTCTGGATCCACTGCT |

| SEQ ID NO | Description | SEQ |
|---|---|---|
| | | TAAATACGGACGAGGACAGGGCCCTGTCTCCTCAGCTTCAGGCACCACCA<br>CTGACCTGGGACAGTGAATC |
| 40. | CBA Promoter-AAT Exon-hBGI-hBG Exon | TGGTCGAGGTGAGCCCCACGTTCTGCTTCACTCTCCCCATCTCCCCCCCC<br>TCCCCACCCCCAATTTTGTATTTATTTATTTTTTAATTATTTTGTGCAGC<br>GATGGGGGCGGGGGGGGGGGGGGCGCGCGCCAGGCGGGGCGGGGCGGGGC<br>GAGGGGCGGGGGGGGCGAGGCGGAGAGGTGCGGCGGCAGCCAATCAGAGC<br>GGCGCGCTCCGAAAGTTTCCTTTTATGGCGAGGCGGCGGCGGCGGCGGCC<br>CTATAAAAAGCGAAGCGCGCGGCGGGCGGGAGTCTCTGGATCCACTGCTT<br>AAATACGGACGAGGACAGGGCCCTGTCTCCTCAGCTTCAGGCACCACCAC<br>TGACCTGGGACAGTGAATCGTAAGTACTAGCAGCTACAATCCAGCTACCA<br>TTCTGCTTTTATTTTATGGTTGGGATAAGGCTGGATTATTCTGAGTCCAA<br>GCTAGGCCCTTTTGCTAATCATGTTCATACCTCTTATCTTCCTCCCACAG<br>CTCCTGGGCAACGTGCTGGTCTGTGTGCTGGCCCATCACTTTGGCAAAGA<br>ATTGCGATCGCCACC |
| 41. | CAG | CGTTACATAACTTACGGTAAATGGCCCGCCTGGCTGACCGCCCAACGACC<br>CCCGCCCATTGACGTCAATAATGACGTATGTTCCCATAGTAACGCCAATA<br>GGGACTTTCCATTGACGTCAATGGGTGGAGTATTTACGGTAAACTGCCCA<br>CTTGGCAGTACATCAAGTGTATCATATGCCAAGTACGCCCCCTATTGACG<br>TCAATGACGGTAAATGGCCCGCCTGGCATTATGCCCAGTACATGACCTTA<br>TGGGACTTTCCTACTTGGCAGTACATCTACGTATTAGTCATCGCTATTAC<br>CATGGTCGAGGTGAGCCCCACGTTCTGCTTCACTCTCCCCATCTCCCCCC<br>CCTCCCCACCCCCAATTTTGTATTTATTTATTTTTTAATTATTTTGTGCA<br>GCGATGGGGGCGGGGGGGGGGGGGGGGCGCGCCAGGCGGGGCGGGGCGGG<br>GCGAGGGGCGGGGCGGGGCGAGGCGGAGAGGTGCGGCGGCAGCCAATCAGA<br>GCGGCGCGCTCCGAAAGTTTCCTTTTATGGCGAGGCGGCGGCGGCGGCGG<br>CCCTATAAAAAGCGAAGCGCGCGGCGGGCGGGAGTCGCTGCGCGCTGCCT<br>TCGCCCCGTGCCCCGCTCCGCCGCCGCCTCGCGCCGCCCGCCCCGGCTCT<br>GACTGACCGCGTTACTCCCACAGGTGAGCGGGCGGGACGGCCCTTCTCCT<br>CCGGGCTGTAATTAGCGCTTGGTTTAATGACGGCTTGTTTCTTTTCTGTG<br>GCTGCGTGAAAGCCTTGAGGGGCTCCGGGAGGGCCCTTTGTGCGGGGGGA<br>GCGGCTCGGGGGGTGCGTGCGTGTGTGTGTGCGTGGGGAGCGCCGCGTGC<br>GGCTCCGCGCTGCCCGGCGGCTGTGAGCGCTGCGGGCGCGGCGCGGGGCT<br>TTGTGCGCTCCGCAGTGTGCGCGAGGGGAGCGCGGCCGGGGGCGGTGCCC<br>CGCGGTGCGGGGGGGGCTGCGAGGGGAACAAAGGCTGCGTGCGGGGTGTG<br>TGCGTGGGGGGGTGAGCAGGGGGTGTGGGCGCGTCGGTCGGGCTGCAACC<br>CCCCCTGCACCCCCCTCCCCGAGTTGCTGAGCACGGCCCGGCTTCGGGTG<br>CGGGGCTCCGTACGGGGCGTGGCGCGGGGCTCGCCGTGCCGGGCGGGGGG<br>TGGCGGCAGGTGGGGGTGCCGGGCGGGGCGGGGCCGCCTCGGGCCGGGGA<br>GGGCTCGGGGGAGGGGCGCGGCGGCCCCCGGAGCGCCGGCGGCTGTCGAG<br>GCGCGGCGAGCCGCAGCCATTGCCTTTTATGGTAATCGTGCGAGAGGGCG<br>CAGGGACTTCCTTTGTCCCAAATCTGTGCGGAGCCGAAATCTGGGAGGCG<br>CCGCCGCACCCCCTCTAGCGGGCGCGGGGCGAAGCGGTGCGGCGCCGGCA<br>GGAAGGAAATGGGCGGGGAGGGCCTTCGTGCGTCGCCGCGCCGCCGTCCC<br>CTTCTCCCTCTCCAGCCTCGGGGCTGTCCGCGGGGGGACGGCTGCCTTCG<br>GGGGGGACGGGGCAGGGCGGGGTTCGGCTTCTGGCGTGTGACCGGCGGCTC<br>TAGAGCCTCTGCTAACCATGTTCATGCCTTCTTCTTTTTCCTACAGCTCC<br>TGGGCAACGTGCTGGTTATTGTGCTGTCTCATCATTTTGGCAAAGAACGC |
| 42. | NP-CAG-EGFP-P2A-Fluc-WPRE3-DTS | GTACAGTAGAATTGGTAAAGAGAGTTGTGTAAAATATTGAGTTCGCACAT<br>CTTGTTGTCTGATTATTGATTTTTGGCGAAACCATTTGATCATATGACAA<br>GATGTGTATCTACCTTAACTTAATGATTTTGATAAAAATCATTAGGTACC<br>TCGCGAATGCATCTAGATCCGACGTTACATAACTTACGGTAAATGGCCCG<br>CCTGGCTGACCGCCCAACGACCCCCGCCCATTGACGTCAATAATGACGTA<br>TGTTCCCATAGTAACGCCAATAGGGACTTTCCATTGACGTCAATGGGTGG<br>AGTATTTACGGTAAACTGCCCACTTGGCAGTACATCAAGTGTATCATATG<br>CCAAGTACGCCCCCTATTGACGTCAATGACGGTAAATGGCCCGCCTGGCA<br>TTATGCCCAGTACATGACCTTATGGGACTTTCCTACTTGGCAGTACATCT<br>ACGTATTAGTCATCGCTATTACCATGGTCGAGGTGAGCCCCACGTTCTGC<br>TTCACTCTCCCCATCTCCCCCCCCTCCCCACCCCCAATTTTGTATTTATT<br>TATTTTTTAATTATTTTGTGCAGCGATGGGGGCGGGGGGGGGGGGGGCGC<br>GCGCCAGGCGGGGGGGGGGGGGGCGAGGGGCGGGGCGGGGCGAGGCGGAG<br>AGGTGCGGCGGCAGCCAATCAGAGCGGCGCGCTCCGAAAGTTTCCTTTTA<br>TGGCGAGGCGGCGGCGGCGGCGGCCCTATAAAAAGCGAAGCGCGCGGCGG<br>GCGGGAGTCGCTGCGCGCTGCCTTCGCCCCGTGCCCCGCTCCGCCGCCGC<br>CTCGCGCCGCCCGCCCCGGCTCTGACTGACCGCGTTACTCCCACAGGTGA<br>GCGGGCGGGACGGCCCTTCTCCTCCGGGCTGTAATTAGCGCTTGGTTTAA<br>TGACGGCTTGTTTCTTTTCTGTGGCTGCGTGAAAGCCTTGAGGGGCTCCG<br>GGAGGGCCCTTTGTGCGGGGGGAGCGGCTCGGGGGGTGCGTGCGTGTGTG<br>TGTGCGTGGGGAGCGCCGCGTGCGGCTCCGCGCTGCCCGGCGGCTGTGAG<br>CGCTGCGGGCGCGGCGCGGGGCTTTGTGCGCTCCGCAGTGTGCGCGAGGG<br>GAGCGCGGCCGGGGGCGGTGCCCCGCGGTGCGGGGGGGGCTGCGAGGGGA<br>ACAAAGGCTGCGTGCGGGGTGTGTGCGTGGGGGGGTGAGCAGGGGGTGTG<br>GGCGCGTCGGTCGGGCTGCAACCCCCCCTGCACCCCCCTCCCCGAGTTGC |

| SEQ ID NO | Description | SEQ |
|---|---|---|
| | | TGAGCACGGCCCGGCTTCGGGTGCGGGGCTCCGTACGGGGCGTGGCGCGG GGCTCGCCGTGCCGGGCGGGGGGTGGCGGCAGGTGGGGGTGCCGGGCGGG GCGGGGCCGCCTCGGGCCGGGGAGGGCTCGGGGGAGGGGCGCGGCGGCCC CCGGAGCGCCGGCGGCTGTCGAGGCGCGGCGAGCCGCAGCCATTGCCTTT TATGGTAATCGTGCGAGAGGGCGCAGGGACTTCCTTTGTCCCAAATCTGT GCGGAGCCGAAATCTGGGAGGCGCCGCCGCACCCCCTCTAGCGGGCGCGG GGCGAAGCGGTGCGGCGCCGGCAGGAAGGAAATGGGCGGGGAGGGCCTTC GTGCGTCGCCGCGCCGCCGTCCCCTTCTCCCTCTCCAGCCTCGGGGCTGT CCGCGGGGGGACGGCTGCCTTCGGGGGGGACGGGGCAGGGCGGGGTTCGG CTTCTGGCGTGTGACCGGCGGCTCTAGAGCCTCTGCTAACCATGTTCATG CCTTCTTCTTTTTCCTACAGCTCCTGGGCAACGTGCTGGTTATTGTGCTG TCTCATCATTTTGGCAAAGAACGCGCGATCGCCACCATGGTGAGCAAGGG CGAGGAGCTGTTCACCGGGGTGGTGCCCATCCTGGTCGAGCTGGACGGCG ACGTAAACGGCCACAAGTTCAGCGTGTCCGGCGAGGGCGAGGGCGATGCC ACCTACGGCAAGCTGACCCTGAAGTTCATCTGCACCACCGGCAAGCTGCC CGTGCCCTGGCCCACCCTCGTGACCACCCTGACCTACGGCGTGCAGTGCT TCAGCCGCTACCCCGACCACATGAAGCAGCACGACTTCTTCAAGTCCGCC ATGCCCGAAGGCTACGTCCAGGAGCGCACCATCTTCTTCAAGGACGACGG CAACTACAAGACCCGCGCCGAGGTGAAGTTCGAGGGCGACACCCTGGTGA ACCGCATCGAGCTGAAGGGCATCGACTTCAAGGAGGACGGCAACATCCTG GGGCACAAGCTGGAGTACAACTACAACAGCCACAACGTCTATATCATGGC CGACAAGCAGAAGAACGGCATCAAGGTGAACTTCAAGATCCGCCACAACA TCGAGGACGGCAGCGTGCAGCTCGCCGACCACTACCAGCAGAACACCCCC ATCGGCGACGGCCCCGTGCTGCTGCCCGACAACCACTACCTGAGCACCCA GTCCGCCCTGAGCAAAGACCCCAACGAGAAGCGCGATCACATGGTCCTGC TGGAGTTCGTGACCGCCGCCGGGATCACTCTCGGCATGGACGAGCTGTAC AAGAATCGCGCTACTAACTTCAGCCTGCTGAAGCAGGCTGGAGACGTGGA GGAGAACCCTGGACCTATGGAAGACGCCAAAAACATAAAGAAAGGCCCGG CGCCATTCTATCCGCTGGAAGATGGAACCGCTGGAGAGCAACTGCATAAG GCTATGAAGAGATACGCCCTGGTTCCTGGAACAATTGCTTTTACAGATGC ACATATCGAGGTGGACATCACTTACGCTGAGTACTTCGAAATGTCCGTTC GGTTGGCAGAAGCTATGAAACGATATGGGCTGAATACAAATCACAGAATC GTCGTATGCAGTGAAAACTCTCTTCAATTCTTTATGCCGGTGTTGGGCGC GTTATTTATCGGAGTTGCAGTTGCGCCCGCGAACGACATTTATAATGAAC GTGAATTGCTCAACAGTATGGGCATTTCGCAGCCTACCGTGGTGTTCGTT TCCAAAAAGGGGTTGCAAAAAATTTTGAACGTGCAAAAAAAGCTCCCAAT CATCCAAAAAATTATTATCATGGATTCTAAAACGGATTACCAGGGATTTC AGTCGATGTACACGTTCGTCACATCTCATCTACCTCCCGGTTTTAATGAA TACGATTTTGTGCCAGAGTCCTTCGATAGGGACAAGACAATTGCACTGAT CATGAACTCCTCTGGATCTACTGGTCTGCCTAAAGGTGTCGCTCTGCCTC ATAGAACTGCCTGCGTGAGATTCTCGCATGCCAGAGATCCTATTTTTGGC AATCAAATCATTCCGGATACTGCGATTTTAAGTGTTGTTCCATTCCATCA CGGTTTTGGAATGTTTACTACACTCGGATATTTGATATGTGGATTTCGAG TCGTCTTAATGTATAGATTTGAAGAAGAGCTGTTTCTGAGGAGCCTTCAG GATTACAAGATTCAAAGTGCGCTGCTGGTGCCAACCCTATTCTCCTTCTT CGCCAAAAGCACTCTGATTGACAAATACGATTTATCTAATTTACACGAAA TTGCTTCTGGTGGCGCTCCCCTCTCTAAGGAAGTCGGGGAAGCGGTTGCC AAGAGGTTCCATCTGCCAGGTATCAGGCAAGGATATGGGCTCACTGAGAC TACATCAGCTATTCTGATTACACCCGAGGGGGATGATAAACCGGGCGCGG TCGGTAAAGTTGTTCCATTTTTTGAAGCGAAGGTTGTGGATCTGGATACC GGGAAAACGCTGGGCGTTAATCAAAGAGGCGAACTGTGTGTGAGAGGTCC TATGATTATGTCCGGTTATGTAAACAATCCGGAAGCGACCAACGCCTTGA TTGACAAGGATGGATGGCTACATTCTGGAGACATAGCTTACTGGGACGAA GACGAACACTTCTTCATCGTTGACCGCCTGAAGTCTCTGATTAAGTACAA AGGCTATCAGGTGGCTCCCGCTGAATTGGAATCCATCTTGCTCCAACACC CCAACATCTTCGACGCAGGTGTCGCAGGTCTTCCCGACGATGACGCCGGT GAACTTCCCGCCGCCGTTGTTGTTTTGGAGCACGGAAAGACGATGACGGA AAAAGAGATCGTGGATTACGTCGCCAGTCAAGTAACAACCGCGAAAAAGT TGCGCGGAGGAGTTGTGTTTGTGGACGAAGTACCGAAAGGTCTTACCGGA AAACTCGACGCAAGAAAAATCAGAGAGATCCTCATAAAGGCCAAGAAGGG CGGAAAGATCGCCGTGTAACTCGAGAATCAACCTCTGGATTACAAAATTT GTGAAAGATTGACTGGTATTCTTAACTATGTTGCTCCTTTTACGCTATGT GGATACGCTGCTTTAATGCCTTTGTATCATGCTATTGCTTCCCGTATGGC TTTCATTTTCTCCTCCTTGTATAAATCCTGGTTGCTGTCTCTTTATGAGG AGTTGTGGCCCGTTGTCAGGCAACGTGGCGTGGTGTGCACTGTGTTTGCT GACGCAACCCCCACTGGTTGGGGCATTGCCACCACCTGTCAGCTCCTTTC CGGGACTTTCGCTTTCCCCCTCCCTATTGCCACGGCGGAACTCATCGCCG CCTGCCTTGCCCGCTGCTGGACAGGGGCTCGGCTGTTGGGCACTGACAAT TCCGTGGGGTGTGCCTTCTAGTTGCCAGCCATCTGTTGTTTGCCCCTCCC CCGTGCCTTCCTTGACCCTGGAAGGTGCCACTCCCACTGTCCTTTCCTAA TAAAATGAGGAAATTGCATCGCATTGTCTGAGTAGGTGTCATTCTATTCT GGGGGGTGGGGTGGGGCAGGACAGCAAGGGGGAGGATTGGGAAGACAATA GCAGGCATGCTGGGGATGCGGTGGGCTCTATGGGAAGATGTCTACTGAGC TGTGCGATCCCTGCTGGGGACTTTCCGCTGGGGACTTTCCGCTGGGGACT TTCCGCCTTCAGCTAAGGAAGCTACCAATATTTAGAGGTACATTTTGTTC |

| SEQ ID NO | Description | SEQ |
|---|---|---|
| | | TAGAACAAAATGTACCGGTACATTTTGTTCTGGTACATTTTGTTCTATTA<br>AGGACAACGTAAGTATAGCGCATAGACACGTGGCGCCATCGGATCCCGGG<br>TGGCTTGTTGTCCACAACCATTAAACCTTAAAAGCTTTAAAAGCCTTATA<br>TATTCTTTTTTTTCTTATAAAACTTAAAACCTTAGAGGCTATTTAAGTTG<br>CTGATTTATATTAATTTTATTGTTCAAACATGAGAGCTTAGTACGTGAAA<br>CATGAGAGCTTAGTACATTAGCCATGAGAGCTTAGTACATTAGCCATGAG<br>GGTTTAGTTCATTAAACATGAGAGCTTAGTACATTAAACATGAGAGCTTA<br>GTACATTAAACATGAGAGCTTAGTACATACTATCAACAGGTTGAACTGCT<br>GATCT |
| 43. | NP-CBA-hBGi-EGFP-P2A-Fluc-WPRE3-DTS | TGCATGCGGCCGCCGTTACATAACTTACGGTAAATGGCCCGCCTGGCTGA<br>CCGCCCAACGACCCCCGCCCATTGACGTCAATAATGACGTATGTTCCCAT<br>AGTAACGCCAATAGGGACTTTCCATTGACGTCAATGGGTGGAGTATTTAC<br>GGTAAACTGCCCACTTGGCAGTACATCAAGTGTATCATATGCCAAGTACG<br>CCCCCTATTGACGTCAATGACGGTAAATGGCCCGCCTGGCATTATGCCCA<br>GTACATGACCTTATGGGACTTTCCTACTTGGCAGTACATCTACGTATTAG<br>TCATCGCTATTACCATGGTCGAGGTGAGCCCCACGTTCTGCTTCACTCTC<br>CCCATCTCCCCCCCCTCCCCACCCCCAATTTTGTATTTATTTATTTTTTA<br>ATTATTTTGTGCAGCGATGGGGGCGGGGGGGGGGGGGGCGCGCGCCAGGC<br>GGGGCGGGGCGGGGCGAGGGGGGGGGGGGGGCGAGGCGGAGAGGTGCGGC<br>GGCAGCCAATCAGAGCGGCGCGCTCCGAAAGTTTCCTTTTATGGCGAGGC<br>GGCGGCGGCGGCGGCCCTATAAAAAGCGAAGCGCGCGGCGGGCGGGAGTC<br>TCTGGATCCACTGCTTAAATACGGACGAGGACAGGGCCCTGTCTCCTCAG<br>CTTCAGGCACCACCACTGACCTGGGACAGTGAATCGTAAGTACTAGCAGC<br>TACAATCCAGCTACCATTCTGCTTTTATTTTATGGTTGGGATAAGGCTGG<br>ATTATTCTGAGTCCAAGCTAGGCCCTTTTGCTAATCATGTTCATACCTCT<br>TATCTTCCTCCCACAGCTCCTGGGCAACGTGCTGGTCTGTGTGCTGGCCC<br>ATCACTTTGGCAAAGAATTGCGATCGCCACCATGGTGAGCAAGGGCGAGG<br>AGCTGTTCACCGGGGTGGTGCCCATCCTGGTCGAGCTGGACGGCGACGTA<br>AACGGCCACAAGTTCAGCGTGTCCGGCGAGGGCGAGGGCGATGCCACCTA<br>CGGCAAGCTGACCCTGAAGTTCATCTGCACCACCGGCAAGCTGCCCGTGC<br>CCTGGCCCACCCTCGTGACCACCCTGACCTACGGCGTGCAGTGCTTCAGC<br>CGCTACCCCGACCACATGAAGCAGCACGACTTCTTCAAGTCCGCCATGCC<br>CGAAGGCTACGTCCAGGAGCGCACCATCTTCTTCAAGGACGACGGCAACT<br>ACAAGACCCGCGCCGAGGTGAAGTTCGAGGGCGACACCCTGGTGAACCGC<br>ATCGAGCTGAAGGGCATCGACTTCAAGGAGGACGGCAACATCCTGGGGCA<br>CAAGCTGGAGTACAACTACAACAGCCACAACGTCTATATCATGGCCGACA<br>AGCAGAAGAACGGCATCAAGGTGAACTTCAAGATCCGCCACAACATCGAG<br>GACGGCAGCGTGCAGCTCGCCGACCACTACCAGCAGAACACCCCCATCGG<br>CGACGGCCCCGTGCTGCTGCCCGACAACCACTACCTGAGCACCCAGTCCG<br>CCCTGAGCAAAGACCCCAACGAGAAGCGCGATCACATGGTCCTGCTGGAG<br>TTCGTGACCGCCGCCGGGATCACTCTCGGCATGGACGAGCTGTACAAGAA<br>TCGCGCTACTAACTTCAGCCTGCTGAAGCAGGCTGGAGACGTGGAGGAGA<br>ACCCTGGACCTATGGAAGACGCCAAAAACATAAAGAAAGGCCCGGCGCCA<br>TTCTATCCGCTGGAAGATGGAACCGCTGGAGAGCAACTGCATAAGGCTAT<br>GAAGAGATACGCCCTGGTTCCTGGAACAATTGCTTTTACAGATGCACATA<br>TCGAGGTGGACATCACTTACGCTGAGTACTTCGAAATGTCCGTTCGGTTG<br>GCAGAAGCTATGAAACGATATGGGCTGAATACAAATCACAGAATCGTCGT<br>ATGCAGTGAAAACTCTCTTCAATTCTTTATGCCGGTGTTGGGCGCGTTAT<br>TTATCGGAGTTGCAGTTGCGCCCGCGAACGACATTTATAATGAACGTGAA<br>TTGCTCAACAGTATGGGCATTTCGCAGCCTACCGTGGTGTTCGTTTCCAA<br>AAAGGGGTTGCAAAAAATTTTGAACGTGCAAAAAAAGCTCCCAATCATCC<br>AAAAAATTATTATCATGGATTCTAAAACGGATTACCAGGGATTTCAGTCG<br>ATGTACACGTTCGTCACATCTCATCTACCTCCCGGTTTTAATGAATACGA<br>TTTTGTGCCAGAGTCCTTCGATAGGGACAAGACAATTGCACTGATCATGA<br>ACTCCTCTGGATCTACTGGTCTGCCTAAAGGTGTCGCTCTGCCTCATAGA<br>ACTGCCTGCGTGAGATTCTCGCATGCCAGAGATCCTATTTTTGGCAATCA<br>AATCATTCCGGATACTGCGATTTTAAGTGTTGTTCCATTCCATCACGGTT<br>TTGGAATGTTTACTACACTCGGATATTTGATATGTGGATTTCGAGTCGTC<br>TTAATGTATAGATTTGAAGAAGAGCTGTTTCTGAGGAGCCTTCAGGATTA<br>CAAGATTCAAAGTGCGCTGCTGGTGCCAACCCTATTCTCCTTCTTCGCCA<br>AAAGCACTCTGATTGACAAATACGATTTATCTAATTTACACGAAATTGCT<br>TCTGGTGGCGCTCCCCTCTCTAAGGAAGTCGGGGAAGCGGTTGCCAAGAG<br>GTTCCATCTGCCAGGTATCAGGCAAGGATATGGGCTCACTGAGACTACAT<br>CAGCTATTCTGATTACACCCGAGGGGGATGATAAACCGGGCGCGGTCGGT<br>AAAGTTGTTCCATTTTTTGAAGCGAAGGTTGTGGATCTGGATACCGGGAA<br>AACGCTGGGCGTTAATCAAAGAGGCGAACTGTGTGTGAGAGGTCCTATGA<br>TTATGTCCGGTTATGTAAACAATCCGGAAGCGACCAACGCCTTGATTGAC<br>AAGGATGGATGGCTACATTCTGGAGACATAGCTTACTGGGACGAAGACGA<br>ACACTTCTTCATCGTTGACCGCCTGAAGTCTCTGATTAAGTACAAAGGCT<br>ATCAGGTGGCTCCCGCTGAATTGGAATCCATCTTGCTCCAACACCCCAAC<br>ATCTTCGACGCAGGTGTCGCAGGTCTTCCCGACGATGACGCCGGTGAACT<br>TCCCGCCGCCGTTGTTGTTTTGGAGCACGGAAAGACGATGACGGAAAAAG<br>AGATCGTGGATTACGTCGCCAGTCAAGTAACAACCGCGAAAAAGTTGCGC<br>GGAGGAGTTGTGTTTGTGGACGAAGTACCGAAAGGTCTTACCGGAAAACT |

-continued

| SEQ ID NO | Description | SEQ |
|---|---|---|
| | | CGACGCAAGAAAAATCAGAGAGATCCTCATAAAGGCCAAGAAGGGCGGAA<br>AGATCGCCGTGTAACTCGAGAATCAACCTCTGGATTACAAAATTTGTGAA<br>AGATTGACTGGTATTCTTAACTATGTTGCTCCTTTTACGCTATGTGGATA<br>CGCTGCTTTAATGCCTTTGTATCATGCTATTGCTTCCCGTATGGCTTTCA<br>TTTTCTCCTCCTTGTATAAATCCTGGTTGCTGTCTCTTTATGAGGAGTTG<br>TGGCCCGTTGTCAGGCAACGTGGCGTGGTGTGCACTGTGTTTGCTGACGC<br>AACCCCCACTGGTTGGGGCATTGCCACCACCTGTCAGCTCCTTTCCGGGA<br>CTTTCGCTTTCCCCCTCCCTATTGCCACGGCGGAACTCATCGCCGCCTGC<br>CTTGCCCGCTGCTGGACAGGGGCTCGGCTGTTGGGCACTGACAATTCCGT<br>GGGGTGTGCCTTCTAGTTGCCAGCCATCTGTTGTTTGCCCCTCCCCCGTG<br>CCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGG<br>GTGGGGTGGGGCAGGACAGCAAGGGGGAGGATTGGGAAGACAATAGCAGG<br>CATGCTGGGGATGCGGTGGGCTCTATGGGAAGATGTCTACTGAGCTGTGC<br>GATCCCTGCTGGGGACTTTCCGCTGGGGACTTTCCGCTGGGGACTTTCCG<br>CCTTCAGCTAAGGAAGCTACCAATATTTAGAGGTACATTTTGTTCTAGAA<br>CAAAATGTACCGGTACATTTTGTTCTGGTACATTTTGTTCTATTAAGGAC<br>AACGTAAGTATAGCGCATAGACACGTGGCGCCATCGGATCCCGGGTGGCT<br>TGTTGTCCACAACCATTAAACCTTAAAAGCTTTAAAAGCCTTATATATTC<br>TTTTTTTTCTTATAAAACTTAAAACCTTAGAGGCTATTTAAGTTGCTGAT<br>TTATATTAATTTTATTGTTCAAACATGAGAGCTTAGTACGTGAAACATGA<br>GAGCTTAGTACATTAGCCATGAGAGCTTAGTACATTAGCCATGAGGGTTT<br>AGTTCATTAAACATGAGAGCTTAGTACATTAAACATGAGAGCTTAGTACA<br>TTAAACATGAGAGCTTAGTACATACTATCAACAGGTTGAACTGCTGATCT<br>GTACAGTAGAATTGGTAAAGAGAGTTGTGTAAAATATTGAGTTCGCACAT<br>CTTGTTGTCTGATTATTGATTTTTGGCGAAACCATTTGATCATATGACAA<br>GATGTGTATCTACCTTAACTTAATGATTTTGATAAAAATCATTA |
| 44. | hNPHS1-<br>hBGi | CACCTGAGGTCAGGAGTTCGAGACCAGCGTGGCCAACATGATGAAACCCC<br>GTCTCTAGTAAAAATACAAAAATTAGCCAGGCATGGTGCTATATACCTGT<br>AGCACCAGCTACTTGGGAGACAGAGGTGGGAGAATTACTTGAACCTGGGA<br>GGTTCAAGCCATGGGAGGTGGAAGTTGCAGTGAGCCGAGATGCCACTGCA<br>CTCCAGCCTGAGCAACAGAGCAAGACTATCTCAAGAAAAGAAAGAAAGAA<br>AGAAAGAGACTTGCCAAGGTCATGTATCAGGGCAAGGAAGAGCTGGGGGC<br>CCAGCTGGCTGCTCCCCTGCTGAGCTGGGAGACCACCTTGATCTGACTTC<br>TCCCATCTTCCCAGCCTAAGCCAGGCCCTGGGGTCACGGAGGCTGGGGAG<br>GCACCGAGGAACGCGCCTGGCATGTGCTGACAGGGGATTTTATGCTCCAG<br>CTGGGCCAGCTGGGAGGAGCCTGCTGGGCAGAGGCCAGAGCTGGGGGCTC<br>TGGAAGGTACCTGGGGGAGGTTGCACTGTGAGAATGAGCTCAAGCTGGGT<br>CAGAGAGCAGGGCTGACTCTGCCAGTGCCTGCATCAGCCTCATCGCTCTC<br>CTAGGCTCCTGGCCTGCTGGACTCTGGGCTGCAGGTCCTTCTTGAAAGGC<br>TGTGAGTAGTGAGACAAGGAGCAGGAGTGAGGGGTGGCAGGAGAGAAGAT<br>AGAGATTGAGAGAGAGAGAGAGAGAGAGACAGAGAGAGAGGAAGAGACAG<br>AGACAAAAGGAGAGAGAACGGCTTAGACAAGGAGAGAAAGATGGAAAGAT<br>AAAGAGACTGGGCGCAGTGGCTCACGCCTGTAATCCCAACACTTGGGGAG<br>GCCAAGGTGGGAGGATGGCTTGAAGGAAAGAGTCTGAGATCAACCTGGCC<br>AACATAGTGAGACCCTGTCTCTAAAAAAAAAAAAAAGAAAAAAAAAAAGAA<br>AAAAGAAAAAAAAGTTTTTTTAAAGAGACAGAGAAAGAGACTCAGAGATT<br>GAGACTGAGAGCAAGACAGAGAGAGATACTCACAGGGAAGAGGGGAAGAG<br>GAAAACGAGAAAGGGAGGAGAGTAACGGAAAGAGATAAAAAAGAAAAGCA<br>GGTGGCAGAGACACACAGAGAGGGACCCAGAGAAAGCCAGACAGACGCAG<br>GTGGCTGGCAGCGGGCGCTGTGGGGGTCACAGTAGGGGGACCTGTGTCTG<br>GATCCACTGCTTAAATACGGACGAGGACAGGGCCCTGTCTCCTCAGCTTC<br>AGGCACCACCACTGACCTGGGACAGTGAATCGTAAGTACTAGCAGCTACA<br>ATCCAGCTACCATTCTGCTTTTATTTTATGGTTGGGATAAGGCTGGATTA<br>TTCTGAGTCCAAGCTAGGCCCTTTTGCTAATCATGTTCATACCTCTTATC<br>TTCCTCCCACAGCTCCTGGGCAACGTGCTGGTCTGTGTGCTGGCCCATCA<br>CTTTGGCAAAGAATTGCGATCGCCACC |
| 45. | NP-<br>hNPHS1-<br>hBGi-<br>EGFP-P2A-<br>Fluc-<br>WPRE3-<br>DTS | GCCACCTGAGGTCAGGAGTTCGAGACCAGCGTGGCCAACATGATGAAACC<br>CCGTCTCTAGTAAAAATACAAAAATTAGCCAGGCATGGTGCTATATACCT<br>GTAGCACCAGCTACTTGGGAGACAGAGGTGGGAGAATTACTTGAACCTGG<br>GAGGTTCAAGCCATGGGAGGTGGAAGTTGCAGTGAGCCGAGATGCCACTG<br>CACTCCAGCCTGAGCAACAGAGCAAGACTATCTCAAGAAAAGAAAGAAAG<br>AAAGAAAGAGACTTGCCAAGGTCATGTATCAGGGCAAGGAAGAGCTGGGG<br>GCCCAGCTGGCTGCTCCCCTGCTGAGCTGGGAGACCACCTTGATCTGACT<br>TCTCCCATCTTCCCAGCCTAAGCCAGGCCCTGGGGTCACGGAGGCTGGGG<br>AGGCACCGAGGAACGCGCCTGGCATGTGCTGACAGGGGATTTTATGCTCC<br>AGCTGGGCCAGCTGGGAGGAGCCTGCTGGGCAGAGGCCAGAGCTGGGGGC<br>TCTGGAAGGTACCTGGGGGAGGTTGCACTGTGAGAATGAGCTCAAGCTGG<br>GTCAGAGAGCAGGGCTGACTCTGCCAGTGCCTGCATCAGCCTCATCGCTC<br>TCCTAGGCTCCTGGCCTGCTGGACTCTGGGCTGCAGGTCCTTCTTGAAAG<br>GCTGTGAGTAGTGAGACAAGGAGCAGGAGTGAGGGGTGGCAGGAGAGAAG<br>ATAGAGATTGAGAGAGAGAGAGAGAGAGAGACAGAGAGAGAGGAAGAGAC<br>AGAGACAAAAGGAGAGAGAACGGCTTAGACAAGGAGAGAAAGATGGAAAG |

-continued

| SEQ ID NO | Description | SEQ |
|---|---|---|
| | | ATAAAGAGACTGGGCGCAGTGGCTCACGCCTGTAATCCCAACACTTGGGG<br>AGGCCAAGGTGGGAGGATGGCTTGAAGGAAAGAGTCTGAGATCAACCTGG<br>CCAACATAGTGAGACCCTGTCTCTAAAAAAAAAAAAAAAGAAAAAAAAAAG<br>AAAAAAGAAAAAAAAAGTTTTTTAAAGAGACAGAGAAAGAGACTCAGAGA<br>TTGAGACTGAGAGCAAGACAGAGAGAGATACTCACAGGGAAGAGGGGAAG<br>AGGAAAACGAGAAAGGGAGGAGAGTAACGGAAAGAGATAAAAAAGAAAAG<br>CAGGTGGCAGAGACACACAGAGAGGGACCCAGAGAAAGCCAGACAGACGC<br>AGGTGGCTGGCAGCGGGCGCTGTGGGGGTCACAGTAGGGGGACCTGTGTC<br>TGGATCCACTGCTTAAATACGGACGAGGACAGGGCCCTGTCTCCTCAGCT<br>TCAGGCACCACCACTGACCTGGGACAGTGAATCGTAAGTACTAGCAGCTA<br>CAATCCAGCTACCATTCTGCTTTTATTTTATGGTTGGGATAAGGCTGGAT<br>TATTCTGAGTCCAAGCTAGGCCCTTTTGCTAATCATGTTCATACCTCTTA<br>TCTTCCTCCCACAGCTCCTGGGCAACGTGCTGGTCTGTGTGCTGGCCCAT<br>CACTTTGGCAAAGAATTGCGATCGCCACCATGGTGAGCAAGGGCGAGGAG<br>CTGTTCACCGGGGTGGTGCCCATCCTGGTCGAGCTGGACGGCGACGTAAA<br>CGGCCACAAGTTCAGCGTGTCCGGCGAGGGCGAGGGCGATGCCACCTACG<br>GCAAGCTGACCCTGAAGTTCATCTGCACCACCGGCAAGCTGCCCGTGCCC<br>TGGCCCACCCTCGTGACCACCCTGACCTACGGCGTGCAGTGCTTCAGCCG<br>CTACCCCGACCACATGAAGCAGCACGACTTCTTCAAGTCCGCCATGCCCG<br>AAGGCTACGTCCAGGAGCGCACCATCTTCTTCAAGGACGACGGCAACTAC<br>AAGACCCGCGCCGAGGTGAAGTTCGAGGGCGACACCCTGGTGAACCGCAT<br>CGAGCTGAAGGGCATCGACTTCAAGGAGGACGGCAACATCCTGGGGCACA<br>AGCTGGAGTACAACTACAACAGCCACAACGTCTATATCATGGCCGACAAG<br>CAGAAGAACGGCATCAAGGTGAACTTCAAGATCCGCCACAACATCGAGGA<br>CGGCAGCGTGCAGCTCGCCGACCACTACCAGCAGAACACCCCCATCGGCG<br>ACGGCCCCGTGCTGCTGCCCGACAACCACTACCTGAGCACCCAGTCCGCC<br>CTGAGCAAAGACCCCAACGAGAAGCGCGATCACATGGTCCTGCTGGAGTT<br>CGTGACCGCCGCCGGGATCACTCTCGGCATGGACGAGCTGTACAAGAATC<br>GCGCTACTAACTTCAGCCTGCTGAAGCAGGCTGGAGACGTGGAGGAGAAC<br>CCTGGACCTATGGAAGACGCCAAAAACATAAAGAAAGGCCCGGCGCCATT<br>CTATCCGCTGGAAGATGGAACCGCTGGAGAGCAACTGCATAAGGCTATGA<br>AGAGATACGCCCTGGTTCCTGGAACAATTGCTTTTACAGATGCACATATC<br>GAGGTGGACATCACTTACGCTGAGTACTTCGAAATGTCCGTTCGGTTGGC<br>AGAAGCTATGAAACGATATGGGCTGAATACAAATCACAGAATCGTCGTAT<br>GCAGTGAAAACTCTCTTCAATTCTTTATGCCGGTGTTGGGCGCGTTATTT<br>ATCGGAGTTGCAGTTGCGCCCGCGAACGACATTTATAATGAACGTGAATT<br>GCTCAACAGTATGGGCATTTCGCAGCCTACCGTGGTGTTCGTTTCCAAAA<br>AGGGGTTGCAAAAAATTTTGAACGTGCAAAAAAAGCTCCCAATCATCCAA<br>AAAATTATTATCATGGATTCTAAAACGGATTACCAGGGATTTCAGTCGAT<br>GTACACGTTCGTCACATCTCATCTACCTCCCGGTTTTAATGAATACGATT<br>TTGTGCCAGAGTCCTTCGATAGGGACAAGACAATTGCACTGATCATGAAC<br>TCCTCTGGATCTACTGGTCTGCCTAAAGGTGTCGCTCTGCCTCATAGAAC<br>TGCCTGCGTGAGATTCTCGCATGCCAGAGATCCTATTTTTGGCAATCAAA<br>TCATTCCGGATACTGCGATTTTAAGTGTTGTTCCATTCCATCACGGTTTT<br>GGAATGTTTACTACACTCGGATATTTGATATGTGGATTTCGAGTCGTCTT<br>AATGTATAGATTTGAAGAAGAGCTGTTTCTGAGGAGCCTTCAGGATTACA<br>AGATTCAAAGTGCGCTGCTGGTGCCAACCCTATTCTCCTTCTTCGCCAAA<br>AGCACTCTGATTGACAAATACGATTTATCTAATTTACACGAAATTGCTTC<br>TGGTGGCGCTCCCCTCTCTAAGGAAGTCGGGGAAGCGGTTGCCAAGAGGT<br>TCCATCTGCCAGGTATCAGGCAAGGATATGGGCTCACTGAGACTACATCA<br>GCTATTCTGATTACACCCGAGGGGGATGATAAACCGGGCGCGGTCGGTAA<br>AGTTGTTCCATTTTTTGAAGCGAAGGTTGTGGATCTGGATACCGGGAAAA<br>CGCTGGGCGTTAATCAAAGAGGCGAACTGTGTGTGAGAGGTCCTATGATT<br>ATGTCCGGTTATGTAAACAATCCGGAAGCGACCAACGCCTTGATTGACAA<br>GGATGGATGGCTACATTCTGGAGACATAGCTTACTGGGACGAAGACGAAC<br>ACTTCTTCATCGTTGACCGCCTGAAGTCTCTGATTAAGTACAAAGGCTAT<br>CAGGTGGCTCCCGCTGAATTGGAATCCATCTTGCTCCAACACCCCAACAT<br>CTTCGACGCAGGTGTCGCAGGTCTTCCCGACGATGACGCCGGTGAACTTC<br>CCGCCGCCGTTGTTGTTTTGGAGCACGGAAAGACGATGACGGAAAAAGAG<br>ATCGTGGATTACGTCGCCAGTCAAGTAACAACCGCGAAAAAGTTGCGCGG<br>AGGAGTTGTGTTTGTGGACGAAGTACCGAAAGGTCTTACCGGAAAACTCG<br>ACGCAAGAAAAATCAGAGAGATCCTCATAAAGGCCAAGAAGGGCGGAAAG<br>ATCGCCGTGTAACTCGAGAATCAACCTCTGGATTACAAAATTTGTGAAAG<br>ATTGACTGGTATTCTTAACTATGTTGCTCCTTTTACGCTATGTGGATACG<br>CTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTG<br>GCCCGTTGTCAGGCAACGTGGCGTGGTGTGCACTGTGTTTGCTGACGCAA<br>CCCCCACTGGTTGGGGCATTGCCACCACCTGTCAGCTCCTTTCCGGGACT<br>TTCGCTTTCCCCCTCCCTATTGCCACGGCGGAACTCATCGCCGCCTGCCT<br>TGCCCGCTGCTGGACAGGGGCTCGGCTGTTGGGCACTGACAATTCCGTGG<br>GGTGTGCCTTCTAGTTGCCAGCCATCTGTTGTTTGCCCCTCCCCCGTGCC<br>TTCCTTGACCCTGGAAGGTGCCACTCCCACTGTCCTTTCCTAATAAAATG<br>AGGAAATTGCATCGCATTGTCTGAGTAGGTGTCATTCTATTCTGGGGGGT<br>GGGGTGGGGCAGGACAGCAAGGGGGAGGATTGGGAAGACAATAGCAGGCA<br>TGCTGGGGATGCGGTGGGCTCTATGGGAAGATGTCTACTGAGCTGTGCGA |

-continued

| SEQ ID NO | Description | SEQ |
|---|---|---|
| | | TCCCTGCTGGGGACTTTCCGCTGGGGACTTTCCGCTGGGGACTTTCCGCC TTCAGCTAAGGAAGCTACCAATATTTAGAGGTACATTTTGTTCTAGAACA AAATGTACCGGTACATTTTGTTCTGGTACATTTTGTTCTATTAAGGACAA CGTAAGTATAGCGCATAGACACTGGCTTGTTGTCCACAACCATTAAACCT TAAAAGCTTTAAAAGCCTTATATATTCTTTTTTTTCTTATAAAACTTAAA ACCTTAGAGGCTATTTAAGTTGCTGATTTATATTAATTTTATTGTTCAAA CATGAGAGCTTAGTACGTGAAACATGAGAGCTTAGTACATTAGCCATGAG AGCTTAGTACATTAGCCATGAGGGTTTAGTTCATTAAACATGAGAGCTTA GTACATTAAACATGAGAGCTTAGTACATTAAACATGAGAGCTTAGTACAT ACTATCAACAGGTTGAACTGCTGATCTGTACAGTAGAATTGGTAAAGAGA GTTGTGTAAAATATTGAGTTCGCACATCTTGTTGTCTGATTATTGATTTT TGGCGAAACCATTTGATCATATGACAAGATGTGTATCTACCTTAACTTAA TGATTTTGATAAAAATCATTA |
| 46. | MHCK Promoter | CTAGAAGCTGCATGTCTAAGCTAGACCCTTCAGATTAAAAATAACTGAGG TAAGGGCCTGGGTAGGGGAGGTGGTGTGAGACGCTCCTGTCTCTCCTCTA TCTGCCCATCGGCCCTTTGGGGAGGAGGAATGTGCCCAAGGACTAAAAAA AGGCCATGGAGCCAGAGGGGCGAGGGCAACAGACCTTTCATGGGCAAACC TTGGGGCCCTGCTGTCTAGCATGCCCCACTACGGGTCTAGGCTGCCCATG TAAGGAGGCAAGGCCTGGGGACACCCGAGATGCCTGGTTATAATTAACCC AGACATGTGGCTGCCCCCCCCCCCCCAACACCTGCTGCCTCTAAAAATAA CCCTGTCCCTGGTGGATCCCCTGCATGCGAAGATCTTCGAACAAGGCTGT GGGGGACTGAGGGCAGGCTGTAACAGGCTTGGGGGCCAGGGCTTATACGT GCCTGGGACTCCCAAAGTATTACTGTTCCATGTTCCCGGCGAAGGGCCAG CTGTCCCCCGCCAGCTAGACTCAGCACTTAGTTTAGGAACCAGTGAGCAA GTCAGCCCTTGGGGCAGCCCATACAAGGCCATGGGGCTGGGCAAGCTGCA CGCCTGGGTCCGGGGTGGGCACGGTGCCCGGGCAACGAGCTGAAAGCTCA TCTGCTCTCAGGGGCCCCTCCCTGGGGACAGCCCCTCCTGGCTAGTCACA CCCTGTAGGCTCCTCTATATAACCCAGGGGCACAGGGGCTGCCCTCATTC TACCACCACCTCCACAGCACTCTGGATCCACTGCTTAAATACGGACGAGG ACAGGGCCCTGTCTCCTCAGCTTCAGGCACCACCACTGACCTGGGACAGT GAATCGTAAGTACTAGCAGCTACAATCCAGCTACCATTCTGCTTTTATTT TATGGTTGGGATAAGGCTGGATTATTCTGAGTCCAAGCTAGGCCCTTTTG CTAATCATGTTCATACCTCTTATCTTCCTCCCACAGCTCCTGGGCAACGT GCTGGTCTGTGTGCTGGCCCATCACTTTGGCAAAGAATTGCGATCGCCAC C |
| 47. | NP-CBA- hBGi- EGFP-P2A- Fluc- WPRE3- DTS | TGCATGCGGCCGCCGTTACATAACTTACGGTAAATGGCCCGCCTGGCTGA CCGCCCAACGACCCCCGCCCATTGACGTCAATAATGACGTATGTTCCCAT AGTAACGCCAATAGGGACTTTCCATTGACGTCAATGGGTGGAGTATTTAC GGTAAACTGCCCACTTGGCAGTACATCAAGTGTATCATATGCCAAGTACG CCCCCTACTCTCCCCATCTCCCCCCCCTCCCCACCCCCAATTTTGTATTT ATTTATTTTTTAATTATTTTGTGCAGCATTGACGTCAATGACGGTAAATG GCCCGCCTGGCATTATGCCCAGTACATGACCTTATGGGACTTTCCTACTT GGCAGTACATCTACGTATTAGTCATCGCTATTACCATGGTCGAGGTGAGC CCCACGTTCTGCTTCGATGGGGGCGGGGGGGGGGGGGGCGCGCGCCAGGC GGGGCGGGGCGGGGCGAGGGGGGGGGGGGGGCGAGGCGGAGAGGTGCGGC GGCAGCCAATCAGAGCGGCGCGCTCCGAAAGTTTCCTTTTATGGCGAGGC GGCGGCGGCGGCGGCCCTATAAAAAGCGAAGCGCGCGGCGGGCGGGAGTC TCTGGATCCACTGCTTAAATACGGACGAGGACAGGGCCCTGTCTCCTCAG CTTCAGGCACCACCACTGACCTGGGACAGTGAATCGTAAGTACTAGCAGC TACAATCCAGCTACCATTCTGCTTTTATTTTATGGTTGGGATAAGGCTGG ATTATTCTGAGTCCAAGCTAGGCCCTTTTGCTAATCATGTTCATACCTCT TATCTTCCTCCCACAGCTCCTGGGCAACGTGCTGGTCTGTGTGCTGGCCC ATCACTTTGGCAAAGAATTGCGATCGCCACCATGGTGAGCAAGGGCGAGG AGCTGTTCACCGGGGTGGTGCCCATCCTGGTCGAGCTGGACGGCGACGTA AACGGCCACAAGTTCAGCGTGTCCGGCGAGGGCGAGGGCGATGCCACCTA CGGCAAGCTGACCCTGAAGTTCATCTGCACCACCGGCAAGCTGCCCGTGC CCTGGCCCACCCTCGTGACCACCCTGACCTACGGCGTGCAGTGCTTCAGC CGCTACCCCGACCACATGAAGCAGCACGACTTCTTCAAGTCCGCCATGCC CGAAGGCTACGTCCAGGAGCGCACCATCTTCTTCAAGGACGACGGCAACT ACAAGACCCGCGCCGAGGTGAAGTTCGAGGGCGACACCCTGGTGAACCGC ATCGAGCTGAAGGGCATCGACTTCAAGGAGGACGGCAACATCCTGGGGCA CAAGCTGGAGTACAACTACAACAGCCACAACGTCTATATCATGGCCGACA AGCAGAAGAACGGCATCAAGGTGAACTTCAAGATCCGCCACAACATCGAG GACGGCAGCGTGCAGCTCGCCGACCACTACCAGCAGAACACCCCCATCGG CGACGGCCCCGTGCTGCTGCCCGACAACCACTACCTGAGCACCCAGTCCG CCCTGAGCAAAGACCCCAACGAGAAGCGCGATCACATGGTCCTGCTGGAG TTCGTGACCGCCGCCGGGATCACTCTCGGCATGGACGAGCTGTACAAGAA TCGCGCTACTAACTTCAGCCTGCTGAAGCAGGCTGGAGACGTGGAGGAGA ACCCTGGACCTATGGAAGACGCCAAAAACATAAAGAAAGGCCCGGCGCCA TTCTATCCGCTGGAAGATGGAACCGCTGGAGAGCAACTGCATAAGGCTAT GAAGAGATACGCCCTGGTTCCTGGAACAATTGCTTTTACAGATGCACATA TCGAGGTGGACATCACTTACGCTGAGTACTTCGAAATGTCCGTTCGGTTG GCAGAAGCTATGAAACGATATGGGCTGAATACAAATCACAGAATCGTCGT |

-continued

| SEQ ID NO | Description | SEQ |
|---|---|---|
| | | ATGCAGTGAAAACTCTCTTCAATTCTTTATGCCGGTGTTGGGCGCGTTAT<br>TTATCGGAGTTGCAGTTGCGCCCGCGAACGACATTTATAATGAACGTGAA<br>TTGCTCAACAGTATGGGCATTTCGCAGCCTACCGTGGTGTTCGTTTCCAA<br>AAAGGGGTTGCAAAAAATTTTGAACGTGCAAAAAAAGCTCCCAATCATCC<br>AAAAAATTATTATCATGGATTCTAAAACGGATTACCAGGGATTTCAGTCG<br>ATGTACACGTTCGTCACATCTCATCTACCTCCCGGTTTTAATGAATACGA<br>TTTTGTGCCAGAGTCCTTCGATAGGGACAAGACAATTGCACTGATCATGA<br>ACTCCTCTGGATCTACTGGTCTGCCTAAAGGTGTCGCTCTGCCTCATAGA<br>ACTGCCTGCGTGAGATTCTCGCATGCCAGAGATCCTATTTTTGGCAATCA<br>AATCATTCCGGATACTGCGATTTTAAGTGTTGTTCCATTCCATCACGGTT<br>TTGGAATGTTTACTACACTCGGATATTTGATATGTGGATTTCGAGTCGTC<br>TTAATGTATAGATTTGAAGAAGAGCTGTTTCTGAGGAGCCTTCAGGATTA<br>CAAGATTCAAAGTGCGCTGCTGGTGCCAACCCTATTCTCCTTCTTCGCCA<br>AAAGCACTCTGATTGACAAATACGATTTATCTAATTTACACGAAATTGCT<br>TCTGGTGGCGCTCCCCTCTCTAAGGAAGTCGGGGAAGCGGTTGCCAAGAG<br>GTTCCATCTGCCAGGTATCAGGCAAGGATATGGGCTCACTGAGACTACAT<br>CAGCTATTCTGATTACACCCGAGGGGGATGATAAACCGGGCGCGGTCGGT<br>AAAGTTGTTCCATTTTTTGAAGCGAAGGTTGTGGATCTGGATACCGGGAA<br>AACGCTGGGCGTTAATCAAAGAGGCGAACTGTGTGTGAGAGGTCCTATGA<br>TTATGTCCGGTTATGTAAACAATCCGGAAGCGACCAACGCCTTGATTGAC<br>AAGGATGGATGGCTACATTCTGGAGACATAGCTTACTGGGACGAAGACGA<br>ACACTTCTTCATCGTTGACCGCCTGAAGTCTCTGATTAAGTACAAAGGCT<br>ATCAGGTGGCTCCCGCTGAATTGGAATCCATCTTGCTCCAACACCCCAAC<br>ATCTTCGACGCAGGTGTCGCAGGTCTTCCCGACGATGACGCCGGTGAACT<br>TCCCGCCGCCGTTGTTGTTTTGGAGCACGGAAAGACGATGACGGAAAAAG<br>AGATCGTGGATTACGTCGCCAGTCAAGTAACAACCGCGAAAAAGTTGCGC<br>GGAGGAGTTGTGTTTGTGGACGAAGTACCGAAAGGTCTTACCGGAAAACT<br>CGACGCAAGAAAAATCAGAGAGATCCTCATAAAGGCCAAGAAGGGCGGAA<br>AGATCGCCGTGTAACTCGAGAATCAACCTCTGGATTACAAAATTTGTGAA<br>AGATTGACTGGTATTCTTAACTATGTTGCTCCTTTTACGCTATGTGGATA<br>CGCTGCTTTAATGCCTTTGTATCATGCTATTGCTTCCCGTATGGCTTTCA<br>TTTTCTCCTCCTTGTATAAATCCTGGTTGCTGTCTCTTTATGAGGAGTTG<br>TGGCCCGTTGTCAGGCAACGTGGCGTGGTGTGCACTGTGTTTGCTGACGC<br>AACCCCCACTGGTTGGGGCATTGCCACCACCTGTCAGCTCCTTTCCGGGA<br>CTTTCGCTTTCCCCCTCCCTATTGCCACGGCGGAACTCATCGCCGCCTGC<br>CTTGCCCGCTGCTGGACAGGGGCTCGGCTGTTGGGCACTGACAATTCCGT<br>GGGGTGTGCCTTCTAGTTGCCAGCCATCTGTTGTTTGCCCCTCCCCCGTG<br>CCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGG<br>GTGGGGTGGGGCAGGACAGCAAGGGGGAGGATTGGGAAGACAATAGCAGG<br>CATGCTGGGGATGCGGTGGGCTCTATGGGAAGATGTCTACTGAGCTGTGC<br>GATCCCTGCTGGGGACTTTCCGCTGGGGACTTTCCGCTGGGGACTTTCCG<br>CCTTCAGCTAAGGAAGCTACCAATATTTAGAGGTACATTTTGTTCTAGAA<br>CAAAATGTACCGGTACATTTTGTTCTGGTACATTTTGTTCTATTAAGGAC<br>AACGTAAGTATAGCGCATAGACACGTGGCGCCATCGGATCCCGGGTGGCT<br>TGTTGTCCACAACCATTAAACCTTAAAAGCTTTAAAAGCCTTATATATTC<br>TTTTTTTTCTTATAAAACTTAAAACCTTAGAGGCTATTTAAGTTGCTGAT<br>TTATATTAATTTTATTGTTCAAACATGAGAGCTTAGTACGTGAAACATGA<br>GAGCTTAGTACATTAGCCATGAGAGCTTAGTACATTAGCCATGAGGGTTT<br>AGTTCATTAAACATGAGAGCTTAGTACATTAAACATGAGAGCTTAGTACA<br>TTAAACATGAGAGCTTAGTACATACTATCAACAGGTTGAACTGCTGATCT<br>GTACAGTAGAATTGGTAAAGAGAGTTGTGTAAAATATTGAGTTCGCACAT<br>CTTGTTGTCTGATTATTGATTTTTGGCGAAACCATTTGATCATATGACAA<br>GATGTGTATCTACCTTAACTTAATGATTTTGATAAAAATCATTA |
| 48. | NP-<br>MHCK7-<br>hBGi-<br>EGFP-P2A-<br>Fluc-<br>WPRE3-<br>DTS | CTAGAAGCTGCATGTCTAAGCTAGACCCTTCAGATTAAAAATAACTGAGG<br>TAAGGGCCTGGGTAGGGGAGGTGGTGTGAGACGCTCCTGTCTCTCCTCTA<br>TCTGCCCATCGGCCCTTTGGGGAGGAGGAATGTGCCCAAGGACTAAAAAA<br>AGGCCATGGAGCCAGAGGGGCGAGGGCAACAGACCTTTCATGGGCAAACC<br>TTGGGGCCCTGCTGTCTAGCATGCCCCACTACGGGTCTAGGCTGCCCATG<br>TAAGGAGGCAAGGCCTGGGGACACCCGAGATGCCTGGTTATAATTAACCC<br>AGACATGTGGCTGCCCCCCCCCCCCCAACACCTGCTGCCTCTAAAAATAA<br>CCCTGTCCCTGGTGGATCCCCTGCATGCGAAGATCTTCGAACAAGGCTGT<br>GGGGGACTGAGGGCAGGCTGTAACAGGCTTGGGGGCCAGGGCTTATACGT<br>GCCTGGGACTCCCAAAGTATTACTGTTCCATGTTCCCGGCGAAGGGCCAG<br>CTGTCCCCCGCCAGCTAGACTCAGCACTTAGTTTAGGAACCAGTGAGCAA<br>GTCAGCCCTTGGGGCAGCCCATACAAGGCCATGGGGCTGGGCAAGCTGCA<br>CGCCTGGGTCCGGGGTGGGCACGGTGCCCGGGCAACGAGCTGAAAGCTCA<br>TCTGCTCTCAGGGGCCCCTCCCTGGGGACAGCCCCTCCTGGCTAGTCACA<br>CCCTGTAGGCTCCTCTATATAACCCAGGGGCACAGGGGCTGCCCTCATTC<br>TACCACCACCTCCACAGCACTCTGGATCCACTGCTTAAATACGGACGAGG<br>ACAGGGCCCTGTCTCCTCAGCTTCAGGCACCACCACTGACCTGGGACAGT<br>GAATCGTAAGTACTAGCAGCTACAATCCAGCTACCATTCTGCTTTTATTT<br>TATGGTTGGGATAAGGCTGGATTATTCTGAGTCCAAGCTAGGCCCTTTTG<br>CTAATCATGTTCATACCTCTTATCTTCCTCCCACAGCTCCTGGGCAACGT |

-continued

| SEQ ID NO | Description | SEQ |
|---|---|---|
| | | GCTGGTCTGTGTGCTGGCCCATCACTTTGGCAAAGAATTGCGATCGCCAC |
| | | CATGGTGAGCAAGGGCGAGGAGCTGTTCACCGGGGTGGTGCCCATCCTGG |
| | | TCGAGCTGGACGGCGACGTAAACGGCCACAAGTTCAGCGTGTCCGGCGAG |
| | | GGCGAGGGCGATGCCACCTACGGCAAGCTGACCCTGAAGTTCATCTGCAC |
| | | CACCGGCAAGCTGCCCGTGCCCTGGCCCACCCTCGTGACCACCCTGACCT |
| | | ACGGCGTGCAGTGCTTCAGCCGCTACCCCGACCACATGAAGCAGCACGAC |
| | | TTCTTCAAGTCCGCCATGCCCGAAGGCTACGTCCAGGAGCGCACCATCTT |
| | | CTTCAAGGACGACGGCAACTACAAGACCCGCGCCGAGGTGAAGTTCGAGG |
| | | GCGACACCCTGGTGAACCGCATCGAGCTGAAGGGCATCGACTTCAAGGAG |
| | | GACGGCAACATCCTGGGGCACAAGCTGGAGTACAACTACAACAGCCACAA |
| | | CGTCTATATCATGGCCGACAAGCAGAAGAACGGCATCAAGGTGAACTTCA |
| | | AGATCCGCCACAACATCGAGGACGGCAGCGTGCAGCTCGCCGACCACTAC |
| | | CAGCAGAACACCCCCATCGGCGACGGCCCCGTGCTGCTGCCCGACAACCA |
| | | CTACCTGAGCACCCAGTCCGCCCTGAGCAAAGACCCCAACGAGAAGCGCG |
| | | ATCACATGGTCCTGCTGGAGTTCGTGACCGCCGCCGGGATCACTCTCGGC |
| | | ATGGACGAGCTGTACAAGAATCGCGCTACTAACTTCAGCCTGCTGAAGCA |
| | | GGCTGGAGACGTGGAGGAGAACCCTGGACCTATGGAAGACGCCAAAAACA |
| | | TAAAGAAAGGCCCGGCGCCATTCTATCCGCTGGAAGATGGAACCGCTGGA |
| | | GAGCAACTGCATAAGGCTATGAAGAGATACGCCCTGGTTCCTGGAACAAT |
| | | TGCTTTTACAGATGCACATATCGAGGTGGACATCACTTACGCTGAGTACT |
| | | TCGAAATGTCCGTTCGGTTGGCAGAAGCTATGAAACGATATGGGCTGAAT |
| | | ACAAATCACAGAATCGTCGTATGCAGTGAAAACTCTCTTCAATTCTTTAT |
| | | GCCGGTGTTGGGCGCGTTATTTATCGGAGTTGCAGTTGCGCCCGCGAACG |
| | | ACATTTATAATGAACGTGAATTGCTCAACAGTATGGGCATTTCGCAGCCT |
| | | ACCGTGGTGTTCGTTTCCAAAAAGGGGTTGCAAAAAATTTTGAACGTGCA |
| | | AAAAAAGCTCCCAATCATCCAAAAAATTATTATCATGGATTCTAAAACGG |
| | | ATTACCAGGGATTTCAGTCGATGTACACGTTCGTCACATCTCATCTACCT |
| | | CCCGGTTTTAATGAATACGATTTTGTGCCAGAGTCCTTCGATAGGGACAA |
| | | GACAATTGCACTGATCATGAACTCCTCTGGATCTACTGGTCTGCCTAAAG |
| | | GTGTCGCTCTGCCTCATAGAACTGCCTGCGTGAGATTCTCGCATGCCAGA |
| | | GATCCTATTTTTGGCAATCAAATCATTCCGGATACTGCGATTTTAAGTGT |
| | | TGTTCCATTCCATCACGGTTTTGGAATGTTTACTACACTCGGATATTTGA |
| | | TATGTGGATTTCGAGTCGTCTTAATGTATAGATTTGAAGAAGAGCTGTTT |
| | | CTGAGGAGCCTTCAGGATTACAAGATTCAAAGTGCGCTGCTGGTGCCAAC |
| | | CCTATTCTCCTTCTTCGCCAAAAGCACTCTGATTGACAAATACGATTTAT |
| | | CTAATTTACACGAAATTGCTTCTGGTGGCGCTCCCCTCTCTAAGGAAGTC |
| | | GGGGAAGCGGTTGCCAAGAGGTTCCATCTGCCAGGTATCAGGCAAGGATA |
| | | TGGGCTCACTGAGACTACATCAGCTATTCTGATTACACCCGAGGGGGATG |
| | | ATAAACCGGGCGCGGTCGGTAAAGTTGTTCCATTTTTTGAAGCGAAGGTT |
| | | GTGGATCTGGATACCGGGAAAACGCTGGGCGTTAATCAAAGAGGCGAACT |
| | | GTGTGTGAGAGGTCCTATGATTATGTCCGGTTATGTAAACAATCCGGAAG |
| | | CGACCAACGCCTTGATTGACAAGGATGGATGGCTACATTCTGGAGACATA |
| | | GCTTACTGGGACGAAGACGAACACTTCTTCATCGTTGACCGCCTGAAGTC |
| | | TCTGATTAAGTACAAAGGCTATCAGGTGGCTCCCGCTGAATTGGAATCCA |
| | | TCTTGCTCCAACACCCCAACATCTTCGACGCAGGTGTCGCAGGTCTTCCC |
| | | GACGATGACGCCGGTGAACTTCCCGCCGCCGTTGTTGTTTTGGAGCACGG |
| | | AAAGACGATGACGGAAAAAGAGATCGTGGATTACGTCGCCAGTCAAGTAA |
| | | CAACCGCGAAAAAGTTGCGCGGAGGAGTTGTGTTTGTGGACGAAGTACCG |
| | | AAAGGTCTTACCGGAAAACTCGACGCAAGAAAAATCAGAGAGATCCTCAT |
| | | AAAGGCCAAGAAGGGCGGAAAGATCGCCGTGTAACTCGAGAATCAACCTC |
| | | TGGATTACAAAATTTGTGAAAGATTGACTGGTATTCTTAACTATGTTGCT |
| | | CCTTTTACGCTATGTGGATACGCTGCTTTAATGCCTTTGTATCATGCTAT |
| | | TGCTTCCCGTATGGCTTTCATTTTCTCCTCCTTGTATAAATCCTGGTTGC |
| | | TGTCTCTTTATGAGGAGTTGTGGCCCGTTGTCAGGCAACGTGGCGTGGTG |
| | | TGCACTGTGTTTGCTGACGCAACCCCCACTGGTTGGGGCATTGCCACCAC |
| | | CTGTCAGCTCCTTTCCGGGACTTTCGCTTTCCCCCTCCCTATTGCCACGG |
| | | CGGAACTCATCGCCGCCTGCCTTGCCCGCTGCTGGACAGGGGCTCGGCTG |
| | | TTGGGCACTGACAATTCCGTGGGGTGTGCCTTCTAGTTGCCAGCCATCTG |
| | | TTGTTTGCCCCTCCCCCGTGCCTTCCTTGACCCTGGAAGGTGCCACTCCC |
| | | ACTGTCCTTTCCTAATAAAATGAGGAAATTGCATCGCATTGTCTGAGTAG |
| | | GTGTCATTCTATTCTGGGGGGTGGGGTGGGGCAGGACAGCAAGGGGGAGG |
| | | ATTGGGAAGACAATAGCAGGCATGCTGGGGATGCGGTGGGCTCTATGGGA |
| | | AGATGTCTACTGAGCTGTGCGATCCCTGCTGGGGACTTTCCGCTGGGGAC |
| | | TTTCCGCTGGGGACTTTCCGCCTTCAGCTAAGGAAGCTACCAATATTTAG |
| | | AGGTACATTTTGTTCTAGAACAAAATGTACCGGTACATTTTGTTCTGGTA |
| | | CATTTTGTTCTATTAAGGACAACGTAAGTATAGCGCATAGACACGTGGCG |
| | | CCATCGGATCCCGGGCCCGTCGACTTAAGTGGCTTGTTGTCCACAACCAT |
| | | TAAACCTTAAAAGCTTTAAAAGCCTTATATATTCTTTTTTTTCTTATAAA |
| | | ACTTAAAACCTTAGAGGCTATTTAAGTTGCTGATTTATATTAATTTTATT |
| | | GTTCAAACATGAGAGCTTAGTACGTGAAACATGAGAGCTTAGTACATTAG |
| | | CCATGAGAGCTTAGTACATTAGCCATGAGGGTTTAGTTCATTAAACATGA |
| | | GAGCTTAGTACATTAAACATGAGAGCTTAGTACATTAAACATGAGAGCTT |
| | | AGTACATACTATCAACAGGTTGAACTGCTGATCTGTACAGTAGAATTGGT |

-continued

| SEQ ID NO | Description | SEQ |
|---|---|---|
| | | AAAGAGAGTTGTGTAAAATATTGAGTTCGCACATCTTGTTGTCTGATTAT |
| | | TGATTTTTGGCGAAACCATTTGATCATATGACAAGATGTGTATCTACCTT |
| | | AACTTAATGATTTTGATAAAAATCATTAGCGGCCGC |
| 49. | pUC57- | TCTGGATCCACTGCTTAAATACGGACGAGGACAGGGCCCTGTCTCCTCAG |
| | CBA-hBGi- | CTTCAGGCACCACCACTGACCTGGGACAGTGAATCGTAAGTACTAGCAGC |
| | DMD-4- | TACAATCCAGCTACCATTCTGCTTTTATTTTATGGTTGGGATAAGGCTGG |
| | WPRE3- | ATTATTCTGAGTCCAAGCTAGGCCCTTTTGCTAATCATGTTCATACCTCT |
| | DTS | TATCTTCCTCCCACAGCTCCTGGGCAACGTGCTGGTCTGTGTGCTGGCCC |
| | | ATCACTTTGGCAAAGAATTGCGATCGCCACCATGCTTTGGTGGGAAGAAG |
| | | TCGAGGACTGCTACGAGCGCGAGGACGTGCAGAAGAAAACCTTCACCAAA |
| | | TGGGTCAACGCCCAGTTCAGCAAGTTCGGCAAGCAGCACATCGAGAACCT |
| | | GTTCAGCGACCTGCAGGATGGCAGAAGGCTGCTGGATCTGCTGGAAGGCC |
| | | TGACAGGACAGAAGCTGCCCAAAGAGAAGGGCAGCACAAGAGTGCACGCC |
| | | CTGAACAACGTGAACAAGGCCCTGAGAGTGCTGCAGAACAACAACGTGGA |
| | | CCTGGTCAACATCGGCAGCACCGACATCGTGGACGGCAACCACAAACTGA |
| | | CCCTGGGCCTGATCTGGAACATCATCCTGCACTGGCAAGTGAAGAACGTG |
| | | ATGAAGAACATCATGGCCGGCCTGCAGCAGACCAACAGCGAGAAGATTCT |
| | | GCTGAGCTGGGTCCGACAGAGCACCCGGAATTACCCTCAAGTGAACGTGA |
| | | TCAACTTCACCACCTCTTGGAGCGACGGACTGGCCCTGAATGCCCTGATC |
| | | CACAGCCACAGACCTGACCTGTTCGACTGGAACAGCGTCGTGTGTCAGCA |
| | | GAGCGCCACACAGAGGCTGGAACACGCCTTCAATATCGCCAGATACCAGC |
| | | TGGGCATCGAGAAACTGCTGGACCCCGAGGATGTGGACACCACCTATCCT |
| | | GACAAGAAATCCATCCTCATGTACATCACCAGCCTGTTCCAGGTGCTGCC |
| | | CCAGCAGGTTTCCATCGAGGCCATTCAAGAGGTCGAGATGCTGCCCAGAC |
| | | CTCCTAAAGTGACCAAAGAGGAACACTTCCAGCTGCACCACCAGATGCAC |
| | | TACTCTCAGCAGATCACCGTGTCTCTGGCCCAGGGCTACGAGAGAACAAG |
| | | CAGCCCCAAGCCTCGGTTCAAGAGCTACGCCTATACACAGGCCGCCTACG |
| | | TGACCACCAGCGATCCTACAAGAAGCCCATTTCCTAGCCAGCATCTGGAA |
| | | GCCCCTGAGGACAAGAGCTTTGGCAGCAGCCTGATGGAAAGCGAAGTGAA |
| | | CCTGGACCGCTACCAGACAGCCCTGGAAGAGGTTCTGAGCTGGCTGCTGT |
| | | CTGCCGAGGATACACTGCAGGCTCAGGGCGAGATCAGCAACGACGTGGAA |
| | | GTGGTCAAGGACCAGTTTCACACCCACGAGGGCTACATGATGGACCTGAC |
| | | AGCCCACCAGGGCAGAGTGGGCAATATTCTGCAGCTGGGCTCCAAGCTGA |
| | | TCGGCACAGGCAAGCTGAGCGAGGACGAAGAGACAGAGGTGCAAGAGCAG |
| | | ATGAACCTGCTGAACAGCAGATGGGAGTGTCTGAGAGTGGCCAGCATGGA |
| | | AAAGCAGAGCAACCTGCACCGGGTGCTGATGGATCTCCAGAACCAGAAGC |
| | | TGAAAGAGCTGAACGACTGGCTGACCAAGACCGAGGAACGGACCCGGAAG |
| | | ATGGAAGAGGAACCTCTGGGACCCGACCTGGAAGATCTGAAAAGACAGGT |
| | | GCAGCAGCATAAGGTGCTGCAAGAGGACCTCGAACAAGAGCAAGTGCGCG |
| | | TGAACAGCCTGACACACATGGTGGTGGTCGTGGATGAGAGCAGCGGAGAT |
| | | CATGCCACAGCCGCTCTGGAAGAACAGCTGAAGGTGCTGGGAGACAGATG |
| | | GGCCAATATCTGCCGGTGGACCGAGGATAGATGGGTGCTGCTCCAGGACA |
| | | TCCTGCTGAAGTGGCAGCGGCTGACAGAGGAACAGTGCCTGTTTAGCGCC |
| | | TGGCTGTCCGAGAAAGAGGACGCCGTCAACAAGATCCACACCACCGGCTT |
| | | CAAGGATCAGAATGAGATGCTGAGCAGCCTGCAGAAACTGGCCGTGCTGA |
| | | AGGCTGACCTGGAAAAGAAAAAGCAGTCCATGGGCAAGCTGTACTCCCTG |
| | | AAGCAGGACCTGCTGAGCACACTGAAGAACAAGTCTGTGACCCAGAAAAC |
| | | CGAGGCCTGGCTGGACAACTTCGCCCGGTGTTGGGATAACCTGGTGCAGA |
| | | AGCTGGAAAAGTCCACCGCTCAGATCTCTCAGGCCGTGACCACAACACAG |
| | | CCTTCTCTGACCCAGACCACCGTGATGGAAACAGTGACCACAGTGACAAC |
| | | CCGCGAGCAGATCCTGGTCAAGCACGCCCAAGAAGAACTGCCTCCTCCAC |
| | | CTCCTCAGAAGAAACGGCAGATCACAGTGGACAGCGAGATCCGGAAGAGA |
| | | CTGGACGTGGACATCACCGAGCTGCACAGCTGGATCACCAGATCCGAAGC |
| | | CGTGCTGCAGTCCCCTGAGTTCGCCATCTTCAGAAAAGAGGGCAACTTCT |
| | | CCGACCTGAAAGAGAAAGTCAACGCCATCGAGAGAGAGAAGGCCGAGAAG |
| | | TTCCGGAAGCTGCAGGACGCCTCTAGATCTGCCCAGGCTCTGGTGGAACA |
| | | GATGGTCAACGAAGGCGTGAACGCCGACAGCATCAAGCAGGCCTCAGAGC |
| | | AGCTGAACTCCCGGTGGATCGAGTTCTGTCAGCTCCTGAGCGAGAGACTG |
| | | AACTGGCTGGAATACCAGAACAATATCATTGCCTTCTACAACCAGCTCCA |
| | | GCAGCTCGAACAGATGACCACCACAGCCGAGAATTGGCTGAAGATCCAGC |
| | | CTACCACACCTAGCGAGCCCACCGCCATTAAGAGCCAGCTGAAAATCTGC |
| | | AAGGACGAAGTGAATCGGCTGAGCGATCTGCAGCCCCAGATCGAAAGACT |
| | | GAAAATCCAGTCTATCGCCCTCAAAGAGAAAGGACAGGGCCCCATGTTCC |
| | | TGGACGCCGATTTTGTGGCCTTTACCAACCACTTCAAACAGGTGTTCTCC |
| | | GACGTGCAGGCCCGGGAAAAAGAGCTGCAGACCATCTTCGACACCCTGCC |
| | | TCCAATGAGATACCAAGAGACAATGAGCGCCATCCGGACCTGGGTGCAGC |
| | | AAAGCGAGACAAAGCTGAGCATCCCACAGCTGAGCGTGACCGACTACGAG |
| | | ATCATGGAACAGAGACTGGGCGAACTGCAGGCCCTCCAGTCTAGCCTGCA |
| | | AGAACAGCAGTCCGGCCTGTACTACCTGAGCACAACCGTGAAAGAGATGA |
| | | GCAAGAAGGCCCCTAGCGAGATCTCCCGGAAGTACCAGAGCGAGTTCGAA |
| | | GAGATCGAAGGCCGGTGGAAGAAGCTGTCTAGCCAGCTGGTTGAGCACTG |
| | | CCAGAAACTCGAAGAACAAATGAACAAGCTGCGCAAGATCCAGAATCACA |
| | | TCCAGACGCTGAAGAAATGGATGGCCGAGGTGGACGTGTTCCTGAAAGAA |
| | | GAGTGGCCCGCTCTGGGCGACTCCGAGATTCTGAAGAAACAGCTCAAACA |

-continued

| SEQ ID NO | Description | SEQ |
|---|---|---|
| | | GTGCCGGCTGCTGGTGTCCGATATCCAGACAATCCAGCCAAGCCTGAACT CCGTGAATGAAGGCGGCCAGAAGATCAAGAACGAGGCCGAGCCTGAGTTT GCCAGCAGACTGGAAACCGAACTGAAAGAACTCAACACCCAGTGGGACCA CATGTGCCAGCAAGTGTACGCCCGGAAAGAGGCCCTGAAAGGCGGACTCG AAAAGACTGTGTCTCTGCAGAAAGACCTGTCTGAGATGCACGAGTGGATG ACCCAGGCCGAAGAGGAATACCTGGAACGGGACTTCGAGTACAAGACCCC TGATGAGCTGCAAAAAGCCGTCGAGGAAATGAAGCGGGCCAAAGAAGAGG CCCAGCAGAAAGAAGCCAAAGTCAAGCTGCTGACCGAGTCCGTGAATAGC GTTATCGCTCAGGCCCCTCCTGTGGCTCAAGAGGCTCTCAAGAAAGAACT GGAAACTCTGACCACCAACTACCAGTGGCTGTGCACCAGACTGAACGGCA AGTGCAAGACACTGGAAGAAGTGTGGGCCTGCTGGCACGAACTGCTGTCC TATCTGGAAAAGGCCAACAAGTGGCTGAACGAGGTGGAATTCAAGCTGAA AACCACCGAGAACATCCCTGGCGGCGCTGAAGAGATTAGCGAGGTGCTGG ACAGCCTGGAAAACCTGATGAGACACAGCGAGGACAACCCCAATCAGATC AGAATCCTGGCTCAGACCCTGACCGATGGCGGCGTGATGGACGAGCTGAT CAACGAGGAACTCGAAACCTTCAACAGCCGGTGGCGGGAACTGCACGAGG AAGCTGTTCGGAGGCAGAAGTTGCTGGAACAGTCTATCCAGAGCGCACAA GAAACCGAGAAGTCCCTGCACCTGATCCAAGAGAGCCTGACCTTCATCGA CAAGCAGCTGGCCGCTTATATCGCCGACAAGGTGGACGCTGCTCAGATGC CCCAAGAGGCACAGAAGATTCAGAGCGACCTGACCAGCCACGAGATTAGC CTGGAAGAAATGAAGAAGCACAACCAGGGCAAAGAGGCCGCTCAGAGAGT CCTGAGCCAGATCGATGTGGCACAGAAAAAGCTCCAGGATGTGTCCATGA AGTTTCGGCTGTTTCAGAAGCCCGCCAACTTCGAGCAGAGACTGCAAGAG TCCAAGATGATCCTGGACGAAGTCAAAATGCATCTGCCCGCACTGGAAAC AAAGTCCGTGGAACAAGAAGTGGTGCAGTCCCAGCTGAACCACTGCGTGA ACCTGTACAAGAGCCTGTCCGAAGTGAAGTCTGAGGTGGAAATGGTCATC AAGACCGGCAGGCAGATCGTCCAGAAGAAGCAGACCGAGAATCCCAAAGA ACTCGACGAGAGAGTGACCGCTCTGAAGCTGCACTACAATGAGCTGGGCG CCAAAGTGACCGAGCGGAAGCAACAGCTTGAGAAGTGCCTGAAACTGTCT CGGAAGATGCGGAAAGAAATGAACGTGCTGACAGAGTGGCTGGCCGCCAC CGATATGGAACTGACTAAGAGAAGCGCCGTGGAAGGCATGCCCAGCAACC TGGATAGTGAAGTGGCCTGGGGCAAAGCCACTCAGAAAGAGATTGAGAAG CAGAAGGTCCACCTGAAGTCCATCACCGAAGTGGGCGAAGCCCTGAAAAC CGTGCTGGGAAAGAAAGAGACACTGGTCGAGGACAAGCTGTCCCTGCTGA ATTCCAACTGGATCGCCGTGACCTCCAGAGCTGAGGAATGGCTGAATCTG CTGCTTGAGTACCAGAAACACATGGAAACGTTCGACCAGAACGTCGACCA CATCACAAAGTGGATCATCCAGGCTGATACCCTGCTGGACGAGTCCGAGA AGAAGAAACCCCAACAAAAAGAAGATGTGCTGAAGCGGCTGAAAGCCGAG CTGAATGACATCCGGCCTAAGGTGGACAGCACCAGAGATCAGGCAGCCAA CCTGATGGCCAACAGAGGCGACCACTGTCGGAAGCTCGTGGAACCTCAGA TCAGCGAGCTTAACCACAGATTTGCCGCCATCAGCCACCGGATCAAGACA GGCAAGGCCAGCATTCCTCTCAAAGAGCTTGAGCAGTTCAACAGCGACAT CCAAAAGCTGCTCGAACCCCTGGAAGCCGAGATCCAACAGGGCGTCAACC TCAAAGAAGAAGATTTCAACAAGGACATGAACGAGGACAATGAGGGCACC GTCAAAGAACTGCTGCAGCGGGGCGATAATCTGCAGCAGCGGATTACCGA TGAGCGCAAGCGGGAAGAGATCAAGATTAAGCAGCAGCTGCTGCAGACCA AGCACAACGCCCTGAAGGACCTGCGGAGCCAGAGAAGAAAGAAGGCCCTG GAAATCAGCCACCAGTGGTATCAGTACAAGCGGCAGGCCGACGACCTGCT GAAGTGCCTGGATGACATCGAGAAGAAGCTGGCCTCTCTGCCCGAGCCTA GGGACGAGAGAAAGATCAAAGAGATCGACCGCGAGCTGCAGAAAAAGAAA GAGGAACTGAACGCCGTCCGCAGACAGGCCGAAGGACTTTCTGAAGATGG CGCCGCTATGGCCGTGGAACCCACACAGATTCAGCTGAGCAAGCGGTGGC GGGAAATCGAGAGCAAGTTCGCCCAGTTCCGGCGGCTGAATTTCGCCCAG ATCCACACCGTGCGGGAAGAGACAATGATGGTCATGACAGAGGACATGCC CCTTGAGATCAGCTACGTGCCCAGCACCTACCTGACCGAGATCACCCATG TGTCTCAGGCCCTGCTGGAAGTGGAACAGCTGCTGAATGCCCCTGACCTG TGCGCCAAGGACTTCGAGGACCTGTTCAAGCAAGAGGAAAGCCTGAAGAA CATCAAGGACAGCCTGCAGCAGAGCAGCGGCCGGATCGATATCATCCACA GCAAGAAAACCGCCGCACTGCAGAGCGCCACACCTGTGGAAAGAGTGAAG CTGCAAGAGGCCCTGAGCCAGCTGGATTTCCAGTGGGAGAAAGTGAACAA GATGTACAAGGACCGGCAGGGCAGATTCGACCGCAGCGTTGAAAAGTGGC GGCGGTTCCACTACGACATCAAGATCTTCAACCAGTGGCTGACCGAGGCC GAGCAGTTCCTGAGAAAGACACAGATCCCCGAGAACTGGGAGCACGCCAA GTACAAGTGGTATCTGAAAGAGCTGCAGGACGGCATCGGCCAGAGACAGA CAGTCGTGCGGACACTGAATGCCACCGGCGAGGAAATCATCCAGCAGTCC AGCAAGACCGACGCCAGCATCCTGCAAGAGAAGCTGGGCAGCCTGAACCT GCGGTGGCAAGAAGTGTGCAAGCAGCTGAGCGACCGGAAGAAGCGGCTGG AAGAACAGAAGAATATCCTGAGCGAGTTCCAGCGGGACCTGAACGAGTTC GTGCTGTGGCTCGAAGAGGCCGACAATATCGCCAGCATTCCCCTGGAACC TGGCAAAGAGCAGCAGCTGAAAGAAAAGCTGGAACAAGTGAAACTGCTGG TCGAGGAACTGCCCCTGAGACAGGGAATCCTGAAACAGCTGAACGAGACA GGCGGCCCTGTGCTGGTGTCTGCCCCTATTTCTCCCGAGGAACAGGACAA GCTGGAAAACAAGCTGAAGCAGACCAACCTGCAGTGGATCAAGGTGTCCA GAGCACTGCCTGAGAAGCAGGGCGAGATCGAGGCCCAGATCAAGGACCTG GGACAGCTCGAAAAGAAGCTTGAGGACCTCGAAGAACAGCTCAACCATCT |

-continued

| SEQ ID NO | Description | SEQ |
|---|---|---|
| | | GCTGCTTTGGCTGAGCCCCATCCGGAACCAGCTGGAAATCTACAACCAGC |
| | | CTAATCAAGAGGGCCCCTTCGACGTGAAAGAAACCGAGATTGCCGTGCAG |
| | | GCCAAGCAGCCCGATGTGGAAGAGATCCTGTCTAAGGGCCAGCACCTGTA |
| | | CAAAGAGAAGCCCGCCACACAGCCCGTGAAGCGGAAACTGGAAGATCTGA |
| | | GCAGCGAGTGGAAGGCCGTGAACCGGCTGCTGCAAGAACTGAGAGCCAAA |
| | | CAGCCTGATCTGGCCCCTGGCCTGACAACAATTGGCGCCTCTCCTACACA |
| | | GACCGTGACACTGGTCACACAGCCTGTGGTCACCAAAGAGACAGCCATCA |
| | | GCAAACTGGAAATGCCCAGCAGTCTGATGCTCGAAGTGCCCGCACTGGCC |
| | | GACTTCAATAGAGCCTGGACCGAGCTGACCGACTGGCTCAGTCTGCTGGA |
| | | CCAAGTCATCAAGTCCCAGAGAGTGATGGTCGGAGATCTTGAGGACATCA |
| | | ACGAGATGATCATTAAGCAGAAAGCCACCATGCAGGACCTTGAGCAGAGA |
| | | AGGCCCCAGCTTGAAGAACTGATCACCGCCGCTCAGAACCTGAAAAACAA |
| | | GACCAGCAATCAAGAAGCCCGGACCATCATCACCGACCGGATCGAGAGAA |
| | | TCCAGAACCAGTGGGACGAAGTGCAAGAGCATCTGCAGAACAGACGGCAG |
| | | CAGCTCAATGAGATGCTGAAGGACAGCACACAGTGGCTGGAAGCCAAAGA |
| | | AGAAGCCGAGCAGGTTCTCGGACAGGCCAGAGCTAAGCTGGAATCTTGGA |
| | | AAGAGGGACCCTACACCGTCGACGCCATCCAGAAGAAGATCACCGAGACA |
| | | AAGCAGCTGGCCAAGGATCTGAGACAGTGGCAGACCAATGTGGACGTGGC |
| | | CAACGACCTGGCTCTGAAGCTGCTGAGAGACTACAGCGCCGACGACACCA |
| | | GAAAGGTGCACATGATCACCGAAAACATCAACGCCTCTTGGCGGAGCATC |
| | | CACAAGCGGGTGTCAGAGAGAGAAGCCGCTCTGGAAGAAACACATAGACT |
| | | GCTCCAGCAGTTCCCACTCGACCTGGAAAAGTTCCTGGCCTGGCTGACAG |
| | | AAGCCGAAACCACCGCTAACGTGCTCCAGGATGCCACCAGAAAAGAGCGG |
| | | CTGTTGGAGGACAGCAAGGGCGTCAAAGAACTCATGAAGCAGTGGCAGGA |
| | | TCTGCAAGGGGAGATTGAAGCCCACACCGACGTGTACCACAACCTGGACG |
| | | AGAACAGCCAGAAGATCCTGCGGTCCCTGGAAGGCTCTGATGATGCTGTG |
| | | CTGCTTCAGAGGCGGCTGGACAACATGAACTTCAAGTGGAGCGAGCTGCG |
| | | GAAGAAGTCCCTGAACATCAGAAGCCACCTGGAAGCCTCCAGCGACCAGT |
| | | GGAAAAGACTGCACCTGTCTCTCCAAGAGCTGCTCGTGTGGCTGCAGCTG |
| | | AAGGATGACGAGCTGAGTAGACAGGCCCCTATCGGCGGAGATTTTCCCGC |
| | | CGTGCAGAAACAGAACGACGTGCACCGGGCCTTCAAGAGAGAGCTGAAAA |
| | | CAAAAGAACCCGTCATCATGAGCACCCTGGAAACCGTGCGGATCTTTCTG |
| | | ACCGAGCAGCCTCTGGAAGGACTGGAAAAGCTGTACCAAGAGCCTAGAGA |
| | | GCTGCCTCCTGAAGAAAGGGCCCAGAACGTGACACGGCTGCTTAGAAAGC |
| | | AGGCCGAGGAAGTGAACACCGAATGGGAGAAGCTGAACCTCCACTCCGCC |
| | | GACTGGCAGCGGAAGATCGATGAGACACTGGAACGGCTGCGGGAACTGCA |
| | | AGAAGCCACAGACGAGCTGGACCTGAAACTGCGGCAGGCTGAAGTGATCA |
| | | AAGGCTCCTGGCAGCCAGTGGGCGATCTGCTGATCGATAGCCTGCAGGAC |
| | | CATCTGGAAAAAGTCAAGGCCCTGCGGGGAGAGATCGCCCCTCTCAAAGA |
| | | AAACGTGTCCCACGTGAACGATCTGGCCAGGCAGCTGACAACACTGGGCA |
| | | TCCAGCTGAGCCCTTACAACCTGTCTACCTTGGAGGACCTGAATACCCGG |
| | | TGGAAGCTGCTCCAAGTGGCCGTCGAGGATAGAGTGCGGCAGCTGCATGA |
| | | GGCTCACAGAGATTTTGGACCCGCCAGCCAGCACTTCCTGAGCACATCTG |
| | | TTCAAGGCCCCTGGGAGAGAGCTATCAGCCCTAACAAGGTGCCCTACTAC |
| | | ATCAACCACGAGACACAGACCACCTGTTGGGATCACCCCAAGATGACCGA |
| | | ACTGTATCAGTCCCTGGCCGACCTGAACAACGTGCGGTTTAGCGCCTACC |
| | | GGACCGCCATGAAGCTGCGCAGACTGCAGAAAGCTCTGTGCCTGGACCTG |
| | | CTGTCTCTGAGCGCTGCTTGTGATGCCCTGGACCAGCATAACCTCAAGCA |
| | | GAACGACCAGCCTATGGACATCCTGCAGATCATCAACTGCCTGACCACCA |
| | | TCTACGACCGGCTCGAACAAGAGCACAACAACCTGGTCAACGTGCCCCTG |
| | | TGCGTGGACATGTGCCTGAATTGGCTGCTGAACGTGTACGACACCGGCAG |
| | | AACCGGCAGGATCAGAGTGCTGAGCTTCAAGACCGGCATCATCTCCCTGT |
| | | GCAAGGCCCACCTTGAGGATAAGTACCGCTACCTGTTTAAGCAGGTCGCC |
| | | AGCAGCACCGGCTTTTGCGACCAAAGAAGGCTGGGACTGCTGCTCCACGA |
| | | CAGCATTCAGATCCCTAGACAGCTGGGCGAAGTGGCCTCTTTCGGCGGCT |
| | | CTAATATCGAGCCTAGCGTGCGGAGCTGCTTCCAGTTCGCCAACAACAAG |
| | | CCCGAGATTGAGGCCGCACTGTTCCTGGACTGGATGAGACTGGAACCCCA |
| | | GAGCATGGTCTGGCTGCCTGTGCTGCATAGAGTGGCCGCAGCCGAAACAG |
| | | CCAAGCACCAGGCCAAGTGCAACATCTGCAAAGAGTGCCCCATCATCGGC |
| | | TTCCGGTACAGATCCCTGAAGCACTTCAACTACGATATCTGCCAGTCCTG |
| | | CTTCTTCAGCGGCAGAGTGGCCAAGGGCCACAAGATGCACTACCCCATGG |
| | | TGGAATACTGCACCCCTACCACCTCTGGCGAGGACGTGCGGGATTTTGCC |
| | | AAGGTGCTCAAGAACAAGTTCCGGACCAAGCGCTACTTCGCTAAGCACCC |
| | | CAGAATGGGCTACCTGCCAGTGCAGACAGTGCTTGAGGGCGACAACATGG |
| | | AAACCCCTGTGACTCTGATCAACTTCTGGCCCGTGGATAGCGCCCCTGCT |
| | | AGTTCTCCTCAGCTGTCTCACGACGATACCCACAGCAGAATCGAGCACTA |
| | | CGCCTCCAGACTGGCCGAGATGGAAAACAGCAACGGCAGCTACCTGAATG |
| | | ACAGCATCAGCCCCAACGAGAGCATCGACGACGAACATCTGCTCATTCAG |
| | | CACTACTGCCAGAGCCTGAATCAGGACAGCCCTCTGTCTCAGCCTAGAAG |
| | | CCCTGCACAGATCCTGATCAGCCTGGAAAGCGAGGAACGCGGCGAGCTGG |
| | | AAAGAATCCTGGCAGACCTGGAAGAGGAAAACCGGAACCTGCAGGCCGAA |
| | | TACGACAGACTCAAGCAGCAGCACGAGCACAAGGGACTGTCTCCACTGCC |
| | | TTCTCCACCTGAAATGATGCCCACCTCTCCACAGAGCCCCAGAGATGCCG |
| | | AGCTGATTGCCGAAGCCAAACTGCTGAGGCAGCACAAAGGCAGACTCGAA |
| | | GCCAGAATGCAGATTCTCGAAGATCACAACAAGCAGCTCGAATCCCAGCT |

-continued

| SEQ ID NO | Description | SEQ |
|---|---|---|
| | | GCACAGACTTAGGCAGCTGCTGGAACAGCCTCAGGCAGAGGCCAAAGTGA ATGGCACCACCGTGTCTAGCCCTAGCACAAGCCTGCAGAGATCCGACAGC AGCCAGCCAATGCTTCTGAGAGTCGTGGGCTCCCAGACCAGCGATTCTAT GGGCGAAGAGGACCTGCTCAGCCCTCCTCAGGATACAAGCACCGGCCTGG AAGAAGTGATGGAACAACTGAACAACAGCTTCCCCAGCAGCAGAGGCAGA AACACCCCTGGCAAGCCCATGCGCGAGGACACCATGTGATAACTCGAGAA TCAACCTCTGGATTACAAAATTTGTGAAAGATTGACTGGTATTCTTAACT ATGTTGCTCCTTTTACGCTATGTGGATACGCTGCTTTAATGCCTTTGTAT CATGCTATTGCTTCCCGTATGGCTTTCATTTTCTCCTCCTTGTATAAATC CTGGTTGCTGTCTCTTTATGAGGAGTTGTGGCCCGTTGTCAGGCAACGTG GCGTGGTGTGCACTGTGTTTGCTGACGCAACCCCCACTGGTTGGGGCATT GCCACCACCTGTCAGCTCCTTTCCGGGACTTTCGCTTTCCCCCTCCCTAT TGCCACGGCGGAACTCATCGCCGCCTGCCTTGCCCGCTGCTGGACAGGGG CTCGGCTGTTGGGCACTGACAATTCCGTGGGGTGTGCCTTCTAGTTGCCA GCCATCTGTTGTTTGCCCCTCCCCCGTGCCTTCCTTGACCCTGGAAGGTG CCACTCCCACTGTCCTTTCCTAATAAAATGAGGAAATTGCATCGCATTGT CTGAGTAGGTGTCATTCTATTCTGGGGGGTGGGGTGGGGCAGGACAGCAA GGGGGAGGATTGGGAAGACAATAGCAGGCATGCTGGGGATGCGGTGGGCT CTATGGGAAGATGTCTACTGAGCTGTGCGATCCCTGCTGGGGACTTTCCG CTGGGGACTTTCCGCTGGGGACTTTCCGCCTTCAGCTAAGGAAGCTACCA ATATTTAGAGGTACATTTTGTTCTAGAACAAAATGTACCGGTACATTTTG TTCTGGTACATTTTGTTCTATTAAGGACAACGTAAGTATAGCGCATAGAC ACGTGGCGCCATCGGATCCCGGGCCCGTCGACTGCAGAGGCCTGCATGCA AGCTTGGCGTAATCATGGTCATAGCTGTTTCCTGTGTGAAATTGTTATCC GCTCACAATTCCACACAACATACGAGCCGGAAGCATAAAGTGTAAAGCCT GGGGTGCCTAATGAGTGAGCTAACTCACATTAATTGCGTTGCGCTCACTG CCCGCTTTCCAGTCGGGAAACCTGTCGTGCCAGCTGCATTAATGAATCGG CCAACGCGCGGGGAGAGGCGGTTTGCGTATTGGGCGCTCTTCCGCTTCCT CGCTCACTGACTCGCTGCGCTCGGTCGTTCGGCTGCGGCGAGCGGTATCA GCTCACTCAAAGGCGGTAATACGGTTATCCACAGAATCAGGGGATAACGC AGGAAAGAACATGTGAGCAAAAGGCCAGCAAAAGGCCAGGAACCGTAAAA AGGCCGCGTTGCTGGCGTTTTTCCATAGGCTCCGCCCCCCTGACGAGCAT CACAAAAATCGACGCTCAAGTCAGAGGTGGCGAAACCCGACAGGACTATA AAGATACCAGGCGTTTCCCCCTGGAAGCTCCCTCGTGCGCTCTCCTGTTC CGACCCTGCCGCTTACCGGATACCTGTCCGCCTTTCTCCCTTCGGGAAGC GTGGCGCTTTCTCATAGCTCACGCTGTAGGTATCTCAGTTCGGTGTAGGT CGTTCGCTCCAAGCTGGGCTGTGTGCACGAACCCCCCGTTCAGCCCGACC GCTGCGCCTTATCCGGTAACTATCGTCTTGAGTCCAACCCGGTAAGACAC GACTTATCGCCACTGGCAGCAGCCACTGGTAACAGGATTAGCAGAGCGAG GTATGTAGGCGGTGCTACAGAGTTCTTGAAGTGGTGGCCTAACTACGGCT ACACTAGAAGAACAGTATTTGGTATCTGCGCTCTGCTGAAGCCAGTTACC TTCGGAAAAAGAGTTGGTAGCTCTTGATCCGGCAAACAAACCACCGCTGG TAGCGGTGGTTTTTTTGTTTGCAAGCAGCAGATTACGCGCAGAAAAAAAG GATCTCAAGAAGATCCTTTGATCTTTTCTACGGGGTCTGACGCTCAGTGG AACGAAAACTCACGTTAAGGGATTTTGGTCATGAGATTATCAAAAAGGAT CTTCACCTAGATCCTTTTAAATTAAAAATGAAGTTTTAAATCAATCTAAA GTATATATGAGTAAACTTGGTCTGACAGTTACCAATGCTTAATCAGTGAG GCACCTATCTCAGCGATCTGTCTATTTCGTTCATCCATAGTTGCCTGACT CCCCGTCGTGTAGATAACTACGATACGGGAGGGCTTACCATCTGGCCCCA GTGCTGCAATGATACCGCGAGACCCACGCTCACCGGCTCCAGATTTATCA GCAATAAACCAGCCAGCCGGAAGGGCCGAGCGCAGAAGTGGTCCTGCAAC TTTATCCGCCTCCATCCAGTCTATTAATTGTTGCCGGGAAGCTAGAGTAA GTAGTTCGCCAGTTAATAGTTTGCGCAACGTTGTTGCCATTGCTACAGGC ATCGTGGTGTCACGCTCGTCGTTTGGTATGGCTTCATTCAGCTCCGGTTC CCAACGATCAAGGCGAGTTACATGATCCCCCATGTTGTGCAAAAAAGCGG TTAGCTCCTTCGGTCCTCCGATCGTTGTCAGAAGTAAGTTGGCCGCAGTG TTATCACTCATGGTTATGGCAGCACTGCATAATTCTCTTACTGTCATGCC ATCCGTAAGATGCTTTTCTGTGACTGGTGAGTACTCAACCAAGTCATTCT GAGAATAGTGTATGCGGCGACCGAGTTGCTCTTGCCCGGCGTCAATACGG GATAATACCGCGCCACATAGCAGAACTTTAAAAGTGCTCATCATTGGAAA ACGTTCTTCGGGGCGAAAACTCTCAAGGATCTTACCGCTGTTGAGATCCA GTTCGATGTAACCCACTCGTGCACCCAACTGATCTTCAGCATCTTTTACT TTCACCAGCGTTTCTGGGTGAGCAAAAACAGGAAGGCAAAATGCCGCAAA AAAGGGAATAAGGGCGACACGGAAATGTTGAATACTCATACTCTTCCTTT TTCAATATTATTGAAGCATTTATCAGGGTTATTGTCTCATGAGCGGATAC ATATTTGAATGTATTTAGAAAAATAAACAAATAGGGGTTCCGCGCACATT TCCCCGAAAAGTGCCACCTGACGTCTAAGAAACCATTATTATCATGACAT TAACCTATAAAAATAGGCGTATCACGAGGCCCTTTCGTCTCGCGCGTTTC GGTGATGACGGTGAAAACCTCTGACACATGCAGCTCCCGGAGACGGTCAC AGCTTGTCTGTAAGCGGATGCCGGGAGCAGACAAGCCCGTCAGGGCGCGT CAGCGGGTGTTGGCGGGTGTCGGGGCTGGCTTAACTATGCGGCATCAGAG CAGATTGTACTGAGAGTGCACCATATGCGGTGTGAAATACCGCACAGATG CGTAAGGAGAAAATACCGCATCAGGCGCCATTCGCCATTCAGGCTGCGCA ACTGTTGGGAAGGGCGATCGGTGCGGGCCTCTTCGCTATTACGCCAGCTG GCGAAAGGGGGATGTGCTGCAAGGCGATTAAGTTGGGTAACGCCAGGGTT |

-continued

| SEQ ID NO | Description | SEQ |
|---|---|---|
| | | TTCCCAGTCACGACGTTGTAAAACGACGGCCAGTGAATTCGAGCTCGGTA |
| | | CCTCGCGAATGCATGCGGCCGCCGTTACATAACTTACGGTAAATGGCCCG |
| | | CCTGGCTGACCGCCCAACGACCCCCGCCCATTGACGTCAATAATGACGTA |
| | | TGTTCCCATAGTAACGCCAATAGGGACTTTCCATTGACGTCAATGGGTGG |
| | | AGTATTTACGGTAAACTGCCCACTTGGCAGTACATCAAGTGTATCATATG |
| | | CCAAGTACGCCCCCTATTGACGTCAATGACGGTAAATGGCCCGCCTGGCA |
| | | TTATGCCCAGTACATGACCTTATGGGACTTTCCTACTTGGCAGTACATCT |
| | | ACGTATTAGTCATCGCTATTACCATGGTCGAGGTGAGCCCCACGTTCTGC |
| | | TTCACTCTCCCCATCTCCCCCCCCTCCCCACCCCCAATTTTGTATTTATT |
| | | TATTTTTTAATTATTTTGTGCAGCGATGGGGGCGGGGGGGGGGGGGGCGC |
| | | GCGCCAGGCGGGGCGGGGCGGGGCGAGGGGCGGGGCGGGGCGAGGCGGAG |
| | | AGGTGCGGCGGCAGCCAATCAGAGCGGCGCGCTCCGAAAGTTTCCTTTTA |
| | | TGGCGAGGCGGCGGCGGCGGCGGCCCTATAAAAAGCGAAGCGCGCGGCGG |
| | | GCGGGAGTC |
| 50. | pUC57-MHCK7-hBGi-DMD-4-WPRE3-DTS | TCTGGATCCACTGCTTAAATACGGACGAGGACAGGGCCCTGTCTCCTCAG |
| | | CTTCAGGCACCACCACTGACCTGGGACAGTGAATCGTAAGTACTAGCAGC |
| | | TACAATCCAGCTACCATTCTGCTTTTATTTTATGGTTGGGATAAGGCTGG |
| | | ATTATTCTGAGTCCAAGCTAGGCCCTTTTGCTAATCATGTTCATACCTCT |
| | | TATCTTCCTCCCACAGCTCCTGGGCAACGTGCTGGTCTGTGTGCTGGCCC |
| | | ATCACTTTGGCAAAGAATTGCGATCGCCACCATGCTTTGGTGGGAAGAAG |
| | | TCGAGGACTGCTACGAGCGCGAGGACGTGCAGAAGAAAACCTTCACCAAA |
| | | TGGGTCAACGCCCAGTTCAGCAAGTTCGGCAAGCAGCACATCGAGAACCT |
| | | GTTCAGCGACCTGCAGGATGGCAGAAGGCTGCTGGATCTGCTGGAAGGCC |
| | | TGACAGGACAGAAGCTGCCCAAAGAGAAGGGCAGCACAAGAGTGCACGCC |
| | | CTGAACAACGTGAACAAGGCCCTGAGAGTGCTGCAGAACAACAACGTGGA |
| | | CCTGGTCAACATCGGCAGCACCGACATCGTGGACGGCAACCACAAACTGA |
| | | CCCTGGGCCTGATCTGGAACATCATCCTGCACTGGCAAGTGAAGAACGTG |
| | | ATGAAGAACATCATGGCCGGCCTGCAGCAGACCAACAGCGAGAAGATTCT |
| | | GCTGAGCTGGGTCCGACAGAGCACCCGGAATTACCCTCAAGTGAACGTGA |
| | | TCAACTTCACCACCTCTTGGAGCGACGGACTGGCCCTGAATGCCCTGATC |
| | | CACAGCCACAGACCTGACCTGTTCGACTGGAACAGCGTCGTGTGTCAGCA |
| | | GAGCGCCACACAGAGGCTGGAACACGCCTTCAATATCGCCAGATACCAGC |
| | | TGGGCATCGAGAAACTGCTGGACCCCGAGGATGTGGACACCACCTATCCT |
| | | GACAAGAAATCCATCCTCATGTACATCACCAGCCTGTTCCAGGTGCTGCC |
| | | CCAGCAGGTTTCCATCGAGGCCATTCAAGAGGTCGAGATGCTGCCCAGAC |
| | | CTCCTAAAGTGACCAAAGAGGAACACTTCCAGCTGCACCACCAGATGCAC |
| | | TACTCTCAGCAGATCACCGTGTCTCTGGCCCAGGGCTACGAGAGAACAAG |
| | | CAGCCCCAAGCCTCGGTTCAAGAGCTACGCCTATACACAGGCCGCCTACG |
| | | TGACCACCAGCGATCCTACAAGAAGCCCATTTCCTAGCCAGCATCTGGAA |
| | | GCCCCTGAGGACAAGAGCTTTGGCAGCAGCCTGATGGAAAGCGAAGTGAA |
| | | CCTGGACCGCTACCAGACAGCCCTGGAAGAGGTTCTGAGCTGGCTGCTGT |
| | | CTGCCGAGGATACACTGCAGGCTCAGGGCGAGATCAGCAACGACGTGGAA |
| | | GTGGTCAAGGACCAGTTTCACACCCACGAGGGCTACATGATGGACCTGAC |
| | | AGCCCACCAGGGCAGAGTGGGCAATATTCTGCAGCTGGGCTCCAAGCTGA |
| | | TCGGCACAGGCAAGCTGAGCGAGGACGAAGAGACAGAGGTGCAAGAGCAG |
| | | ATGAACCTGCTGAACAGCAGATGGGAGTGTCTGAGAGTGGCCAGCATGGA |
| | | AAAGCAGAGCAACCTGCACCGGGTGCTGATGGATCTCCAGAACCAGAAGC |
| | | TGAAAGAGCTGAACGACTGGCTGACCAAGACCGAGGAACGGACCCGGAAG |
| | | ATGGAAGAGGAACCTCTGGGACCCGACCTGGAAGATCTGAAAAGACAGGT |
| | | GCAGCAGCATAAGGTGCTGCAAGAGGACCTCGAACAAGAGCAAGTGCGCG |
| | | TGAACAGCCTGACACACATGGTGGTGGTCGTGGATGAGAGCAGCGGAGAT |
| | | CATGCCACAGCCGCTCTGGAAGAACAGCTGAAGGTGCTGGGAGACAGATG |
| | | GGCCAATATCTGCCGGTGGACCGAGGATAGATGGGTGCTGCTCCAGGACA |
| | | TCCTGCTGAAGTGGCAGCGGCTGACAGAGGAACAGTGCCTGTTTAGCGCC |
| | | TGGCTGTCCGAGAAAGAGGACGCCGTCAACAAGATCCACACCACCGGCTT |
| | | CAAGGATCAGAATGAGATGCTGAGCAGCCTGCAGAAACTGGCCGTGCTGA |
| | | AGGCTGACCTGGAAAAGAAAAAGCAGTCCATGGGCAAGCTGTACTCCCTG |
| | | AAGCAGGACCTGCTGAGCACACTGAAGAACAAGTCTGTGACCCAGAAAAC |
| | | CGAGGCCTGGCTGGACAACTTCGCCCGGTGTTGGGATAACCTGGTGCAGA |
| | | AGCTGGAAAAGTCCACCGCTCAGATCTCTCAGGCCGTGACCACAACACAG |
| | | CCTTCTCTGACCCAGACCACCGTGATGGAAACAGTGACCACAGTGACAAC |
| | | CCGCGAGCAGATCCTGGTCAAGCACGCCCAAGAAGAACTGCCTCCTCCAC |
| | | CTCCTCAGAAGAAACGGCAGATCACAGTGGACAGCGAGATCCGGAAGAGA |
| | | CTGGACGTGGACATCACCGAGCTGCACAGCTGGATCACCAGATCCGAAGC |
| | | CGTGCTGCAGTCCCCTGAGTTCGCCATCTTCAGAAAAGAGGGCAACTTCT |
| | | CCGACCTGAAAGAGAAAGTCAACGCCATCGAGAGAGAGAAGGCCGAGAAG |
| | | TTCCGGAAGCTGCAGGACGCCTCTAGATCTGCCCAGGCTCTGGTGGAACA |
| | | GATGGTCAACGAAGGCGTGAACGCCGACAGCATCAAGCAGGCCTCAGAGC |
| | | AGCTGAACTCCCGGTGGATCGAGTTCTGTCAGCTCCTGAGCGAGAGACTG |
| | | AACTGGCTGGAATACCAGAACAATATCATTGCCTTCTACAACCAGCTCCA |
| | | GCAGCTCGAACAGATGACCACCACAGCCGAGAATTGGCTGAAGATCCAGC |
| | | CTACCACACCTAGCGAGCCCACCGCCATTAAGAGCCAGCTGAAAATCTGC |
| | | AAGGACGAAGTGAATCGGCTGAGCGATCTGCAGCCCCAGATCGAAAGACT |
| | | GAAAATCCAGTCTATCGCCCTCAAAGAGAAAGGACAGGGCCCCATGTTCC |

-continued

| SEQ ID NO | Description | SEQ |
|---|---|---|
| | | TGGACGCCGATTTTGTGGCCTTTACCAACCACTTCAAACAGGTGTTCTCC |
| | | GACGTGCAGGCCCGGGAAAAAGAGCTGCAGACCATCTTCGACACCCTGCC |
| | | TCCAATGAGATACCAAGAGACAATGAGCGCCATCCGGACCTGGGTGCAGC |
| | | AAAGCGAGACAAAGCTGAGCATCCCACAGCTGAGCGTGACCGACTACGAG |
| | | ATCATGGAACAGAGACTGGGCGAACTGCAGGCCCTCCAGTCTAGCCTGCA |
| | | AGAACAGCAGTCCGGCCTGTACTACCTGAGCACAACCGTGAAAGAGATGA |
| | | GCAAGAAGGCCCCTAGCGAGATCTCCCGGAAGTACCAGAGCGAGTTCGAA |
| | | GAGATCGAAGGCCGGTGGAAGAAGCTGTCTAGCCAGCTGGTTGAGCACTG |
| | | CCAGAAACTCGAAGAACAAATGAACAAGCTGCGCAAGATCCAGAATCACA |
| | | TCCAGACGCTGAAGAAATGGATGGCCGAGGTGGACGTGTTCCTGAAAGAA |
| | | GAGTGGCCCGCTCTGGGCGACTCCGAGATTCTGAAGAAACAGCTCAAACA |
| | | GTGCCGGCTGCTGGTGTCCGATATCCAGACAATCCAGCCAAGCCTGAACT |
| | | CCGTGAATGAAGGCGGCCAGAAGATCAAGAACGAGGCCGAGCCTGAGTTT |
| | | GCCAGCAGACTGGAAACCGAACTGAAAGAACTCAACACCCAGTGGGACCA |
| | | CATGTGCCAGCAAGTGTACGCCCGGAAAGAGGCCCTGAAAGGCGGACTCG |
| | | AAAAGACTGTGTCTCTGCAGAAAGACCTGTCTGAGATGCACGAGTGGATG |
| | | ACCCAGGCCGAAGAGGAATACCTGGAACGGGACTTCGAGTACAAGACCCC |
| | | TGATGAGCTGCAAAAAGCCGTCGAGGAAATGAAGCGGGCCAAAGAAGAGG |
| | | CCCAGCAGAAAGAAGCCAAAGTCAAGCTGCTGACCGAGTCCGTGAATAGC |
| | | GTTATCGCTCAGGCCCCTCCTGTGGCTCAAGAGGCTCTCAAGAAAGAACT |
| | | GGAAACTCTGACCACCAACTACCAGTGGCTGTGCACCAGACTGAACGGCA |
| | | AGTGCAAGACACTGGAAGAAGTGTGGGCCTGCTGGCACGAACTGCTGTCC |
| | | TATCTGGAAAAGGCCAACAAGTGGCTGAACGAGGTGGAATTCAAGCTGAA |
| | | AACCACCGAGAACATCCCTGGCGGCGCTGAAGAGATTAGCGAGGTGCTGG |
| | | ACAGCCTGGAAAACCTGATGAGACACAGCGAGGACAACCCCAATCAGATC |
| | | AGAATCCTGGCTCAGACCCTGACCGATGGCGGCGTGATGGACGAGCTGAT |
| | | CAACGAGGAACTCGAAACCTTCAACAGCCGGTGGCGGGAACTGCACGAGG |
| | | AAGCTGTTCGGAGGCAGAAGTTGCTGGAACAGTCTATCCAGAGCGCACAA |
| | | GAAACCGAGAAGTCCCTGCACCTGATCCAAGAGAGCCTGACCTTCATCGA |
| | | CAAGCAGCTGGCCGCTTATATCGCCGACAAGGTGGACGCTGCTCAGATGC |
| | | CCCAAGAGGCACAGAAGATTCAGAGCGACCTGACCAGCCACGAGATTAGC |
| | | CTGGAAGAAATGAAGAAGCACAACCAGGGCAAAGAGGCCGCTCAGAGAGT |
| | | CCTGAGCCAGATCGATGTGGCACAGAAAAAGCTCCAGGATGTGTCCATGA |
| | | AGTTTCGGCTGTTTCAGAAGCCCGCCAACTTCGAGCAGAGACTGCAAGAG |
| | | TCCAAGATGATCCTGGACGAAGTCAAAATGCATCTGCCCGCACTGGAAAC |
| | | AAAGTCCGTGGAACAAGAAGTGGTGCAGTCCCAGCTGAACCACTGCGTGA |
| | | ACCTGTACAAGAGCCTGTCCGAAGTGAAGTCTGAGGTGGAAATGGTCATC |
| | | AAGACCGGCAGGCAGATCGTCCAGAAGAAGCAGACCGAGAATCCCAAAGA |
| | | ACTCGACGAGAGAGTGACCGCTCTGAAGCTGCACTACAATGAGCTGGGCG |
| | | CCAAAGTGACCGAGCGGAAGCAACAGCTTGAGAAGTGCCTGAAACTGTCT |
| | | CGGAAGATGCGGAAAGAAATGAACGTGCTGACAGAGTGGCTGGCCGCCAC |
| | | CGATATGGAACTGACTAAGAGAAGCGCCGTGGAAGGCATGCCCAGCAACC |
| | | TGGATAGTGAAGTGGCCTGGGGCAAAGCCACTCAGAAAGAGATTGAGAAG |
| | | CAGAAGGTCCACCTGAAGTCCATCACCGAAGTGGGCGAAGCCCTGAAAAC |
| | | CGTGCTGGGAAAGAAAGAGACACTGGTCGAGGACAAGCTGTCCCTGCTGA |
| | | ATTCCAACTGGATCGCCGTGACCTCCAGAGCTGAGGAATGGCTGAATCTG |
| | | CTGCTTGAGTACCAGAAACACATGGAAACGTTCGACCAGAACGTCGACCA |
| | | CATCACAAAGTGGATCATCCAGGCTGATACCCTGCTGGACGAGTCCGAGA |
| | | AGAAGAAACCCCAACAAAAAGAAGATGTGCTGAAGCGGCTGAAAGCCGAG |
| | | CTGAATGACATCCGGCCTAAGGTGGACAGCACCAGAGATCAGGCAGCCAA |
| | | CCTGATGGCCAACAGAGGCGACCACTGTCGGAAGCTCGTGGAACCTCAGA |
| | | TCAGCGAGCTTAACCACAGATTTGCCGCCATCAGCCACCGGATCAAGACA |
| | | GGCAAGGCCAGCATTCCTCTCAAAGAGCTTGAGCAGTTCAACAGCGACAT |
| | | CCAAAAGCTGCTCGAACCCCTGGAAGCCGAGATCCAACAGGGCGTCAACC |
| | | TCAAAGAAGAAGATTTCAACAAGGACATGAACGAGGACAATGAGGGCACC |
| | | GTCAAAGAACTGCTGCAGCGGGGCGATAATCTGCAGCAGCGGATTACCGA |
| | | TGAGCGCAAGCGGGAAGAGATCAAGATTAAGCAGCAGCTGCTGCAGACCA |
| | | AGCACAACGCCCTGAAGGACCTGCGGAGCCAGAGAAGAAAGAAGGCCCTG |
| | | GAAATCAGCCACCAGTGGTATCAGTACAAGCGGCAGGCCGACGACCTGCT |
| | | GAAGTGCCTGGATGACATCGAGAAGAAGCTGGCCTCTCTGCCCGAGCCTA |
| | | GGGACGAGAGAAAGATCAAAGAGATCGACCGCGAGCTGCAGAAAAAGAAA |
| | | GAGGAACTGAACGCCGTCCGCAGACAGGCCGAAGGACTTTCTGAAGATGG |
| | | CGCCGCTATGGCCGTGGAACCCACACAGATTCAGCTGAGCAAGCGGTGGC |
| | | GGGAAATCGAGAGCAAGTTCGCCCAGTTCCGGCGGCTGAATTTCGCCCAG |
| | | ATCCACACCGTGCGGGAAGAGACAATGATGGTCATGACAGAGGACATGCC |
| | | CCTTGAGATCAGCTACGTGCCCAGCACCTACCTGACCGAGATCACCCATG |
| | | TGTCTCAGGCCCTGCTGGAAGTGGAACAGCTGCTGAATGCCCCTGACCTG |
| | | TGCGCCAAGGACTTCGAGGACCTGTTCAAGCAAGAGGAAAGCCTGAAGAA |
| | | CATCAAGGACAGCCTGCAGCAGAGCAGCGGCCGGATCGATATCATCCACA |
| | | GCAAGAAAACCGCCGCACTGCAGAGCGCCACACCTGTGGAAAGAGTGAAG |
| | | CTGCAAGAGGCCCTGAGCCAGCTGGATTTCCAGTGGGAGAAAGTGAACAA |
| | | GATGTACAAGGACCGGCAGGGCAGATTCGACCGCAGCGTTGAAAAGTGGC |
| | | GGCGGTTCCACTACGACATCAAGATCTTCAACCAGTGGCTGACCGAGGCC |
| | | GAGCAGTTCCTGAGAAAGACACAGATCCCCGAGAACTGGGAGCACGCCAA |
| | | GTACAAGTGGTATCTGAAAGAGCTGCAGGACGGCATCGGCCAGAGACAGA |

-continued

| SEQ ID NO | Description | SEQ |
|---|---|---|
| | | CAGTCGTGCGGACACTGAATGCCACCGGCGAGGAAATCATCCAGCAGTCC<br>AGCAAGACCGACGCCAGCATCCTGCAAGAGAAGCTGGGCAGCCTGAACCT<br>GCGGTGGCAAGAAGTGTGCAAGCAGCTGAGCGACCGGAAGAAGCGGCTGG<br>AAGAACAGAAGAATATCCTGAGCGAGTTCCAGCGGGACCTGAACGAGTTC<br>GTGCTGTGGCTCGAAGAGGCCGACAATATCGCCAGCATTCCCCTGGAACC<br>TGGCAAAGAGCAGCAGCTGAAAGAAAAGCTGGAACAAGTGAAACTGCTGG<br>TCGAGGAACTGCCCCTGAGACAGGGAATCCTGAAACAGCTGAACGAGACA<br>GGCGGCCCTGTGCTGGTGTCTGCCCCTATTTCTCCCGAGGAACAGGACAA<br>GCTGGAAAACAAGCTGAAGCAGACCAACCTGCAGTGGATCAAGGTGTCCA<br>GAGCACTGCCTGAGAAGCAGGGCGAGATCGAGGCCCAGATCAAGGACCTG<br>GGACAGCTCGAAAAGAAGCTTGAGGACCTCGAAGAACAGCTCAACCATCT<br>GCTGCTTTGGCTGAGCCCCATCCGGAACCAGCTGGAAATCTACAACCAGC<br>CTAATCAAGAGGGCCCCTTCGACGTGAAAGAAACCGAGATTGCCGTGCAG<br>GCCAAGCAGCCCGATGTGGAAGAGATCCTGTCTAAGGGCCAGCACCTGTA<br>CAAAGAGAAGCCCGCCACACAGCCCGTGAAGCGGAAACTGGAAGATCTGA<br>GCAGCGAGTGGAAGGCCGTGAACCGGCTGCTGCAAGAACTGAGAGCCAAA<br>CAGCCTGATCTGGCCCCTGGCCTGACAACAATTGGCGCCTCTCCTACACA<br>GACCGTGACACTGGTCACACAGCCTGTGGTCACCAAAGAGACAGCCATCA<br>GCAAACTGGAAATGCCCAGCAGTCTGATGCTCGAAGTGCCCGCACTGGCC<br>GACTTCAATAGAGCCTGGACCGAGCTGACCGACTGGCTCAGTCTGCTGGA<br>CCAAGTCATCAAGTCCCAGAGAGTGATGGTCGGAGATCTTGAGGACATCA<br>ACGAGATGATCATTAAGCAGAAAGCCACCATGCAGGACCTTGAGCAGAGA<br>AGGCCCCAGCTTGAAGAACTGATCACCGCCGCTCAGAACCTGAAAAACAA<br>GACCAGCAATCAAGAAGCCCGGACCATCATCACCGACCGGATCGAGAGAA<br>TCCAGAACCAGTGGGACGAAGTGCAAGAGCATCTGCAGAACAGACGGCAG<br>CAGCTCAATGAGATGCTGAAGGACAGCACACAGTGGCTGGAAGCCAAAGA<br>AGAAGCCGAGCAGGTTCTCGGACAGGCCAGAGCTAAGCTGGAATCTTGGA<br>AAGAGGGACCCTACACCGTCGACGCCATCCAGAAGAAGATCACCGAGACA<br>AAGCAGCTGGCCAAGGATCTGAGACAGTGGCAGACCAATGTGGACGTGGC<br>CAACGACCTGGCTCTGAAGCTGCTGAGAGACTACAGCGCCGACGACACCA<br>GAAAGGTGCACATGATCACCGAAAACATCAACGCCTCTTGGCGGAGCATC<br>CACAAGCGGGTGTCAGAGAGAGAAGCCGCTCTGGAAGAAACACATAGACT<br>GCTCCAGCAGTTCCCACTCGACCTGGAAAAGTTCCTGGCCTGGCTGACAG<br>AAGCCGAAACCACCGCTAACGTGCTCCAGGATGCCACCAGAAAAGAGCGG<br>CTGTTGGAGGACAGCAAGGGCGTCAAAGAACTCATGAAGCAGTGGCAGGA<br>TCTGCAAGGGGAGATTGAAGCCCACACCGACGTGTACCACAACCTGGACG<br>AGAACAGCCAGAAGATCCTGCGGTCCCTGGAAGGCTCTGATGATGCTGTG<br>CTGCTTCAGAGGCGGCTGGACAACATGAACTTCAAGTGGAGCGAGCTGCG<br>GAAGAAGTCCCTGAACATCAGAAGCCACCTGGAAGCCTCCAGCGACCAGT<br>GGAAAAGACTGCACCTGTCTCTCCAAGAGCTGCTCGTGTGGCTGCAGCTG<br>AAGGATGACGAGCTGAGTAGACAGGCCCCTATCGGCGGAGATTTTCCCGC<br>CGTGCAGAAACAGAACGACGTGCACCGGGCCTTCAAGAGAGAGCTGAAAA<br>CAAAAGAACCCGTCATCATGAGCACCCTGGAAACCGTGCGGATCTTTCTG<br>ACCGAGCAGCCTCTGGAAGGACTGGAAAAGCTGTACCAAGAGCCTAGAGA<br>GCTGCCTCCTGAAGAAAGGGCCCAGAACGTGACACGGCTGCTTAGAAAGC<br>AGGCCGAGGAAGTGAACACCGAATGGGAGAAGCTGAACCTCCACTCCGCC<br>GACTGGCAGCGGAAGATCGATGAGACACTGGAACGGCTGCGGGAACTGCA<br>AGAAGCCACAGACGAGCTGGACCTGAAACTGCGGCAGGCTGAAGTGATCA<br>AAGGCTCCTGGCAGCCAGTGGGCGATCTGCTGATCGATAGCCTGCAGGAC<br>CATCTGGAAAAAGTCAAGGCCCTGCGGGGAGAGATCGCCCCTCTCAAAGA<br>AAACGTGTCCCACGTGAACGATCTGGCCAGGCAGCTGACAACACTGGGCA<br>TCCAGCTGAGCCCTTACAACCTGTCTACCTTGGAGGACCTGAATACCCGG<br>TGGAAGCTGCTCCAAGTGGCCGTCGAGGATAGAGTGCGGCAGCTGCATGA<br>GGCTCACAGAGATTTTGGACCCGCCAGCCAGCACTTCCTGAGCACATCTG<br>TTCAAGGCCCCTGGGAGAGAGCTATCAGCCCTAACAAGGTGCCCTACTAC<br>ATCAACCACGAGACACAGACCACCTGTTGGGATCACCCCAAGATGACCGA<br>ACTGTATCAGTCCCTGGCCGACCTGAACAACGTGCGGTTTAGCGCCTACC<br>GGACCGCCATGAAGCTGCGCAGACTGCAGAAAGCTCTGTGCCTGGACCTG<br>CTGTCTCTGAGCGCTGCTTGTGATGCCCTGGACCAGCATAACCTCAAGCA<br>GAACGACCAGCCTATGGACATCCTGCAGATCATCAACTGCCTGACCACCA<br>TCTACGACCGGCTCGAACAAGAGCACAACAACCTGGTCAACGTGCCCCTG<br>TGCGTGGACATGTGCCTGAATTGGCTGCTGAACGTGTACGACACCGGCAG<br>AACCGGCAGGATCAGAGTGCTGAGCTTCAAGACCGGCATCATCTCCCTGT<br>GCAAGGCCCACCTTGAGGATAAGTACCGCTACCTGTTTAAGCAGGTCGCC<br>AGCAGCACCGGCTTTTGCGACCAAAGAAGGCTGGGACTGCTGCTCCACGA<br>CAGCATTCAGATCCCTAGACAGCTGGGCGAAGTGGCCTCTTTCGGCGGCT<br>CTAATATCGAGCCTAGCGTGCGGAGCTGCTTCCAGTTCGCCAACAACAAG<br>CCCGAGATTGAGGCCGCACTGTTCCTGGACTGGATGAGACTGGAACCCCA<br>GAGCATGGTCTGGCTGCCTGTGCTGCATAGAGTGGCCGCAGCCGAAACAG<br>CCAAGCACCAGGCCAAGTGCAACATCTGCAAAGAGTGCCCCATCATCGGC<br>TTCCGGTACAGATCCCTGAAGCACTTCAACTACGATATCTGCCAGTCCTG<br>CTTCTTCAGCGGCAGAGTGGCCAAGGGCCACAAGATGCACTACCCCATGG<br>TGGAATACTGCACCCCTACCACCTCTGGCGAGGACGTGCGGGATTTTGCC<br>AAGGTGCTCAAGAACAAGTTCCGGACCAAGCGCTACTTCGCTAAGCACCC<br>CAGAATGGGCTACCTGCCAGTGCAGACAGTGCTTGAGGGCGACAACATGG |

-continued

| SEQ ID NO | Description | SEQ |
|---|---|---|
| | | AAACCCCTGTGACTCTGATCAACTTCTGGCCCGTGGATAGCGCCCCTGCT<br>AGTTCTCCTCAGCTGTCTCACGACGATACCCACAGCAGAATCGAGCACTA<br>CGCCTCCAGACTGGCCGAGATGGAAAACAGCAACGGCAGCTACCTGAATG<br>ACAGCATCAGCCCCAACGAGAGCATCGACGACGAACATCTGCTCATTCAG<br>CACTACTGCCAGAGCCTGAATCAGGACAGCCCTCTGTCTCAGCCTAGAAG<br>CCCTGCACAGATCCTGATCAGCCTGGAAAGCGAGGAACGCGGCGAGCTGG<br>AAAGAATCCTGGCAGACCTGGAAGAGGAAAACCGGAACCTGCAGGCCGAA<br>TACGACAGACTCAAGCAGCAGCACGAGCACAAGGGACTGTCTCCACTGCC<br>TTCTCCACCTGAAATGATGCCCACCTCTCCACAGAGCCCCAGAGATGCCG<br>AGCTGATTGCCGAAGCCAAACTGCTGAGGCAGCACAAAGGCAGACTCGAA<br>GCCAGAATGCAGATTCTCGAAGATCACAACAAGCAGCTCGAATCCCAGCT<br>GCACAGACTTAGGCAGCTGCTGGAACAGCCTCAGGCAGAGGCCAAAGTGA<br>ATGGCACCACCGTGTCTAGCCCTAGCACAAGCCTGCAGAGATCCGACAGC<br>AGCCAGCCAATGCTTCTGAGAGTCGTGGGCTCCCAGACCAGCGATTCTAT<br>GGGCGAAGAGGACCTGCTCAGCCCTCCTCAGGATACAAGCACCGGCCTGG<br>AAGAAGTGATGGAACAACTGAACAACAGCTTCCCCAGCAGCAGAGGCAGA<br>AACACCCCTGGCAAGCCCATGCGCGAGGACACCATGTGATAACTCGAGAA<br>TCAACCTCTGGATTACAAAATTTGTGAAAGATTGACTGGTATTCTTAACT<br>ATGTTGCTCCTTTTACGCTATGTGGATACGCTGCTTTAATGCCTTTGTAT<br>CATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTG<br>GCGTGGTGTGCACTGTGTTTGCTGACGCAACCCCCACTGGTTGGGGCATT<br>GCCACCACCTGTCAGCTCCTTTCCGGGACTTTCGCTTTCCCCCTCCCTAT<br>TGCCACGGCGGAACTCATCGCCGCCTGCCTTGCCCGCTGCTGGACAGGGG<br>CTCGGCTGTTGGGCACTGACAATTCCGTGGGGTGTGCCTTCTAGTTGCCA<br>GCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAA<br>GGGGGAGGATTGGGAAGACAATAGCAGGCATGCTGGGGATGCGGTGGGCT<br>CTATGGGAAGATGTCTACTGAGCTGTGCGATCCCTGCTGGGGACTTTCCG<br>CTGGGGACTTTCCGCTGGGGACTTTCCGCCTTCAGCTAAGGAAGCTACCA<br>ATATTTAGAGGTACATTTTGTTCTAGAACAAAATGTACCGGTACATTTTG<br>TTCTGGTACATTTTGTTCTATTAAGGACAACGTAAGTATAGCGCATAGAC<br>ACGTGGCGCCATCGGATCCCGGGCCCGTCGACTGCAGAGGCCTGCATGCA<br>AGCTTGGCGTAATCATGGTCATAGCTGTTTCCTGTGTGAAATTGTTATCC<br>GCTCACAATTCCACACAACATACGAGCCGGAAGCATAAAGTGTAAAGCCT<br>GGGGTGCCTAATGAGTGAGCTAACTCACATTAATTGCGTTGCGCTCACTG<br>CCCGCTTTCCAGTCGGGAAACCTGTCGTGCCAGCTGCATTAATGAATCGG<br>CCAACGCGCGGGGAGAGGCGGTTTGCGTATTGGGCGCTCTTCCGCTTCCT<br>CGCTCACTGACTCGCTGCGCTCGGTCGTTCGGCTGCGGCGAGCGGTATCA<br>GCTCACTCAAAGGCGGTAATACGGTTATCCACAGAATCAGGGGATAACGC<br>AGGAAAGAACATGTGAGCAAAAGGCCAGCAAAAGGCCAGGAACCGTAAAA<br>AGGCCGCGTTGCTGGCGTTTTTCCATAGGCTCCGCCCCCCTGACGAGCAT<br>CACAAAAATCGACGCTCAAGTCAGAGGTGGCGAAACCCGACAGGACTATA<br>AAGATACCAGGCGTTTCCCCCTGGAAGCTCCCTCGTGCGCTCTCCTGTTC<br>CGACCCTGCCGCTTACCGGATACCTGTCCGCCTTTCTCCCTTCGGGAAGC<br>GTGGCGCTTTCTCATAGCTCACGCTGTAGGTATCTCAGTTCGGTGTAGGT<br>CGTTCGCTCCAAGCTGGGCTGTGTGCACGAACCCCCCGTTCAGCCCGACC<br>GCTGCGCCTTATCCGGTAACTATCGTCTTGAGTCCAACCCGGTAAGACAC<br>GACTTATCGCCACTGGCAGCAGCCACTGGTAACAGGATTAGCAGAGCGAG<br>GTATGTAGGCGGTGCTACAGAGTTCTTGAAGTGGTGGCCTAACTACGGCT<br>ACACTAGAAGAACAGTATTTGGTATCTGCGCTCTGCTGAAGCCAGTTACC<br>TTCGGAAAAAGAGTTGGTAGCTCTTGATCCGGCAAACAAACCACCGCTGG<br>TAGCGGTGGTTTTTTTGTTTGCAAGCAGCAGATTACGCGCAGAAAAAAAG<br>GATCTCAAGAAGATCCTTTGATCTTTTCTACGGGGTCTGACGCTCAGTGG<br>AACGAAAACTCACGTTAAGGGATTTTGGTCATGAGATTATCAAAAAGGAT<br>CTTCACCTAGATCCTTTTAAATTAAAAATGAAGTTTTAAATCAATCTAAA<br>GTATATATGAGTAAACTTGGTCTGACAGTTACCAATGCTTAATCAGTGAG<br>GCACCTATCTCAGCGATCTGTCTATTTCGTTCATCCATAGTTGCCTGACT<br>CCCCGTCGTGTAGATAACTACGATACGGGAGGGCTTACCATCTGGCCCCA<br>GTGCTGCAATGATACCGCGAGACCCACGCTCACCGGCTCCAGATTTATCA<br>GCAATAAACCAGCCAGCCGGAAGGGCCGAGCGCAGAAGTGGTCCTGCAAC<br>TTTATCCGCCTCCATCCAGTCTATTAATTGTTGCCGGGAAGCTAGAGTAA<br>GTAGTTCGCCAGTTAATAGTTTGCGCAACGTTGTTGCCATTGCTACAGGC<br>ATCGTGGTGTCACGCTCGTCGTTTGGTATGGCTTCATTCAGCTCCGGTTC<br>CCAACGATCAAGGCGAGTTACATGATCCCCCATGTTGTGCAAAAAAGCGG<br>TTAGCTCCTTCGGTCCTCCGATCGTTGTCAGAAGTAAGTTGGCCGCAGTG<br>TTATCACTCATGGTTATGGCAGCACTGCATAATTCTCTTACTGTCATGCC<br>ATCCGTAAGATGCTTTTCTGTGACTGGTGAGTACTCAACCAAGTCATTCT<br>GAGAATAGTGTATGCGGCGACCGAGTTGCTCTTGCCCGGCGTCAATACGG<br>GATAATACCGCGCCACATAGCAGAACTTTAAAAGTGCTCATCATTGGAAA<br>ACGTTCTTCGGGGCGAAAACTCTCAAGGATCTTACCGCTGTTGAGATCCA<br>GTTCGATGTAACCCACTCGTGCACCCAACTGATCTTCAGCATCTTTTACT<br>TTCACCAGCGTTTCTGGGTGAGCAAAAACAGGAAGGCAAAATGCCGCAAA<br>AAAGGGAATAAGGGCGACACGGAAATGTTGAATACTCATACTCTTCCTTT |

-continued

| SEQ ID NO | Description | SEQ |
|---|---|---|
| | | TTCAATATTATTGAAGCATTTATCAGGGTTATTGTCTCATGAGCGGATAC ATATTTGAATGTATTTAGAAAAATAAACAAATAGGGGTTCCGCGCACATT TCCCCGAAAAGTGCCACCTGACGTCTAAGAAACCATTATTATCATGACAT TAACCTATAAAAATAGGCGTATCACGAGGCCCTTTCGTCTCGCGCGTTTC GGTGATGACGGTGAAAACCTCTGACACATGCAGCTCCCGGAGACGGTCAC AGCTTGTCTGTAAGCGGATGCCGGGAGCAGACAAGCCCGTCAGGGCGCGT CAGCGGGTGTTGGCGGGTGTCGGGGCTGGCTTAACTATGCGGCATCAGAG CAGATTGTACTGAGAGTGCACCATATGCGGTGTGAAATACCGCACAGATG CGTAAGGAGAAAATACCGCATCAGGCGCCATTCGCCATTCAGGCTGCGCA ACTGTTGGGAAGGGCGATCGGTGCGGGCCTCTTCGCTATTACGCCAGCTG GCGAAAGGGGGATGTGCTGCAAGGCGATTAAGTTGGGTAACGCCAGGGTT TTCCCAGTCACGACGTTGTAAAACGACGGCCAGTGAATTCGAGCTCGGTA CCTCGCGAATGCATCTAGAAGCTGCATGTCTAAGCTAGACCCTTCAGATT AAAAATAACTGAGGTAAGGGCCTGGGTAGGGGAGGTGGTGTGAGACGCTC CTGTCTCTCCTCTATCTGCCCATCGGCCCTTTGGGGAGGAGGAATGTGCC CAAGGACTAAAAAAAGGCCATGGAGCCAGAGGGGCGAGGGCAACAGACCT TTCATGGGCAAACCTTGGGGCCCTGCTGTCTAGCATGCCCCACTACGGGT CTAGGCTGCCCATGTAAGGAGGCAAGGCCTGGGGACACCCGAGATGCCTG GTTATAATTAACCCAGACATGTGGCTGCCCCCCCCCCCCCAACACCTGCT GCCTCTAAAAATAACCCTGTCCCTGGTGGATCCCCTGCATGCGAAGATCT TCGAACAAGGCTGTGGGGGACTGAGGGCAGGCTGTAACAGGCTTGGGGGC CAGGGCTTATACGTGCCTGGGACTCCCAAAGTATTACTGTTCCATGTTCC CGGCGAAGGGCCAGCTGTCCCCCGCCAGCTAGACTCAGCACTTAGTTTAG GAACCAGTGAGCAAGTCAGCCCTTGGGGCAGCCCATACAAGGCCATGGGG CTGGGCAAGCTGCACGCCTGGGTCCGGGGTGGGCACGGTGCCCGGGCAAC GAGCTGAAAGCTCATCTGCTCTCAGGGGCCCCTCCCTGGGGACAGCCCCT CCTGGCTAGTCACACCCTGTAGGCTCCTCTATATAACCCAGGGGCACAGG GGCTGCCCTCATTCTACCACCACCTCCACAGCAC |
| 51. | hBGi intron | TCTGGATCCACTGCTTAAATACGGACGAGGACAGGGCCCTGTCTCCTCAG CTTCAGGCACCACCACTGACCTGGGACAGTGAATCGTAAGTACTAGCAGC TACAATCCAGCTACCATTCTGCTTTTATTTTATGGTTGGGATAAGGCTGG ATTATTCTGAGTCCAAGCTAGGCCCTTTTGCTAATCATGTTCATACCTCT TATCTTCCTCCCACAGCTCCTGGGCAACGTGCTGGTCTGTGTGCTGGCCC ATCACTTTGGCAAAGAATTGCGATCGCCACC |

What is claimed is:

1. A nucleic acid comprising a nucleic acid sequence having at least 90% sequence identity to SEQ ID NO: 34.

2. The nucleic acid of claim 1, wherein the nucleic acid sequence has at least 91% sequence identity to SEQ ID NO: 34.

3. The nucleic acid of claim 1, wherein the nucleic acid sequence has at least 92% sequence identity to SEQ ID NO: 34.

4. The nucleic acid of claim 1, wherein the nucleic acid sequence has at least 93% sequence identity to SEQ ID NO: 34.

5. The nucleic acid of claim 1, wherein the nucleic acid sequence has at least 95% sequence identity to SEQ ID NO: 34.

6. The nucleic acid of claim 1, wherein the nucleic acid sequence has at least 97% sequence identity to SEQ ID NO: 34.

7. The nucleic acid of claim 1, wherein the nucleic acid sequence has at least 99% sequence identity to SEQ ID NO: 34.

8. The nucleic acid of claim 1, wherein the nucleic acid sequence is SEQ ID NO: 34.

9. The nucleic acid of claim 1, wherein the nucleic acid sequence encodes a dystrophin protein.

10. The nucleic acid of claim 1, wherein the nucleic acid sequence encodes a full length dystrophin protein.

11. The nucleic acid of claim 1, wherein the nucleic acid sequence encodes a dystrophin protein at least 3500 amino acids in length.

12. The nucleic acid of claim 1, wherein the nucleic acid sequence encodes a protein having at least 90% sequence identity to SEQ ID NO: 13.

13. The nucleic acid of claim 1, wherein the nucleic acid sequence comprises a muscle tissue specific promoter sequence.

14. The nucleic acid of claim 13, wherein the muscle tissue specific promoter sequence enhances expression of a dystrophin protein in a muscle cell compared to a nucleic acid without the muscle tissue specific promoter sequence.

15. The nucleic acid of claim 14, wherein the muscle cell comprises a myocyte, a cardiomyocyte, or a smooth muscle cell.

16. The nucleic acid of claim 1, wherein the nucleic acid sequence is an expression cassette for a dystrophin protein.

17. The nucleic acid of claim 1, wherein the nucleic acid sequence is an expression cassette for a dystrophin protein optimized for expression of the dystrophin protein in mammalian cells.

18. The nucleic acid of claim 1, wherein the nucleic acid sequence is an expression cassette for a dystrophin protein optimized for expression of the dystrophin protein in myocytes.

19. The nucleic acid of claim 1, wherein the nucleic acid sequence is comprised within a nucleic acid delivery vector having the nucleic acid sequence of SEQ ID NO: 17.

* * * * *